US011236046B2

(12) United States Patent
Chen et al.

(10) Patent No.: US 11,236,046 B2
(45) Date of Patent: Feb. 1, 2022

(54) SUBSTITUTED HETEROCYCLIC SULFONAMIDE COMPOUNDS USEFUL AS TRPA1 MODULATORS

(71) Applicant: Genentech, Inc., South San Francisco, CA (US)

(72) Inventors: Huifen Chen, South San Francisco, CA (US); Yanyan Chu, Beijing (CN); Steven Do, South San Francisco, CA (US); Anthony Estrada, San Mateo, CA (US); Baihua Hu, Beijing (CN); Aleksandr Kolesnikov, South San Francisco, CA (US); Xingyu Lin, Beijing (CN); Joseph P. Lyssikatos, Piedmont, CA (US); Daniel Shore, South San Francisco, CA (US); Vishal Verma, South San Francisco, CA (US); Lan Wang, South San Francisco, CA (US); Guosheng Wu, Beijing (CN); Po-wai Yuen, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/657,102

(22) Filed: Oct. 18, 2019

(65) Prior Publication Data

US 2020/0048197 A1 Feb. 13, 2020

Related U.S. Application Data

(63) Continuation of application No. 16/001,770, filed on Jun. 6, 2018, now abandoned, which is a continuation of application No. 15/851,322, filed on Dec. 21, 2017, now abandoned, which is a continuation of application No. PCT/EP2014/071593, filed on Oct. 9, 2014.

(60) Provisional application No. 61/890,127, filed on Oct. 11, 2013.

(30) Foreign Application Priority Data

Sep. 12, 2014 (WO) ................ PCT/CN2014/086380

(51) Int. Cl.

| | |
|---|---|
| ***C07D 207/48*** | (2006.01) |
| ***C07D 403/12*** | (2006.01) |
| ***C07D 401/14*** | (2006.01) |
| ***C07D 401/12*** | (2006.01) |
| ***C07D 403/14*** | (2006.01) |
| ***C07D 417/12*** | (2006.01) |
| ***C07D 451/02*** | (2006.01) |
| ***C07D 491/048*** | (2006.01) |
| ***C07D 405/14*** | (2006.01) |

(52) U.S. Cl.

CPC ......... *C07D 207/48* (2013.01); *C07D 401/12* (2013.01); *C07D 401/14* (2013.01); *C07D 403/12* (2013.01); *C07D 403/14* (2013.01); *C07D 405/14* (2013.01); *C07D 417/12* (2013.01); *C07D 451/02* (2013.01); *C07D 491/048* (2013.01)

(58) Field of Classification Search

CPC .. C07D 207/48; C07D 401/12; C07D 401/14; C07D 403/12; C07D 403/14; C07D 417/12; C07D 491/048; C07D 405/14; C07D 451/02; A61K 31/4025; A61K 31/4155; A61K 31/506

See application file for complete search history.

(56) References Cited

U.S. PATENT DOCUMENTS

2012/0083474 A1 * 4/2012 Berthelot ................ A61P 29/00
514/157

* cited by examiner

*Primary Examiner* — Jean P Cornet
(74) *Attorney, Agent, or Firm* — Robert C. Hall

(57) ABSTRACT

The invention is concerned with the compounds of formula I or II:

I or II

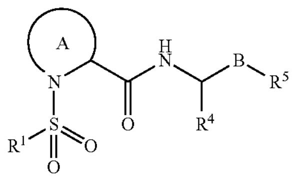

and salts thereof. In addition, the present invention relates to methods of manufacturing and methods of using the compounds of formula I or II as well as pharmaceutical compositions containing such compounds. The compounds may be useful in treating diseases and conditions mediated by TRPA1, such as pain.

1 Claim, No Drawings

SUBSTITUTED HETEROCYCLIC SULFONAMIDE COMPOUNDS USEFUL AS TRPA1 MODULATORS

CROSS REFERENCE TO RELATED APPLICATIONS

This application is a continuation of U.S. patent application Ser. No. 16/001,770 filed on Jun. 6, 2018, which is a continuation of U.S. patent application Ser. No. 15/851,322 filed on Dec. 21, 2017, which is a continuation of International Application No. PCT/EP2014/071593 having an international filing date of Oct. 9, 2014, the entire contents of which are incorporated herein by reference, and which claims the benefit of and priority to U.S. Provisional Application Ser. No. 61/890,127, filed Oct. 11, 2013, and to Chinese International Application Serial No. PCT/CN2014/086380, filed Sep. 12, 2014, both of which are hereby incorporated by reference in their entireties.

FIELD OF THE INVENTION

The present invention relates to substituted sulfonamide compounds, their manufacture, pharmaceutical compositions containing them and their use as Transient Receptor Potential (TRP) channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor.'

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., *J. Neurosci* 27, (2007) 4443-4451; Kremayer et al., *Neuron* 66 (2010) 671-680; Wei et al., *Pain* 152 (2011) 582-591); Wei et al., *Neurosci Lett* 479 (2010) 253-256)) providing additional rationale for the utility of small molecule TRPA1 inhibitors in the treatment of pain disorders.

SUMMARY OF THE INVENTION

The invention provides a compound of the invention which is a compound of Formula I:

I

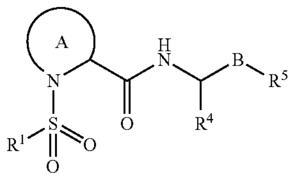

wherein:

(1) A is

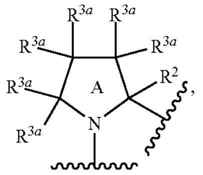

B is $B^1$ and $R^5$ is $R^{5a}$; or (2) A is

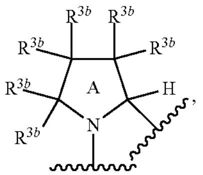

B is $B^2$ and $R^5$ is $R^{5b}$; or (3) A is

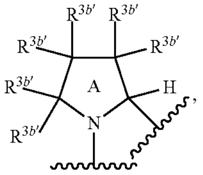

B is $B^3$ and $R^5$ is $R^{5a}$; or (4) A is

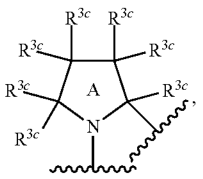

B is $B^4$ and $R^5$ is $R^{5a}$; or (5) A is

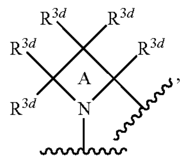

B is $B^1$ and $R^5$ is $R^{5a}$;

B is $B^1$, $B^2$, $B^3$ or $B^4$;

$B^1$ is a 5-membered heteroaryl comprising 2 or 3 nitrogen atoms in the ring or a 6-membered heteroaryl, wherein any 5-membered heteroaryl or 6-membered heteroaryl of $B^1$ is optionally substituted with one or more groups independently selected from halogen, $(C_1$-$C_6)$alkyl, —O$(C_1$-$C_6)$alkyl and $(C_3$-$C_7)$cycloalkyl;

$B^2$ is a pyridinyl, wherein any pyridinyl of $B^2$ is optionally substituted with one or more groups independently selected from halogen, $(C_1$-$C_6)$alkyl, —O$(C_1$-$C_6)$alkyl and $(C_3$-$C_7)$cycloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1$-$C_6)$alkyl, —O$(C_1$-$C_6)$alkyl and $(C_3$-$C_7)$cycloalkyl, and wherein when $B^3$ is pyrimidinyl which is attached to the remainder of formula I at the 4 and 6 positions of the pyrimidinyl, then $R^{5a}$ is not pyrrolidinyl or substituted pyrrolidinyl;

$B^4$ is a 5-membered heteroaryl or 6-membered heteroaryl, wherein any 5-membered heteroaryl or 6-membered heteroaryl of $B^4$ is optionally substituted with one or more groups independently selected from halogen, $(C_1$-$C_6)$alkyl, —O$(C_1$-$C_6)$alkyl and $(C_3$-$C_7)$cycloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1$-$C_6)$alkyl and $(C_1$-$C_6)$haloalkyl;

$R^2$ is halogen, $(C_1$-$C_6)$alkyl or CN, wherein any $(C_1$-$C_6)$alkyl of $R^2$ is optionally substituted with one or more groups independently selected from halogen, —OH and —O$(C_1$-$C_6)$alkyl;

each $R^{3a}$ is independently selected from H, halogen and $(C_1$-$C_6)$alkyl;

one $R^{3b}$ group is halogen or $(C_1$-$C_6)$alkyl and the remaining $R^{3b}$ groups are independently selected from H and $(C_1$-$C_6)$alkyl;

one $R^{3b'}$ group is halogen or $(C_1$-$C_6)$alkyl and the remaining $R^{3b'}$ groups are independently selected from H and $(C_1$-$C_6)$alkyl;

two $R^{3c}$ groups attached to different non-adjacent carbon atoms are combined to form a $(C_2$-$C_4)$alkyl linker, wherein the $(C_2$-$C_4)$alkyl linker is optionally substituted with one or more groups independently selected from halogen and $(C_1$-$C_6)$alkyl, and the remaining $R^{3c}$ groups are independently selected from H, halogen and $(C_1$-$C_6)$alkyl;

one $R^{3d}$ group is halogen, $(C_1$-$C_6)$alkyl or CN and the remaining $R^{3d}$ groups are independently selected from H, halogen and $(C_1$-$C_6)$alkyl, wherein any $(C_1$-$C_6)$alkyl of $R^{3d}$ is optionally substituted with one or more groups independently selected from halogen, —OH and —O$(C_1$-$C_6)$alkyl;

$R^4$ is H, $(C_1$-$C_6)$alkyl or $(C_1$-$C_6)$haloalkyl;

$R^5$ is $R^{5a}$ or $R^{5b}$;

$R^{5a}$ is a phenyl, 5-membered heteroaryl, 6-membered heteroaryl, 4, 5, 6 or 7-membered heterocycle or $(C_3$-$C_7)$cycloalkyl, wherein any phenyl, 5-membered heteroaryl, 6-membered heteroaryl, 4, 5, 6 or 7-membered heterocycle or $(C_3$-$C_7)$cycloalkyl of $R^{5a}$ is optionally substituted with one or more groups independently selected from halogen, $(C_1$-$C_6)$alkyl, $(C_1$-$C_6)$haloalkyl, —CN, $(C_3$-$C_7)$cycloalkyl, —O$(C_1$-$C_6)$alkyl, —O$(C_1$-$C_6)$haloalkyl, —S$(C_1$-$C_6)$alkyl and —S$(C_1$-$C_6)$haloalkyl; and $R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6 or 7-membered heterocycle of $R^{5b}$ is optionally substituted with one or more groups independently selected from halogen, $(C_1$-$C_6)$alkyl, $(C_1$-$C_6)$haloalkyl, —CN, $(C_3$-$C_7)$cycloalkyl, —O$(C_1$-$C_6)$alkyl, —O$(C_1$-$C_6)$haloalkyl, —S$(C_1$-$C_6)$alkyl and —S$(C_1$-$C_6)$haloalkyl, and wherein any 5-membered heterocycle of $R^{5b}$ is substituted with one or more groups independently selected from halogen, $(C_1$-$C_6)$alkyl, $(C_1$-$C_6)$haloalkyl, —CN, $(C_3$-$C_7)$cycloalkyl, —O$(C_1$-$C_6)$alkyl, —O$(C_1$-$C_6)$haloalkyl, —S$(C_1$-$C_6)$alkyl and —S$(C_1$-$C_6)$haloalkyl;

or a pharmaceutically acceptable salt thereof.

The invention also provides a compound of the invention which is a compound of formula II:

II

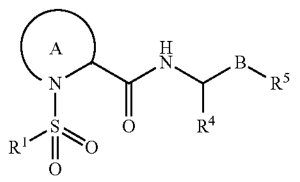

wherein:

(1) A is

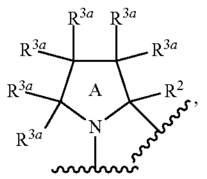

B is $B^1$ and $R^5$ is $R^{5a}$; or (2) A is

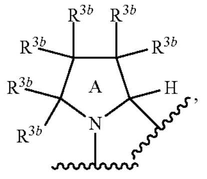

B is $B^2$ and $R^5$ is $R^{5b}$; or (3) A is

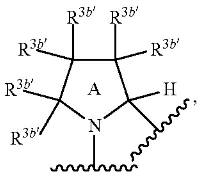

B is $B^3$ and $R^5$ is $R^{5a}$; or (4) A is

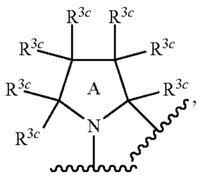

B is $B^4$ and $R^5$ is $R^{5a}$; or (5) A is

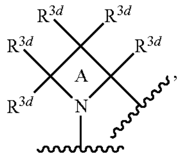

B is $B^1$ and $R^5$ is $R^{5a}$; or (6) A is

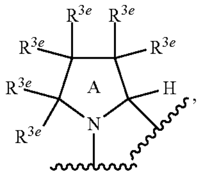

B is $B^5$ and $R^5$ is $R^{5a}$; or (7) A is

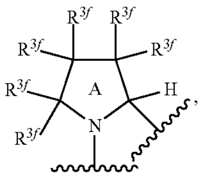

B is $B^3$ and $R^5$ is $R^{5a}$;

B is $B^1$, $B^2$, $B^3$, $B^4$, or $B^5$;

$B^1$ is a 5-membered heteroaryl comprising 2 or 3 nitrogen atoms in the ring or a 6-membered heteroaryl, wherein any 5-membered heteroaryl or 6-membered heteroaryl of B' is optionally substituted with one or more groups independently selected from halogen, $(C_1\text{-}C_6)$alkyl, —O$(C_1\text{-}C_6)$alkyl and $(C_3\text{-}C_7)$cycloalkyl;

$B^2$ is a pyridinyl, wherein any pyridinyl of $B^2$ is optionally substituted with one or more groups independently selected from halogen, $(C_1\text{-}C_6)$alkyl, —O$(C_1\text{-}C_6)$alkyl, —O$(C_1\text{-}C_6)$alkyl-O$(C_1\text{-}C_6)$alkyl, $(C_3\text{-}C_7)$cycloalkyl, $(C_1\text{-}C_6)$haloalkyl, —CN, and 6-membered heteroaryl, wherein any 6-membered heteroaryl is optionally substituted with one or more $(C_1\text{-}C_6)$alkyl or $(C_1\text{-}C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1\text{-}C_6)$alkyl, —O$(C_1\text{-}C_6)$alkyl, $(C_3\text{-}C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^4$ is a 5-membered heteroaryl, 6-membered heteroaryl, or phenyl, wherein any 5-membered heteroaryl, 6-membered heteroaryl, or phenyl of $B^4$ is optionally substituted with one or more groups independently selected from halogen, —CN, $(C_1\text{-}C_6)$alkyl, —O$(C_1\text{-}C_6)$alkyl and $(C_3\text{-}C_7)$cycloalkyl;

$B^5$ is a phenyl optionally substituted with one or more groups independently selected from —CN, halogen, $(C_1\text{-}C_6)$alkyl, $(C_1\text{-}C_6)$haloalkyl, —O$(C_1\text{-}C_6)$alkyl, and —O$(C_1\text{-}C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1\text{-}C_6)$alkyl and $(C_1\text{-}C_6)$haloalkyl;

$R^2$ is halogen, $(C_1\text{-}C_6)$alkyl or CN, wherein any $(C_1\text{-}C_6)$alkyl of $R^2$ is optionally substituted with one or more groups independently selected from halogen, —OH and —O$(C_1\text{-}C_6)$alkyl;

each $R^{3a}$ is independently selected from H, halogen and $(C_1\text{-}C_6)$alkyl;

one $R^{3b}$ group is halogen, —CN, or $(C_1\text{-}C_6)$alkyl and the remaining $R^{3b}$ groups are independently selected from H, $(C_1\text{-}C_6)$alkyl and $(C_1\text{-}C_6)$haloalkyl;

one $R^{3b'}$ group is halogen, $(C_1\text{-}C_6)$alkyl, —CN, or $(C_1\text{-}C_6)$haloalkyl and the remaining $R^{3b'}$ groups are independently selected from H, $(C_1\text{-}C_6)$alkyl and $(C_1\text{-}C_6)$haloalkyl;

two $R^{3c}$ groups attached to different non-adjacent carbon atoms or adjacent carbon atoms are combined to form a $(C_1\text{-}C_4)$alkyl linker or a $(C_1\text{-}C_2)$alkyl-O—$(C_1\text{-}C_2)$alkyl linker, wherein the $(C_1\text{-}C_4)$alkyl linker or $(C_1\text{-}C_2)$alkyl-O—$(C_1\text{-}C_2)$alkyl linker is optionally substituted with one or more groups independently selected from halogen and $(C_1\text{-}C_6)$alkyl, and the remaining $R^{3c}$ groups are independently selected from H, halogen and $(C_1\text{-}C_6)$alkyl;

each $R^{3d}$ group is independently selected from H, halogen, $(C_1\text{-}C_6)$alkyl, and —CN, wherein any $(C_1\text{-}C_6)$alkyl of $R^{3d}$ is optionally substituted with one or more groups independently selected from halogen, —OH and —O$(C_1\text{-}C_6)$alkyl;

one $R^{3e}$ group is halogen, —CN or $(C_1\text{-}C_6)$alkyl and the remaining $R^{3e}$ groups are independently selected from H, $(C_1\text{-}C_6)$alkyl and $(C_1\text{-}C_6)$haloalkyl;

two $R^{3f}$ groups attached to the same carbon atom are combined to form a $(C_2\text{-}C_4)$alkyl linker, wherein the $(C_2\text{-}C_4)$alkyl linker is optionally substituted with one or more groups independently selected from halogen and $(C_1\text{-}C_6)$alkyl, and the remaining $R^{3f}$ groups are independently selected from H, halogen and $(C_1\text{-}C_6)$alkyl;

$R^4$ is H, $(C_1-C_6)$alkyl or $(C_1-C_6)$haloalkyl;

$R^5$ is $R^{5a}$ or $R^{5b}$;

$R^{5a}$ is a phenyl, 5-membered heteroaryl, 6-membered heteroaryl, 4, 5, 6 or 7-membered heterocycle or $(C_3-C_8)$cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$alkyl-O$(C_1-C_6)$alkyl, —O$(C_1-C_6)$haloalkyl, —S$(C_1-C_6)$alkyl, —S$(C_1-C_6)$haloalkyl, oxo, and —O—$(C_1-C_2)$alkyl-O— optionally substituted with one or more halogen, which —O—$(C_1-C_2)$alkyl-O— group is bonded to two adjacent carbon atoms of any phenyl, 5-membered heteroaryl, 6-membered heteroaryl, 4, 5, 6 or 7-membered heterocycle or $(C_3-C_8)$cycloalkyl of $R^{5a}$;

$R^{5b}$ is a phenyl, 5-membered heteroaryl, 6-membered heteroaryl or 4, 5, 6, 7 or 8-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, —O$(C_1-C_6)$alkyl, —O$(C_1-C_6)$haloalkyl, —OH, —S$(C_1-C_6)$alkyl, —S$(C_1-C_6)$haloalkyl, and $NR^6_2$, and wherein any 5-membered heterocycle of $R^{5b}$ is substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl; and each $R^6$ is independently H or $(C_1-C_6)$alkyl;

or a salt or pharmaceutically acceptable salt thereof.

The invention also provides a pharmaceutical composition comprising a compound of the invention and a pharmaceutically acceptable carrier.

The invention also provides a compound of the invention or a pharmaceutically acceptable salt thereof for use in medical therapy.

The invention also provides for a compound of the invention or a pharmaceutically acceptable salt thereof for the treatment or prophylaxis of a respiratory disorder.

The invention provides for the use of a compound of the invention or a pharmaceutically acceptable salt thereof for the preparation of a medicament for the treatment or prophylaxis of a respiratory disorder.

The invention also provides for a method for treating a respiratory disorder in a mammal (e.g., a human) comprising, administering a compound of the invention or a pharmaceutically acceptable salt thereof to the mammal.

The invention also provides for a compound of the invention or a pharmaceutically acceptable salt thereof for modulating TRPA1 activity.

In another embodiment, the invention provides for a method for modulating TRPA1 activity, comprising contacting TRPA1 with a compound of the invention or a salt thereof.

In another embodiment, the invention provides for a compound of the invention or a pharmaceutically acceptable salt thereof for the treatment or prophylaxis of a disease or condition mediated by TRPA1 activity. Within aspects of this embodiment, the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain, arthritis, itch, cough, asthma, inflammatory bowel disease, or an inner ear disorder.

In another embodiment, the invention provides for the use of a compound of the invention or a pharmaceutically acceptable salt thereof for the preparation of a medicament for the treatment or prophylaxis of a disease or condition that is mediated by TRPA1 activity. Within aspects of this embodiment, the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain, arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound of the invention or a pharmaceutically acceptable salt thereof to the mammal. Within certain aspects of this embodiment, the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain, arthritis, itch, cough, asthma, inflammatory bowel disease, or an inner ear disorder.

The invention also provides a compound of formula I or formula II or a salt thereof.

The invention also provides a compound of formula I or formula II or a pharmaceutically acceptable salt thereof.

The invention also provides processes and intermediates disclosed herein that are useful for preparing a compound of formula I or formula II or a salt thereof.

The invention also provides an invention as described herein.

DETAILED DESCRIPTION OF THE INVENTION

Definitions

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$ to $R^5$ of formula I or II refer to moieties that are attached to the core structure of formula I or II by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms.

The term "alkoxy" denotes a group of the formula —O—R', wherein R' is an alkyl group. Examples of alkoxy moieties include methoxy, ethoxy, isopropoxy, and tert-butoxy.

"Aryl" means a cyclic aromatic hydrocarbon moiety having a mono-, bi- or tricyclic aromatic ring of 6 to 16 carbon ring atoms. The aryl group can be optionally substituted as defined herein. Examples of aryl moieties include, but are not limited to, phenyl, naphthyl, phenanthryl, fluorenyl, indenyl, pentalenyl, azulenyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted. In one embodiment the aryl has 6 to 14 carbon ring atoms (i.e., $(C_6-C_{14})$ aryl). In another embodiment the aryl has 6 to 10 carbon ring atoms (i.e., $(C_6-C_{10})$aryl)

The term "heteroaryl" denotes an aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

"Cycloalkyl" means a saturated or partially unsaturated carbocyclic moiety having mono- or bicyclic (including bridged bicyclic) rings and 3 to 10 carbon atoms in the ring. The cycloalkyl moiety can optionally be substituted with one or more substituents. In particular embodiments cycloalkyl contains from 3 to 8 carbon atoms (i.e., $(C_3-C_8)$cycloalkyl). In other particular embodiments cycloalkyl contains from 3 to 6 carbon atoms (i.e., $(C_3-C_6)$cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a "spirocycloakyl" fashion such as "spirocyclopropyl":

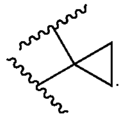 [SMILES: *C1(*)CC1]

"Heterocycle" refers to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4 heteroatoms selected from oxygen, nitrogen and sulfur in the ring with the remaining ring atoms being carbon. When used in reference to a ring atom of a heterocycle, a nitrogen or sulfur may also be in an oxidized form, and a nitrogen may be substituted with one or more $(C_1-C_6)$alkyl or groups. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, 2-azabicyclo[2.2.1]heptanyl, octahydroindolyl, or tetrahydroquinolinyl.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula I or II, which can be useful as an intermediate for isolating or purifying a compound of Formula I or II. The compounds of the present invention can also be present in the form of pharmaceutically acceptable esters (i.e., the methyl and ethyl esters of the acids of Formula I or II to be used as prodrugs). The compounds of the present invention can also be solvated, i.e. hydrated. The solvation can be effected in the course of the manufacturing process or can take place i.e. as a consequence of hygroscopic properties of an initially anhydrous compound of Formula I or II.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

In one aspect the present invention provides for compounds of formula I as described herein below as a first embodiment of the invention (embodiment "E1"):

E1: A compound of formula I:

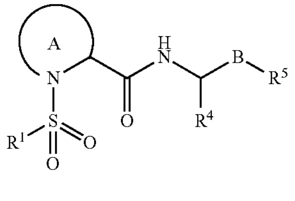

I wherein:

(1) A is

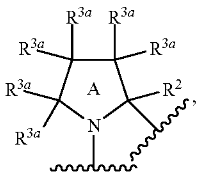

B is $B^1$ and $R^5$ is $R^{5a}$; or (2) A is

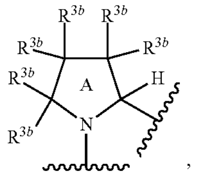

B is $B^2$ and $R^5$ is $R^{5b}$; or (3) A is

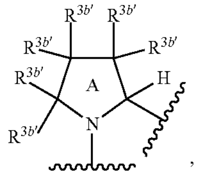

B is $B^3$ and $R^5$ is $R^{5a}$; or (4) A is

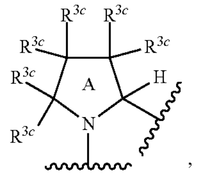

B is $B^4$ and $R^5$ is $R^{5a}$; or (5) A is

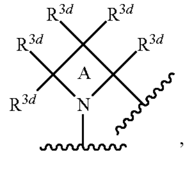

B is $B^1$ and $R^5$ is $R^{5a}$;

B is $B^1$, $B^2$, $B^3$ or $B^4$;

$B^1$ is a 5-membered heteroaryl comprising 2 or 3 nitrogen atoms in the ring or a 6-membered heteroaryl, wherein any 5-membered heteroaryl or 6-membered heteroaryl of $B^1$ is optionally substituted with one or more groups independently selected from halogen, $(C_1$-$C_6)$alkyl, —$O(C_1$-$C_6)$alkyl and $(C_3$-$C_7)$cycloalkyl;

$B^2$ is a pyridinyl, wherein any pyridinyl of $B^2$ is optionally substituted with one or more groups independently selected from halogen, $(C_1$-$C_6)$alkyl, —$O(C_1$-$C_6)$alkyl and $(C_3$-$C_7)$cycloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1$-$C_6)$alkyl, —$O(C_1$-$C_6)$alkyl and $(C_3$-$C_7)$cycloalkyl, and wherein when $B^3$ is pyrimidinyl which is attached to the remainder of formula I at the 4 and 6 positions of the pyrimidinyl, then $R^{5a}$ is not pyrrolidinyl or substituted pyrrolidinyl;

$B^4$ is a 5-membered heteroaryl or 6-membered heteroaryl, wherein any 5-membered heteroaryl or 6-membered heteroaryl of $B^4$ is optionally substituted with one or more groups independently selected from halogen, $(C_1$-$C_6)$alkyl, —$O(C_1$-$C_6)$alkyl and $(C_3$-$C_7)$cycloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1$-$C_6)$alkyl and $(C_1$-$C_6)$haloalkyl;

$R^2$ is halogen, $(C_1$-$C_6)$alkyl or CN, wherein any $(C_1$-$C_6)$alkyl of $R^2$ is optionally substituted with one or more groups independently selected from halogen, —OH and —$O(C_1$-$C_6)$alkyl;

each $R^{3a}$ is independently selected from H, halogen and $(C_1$-$C_6)$alkyl;

one $R^{3b}$ group is halogen or $(C_1$-$C_6)$alkyl and the remaining $R^{3b}$ groups are independently selected from H and $(C_1$-$C_6)$alkyl;

one $R^{3b'}$ group is halogen or $(C_1$-$C_6)$alkyl and the remaining $R^{3b'}$ groups are independently selected from H and $(C_1$-$C_6)$alkyl;

two $R^{3c}$ groups attached to different non-adjacent carbon atoms are combined to form a $(C_2$-$C_4)$alkyl linker, wherein the $(C_2$-$C_4)$alkyl linker is optionally substituted with one or more groups independently selected from halogen and $(C_1$-$C_6)$alkyl, and the remaining $R^{3c}$ groups are independently selected from H, halogen and $(C_1$-$C_6)$alkyl;

one $R^{3d}$ group is halogen, $(C_1$-$C_6)$alkyl or CN and the remaining $R^{3d}$ groups are independently selected from H, halogen and $(C_1$-$C_6)$alkyl, wherein any $(C_1$-$C_6)$alkyl of $R^{3d}$ is optionally substituted with one or more groups independently selected from halogen, —OH and —$O(C_1$-$C_6)$alkyl;

$R^4$ is H, $(C_1$-$C_6)$alkyl or $(C_1$-$C_6)$haloalkyl;

$R^5$ is $R^{5a}$ or $R^{5b}$;

$R^{5a}$ is a phenyl, 5-membered heteroaryl, 6-membered heteroaryl, 4, 5, 6 or 7-membered heterocycle or $(C_3$-$C_7)$cycloalkyl, wherein any phenyl, 5-membered heteroaryl, 6-membered heteroaryl, 4, 5, 6 or 7-membered heterocycle or $(C_3$-$C_7)$cycloalkyl of $R^{5a}$ is optionally substituted with one or more groups independently selected from halogen, $(C_1$-$C_6)$alkyl, $(C_1$-$C_6)$haloalkyl, —CN, $(C_3$-$C_7)$cycloalkyl, —$O(C_1$-$C_6)$alkyl, —$O(C_1$-$C_6)$haloalkyl, —$S(C_1$-$C_6)$alkyl and —$S(C_1$-$C_6)$haloalkyl; and $R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6 or 7-membered heterocycle of $R^{5b}$ is optionally substituted with one or more groups independently selected from halogen, $(C_1$-$C_6)$alkyl, $(C_1$-$C_6)$haloalkyl, —CN, $(C_3$-$C_7)$cycloalkyl, —$O(C_1$-$C_6)$alkyl, —$O(C_1$-$C_6)$haloalkyl, —$S(C_1$-$C_6)$alkyl and —$S(C_1$-$C_6)$haloalkyl, and wherein any 5-membered heterocycle of $R^{5b}$ is substituted with one or more groups independently selected from halogen, ($C_1$-$C_6$)alkyl, ($C_1$-$C_6$)haloalkyl, —CN, ($C_3$-$C_7$)cycloalkyl, —O($C_1$-$C_6$)alkyl, —O($C_1$-$C_6$)haloalkyl, —S($C_1$-$C_6$)alkyl and —S($C_1$-$C_6$)haloalkyl;

or a pharmaceutically acceptable salt thereof.

Additional embodiments of the invention are set forth below.

E2: The compound according to E1 which is a compound of formula I':

I'

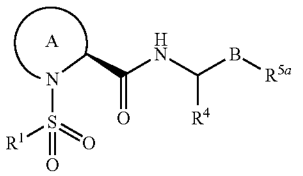

wherein:

(1) A is

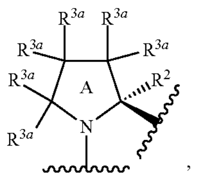

,

B is $B^1$ and $R^5$ is $R^{5a}$; or (2) A is

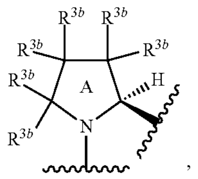

,

B is $B^2$ and $R^5$ is $R^{5b}$; or (3) A is

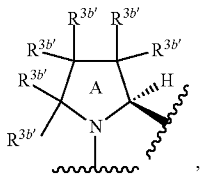

,

B is $B^3$ and $R^5$ is $R^{5a}$.

(4) A is

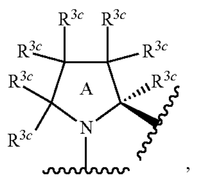

,

B is $B^4$ and $R^5$ is $R^{5a}$; or (5) A is

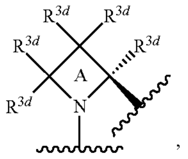

,

B is $B^1$ and $R^5$ is $R^{5a}$;

B is $B^1$, $B^2$, $B^3$ or $B^4$;

$B^1$ is a 5-membered heteroaryl comprising 2 or 3 nitrogen atoms in the ring or a 6-membered heteroaryl, wherein any 5-membered heteroaryl or 6-membered heteroaryl of $B^1$ is optionally substituted with one or more groups independently selected from halogen, ($C_1$-$C_6$)alkyl, —O($C_1$-$C_6$)alkyl and ($C_3$-$C_7$)cycloalkyl;

$B^2$ is a pyridinyl, wherein any pyridinyl of $B^2$ is optionally substituted with one or more groups independently selected from halogen, ($C_1$-$C_6$)alkyl, —O($C_1$-$C_6$)alkyl and ($C_3$-$C_7$)cycloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, ($C_1$-$C_6$)alkyl, —O($C_1$-$C_6$)alkyl and ($C_3$-$C_7$)cycloalkyl, and wherein when $B^3$ is pyrimidinyl which is attached to the remainder of formula I at the 4 and 6 positions of the pyrimidinyl, then $R^{5a}$ is not pyrrolidinyl or substituted pyrrolidinyl;

$B^4$ is a 5-membered heteroaryl or 6-membered heteroaryl, wherein any 5-membered heteroaryl or 6-membered heteroaryl of $B^4$ is optionally substituted with one or more groups independently selected from halogen, ($C_1$-$C_6$)alkyl, —O($C_1$-$C_6$)alkyl and ($C_3$-$C_7$)cycloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, ($C_1$-$C_6$)alkyl and ($C_1$-$C_6$)haloalkyl;

$R^2$ is halogen, ($C_1$-$C_6$)alkyl or CN, wherein any ($C_1$-$C_6$)alkyl of $R^2$ is optionally substituted with one or more groups independently selected from halogen, —OH and —O($C_1$-$C_6$)alkyl;

each $R^{3a}$ is independently selected from H, halogen and ($C_1$-$C_6$)alkyl;

one $R^{3b}$ group is halogen or ($C_1$-$C_6$)alkyl and the remaining $R^{3b}$ groups are independently selected from H and ($C_1$-$C_6$)alkyl;

one $R^{3b'}$ group is halogen or ($C_1$-$C_6$)alkyl and the remaining $R^{3b'}$ groups are independently selected from H and ($C_1$-$C_6$)alkyl;

two $R^{3c}$ groups attached to different non-adjacent carbon atoms are combined to form a ($C_2$-$C_4$)alkyl linker, wherein the ($C_2$-$C_4$)alkyl linker is optionally substituted with one or more groups independently selected from halogen and ($C_1$-$C_6$)alkyl, and the remaining $R^{3c}$ groups are independently selected from H, halogen and ($C_1$-$C_6$)alkyl;

one $R^{3d}$ group is halogen, ($C_1$-$C_6$)alkyl or CN and the remaining $R^{3d}$ groups are independently selected from H, halogen and ($C_1$-$C_6$)alkyl, wherein any ($C_1$-$C_6$)alkyl of $R^{3d}$ is optionally substituted with one or more groups independently selected from halogen, —OH and —O($C_1$-$C_6$)alkyl;

$R^4$ is H, $(C_1\text{-}C_6)$alkyl or $(C_1\text{-}C_6)$haloalkyl;

$R^5$ is $R^{5a}$ or $R^{5b}$;

$R^{5a}$ is a phenyl, 5-membered heteroaryl, 6-membered heteroaryl, 4, 5, 6 or 7-membered heterocycle or $(C_3\text{-}C_7)$cycloalkyl, wherein any phenyl, 5-membered heteroaryl, 6-membered heteroaryl, 4, 5, 6 or 7-membered heterocycle or $(C_3\text{-}C_7)$cycloalkyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —$O(C_1\text{-}C_6)$alkyl, —$O(C_1\text{-}C_6)$haloalkyl, —$S(C_1\text{-}C_6)$alkyl and —$S(C_1\text{-}C_6)$haloalkyl; and $R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6 or 7-membered heterocycle of $R^{5b}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —$O(C_1\text{-}C_6)$alkyl, —$O(C_1\text{-}C_6)$haloalkyl, —$S(C_1\text{-}C_6)$alkyl and —$S(C_1\text{-}C_6)$haloalkyl, and wherein any 5-membered heterocycle of $R^{5b}$ is substituted with one or more groups independently selected from halogen, $(C_1\text{-}C_6)$alkyl, $(C_1\text{-}C_6)$haloalkyl, —CN, $(C_3\text{-}C_7)$cycloalkyl, —$O(C_1\text{-}C_6)$alkyl, —$O(C_1\text{-}C_6)$haloalkyl, —$S(C_1\text{-}C_6)$alkyl and —$S(C_1\text{-}C_6)$haloalkyl;

or a pharmaceutically acceptable salt thereof.

E3: The compound according to E1 or E2, wherein each $R^{3a}$ is independently H or F.

E4: The compound according to E1 or E2, wherein one $R^{3a}$ is F and the remaining $R^{3a}$ groups are H.

E5: The compound according to E1 or E2, wherein each $R^{3a}$ is H.

E6: The compound according to any one of E1-E5, wherein $R^2$ is $(C_1\text{-}C_6)$alkyl or CN, wherein any $(C_1\text{-}C_6)$alkyl of $R^2$ is optionally substituted with one or more groups independently selected from halogen, —OH and —$O(C_1\text{-}C_6)$alkyl.

E7: The compound according to any one of E1-E5, wherein $R^2$ is —$CH_3$, —$CH_2OH$, —$CHF_2$, —$CH_2OCH_3$ or CN.

E8: The compound according to any one of E1-E5, wherein $R^2$ is —$CH_3$.

E9: The compound according to any one of E1-E8, wherein $B^1$ is a pyrazolyl, triazolyl, pyridinyl or pyrimidinyl, wherein any pyrazolyl, triazolyl, pyridinyl or pyrimidinyl of $B^1$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E10: The compound according to any one of E1-E8, wherein $B^1$ is a pyridinyl or pyrimidinyl, wherein any pyridinyl or pyrimidinyl of $B^1$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E11: The compound according to any one of E1-E8, wherein $B^1$ is:

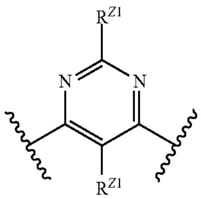

,

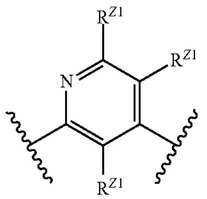

or

-continued

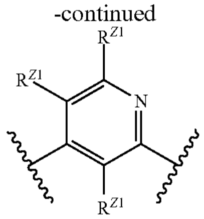

wherein each $R^{Z1}$ is independently selected from H, halogen, $(C_1\text{-}C_6)$alkyl, —$O(C_1\text{-}C_6)$alkyl and $(C_3\text{-}C_7)$cycloalkyl.

E12: The compound according to any one of E1-E8, wherein $B^1$ is:

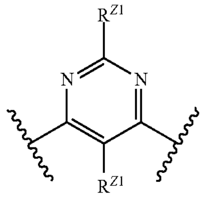

wherein each $R^{Z1}$ is independently selected from H, halogen, $(C_1\text{-}C_6)$alkyl, —$O(C_1\text{-}C_6)$alkyl and $(C_3\text{-}C_7)$cycloalkyl.

E13: The compound according to any one of E1-E8, wherein $B^1$ is a pyrazolyl or a triazolyl, wherein any pyrazolyl or triazolyl of $B^1$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E14: The compound according to any one of E1-E8, wherein $B^1$ is a pyrazolyl, wherein any pyrazolyl of $B^1$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E15: The compound according to any one of E1-E8, wherein $B^1$ is:

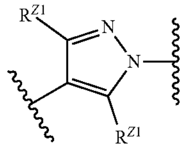

wherein each $R^{Z1}$ is independently selected from H, halogen, $(C_1\text{-}C_6)$alkyl, —$O(C_1\text{-}C_6)$alkyl and $(C_3\text{-}C_7)$cycloalkyl.

E16: The compound according to any one of E1-E15, wherein one $R^{3b}$ group is F, one $R^{3b'}$ group is F and the remaining $R^{3b}$ groups and $R^{3b'}$ groups are H.

E17: The compound according to any one of E1-E15, wherein (1) the A group

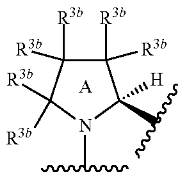

is:

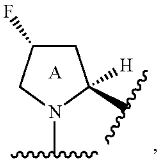

B is $B^2$ and $R^5$ is $R^{5b}$; and (2) the A group

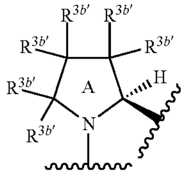

is:

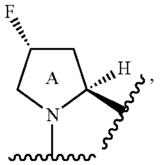

B is $B^3$ and $R^5$ is $R^{5a}$.

E18: The compound according to any one of E1-E15, wherein $B^2$ is pyridinyl, wherein any pyridinyl of $B^2$ is optionally substituted with one or more groups independently selected from halogen, $(C_1\text{-}C_6)$alkyl and $(C_3\text{-}C_7)$cycloalkyl.

E19: The compound according to any one of E1-E15, wherein $B^2$ is:

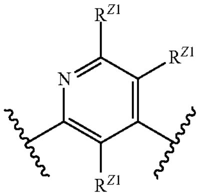

or

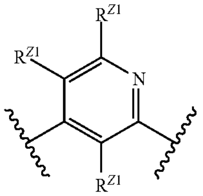

wherein each $R^{Z1}$ is independently selected from H, halogen, $(C_1\text{-}C_6)$alkyl, —$O(C_1\text{-}C_6)$alkyl and $(C_3\text{-}C_7)$cycloalkyl.

E20: The compound according to any one of E1-E19, wherein $B^3$ is pyrazolyl, triazolyl or pyrimidinyl, wherein any pyrazolyl, triazolyl or pyrimidinyl of $B^3$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E21: The compound according to any one of E1-E19, wherein $B^3$ is a pyrimidinyl, wherein any pyrimidinyl of $B^3$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E22: The compound according to any one of E1-E19, wherein $B^3$ is:

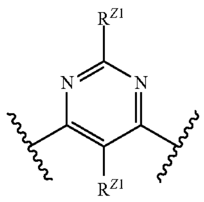

wherein each $R^{Z1}$ is independently selected from hydrogen halogen, $(C_1\text{-}C_6)$alkyl, —$O(C_1\text{-}C_6)$alkyl and $(C_3\text{-}C_7)$cycloalkyl.

E23: The compound according to any one of E1-E19, wherein $B^3$ is a pyrazolyl or a triazolyl, wherein any pyrazolyl or triazolyl of $B^3$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E24: The compound according to any one of E1-E19, wherein $B^3$ is a pyrazolyl, wherein any pyrazolyl of $B^3$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

E25: The compound according to any one of E1-E19, wherein $B^3$ is:

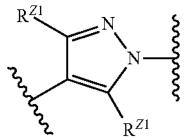

wherein each $R^{Z1}$ is independently selected from H, halogen, $(C_1\text{-}C_6)$alkyl, —$O(C_1\text{-}C_6)$alkyl and $(C_3\text{-}C_7)$cycloalkyl.

E26: The compound according to any one of E1-E25, wherein one two $R^{3c}$ groups attached to different non-adjacent carbon atoms are combined to form a —$CH_2CH_2$— linker and the remaining $R^{3c}$ groups are each H.

E27: The compound according to any one of E1-E25, wherein the

A group

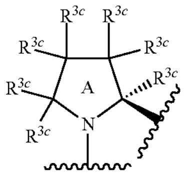

is:

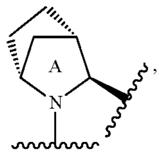,
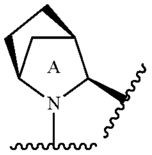
or
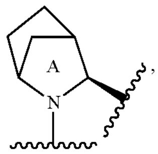,

B is $B^4$ and $R^5$ is $R^{5a}$.

E28: The compound according to any one of E1-E27, wherein $B^4$ is a pyrazolyl, triazolyl, pyridinyl or pyrimidinyl, wherein any pyrazolyl, triazolyl, pyridinyl or pyrimidinyl of $B^4$ is optionally substituted with one or more groups independently selected from halogen, $(C_1-C_6)$alkyl, —O$(C_1-C_6)$alkyl and $(C_3-C_7)$cycloalkyl.

E29: The compound according to any one of E1-E27, wherein $B^4$ is a pyrimidinyl, wherein any pyrimidinyl of $B^4$ is optionally substituted with one or more groups independently selected from halogen, $(C_1-C_6)$alkyl, —O$(C_1-C_6)$alkyl and $(C_3-C_7)$cycloalkyl.

E30: The compound according to any one of E1-E27, wherein $B^4$ is:

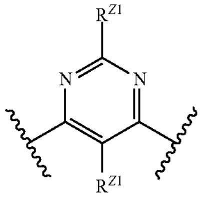

wherein each $R^{Z1}$ is independently selected from hydrogen halogen, $(C_1-C_6)$alkyl, —O$(C_1-C_6)$alkyl and $(C_3-C_7)$cycloalkyl.

E31: The compound according to any one of E1-E30, wherein one $R^{3d}$ group is halogen or $(C_1-C_6)$alkyl and the remaining $R^{3d}$ groups are H.

E32: The compound according to any one of E1-E30, wherein one $R^{3d}$ group is methyl and the remaining $R^{3d}$ groups are H.

E33: The compound according to any one of E1-E30, wherein the

A group

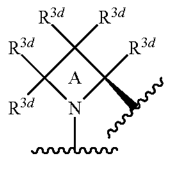

is:

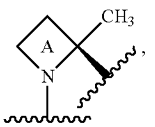

B is $B^1$ and $R^5$ is $R^{5a}$.

E34: The compound of any one of E11, E12, E15, E19, E22, E25 or E30, wherein each $R^{Z1}$ is independently selected from H, halogen, $(C_1-C_6)$alkyl, and $(C_3-C_7)$cycloalkyl.

E35: The compound of any one of E11, E12, E15, E19, E22, E25 or E30, wherein each $R^{Z1}$ is independently selected from H, fluoro, chloro, methyl and cyclopropyl.

E36: The compound of any one of 12, 22 or 30, wherein each $R^{Z1}$ is H.

E37: The compound according to any one of E1-E36, wherein $R^4$ is H.

E38: The compound according to any one of E1-E37, wherein $R^1$ is a phenyl or thiophenyl, wherein any phenyl or thiophenyl of $R^1$ is optionally substituted with one or more groups independently selected from halogen, —CN, $(C_1-C_6)$alkyl and $(C_1-C_6)$haloalkyl.

E39: The compound according to any one of E1-E37, wherein $R^1$ is a phenyl or thiophenyl, wherein any phenyl or thiophenyl of $R^1$ is optionally substituted with one or more groups independently selected from halogen and —CN.

E40: The compound according to any one of E1-E37, wherein $R^1$ is a phenyl or thiophenyl, wherein any phenyl or thiophenyl of $R^1$ is optionally substituted with one or more groups independently selected from fluoro, chloro and —CN.

E41: The compound according to any one of E1-E37, wherein $R^1$ is 4-fluorophenyl, 3-fluorophenyl, 4-cyanophenyl, 2-chlorothiophen-5-yl, 3,4,-difluorophenyl or 3-fluoropyridin-5-yl.

E42: The compound according to any one of E1-E41, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl; and $R^{5b}$ is phenyl, 6-membered heteroaryl or 6-membered heterocycle, wherein any phenyl, 6-membered heteroaryl or 6-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl.

E43: The compound according to any one of E1-E41, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl; and $R^{5b}$ is phenyl, 6-membered heteroaryl or 6-membered heterocycle, wherein any phenyl, 6-membered heteroaryl or 6-membered heterocycle of $R^{5b}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E44: The compound according to any one of E1-E41, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl; and $R^{5b}$ is phenyl, pyridinyl or piperidinyl, wherein any phenyl, pyridinyl or piperidinyl of $R^{5b}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E45: The compound according to any one of E1-E41, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from —$CF_3$, —$SCF_3$, —$OCF_3$ or cyclopropyl; and $R^{5b}$ is phenyl, pyridinyl or piperidinyl, wherein any phenyl, pyridinyl or piperidinyl of $R^{5b}$ is optionally substituted with one or more groups independently selected from —$CF_3$, —$SCF_3$, —$OCF_3$ or cyclopropyl.

E46: The compound according to any one of E1-E41, wherein $R^{5a}$ or $R^{5b}$ is phenyl or pyridinyl, wherein any phenyl or pyridinyl of $R^{5a}$ or $R^{5b}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$haloalkyl, —S$(C_1\text{-}C_6)$alkyl and —S$(C_1\text{-}C_6)$haloalkyl.

E47: The compound according to any one of E1-E41, wherein $R^{5a}$ or $R^{5b}$ is phenyl or pyridinyl, wherein any phenyl or pyridinyl of $R^{5a}$ or $R^{5b}$ is optionally substituted with one or more groups independently selected from $(C_1\text{-}C_6)$haloalkyl, $(C_3\text{-}C_7)$cycloalkyl, —O$(C_1\text{-}C_6)$haloalkyl and —S$(C_1\text{-}C_6)$haloalkyl.

E48: The compound according to any one of E1-E41, wherein $R^{5a}$ or $R^{5b}$ is phenyl or pyridinyl, wherein any phenyl or pyridinyl of $R^{5a}$ or $R^{5b}$ is optionally substituted with one or more groups independently selected from —$CF_3$, —$SCF_3$, —$OCF_3$ or cyclopropyl.

E49: The compound according to any one of E1-E41, wherein $R^{5a}$ is

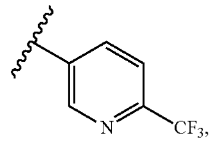,
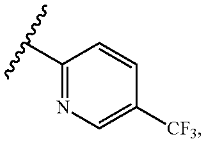,
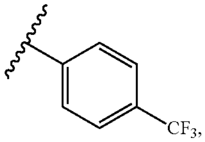,
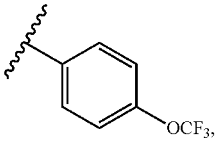,
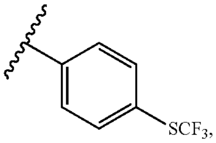,
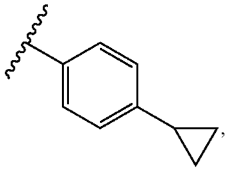,
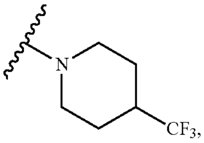,
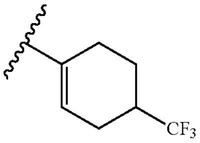 or
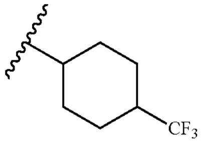

E50: The compound according to any one of E1-E41, wherein $R^{5b}$ is

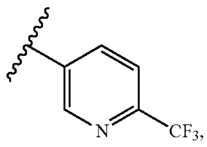,
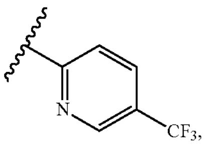,
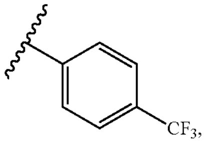,
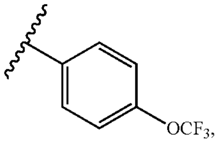,

-continued

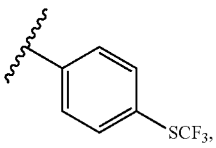,
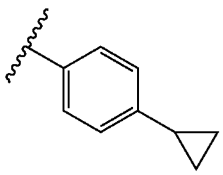 or
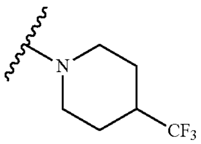

E1A: The compound according to E1, wherein A is

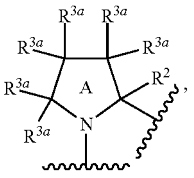,

B is $B^1$ and $R^5$ is $R^{5a}$.

E2A: The compound according to E1, wherein A is

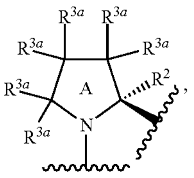,

B is $B^1$ and $R^5$ is $R^{5a}$.

E3A: The compound according to E1 which is a compound of formula Ia:

Ia

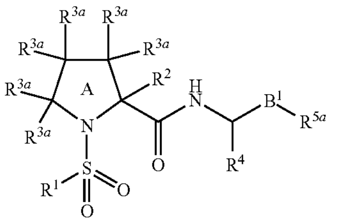

or a pharmaceutically acceptable salt thereof.

E4A: The compound according to E1 which is a compound of formula Ia':

Ia'

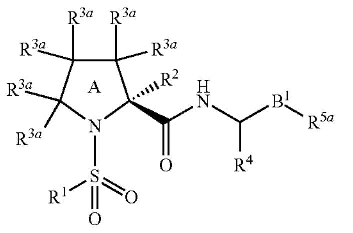

or a pharmaceutically acceptable salt thereof.

E5A: The compound according to any one of E1A-E4A, wherein one $R^{3a}$ is F and the remaining $R^{3a}$ groups are H.

E6A: The compound according to any one of E1A-E4A, wherein each $R^{3a}$ is H.

E7A: The compound according to any one of E1A-E6A, wherein $R^2$ is $(C_1\text{-}C_6)$alkyl or CN, wherein any $(C_1\text{-}C_6)$alkyl of $R^2$ is optionally substituted with one or more groups independently selected from halogen, —OH and —O$(C_1\text{-}C_6)$alkyl.

E8A: The compound according to any one of E1A-E6A, wherein $R^2$ is —$CH_3$, —$CH_2OH$, —$CHF_2$, —$CH_2OCH_3$ or CN.

E9A: The compound according to any one of E1A-E6A, wherein $R^2$ is —$CH_3$.

E10A: The compound according to any one of E1A-E9A, wherein $B^1$ is a pyrazolyl, triazolyl, pyridinyl or pyrimidinyl, wherein any pyrazolyl, triazolyl, pyridinyl or pyrimidinyl of $B^1$ is optionally substituted with one or more groups independently selected from halogen, $(C_1\text{-}C_6)$alkyl, —O$(C_1\text{-}C_6)$alkyl and $(C_3\text{-}C_7)$cycloalkyl.

E11A: The compound according to any one of E1A-E9A, wherein $B^1$ is a pyridinyl or pyrimidinyl, wherein any pyridinyl or pyrimidinyl of $B^1$ is optionally substituted with one or more groups independently selected from halogen, $(C_1\text{-}C_6)$alkyl, —O$(C_1\text{-}C_6)$alkyl and $(C_3\text{-}C_7)$cycloalkyl.

E12A: The compound according to any one of E1A-E9A, wherein $B^1$ is:

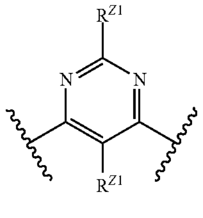

,

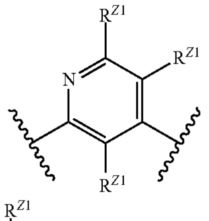

or

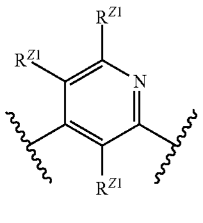

wherein each $R^{Z1}$ is independently selected from H, halogen, $(C_1\text{-}C_6)$alkyl, —O$(C_1\text{-}C_6)$alkyl and $(C_3\text{-}C_7)$cycloalkyl.

E13A: The compound according to any one of E1A-E9A, wherein $B^1$ is:

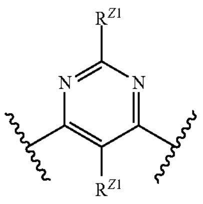

wherein each $R^{Z1}$ is independently selected from H, halogen, $(C_1\text{-}C_6)$alkyl, —O$(C_1\text{-}C_6)$alkyl and $(C_3\text{-}C_7)$cycloalkyl.

E14A: The compound according to any one of E1A-E9A, wherein $B^1$ is a pyrazolyl or a triazolyl, wherein any pyrazolyl or triazolyl of $B^1$ is optionally substituted with one or more groups independently selected from halogen, $(C_1\text{-}C_6)$alkyl, —O$(C_1\text{-}C_6)$alkyl and $(C_3\text{-}C_7)$cycloalkyl.

E15A: The compound according to any one of E1A-E9A, wherein $B^1$ is a pyrazolyl, wherein any pyrazolyl of $B^1$ is optionally substituted with one or more groups independently selected from halogen, $(C_1\text{-}C_6)$alkyl, —O$(C_1\text{-}C_6)$alkyl and $(C_3\text{-}C_7)$cycloalkyl.

E16A: The compound according to any one of E1A-E9A, wherein $B^1$ is:

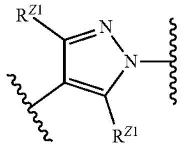

wherein each $R^{Z1}$ is independently selected from H, halogen, $(C_1\text{-}C_6)$alkyl, —O$(C_1\text{-}C_6)$alkyl and $(C_3\text{-}C_7)$cycloalkyl.

E17A: The compound according to any one E12A, E13A or E14A, wherein each $R^{Z1}$ is independently selected from H, halogen, $(C_1\text{-}C_6)$alkyl, and $(C_3\text{-}C_7)$cycloalkyl.

E18A: The compound according to any one E12A, E1A or E14A, wherein each $R^{Z1}$ is independently selected from H, fluoro, chloro, methyl and cyclopropyl.

E19A: The compound according to E12A or E13A, wherein each $R^{Z1}$ is H.

E20A: The compound according to any one of E1A-E19A, wherein $R^4$ is H.

E21A: The compound according to any one of E1A-E20A, wherein $R^1$ is a phenyl or thiophenyl, wherein any phenyl or thiophenyl of $R^1$ is optionally substituted with one or more groups independently selected from halogen, —CN, $(C_1\text{-}C_6)$alkyl and $(C_1\text{-}C_6)$haloalkyl.

E22A: The compound according to any one of E1A-E20A, wherein $R^1$ is a phenyl or thiophenyl, wherein any phenyl or thiophenyl of $R^1$ is optionally substituted with one or more groups independently selected from halogen and —CN.

E23A: The compound according to any one of E1A-E20A, wherein $R^1$ is a phenyl or thiophenyl, wherein any phenyl or thiophenyl of $R^1$ is optionally substituted with one or more groups independently selected from fluoro, chloro and —CN.

E24A: The compound according to any one of E1A-E20A, wherein $R^1$ is 4-fluorophenyl, 3-fluorophenyl, 4-cyanophenyl, 2-chlorothiophen-5-yl, 3,4,-difluorophenyl or 3-fluoropyridin-5-yl.

E25A: The compound according to any one of E1A-E24A, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl.

E26A: The compound according to any one of E1A-E24A, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E27A: The compound according to any one of E1A-E24A, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl.

E28A: The compound according to any one of E1A-E24A, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E29A: The compound according to any one of E1A-E24A, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from —$CF_3$, —$SCF_3$, —$OCF_3$ or cyclopropyl.

E30A: The compound according to any one of E1A-E24A, wherein $R^{5a}$ is phenyl or pyridinyl, wherein any phenyl or pyridinyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl.

E31A: The compound according to any one of E1A-E24A, wherein $R^{5a}$ is phenyl or pyridinyl, wherein any phenyl or pyridinyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E32A: The compound according to any one of E1A-E24A, wherein $R^{5a}$ is phenyl or pyridinyl, wherein any phenyl or pyridinyl of $R^{5a}$ is optionally substituted with one or more groups independently selected from —$CF_3$, —$SCF_3$, —$OCF_3$ or cyclopropyl.

E33A: The compound according to any one of E1A-E24A, wherein $R^{5a}$ is

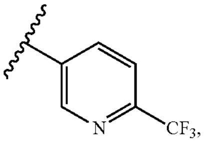
,
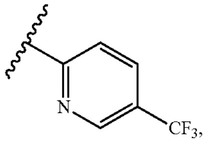
,

-continued

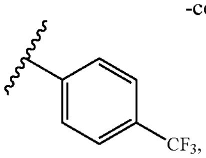
,
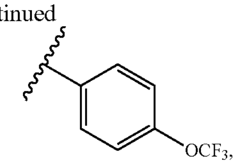
,
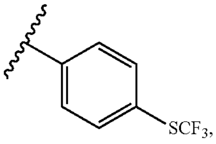
,
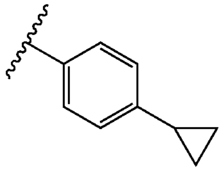

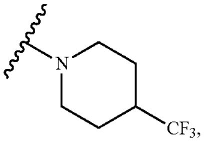
,
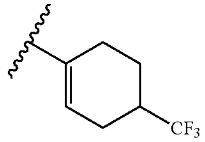
or

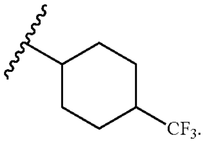
.

E1B: The compound of E1 wherein:

A is

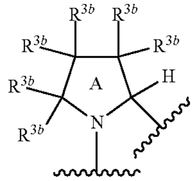
,

B is $B^2$ and $R^5$ is $R^{5b}$.

E2B: The compound of E1 wherein:

A is

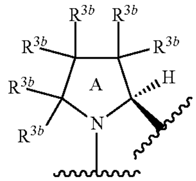
,

B is $B^2$ and $R^5$ is $R^{5b}$.

E3B: The compound according to E1 which is a compound of formula Ib:

Ib

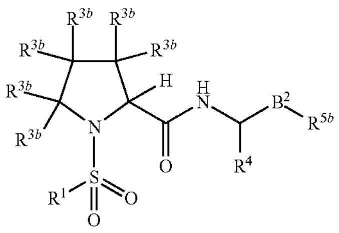

or a pharmaceutically acceptable salt thereof.

E4B: The compound according to E1 which is a compound of formula Ib':

Ib'

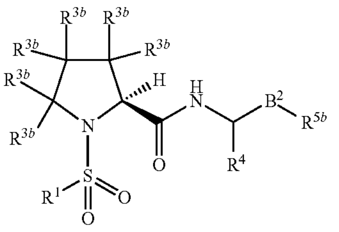

or a pharmaceutically acceptable salt thereof.

E5B: The compound according to any one of E1B-E4B, wherein one $R^{3b}$ group is F and the remaining $R^{3b}$ groups are H.

E6B: The compound according to E2B or E4B, wherein the A group

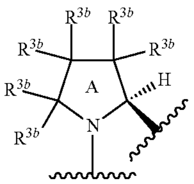

is

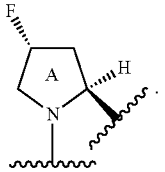

E7B: The compound according to any one of E1B-E7B, wherein $B^2$ is pyridinyl, wherein any pyridinyl of $B^2$ is optionally substituted with one or more groups independently selected from halogen, $(C_1$-$C_6)$alkyl and $(C_3$-$C_7)$cycloalkyl.

E8B: The compound according to any one of E1B-E7B, wherein $B^2$ is:

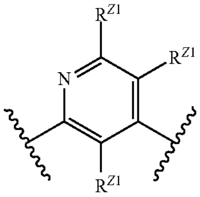

or

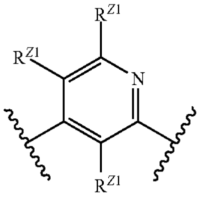

wherein each $R^{Z1}$ is independently selected from H, halogen, $(C_1$-$C_6)$alkyl, —$O(C_1$-$C_6)$alkyl and $(C_3$-$C_7)$cycloalkyl.

E9B: The compound according to E8B, wherein each $R^{Z1}$ is independently selected from H, halogen, $(C_1$-$C_6)$alkyl and $(C_3$-$C_7)$cycloalkyl.

E10B: The compound according to E8B, wherein each $R^{Z1}$ is H.

E11B: The compound according to any one of E1B-E10B, wherein $R^4$ is H.

E12B: The compound according to any one of E1B-E11B, wherein $R^1$ is a phenyl or thiophenyl, wherein any phenyl or thiophenyl of $R^1$ is optionally substituted with one or more groups independently selected from halogen, —CN, $(C_1$-$C_6)$alkyl and $(C_1$-$C_6)$haloalkyl.

E13B: The compound according to any one of E1B-E11B, wherein $R^1$ is a phenyl or thiophenyl, wherein any phenyl or thiophenyl of $R^1$ is optionally substituted with one or more groups independently selected from halogen and —CN.

E14B: The compound according to any one of E1B-E11B, wherein $R^1$ is a phenyl or thiophenyl, wherein any phenyl or thiophenyl of $R^1$ is optionally substituted with one or more groups independently selected from fluoro, chloro and —CN.

E15B: The compound according to any one of E1B-E11B, wherein $R^1$ is 4-fluorophenyl, 3-fluorophenyl, 4-cyanophenyl, 2-chlorothiophen-5-yl, 3,4,-difluorophenyl or 3-fluoropyridin-5-yl.

E16B: The compound according to any one of E1B-E15B, wherein $R^{5b}$ is phenyl, 6-membered heteroaryl or 6-membered heterocycle, wherein any phenyl, 6-membered heteroaryl or 6-membered heterocycle of $R^{5b}$ is optionally substituted with one or more groups independently selected from halogen, $(C_1$-$C_6)$alkyl, $(C_1$-$C_6)$haloalkyl, —CN, $(C_3$-$C_7)$cycloalkyl, —$O(C_1$-$C_6)$alkyl, —$O(C_1$-$C_6)$haloalkyl, —$S(C_1$-$C_6)$alkyl and —$S(C_1$-$C_6)$haloalkyl.

E17B: The compound according to any one of E1B-E15B, wherein $R^{5b}$ is phenyl, 6-membered heteroaryl or 6-membered heterocycle, wherein any phenyl, 6-membered heteroaryl or 6-membered heterocycle of $R^{5b}$ is optionally substituted with one or more groups independently selected from $(C_1$-$C_6)$haloalkyl, $(C_3$-$C_7)$cycloalkyl, —$O(C_1$-$C_6)$haloalkyl and —$S(C_1$-$C_6)$haloalkyl.

E18B: The compound according to any one of E1B-E15B, wherein $R^{5b}$ is phenyl, pyridinyl, or piperidinyl, wherein any phenyl, pyridinyl or piperidinyl of $R^{5b}$ is optionally substituted with one or more groups independently selected from halogen, $(C_1$-$C_6)$alkyl, $(C_1$-$C_6)$haloalkyl, —CN, $(C_3$-$C_7)$cycloalkyl, —$O(C_1$-$C_6)$alkyl, —$O(C_1$-$C_6)$haloalkyl, —$S(C_1$-$C_6)$alkyl and —$S(C_1$-$C_6)$haloalkyl.

E19B: The compound according to any one of E1B-E15B, wherein $R^{5b}$ is phenyl, pyridinyl, or piperidinyl, wherein any phenyl, pyridinyl or piperidinyl of $R^{5b}$ is optionally substituted with one or more groups independently selected from $(C_1$-$C_6)$haloalkyl, $(C_3$-$C_7)$cycloalkyl, —$O(C_1$-$C_6)$haloalkyl and —$S(C_1$-$C_6)$haloalkyl.

E20B: The compound according to any one of E1B-E15B, wherein $R^{5b}$ is phenyl, pyridinyl, or piperidinyl, wherein any phenyl, pyridinyl or piperidinyl of $R^{5b}$ is optionally substituted with one or more groups independently selected from —$CF_3$, —$SCF_3$, —$OCF_3$ or cyclopropyl.

E21B: The compound according to any one of E1B-E15B, wherein $R^{5b}$ is phenyl or pyridinyl, wherein any phenyl or pyridinyl of $R^{5b}$ is optionally substituted with one or more groups independently selected from halogen, $(C_1$-$C_6)$alkyl, $(C_1$-$C_6)$haloalkyl, —CN, $(C_3$-$C_7)$cycloalkyl, —$O(C_1$-$C_6)$alkyl, —$O(C_1$-$C_6)$haloalkyl, —$S(C_1$-$C_6)$alkyl and —$S(C_1$-$C_6)$ haloalkyl.

E22B: The compound according to any one of E1B-E15B, wherein $R^{5b}$ is phenyl or pyridinyl, wherein any phenyl or pyridinyl of $R^{5b}$ is optionally substituted with one or more groups independently selected from $(C_1$-$C_6)$haloalkyl, $(C_3$-$C_7)$cycloalkyl, —$O(C_1$-$C_6)$haloalkyl and —$S(C_1$-$C_6)$haloalkyl.

E23B: The compound according to any one of E1B-E15B, wherein $R^{5b}$ is phenyl or pyridinyl, wherein any phenyl or pyridinyl of $R^{5b}$ is optionally substituted with one or more groups independently selected from —$CF_3$, —$SCF_3$, —$OCF_3$ or cyclopropyl.

E24B: The compound according to any one of E1B-E15B, wherein $R^{5b}$ is

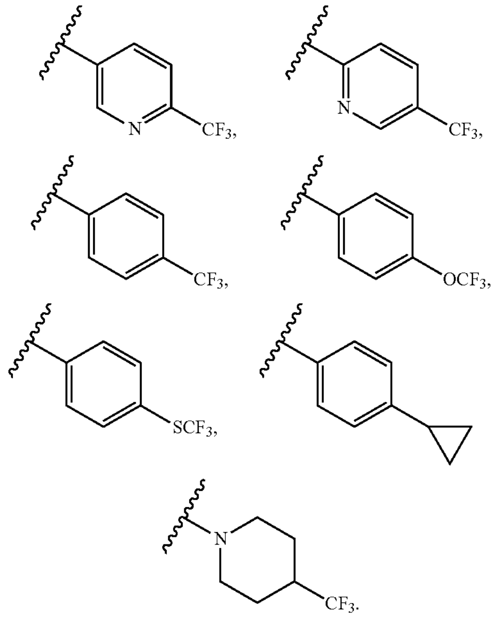

or

E1C: The compound of E1 wherein:

A is

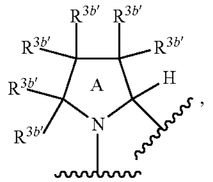

B is $B^3$ and $R^5$ is $R^{5a}$.

E2C: The compound of E1 wherein:

A is

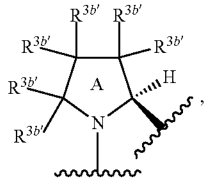

B is $B^3$ and $R^5$ is $R^{5a}$.

E3C: The compound according to E1 which is a compound of formula Ic:

Ic

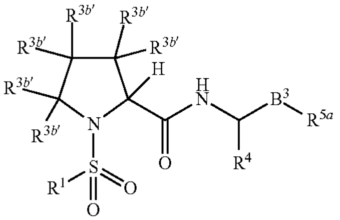

or a pharmaceutically acceptable salt thereof.

E4C: The compound according to E1 which is a compound of formula Ic':

Ic'

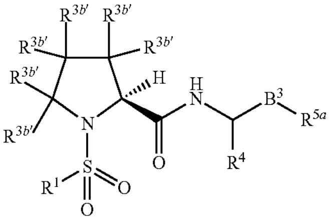

or a pharmaceutically acceptable salt thereof.

ESC: The compound according to any one of E1C-E4C, wherein one $R^{3b'}$ group is F and the remaining $R^{3b'}$ groups are H.

E6C: The compound according to E2C or E4C, wherein the A group

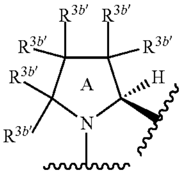

is

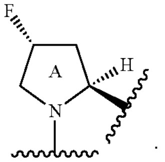

E7C: The compound according to any one of E1C-E6C, wherein $B^3$ is pyrazolyl, triazolyl or pyrimidinyl, wherein any pyrazolyl, triazolyl or pyrimidinyl of $B^3$ is optionally substituted with one or more groups independently selected from halogen, $(C_1-C_6)$alkyl, —$O(C_1-C_6)$alkyl and $(C_3-C_7)$cycloalkyl.

E8C: The compound according to any one of E1C-E6C, wherein $B^3$ is a pyrimidinyl, wherein any pyrimidinyl of $B^3$ is optionally substituted with one or more groups independently selected from halogen, $(C_1-C_6)$alkyl, —$O(C_1-C_6)$alkyl and $(C_3-C_7)$cycloalkyl.

E9C: The compound according to any one of E1C-E6C, wherein $B^3$ is:

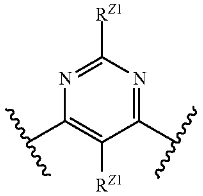

wherein each $R^{Z1}$ is independently selected from hydrogen halogen, $(C_1-C_6)$alkyl, —O$(C_1-C_6)$alkyl and $(C_3-C_7)$cycloalkyl.

E10C: The compound according to any one of E1C-E6C, wherein $B^3$ is a pyrazolyl or a triazolyl, wherein any pyrazolyl or triazolyl of $B^3$ is optionally substituted with one or more groups independently selected from halogen, $(C_1-C_6)$alkyl, —O$(C_1-C_6)$alkyl and $(C_3-C_7)$cycloalkyl.

E11C: The compound according to any one of E1C-E6C, wherein $B^3$ is a pyrazolyl, wherein any pyrazolyl of $B^3$ is optionally substituted with one or more groups independently selected from halogen, $(C_1-C_6)$alkyl, —O$(C_1-C_6)$alkyl and $(C_3-C_7)$cycloalkyl.

E12C: The compound according to any one of E1C-E6C, wherein $B^3$ is:

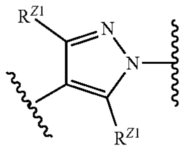

wherein each $R^{Z1}$ is independently selected from H, halogen, $(C_1-C_6)$alkyl, —O$(C_1-C_6)$alkyl and $(C_3-C_7)$cycloalkyl.

E13C: The compound according to E9C or E12C, wherein each $R^{Z1}$ is independently selected from H, halogen, $(C_1-C_6)$alkyl, and $(C_3-C_7)$cycloalkyl.

E14C: The compound according to E9C or E12C, wherein each $R^{Z1}$ is independently selected from H, fluoro, chloro, methyl and cyclopropyl.

E15C: The compound according to E9C, wherein each $R^{Z1}$ is H.

E16C: The compound according to any one of E1C-E15C, wherein $R^4$ is H.

E17C: The compound according to any one of E1C-E16C, wherein $R^1$ is a phenyl or thiophenyl, wherein any phenyl or thiophenyl of $R^1$ is optionally substituted with one or more groups independently selected from halogen, —CN, $(C_1-C_6)$alkyl and $(C_1-C_6)$haloalkyl.

E18C: The compound according to any one of E1C-E16C, wherein $R^1$ is a phenyl or thiophenyl, wherein any phenyl or thiophenyl of $R^1$ is optionally substituted with one or more groups independently selected from halogen and —CN.

E19C: The compound according to any one of E1C-E16C, wherein $R^1$ is a phenyl or thiophenyl, wherein any phenyl or thiophenyl of $R^1$ is optionally substituted with one or more groups independently selected from fluoro, chloro and —CN.

E20C: The compound according to any one of E1C-E16C, wherein $R^1$ is 4-fluorophenyl, 3-fluorophenyl, 4-cyanophenyl, 2-chlorothiophen-5-yl, 3,4,-difluorophenyl or 3-fluoropyridin-5-yl.

E21C: The compound according to any one of E1C-E20C, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl.

E22C: The compound according to any one of E1C-E20C, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E23C: The compound according to any one of E1C-E20C, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl.

E24C: The compound according to any one of E1C-E20C, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E25C: The compound according to any one of E1C-E20C, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from —$CF_3$, —$SCF_3$, —$OCF_3$ or cyclopropyl.

E26C: The compound according to any one of E1C-E20C, wherein $R^{5a}$ is phenyl or pyridinyl, wherein any phenyl or pyridinyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl.

E27C: The compound according to any one of E1C-E20C, wherein $R^{5a}$ is phenyl or pyridinyl, wherein any phenyl or pyridinyl of $R^{5a}$ is optionally substituted with one or more groups independently selected from $(C_1-C_6)$haloalkyl, $(C_3-C_7)$cycloalkyl, —O$(C_1-C_6)$haloalkyl and —S$(C_1-C_6)$haloalkyl.

E28C: The compound according to any one of E1C-E20C, wherein $R^{5a}$ is phenyl or pyridinyl, wherein any phenyl or pyridinyl of $R^{5a}$ is optionally substituted with one or more groups independently selected from —$CF_3$, —$SCF_3$, —$OCF_3$ or cyclopropyl.

E29C: The compound according to any one of E1C-E20C, wherein $R^{5a}$ is

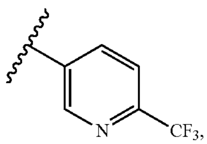,
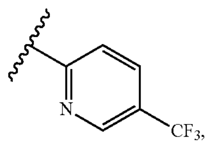,

-continued

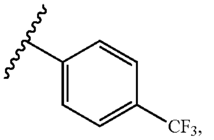

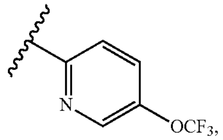

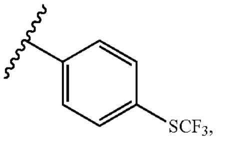

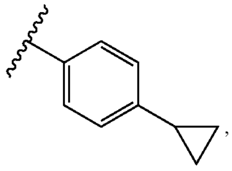

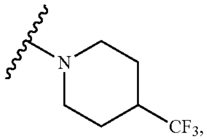

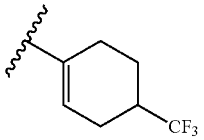

or

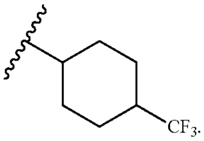

E1D: The compound of E1 wherein:

A is

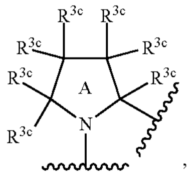

B is $B^4$ and $R^5$ is $R^{5a}$.

E2D: The compound of E1 wherein:

A is

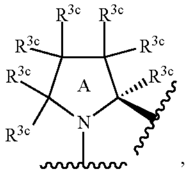

B is $B^4$ and $R^5$ is $R^{5a}$.

E3D: The compound according to E1 which is a compound of formula Id:

Id

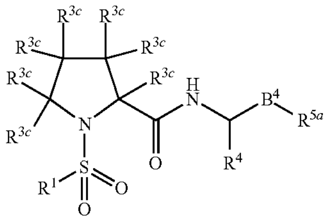

or a pharmaceutically acceptable salt thereof.

E4D: The compound according to E1 which is a compound of formula Id':

Id'

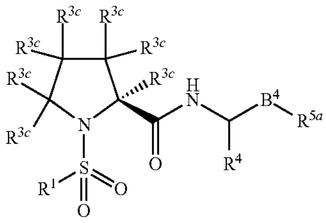

or a pharmaceutically acceptable salt thereof.

E5D: The compound according to any one of E1D-E4D, wherein two $R^{3c}$ groups attached to different non-adjacent carbon atoms are combined to form a $—CH_2CH_2—$ linker and the remaining $R^{3c}$ groups are each H.

E6D: The compound according to E2D or E4D, wherein the

A group

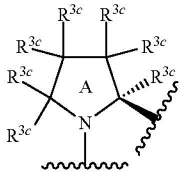

is

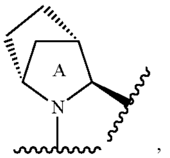

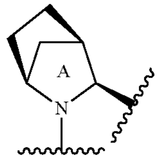

or

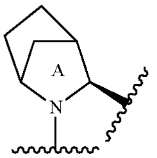

E7D: The compound according to any one of E1D-E6D, wherein $B^4$ is a pyrazolyl, triazolyl, pyridinyl or pyrimidinyl, wherein any pyrazolyl, triazolyl, pyridinyl or pyrimidinyl of $B^4$ is optionally substituted with one or more groups independently selected from halogen, $(C_1\text{-}C_6)$alkyl, $—O(C_1\text{-}C_6)$alkyl and $(C_3\text{-}C_7)$cycloalkyl.

EBD: The compound according to any one of E1D-E6D, wherein $B^4$ is a pyrimidinyl, wherein any pyrimidinyl of $B^4$ is optionally substituted with one or more groups independently selected from halogen, $(C_1\text{-}C_6)$alkyl, $—O(C_1\text{-}C_6)$alkyl and $(C_3\text{-}C_7)$cycloalkyl.

E9D: The compound according to any one of E1D-E6D, wherein $B^4$ is:

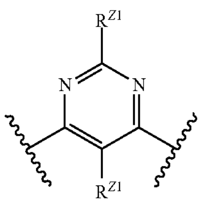

wherein each $R^{Z1}$ is independently selected from hydrogen halogen, $(C_1\text{-}C_6)$alkyl, $—O(C_1\text{-}C_6)$alkyl and $(C_3\text{-}C_7)$cycloalkyl.

E10D: The compound according to E9D, wherein each $R^{Z1}$ is independently selected from H, halogen, $(C_1\text{-}C_6)$ alkyl, and $(C_3\text{-}C_7)$cycloalkyl.

E11D: The compound according to E9D, wherein each $R^{Z1}$ is independently selected from H, fluoro, chloro, methyl and cyclopropyl.

E12D: The compound according to E9D, wherein each $R^{Z1}$ is H.

E13D: The compound according to any one of E1D-E12D, wherein $R^4$ is H.

E14D: The compound according to any one of E1D-E13D, wherein $R^1$ is a phenyl or thiophenyl, wherein any phenyl or thiophenyl of $R^1$ is optionally substituted with one or more groups independently selected from halogen, —CN, $(C_1\text{-}C_6)$alkyl and $(C_1\text{-}C_6)$haloalkyl.

E15D: The compound according to any one of E1D-E13D, wherein $R^1$ is a phenyl or thiophenyl, wherein any phenyl or thiophenyl of $R^1$ is optionally substituted with one or more groups independently selected from halogen and —CN.

E16D: The compound according to any one of E1D-E13D, wherein $R^1$ is a phenyl or thiophenyl, wherein any phenyl or thiophenyl of $R^1$ is optionally substituted with one or more groups independently selected from fluoro, chloro and —CN.

E17D: The compound according to any one of E1D-E13D, wherein $R^1$ is 4-fluorophenyl, 3-fluorophenyl, 4-cyanophenyl, 2-chlorothiophen-5-yl, 3,4,-difluorophenyl or 3-fluoropyridin-5-yl.

E18D: The compound according to any one of E1D-E17D, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from halogen, $(C_1\text{-}C_6)$ alkyl, $(C_1\text{-}C_6)$haloalkyl, —CN, $(C_3\text{-}C_7)$cycloalkyl, $—O(C_1\text{-}C_6)$alkyl, $—O(C_1\text{-}C_6)$haloalkyl, $—S(C_1\text{-}C_6)$alkyl and $—S(C_1\text{-}C_6)$haloalkyl.

E19D: The compound according to any one of E1D-E17D, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from $(C_1\text{-}C_6)$haloalkyl, $(C_3\text{-}C_7)$cycloalkyl, $—O(C_1\text{-}C_6)$haloalkyl and $—S(C_1\text{-}C_6)$ haloalkyl.

E20D: The compound according to any one of E1D-E17D, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, $—O(C_1\text{-}C_6)$alkyl, $—O(C_1\text{-}C_6)$haloalkyl, $—S(C_1\text{-}C_6)$alkyl and $—S(C_1\text{-}C_6)$haloalkyl.

E21D: The compound according to any one of E1D-E17D, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from $(C_1\text{-}C_6)$haloalkyl, $(C_3\text{-}C_7)$cycloalkyl, $—O(C_1\text{-}C_6)$haloalkyl and $—S(C_1\text{-}C_6)$haloalkyl.

E22D: The compound according to any one of E1D-E17D, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from $—CF_3$, $—SCF_3$, $—OCF_3$ or cyclopropyl.

E23D: The compound according to any one of E1D-E17D, wherein $R^{5a}$ is phenyl or pyridinyl, wherein any phenyl or pyridinyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, $—O(C_1\text{-}C_6)$alkyl, $—O(C_1\text{-}C_6)$haloalkyl, $—S(C_1\text{-}C_6)$alkyl and $—S(C_1\text{-}C_6)$haloalkyl.

E24D: The compound according to any one of E1D-E17D, wherein $R^{5a}$ is phenyl or pyridinyl, wherein any phenyl or pyridinyl of $R^{5a}$ is optionally substituted with one or more groups independently selected from $(C_1\text{-}C_6)$haloalkyl, $(C_3\text{-}C_7)$cycloalkyl, $—O(C_1\text{-}C_6)$haloalkyl and $—S(C_1\text{-}C_6)$haloalkyl.

E25D: The compound according to any one of E1D-E17D, wherein $R^{5a}$ is phenyl or pyridinyl, wherein any phenyl or pyridinyl of $R^{5a}$ is optionally substituted with one or more groups independently selected from $—CF_3$, $—SCF_3$, $—OCF_3$ or cyclopropyl.

E26D: The compound according to any one of E1D-E17D, wherein $R^{5a}$ is

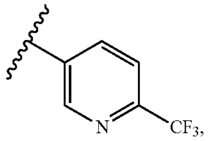
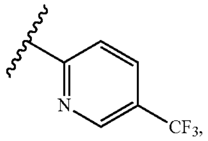
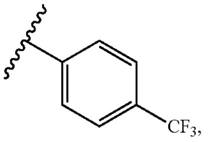
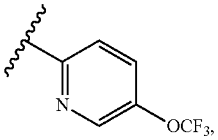
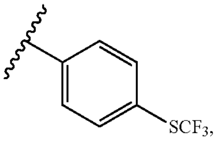
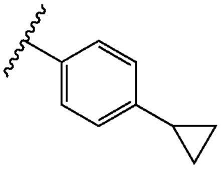
,
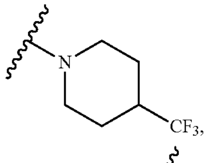
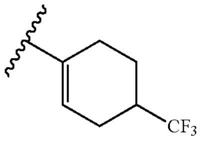
or
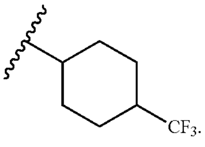

E1E: The compound according to E1, wherein A is

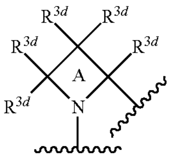
,

B is $B^1$ and $R^5$ is $R^{5a}$.

E2E: The compound according to E1, wherein A is

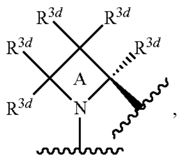

B is $B^1$ and $R^5$ is $R^{5a}$.

E3E: The compound according to E1 which is a compound of formula Ie:

Ie

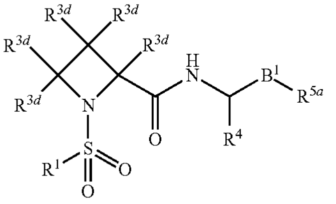

or a pharmaceutically acceptable salt thereof.

E4E: The compound according to E1 which is a compound of formula Ie':

Ie'

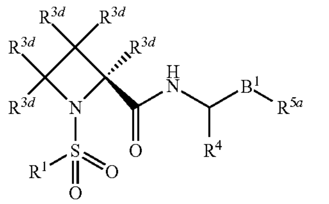

or a pharmaceutically acceptable salt thereof.

E5E: The compound according to any one of E1E-E5E, wherein one $R^{3d}$ group is halogen or $(C_1-C_6)$alkyl and the remaining $R^{3d}$ groups are H. E5E:

E6E: The compound according to any one of E1E-E5E, wherein one $R^{3d}$ group is halogen and the remaining $R^{3d}$ groups are H.

E7E: The compound according to any one of E1E-E5E, wherein one $R^{3d}$ $(C_1-C_6)$alkyl and the remaining $R^{3d}$ groups are H.

E8E: The compound according to any one of E1E-E5E, wherein one $R^{3d}$ group is methyl and the remaining $R^{3d}$ groups are H.

E9E: The compound according to E2E or E4E, wherein the A group

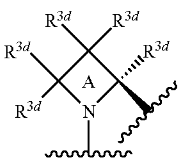

is

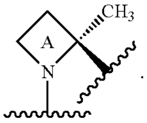

E10E: The compound according to any one of E1E-E9E, wherein $B^1$ is a pyrazolyl, triazolyl, pyridinyl or pyrimidinyl, wherein any pyrazolyl, triazolyl, pyridinyl or pyrimidinyl of $B^1$ is optionally substituted with one or more groups independently selected from halogen, $(C_1-C_6)$alkyl, $-O(C_1-C_6)$alkyl and $(C_3-C_7)$cycloalkyl.

E11E: The compound according to any one of E1E-E9E, wherein $B^1$ is a pyridinyl or pyrimidinyl, wherein any pyridinyl or pyrimidinyl of $B^1$ is optionally substituted with one or more groups independently selected from halogen, $(C_1-C_6)$alkyl, $-O(C_1-C_6)$alkyl and $(C_3-C_7)$cycloalkyl.

E12E: The compound according to any one of E1E-E9E, wherein $B^1$ is:

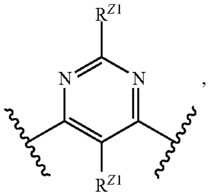

,

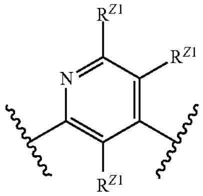

or

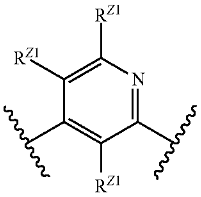

wherein each $R^{Z1}$ is independently selected from H, halogen, $(C_1-C_6)$alkyl, $-O(C_1-C_6)$alkyl and $(C_3-C_7)$cycloalkyl.

E13E: The compound according to any one of E1E-E9E, wherein $B^1$ is:

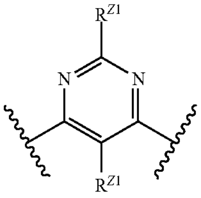

wherein each $R^{Z1}$ is independently selected from H, halogen, $(C_1-C_6)$alkyl, $-O(C_1-C_6)$alkyl and $(C_3-C_7)$cycloalkyl.

E14E: The compound according to any one of E1E-E9E, wherein $B^1$ is a pyrazolyl or a triazolyl, wherein any pyrazolyl or triazolyl of $B^1$ is optionally substituted with one or more groups independently selected from halogen, $(C_1-C_6)$alkyl, $-O(C_1-C_6)$alkyl and $(C_3-C_7)$cycloalkyl.

E15E: The compound according to any one of E1E-E9E, wherein $B^1$ is a pyrazolyl, wherein any pyrazolyl of $B^1$ is optionally substituted with one or more groups independently selected from halogen, $(C_1-C_6)$alkyl, $-O(C_1-C_6)$alkyl and $(C_3-C_7)$cycloalkyl.

E16E: The compound according to any one of E1E-E9E, wherein $B^1$ is:

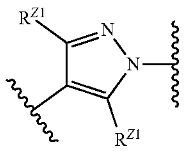

wherein each $R^{Z1}$ is independently selected from H, halogen, $(C_1\text{-}C_6)$alkyl, —O$(C_1\text{-}C_6)$alkyl and $(C_3\text{-}C_7)$cycloalkyl.

E17E: The compound according to E12E, E13E or E16E, wherein each $R^{Z1}$ is independently selected from H, halogen, $(C_1\text{-}C_6)$alkyl, and $(C_3\text{-}C_7)$cycloalkyl.

E18E: The compound according to E12E, E13E or E16E, wherein each $R^{Z1}$ is independently selected from H, fluoro, chloro, methyl and cyclopropyl.

E19E: The compound according to E12E or E13E, wherein each $R^{Z1}$ is H.

E20E: The compound according to any one of E1E-E19E, wherein $R^4$ is H.

E21E: The compound according to any one of E1E-E20E, wherein $R^1$ is a phenyl or thiophenyl, wherein any phenyl or thiophenyl of $R^1$ is optionally substituted with one or more groups independently selected from halogen, —CN, $(C_1\text{-}C_6)$alkyl and $(C_1\text{-}C_6)$haloalkyl.

E22E: The compound according to any one of E1E-E20E, wherein $R^1$ is a phenyl or thiophenyl, wherein any phenyl or thiophenyl of $R^1$ is optionally substituted with one or more groups independently selected from halogen and —CN.

E23E: The compound according to any one of E1E-E20E, wherein $R^1$ is a phenyl or thiophenyl, wherein any phenyl or thiophenyl of $R^1$ is optionally substituted with one or more groups independently selected from fluoro, chloro and —CN.

E24E: The compound according to any one of E1E-E20E, wherein $R^1$ is 4-fluorophenyl, 3-fluorophenyl, 4-cyanophenyl, 2-chlorothiophen-5-yl, 3,4,-difluorophenyl or 3-fluoropyridin-5-yl.

E25E: The compound according to any one of E1E-E24E, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$haloalkyl, —S$(C_1\text{-}C_6)$alkyl and —S$(C_1\text{-}C_6)$haloalkyl.

E26E: The compound according to any one of E1E-E24E, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from $(C_1\text{-}C_6)$haloalkyl, $(C_3\text{-}C_7)$cycloalkyl, —O$(C_1\text{-}C_6)$haloalkyl and —S$(C_1\text{-}C_6)$haloalkyl.

E27E: The compound according to any one of E1E-E24E, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$haloalkyl, —S$(C_1\text{-}C_6)$alkyl and —S$(C_1\text{-}C_6)$haloalkyl.

E28E: The compound according to any one of E1E-E24E, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from $(C_1\text{-}C_6)$haloalkyl, $(C_3\text{-}C_7)$cycloalkyl, —O$(C_1\text{-}C_6)$haloalkyl and —S$(C_1\text{-}C_6)$haloalkyl.

E29E: The compound according to any one of E1E-E24E, wherein $R^{5a}$ is phenyl, pyridinyl, piperidinyl, cyclohexenyl or cyclohexanyl, wherein any phenyl, pyridinyl, piperidinyl, cyclohexenyl or cyclohexanyl of $R^{5a}$ is optionally substituted with one or more groups independently selected from —$CF_3$, —$SCF_3$, —$OCF_3$ or cyclopropyl.

E30E: The compound according to any one of E1E-E24E, wherein $R^{5a}$ is phenyl or pyridinyl, wherein any phenyl or pyridinyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$haloalkyl, —S$(C_1\text{-}C_6)$alkyl and —S$(C_1\text{-}C_6)$haloalkyl.

E31E: The compound according to any one of E1E-E24E, wherein $R^{5a}$ is phenyl or pyridinyl, wherein any phenyl or pyridinyl of $R^{5a}$ is optionally substituted with one or more groups independently selected from $(C_1\text{-}C_6)$haloalkyl, $(C_3\text{-}C_7)$cycloalkyl, —O$(C_1\text{-}C_6)$haloalkyl and —S$(C_1\text{-}C_6)$haloalkyl.

E32E: The compound according to any one of E1E-E24E, wherein $R^{5a}$ is phenyl or pyridinyl, wherein any phenyl or pyridinyl of $R^{5a}$ is optionally substituted with one or more groups independently selected from —$CF_3$, —$SCF_3$, —$OCF_3$ or cyclopropyl.

E33E: The compound according to any one of E1E-E24E, wherein $R^{5a}$ is

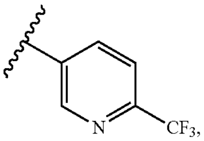,
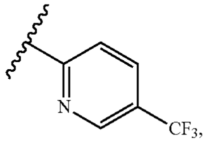,
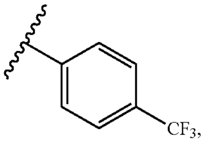,
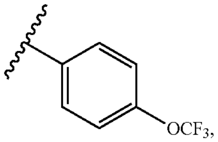,
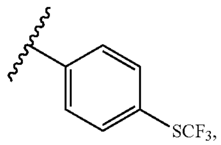,
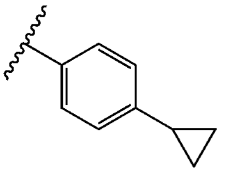,
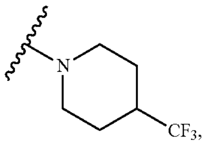,
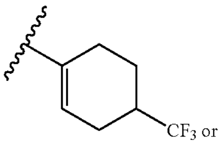 or
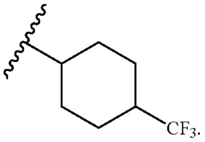.

In another embodiment, compounds of formula I or formula II are selected from the compound in the Table 1 below or a salt or a pharmaceutically acceptable salt thereof.

TABLE 1

| Example Number | Chemical Name via ChemDraw | Structure |
|---|---|---|
| 1 | (S)-1-(4-fluorophenylsulfonyl)-2-methyl-N-((6-(6-(trifluoromethyl)pyridin-3-yl)pyrimidin-4-yl)methyl)pyrrolidine-2-carboxamide | 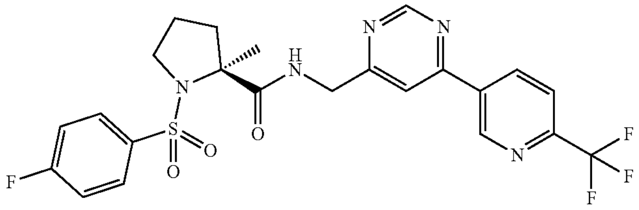 [SMILES: C[C@@]1(C(=O)NCc2cc(-c3ccc(C(F)(F)F)nc3)ncn2)CCCN1S(=O)(=O)c1ccc(F)cc1] |
| 2 | (S)-1-(4-fluorophenylsulfonyl)-2-methyl-N-((6-(6-(trifluoromethyl)pyridin-3-yl)pyrimidin-4-yl)methyl)azetidine-2-carboxamide | 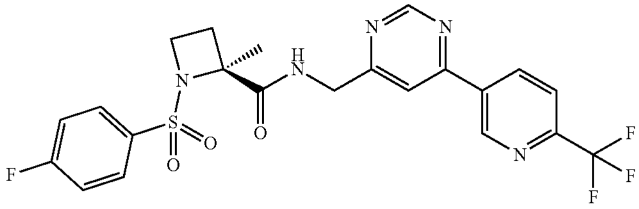 [SMILES: C[C@@]1(C(=O)NCc2cc(-c3ccc(C(F)(F)F)nc3)ncn2)CCN1S(=O)(=O)c1ccc(F)cc1] |
| 4 | (2S,4S)-4-fluoro-1-(4-fluorophenylsulfonyl)-N-((6-(6-(trifluoromethyl)pyridin-3-yl)pyrimidin-4-yl)methyl)pyrrolidine-2-carboxamide | 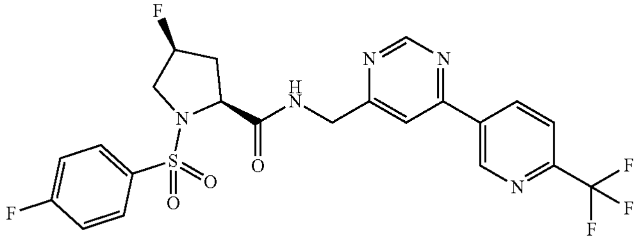 [SMILES: O=C(NCc1cc(-c2ccc(C(F)(F)F)nc2)ncn1)[C@@H]1C[C@H](F)CN1S(=O)(=O)c1ccc(F)cc1] |
| 3 | (2S,4R)-4-fluoro-1-(4-fluorophenylsulfonyl)-N-((6-(6-(trifluoromethyl)pyridin-3-yl)pyrimidin-4-yl)methyl)pyrrolidine-2-carboxamide | 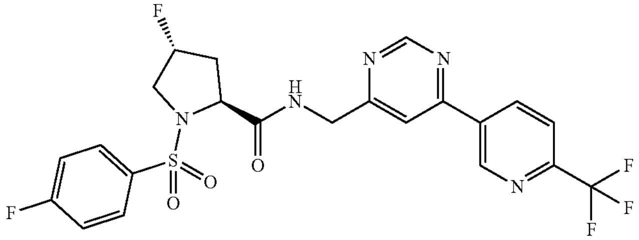 [SMILES: O=C(NCc1cc(-c2ccc(C(F)(F)F)nc2)ncn1)[C@@H]1C[C@@H](F)CN1S(=O)(=O)c1ccc(F)cc1] |
| 5 | (2S,4R)-4-fluoro-1-(4-fluorophenylsulfonyl)-N-((6-(4-(trifluoromethyl)phenyl) pyrimidin-4-yl)methyl)pyrrolidine-2-carboxamide | 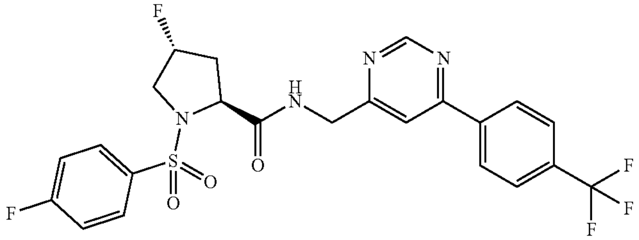 [SMILES: O=C(NCc1cc(-c2ccc(C(F)(F)F)cc2)ncn1)[C@@H]1C[C@@H](F)CN1S(=O)(=O)c1ccc(F)cc1] |
| 6 | (2S,4R)-4-fluoro-1-(3-fluorophenylsulfonyl)-N-((6-(4-(trifluoromethyl)phenyl) pyrimidin-4-yl)methyl)pyrrolidine-2-carboxamide | 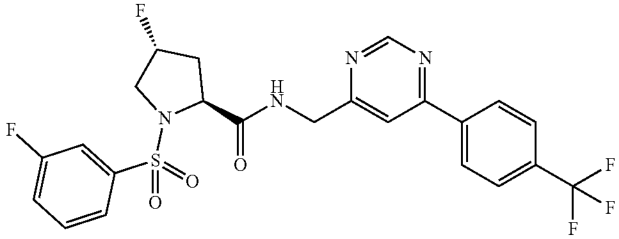 [SMILES: O=C(NCc1cc(-c2ccc(C(F)(F)F)cc2)ncn1)[C@@H]1C[C@@H](F)CN1S(=O)(=O)c1cccc(F)c1] |

TABLE 1-continued

| Example Number | Chemical Name via ChemDraw | Structure |
|---|---|---|
| 14 | (S)-1-(4-fluorophenylsulfonyl)-2-methyl-N-((6-(5-(trifluoromethyl)pyridin-2-yl)pyrimidin-4-yl)methyl)pyrrolidine-2-carboxamide | 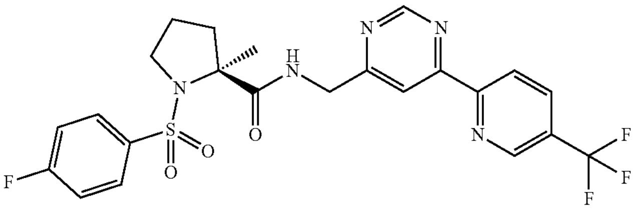 [SMILES: C[C@@]1(C(=O)NCc2cc(-c3ccc(C(F)(F)F)cn3)ncn2)CCCN1S(=O)(=O)c1ccc(F)cc1] |
| 7 | (R)-1-(4-fluorophenylsulfonyl)-2-(hydroxymethyl)-N-((6-(6-(trifluoromethyl)pyridin-3-yl)pyrimidin-4-yl)methyl)pyrrolidine-2-carboxamide | 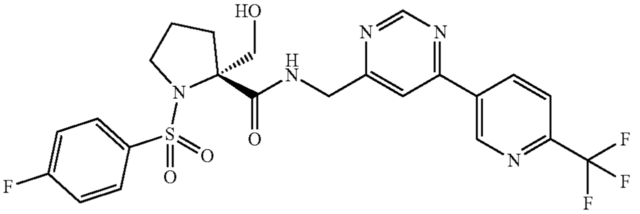 [SMILES: O=C(NCc1cc(-c2ccc(C(F)(F)F)nc2)ncn1)[C@]1(CO)CCCN1S(=O)(=O)c1ccc(F)cc1] |
| 9 | (2S,4R)-4-fluoro-N-((5'-fluoro-6-(trifluoromethyl)-3,4'-bipyridin-2'-yl)methyl)-1-(4-fluorophenylsulfonyl) pyrrolidine-2-carboxamide | 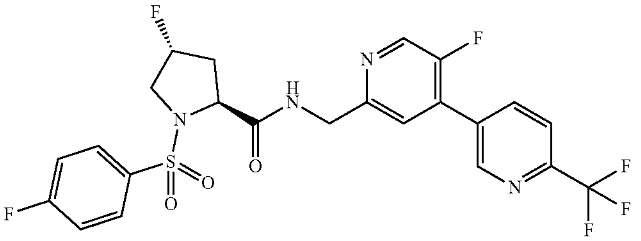 [SMILES: O=C(NCc1cc(-c2ccc(C(F)(F)F)nc2)c(F)cn1)[C@@H]1C[C@@H](F)CN1S(=O)(=O)c1ccc(F)cc1] |
| 8 | (2S,4R)-4-fluoro-N-((5-fluoro-6'-(trifluoromethyl)-2,3'-bipyridin-4-yl)methyl)-1-(4-fluorophenylsulfonyl) pyrrolidine-2-carboxamide | 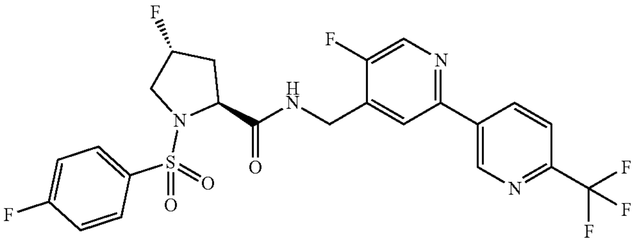 [SMILES: O=C(NCc1cc(-c2ccc(C(F)(F)F)nc2)ncc1F)[C@@H]1C[C@@H](F)CN1S(=O)(=O)c1ccc(F)cc1] |
| 17 | (2S,4R)-N-((3-cyclopropyl-1-(6-(trifluoromethyl)pyridin-3-yl)-1H-pyrazol-4-yl)methyl)-4-fluoro-1-(4-fluorophenylsulfonyl) pyrrolidine-2-carboxamide | 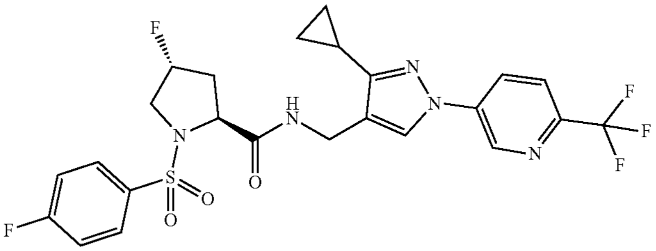 [SMILES: O=C(NCc1cn(-c2ccc(C(F)(F)F)nc2)nc1C1CC1)[C@@H]1C[C@@H](F)CN1S(=O)(=O)c1ccc(F)cc1] |
| 15 | (2S,4R)-N-((3-chloro-1-(6-(trifluoromethyl)pyridin-3-yl)-1H-pyrazol-4-yl)methyl)-4-fluoro-1-(4-fluorophenylsulfonyl) pyrrolidine-2-carboxamide | 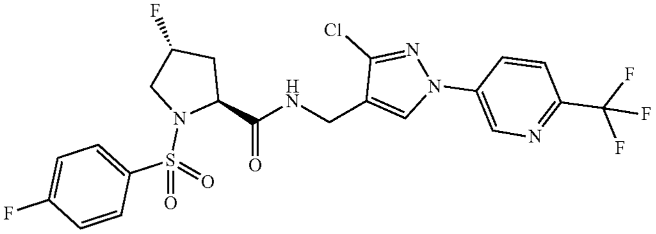 [SMILES: O=C(NCc1cn(-c2ccc(C(F)(F)F)nc2)nc1Cl)[C@@H]1C[C@@H](F)CN1S(=O)(=O)c1ccc(F)cc1] |

TABLE 1-continued

| Example Number | Chemical Name via ChemDraw | Structure |
| --- | --- | --- |
| 16 | (2S,4R)-N-((3-chloro-1-(4-(trifluoromethyl)phenyl)-1H-pyrazol-4-yl)methyl)-4-fluoro-1-(4-fluorophenylsulfonyl) pyrrolidine-2-carboxamide | 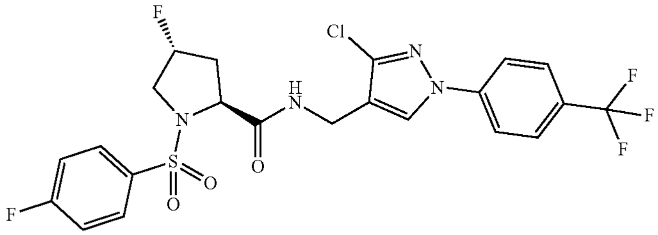 [SMILES: O=C(NCc1cn(-c2ccc(C(F)(F)F)cc2)nc1Cl)[C@@H]1C[C@@H](F)CN1S(=O)(=O)c1ccc(F)cc1] |
| 18 | (2S,4R)-N-((3-chloro-1-(4-(trifluoromethyl)phenyl)-1H-pyrazol-4-yl)methyl)-1-(4-cyanophenylsulfonyl)-4-fluoropyrrolidine-2-carboxamide | 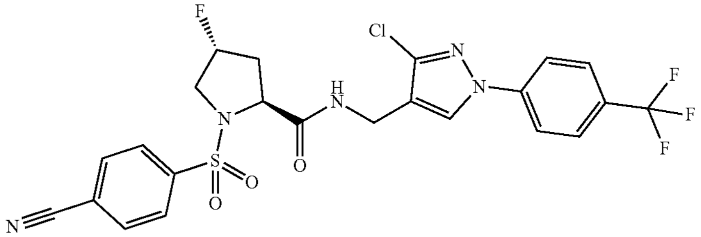 [SMILES: N#Cc1ccc(S(=O)(=O)N2C[C@H](F)C[C@H]2C(=O)NCc2cn(-c3ccc(C(F)(F)F)cc3)nc2Cl)cc1] |
| 19 | (2S,4R)-4-fluoro-1-(4-fluorophenylsulfonyl)-2-methyl-N-((6-(6-(trifluoromethyl)pyridin-3-yl)pyrimidin-4-yl)methyl)pyrrolidine-2-carboxamide | 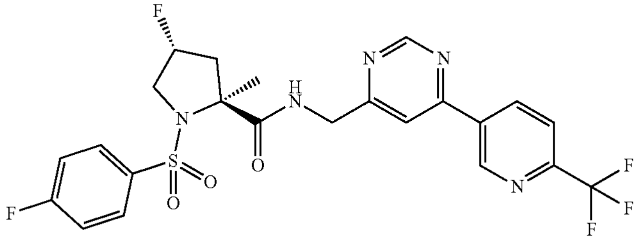 [SMILES: C[C@@]1(C(=O)NCc2cc(-c3ccc(C(F)(F)F)nc3)ncn2)C[C@@H](F)CN1S(=O)(=O)c1ccc(F)cc1] |
| 10 | (2S,4R)-N-((6-(4-cyclopropylphenyl)pyrimidin-4-yl)methyl)-4-fluoro-1-(4-fluorophenylsulfonyl) pyrrolidine-2-carboxamide | 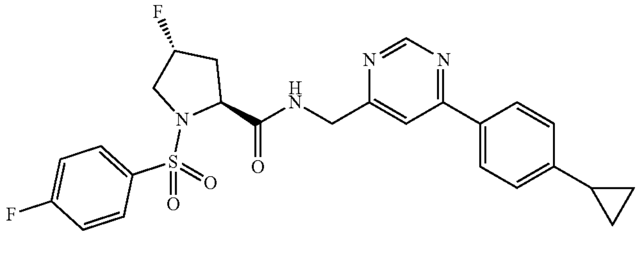 [SMILES: O=C(NCc1cc(-c2ccc(C3CC3)cc2)ncn1)[C@@H]1C[C@@H](F)CN1S(=O)(=O)c1ccc(F)cc1] |
| 11 | (2S,4R)-4-fluoro-1-(4-fluorophenylsulfonyl)-N-((6-(4-(trifluoromethyl)piperidin-1-yl)pyrimidin-4-yl)methyl)pyrrolidine-2-carboxamide | 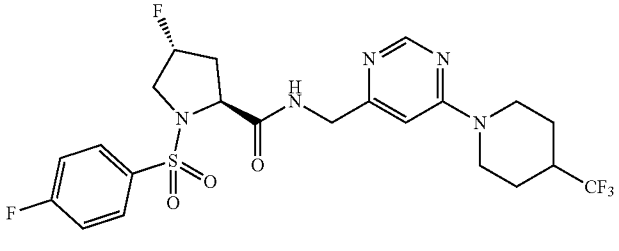 [SMILES: O=C(NCc1cc(N2CCC(C(F)(F)F)CC2)ncn1)[C@@H]1C[C@@H](F)CN1S(=O)(=O)c1ccc(F)cc1] |
| 20 | (2S,4R)-4-fluoro-1-(4-fluorophenylsulfonyl)-2-methyl-N-((6-(4-(trifluoromethyl)phenyl) pyrimidin-4-yl)methyl)pyrrolidine-2-carboxamide | 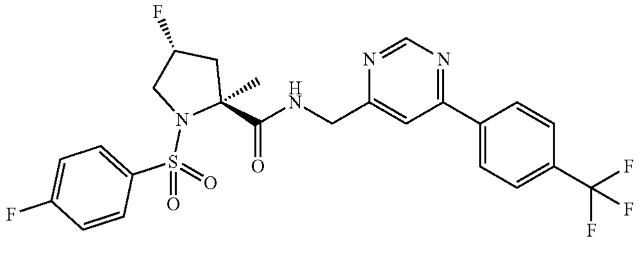 [SMILES: C[C@@]1(C(=O)NCc2cc(-c3ccc(C(F)(F)F)cc3)ncn2)C[C@@H](F)CN1S(=O)(=O)c1ccc(F)cc1] |

TABLE 1-continued

| Example Number | Chemical Name via ChemDraw | Structure |
|---|---|---|
| 21 | (2S,4R)-4-fluoro-1-(4-fluorophenylsulfonyl)-N-((6-(4-(trifluoromethoxy)phenyl) pyrimidin-4-yl)methyl)pyrrolidine-2-carboxamide | 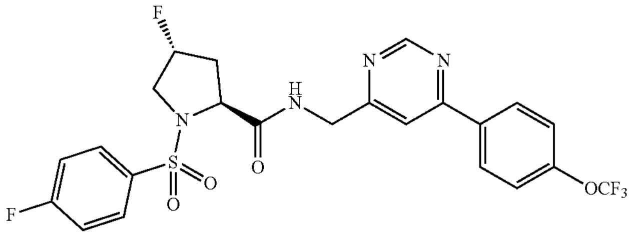 [SMILES: O=C(NCc1cc(-c2ccc(OC(F)(F)F)cc2)ncn1)[C@@H]1C[C@@H](F)CN1S(=O)(=O)c1ccc(F)cc1] |
| 22 | (2S,4R)-4-fluoro-1-(4-fluorophenylsulfonyl)-N-((2-methyl-6-(6-(trifluoromethyl)pyridin-3-yl)pyrimidin-4-yl)methyl)pyrrolidine-2-carboxamide | 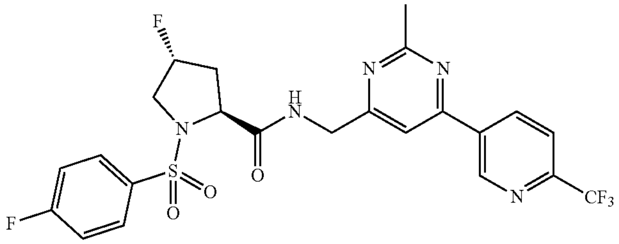 [SMILES: Cc1nc(CNC(=O)[C@@H]2C[C@@H](F)CN2S(=O)(=O)c2ccc(F)cc2)cc(-c2ccc(C(F)(F)F)nc2)n1] |
| 23 | (2S,4R)-N-((6-(6-cyclopropylpyridin-3-yl)pyrimidin-4-yl)methyl)-4-fluoro-1-(4-fluorophenylsulfonyl) pyrrolidine-2-carboxamide | 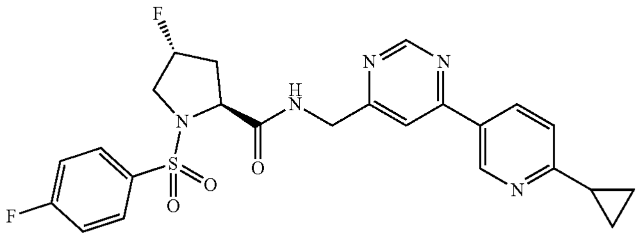 [SMILES: O=C(NCc1cc(-c2ccc(C3CC3)nc2)ncn1)[C@@H]1C[C@@H](F)CN1S(=O)(=O)c1ccc(F)cc1] |
| 24 | (2S,4R)-1-(5-chlorothiophen-2-ylsulfonyl)-4-fluoro-N-((6-(6-(trifluoromethyl)pyridin-3-yl)pyrimidin-4-yl)methyl)pyrrolidine-2-carboxamide | 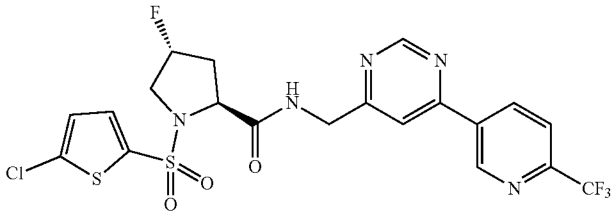 [SMILES: O=C(NCc1cc(-c2ccc(C(F)(F)F)nc2)ncn1)[C@@H]1C[C@@H](F)CN1S(=O)(=O)c1ccc(Cl)s1] |
| 25 | (2S,4R)-1-(3,4-difluorophenylsulfonyl)-4-fluoro-N-((6-(6-(trifluoromethyl)pyridin-3-yl)pyrimidin-4-yl)methyl)pyrrolidine-2-carboxamide | 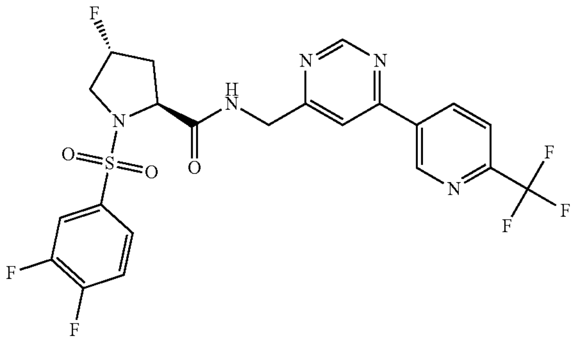 [SMILES: O=C(NCc1cc(-c2ccc(C(F)(F)F)nc2)ncn1)[C@@H]1C[C@@H](F)CN1S(=O)(=O)c1ccc(F)c(F)c1] |

TABLE 1-continued

| Example Number | Chemical Name via ChemDraw | Structure |
|---|---|---|
| 26 | (2S,4R)-1-(3,4-difluorophenylsulfonyl)-4-fluoro-N-((6-(4-(trifluoromethyl)phenyl) pyrimidin-4-yl)methyl)pyrrolidine-2-carboxamide | 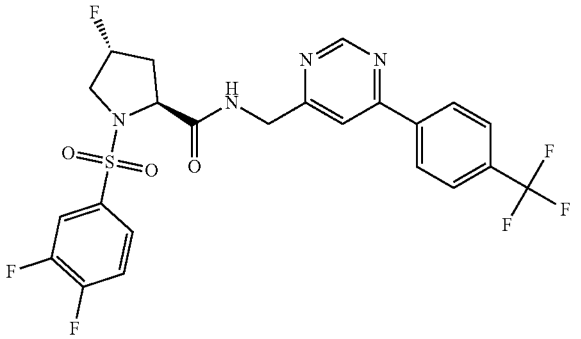 [SMILES: O=C(NCc1cc(-c2ccc(C(F)(F)F)cc2)ncn1)[C@@H]1C[C@@H](F)CN1S(=O)(=O)c1ccc(F)c(F)c1] |
| 27 | (2S,4R)-4-fluoro-1-(5-fluoropyridin-3-ylsulfonyl)-N-((6-(6-(trifluoromethyl)pyridin-3-yl)pyrimidin-4-yl)methyl)pyrrolidine-2-carboxamide | 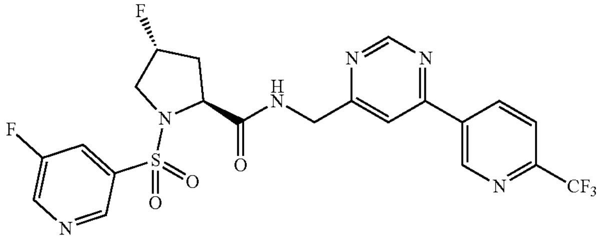 |
| 28 | (2S,4R)-4-fluoro-1-(5-fluoropyridin-3-ylsulfonyl)-N-((6-(4-(trifluoromethyl)phenyl) pyrimidin-4-yl)methyl)pyrrolidine-2-carboxamide | 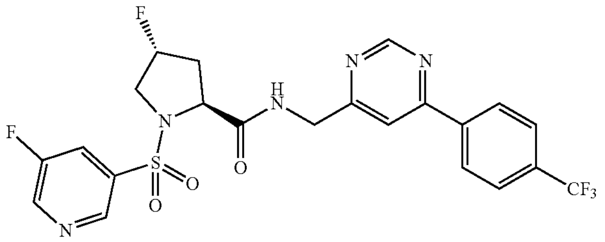 [SMILES: O=C(NCc1cc(-c2ccc(C(F)(F)F)cc2)ncn1)[C@@H]1C[C@@H](F)CN1S(=O)(=O)c1cncc(F)c1] |
| 29 | (2S,4R)-4-fluoro-1-(4-fluorophenylsulfonyl)-N-((6-(4-(trifluoromethylthio)phenyl) pyrimidin-4-yl)methyl)pyrrolidine-2-carboxamide | 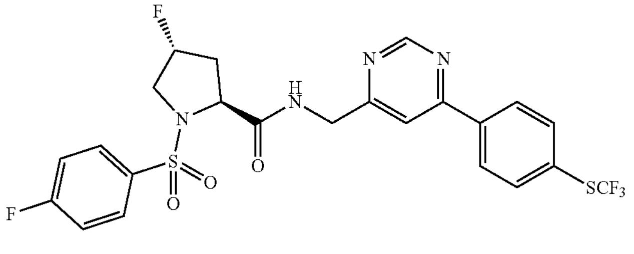 |
| 12 | (2S,4R)-4-fluoro-1-(4-fluorophenylsulfonyl)-N-((6-(4-(trifluoromethyl)cyclohex-1-enyl)pyrimidin-4-yl)methyl)pyrrolidine-2-carboxamide | 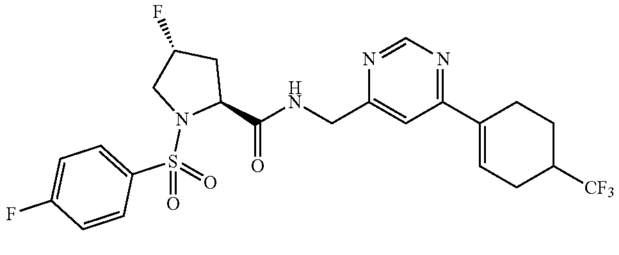 [SMILES: O=C(NCc1cc(C2=CCC(C(F)(F)F)CC2)ncn1)[C@@H]1C[C@@H](F)CN1S(=O)(=O)c1ccc(F)cc1] |
| 13 | (2S,4R)-4-fluoro-1-(4-fluorophenylsulfonyl)-N-((6-((1s,4R)-4-(trifluoromethyl)cyclohexyl) pyrimidin-4-yl)methyl)pyrrolidine-2-carboxamide | 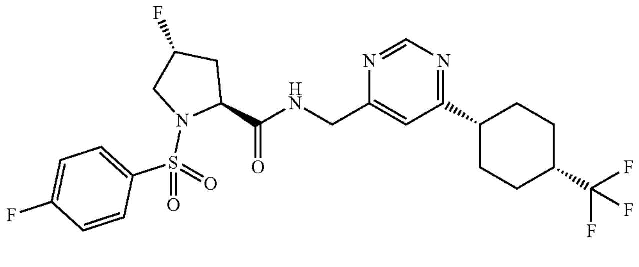 [SMILES: O=C(NCc1cc([C@H]2CC[C@@H](C(F)(F)F)CC2)ncn1)[C@@H]1C[C@@H](F)CN1S(=O)(=O)c1ccc(F)cc1] |

TABLE 1-continued

| Example Number | Chemical Name via ChemDraw | Structure |
|---|---|---|
| 13 | (2S,4R)-4-fluoro-1-(4-fluorophenylsulfonyl)-N-((6-((1r,4S)-4-(trifluoromethyl)cyclohexyl)pyrimidin-4-yl)methyl)pyrrolidine-2-carboxamide | 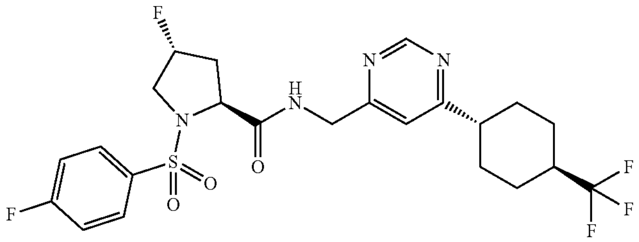 [SMILES: O=C(NCc1cc([C@H]2CC[C@H](C(F)(F)F)CC2)ncn1)[C@@H]1C[C@@H](F)CN1S(=O)(=O)c1ccc(F)cc1] |
| 30 | (R)-1-(4-fluorophenylsulfonyl)-2-(methoxymethyl)-N-((6-(6-(trifluoromethyl)pyridin-3-yl)pyrimidin-4-yl)methyl)pyrrolidine-2-carboxamide | 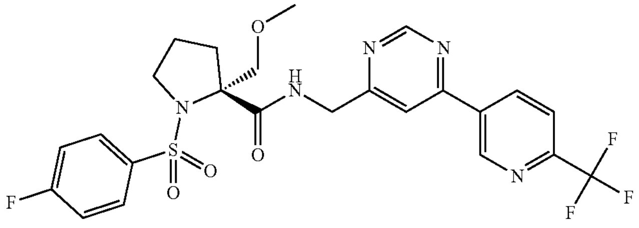 [SMILES: COC[C@@]1(C(=O)NCc2cc(-c3ccc(C(F)(F)F)nc3)ncn2)CCCN1S(=O)(=O)c1ccc(F)cc1] |
| 31 | (S)-2-(difluoromethyl)-1-(4-fluorophenylsulfonyl)-N-((6-(6-(trifluoromethyl)pyridin-3-yl)pyrimidin-4-yl)methyl)pyrrolidine-2-carboxamide | 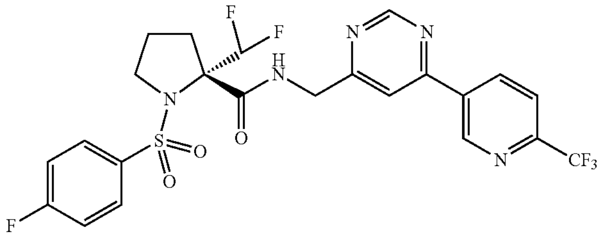 [SMILES: O=C(NCc1cc(-c2ccc(C(F)(F)F)nc2)ncn1)[C@]1(C(F)F)CCCN1S(=O)(=O)c1ccc(F)cc1] |
| 32 | (R)-2-cyano-1-(4-fluorophenylsulfonyl)-N-((6-(6-(trifluoromethyl)pyridin-3-yl)pyrimidin-4-yl)methyl)pyrrolidine-2-carboxamide | 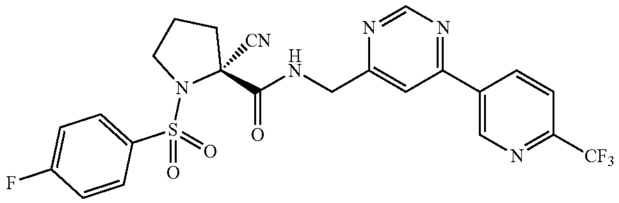 [SMILES: N#C[C@@]1(C(=O)NCc2cc(-c3ccc(C(F)(F)F)nc3)ncn2)CCCN1S(=O)(=O)c1ccc(F)cc1] |
| 35 | (2R,3S)-3-fluoro-1-(4-fluorophenylsulfonyl)-N-((6-(6-(trifluoromethyl)pyridin-3-yl)pyrimidin-4-yl)methyl)pyrrolidine-2-carboxamide | 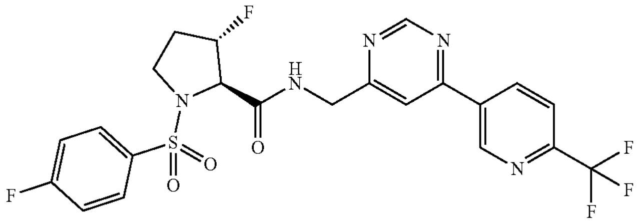 [SMILES: O=C(NCc1cc(-c2ccc(C(F)(F)F)nc2)ncn1)[C@@H]1[C@@H](F)CCN1S(=O)(=O)c1ccc(F)cc1] |
| 33 | (1R,3S,4S)-2-(4-fluorophenylsulfonyl)-N-((6-(4-(trifluoromethyl)phenyl)pyrimidin-4-yl)methyl)-2-azabicyclo[2.2.1]heptane-3-carboxamide | 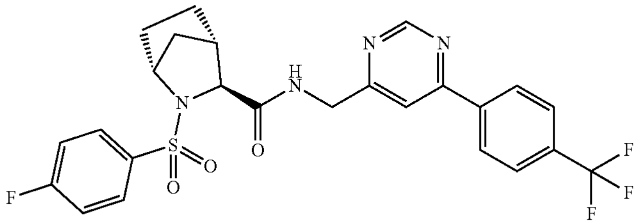 [SMILES: O=C(NCc1cc(-c2ccc(C(F)(F)F)cc2)ncn1)[C@@H]1[C@H]2CC[C@H](C2)N1S(=O)(=O)c1ccc(F)cc1] |

TABLE 1-continued

| Example Number | Chemical Name via ChemDraw | Structure |
|---|---|---|
| 34 | (1R,3S,4S)-2-(4-fluorophenylsulfonyl)-N-((6-(6-(trifluoromethyl)pyridin-3-yl)pyrimidin-4-yl)methyl)-2-azabicyclo[2.2.1]heptane-3-carboxamide | 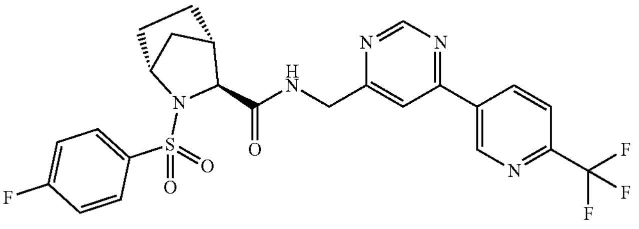 [SMILES: O=C(NCc1cc(-c2ccc(C(F)(F)F)nc2)ncn1)[C@@H]1[C@H]2CC[C@H](C2)N1S(=O)(=O)c1ccc(F)cc1] |
| 36 | (2R,3R)-3-fluoro-1-(4-fluorophenylsulfonyl)-N-((6-(6-(trifluoromethyl)pyridin-3-yl)pyrimidin-4-yl)methyl)pyrrolidine-2-carboxamide | 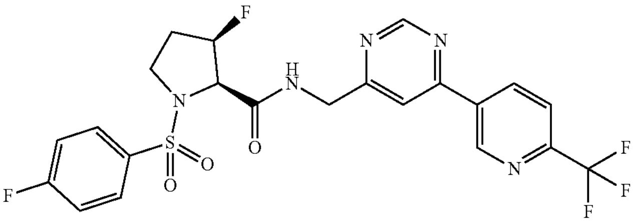 [SMILES: O=C(NCc1cc(-c2ccc(C(F)(F)F)nc2)ncn1)[C@@H]1[C@H](F)CCN1S(=O)(=O)c1ccc(F)cc1] |
| 37 | (2S,4R)-4-fluoro-N-((5-fluoro-4-(4-(trifluoromethyl)piperidin-1-yl)pyridin-2-yl)methyl)-1-(4-fluorophenylsulfonyl) pyrrolidine-2-carboxamide | 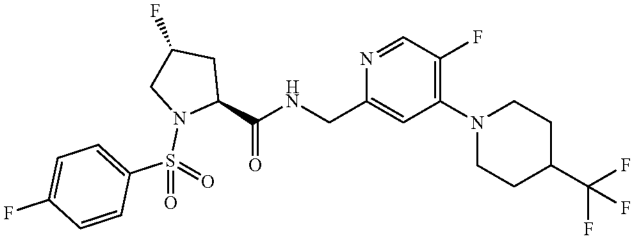 [SMILES: O=C(NCc1cc(N2CCC(C(F)(F)F)CC2)c(F)cn1)[C@@H]1C[C@@H](F)CN1S(=O)(=O)c1ccc(F)cc1] |

In another aspect the present invention provides for compounds of formula II as described herein below as a second embodiment of the invention (embodiment "EE1"):

EE1. A compound of formula II:

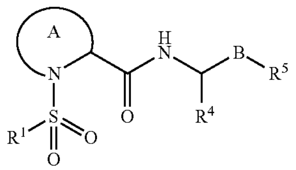

II wherein:

(1) A is

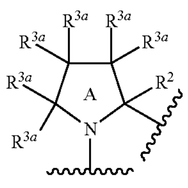

,

B is $B^1$ and $R^5$ is $R^{5a}$; or (2) A is

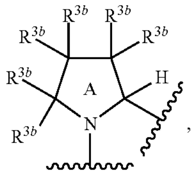

,

B is $B^2$ and $R^5$ is $R^{5b}$; or (3) A is

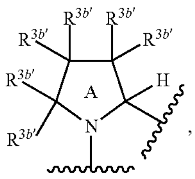

,

B is $B^3$ and $R^5$ is $R^{5a}$; or (4) A is

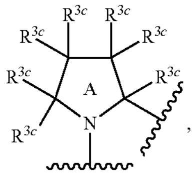
,

B is $B^4$ and $R^5$ is $R^{5a}$; or (5) A is

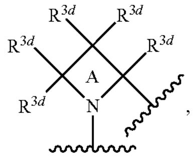
,

B is $B^1$ and $R^5$ is $R^{5a}$; or (6) A is

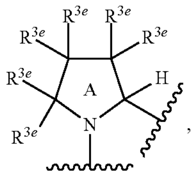
,

B is $B^5$ and $R^5$ is $R^{5a}$; or (7) A is

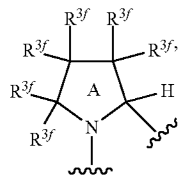

B is $B^3$ and $R^5$ is $R^{5a}$;

B is $B^1$, $B^2$, $B^3$, $B^4$, or $B^5$;

$B^1$ is a 5-membered heteroaryl comprising 2 or 3 nitrogen atoms in the ring or a 6-membered heteroaryl, wherein any 5-membered heteroaryl or 6-membered heteroaryl of $B^1$ is optionally substituted with one or more groups independently selected from halogen, $(C_1-C_6)$alkyl, —O$(C_1-C_6)$alkyl and $(C_3-C_7)$cycloalkyl;

$B^2$ is a pyridinyl, wherein any pyridinyl of $B^2$ is optionally substituted with one or more groups independently selected from halogen, $(C_1-C_6)$alkyl, —O$(C_1-C_6)$alkyl, —O$(C_1-C_6)$alkyl-O$(C_1-C_6)$alkyl, $(C_3-C_7)$cycloalkyl, $(C_1-C_6)$haloalkyl, —CN, and 6-membered heteroaryl, wherein any 6-membered heteroaryl is optionally substituted with one or more $(C_1-C_6)$alkyl or $(C_1-C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1-C_6)$alkyl, —O$(C_1-C_6)$alkyl, $(C_3-C_7)$cycloalkyl, —CN, and $NR^6{}_2$, and wherein when $B^3$ is pyrimidinyl which is attached to the remainder of Formula II at the 4 and 6 positions of the pyrimidinyl, then $R^{5a}$ is not pyrrolidinyl or substituted pyrrolidinyl;

$B^4$ is a 5-membered heteroaryl, 6-membered heteroaryl, or phenyl, wherein any 5-membered heteroaryl, 6-membered heteroaryl, or phenyl of $B^4$ is optionally substituted with one or more groups independently selected from halogen, —CN, $(C_1-C_6)$alkyl, —O$(C_1-C_6)$alkyl and $(C_3-C_7)$cycloalkyl;

$B^5$ is a phenyl optionally substituted with one or more groups independently selected from —CN, halogen, $(C_1-C_6)$alkyl, $(C_1-C_6)$haloalkyl, —O$(C_1-C_6)$alkyl, and —O$(C_1-C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1-C_6)$alkyl and $(C_1-C_6)$haloalkyl;

$R^2$ is halogen, $(C_1-C_6)$alkyl or CN, wherein any $(C_1-C_6)$alkyl of $R^2$ is optionally substituted with one or more groups independently selected from halogen, —OH and —O$(C_1-C_6)$alkyl;

each $R^{3a}$ is independently selected from H, halogen and $(C_1-C_6)$alkyl;

one $R^{3b}$ group is halogen, —CN, or $(C_1-C_6)$alkyl and the remaining $R^{3b}$ groups are independently selected from H, $(C_1-C_6)$alkyl and $(C_1-C_6)$haloalkyl;

one $R^{3b'}$ group is halogen, $(C_1-C_6)$alkyl, —CN, or $(C_1-C_6)$haloalkyl and the remaining $R^{3b'}$ groups are independently selected from H, $(C_1-C_6)$alkyl and $(C_1-C_6)$haloalkyl;

two $R^{3c}$ groups attached to different non-adjacent carbon atoms or adjacent carbon atoms are combined to form a $(C_1-C_4)$alkyl linker or a $(C_1-C_2)$alkyl-O—$(C_1-C_2)$alkyl linker, wherein the $(C_1-C_4)$alkyl linker or $(C_1-C_2)$alkyl-O—$(C_1-C_2)$alkyl linker is optionally substituted with one or more groups independently selected from halogen and $(C_1-C_6)$alkyl, and the remaining $R^{3c}$ groups are independently selected from H, halogen and $(C_1-C_6)$alkyl;

each $R^{3d}$ group is independently selected from H, halogen, $(C_1-C_6)$alkyl, and —CN, wherein any $(C_1-C_6)$alkyl of $R^{3d}$ is optionally substituted with one or more groups independently selected from halogen, —OH and —O$(C_1-C_6)$alkyl;

one $R^{3e}$ group is halogen, —CN or $(C_1-C_6)$alkyl and the remaining $R^{3e}$ groups are independently selected from H, $(C_1-C_6)$alkyl and $(C_1-C_6)$haloalkyl;

two $R^{3f}$ groups attached to the same carbon atom are combined to form a $(C_2-C_4)$alkyl linker, wherein the $(C_2-C_4)$alkyl linker is optionally substituted with one or more groups independently selected from halogen and $(C_1-C_6)$alkyl, and the remaining $R^{3f}$ groups are independently selected from H, halogen and $(C_1-C_6)$alkyl;

$R^4$ is H, $(C_1-C_6)$alkyl or $(C_1-C_6)$haloalkyl;

$R^5$ is $R^{5a}$ or $R^{5b}$;

$R^{5a}$ is a phenyl, 5-membered heteroaryl, 6-membered heteroaryl, 4, 5, 6 or 7-membered heterocycle or $(C_3-C_8)$cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$alkyl-O$(C_1-C_6)$alkyl, —O$(C_1-C_6)$haloalkyl, —S$(C_1-C_6)$alkyl, —S$(C_1-C_6)$haloalkyl, oxo and —O—$(C_1-C_2)$alkyl-O— optionally substituted with one or more halogen, which —O—$(C_1-C_2)$alkyl-O— group is bonded to two adjacent carbon atoms of any phenyl, 5-membered heteroaryl, 6-membered heteroaryl, 4, 5, 6 or 7-membered heterocycle or $(C_3-C_8)$cycloalkyl of $R^{5a}$;

$R^{5b}$ is a phenyl, 5-membered heteroaryl, 6-membered heteroaryl or 4, 5, 6, 7 or 8-membered heterocycle, wherein any phenyl, 5-membered heteroaryl, 6-membered heteroaryl or 4, 6, 7 or 8-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, $—O(C_1-C_6)$alkyl, $—O(C_1-C_6)$haloalkyl, —OH, $—S(C_1-C_6)$alkyl, $—S(C_1-C_6)$haloalkyl, and $NR^6_2$, and wherein any 5-membered heterocycle of $R^{5b}$ is substituted with one or more groups independently selected from halogen, $(C_1-C_6)$alkyl, $(C_1-C_6)$haloalkyl, —CN, $(C_3-C_7)$cycloalkyl, $—O(C_1-C_6)$alkyl, $—O(C_1-C_6)$haloalkyl, $—S(C_1-C_6)$alkyl and $—S(C_1-C_6)$haloalkyl; and each $R^6$ is independently H or $(C_1-C_6)$alkyl;

or a salt thereof.

Additional embodiments of the invention are set forth below.

EE2. The compound of embodiment EE1, wherein:

(1) A is

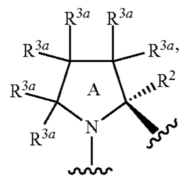

B is $B^1$ and $R^5$ is $R^{5a}$; or (2) A is

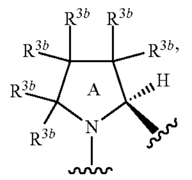

B is $B^2$ and $R^5$ is $R^{5b}$; or (3) A is

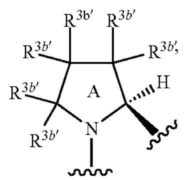

B is $B^3$ and $R^5$ is $R^{5a}$ or (4) A is

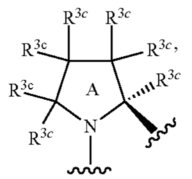

B is $B^4$ and $R^5$ is $R^{5a}$; or (5) A is

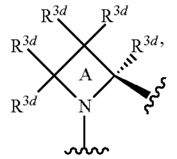

B is $B^1$ and $R^5$ is $R^{5a}$; or (6) A is

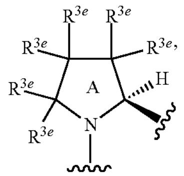

B is $B^5$ and $R^5$ is $R^{5a}$; or (7) A is

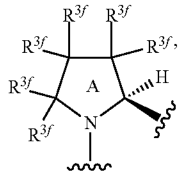

B is $B^3$ and $R^5$ is $R^{5a}$.

EE3. The compound of embodiment EE1 or embodiment EE2, wherein each $R^{3a}$ is independently H or F.

EE4. The compound of embodiment EE1 or embodiment EE2, wherein one $R^{3a}$ is F and the remaining $R^{3a}$ groups are H.

EE5. The compound of embodiment EE1 or embodiment EE2, wherein each $R^{3a}$ is H.

EE6. The compound of any one of embodiments EE1-EE5, wherein $R^2$ is $(C_1-C_6)$alkyl or CN, wherein any $(C_1-C_6)$alkyl of $R^2$ is optionally substituted with one or more groups independently selected from halogen, —OH and $—O(C_1-C_6)$alkyl.

EE7. The compound of any one of embodiments EE1-EE5, wherein $R^2$ is $—CH_3$, $—CH_2OH$, $—CHF_2$, $—CH_2OCH_3$ or CN.

EE8. The compound of any one of embodiments EE1-EE5, wherein $R^2$ is $—CH_3$.

EE9. The compound of any one of embodiments EE1-EE8, wherein $B^1$ is a pyrazolyl, triazolyl, pyridinyl or pyrimidinyl, wherein any pyrazolyl, triazolyl, pyridinyl or pyrimidinyl of $B^1$ is optionally substituted with one or more groups independently selected from halogen, $(C_1-C_6)$alkyl, $—O(C_1-C_6)$alkyl and $(C_3-C_7)$cycloalkyl.

EE10. The compound of any one of embodiments EE1-EE8, wherein $B^1$ is a pyridinyl or pyrimidinyl wherein any pyridinyl or pyrimidinyl of $B^1$ is optionally substituted with one or more groups independently selected from halogen, $(C_1-C_6)$alkyl, $—O(C_1-C_6)$alkyl and $(C_3-C_7)$cycloalkyl.

EE11. The compound of any one of embodiments EE1-EE8, wherein $B^1$ is:

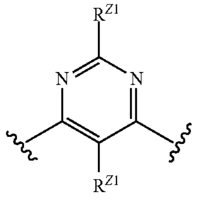
,
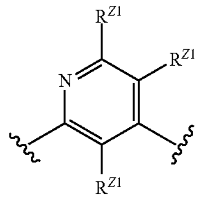
or
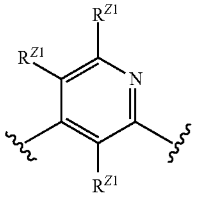

wherein each $R^{Z1}$ is independently selected from H, halogen, $(C_1-C_6)$alkyl, —O$(C_1-C_6)$alkyl and $(C_3-C_7)$cycloalkyl.

EE12. The compound of any one of embodiments EE1-EE8 1-8, wherein $B^1$ is:

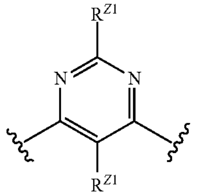

wherein each $R^{Z1}$ is independently selected from H, halogen, $(C_1-C_6)$alkyl, —O$(C_1-C_6)$alkyl and $(C_3-C_7)$cycloalkyl.

EE13. The compound of any one of embodiments EE1-EE8, wherein $B^1$ is a pyrazolyl or a triazolyl, wherein any pyrazolyl or triazolyl of $B^1$ is optionally substituted with one or more groups independently selected from halogen, $(C_1-C_6)$alkyl, —O$(C_1-C_6)$alkyl and $(C_3-C_7)$cycloalkyl.

EE14. The compound of any one of embodiments EE1-EE8, wherein $B^1$ is a pyrazolyl, wherein any pyrazolyl of $B^1$ is optionally substituted with one or more groups independently selected from halogen, $(C_1-C_6)$alkyl, —O$(C_1-C_6)$alkyl and $(C_3-C_7)$cycloalkyl.

EE15. The compound of any one of embodiments EE1-EE8, wherein $B^1$ is:

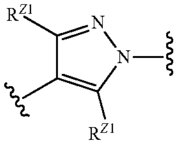

wherein each $R^{Z1}$ is independently selected from H, halogen, $(C_1-C_6)$alkyl, —O$(C_1-C_6)$alkyl and $(C_3-C_7)$cycloalkyl.

EE16. The compound of any one of embodiments EE1-EE15, wherein one $R^{3b}$ group is F and the remaining $R^{3b}$ groups are H, and one $R^{3b'}$ group is F and the remaining $R^{3b'}$ groups are H.

EE16a. The compound of any one of embodiments EE1-EE15, wherein one $R^{3b}$ group is halogen, —CN, or $(C_1-C_6)$alkyl and the remaining $R^{3b}$ groups are independently selected from H, $(C_1-C_6)$alkyl and $(C_1-C_6)$haloalkyl, and one $R^{3b'}$ group is halogen, $(C_1-C_6)$alkyl, —CN, or $(C_1-C_6)$haloalkyl and the remaining $R^{3b'}$ groups are independently selected from H, $(C_1-C_6)$alkyl and $(C_1-C_6)$haloalkyl.

EE16b. The compound of any one of embodiments EE1-EE15, wherein one $R^{3b}$ group is halogen or $(C_1-C_6)$alkyl and the remaining $R^{3b}$ groups are independently selected from H and $(C_1-C_6)$alkyl, and one $R^{3b'}$ group is halogen, $(C_1-C_6)$alkyl, —CN, or $(C_1-C_6)$haloalkyl and the remaining $R^{3b'}$ groups are independently selected from H and $(C_1-C_6)$alkyl.

EE17. The compound of any one of embodiments EE1-EE15, wherein (1) the A group

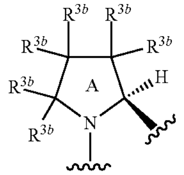

is:

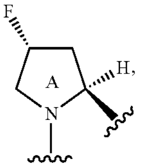

B is $B^2$ and $R^5$ is $R^{5b}$;

(2) the A group

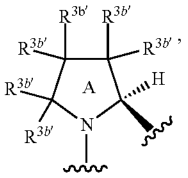

is:

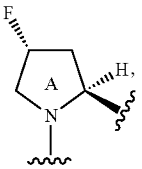

B is $B^3$ and $R^5$ is $R^{5a}$; and (3) the A group

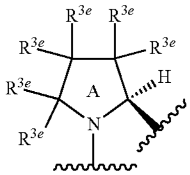

, is:

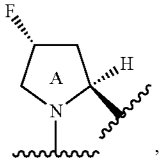

,

B is $B^5$ and $R^5$ is $R^{5a}$.

EE17a. The compound of any one of embodiments EE1-EE15, wherein (1) the A group

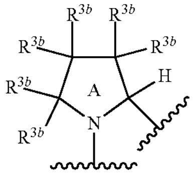

, is:

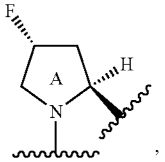

,

B is $B^2$ and $R^5$ is $R^{5b}$;

(2) the A group

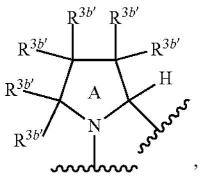

, is:

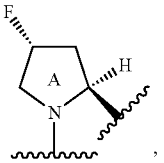

,

B is $B^3$ and $R^5$ is $R^{5a}$; and (3) the A group

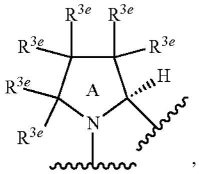

, is:

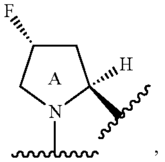

,

B is $B^5$ and $R^5$ is $R^{5a}$.

EE18. The compound of any one of embodiments EE1-EE17, wherein $B^2$ is pyridinyl, wherein any pyridinyl of $B^2$ is optionally substituted with one or more groups independently selected from halogen, $(C_1\text{-}C_6)$alkyl, —O$(C_1\text{-}C_6)$alkyl, —O$(C_1\text{-}C_6)$alkyl-O$(C_1\text{-}C_6)$alkyl, $(C_3\text{-}C_7)$cycloalkyl, $(C_1\text{-}C_6)$haloalkyl, —CN, and 6-membered heteroaryl, wherein any 6-membered heteroaryl is optionally substituted with one or more $(C_1\text{-}C_6)$alkyl or $(C_1\text{-}C_6)$haloalkyl.

EE18a. The compound of any one of embodiments EE1-EE17, wherein $B^2$ is pyridinyl, wherein any pyridinyl of $B^2$ is optionally substituted with one or more groups independently selected from halogen, $(C_1\text{-}C_6)$alkyl, —O$(C_1\text{-}C_6)$alkyl, —O$(C_1\text{-}C_6)$alkyl-O$(C_1\text{-}C_6)$alkyl, $(C_1\text{-}C_6)$haloalkyl, —CN, and 6-membered heteroaryl, wherein any 6-membered heteroaryl is optionally substituted with one or more $(C_1\text{-}C_6)$alkyl or $(C_1\text{-}C_6)$haloalkyl.

EE19. The compound of any one of embodiments EE1-EE17 wherein $B^2$ is:

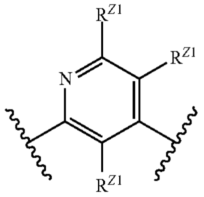

or

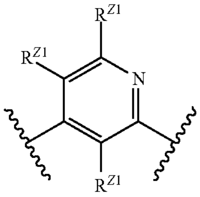

wherein each $R^{Z1}$ is independently selected from H, halogen, $(C_1\text{-}C_6)$alkyl, —O$(C_1\text{-}C_6)$alkyl, —O$(C_1\text{-}C_6)$alkyl-O$(C_1\text{-}C_6)$alkyl, $(C_3\text{-}C_7)$cycloalkyl, $(C_1\text{-}C_6)$haloalkyl, —CN, and 6-membered heteroaryl, wherein any 6-membered heteroaryl is optionally substituted with ($C_1$-$C_6$)alkyl or ($C_1$-$C_6$)haloalkyl.

EE20. The compound of any one of embodiments EE1-EE19, wherein $B^3$ is pyrazolyl, triazolyl or pyrimidinyl, wherein any pyrazolyl, triazolyl or pyrimidinyl of $B^3$ is optionally substituted with one or more groups independently selected from halogen, ($C_1$-$C_6$)alkyl, —O($C_1$-$C_6$)alkyl, ($C_3$-$C_7$)cycloalkyl, —CN, and $NR^6_2$.

EE21. The compound of any one of embodiments EE1-EE19, wherein $B^3$ is a pyrimidinyl, wherein any pyrimidinyl of $B^3$ is optionally substituted with one or more groups independently selected from halogen, ($C_1$-$C_6$)alkyl, —O($C_1$-$C_6$)alkyl, ($C_3$-$C_7$)cycloalkyl, —CN, and $NR^6_2$.

EE22. The compound of any one of embodiments EE1-EE19 wherein $B^3$ is:

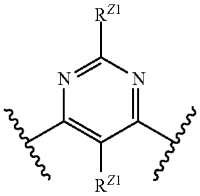

wherein each $R^{Z1}$ is independently selected from hydrogen, halogen, ($C_1$-$C_6$)alkyl, —O($C_1$-$C_6$)alkyl, ($C_3$-$C_7$)cycloalkyl, —CN, and $NR^6_2$.

EE23. The compound of any one of embodiments EE1-EE19, wherein $B^3$ is a pyrazolyl or a triazolyl, wherein any pyrazolyl or triazolyl of $B^3$ is optionally substituted with one or more groups independently selected from halogen, ($C_1$-$C_6$)alkyl, —O($C_1$-$C_6$)alkyl and ($C_3$-$C_7$)cycloalkyl.

EE24. The compound of any one of embodiments EE1-EE19, wherein $B^3$ is a pyrazolyl, wherein any pyrazolyl of $B^3$ is optionally substituted with one or more groups independently selected from halogen, ($C_1$-$C_6$)alkyl, —O($C_1$-$C_6$)alkyl and ($C_3$-$C_7$)cycloalkyl.

EE25. The compound of any one of embodiments EE1-EE19, wherein $B^3$ is:

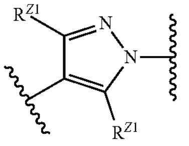

wherein each $R^{Z1}$ is independently selected from H, halogen, ($C_1$-$C_6$)alkyl, —O($C_1$-$C_6$)alkyl and ($C_3$-$C_7$)cycloalkyl.

EE26. The compound of any one of embodiments EE1-EE25, wherein two $R^{3c}$ groups attached to different non-adjacent carbon atoms or different adjacent carbon atoms are combined to form a —$CH_2$, —$CH_2CH_2$— or a —$CH_2OCH_2$— linker, wherein the —$CH_2$—, —$CH_2CH_2$— or a —$CH_2OCH_2$— linker is optionally substituted with one or more independent halogen groups and the remaining $R^{3c}$ groups are each H.

EE27. The compound of any one of embodiments EE1-EE25, wherein the A group

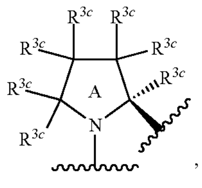

, is:

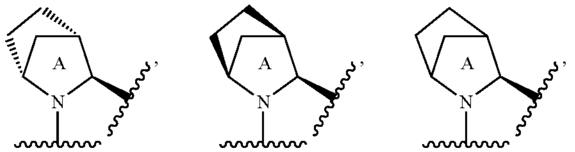

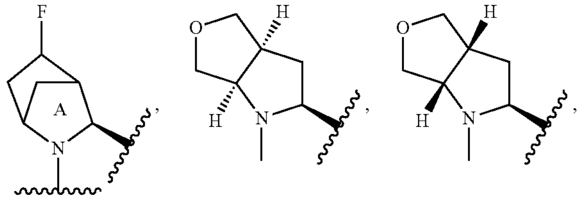

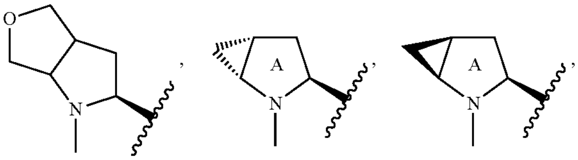

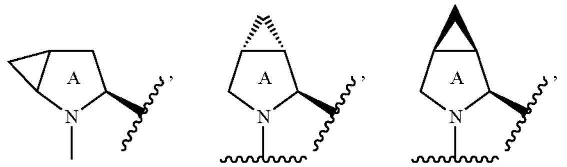

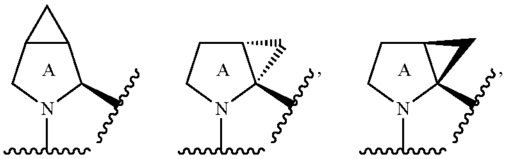

or

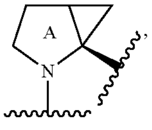

B is $B^4$ and $R^5$ is $R^{5a}$.

EE27a. The compound of any one of embodiments EE1-EE25, wherein the A group

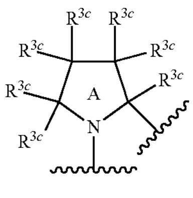

is:

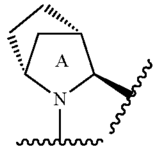,
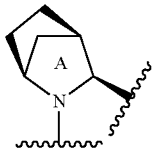,
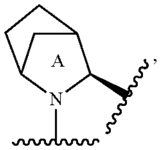,
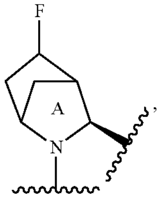,
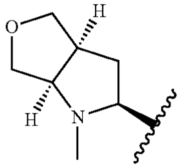,
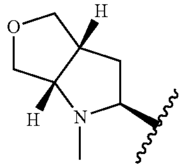,
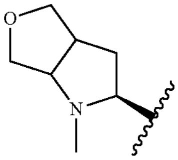,
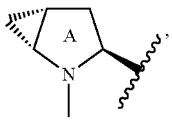,
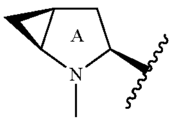,
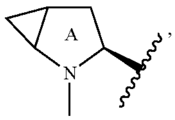,
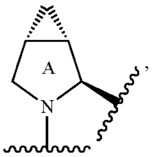,
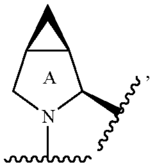,
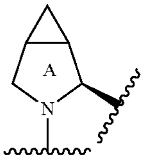
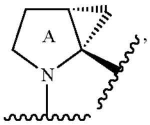,
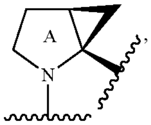, or
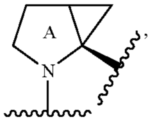, B is $B^4$ and $R^5$ is $R^{5a}$.

EE28. The compound of any one of embodiments EE1-EE27, wherein $B^4$ is a pyrazolyl, triazolyl, pyridinyl, pyrimidinyl, or phenyl wherein any pyrazolyl, triazolyl, pyridinyl, pyrimidinyl, or phenyl of $B^4$ is optionally substituted with one or more groups independently selected from halogen, $(C_1\text{-}C_6)$alkyl, —$O(C_1\text{-}C_6)$alkyl and $(C_3\text{-}C_7)$cycloalkyl.

EE29. The compound of any one of embodiments EE1-EE27, wherein $B^4$ is a pyrimidinyl, wherein any pyrimidinyl of $B^4$ is optionally substituted with one or more groups independently selected from halogen, —CN, $(C_1\text{-}C_6)$alkyl, —$O(C_1\text{-}C_6)$alkyl and $(C_3\text{-}C_7)$cycloalkyl.

EE30. The compound of any one of embodiments EE1-EE27, wherein $B^4$ is:

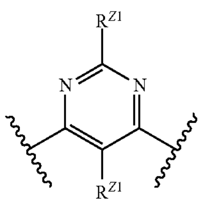

wherein each $R^{Z1}$ is independently selected from hydrogen, halogen, $(C_1\text{-}C_6)$alkyl, —$O(C_1\text{-}C_6)$alkyl and $(C_3\text{-}C_7)$cycloalkyl.

EE30a. The compound of any one of embodiments EE1-EE27, wherein $B^4$ is:

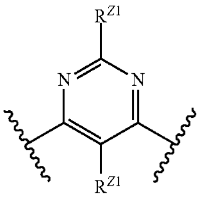

wherein each $R^{Z1}$ is independently selected from hydrogen, halogen, —CN, $(C_1\text{-}C_6)$alkyl, —$O(C_1\text{-}C_6)$alkyl and $(C_3\text{-}C_7)$ cycloalkyl.

EE31. The compound of any one of embodiments EE1-EE30 wherein one $R^{3d}$ group is halogen or $(C_1\text{-}C_6)$alkyl and the remaining $R^{3d}$ groups are H.

EE32. The compound of any one of embodiments EE1-EE30 wherein one $R^{3d}$ group is methyl and the remaining $R^{3d}$ groups are H.

EE33. The compound of any one of embodiments EE1-EE30, wherein the

A group

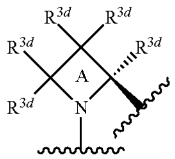

is:

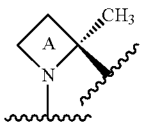 or 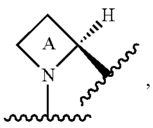,

B is $B^1$ and $R^5$ is $R^{5a}$.

EE33a. The compound of any one of embodiments EE1-EE30, wherein the

A group

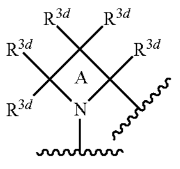

is:

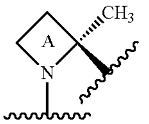

or

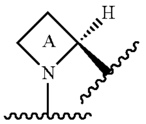

,

B is $B^1$ and $R^5$ is $R^{5a}$.

EE34. The compound of any one of embodiments EE11, EE12, EE15, EE19, EE22, EE25 or EE30, wherein each $R^{Z1}$ is independently selected from H, halogen, $(C_1\text{-}C_6)$alkyl, and $(C_3\text{-}C_7)$cycloalkyl.

EE35. The compound of any one of embodiments EE11, EE12, EE15, EE19, EE22, EE25 or EE30, wherein each $R^{Z1}$ is independently selected from H, fluoro, chloro, methyl, $O(CH_3)$, —CN, (trifluoromethyl)pyrimidin-5-yl, —NH$(CH_3)$, 2-methoxyethoxy, and cyclopropyl.

EE35a. The compound of any one of embodiments EE11, EE12, EE15, EE19, EE22, EE25 or EE30, wherein each $R^{Z1}$ is independently selected from H, fluoro, chloro, methyl, trifluoromethyl, —$O(CH_3)$, —CN, 2-(trifluoromethyl)pyrimidin-5-yl, 2-(trifluoromethyl)pyrinin-5-yl, —$NH(CH_3)$, 2-methoxyethoxy, and cyclopropyl.

EE36. The compound of any one of embodiments EE12, EE22 or EE30, wherein each $R^{Z1}$ is H.

EE37. The compound of any one of embodiments EE1-EE36, wherein $R^4$ is H.

EE38. The compound of any one of embodiments EE1-EE37, wherein $R^1$ is a phenyl or thiophenyl, wherein any phenyl or thiophenyl of $R^1$ is optionally substituted with one or more groups independently selected from halogen, —CN, $(C_1\text{-}C_6)$alkyl and $(C_1\text{-}C_6)$haloalkyl.

EE39. The compound of any one of embodiments EE1-EE37, wherein $R^1$ is a phenyl or thiophenyl, wherein any phenyl or thiophenyl of $R^1$ is optionally substituted with one or more groups independently selected from halogen and —CN.

EE40. The compound of any one of embodiments EE1-EE37, wherein $R^1$ is a phenyl or thiophenyl, wherein any phenyl or thiophenyl of $R^1$ is optionally substituted with one or more groups independently selected from fluoro, chloro and —CN.

EE41. The compound of any one of embodiments EE1-EE37, wherein $R^1$ is 4-fluorophenyl, 3-fluorophenyl, 4-cyanophenyl, 2-chlorothiophen-5-yl, 3,4,-difluorophenyl or 3-fluoropyridin-5-yl.

EE42. The compound of any one of embodiments EE1-EE41, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —$O(C_1\text{-}C_6)$alkyl, —$O(C_1\text{-}C_6)$alkyl-$O(C_1\text{-}C_6)$alkyl, —$O(C_1\text{-}C_6)$haloalkyl, —$S(C_1\text{-}C_6)$alkyl, —$S(C_1\text{-}C_6)$haloalkyl, oxo, and —O—$(C_1\text{-}C_2)$alkyl-O— optionally substituted with one or more halogen; and $R^{5b}$ is phenyl, 6-membered heteroaryl or 6-membered heterocycle, wherein any phenyl, 6-membered heteroaryl or 6-membered heterocycle of $R^{5b}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl optionally substituted with one or more halogen, —$O(C_1\text{-}C_6)$alkyl, —$O(C_1\text{-}C_6)$haloalkyl, —OH, —$S(C_1\text{-}C_6)$alkyl, —$S(C_1\text{-}C_6)$haloalkyl, and $NR^6{}_2$.

EE42a. The compound of any one of embodiments EE1-EE41, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —$O(C_1\text{-}C_6)$alkyl, —$O(C_1\text{-}C_6)$alkyl-$O(C_1\text{-}C_6)$alkyl, —$O(C_1\text{-}C_6)$haloalkyl, —$S(C_1\text{-}C_6)$alkyl, —$S(C_1\text{-}C_6)$haloalkyl, oxo, and —O—$(C_1\text{-}C_2)$alkyl-O— optionally substituted with one or more halogen, which —O—$(C_1\text{-}C_2)$alkyl-O— is bonded to two adjacent atoms of any $R^{5a}$ group; and $R^{5b}$ is phenyl, 6-membered heteroaryl or 6-membered heterocycle, wherein any phenyl, 6-membered heteroaryl or 6-membered heterocycle of $R^{5b}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl optionally substituted with one or more halogen, —$O(C_1\text{-}C_6)$alkyl, —$O(C_1\text{-}C_6)$haloalkyl, —OH, —$S(C_1\text{-}C_6)$alkyl, —$S(C_1\text{-}C_6)$haloalkyl, and $NR^6{}_2$.

EE43. The compound of any one of embodiments EE1-EE41, wherein $R^{5a}$ is phenyl, 6-membered heteroaryl, 6-membered heterocycle or $(C_6)$cycloalkyl, wherein any phenyl, 6-membered heteroaryl, 6-membered heterocycle or $(C_6)$cycloalkyl of $R^{5a}$ is optionally substituted with one or more groups independently selected from $(C_1\text{-}C_6)$haloalkyl, $(C_3\text{-}C_7)$cycloalkyl, —$O(C_1\text{-}C_6)$haloalkyl and —$S(C_1\text{-}C_6)$haloalkyl; and $R^{5b}$ is phenyl, 6-membered heteroaryl or 6-membered heterocycle, wherein any phenyl, 6-membered heteroaryl or 6-membered heterocycle of $R^{5b}$ is optionally substituted with one or more groups independently selected from $(C_1\text{-}C_6)$haloalkyl, $(C_3\text{-}C_7)$cycloalkyl, —$O(C_1\text{-}C_6)$haloalkyl and —$S(C_1\text{-}C_6)$haloalkyl.

EE44. The compound of any one of embodiments EE1-EE41, wherein $R^{5a}$ is phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl wherein any phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —$O(C_1\text{-}C_6)$alkyl, —$O(C_1\text{-}C_6)$alkyl-$O(C_1\text{-}C_6)$alkyl, —$O(C_1\text{-}C_6)$haloalkyl, —$S(C_1\text{-}C_6)$alkyl, —$S(C_1\text{-}C_6)$haloalkyl, oxo, and —O—$(C_1\text{-}C_2)$alkyl-O— optionally substituted with one or more halogen; and $R^{5b}$ is phenyl, pyridinyl, piperidinyl, pyrimidinyl, pyridazinyl, pyrazinyl, 6-azaspiro[2.5]octan-6-yl, or 8-azabicyclo[3.2.1]octan-8-yl, wherein any phenyl, pyridinyl, piperidinyl, pyrimidinyl, pyridazinyl, pyrazinyl, 6-azaspiro[2.5]octan-6-yl, or 8-azabicyclo[3.2.1]octan-8-yl of $R^{5b}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl optionally substituted with one or more halogen, —$O(C_1\text{-}C_6)$alkyl, —$O(C_1\text{-}C_6)$haloalkyl, —OH, —$S(C_1\text{-}C_6)$alkyl, —$S(C_1\text{-}C_6)$haloalkyl, and $NR^6{}_2$.

EE44. The compound of any one of embodiments EE1-EE41, wherein $R^{5a}$ is phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl wherein any phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —$O(C_1\text{-}C_6)$alkyl, —$O(C_1\text{-}C_6)$alkyl-$O(C_1\text{-}C_6)$alkyl, —$O(C_1\text{-}C_6)$haloalkyl, —$S(C_1\text{-}C_6)$alkyl, —$S(C_1\text{-}C_6)$haloalkyl, oxo, and —O—($C_1$-$C_2$)alkyl-O— optionally substituted with one or more halogen, which —O—($C_1$-$C_2$)alkyl-O— is bonded to two adjacent atoms of any $R^{5a}$ group; and $R^{5b}$ is phenyl, pyridinyl, piperidinyl, pyrimidinyl, pyridazinyl, pyrazinyl, 6-azaspiro[2.5]octan-6-yl, or 8-azabicyclo[3.2.1]octan-8-yl, wherein any phenyl, pyridinyl, piperidinyl, pyrimidinyl, pyridazinyl, pyrazinyl, 6-azaspiro[2.5]octan-6-yl, or 8-azabicyclo[3.2.1]octan-8-yl of $R^{5b}$ is optionally substituted with one or more groups independently selected from halogen, ($C_1$-$C_6$)alkyl, ($C_1$-$C_6$)haloalkyl, —CN, ($C_3$-$C_7$)cycloalkyl optionally substituted with one or more halogen, —O($C_1$-$C_6$)alkyl, —O($C_1$-$C_6$)haloalkyl, —OH, —S($C_1$-$C_6$)alkyl, —S($C_1$-$C_6$)haloalkyl, and $NR^6{}_2$.

EE45. The compound of any one of embodiments EE1-EE41, wherein $R^{5a}$ is phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl wherein any phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl of $R^{5a}$ is optionally substituted with one or more groups independently selected from —F, —$CHF_2$, —$CF_3$, —$SCF_3$, —$OCHF_2$, —$OCF_3$, oxo, —O—$CF_2$—O—, —$OCH_2CH_2OCH_3$, cyclopropyl, or spirocyclopropyl; and $R^{5b}$ is phenyl, pyridinyl, piperidinyl, pyrimidinyl, pyridazinyl, pyrazinyl, 6-azaspiro[2.5]octan-6-yl, or 8-azabicyclo[3.2.1]octan-8-yl, wherein any phenyl, pyridinyl, piperidinyl, pyrimidinyl, pyridazinyl, pyrazinyl, 6-azaspiro[2.5]octan-6-yl, or 8-azabicyclo[3.2.1]octan-8-yl of $R^{5b}$ is optionally substituted with one or more groups independently selected from —F, —$CHF_2$, —$CF_3$, —$SCF_3$, —$OCH_3$, —$OCHF_2$, —$OCF_3$, —OH, —$NH_2$, —$NHCH_3$, cyclopropyl, or 2,2-difluoro-spirocyclopropyl.

EE46. The compound of any one of embodiments EE1-EE41, wherein $R^{5a}$ or $R^{5b}$ is phenyl, pyridinyl, pyrimidinyl, pyridazinyl, or pyrazinyl wherein any phenyl, pyridinyl pyrimidinyl, pyridazinyl, or pyrazinyl of $R^{5a}$ or $R^{5b}$ is optionally substituted with one or more groups independently selected from halogen, ($C_1$-$C_6$)alkyl, ($C_1$-$C_6$)haloalkyl, —CN, ($C_3$-$C_7$)cycloalkyl, —O($C_1$-$C_6$)alkyl, —O($C_1$-$C_6$)haloalkyl, —S($C_1$-$C_6$)alkyl and —S($C_1$-$C_6$)haloalkyl.

EE47. The compound of any one of embodiments EE1-EE41, wherein $R^{5a}$ or $R^{5b}$ is phenyl, pyridinyl, pyrimidinyl, pyridazinyl, or pyrazinyl wherein any phenyl, pyridinyl pyrimidinyl, pyridazinyl, or pyrazinyl of $R^{5a}$ or $R^{5b}$ is optionally substituted with one or more groups independently selected from ($C_1$-$C_6$)haloalkyl, ($C_3$-$C_7$)cycloalkyl, —O($C_1$-$C_6$)haloalkyl and —S($C_1$-$C_6$)haloalkyl.

EE48. The compound of any one of embodiments EE1-EE41, wherein $R^{5a}$ or $R^{5b}$ is phenyl, pyridinyl, pyrimidinyl, pyridazinyl, or pyrazinyl wherein any phenyl, pyridinyl pyrimidinyl, pyridazinyl, or pyrazinyl of $R^{5a}$ or $R^{5b}$ is optionally substituted with one or more groups independently selected from —F, —$CHF_2$, —$CF_3$, —$SCF_3$, —$OCF_3$ or cyclopropyl.

EE49. The compound of any one of embodiments EE1-EE41, wherein $R^{5a}$ is

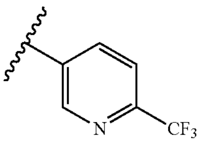
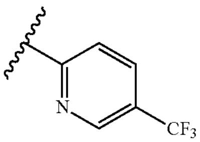

-continued

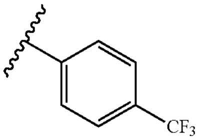
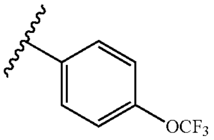
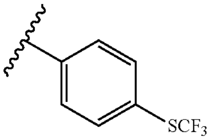
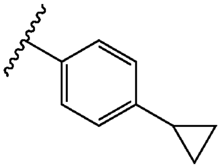
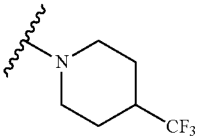
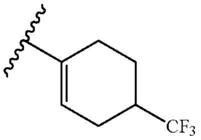
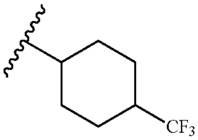
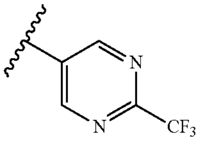
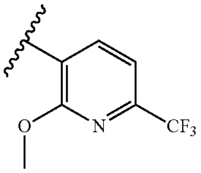
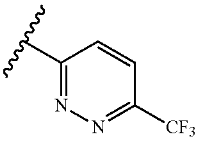
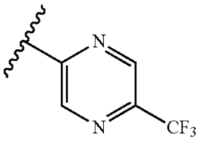
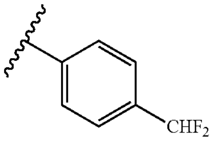
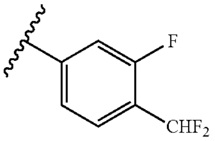
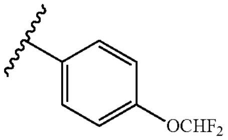
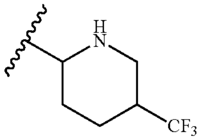
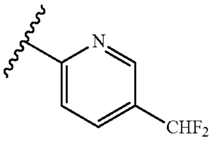
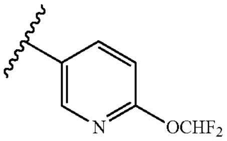
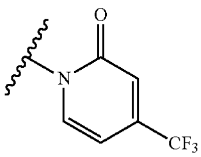
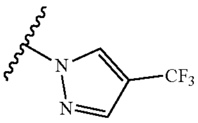
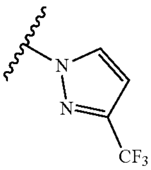

-continued
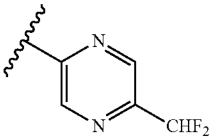
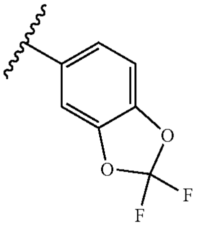
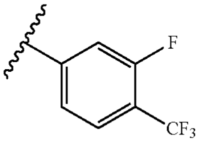
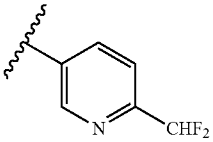
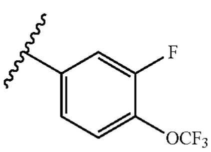
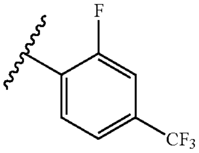
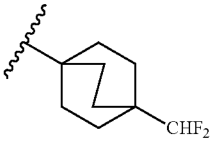
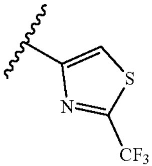
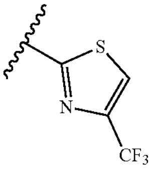
or
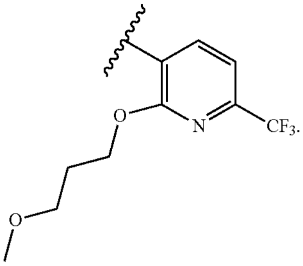
EE50. The compound of any one of embodiments EE1-EE41, wherein $R^{5b}$ is
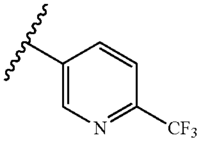
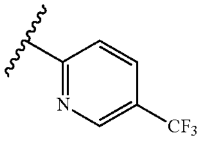
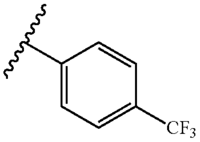
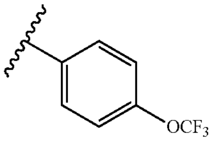
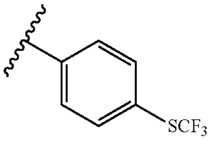
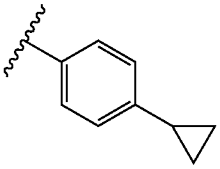
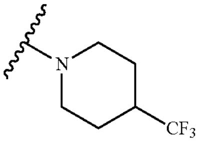
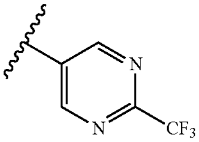
-continued
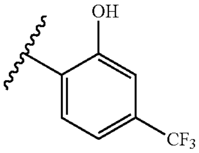
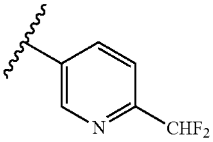
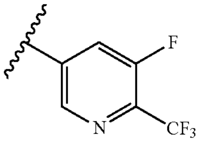
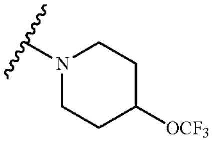
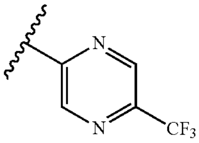
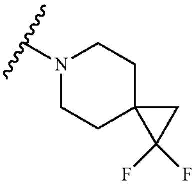
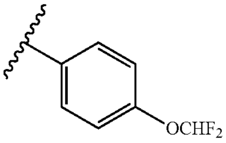
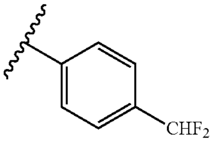
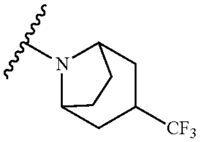
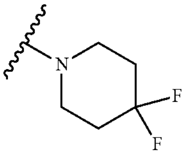
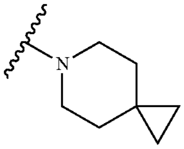
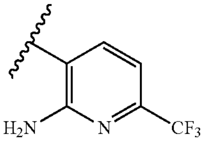
or
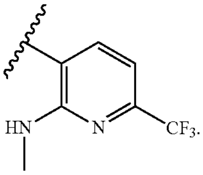
EE51. The compound according to embodiment EE1, which is:
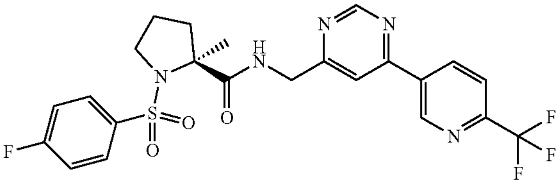
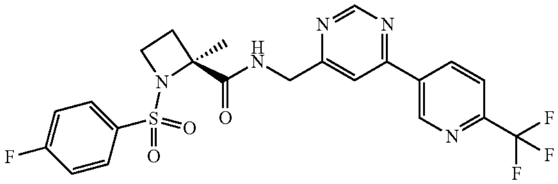

-continued
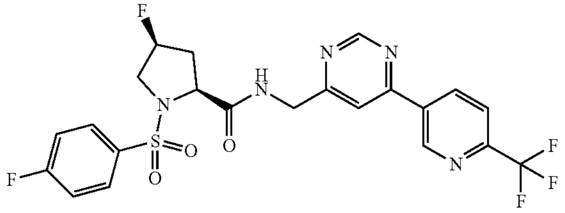
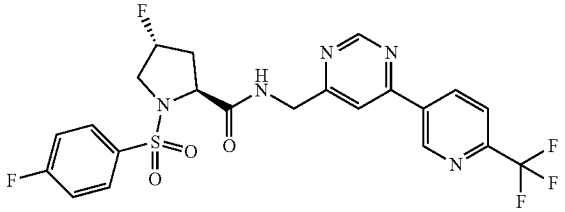
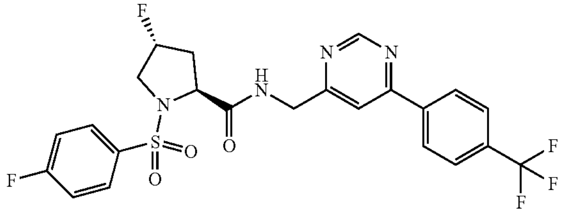
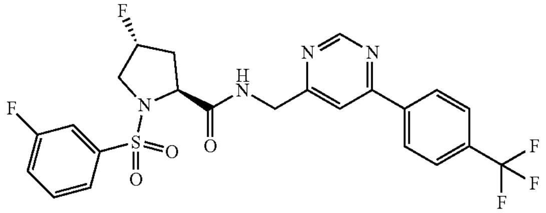
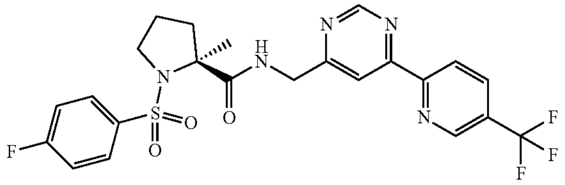
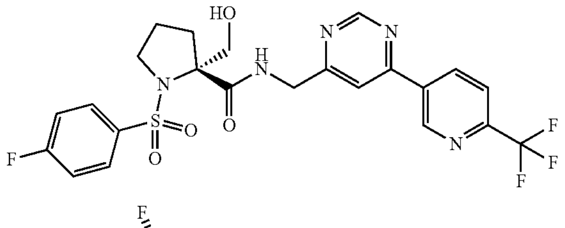
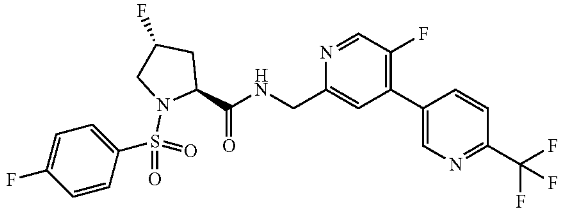
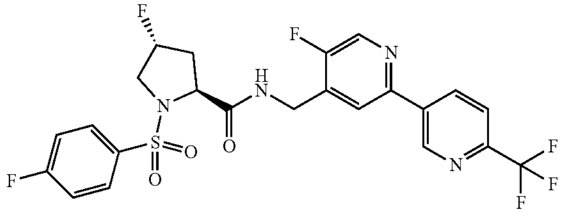
-continued
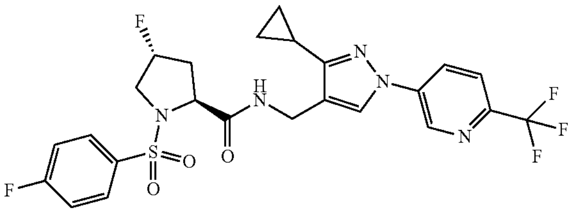
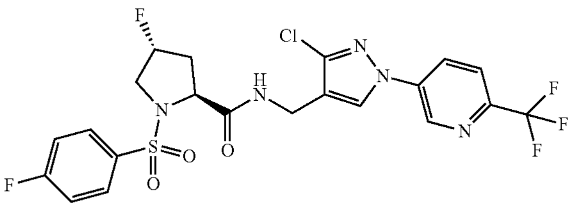
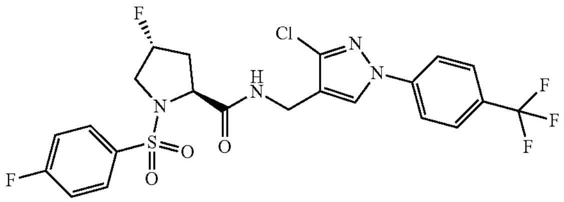
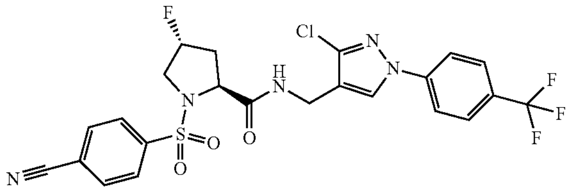
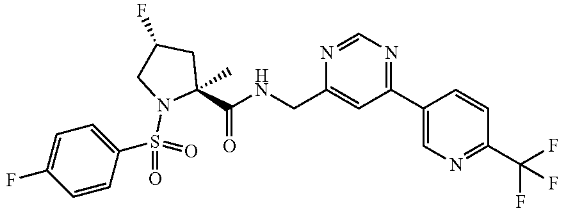
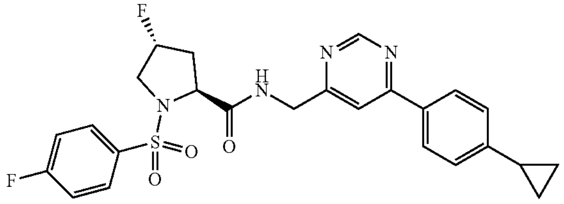
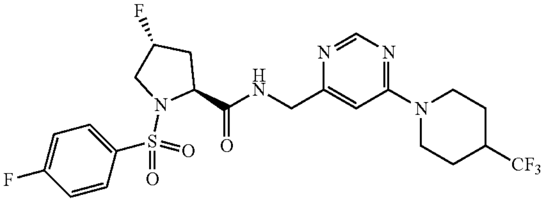
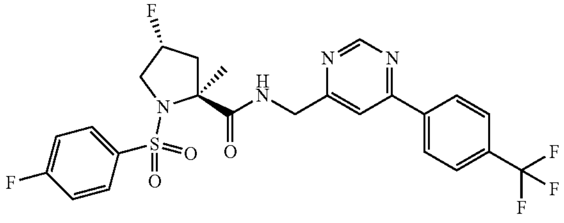

-continued
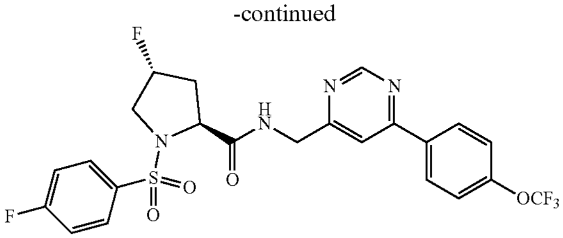
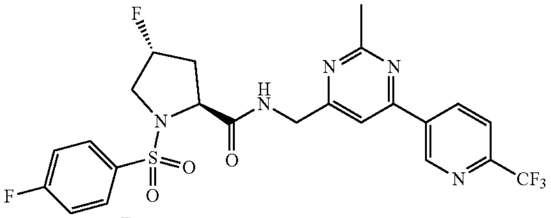
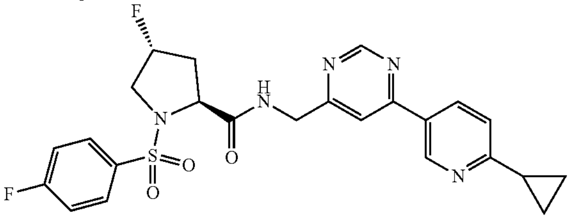
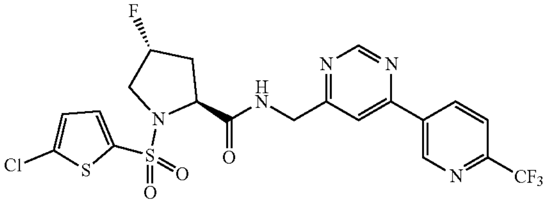
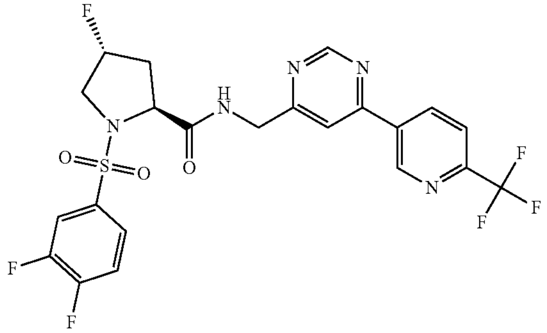
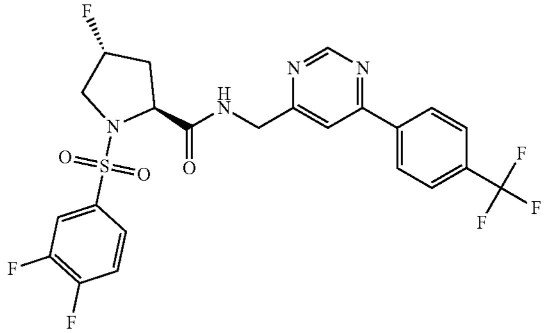
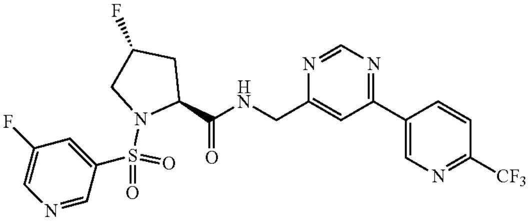
-continued
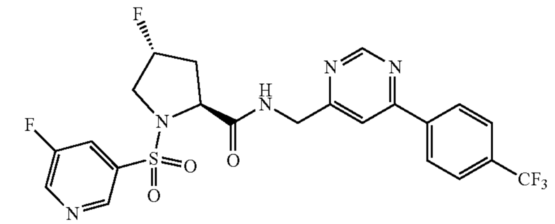
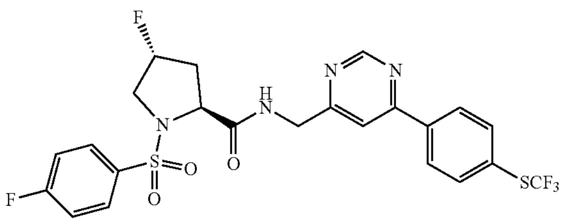
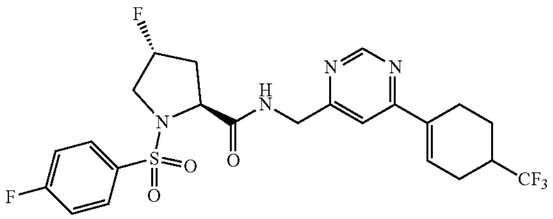
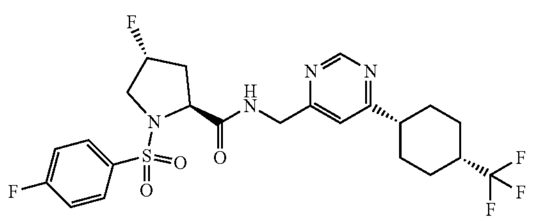
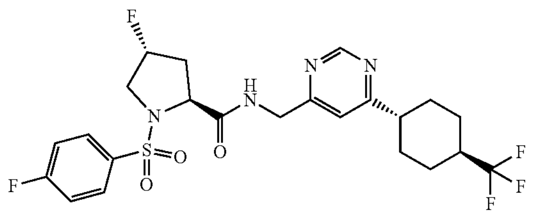
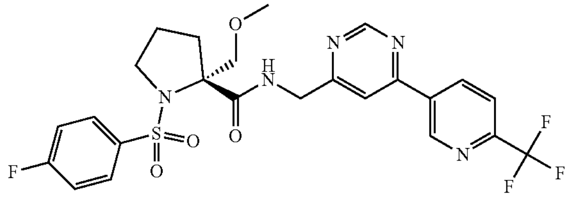
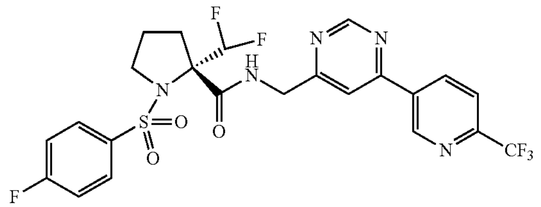
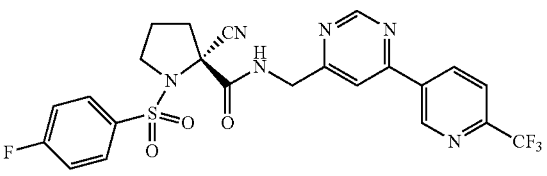

-continued

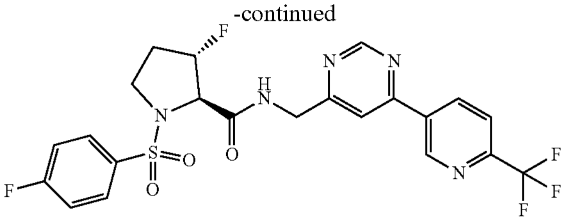

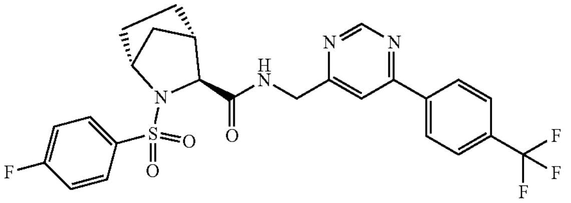

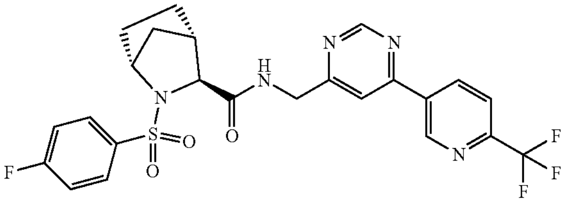

-continued

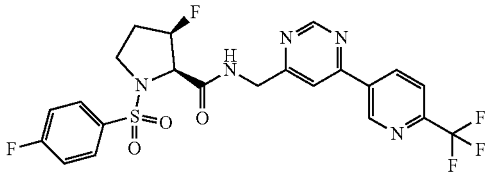

or

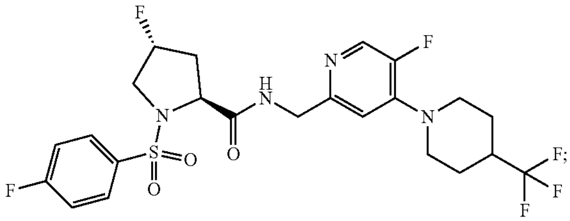

or a salt or a pharmaceutically acceptable salt thereof.

EE52. The compound according to embodiment EE1, which are selected from the compound in the Table 2 below or a salt or a pharmaceutically acceptable salt thereof:

TABLE 2

| Example Number | Chemical Name via ChemDraw | Structure |
|---|---|---|
| 38 | (2R,3S)-N-[[2-cyano-5-[2-(trifluoromethyl)pyrimidin-5-yl]phenyl]methyl]-3-fluoro-1-(4-fluorophenyl)sulfonyl-pyrrolidine-2-carboxamide | 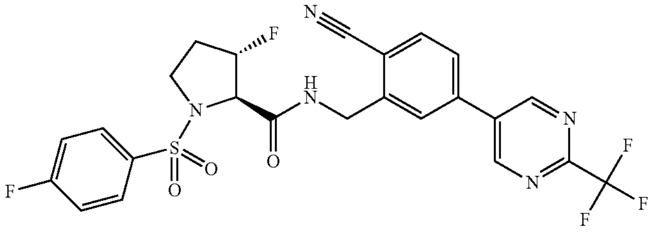 [SMILES: N#Cc1ccc(-c2cnc(C(F)(F)F)nc2)cc1CNC(=O)[C@@H]1[C@@H](F)CCN1S(=O)(=O)c1ccc(F)cc1] |
| 39 | (2S,5R)-1-(4-fluorophenyl)sulfonyl-5-methyl-N-[[6-[6-(trifluoromethyl)-3-pyridyl]pyrimidin-4-yl]methyl]pyrrolidine-2-carboxamide | 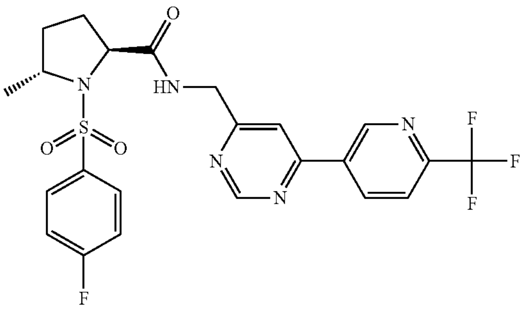 [SMILES: C[C@@H]1CC[C@@H](C(=O)NCc2cc(-c3ccc(C(F)(F)F)nc3)ncn2)N1S(=O)(=O)c1ccc(F)cc1] |
| 40 | (2S,4S)-4-fluoro-4-(fluoromethyl)-1-(4-fluorophenyl)sulfonyl-N-[[6-[6-(trifluoromethyl)-3-pyridyl]pyrimidin-4-yl]methyl]pyrrolidine-2-carboxamide | 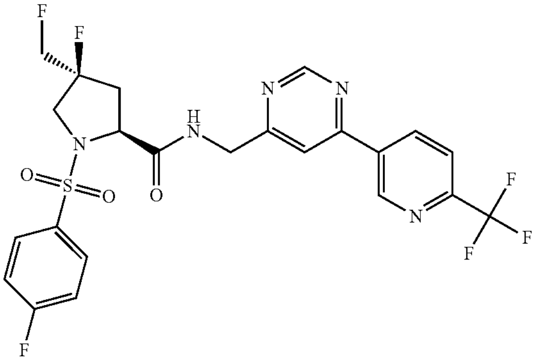 [SMILES: O=C(NCc1cc(-c2ccc(C(F)(F)F)nc2)ncn1)[C@@H]1C[C@@](F)(CF)CN1S(=O)(=O)c1ccc(F)cc1] |

TABLE 2-continued

| Example Number | Chemical Name via ChemDraw | Structure |
| --- | --- | --- |
| 41 | (2S,5S)-1-(4-fluorophenyl)sulfonyl-5-methyl-N-[[6-[6-(trifluoromethyl)-3-pyridyl]pyrimidin-4-yl]methyl]pyrrolidine-2-carboxamide | 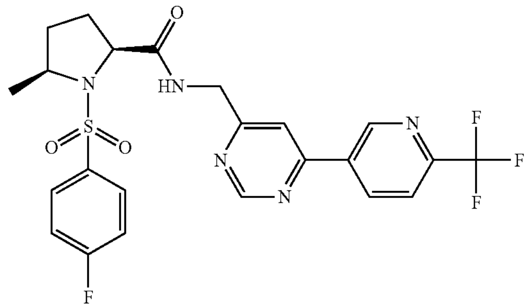 [SMILES: C[C@H]1CC[C@@H](C(=O)NCc2cc(-c3ccc(C(F)(F)F)nc3)ncn2)N1S(=O)(=O)c1ccc(F)cc1] |
| 42 | (2S,4R)-4-fluoro-1-(4-fluorophenyl)sulfonyl-N-[[6-[2-(trifluoromethyl)pyrimidin-5-yl]pyrimidin-4-yl]methyl]pyrrolidine-2-carboxamide | 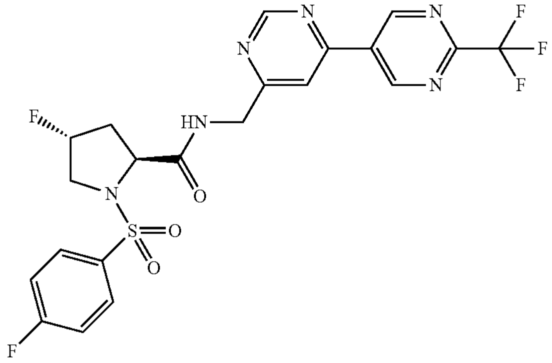 |
| 43 | (2S,4R)-4-fluoro-1-(4-fluorophenyl)sulfonyl-N-[[2-methyl-6-[2-(trifluoromethyl)pyrimidin-5-yl]-4-pyridyl]methyl]pyrrolidine-2-carboxamide | 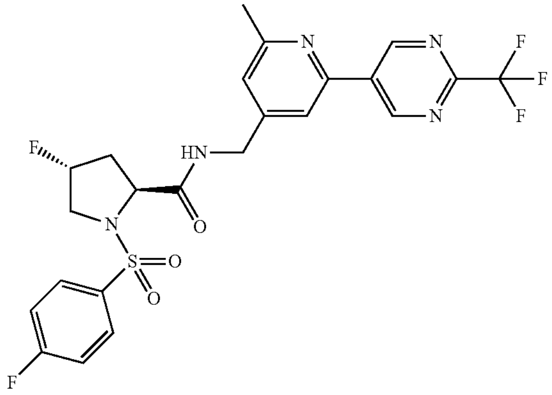 [SMILES: Cc1cc(CNC(=O)[C@@H]2C[C@@H](F)CN2S(=O)(=O)c2ccc(F)cc2)cc(-c2cnc(C(F)(F)F)nc2)n1] |
| 44 | (2S,4R)-4-fluoro-N-[[3-fluoro-5-[2-methoxy-6-(trifluoromethyl)-3-pyridyl]phenyl]methyl]-1-(4-fluorophenyl)sulfonyl-pyrrolidine-2-carboxamide | 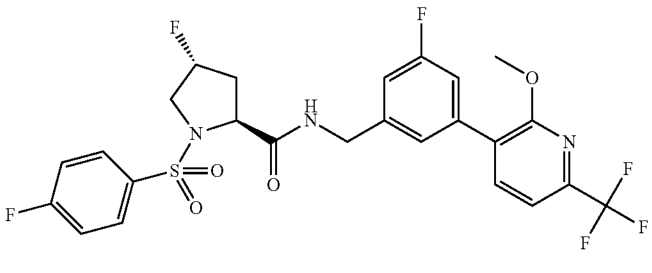 [SMILES: COc1nc(C(F)(F)F)ccc1-c1cc(F)cc(CNC(=O)[C@@H]2C[C@@H](F)CN2S(=O)(=O)c2ccc(F)cc2)c1] |

TABLE 2-continued

| Example Number | Chemical Name via ChemDraw | Structure |
|---|---|---|
| 45 | (2S,4R)-4-fluoro-1-(4-fluorophenyl)sulfonyl-N-[[3-fluoro-5-[6-(trifluoromethyl)pyridazin-3-yl]phenyl]methyl]-4-methyl-pyrrolidine-2-carboxamide | 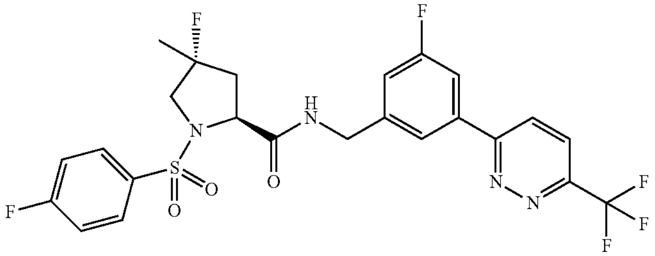 [SMILES: C[C@@]1(F)C[C@@H](C(=O)NCc2cc(F)cc(-c3ccc(C(F)(F)F)nn3)c2)N(S(=O)(=O)c2ccc(F)cc2)C1] |
| 46 | (2S)-4-fluoro-1-(4-fluorophenyl)sulfonyl-4-methyl-N-[[6-[4-(trifluoromethoxy)phenyl] pyrimidin-4-yl] methyl]pyrrolidine-2-carboxamide | 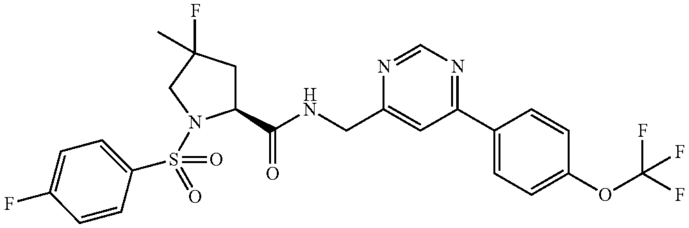 [SMILES: CC1(F)C[C@@H](C(=O)NCc2cc(-c3ccc(OC(F)(F)F)cc3)ncn2)N(S(=O)(=O)c2ccc(F)cc2)C1] |
| 47 | (2S,4R)-4-fluoro-1-(4-fluorophenyl)sulfonyl-N-[[3-fluoro-5-[5-(trifluoromethyl)pyrazin-2-yl]phenyl]methyl]-4-methyl-pyrrolidine-2-carboxamide | 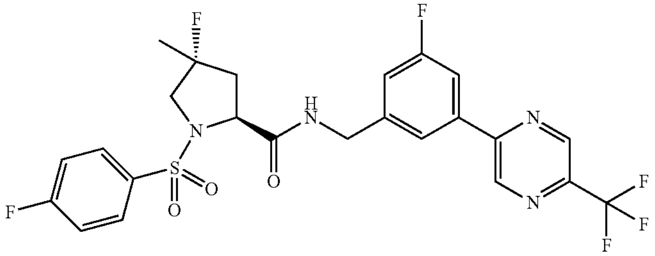 [SMILES: C[C@@]1(F)C[C@@H](C(=O)NCc2cc(F)cc(-c3cnc(C(F)(F)F)cn3)c2)N(S(=O)(=O)c2ccc(F)cc2)C1] |
| 48 | (2S,4R)-4-fluoro-1-(4-fluorophenyl)sulfonyl-N-[[6-methyl-4-[2-(trifluoromethyl)pyrimidin-5-yl]-2-pyridyl]methyl]pyrrolidine-2-carboxamide | 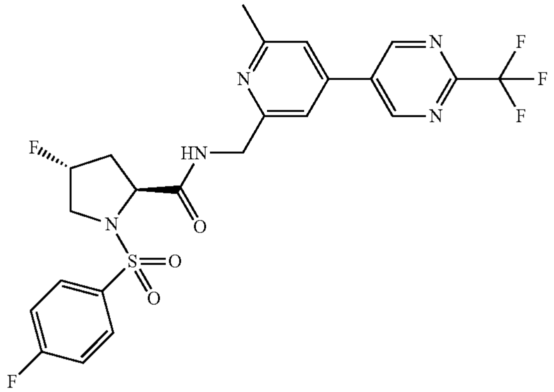 [SMILES: Cc1cc(-c2cnc(C(F)(F)F)nc2)cc(CNC(=O)[C@@H]2C[C@@H](F)CN2S(=O)(=O)c2ccc(F)cc2)n1] |
| 49 | (2S,4R)-4-fluoro-1-(4-fluorophenyl)sulfonyl-N-[[6-fluoro-4-[5-(trifluoromethyl)-2-pyridyl]-2-pyridyl]methyl]pyrrolidine-2-carboxamide | 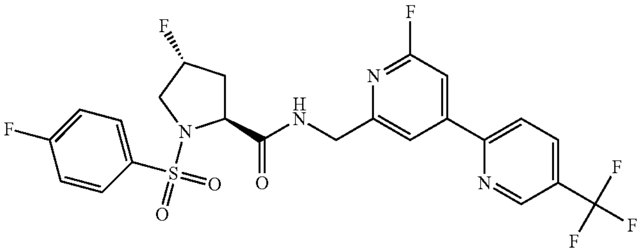 [SMILES: O=C(NCc1cc(-c2ccc(C(F)(F)F)cn2)cc(F)n1)[C@@H]1C[C@@H](F)CN1S(=O)(=O)c1ccc(F)cc1] |

TABLE 2-continued

| Example Number | Chemical Name via ChemDraw | Structure |
|---|---|---|
| 50 | (2S,4R)-N-[[3-cyano-1-[4-(trifluoromethyl)phenyl]pyrazol-4-yl]methyl]-4-fluoro-1-(4-fluorophenyl)sulfonyl-pyrrolidine-2-carboxamide | 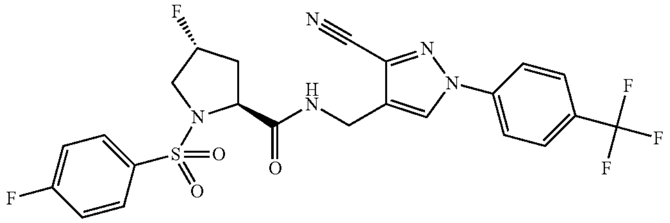 [SMILES: N#Cc1nn(-c2ccc(C(F)(F)F)cc2)cc1CNC(=O)[C@@H]1C[C@@H](F)CN1S(=O)(=O)c1ccc(F)cc1] |
| 51 | 5-fluoro-2-(4-fluorophenyl)sulfonyl-N-[[6-[6-(trifluoromethyl)-3-pyridyl]pyrimidin-4-yl]methyl]-2-azabicyclo[2.2.1]heptane-3-carboxamide | 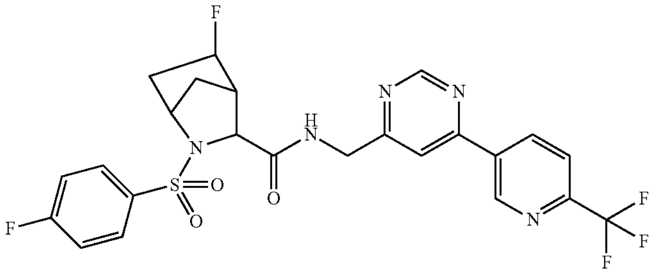 [SMILES: O=C(NCc1cc(-c2ccc(C(F)(F)F)nc2)ncn1)C1C2CC(CC2F)N1S(=O)(=O)c1ccc(F)cc1] |
| 52 | (2S,4R)-4-fluoro-1-(4-fluorophenyl)sulfonyl-N-[[3-fluoro-5-[2-(trifluoromethyl)pyrimidin-5-yl]phenyl]methyl]-4-methyl-pyrrolidine-2-carboxamide | 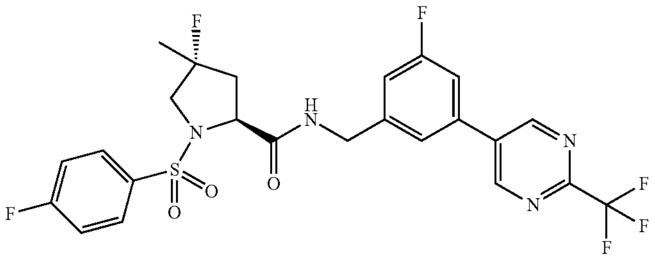 [SMILES: C[C@@]1(F)C[C@@H](C(=O)NCc2cc(F)cc(-c3cnc(C(F)(F)F)nc3)c2)N(S(=O)(=O)c2ccc(F)cc2)C1] |
| 53 | (2S,4R)-4-fluoro-1-(4-fluorophenyl)sulfonyl-N-[[4-[2-(trifluoromethyl)pyrimidin-5-yl]-2-pyridyl]methyl]pyrrolidine-2-carboxamide | 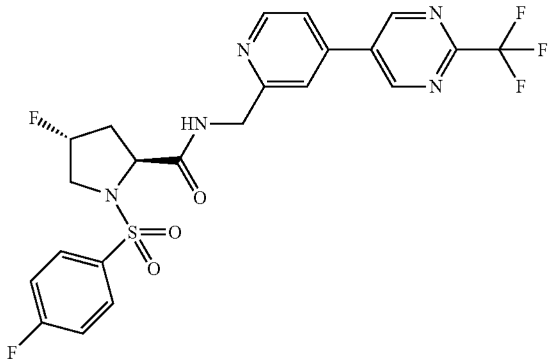 [SMILES: O=C(NCc1cc(-c2cnc(C(F)(F)F)nc2)ccn1)[C@@H]1C[C@@H](F)CN1S(=O)(=O)c1ccc(F)cc1] |
| 54 | (2S,4R)-4-fluoro-1-(4-fluorophenyl)sulfonyl-N-[[2-fluoro-5-[5-(trifluoromethyl)pyrazin-2-yl]phenyl]methyl]pyrrolidine-2-carboxamide | 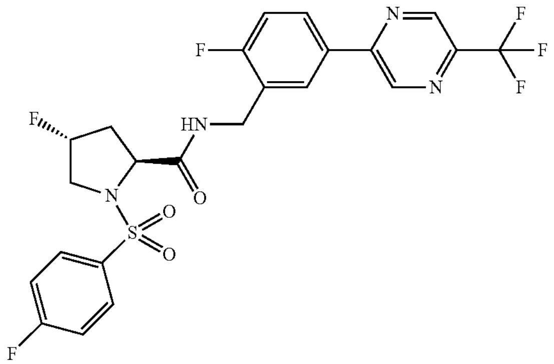 [SMILES: O=C(NCc1cc(-c2cnc(C(F)(F)F)cn2)ccc1F)[C@@H]1C[C@@H](F)CN1S(=O)(=O)c1ccc(F)cc1] |

TABLE 2-continued

| Example Number | Chemical Name via ChemDraw | Structure |
| --- | --- | --- |
| 55 | (2R,3S)-N-[[6-[4-(difluoromethyl)phenyl]pyrimidin-4-yl]methyl]-3-fluoro-1-(4-fluorophenyl)sulfonyl-pyrrolidine-2-carboxamide | 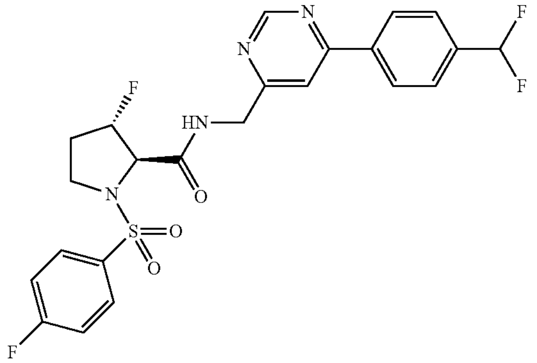 [SMILES: O=C(NCc1cc(-c2ccc(C(F)F)cc2)ncn1)[C@@H]1[C@@H](F)CCN1S(=O)(=O)c1ccc(F)cc1] |
| 56 | (2S,4R)-4-fluoro-1-(4-fluorophenyl)sulfonyl-N-[[2-fluoro-5-[2-(trifluoromethyl)pyrimidin-5-yl]phenyl]methyl]pyrrolidine-2-carboxamide | 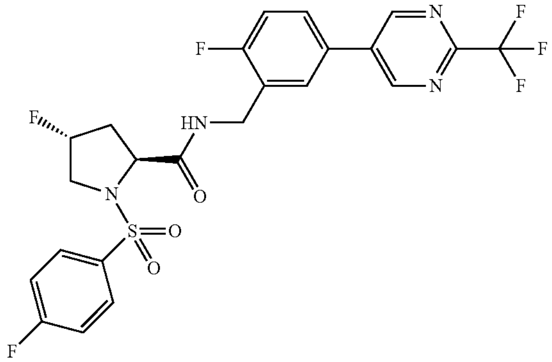 [SMILES: O=C(NCc1cc(-c2cnc(C(F)(F)F)nc2)ccc1F)[C@@H]1C[C@@H](F)CN1S(=O)(=O)c1ccc(F)cc1] |
| 57 | (2S,4R)-4-fluoro-1-(4-fluorophenyl)sulfonyl-N-[[2-[2-hydroxy-4-(trifluoromethyl)phenyl]-4-pyridyl]methyl]pyrrolidine-2-carboxamide | 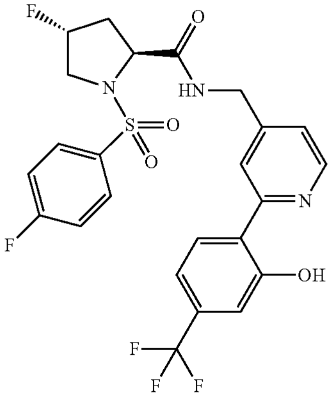 [SMILES: O=C(NCc1ccnc(-c2ccc(C(F)(F)F)cc2O)c1)[C@@H]1C[C@@H](F)CN1S(=O)(=O)c1ccc(F)cc1] |
| 58 | (2S,4R)-4-fluoro-1-(4-fluorophenyl)sulfonyl-N-[[3-methoxy-1-[5-(trifluoromethyl)pyrazin-2-yl]pyrazol-4-yl]methyl]pyrrolidine-2-carboxamide | 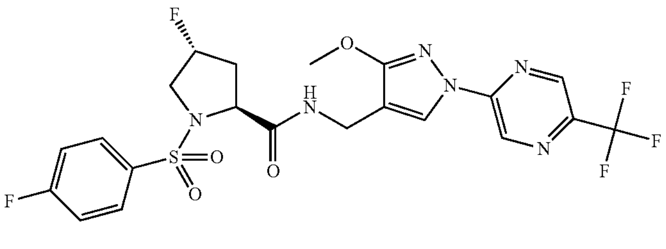 [SMILES: COc1nn(-c2cnc(C(F)(F)F)cn2)cc1CNC(=O)[C@@H]1C[C@@H](F)CN1S(=O)(=O)c1ccc(F)cc1] |

TABLE 2-continued

| Example Number | Chemical Name via ChemDraw | Structure |
|---|---|---|
| 59 | (2S,4R)-N-[[6-[4-(difluoromethyl)-3-fluoro-phenyl]pyrimidin-4-yl]methyl]-4-fluoro-1-(4-fluorophenyl)sulfonyl-pyrrolidine-2-carboxamide | 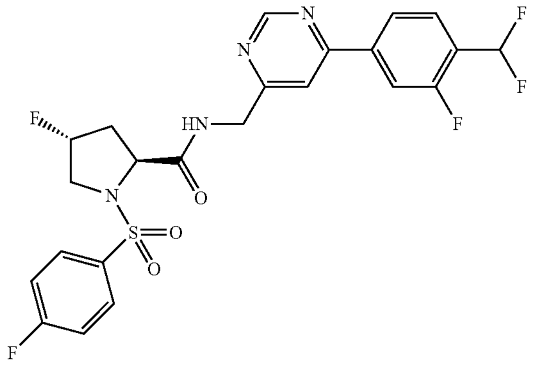 [SMILES: O=C(NCc1cc(-c2ccc(C(F)F)c(F)c2)ncn1)[C@@H]1C[C@@H](F)CN1S(=O)(=O)c1ccc(F)cc1] |
| 60 | (2S,4R)-N-[[2-chloro-6-[6-(difluoromethyl)-3-pyridyl]-4-pyridyl]methyl]-4-fluoro-1-(4-fluorophenyl)sulfonyl-pyrrolidine-2-carboxamide | 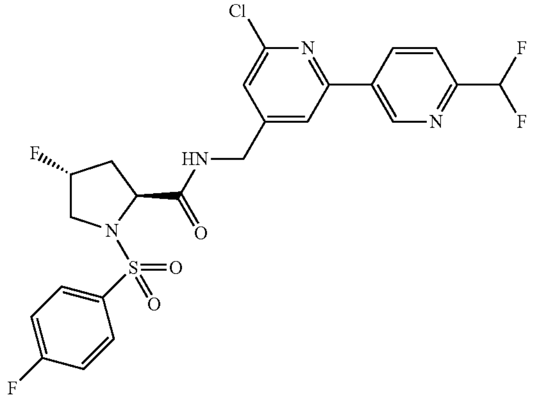 [SMILES: O=C(NCc1cc(Cl)nc(-c2ccc(C(F)F)nc2)c1)[C@@H]1C[C@@H](F)CN1S(=O)(=O)c1ccc(F)cc1] |
| 61 | (2S,4R)-N-[[2,6-bis[2-(trifluoromethyl)pyrimidin-5-yl]-4-pyridyl]methyl]-4-fluoro-1-(4-fluorophenyl)sulfonyl-pyrrolidine-2-carboxamide | 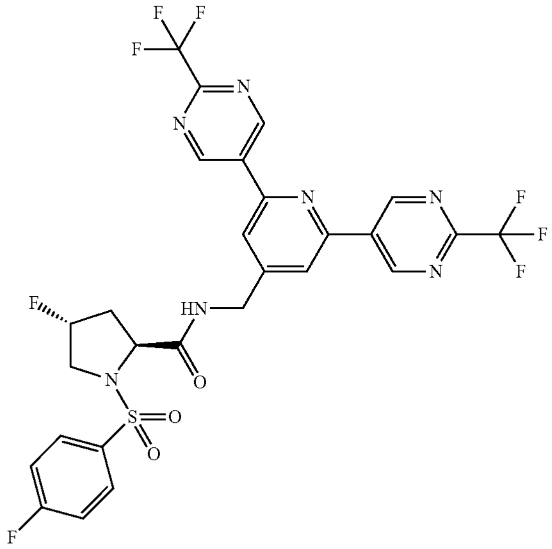 [SMILES: O=C(NCc1cc(-c2cnc(C(F)(F)F)nc2)nc(-c2cnc(C(F)(F)F)nc2)c1)[C@@H]1C[C@@H](F)CN1S(=O)(=O)c1ccc(F)cc1] |

TABLE 2-continued

| Example Number | Chemical Name via ChemDraw | Structure |
|---|---|---|
| 62 | (2S,4R)-N-[[2-chloro-6-[2-(trifluoromethyl)pyrimidin-5-yl]-4-pyridyl]methyl]-4-fluoro-1-(4-fluorophenyl)sulfonyl-pyrrolidine-2-carboxamide | 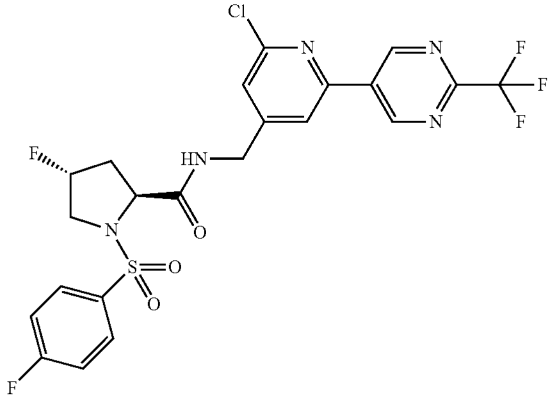 [SMILES: O=C(NCc1cc(Cl)nc(-c2cnc(C(F)(F)F)nc2)c1)[C@@H]1C[C@@H](F)CN1S(=O)(=O)c1ccc(F)cc1] |
| 63 | (2S,4R)-N-[[6-[4-(difluoromethyl)phenyl]pyrimidin-4-yl]methyl]-4-fluoro-1-(4-fluorophenyl)sulfonyl-pyrrolidine-2-carboxamide | 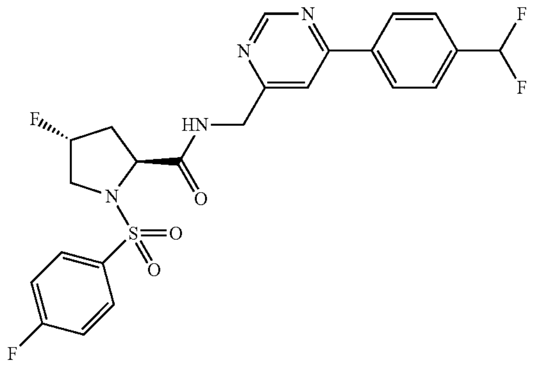 [SMILES: O=C(NCc1cc(-c2ccc(C(F)F)cc2)ncn1)[C@@H]1C[C@@H](F)CN1S(=O)(=O)c1ccc(F)cc1] |
| 64 | (2S,4R)-N-[[6-[4-(difluoromethoxy)phenyl]pyrimidin-4-yl]methyl]-4-fluoro-1-(4-fluorophenyl)sulfonyl-pyrrolidine-2-carboxamide | 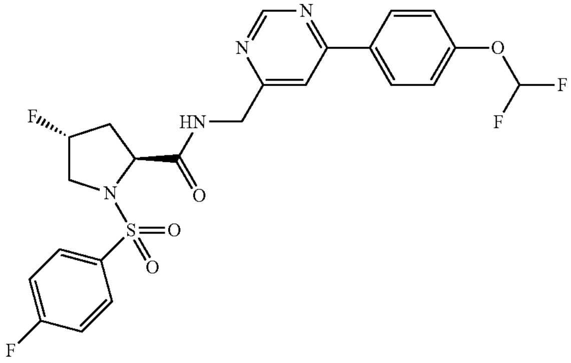 [SMILES: O=C(NCc1cc(-c2ccc(OC(F)F)cc2)ncn1)[C@@H]1C[C@@H](F)CN1S(=O)(=O)c1ccc(F)cc1] |
| 65 | (2S,4R)-4-fluoro-N-[[5-fluoro-4-[5-fluoro-6-(trifluoromethyl)-3-pyridyl]-2-pyridyl]methyl]-1-(4-fluorophenyl)sulfonyl-pyrrolidine-2-carboxamide | 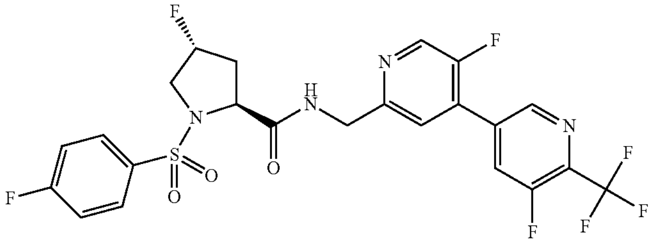 [SMILES: O=C(NCc1cc(-c2cnc(C(F)(F)F)c(F)c2)c(F)cn1)[C@@H]1C[C@@H](F)CN1S(=O)(=O)c1ccc(F)cc1] |

TABLE 2-continued

| Example Number | Chemical Name via ChemDraw | Structure |
|---|---|---|
| 66 | (2S,4R)-4-fluoro-1-(4-fluorophenyl)sulfonyl-N-[[5-fluoro-4-[4-(trifluoromethoxy)-1-piperidyl]-2-pyridyl]methyl]pyrrolidine-2-carboxamide | 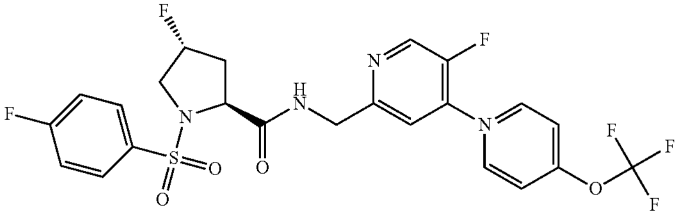 |
| 67 | (2S,4R)-4-fluoro-1-(4-fluorophenyl)sulfonyl-N-[[2-[5-(trifluoromethyl)pyrazin-2-yl]-4-pyridyl]methyl]pyrrolidine-2-carboxamide | 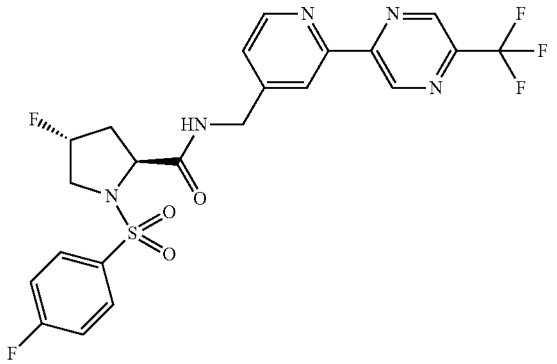 [SMILES: O=C(NCc1ccnc(-c2cnc(C(F)(F)F)cn2)c1)[C@@H]1C[C@@H](F)CN1S(=O)(=O)c1ccc(F)cc1] |
| 68 | (2R,3S)-3-fluoro-1-(4-fluorophenyl)sulfonyl-N-[[3-fluoro-5-[2-(trifluoromethyl)pyrimidin-5-yl]phenyl]methyl]pyrrolidine-2-carboxamide | 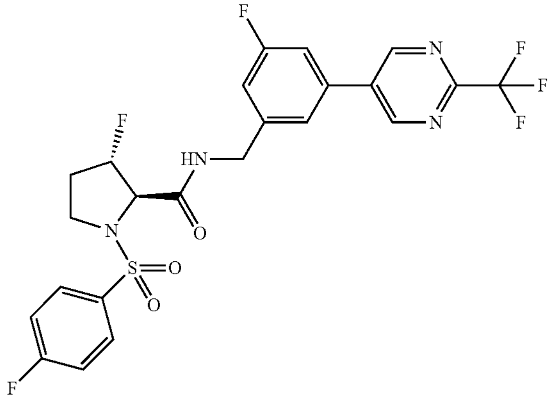 [SMILES: O=C(NCc1cc(F)cc(-c2cnc(C(F)(F)F)nc2)c1)[C@@H]1[C@@H](F)CCN1S(=O)(=O)c1ccc(F)cc1] |
| 69 | (2S,4R)-N-[[4-(2,2-difluoro-6-azaspiro[2.5]octan-6-yl)-5-fluoro-2-pyridyl]methyl]-4-fluoro-1-(4-fluorophenyl)sulfonyl-pyrrolidine-2-carboxamide | 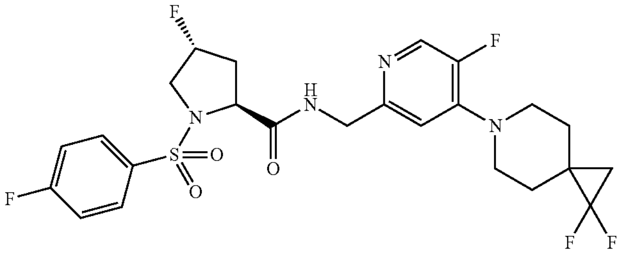 [SMILES: O=C(NCc1cc(N2CCC3(CC2)CC3(F)F)c(F)cn1)[C@@H]1C[C@@H](F)CN1S(=O)(=O)c1ccc(F)cc1] |
| 70 | (2S,4R)-N-[[5-cyano-4-[4-(trifluoromethyl)phenyl]-2-pyridyl]methyl]-4-fluoro-1-(4-fluorophenyl)sulfonyl-pyrrolidine-2-carboxamide | 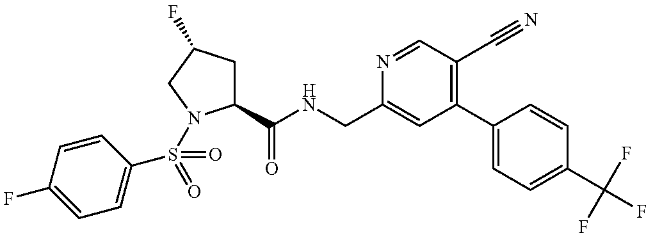 |

TABLE 2-continued

| Example Number | Chemical Name via ChemDraw | Structure |
| --- | --- | --- |
| 71 | (2S,4R)-N-[[5-cyano-4-[6-(trifluoromethyl)-3-pyridyl]-2-pyridyl]methyl]-4-fluoro-1-(4-fluorophenyl)sulfonyl-pyrrolidine-2-carboxamide | 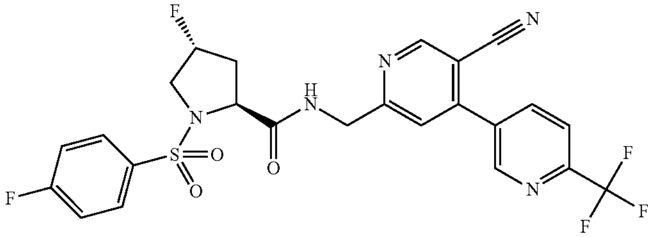 [SMILES: N#Cc1cnc(CNC(=O)[C@@H]2C[C@@H](F)CN2S(=O)(=O)c2ccc(F)cc2)cc1-c1ccc(C(F)(F)F)nc1] |
| 72 | (2R,3S)-3-fluoro-1-(4-fluorophenyl)sulfonyl-N-[[4-[5-(trifluoromethyl)-2-pyridyl]-2-pyridyl]methyl]pyrrolidine-2-carboxamide | 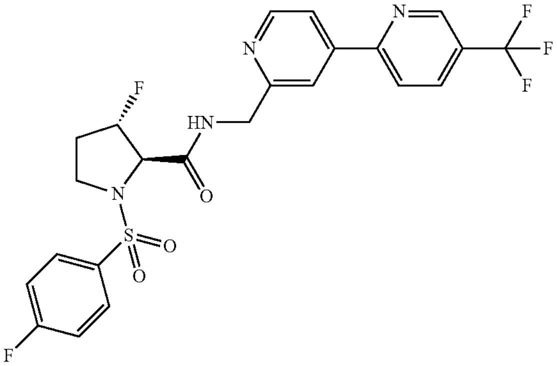 [SMILES: O=C(NCc1cc(-c2ccc(C(F)(F)F)cn2)ccn1)[C@@H]1[C@@H](F)CCN1S(=O)(=O)c1ccc(F)cc1] |
| 73 | (2S,4R)-4-fluoro-1-(4-fluorophenyl)sulfonyl-N-[[2-[2-(trifluoromethyl)pyrimidin-5-yl]-4-pyridyl]methyl]pyrrolidine-2-carboxamide | 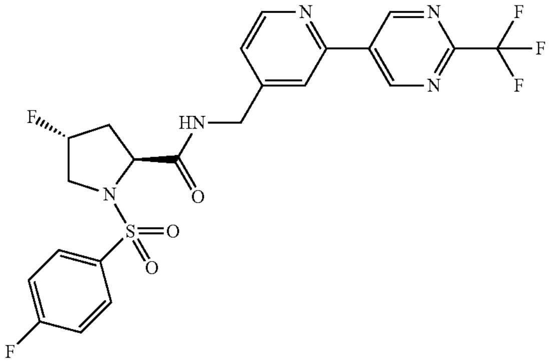 [SMILES: O=C(NCc1ccnc(-c2cnc(C(F)(F)F)nc2)c1)[C@@H]1C[C@@H](F)CN1S(=O)(=O)c1ccc(F)cc1] |
| 74 | (2S,4R)-4-fluoro-1-(4-fluorophenyl)sulfonyl-N-[[3-fluoro-5-[5-(trifluoromethyl)-2-piperidyl]phenyl]methyl] pyrrolidine-2-carboxamide | 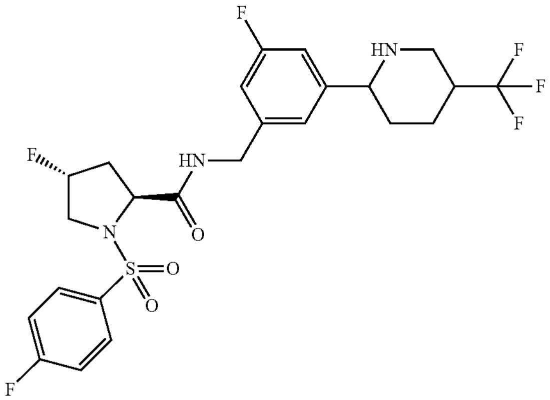 [SMILES: O=C(NCc1cc(F)cc(C2CCC(C(F)(F)F)CN2)c1)[C@@H]1C[C@@H](F)CN1S(=O)(=O)c1ccc(F)cc1] |

TABLE 2-continued

| Example Number | Chemical Name via ChemDraw | Structure |
| --- | --- | --- |
| 75 | (2S,4R)-N-[[3-[5-(difluoromethyl)-2-pyridyl]-5-fluoro-phenyl]methyl]-4-fluoro-1-(4-fluorophenyl)sulfonyl-pyrrolidine-2-carboxamide | 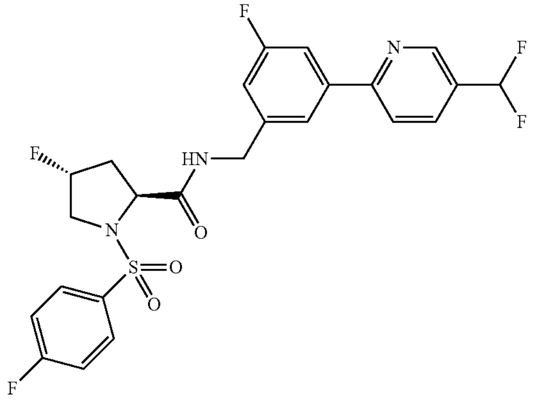 [SMILES: O=C(NCc1cc(F)cc(-c2ccc(C(F)F)cn2)c1)[C@@H]1C[C@@H](F)CN1S(=O)(=O)c1ccc(F)cc1] |
| 76 | (2S,4R)-N-[[3-[6-(difluoromethoxy)-3-pyridyl]-5-fluoro-phenyl]methyl]-4-fluoro-1-(4-fluorophenyl)sulfonyl-pyrrolidine-2-carboxamide | 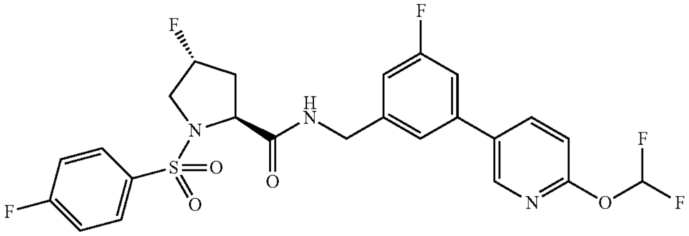 [SMILES: O=C(NCc1cc(F)cc(-c2ccc(OC(F)F)nc2)c1)[C@@H]1C[C@@H](F)CN1S(=O)(=O)c1ccc(F)cc1] |
| 77 | (2S,4R)-N-[[4-[4-(difluoromethoxy)phenyl]-5-fluoro-2-pyridyl]methyl]-4-fluoro-1-(4-fluorophenyl)sulfonyl-pyrrolidine-2-carboxamide | 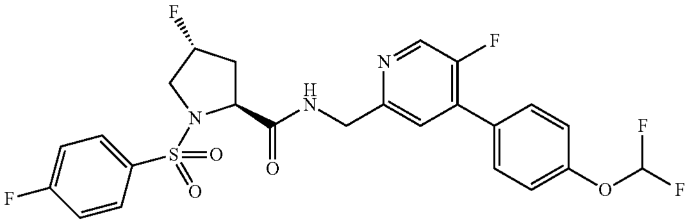 [SMILES: O=C(NCc1cc(-c2ccc(OC(F)F)cc2)c(F)cn1)[C@@H]1C[C@@H](F)CN1S(=O)(=O)c1ccc(F)cc1] |
| 78 | (2S,4R)-N-[[5-cyano-2-[4-(trifluoromethyl)phenyl]-4-pyridyl]methyl]-4-fluoro-1-(4-fluorophenyl)sulfonyl-pyrrolidine-2-carboxamide | 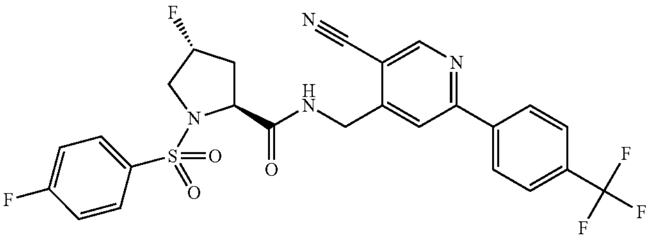 [SMILES: N#Cc1cnc(-c2ccc(C(F)(F)F)cc2)cc1CNC(=O)[C@@H]1C[C@@H](F)CN1S(=O)(=O)c1ccc(F)cc1] |
| 79 | (2S,4R)-N-[[5-cyano-2-[6-(trifluoromethyl)-3-pyridyl]-4-pyridyl]methyl]-4-fluoro-1-(4-fluorophenyl)sulfonyl-pyrrolidine-2-carboxamide | 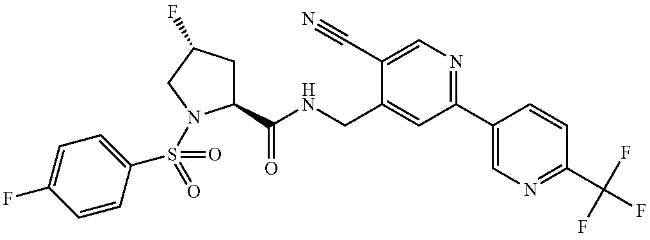 [SMILES: N#Cc1cnc(-c2ccc(C(F)(F)F)nc2)cc1CNC(=O)[C@@H]1C[C@@H](F)CN1S(=O)(=O)c1ccc(F)cc1] |

TABLE 2-continued

| Example Number | Chemical Name via ChemDraw | Structure |
|---|---|---|
| 80 | (6S)-5-(4-fluorophenyl)sulfonyl-N-[[6-[6-(trifluoromethyl)-3-pyridyl]pyrimidin-4-yl]methyl]-5-azaspiro[2.4]heptane-6-carboxamide | 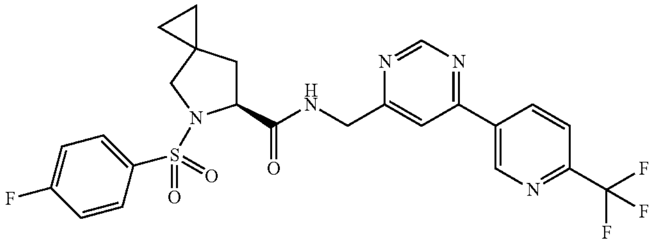 [SMILES: O=C(NCc1cc(-c2ccc(C(F)(F)F)nc2)ncn1)[C@@H]1CC2(CC2)CN1S(=O)(=O)c1ccc(F)cc1] |
| 81 | (2S,4R)-4-fluoro-1-(4-fluorophenyl)sulfonyl-N-[[4-[6-(trifluoromethyl)-3-pyridyl]-2-pyridyl]methyl]pyrrolidine-2-carboxamide | 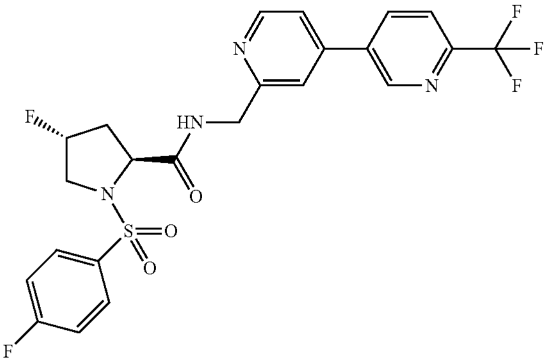 [SMILES: O=C(NCc1cc(-c2ccc(C(F)(F)F)nc2)ccn1)[C@@H]1C[C@@H](F)CN1S(=O)(=O)c1ccc(F)cc1] |
| 82 | (2S,4R)-4-fluoro-1-(4-fluorophenyl)sulfonyl-N-[[4-[5-(trifluoromethyl)pyrazin-2-yl]-2-pyridyl]methyl]pyrrolidine-2-carboxamide | 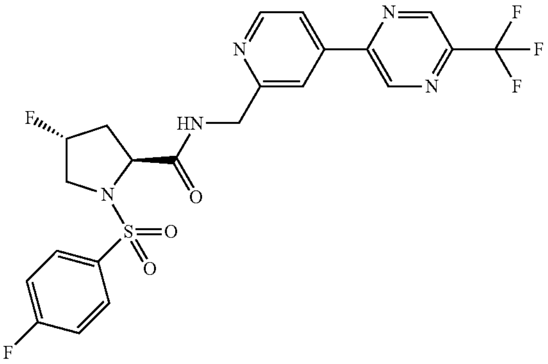 [SMILES: O=C(NCc1cc(-c2cnc(C(F)(F)F)cn2)ccn1)[C@@H]1C[C@@H](F)CN1S(=O)(=O)c1ccc(F)cc1] |
| 83 | (2S,4R)-N-[[2,6-bis[6-(trifluoromethyl)-3-pyridyl]-4-pyridyl]methyl]-4-fluoro-1-(4-fluorophenyl)sulfonyl-pyrrolidine-2-carboxamide | 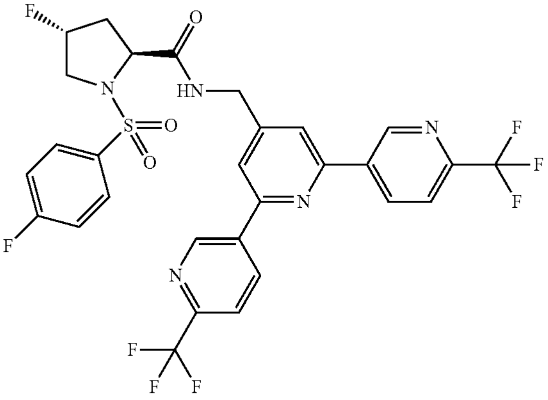 [SMILES: O=C(NCc1cc(-c2ccc(C(F)(F)F)nc2)nc(-c2ccc(C(F)(F)F)nc2)c1)[C@@H]1C[C@@H](F)CN1S(=O)(=O)c1ccc(F)cc1] |

TABLE 2-continued

| Example Number | Chemical Name via ChemDraw | Structure |
|---|---|---|
| 84 | (2S,4R)-N-[[2-chloro-6-[6-(trifluoromethyl)-3-pyridyl]-4-pyridyl]methyl]-4-fluoro-1-(4-fluorophenyl)sulfonyl-pyrrolidine-2-carboxamide | 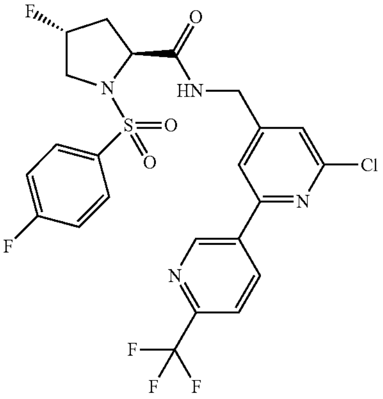 [SMILES: O=C(NCc1cc(Cl)nc(-c2ccc(C(F)(F)F)nc2)c1)[C@@H]1C[C@@H](F)CN1S(=O)(=O)c1ccc(F)cc1] |
| 85 | (2S,4R)-4-fluoro-N-[[3-fluoro-5-[2-oxo-4-(trifluoromethyl)-1-pyridyl]phenyl]methyl]-1-(4-fluorophenyl)sulfonyl-pyrrolidine-2-carboxamide | 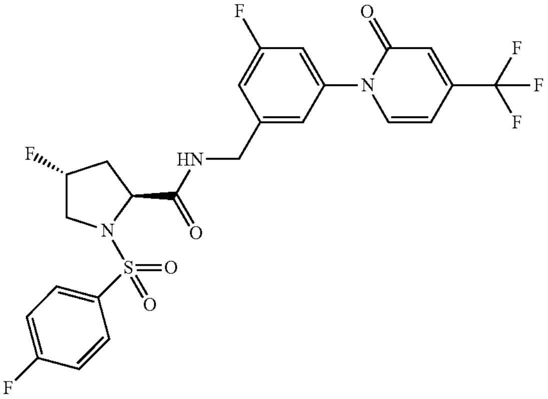 [SMILES: O=C(NCc1cc(F)cc(-n2ccc(C(F)(F)F)cc2=O)c1)[C@@H]1C[C@@H](F)CN1S(=O)(=O)c1ccc(F)cc1] |
| 86 | (2S,4R)-4-fluoro-1-(4-fluorophenyl)sulfonyl-N-[[3-fluoro-5-[4-(trifluoromethyl)pyrazol-1-yl]phenyl]methyl]pyrrolidine-2-carboxamide | 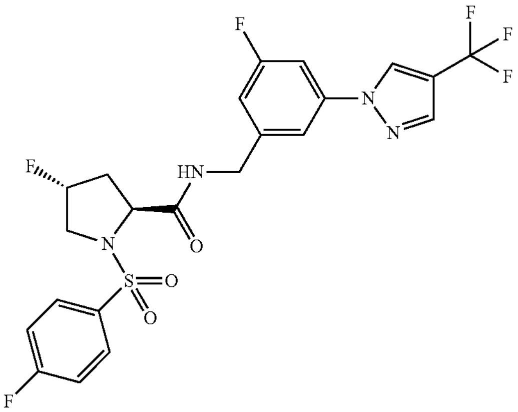 [SMILES: O=C(NCc1cc(F)cc(-n2cc(C(F)(F)F)cn2)c1)[C@@H]1C[C@@H](F)CN1S(=O)(=O)c1ccc(F)cc1] |

TABLE 2-continued

| Example Number | Chemical Name via ChemDraw | Structure |
| --- | --- | --- |
| 87 | (2S,4R)-4-fluoro-1-(4-fluorophenyl)sulfonyl-N-[[3-fluoro-5-[3-(trifluoromethyl)pyrazol-1-yl]phenyl]methyl]pyrrolidine-2-carboxamide | 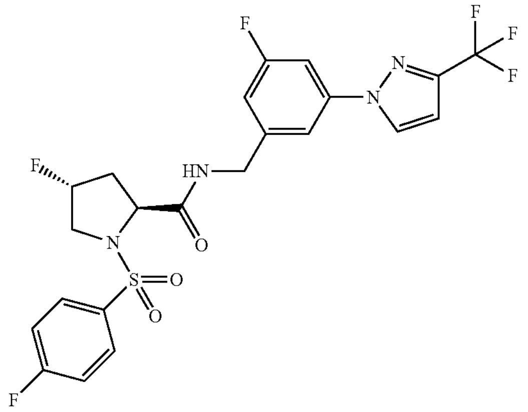 [SMILES: O=C(NCc1cc(F)cc(-n2ccc(C(F)(F)F)n2)c1)[C@@H]1C[C@@H](F)CN1S(=O)(=O)c1ccc(F)cc1] |
| 88 | (2S,4R)-N-[[4-[4-(difluoromethyl)phenyl]-5-fluoro-2-pyridyl]methyl]-4-fluoro-1-(4-fluorophenyl)sulfonyl-pyrrolidine-2-carboxamide | 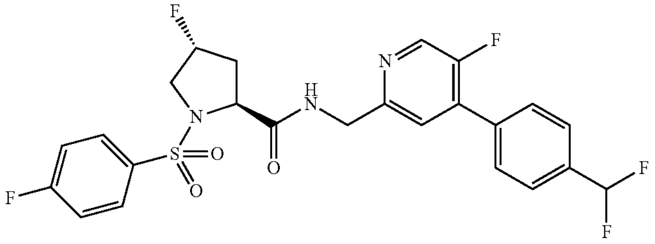 [SMILES: O=C(NCc1cc(-c2ccc(C(F)F)cc2)c(F)cn1)[C@@H]1C[C@@H](F)CN1S(=O)(=O)c1ccc(F)cc1] |
| 89 | (2S,4R)-4-fluoro-1-(4-fluorophenyl)sulfonyl-N-[[3-fluoro-5-[6-(trifluoromethyl)pyridazin-3-yl]phenyl]methyl]pyrrolidine-2-carboxamide | 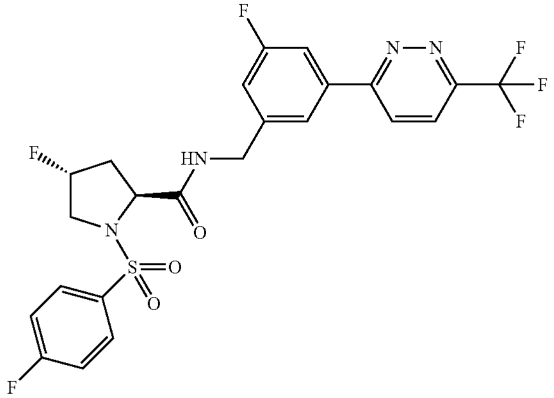 [SMILES: O=C(NCc1cc(F)cc(-c2ccc(C(F)(F)F)nn2)c1)[C@@H]1C[C@@H](F)CN1S(=O)(=O)c1ccc(F)cc1] |
| 90 | (2S,4R)-N-[[3-[5-(difluoromethyl)pyrazin-2-yl]-5-fluoro-phenyl]methyl]-4-fluoro-1-(4-fluorophenyl)sulfonyl-pyrrolidine-2-carboxamide | 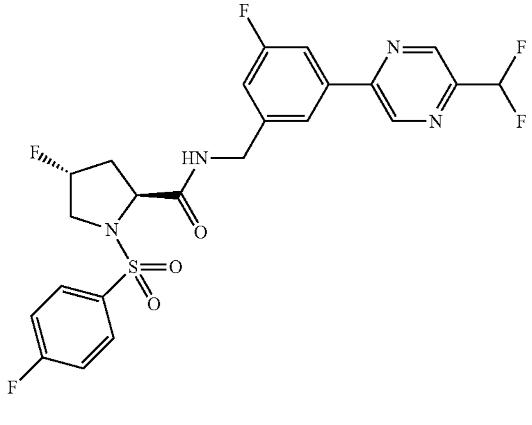 [SMILES: O=C(NCc1cc(F)cc(-c2cnc(C(F)F)cn2)c1)[C@@H]1C[C@@H](F)CN1S(=O)(=O)c1ccc(F)cc1] |

TABLE 2-continued

| Example Number | Chemical Name via ChemDraw | Structure |
|---|---|---|
| 91 | (2S,4R)-4-fluoro-1-(4-fluorophenyl)sulfonyl-N-[[3-fluoro-5-[2-(trifluoromethyl)pyrimidin-5-yl]phenyl]methyl]pyrrolidine-2-carboxamide | 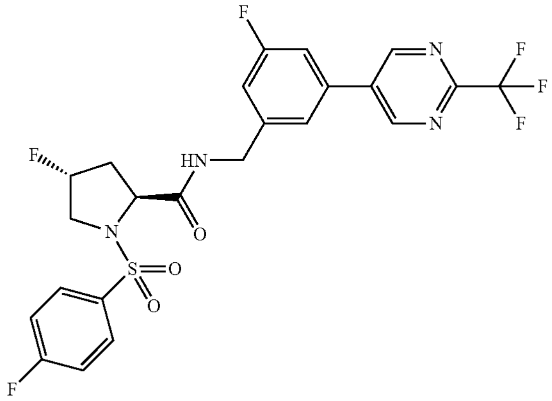 [SMILES: O=C(NCc1cc(F)cc(-c2cnc(C(F)(F)F)nc2)c1)[C@@H]1C[C@@H](F)CN1S(=O)(=O)c1ccc(F)cc1] |
| 92 | (2S,4R)-N-[[6-(2,2-difluoro-1,3-benzodioxol-5-yl)pyrimidin-4-yl]methyl]-4-fluoro-1-(4-fluorophenyl)sulfonyl-pyrrolidine-2-carboxamide | 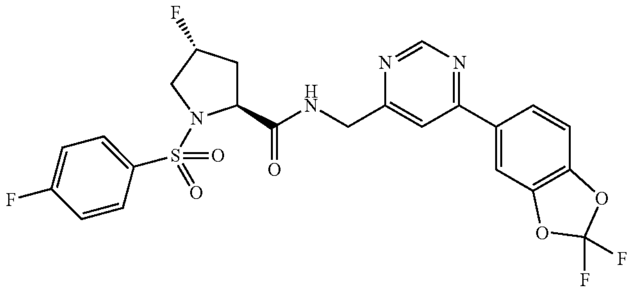 [SMILES: O=C(NCc1cc(-c2ccc3c(c2)OC(F)(F)O3)ncn1)[C@@H]1C[C@@H](F)CN1S(=O)(=O)c1ccc(F)cc1] |
| 93 | (2R,3S)-3-fluoro-1-(4-fluorophenyl)sulfonyl-N-[[6-[3-fluoro-4-(trifluoromethyl)phenyl] pyrimidin-4-yl] methyl]pyrrolidine-2-carboxamide | 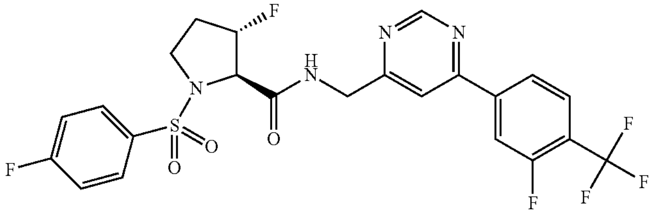 [SMILES: O=C(NCc1cc(-c2ccc(C(F)(F)F)c(F)c2)ncn1)[C@@H]1[C@@H](F)CCN1S(=O)(=O)c1ccc(F)cc1] |
| 94 | (2S,4R)-N-[[3-[6-(difluoromethyl)-3-pyridyl]-5-fluoro-phenyl]methyl]-4-fluoro-1-(4-fluorophenyl)sulfonyl-pyrrolidine-2-carboxamide | 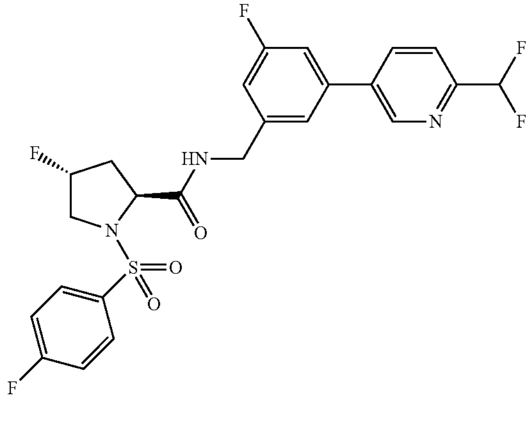 [SMILES: O=C(NCc1cc(F)cc(-c2ccc(C(F)F)nc2)c1)[C@@H]1C[C@@H](F)CN1S(=O)(=O)c1ccc(F)cc1] |

TABLE 2-continued

| Example Number | Chemical Name via ChemDraw | Structure |
|---|---|---|
| 95 | (2S,4R)-4-fluoro-1-(4-fluorophenyl)sulfonyl-N-[[3-fluoro-5-[5-(trifluoromethyl)-2-pyridyl]phenyl]methyl] pyrrolidine-2-carboxamide | 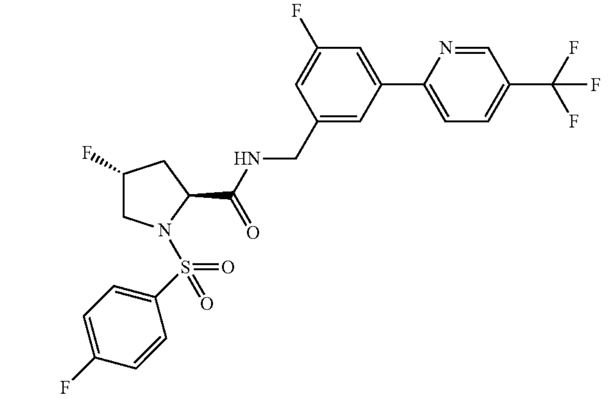 [SMILES: O=C(NCc1cc(F)cc(-c2ccc(C(F)(F)F)cn2)c1)[C@@H]1C[C@@H](F)CN1S(=O)(=O)c1ccc(F)cc1] |
| 96 | (2S,4R)-4-fluoro-1-(4-fluorophenyl)sulfonyl-N-[[5-methyl-4-[6-(trifluoromethyl)-3-pyridyl]-2-pyridyl]methyl]pyrrolidine-2-carboxamide | 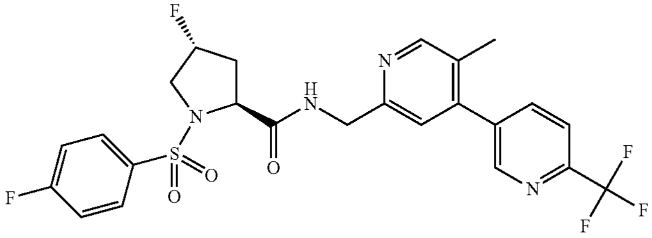 [SMILES: Cc1cnc(CNC(=O)[C@@H]2C[C@@H](F)CN2S(=O)(=O)c2ccc(F)cc2)cc1-c1ccc(C(F)(F)F)nc1] |
| 97 | (2R,3S)-3-fluoro-1-(4-fluorophenyl)sulfonyl-N-[[4-fluoro-3-[5-(trifluoromethyl)pyrazin-2-yl]phenyl]methyl]pyrrolidine-2-carboxamide | 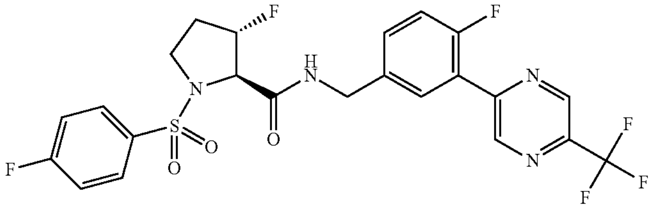 [SMILES: O=C(NCc1ccc(F)c(-c2cnc(C(F)(F)F)cn2)c1)[C@@H]1[C@@H](F)CCN1S(=O)(=O)c1ccc(F)cc1] |
| 98 | (2R,3S)-3-fluoro-1-(4-fluorophenyl)sulfonyl-N-[[3-fluoro-5-[5-(trifluoromethyl)pyrazin-2-yl]phenyl]methyl]pyrrolidine-2-carboxamide | 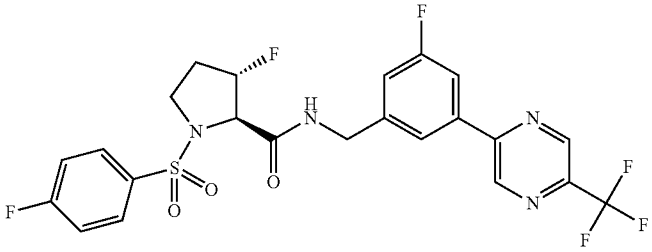 [SMILES: O=C(NCc1cc(F)cc(-c2cnc(C(F)(F)F)cn2)c1)[C@@H]1[C@@H](F)CCN1S(=O)(=O)c1ccc(F)cc1] |
| 99 | (2S,3aS,6aR)-1-(4-fluorophenyl)sulfony]-N-[[6-[4-(trifluoromethyl)phenyl] pyrimidin-4-yl]methyl]-2,3,3a,4,6,6a-hexahydrofuro[3,4-b]pyrrole-2-carboxamide | 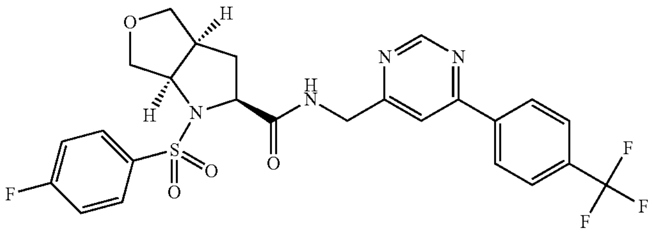 [SMILES: O=C(NCc1cc(-c2ccc(C(F)(F)F)cc2)ncn1)[C@@H]1C[C@@H]2COC[C@@H]2N1S(=O)(=O)c1ccc(F)cc1] |

TABLE 2-continued

| Example Number | Chemical Name via ChemDraw | Structure |
|---|---|---|
| 100 | (2S,3aR,6aS)-1-(4-fluorophenyl)sulfonyl-N-[[6-[4-(trifluoromethyl)phenyl] pyrimidin-4-yl]methyl]-2,3,3a,4,6,6a-hexahydrofuro[3,4-b]pyrrole-2-carboxamide | 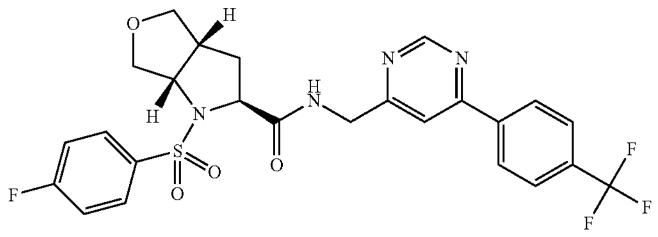 [SMILES: O=C(NCc1cc(-c2ccc(C(F)(F)F)cc2)ncn1)[C@@H]1C[C@H]2COC[C@H]2N1S(=O)(=O)c1ccc(F)cc1] |
| 101 | (2S,4R)-N-[[5-chloro-4-[6-(trifluoromethyl)-3-pyridyl]-2-pyridyl]methyl]-4-fluoro-1-(4-fluorophenyl)sulfonyl-pyrrolidine-2-carboxamide | 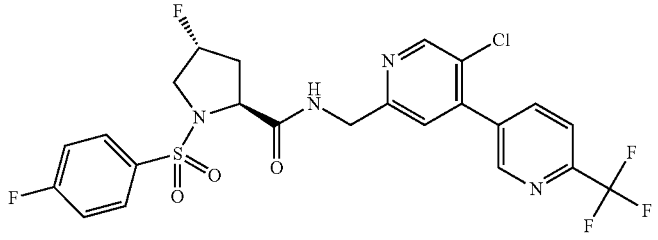 [SMILES: O=C(NCc1cc(-c2ccc(C(F)(F)F)nc2)c(Cl)cn1)[C@@H]1C[C@@H](F)CN1S(=O)(=O)c1ccc(F)cc1] |
| 102 | (2S,4R)-4-fluoro-1-(4-fluorophenyl)sulfonyl-N-[[5-fluoro-4-[5-(trifluoromethyl)pyrazin-2-yl]-2-pyridyl]methyl]pyrrolidine-2-carboxamide | 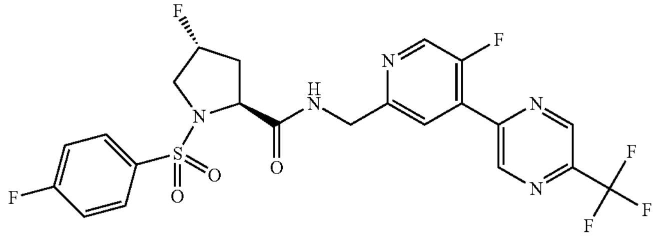 [SMILES: O=C(NCc1cc(-c2cnc(C(F)(F)F)cn2)c(F)cn1)[C@@H]1C[C@@H](F)CN1S(=O)(=O)c1ccc(F)cc1] |
| 103 | (2R,3S)-3-fluoro-1-(4-fluorophenyl)sulfonyl-N-[[3-methoxy-1-[6-(trifluoromethyl)-3-pyridyl]pyrazol-4-yl]methyl]pyrrolidine-2-carboxamide | 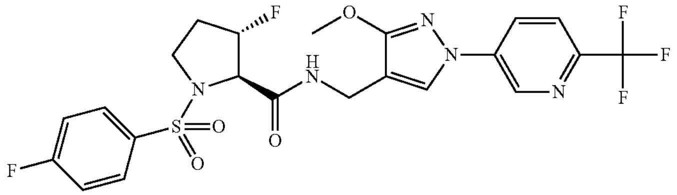 [SMILES: COc1nn(-c2ccc(C(F)(F)F)nc2)cc1CNC(=O)[C@@H]1[C@@H](F)CCN1S(=O)(=O)c1ccc(F)cc1] |
| 104 | (2S,4R)-4-fluoro-1-(4-fluorophenyl)sulfonyl-N-[[6-[3-fluoro-4-(trifluoromethoxy)phenyl] pyrimidin-4-yl] methyl]pyrrolidine-2-carboxamide | 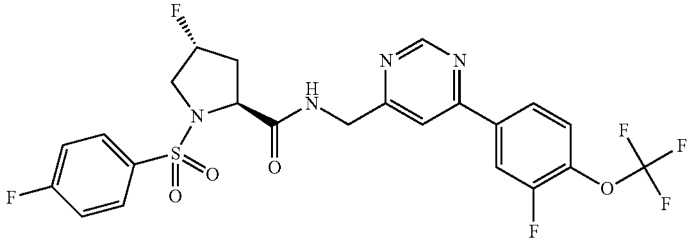 [SMILES: O=C(NCc1cc(-c2ccc(OC(F)(F)F)c(F)c2)ncn1)[C@@H]1C[C@@H](F)CN1S(=O)(=O)c1ccc(F)cc1] |
| 105 | (2S,4R)-4-fluoro-1-(4-fluorophenyl)sulfonyl-N-[[2-(methylamino)-6-[4-(trifluoromethyl)phenyl] pyrimidin-4-yl]methyl] pyrrolidine-2-carboxamide | 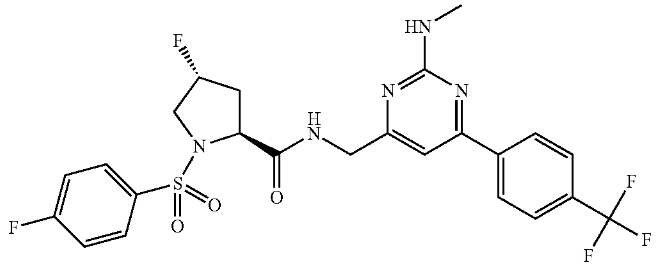 [SMILES: CNc1nc(CNC(=O)[C@@H]2C[C@@H](F)CN2S(=O)(=O)c2ccc(F)cc2)cc(-c2ccc(C(F)(F)F)cc2)n1] |

TABLE 2-continued

| Example Number | Chemical Name via ChemDraw | Structure |
|---|---|---|
| 106 | (2S,3R,4R)-4-fluoro-1-(4-fluorophenyl)sulfonyl-3-methyl-N-[[6-[6-(trifluoromethyl)-3-pyridyl]pyrimidin-4-yl]methyl]pyrrolidine-2-carboxamide | 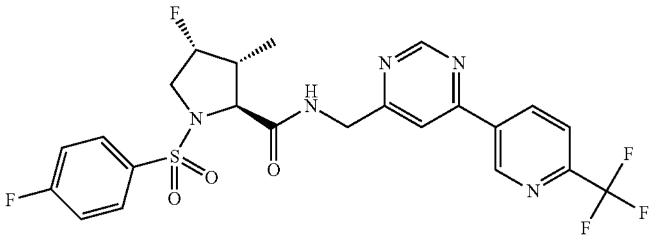 [SMILES: C[C@@H]1[C@@H](C(=O)NCc2cc(-c3ccc(C(F)(F)F)nc3)ncn2)N(S(=O)(=O)c2ccc(F)cc2)C[C@@H]1F] |
| 107 | (2S,4R)-4-fluoro-1-(4-fluorophenyl)sulfonyl-4-methyl-N-[[6-[6-(trifluoromethyl)-3-pyridyl]pyrimidin-4-yl]methyl]pyrrolidine-2-carboxamide | 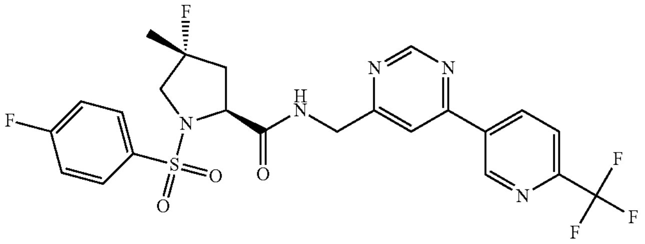 [SMILES: C[C@@]1(F)C[C@@H](C(=O)NCc2cc(-c3ccc(C(F)(F)F)nc3)ncn2)N(S(=O)(=O)c2ccc(F)cc2)C1] |
| 108 | (2S,4R)-4-fluoro-1-(4-fluorophenyl)sulfonyl-N-[[5-methoxy-4-[6-(trifluoromethyl)-3-pyridyl]-2-pyridyl]methyl]pyrrolidine-2-carboxamide | 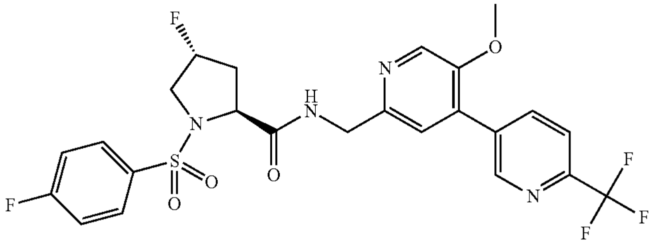 [SMILES: COc1cnc(CNC(=O)[C@@H]2C[C@@H](F)CN2S(=O)(=O)c2ccc(F)cc2)cc1-c1ccc(C(F)(F)F)nc1] |
| 109 | (2S,4R)-4-fluoro-1-(4-fluorophenyl)sulfonyl-N-[[5-methoxy-4-[6-(trifluoromethyl)-3-pyridyl]-2-pyridyl]methyl]-2-methyl-pyrrolidine-2-carboxamide | 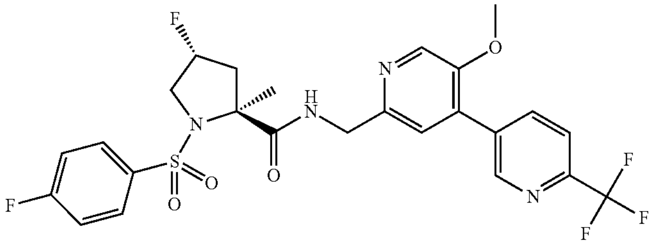 [SMILES: COc1cnc(CNC(=O)[C@]2(C)C[C@@H](F)CN2S(=O)(=O)c2ccc(F)cc2)cc1-c1ccc(C(F)(F)F)nc1] |
| 110 | (2S,4R)-4-cyano-1-(4-fluorophenyl)sulfonyl-N-[[3-methoxy-1-[4-(trifluoromethyl)phenyl]pyrazol-4-yl]methyl]pyrrolidine-2-carboxamide | 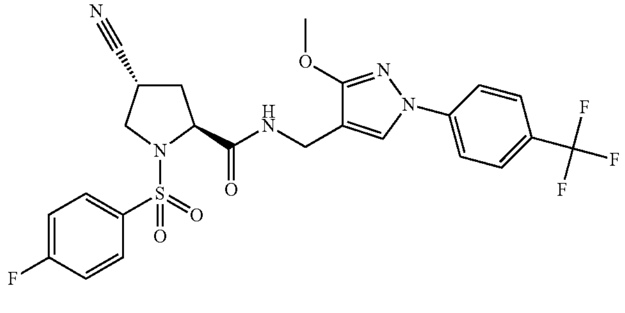 [SMILES: COc1nn(-c2ccc(C(F)(F)F)cc2)cc1CNC(=O)[C@@H]1C[C@@H](C#N)CN1S(=O)(=O)c1ccc(F)cc1] |
| 111 | (2R,3S)-3-fluoro-1-(4-fluorophenyl)sulfonyl-N-[[6-[4-(trifluoromethoxy)phenyl]pyrimidin-4-yl]methyl]pyrrolidine-2-carboxamide | 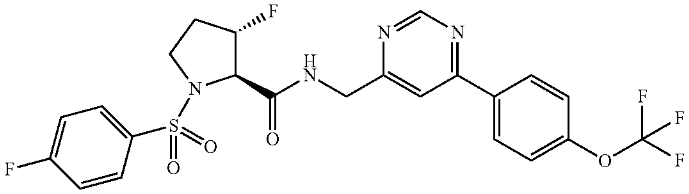 [SMILES: O=C(NCc1cc(-c2ccc(OC(F)(F)F)cc2)ncn1)[C@@H]1[C@@H](F)CCN1S(=O)(=O)c1ccc(F)cc1] |

TABLE 2-continued

| Example Number | Chemical Name via ChemDraw | Structure |
|---|---|---|
| 112 | (2S,4R)-N-[[3-cyano-5-[6-(trifluoromethyl)-3-pyridyl]phenyl]methyl]-4-fluoro-1-(4-fluorophenyl)sulfonyl-pyrrolidine-2-carboxamide | 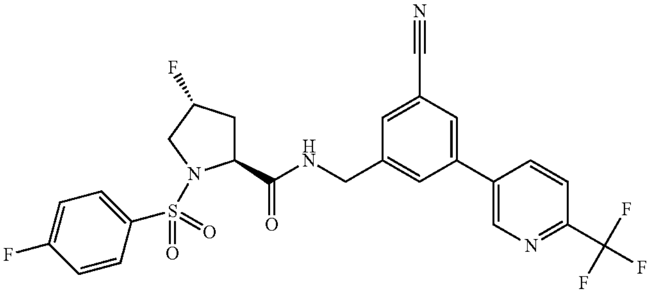 [SMILES: N#Cc1cc(CNC(=O)[C@@H]2C[C@@H](F)CN2S(=O)(=O)c2ccc(F)cc2)cc(-c2ccc(C(F)(F)F)nc2)c1] |
| 113 | (2S,4R)-4-fluoro-1-(4-fluorophenyl)sulfonyl-N-[[6-[2-fluoro-4-(trifluoromethyl)phenyl] pyrimidin-4-yl] methyl]pyrrolidine-2-carboxamide | 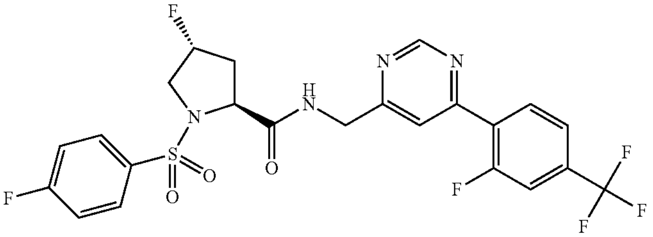 [SMILES: O=C(NCc1cc(-c2ccc(C(F)(F)F)cc2F)ncn1)[C@@H]1C[C@@H](F)CN1S(=O)(=O)c1ccc(F)cc1] |
| 114 | (2S,4R)-4-fluoro-1-(4-fluorophenyl)sulfonyl-N-[[6-[3-fluoro-4-(trifluoromethyl)phenyl] pyrimidin-4-yl]methyl] pyrrolidine-2-carboxamide | 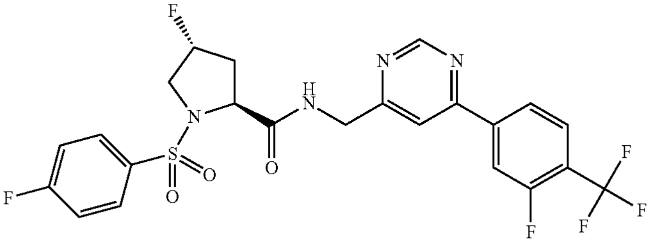 [SMILES: O=C(NCc1cc(-c2ccc(C(F)(F)F)c(F)c2)ncn1)[C@@H]1C[C@@H](F)CN1S(=O)(=O)c1ccc(F)cc1] |
| 115 | (2R,3S)-3-fluoro-1-(4-fluorophenyl)sulfonyl-N-[[5-fluoro-4-[6-(trifluoromethyl)-3-pyridyl]-2-pyridyl]methyl]pyrrolidine-2-carboxamide | 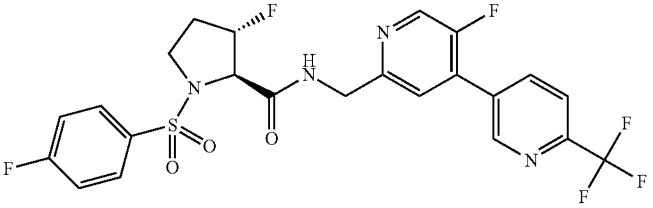 [SMILES: O=C(NCc1cc(-c2ccc(C(F)(F)F)nc2)c(F)cn1)[C@@H]1[C@@H](F)CCN1S(=O)(=O)c1ccc(F)cc1] |
| 116 | (2S,4R)-4-fluoro-1-(4-fluorophenyl)sulfonyl-N-[[3-methoxy-5-[6-(trifluoromethyl)-3-pyridyl]phenyl]methyl] pyrrolidine-2-carboxamide | 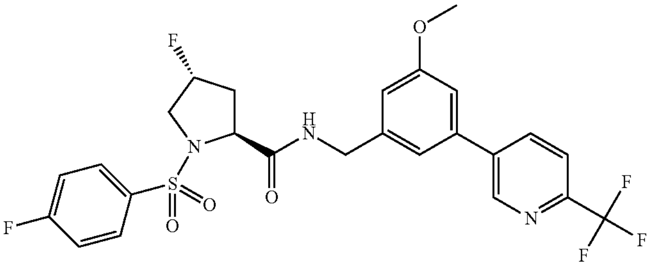 [SMILES: COc1cc(CNC(=O)[C@@H]2C[C@@H](F)CN2S(=O)(=O)c2ccc(F)cc2)cc(-c2ccc(C(F)(F)F)nc2)c1] |
| 117 | (2S,4R)-N-[[3,5-difluoro-4-[6-(trifluoromethyl)-3-pyridyl]-2-pyridyl]methyl]-4-fluoro-1-(4-fluorophenyl)sulfonyl-pyrrolidine-2-carboxamide | 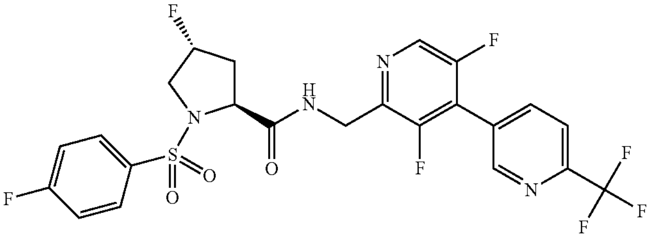 [SMILES: O=C(NCc1ncc(F)c(-c2ccc(C(F)(F)F)nc2)c1F)[C@@H]1C[C@@H](F)CN1S(=O)(=O)c1ccc(F)cc1] |

TABLE 2-continued

| Example Number | Chemical Name via ChemDraw | Structure |
|---|---|---|
| 118 | (2S,4R)-4-fluoro-1-(4-fluorophenyl)sulfonyl-N-[[6-methoxy-4-[6-(trifluoromethyl)-3-pyridyl]-2-pyridyl]methyl]pyrrolidine-2-carboxamide | 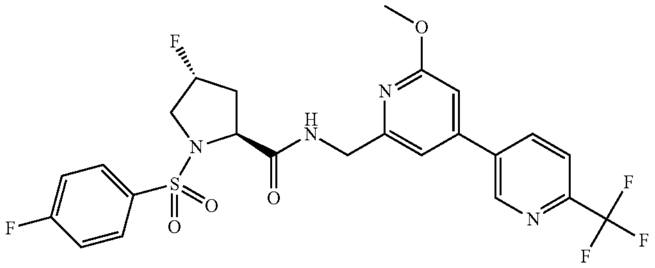 [SMILES: COc1cc(-c2ccc(C(F)(F)F)nc2)cc(CNC(=O)[C@@H]2C[C@@H](F)CN2S(=O)(=O)c2ccc(F)cc2)n1] |
| 119 | (2S,4R)-4-fluoro-1-(4-fluorophenyl)sulfonyl-N-[[2-fluoro-6-[6-(trifluoromethyl)-3-pyridyl]-4-pyridyl]methyl]pyrrolidine-2-carboxamide | 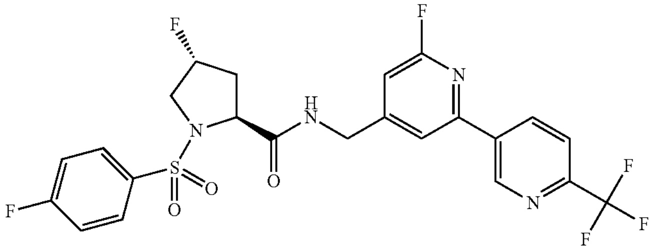 [SMILES: O=C(NCc1cc(F)nc(-c2ccc(C(F)(F)F)nc2)c1)[C@@H]1C[C@@H](F)CN1S(=O)(=O)c1ccc(F)cc1] |
| 120 | (2S,4R)-4-fluoro-1-(4-fluorophenyl)sulfonyl-N-[[6-fluoro-4-[6-(trifluoromethyl)-3-pyridyl]-2-pyridyl]methyl]pyrrolidine-2-carboxamide | 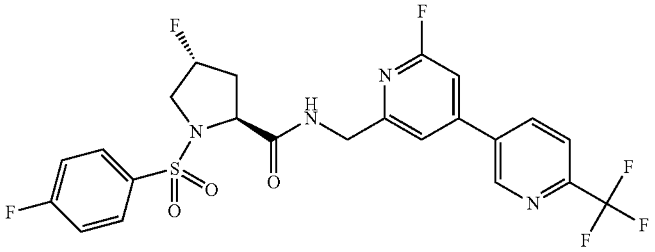 |
| 121 | (2S,4R)-4-fluoro-1-(4-fluorophenyl)sulfonyl-N-[[5-fluoro-4-[3-(trifluoromethyl)-8-azabicyclo[3.2.1]octan-8-yl]-2-pyridyl]methyl]pyrrolidine-2-carboxamide | 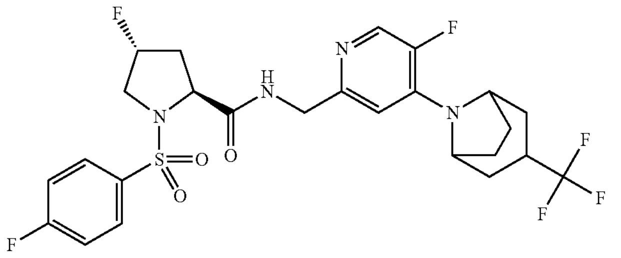 [SMILES: O=C(NCc1cc(N2C3CCC2CC(C(F)(F)F)C3)c(F)cn1)[C@@H]1C[C@@H](F)CN1S(=O)(=O)c1ccc(F)cc1] |
| 122 | (2S,4R)-4-fluoro-1-(4-fluorophenyl)sulfonyl-N-[[3-fluoro-5-[5-(trifluoromethyl)pyrazin-2-yl]phenyl]methyl]pyrrolidine-2-carboxamide | 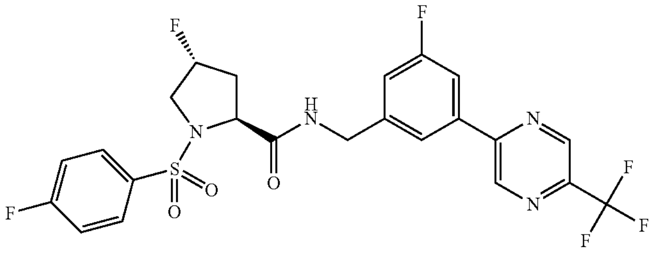 [SMILES: O=C(NCc1cc(F)cc(-c2cnc(C(F)(F)F)cn2)c1)[C@@H]1C[C@@H](F)CN1S(=O)(=O)c1ccc(F)cc1] |

TABLE 2-continued

| Example Number | Chemical Name via ChemDraw | Structure |
|---|---|---|
| 123 | (1R,3S,5R)-2-(4-fluorophenyl)sulfonyl-N-[[6-[6-(trifluoromethyl)-3-pyridyl]pyrimidin-4-yl]methyl]-2-azabicyclo[3.1.0]hexane-3-carboxamide | 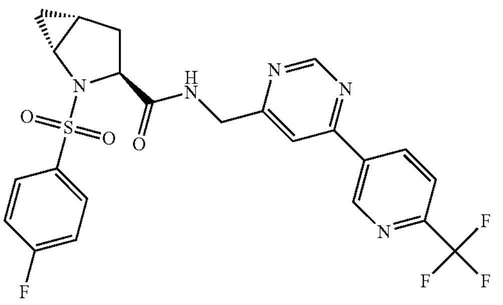 |
| 124 | (3R,6S)-2,2-difluoro-5-(4-fluorophenyl)sulfonyl-N-[[6-[6-(trifluoromethyl)-3-pyridyl]pyrimidin-4-yl]methyl]-5-azaspiro[2.4]heptane-6-carboxamide | 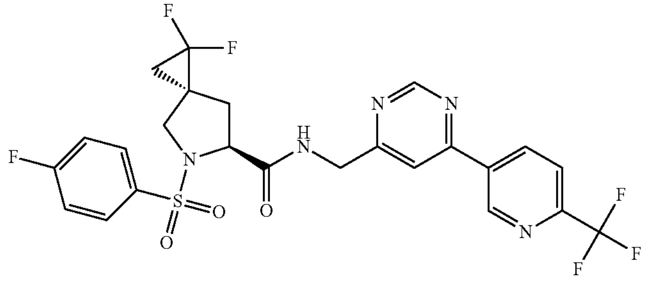 [SMILES: O=C(NCc1cc(-c2ccc(C(F)(F)F)nc2)ncn1)[C@@H]1C[C@]2(CN1S(=O)(=O)c1ccc(F)cc1)CC2(F)F] |
| 125 | (2S,4R)-4-fluoro-1-(4-fluorophenyl)sulfonyl-N-[[3-methoxy-1-[6-(trifluoromethyl)-3-pyridyl]pyrazol-4-yl]methyl]-2-methyl-pyrrolidine-2-carboxamide | 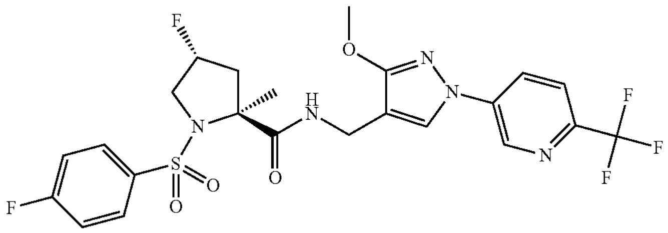 [SMILES: COc1nn(-c2ccc(C(F)(F)F)nc2)cc1CNC(=O)[C@]1(C)C[C@@H](F)CN1S(=O)(=O)c1ccc(F)cc1] |
| 126 | (2S,4R)-4-fluoro-1-(4-fluorophenyl)sulfonyl-N-[[5-fluoro-4-[6-(trifluoromethyl)-3-pyridyl]-2-pyridyl]methyl]-2-methyl-pyrrolidine-2-carboxamide | 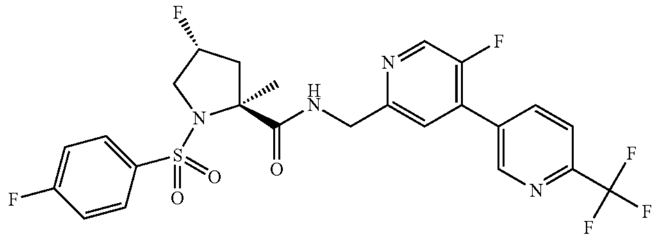 |
| 127 | (2S,4R)-4-fluoro-1-(4-fluorophenyl)sulfonyl-N-[[2-methoxy-6-[6-(trifluoromethyl)-3-pyridyl]pyrimidin-4-yl]methyl]pyrrolidine-2-carboxamide | 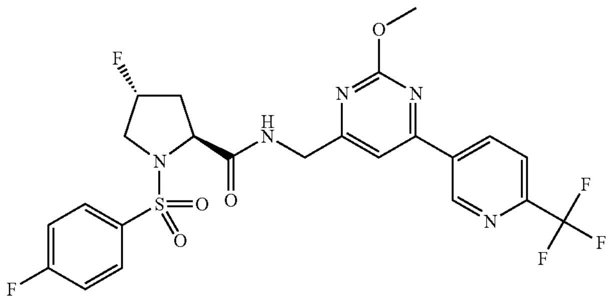 [SMILES: COc1nc(CNC(=O)[C@@H]2C[C@@H](F)CN2S(=O)(=O)c2ccc(F)cc2)cc(-c2ccc(C(F)(F)F)nc2)n1] |

TABLE 2-continued

| Example Number | Chemical Name via ChemDraw | Structure |
|---|---|---|
| 128 | (2S,4R)-N-[[4-(4,4-difluoro-1-piperidyl)-5-fluoro-2-pyridyl]methyl]-4-fluoro-1-(4-fluorophenyl)sulfonyl-pyrrolidine-2-carboxamide | 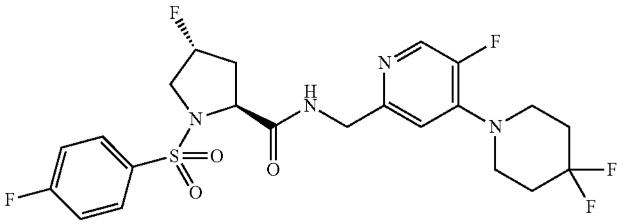 [SMILES: O=C(NCc1cc(N2CCC(F)(F)CC2)c(F)cn1)[C@@H]1C[C@@H](F)CN1S(=O)(=O)c1ccc(F)cc1] |
| 129 | (2S,4R)-N-[[4-(6-azaspiro[2.5]octan-6-yl)-5-fluoro-2-pyridyl]methyl]-4-fluoro-1-(4-fluorophenyl)sulfonyl-pyrrolidine-2-carboxamide | 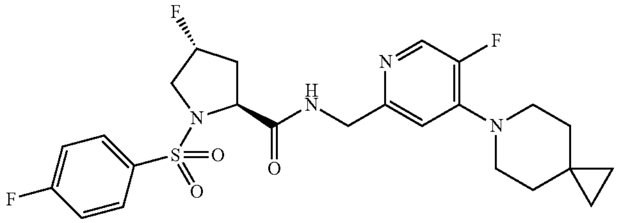 [SMILES: O=C(NCc1cc(N2CCC3(CC2)CC3)c(F)cn1)[C@@H]1C[C@@H](F)CN1S(=O)(=O)c1ccc(F)cc1] |
| 130 | (2S,4R)-4-fluoro-1-(4-fluorophenyl)sulfonyl-N-[[5-(trifluoromethyl)-4-[4-(trifluoromethyl)-1-piperidyl]-2-pyridyl]methyl]pyrrolidine-2-carboxamide | 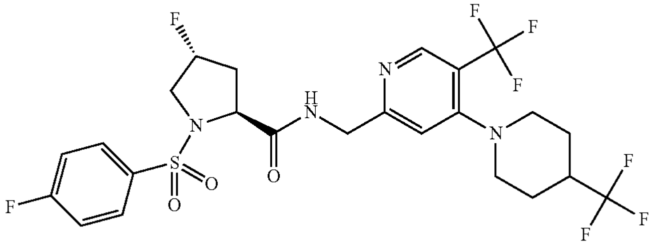 [SMILES: O=C(NCc1cc(N2CCC(C(F)(F)F)CC2)c(C(F)(F)F)cn1)[C@@H]1C[C@@H](F)CN1S(=O)(=O)c1ccc(F)cc1] |
| 131 | (2S,4R)-4-fluoro-1-(4-fluorophenyl)sulfonyl-N-[[4-[5-(trifluoromethyl)-2-pyridyl]-2-pyridyl]methyl]pyrrolidine-2-carboxamide | 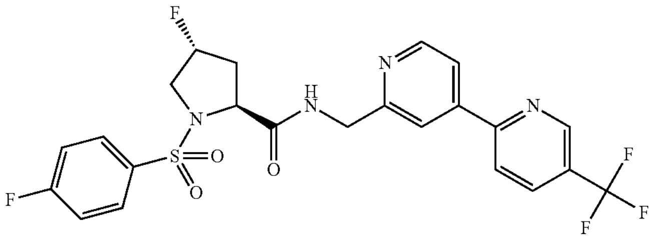 [SMILES: O=C(NCc1cc(-c2ccc(C(F)(F)F)cn2)ccn1)[C@@H]1C[C@@H](F)CN1S(=O)(=O)c1ccc(F)cc1] |
| 132 | (2S,4R)-4-fluoro-1-(4-fluorophenyl)sulfonyl-N-[[3-methoxy-1-[2-(trifluoromethyl)pyrimidin-5-yl]pyrazol-4-yl]methyl]pyrrolidine-2-carboxamide | 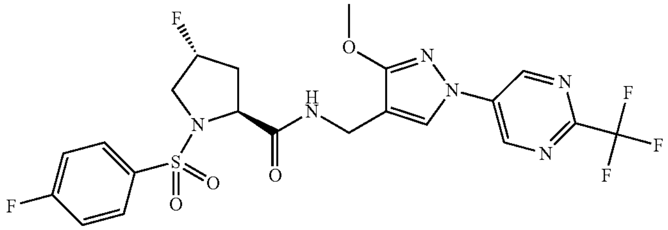 [SMILES: COc1nn(-c2cnc(C(F)(F)F)nc2)cc1CNC(=O)[C@@H]1C[C@@H](F)CN1S(=O)(=O)c1ccc(F)cc1] |
| 133 | (2S,4R)-N-[[6-[4-(difluoromethyl)-1-bicyclo[2.2.2]octanyl]pyrimidin-4-yl]methyl]-4-fluoro-1-(4-fluorophenyl)sulfonyl-pyrrolidine-2-carboxamide | 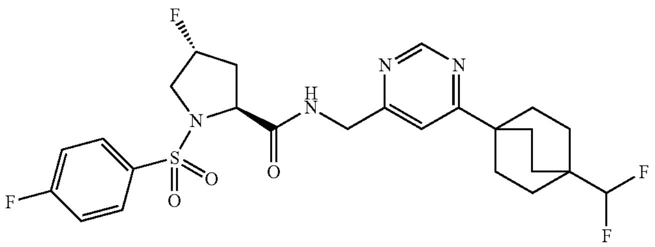 [SMILES: O=C(NCc1cc(C23CCC(C(F)F)(CC2)CC3)ncn1)[C@@H]1C[C@@H](F)CN1S(=O)(=O)c1ccc(F)cc1] |

TABLE 2-continued

| Example Number | Chemical Name via ChemDraw | Structure |
|---|---|---|
| 134 | (2S,4R)-4-fluoro-1-(3-fluorophenyl)sulfonyl-N-[[3-methoxy-1-[4-(trifluoromethyl)phenyl]pyrazol-4-yl]methyl]pyrrolidine-2-carboxamide | 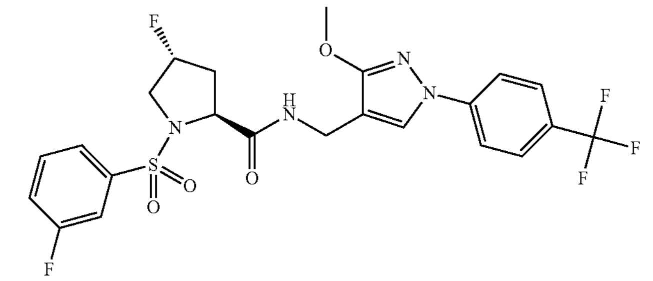 [SMILES: COc1nn(-c2ccc(C(F)(F)F)cc2)cc1CNC(=O)[C@@H]1C[C@@H](F)CN1S(=O)(=O)c1cccc(F)c1] |
| 135 | (2S,4R)-4-fluoro-1-(4-fluorophenyl)sulfonyl-N-[[3-methoxy-1-[4-(trifluoromethyl)phenyl]pyrazol-4-yl]methyl]pyrrolidine-2-carboxamide | 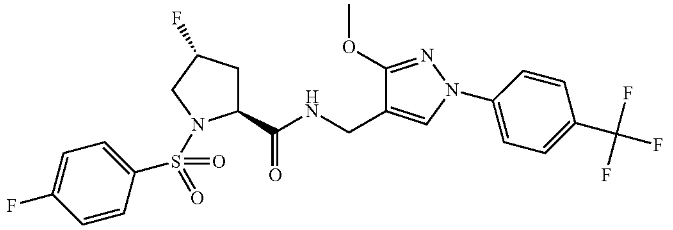 [SMILES: COc1nn(-c2ccc(C(F)(F)F)cc2)cc1CNC(=O)[C@@H]1C[C@@H](F)CN1S(=O)(=O)c1ccc(F)cc1] |
| 136 | (2R,3S)-3-fluoro-1-(4-fluorophenyl)sulfonyl-N-[[6-[6-(trifluoromethyl)-3-pyridyl]pyrimidin-4-yl]methyl]pyrrolidine-2-carboxamide | 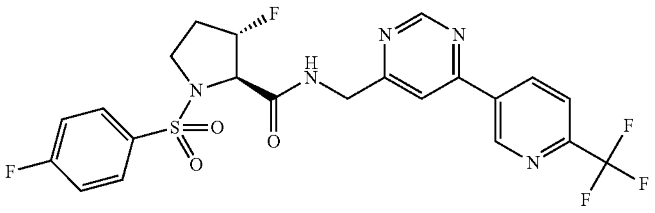 [SMILES: O=C(NCc1cc(-c2ccc(C(F)(F)F)nc2)ncn1)[C@@H]1[C@@H](F)CCN1S(=O)(=O)c1ccc(F)cc1] |
| 137 | (2S,4R)-N-[[3-chloro-1-[4-(trifluoromethyl)phenyl]pyrazol-4-yl]methyl]-4-fluoro-1-(4-fluorophenyl)sulfonyl-pyrrolidine-2-carboxamide | 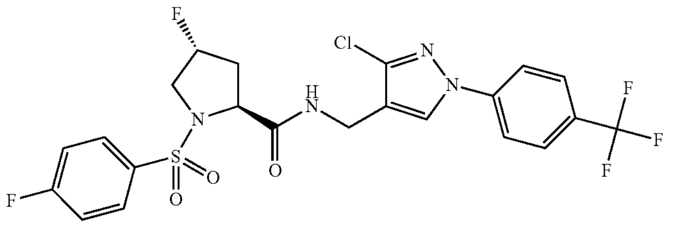 [SMILES: O=C(NCc1cn(-c2ccc(C(F)(F)F)cc2)nc1Cl)[C@@H]1C[C@@H](F)CN1S(=O)(=O)c1ccc(F)cc1] |
| 138 | (2S,4R)-4-fluoro-1-(4-fluorophenyl)sulfonyl-2-methyl-N-[[6-[4-(trifluoromethyl)phenyl] pyrimidin-4-yl]methyl] pyrrolidine-2-carboxamide | 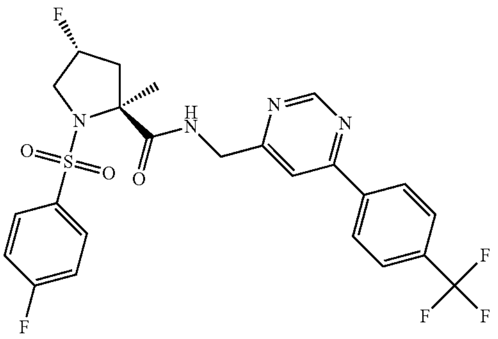 [SMILES: C[C@@]1(C(=O)NCc2cc(-c3ccc(C(F)(F)F)cc3)ncn2)C[C@@H](F)CN1S(=O)(=O)c1ccc(F)cc1] |
| 139 | (2S,4R)-4-fluoro-1-(4-fluorophenyl)sulfonyl-N-[[3-fluoro-5-[6-(trifluoromethyl)-3-pyridyl]phenyl]methyl] pyrrolidine-2-carboxamide | 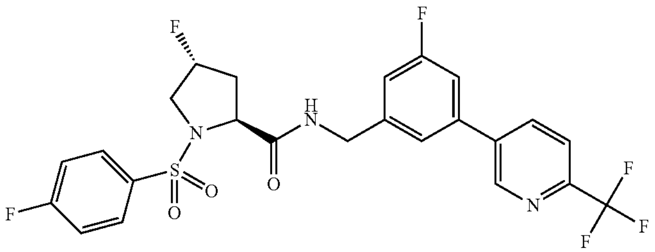 [SMILES: O=C(NCc1cc(F)cc(-c2ccc(C(F)(F)F)nc2)c1)[C@@H]1C[C@@H](F)CN1S(=O)(=O)c1ccc(F)cc1] |

TABLE 2-continued

| Example Number | Chemical Name via ChemDraw | Structure |
|---|---|---|
| 140 | (2S,4R)-4-fluoro-1-(4-fluorophenyl)sulfonyl-N-[[5-fluoro-4-[6-(trifluoromethyl)-3-pyridyl]-2-pyridyl]methyl]pyrrolidine-2-carboxamide | 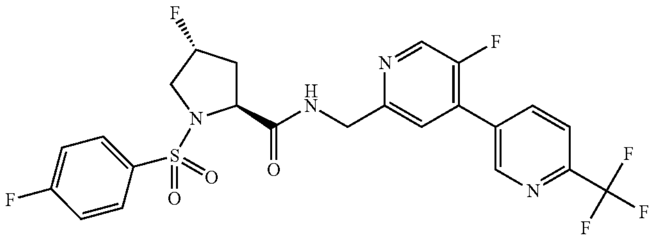 |
| 141 | (2S,4R)-4-fluoro-1-(4-fluorophenyl)sulfonyl-N-[[5-fluoro-2-[6-(trifluoromethyl)-3-pyridyl]-4-pyridyl]methyl]pyrrolidine-2-carboxamide | 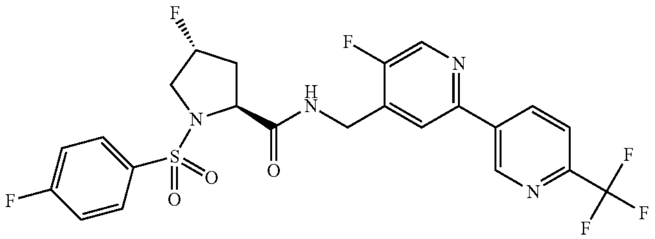 [SMILES: O=C(NCc1cc(-c2ccc(C(F)(F)F)nc2)ncc1F)[C@@H]1C[C@@H](F)CN1S(=O)(=O)c1ccc(F)cc1] |
| 142 | (2S,4R)-4-fluoro-1-(4-fluorophenyl)sulfonyl-2-methyl-N-[[6-[6-(trifluoromethyl)-3-pyridyl]pyrimidin-4-yl]methyl]pyrrolidine-2-carboxamide | 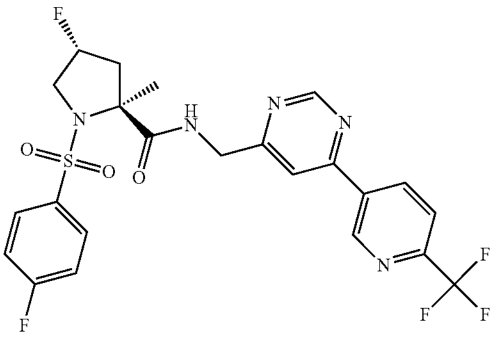 [SMILES: C[C@@]1(C(=O)NCc2cc(-c3ccc(C(F)(F)F)nc3)ncn2)C[C@@H](F)CN1S(=O)(=O)c1ccc(F)cc1] |
| 143 | (2S,4R)-4-fluoro-1-(4-fluorophenyl)sulfonyl-N-[[6-[4-(trifluoromethyl)phenyl] pyrimidin-4-yl] methyl]pyrrolidine-2-carboxamide | 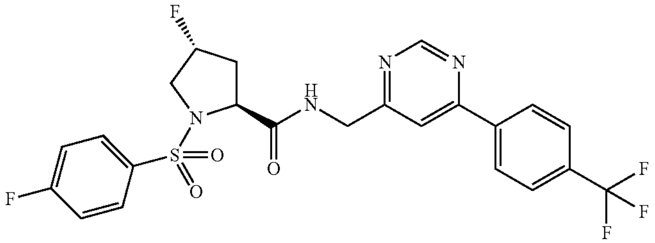 [SMILES: O=C(NCc1cc(-c2ccc(C(F)(F)F)cc2)ncn1)[C@@H]1C[C@@H](F)CN1S(=O)(=O)c1ccc(F)cc1] |
| 144 | (2S,4R)-4-fluoro-1-(4-fluorophenyl)sulfonyl-N-[[5-fluoro-4-[4-(trifluoromethyl)-1-piperidyl]-2-pyridyl]methyl]pyrrolidine-2-carboxamide | 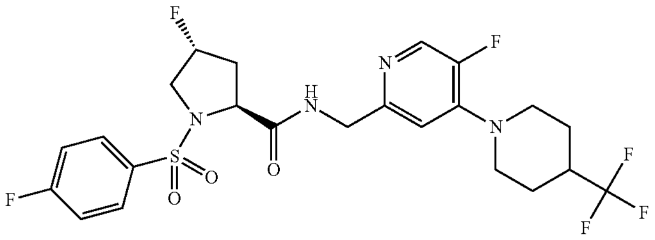 [SMILES: O=C(NCc1cc(N2CCC(C(F)(F)F)CC2)c(F)cn1)[C@@H]1C[C@@H](F)CN1S(=O)(=O)c1ccc(F)cc1] |
| 145 | (2S,4R)-4-fluoro-1-(4-fluorophenyl)sulfonyl-N-[[6-[4-(trifluoromethoxy)phenyl] pyrimidin-4-yl]methyl] pyrrolidine-2-carboxamide | 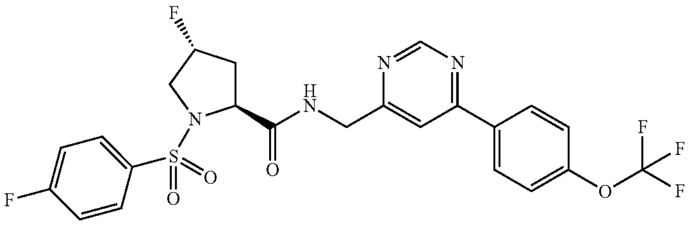 [SMILES: O=C(NCc1cc(-c2ccc(OC(F)(F)F)cc2)ncn1)[C@@H]1C[C@@H](F)CN1S(=O)(=O)c1ccc(F)cc1] |

TABLE 2-continued

| Example Number | Chemical Name via ChemDraw | Structure |
|---|---|---|
| 146 | (2S,4R)-N-[[3-chloro-1-[6-(trifluoromethyl)-3-pyridyl]pyrazol-4-yl]methyl]-4-fluoro-1-(4-fluorophenyl)sulfonyl-pyrrolidine-2-carboxamide | 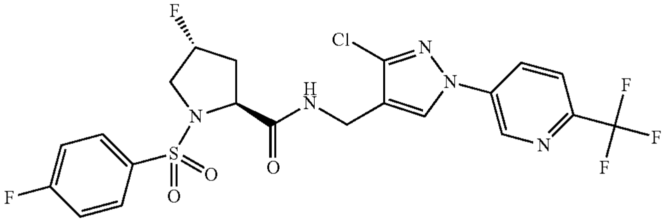 [SMILES: O=C(NCc1cn(-c2ccc(C(F)(F)F)nc2)nc1Cl)[C@@H]1C[C@@H](F)CN1S(=O)(=O)c1ccc(F)cc1] |
| 147 | (2S,4R)-4-fluoro-1-(4-fluorophenyl)sulfonyl-N-[[6-[4-(trifluoromethylsulfanyl)phenyl] pyrimidin-4-yl]methyl]pyrrolidine-2-carboxamide | 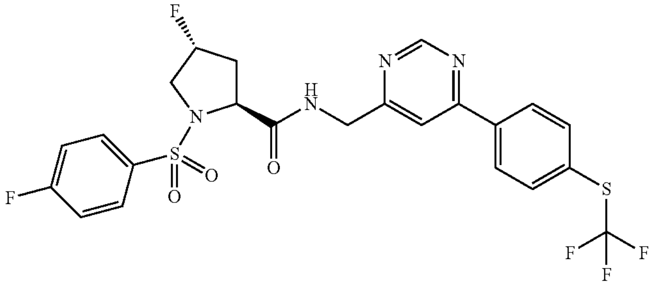 [SMILES: O=C(NCc1cc(-c2ccc(SC(F)(F)F)cc2)ncn1)[C@@H]1C[C@@H](F)CN1S(=O)(=O)c1ccc(F)cc1] |
| 148 | (2S,4R)-4-fluoro-1-(4-fluorophenyl)sulfonyl-N-[[6-[4-(trifluoromethyl)cyclohexen-1-yl]pyrimidin-4-yl]methyl]pyrrolidine-2-carboxamide | 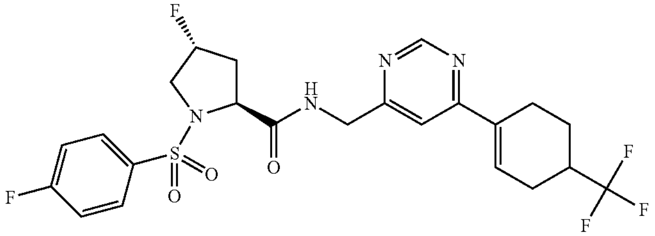 [SMILES: O=C(NCc1cc(C2=CCC(C(F)(F)F)CC2)ncn1)[C@@H]1C[C@@H](F)CN1S(=O)(=O)c1ccc(F)cc1] |
| 149 | (2S,4R)-4-fluoro-1-(4-fluorophenyl)sulfonyl-N-[[6-[4-(trifluoromethyl)cyclohexyl] pyrimidin-4-yl]methyl] pyrrolidine-2-carboxamide | 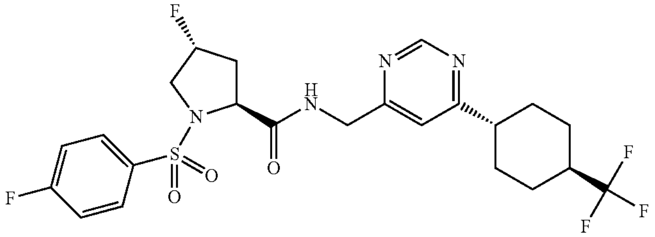 [SMILES: O=C(NCc1cc([C@H]2CC[C@H](C(F)(F)F)CC2)ncn1)[C@@H]1C[C@@H](F)CN1S(=O)(=O)c1ccc(F)cc1] |
| 150 | (2S,4R)-1-(3,4-difluorophenyl)sulfonyl-4-fluoro-N-[[6-[4-(trifluoromethyl)phenyl] pyrimidin-4-yl]methyl] pyrrolidine-2-carboxamide | 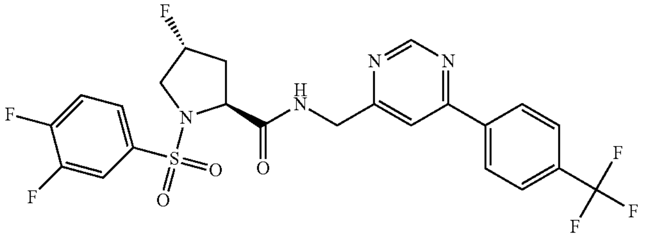 [SMILES: O=C(NCc1cc(-c2ccc(C(F)(F)F)cc2)ncn1)[C@@H]1C[C@@H](F)CN1S(=O)(=O)c1ccc(F)c(F)c1] |
| 151 | (2S,4R)-N-[[3-cyclopropyl-1-[6-(trifluoromethyl)-3-pyridyl]pyrazol-4-yl]methyl]-4-fluoro-1-(4-fluorophenyl)sulfonyl-pyrrolidine-2-carboxamide | 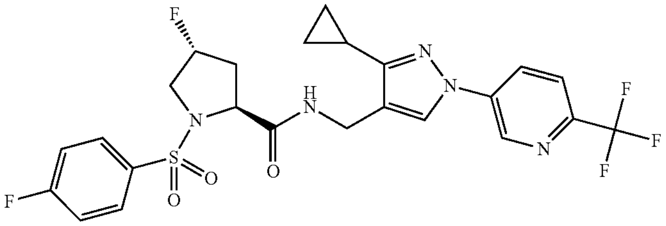 [SMILES: O=C(NCc1cn(-c2ccc(C(F)(F)F)nc2)nc1C1CC1)[C@@H]1C[C@@H](F)CN1S(=O)(=O)c1ccc(F)cc1] |

TABLE 2-continued

| Example Number | Chemical Name via ChemDraw | Structure |
|---|---|---|
| 152 | (2S,4R)-4-fluoro-1-(4-fluorophenyl)sulfonyl-N-[[2-methyl-6-[6-(trifluoromethyl)-3-pyridyl]pyrimidin-4-yl]methyl]pyrrolidine-2-carboxamide | 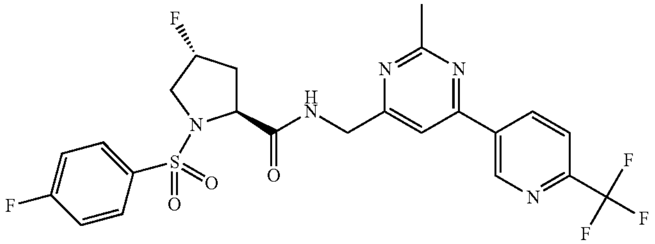 [SMILES: Cc1nc(CNC(=O)[C@@H]2C[C@@H](F)CN2S(=O)(=O)c2ccc(F)cc2)cc(-c2ccc(C(F)(F)F)nc2)n1] |
| 153 | (2S,4R)-4-fluoro-1-(4-fluorophenyl)sulfonyl-N-[[3-methoxy-1-[6-(trifluoromethyl)-3-pyridyl]pyrazol-4-yl]methyl]pyrrolidine-2-carboxamide | 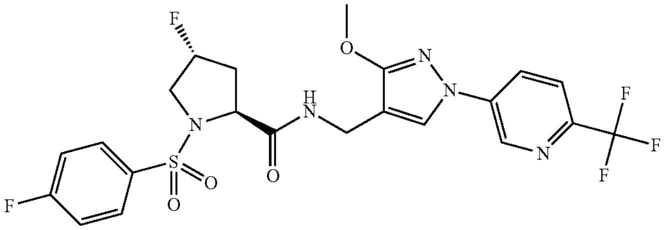 [SMILES: COc1nn(-c2ccc(C(F)(F)F)nc2)cc1CNC(=O)[C@@H]1C[C@@H](F)CN1S(=O)(=O)c1ccc(F)cc1] |
| 154 | (2S,4R)-4-fluoro-1-(4-fluorophenyl)sulfonyl-N-[[6-[6-(trifluoromethyl)-3-pyridyl]pyrimidin-4-yl]methyl]pyrrolidine-2-carboxamide | 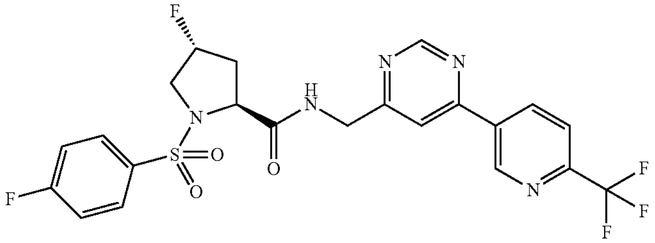 [SMILES: O=C(NCc1cc(-c2ccc(C(F)(F)F)nc2)ncn1)[C@@H]1C[C@@H](F)CN1S(=O)(=O)c1ccc(F)cc1] |
| 155 | (2S,4R)-N-[[6-(4-cyclopropylphenyl)pyrimidin-4-yl]methyl]-4-fluoro-1-(4-fluorophenyl)sulfonyl-pyrrolidine-2-carboxamide | 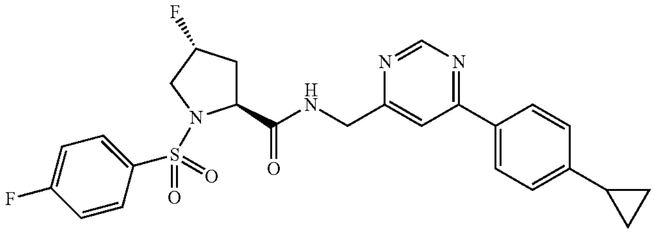 [SMILES: O=C(NCc1cc(-c2ccc(C3CC3)cc2)ncn1)[C@@H]1C[C@@H](F)CN1S(=O)(=O)c1ccc(F)cc1] |
| 156 | (2S,4R)-1-(3,4-difluorophenyl)sulfonyl-4-fluoro-N-[[6-[6-(trifluoromethyl)-3-pyridyl]pyrimidin-4-yl]methyl]pyrrolidine-2-carboxamide | 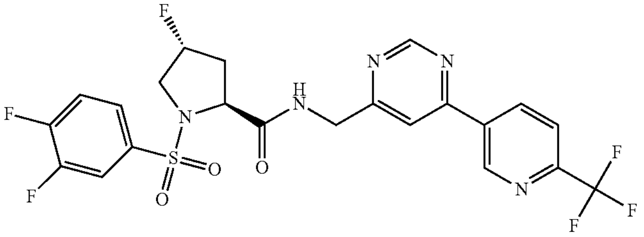 [SMILES: O=C(NCc1cc(-c2ccc(C(F)(F)F)nc2)ncn1)[C@@H]1C[C@@H](F)CN1S(=O)(=O)c1ccc(F)c(F)c1] |
| 157 | (2R,3S)-3-fluoro-1-(4-fluorophenyl)sulfonyl-N-[[4-[2-(trifluoromethyl)pyrimidin-5-yl]-2-pyridyl]methyl]pyrrolidine-2-carboxamide | 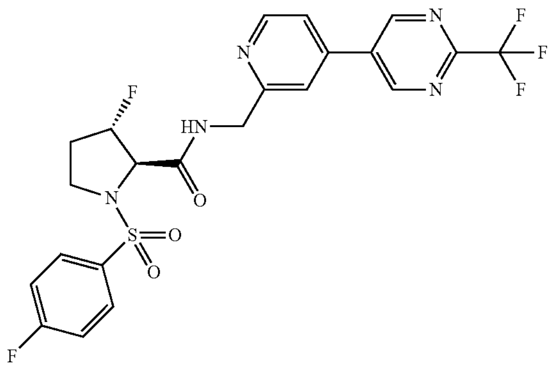 [SMILES: O=C(NCc1cc(-c2cnc(C(F)(F)F)nc2)ccn1)[C@@H]1[C@@H](F)CCN1S(=O)(=O)c1ccc(F)cc1] |

TABLE 2-continued

| Example Number | Chemical Name via ChemDraw | Structure |
|---|---|---|
| 158 | (2S,4R)-N-[[2-chloro-5-[2-(trifluoromethyl)pyrimidin-5-yl]phenyl]methyl]-4-fluoro-1-(4-fluorophenyl)sulfonyl-pyrrolidine-2-carboxamide | 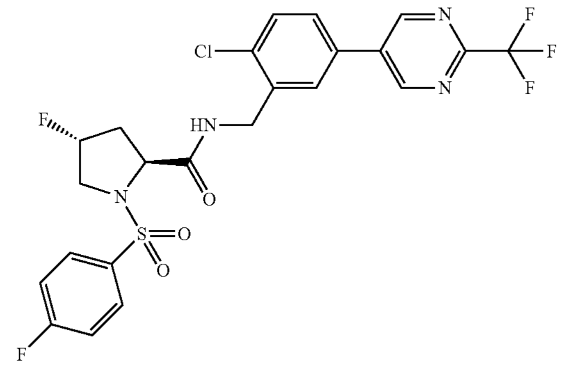 |
| 159 | (2S,4R)-4-fluoro-1-(4-fluorophenyl)sulfony]-N-[[2-[4-(trifluoromethoxy)phenyl]-4-pyridyl]methyl]pyrrolidine-2-carboxamide | 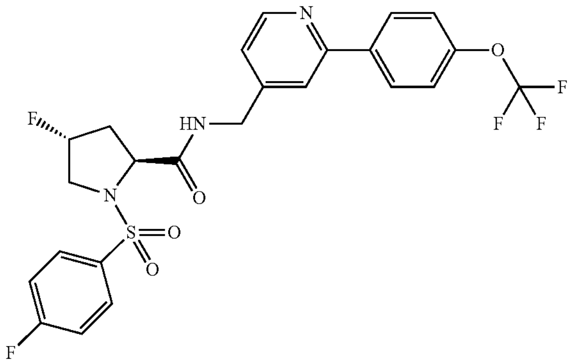 [SMILES: O=C(NCc1ccnc(-c2ccc(OC(F)(F)F)cc2)c1)[C@@H]1C[C@@H](F)CN1S(=O)(=O)c1ccc(F)cc1] |
| 160 | (2S,4R)-N-[[2-[4-(difluoromethoxy)phenyl]-4-pyridyl]methyl]-4-fluoro-1-(4-fluorophenyl)sulfonyl-pyrrolidine-2-carboxamide | 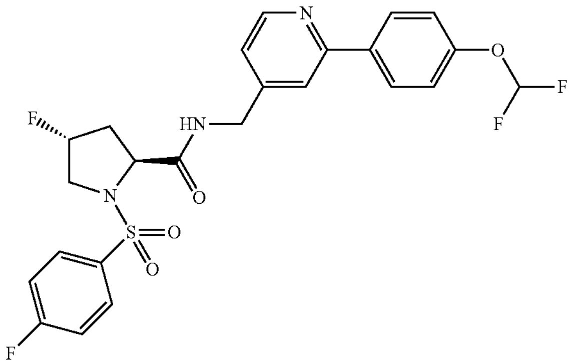 |
| 161 | (2S,4R)-4-fluoro-1-(4-fluorophenyl)sulfonyl-N-[[2-fluoro-5-[6-(trifluoromethyl)-3-pyridyl]phenyl]methyl] pyrrolidine-2-carboxamide | 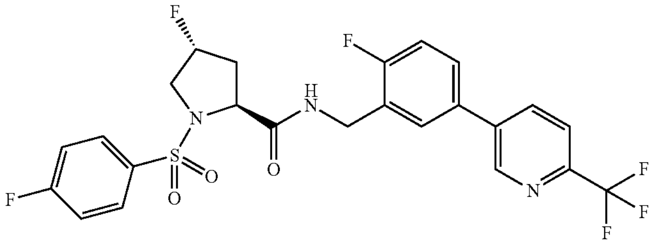 |

TABLE 2-continued

| Example Number | Chemical Name via ChemDraw | Structure |
|---|---|---|
| 162 | (2S,4R)-4-fluoro-1-(4-fluorophenyl)sulfonyl-N-[[2-fluoro-5-[5-(trifluoromethyl)-2-pyridyl]phenyl]methyl]pyrrolidine-2-carboxamide | 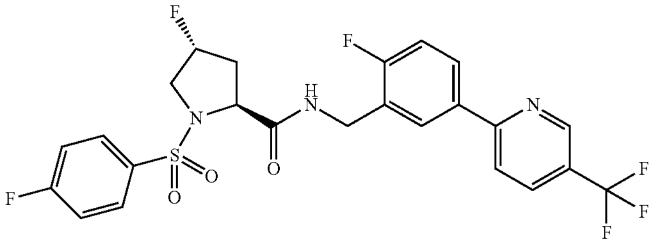 [SMILES: O=C(NCc1cc(-c2ccc(C(F)(F)F)cn2)ccc1F)[C@@H]1C[C@@H](F)CN1S(=O)(=O)c1ccc(F)cc1] |
| 163 | (2S,4R)-4-fluoro-1-(4-fluorophenyl)sulfonyl-N-[[2-fluoro-5-[6-(trifluoromethyl)pyridazin-3-yl]phenyl]methyl]pyrrolidine-2-carboxamide | 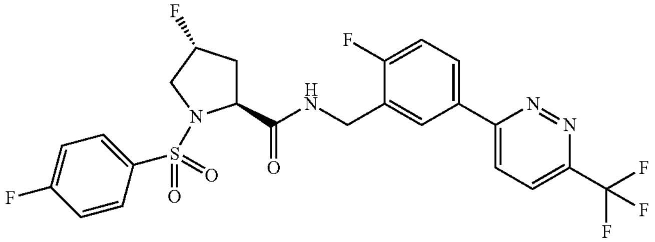 [SMILES: O=C(NCc1cc(-c2ccc(C(F)(F)F)nn2)ccc1F)[C@@H]1C[C@@H](F)CN1S(=O)(=O)c1ccc(F)cc1] |
| 164 | (2S,4R)-N-[[2-cyano-5-[2-(trifluoromethyl)pyrimidin-5-yl]phenyl]methyl]-4-fluoro-1-(4-fluorophenyl)sulfonyl-pyrrolidine-2-carboxamide | 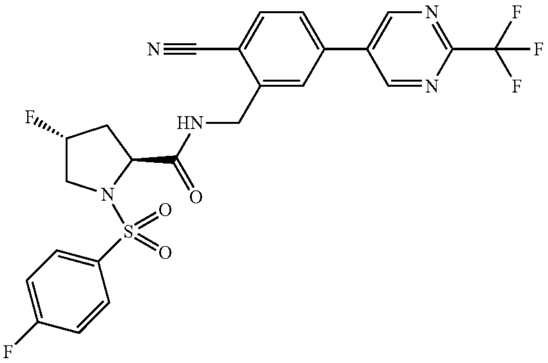 [SMILES: N#Cc1ccc(-c2cnc(C(F)(F)F)nc2)cc1CNC(=O)[C@@H]1C[C@@H](F)CN1S(=O)(=O)c1ccc(F)cc1] |
| 165 | (2S,4R)-N-[[2-chloro-6-[4-(difluoromethoxy)phenyl]-4-pyridyl]methyl]-4-fluoro-1-(4-fluorophenyl)sulfonyl-pyrrolidine-2-carboxamide | 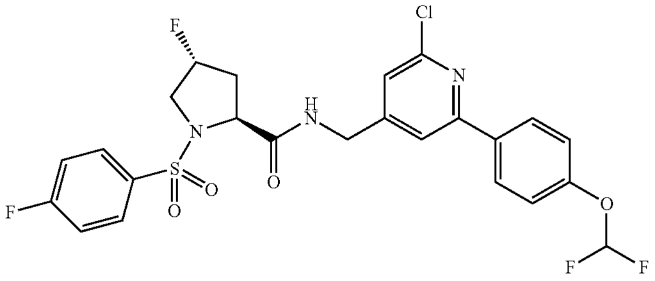 [SMILES: O=C(NCc1cc(Cl)nc(-c2ccc(OC(F)F)cc2)c1)[C@@H]1C[C@@H](F)CN1S(=O)(=O)c1ccc(F)cc1] |
| 166 | (2R,3S)-N-[[5-cyano-2-[6-(trifluoromethyl)-3-pyridyl]-4-pyridyl]methyl]-3-fluoro-1-(4-fluorophenyl)sulfonyl-pyrrolidine-2-carboxamide | 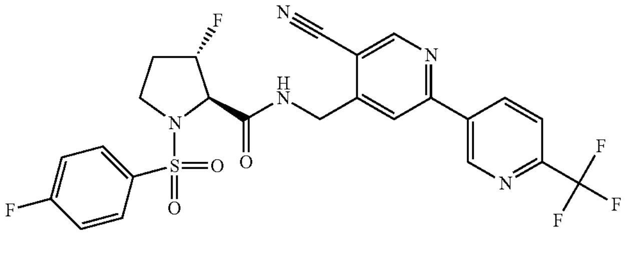 [SMILES: N#Cc1cnc(-c2ccc(C(F)(F)F)nc2)cc1CNC(=O)[C@@H]1[C@@H](F)CCN1S(=O)(=O)c1ccc(F)cc1] |

TABLE 2-continued

| Example Number | Chemical Name via ChemDraw | Structure |
| --- | --- | --- |
| 167 | (2S,4R)-4-fluoro-1-(4-fluorophenyl)sulfonyl-N-[[5-fluoro-4-[2-(trifluoromethyl)pyrimidin-5-yl]-2-pyridyl]methyl]pyrrolidine-2-carboxamide | 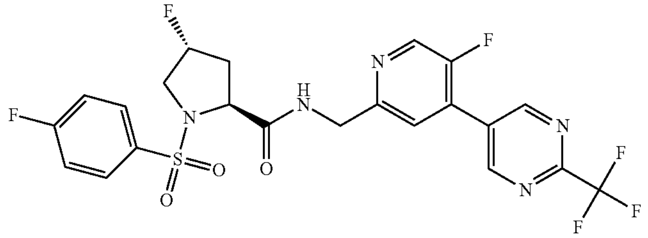 [SMILES: O=C(NCc1cc(-c2cnc(C(F)(F)F)nc2)c(F)cn1)[C@@H]1C[C@@H](F)CN1S(=O)(=O)c1ccc(F)cc1] |
| 168 | (2R,3S)-3-fluoro-1-(4-fluorophenyl)sulfonyl-N-[[2-[2-(trifluoromethyl)pyrimidin-5-yl]-4-pyridyl]methyl]pyrrolidine-2-carboxamide | 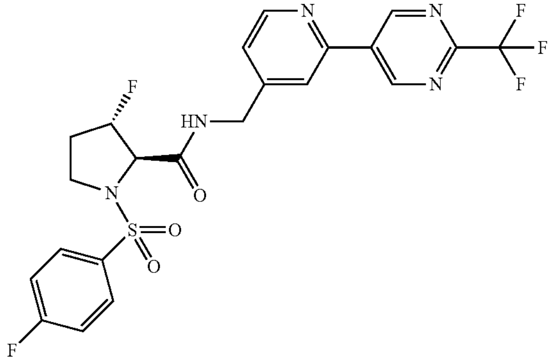 [SMILES: O=C(NCc1ccnc(-c2cnc(C(F)(F)F)nc2)c1)[C@@H]1[C@@H](F)CCN1S(=O)(=O)c1ccc(F)cc1] |
| 169 | (2S,4R)-4-fluoro-1-(4-fluorophenyl)sulfonyl-N-[[5-methyl-2-[2-(trifluoromethyl)pyrimidin-5-yl]-4-pyridyl]methyl]pyrrolidine-2-carboxamide | 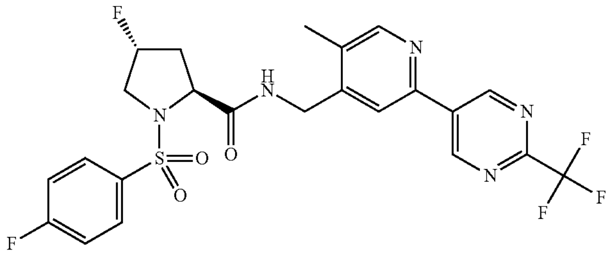 [SMILES: Cc1cnc(-c2cnc(C(F)(F)F)nc2)cc1CNC(=O)[C@@H]1C[C@@H](F)CN1S(=O)(=O)c1ccc(F)cc1] |
| 170 | (2S,4R)-4-fluoro-1-(4-fluorophenyl)sulfonyl-N-[[6-(2-methoxyethoxy)-4-[6-(trifluoromethyl)-3-pyridyl]-2-pyridyl]methyl]pyrrolidine-2-carboxamide | 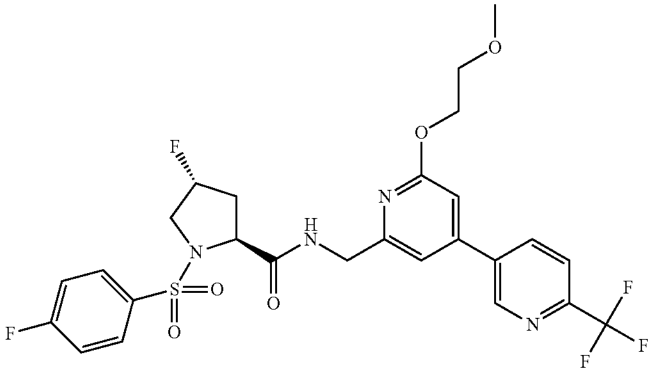 [SMILES: COCCOc1cc(-c2ccc(C(F)(F)F)nc2)cc(CNC(=O)[C@@H]2C[C@@H](F)CN2S(=O)(=O)c2ccc(F)cc2)n1] |

TABLE 2-continued

| Example Number | Chemical Name via ChemDraw | Structure |
|---|---|---|
| 171 | (2S,4R)-4-fluoro-1-(4-fluorophenyl)sulfonyl-N-[[2-fluoro-5-[2-(trifluoromethyl)pyrimidin-5-yl]-3-pyridyl]methyl]pyrrolidine-2-carboxamide | 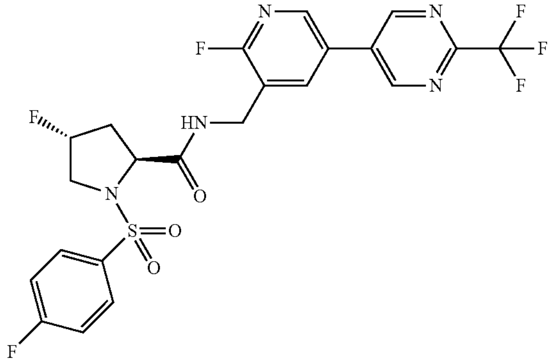 [SMILES: O=C(NCc1cc(-c2cnc(C(F)(F)F)nc2)cnc1F)[C@@H]1C[C@@H](F)CN1S(=O)(=O)c1ccc(F)cc1] |
| 172 | (1R,4S,5S)-3-(4-fluorophenyl)sulfonyl-N-[[2-[2-(trifluoromethyl)pyrimidin-5-yl]-4-pyridyl]methyl]-3-azabicyclo[3.1.0]hexane-4-carboxamide | 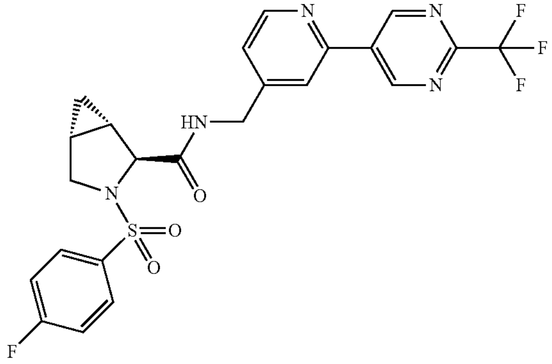 [SMILES: O=C(NCc1ccnc(-c2cnc(C(F)(F)F)nc2)c1)[C@@H]1[C@H]2C[C@H]2CN1S(=O)(=O)c1ccc(F)cc1] |
| 173 | (2S,4R)-4-fluoro-1-(4-fluorophenyl)sulfonyl-N-[[3-fluoro-5-[2-(trifluoromethyl)thiazol-4-yl]phenyl]methyl]pyrrolidine-2-carboxamide | 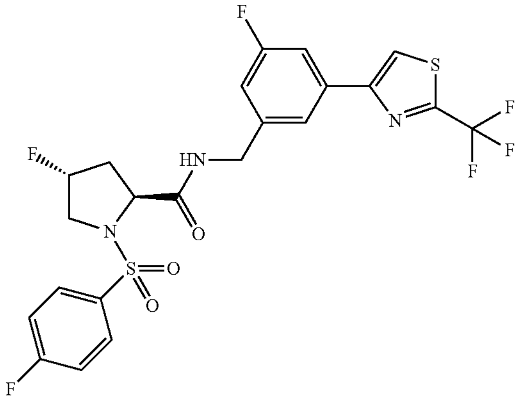 [SMILES: O=C(NCc1cc(F)cc(-c2csc(C(F)(F)F)n2)c1)[C@@H]1C[C@@H](F)CN1S(=O)(=O)c1ccc(F)cc1] |
| 174 | (2S,4R)-4-fluoro-1-(4-fluorophenyl)sulfonyl-N-[[3-fluoro-5-[2-(trifluoromethyl)thiazol-5-yl]phenyl]methyl]pyrrolidine-2-carboxamide | 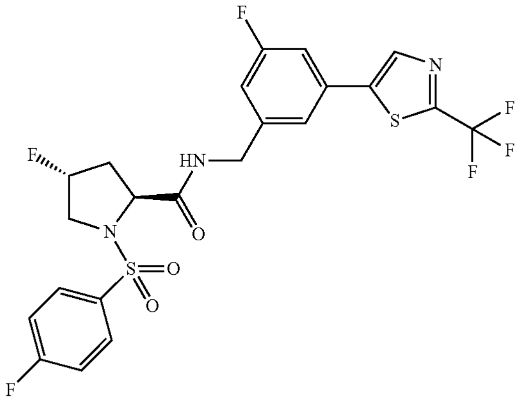 [SMILES: O=C(NCc1cc(F)cc(-c2cnc(C(F)(F)F)s2)c1)[C@@H]1C[C@@H](F)CN1S(=O)(=O)c1ccc(F)cc1] |

TABLE 2-continued

| Example Number | Chemical Name via ChemDraw | Structure |
|---|---|---|
| 175 | (2S,4R)-4-fluoro-1-(4-fluorophenyl)sulfonyl-N-[[3-fluoro-5-[4-(trifluoromethyl)thiazol-2-yl]phenyl]methyl]pyrrolidine-2-carboxamide | 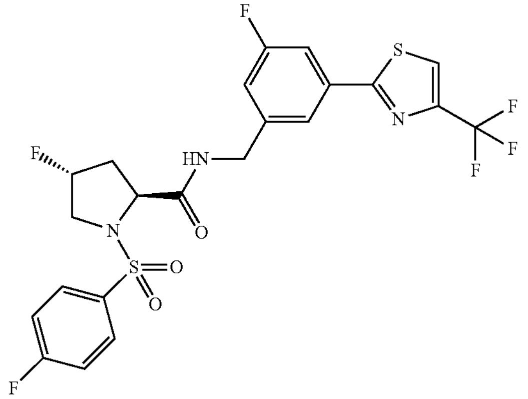 [SMILES: O=C(NCc1cc(F)cc(-c2nc(C(F)(F)F)cs2)c1)[C@@H]1C[C@@H](F)CN1S(=O)(=O)c1ccc(F)cc1] |
| 176 | (1S,2S,5R)-N-[[2-cyano-5-[2-(trifluoromethyl)pyrimidin-5-yl]phenyl]methyl]-3-(4-fluorophenyl)sulfonyl-3-azabicyclo[3.1.0]hexane-2-carboxamide | 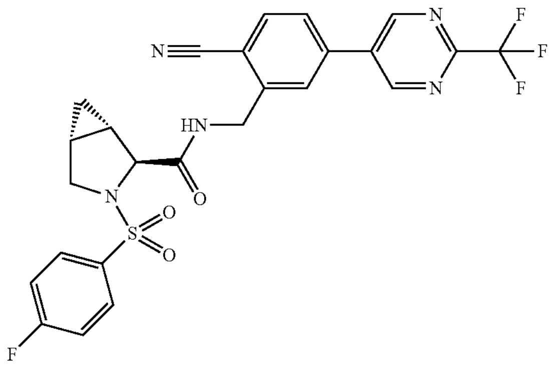 [SMILES: N#Cc1ccc(-c2cnc(C(F)(F)F)nc2)cc1CNC(=O)[C@@H]1[C@H]2C[C@H]2CN1S(=O)(=O)c1ccc(F)cc1] |
| 177 | (2S,4R)-4-fluoro-1-(4-fluorophenyl)sulfonyl-N-[[2-fluoro-5-[4-(trifluoromethyl)phenyl]phenyl]methyl]pyrrolidine-2-carboxamide | 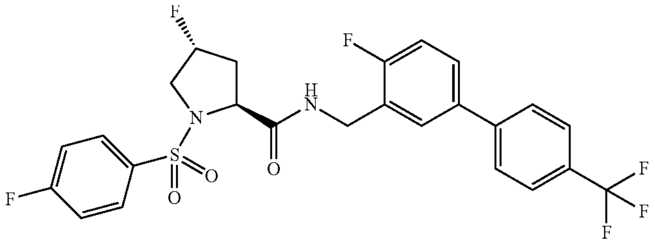 [SMILES: O=C(NCc1cc(-c2ccc(C(F)(F)F)cc2)ccc1F)[C@@H]1C[C@@H](F)CN1S(=O)(=O)c1ccc(F)cc1] |
| 178 | (2S,4R)-N-[[2-[2-amino-6-(trifluoromethyl)-3-pyridyl]-4-pyridyl]methyl]-4-fluoro-1-(4-fluorophenyl)sulfonyl-pyrrolidine-2-carboxamide | 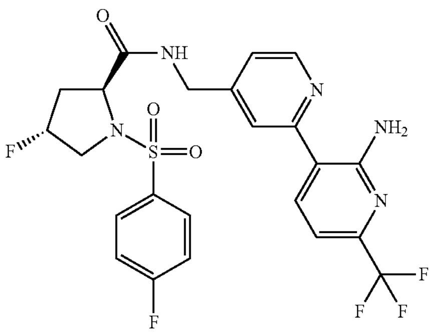 [SMILES: Nc1nc(C(F)(F)F)ccc1-c1cc(CNC(=O)[C@@H]2C[C@@H](F)CN2S(=O)(=O)c2ccc(F)cc2)ccn1] |

TABLE 2-continued

| Example Number | Chemical Name via ChemDraw | Structure |
|---|---|---|
| 179 | (2S,4R)-4-fluoro-1-(4-fluorophenyl)sulfonyl-N-[[2-[2-(methylamino)-6-(trifluoromethyl)-3-pyridyl]-4-pyridyl]methyl]pyrrolidine-2-carboxamide | 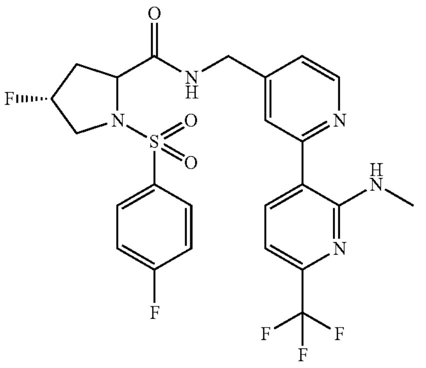 [SMILES: CNc1nc(C(F)(F)F)ccc1-c1cc(CNC(=O)C2C[C@@H](F)CN2S(=O)(=O)c2ccc(F)cc2)ccn1] |
| 180 | (2S,4R)-4-fluoro-1-(4-fluorophenyl)sulfonyl-N-[[5-fluoro-2-[2-(trifluoromethyl)pyrimidin-5-yl]-4-pyridyl]methyl]pyrrolidine-2-carboxamide | 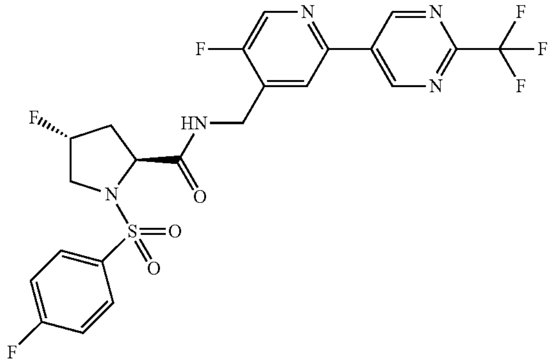 [SMILES: O=C(NCc1cc(-c2cnc(C(F)(F)F)nc2)ncc1F)[C@@H]1C[C@@H](F)CN1S(=O)(=O)c1ccc(F)cc1] |
| 181 | (1R,5S)-4-(4-fluorophenyl)sulfonyl-N-[[3-fluoro-5-[2-(trifluoromethyl)pyrimidin-5-yl]phenyl]methyl]-4-azabicyclo[3.1.0]hexane-5-carboxamide | 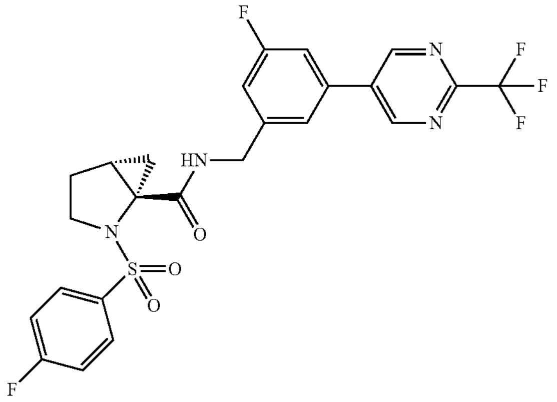 [SMILES: O=C(NCc1cc(F)cc(-c2cnc(C(F)(F)F)nc2)c1)[C@]12C[C@H]1CCN2S(=O)(=O)c1ccc(F)cc1] |
| 182 | (1R,5S)-4-(4-fluorophenyl)sulfonyl-N-[[2-fluoro-5-[2-(trifluoromethyl)pyrimidin-5-yl]phenyl]methyl]-4-azabicyclo[3.1.0]hexane-5-carboxamide | 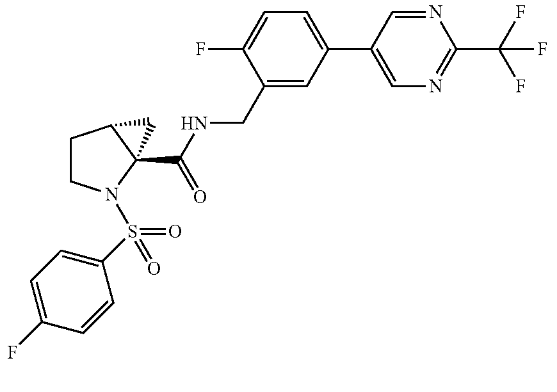 [SMILES: O=C(NCc1cc(-c2cnc(C(F)(F)F)nc2)ccc1F)[C@]12C[C@H]1CCN2S(=O)(=O)c1ccc(F)cc1] |

TABLE 2-continued

| Example Number | Chemical Name via ChemDraw | Structure |
|---|---|---|
| 183 | (1S,2S,5R)-3-(4-fluorophenyl)sulfonyl-N-[[2-fluoro-5-[2-(trifluoromethyl)pyrimidin-5-yl]phenyl]methyl]-3-azabicyclo[3.1.0]hexane-2-carboxamide | 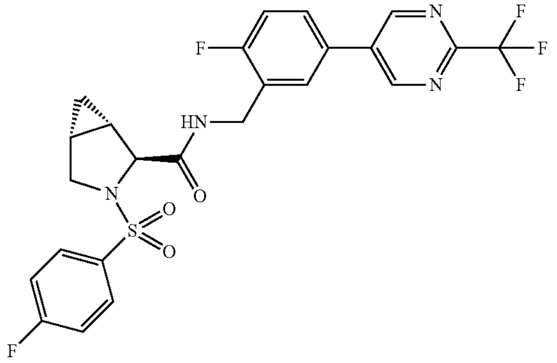 [SMILES: O=C(NCc1cc(-c2cnc(C(F)(F)F)nc2)ccc1F)[C@@H]1[C@H]2C[C@H]2CN1S(=O)(=O)c1ccc(F)cc1] |
| 184 | (2S,4R)-N-[[5-chloro-2-[2-(trifluoromethyl)pyrimidin-5-yl]-4-pyridyl]methyl]-4-fluoro-1-(4-fluorophenyl)sulfonyl-pyrrolidine-2-carboxamide | Chiral 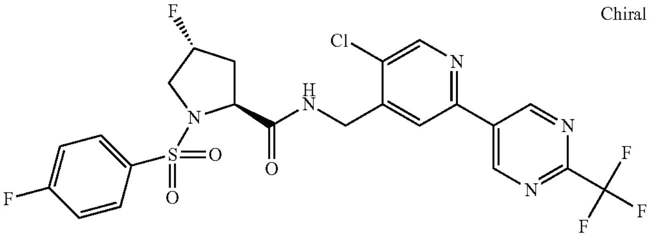 [SMILES: O=C(NCc1cc(-c2cnc(C(F)(F)F)nc2)ncc1Cl)[C@@H]1C[C@@H](F)CN1S(=O)(=O)c1ccc(F)cc1] |
| 185 | 5-fluoro-2-(4-fluorophenyl)sulfonyl-N-[[5-fluoro-2-[2-(trifluoromethyl)pyrimidin-5-yl]-4-pyridyl]methyl]-2-azabicyclo[2.2.1]heptane-3-carboxamide | 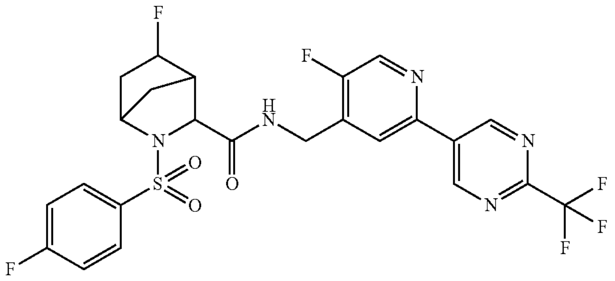 [SMILES: O=C(NCc1cc(-c2cnc(C(F)(F)F)nc2)ncc1F)C1C2CC(CC2F)N1S(=O)(=O)c1ccc(F)cc1] |
| 186 | (2S,5S)-1-(4-fluorophenyl)sulfonyl-5-methyl-N-[[2-[2-(trifluoromethyl)pyrimidin-5-yl]-4-pyridyl]methyl]pyrrolidine-2-carboxamide | Chiral 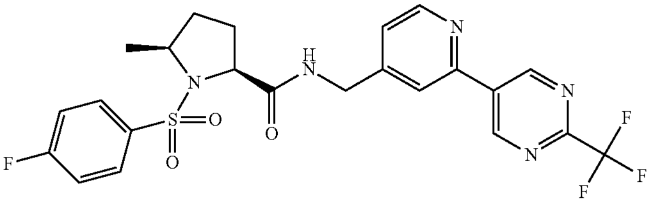 |
| 187 | (2S,4R)-4-fluoro-1-(4-fluorophenyl)sulfonyl-N-[[2-fluoro-5-[2-(trifluoromethyl)pyrimidin-5-yl]phenyl]methyl]-4-methyl-pyrrolidine-2-carboxamide | 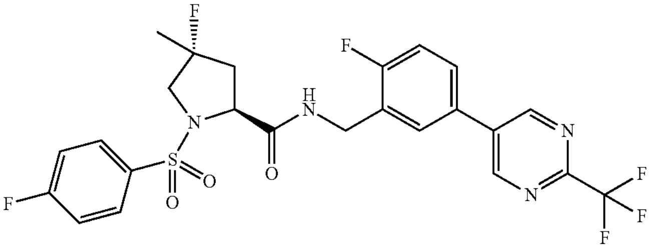 [SMILES: C[C@@]1(F)C[C@@H](C(=O)NCc2cc(-c3cnc(C(F)(F)F)nc3)ccc2F)N(S(=O)(=O)c2ccc(F)cc2)C1] |

TABLE 2-continued

| Example Number | Chemical Name via ChemDraw | Structure |
| --- | --- | --- |
| 188 | (2S,4R)-4-fluoro-1-(4-fluorophenyl)sulfonyl-N-[[2-methoxy-6-[2-(trifluoromethyl)pyrimidin-5-yl]-4-pyridyl]methyl]pyrrolidine-2-carboxamide | 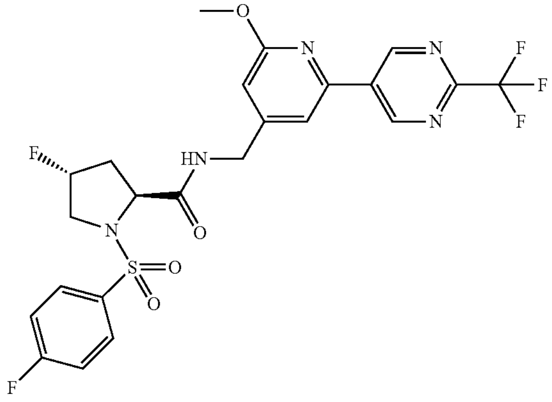 [SMILES: COc1cc(CNC(=O)[C@@H]2C[C@@H](F)CN2S(=O)(=O)c2ccc(F)cc2)cc(-c2cnc(C(F)(F)F)nc2)n1] |
| 189 | (2S,4R)-N-[[5-cyano-2-[2-(trifluoromethyl)pyrimidin-5-yl]-4-pyridyl]methyl]-4-fluoro-1-(4-fluorophenyl)sulfonyl-pyrrolidine-2-carboxamide | 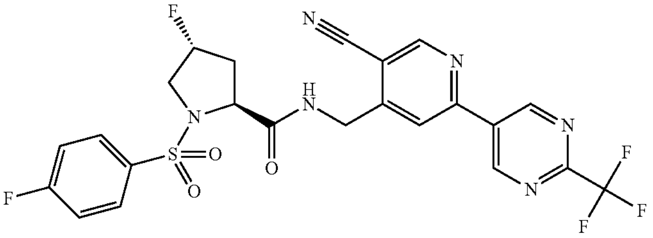 |
| 190 | (2S,4R)-4-fluoro-N-[[3-fluoro-5-[2-(2-methoxyethoxy)-6-(trifluoromethyl)-3-pyridyl]phenyl]methyl]-1-(4-fluorophenyl)sulfonyl-pyrrolidine-2-carboxamide | 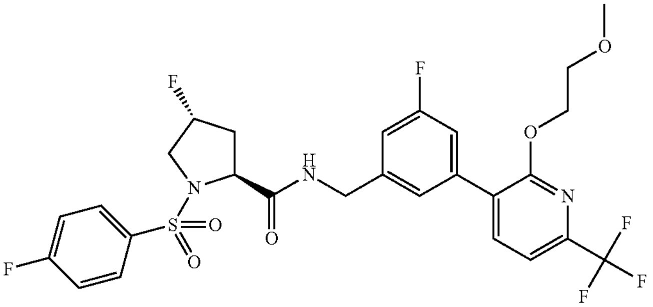 [SMILES: COCCOc1nc(C(F)(F)F)ccc1-c1cc(F)cc(CNC(=O)[C@@H]2C[C@@H](F)CN2S(=O)(=O)c2ccc(F)cc2)c1] |
| 191 | (2R,3S)-3-fluoro-1-(4-fluorophenyl)sulfonyl-N-[[6-methyl-4-[2-(trifluoromethyl)pyrimidin-5-yl]-2-pyridyl]methyl]pyrrolidine-2-carboxamide | 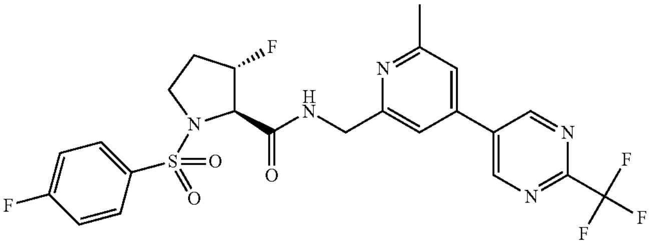 [SMILES: Cc1cc(-c2cnc(C(F)(F)F)nc2)cc(CNC(=O)[C@@H]2[C@@H](F)CCN2S(=O)(=O)c2ccc(F)cc2)n1] |
| 192 | (2S,4R)-N-[[5-chloro-4-[2-(trifluoromethyl)pyrimidin-5-yl]-2-pyridyl]methyl]-4-fluoro-1-(4-fluorophenyl)sulfonyl-pyrrolidine-2-carboxamide | 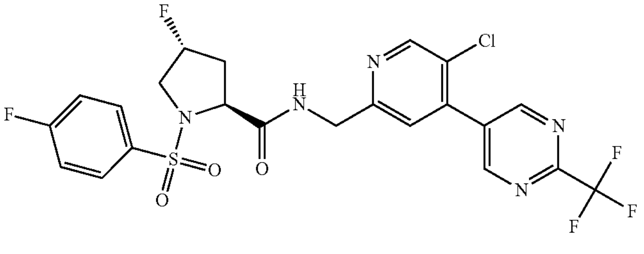 [SMILES: O=C(NCc1cc(-c2cnc(C(F)(F)F)nc2)c(Cl)cn1)[C@@H]1C[C@@H](F)CN1S(=O)(=O)c1ccc(F)cc1] |

TABLE 2-continued

| Example Number | Chemical Name via ChemDraw | Structure |
|---|---|---|
| 193 | (2S,4R,5S)-4-fluoro-1-(4-fluorophenyl)sulfonyl-5-methyl-N-[[2-[2-(trifluoromethyl)pyrimidin-5-yl]-4-pyridyl]methyl]pyrrolidine-2-carboxamide | 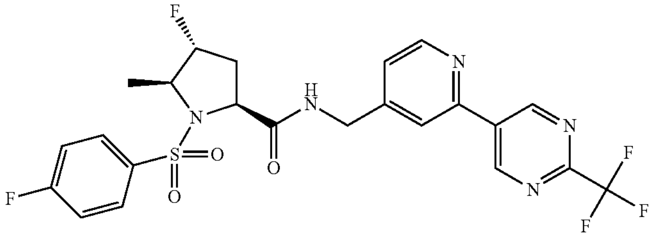 [SMILES: C[C@H]1[C@H](F)C[C@@H](C(=O)NCc2ccnc(-c3cnc(C(F)(F)F)nc3)c2)N1S(=O)(=O)c1ccc(F)cc1] |
| 194 | (2S)-1-(4-fluorophenyl)sulfonyl-5,5-dimethyl-N-[[6-[6-(trifluoromethyl)-3-pyridyl]pyrimidin-4-yl]methyl]pyrrolidine-2-carboxamide | 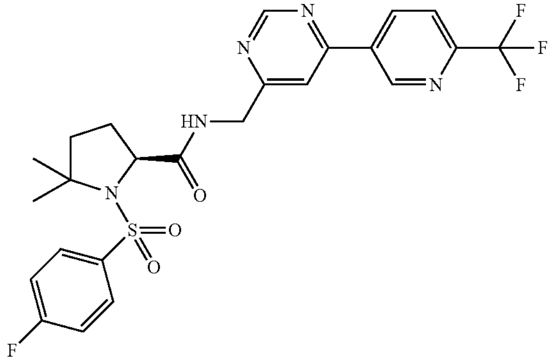 [SMILES: CC1(C)CC[C@@H](C(=O)NCc2cc(-c3ccc(C(F)(F)F)nc3)ncn2)N1S(=O)(=O)c1ccc(F)cc1] |
| 195 | (2S,4R)-4-fluoro-1-(4-fluorophenyl)sulfonyl-N-[[5-[2-(trifluoromethyl)pyrimidin-5-yl]-3-pyridyl]methyl]pyrrolidine-2-carboxamide | 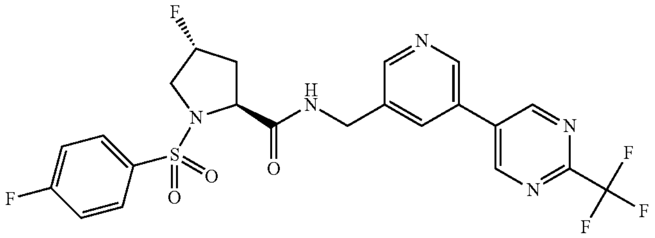 [SMILES: O=C(NCc1cncc(-c2cnc(C(F)(F)F)nc2)c1)[C@@H]1C[C@@H](F)CN1S(=O)(=O)c1ccc(F)cc1] |
| 196 | (2S,4R)-4-fluoro-1-(4-fluorophenyl)sulfonyl-N-[[5-methoxy-2-[2-(trifluoromethyl)pyrimidin-5-yl]-4-pyridyl]methyl]pyrrolidine-2-carboxamide | 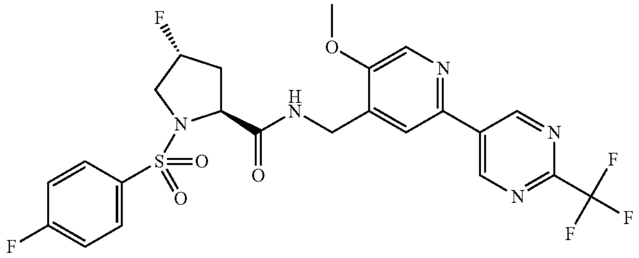 [SMILES: COc1cnc(-c2cnc(C(F)(F)F)nc2)cc1CNC(=O)[C@@H]1C[C@@H](F)CN1S(=O)(=O)c1ccc(F)cc1] |
| 197 | (2S)-N-[[3-chloro-1-[4-(trifluoromethyl)phenyl]pyrazol-4-yl]methyl]-1-(4-fluorophenyl)sulfonyl-azetidine-2-carboxamide | 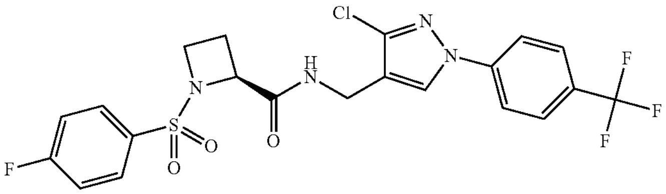 [SMILES: O=C(NCc1cn(-c2ccc(C(F)(F)F)cc2)nc1Cl)[C@@H]1CCN1S(=O)(=O)c1ccc(F)cc1] |
| 198 | (2S)-1-(4-fluorophenyl)sulfonyl-2-methyl-N-[[6-[6-(trifluoromethyl)-3-pyridyl]pyrimidin-4-yl]methyl]azetidine-2-carboxamide | 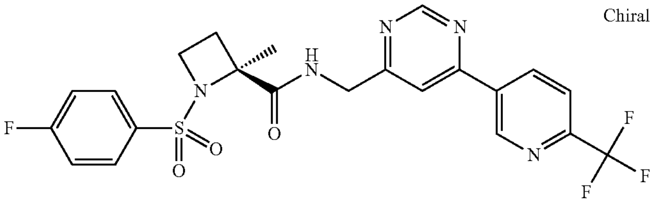 [SMILES: C[C@@]1(C(=O)NCc2cc(-c3ccc(C(F)(F)F)nc3)ncn2)CCN1S(=O)(=O)c1ccc(F)cc1] Chiral |

TABLE 2-continued

| Example Number | Chemical Name via ChemDraw | Structure |
|---|---|---|
| 199 | (2S)-N-[[3-chloro-1-[6-(trifluoromethyl)-3-pyridyl]pyrazol-4-yl]methyl]-1-(4-fluorophenyl)sulfonyl-azetidine-2-carboxamide | 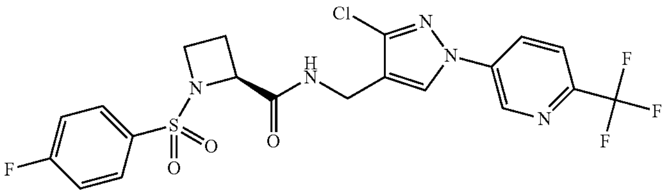 |
| 200 | (2S,4R)-1-(4-fluorophenyl)sulfonyl-4-methyl-N-[[6-[6-(trifluoromethyl)-3-pyridyl]pyrimidin-4-yl]methyl]azetidine-2-carboxamide | 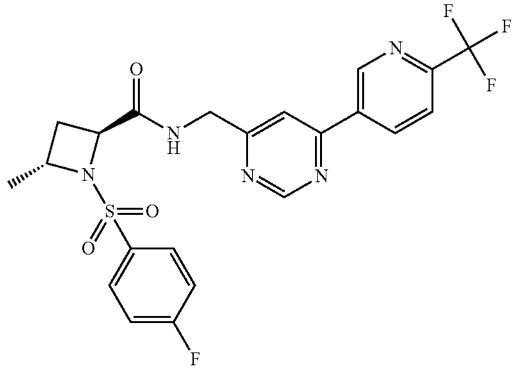 [SMILES: C[C@@H]1C[C@@H](C(=O)NCc2cc(-c3ccc(C(F)(F)F)nc3)ncn2)N1S(=O)(=O)c1ccc(F)cc1] |
| 201 | (2S)-1-(4-fluorophenyl)sulfonyl-N-[[6-[6-(trifluoromethyl)-3-pyridyl]pyrimidin-4-yl]methyl]azetidine-2-carboxamide | 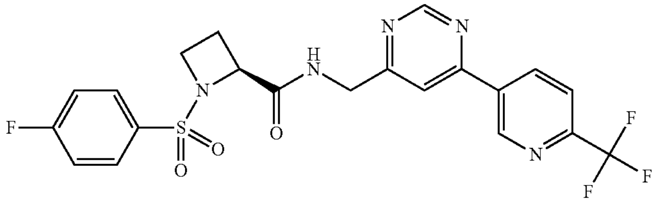 [SMILES: O=C(NCc1cc(-c2ccc(C(F)(F)F)nc2)ncn1)[C@@H]1CCN1S(=O)(=O)c1ccc(F)cc1] |

EE53. A compound of formula II:

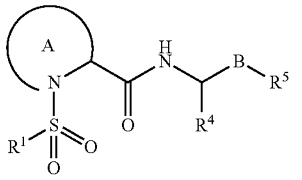

II wherein:

B is $B^2$, $B^3$, or $B^5$;

(1) the A group is:

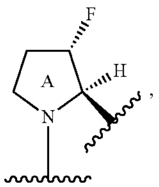

B is $B^2$ and $R^5$ is $R^{5b}$;

(2) the A group is:

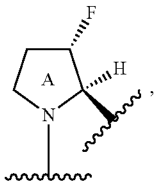

B is $B^3$ and $R^5$ is $R^{5a}$;

(3) the A group is:

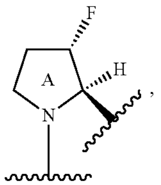

B is $B^5$ and $R^5$ is $R^{5a}$;

$B^2$ is a pyridinyl, wherein any pyridinyl of $B^2$ is optionally substituted with one or more groups independently selected from halogen, $(C_1\text{-}C_6)$alkyl, —O$(C_1\text{-}C_6)$alkyl, —O$(C_1\text{-}C_6)$alkyl-O$(C_1\text{-}C_6)$alkyl, $(C_3\text{-}C_7)$cycloalkyl, $(C_1\text{-}C_6)$haloalkyl, —CN, and 6-membered heteroaryl, wherein any 6-membered heteroaryl is optionally substituted with one or more $(C_1\text{-}C_6)$alkyl or $(C_1\text{-}C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1\text{-}C_6)$alkyl, —O$(C_1\text{-}C_6)$alkyl, $(C_3\text{-}C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1\text{-}C_6)$alkyl, $(C_1\text{-}C_6)$haloalkyl, —O$(C_1\text{-}C_6)$alkyl, and —O$(C_1\text{-}C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1\text{-}C_6)$alkyl and $(C_1\text{-}C_6)$haloalkyl;

$R^4$ is H, $(C_1\text{-}C_6)$alkyl or $(C_1\text{-}C_6)$haloalkyl;

$R^{5a}$ is a phenyl, 5-membered heteroaryl, 6-membered heteroaryl, 4, 5, 6 or 7-membered heterocycle or $(C_3\text{-}C_8)$cycloalkyl, wherein any phenyl, 5-membered heteroaryl, 6-membered heteroaryl, 4, 5, 6 or 7-membered heterocycle or $(C_3\text{-}C_8)$cycloalkyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$alkyl-O$(C_1\text{-}C_6)$alkyl, —O$(C_1\text{-}C_6)$haloalkyl, —S$(C_1\text{-}C_6)$alkyl, —S$(C_1\text{-}C_6)$haloalkyl, oxo, and —O—$(C_1\text{-}C_2)$alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl optionally substituted with one or more halogen, —O$(C_1\text{-}C_6)$alkyl, —O$(C_1\text{-}C_6)$haloalkyl, —OH, —S$(C_1\text{-}C_6)$alkyl, —S$(C_1\text{-}C_6)$haloalkyl, and $NR^6_2$, and wherein any 5-membered heterocycle of $R^{5b}$ is substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$haloalkyl, —S$(C_1\text{-}C_6)$alkyl and —S$(C_1\text{-}C_6)$haloalkyl; and $R^6$ is H or $(C_1\text{-}C_6)$alkyl;

or a pharmaceutically acceptable salt thereof.

EE54. A compound of formula II:

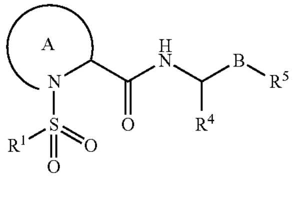

II wherein:

B is $B^2$, $B^3$, or $B^5$;

(1) the A group is:

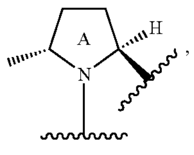

B is $B^2$ and $R^5$ is $R^{5b}$;

(2) the A group is:

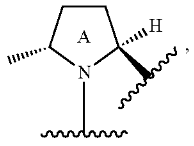

B is $B^3$ and $R^5$ is $R^{5a}$;

(3) the A group is:

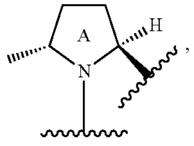

B is $B^5$ and $R^5$ is $R^{5a}$;

$B^2$ is a pyridinyl, wherein any pyridinyl of $B^2$ is optionally substituted with one or more groups independently selected from halogen, $(C_1\text{-}C_6)$alkyl, —O$(C_1\text{-}C_6)$alkyl, —O$(C_1\text{-}C_6)$alkyl-O$(C_1\text{-}C_6)$alkyl, $(C_3\text{-}C_7)$cycloalkyl, $(C_1\text{-}C_6)$haloalkyl, —CN, and 6-membered heteroaryl, wherein any 6-membered heteroaryl is optionally substituted with one or more $(C_1\text{-}C_6)$alkyl or $(C_1\text{-}C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1\text{-}C_6)$alkyl, —O$(C_1\text{-}C_6)$alkyl, $(C_3\text{-}C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1\text{-}C_6)$alkyl, $(C_1\text{-}C_6)$haloalkyl, —O$(C_1\text{-}C_6)$alkyl, and —O$(C_1\text{-}C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1\text{-}C_6)$alkyl and $(C_1\text{-}C_6)$haloalkyl;

$R^4$ is H, $(C_1\text{-}C_6)$alkyl or $(C_1\text{-}C_6)$haloalkyl;

$R^{5a}$ is a phenyl, 5-membered heteroaryl, 6-membered heteroaryl, 4, 5, 6 or 7-membered heterocycle or $(C_3\text{-}C_8)$cycloalkyl, wherein any phenyl, 5-membered heteroaryl, 6-membered heteroaryl, 4, 5, 6 or 7-membered heterocycle or $(C_3\text{-}C_8)$cycloalkyl of $R^{5a}$ is optionally substituted with one or more groups independently selected from halogen, ($C_1$-$C_6$)alkyl, ($C_1$-$C_6$)haloalkyl, —CN, ($C_3$-$C_7$)cycloalkyl, —O($C_1$-$C_6$)alkyl, —O($C_1$-$C_6$)alkyl-O($C_1$-$C_6$)alkyl, —O($C_1$-$C_6$)haloalkyl, —S($C_1$-$C_6$)alkyl, —S($C_1$-$C_6$)haloalkyl, oxo, and —O—($C_1$-$C_2$)alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, ($C_1$-$C_6$)alkyl, ($C_1$-$C_6$)haloalkyl, —CN, ($C_3$-$C_7$)cycloalkyl optionally substituted with one or more halogen, —O($C_1$-$C_6$)alkyl, —O($C_1$-$C_6$)haloalkyl, —OH, —S($C_1$-$C_6$)alkyl, —S($C_1$-$C_6$)haloalkyl, and $NR^6_2$, and wherein any 5-membered heterocycle of $R^{5b}$ is substituted with one or more groups independently selected from halogen, ($C_1$-$C_6$)alkyl, ($C_1$-$C_6$)haloalkyl, —CN, ($C_3$-$C_7$)cycloalkyl, —O($C_1$-$C_6$)alkyl, —O($C_1$-$C_6$)haloalkyl, —S($C_1$-$C_6$)alkyl and —S($C_1$-$C_6$)haloalkyl; and $R^6$ is H or ($C_1$-$C_6$)alkyl;

or a pharmaceutically acceptable salt thereof.

EE55. A compound of formula II:

II

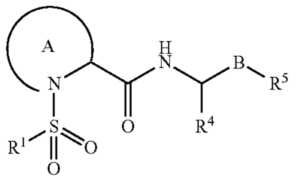

wherein:

B is $B^2$, $B^3$, or $B^5$;

(1) the A group is:

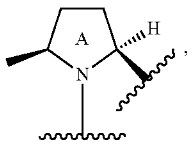

B is $B^2$ and $R^5$ is $R^{5b}$;

(2) the A group is:

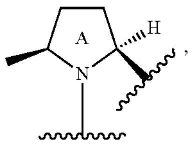

B is $B^3$ and $R^5$ is $R^{5a}$;

(3) the A group is:

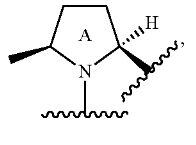

B is $B^5$ and $R^5$ is $R^{5a}$;

$B^2$ is a pyridinyl, wherein any pyridinyl of $B^2$ is optionally substituted with one or more groups independently selected from halogen, ($C_1$-$C_6$)alkyl, —O($C_1$-$C_6$)alkyl, —O($C_1$-$C_6$)alkyl-O($C_1$-$C_6$)alkyl, ($C_3$-$C_7$)cycloalkyl, ($C_1$-$C_6$)haloalkyl, —CN, and 6-membered heteroaryl, wherein any 6-membered heteroaryl is optionally substituted with one or more ($C_1$-$C_6$)alkyl or ($C_1$-$C_6$)haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, ($C_1$-$C_6$)alkyl, —O($C_1$-$C_6$)alkyl, ($C_3$-$C_7$)cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, ($C_1$-$C_6$)alkyl, ($C_1$-$C_6$)haloalkyl, —O($C_1$-$C_6$)alkyl, and —O($C_1$-$C_6$)haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, ($C_1$-$C_6$)alkyl and ($C_1$-$C_6$)haloalkyl;

$R^4$ is H, ($C_1$-$C_6$)alkyl or ($C_1$-$C_6$)haloalkyl;

$R^{5a}$ is a phenyl, 5-membered heteroaryl, 6-membered heteroaryl, 4, 5, 6 or 7-membered heterocycle or ($C_3$-$C_8$)cycloalkyl, wherein any phenyl, 5-membered heteroaryl, 6-membered heteroaryl, 4, 5, 6 or 7-membered heterocycle or ($C_3$-$C_8$)cycloalkyl of $R^{5a}$ is optionally substituted with one or more groups independently selected from halogen, ($C_1$-$C_6$)alkyl, ($C_1$-$C_6$)haloalkyl, —CN, ($C_3$-$C_7$)cycloalkyl, —O($C_1$-$C_6$)alkyl, —O($C_1$-$C_6$)alkyl-O($C_1$-$C_6$)alkyl, —O($C_1$-$C_6$)haloalkyl, —S($C_1$-$C_6$)alkyl, —S($C_1$-$C_6$)haloalkyl, oxo, and —O—($C_1$-$C_2$)alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, ($C_1$-$C_6$)alkyl, ($C_1$-$C_6$)haloalkyl, —CN, ($C_3$-$C_7$)cycloalkyl optionally substituted with one or more halogen, —O($C_1$-$C_6$)alkyl, —O($C_1$-$C_6$)haloalkyl, —OH, —S($C_1$-$C_6$)alkyl, —S($C_1$-$C_6$)haloalkyl, and $NR^6_2$, and wherein any 5-membered heterocycle of $R^{5b}$ is substituted with one or more groups independently selected from halogen, ($C_1$-$C_6$)alkyl, ($C_1$-$C_6$)haloalkyl, —CN, ($C_3$-$C_7$)cycloalkyl, —O($C_1$-$C_6$)alkyl, —O($C_1$-$C_6$)haloalkyl, —S($C_1$-$C_6$)alkyl and —S($C_1$-$C_6$)haloalkyl; and $R^6$ is H or ($C_1$-$C_6$)alkyl;

or a pharmaceutically acceptable salt thereof.

EE56. A compound of formula II:

II

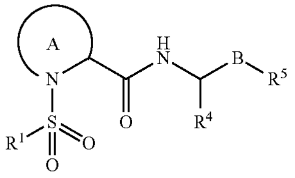

wherein:

B is $B^2$, $B^3$, or $B^5$;

(1) the A group is:

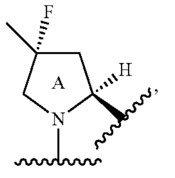

B is $B^2$ and $R^5$ is $R^{5b}$;

(2) the A group is:

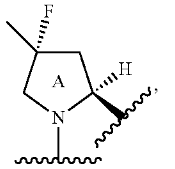

B is $B^3$ and $R^5$ is $R^{5a}$;

(3) the A group is:

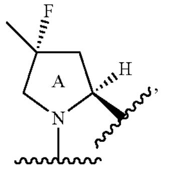

B is $B^5$ and $R^5$ is $R^{5a}$;

$B^2$ is a pyridinyl, wherein any pyridinyl of $B^2$ is optionally substituted with one or more groups independently selected from halogen, $(C_1\text{-}C_6)$alkyl, —O$(C_1\text{-}C_6)$alkyl, —O$(C_1\text{-}C_6)$alkyl-O$(C_1\text{-}C_6)$alkyl, $(C_3\text{-}C_7)$cycloalkyl, $(C_1\text{-}C_6)$haloalkyl, —CN, and 6-membered heteroaryl, wherein any 6-membered heteroaryl is optionally substituted with one or more $(C_1\text{-}C_6)$alkyl or $(C_1\text{-}C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1\text{-}C_6)$alkyl, —O$(C_1\text{-}C_6)$alkyl, $(C_3\text{-}C_7)$cycloalkyl, —CN, and $NR^6{}_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1\text{-}C_6)$alkyl, $(C_1\text{-}C_6)$haloalkyl, —O$(C_1\text{-}C_6)$alkyl, and —O$(C_1\text{-}C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1\text{-}C_6)$alkyl and $(C_1\text{-}C_6)$haloalkyl;

$R^4$ is H, $(C_1\text{-}C_6)$alkyl or $(C_1\text{-}C_6)$haloalkyl;

$R^{5a}$ is a phenyl, 5-membered heteroaryl, 6-membered heteroaryl, 4, 5, 6 or 7-membered heterocycle or $(C_3\text{-}C_8)$cycloalkyl, wherein any phenyl, 5-membered heteroaryl, 6-membered heteroaryl, 4, 5, 6 or 7-membered heterocycle or $(C_3\text{-}C_8)$cycloalkyl of $R^{5a}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$alkyl-O$(C_1\text{-}C_6)$alkyl, —O$(C_1\text{-}C_6)$haloalkyl, —S$(C_1\text{-}C_6)$alkyl, —S$(C_1\text{-}C_6)$haloalkyl, oxo, and —O—$(C_1\text{-}C_2)$alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1\text{-}C_6)$alkyl, $(C_1\text{-}C_6)$haloalkyl, —CN, $(C_3\text{-}C_7)$cycloalkyl optionally substituted with one or more halogen, —O$(C_1\text{-}C_6)$alkyl, —O$(C_1\text{-}C_6)$haloalkyl, —OH, —S$(C_1\text{-}C_6)$alkyl, —S$(C_1\text{-}C_6)$haloalkyl, and $NR^6{}_2$, and wherein any 5-membered heterocycle of $R^{5b}$ is substituted with one or more groups independently selected from halogen, $(C_1\text{-}C_6)$alkyl, $(C_1\text{-}C_6)$haloalkyl, —CN, $(C_3\text{-}C_7)$cycloalkyl, —O$(C_1\text{-}C_6)$alkyl, —O$(C_1\text{-}C_6)$haloalkyl, —S$(C_1\text{-}C_6)$alkyl and —S$(C_1\text{-}C_6)$haloalkyl; and $R^6$ is H or $(C_1\text{-}C_6)$alkyl;

or a pharmaceutically acceptable salt thereof.

EE57. A compound of formula II:

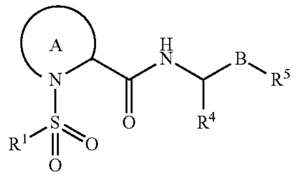

II wherein:

B is $B^2$, $B^3$, or $B^5$;

(1) the A group is:

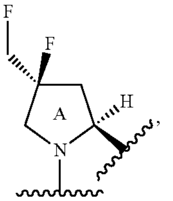

B is $B^2$ and $R^5$ is $R^{5b}$;

(2) the A group is:

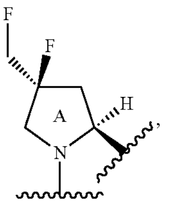

B is $B^3$ and $R^5$ is $R^{5a}$;

(3) the A group is:

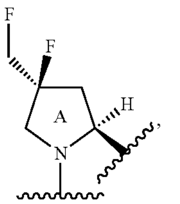

B is $B^5$ and $R^5$ is $R^{5a}$;

$B^2$ is a pyridinyl, wherein any pyridinyl of $B^2$ is optionally substituted with one or more groups independently selected from halogen, $(C_1-C_6)$alkyl, —O$(C_1-C_6)$alkyl, —O$(C_1-C_6)$alkyl-O$(C_1-C_6)$alkyl, $(C_3-C_7)$cycloalkyl, $(C_1-C_6)$haloalkyl, —CN, and 6-membered heteroaryl, wherein any 6-membered heteroaryl is optionally substituted with one or more $(C_1-C_6)$alkyl or $(C_1-C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1-C_6)$alkyl, —O$(C_1-C_6)$alkyl, $(C_3-C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1-C_6)$alkyl, $(C_1-C_6)$haloalkyl, —O$(C_1-C_6)$alkyl, and —O$(C_1-C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1-C_6)$alkyl and $(C_1-C_6)$haloalkyl;

$R^4$ is H, $(C_1-C_6)$alkyl or $(C_1-C_6)$haloalkyl;

$R^{5a}$ is a phenyl, 5-membered heteroaryl, 6-membered heteroaryl, 4, 5, 6 or 7-membered heterocycle or $(C_3-C_8)$cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$alkyl-O$(C_1-C_6)$alkyl, —O$(C_1-C_6)$haloalkyl, —S$(C_1-C_6)$alkyl, —S$(C_1-C_6)$haloalkyl, oxo, and —O—$(C_1-C_2)$alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, —O$(C_1-C_6)$alkyl, —O$(C_1-C_6)$haloalkyl, —OH, —S$(C_1-C_6)$alkyl, —S$(C_1-C_6)$haloalkyl, and $NR^6_2$, and wherein any 5-membered heterocycle of $R^{5b}$ is substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl; and $R^6$ is H or $(C_1-C_6)$alkyl;

or a pharmaceutically acceptable salt thereof.

EE58. A compound of formula II:

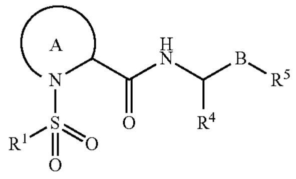

II wherein:

B is $B^2$, $B^3$, or $B^5$;

(1) the A group is:

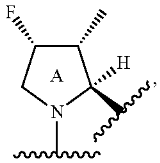

B is $B^2$ and $R^5$ is $R^{5b}$;

(2) the A group is:

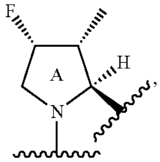

B is $B^3$ and $R^5$ is $R^{5a}$;

(3) the A group is:

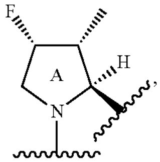

B is $B^5$ and $R^5$ is $R^{5a}$;

$B^2$ is a pyridinyl, wherein any pyridinyl of $B^2$ is optionally substituted with one or more groups independently selected from halogen, $(C_1-C_6)$alkyl, —O$(C_1-C_6)$alkyl, —O$(C_1-C_6)$alkyl-O$(C_1-C_6)$alkyl, $(C_3-C_7)$cycloalkyl, $(C_1-C_6)$haloalkyl, —CN, and 6-membered heteroaryl, wherein any 6-membered heteroaryl is optionally substituted with one or more $(C_1-C_6)$alkyl or $(C_1-C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1-C_6)$alkyl, —O$(C_1-C_6)$alkyl, $(C_3-C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1-C_6)$alkyl, $(C_1-C_6)$haloalkyl, —O$(C_1-C_6)$alkyl, and —O$(C_1-C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1-C_6)$alkyl and $(C_1-C_6)$haloalkyl;

$R^4$ is H, $(C_1-C_6)$alkyl or $(C_1-C_6)$haloalkyl;

$R^{5a}$ is a phenyl, 5-membered heteroaryl, 6-membered heteroaryl, 4, 5, 6 or 7-membered heterocycle or $(C_3-C_8)$ cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$alkyl-O$(C_1-C_6)$alkyl, —O$(C_1-C_6)$haloalkyl, —S$(C_1-C_6)$alkyl, —S$(C_1-C_6)$haloalkyl, oxo, and —O—$(C_1-C_2)$alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, —O$(C_1-C_6)$alkyl, —O$(C_1-C_6)$haloalkyl, —OH, —S$(C_1-C_6)$alkyl, —S$(C_1-C_6)$haloalkyl, and $NR^6_2$, and wherein any 5-membered heterocycle of $R^{5b}$ is substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl; and $R^6$ is H or $(C_1-C_6)$alkyl;

or a pharmaceutically acceptable salt thereof.

EE59. A compound of formula II:

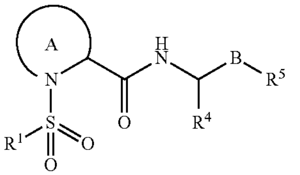

II wherein:

B is $B^2$, $B^3$, or $B^5$;

(1) the A group is:

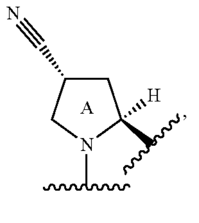

B is $B^2$ and $R^5$ is $R^{5b}$;

(2) the A group is:

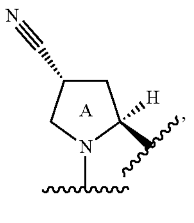

B is $B^3$ and $R^5$ is $R^{5a}$;

(3) the A group is:

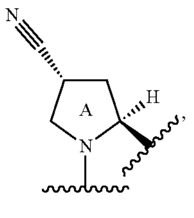

B is $B^5$ and $R^5$ is $R^{5a}$;

$B^2$ is a pyridinyl, wherein any pyridinyl of $B^2$ is optionally substituted with one or more groups independently selected from halogen, $(C_1-C_6)$alkyl, —O$(C_1-C_6)$alkyl, —O$(C_1-C_6)$alkyl-O$(C_1-C_6)$alkyl, $(C_3-C_7)$cycloalkyl, $(C_1-C_6)$haloalkyl, —CN, and 6-membered heteroaryl, wherein any 6-membered heteroaryl is optionally substituted with one or more $(C_1-C_6)$alkyl or $(C_1-C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1-C_6)$alkyl, —O$(C_1-C_6)$alkyl, $(C_3-C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1-C_6)$alkyl, $(C_1-C_6)$haloalkyl, —O$(C_1-C_6)$alkyl, and —O$(C_1-C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1-C_6)$alkyl and $(C_1-C_6)$haloalkyl;

$R^4$ is H, $(C_1-C_6)$alkyl or $(C_1-C_6)$haloalkyl;

$R^{5a}$ is a phenyl, 5-membered heteroaryl, 6-membered heteroaryl, 4, 5, 6 or 7-membered heterocycle or $(C_3-C_8)$ cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$alkyl-O$(C_1-C_6)$alkyl, —O$(C_1-C_6)$haloalkyl, —S$(C_1-C_6)$alkyl, —S$(C_1-C_6)$haloalkyl, oxo, and —O—$(C_1-C_2)$alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, —$O(C_1-C_6)$alkyl, —$O(C_1-C_6)$haloalkyl, —OH, —$S(C_1-C_6)$alkyl, —$S(C_1-C_6)$haloalkyl, and $NR^6_2$, and wherein any 5-membered heterocycle of $R^{5b}$ is substituted with one or more groups independently selected from halogen, $(C_1-C_6)$alkyl, $(C_1-C_6)$haloalkyl, —CN, $(C_3-C_7)$cycloalkyl, —$O(C_1-C_6)$alkyl, —$O(C_1-C_6)$haloalkyl, —$S(C_1-C_6)$alkyl and —$S(C_1-C_6)$haloalkyl; and $R^6$ is H or $(C_1-C_6)$alkyl;

or a pharmaceutically acceptable salt thereof.

EE60. A compound of formula II:

II

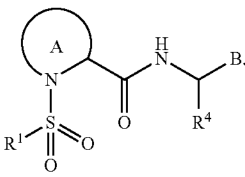

wherein:

B is $B^2$, $B^3$, or $B^5$;

(1) the A group is:

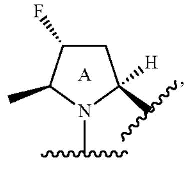

B is $B^2$ and $R^5$ is $R^{5b}$;

(2) the A group is:

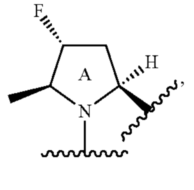

B is $B^3$ and $R^5$ is $R^{5a}$;

(3) the A group is:

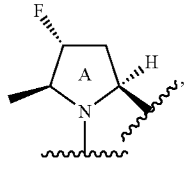

B is $B^5$ and $R^5$ is $R^{5a}$;

$B^2$ is a pyridinyl, wherein any pyridinyl of $B^2$ is optionally substituted with one or more groups independently selected from halogen, $(C_1-C_6)$alkyl, —$O(C_1-C_6)$alkyl, —$O(C_1-C_6)$alkyl-$O(C_1-C_6)$alkyl, $(C_3-C_7)$cycloalkyl, $(C_1-C_6)$haloalkyl, —CN, and 6-membered heteroaryl, wherein any 6-membered heteroaryl is optionally substituted with one or more $(C_1-C_6)$alkyl or $(C_1-C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1-C_6)$alkyl, —$O(C_1-C_6)$alkyl, $(C_3-C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1-C_6)$alkyl, $(C_1-C_6)$haloalkyl, —$O(C_1-C_6)$alkyl, and —$O(C_1-C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1-C_6)$alkyl and $(C_1-C_6)$haloalkyl;

$R^4$ is H, $(C_1-C_6)$alkyl or $(C_1-C_6)$haloalkyl;

$R^{5a}$ is a phenyl, 5-membered heteroaryl, 6-membered heteroaryl, 4, 5, 6 or 7-membered heterocycle or $(C_3-C_8)$ cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —$O(C_1-C_6)$alkyl, —$O(C_1-C_6)$alkyl-$O(C_1-C_6)$alkyl, —$O(C_1-C_6)$haloalkyl, —$S(C_1-C_6)$alkyl, —$S(C_1-C_6)$haloalkyl, oxo, and —O—$(C_1-C_2)$alkyl-O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, —$O(C_1-C_6)$alkyl, —$O(C_1-C_6)$haloalkyl, —OH, —$S(C_1-C_6)$alkyl, —$S(C_1-C_6)$haloalkyl, and $NR^6_2$, and wherein any 5-membered heterocycle of $R^{5b}$ is substituted with one or more groups independently selected from halogen, $(C_1-C_6)$alkyl, $(C_1-C_6)$haloalkyl, —CN, $(C_3-C_7)$cycloalkyl, —$O(C_1-C_6)$alkyl, —$O(C_1-C_6)$haloalkyl, —$S(C_1-C_6)$alkyl and —$S(C_1-C_6)$haloalkyl; and $R^6$ is H or $(C_1-C_6)$alkyl;

or a pharmaceutically acceptable salt thereof.

EE61. A compound of formula II:

II

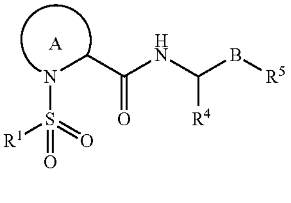

wherein:

B is $B^2$, $B^3$, or $B^5$;

(1) the A group is:

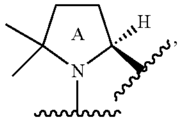

B is $B^2$ and $R^5$ is $R^{5b}$;

(2) the A group is:

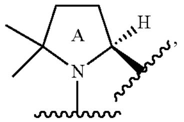

B is $B^3$ and $R^5$ is $R^{5a}$;

(3) the A group is:

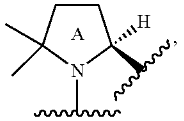

B is $B^5$ and $R^5$ is $R^{5a}$;

$B^2$ is a pyridinyl, wherein any pyridinyl of $B^2$ is optionally substituted with one or more groups independently selected from halogen, $(C_1-C_6)$alkyl, —O$(C_1-C_6)$alkyl, —O$(C_1-C_6)$alkyl-O$(C_1-C_6)$alkyl, $(C_3-C_7)$cycloalkyl, $(C_1-C_6)$haloalkyl, —CN, and 6-membered heteroaryl, wherein any 6-membered heteroaryl is optionally substituted with one or more $(C_1-C_6)$alkyl or $(C_1-C_6)$haloalkyl;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1-C_6)$alkyl, —O$(C_1-C_6)$alkyl, $(C_3-C_7)$cycloalkyl, —CN, and $NR^6{}_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$B^5$ is a phenyl optionally substituted with one or more groups independently selected from —CN, halogen, $(C_1-C_6)$alkyl, $(C_1-C_6)$haloalkyl, —O$(C_1-C_6)$alkyl, and —O$(C_1-C_6)$haloalkyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1-C_6)$alkyl and $(C_1-C_6)$haloalkyl;

$R^4$ is H, $(C_1-C_6)$alkyl or $(C_1-C_6)$haloalkyl;

$R^{5a}$ is a phenyl, 5-membered heteroaryl, 6-membered heteroaryl, 4, 5, 6 or 7-membered heterocycle or $(C_3-C_8)$cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$alkyl-O$(C_1-C_6)$alkyl, —O$(C_1-C_6)$haloalkyl, —S$(C_1-C_6)$alkyl, —S$(C_1-C_6)$haloalkyl, oxo, and —O—$(C_1-C_2)$—O— optionally substituted with one or more halogen;

$R^{5b}$ is a phenyl, 5-membered heteroaryl, 6-membered heteroaryl or 4, 5, 6 or 7-membered heterocycle, wherein any phenyl, 5-membered heteroaryl, 6-membered heteroaryl or 4, 6, 7, or 8-membered heterocycle of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, —O$(C_1-C_6)$alkyl, —O$(C_1-C_6)$haloalkyl, —OH, —S$(C_1-C_6)$alkyl, —S$(C_1-C_6)$haloalkyl, and $NR^6{}_2$, and wherein any 5-membered heterocycle of $R^{5b}$ is substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$haloalkyl, —S$(C_1-C_6)$alkyl and —S$(C_1-C_6)$haloalkyl; and $R^6$ is H or $(C_1-C_6)$alkyl;

or a pharmaceutically acceptable salt thereof.

EE62. The compound of any one of embodiments EE53-EE61, wherein:

$B^2$ is pyridinyl, wherein any pyridinyl of $B^2$ is optionally substituted with one or more groups independently selected from halogen, $(C_1-C_6)$alkyl, —O$(C_1-C_6)$alkyl, —O$(C_1-C_6)$alkyl-O$(C_1-C_6)$alkyl, $(C_3-C_7)$cycloalkyl, $(C_1-C_6)$haloalkyl, —CN, and 6-membered heteroaryl, wherein any 6-membered heteroaryl is optionally substituted with $(C_1-C_6)$alkyl or $(C_1-C_6)$haloalkyl;

$B^3$ is a pyrimidinyl, wherein any pyrimidinyl of $B^3$ is optionally substituted with one or more groups independently selected from halogen, $(C_1-C_6)$alkyl, —O$(C_1-C_6)$alkyl, $(C_3-C_7)$cycloalkyl, —CN, and $NR^6{}_2$;

$B^5$ is a phenyl optionally substituted with one or more groups independently selected from —CN, halogen, $(C_1-C_6)$alkyl, $(C_1-C_6)$haloalkyl, —O$(C_1-C_6)$alkyl, and —O$(C_1-C_6)$haloalkyl;

$R^{5a}$ is phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl wherein any phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —O$(C_1-C_6)$alkyl, —O$(C_1-C_6)$alkyl-O$(C_1-C_6)$alkyl, —O$(C_1-C_6)$haloalkyl, —S$(C_1-C_6)$alkyl, —S$(C_1-C_6)$haloalkyl, oxo, and —O—$(C_1-C_2)$—O— optionally substituted with one or more halogen;

$R^{5b}$ is phenyl, pyridinyl, piperidinyl, pyrimidinyl, pyridazinyl, pyrazinyl, 6-azaspiro[2.5]octan-6-yl, or 8-azabicyclo[3.2.1]octan-8-yl, wherein any phenyl, pyridinyl, piperidinyl, pyrimidinyl, pyridazinyl, pyrazinyl, 6-azaspiro[2.5]octan-6-yl, or 8-azabicyclo[3.2.1]octan-8-yl of $R^{5b}$ is optionally substituted with one or more groups independently selected from halogen, $(C_1-C_6)$alkyl, $(C_1-C_6)$haloalkyl, —CN, $(C_3-C_7)$cycloalkyl optionally substituted with one or more halogen, —O$(C_1-C_6)$alkyl, —O$(C_1-C_6)$haloalkyl, —OH, —S$(C_1-C_6)$alkyl, —S$(C_1-C_6)$haloalkyl, and $NR^6{}_2$;

$R^1$ is a phenyl or thiophenyl, wherein any phenyl or thiophenyl of $R^1$ is optionally substituted with one or more groups independently selected from fluoro, chloro and —CN; and $R^4$ is H.

EE63. The compound of any one of embodiments EE53-EE62, wherein $R^{5a}$ is
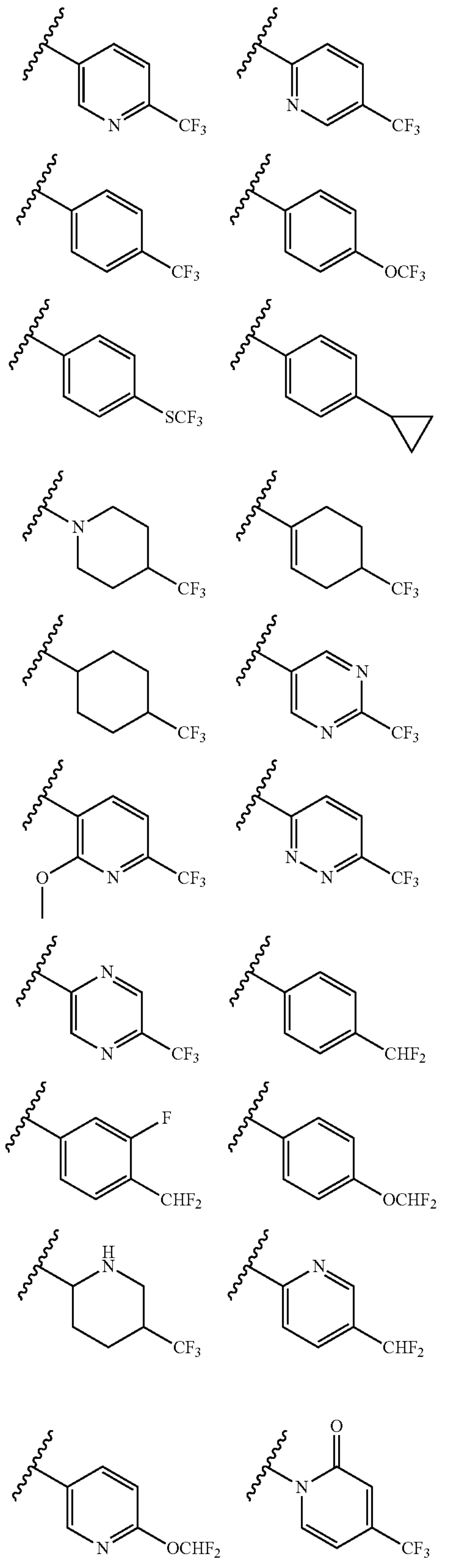
-continued
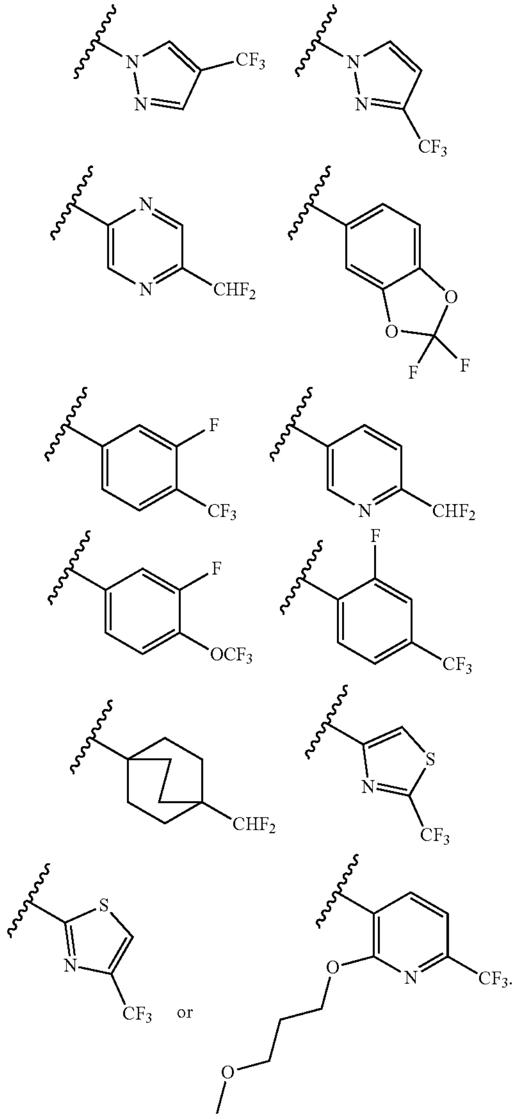
or
EE64. The compound of any one of embodiments EE53-EE62, wherein $R^{5b}$ is
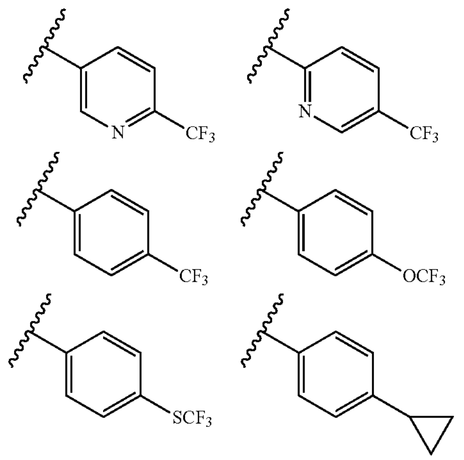

-continued

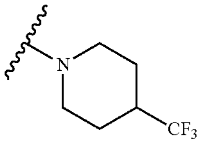
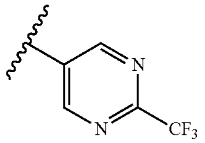
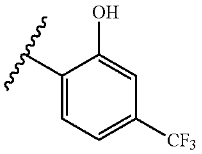
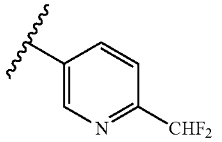
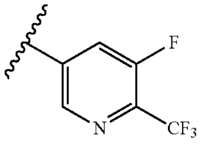
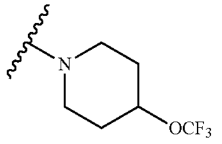
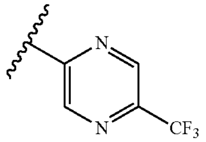
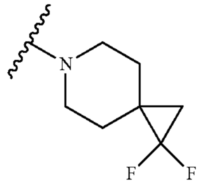
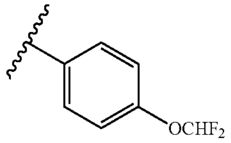
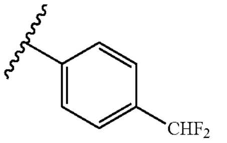
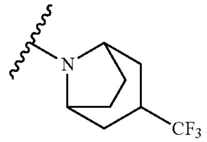
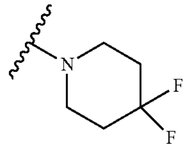
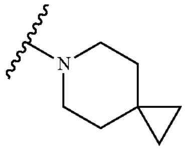
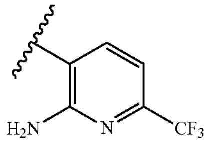 or

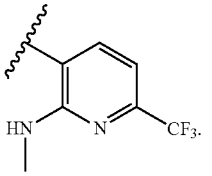

EE65. A compound of formula II:

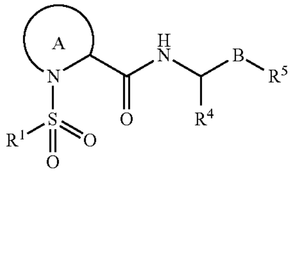

II wherein:

B is $B^3$;

the A group is:

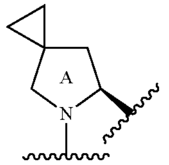 or 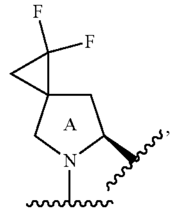

B is $B^3$ and $R^5$ is $R^{5a}$;

$B^3$ is a 5-membered heteroaryl comprising 2 or 3 nitrogen atoms in the ring or a 6-membered heteroaryl comprising 2 nitrogen atoms in the ring, wherein any 5-membered heteroaryl or 6-membered heteroaryl of $B^3$ is optionally substituted with one or more groups independently selected from halogen, $(C_1-C_6)$alkyl, —$O(C_1-C_6)$alkyl, $(C_3-C_7)$cycloalkyl, —CN, and $NR^6_2$, and wherein when $B^3$ is pyrimidinyl which is attached to the remainder of formula II at the 4 and 6 positions of the pyrimidinyl, then $R^{5a}$ is not pyrrolidinyl or substituted pyrrolidinyl;

$R^1$ is a phenyl, 5-membered heteroaryl or 6-membered heteroaryl, wherein any phenyl, 5-membered heteroaryl or 6-membered heteroaryl of $R^1$ is optionally substituted with one or more groups independently selected from halogen, —CN, $(C_1-C_6)$alkyl and $(C_1-C_6)$haloalkyl;

$R^4$ is H, $(C_1-C_6)$alkyl or $(C_1-C_6)$haloalkyl; and $R^{5a}$ is a phenyl, 5-membered heteroaryl, 6-membered heteroaryl, 4, 5, 6 or 7-membered heterocycle or $(C_3-C_8)$ cycloalkyl, wherein any phenyl, 5-membered heteroaryl, 6-membered heteroaryl, 4, 5, 6 or 7-membered heterocycle or $(C_3-C_8)$cycloalkyl of $R^{5a}$ is optionally substituted with one or more groups independently selected from halogen, $(C_1-C_6)$alkyl, $(C_1-C_6)$haloalkyl, —CN, $(C_3-C_7)$cycloalkyl, —$O(C_1-C_6)$alkyl, —$O(C_1-C_6)$alkyl-$O(C_1-C_6)$alkyl, —$O(C_1-C_6)$haloalkyl, —$S(C_1-C_6)$alkyl, —$S(C_1-C_6)$haloalkyl, oxo, and —O—$(C_1-C_2)$alkyl-O— optionally substituted with one or more halogen;

or a pharmaceutically acceptable salt thereof.

EE66. The compound of embodiment EE65, wherein:

$B^3$ is a pyrimidinyl, wherein any pyrimidinyl of $B^3$ is optionally substituted with one or more groups independently selected from halogen, $(C_1-C_6)$alkyl, —$O(C_1-C_6)$ alkyl, $(C_3-C_7)$cycloalkyl, —CN, and $NR^6_2$; and $R^{5a}$ is phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl wherein any phenyl, pyridinyl, piperidinyl, pyrimidinyl, pyridazinyl, pyrazinyl, pyrazolyl, thiazolyl, cyclohexenyl, cyclohexanyl, or bicyclo[2.2.2]octanyl of $R^{5a}$ is optionally substituted with one or more groups independently selected from halogen, $(C_1-C_6)$ alkyl, $(C_1-C_6)$haloalkyl, —CN, $(C_3-C_7)$cycloalkyl, —$O(C_1-C_6)$alkyl, —$O(C_1-C_6)$alkyl-$O(C_1-C_6)$alkyl, —$O(C_1-C_6)$haloalkyl, —$S(C_1-C_6)$alkyl, —$S(C_1-C_6)$haloalkyl, oxo, and —O—$(C_1-C_2)$—Oalkyl- optionally substituted with one or more halogen.

EE67. The compound of embodiment EE66, wherein $R^{5a}$ is

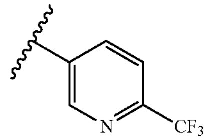
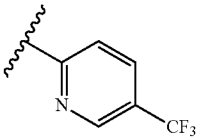

-continued

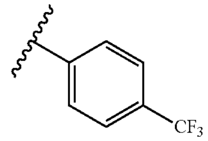
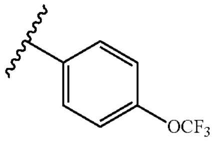
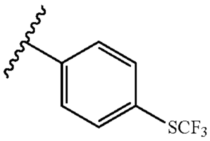
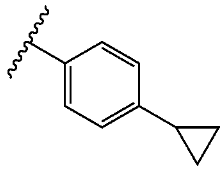
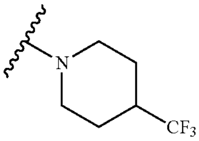
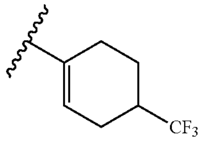
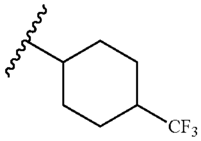
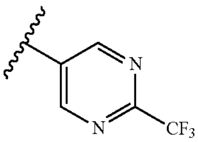
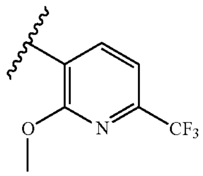
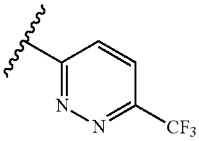
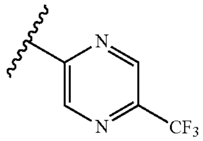
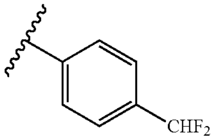
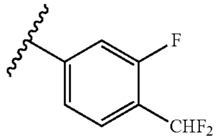
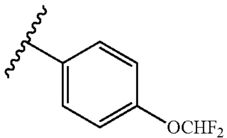
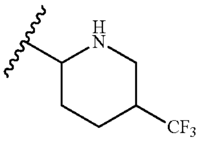
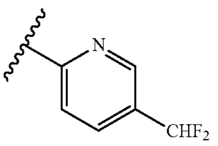
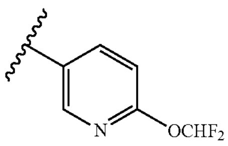
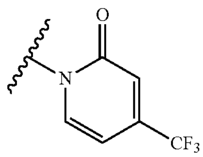
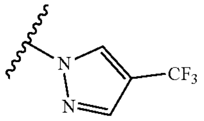
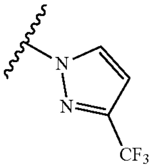

-continued

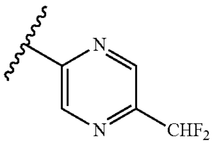
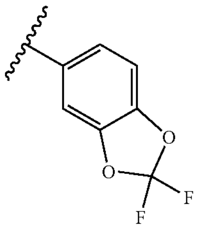
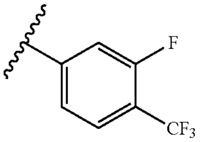
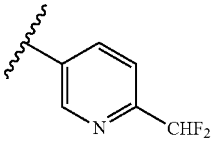
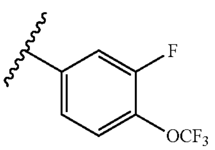
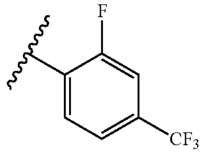
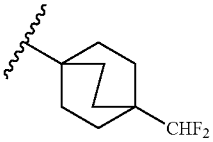
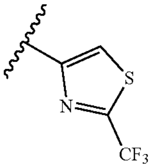
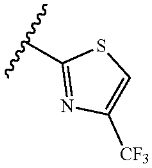
or
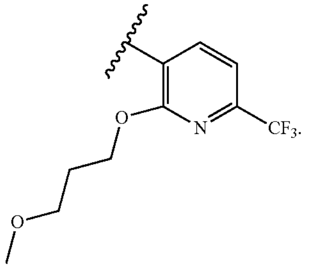

EE68. The compound of any one of embodiments EE1-EE30 wherein one $R^{3e}$ group is halogen, —CN or $(C_1$-$C_6)$alkyl and the remaining $R^{3e}$ groups are independently selected from H, $(C_1$-$C_6)$alkyl and $(C_1$-$C_6)$haloalkyl.

EE69. The compound of any one of embodiments EE1-EE30 wherein one $R^{3e}$ group is halogen or $(C_1$-$C_6)$alkyl and the remaining $R^{3e}$ groups are independently selected from H and $(C_1$-$C_6)$alkyl.

In another embodiment of the invention, the compounds of Formula I or II are isotopically-labeled by having one or more atoms therein replaced by an atom having a different atomic mass or mass number. Such isotopically-labeled (i.e., radiolabelled) compounds of Formula I or II are considered to be within the scope of this invention. Examples of isotopes that can be incorporated into the compounds of Formula I or II include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of Formula I or II, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of Formula I or II can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula I or II can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to Formula I or II and a pharmaceutically acceptable carrier.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, $—P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the invention also provides for compositions and medicaments comprising a compound of Formula I or II or and embodiment thereof and at least one pharmaceutically acceptable carrier. The compositions of the invention can be used to selectively inhibit TRPA1 in patients (e.g., humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions or medicaments comprising a compound of Formula I or II or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I or II or its embodiments and compositions comprising compounds of Formula I or II or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of Formula I or II or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of Formula I or II or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include Sustained-release preparations of a compound of the invention (e.g., compound of Formula I or II or an embodiment thereof) can be prepared. Suitable examples of sustained-release preparations include semipermeable matrices of solid hydrophobic polymers containing a compound of Formula I or II or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of Formula I or II or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I or II (or an embodiment thereof) is formulated in an acetate buffer, at pH 5. In another embodiment, the compounds of Formula I or II or an embodiment thereof are sterile. The compound may be stored, for example, as a solid or amorphous composition, as a lyophilized formulation or as an aqueous solution.

Formulations of a compound of the invention (e.g., compound of Formula I or II or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I or II or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of Formula I or II (or an embodiment thereof) to traverse the blood-brain barrier. Certain neurodegenerative diseases are associated with an increase in permeability of the blood-brain barrier, such that a compound of Formula I or II (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of Formula I or II (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford. Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of Formula I or II (or an embodiment thereof) across the blood-brain barrier include, but are not limited to, encapsulating the a compound of Formula I or II (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of Formula I or II (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of Formula I or II (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of Formula I or II (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA1 activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn (Bolcskei et al., *Pain* 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, G1 tract disorders, cystitis, interstitial cystitis, cholecystitis, urinary tract infection, urethral colic, renal colic, pharyngitis, cold sores, stomatitis, external otitis, otitis media (Chan et al., *Lancet,* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J Pharmacal Exp Ther.,* 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. *J. Pharmacal. Exp. Ther.* 2003, 306, 387; Walker, K. M. et al., *J. Pharmacal. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., *Br. J. Pharmacal.* 2004, 141, 1313-20; Yiangou, Y. et al., *Lancet*2001, 357, 1338-39; Kimball, E. S. etal., *Neurogastroenterol. Motif.,* 2004, 16, 811), osteoarthritis (Szabo, A. et al., *J. Pharmacal. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

For example, compounds of the invention can be administered to treat tracheobronchial and diaphragmatic dysfunctions including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacal.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., *J Neurosci.,* 2004, 24, 11253-11263), interstitial cystitis (Sculptoreanu, A. et al., *Neurosci Lett.,* 2005, 381, 42-46), inflammatory prostate disease, prostatitis (Sanchez, M. et al., *Eur J Pharmacal.,* 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound according to Formula I or II (e.g., a compound as described in any one of E1-E50, E1A-E33A, E1B-E24B, E1C-E29C, E1D-E26D, E1E-E33E, Table 1, Table 2, or EE1-EE67 above) to a subject in need thereof.

In another embodiment, the invention provides for a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above) or a pharmaceutically acceptable salt thereof for modulating TRPA1 activity.

In another embodiment, the invention provides for a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above), or a pharmaceutically acceptable salt thereof for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to Formula I or II (e.g., a compound as described in any one of E1-E50, E1A-E33A, E1B-E24B, E1C-E29C, E1D-E26D, E1E-E33E, Table 1, Table 2, or EE1-EE67 above) to a subject in need thereof.

In another embodiment, the invention provides for a compound of Formula I or II (e.g., a compound as described in any one of E1-E50, E1A-E33A, E1B-E24B, E1D-E26D, E1E-E33E, Table 1, Table 2, or EE1-EE67 above) or a pharmaceutically acceptable salt thereof for the treatment or prophylaxis of a respiratory disorder.

In another embodiment, the invention provides for the use of a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above) or a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above) or a pharmaceutically acceptable salt thereof to the mammal.

In another embodiment, the invention provides for a method for modulating TRPA1 activity, comprising contacting TRPA1 with a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above) or a salt thereof.

In another embodiment, the invention provides for a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above) or a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above) or a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound of Formula I or II (e.g., a compound as described in any one of E1-E50, E1A-E33A, E1B-E24B, E1C-E29C, E1D-E26D, E1E-E33E, Table 1, Table 2, or EE1-EE67 above) or a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder.

In one aspect, compounds of the invention demonstrate surprisingly superior stability in in vivo rat pharmacokinetic (PK) studies over related compounds. Monofluorination, specifically at the 4-position of the proline ring, enhances the stability of the compounds, such that the compounds do not clear as rapidly from the blood as other related compounds. For example, a monofluorinated compound at the proline 3-position, (2S,4R)-4-fluoro-1-(4-fluorophenyl)sulfonyl-N-[[6-[6-(trifluoromethyl)-3-pyridyl]pyrimidin-4-yl]methyl]pyrrolidine-2-carboxamide, possess the highest stability (slowest clearance) over related difluorinated, non-fluorinated, and 3-fluorinated compounds as shown below:

| Structure | Name | Rat PK Clp (ml/min/kg) |
|---|---|---|
| 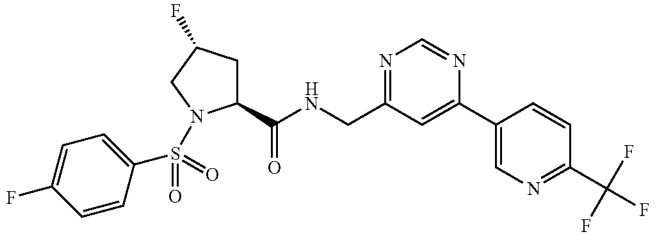 [SMILES: O=C(NCc1cc(-c2ccc(C(F)(F)F)nc2)ncn1)[C@@H]1C[C@@H](F)CN1S(=O)(=O)c1ccc(F)cc1] | (2S,4R)-4-fluoro-1-(4-fluorophenyl)sulfonyl-N-[[6-[6-(trifluoromethyl)-3-pyridyl]pyrimidin-4-yl]methyl]pyrrolidine-2-carboxamide | 15 |
| 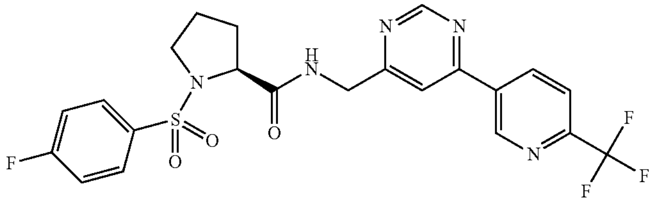 [SMILES: O=C(NCc1cc(-c2ccc(C(F)(F)F)nc2)ncn1)[C@@H]1CCCN1S(=O)(=O)c1ccc(F)cc1] | (2S)-1-(4-fluorophenyl)sulfonyl-N-[[6-[6-(trifluoromethyl)-3-pyridyl]pyrimidin-4-yl]methyl]pyrrolidine-2-carboxamide | 98 |
| 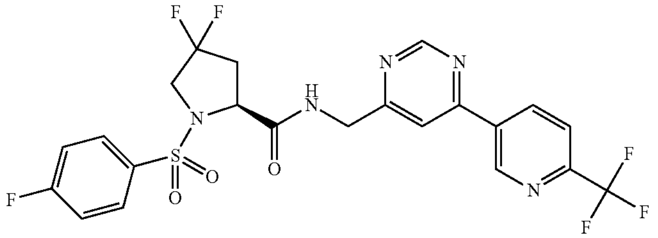 [SMILES: O=C(NCc1cc(-c2ccc(C(F)(F)F)nc2)ncn1)[C@@H]1CC(F)(F)CN1S(=O)(=O)c1ccc(F)cc1] | (2S)-4,4-difluoro-1-(4-fluorophenyl)sulfonyl-N-[[6-[6-(trifluoromethyl)-3-pyridyl]pyrimidin-4-yl]methyl]pyrrolidine-2-carboxamide | 30 |
| 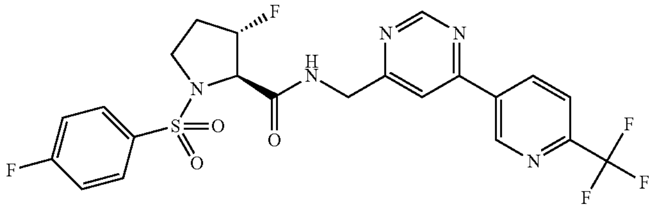 [SMILES: O=C(NCc1cc(-c2ccc(C(F)(F)F)nc2)ncn1)[C@@H]1[C@@H](F)CCN1S(=O)(=O)c1ccc(F)cc1] | (2R,3S)-3-fluoro-1-(4-fluorophenyl)sulfonyl-N-[[6-[6-(trifluoromethyl)-3-pyridyl]pyrimidin-4-yl]methyl]pyrrolidine-2-carboxamide | 101 |

Other representative compounds, commensurate in scope of the present invention, demonstrate similar surprisingly enhanced PK stability as (2S,4R)-4-fluoro-1-(4-fluorophenyl)sulfonyl-N-[[6-[6-(trifluoromethyl)-3-pyridyl]pyrimidin-4-yl]methyl]pyrrolidine-2-carboxamide, shown below:

| Structure | Name | Rat PK Clp (ml/min/kg) |
|---|---|---|
| 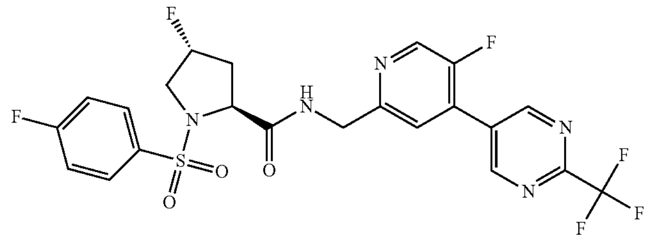 [SMILES: O=C(NCc1cc(-c2cnc(C(F)(F)F)nc2)c(F)cn1)[C@@H]1C[C@@H](F)CN1S(=O)(=O)c1ccc(F)cc1] | (2S,4R)-4-fluoro-1-(4-fluorophenyl)sulfonyl-N-[[5-fluoro-4-[2-(trifluoromethyl)pyrimidin-5-yl]-2-pyridyl]methyl]pyrrolidine-2-carboxamide | 5.9 |

-continued

| Structure | Name | Rat PK Clp (ml/min/kg) |
|---|---|---|
| 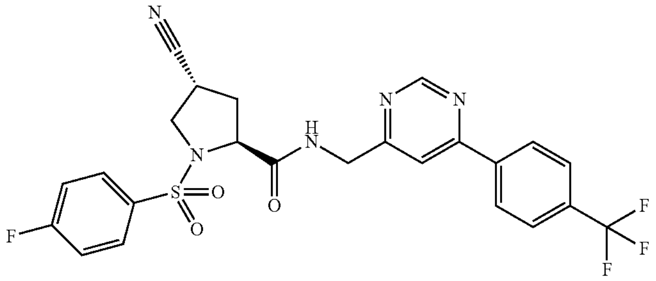 [SMILES: N#C[C@@H]1C[C@@H](C(=O)NCc2cc(-c3ccc(C(F)(F)F)cc3)ncn2)N(S(=O)(=O)c2ccc(F)cc2)C1] | (2S,4R)-4-cyano-1-(4-fluorophenyl)sulfonyl-N-[[6-[4-(trifluoromethyl)phenyl]pyrimidin-4-yl]methyl]pyrrolidine-2-carboxamide | 7.6 |
| 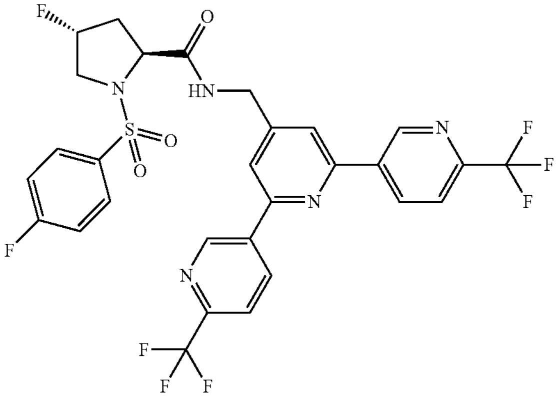 [SMILES: O=C(NCc1cc(-c2ccc(C(F)(F)F)nc2)nc(-c2ccc(C(F)(F)F)nc2)c1)[C@@H]1C[C@@H](F)CN1S(=O)(=O)c1ccc(F)cc1] | (2S,4R)-N-[[2,6-bis[6-(trifluoromethyl)-3-pyridyl]-4-pyridyl]methyl]-4-fluoro-1-(4-fluorophenyl)sulfonyl-pyrrolidine-2-carboxamide | 9.1 |
| 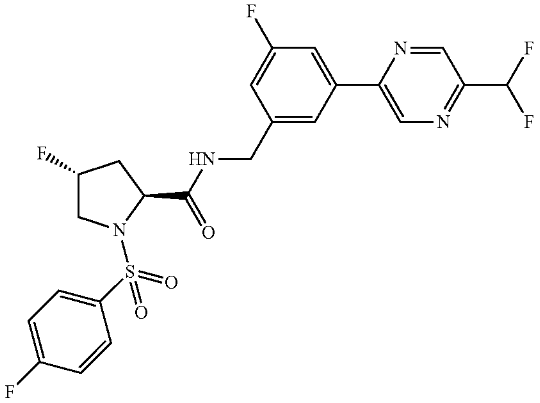 [SMILES: O=C(NCc1cc(F)cc(-c2cnc(C(F)F)cn2)c1)[C@@H]1C[C@@H](F)CN1S(=O)(=O)c1ccc(F)cc1] | (2S,4R)-N-[[3-[5-(difluoromethyl)pyrazin-2-yl]-5-fluoro-phenyl]methyl]4-fluoro-1-(4-fluorophenyl)sulfonyl-pyrrolidine-2-carboxamide | 9.9 |
| 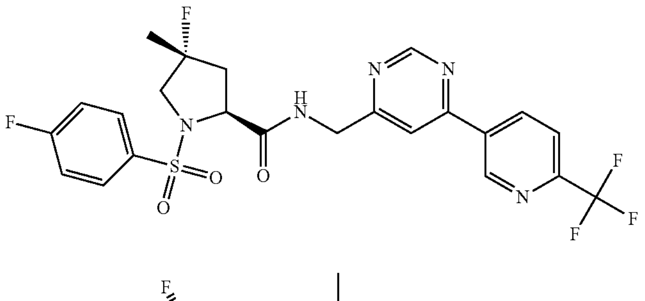 | (2S,4R)-4-fluoro-1-(4-fluorophenyl)sulfonyl-4-methyl-N-[[6-[6-(trifluoromethyl)-3-pyridyl]pyrimidin-4-yl]methyl]pyrrolidine-2-carboxamide | 11.3 |
| 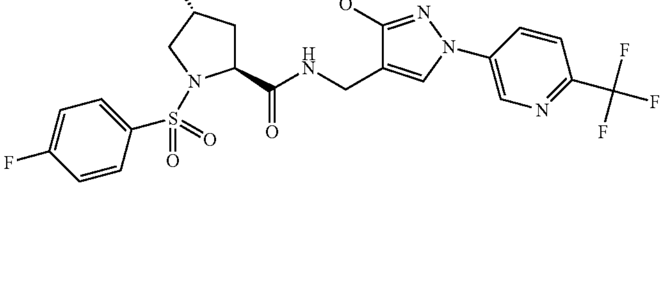 | (2S,4R)-4-fluoro-1-(4-fluorophenyl)sulfonyl-N-[[3-methoxy-1-[6-(trifluoromethyl)-3-pyridyl]pyrazol-4-yl]methyl]pyrrolidine-2-carboxamide | 13 |

-continued

| Structure | Name | Rat PK Clp (ml/min/kg) |
|---|---|---|
| 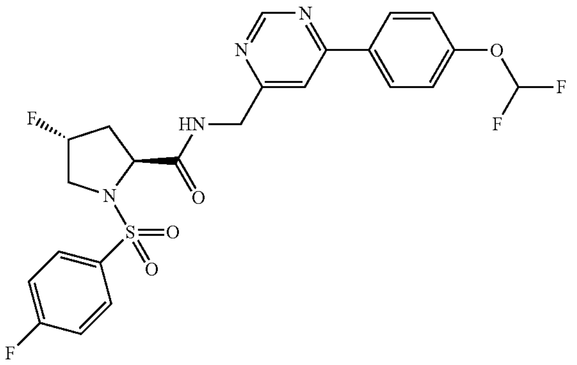 [SMILES: O=C(NCc1cc(-c2ccc(OC(F)F)cc2)ncn1)[C@@H]1C[C@@H](F)CN1S(=O)(=O)c1ccc(F)cc1] | (2S,4R)-N-[[6-[4-(difluoromethoxy)phenyl]pyrimidin-4-yl]methyl]-4-fluoro-1-(4-fluorophenyl)sulfonyl-pyrrolidine-2-carboxamide | 13.2 |
| 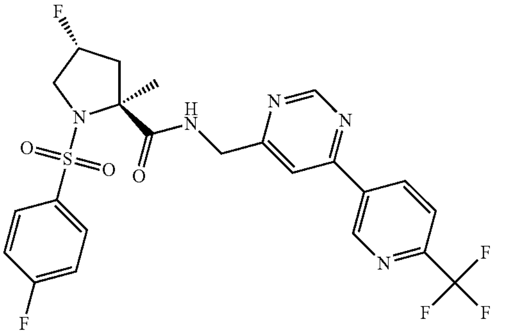 [SMILES: C[C@@]1(C(=O)NCc2cc(-c3ccc(C(F)(F)F)nc3)ncn2)C[C@@H](F)CN1S(=O)(=O)c1ccc(F)cc1] | (2S,4R)-4-fluoro-1-(4-fluorophenyl)sulfonyl-2-methyl-N-[[6-[6-(trifluoromethyl)-3-pyridyl]pyrimidin-4-yl]methyl]pyrrolidine-2-carboxamide | 15 |
| 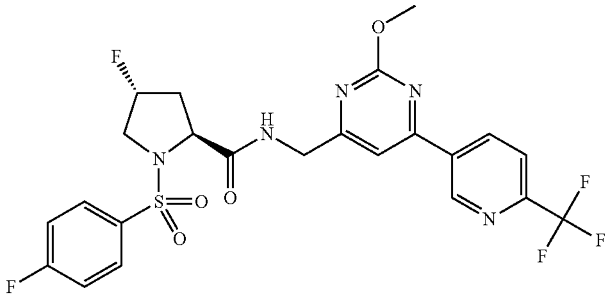 [SMILES: COc1nc(CNC(=O)[C@@H]2C[C@@H](F)CN2S(=O)(=O)c2ccc(F)cc2)cc(-c2ccc(C(F)(F)F)nc2)n1] | (2S,4R)-4-fluoro-1-(4-fluorophenyl)sulfonyl-N-[[2-methoxy-6-[6-(trifluoromethyl)-3-pyridyl]pyrimidin-4-yl]methyl]pyrrolidine-2-carboxamide | 16.5 |

Combination Therapy

The compounds of the invention may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with other therapeutic agents, including, but not limited to:

- opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;
- non-opiate analgesics, e.g., acetomeniphen, salicylates (e.g., aspirin);
- nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;
- anticonvulsants, e.g., carbamazepine, oxcarbazepine, lamotrigine, valproate, topiramate, gabapentin and pregabalin;
- antidepressants such as tricyclic antidepressants, e.g., amitriptyline, clomipramine, despramine, imipramine and nortriptyline;
- COX-2 selective inhibitors, e.g., celecoxib, rofecoxib, parecoxib, valdecoxib, deracoxib, etoricoxib, and lumiracoxib;
- alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (□R, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT3 antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotine) analgesics;

alpha-2-delta ligands;

prostaglandin E2 subtype antagonists;

leukotriene B4 antagonists;

5-lipoxygenase inhibitors; and

5-HT3 antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In another embodiment, provided is an invention as hereinbefore described.

General Preparation of Compounds of Formula I or II

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention can be made according methods known in art. In one aspect, compounds of the invention can be made as outlined in Schemes 1-4 herein. In Schemes 1-4, the variable A, B, $R^1$, $R^4$, $R^{z1}$ and $R^5$ have the meaning as defined for Formula I or II. R is an non-interfering group and Hal represents halogen.

Scheme 1

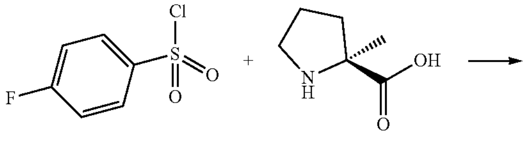

-continued

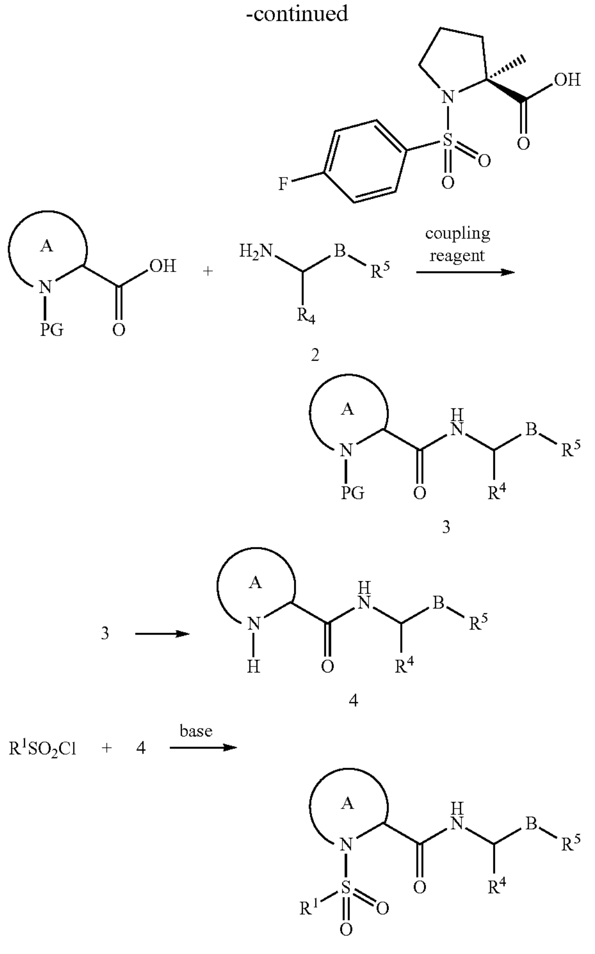

2

3

4

1

According to Scheme 1, an N-PG-substituted carboxylic acid, where the amine may be protected using well known protecting groups (PG) as described in "Protective Groups in Organic Synthesis" [T. W. Greene and P. G. M. Wuts, $3^{rd}$ Edition, John Wiley and Sons, N.Y. 1999], may be reacted with an amine of formula 2 to yield an amide of formula 3. This transformation is well-documented in the chemical literature and familiar to those skilled in the art. It proceeds under various reactions conditions, for example, the carboxylic acid and amine can be combined in an aprotic solvent such as N,N-dimethylformamide and treated with any number of peptide coupling reagents such as 2-(1H-7-azabenzotriazol-1-yl)-1,1,3,3-tetramethyl uronium hexafluorophosphate methanaminium or bromo-tris-pyrrolidino phosphoniumhexafluorophosphate. A large variety and number of N-PG-substituted carboxylic acids may be purchased from commercial sources. Examples include (2S,4R)-1-(tert-butoxycarbonyl)-4-fluoropyrrolidine-2-carboxylic acid, 1-(tert-butoxycarbonyl)-2-methylazetidine-2-carboxylic acid, and (2S,4S)-1-(tert-butoxycarbonyl)-4-fluoropyrrolidine-2-carboxylic acid. The amine coupling partner of formula 2 in Scheme 1 can be purchased or made from the methods described in Scheme 3. An intermediate of formula 4 can then be made by a variety of well-established methods. For example, an intermediate of formula 3 can be treated with hydrochloric acid, trifluoroacetic acid, or other reagent to provide an intermediate of formula 4. An intermediate of formula 4 can then be coupled with a $R^1$-substituted sulfonyl chloride by a variety of well-established methods to yield compounds of formula 1. For example, the sulfonyl chloride and amine can be combined in an aprotic solvent such as dichloromethane and treated with an excess of base such as triethylamine or potassium carbonate. Numerous sulfonyl chlorides can be obtained from commercial sources including benzenesulfonyl chloride, 4-fluorobenzenesulfonyl chloride, 3,4-dichlorobenzenesulfonyl chloride, pyridine-3-sulfonyl chloride, 2-chloropyridine-5-sulfonyl chloride, 3-cyanobenzenesulfonyl chloride and 2-thiazolesulfonyl chloride.

Scheme 2

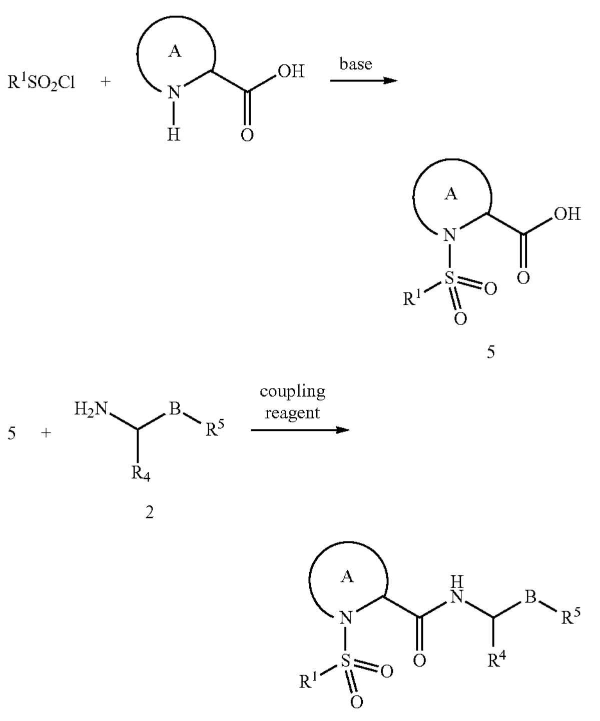

5

2

1

Alternatively, compounds of the invention may be made according to the processes outlined in Scheme 2. According to Scheme 2, sulfonamides of formula 5 can be readily prepared according to well established methods by combining sulfonyl chlorides containing $R^1$ with amino acids. For example, sulfonyl chloride may be added to a solution of the amino acid and an organic base such as triethylamine in a polar, aprotic solvent such as THF. Alternatively, the reagents may be combined in a moderately basic solvent such as pyridine. A large variety and number of amino acids may be purchased from commercial sources. An intermediate of formula 5 may then be reacted with an amine of formula 2. This transformation is well-documented in the chemical literature and familiar to those skilled in the art. It proceeds under various reactions conditions, for example, the carboxylic acid and amine can be combined in an aprotic solvent such as N,N-dimethylformamide and treated with any number of peptide coupling reagents such as 2-(1H-7-azabenzotriazol-1-yl)-1,1,3,3-tetramethyl uronium hexafluorophosphate methanaminium or bromo-tris-pyrrolidino phosphoniumhexafluorophosphate.

Scheme 3

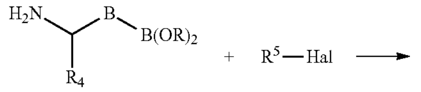

2a

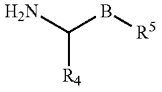

2

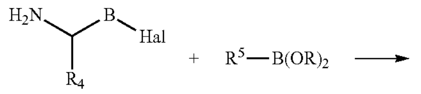

2b

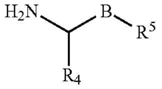

2

As shown in Scheme 3, intermediates of the general structure 2 may be synthesized by well-established methods. For example, the bond between the central aromatic ring and $R^5$ may be created by a number of efficient metal-catalyzed coupling methods such as method that has come to be known as the Suzuki coupling. Under this scheme either of the two groups to be linked may be boronic acid or ester or halogen/pseudo-halogen. The other coupling partner would then be halogen/pseudo-halogen or boronic acid/ester respectively. Conditions for effecting this coupling include heating the boronic acid and aryl halide in a polar solvent mixture such as dioxane/water in the presence of an organic or inorganic base such as triethylamine or potassium carbonate and using a palladium catalyst such as tetrakis [triphenylphosphine] palladium or palladium (II) acetate.

Numerous starting materials of formula 2a and 2b may be purchased commercially. For example, 2-chloro-6-(trifluoromethoxy)-4-pyridinemethanamine, 2-bromo-4-pyridinemethanamine hydrochloride, (3,6-dichloropyridazin-4-yl)methanamine, 4-aminomethyl-6-chloropyrimidine, (3-aminomethylphenyl)boronic acid hydrochloride, 5-(aminomethyl)-2-fluorophenylboronic acid, HCl, [5-(aminomethyl)-2-methylphenyl]boronic acid, (5-bromopyridin-3-yl) methanamine, 3-(aminomethyl)-5-bromopyridin-2-ol, (5-bromo-2-chloro-pyridin-3-yl)-methanamine hydrochloride, (4-bromopyridin-2-yl)methanamine, (4-bromo-6-(trifluoromethyl)pyridin-2-yl)methanamine, 2-bromo-4-pyridinethylamine, (2-bromo-5-chloropyridin-4-yl)methanamine.

Scheme 4

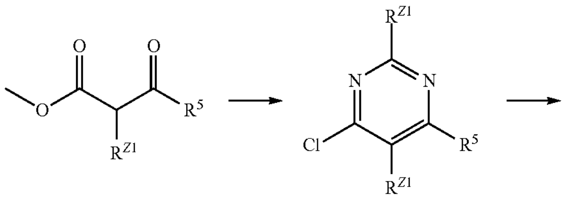

-continued

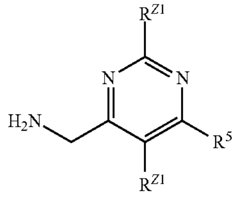

As shown in Scheme 4, compounds of the invention in which B is pyrimidinyl may be made by known methods for synthesizing pyrimidines. For example, they may be made by a process outlined in Scheme 4 in which an arylketoester is reacted with an amidine or an appropriate equivalent to give 4-arylpyrimidinones, wherein $R^{Z1}$ and $R^5$ have values described herein for compounds of formula I and II. This intermediate could then by chlorinated under established conditions such as heating in phosphorus oxychloride. The chloride could then be converted to the nitrile by a number of well-known methods and then reduced to the aminomethyl group. For example, the chloropyrimidine could be heated with potassium cyanide in a polar solvent such as DMSO to yield cyanopyrimidine. Alternatively, the chloropyrimidine could be treated with zinc cyanide and a catalytic amount of a transition metal catalyst such as tetrakis[triphenylphosphine]palladium in a polar solvent such as N-methylpyrrolidinone or THF. The nitrile could be subsequently reduced by dissolving it in a polar solvent such as ethanol and treated with a catalytic amount of metal catalyst such as palladium on carbon and shaken under a hydrogen atmosphere or pressure, for example, 60 psi.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography. Unless otherwise noted, flash chromatography was carried out using pre-packed silica gel cartridges from either ISCO or SiliCycle on an ISCO CombiFlash® chromatography instrument (from Teledyne Isco, Inc.). Reverse-phase preparative HPLC was performed using a (1) Polaris C-18 5 μM column (50×21 mm), or (2) XBridge Prep C-18 OBD 5 μM column (19×150 mm). Supercritical fluid chromatography was carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 μM, (2) 4.6 cm×5 cm, 5 μM, or (3) 15 cm×21.2 mm, 5 μM.

Mass spectrometry (MS) was performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

Example 1

Preparation of (S)-1-(4-fluorophenylsulfonyl)-2-methyl-N-((6-(6-(trifluoromethyl)pyridin-3-yl)pyrimidin-4-yl)methyl)pyrrolidine-2-carboxamide

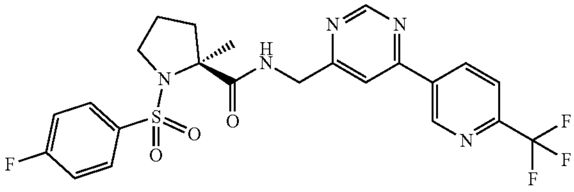

(S)-1-(4-fluorophenylsulfonyl)-2-methyl-N-((6-(6-(trifluoromethyl)pyridin-3-yl)pyrimidin-4-yl)methyl)pyrrolidine-2-carboxamide

Step 1: Preparation of (S)-1-(4-fluorophenylsulfonyl)-2-methylpyrrolidine-2-carboxylic acid

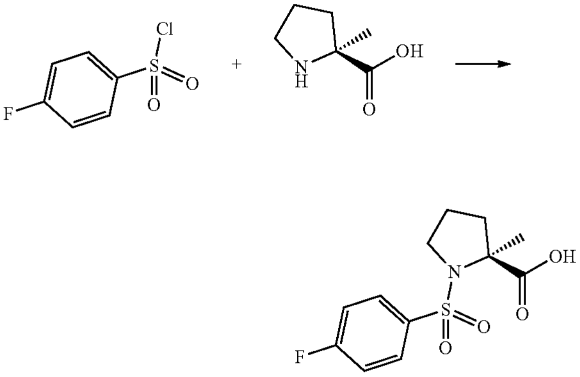

A mixture of (S)-2-methylpyrrolidine-2-carboxylic acid (0.1 g, 0.77 mmol), 4-fluorobenzene-1-sulfonyl chloride (0.16 g, 0.81 mmol) and 10 N NaOH (1.5 mL, 15 mmol) in THF (1.5 mL) was stirred at room temperature for 12 h. The mixture was diluted with EtOAc, acidified with 3 N HCl (pH 2-3) and separated. The aqueous layer was extracted with EtOAc (2×). The combined organic layers were washed with brine (2×), dried ($Na_2SO_4$), filtered, and concentrated to provide crude (S)-1-(4-fluorophenylsulfonyl)-2-methylpyrrolidine-2-carboxylic acid as a white solid, which was used in the next step without any further purification.

Step 2: Preparation of (S)-1-(4-fluorophenylsulfonyl)-2-methyl-N-((6-(6-(trifluoromethyl)pyridin-3-yl)pyrimidin-4-yl)methyl)pyrrolidine-2-carboxamide

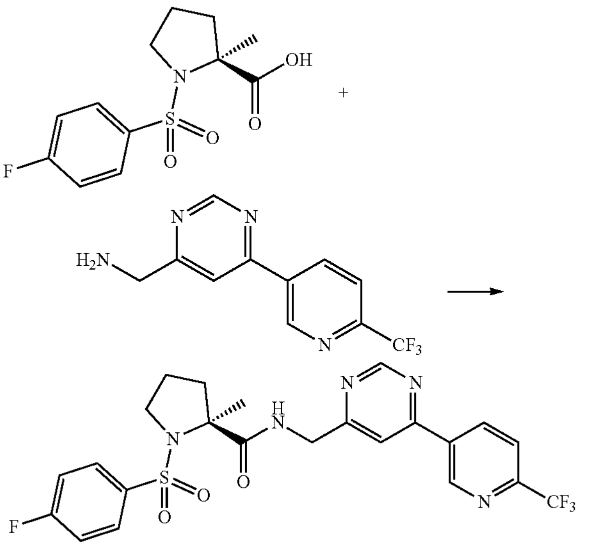

A mixture of crude (S)-1-(4-fluorophenylsulfonyl)-2-methylpyrrolidine-2-carboxylic acid (0.043 g, 0.15 mmol), (6-(6-(trifluoromethyl)pyridin-3-yl)pyrimidin-4-yl)methanamine (0.046 mg, 0.18 mmol), EDC (0.057 mg, 0.3 mmol), HOAt (0.042 mg, 0.3 mmol) and $Et_3N$ (0.063 mL, 0.45 mmol) in DMF (1.5 mL) was stirred at room temperature for 48 h. The mixture was diluted with water and extracted with EtOAc (2×). The combined organic layers were dried ($Na_2SO_4$), filtered, and concentrated. The resulting residue was purified by reverse phase HPLC affording the title compound (37 mg, 9%, two steps): $^1$H-NMR (400 MHz, DMSO-$d_6$) δ 9.47 (d, J=1.9 Hz, 1H), 9.29 (d, J=1.2 Hz, 1H), 8.78 (dd, J=8.2, 1.7 Hz, 1H), 8.62 (t, J=5.8 Hz, 1H), 8.25 (d, J=0.9 Hz, 1H), 8.09 (d, J=8.0 Hz, 1H), 8.02-7.93 (m, 2H), 7.48-7.39 (m, 2H), 4.61 (dd, J=17.4, 6.3 Hz, 1H), 4.41 (dd, J=17.4, 5.4 Hz, 1H), 3.67-3.58 (m, 1H), 3.38-3.31 (m, 1H), 2.22-2.13 (m, 1H), 2.06-1.95 (m, 1H), 1.94-1.80 (m, 2H), 1.50 (s, 3H).

Example 2

Preparation of (S)-1-(4-fluorophenylsulfonyl)-2-methyl-N-((6-(6-(trifluoromethyl)pyridin-3-yl)pyrimidin-4-yl)methyl)azetidine-2-carboxamide

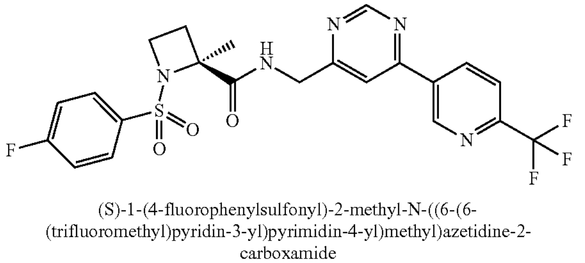 [SMILES: C[C@@]1(C(=O)NCc2cc(-c3ccc(C(F)(F)F)nc3)ncn2)CCN1S(=O)(=O)c1ccc(F)cc1]

(S)-1-(4-fluorophenylsulfonyl)-2-methyl-N-((6-(6-(trifluoromethyl)pyridin-3-yl)pyrimidin-4-yl)methyl)azetidine-2-carboxamide Step 1: Preparation of tert-butyl 2-methyl-2-((6-(6-(trifluoromethyl)pyridin-3-yl)pyrimidin-4-yl)methyl-carbamoyl)azetidine-1-carboxylate

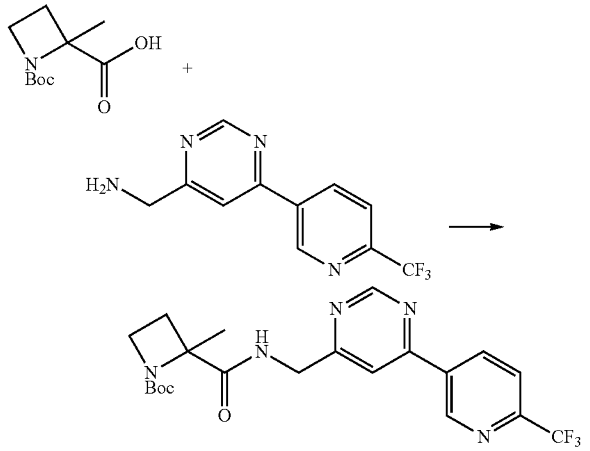

A mixture of 1-(tert-butoxycarbonyl)-2-methylazetidine-2-carboxylic acid (0.1 g, 0.51 mmol), (6-(6-(trifluoromethyl)pyridin-3-yl)pyrimidin-4-yl)methanamine (0.13 mg, 0.51 mmol), $iPr_2NEt$ (0.17 mL, 0.98 mmol), PyAOP (0.29 mg, 0.54 mmol) and 4-DMAP (0.006 mg, 0.05 mmol) in DMF (3 mL) was stirred at room temperature for 3 h. The mixture was washed with saturated aqueous $NaHCO_3$ solution and brine, and extracted with EtOAc (2×). The combined organic layers were dried ($Na_2SO_4$) filtered, passed through a silica gel plug washing with EtOAc, and concentrated to provide crude tert-butyl 2-methyl-2-((6-(6-(trifluoromethyl)pyridin-3-yl)pyrimidin-4-yl)methylcarbamoyl) azetidine-1-carboxylate, which was used in the next step without any further purification.

Step 2: Preparation of 2-methyl-2-((6-(6-(trifluoromethyl)pyridin-3-yl)pyrimidin-4-yl)methylcarbamoyl)azetidinium chloride

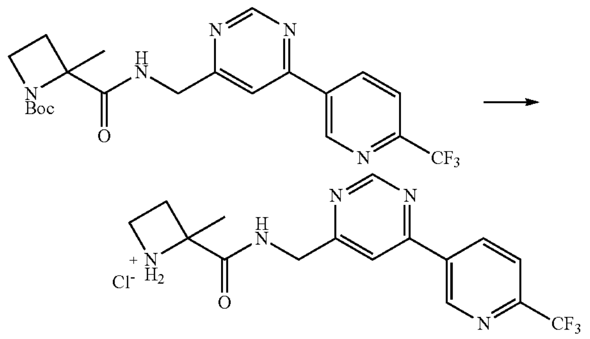

To a solution of crude tert-butyl 2-methyl-2-((6-(6-(trifluoromethyl)pyridin-3-yl)pyrimidin-4-yl)methylcarbamoyl) azetidine-1-carboxylate (0.22 g, 0.49 mmol), in $CH_2Cl_2$ (2 mL) was added 4 N HCl in dioxane (1 mL, 4 mmol) and the mixture stirred at room temperature for 3 h. The mixture was concentrated under reduced pressure to provide 2-methyl-2-((6-(6-(trifluoromethyl)pyridin-3-yl)pyrimidin-4-yl)methylcarbamoyl)azetidinium chloride as a crude salt, which was used in the next step without any further purification.

Step 3: Preparation of (S)-1-(4-fluorophenylsulfonyl)-2-methyl-N-((6-(6-(trifluoromethyl)pyridin-3-yl)pyrimidin-4-yl)methyl)azetidine-2-carboxamide

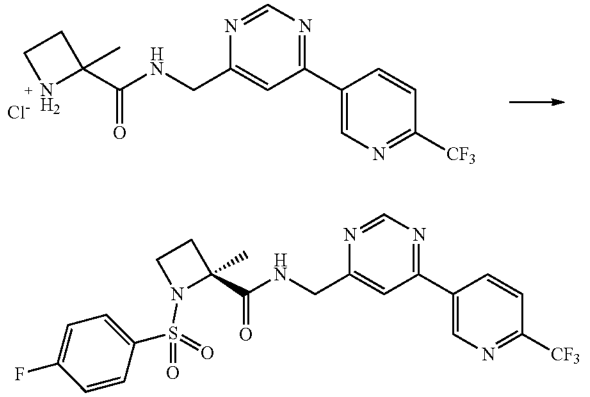

A mixture of crude 2-methyl-2-((6-(6-(trifluoromethyl) pyridin-3-yl)pyrimidin-4-yl)methylcarbamoyl)azetidinium chloride (0.085 g, 0.22 mmol), 4-fluorobenzene-1-sulfonyl chloride (0.047 mg, 0.24 mmol), and $Et_3N$ (0.15 mL, 1.1 mmol) in $CH_2Cl_2$ (2 mL) was stirred at room temperature for 12 h. The mixture was diluted with water and extracted with $CH_2Cl_2$ (2×). The combined organic layers were dried ($Na_2SO_4$), filtered, and concentrated. The resulting residue was purified by chiral SFC affording the title compound (22 mg) as the slower eluting isomer: $^1$H-NMR (400 MHz, DMSO-$d_6$) δ 9.48 (d, J=1.9 Hz, 1H), 9.32 (d, J=1.2 Hz, 1H), 8.79 (dd, J=8.2, 1.7 Hz, 1H), 8.74 (t, J=5.9 Hz, 1H), 8.18 (d, J=0.9 Hz, 1H), 8.11 (d, J=8.2 Hz, 1H), 8.03-7.95 (m, 2H), 7.54-7.43 (m, 2H), 4.66 (dd, J=17.4, 6.4 Hz, 1H), 4.49 (dd, J=17.4, 5.4 Hz, 1H), 3.97-3.86 (m, 1H), 3.82-3.74 (m, 1H), 2.10-1.98 (m, 1H), 1.54 (s, 3H).

Example 3

Preparation of (2S,4R)-4-fluoro-1-(4-fluorophenylsulfonyl)-N-((6-(6-(trifluoromethyl)pyridin-3-yl) pyrimidin-4-yl)methyl)pyrrolidine-2-carboxamide

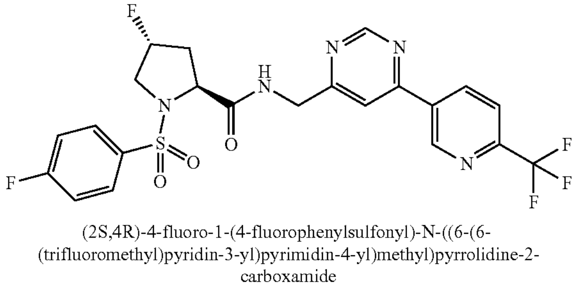 [SMILES: O=C(NCc1cc(-c2ccc(C(F)(F)F)nc2)ncn1)[C@@H]1C[C@@H](F)CN1S(=O)(=O)c1ccc(F)cc1]

(2S,4R)-4-fluoro-1-(4-fluorophenylsulfonyl)-N-((6-(6-(trifluoromethyl)pyridin-3-yl)pyrimidin-4-yl)methyl)pyrrolidine-2-carboxamide Step 1: Preparation of (2S,4R)-tert-butyl 4-fluoro-2-((6-(6-(trifluoromethyl)pyridin-3-yl)pyrimidin-4-yl)methylcarbamoyl)pyrrolidine-1-carboxylate

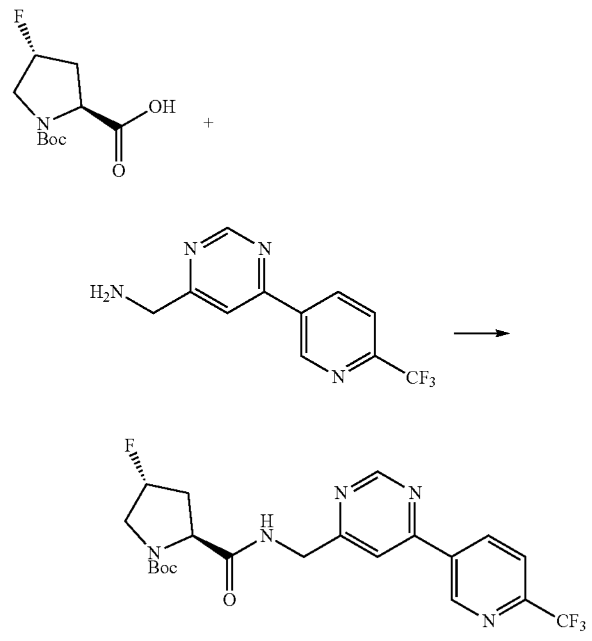

(2S,4R)-tert-butyl 4-fluoro-2-((6-(6-(trifluoromethyl)pyridin-3-yl)pyrimidin-4-yl)methylcarbamoyl)pyrrolidine-1-carboxylate was prepared by the procedure described in Example 2, step 1 using (2S,4R)-1-(tert-butoxycarbonyl)-4-fluoropyrrolidine-2-carboxylic acid.

Step 2: Preparation of (2S,4R)-4-fluoro-2-((6-(6-(trifluoromethyl)pyridin-3-yl)pyrimidin-4-yl)methylcarbamoyl)pyrrolidinium chloride

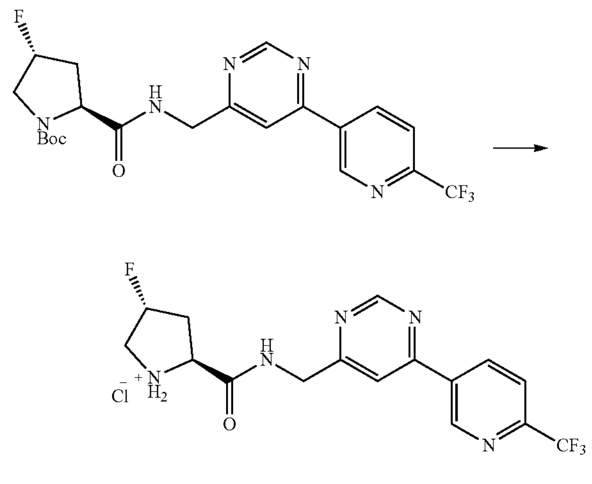

(2S,4R)-4-fluoro-N-((6-(6-(trifluoromethyl)pyridin-3-yl)pyrimidin-4-yl)methyl)pyrrolidine-2-carboxamide was prepared by the procedure described in Example 2, step 2.

Step 3: Preparation of (2S,4R)-4-fluoro-1-(4-fluorophenylsulfonyl)-N-((6-(6-(trifluoromethyl)pyridin-3-yl)pyrimidin-4-yl)methyl)pyrrolidine-2-carboxamide

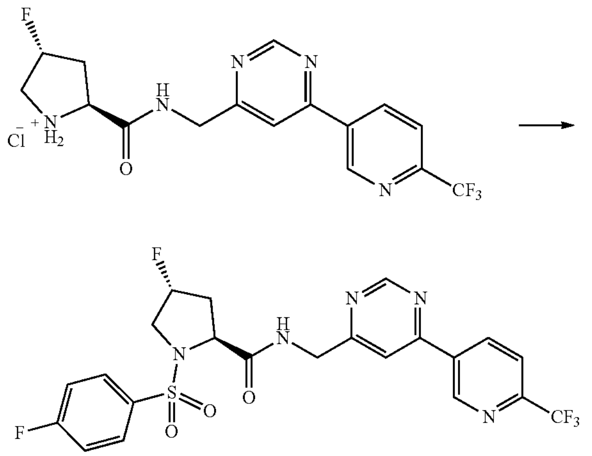

The title compound was prepared by the procedure described in Example 2, step 3 (29 mg): $^{1}$H-NMR (400 MHz, DMSO-$d_6$) δ 9.48 (d, J=1.9 Hz, 1H), 9.30 (d, J=1.2 Hz, 1H), 9.11 (t, J=5.9 Hz, 1H), 8.79 (dd, J=8.3, 1.7 Hz, 1H), 8.23 (s, 1H), 8.08 (d, J=8.3 Hz, 1H), 8.05-7.98 (m, 2H), 7.47 (t, J=8.8 Hz, 2H), 5.21 (d, J=52.4 Hz, 1H), 4.53 (d, J=5.9 Hz, 2H), 4.25 (dd, J=9.8, 7.2 Hz, 1H), 3.79-3.60 (m, 2H), 2.46-2.37 (m, 1H), 2.25-2.04 (m, 1H).

Example 4

Preparation of (2S,4S)-4-fluoro-1-(4-fluorophenylsulfonyl)-N-((6-(6-(trifluoromethyl)pyridin-3-yl)pyrimidin-4-yl)methyl)pyrrolidine-2-carboxamide

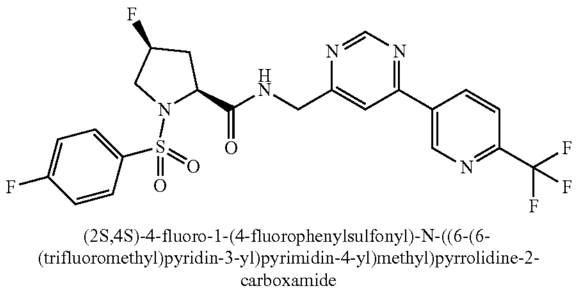 [SMILES: O=C(NCc1cc(-c2ccc(C(F)(F)F)nc2)ncn1)[C@@H]1C[C@H](F)CN1S(=O)(=O)c1ccc(F)cc1]

(2S,4S)-4-fluoro-1-(4-fluorophenylsulfonyl)-N-((6-(6-(trifluoromethyl)pyridin-3-yl)pyrimidin-4-yl)methyl)pyrrolidine-2-carboxamide The title compound was prepared by the procedures described in Example 2, step 1 using (2S,4S)-1-(tert-butoxycarbonyl)-4-fluoropyrrolidine-2-carboxylic acid, and Example 2, steps 2 and 3 (37 mg): $^{1}$H-NMR (400 MHz, DMSO-$d_6$) δ 9.43 (d, J=1.9 Hz, 1H), 9.28 (d, J=1.2 Hz, 1H), 8.89 (t, J=6.1 Hz, 1H), 8.75 (dd, J=8.1, 1.8 Hz, 1H), 8.14-8.01 (m, 4H), 7.55-7.43 (m, 2H), 5.26 (dt, J=53.3, 3.7 Hz, 1H), 4.61-4.44 (m, 2H), 4.39 (d, J=9.5 Hz, 1H), 3.81 (dd, J=22.4, 12.2 Hz, 1H), 3.45 (ddd, J=36.0, 12.3, 3.8 Hz, 1H), 2.37-2.24 (m, 1H), 2.07-1.85 (m, 1H).

Example 5

Preparation of (2S,4R)-4-fluoro-1-(4-fluorophenylsulfonyl)-N-((6-(4-(trifluoromethyl)phenyl)pyrimidin-4-yl)methyl)pyrrolidine-2-carboxamide

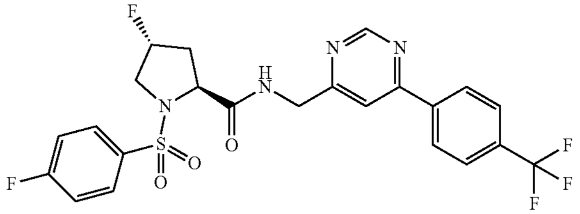

(2S,4R)-4-fluoro-1-(4-fluorophenylsulfonyl)-N-((6-(4-(trifluoromethyl)phenyl)pyrimidin-4-yl)methyl)pyrrolidine-2-carboxamide The title compound was prepared by the procedures described in Example 2, step 1 using (2S,4R)-1-(tert-butoxycarbonyl)-4-fluoropyrrolidine-2-carboxylic acid and (6-(4-(trifluoromethyl)phenyl)pyrimidin-4-yl)methanamine, and Example 2, steps 2 and 3 (107 mg): $^1$H-NMR (400 MHz, DMSO-$d_6$) δ 9.25 (s, 1H), 9.11 (t, J=5.7 Hz, 1H), 8.40 (d, J=8.1 Hz, 2H), 8.15 (s, 1H), 8.07-7.99 (m, 2H), 7.88 (d, J=8.1 Hz, 2H), 7.47 (t, J=8.6 Hz, 2H), 5.21 (d, J=52.4 Hz, 1H), 4.51 (d, J=5.8 Hz, 2H), 4.31-4.22 (m, 1H), 3.78-3.59 (m, 2H), 2.48-2.38 (m, 1H), 2.23-2.05 (m, 1H).

Example 6

Preparation of (2S,4R)-4-fluoro-1-(3-fluorophenylsulfonyl)-N-((6-(4-(trifluoromethyl)phenyl)pyrimidin-4-yl)methyl)pyrrolidine-2-carboxamide

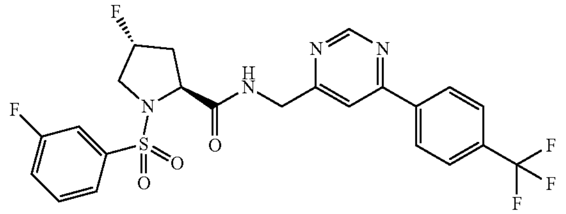

(2S,4R)-4-fluoro-1-(3-fluorophenylsulfonyl)-N-((6-(4-(trifluoromethyl)phenyl)pyrimidin-4-yl)methyl)pyrrolidine-2-carboxamide The title compound was prepared by the procedures described in Example 2, step 1 using (2S,4R)-1-(tert-butoxycarbonyl)-4-fluoropyrrolidine-2-carboxylic acid and (6-(4-(trifluoromethyl)phenyl)pyrimidin-4-yl)methanamine, Example 2, step 2 and Example 2, step 3 using 3-fluorobenzene-1-sulfonyl chloride (108 mg): $^1$H-NMR (400 MHz, DMSO-$d_6$) δ 9.25 (d, J=1.1 Hz, 1H), 9.13 (t, J=5.8 Hz, 1H), 8.40 (d, J=8.1 Hz, 2H), 8.15 (s, 1H), 7.88 (d, J=8.3 Hz, 2H), 7.85-7.77 (m, 2H), 7.73-7.65 (m, 1H), 7.63-7.56 (m, 1H), 5.22 (d, J=52.3 Hz, 1H), 4.59-4.45 (m, 2H), 4.31 (dd, J=9.9, 7.1 Hz, 1H), 3.83-3.58 (m, 2H), 2.48-2.39 (m, 1H), 2.23-2.05 (m, 1H).

Example 7

Preparation of (R)-1-(4-fluorophenylsulfonyl)-2-(hydroxymethyl)-N-((6-(6-(trifluoromethyl)pyridin-3-yl)pyrimidin-4-yl)methyl)pyrrolidine-2-carboxamide

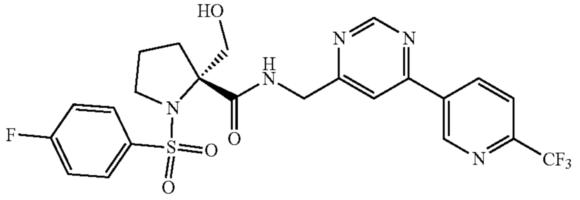 [SMILES: O=C(NCc1cc(-c2ccc(C(F)(F)F)nc2)ncn1)[C@]1(CO)CCCN1S(=O)(=O)c1ccc(F)cc1]

Step 1: Preparation of (3R,7aS)-3-(trichloromethyl)-tetrahydropyrrolo[1,2-c]oxazol-1(3H)-one

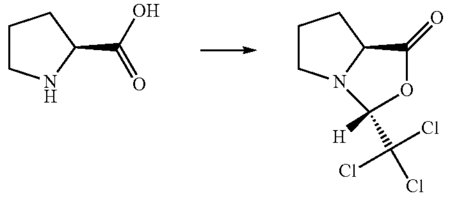 [SMILES: O=C(O)[C@@H]1CCCN1 ; O=C1O[C@H](C(Cl)(Cl)Cl)N2CCC[C@@H]12]

A solution of (2S)-pyrrolidine-2-carboxylic acid (5.8 g, 50.38 mmol), 2,2,2-trichloroacetaldehyde (12.4 g, 84.13 mmol) in chloroform (100 mL) was stirred for 18 h at 75° C. in an oil bath. The resulting mixture was washed with water (2×) and brine, dried ($Na_2SO_4$) and concentrated under reduced pressure. The crude product was recrystallized from ethanol to afford the title compound (6.2 g, 50%) as a white solid.

Step 2: Preparation of (3R,7aR)-7a-(benzyloxymethyl)-3-(trichloromethyl)-tetrahydropyrrolo[1,2-c]oxazol-1(3H)-one

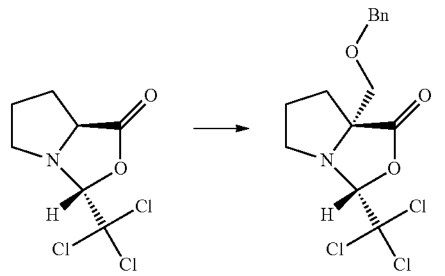 [SMILES: O=C1O[C@H](C(Cl)(Cl)Cl)N2CCC[C@@H]12 ; O=C1O[C@H](C(Cl)(Cl)Cl)N2CCC[C@@]12COCc1ccccc1]

n-BuLi (36 mL, 90 mmol) was added dropwise to a solution of diisopropylamine (9.1 g, 89.93 mmol,) in THF (60 mL) with stirring at −78° C. under nitrogen and the reaction mixture was stirred for another 15 min at 0° C. The resulting solution was added dropwise into a solution of (3R,7aS)-3-(trichloromethyl)-hexahydropyrrolo[1,2-c][1,3]oxazol-1-one (14.6 g, 59.71 mmol) in THF (100 mL) within 30 min at −78° C. and stirred for another 30 min at −78° C. Then [(chloromethoxy)methyl]benzene (14.1 g, 90.03 mmol) was added dropwise. The resulting solution was stirred for an additional 2 h at −40° C. and quenched by the addition of water (150 mL), extracted with EtOAc (3×200 mL) and separated. The combined organic layers were dried ($Na_2SO_4$) and concentrated under reduced pressure. The residue was purified by flash chromatography on silica gel eluting with EtOAc/petroleum ether (1:10) to afford the title compound (10 g, 38%) as light yellow oil.

Step 3: Preparation of (R)-methyl 2-(benzyloxymethyl)pyrrolidine-2-carboxylate

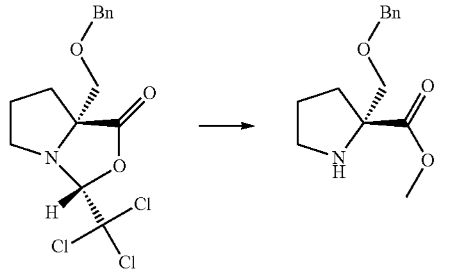 [SMILES: O=C1O[C@H](C(Cl)(Cl)Cl)N2CCC[C@@]12COCc1ccccc1 ; COC(=O)[C@]1(COCc2ccccc2)CCCN1]

Sodium methoxide (890 mg, 16.47 mmol) was added portionwise to a solution of (3R,7aR)-7a-[(benzyloxy)methyl]-3-(trichloromethyl)-hexahydropyrrolo[1,2-c][1,3]oxazol-1-one (10 g, 27.42 mmol) in methanol (100 mL). The resulting solution was stirred for 30 min at room temperature and acetyl chloride (38 mL, 532.50 mmol) was added dropwise with stirring over 1 h at 0° C. The resulting solution was allowed to react for an additional 24 h at room temperature and concentrated under reduced pressure. The residue was diluted with EtOAc (50 mL) and saturated aqueous sodium carbonate (100 mL), extracted with EtOAc (3×100 mL). The combined organic layers were washed with brine (100 mL), dried ($Na_2SO_4$), filtered and concentrated under reduced pressure to afford the title compound (5.85 g, 86%) as light red oil.

Step 4: Preparation of (R)-methyl 2-(benzyloxymethyl)-1-(4-fluorophenylsulfonyl)pyrrolidine-2-carboxylate

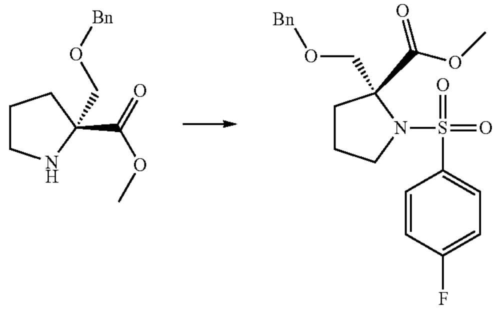 [SMILES: COC(=O)[C@]1(COCc2ccccc2)CCCN1 ; COC(=O)[C@]1(COCc2ccccc2)CCCN1S(=O)(=O)c1ccc(F)cc1]

4-Fluorobenzene-1-sulfonyl chloride (6.8 g, 34.94 mmol) was added dropwise to a solution of methyl (2R)-2-[(benzyloxy)methyl]pyrrolidine-2-carboxylate (5.8 g, 23.26 mmol), DIPEA (9 g, 69.64 mmol), 4-dimethylaminopyridine (280 mg, 2.29 mmol) in $CH_2Cl_2$ (150 mL) with stirring at 0° C. The resulting solution was stirred for 18 h at room temperature and diluted with $CH_2Cl_2$ (150 mL), washed with 2 N HCl (2×) and brine. The mixture was dried ($Na_2SO_4$), filtered and concentrated under reduced pressure to afford the title compound (8.3 g, 88%) as yellow oil Step 5: Preparation of (R)-methyl 1-(4-fluorophenylsulfonyl)-2-(hydroxymethyl)pyrrolidine-2-carboxylate

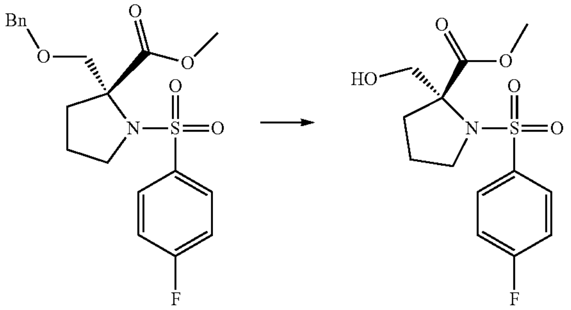 [SMILES: COC(=O)[C@]1(COCc2ccccc2)CCCN1S(=O)(=O)c1ccc(F)cc1 ; COC(=O)[C@]1(CO)CCCN1S(=O)(=O)c1ccc(F)cc1]

A mixture of methyl (2R)-2-[(benzyloxy)methyl]-1-[(4-fluorobenzene)sulfonyl]pyrrolidine-2-carboxylate (510 mg, 1.3 mmol), 10% palladium carbon (100 mg) in methanol (30 mL) was stirred for 18 h at room temperature under an atmosphere of hydrogen gas. The solids were filtered off and the filtrate was concentrated under reduced pressure to afford the title compound (400 mg) as light yellow oil, which was used in the next step without any further purification.

Step 6: Preparation of (R)-1-(4-fluorophenylsulfonyl)-2-(hydroxymethyl)pyrrolidine-2-carboxylic acid

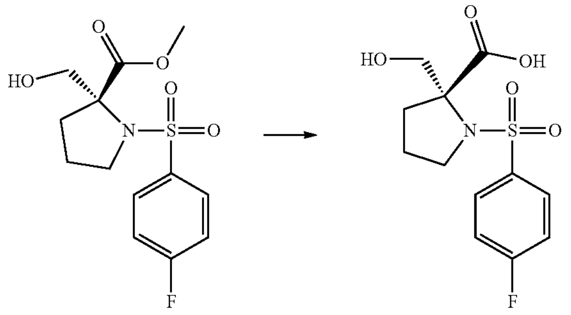 [SMILES: COC(=O)[C@]1(CO)CCCN1S(=O)(=O)c1ccc(F)cc1 ; O=C(O)[C@]1(CO)CCCN1S(=O)(=O)c1ccc(F)cc1]

A mixture of methyl (2R)-1-[(4-fluorobenzene)sulfonyl]-2-(hydroxymethyl)pyrrolidine-2-carboxylate (40 mg, 0.13 mmol), LiOH (30 mg, 1.25 mmol) in methanol (1 mL), water (1 mL) was stirred for 18 h at room temperature. The solution was acidified (pH~5) with 2 N HCl and concentrated under reduced pressure. The resulting solution was extracted with EtOAc (3×10 mL), and the organic layers were combined, dried ($Na_2SO_4$) and concentrated under reduced pressure to afford the title compound (40 mg) as a light yellow syrup, which was used in the next step without any further purification.

Step 7: Preparation of (2R)-1-(4-fluorophenylsulfonyl)-2-(hydroxymethyl)-N-((6-(6-(trifluoromethyl) pyridin-3-yl)pyrimidin-4-yl)methyl)pyrrolidine-2-carboxamide

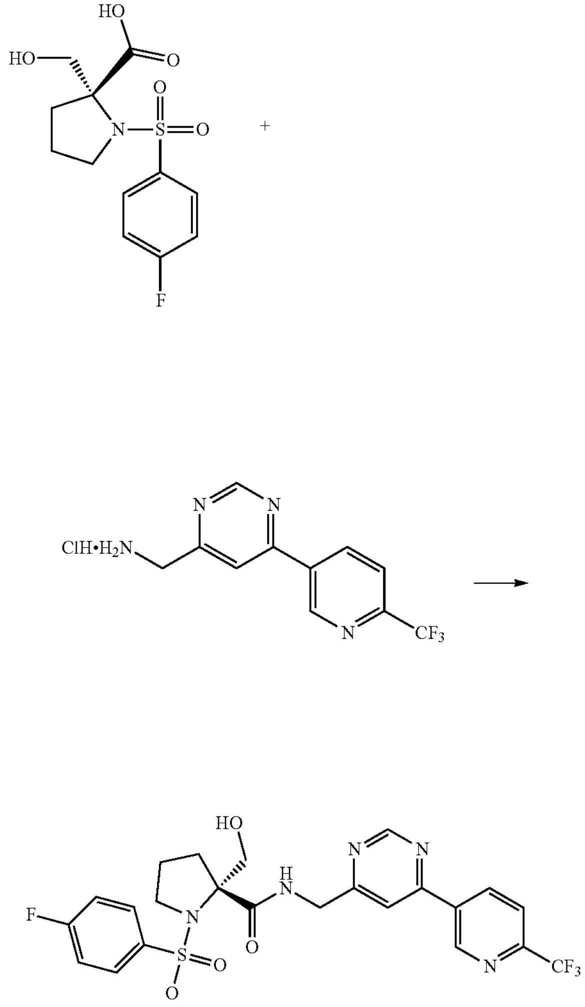

A solution of (2R)-1-[(4-fluorobenzene)sulfonyl]-2-(hydroxymethyl)pyrrolidine-2-carboxylic acid (40 mg, 0.13 mmol), HATU (62.7 mg, 0.16 mmol), DIPEA (57 mg, 0.44 mmol) and [6-[6-(trifluoromethyl)pyridin-3-yl]pyrimidin-4-yl]methanamine hydrochloride (32 mg, 0.11 mmol) in DMF (2 mL) was stirred for 2 h at room temperature. The resulting solution was diluted with water (10 mL), extracted with EtOAc (3×). The combined organic layers were washed with brine (3×), dried ($Na_2SO_4$) and concentrated under reduced pressure. The crude product (70 mg) was purified by Prep-HPLC high pH to afford the title compound (24.7 mg) as a white solid. $^1$H-NMR (400 MHz, DMSO-$d_6$) δ 9.47 (s, 1H), 9.28 (s, 1H), 8.78 (d, J=8 Hz, 1H), 8.57-8.56 (m, 1H), 8.25 (s, 1H), 8.08 (d, J=8.4 Hz, 1H), 7.96-7.92 (m, 2H), 7.38 (t, J=8.8 Hz, 2H), 5.20-5.17 (m, 1H), 4.59-4.57 (m, 1H), 4.47-4.46 (m, 1H), 4.06-4.03 (m, 1H), 3.87-3.85 (m, 1H), 3.53-3.52 (m, 1H), 3.24-3.22 (m, 1H), 2.34-2.33 (m, 1H), 2.04-1.90 (m, 3H).

Example 8

Preparation of (2S,4R)-4-fluoro-N-((5-fluoro-6'-(trifluoromethyl)-2,3'-bipyridin-4-yl)methyl)-1-(4-fluorophenylsulfonyl)pyrrolidine-2-carboxamide

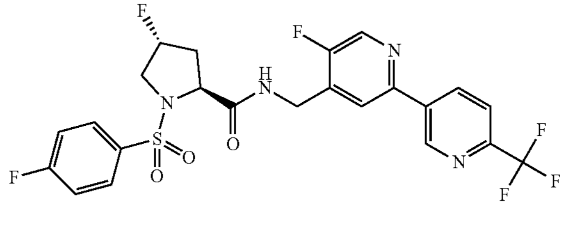 [SMILES: O=C(NCc1cc(-c2ccc(C(F)(F)F)nc2)ncc1F)[C@@H]1C[C@@H](F)CN1S(=O)(=O)c1ccc(F)cc1]

Step 1: Preparation of 5-fluoro-6'-(trifluoromethyl)-2,3'-bipyridine-4-carbaldehyde

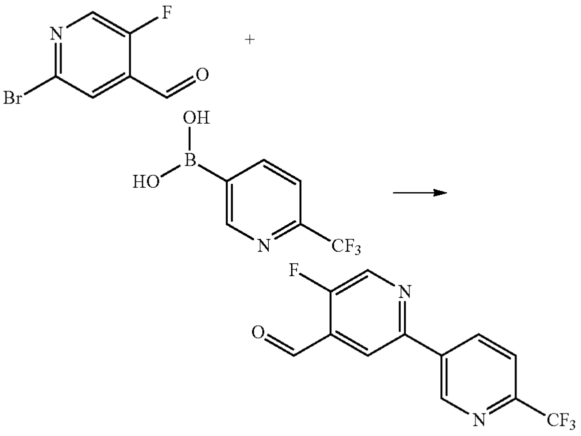

A mixture of 2-bromo-5-fluoropyridine-4-carbaldehyde (300 mg, 1.47 mmol), [6-(trifluoromethyl)pyridin-3-yl]boronic acid (420 mg, 2.20 mmol), $Pd(dppf)Cl_2.CH_2Cl_2$ (60 mg, 0.07 mmol), $Cs_2CO_3$ (1.44 g, 0.09 mmol) in water (2 mL) and 1,4-Dioxane (6 mL) was stirred overnight at 90° C. in an oil bath under nitrogen. The resulting mixture was quenched with water (20 mL), extracted with $CH_2Cl_2$ (3×) and separated. The combined organic layers were washed with brine (50 mL), dried ($Na_2SO_4$) and concentrated under reduce pressure. The residue was purified by flash chromatography on silica gel with EtOAc/petroleum ether (12:88) to afford the title compound (110 mg) as a light yellow solid.

Step 2: Preparation of (5-fluoro-6'-(trifluoromethyl)-2,3'-bipyridin-4-yl)methanamine

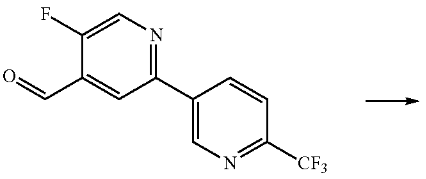

-continued

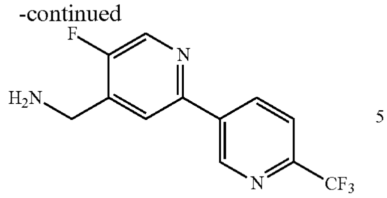

A mixture of 5-fluoro-2-[6-(trifluoromethyl)pyridin-3-yl] pyridine-4-carbaldehyde (363 mg, 1.34 mmol), $NH_2OH.HCl$ (187 mg, 2.69 mmol) in ethanol (15 mL) and water (3 mL) was stirred for 30 min at 25° C. Then concentrated HCl (0.08 mL, 36%), Pd/C (300 mg, 10%) was added and the reaction mixture was stirred for 50 min at 25° C. under an atmosphere of hydrogen gas. The solids were filtered off and the filtrate was concentrated under reduced pressure. The resulting mixture was diluted with $H_2O$ (20 mL), and adjusted to pH ~7-8 with 5 N $NaHCO_3$, extracted with EtOAc (3×). The combined organic layers were washed with brine (50 mL), dried ($Na_2SO_4$) and concentrated under reduced pressure to afford the crude title compound (300 mg) as yellow oil, which was used in the next step without any further purification.

Step 3: Preparation of (2S,4R)-4-fluoro-N-((5-fluoro-6'-(trifluoromethyl)-2,3'-bipyridin-4-yl) methyl)-1-(4-fluorophenylsulfonyl)pyrrolidine-2-carboxamide

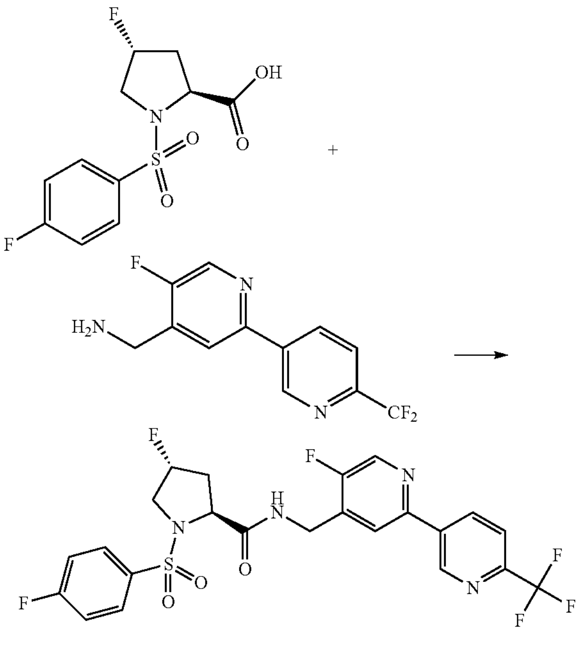

A mixture of (2S,4R)-4-fluoro-1-[(4-fluorobenzene) sulfonyl]pyrrolidine-2-carboxylic acid (129 mg, 0.44 mmol), HATU (169 mg, 0.44 mmol), DIPEA (143 mg, 1.11 mmol), [5-fluoro-2-[6-(trifluoromethyl)pyridin-3-yl]pyridin-4-yl]methanamine (100 mg, 0.37 mmol) in DMF (2 mL) was stirred for overnight at 25° C. The reaction mixture was quenched with water (20 mL), extracted with dichloromethane (3×). The combined organic layers were washed with brine (20 mL), dried ($Na_2SO_4$) and concentrated under reduced pressure. The residue was purified by flash chromatography on silica gel eluting with EtOAc/petroleum ether (6:4). The crude product was recrystallized from methanol to afford the title compound (67 mg) as an off-white solid. $^1$H-NMR (300 MHz, $CD_3OD$) δ 9.08 (s, 1H), 8.61 (d, J=3 Hz, 1H), 8.43 (d, J=6 Hz, 1H), 8.02-7.92 (m, 4H), 7.38-7.32 (m, 2H), 5.16 (d, J=54 Hz, 1H), 4.65 (s, 2H), 4.31-4.26 (m, 1H), 3.86-3.68 (m, 2H). 2.54-2.52 (m, 1H), 2.32-2.06 (m, 1H).

Example 9

Preparation of (2S,4R)-4-fluoro-N-((5'-fluoro-6-(trifluoromethyl)-3,4'-bipyridin-2'-yl)methyl)-1-(4-fluorophenylsulfonyl)pyrrolidine-2-carboxamide

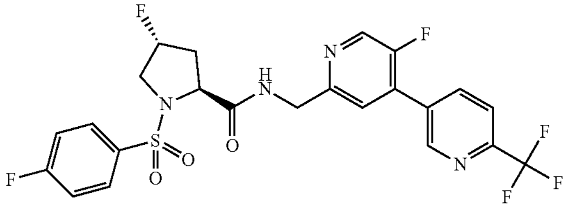 [SMILES: O=C(NCc1cc(-c2ccc(C(F)(F)F)nc2)c(F)cn1)[C@@H]1C[C@@H](F)CN1S(=O)(=O)c1ccc(F)cc1]

Step 1: Preparation of 2'-chloro-5'-fluoro-6-(trifluoromethyl)-3,4'-bipyridine

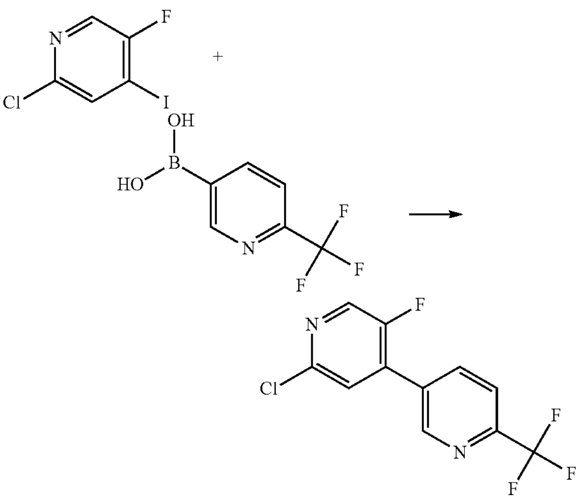

A mixture of 2-chloro-5-fluoro-4-iodopyridine (2.57 g, 9.98 mmol), [6-(trifluoromethyl)pyridin-3-yl]boronic acid (2.00 g, 10.48 mmol), $Pd(dppf)Cl_2.CH_2Cl_2$ (407.63 mg, 0.50 mmol), sodium carbonate (2.12 g, 20.00 mmol) in water (10 mL) and toluene (25 mL) was stirred for overnight at 90° C. under nitrogen. The reaction mixture was concentrated under reduced pressure, diluted with water (100 mL), extracted with dichloromethane (2×100 mL), and separated. The combined organic layers were washed with brine (200 mL), dried ($Na_2SO_4$) and concentrated under reduced pressure. The residue was purified by flash chromatography on silica gel eluting with EtOAc/petroleum ether (1:5) to afford the title compound (2.31 g) as colorless oil.

Step 2: Preparation of 5'-fluoro-6-(trifluoromethyl)-3,4'-bipyridine-2'-carbonitrile

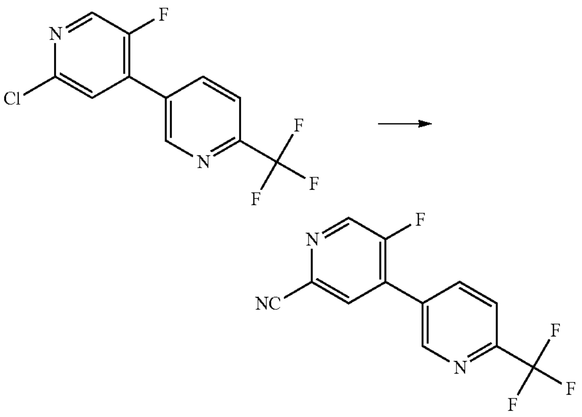

A mixture of 2-chloro-5-fluoro-4-[6-(trifluoromethyl)pyridin-3-yl]pyridine (1 g, 3.62 mmol), $Pd_2(dba)_3.CHCl_3$ (187 mg, 0.18 mmol), $Zn(CN)_2$ (254 mg, 2.16 mmol), DPPF (200 mg, 0.36 mmol), and Zn (24 mg, 0.37 mmol) in DMA (10 mL) was irradiated with microwave radiation for 1 h at 125° C. under nitrogen. The reaction was then quenched with water (100 mL), extracted with EtOAc (3×100 mL). The organic layers were combined and washed with brine (100 mL), dried ($Na_2SO_4$) and concentrated under reduced pressure. The residue was purified by flash chromatography on silica gel eluting with EtOAc/petroleum ether (1:5) to afford the title compound (860 mg) as a yellow solid.

Step 3: Preparation of (5'-fluoro-6-(trifluoromethyl)-3,4'-bipyridin-2'-yl)methanamine

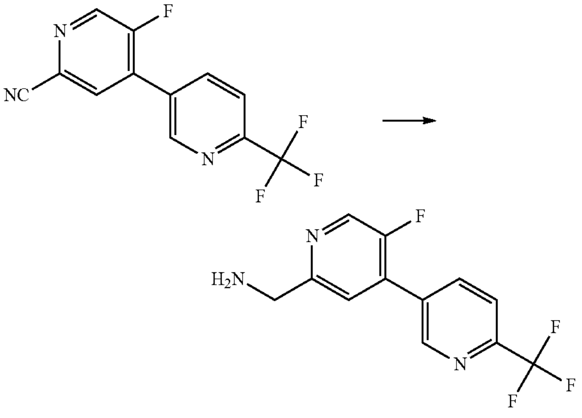

A mixture of 5-fluoro-4-[6-(trifluoromethyl)pyridin-3-yl]pyridine-2-carbonitrile (250 mg, 0.94 mmol), Raney Ni (100 mg, 1.17 mmol) in methanol (10 mL) was stirred for 1 h at room temperature under an atmosphere of hydrogen. The solids were filtered off and the filtrate was concentrated under reduced pressure to afford the crude title compound (250 mg) as brown oil, which was used in the next step without any further purification.

Step 4: Preparation of (2S,4R)-4-fluoro-N-((5'-fluoro-6-(trifluoromethyl)-3,4'-bipyridin-2'-yl)methyl)-1-(4-fluorophenylsulfonyl)pyrrolidine-2-carboxamide

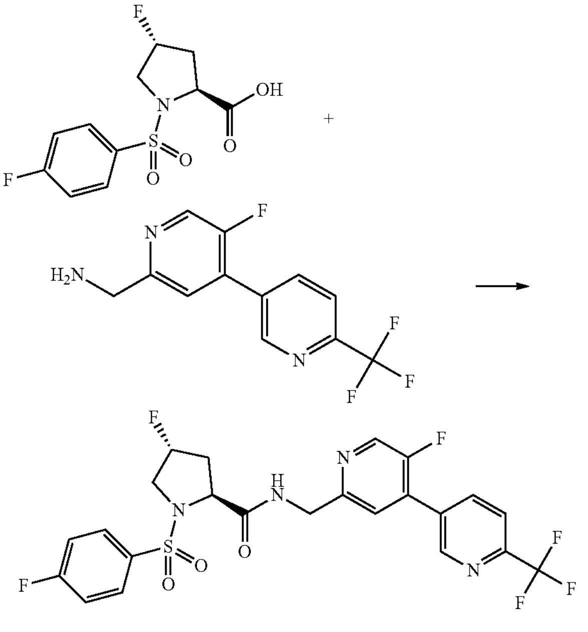

A mixture of [5-fluoro-4-[6-(trifluoromethyl)pyridin-3-yl]pyridin-2-yl]methanamine (141 mg, 0.52 mmol), HATU (231 mg, 0.61 mmol), DIPEA (157 mg, 1.21 mmol), (3R,4R)-4-fluoro-1-[(4-fluorobenzene)sulfonyl]pyrrolidine-3-carboxylic acid (110 mg, 0.38 mmol) in DMF (5 mL) was stirred overnight at 25° C. The reaction mixture was quenched with water (20 mL), extracted with $CH_2Cl_2$ (3×20 mL). The combined organic layers were washed with brine (20 mL), dried ($Na_2SO_4$) and concentrated under reduced pressure. The residue was purified by Prep-HPLC to afford the title compound (32.4 mg) as a white solid. $^1$H-NMR (300 MHz, $CD_3OD$) δ 9.41 (s, 1H), 8.72 (d, J=9.9 Hz, 2H), 8.58 (d, J=1.2 Hz, 1H), 8.28 (d, J=5.7 Hz, 1H), 8.04-7.99 (m, 2H), 7.86 (d, J=8.4 Hz, 1H), 7.37-7.31 (m, 2H), 5.16 (d, J=51.9 Hz, 1H), 4.74-4.56 (m, 2H), 4.33-4.27 (m, 1H), 3.86-3.67 (m, 2H), 2.54-2.52 (m, 1H), 2.30-2.12 (m, 1H).

Example 10

Preparation of (2S,4R)—N-((6-(4-cyclopropylphenyl)pyrimidin-4-yl)methyl)-4-fluoro-1-(4-fluorophenylsulfonyl)pyrrolidine-2-carboxamide

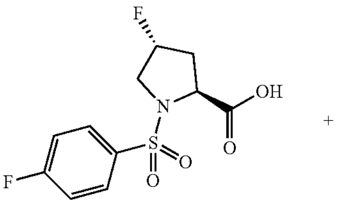

-continued

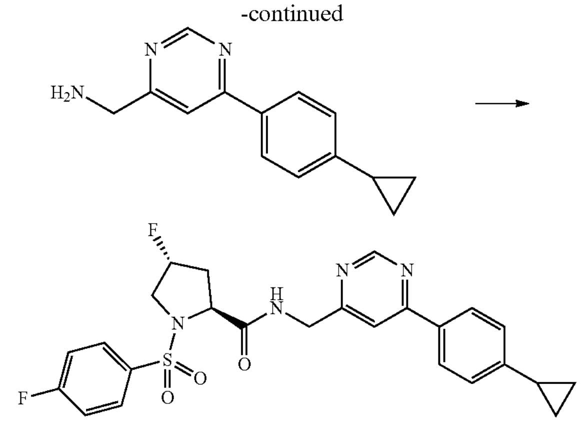

A mixture of (2S,4R)-4-fluoro-1-[(4-fluorobenzene)sulfonyl]pyrrolidine-2-carboxylic acid (155.2 mg, 0.53 mmol), HATU (253.3 mg, 0.67 mmol), DIPEA (172 mg, 1.33 mmol), [6-(4-cyclopropylphenyl)pyrimidin-4-yl]methanamine (100 mg, 0.44 mmol) in DMF (5 mL) was stirred overnight at 25° C. The reaction mixture was quenched with water (20 mL), extracted with $CH_2Cl_2$ (3×) and separated. The combined organic layers were washed with brine (20 mL), dried over anhydrous $Na_2SO_4$ and concentrated under reduced pressure. The residue was purified by Prep-HPLC to afford the title compound (36.4 mg) as a white solid. $^1$H-NMR (400 MHz, $CD_3OD$) δ 8.94 (s, 1H), 8.04 (d, J=8 Hz, 3H), 7.94-7.90 (m, 2H), 7.26-7.21 (m, 2H), 7.05 (d, J=8.4 Hz, 2H), 5.06 (d, J=52 Hz, 1H), 4.48 (dd, J=17.6, 8.8 Hz, 2H), 4.23-4.18 (m, 1H), 3.76-3.63 (m, 2H), 2.43-2.39 (m, 1H), 2.17-2.04 (m, 1H), 1.86-1.81 (m, 1H), 0.92-0.90 (m, 2H), 0.65-0.63 (m, 2H).

Example 11

Preparation of (2S,4R)-4-fluoro-1-(4-fluorophenylsulfonyl)-N-((6-(4-(trifluoromethyl)piperidin-1-yl)pyrimidin-4-yl)methyl)pyrrolidine-2-carboxamide

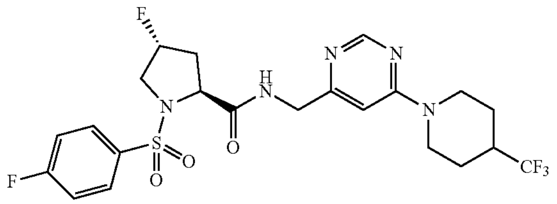 [SMILES: O=C(NCc1cc(N2CCC(C(F)(F)F)CC2)ncn1)[C@@H]1C[C@@H](F)CN1S(=O)(=O)c1ccc(F)cc1]

Step 1: Preparation of 4-chloro-6-(4-(trifluoromethyl)piperidin-1-yl)pyrimidine

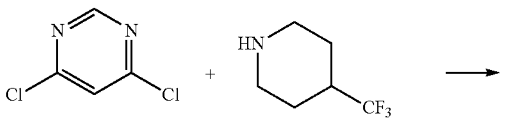

-continued

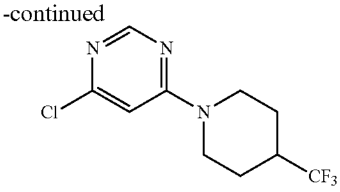

A mixture of 4,6-dichloropyrimidine (2 g, 13.42 mmol), DIPEA (0.65 mL, 3.93 mmol), 4-(trifluoromethyl)piperidine (9.74 g, 63.60 mmol) in DMF (20 mL) was stirred for 3 h at 25° C. The reaction mixture was then quenched with water (100 mL), extracted with EtOAc (3×100 mL). The combined organic layers were washed with water (3×) and brine, dried over anhydrous $Na_2SO_4$ and concentrated under reduced pressure. The residue was purified by flash chromatography on silica gel eluting with EtOAc/petroleum ether (3:7) to afford the title compound (3.4 g) as a white solid.

Step 2: Preparation of 6-(4-(trifluoromethyl)piperidin-1-yl)pyrimidine-4-carbonitrile

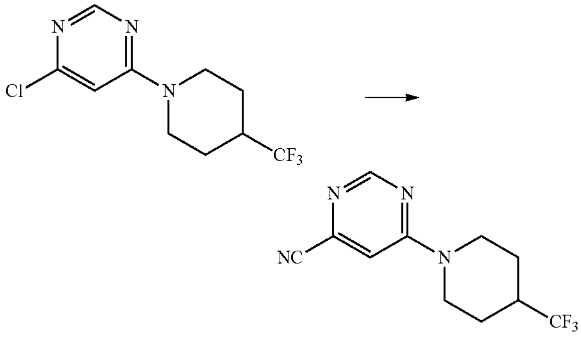

A mixture of 4-chloro-6-[4-(trifluoromethyl)piperidin-1-yl]pyrimidine (2.6 g, 9.79 mmol), $Pd_2(dba)_3.CHCl_3$ (506 mg, 0.49 mmol), $Zn(CN)_2$ (686 mg, 5.84 mmol), DPPF (540 mg, 0.97 mmol), and Zn (64 mg, 0.98 mmol) in DMA (26 mL) was irradiated with microwave radiation for 1 h at 125° C. under nitrogen. The reaction mixture was then quenched with water (100 mL), extracted with EtOAc (3×100 mL). The combined organic layers were washed with water (3×) and brine, dried over anhydrous $Na_2SO_4$ and concentrated under reduced pressure. The residue was purified by flash chromatography on silica gel with EtOAc/petroleum ether (35:65) to afford the title compound (3.4 g) as a light yellow solid.

Step 3: Preparation of (6-(4-(trifluoromethyl)piperidin-1-yl)pyrimidin-4-yl)methanamine

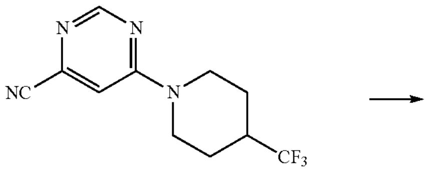

-continued

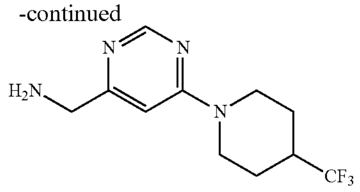

A mixture of 6-[4-(trifluoromethyl)piperidin-1-yl]pyrimidine-4-carbonitrile (500 mg, 1.95 mmol), 10% Pa/C (500 mg), conc. HCl (0.2 mL) in methanol (10 mL) was stirred for 20 min at 25° C. under an atmosphere of hydrogen gas. The solids were filtered off and the mixture was concentrated under reduced pressure to afford the crude title compound (500 mg) as purple oil, which was used in the next step without any further purification.

Step 4: Preparation of (2S,4R)-4-fluoro-1-(4-fluorophenylsulfonyl)-N-((6-(4-(trifluoromethyl)piperidin-1-yl)pyrimidin-4-yl)methyl)pyrrolidine-2-carboxamide

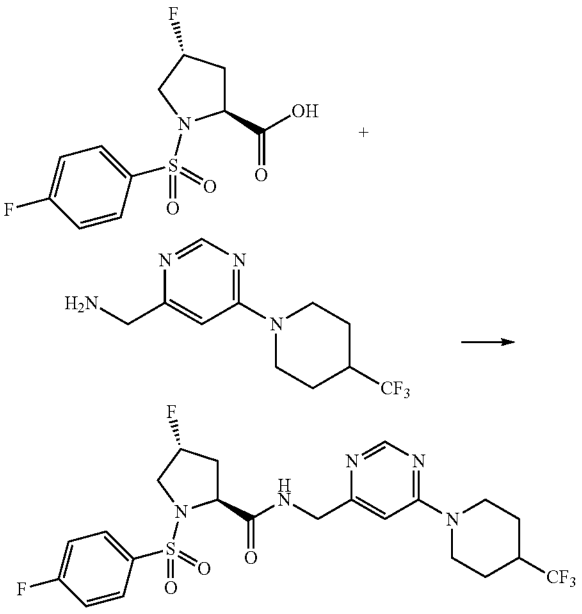

A mixture of [6-[4-(trifluoromethyl)piperidin-1-yl]pyrimidin-4-yl]methanamine (178.7 mg, 0.69 mmol), (2S,4R)-4-fluoro-1-[(4-fluorobenzene)sulfonyl]pyrrolidine-2-carboxylic acid (200 mg, 0.69 mmol), HOBT (102 mg, 0.75 mmol), EDC.HCl (213 mg, 1.11 mmol) and DIPEA (117.2 mg, 0.91 mmol), in DMF (5 mL) was stirred overnight at 25° C. The reaction mixture was quenched with water (20 mL), extracted with EtOAc (3x20 mL). The combined organic layers were washed with brine (20 mL), dried over anhydrous $Na_2SO_4$ and concentrated under reduced pressure. The residue was purified by flash chromatography on silica gel eluting with dichloromethane/methanol (85:15) to afford the crude product (101 mg), which was then purified by Prep-HPLC to afford the title compound (45.5 mg) as a white solid. $^1$H-NMR (400 MHz, $CD_3OD$) δ 8.42 (s, 1H), 8.04-8.01 (m, 2H), 7.39-7.35 (m, 2H), 7.05 (s, 1H), 5.15 (d, J=39 Hz, 1H), 4.74 (m, 2H), 4.44-4.27 (m, 3H), 3.84-3.73 (m, 2H), 3.00-2.94 (m, 2H), 2.56-2.51 (m, 2H), 2.40-2.11 (m, 1H), 1.88-1.82 (m, 2H), 1.50-1.43 (m, 2H).

Example 12

Preparation of (2S,4R)-4-fluoro-1-(4-fluorophenylsulfonyl)-N-((6-(4-(trifluoromethyl)cyclohex-1-enyl)pyrimidin-4-yl)methyl)pyrrolidine-2-carboxamide

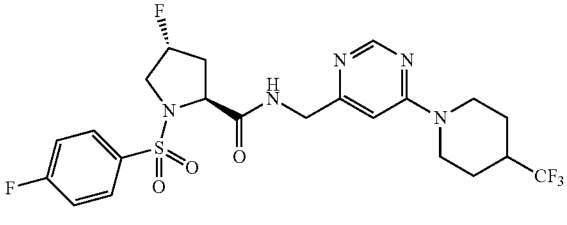 [SMILES: O=C(NCc1cc(N2CCC(C(F)(F)F)CC2)ncn1)[C@@H]1C[C@@H](F)CN1S(=O)(=O)c1ccc(F)cc1]

Step 1: Preparation of [6-[4-(trifluoromethyl)cyclohex-1-en-1-yl]pyrimidin-4-yl]methanol

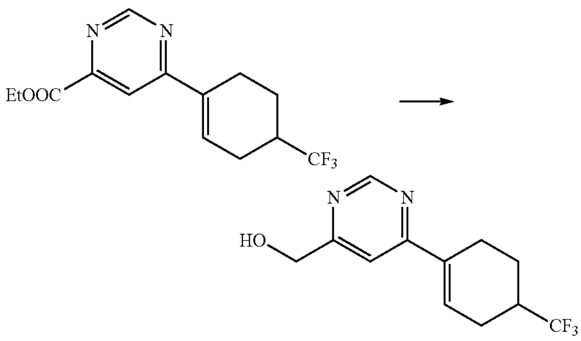

$NaBH_4$ (76 mg, 2.01 mmol) was added portionwise to a solution of ethyl 6-[4-(trifluoromethyl) cyclohex-1-en-1-yl] pyrimidine-4-carboxylate (300 mg, 1.00 mmol) in methanol (10 mL) with stirring. The resulting mixture was stirred for 2 h at 25° C., and concentrated under reduced pressure. The residue was purified by flash chromatography on silica gel eluting with EtOAc/petroleum ether (1:1) to afford the title compound (254 mg) as a white solid.

Step 2: Preparation of 2-([6-[4-(trifluoromethyl) cyclohex-1-en-1-yl]pyrimidin-4-yl]methyl)-2,3-dihydro-1H-isoindole-1,3-dione

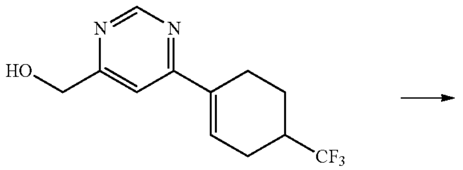

-continued

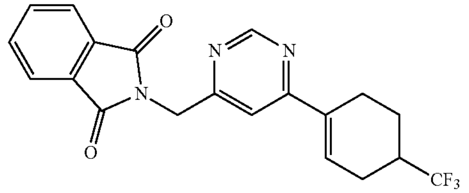

DIAD (235 mg, 1.16 mmol) was added dropwise to a solution of [6-[4-(trifluoromethyl)cyclohex-1-en-1-yl]pyrimidin-4-yl]methanol (150 mg, 0.58 mmol), 2,3-dihydro-1H-isoindole-1,3-dione (94 mg, 0.64 mmol), $PPh_3$ (305 mg, 1.16 mmol) in THF (10 mL) at 0° C. with stirring. The resulting mixture was stirred for 2 h at 25° C., then diluted with water (20 mL), extracted with dichloromethane (3×20 mL). The organic layers were combined and washed with brine (20 mL), dried over anhydrous $Na_2SO_4$ and concentrated under reduced pressure. The residue was purified by flash chromatography on silica gel eluting with EtOAc/petroleum ether (1:1) to afford the title compound (425 mg) as a white solid.

Step 3: Preparation of [6-[4-(trifluoromethyl)cyclohex-1-en-1-yl]pyrimidin-4-yl]methanamine

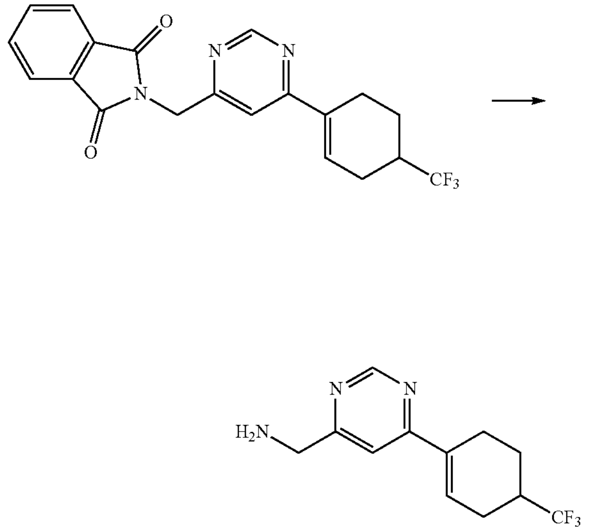

A mixture of 2-([6-[4-(trifluoromethyl)cyclohex-1-en-1-yl]pyrimidin-4-yl]methyl)-2,3-dihydro-1H-isoindole-1,3-dione (425 mg, 1.10 mmol), hydrazine hydrate (80%) (0.5 mL) in methanol (10 mL) was stirred for 3 h at 25° C., and concentrated under reduced pressure. The residue was dissolved in EtOAc (3 mL), and the solids were filtered out. The filtrate was concentrated under reduced pressure to afford the crude title compound (210 mg) as a white solid, which was used in the next step without any further purification.

Step 4: Preparation of (2S,4R)-4-fluoro-1-(4-fluorophenylsulfonyl)-N-((6-(4-(trifluoromethyl)cyclohex-1-enyl)pyrimidin-4-yl)methyl)pyrrolidine-2-carboxamide

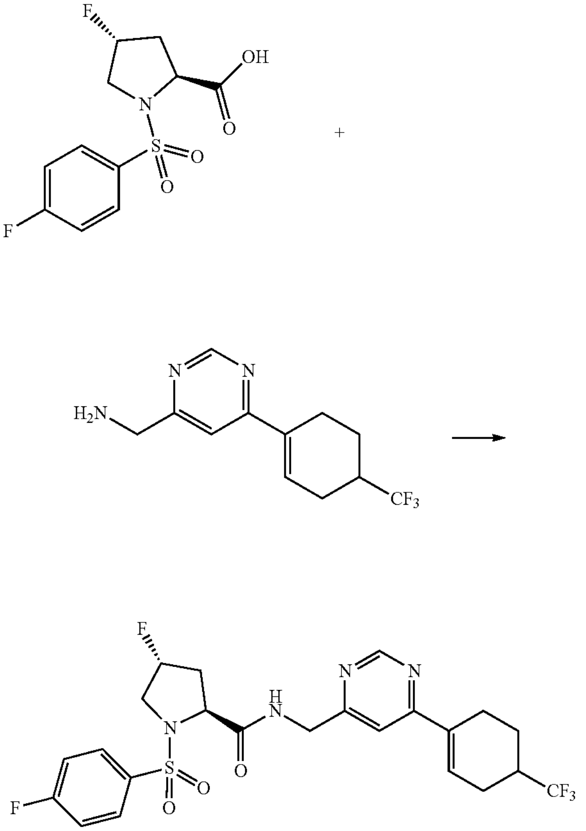

A mixture of [6-[4-(trifluoromethyl) cyclohex-1-en-1-yl] pyrimidin-4-yl]methanamine (284 mg, 1.10 mmol), HATU (465.8 mg, 1.23 mmol), DIPEA (317 mg, 2.45 mmol) in DMF (5 mL) was stirred for 10 min at 25° C. Then (2S,4R)-4-fluoro-1-[(4-fluorobenzene)sulfonyl]pyrrolidine-2-carboxylic acid (210 mg, 0.72 mmol) was added and the resulting mixture was a stirred overnight at 25° C. The reaction mixture was then quenched with water (10 mL), extracted with dichloromethane (3×10 mL). The combined organic layers were washed with brine (2×10 mL), dried over anhydrous $Na_2SO_4$ and concentrated under reduced pressure. The crude product (120 mg) was purified by Flash-Prep-HPLC with the following conditions (IntelFlash-1): Column, C18 silica gel; mobile phase, $CH_3CN:H_2O$ from 10% to 65% within 30 min; Detector, UV 254 nm to afford the title compound (25.8 mg) as a white solid. $^1$H-NMR (300 MHz, $CD_3OD$) δ 8.99 (s, 1H), 8.04 (q, J=6 Hz, 2H), 7.84 (s, 1H), 7.38 (t, J=9 Hz, 2H), 7.15 (s, 1H), 5.16 (d, J=51 Hz, 1H), 4.88-4.86 (d, J=6 Hz, 2H), 4.31 (t, J=9 Hz, 1H), 3.86-3.72 (m, 2H), 2.84 (m, 1H), 2.59-2.47 (m, 4H), 2.32-2.14 (m, 3H), 1.67-1.61 (m, 1H).

Example 13

Preparation of (2S,4R)-4-fluoro-1-(4-fluorophenylsulfonyl)-N-((6-((1s,4R)-4-(trifluoromethyl)cyclohexyl)pyrimidin-4-yl)methyl)pyrrolidine-2-carboxamide and ((2S,4R)-4-fluoro-1-(4-fluorophenylsulfonyl)-N-((6-((1r,4S)-4 (trifluoromethyl)cyclohexyl)-pyrimidin-4-yl)methyl) pyrrolidine-2-carboxamide

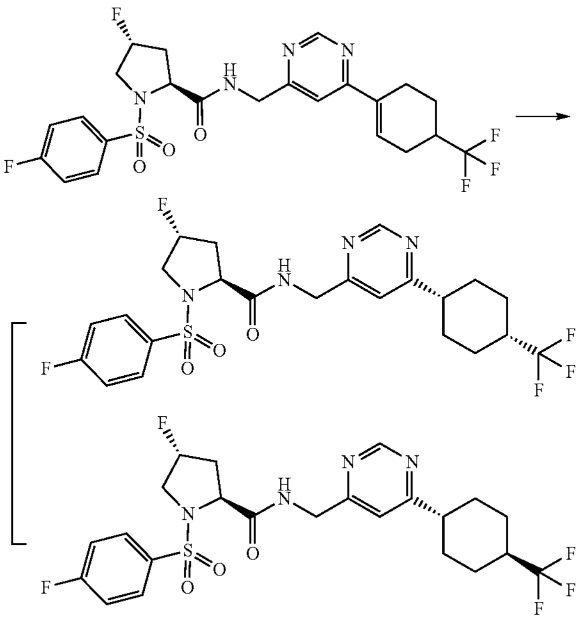

A mixture of (2S,4R)-4-fluoro-1-[(4-fluorobenzene) sulfonyl]-N-([6-[4-(trifluoromethyl)cyclohex-1-en-1-yl]pyrimidin-4-yl]methyl)pyrrolidine-2-carboxamide (180 mg, 0.34 mmol), 10% $Pd(OH)_2/C$ (30 mg) in methanol (20 mL) was stirred for 15 min at 25° C. under an atmosphere of hydrogen gas. The solids were filtered off and the filtrate was concentrated under reduced pressure. The residue (260 mg) was purified by Flash-Prep-HPLC with the following conditions: Column, C18 silica gel; mobile phase, $CH_3CN$:$H_2O$ from 10% to 55% within 30 min; Detector, UV 254 nm to afford a mixture of cis/trans-isomers (120 mg). The isomers were separated by Chiral-Prep-HPLC with the following conditions (Prep-HPLC-004): Column, Chiralpak IA, 2*25 cm, 5 um; mobile phase, Hex and IPA (hold 30.0% IPA in 20 min); Detector, UV 254/220 nm.

Faster eluting isomer (33.6 mg) arbitrarily assigned as trans isomer (2S,4R)-4-fluoro-1-[(4-fluorobenzene) sulfonyl]-N-([6-[(1r,4S)-4-(trifluoromethyl) cyclohexyl]pyrimidin-4-yl]methyl) pyrrolidine-2-carboxamide: $^1$H-NMR (300 MHz, $CD_3OD$) δ 8.97 (s, 1H), 8.04 (q, J=6 Hz, 2H), 7.71 (s, 1H), 7.37 (t, J=9 Hz, 2H), 5.16 (d, J=54 Hz, 1H), 4.54 (s, 2H), 4.32 (t, J=9 Hz, 1H), 3.86-3.72 (m, 2H), 2.72 (t, J=3 Hz, 1H), 2.51 (m, 1H), 2.27-2.04 (m, 6H), 1.74-1.53 (m, 2H), 1.50-1.44 (m, 2H).

Slower eluting isomer (18 mg), arbitrarily assigned as cis isomer (2S,4R)-4-fluoro-1-[(4-fluorobenzene)sulfonyl]-N-([6-[(1s,4R)-4-(trifluoromethyl)cyclohexyl]pyrimidin-4-yl] methyl)pyrrolidine-2-carboxamide: $^1$H-NMR (300 MHz, $CD_3OD$) δ 9.02 (s, 1H), 8.01 (q, J=6 Hz, 2H), 7.74 (s, 1H), 7.36 (t, J=9 Hz, 2H), 5.15 (d, J=54 Hz, 1H), 4.56 (d, J=3 Hz, 2H), 4.27 (t, J=9 Hz, 1H), 3.86-3.72 (m, 2H), 3.03-3.00 (m, 1H), 2.53-2.51 (m, 1H), 2.35-2.06 (m, 5H), 1.88-1.61 (m, 6H).

Example 14

Preparation of (S)-1-(4-fluorophenylsulfonyl)-2-methyl-N-((6-(5-(trifluoromethyl)pyridin-2-yl)pyrimidin-4-yl)methyl)pyrrolidine-2-carboxamide

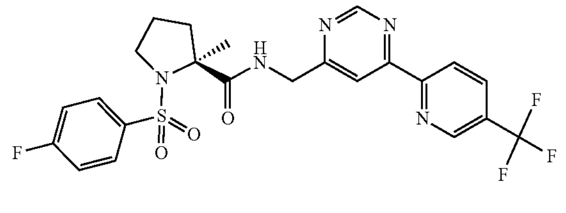 [SMILES: C[C@@]1(C(=O)NCc2cc(-c3ccc(C(F)(F)F)cn3)ncn2)CCCN1S(=O)(=O)c1ccc(F)cc1]

Step 1: Preparation of ethyl 6-hydroxypyrimidine-4-carboxulate

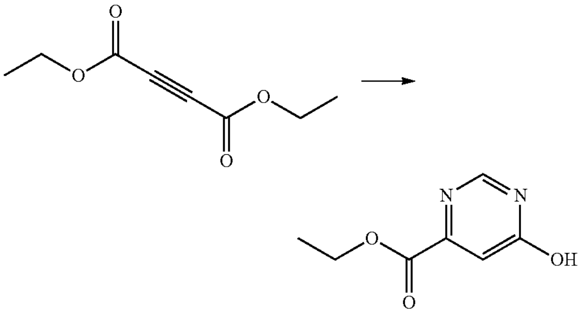

Triethylamine (19 g, 187.8 mmol) was added dropwise to a mixture of 1,4-diethyl but-2-ynedioate (25 g, 146.92 mmol), methanimidamide hydrochloride (11.83 g, 146.93 mmol), $CH_3CN$ (500 mL). The reaction was stirred for 2.5 h at 80° C. in an oil bath and then cooled to 5° C. The crude products were collected by filtration and re-crystallized from $CH_3CN$ to afford the title compound (18.0 g, 73%) as a white solid.

Step 2: Preparation of ethyl 6-chloropyrimidine-4-carboxylate

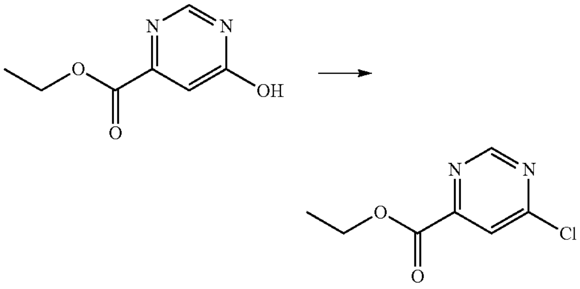

To a mixture of ethyl 6-hydroxypyrimidine-4-carboxylate (5.0 g, 29.74 mmol), EtOAc (150 mL) and N,N-dimethylformamide (0.2 mL) was added $(COCl)_2$ (11.3 g, 89.03 mmol) dropwise with stirring. The reaction was stirred overnight at 75° C. The reaction was cooled and the solids were filtered off. The filtrate was concentrated and purified by a flash chromatography on a silica gel eluting with petroleum ether:EtOAc (10:1-5:1) to afford the title compound (2.2 g, 40%) as a light yellow solid.

Step 3: Preparation of ethyl 6-[5-(trifluoromethyl)pyridin-2-yl]pyrimidine-4-carboxylate

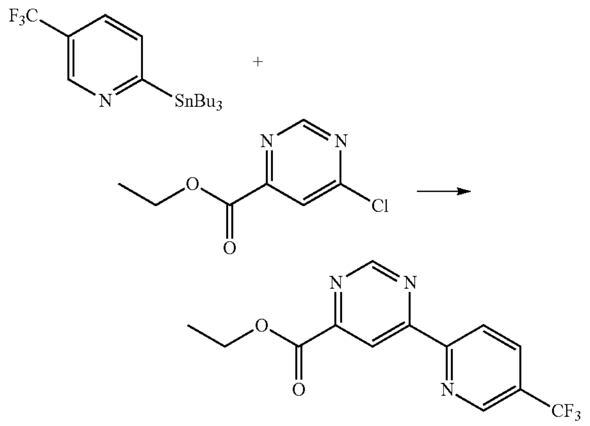

A mixture of 2-(tributylstannyl)-5-(trifluoromethyl)pyridine (8.4 g, 19.26 mmol), $Pd(PPh_3)_2Cl_2$ (558 mg, 0.79 mmol), CuI (168 mg, 0.88 mmol), and ethyl 6-chloropyrimidine-4-carboxylate (900 mg, 4.82 mmol) in DMF (72 mL) was irradiated with microwave radiation for 30 min at 60° C. under nitrogen. The reaction was diluted EtOAc (300 mL), washed with brine (2×), dried over anhydrous $Na_2SO_4$ and concentrated. The residue was purified by flash chromatography on a silica gel eluting with EtOAc/petroleum (10/1) to afford the title compound (300 mg, 21%) as a yellow solid.

Step 4: Preparation of [6-[5-(trifluoromethyl)pyridin-2-yl]pyrimidin-4-yl]methanol

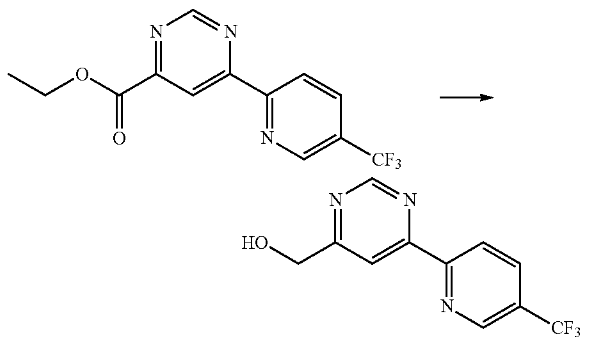

$NaBH_4$ (55 mg, 1.45 mmol) was added to a mixture of ethyl 6-[5-(trifluoromethyl)pyridin-2-yl]pyrimidine-4-carboxylate (290 mg, 0.98 mmol) in THF (30 mL) in portionwise at 0-5° C. The reaction was stirred for 0.5 h at room temperature. The reaction was then quenched with the addition of water (50 mL) at 0-5° C., extracted with EtOAc (3×50 mL), washed with brine (3×30 mL), dried over anhydrous $Na_2SO_4$ and concentrated. The residue was purified by flash chromatography on a silica gel eluting with petroleum ether:EtOAc (5:1) to afford the title compound (216 mg, 87%) as a light yellow solid.

Step 5: Preparation of 2-([6-[5-(trifluoromethyl)pyridin-2-yl]pyrimidin-4-yl]methyl)-2,3-dihydro-1H-isoindole-1,3-dione

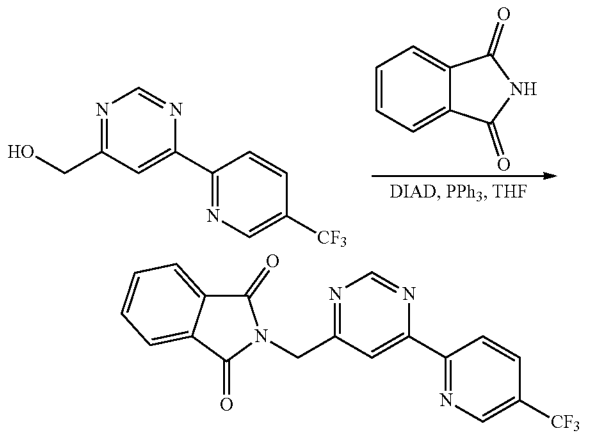

DIAD (326 mg, 1.61 mmol) was added dropwise into a mixture of [6-[5-(trifluoromethyl)pyridin-2-yl]pyrimidin-4-yl]methanol (206 mg, 0.81 mmol), THF (20 mL), $PPh_3$ (423 mg, 1.61 mmol) and 2,3-dihydro-1H-isoindole-1,3-dione (142 mg, 0.97 mmol) with stirring at 0° C. The reaction was stirred for 2 h at room temperature and concentrated. The residue was purified by flash chromatography on a silica gel eluting with petroleum ether:EtOAc (20:1) to afford the title compound (300 mg, 97%) as a white solid.

Step 6: Preparation of [6-[5-(trifluoromethyl)pyridin-2-yl]pyrimidin-4-yl]methanamine

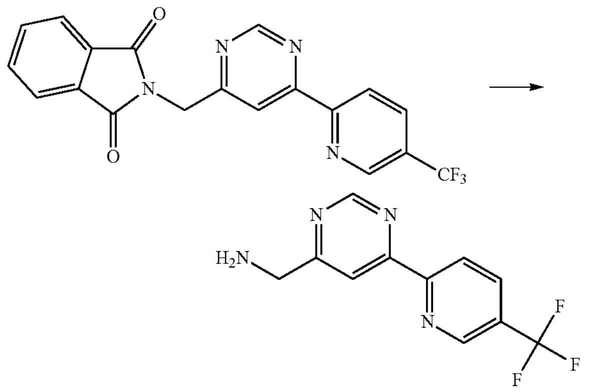

A mixture of 2-([6-[5-(trifluoromethyl)pyridin-2-yl]pyrimidin-4-yl]methyl)-2,3-dihydro-1H-isoindole-1,3-dione (290 mg, 0.75 mmol), methanol (15 mL) and hydrazine hydrate (472 mg, 9.43 mmol) was stirred for 4 h at 40° C. The mixture was concentrated, diluted with water (20 mL), extracted with EtOAc (3x30 mL). The combined organic layers were dried over anhydrous $Na_2SO_4$, concentrated to afford the title compound (360 mg) as a green solid, which was used in the next step without any further purification.

Step 7: Preparation of (2S)-1-[(4-fluorobenzene)sulfonyl]-2-methyl-N-([6-[5-(trifluoromethyl)pyridin-2-yl]pyrimidin-4-yl]methyl)pyrrolidine-2-carboxamide

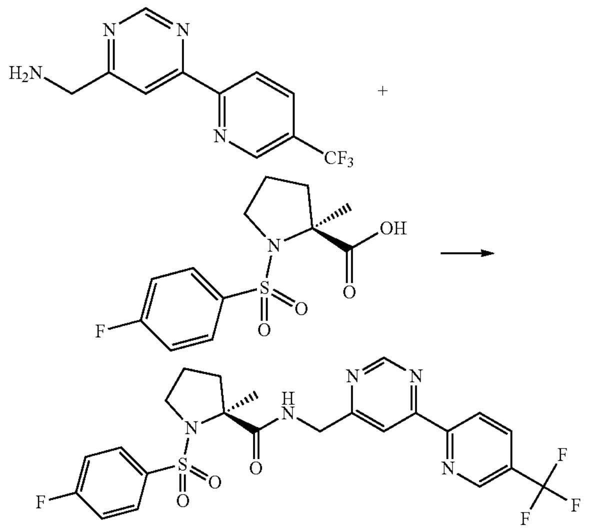

A mixture of (2S)-1-[(4-fluorobenzene)sulfonyl]-2-methylpyrrolidine-2-carboxylic acid (190 mg, 0.66 mmol), N,N-dimethylformamide (5 mL), DIPEA (213 mg, 1.65 mmol, 3.00 equiv), HATU (314 mg, 0.83 mmol) and [6-[5-(trifluoromethyl)pyridin-2-yl]pyrimidin-4-yl]methanamine (140 mg, 0.55 mmol) was stirred overnight at room temperature. The crude solution was purified directly by Prep-HPLC to afford the title compound (7.6 mg, 3%) as a white solid. $^1$H-NMR (300 MHz, DMSO-$d_6$) δ 9.35 (s, 1H), 9.17 (s, 1H), 8.69 (d, J=3 Hz, 1H), 8.60-8.57 (m, 1H), 8.53-8.50 (m, 1H), 8.49 (s, 1H), 8.01-7.96 (m, 2H), 7.50-7.44 (m, 2H), 4.58-4.55 (m, 2H), 3.70-3.50 (m, 2H), 2.31-2.26 (m, 1H), 2.06-1.95 (m, 3H), 1.58 (s, 3H), 1.40-1.20 (m, 1H).

Example 15

Preparation of (2S,4R)—N-([3-chloro-1-[6-(trifluoromethyl)pyridin-3-yl]-1H-pyrazol-4-yl]methyl)-4-fluoro-1-[(4-fluorobenzene)sulfonyl]pyrrolidine-2-carboxamide

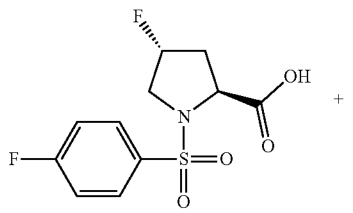

-continued

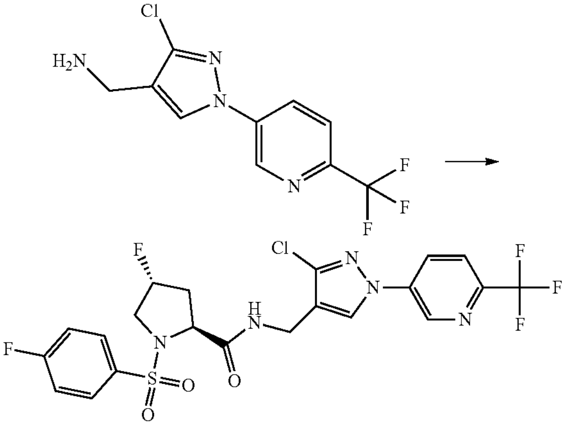

A mixture of (2S,4R)-4-fluoro-1-[(4-fluorobenzene)sulfonyl]-pyrrolidine-2-carboxylic acid (48 mg, 0.16 mmol), DIPEA (63 mg, 0.49 mmol), DMF (3 mL), HATU (94 mg, 0.25 mmol) and [3-chloro-1-[6-(trifluoromethyl)pyridin-3-yl]-1H-pyrazol-4-yl]methanamine (46 mg, 0.17 mmol) was stirred for 2 h at room temperature. The reaction mixture was purified directly by Prep-HPLC to afford the title compound (40 mg, 44%) as a white solid. $^1$H-NMR (300 MHz, $CD_3OD$) δ 9.16 (s, 1H), 8.55 (s, 1H), 8.33-8.37 (m, 1H), 7.94-8.02 (m, 3H), 7.32-7.38 (m, 2H), 5.15 (d, J=52.5 Hz, 1H), 4.39 (s, 2H), 4.25-4.19 (m, 1H), 3.85-3.67 (m, 2H), 2.53-2.42 (m, 1H), 2.29-2.10 (m, 1H).

Example 16

Preparation of (2S,4R)—N-([3-chloro-1-[4-(trifluoromethyl)phenyl]-1H-pyrazol-4-yl]methyl)-4-fluoro-1-[(4-fluorobenzene)sulfonyl]pyrrolidine-2-carboxamide

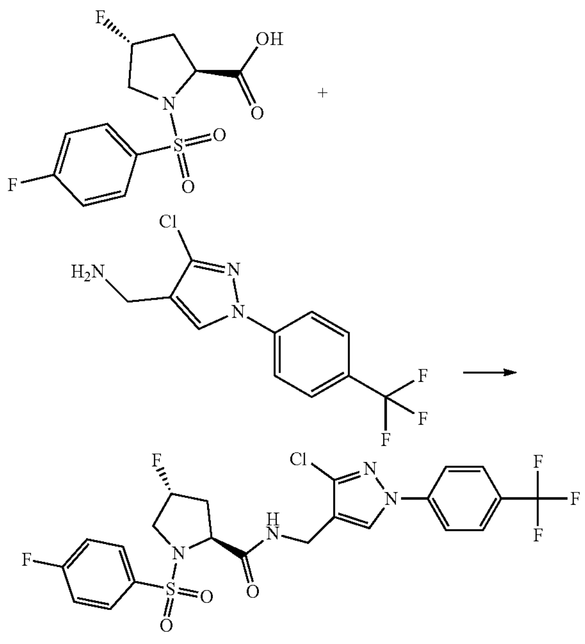

A mixture of (2S,4R)-4-fluoro-1-[(4-fluorobenzene)sulfonyl]-pyrrolidine-2-carboxylic acid (100 mg, 0.34 mmol), DMF (2 mL), DIPEA (132 mg, 1.02 mmol), HATU (194 mg, 0.51 mmol) and [3-chloro-1-[4-(trifluoromethyl) phenyl]-1H-pyrazol-4-yl]methanamine (187 mg, 0.68 mmol) was stirred for 2 h at room temperature. The reaction mixture was purified directly by Prep-HPLC to afford the title compound (38 mg, 20%) as a white solid. $^1$H-NMR (400 MHz, $CD_3OD$) δ 8.45 (s, 1H), 8.00-7.79 (m, 6H), 7.42-7.31 (m, 2H), 5.14 (d, J=52 Hz, 1H), 4.37 (s, 2H), 4.30-4.19 (m, 1H), 3.87-3.69 (m, 3H), 2.52-2.43 (m, 1H), 2.25-2.08 (m, 1H).

Example 17

Preparation of (2S,4R)—N-([3-cyclopropyl-1-[6-(trifluoromethyl)pyridin-3-yl]-1H-pyrazol-4-yl] methyl)-4-fluoro-1-[(4-fluorobenzene)sulfonyl]pyrrolidine-2-carboxamide

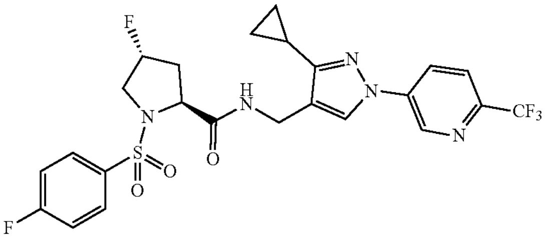 [SMILES: O=C(NCc1cn(-c2ccc(C(F)(F)F)nc2)nc1C1CC1)[C@@H]1C[C@@H](F)CN1S(=O)(=O)c1ccc(F)cc1]

Step 1: Preparation of 2-(cyclopropanecarbonyl)-3-ethoxyprop-2-enenitrile

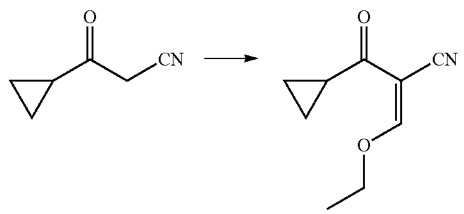

A mixture of 3-cyclopropyl-3-oxopropanenitrile (5.5 g, 50.40 mmol), (diethoxymethoxy)ethane (74.7 g, 504.05 mmol), acetic anhydride (60 mL, 634.74 mmol) was stirred for 2 h at 150° C. The mixture was cooled, concentrated under reduced pressure. The residue was recrystallized from ethanol to afford the title compound (6 g, 72%) as a light yellow solid.

Step 2: Preparation of 3-cyclopropyl-1H-pyrazole-4-carbonitrile

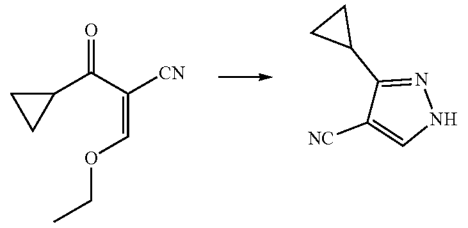

A mixture of 2(cyclopropanecarbonyl)-3-ethoxyprop-2-enenitrile (2 g, 12.11 mmol), hydrazine hydrate (85%) (6.1 g, 121.85 mmol) and ethanol (20 mL) was stirred for 10 min at room temperature. The mixture was concentrated under reduced pressure. The residue was re-crystallized from toluene to afford the title compound (1 g, 62%) as a yellow solid.

Step 3: Preparation of 3-cyclopropyl-1-[6-(trifluoromethyl)pyridin-3-yl]-1H-pyrazole-4-carbonitrile

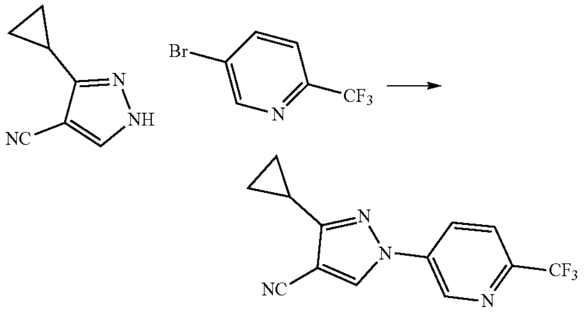

A mixture of 3-cyclopropyl-1H-pyrazole-4-carbonitrile (1 g, 7.51 mmol), 5-bromo-2-(trifluoromethyl)pyridine (2.88 g, 12.74 mmol), CuI (143 mg, 0.75 mmol), L-proline (173 mg, 1.50 mmol), potassium carbonate (2.28 g, 16.50 mmol) and DMSO (50 mL) was stirred for 12 h at 100° C. under nitrogen. The mixture was cooled, diluted with EtOAc (200 mL), washed with brine (3×100 mL), dried over anhydrous $Na_2SO_4$ and concentrated under reduced pressure. The residue was purified by flash chromatography on a silica gel eluting with petroleum ether/EtOAc (50/1) to afford the title compound (1.1 g, 53%) as a white solid.

Step 4: Preparation of [3-cyclopropyl-1-[6-(trifluoromethyl)pyridin-3-yl]-1H-pyrazol-4-yl]methanamine

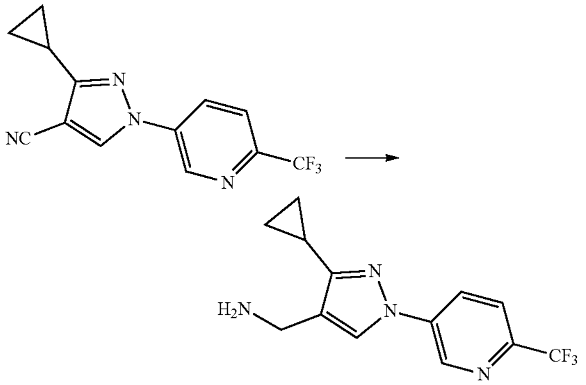

A mixture of 3-cyclopropyl-1-[6-(trifluoromethyl)pyridin-3-yl]-1H-pyrazole-4-carbonitrile (1 g, 3.59 mmol), methanol (50 mL) and RaneyNi (500 mg, 5.84 mmol) was stirred for 15 min at room temperature under an atmosphere of hydrogen gas. The solids were filtered off, and the filtrate was concentrated under reduced pressure to afford the title compound (900 mg) as a white solid, which was used in the next step without any further purification.

Step 5: Preparation of (2S,4R)—N-([3-cyclopropyl-1-[6-(trifluoromethyl)pyridin-3-yl]-1H-pyrazol-4-yl]methyl)-4-fluoro-1-[(4-fluorobenzene)sulfonyl]pyrrolidine-2-carboxamide

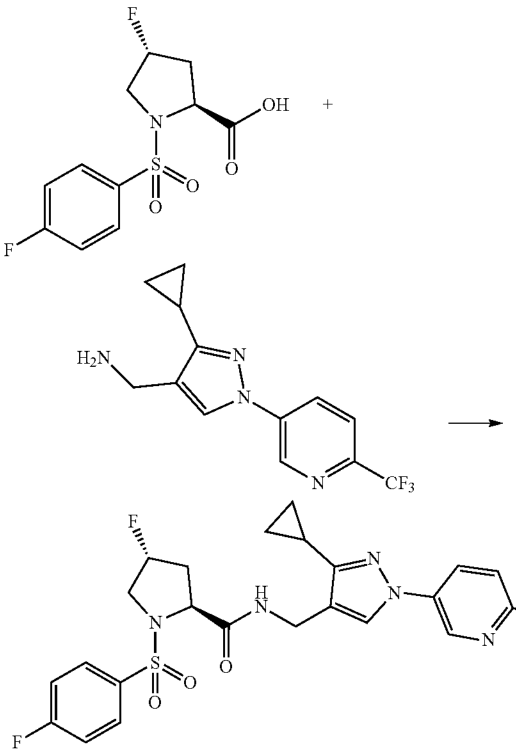

A mixture of (2S,4R)-4-fluoro-1-[(4-fluorobenzene)sulfonyl]pyrrolidine-2-carboxylic acid (80 mg, 0.27 mmol), DMF (5 mL), DIPEA (106.8 mg, 0.83 mmol), HATU (156.6 mg, 0.41 mmol) and 3-cyclopropyl-1-[6-(trifluoromethyl)pyridin-3-yl]-1H-pyrazol-4-ylmethanamine (77.55 mg, 0.27 mmol) was stirred for 1 h at room temperature. The crude solution was purified directly by Prep-HPLC to afford the title compound (50 mg, 33%) as a white solid. $^1$H-NMR (300 MHz, DMSO-$d_6$) δ 9.14 (s, 1H), 8.66 (s, 1H), 8.49 (s, 1H), 8.32 (d, J=7.8 Hz, 1H), 8.02-7.96 (m, 3H), 7.74 (m, 1H), 5.27-5.10 (m, 1H), 4.33-4.30 (m, 2H), 4.19-4.14 (m, 1H), 3.71-3.67 (m, 1H), 3.62-3.58 (m, 1H), 2.51 (m, 1H), 2.42-2.29 (m, 1H), 2.18-1.94 (m, 1H), 0.96-0.90 (m, 4H).

Example 18

Preparation of (2S,4R)—N-([3-chloro-1-[4-(trifluoromethyl)phenyl]-1H-pyrazol-4-yl]methyl)-1-[(4-cyanobenzene)sulfonyl]-4-fluoropyrrolidine-2-carboxamide

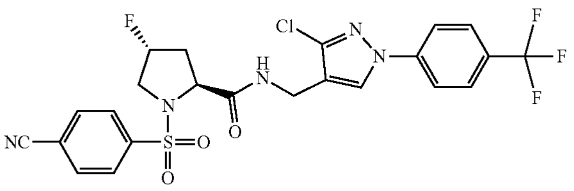 [SMILES: N#Cc1ccc(S(=O)(=O)N2C[C@H](F)C[C@H]2C(=O)NCc2cn(-c3ccc(C(F)(F)F)cc3)nc2Cl)cc1]

Step 1: Preparation of (2S,4R)-1-[(4-cyanobenzene)sulfonyl]-4-fluoropyrrolidine-2-carboxylic acid

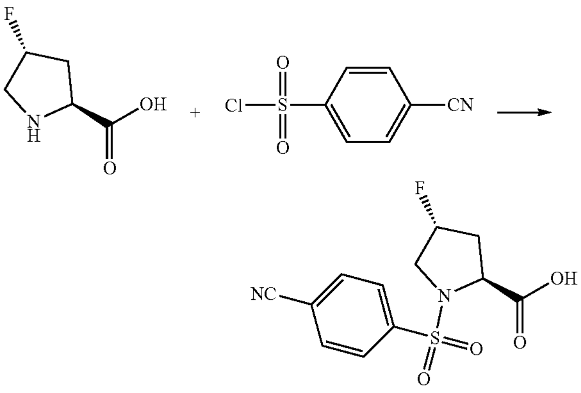

A mixture of (2S,4R)-4-fluoropyrrolidine-2-carboxylic acid (79 mg, 0.59 mmol), tetrahydrofuran (5 mL), water (2 mL), sodium carbonate (121 mg, 1.13 mmol) and 4-cyanobenzene-1-sulfonyl chloride (100 mg, 0.50 mmol) was stirred for 1 h at 0° C. The mixture was diluted with water, extracted with ether (30 mL). The aqueous layers was acidified with 3 N HCl to pH=2-3, extracted with EtOAc (3×50 mL). The combined organic layers were dried over anhydrous Na2SO4 and concentrated to afford the title compound (100 mg, 68%) as a white solid, which was used in the next step without any further purification.

Step 2: Preparation of (2S,4R)—N-([3-chloro-1-[4-(trifluoromethyl)phenyl]-1H-pyrazol-4-yl]methyl)-1-[(4-cyanobenzene)sulfonyl]-4-fluoropyrrolidine-2-carboxamide

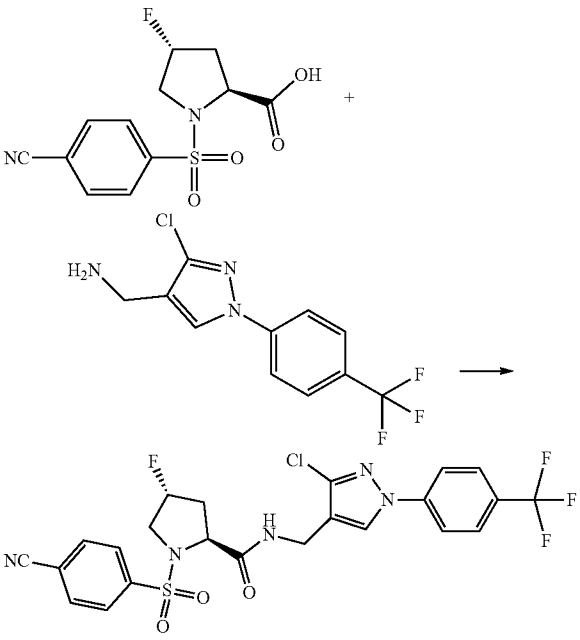

A mixture of (2S,4R)-1-[(4-cyanobenzene)sulfonyl]-4-fluoropyrrolidine-2-carboxylic acid (180 mg, 0.60 mmol), N,N-dimethylformamide (5 mL), DIPEA (234 mg, 1.81 mmol), HATU (234 mg, 0.62 mmol) and [3-chloro-1-[4-(trifluoromethyl)phenyl]-1H-pyrazol-4-yl]methanamine (234 mg, 0.85 mmol) was stirred overnight at room temperature. The reaction mixture was purified by Prep-HPLC to afford the title compound (85.1 mg, 25%) as a white solid. $^1$H-NMR (300 MHz, DMSO-$d_6$) δ 8.74 (m, 1H), 8.60 (s, 1H), 8.12-8.04 (m, 4H), 7.99-7.88 (m, 4H), 5.20 (d, J=51.9 Hz, 1H), 4.21-4.17 (m, 3H), 3.85-3.55 (m, 2H), 2.77-2.33 (m, 1H), 2.19-1.98 (m, 1H).

Example 19

Preparation of (2S,4R)-4-fluoro-1-(4-fluorophenylsulfonyl)-2-methyl-N-((6-(6-(trifluoromethyl)pyridin-3-yl)pyrimidin-4-yl)methyl)pyrrolidine-2-carboxamide

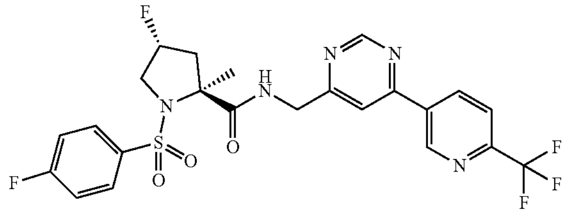 [SMILES: C[C@@]1(C(=O)NCc2cc(-c3ccc(C(F)(F)F)nc3)ncn2)C[C@@H](F)CN1S(=O)(=O)c1ccc(F)cc1]

Step 1: Preparation of 1-tert-Butyl 2-methyl (2S,4R)-4-fluoropyrrolidine-1,2-dicarboxylate

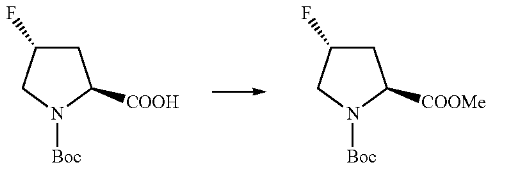 [SMILES: CC(C)(C)OC(=O)N1C[C@H](F)C[C@H]1C(=O)O ; COC(=O)[C@@H]1C[C@@H](F)CN1C(=O)OC(C)(C)C]

A mixture of (2S,4R)-1-[(tert-butoxy)carbonyl]-4-fluoropyrrolidine-2-carboxylic acid (2 g, 8.57 mmol), potassium carbonate (5.9 g, 42.69 mmol), THF (80 mL) and $CH_3I$ (6.1 g, 42.98 mmol) was stirred for 12 h at room temperature. The solids were filtered off and the filtrate was concentrated under reduced pressure. The residue was purified by flash chromatography on silica gel eluting with EtOAc/petroleum ether (1:5) to afford the title compound (800 mg, 38%) as colorless oil.

Step 2: Preparation of 1-tert-butyl 2-methyl (4R)-4-fluoro-2-methylpyrrolidine-1,2-dicarboxylate

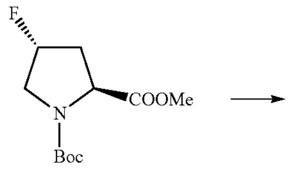

-continued

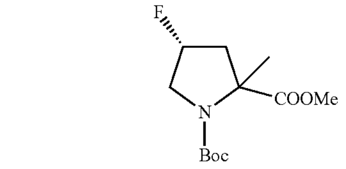

A 1 M solution of LiHMDS (4.85 mL, 4.85 mmol) was added dropwise into a mixture of 1-tert-butyl 2-methyl (2S,4R)-4-fluoropyrrolidine-1,2-dicarboxylate (400 mg, 1.62 mmol) in THF (20 mL) with stirring at −78° C. under nitrogen. The reaction solution was stirred for 30 min at −78° C. To this was added $CH_3I$ (690 mg, 4.86 mmol) dropwise at −78° C. The reaction mixture stirred for 12 h at room temperature, quenched with water (20 mL), extracted with EtOAc (3×30 mL), dried over anhydrous $Na_2SO_4$ and concentrated. The residue was purified by flash chromatography on silica gel eluting with EtOAc/petroleum ether (1:5) to afford the title compound (360 mg, 85%) as colorless oil.

Step 3: Preparation of 4R-4-fluoro-2-methylpyrrolidine-2-carboxylic acid hydrochloride

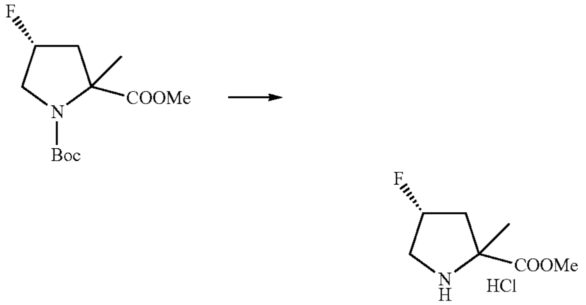 [SMILES: COC(=O)C1(C)C[C@@H](F)CN1C(=O)OC(C)(C)C ; COC(=O)C1(C)C[C@@H](F)CN1 ; Cl]

A mixture of 1-tert-butyl 2-methyl (4R)-4-fluoro-2-methylpyrrolidine-1,2-dicarboxylate (360 mg, 1.38 mmol) and HCl in dioxane (10 mL, 1 mol/L) was stirred for 2 h at room temperature. The mixture was concentrated to afford the crude product (315 mg) as a light yellow solid, which was used in the next step without any further purification.

Step 4: Preparation of methyl (4R)-4-fluoro-[4(4-fluorobenzene)sulfonyl]-2-methylpyrrolidine-2-carboxylate

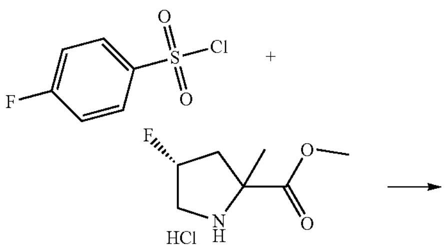

-continued

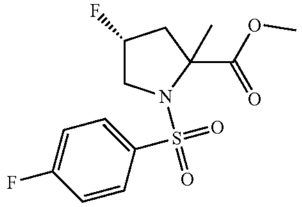

A mixture of 4R-4-fluoro-2-methylpyrrolidine-2-carboxylate hydrochloride (315 mg, 1.60 mmol), triethylamine (485 mg, 4.80 mmol), dichloromethane (20 mL) and 4-fluorobenzene-1-sulfonyl chloride (310 mg, 1.60 mmol) was stirred for 12 h at room temperature. The reaction was diluted with dichloromethane (100 mL), washed with brine (3×20 mL), dried over anhydrous $Na_2SO_4$ and concentrated. The residue was purified by flash chromatography on silica gel eluting with EtOAc/petroleum ether (1:4) to afford the title compound (380 mg) as colorless oil, which was used in the next step without any further purification.

Step 5: Preparation of (4R)-4-fluoro-1-[(4-fluorobenzene)sulfonyl]-2-methylpyrrolidine-2-carboxylic acid

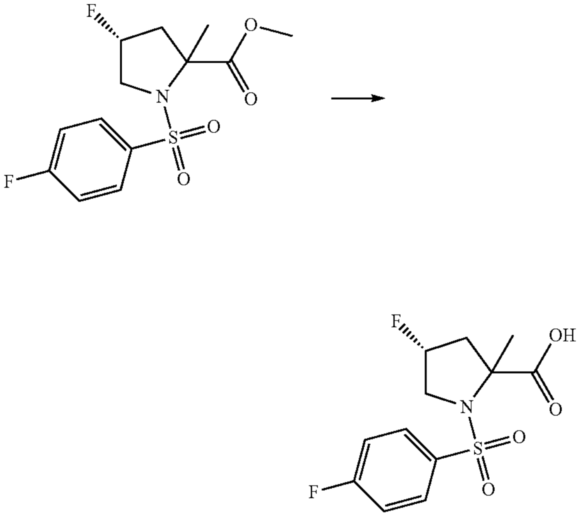

A mixture of methyl (4R)-4-fluoro-1-[(4-fluorobenzene) sulfonyl]-2-methylpyrrolidine-2-carboxylate (380 mg, 1.19 mmol), LiOH (58 mg, 2.42 mmol), methanol (8 mL), water (2 mL) was stirred for 12 h at room temperature. The reaction mixture was concentrated, dissolved in water (20 mL), extracted with ether (3×20 mL). The aqueous layers was acidified with 3 N HCl (pH 2-3), extracted with EtOAc (3×50 mL), dried over anhydrous $Na_2SO_4$ and concentrated to afford the title compound (260 mg, 72%) as yellow oil, which was used in the next step without any further purification.

Step 6: Preparation of (2S,4R)-4-fluoro-1-(4-fluorophenylsulfonyl)-2-methyl-N-((6-(6-(trifluoromethyl) pyridin-3-yl)pyrimidin-4-yl)methyl)pyrrolidine-2-carboxamide

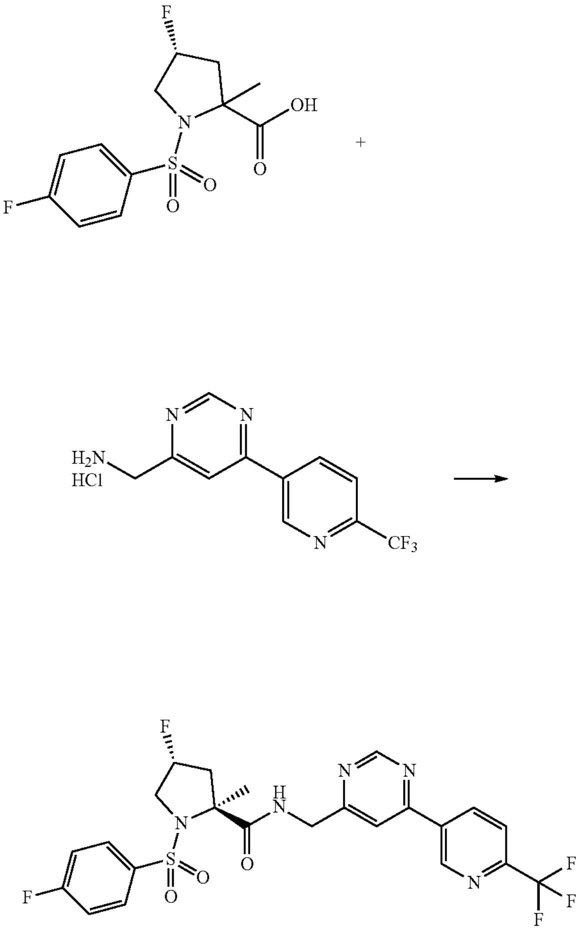

A mixture of (4R)-4-fluoro-1-[(4-fluorobenzene)sulfonyl]-2-methylpyrrolidine-2-carboxylic acid (125 mg, 0.41 mmol), DMF (4 mL), HATU (228 mg, 0.60 mmol), DIPEA (206 mg, 1.59 mmol) and [6-[6-(trifluoromethyl)pyridin-3-yl]pyrimidin-4-yl]methanamine hydrochloride (104 mg, 0.36 mmol) was stirred for 12 h at room temperature. The mixture was diluted with water (20 mL), extracted with EtOAc (3×50 mL). The combined organic layers were washed with brine, dried over anhydrous $Na_2SO_4$ and concentrated. The residue was purified by flash chromatography on silica gel eluting with EtOAc/petroleum ether (1:1 to 2:1).

Slower eluting isomer (72.7 mg) was assigned by potency as (2S,4R)-4-fluoro-1-(4-fluorophenylsulfonyl)-2-methyl-N-((6-(6-(trifluoromethyl)pyridin-3-yl)pyrimidin-4-yl) methyl)pyrrolidine-2-carboxamide: $^1$H-NMR (300 MHz, $CD_3OD$) δ 9.50 (s, 1H), 9.20 (s, 1H), 8.83 (d, J=8.4 Hz, 1H), 8.31 (s, 1H), 8.06-7.98 (m, 3H), 7.37 (t, J=17.4 Hz, 2H), 5.26 (d, J=51 Hz, 1H), 4.80 (d, J=15 Hz, 1H), 4.54 (d, J=17.4 Hz, 1H), 4.19-4.07 (m, 1H), 3.76-3.60 (m, 1H), 2.76-2.64 (m, 1H), 2.33-2.14 (m, 1H), 1.61 (s, 3H).

Example 20

Preparation of (2S,4R)-4-fluoro-1-(4-fluorophenylsulfonyl)-2-methyl-N-((6-(4-(trifluoromethyl)phenyl)pyrimidin-4-yl)methyl)pyrrolidine-2-carboxamide

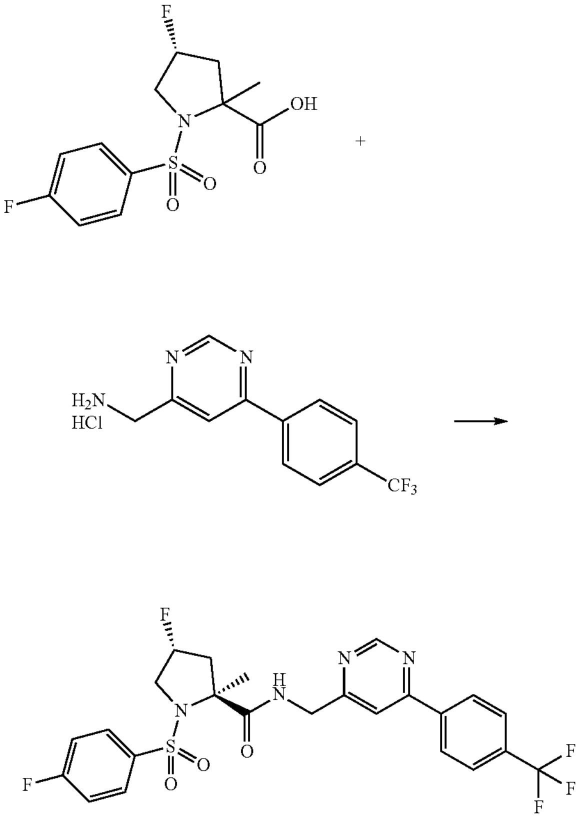

A mixture of (4R)-4-fluoro-1-[(4-fluorobenzene)sulfonyl]-2-methylpyrrolidine-2-carboxylic acid (125 mg, 0.41 mmol), DMF (4 mL), HATU (234 mg, 0.62 mmol), DIPEA (212 mg, 1.64 mmol) and [6-[4-(trifluoromethyl)phenyl]pyrimidin-4-yl]methanamine hydrochloride (106 mg, 0.37 mmol) was stirred for 12 h at room temperature. The mixture was diluted with water (20 mL), extracted with EtOAc (3×50 mL), washed with brine (3×20 mL), dried over anhydrous $Na_2SO_4$ and concentrated. The residue was purified by flash chromatography on silica gel eluting with EtOAc/petroleum ether (1:1).

Faster eluting isomer (24.8 mg) (2S,4R)-4-fluoro-1-(4-fluorophenylsulfonyl)-2-methyl-N-((6-(4-(trifluoromethyl)phenyl)pyrimidin-4-yl)methyl)pyrrolidine-2-carboxamide: $^1$H-NMR (300 MHz, $CD_3OD$) δ 9.19 (d, J=1.2 Hz, 1H), 8.45 (d, J=7.8 Hz, 2H), 8.34 (s, 1H), 8.05-8.01 (m, 2H), 7.77 (d, J=8.4 Hz, 2H), 7.32 (t, J=8.7 Hz, 2H), 5.30 (d, J=51.9 Hz, 1H), 4.71-4.51 (m, 2H), 3.94-3.90 (m, 1H), 3.82 (d, J=2.4 Hz, 1H), 2.72-2.34 (m, 2H), 1.82 (s, 3H).

Example 21

Preparation of (2S,4R)-4-fluoro-1-(4-fluorophenylsulfonyl)-N-((6-(4-(trifluoromethoxy)phenyl)pyrimidin-4-yl)methyl)pyrrolidine-2-carboxamide

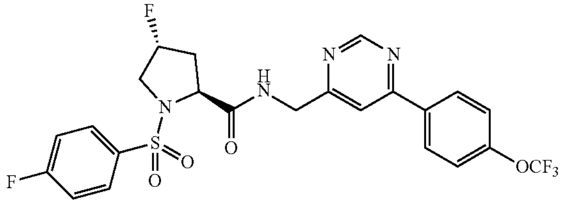 [SMILES: O=C(NCc1cc(-c2ccc(OC(F)(F)F)cc2)ncn1)[C@@H]1C[C@@H](F)CN1S(=O)(=O)c1ccc(F)cc1]

Step 1: Preparation of 4-chloro-6-[4-(trifluoromethoxy)phenyl]pyrimidine

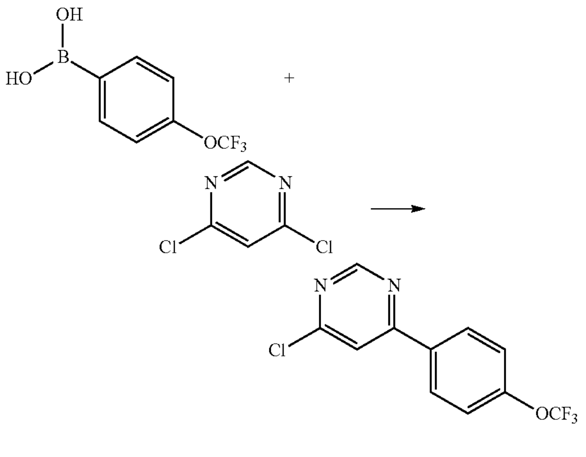

A mixture of 4,6-dichloropyrimidine (2.17 g, 14.57 mmol), [4-(trifluoromethoxy)phenyl]boronic acid (1 g, 4.86 mmol), Pd(dppf)$Cl_2$ (731 mg, 1.00 mmol), potassium carbonate (5 g, 36.18 mmol), dioxane (40 mL) and water (4 mL) was stirred for 12 h at 100° C. under nitrogen. The mixture was diluted with EtOAc (150 mL), washed with brine (3×), dried and concentrated. The residue was purified by flash chromatography on silica gel eluting with EtOAc/petroleum ether (1/50) to afford the title compound (1.1 g, 82%) as a white solid.

Step 2: Preparation of 6-[4-(trifluoromethoxy)phenyl]pyrimidine-4-carbonitrile

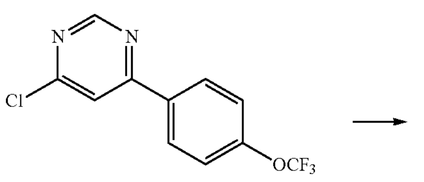

-continued

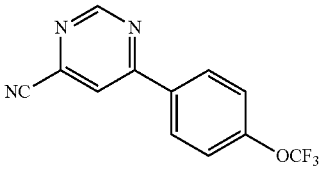

A mixture of 4-chloro-6-[4-(trifluoromethoxy)phenyl]pyrimidine (820 mg, 2.99 mmol), $Zn(CN)_2$ (421 mg, 3.58 mmol), $Pd(PPh_3)_4$ (347 mg, 0.30 mmol), DMF (6 mL) was stirred for 9 h at 100° C. under nitrogen. The reaction was cooled, diluted with water (30 mL), extracted with EtOAc (3×50 mL). The combined organic layers were washed with brine, dried over anhydrous $Na_2SO_4$ and concentrated. The residue was purified by flash chromatography on silica gel eluting with EtOAc/petroleum ether (1/50) to afford the title compound (320 mg, 40%) as a white solid.

Step 3: Preparation of (6-(4-(trifluoromethoxy)phenyl)pyrimidin-4-yl)methanamine hydrochloride

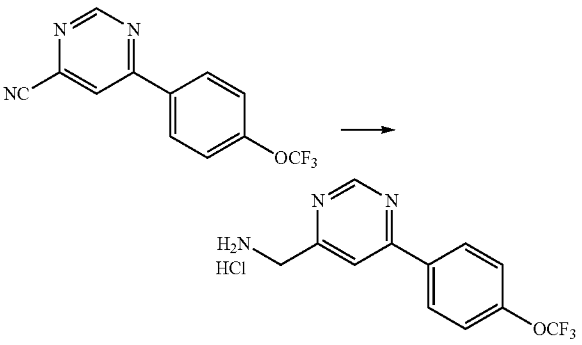

A mixture of 6-[4-(trifluoromethoxy)phenyl]pyrimidine-4-carbonitrile (160 mg, 0.60 mmol), ethanol (10 mL), concentrated HCl solution (0.02 mL), 10% Palladium over carbon (100 mg) was stirred for 10 min at room temperature under an atmosphere of hydrogen gas. The solids were filtered off and the filtrate was concentrated to afford the crude product (200 mg) as a solid, which was used in the next step without any further purification.

Step 4: Preparation of (2S,4R)-4-fluoro-1-(4-fluorophenylsulfonyl)-N-((6-(4-(trifluoromethoxy)phenyl)pyrimidin-4-yl)methyl)pyrrolidine-2-carboxamide

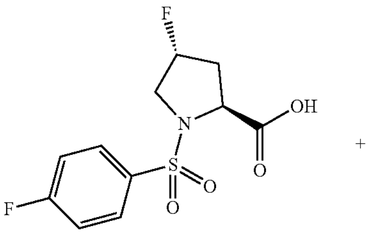

-continued

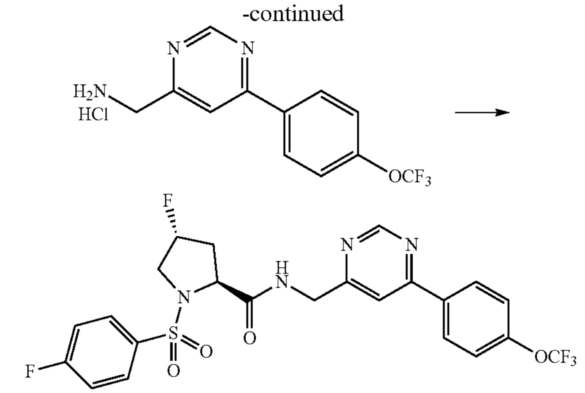

A mixture of (2S,4R)-4-fluoro-1-[(4-fluorobenzene)sulfonyl]pyrro-lidine-2-carboxylic acid (150 mg, 0.51 mmol), DMF (4 mL), DIPEA (263 mg, 2.03 mmol), HATU (294 mg, 0.77 mmol) and [6-[4-(trifluoromethoxy)phenyl]pyrimidin-4-yl]methanamine (200 mg, 0.74 mmol) was stirred for 12 h at room temperature. The crude solution was purified directly by Prep-HPLC to afford the title compound (51 mg, 13%) as a white solid. $^1$H-NMR (300 MHz, $CD_3OD$) δ 9.15 (s, 1H), 8.41 (d, J=8.7 Hz, 6H), 8.25 (s, 1H), 8.08-8.03 (m, 2H), 7.40-7.34 (m, 4H), 5.17 (d, J=51.6 Hz, 1H), 4.63 (d, J=4.8 Hz, 2H), 4.37-4.31 (m, 1H), 3.88-3.75 (m, 2H), 2.61-2.48 (m, 1H), 2.35-2.11 (m, 1H).

Example 22

Preparation of (2S,4R)-4-fluoro-1-(4-fluorophenylsulfonyl)-N-((2-methyl-6-(6-(trifluoromethyl)pyridin-3-yl)pyrimidin-4-yl)methyl)pyrrolidine-2-carboxamide

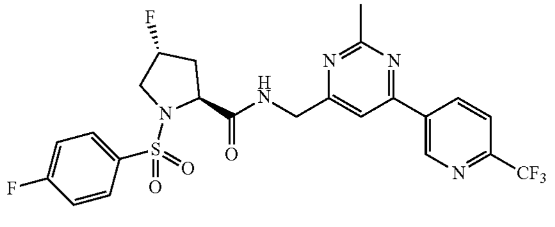 [SMILES: Cc1nc(CNC(=O)[C@@H]2C[C@@H](F)CN2S(=O)(=O)c2ccc(F)cc2)cc(-c2ccc(C(F)(F)F)nc2)n1]

Step 1: Preparation of 4-chloro-2-methyl-6-[6-(trifluoromethyl)pyridin-3-yl]pyrimidine

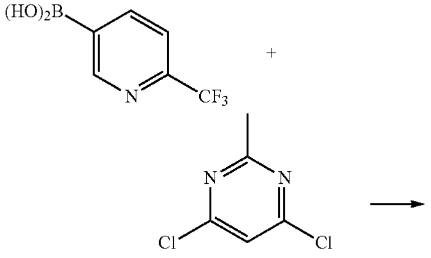

-continued

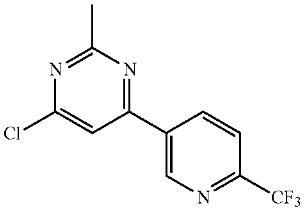

A mixture of 4,6-dichloro-2-methylpyrimidine (1 g, 6.13 mmol), [6-(trifluoromethyl)pyridin-3-yl]boronic acid (229 mg, 1.20 mmol), potassium carbonate (2.07 g, 14.98 mmol), dioxane (50 mL), water (2 mL) and $Pd(dppf)Cl_2$ (320 mg, 0.44 mmol) was irradiated with microwave radiation for 3 h at 100° C. under nitrogen. The mixture was diluted with EtOAc (150 mL), washed with brine (3×50 mL), dried over anhydrous $Na_2SO_4$ and concentrated. The residue was purified by flash chromatography on silica gel eluting with EtOAc/petroleum ether (1/10) to afford the title compound (1.1 g, 66%) as a white solid.

Step 2: Preparation of 2-methyl-6-[6-(trifluoromethyl)pyridin-3-yl]pyrimidine-4-carbonitrile

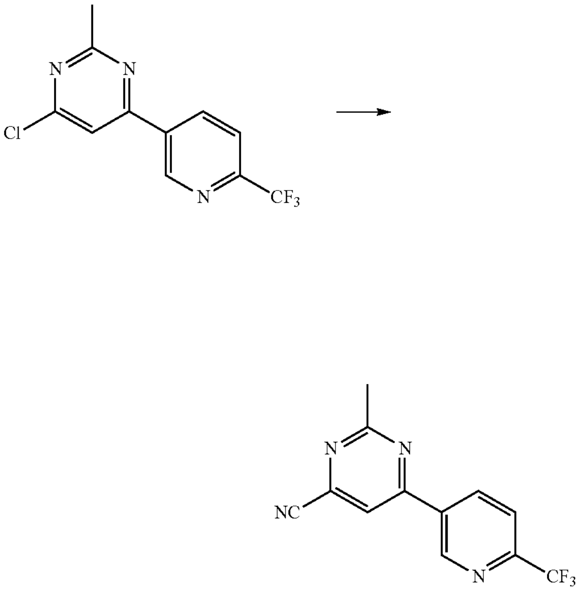

A mixture of 4-chloro-2-methyl-6-[6-(trifluoromethyl) pyridin-3-yl]pyrimidine (300 mg, 1.10 mmol), DMF (5 mL), $Zn(CN)_2$ (128.7 mg, 1.10 mmol), dppf (60.9 mg, 0.11 mmol) and $Pd_2(dba)_3CHCl_3$ (113.9 mg, 0.11 mmol) was irradiated with microwave radiation for 3 h at 120° C. under nitrogen. The mixture was diluted with EtOAc (100 mL), washed with brine (3×), dried over anhydrous $Na_2SO_4$ and concentrated. The residue was purified by flash chromatography on silica gel eluting with EtOAc/petroleum ether (1/10) to afford the title compound (250 mg, 86%) as a white solid.

Step 3: Preparation of [2-methyl-6-[6-(trifluoromethyl)pyridin-3-yl]pyrimidin-4-yl]methanamine hydrogen chloride

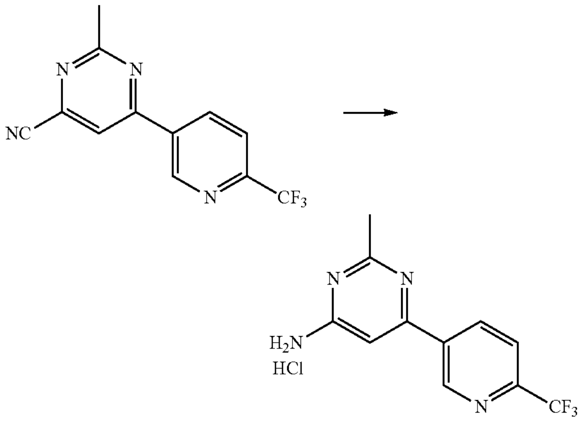

A mixture of 2-methyl-6-[6-(trifluoromethyl)pyridin-3-yl]pyrimidine-4-carbonitrile (250 mg, 0.94 mmol), ethanol (20 mL), concentrated HCl (0.2 mL) and 10% Palladium carbon (200 mg) was stirred for 5 min at room temperature under an atmosphere of hydrogen gas. The solids were filtered off and the filtrate was concentrated to afford the crude product (200 mg) as a black solid, which was used in the next step without any further purification.

Step 4: Preparation of (2S,4R)-4-fluoro-1-(4-fluorophenylsulfonyl)-N-((2-methyl-6-(6-(trifluoromethyl) pyridin-3-yl)pyrimidin-4-yl)methyl)pyrrolidine-2-carboxamide

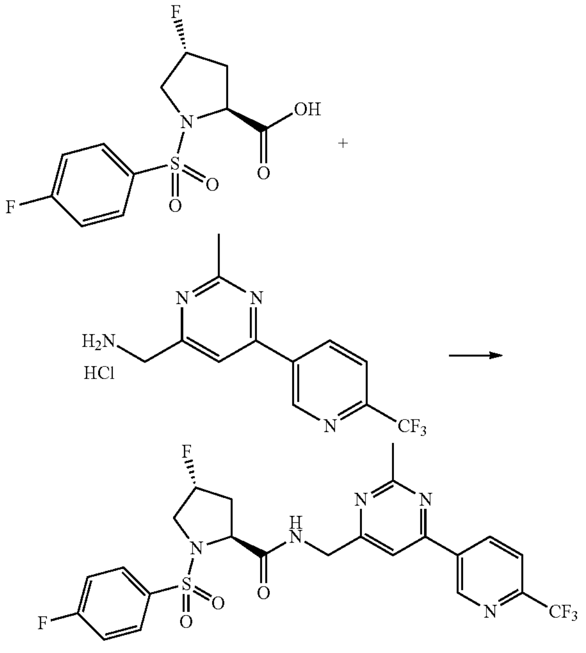

A mixture of (2S,4R)-4-fluoro-1-[(4-fluorobenzene) sulfonyl]pyrrolidine-2-carboxylic acid (107.7 mg, 0.37 mmol), DMF (5 mL), DIPEA (144.4 mg, 1.12 mmol), HATU (212.8 mg, 0.56 mmol) and [2-methyl-6-[6-(trifluoromethyl)pyridin-3-yl]pyrimidin-4-yl]methanamine hydrogen chloride (112 mg, 0.37 mmol) was stirred for 1 h at room temperature. The crude solution was purified directly by Prep-HPLC to afford the title compound (32.9 mg, 16%) as a white solid. $^1$H-NMR (300 MHz, DMSO-$d_6$) δ 9.46 (s, 1H), 8.69 (d, J=7.2 Hz, 1H), 7.94-7.91 (m, 3H), 7.89 (d, J=8.1 Hz, 1H), 7.61 (s, 1H), 7.28-7.23 (m, 1H), 5.09 (d, J=52.2 Hz, 1H), 4.94-4.89 (m, 1H), 4.50-4.45 (m, 1H), 4.37-4.31 (m, 1H), 3.96-3.62 (m, 2H), 2.83 (s, 3H), 2.64-2.54 (m, 1H), 2.34-1.52 (m, 1H).

Example 23

Preparation of (2S,4R)—N-((6-(6-cyclopropylpyridin-3-yl)pyrimidin-4-yl)methyl)-4-fluoro-1-(4-fluorophenylsulfonyl)pyrrolidine-2-carboxamide

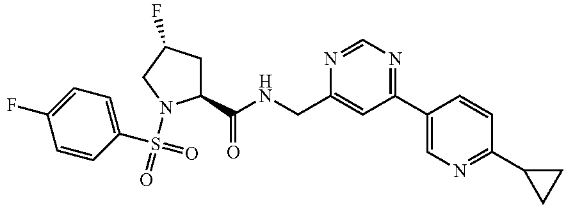 [SMILES: O=C(NCc1cc(-c2ccc(C3CC3)nc2)ncn1)[C@@H]1C[C@@H](F)CN1S(=O)(=O)c1ccc(F)cc1]

Step 1: Preparation of 2-cyclopropyl-5-(tetramethyl-1,3,2-dioxaborolan-2-yl)pyridine

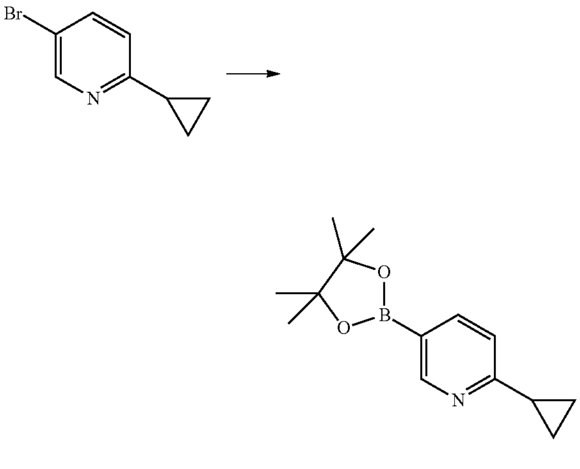

A mixture of 4,4,5,5-tetramethyl-2-(tetramethyl-1,3,2-dioxaborolan-2-yl)-1,3,2-dioxaborolane (2.7 g, 10.63 mmol), Pd(dppf)$Cl_2$ (519 mg, 0.71 mmol), KOAc (1.39 g, 14.16 mmol), 1,4-dioxane (100 mL) and 5-bromo-2-cyclopropylpyridine (1.4 g, 7.07 mmol) was stirred for 6 h at 90° C. under nitrogen. The mixture was concentrated and purified by flash chromatography on a silica gel eluting with petroleum ether/EtOAc (10/1) to afford the title compound (1.5 g, 87%) as brown oil.

Step 2: Preparation of 6-(6-cyclopropylpyridin-3-yl)pyrimidine-4-carboxylic acid

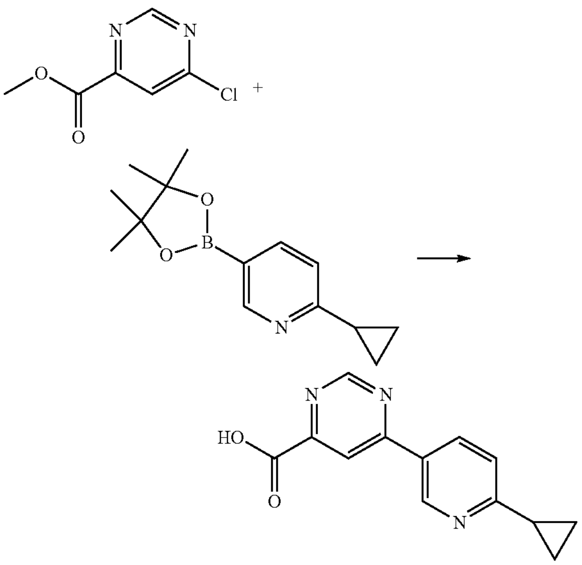

A mixture of 2-cyclopropyl-5-(tetramethyl-1,3,2-dioxaborolan-2-yl)pyridine (1.5 g, 6.12 mmol), ethyl 6-chloropyrimidine-4-carboxylate (1.3 g, 6.97 mmol), Pd($PPh_3$)$_4$ (1.04 g, 0.90 mmol), $K_3PO_4$ (3.18 g, 14.98 mmol), 1,4-dioxane (100 mL) and water (10 mL) was stirred overnight at 65° C. under nitrogen. The mixture was concentrated, diluted with water (50 mL), acidified with 3 N HCl (pH 2-3), extracted with EtOAc (3×100 mL). The combined organic layers were dried over anhydrous $Na_2SO_4$ and concentrated to afford the title compound (2.6 g) as a brown solid, which was used in the next step without any further purification.

Step 3: Preparation of methyl 6-(6-cyclopropylpyridin-3-yl)pyrimidine-4-carboxylate

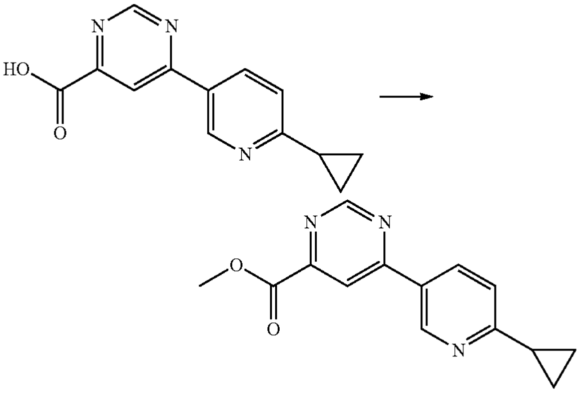

A mixture of 6-(6-cyclopropylpyridin-3-yl)pyrimidine-4-carboxylic acid (2.6 g, 10.78 mmol), methanol (60 mL, 1.48 mol), concentrated $H_2SO_4$ (0.5 mL, 98%) was stirred overnight at 70° C. The mixture was concentrated under reduced pressure, dissolved with EtOAc (150 mL), washed with saturated $NaHCO_3$ (3×30 mL), dried over anhydrous $Na_2SO_4$ and concentrated to afford the title compound (310 mg) as a brown solid, which was used in the next step without any further purification.

Step 4: Preparation of [6-(6-cyclopropylpyridin-3-yl)pyrimidin-4-yl]methanol

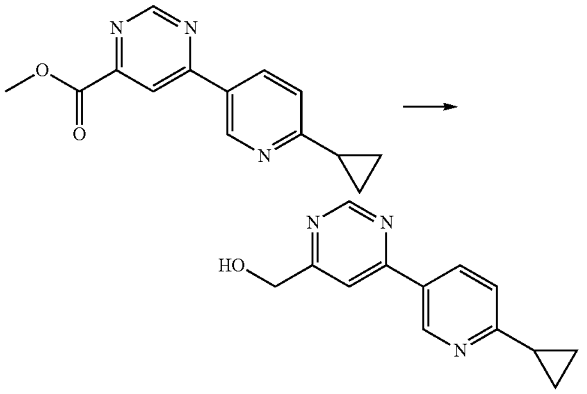

$NaBH_4$ (136 mg, 3.69 mmol) was added into a solution of 6-(6-cyclopropylpyridin-3-yl)pyrimidine-4-carboxylate (310 mg, 1.21 mmol) and methanol (10 mL) with stirring at room temperature. The reaction was stirred for 30 min and quenched with water (20 mL), extracted with EtOAc (3×30 mL), washed with brine (3×20 mL), dried over anhydrous $Na_2SO_4$ and concentrated. The residue was purified by flash chromatography on silica gel eluting with dichloromethane/methanol (10/1) to afford the title compound (230 mg, 83%) as a brown solid.

Step 5: Preparation of 2-[[6-(6-cyclopropylpyridin-3-yl)pyrimidin-4-yl]methyl]-2,3-dihydro-1H-isoindole-1,3-dione

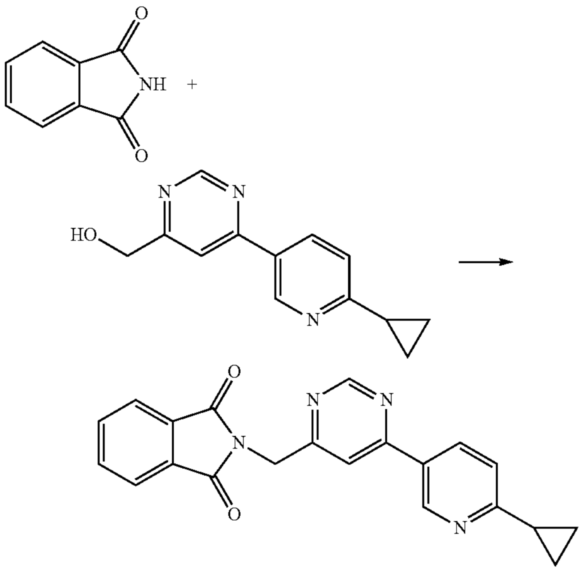

DIAD (266 mg, 1.32 mmol) was added dropwise into a mixture of [6-(6-cyclopropylpyridin-3-yl)pyrimidin-4-yl]

methanol (100 mg, 0.44 mmol), 2,3-dihydro-1H-isoindole-1,3-dione (98 mg, 0.67 mmol), $PPh_3$ (346 mg, 1.32 mmol) and THF (10 mL) with stirring at 0° C. The resulting solution was stirred for 5 h at room temperature. The mixture was concentrated under reduced pressure, and the residue was purified by flash chromatography on silica gel eluting with EtOAc/petroleum ether (1/1) to afford the title compound (102 mg, 65%) as a yellow solid.

Step 6: Preparation of [6-(6-cyclopropylpyridin-3-yl)pyrimidin-4-yl]methanamine

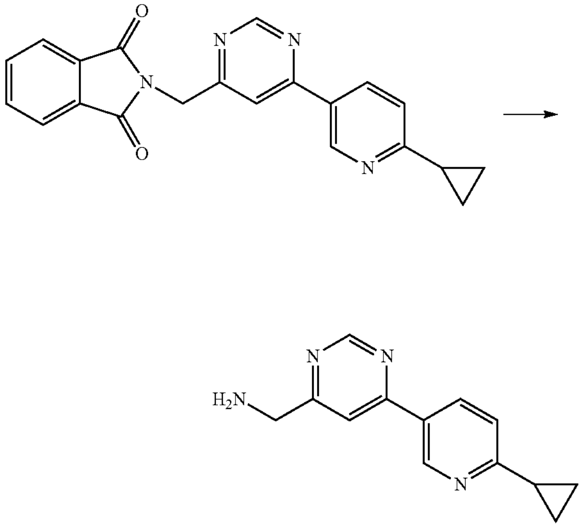

A mixture of 2-[[6-(6-cyclopropylpyridin-3-yl)pyrimidin-4-yl]methyl]-2,3-dihydro-1H-isoindole-1,3-dione (102 mg, 0.29 mmol), methanol (20 mL) and hydrazine hydrate (140 mg, 80%) was stirred for 5 h at 40° C. The resulting mixture was concentrated, diluted with 1 N HCl (20 mL), washed with EtOAc (30 mL). The aqueous layer was basified with 3 N NaOH (pH~8-9), extracted with EtOAc (3×50 mL). The organic layer combined, dried over anhydrous $Na_2SO_4$ and concentrated to afford the crude product (35 mg, 54%) as a yellow solid, which was used in the next step without any further purification.

Step 7: Preparation of (2S,4R)—N-((6-(6-cyclopropylpyridin-3-yl)pyrimidin-4-yl)methyl)-4-fluoro-1-(4-fluorophenylsulfonyl)pyrrolidine-2-carboxamide

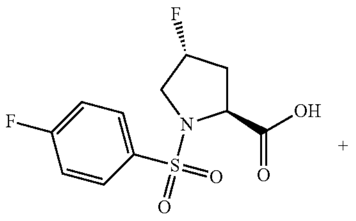

-continued

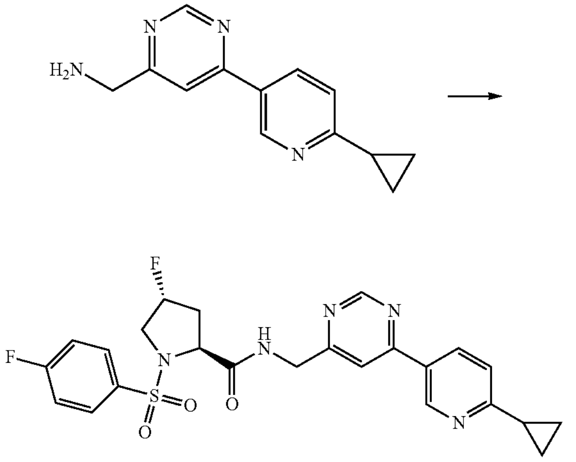

A mixture of (2S,4R)-4-fluoro-1-[(4-fluorobenzene)sulfonyl]pyrrolidine-2-carboxylic acid (52 mg, 0.18 mmol), DMF(5 mL), DIPEA (38.7 mg, 0.30 mmol), HATU (85.5 mg, 0.22 mmol) and [6-(6-cyclopropylpyridin-3-yl)pyrimidin-4-yl]methanamine (35 mg, 0.15 mmol) was stirred overnight at room temperature. The crude solution was purified directly by Prep-HPLC to afford the title compound (16.5 mg, 21%) as a white solid. $^1$H-NMR (300 MHz, DMSO-$d_6$) δ 9.21 (s, 2H), 9.39 (d, J=9.0 Hz, 1H), 7.96-7.91 (m, 3H), 7.64 (d, J=9.0 Hz, 1H), 7.25 (t, J=3.9 Hz, 3H), 5.09 (d, J=51.9 Hz, 1H), 4.89-4.81 (m, 1H), 4.59-4.52 (m, 1H), 4.34 (t, J=9 Hz, 1H), 3.98-3.63 (m, 2H), 2.66-2.52 (m, 1H), 2.37-2.17 (m, 2H), 1.14-1.05 (m, 4H).

Example 24

Preparation of (2S,4R)-1-(5-chlorothiophen-2-ylsulfonyl)-4-fluoro-N-((6-(6-(trifluoromethyl)pyridin-3-yl)pyrimidin-4-yl)methyl)pyrrolidine-2-carboxamide

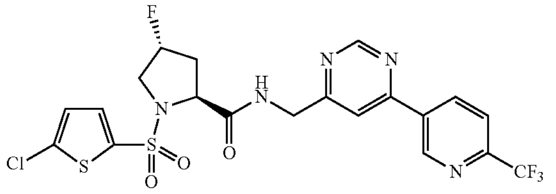 [SMILES: O=C(NCc1cc(-c2ccc(C(F)(F)F)nc2)ncn1)[C@@H]1C[C@@H](F)CN1S(=O)(=O)c1ccc(Cl)s1]

The title compound was prepared by the procedures described in Example 2, step 1 using (2S,4R)-1-(tert-butoxycarbonyl)-4-fluoropyrrolidine-2-carboxylic acid and (6-(6-(trifluoromethyl)pyridin-3-yl)pyrimidin-4-yl)methanamine, Example 2, step 2 and Example 2, step 3 using 5-chlorothiophene-2-sulfonyl chloride (50.9 mg) as a light yellow solid. $^1$H-NMR (300 MHz, DMSO-$d_6$) δ 9.46 (s, 1H), 9.30 (s, 1H), 9.12 (t, J=5.7 Hz, 1H), 8.80-8.76 (m, 1H), 8.13 (t, J=8.1 Hz, 2H), 7.78 (s, 1H), 7.40 (s, 1H), 5.27 (d, J=51 Hz, 1H), 4.52 (d, J=5.7 Hz, 2H), 4.32-4.26 (m, 1H), 3.86-3.75 (m, 1H), 3.70 (s, 1H), 2.59-2.47 (m, 1H), 2.29-2.06 (m, 1H).

Example 25

Preparation of (2S,4R)-1-(3,4-difluorophenylsulfonyl)-4-fluoro-N-((6-(6-(trifluoromethyl)pyridin-3-yl)pyrimidin-4-yl)methyl)pyrrolidine-2-carboxamide

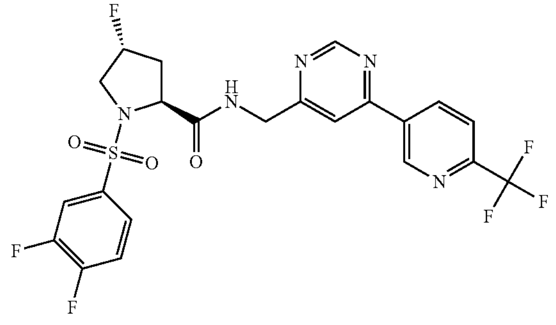 [SMILES: O=C(NCc1cc(-c2ccc(C(F)(F)F)nc2)ncn1)[C@@H]1C[C@@H](F)CN1S(=O)(=O)c1ccc(F)c(F)c1]

The title compound was prepared by the procedures described in Example 2, step 1 using (2S,4R)-1-(tert-butoxycarbonyl)-4-fluoropyrrolidine-2-carboxylic acid and(6-(6-(trifluoromethyl)pyridin-3-yl)pyrimidin-4-yl)methanamine, Example 2, step 2 and Example 2, step 3 using 3,4-difluorobenzene-1-sulfonyl chloride as a light yellow solid. $^1$H-NMR (300 MHz, $CDCl_3$) δ 9.52 (s, 1H), 9.28 (s, 1H), 8.70 (d, J=7.8 Hz, 1H), 8.09 (s, 1H), 7.83-7.68 (m, 3H), 7.61-7.58 (m, 1H), 7.42-7.33 (m, 1H), 5.11 (d, J=51.6 Hz, 1H), 4.99-4.92 (m, 1H), 4.62-4.55 (m, 1H), 4.35 (t, J=9 Hz, 1H), 3.95-3.64 (m, 2H), 2.65-2.57 (m, 1H), 2.37-2.02 (m, 1H).

Example 26

Preparation of (2S,4R)-1-(3,4-difluorophenylsulfonyl)-4-fluoro-N-((6-(4-(trifluoromethyl)phenyl)pyrimidin-4-yl)methyl)pyrrolidine-2-carboxamide

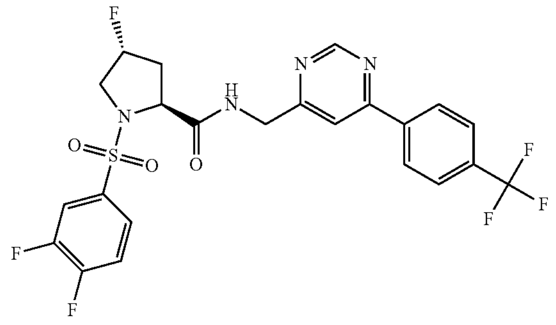 [SMILES: O=C(NCc1cc(-c2ccc(C(F)(F)F)cc2)ncn1)[C@@H]1C[C@@H](F)CN1S(=O)(=O)c1ccc(F)c(F)c1]

The title compound was prepared by the procedures described in Example 2, step 1 using (2S,4R)-1-(tert-butoxycarbonyl)-4-fluoropyrrolidine-2-carboxylic acid and (6-(4-(trifluoromethyl)phenyl)pyrimidin-4-yl)methanamine, and Example 2, steps 2 and 3 using 3,4-difluorobenzene-1-sulfonyl chloride as a white solid. $^1$H-NMR (300 MHz, $CDCl_3$) δ 9.29 (s, 1H), 8.33 (d, J=8.1 Hz, 2H), 8.08 (s, 1H), 7.82-7.61 (m, 5H), 7.41-7.33 (m, 1H), 5.11 (d, J=51.9 Hz, 1H), 4.95-4.88 (m, 1H), 4.71-4.65 (m, 1H), 4.33 (dd, J=7.4, 9.9 Hz, 1H), 3.94-3.69 (m, 2H), 2.67-2.53 (m, 1H), 2.40-2.23 (m, 1H).

Example 27

Preparation of (2S,4R)-4-fluoro-1-(5-fluoropyridin-3-ylsulfonyl)-N-((6-(6-(trifluoromethyl)pyridin-3-yl)pyrimidin-4-yl)methyl)pyrrolidine-2-carboxamide

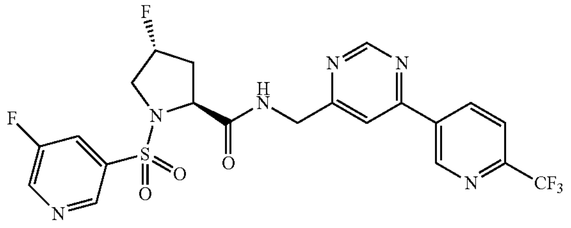 [SMILES: O=C(NCc1cc(-c2ccc(C(F)(F)F)nc2)ncn1)[C@@H]1C[C@@H](F)CN1S(=O)(=O)c1cncc(F)c1]

The title compound was prepared by the procedures described in Example 2, step 1 using (2S,4R)-1-(tert-butoxycarbonyl)-4-fluoropyrrolidine-2-carboxylic acid and(6-(6-(trifluoromethyl)pyridin-3-yl)pyrimidin-4-yl)methanamine, Example 2, step 2 and Example 2, step 3 using 5-fluoropyridine-3-sulfonyl chloride as a white solid. $^1$H-NMR (300 MHz, DMSO-$d_6$) δ 9.49 (s, 1H), 9.31 (s, 1H), 9.20-9.10 (m, 1H), 9.01 (s, 1H), 8.94 (d, J=2.7 Hz, 1H), 8.80 (m, 1H), 8.40 (m, 1H), 8.21 (d, J=2.7 Hz, 1H), 8.10 (m, 1H), 5.24 (d, J=51.3 Hz, 1H), 4.40-4.38 (m, 2H), 4.36-4.33 (m, 2H), 3.97-3.59 (m, 2H), 2.44-2.04 (m, 2H).

Example 28

Preparation of (2S,4R)-4-fluoro-1-(5-fluoropyridin-3-ylsulfonyl)-N-((6-(4-(trifluoromethyl)phenyl)pyrimidin-4-yl)methyl)pyrrolidine-2-carboxamide

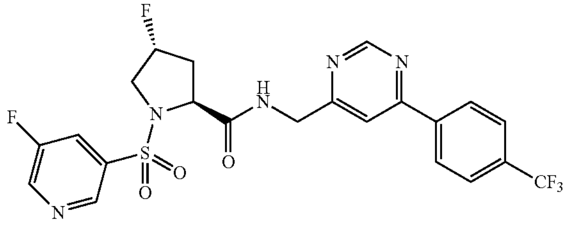 [SMILES: O=C(NCc1cc(-c2ccc(C(F)(F)F)cc2)ncn1)[C@@H]1C[C@@H](F)CN1S(=O)(=O)c1cncc(F)c1]

The title compound was prepared by the procedures described in Example 2, step 1 using (2S,4R)-1-(tert-butoxycarbonyl)-4-fluoropyrrolidine-2-carboxylic acid and (6-(4-(trifluoromethyl)phenyl)pyrimidin-4-yl)methanamine, and Example 2, steps 2 and 3 using 5-fluoropyridine-3-sulfonyl chloride. $^1$H-NMR (300 MHz, $CDCl_3$) δ 9.26 (s, 1H), 8.94 (s, 1H), 8.75 (s, 1H), 8.29 (d, J=8.1 Hz, 2H), 7.94-7.89 (m, 2H), 7.77 (d, J=8.1 Hz, 2H), 7.61 (s, 1H), 5.13 (d, J=51 Hz, 1H), 4.82 (m, 1H), 4.75 (m, 1H), 4.39 (m, 1H), 4.29 (m, 1H), 3.97-3.6 (m, 2H), 2.63-2.2 (m, 2H).

Example 29

Preparation of (2S,4R)-4-fluoro-1-(4-fluorophenylsulfonyl)-N-((6-(4-(trifluoromethylthio)phenyl)pyrimidin-4-yl)methyl)pyrrolidine-2-carboxamide

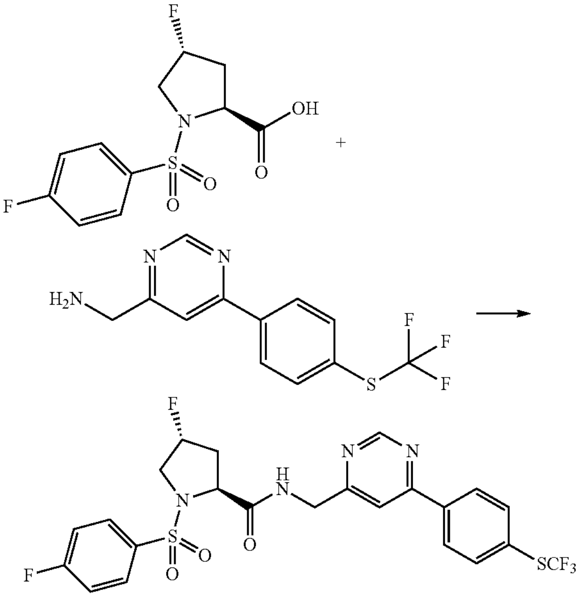

A mixture of (2S,4R)-4-fluoro-1-[(4-fluorobenzene)sulfonyl]pyrrolidine-2-carboxylic acid (102 mg, 0.35 mmol), DMF(5 mL), DIPEA (136 mg, 1.05 mmol), HATU (200 mg, 0.53 mmol) and (6-[4-[(trifluoromethyl)sulfanyl]phenyl]pyrimidin-4-yl)methanamine (100 mg, 0.35 mmol) was stirred for 1 h at room temperature. The crude solution was purified directly by Prep-HPLC high to afford the title compound (75.4 mg, 39%) as a white solid. $^1$H-NMR (300 MHz, $CD_3OD$) δ 9.16 (s, 1H), 8.39 (d, J=8.4 Hz, 2H), 8.27 (s, 1H), 8.07-8.01 (m, 2H), 7.79 (d, J=8.4 Hz, 2H), 7.38-7.32 (m, 2H), 5.16 (d, J=51.9 Hz, 1H), 4.63 (d, J=4.2 Hz, 2H), 4.32 (dd, J=10.2, 7.2 Hz, 1H), 3.87-3.9 (m, 2H), 2.57-2.15 (m, 2H).

Example 30

Preparation of (R)-1-(4-fluorophenylsulfonyl)-2-(methoxymethyl)-N-((6-(6-(trifluoromethyl)pyridin-3-yl)pyrimidin-4-yl)methyl)pyrrolidine-2-carboxamide

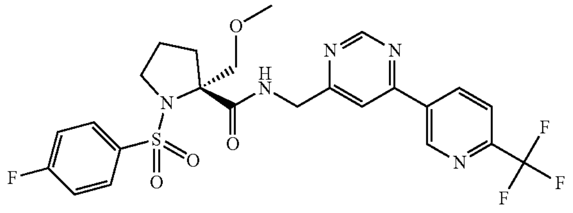 [SMILES: COC[C@@]1(C(=O)NCc2cc(-c3ccc(C(F)(F)F)nc3)ncn2)CCCN1S(=O)(=O)c1ccc(F)cc1]

Step 1: Preparation of 1-[(4-fluorobenzene)sulfonyl]-2-(methoxymethyl)pyrrolidine-2-carboxylic acid

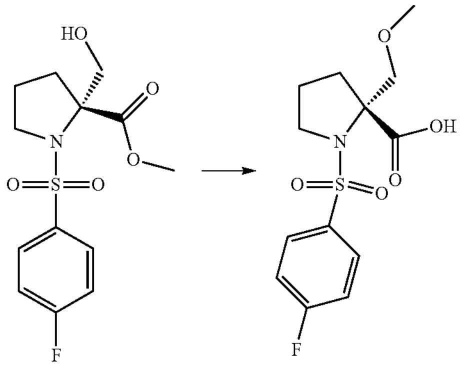 [SMILES: COC(=O)[C@]1(CO)CCCN1S(=O)(=O)c1ccc(F)cc1 ; COC[C@@]1(C(=O)O)CCCN1S(=O)(=O)c1ccc(F)cc1]

Sodium hydride (379 mg, 9.47 mmol, 60% in mineral oil) was added to a solution of methyl 1-[(4-fluorobenzene) sulfonyl]-2-(hydroxymethyl)pyrrolidine-2-carboxylate (100 mg, 0.32 mmol), THF (7 mL). The mixture was stirred for 20 min at room temperature, and $CH_3I$ (222.8 mg, 1.57 mmol) was added. The resulting solution was stirred for 2 h at room temperature. The reaction was then quenched with 5% HCl (15 m), extracted with EtOAc (3×30 mL). The combined organic layers were dried over anhydrous $Na_2SO_4$, concentrated to afford the title compound (75 mg) as a white solid, which was used in the next step without any further purification.

Step 2: Preparation of (R)-1-(4-fluorophenylsulfonyl)-2-(methoxymethyl)-N-((6-(6-(trifluoromethyl) pyridin-3-yl)pyrimidin-4-yl)methyl)pyrrolidine-2-carboxamide

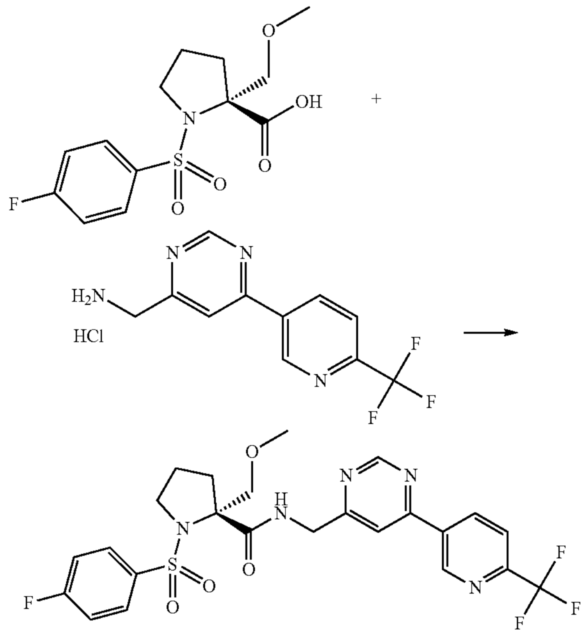

A mixture of (2R)-1-[(4-fluorobenzene)sulfonyl]-2-(methoxymethyl)pyrrolidine-2-carboxylic acid (70 mg, 0.22 mmol), DMF (2 mL), DIPEA (113.9 mg, 0.88 mmol), HATU (125.86 mg, 0.33 mmol) and [6-[6-(trifluoromethyl)pyridin-3-yl]pyrimidin-4-yl]methanamine hydrochloride (77.1 mg, 0.27 mmol) was stirred for 12 h at room temperature. The reaction mixture was purified directly by Prep-HPLC to afford the title compound (51.8 mg, 42%) as a light yellow solid. $^1$H-NMR (300 MHz, $CDCl_3$) δ 9.50 (s, 1H), 9.25 (s, 1H), 8.70 (d, J=7.8 Hz, 1H), 8.15 (s, 1H), 7.99-7.94 (m, 2H), 7.77-7.71 (m, 1H), 7.21-7.15 (m, 2H), 4.82-4.64 (m, 2H), 4.00 (dd, J=67.5, 9.6 Hz, 2H), 3.57-3.52 (m, 1H), 3.38-3.29 (m, 4H), 2.48-2.41 (m, 1H), 2.23-2.19 (m, 1H), 2.05-1.98 (m, 2H).

Example 31

Preparation of (S)-2-(difluoromethyl)-1-(4-fluorophenylsulfonyl)-N-((6-(6-(trifluoromethyl)pyridin-3-yl)pyrimidin-4-yl)methyl)pyrrolidine-2-carboxamide

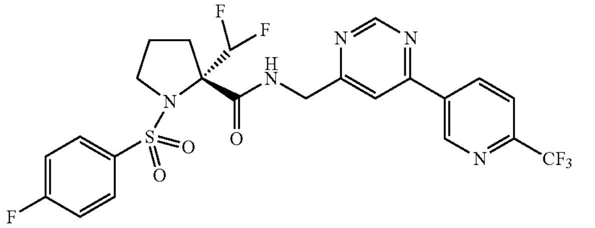 [SMILES: O=C(NCc1cc(-c2ccc(C(F)(F)F)nc2)ncn1)[C@]1(C(F)F)CCCN1S(=O)(=O)c1ccc(F)cc1]

Step 1: Preparation of methyl (2R)-1-[(4-fluorobenzene)sulfonyl]-2-formylpyrrolidine-2-carboxylate

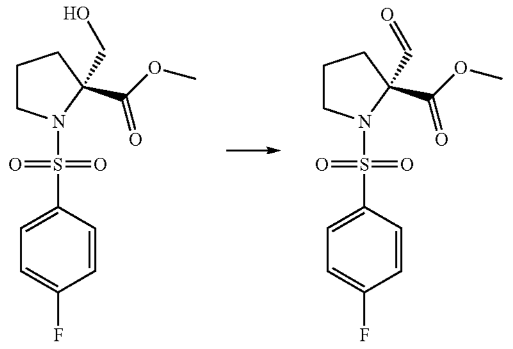 [SMILES: COC(=O)[C@]1(CO)CCCN1S(=O)(=O)c1ccc(F)cc1 ; COC(=O)[C@]1(C=O)CCCN1S(=O)(=O)c1ccc(F)cc1]

A mixture of methyl (2R)-1-[(4-fluorobenzene)sulfonyl]-2-(hydroxymethyl)pyrrolidine-2-carboxylate (100 mg, 0.32 mmol), dichloromethane (20 mL), silica gel (1 g), PCC (136 mg, 0.63 mmol) was stirred overnight at room temperature. The mixture was concentrated, purified by flash chromatography on a silica gel eluting with EtOAc/petroleum ether (1/5) to afford the title compound (70 mg, 70%) as colorless oil.

Step 2: Preparation of methyl (2S)-2-(difluoromethyl)-1-[(4-fluorobenzene)sulfonyl]pyrrolidine-2-carboxylate

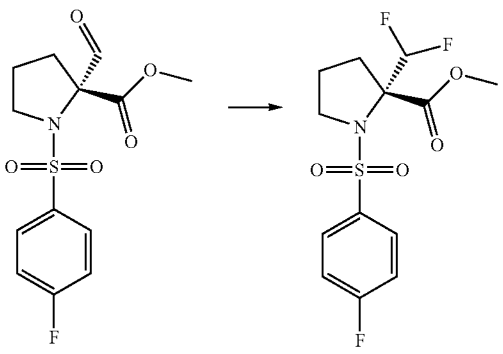 [SMILES: COC(=O)[C@]1(C=O)CCCN1S(=O)(=O)c1ccc(F)cc1 ; COC(=O)[C@]1(C(F)F)CCCN1S(=O)(=O)c1ccc(F)cc1]

A mixture of methyl (2R)-1-[(4-fluorobenzene)sulfonyl]-2-formylpyrrolidine-2-carboxylate (120 mg, 0.38 mmol), dichloromethane (20 mL), DAST (123 mg, 2.00 equiv) was stirred overnight at room temperature. The mixture was concentrated and the residue was purified by flash chromatography on silica gel eluting with EtOAc/petroleum ether (1/5) to afford the title compound (90 mg, 70%) as a white solid.

Step 3: Preparation of (2S)-2-(difluoromethyl)-1-[(4-fluorobenzene)sulfonyl]pyrrolidine-2-carboxylic acid

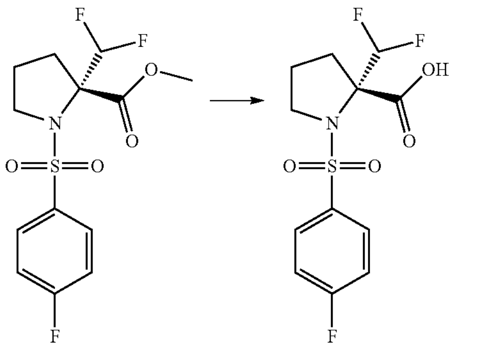 [SMILES: COC(=O)[C@]1(C(F)F)CCCN1S(=O)(=O)c1ccc(F)cc1 ; O=C(O)[C@]1(C(F)F)CCCN1S(=O)(=O)c1ccc(F)cc1]

A mixture of methyl (2S)-2-(difluoromethyl)-1-[(4-fluorobenzene)sulfonyl]pyrrolidine-2-carboxylate (90 mg, 0.27 mmol), methanol (10 mL) and LiOH (20 mg, 0.83 mmol) was stirred overnight at room temperature. The mixture was concentrated, diluted with water (20 mL), extracted with ether (30 mL). The aqueous layers was acidified with 3N HCl to pH~2-3, extracted with EtOAc (3x30 mL). The organic phases were dried over anhydrous $Na_2SO_4$ and concentrated to afford the title compound (30 mg) as colorless oil, which was used in the next step without any further purification.

Step 4: Preparation of (S)-2-(difluoromethyl)-1-(4-fluorophenylsulfonyl)-N-((6-(6-(trifluoromethyl)pyridin-3-yl)pyrimidin-4-yl)methyl)pyrrolidine-2-carboxamide

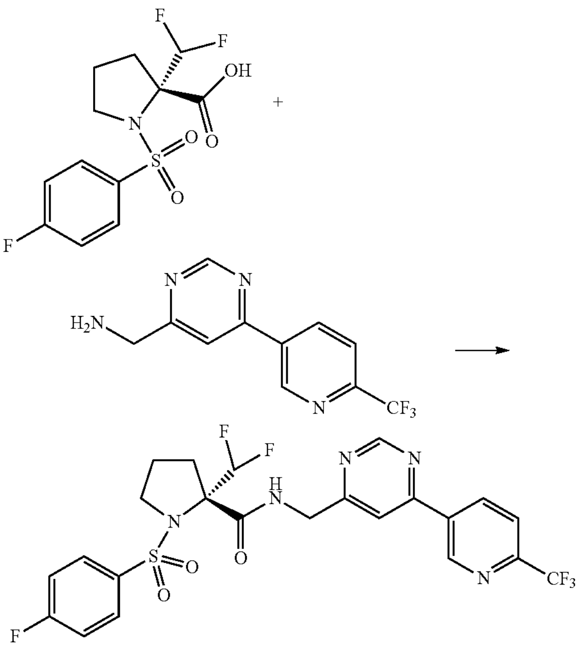

A mixture of (2S)-2-(difluoromethyl)-1-[(4-fluorobenzene)sulfonyl]pyrrolidine-2-carboxylic acid (110 mg, 0.34 mmol), HOBt (55 mg, 0.41 mmol), DIPEA (2 mL, 12.10 mmol), N,N-dimethylformamide (10 mL), EDC.HCl (78 mg, 0.41 mmol) and [6-[6-(trifluoromethyl)pyridin-3-yl]pyrimidin-4-yl]methanamine (95 mg, 0.37 mmol) was stirred overnight at room temperature. The mixture was diluted with EtOAc (100 mL), washed with brine (3x20 mL), dried over $Na_2SO_4$ and concentrated. The residue was purified by Prep-HPLC to afford the title compound (12.3 mg) as a light yellow solid. $^1$H-NMR (300 MHz, $CDCl_3$) δ 9.47 (d, J=1.8 Hz, 1H), 9.26 (d, J=1.2 Hz, 1H), 8.66 (dd, J=1.5, 8.1 Hz, 1H), 8.07 (s, 1H), 7.95-7.90 (m, 2H), 7.79 (d, J=8.1 Hz, 1H), 7.25-7.20 (m, 2H), 6.61 (t, J=56.1 Hz, 1H), 4.93-4.85 (m, 1H), 4.64-4.57 (m, 1H), 3.77-3.71 (m, 1H), 3.29-3.21 (m, 1H), 2.56-2.48 (m, 1H), 2.36-227 (m, 1H), 2.10-2.01 (m, 2H).

Example 32

Preparation of (R)-2-cyano-1-(4-fluorophenylsulfonyl)-N-((6-(6-(trifluoromethyl)pyridin-3-yl)pyrimidin-4-yl)methyl)pyrrolidine-2-carboxamide

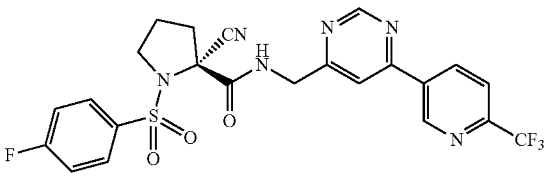

Step 1: Preparation of (2R)-1-[(4-fluorobenzene) sulfonyl]-2-[(1E)-(hydroxyimino)methyl]-N-([6-[6-(trifluoromethyl)pyridin-3-yl]pyrimidin-4-yl]methyl) pyrrolidine-2-carboxamide

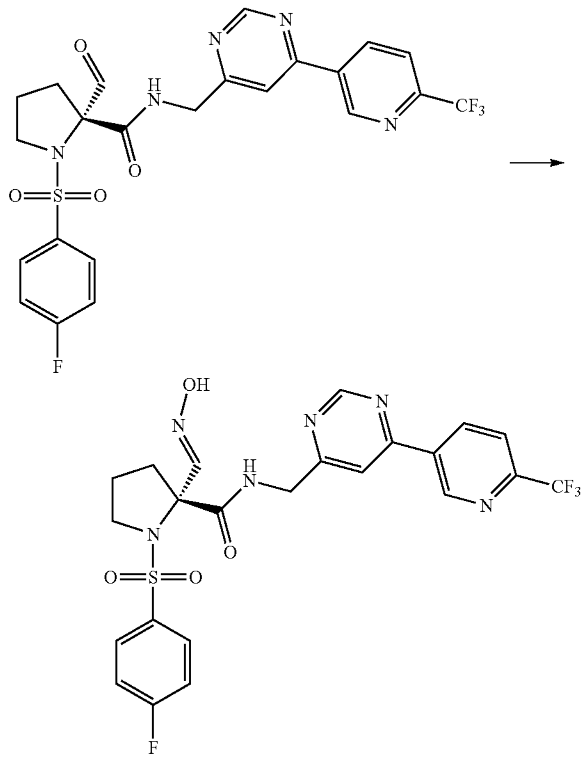

A mixture of (2R)-1-[(4-fluorobenzene)sulfonyl]-2-formyl-N-([6-[6-(trifluoromethyl)pyridin-3-yl]pyrimidin-4-yl]methyl)pyrrolidine-2-carboxamide (60 mg, 0.11 mmol), ethanol (10 mL), $NH_2OH.HCl$ (23 mg, 0.33 mmol) and NaOAc (46 mg, 5.00 equiv) was stirred overnight at room temperature. The mixture was concentrated, diluted with EtOAc (100 mL), washed with brine (30 mL), dried over anhydrous $Na_2SO_4$ and concentrated to afford the title compound (70 mg) as a brown solid, which was used in the next step without any further purification.

Step 2: Preparation of (R)-2-cyano-1-(4-fluorophenylsulfonyl)-N-((6-(6-(trifluoromethyl)pyridin-3-yl) pyrimidin-4-yl)methyl)pyrrolidine-2-carboxamide

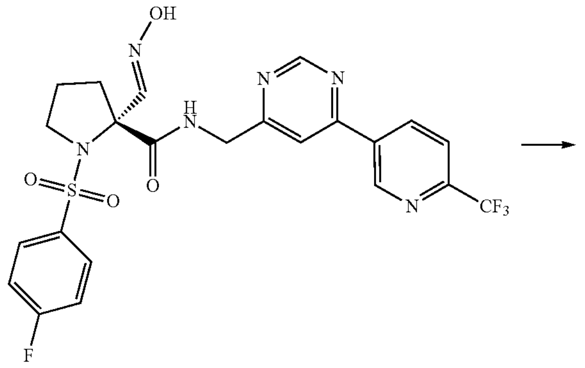

-continued

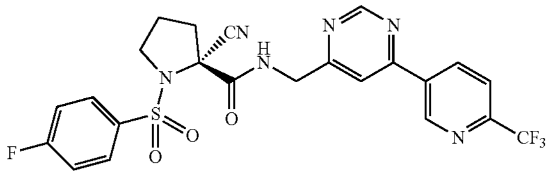 [SMILES: N#C[C@@]1(C(=O)NCc2cc(-c3ccc(C(F)(F)F)nc3)ncn2)CCCN1S(=O)(=O)c1ccc(F)cc1]

A mixture of $Ph_3PO$ (4 mg, 0.01 mmol), chloroform (15 mL), thionyl chloride (45 mg, 0.38 mmol) was stirred for 5 min at 0° C. To this was added a solution of (2R)-1-[(4-fluorobenzene)sulfonyl]-2-[(1E)-(hydroxyimino)methyl]-N-([6-[6-(trifluoromethyl)pyridin-3-yl]pyrimidin-4-yl] methyl)pyrrolidine-2-carboxamide (70 mg, 0.13 mmol) in chloroform (5 mL) dropwise with stirring at 0° C. The resulting solution was stirred for an additional 30 min at room temperature, quenched with saturated $NaHCO_3$ (20 mL), extracted with EtOAc (3×30 mL) and separated. The combined organic layers were dried over anhydrous $Na_2SO_4$ and concentrated. The crude product was purified by Prep-HPLC to afford the title compound (19.6 mg) as a white solid. $^1$H-NMR (400 MHz, $CDCl_3$) δ 9.47 (s, 1H), 9.28 (d, J=0.8 Hz, 1H), 8.65 (dd, J=6.4, 2.0 Hz, 1H), 8.06-8.03 (m, 3H), 7.78 (d, J=8.4 Hz, 1H), 7.48 (t, J=5.4 Hz, 1H), 7.27-7.22 (m, 3H), 4.79 (d, J=5.6 Hz, 2H), 3.69-3.66 (m, 1H), 3.39-3.35 (m, 1H), 2.68-2.64 (m, 2H), 2.28-2.08 (m, 2H).

Example 33

Preparation of (1R,3S,4S)-2-(4-fluorophenylsulfonyl)-N-((6-(4-(trifluoromethyl)phenyl)pyrimidin-4-yl)methyl)-2-azabicyclo[2.2.1]heptane-3-carboxamide

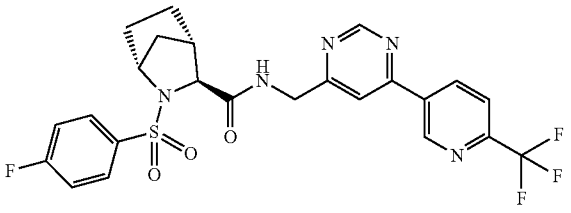 [SMILES: O=C(NCc1cc(-c2ccc(C(F)(F)F)nc2)ncn1)[C@@H]1[C@H]2CC[C@H](C2)N1S(=O)(=O)c1ccc(F)cc1]

The title compound was prepared by the procedures described in Example 2, step 1 using (1R,3S,4S)-2-(tert-butoxycarbonyl)-2-azabicyclo[2.2.1]heptane-3-carboxylic acid and (6-(4-(trifluoromethyl)phenyl)pyrimidin-4-yl) methanamine, and Example 2, steps 2 and 3 (71 mg): $^1$H-NMR (400 MHz, DMSO-$d_6$) δ 9.23 (d, J=1.3 Hz, 1H), 8.78 (t, J=5.9 Hz, 1H), 8.38-8.32 (m, 2H), 8.06-7.99 (m, 3H), 7.84 (d, J=8.3 Hz, 2H), 7.46-7.38 (m, 2H), 4.46 (d, J=6.1 Hz, 2H), 4.07 (s, 1H), 3.92 (s, 1H), 2.64 (d, J=4.1 Hz, 1H), 2.10 (d, J=9.7 Hz, 1H), 1.69-1.59 (m, 1H), 1.52-1.39 (m, 2H), 1.34 (d, J=9.9 Hz, 1H), 1.19-1.08 (m, 1H).

Example 34

Preparation of (1R,3S,4S)-2-(4-fluorophenylsulfonyl)-N-((6-(6-(trifluoromethyl)pyridin-3-yl)pyrimidin-4-yl)methyl)-2-azabicyclo[2.2.1]heptane-3-carboxamide

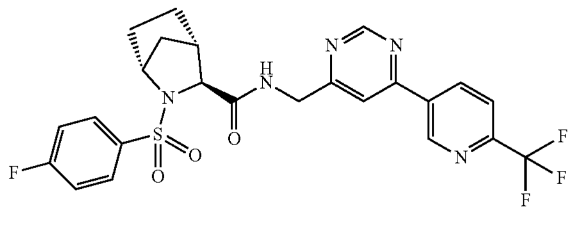 [SMILES: O=C(NCc1cc(-c2ccc(C(F)(F)F)nc2)ncn1)[C@@H]1[C@H]2CC[C@H](C2)N1S(=O)(=O)c1ccc(F)cc1]

The title compound was prepared by the procedures described in Example 2, step 1 using (1R,3S,4S)-2-(tert-butoxycarbonyl)-2-azabicyclo[2.2.1]heptane-3-carboxylic acid, and Example 2, steps 2 and 3 (72 mg): $^{1}$H-NMR (400 MHz, DMSO-$d_6$) δ 9.43 (d, J=2.1 Hz, 1H), 9.28 (d, J=1.3 Hz, 1H), 8.81 (t, J=5.9 Hz, 1H), 8.77-8.72 (m, 1H), 8.14 (d, J=1.2 Hz, 1H), 8.07-7.99 (m, 3H), 7.46-7.39 (m, 2H), 4.48 (d, J=6.0 Hz, 2H), 4.07 (s, 1H), 3.92 (s, 1H), 2.65 (d, J=4.0 Hz, 1H), 2.10 (d, J=10.4 Hz, 1H), 1.70-1.57 (m, 1H), 1.47-1.38 (m, 2H), 1.34 (d, J=10.1 Hz, 1H), 1.17-1.07 (m, 1H).

Example 35

Preparation of (2R,3S)-3-fluoro-1-(4-fluorophenylsulfonyl)-N-((6-(6-(trifluoromethyl)pyridin-3-yl)pyrimidin-4-yl)methyl)pyrrolidine-2-carboxamide

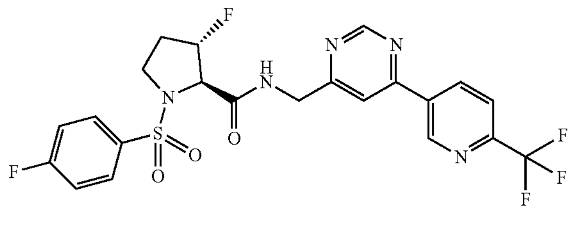 [SMILES: O=C(NCc1cc(-c2ccc(C(F)(F)F)nc2)ncn1)[C@@H]1[C@@H](F)CCN1S(=O)(=O)c1ccc(F)cc1]

Step 1: Preparation of tert-butyl (2S,3R)-3-hydroxy-2-[([6-[6-(trifluoromethyl)pyridin-3-yl]pyrimidin-4-yl]methyl)carbamoyl]pyrrolidine-1-carboxylate

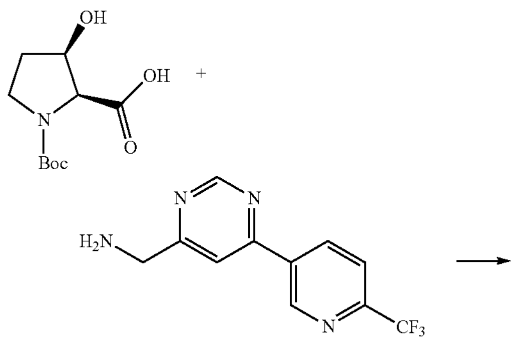

-continued

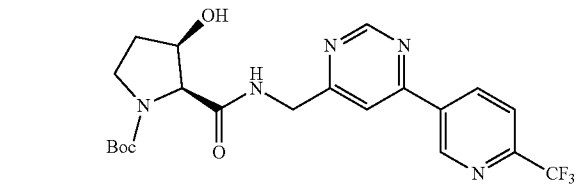

A mixture of (2S,3R)-1-[(tert-butoxy)carbonyl]-3-hydroxypyrrolidine-2-carboxylic acid (200 mg, 0.86 mmol, 1.00 equiv), DMF (10 mL), HATU (493.6 mg, 1.30 mmol, 1.50 equiv), DIEA (446.9 mg, 3.46 mmol, 4.00 equiv), and [6-[6-(trifluoromethyl)pyridin-3-yl]pyrimidin-4-yl]methanamine hydrochloride (302.3 mg, 1.04 mmol, 1.20 equiv) was stirred for 3 h at room temperature. The reaction was quenched by addition of 15 mL of water and extracted with ethyl acetate (3×15 mL). The organic layers were combined, washed with water (2×25 mL) and brine (20 mL), dried over anhydrous sodium sulfate, and concentrated under vacuum. This resulted in 400 mg (99%) of the title compound as orange oil.

Step 2: Preparation of tert-butyl (2R,3S)-3-fluoro-2-[([6-[6-(trifluoromethyl)pyridin-3-yl]pyrimidin-4-yl]methyl)carbamoyl]pyrrolidine-1-carboxylate

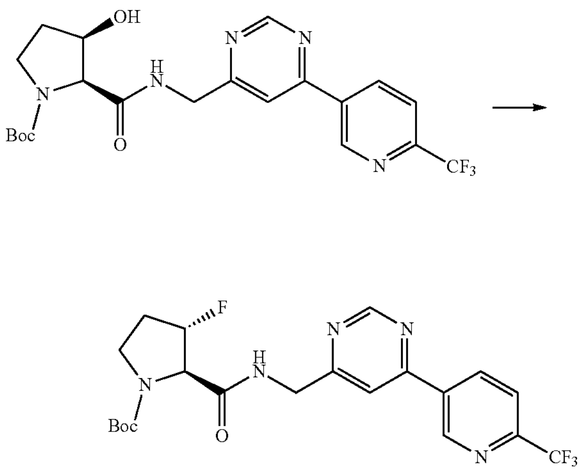

DAST (204 mg, 0.89 mmol, 3.00 equiv) was added dropwise into a solution of tert-butyl(2S,3R)-3-hydroxy-2-[([6-[6-(trifluoromethyl)pyridin-3-yl]pyrimidin-4-yl]methyl)carbamoyl]pyrrolidine-1-carboxylate (200 mg, 0.43 mmol, 1.00 equiv) in 10 mL of DCM at 0° C. The resulting solution was stirred for an additional 30 min at room temperature, quenched by water (15 mL), and extracted with ethyl acetate (3×15 mL). The organic layers were combined, dried over anhydrous sodium sulfate, and concentrated. The residue was applied onto a silica gel column with dichloromethane/methanol (40:1) to afford the title compound (85 mg, 42%) as an orange solid.

Step 3: Preparation of (2R,3S)-3-fluoro-N-([6-[6-(trifluoromethyl)pyridin-3-yl]pyrimidin-4-yl]methyl) pyrrolidine-2-carboxamide hydrochloride

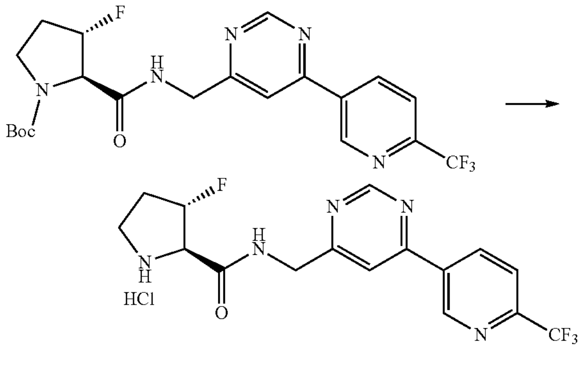

A mixture of tert-butyl (2R,3S)-3-fluoro-2-[([6-[6-(trifluoromethyl)pyridin-3-yl]pyrimidin-4-yl]methyl)carbamoyl]pyrrolidine-1-carboxylate (85 mg, 0.18 mmol, 1.00 equiv) and HCl in dioxane (10 mL, 1 mol/L) was stirred for 3 h at room temperature. The resulting solution was diluted with 5 mL of EtOAc. The solids were collected by filtration to afford the title compound (70 mg, 95%) as an orange solid.

Step 4: Preparation of (2R,3S)-3-fluoro-1-[(4-fluorobenzene)sulfonyl]-N-([6-[6-(trifluoromethyl)pyridin-3-yl]pyrimidin-4-yl]methyl)pyrrolidine-2-carboxamide

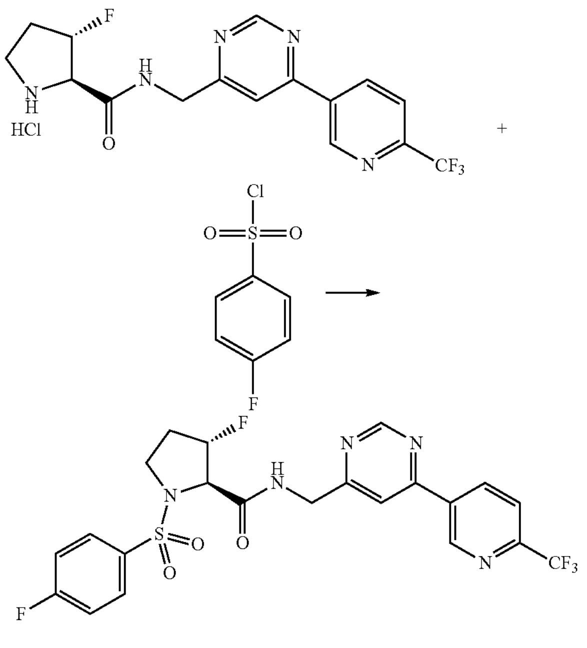

A mixture of (2R,3S)-3-fluoro-N-([6-[6-(trifluoromethyl) pyridin-3-yl]pyrimidin-4-yl]methyl)pyrrolidine-2-carboxamide hydrochloride (70 mg, 0.17 mmol, 1.00 equiv), TEA (51.5 mg, 0.51 mmol, 3.00 equiv), 4-fluorobenzene-1-sulfonyl chloride (39.6 mg, 0.20 mmol, 1.10 equiv), and 4-dimethylaminopyridine (2.1 mg, 0.02 mmol, 0.10 equiv) in DCM (3 mL) was stirred for 3 h at room temperature. The reaction was quenched by water (10 mL) and extracted with ethyl acetate (3×10 mL). The organic layers were combined, dried over anhydrous sodium sulfate, and concentrated under vacuum. The residue was applied onto a silica gel column with ethyl acetate/petroleum ether (1:1) to afford the title compound (40 mg, 44%) as a light yellow solid. $^1$H-NMR (400 MHz, $CDCl_3$) δ 9.49 (s, 1H), 9.28 (s, 1H), 8.69 (d, J=8.4 Hz, 1H), 7.99 (s, 1H), 7.94-7.91 (m, 2H), 7.84-7.80 (m, 2H), 7.29 (t, J=8.4 Hz, 2H), 5.32 (d, J=48 Hz, 1H), 4.96-4.90 (m, 1H), 4.59-4.53 (m, 1H), 4.41 (d, J=22.4 Hz, 1H), 3.84 (t, J=8.8 Hz 1H), 3.34-3.27 (m, 1H), 2.26-2.03 (m, 2H).

Example 36

Preparation of (2R,3R)-3-fluoro-1-(4-fluorophenylsulfonyl)-N-((6-(6-(trifluoromethyl)pyridin-3-yl) pyrimidin-4-yl)methyl)pyrrolidine-2-carboxamide

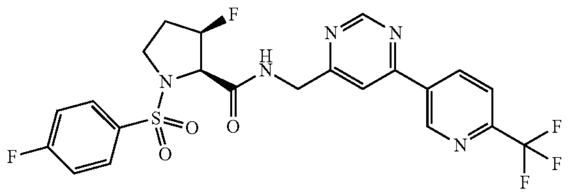 [SMILES: O=C(NCc1cc(-c2ccc(C(F)(F)F)nc2)ncn1)[C@@H]1[C@H](F)CCN1S(=O)(=O)c1ccc(F)cc1]

Step 1: Preparation of tert-butyl (2S,3S)-3-hydroxy-2-[([6-[6-(trifluoromethyl)pyridin-3-yl]pyrimidin-4-yl]methyl)carbamoyl]pyrrolidine-1-carboxylate

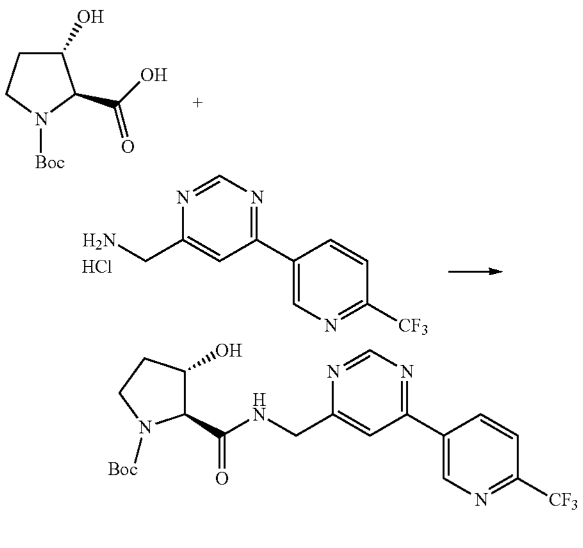

A mixture of (2S,3S)-1-[(tert-butoxy)carbonyl]-3-hydroxypyrrolidine-2-carboxylic acid (200 mg, 0.86 mmol, 1.00 equiv), DMF (10 mL), HATU (493.6 mg, 1.30 mmol, 1.50 equiv), DIEA (446.9 mg, 3.46 mmol, 4.00 equiv), and [6-[6-(trifluoromethyl)pyridin-3-yl]pyrimidin-4-yl]methanamine hydrochloride (302.3 mg, 1.04 mmol, 1.20 equiv) was stirred for 3 h at room temperature. The mixture was quenched by water (15 mL) and extracted with ethyl acetate (3×15 mL). The organic layers were combined, washed with water (2×25 mL) and brine (20 mL), dried over anhydrous sodium sulfate, and concentrated under vacuum. This resulted in 400 mg (99%) of the title compound as an orange oil.

Step 2: Preparation of (2R,3R)-3-fluoro-2-[([6-[6-(trifluoromethyl)pyridin-3-yl]pyrimidin-4-yl]methyl) carbamoyl]pyrrolidine-1-carboxylate

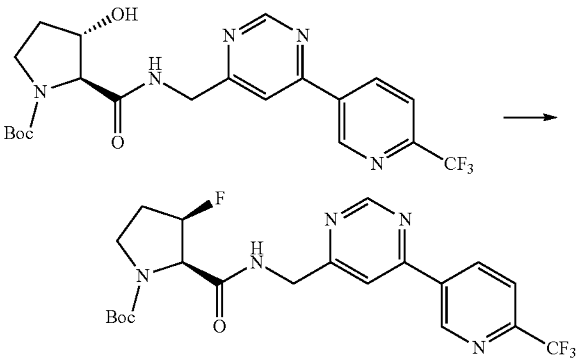

DAST (413.7 mg, 1.81 mmol, 3.00 equiv) was added dropwise into a solution of tert-butyl (2S,3S)-3-hydroxy-2-[([6-[6-(trifluoromethyl)pyridin-3-yl]pyrimidin-4-yl] methyl)carbamoyl]pyrrolidine-1-carboxylate (400 mg, 0.86 mmol, 1.00 equiv) in DCM (15 mL) at −78° C. The resulting solution was warmed slowly to room temperature, quenched by water (20 mL), and extracted with ethyl acetate (3×25 mL). The organic layers were combined, dried over anhydrous sodium sulfate, and concentrated. The residue was applied onto a silica gel column with ethyl acetate/petroleum ether (1:1) to afford the title compound (210 mg, 52%) as a colorless solid.

Step 3: Preparation of (2R,3R)-3-fluoro-N-([6-[4-(trifluoromethyl)-1lambda4,3-fluorazin-1-yl]pyrimidin-4-yl]methyl)pyrrolidine-2-carboxamide hydrochloride

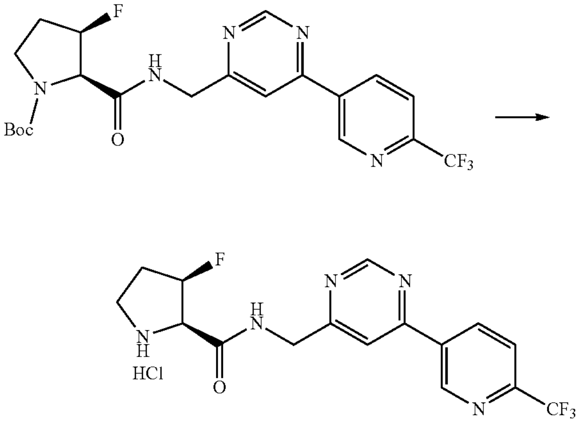

A mixture of tert-butyl (2R,3R)-3-fluoro-2-[([6-[6-(trifluoromethyl)pyridin-3-yl]pyrimidin-4-yl]methyl)carbamoyl]pyrrolidine-1-carboxylate (200 mg, 0.43 mmol, 1.00 equiv) and HCl in dioxane (10 mL, 1 mol/L) was stirred for 5 h at room temperature. The resulting solution was diluted with 10 mL of EA. The solids were collected by filtration to afford the title compound (105 mg, 60%) as a colorless solid.

Step 4: Preparation of (2R,3R)-3-fluoro-1-[(4-fluorobenzene)sulfonyl]-N-([6-[6-(trifluoromethyl)pyridin-3-yl]pyrimidin-4-yl]methyl)pyrrolidine-2-carboxamide

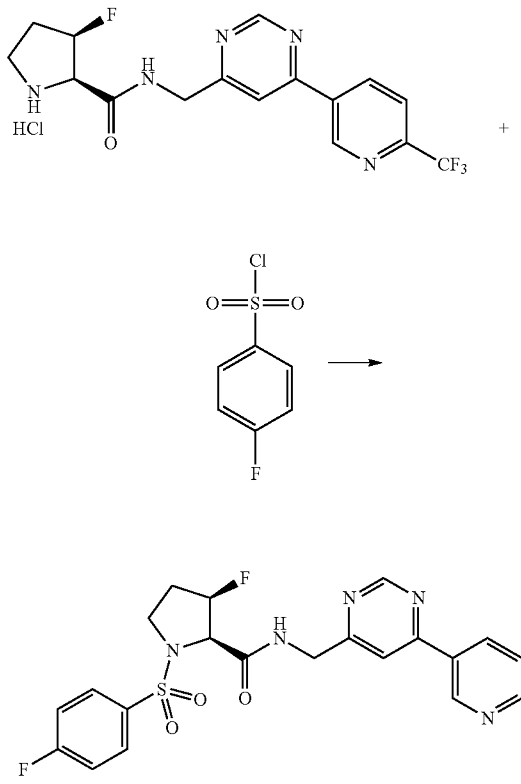

A mixture of (2R,3R)-3-fluoro-N-([6-[6-(trifluoromethyl) pyridin-3-yl]pyrimidin-4-yl]methyl)pyrrolidine-2-carboxamide hydrochloride (100 mg, 0.25 mmol, 1.00 equiv), TEA (101 mg, 1.00 mmol, 4.00 equiv), 4-fluorobenzene-1-sulfonyl chloride (58.3 mg, 0.30 mmol, 1.20 equiv), and 4-dimethylaminopyridine (3 mg, 0.02 mmol, 0.10 equiv) in dichloromethane (10 mL) was stirred for 3 h at room temperature. The mixture was quenched by water (10 mL) and extracted with DCM (3×10 mL). The organic layers were combined, dried over anhydrous sodium sulfate, and concentrated under vacuum. The residue was applied onto a silica gel column with ethyl acetate/petroleum ether (1:1) to afford the title compound (35 mg, 27%) as a light yellow solid. $^1$H-NMR (400 MHz, $CDCl_3$) δ 9.34 (s, 1H), 9.26 (s, 1H), 8.70 (d, J=7.6 Hz, 1H), 8.10 (s, 1H), 7.96-7.93 (m, 2H), 7.80 (d, J=8.0 Hz, 1H), 7.51 (s, 1H), 7.31 (t, J=8 Hz, 2H), 5.46 (d, J=52 Hz, 1H), 4.95-4.91 (m, 1H), 4.75-4.66 (m, 1H), 4.29-4.22 (m, 1H), 3.83 (d, J=8.8 Hz, 2H), 2.32-2.12 (m, 1H), 1.37-1.16 (m, 1H).

Example 37

Preparation of (2S,4R)-4-fluoro-N-((5-fluoro-4-(4-(trifluoromethyl)piperidin-1-yl)pyridin-2-yl)methyl)-1-(4-fluorophenylsulfonyl)pyrrolidine-2-carboxamide

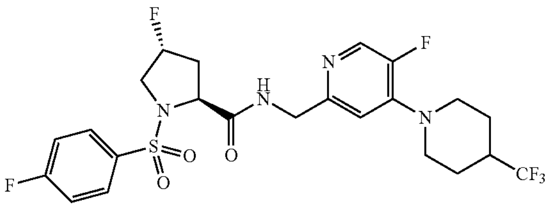 [SMILES: O=C(NCc1cc(N2CCC(C(F)(F)F)CC2)c(F)cn1)[C@@H]1C[C@@H](F)CN1S(=O)(=O)c1ccc(F)cc1]

Step 1: Preparation of 2-chloro-5-fluoro-4-(4-(trifluoromethyl)piperidin-1-yl)pyridine

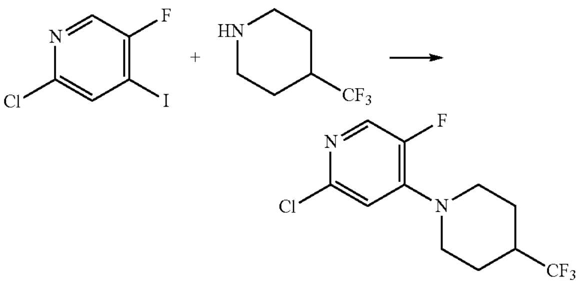

A mixture of 2-chloro-5-fluoro-4-iodopyridine (1.5 g, 5.83 mmol), 4-(trifluoromethyl)piperidine (890 mg, 5.81 mmol), $Pd_2(dba)_3.CHCl_3$ (300 mg, 0.29 mmol), BINAP (360 mg, 0.58 mmol), and t-BuONa (1.4 g, 14.57 mmol) in toluene (15 mL) was irradiated with microwave radiation for 1 h at 125° C. under nitrogen. The reaction was quenched by water (50 mL), extracted with dichloromethane (3×100 mL), dried over anhydrous sodium sulfate, and concentrated under reduced pressure. The residue was purified by flash chromatography on silica gel with ethyl acetate/petroleum ether (1:5) to afford the title compound (960 mg, 55%) as a yellow solid.

Step 2: Preparation of 5-fluoro-4-(4-(trifluoromethyl)piperidin-1-yl)picolinonitrile

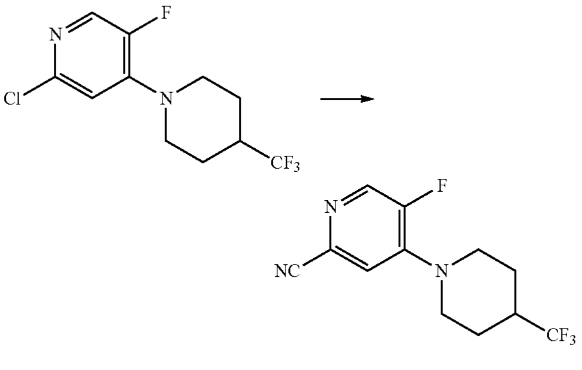

A mixture of 2-chloro-5-fluoro-4-[4-(trifluoromethyl)piperidin-1-yl]pyridine (400 mg, 1.42 mmol), $Pd_2(dba)_3.CHCl_3$ (72 mg, 0.07 mmol), $Zn(CN)_2$ (100 mg, 0.85 mmol), dppf (80 mg, 0.14 mmol), and Zn (8 mg, 0.12 mmol) in DMA (10 mL) was irradiated with microwave radiation for 1 h at 125° C. under nitrogen. The reaction was quenched by water (100 mL), extracted with dichloromethane (3×150 mL), dried over anhydrous sodium sulfate, and concentrated under reduced pressure. The residue was purified by flash chromatography on silica gel with ethyl acetate/petroleum ether (1:5) to afford the title compound (350 mg, 90%) as a yellow solid.

Step 3: Preparation of (5-fluoro-4-(4-(trifluoromethyl)piperidin-1-yl)pyridin-2-yl)methanamine

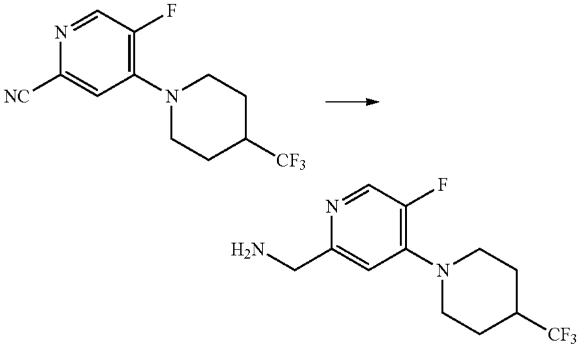

A mixture of 5-fluoro-4-[4-(trifluoromethyl)piperidin-1-yl]pyridine-2-carbonitrile (200 mg, 0.73 mmol), 10% Pd/C (50 mg), and saturated HCl (0.25 mL) in methanol (10 mL) was stirred for 1 h at room temperature under an atmosphere of hydrogen gas. The solids were filtered out and the filtrate was concentrated under reduced pressure to afford the title compound (200 mg) as a brown solid, which was used in the next step without any further purification.

Step 4: Preparation of (2S,4R)-4-fluoro-N-((5-fluoro-4-(4-(trifluoromethyl)piperidin-1-yl)pyridin-2-yl)methyl)-1-(4-fluorophenylsulfonyl)pyrrolidine-2-carboxamide

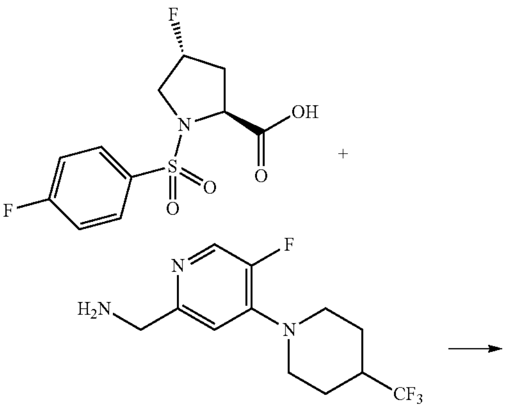

-continued

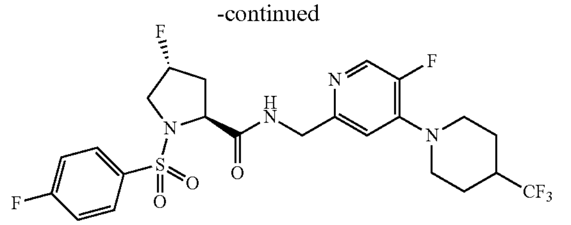

A mixture of (2S,4R)-4-fluoro-1-[(4-fluorobenzene)sulfonyl]pyrrolidine-2-carboxylic acid (315 mg, 1.08 mmol), HATU (410 mg, 1.08 mmol), DIEA (0.8 mL, 4.84 mmol), and [5-fluoro-4-[4-(trifluoromethyl)piperidin-1-yl]pyridin-2-yl]methanamine (250 mg, 0.90 mmol) in DMF (4 mL) was stirred overnight at room temperature. The resulting mixture was purified by Prep-HPLC with the following conditions: Column, X Bridge C18; mobile phase A: water/0.05% $NH_4HCO_3$; mobile phase B: ACN=30% increasing to ACN=70% within 10 min; detector, UV 254 nm. This resulted in the title compound (28.2 mg) as a white solid. $^1$H-NMR (400 MHz, $CD_3OD$) δ 8.09 (s, 1H), 8.03-7.99 (m, 2H), 7.39-7.34 (m, 2H), 7.17 (d, J=7.6 Hz, 2H), 5.14 (d, J=52.4 Hz, 1H), 4.47 (s, 2H), 4.28-4.24 (m, 1H), 4.03 (d, J=12.8 Hz, 2H), 3.83-3.70 (m, 2H), 2.97 (t, J=12.8 Hz, 2H), 2.51-2.40 (m, 2H), 2.25-2.12 (m, 1H), 1.93 (d, J=12.8 Hz, 2H), 1.71-1.65 (m, 2H).

Table 3: $IC_{50}$ Determinations of Exemplified Compounds.

$IC_{50}$s (effective concentration) of compounds on the human TRPA1 channel were determined using a Hamamatsu FDSS fluorescence plate reader. CHO cells expressing human TRPA1 were plated into 384-well plates, incubated overnight at 37 C, and loaded with BD calcium indicator dye for 1 hr at 37° C. followed by 15 minutes. at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using the FDSS while monitoring fluorescence to determine whether any of the test compounds have TRPA1 agonist activity. Plates were then incubated with compound for 20 minutes at room temperature prior to adding agonist. Following this incubation, 100 mM cinnamaldehyde was added to all wells of the plate and block of this cinnamaldehyde induced calcium influx was measured.

$IC_{50}$s were fit with a standard Hill function, keeping the Hill coefficient (n) fixed to 1.5. Fixing the Hill coefficient will generally reduce variability of the $IC_{50}$ determination. The $IC_{50}$s were examined by eye to make sure the MIN and MAX points were set correctly prior to validation of the results. Data for representative compounds of formula I is provided in Table 3 below.

TABLE 3

$IC_{50}$ Determinations of Exemplified Compounds.

| Example Number | Structure | hTRPA1 AUC $IC_{50}$ (μM) |
|---|---|---|
| 1 | 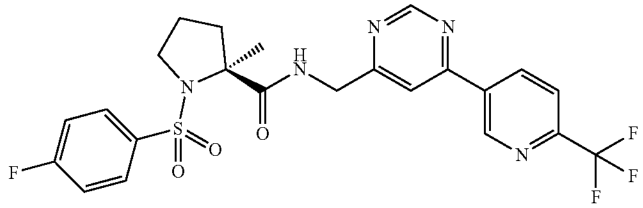 | 0.051 |
| 2 | 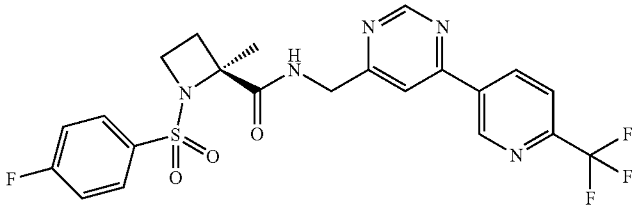 [SMILES: C[C@@]1(C(=O)NCc2cc(-c3ccc(C(F)(F)F)nc3)ncn2)CCN1S(=O)(=O)c1ccc(F)cc1] | 0.059 |
| 4 | 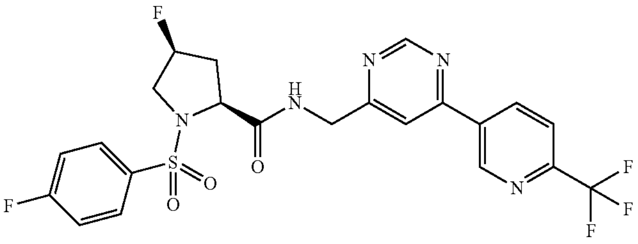 [SMILES: O=C(NCc1cc(-c2ccc(C(F)(F)F)nc2)ncn1)[C@@H]1C[C@H](F)CN1S(=O)(=O)c1ccc(F)cc1] | 0.819 |

TABLE 3-continued
IC$_{50}$ Determinations of Exemplified Compounds.
| Example Number | Structure | hTRPA1 AUC IC$_{50}$ (μM) |
|---|---|---|
| 3 | 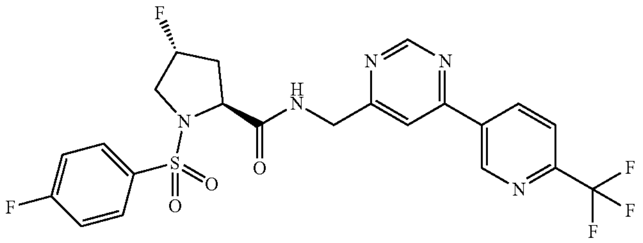 [SMILES: O=C(NCc1cc(-c2ccc(C(F)(F)F)nc2)ncn1)[C@@H]1C[C@@H](F)CN1S(=O)(=O)c1ccc(F)cc1] | 0.097 |
| 5 | 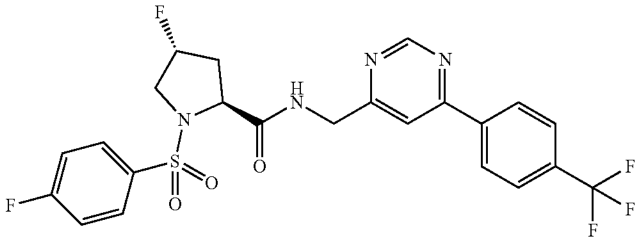 [SMILES: O=C(NCc1cc(-c2ccc(C(F)(F)F)cc2)ncn1)[C@@H]1C[C@@H](F)CN1S(=O)(=O)c1ccc(F)cc1] | 0.015 |
| 6 | 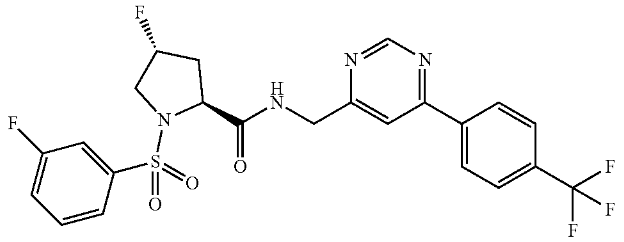 [SMILES: O=C(NCc1cc(-c2ccc(C(F)(F)F)cc2)ncn1)[C@@H]1C[C@@H](F)CN1S(=O)(=O)c1cccc(F)c1] | 0.023 |
| 14 | 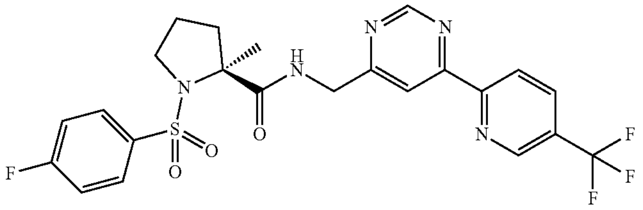 [SMILES: C[C@@]1(C(=O)NCc2cc(-c3ccc(C(F)(F)F)cn3)ncn2)CCCN1S(=O)(=O)c1ccc(F)cc1] | 0.268 |
| 7 | 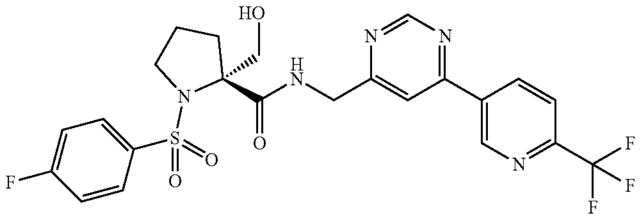 [SMILES: O=C(NCc1cc(-c2ccc(C(F)(F)F)nc2)ncn1)[C@]1(CO)CCCN1S(=O)(=O)c1ccc(F)cc1] | 0.284 |
| 9 | 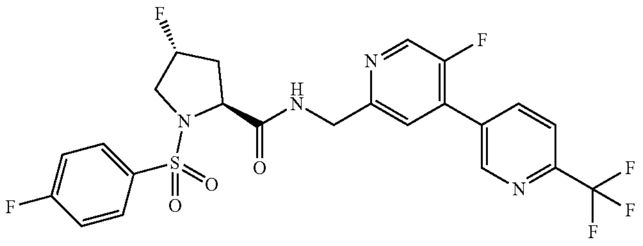 [SMILES: O=C(NCc1cc(-c2ccc(C(F)(F)F)nc2)c(F)cn1)[C@@H]1C[C@@H](F)CN1S(=O)(=O)c1ccc(F)cc1] | 0.020 |

TABLE 3-continued
| IC$_{50}$ Determinations of Exemplified Compounds. | | |
|---|---|---|
| Example Number | Structure | hTRPA1 AUC IC$_{50}$ (μM) |
| 8 | 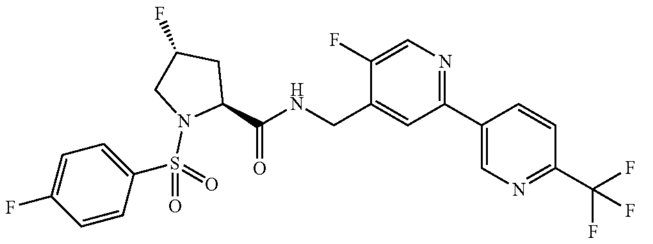 | 0.017 |
| 17 | 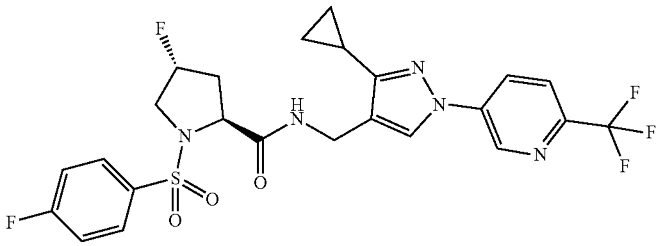 [SMILES: O=C(NCc1cn(-c2ccc(C(F)(F)F)nc2)nc1C1CC1)[C@@H]1C[C@@H](F)CN1S(=O)(=O)c1ccc(F)cc1] | 0.055 |
| 15 | 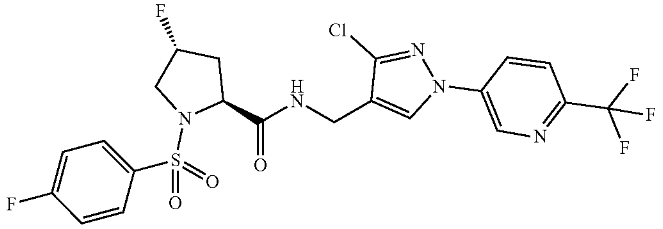 [SMILES: O=C(NCc1cn(-c2ccc(C(F)(F)F)nc2)nc1Cl)[C@@H]1C[C@@H](F)CN1S(=O)(=O)c1ccc(F)cc1] | 0.030 |
| 16 | 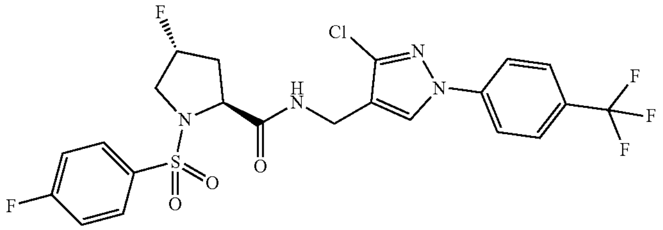 [SMILES: O=C(NCc1cn(-c2ccc(C(F)(F)F)cc2)nc1Cl)[C@@H]1C[C@@H](F)CN1S(=O)(=O)c1ccc(F)cc1] | 0.008 |
| 18 | 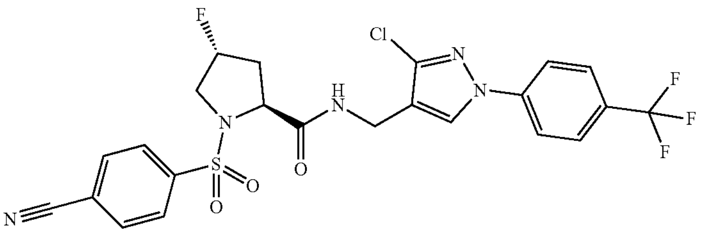 [SMILES: N#Cc1ccc(S(=O)(=O)N2C[C@H](F)C[C@H]2C(=O)NCc2cn(-c3ccc(C(F)(F)F)cc3)nc2Cl)cc1] | 0.049 |
| 19 | 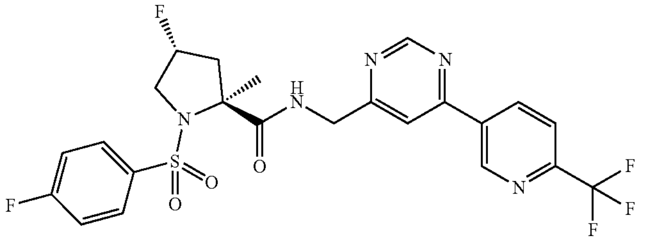 [SMILES: C[C@@]1(C(=O)NCc2cc(-c3ccc(C(F)(F)F)nc3)ncn2)C[C@@H](F)CN1S(=O)(=O)c1ccc(F)cc1] | 0.016 |

TABLE 3-continued
IC$_{50}$ Determinations of Exemplified Compounds.
| Example Number | Structure | hTRPA1 AUC IC$_{50}$ (μM) |
|---|---|---|
| 10 | 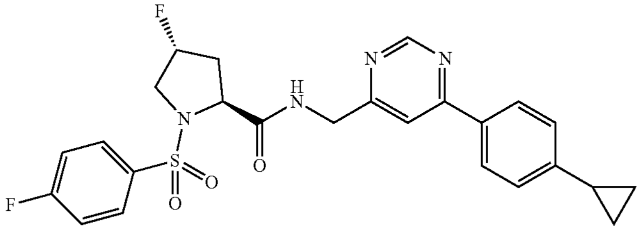 [SMILES: O=C(NCc1cc(-c2ccc(C3CC3)cc2)ncn1)[C@@H]1C[C@@H](F)CN1S(=O)(=O)c1ccc(F)cc1] | 0.107 |
| 11 | 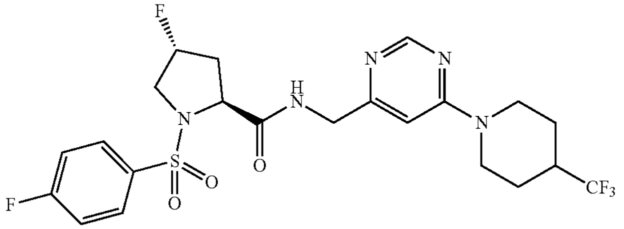 [SMILES: O=C(NCc1cc(N2CCC(C(F)(F)F)CC2)ncn1)[C@@H]1C[C@@H](F)CN1S(=O)(=O)c1ccc(F)cc1] | 0.434 |
| 20 | 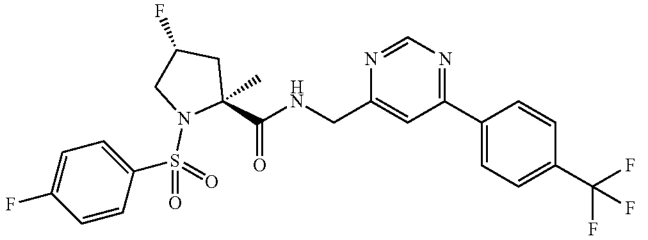 [SMILES: C[C@@]1(C(=O)NCc2cc(-c3ccc(C(F)(F)F)cc3)ncn2)C[C@@H](F)CN1S(=O)(=O)c1ccc(F)cc1] | 0.007 |
| 21 | 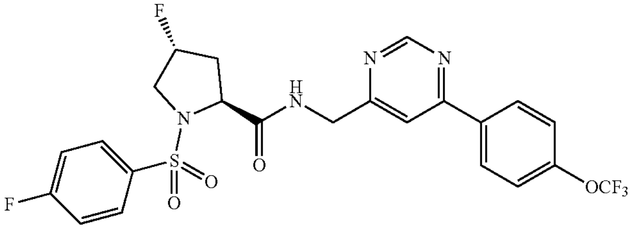 [SMILES: O=C(NCc1cc(-c2ccc(OC(F)(F)F)cc2)ncn1)[C@@H]1C[C@@H](F)CN1S(=O)(=O)c1ccc(F)cc1] | 0.021 |
| 22 | 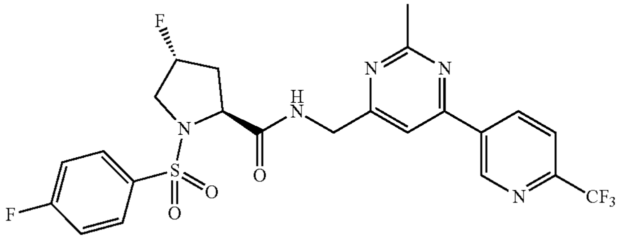 [SMILES: Cc1nc(CNC(=O)[C@@H]2C[C@@H](F)CN2S(=O)(=O)c2ccc(F)cc2)cc(-c2ccc(C(F)(F)F)nc2)n1] | 0.087 |
| 23 | 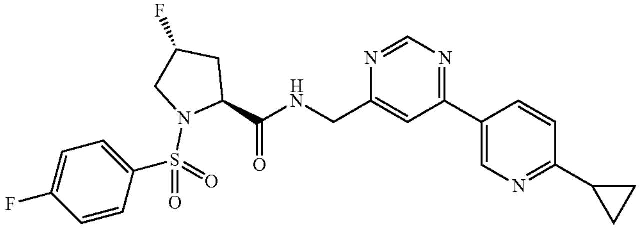 | 2.7 |

TABLE 3-continued
| IC$_{50}$ Determinations of Exemplified Compounds. | | |
|---|---|---|
| Example Number | Structure | hTRPA1 AUC IC$_{50}$ (μM) |
| 24 | 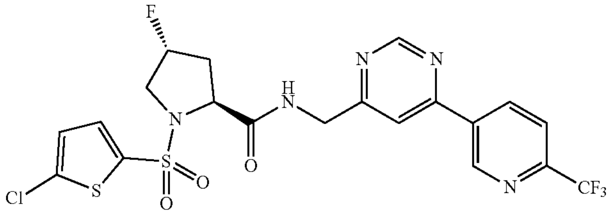 [SMILES: O=C(NCc1cc(-c2ccc(C(F)(F)F)nc2)ncn1)[C@@H]1C[C@@H](F)CN1S(=O)(=O)c1ccc(Cl)s1] | 0.027 |
| 25 | 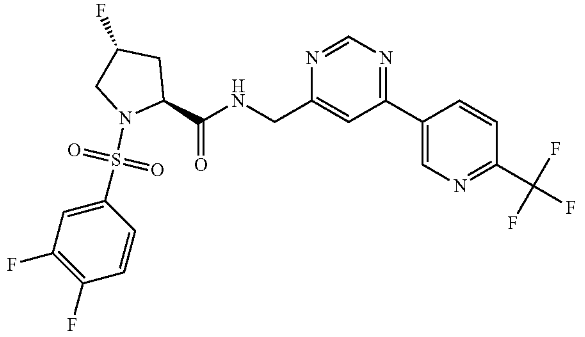 [SMILES: O=C(NCc1cc(-c2ccc(C(F)(F)F)nc2)ncn1)[C@@H]1C[C@@H](F)CN1S(=O)(=O)c1ccc(F)c(F)c1] | 0.126 |
| 26 | 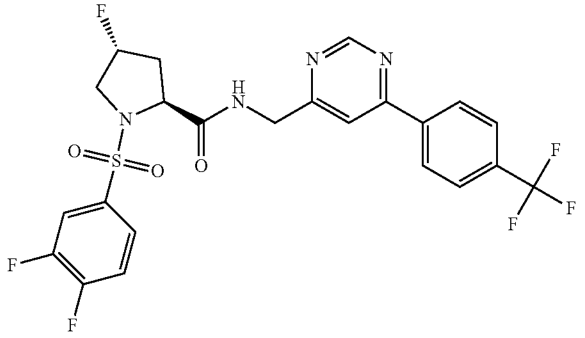 [SMILES: O=C(NCc1cc(-c2ccc(C(F)(F)F)cc2)ncn1)[C@@H]1C[C@@H](F)CN1S(=O)(=O)c1ccc(F)c(F)c1] | 0.030 |
| 27 | 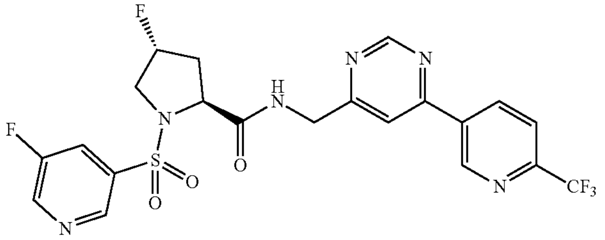 [SMILES: O=C(NCc1cc(-c2ccc(C(F)(F)F)nc2)ncn1)[C@@H]1C[C@@H](F)CN1S(=O)(=O)c1cncc(F)c1] | 3.0 |
| 28 | 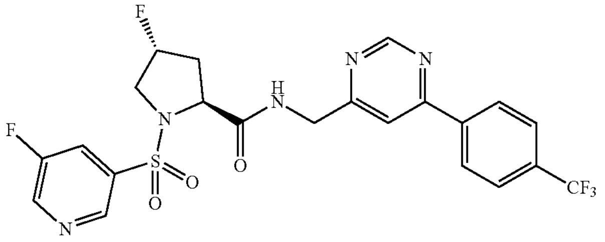 [SMILES: O=C(NCc1cc(-c2ccc(C(F)(F)F)cc2)ncn1)[C@@H]1C[C@@H](F)CN1S(=O)(=O)c1cncc(F)c1] | 0.229 |

TABLE 3-continued
| IC$_{50}$ Determinations of Exemplified Compounds. | | |
|---|---|---|
| Example Number | Structure | hTRPA1 AUC IC$_{50}$ (μM) |
| 29 | 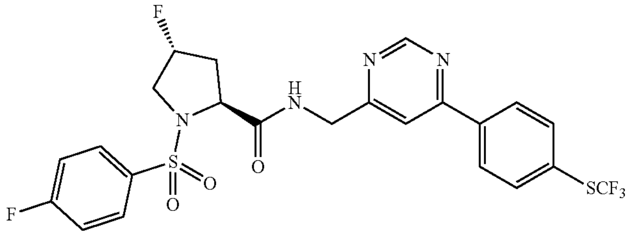 | 0.032 |
| 12 | 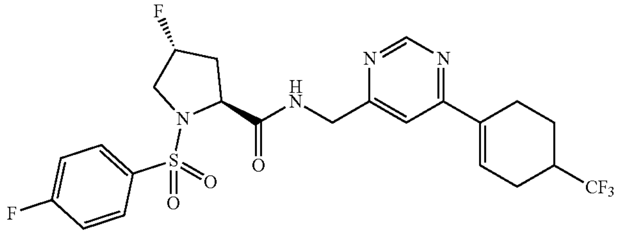 [SMILES: O=C(NCc1cc(C2=CCC(C(F)(F)F)CC2)ncn1)[C@@H]1C[C@@H](F)CN1S(=O)(=O)c1ccc(F)cc1] | 0.030 |
| 13 | 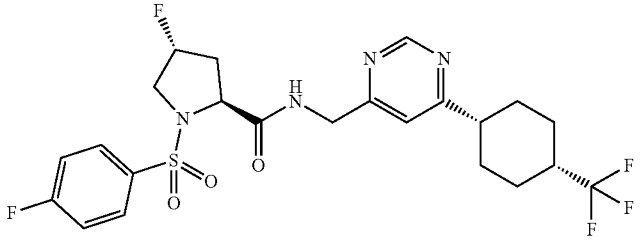 [SMILES: O=C(NCc1cc([C@H]2CC[C@@H](C(F)(F)F)CC2)ncn1)[C@@H]1C[C@@H](F)CN1S(=O)(=O)c1ccc(F)cc1] | 0.308 |
| 13 | 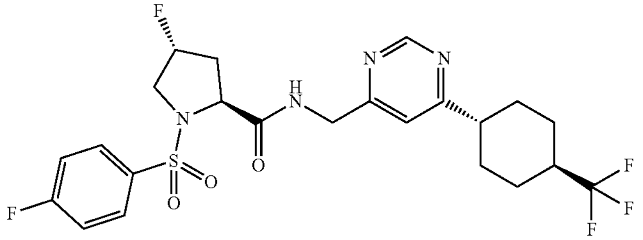 [SMILES: O=C(NCc1cc([C@H]2CC[C@H](C(F)(F)F)CC2)ncn1)[C@@H]1C[C@@H](F)CN1S(=O)(=O)c1ccc(F)cc1] | 0.029 |
| 30 | 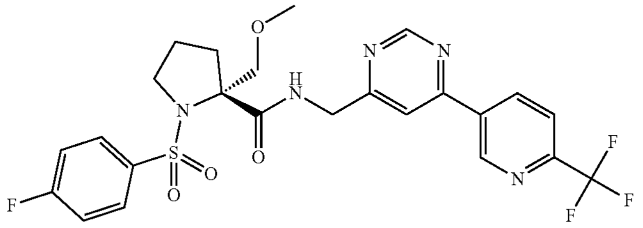 [SMILES: COC[C@@]1(C(=O)NCc2cc(-c3ccc(C(F)(F)F)nc3)ncn2)CCCN1S(=O)(=O)c1ccc(F)cc1] | 0.252 |
| 31 | 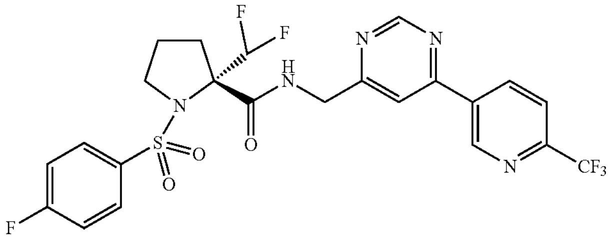 [SMILES: O=C(NCc1cc(-c2ccc(C(F)(F)F)nc2)ncn1)[C@]1(C(F)F)CCCN1S(=O)(=O)c1ccc(F)cc1] | 0.029 |

TABLE 3-continued
IC$_{50}$ Determinations of Exemplified Compounds.
| Example Number | Structure | hTRPA1 AUC IC$_{50}$ (μM) |
|---|---|---|
| 32 | 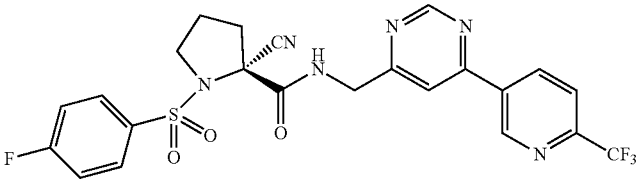 [SMILES: N#C[C@@]1(C(=O)NCc2cc(-c3ccc(C(F)(F)F)nc3)ncn2)CCCN1S(=O)(=O)c1ccc(F)cc1] | 0.867 |
| 35 | 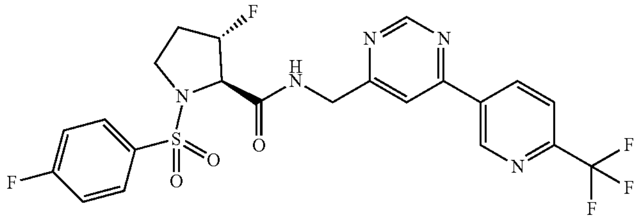 [SMILES: O=C(NCc1cc(-c2ccc(C(F)(F)F)nc2)ncn1)[C@@H]1[C@@H](F)CCN1S(=O)(=O)c1ccc(F)cc1] | 0.023 |
| 33 | 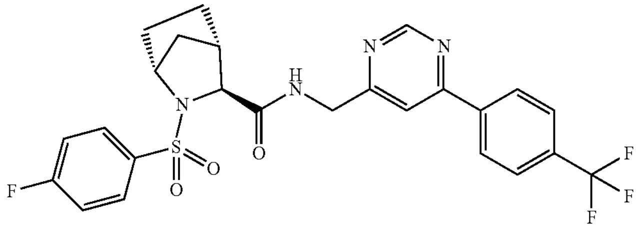 | 0.023 |
| 34 | 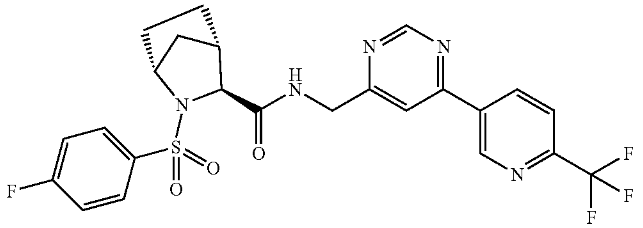 [SMILES: O=C(NCc1cc(-c2ccc(C(F)(F)F)nc2)ncn1)[C@@H]1[C@H]2CC[C@H](C2)N1S(=O)(=O)c1ccc(F)cc1] | 0.040 |
| 36 | 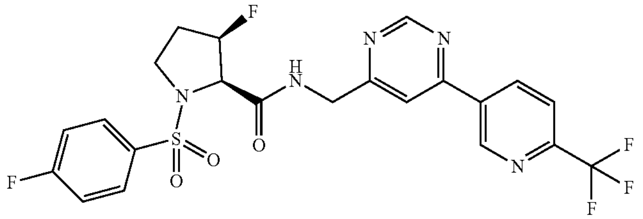 [SMILES: O=C(NCc1cc(-c2ccc(C(F)(F)F)nc2)ncn1)[C@@H]1[C@H](F)CCN1S(=O)(=O)c1ccc(F)cc1] | 0.120 |
| 37 | 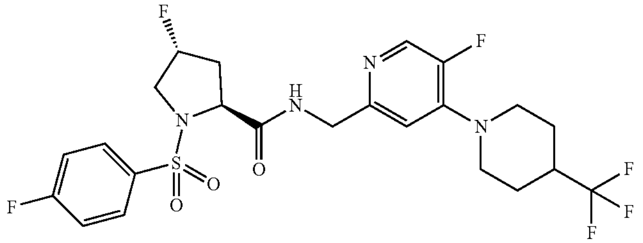 [SMILES: O=C(NCc1cc(N2CCC(C(F)(F)F)CC2)c(F)cn1)[C@@H]1C[C@@H](F)CN1S(=O)(=O)c1ccc(F)cc1] | 0.021 |

Example 38

Preparation of (2R,3S)—N-([2-cyano-5-[2-(trifluoromethyl)pyrimidin-5-yl]phenyl]methyl)-3-fluoro-1-[(4-fluorobenzene)sulfonyl]pyrrolidine-2-carboxamide

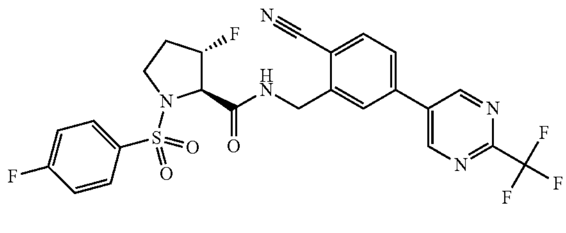 [SMILES: N#Cc1ccc(-c2cnc(C(F)(F)F)nc2)cc1CNC(=O)[C@@H]1[C@@H](F)CCN1S(=O)(=O)c1ccc(F)cc1]

Step 1: Preparation of 5-bromo-2,3-dihydro-1H-isoindol-1-one

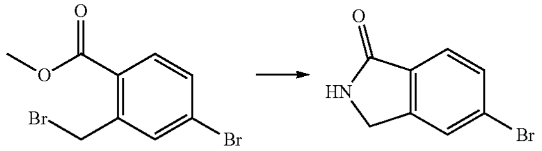

A mixture of methyl 4-bromo-2-(bromomethyl)benzoate (3 g, 9.74 mmol, 1.0 equiv) and ammonium hydroxide (30 mL, 30%) in 1,4-dioxane (250 mL) was stirred for 3 h at 20° C. The resulting mixture was concentrated under vacuum. The crude product was purified by re-crystallization from ethyl acetate to afford the title compound (1.8, 87%) as a white solid.

Step 2: Preparation of tert-butyl 5-bromo-1-oxo-2,3-dihydro-1H-isoindole-2-carboxylate

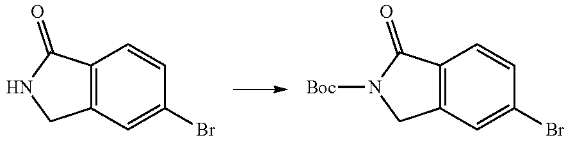 [SMILES: O=C1NCc2cc(Br)ccc21 ; CC(C)(C)OC(=O)N1Cc2cc(Br)ccc2C1=O]

A mixture of 5-bromo-2,3-dihydro-1H-isoindol-1-one (1.38 g, 6.51 mmol, 1.0 equiv), TEA (1.8 g, 17.79 mmol, 2.70 equiv), 4-dimethylaminopyridine (73 mg, 0.60 mmol) and di-tert-butyl dicarbonate (2.6 g, 11.91 mmol, 1.80 equiv) in tetrahydrofuran (50 mL) was stirred for 12 h at 20° C. The resulting mixture was concentrated under vacuum. The residue was dissolved in ethyl acetate, washed with brine, dried over anhydrous sodium sulfate, and concentrated under vacuum. The residue was purified by a silica gel column eluting with ethyl acetate/petroleum ether (1/10) to afford the title compound (1.7 g, 84%) as a white solid.

Step 3: Preparation of 5-bromo-2,3-dihydro-1H-isoindol-1-one

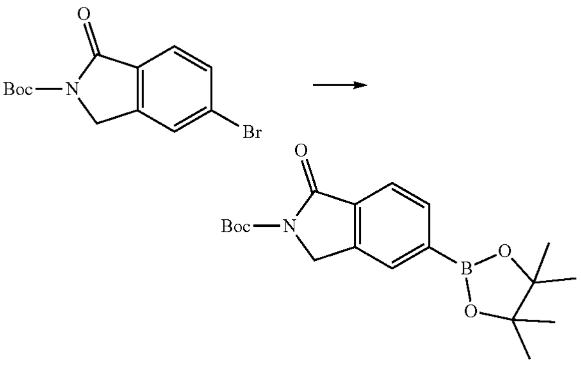

A mixture of tert-butyl 5-bromo-1-oxo-2,3-dihydro-1H-isoindole-2-carboxylate (1.7 g, 5.45 mmol, 1.00 equiv), KOAc (1.6 g, 16.30 mmol, 3.00 equiv), 4,4,5,5-tetramethyl-2-(tetramethyl-1,3,2-dioxaborolan-2-yl)-1,3,2-dioxaborolane (2.08 g, 8.19 mmol, 1.50 equiv), and Pd(dppf)$Cl_2$ (395 mg, 0.54 mmol, 0.10 equiv) in 1,4-dioxane (40 mL) was stirred for 12 h at 90° C. under nitrogen. The resulting mixture was concentrated under vacuum. The residue was dissolved in ethyl acetate, washed with brine, dried over anhydrous sodium sulfate, and concentrated under vacuum. This resulted in the title compound (2 g, crude) as a white solid.

Step 4: Preparation of tert-butyl 1-oxo-5-[2-(trifluoromethyl)pyrimidin-5-yl]-2,3-dihydro-1H-isoindole-2-carboxylate

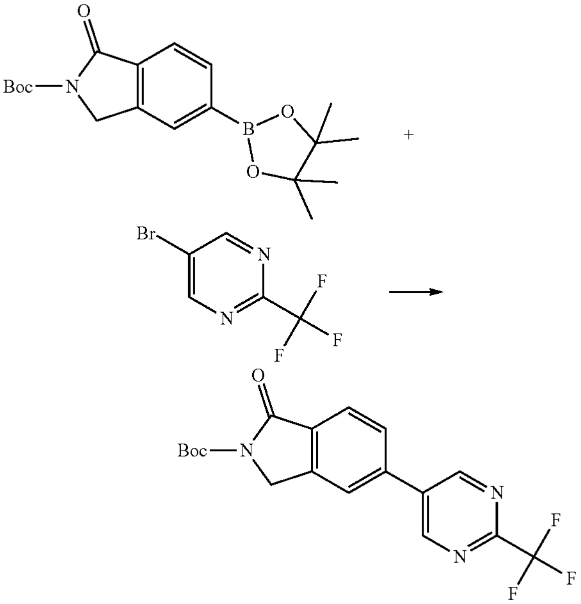

A mixture of tert-butyl 1-oxo-5-(tetramethyl-1,3,2-dioxaborolan-2-yl)-2,3-dihydro-1H-isoindole-2-carboxylate (500 mg, 1.39 mmol, 1.00 equiv), potassium carbonate (575 mg, 4.16 mmol, 3.00 equiv), 5-bromo-2-(trifluoromethyl)pyrimidine (313 mg, 1.38 mmol, 1.00 equiv), and $Pd(dppf)Cl_2$ (106 mg, 0.14 mmol, 0.10 equiv) in dioxane (13 mL)/water (1.3 mL) was stirred for 12 h at 80° C. under nitrogen. The reaction mixture was diluted with ethyl acetate, washed with brine, dried over anhydrous sodium sulfate, and concentrated under vacuum. The residue was purified by a silica gel column eluting with ethyl acetate/petroleum ether (1/10) to afford the title compound (400 mg, 76%) as an off-white solid.

Step 5: Preparation of 2-([[(tert-butoxy)carbonyl]amino]methyl)-4-[2-(trifluoromethyl)pyrimidin-5-yl]benzoic acid

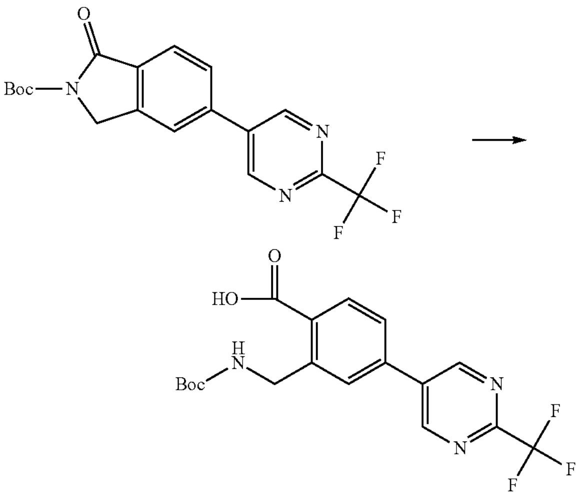

A mixture of tert-butyl 1-oxo-5-[2-(trifluoromethyl)pyrimidin-5-yl]-2,3-dihydro-1H-isoindole-2-carboxylate (250 mg, 0.66 mmol, 1.00 equiv) and LiOH (100 mg, 4.18 mmol, 6.30 equiv) in tetrahydrofuran (3 mL)/water (0.3 mL) was stirred for 12 h at 20° C. The resulting solution was diluted with water and extracted with diethyl ether. The pH value of the aqueous solution was adjusted to 3-4 with 5% HCl. The resulting solution was extracted with ethyl acetate, dried over anhydrous sodium sulfate, and concentrated under vacuum. This resulted in the title compound (180 mg, 69%) as a brown solid.

Step 6: Preparation of tert-butyl N-([2-carbamoyl-5-[2-(trifluoromethyl)pyrimidin-5-yl]phenyl]methyl)carbamate

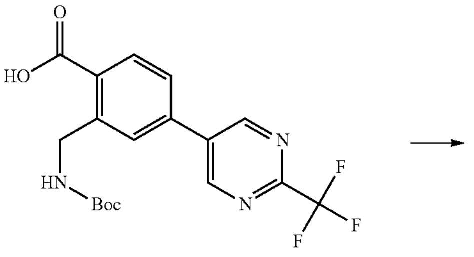

-continued

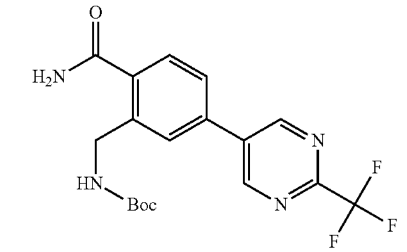

A mixture of 2-([[(tert-butoxy)carbonyl]amino]methyl)-4-[2-(trifluoromethyl)pyrimidin-5-yl]benzoic acid (160 mg, 0.40 mmol, 1.00 equiv), DIEA (600 mg, 4.64 mmol, 11.50 equiv), HATU (183 mg, 0.48 mmol, 1.20 equiv), and $NH_4Cl$ (260 mg, 4.86 mmol, 12.10 equiv) in DMF (5 mL) was stirred for 12 h at 20° C. The resulting solution was diluted with ethyl acetate, washed with brine, dried over anhydrous sodium sulfate, and concentrated under vacuum. The residue was purified by a silica gel column eluting with ethyl acetate/petroleum ether (1/1) to afford the title compound (160 mg, 100%) as a brown solid.

Step 7: Preparation of 2-(aminomethyl)-4-[2-(trifluoromethyl)pyrimidin-5-yl]benzamide hydrochloride

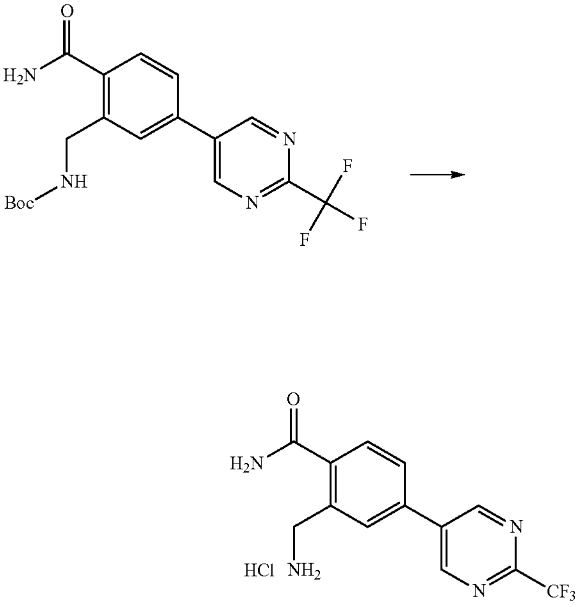

A mixture of tert-butyl N-([2-carbamoyl-5-[2-(trifluoromethyl)pyrimidin-5-yl]phenyl]methyl)carbamate (160 mg, 0.40 mmol, 1.00 equiv) and HCl (saturated solution in 20 mL of 1,4-dioxane) was stirred for 2 h at room temperature. The resulting mixture was concentrated under vacuum to afford the title compound (120 mg, crude) as a white solid.

Step 8: Preparation of tert-butyl (2S,3R)-2-[([2-carbamoyl-5-[2-(trifluoromethyl)pyrimidin-5-yl]phenyl]methyl)carbamoyl]-3-hydroxypyrrolidine-1-carboxylate

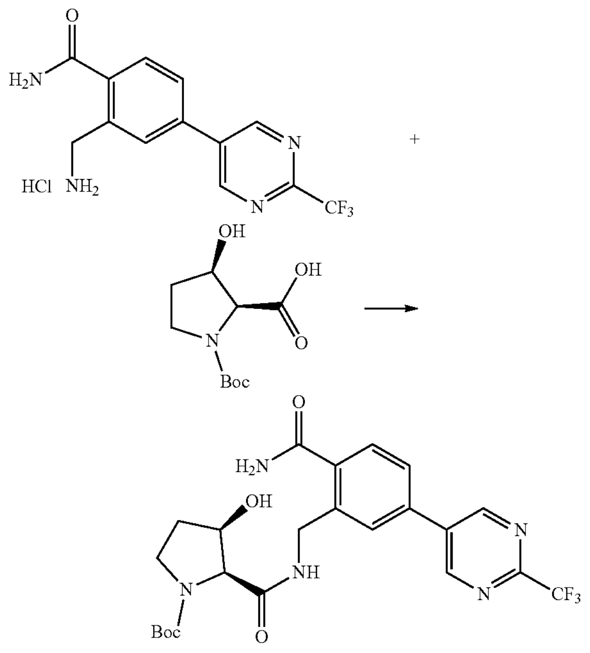

A mixture of (2S,3R)-1-[(tert-butoxy)carbonyl]-3-hydroxypyrrolidine-2-carboxylic acid (93.67 mg, 0.41 mmol, 1.00 equiv), DIEA (157.06 mg, 1.22 mmol, 3.00 equiv), HATU (231.03 mg, 0.61 mmol, 1.50 equiv), and 2-(aminomethyl)-4-[2-(trifluoromethyl)pyrimidin-5-yl]benzamide hydrochloride (120.00 mg, 0.41 mmol, 1.00 equiv) in DMF (5 mL) was stirred for 2 h at room temperature. The resulting solution was diluted with ethyl acetate, washed with brine, dried over anhydrous sodium sulfate, and concentrated under vacuum. The residue was purified by a silica gel column eluting with dichloromethane/methanol (20:1) to afford the title compound (130 mg, 63%) as a white solid.

Step 9: Preparation of tert-butyl (2R,3S)-2-[([2-carbamoyl-5-[2-(trifluoromethyl)pyrimidin-5-yl]phenyl]methyl)carbamoyl]-3-fluoropyrrolidine-1-carboxylate

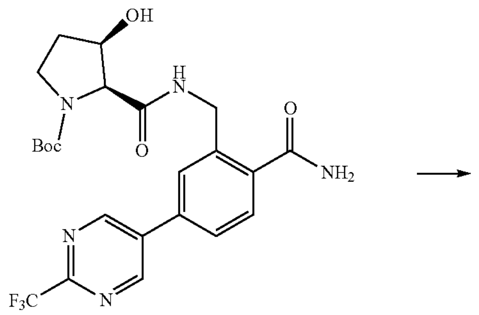

-continued

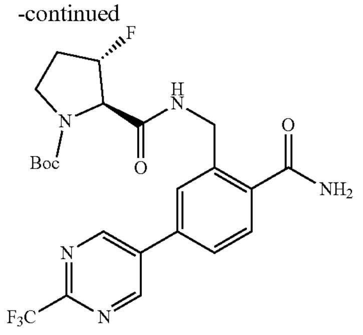

DAST (174.01 mg, 1.08 mmol, 5.00 equiv) was added dropwise into a stirred mixture of tert-butyl (2S,3R)-2-[([2-carbamoyl-5-[2-(trifluoromethyl)pyrimidin-5-yl]phenyl]methyl)carbamoyl]-3-hydroxypyrrolidine-1-carboxylate (110.00 mg, 0.22 mmol, 1.00 equiv) in dichloromethane (5 mL) at −78° C. under nitrogen. The reaction was stirred for 30 min at −78° C. and 12 h at room temperature. The reaction was then quenched by water and extracted with dichloromethane. The combined extracts were washed with saturated aqueous sodium bicarbonate and brine, dried over anhydrous sodium sulfate, and concentrated under vacuum. The residue was purified by a silica gel column eluting with ethyl acetate/petroleum ether (1:1) to afford the title compound (60 mg, 54%) as a white solid.

Step 10: Preparation of tert-butyl (2R,3S)-2-[([2-cyano-5-[2-(trifluoromethyl)pyrimidin-5-yl]phenyl]methyl)carbamoyl]-3-fluoropyrrolidine-1-carboxylate

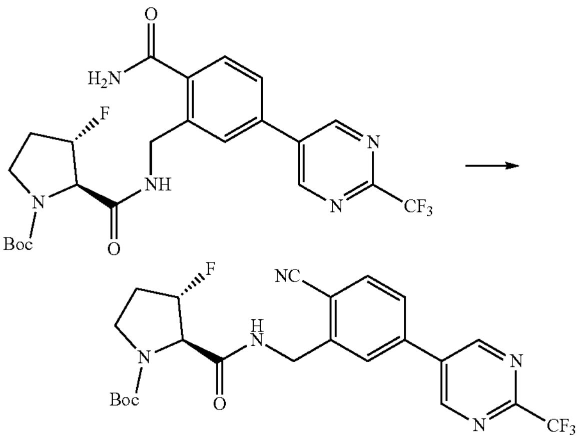

TFAA (49.28 mg, 0.23 mmol, 2.00 equiv) was added to a mixture of tert-butyl (2R,3S)-2-[([2-carbamoyl-5-[2-(trifluoromethyl)pyrimidin-5-yl]phenyl]methyl)carbamoyl]-3-fluoropyrrolidine-1-carboxylate (60.00 mg, 0.12 mmol, 1.00 equiv) in dichloromethane (5 mL)/triethylamine (11.87 mg, 0.12 mmol, 1.00 equiv). The reaction was stirred for 10 min at room temperature, quenched by water, and extracted with dichloromethane. The combined extracts were washed with brine, dried over anhydrous sodium sulfate, and concentrated under vacuum. The residue was purified by a silica gel column eluting with ethyl acetate/petroleum ether (1:5) to afford the title compound (50 mg, 86%) as a white solid.

Step 11: Preparation of (2R,3S)—N-([2-cyano-5-[2-(trifluoromethyl)pyrimidin-5-yl]phenyl]methyl)-3-fluoropyrrolidine-2-carboxamide

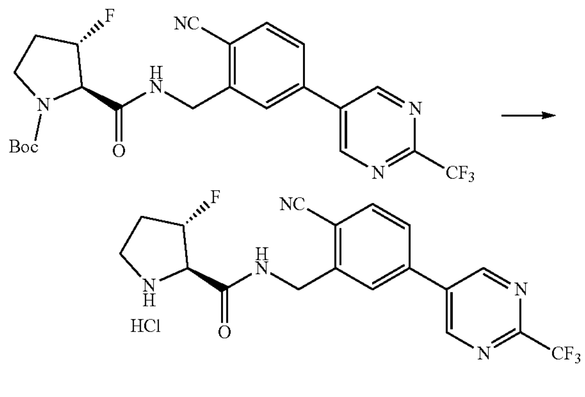

A mixture of tert-butyl (2R,3S)-2-[([2-cyano-5-[2-(trifluoromethyl)pyrimidin-5-yl]phenyl]methyl)carbamoyl]-3-fluoropyrrolidine-1-carboxylate (50 mg, 0.10 mmol, 1.00 equiv) and HCl (saturated solution in 5 mL of 1,4-dioxane) was stirred for 3 h at room temperature. The resulting mixture was concentrated under vacuum to afford the title compound (40 mg, crude) as a white solid.

Step 12: Preparation of (2R,3S)—N-([2-cyano-5-[2-(trifluoromethyl)pyrimidin-5-yl]phenyl]methyl)-3-fluoro-1-[(4-fluorobenzene)sulfonyl]pyrrolidine-2-carboxamide

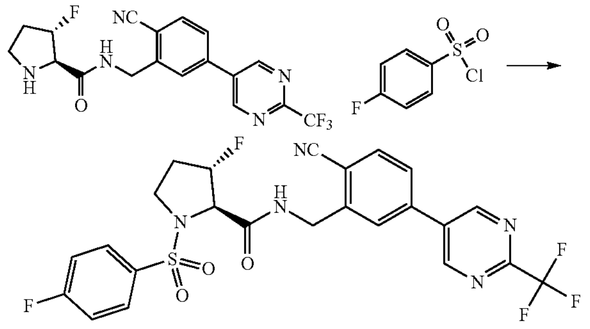

A mixture of (2R,3S)—N-([2-cyano-5-[2-(trifluoromethyl)pyrimidin-5-yl]phenyl]methyl)-3-fluoropyrrolidine-2-carboxamide (47.00 mg, 0.119 mmol, 1.000 equiv), triethylamine (36.27 mg, 0.358 mmol, 3.000 equiv), and 4-fluorobenzene-1-sulfonyl chloride (46.51 mg, 0.239 mmol, 2.000 equiv) in dichloromethane (5 ml) was stirred for 12 h at room temperature. The reaction was then quenched by water and extracted with dichloromethane. The combined extracts were washed with brine, dried over anhydrous sodium sulfate, and concentrated under vacuum. The residue was purified by a silica gel column eluting with ethyl acetate/petroleum ether (1:1). The crude product (40 mg) was re-purified by Prep-HPLC to afford the title compound (25.1 mg, 38%) as a white solid.

$^1$H NMR (400 MHz, $CD_3OD$) δ 9.40 (s, 1H), 8.10 (s, 1H), 8.03-7.91 (m, 4H), 7.41-7.35 (m, 2H), 5.19 (d, J=52 Hz, 1H), 4.92-4.87 (m, 1H), 4.64 (d, J=24.4 Hz, 2H), 4.36 (d, J=24.4 Hz, 1H), 3.80-3.85 (m, 1H), 3.33-3.27 (m, 1H), 2.29-2.14 (m, 2H).

Example 39

Preparation of (2S,5R)-1-[(4-fluorobenzene)sulfonyl]-5-methyl-N-([6-[6-(trifluoromethyl)pyridin-3-yl]pyrimidin-4-yl]methyl)pyrrolidine-2-carboxamide

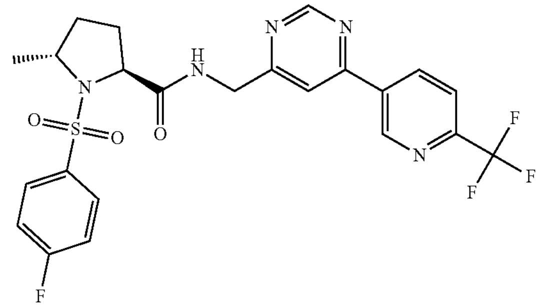 [SMILES: C[C@@H]1CC[C@@H](C(=O)NCc2cc(-c3ccc(C(F)(F)F)nc3)ncn2)N1S(=O)(=O)c1ccc(F)cc1]

Step 1: Preparation of 1-tert-butyl 2-methyl (2S)-5-methoxypyrrolidine-1,2-dicarboxylate

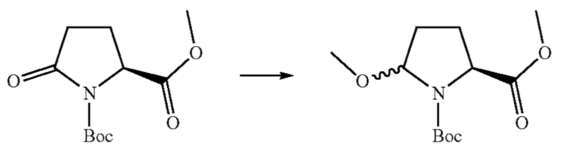 [SMILES: COC(=O)[C@@H]1CCC(=O)N1C(=O)OC(C)(C)C ; COC(=O)[C@@H]1CCC(OC)N1C(=O)OC(C)(C)C]

Lithium triethylborohydride (34.5 mL, 1.20 equiv) was added dropwise into a solution of 1-tert-butyl 2-methyl (2S)-5-oxopyrrolidine-1,2-dicarboxylate (7 g, 1.00 equiv) in tetrahydrofuran (30 mL) at −78° C. under nitrogen. The reaction was stirred for 2 h at −78° C. and quenched by aqueous sodium bicarbonate at 0° C. 30% $H_2O_2$ (15 mL) was added and the reaction was stirred for 20 minutes. The mixture was extracted with $Et_2O$ (2×50 mL), washed with brine, dried over $Na_2SO_4$, and concentrated under vacuum. To the resulting crude aminol in methanol (25 mL) was added PTSA (656 mg, 0.38 mmol, 0.12 equiv). The resulting solution was stirred for 12 h at room temperature, quenched by aqueous sodium bicarbonate, extracted with ether, washed with brine, dried over anhydrous sodium sulfate and concentrated under vacuum. The residue was purified by a silica gel column eluting with ethyl acetate/petroleum ether (1:3). This resulted in the title compound (4.1 g) as light yellow oil.

Step 2: Preparation of 1-tert-butyl 2-methyl (2S)-5-methylpyrrolidine-1,2-dicarboxylate

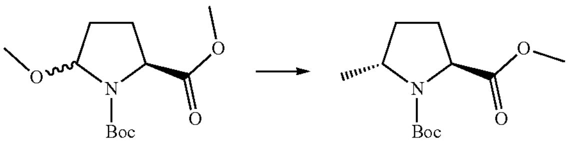

A mixture of copper(I) bromide-dimethyl sulfide (1.05 g, 5.11 mmol, 4.00 equiv) and diethyl ether (13 mL) was added MeMgBr (1.645 mL, 3M in $Et_2O$) dropwise at −40° C. under nitrogen. After 45 min at −40° C. the mixture was cooled to −78° C. and $BF_3.Et_2O$ (0.62 mL, 5.24 mmol, 4.00 equiv) was added dropwise at −78° C. The reaction was stirred for 30 min and 1-tert-butyl 2-methyl (2S)-5-methoxypyrrolidine-1,2-dicarboxylate (320 mg, 1.23 mmol, 1.00 equiv) in diethyl ether (17 mL) was added at −78° C. The resulting solution was stirred for 30 min at −78° C. and 1 h at room temperature. The reaction mixture was then stirred with aqueous $NH_4Cl$ for 1 h at room temperature. The resulting solution was extracted with $Et_2O$, washed with sodium bicarbonate and brine, dried over anhydrous sodium sulfate, and concentrated under vacuum. The residue was purified by a silica gel column eluting with ethyl acetate/petroleum ether (1:4). This resulted in the title compound (180 mg, 60%) as colorless oil.

Step 3: Preparation of (2S)-1-[(tert-butoxy)carbonyl]-5-methylpyrrolidine-2-carboxylic acid

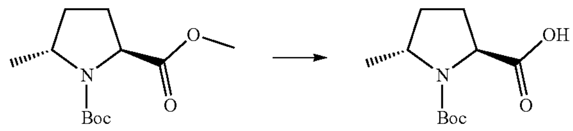

A mixture of 1-tert-butyl 2-methyl (2S)-5-methylpyrrolidine-1,2-dicarboxylate (180 mg, 0.74 mmol, 1.00 equiv) and LiOH (1.6 mg, 0.07 mmol, 0.10 equiv) in methanol (2 mL)/water (0.2 mL) was stirred overnight at room temperature and concentrated under vacuum. The residue was diluted with 10 mL of water and the pH value of the solution was adjusted to 3 with diluted HCl. The resulting solution was extracted with dichloromethane, dried over sodium sulfate, and concentrated under vacuum. This resulted in the title compound (110 mg, 65%) as light yellow oil.

Step 4: Preparation of tert-butyl (2R,5S)-2-methyl-5-[([6-[6-(trifluoromethyl)pyridin-3-yl]pyrimidin-4-yl]methyl)carbamoyl]pyrrolidine-1-carboxylate

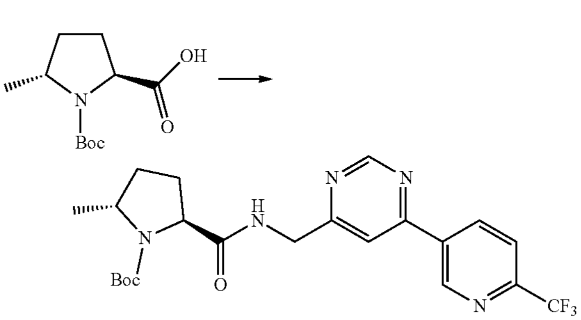

A solution of (2S,5R)-1-[(tert-butoxy)carbonyl]-5-methylpyrrolidine-2-carboxylic acid (120 mg, 0.52 mmol, 1.00 equiv), HATU (298 mg, 0.78 mmol, 1.50 equiv), DIEA (202 mg, 1.56 mmol, 3.00 equiv), and 6-[6-(trifluoromethyl)pyridin-3-yl]pyrimidin-4-ylmethanamine (182 mg, 0.72 mmol, 1.20 equiv) in DMF (5 mL) was stirred overnight at room temperature. The reaction solution was diluted with 40 mL of ethyl acetate, washed with brine, dried over anhydrous sodium sulfate, and concentrated under vacuum. The residue was purified by a silica gel column eluting with ethyl acetate/petroleum ether (1:1) to afford the title compound (90 mg, 37%) as light yellow oil.

Step 5: Preparation of (2S,5R)-5-methyl-N-((6-(6-(trifluoromethyl)pyridin-3-yl)pyrimidin-4-yl)methyl)pyrrolidine-2-carboxamide hydrochloride

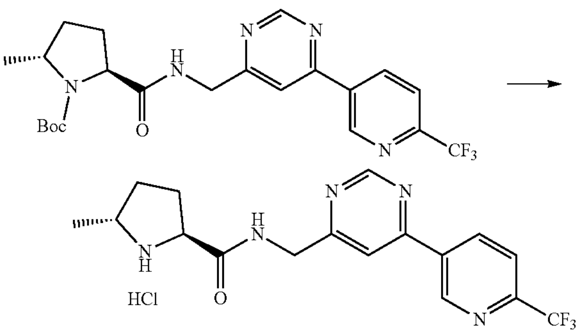

A solution of tert-butyl (2R,5S)-2-methyl-5-[([6-[6-(trifluoromethyl)pyridin-3-yl]pyrimidin-4-yl]methyl)carbamoyl]pyrrolidine-1-carboxylate (90 mg, 0.19 mmol, 1.00 equiv) and saturated HCl in 1,4-dioxane (10 mL) was stirred overnight at room temperature and concentrated under vacuum. This resulted in the title compound (85 mg) as light yellow oil.

Step 6: Preparation of (2S,5R)-1-[(4-fluorobenzene)sulfonyl]-5-methyl-N-([6-[6-(trifluoromethyl)pyridin-3-yl]pyrimidin-4-yl]methyl)pyrrolidine-2-carboxamide

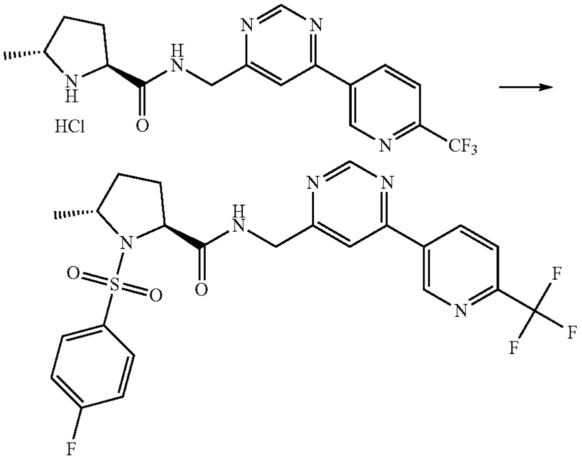

A solution of (2S,5R)-5-methyl-N-([6-[6-(trifluoromethyl)pyridin-3-yl]pyrimidin-4-yl]methyl)pyrrolidine-2-carboxamide hydrochloride (75 mg, 0.19 mmol, 1.0 equiv), TEA (56.6 mg, 0.56 mmol, 3.000 equiv), 4-dimethylaminopyridine (2.28 mg, 0.019 mmol, 0.1 equiv), and 4-fluorobenzene-1-sulfonyl chloride (43.5 mg, 0.224 mmol, 1.2 equiv) in dichloromethane (5 mL) was stirred for 1.5 h at room temperature. The resulting mixture was diluted with DCM, washed with brine, dried over anhydrous sodium sulfate, and concentrated under vacuum. The crude product was purified by Prep-HPLC to afford the title compound (21 mg, 21%) as a white solid.

$^1$H NMR (300 MHz, $CDCl_3$) δ 9.49 (s, 1H), 9.26 (s, 1H), 8.68-8.65 (d, J=8.4 Hz, 1H), 8.15 (s, 1H), 7.97-7.93 (m, 2H), 7.77-7.16 (m, 1H), 7.26-7.16 (m, 3H), 4.94-4.82 (m, 1H), 4.65-4.57 (m, 1H), 4.43-4.41 (m, 1H), 4.28-4.24 (m, 1H), 2.29-2.15 (m, 3H), 1.65-1.59 (m, 1H), 1.14-1.12 (m, 3H).

Example 40

Preparation of (2S,4S)-4-fluoro-1-[(4-fluorobenzene)sulfonyl]-4-(fluoromethyl)-N-([6-[6-(trifluoromethyl)pyridin-3-yl]pyrimidin-4-yl]methyl)pyrrolidine-2-carboxamide

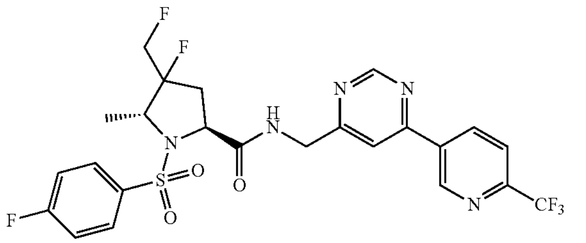 [SMILES: C[C@H]1N(S(=O)(=O)c2ccc(F)cc2)[C@H](C(=O)NCc2cc(-c3ccc(C(F)(F)F)nc3)ncn2)CC1(F)CF]

Step 1: Preparation of 1-tert-butyl 2-methyl 4-hydroxy-4-(hydroxymethyl)pyrrolidine-1,2-dicarboxylate

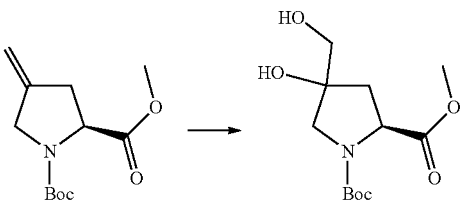 [SMILES: C=C1C[C@@H](C(=O)OC)N(C(=O)OC(C)(C)C)C1 ; COC(=O)[C@@H]1CC(O)(CO)CN1C(=O)OC(C)(C)C]

A mixture of 1-tert-butyl 2-methyl 4-methylidenepyrrolidine-1,2-dicarboxylate (1 g, 4.14 mmol, 1.00 equiv) and 4-methylmorpholin-4-ium-4-olate (1.175 g, 10.03 mmol, 1.60 equiv) in acetone (10 mL)/water(10 mL) was stirred for 7 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:1) to afford the title compound (700 mg, 61%) as orange oil.

Step 2: Preparation of 1-tert-butyl 2-methyl 4-[[(tert-butyldimethylsilyl)oxy]methyl]-4-hydroxypyrrolidine-1,2-dicarboxylate

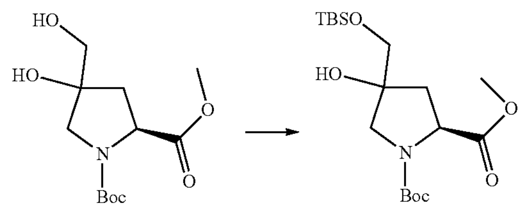 [SMILES: COC(=O)[C@@H]1CC(O)(CO)CN1C(=O)OC(C)(C)C ; COC(=O)[C@@H]1CC(O)(CO[Si](C)(C)C(C)(C)C)CN1C(=O)OC(C)(C)C]

A mixture of 1-tert-butyl 2-methyl 4-hydroxy-4-(hydroxymethyl)pyrrolidine-1,2-dicarboxylate (1.068 g, 3.88 mmol, 1.00 equiv), TBS-Cl (1.165 g, 7.73 mmol, 2.00 equiv), imidazole (528 mg, 7.76 mmol, 2.00 equiv), and 4-dimethylaminopyridine (47 mg, 0.38 mmol, 0.10 equiv) in N,N-dimethylformamide (27 mL) was stirred for 12 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10). This resulted in the title compound (1.37 g, 91%) as light yellow oil.

Step 3: Preparation of 1-tert-butyl 2-methyl (2S)-4-[[(tert-butyldimethylsilyl)oxy]methyl]-4-fluoropyrrolidine-1,2-dicarboxylate

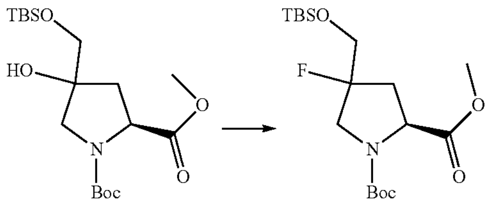 [SMILES: COC(=O)[C@@H]1CC(O)(CO[Si](C)(C)C(C)(C)C)CN1C(=O)OC(C)(C)C ; COC(=O)[C@@H]1CC(F)(CO[Si](C)(C)C(C)(C)C)CN1C(=O)OC(C)(C)C]

DAST (1.13 g, 7.01 mmol, 2.00 equiv) was added dropwise into a solution of 1-tert-butyl 2-methyl (2S)-4-[[(tert-butyldimethylsilyl)oxy]methyl]-4-hydroxypyrrolidine-1,2-dicarboxylate (1.37 g, 3.52 mmol, 1.00 equiv) in dichloromethane (25 mL) at −78° C. under nitrogen. The resulting solution was stirred for 1.5 h at room temperature. The reaction was then quenched by water, extracted with ethyl acetate, washed with brine, dried over anhydrous sodium sulfate, and concentrated under vacuum. This resulted in the title compound (1.25 g, 91%) as light yellow oil.

Step 4: Preparation of 1-tert-butyl 2-methyl (2S)-4-fluoro-4-(hydroxymethyl)pyrrolidine-1,2-dicarboxylate

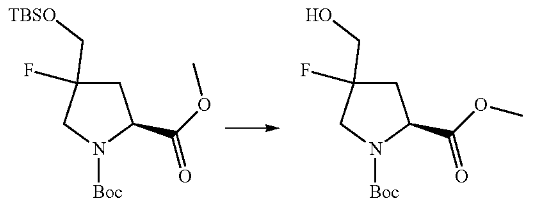 [SMILES: COC(=O)[C@@H]1CC(F)(CO[Si](C)(C)C(C)(C)C)CN1C(=O)OC(C)(C)C ; COC(=O)[C@@H]1CC(F)(CO)CN1C(=O)OC(C)(C)C]

A mixture of 1-tert-butyl 2-methyl (2S)-4-[[(tert-butyldimethylsilyl)oxy]methyl]-4-fluoropyrrolidine-1,2-dicarboxylate (1 g, 2.55 mmol, 1.00 equiv), TBAF (1.335 g, 5.11 mmol, 2.00 equiv) in tetrahydrofuran (5 mL) was stirred for 12 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10) to afford the title compound (520 mg, 73%) as colorless oil.

Step 5: Preparation of 1-tert-butyl 2-methyl (2S)-4-fluoro-4-(fluoromethyl)pyrrolidine-1,2-dicarboxylate

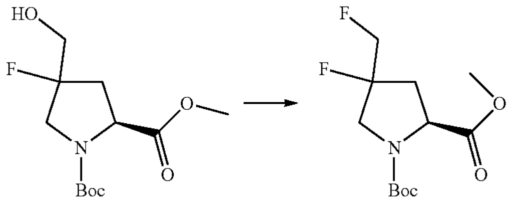 [SMILES: COC(=O)[C@@H]1CC(F)(CO)CN1C(=O)OC(C)(C)C ; COC(=O)[C@@H]1CC(F)(CF)CN1C(=O)OC(C)(C)C]

BAST (1.637 g, 7.40 mmol, 4.00 equiv) was added dropwise into a solution of 1-tert-butyl 2-methyl (2S)-4-fluoro-4-(hydroxymethyl)pyrrolidine-1,2-dicarboxylate (513 mg, 1.85 mmol, 1.00 equiv) in chloroform (10 mL) at 0° C. under nitrogen. The resulting solution was stirred for 5 h at 60° C. The reaction mixture was cooled to room temperature, quenched by water, and extracted with dichloromethane. The combined extracts were washed with brine, dried over anhydrous sodium sulfate, and concentrated under vacuum. The residue was purified by a silica gel column eluting with ethyl acetate/petroleum ether (1:10). This resulted in the title compound (300 mg, 58%) as orange oil.

Step 6: Preparation of (2S)-1-[(tert-butoxy)carbonyl]-4-fluoro-4-(fluoromethyl)pyrrolidine-2-carboxylic acid

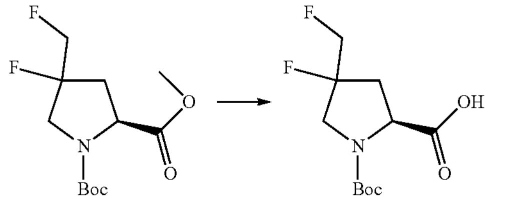 [SMILES: COC(=O)[C@@H]1CC(F)(CF)CN1C(=O)OC(C)(C)C ; CC(C)(C)OC(=O)N1CC(F)(CF)C[C@H]1C(=O)O]

A mixture of 1-tert-butyl 2-methyl (2S)-4-fluoro-4-(fluoromethyl)pyrrolidine-1,2-dicarboxylate (270 mg, 0.97 mmol, 1.00 equiv) and LiOH (116 mg, 4.84 mmol, 5.00 equiv) in tetrahydrofuran (3 mL)/water (2 mL) was stirred for 5 h at room temperature. The resulting solution was diluted with water and extracted with ethyl acetate. The pH value of the aqueous solution was adjusted to 4 with acetic acid. The resulting solution was extracted with ethyl acetate, washed with brine, dried over anhydrous sodium sulfate, and concentrated under vacuum. This resulted in the title compound (250 mg, 97%) as orange oil.

Step 7: Preparation of tert-butyl (2S)-4-fluoro-4-(fluoromethyl)-2-[([6-[6-(trifluoromethyl)pyridin-3-yl]pyrimidin-4-yl]methyl)carbamoyl]pyrrolidine-1-carboxylate

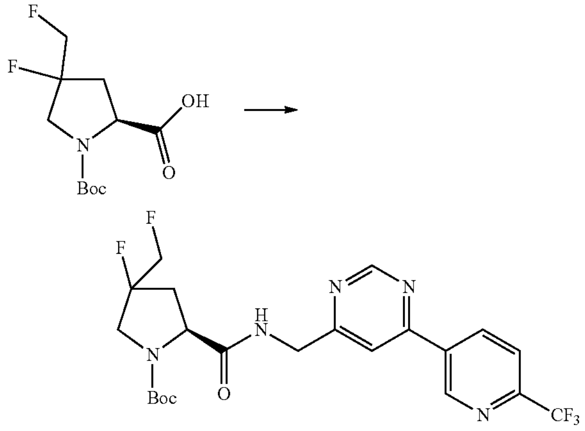

A mixture of (2S)-1-[(tert-butoxy)carbonyl]-4-fluoro-4-(fluoromethyl)pyrrolidine-2-carboxylic acid (110 mg, 0.41 mmol, 1.00 equiv), HATU (173.4 mg, 0.46 mmol, 1.10 equiv), DIEA (160.6 mg, 1.24 mmol, 3.00 equiv), and [6-[6-(trifluoromethyl)pyridin-3-yl]pyrimidin-4-yl]methanamine hydrochloride (120.3 mg, 0.41 mmol, 1.00 equiv) in N,N-dimethylformamide (6 mL) was stirred for 2 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:1) to afford the title compound (170 mg, 82%) as a yellow solid.

Step 8: Preparation of (2S)-4-fluoro-4-(fluoromethyl)-N-([6-[6-(trifluoromethyl)pyridin-3-yl]pyrimidin-4-yl]methyl)pyrrolidine-2-carboxamide hydrochloride

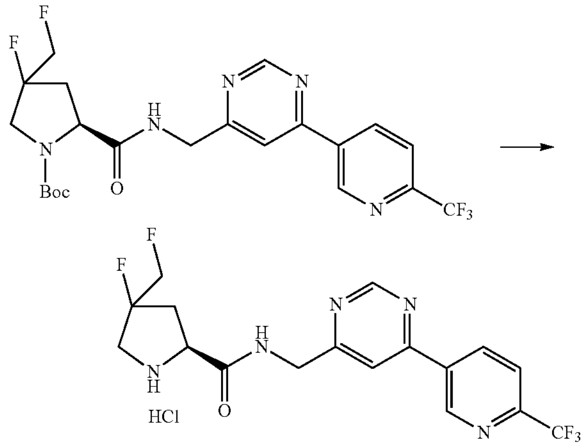

A mixture of tert-butyl (2S)-4-fluoro-4-(fluoromethyl)-2-[([6-[6-(trifluoromethyl)pyridin-3-yl]pyrimidin-4-yl]methyl)carbamoyl]pyrrolidine-1-carboxylate (170 mg, 0.34 mmol, 1.00 equiv) and saturated hydrogen chloride in dioxane (5 mL) was stirred for 20 h at room temperature. The resulting mixture was concentrated under vacuum to afford the title compound (125 mg, 84%) as a pink solid.

Step 9: Preparation of (2S,4S)-4-fluoro-1-[(4-fluorobenzene)sulfonyl]-4-(fluoromethyl)-N-([6-[6-(trifluoromethyl)pyridin-3-yl]pyrimidin-4-yl]methyl)pyrrolidine-2-carboxamide

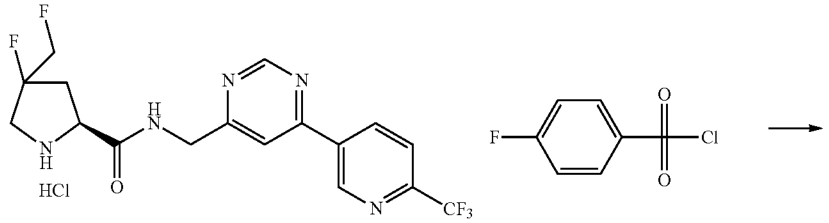

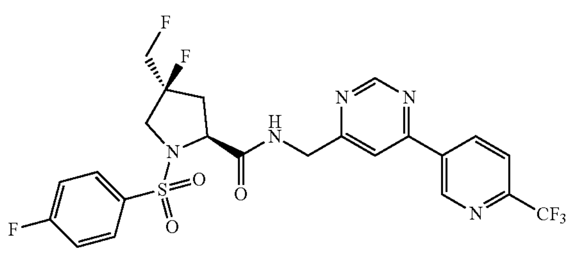

4-Proline Stereochemistry Assumed

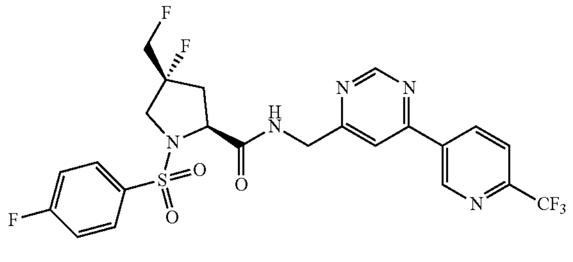

4-Proline Stereochemistry Assumed

A mixture of 4-fluorobenzene-1-sulfonyl chloride (125 mg, 0.642 mmol, 1.00 equiv), TEA (86.6 mg, 0.856 mmol, 3.00 equiv), and (2S)-4-fluoro-4-(fluoromethyl)-N-([6-[6-(trifluoromethyl)pyridin-3-yl]pyrimidin-4-yl]methyl)pyrrolidine-2-carboxamide hydrochloride (61.0 mg, 0.139 mmol, 1.10 equiv) in dichloromethane (5 mL) was stirred for 3 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:1). The crude product was purified by Prep-HPLC to afford the title compound (15.2 mg, 4%) as a white solid. $t_R$=0.93 min (CHIRALPAK AS-3, 4.6×100 cm, 3 μm, MeOH (0.1% DEA)=10% to 40% in 2.0 min, hold 1.0 min at 40%, 4 ml/min).

$^1$H NMR (400 MHz, $CDCl_3$) δ 9.51 (s, 1H), 9.29 (s, 1H), 8.70-8.68 (d, J=8 Hz, 1H), 8.09 (s, 1H), 7.95-7.92 (m, 2H), 7.83-7.81 (d, J=8 Hz, 1H), 7.61 (s, 1H), 7.52-7.28 (m, 2H), 4.97-4.91 (m, 1H), 4.61-4.35 (m, 4H), 3.93-3.71 (m, 2H), 2.52-2.49 (m, 1H), 2.38-2.27 (m, 1H).

And (2S,4R)-4-fluoro-1-[(4-fluorobenzene)sulfonyl]-4-(fluoromethyl)-N-([6-[6-(trifluoromethyl)pyridin-3-yl]pyrimidin-4-yl]methyl)pyrrolidine-2-carboxamide was also isolated (31.8 mg, 9%) as a white solid. $t_R$=1.18 min (CHIRALPAK AS-3, 4.6×100 cm, 3 μm, MeOH (0.1% DEA)=10% to 40% in 2.0 min, hold 1.0 min at 40%, 4 ml/min).

$^1$H NMR (400 MHz, $CDCl_3$) δ 9.50 (s, 1H), 9.27 (s, 1H), 8.68-8.66 (d, J=8 Hz, 1H), 8.00 (s, 1H), 7.96-7.92 (m, 2H), 7.82-7.80 (d, J=8 Hz, 1H), 7.69 (s, 1H), 7.35-7.31 (m, 2H), 4.92-4.85 (m, 1H), 4.70-4.64 (m, 1H), 4.59-4.31 (m, 3H), 4.02-3.94 (m, 1H), 3.45-3.33 (m, 1H), 2.65-2.57 (m, 1H), 2.03-1.72 (m, 1H).

The 4-proline stereochemistry for the above two compounds was arbitrarily assigned. The 2-proline stereochemistry for the above two compounds is as shown.

Example 41

Preparation of (2S,5S)-1-[(4-fluorobenzene)sulfonyl]-5-methyl-N-([6-[6-(trifluoromethyl)pyridin-3-yl]pyrimidin-4-yl]methyl)pyrrolidine-2-carboxamide

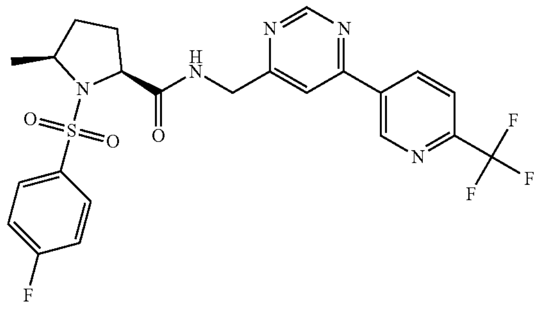 [SMILES: C[C@H]1CC[C@@H](C(=O)NCc2cc(-c3ccc(C(F)(F)F)nc3)ncn2)N1S(=O)(=O)c1ccc(F)cc1]

Step 1: Preparation of methyl (2S)-2-[[(tert-butoxy)carbonyl]amino]-5-oxohexanoate

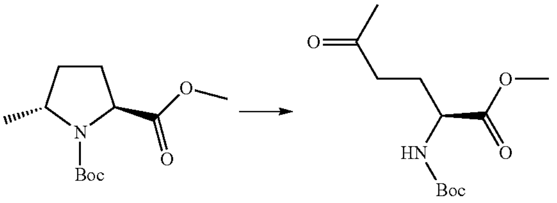

A solution of MeMgBr (1M) (33 mL, 1.00 equiv) was added dropwise to a solution of 1-tert-butyl 2-methyl (2S)-5-oxopyrrolidine-1,2-dicarboxylate (8 g, 32.89 mmol, 1.00 equiv) in tetrahydrofuran (20 mL) at −40° C. The resulting solution was stirred for 2 h at −40° C. The resulting solution was stirred overnight at room temperature. The reaction was then quenched by saturated $NH_4Cl$. The resulting solution was extracted with ethyl acetate and dried over anhydrous sodium sulfate. The solids were filtered off. The filtrate was concentrated under reduced pressure. The residue was purified by a silica gel column eluting with ethyl acetate/petroleum ether (1:5) to afford the title compound (5.1 g, 60%) as light yellow oil.

Step 2: Preparation of methyl (2S)-5-methyl-3,4-dihydro-2H-pyrrole-2-carboxylate

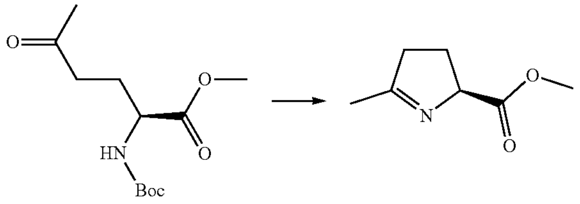

A solution of methyl (2S)-2-[[(tert-butoxy)carbonyl]amino]-5-oxohexanoate (3.7 g, 14.27 mmol, 1.00 equiv) and trifluoroacetic acid (10 mL, 134.63 mmol, 1.00 equiv) in dichloromethane (20 mL) was stirred for 1 day at room temperature. The resulting mixture was concentrated under vacuum to afford the title compound (3.5 g) as light yellow oil.

Step 3: Preparation of methyl (2S,5S)-5-methylpyrrolidine-2-carboxylate

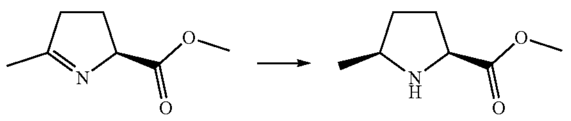

A mixture of methyl (2S)-5-methyl-3,4-dihydro-2H-pyrrole-2-carboxylate (350 mg, 2.48 mmol, 1.00 equiv) and palladium on carbon (300 mg) in methanol (3 mL) was stirred for 8 h at room temperature under hydrogen. The solids were filtered out. The filtrate was concentrated under vacuum to afford the title compound (400 mg) as light yellow oil.

Step 4: Preparation of methyl (2S,5S)-1-[(4-fluorobenzene)sulfonyl]-5-methylpyrrolidine-2-carboxylate

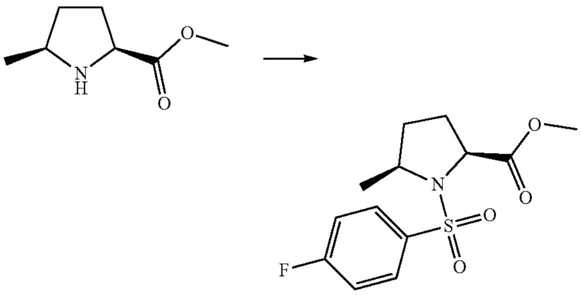

A mixture of methyl (2S,5S)-5-methylpyrrolidine-2-carboxylate (350 mg, 2.44 mmol, 1.00 equiv), TEA (987 mg, 9.75 mmol, 4.00 equiv), 4-dimethylaminopyridine (28 mg, 0.23 mmol, 0.10 equiv), and 4-fluorobenzene-1-sulfonyl chloride (567 mg, 2.91 mmol, 1.20 equiv) in dichloromethane (30 mL) was stirred for 8 h at room temperature. The resulting solution was diluted with ethyl acetate, washed with brine, and dried over anhydrous sodium sulfate. The residue was purified by a silica gel column eluting with ethyl acetate/petroleum ether (1:3) to afford the title compound (190 mg, 26%) as light yellow oil.

Step 5: Preparation of (2S,5S)-1-[(4-fluorobenzene)sulfonyl]-5-methylpyrrolidine-2-carboxylic acid

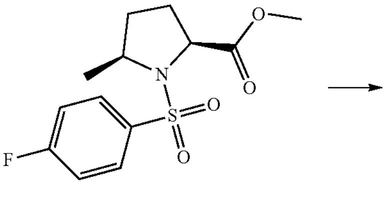

-continued

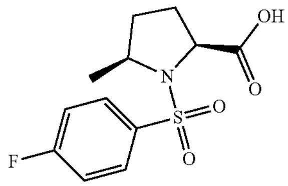

A mixture of methyl (2S,5S)-1-[(4-fluorobenzene)sulfonyl]-5-methylpyrrolidine-2-carboxylate (160 mg, 0.53 mmol, 1.00 equiv) and LiOH (25.5 mg, 1.06 mmol, 1.00 equiv) in methanol (4 mL)/water(0.5 mL) was stirred overnight at room temperature. The resulting solution was diluted with 20 mL of water. The pH value of the solution was adjusted to 9 with $Na_2CO_3$. The resulting solution was extracted with dichloromethane, dried over anhydrous sodium sulfate, and concentrated under vacuum. This resulted in the title compound (180 mg) as a white solid.

Step 6: Preparation of (2S,5S)-1-[(4-fluorobenzene)sulfonyl]-5-methyl-N-([6-[6-(trifluoromethyl)pyridin-3-yl]pyrimidin-4-yl]methyl)pyrrolidine-2-carboxamide

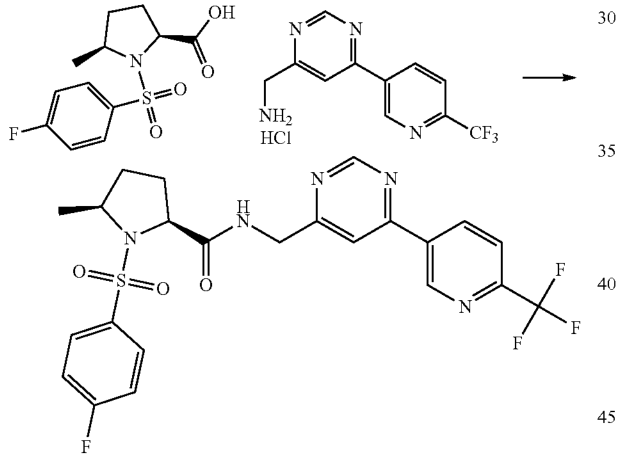

A mixture of (2S,5S)-1-[(4-fluorobenzene)sulfonyl]-5-methylpyrrolidine-2-carboxylic acid (150 mg, 0.522 mmol, 1.00 equiv), HATU (285 mg, 0.750 mmol, 1.50 equiv), DIEA (190 mg, 1.470 mmol, 3.000 equiv), and 6-[6-(trifluoromethyl)pyridin-3-yl]pyrimidin-4-ylmethanamine hydrochloride (182 mg, 0.626 mmol, 1.200 equiv) in N,N-dimethylformamide (4 mL) was stirred for 1 h at room temperature. The resulting solution was diluted with ethyl acetate, washed with brine, dried over anhydrous sodium sulfate, and concentrated under vacuum. The residue was purified by Prep-HPLC to afford the title compound (99.7 mg, 36%) as a white solid.

$^1H$ NMR (300 MHz, $CDCl_3$) δ 9.49 (s, 1H), 9.27 (s, 1H), 8.71-8.70 (d, J=1.5 Hz, 1H), 8.04 (s, 1H), 7.95-7.90 (m, 2H), 7.82-7.80 (m, 1H), 7.69-7.67 (m, 1H), 7.31-7.26 (m, 2H), 5.01-4.92 (m, 1H), 4.60-4.53 (m, 1H), 4.22-4.17 (m, 1H), 3.73-3.71 (m, 1H), 2.19-2.16 (m, 1H), 1.77-1.68 (m, 3H), 1.60-1.51 (m, 3H).

Example 42

Preparation of (2S,4R)-4-fluoro-1-(4-fluorophenyl)sulfonyl-N-[[6-[2-(trifluoromethyl)pyrimidin-5-yl]pyrimidin-4-yl]methyl]pyrrolidine-2-carboxamide

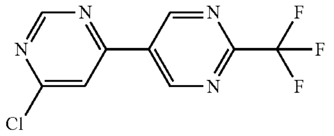 [SMILES: FC(F)(F)c1ncc(-c2cc(Cl)ncn2)cn1]

6-chloro-2'-(trifluoromethyl)-4,5'-bipyrimidine

A solution of 2-(trifluoromethyl)pyrimidin-5-ylboronic acid (100 mg, 0.50 mmol), 4,6-dichloropyrimidine (0.742559 mmol), cesium carbonate (322.595 mg, 0.99 mmol) and [1,1'-bis(diphenylphosphino)ferrocene]dichloropalladium(ii) dichloromethane adduct (0.10 equiv., 0.050 mmol) in acetonitrile (6.0 ml) and water (3.0 mL) was degassed. The reaction mixture was heated at 95° C. for 2 h. The reaction was filtered thru celite. The crude product was purified by flash chromatography (EtOAc/Hex_eluted at 20% EtOAc) to give 74 mg, 57.3% yield. LCMS (ESI) m/z:260.9 [M+H]+

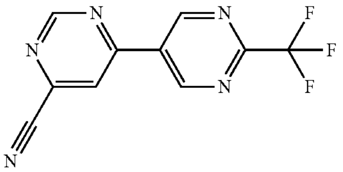 [SMILES: N#Cc1cc(-c2cnc(C(F)(F)F)nc2)ncn1]

2'-(trifluoromethyl)-[4,5'-bipyrimidine]-6-carbonitrile

A solution of 4-chloro-6-[2-(trifluoromethyl)pyrimidin-5-yl]pyrimidine (A, 150 mg, 0.58 mmol), zinc cyanide (82.763 mg, 0.69071 mmol), and 1,1'-bis(diphenylphosphino)ferrocene-palladium(ii)dichloride dichloromethane complex (48.0 mg, 0.058 mmol) in N,N-dimethylformamide (5.7559 mL, 74.4 mmol) was stirred at 150° C. 45 min. The reaction was quenched with water and extracted with EtOAc. The organic layers was dried with sodium sulfate, filtered, and concentrated via rotovap. The crude product was purified by flash chromatography (MeOH/DCM) to give 103 mg, 71.2% yield. LCMS (ESI) m/z:252.0 [M+H]+

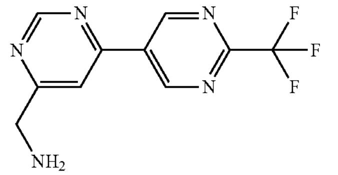 [SMILES: NCc1cc(-c2cnc(C(F)(F)F)nc2)ncn1]

(2'-(trifluoromethyl)-[4,5'-bipyrimidin]-6-yl)methanamine

A solution of 6-[2-(trifluoromethyl)pyrimidin-5-yl]pyrimidine-4-carbonitrile (A, 140 mg, 0.557 mmol) and palladium on Carbon 10% (11.864 mg, 0.0111 mmol) in methanol (11.148 mL) and hydrochloric acid (0.10 mL, 2.7870 mmol) was stirred under H2 10 min. The reaction was filtered thru celite. The crude product was carried to next step. LCMS (ESI) m/z:255.95 [M+H]+

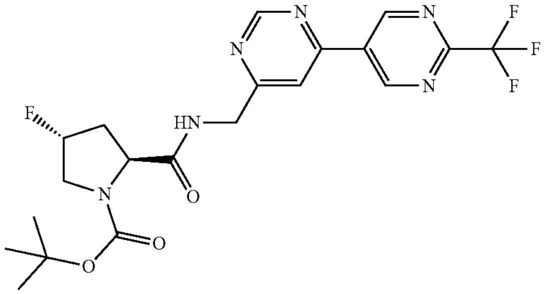 [SMILES: CC(C)(C)OC(=O)N1C[C@H](F)C[C@H]1C(=O)NCc1cc(-c2cnc(C(F)(F)F)nc2)ncn1]

(2S,4R)-tert-butyl 4-fluoro-2-(((2'-(trifluoromethyl)-[4,5'-bipyrimidin]-6-yl)methyl)carbamoyl)pyrrolidine-1-carboxylate To a solution of (2S,4R)-1-tert-butoxycarbonyl-4-fluoro-pyrrolidine-2-carboxylic acid (125 mg, 0.536 mmol) and [6-[2-(trifluoromethyl)pyrimidin-5-yl]pyrimidin-4-yl]methanamine (136.77 mg, 0.536 mmol) in N,N-dimethylformamide (2.0 mL) was added N,N-diisopropylethylamine (0.140 mL, 0.80389 mmol) and HATU (249.52 mg, 0.64311 mmol). The reaction mixture was stirred at RT 2 h. The reaction was quenched with water and extracted with EtOAc. The organic layers was dried with sodium sulfate, filtered, and concentrated via rotovap. The crude product was carried to next step. LCMS (ESI) m/z:471.20 [M+H]+

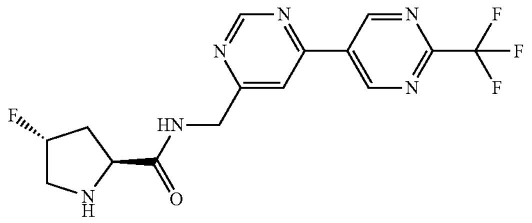 [SMILES: O=C(NCc1cc(-c2cnc(C(F)(F)F)nc2)ncn1)[C@@H]1C[C@@H](F)CN1]

(2S,4R)-4-fluoro-N-((2'-(trifluoromethyl)-[4,5'-bipyrimidin]-6-yl)methyl)pyrrolidine-2-carboxamide To a solution of tert-butyl (2S,4R)-4-fluoro-2-[[6-[2-(trifluoromethyl)pyrimidin-5-yl]pyrimidin-4-yl]methylcarbamoyl]pyrrolidine-1-carboxylate (252 mg, 0.5357 mmol) in 1,4-dioxane (2.7 mL) was added hydrochloric acid (4 mol/L) in 1,4-dioxane (1.34 mL, 5.357 mmol). The reaction mixture was stirred at RT 6 h. The reaction was concentrated and carried to next step. LCMS (ESI) m/z:371.05 [M+H]+

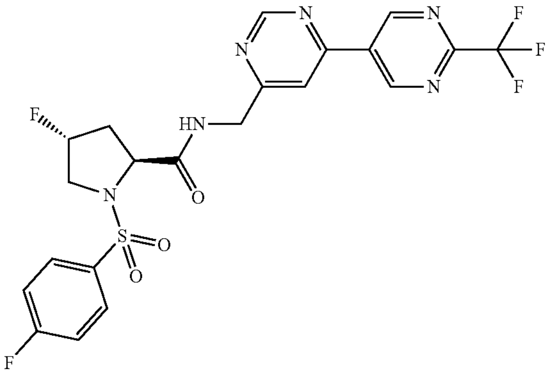 [SMILES: O=C(NCc1cc(-c2cnc(C(F)(F)F)nc2)ncn1)[C@@H]1C[C@@H](F)CN1S(=O)(=O)c1ccc(F)cc1]

(2S,4R)-4-fluoro-1-(4-fluorophenyl)sulfonyl-N-[[6-[2-(trifluoromethyl)pyrimidin-5-yl]pyrimidin-4-yl]methyl]pyrrolidine-2-carboxamide To a solution of (2S,4R)-4-fluoro-N-[[6-[2-(trifluoromethyl)pyrimidin-5-yl]pyrimidin-4-yl]methyl]pyrrolidine-2-carboxamide (198 mg, 0.5347 mmol) in dichloromethane (10.71 mL) was added triethylamine (1.49 mL, 10.71 mmol) then 4-fluorobenzenesulfonyl chloride (156.4 mg, 0.8036 mmol). The reaction was stirred at RT 1 h. The reaction was concentrated and submitted for rHPLC to give 119 mg, 42.03% yield.

1H NMR (400 MHz, DMSO) δ 9.72-9.68 (s, 2H), 9.36-9.33 (d, J=1.2 Hz, 1H), 9.21-9.11 (t, J=6.0 Hz, 1H), 8.30-8.25 (d, J=1.3 Hz, 1H), 8.08-7.99 (m, 2H), 7.52-7.43 (m, 2H), 5.31-5.12 (d, J=52.3 Hz, 1H), 4.61-4.47 (m, 2H), 4.30-4.20 (dd, J=10.0, 7.1 Hz, 1H), 3.80-3.58 (m, 2H), 2.46-2.37 (m, 1H), 2.25-2.03 (dddd, J=42.7, 13.8, 10.0, 3.3 Hz, 1H)., LCMS (ESI) m/z:529.11 [M+H]+.

Example 43

Preparation of (2S,4R)-4-fluoro-1-(4-fluorophenyl)sulfonyl-N-[[2-methyl-6-[2-(trifluoromethyl)pyrimidin-5-yl]-4-pyridyl]methyl]pyrrolidine-2-carboxamide

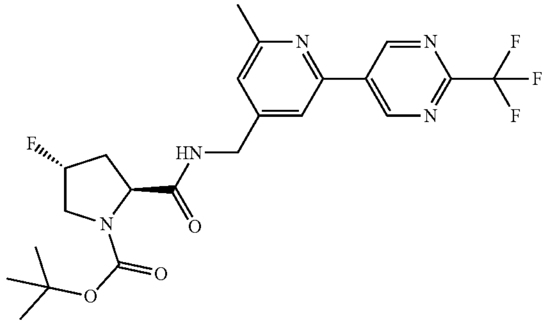 [SMILES: Cc1cc(CNC(=O)[C@@H]2C[C@@H](F)CN2C(=O)OC(C)(C)C)cc(-c2cnc(C(F)(F)F)nc2)n1]

(2S,4R)-tert-butyl 4-fluoro-2-(((2-methyl-6-(2-(trifluoromethyl)pyrimidin-5-yl)pyridin-4-yl)methyl)carbamoyl)pyrrolidine-1-carboxylate To a solution of tert-butyl (2S,4R)-2-[[2-chloro-6-[2-(trifluoromethyl)pyrimidin-5-yl]-4-pyridyl]methylcarbamoyl]-

4-fluoro-pyrrolidine-1-carboxylate (120 mg, 0.2381 mmol) and trimethylboroxine (45.30 mg, 0.0504 mL, 0.3572 mmol) in 1,2-dimethoxyethane (4.763 mL) was added potassium carbonate (99.73 mg, 0.7144 mmol) and [1,1'-bis(diphenylphosphino)ferrocene]dichloropalladium(II) (17.60 mg, 0.02381 mmol). The reaction mixture was degassed then heated microwave at 120° C. 40 min. The reaction was filtered thru celite concentrated. The crude product was purified by flash chromatography (DCM/MeOH) to give 95 mg, 82.5% yield. LCMS (ESI) m/z:484.15 [M+H]+

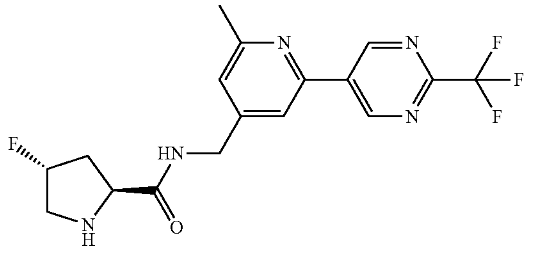 [SMILES: Cc1cc(CNC(=O)[C@@H]2C[C@@H](F)CN2)cc(-c2cnc(C(F)(F)F)nc2)n1]

(2S,4R)-4-fluoro-N-((2-methyl-6-(2-(trifluoromethyl)pyrimidin-5-yl)pyridin-4-yl)methyl)pyrrolidine-2-carboxamide To a solution of tert-butyl (2S,4R)-4-fluoro-2-[[2-methyl-6-[2-(trifluoromethyl)pyrimidin-5-yl]-4-pyridyl]methylcarbamoyl]pyrrolidine-1-carboxylate (A, 95 mg, 0.1965 mmol) in 1,4-dioxane (0.9824 mL) was added hydrochloric acid (4 mol/L) in 1,4-dioxane (0.4912 mL, 1.965 mmol). The reaction mixture was stirred at RT 6 h. The reaction was concentrated and carried to next step. LCMS (ESI) m/z: 384.1 [M+H]+

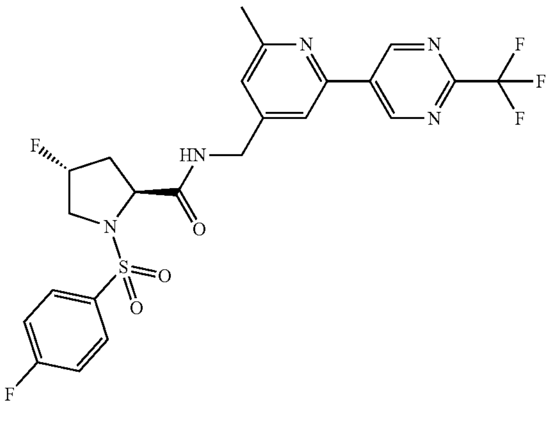 [SMILES: Cc1cc(CNC(=O)[C@@H]2C[C@@H](F)CN2S(=O)(=O)c2ccc(F)cc2)cc(-c2cnc(C(F)(F)F)nc2)n1]

(2S,4R)-4-fluoro-1-(4-fluorophenyl)sulfonyl-N-[[2-methyl-6-[2-(trifluoromethyl)pyrimidin-5-yl]-4-pyridyl]methyl]pyrrolidine-2-carboxamide To a solution of (2S,4R)-4-fluoro-N-[[2-methyl-6-[2-(trifluoromethyl)pyrimidin-5-yl]-4-pyridyl]methyl]pyrrolidine-2-carboxamide (75.31 mg, 0.1965 mmol) in dichloromethane (3.930 mL) was added triethylamine (0.548 mL, 3.930 mmol) then 4-fluorobenzenesulfonyl chloride (57.36 mg, 0.2947 mmol). The reaction was stirred at RT 1 h. The reaction was concentrated and submitted for rHPLC to give 65.4 mg, 61.47% yield.

1H NMR (400 MHz, DMSO) δ 9.67-9.58 (s, 2H), 9.04-8.93 (t, J=6.0 Hz, 1H), 8.06-7.95 (m, 3H), 7.53-7.42 (m, 2H), 7.41-7.36 (d, J=1.3 Hz, 1H), 5.30-5.11 (d, J=52.4 Hz, 1H), 4.55-4.37 (m, 2H), 4.24-4.17 (dd, J=10.0, 7.1 Hz, 1H), 3.76-3.58 (m, 2H), 2.61-2.56 (s, 3H), 2.22-2.00 (m, 1H)., LCMS (ESI) m/z:542.13 [M+H]+

Example 44

Preparation of (2S,4R)-4-fluoro-N-([3-fluoro-5-[2-methoxy-6-(trifluoromethyl)pyridin-3-yl]phenyl]methyl)-1-[(4-fluorobenzene)sulfonyl]pyrrolidine-2-carboxamide

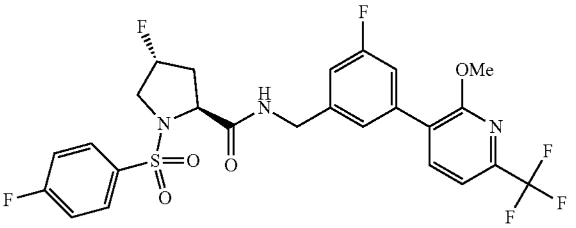 [SMILES: COc1nc(C(F)(F)F)ccc1-c1cc(F)cc(CNC(=O)[C@@H]2C[C@@H](F)CN2S(=O)(=O)c2ccc(F)cc2)c1]

Step 1: Preparation of (2S,4R)-4-fluoro-N-([3-fluoro-5-[2-methoxy-6-(trifluoromethyl)pyridin-3-yl]phenyl]methyl)-1-[(4-fluorobenzene)sulfonyl]pyrrolidine-2-carboxamide

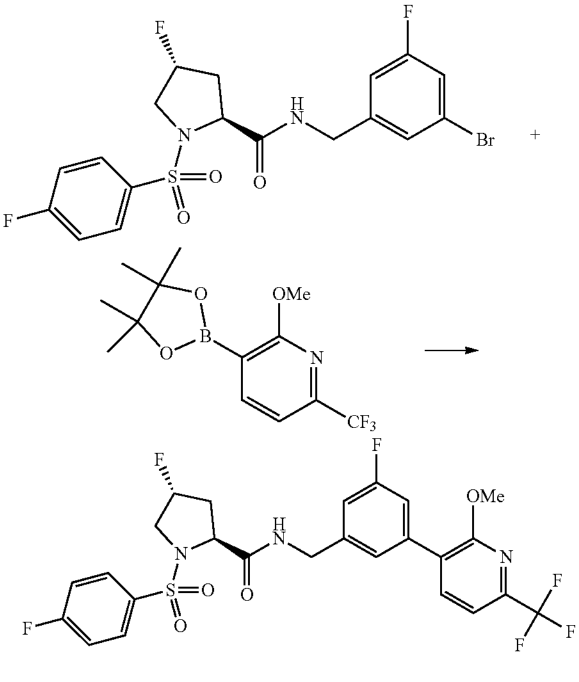

A mixture of (2S,4R)—N-[(3-bromo-5-fluorophenyl)methyl]-4-fluoro-1-[(4-fluorobenzene)sulfonyl]pyrrolidine-2-carboxamide (500 mg, 1.05 mmol, 1.00 equiv), potassium carbonate (430 mg, 3.11 mmol, 3.00 equiv), [2-methoxy-6-(trifluoromethyl)pyridin-3-yl]boronic acid (230 mg, 1.04 mmol, 1.00 equiv), and Pd(dppf)$Cl_2$ (78 mg, 0.11 mmol, 0.10 equiv) in 1,4-dioxane (12 mL)/water(1.2 mL) was stirred for 12 h at 80° C. under nitrogen. The resulting solution was diluted with ethyl acetate, washed with brine, dried over sodium sulfate, and concentrated under vacuum. The residue was purified by Prep-HPLC to afford the title compound (200 mg, 33%) as a white solid.

$^1$H NMR (400 MHz, $CDCl_3$) δ 7.88-7.85 (m, 3H), 7.85-7.78 (m, 1H), 7.35-7.26 (m, 3H), 7.24-7.22 (m, 2H), 7.21-7.07 (d, 1H), 5.10-4.97 (m, 1H), 4.67-4.62 (m, 1H), 4.51-4.48 (m, 1H), 4.29-2.25 (m, 1H), 4.03 (s, 3H), 3.95-3.86 (m, 1H), 3.67-3.42 (s, 1H), 2.52-2.50 (m, 1H), 2.49-2.35 (m, 1H).

Example 45

Preparation of (2S,4R)-4-fluoro-1-(4-fluorophenyl)sulfonyl-N-[[3-fluoro-5-[6-(trifluoromethyl)pyridazin-3-yl]phenyl]methyl]-4-methyl-pyrrolidine-2-carboxamide

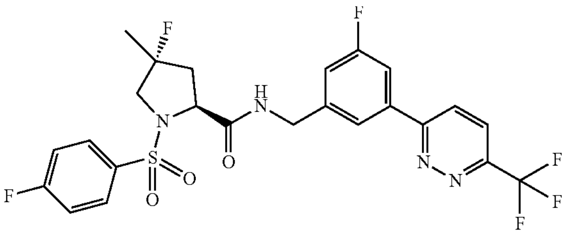 [SMILES: C[C@@]1(F)C[C@@H](C(=O)NCc2cc(F)cc(-c3ccc(C(F)(F)F)nn3)c2)N(S(=O)(=O)c2ccc(F)cc2)C1]

To a microwave vial was added (2S)—N-[(3-bromo-5-fluoro-phenyl)methyl]-4-fluoro-1-(4-fluorophenyl)sulfonyl-4-methyl-pyrrolidine-2-carboxamide (INT-52-5 of Example 52) (60 mg, 0.12 mmol), 3-chloro-6-(trifluoromethyl)pyridazine (29 mg, 0.16 mmol), bis(di-tert-butyl(4-dimethylaminophenyl)phosphine)dichloropalladium(II) (6.3 mg, 0.0089 mmol), sodium carbonate (17 mg, 0.16 mmol) and potassium acetate (15 mg, 0.16 mmol). Acetonitrile (0.8 mL) and water (0.16 mL) were added and nitrogen was bubbled through the reaction mixture for 3 mins then heated to 140° C. in the microwave for 30 mins. The reaction mixture was diluted with dichloromethane, filtered through celite, eluting with dichloromethane and the filtrate was concentrated in vacuo. The residue was adsorbed onto silica and purified by flash column chromatography with 0-100% EtOAc in heptane to afford the partially purified product. The residue was further purified by RP-HPLC to yield the title compound as a white solid (17.0 mg, 27%). MS-ESI: $[M+H]^+$ 559.12

$^1$H NMR (400 MHz, DMSO) δ 8.92 (t, J=6.1 Hz, 1H), 8.57 (d, J=8.9 Hz, 1H), 8.39 (d, J=9.0 Hz, 1H), 8.07 (t, J=1.4 Hz, 1H), 8.04-7.92 (m, 3H), 7.51-7.38 (m, 3H), 4.57-4.42 (m, 2H), 4.25-4.16 (m, 1H), 3.72-3.47 (m, 2H), 2.49-2.32 (m, 1H), 2.14-1.94 (m, 1H), 1.38 (d, J=20.8 Hz, 3H).

Example 46

Preparation of (2S,4R)-4-fluoro-1-((4-fluorophenyl)sulfonyl)-4-methyl-N-((6-(4-(trifluoromethoxy)phenyl)pyrimidin-4-yl)methyl)pyrrolidine-2-carboxamide

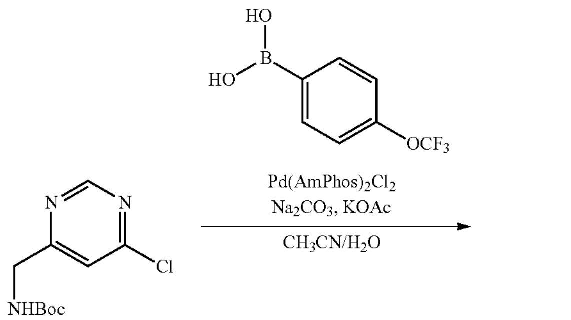

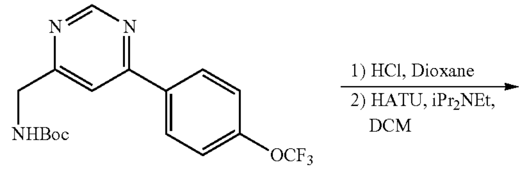

INT-46-7

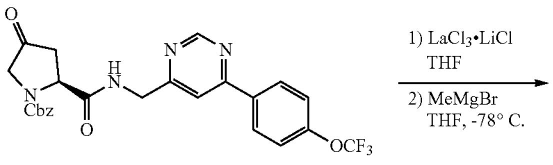

INT-46-8

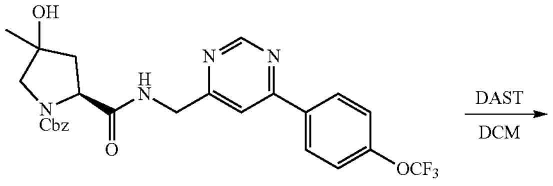

INT-46-9

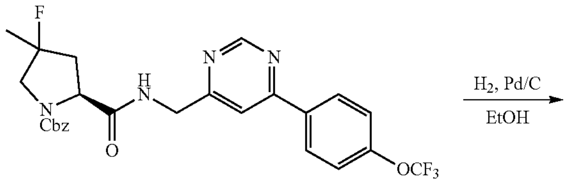

INT-46-10

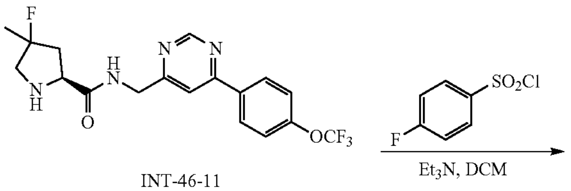

INT-46-11

Et3N, DCM

-continued

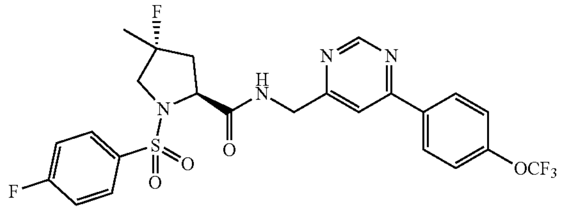 [SMILES: C[C@@]1(F)C[C@@H](C(=O)NCc2cc(-c3ccc(OC(F)(F)F)cc3)ncn2)N(S(=O)(=O)c2ccc(F)cc2)C1]

Step 1: tert-butyl ((6-(4-(trifluoromethoxy)phenyl) pyrimidin-4-yl)methyl)carbamate (INT-46-7)

To a microwave vial was added tert-butyl N-[(6-chloropyrimidin-4-yl)methyl]carbamate (150 mg, 0.58 mmol), 4-(trifluoromethoxy)phenylboronic acid (174 mg, 0.82 mmol), bis(di-tert-butyl(4-dimethylaminophenyl)phosphine)dichloropalladium(II) (33 mg, 0.047 mmol), sodium carbonate (87 mg, 0.82 mmol) and potassium acetate (81 mg, 0.82 mmol). Acetonitrile (3.0 mL) and water (0.6 mL) were added and nitrogen was bubbled through the reaction mixture for 3 mins then heated to 140° C. in the microwave for 30 mins. The reaction mixture was diluted with dichloromethane, filtered through celite, eluting with dichloromethane and the filtrate was concentrated in vacuo. The residue was adsorbed onto silica and purified by flash column chromatography with 0-100% EtOAc in heptane to afford the desired compound as a yellow foam (215 mg, 100%). MS-ESI: $[M+H]^+$ 370.2

Step 2: (S)-benzyl 4-oxo-2-(((6-(4-(trifluoromethoxy)phenyl)pyrimidin-4-yl)methyl)carbamoyl)pyrrolidine-1-carboxylate (INT-46-8)

To a solution of tert-butyl N-[[6-[4-(trifluoromethoxy) phenyl]pyrimidin-4-yl]methyl]carbamate (215 mg, 0.6038 mmol,) in dichloromethane (6 mL) was added hydrochloric acid (4 mol/L) in 1,4-dioxane (3 mL, 12 mmol) and the reaction mixture was stirred for 2 h at room temperature then concentrated in vacuo. The residue was dissolved in dichloromethane (3 mL) and (2S)-1-benzyloxycarbonyl-4-oxo-pyrrolidine-2-carboxylic acid (100 mg, 0.38 mmol) was added followed by N,N-diisopropylethylamine (147.3 mg, 0.199 mL, 1.140 mmol). The reaction mixture was stirred overnight at room temperature then quenched with sat. aq. sodium bicarbonate and extracted with EtOAc (3×). The combined organic extracts were washed with brine then dried over sodium sulfate, filtered and concentrated in vacuo. The residue was adsorbed onto silica and purified by flash column chromatography with 0-10% MeOH in DCM to afford the desired compound as a beige solid (142 mg, 46%). MS-ESI: $[M+H]^+$ 515.2

Step 3: (2S)-benzyl 4-hydroxy-4-methyl-2-(((6-(4-(trifluoromethoxy)phenyl)pyrimidin-4-yl)methyl) carbamoyl)pyrrolidine-1-carboxylate (INT-46-9)

To a solution of benzyl (2S)-4-oxo-2-[[6-[4-(trifluoromethoxy)phenyl]pyrimidin-4-yl]methylcarbamoyl]pyrrolidine-1-carboxylate (142 mg, 0.28 mmol) in tetrahydrofuran (3.0 mL) was added lanthanum(III) chloride bis (lithium chloride) complex solution (0.6 M in THF) (0.51 mL, 0.30 mmol) and the reaction mixture was stirred for 1 h at room temperature. The reaction mixture was then cooled to −78° C. and methylmagnesium bromide (3.0 mol/L in diethyl ether) (0.14 mL, 0.41 mmol) was added dropwise and the reaction mixture was stirred for 30 mins at −78° C. An additional portion of methylmagnesium bromide (3.0 mol/L in diethyl ether) (0.14 mL, 0.41 mmol) was added and the reaction mixture was stirred at −78° C. for an additional 15 min. An additional portion of methylmagnesium bromide (3.0 mol/L in diethyl ether) (0.14 mL, 0.41 mmol) was added an the reaction mixture was stirred at −78° C. for an additional 10 min. The reaction mixture was warmed to room temperature, quenched by the addition of sat. aq. ammonium chloride and extracted with EtOAc (3×). The combined organic layers were washed with brine, dried over sodium sulfate, filtered and concentrated in vacuo. The residue was adsorbed onto silica and purified by flash column chromatography with 0-10% MeOH in DCM to afford the desired compound as a beige foam (100 mg, 68%). MS-ESI: $[M+H]^+$ 531.2

Step 4: (2S)-benzyl 4-fluoro-4-methyl-2-(((6-(4-(trifluoromethoxy)phenyl)pyrimidin-4-yl)methyl) carbamoyl)pyrrolidine-1-carboxylate (INT-46-10)

To a solution of (2S)-benzyl 4-hydroxy-4-methyl-2-[[6-[4-(trifluoromethoxy)phenyl]pyrimidin-4-yl]methylcarbamoyl]pyrrolidine-1-carboxylate (100 mg, 0.19 mmol) in dichloromethane (4 mL) cooled to −78° C. was added diethylaminosulfur trifluoride (0.050 mL, 0.38 mmol) and the reaction mixture was stirred at −78° C. for 2 h. The reaction mixture was quenched by the careful addition of sat. aq. ammonium chloride and extracted with DCM (3×). The combined organic layers were dried over sodium sulfate, filtered and concentrated in vacuo. The residue was adsorbed onto silica and purified by flash column chromatography with 0-10% MeOH in DCM to afford the desired compound as a brown solid (72.5 mg, 72%). MS-ESI: $[M+H]^+$ 399.1

Step 5: (2S)-4-fluoro-4-methyl-N-((6-(4-(trifluoromethoxy)phenyl)pyrimidin-4-yl)methyl)pyrrolidine-2-carboxamide (INT-46-11)

To a solution of (2S)-benzyl 4-fluoro-4-methyl-2-[[6-[4-(trifluoromethoxy)phenyl]pyrimidin-4-yl]methylcarbamoyl]pyrrolidine-1-carboxylate (72.5 mg, 0.14 mmol) in ethanol (4 mL) was added palladium on carbon (10 mass %) (14.5 mg, 0.014 mmol). Hydrogen was bubbled through the reaction mixture for 5 mins then the reaction was stirred at room temp under an atmosphere of hydrogen overnight. The reaction mixture was diluted with dichloromethane, filtered through celite, eluting with dichloromethane and the filtrate was concentrated in vacuo. To the crude mixture was added palladium on carbon (10 mass %) (14.5 mg, 0.014 mmol) and ethanol (4 mL) and hydrogen was bubbled through the reaction mixture for 5 min. The mixture was then heated to 60° C. overnight under an atmosphere of hydrogen. The reaction mixture was diluted with dichloromethane, filtered through celite, eluting with dichloromethane and the filtrate was concentrated in vacuo. The residue was adsorbed onto silica and purified by flash column chromatography with 0-10% MeOH in DCM to afford the desired compound as a yellow foam (37.6 mg, 69%). MS-ESI: $[M+H]^+$ 533.2

Step 6: (2S,4R)-4-fluoro-1-((4-fluorophenyl)sulfonyl)-4-methyl-N-((6-(4-(trifluoromethoxy)phenyl) pyrimidin-4-yl)methyl)pyrrolidine-2-carboxamide To (2S)-4-fluoro-4-methyl-N-[[6-[4-(trifluoromethoxy) phenyl]pyrimidin-4-yl]methyl]pyrrolidine-2-carboxamide (37.6 mg, 0.094 mmol) dissolved in dichloromethane (2 mL)

was added triethylamine (0.026 mL, 0.19 mmol,) and 4-fluorobenzenesulfonyl chloride (20.2 mg, 0.10 mmol) at room temperature for 4 h. The reaction mixture was diluted with DCM and water, the layers were separated and the aqueous layer was extracted with DCM (2×). The combined organic layers were dried over sodium sulfate, filtered and concentrated in vacuo. The residue was adsorbed onto silica and purified by flash column chromatography with 0-10% MeOH in DCM to afford the partially purified title compound. The residue was purified by RP-HPLC to yield the title compound (4.1 mg, 8%) as a white solid. MS-ESI: $[M+H]^+$ 557.13

$^1$H NMR (400 MHz, DMSO) δ 9.20 (d, J=1.3 Hz, 1H), 9.07 (t, J=5.9 Hz, 1H), 8.37-8.28 (m, 2H), 8.09 (d, J=1.4 Hz, 1H), 8.06-7.94 (m, 2H), 7.51-7.43 (m, 4H), 4.57-4.41 (m, 2H), 4.32-4.23 (m, 1H), 3.74-3.48 (m, 2H), 2.49-2.34 (m, 1H), 2.18-1.97 (m, 1H), 1.39 (d, J=20.8 Hz, 3H).

Example 47

Preparation of (2S,4R)-4-fluoro-N-(3-fluoro-5-(5-(trifluoromethyl)pyrazin-2-yl)benzyl)-1-((4-fluorophenyl)sulfonyl)-4-methylpyrrolidine-2-carboxamide

Step 1: (2S,4R)-4-fluoro-N-(3-fluoro-5-(4,4,5,5-tetramethyl-1,3,2-dioxaborolan-2-yl)benzyl)-1-((4-fluorophenyl)sulfonyl)-4-methylpyrrolidine-2-carboxamide (INT-47-6)

To a vial was added (2S,4R)—N-[(3-bromo-5-fluoro-phenyl)methyl]-4-fluoro-1-(4-fluorophenyl)sulfonyl-4-methyl-pyrrolidine-2-carboxamide (INT-52-5) (340 mg, 0.69 mmol), 1,1'-bis(diphenylphosphino)ferrocene-palladium(II)dichloride dichloromethane complex (58 mg, 0.069 mmol), bis(pinacolato)diboron (264 mg, 1.04 mmol) and potassium acetate (204 mg, 2.08 mmol). 1,4-dioxane (10 mL) was added and nitrogen was bubbled through the solution for 3 mins and the reaction mixture was heated to 85° C. for 16 h. The reaction mixture was diluted with dichloromethane, filtered through celite, eluting with dichloromethane and the filtrate was concentrated in vacuo. The residue was adsorbed onto silica and purified by flash column chromatography with 0-100% EtOAc in heptane to afford the desired compound as a brown oil (329 mg, 88%). MS-ESI: $[M+H]^+$ 539.3

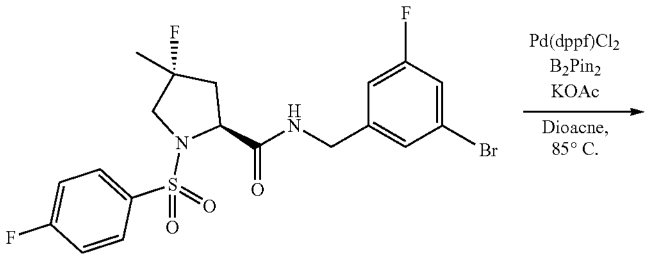

INT-52-5

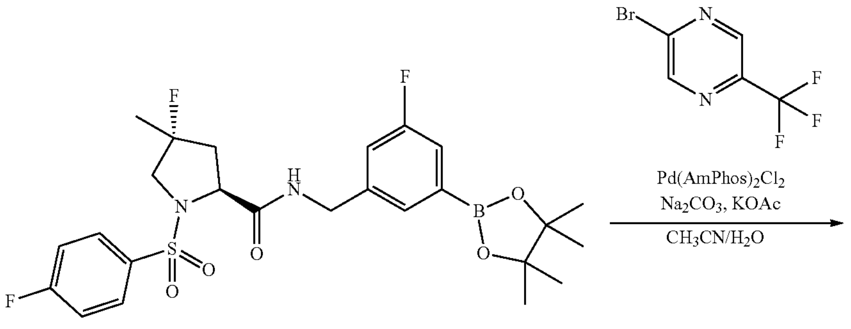

INT-47-6

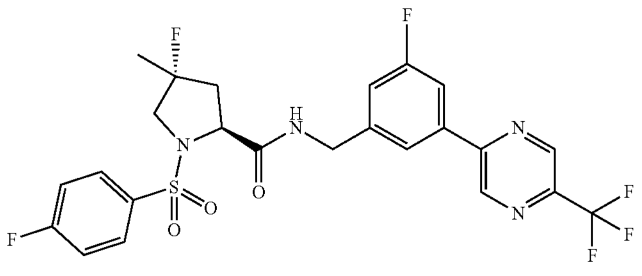

Step 2: (2S,4R)-4-fluoro-N-(3-fluoro-5-(5-(trifluoromethyl)pyrazin-2-yl)benzyl)-1-((4-fluorophenyl)sulfonyl)-4-methylpyrrolidine-2-carboxamide To a microwave vial was added (2S,4R)-4-fluoro-1-(4-fluorophenyl)sulfonyl-N-[[3-fluoro-5-(4,4,5,5-tetramethyl-1,3,2-dioxaborolan-2-yl)phenyl]methyl]-4-methyl-pyrrolidine-2-carboxamide (329 mg, 0.61 mmol), 2-chloro-5-(trifluoromethyl)pyrazine (138 mg, 0.73 mmol), bis(di-tert-butyl(4-dimethylaminophenyl)phosphine) dichloropalladium(II) (35 mg, 0.049 mmol), sodium carbonate (91 mg, 0.86 mmol) and potassium acetate (85 mg, 0.86 mmol). Acetonitrile (8.0 mL) and water (1.6 mL) were added and nitrogen was bubbled through the reaction mixture for 4 mins then heated to 140° C. in the microwave for 30 mins. The reaction mixture was diluted with dichloromethane, filtered through celite, eluting with dichloromethane and the filtrate was concentrated in vacuo. The residue was adsorbed onto silica and purified by flash column chromatography with 0-100% EtOAc in heptane to afford the partially purified product. The residue was purified by RP-HPLC to yield the title compound (108 mg, 32%) as a white solid.

$^1$H NMR (400 MHz, DMSO) δ 9.49 (d, J=1.4 Hz, 1H), 9.25 (d, J=1.4 Hz, 1H), 8.92 (t, J=6.0 Hz, 1H), 8.05 (t, J=1.5 Hz, 1H), 8.00-7.92 (m, 3H), 7.53-7.36 (m, 3H), 4.56-4.40 (m, 2H), 4.25-4.16 (m, 1H), 3.71-3.47 (m, 2H), 2.44-2.34 (m, 1H), 2.14-1.93 (m, 1H), 1.38 (d, J=20.8 Hz, 3H).

Example 48

Preparation of (2S,4R)-4-fluoro-1-(4-fluorophenyl)sulfonyl-N-[[6-methyl-4-[2-(trifluoromethyl)pyrimidin-5-yl]-2-pyridyl]methyl]pyrrolidine-2-carboxamide

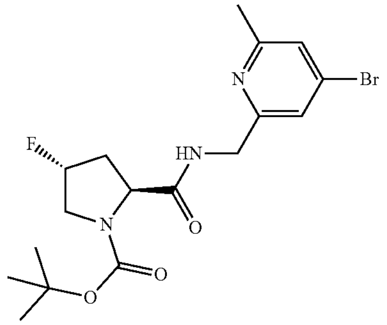 [SMILES: Cc1cc(Br)cc(CNC(=O)[C@@H]2C[C@@H](F)CN2C(=O)OC(C)(C)C)n1]

(2S,4R)-tert-butyl 2-(((4-bromo-6-methylpyridin-2-yl)methyl)carbamoyl)-4-fluoropyrrolidine-1-carboxylate To a solution of (2S,4R)-1-tert-butoxycarbonyl-4-fluoro-pyrrolidine-2-carboxylic acid (100 mg, 0.43 mmol) and (4-bromo-6-methyl-2-pyridyl)methanamine hydrochloride (112.02 mg, 0.47 mmol) in N,N-dimethylformamide (1.7 mL) was added N,N-diisopropylethylamine (0.112 mL, 0.64 mmol) and HATU (199.62 mg, 0.51 mmol). The reaction mixture was stirred at RT 2 h. The reaction was quenched with water and extracted with EtOAc. The organic layers was dried with sodium sulfate, filtered, and concentrated via rotovap. The crude product was purified by flash chromatography (MeOH/DCM) to give 54 mg, 30.2% yield. LCMS (ESI) m/z:416.05 [M+H]+

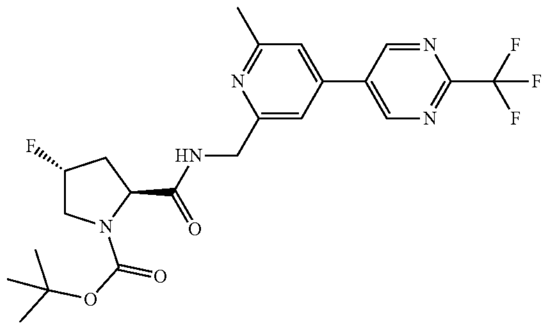 [SMILES: Cc1cc(-c2cnc(C(F)(F)F)nc2)cc(CNC(=O)[C@@H]2C[C@@H](F)CN2C(=O)OC(C)(C)C)n1]

(2S,4R)-tert-butyl 4-fluoro-2-(((6-methyl-4-(2-(trifluoromethyl)pyrimidin-5-yl)pyridin-2-yl)methyl)carbamoyl)pyrrolidine-1-carboxylate A solution of 2-(trifluoromethyl)pyrimidin-5-ylboronic acid (1.2 equiv., 0.3574 mmol), tert-butyl (2S,4R)-2-[(4-bromo-6-methyl-2-pyridyl)methylcarbamoyl]-4-fluoro-pyrrolidine-1-carboxylate (124 mg, 0.2979 mmol), cesium carbonate (194.1 mg, 0.04714 mL, 0.5957 mmol) and [1,1'-bis(diphenylphosphino)ferrocene]dichloropalladium(ii) dichloromethane adduct (0.10 equiv., 0.02979 mmol) in acetonitrile (3.0 mL) and water (1.5 mL) was degassed. The reaction mixture was heated at 95° C. for 2 h. The reaction was filtered thru celite. The crude product was purified by flash chromatography (MeOH/DCM) to give 70 mg, 48.6% yield. LCMS (ESI) m/z:484.15 [M+H]+

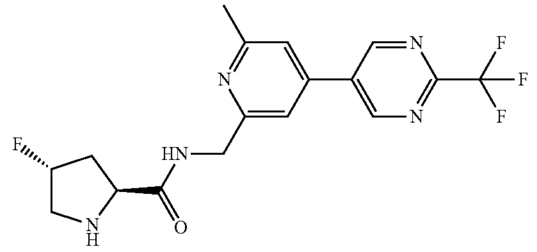 [SMILES: Cc1cc(-c2cnc(C(F)(F)F)nc2)cc(CNC(=O)[C@@H]2C[C@@H](F)CN2)n1]

(2S,4R)-4-fluoro-N-((6-methyl-4-(2-(trifluoromethyl)pyrimidin-5-yl)pyridin-2-yl)methyl)pyrrolidine-2-carboxamide To a solution of tert-butyl (2S,4R)-4-fluoro-2-[[6-methyl-4-[2-(trifluoromethyl)pyrimidin-5-yl]-2-pyridyl]methylcarbamoyl]pyrrolidine-1-carboxylate (70 mg, 0.1448 mmol) in 1,4-dioxane (0.7239 mL) was added hydrochloric acid (4 mol/L) in 1,4-dioxane (0.3619 mL,). The reaction mixture was stirred at RT 6 h. The reaction was concentrated and carried to next step. LCMS (ESI) m/z:384.1 [M+H]+

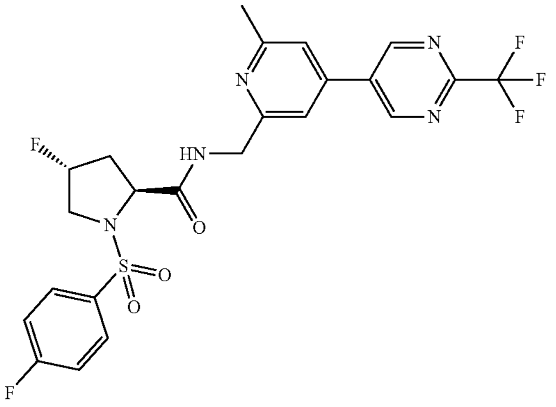 [SMILES: Cc1cc(-c2cnc(C(F)(F)F)nc2)cc(CNC(=O)[C@@H]2C[C@@H](F)CN2S(=O)(=O)c2ccc(F)cc2)n1]

(2S,4R)-4-fluoro-1-(4-fluorophenyl)sulfonyl-N-[[6-methyl-4-[2-(trifluoromethyl)pyrimidin-5-yl]-2-pyridyl]methyl]pyrrolidine-2-carboxamide To a solution of (2S,4R)-4-fluoro-N-[[6-methyl-4-[2-(trifluoromethyl)pyrimidin-5-yl]-2-pyridyl]methyl]pyrrolidine-2-carboxamide (55.5 mg, 0.1448 mmol) in dichloromethane (2.9 mL) was added triethylamine (0.404 mL, 2.896 mmol) then 4-fluorobenzenesulfonyl chloride (42.26 mg, 0.2172 mmol). The reaction was stirred at RT 1 h. The reaction was concentrated and submitted for rHPLC to give 61.4 mg, 78.32% yield.

1H NMR (400 MHz, DMSO) δ 9.51-9.41 (s, 2H), 9.06-8.95 (t, J=6.0 Hz, 1H), 8.05-7.95 (m, 2H), 7.77-7.68 (dd, J=9.2, 1.5 Hz, 2H), 7.49-7.42 (m, 2H), 5.31-5.09 (d, J=52.4 Hz, 1H), 4.56-4.40 (m, 2H), 4.30-4.20 (dd, J=9.9, 7.1 Hz, 1H), 3.78-3.57 (m, 2H), 2.62-2.56 (s, 3H), 2.44-2.30 (m, 1H), 2.24-2.00 (dddd, J=42.5, 14.0, 9.9, 3.4 Hz, 1H)., LCMS (ESI) m/z:542.13 [M+H]+

Example 49

Preparation of (2S,4R)-4-fluoro-N-([6-fluoro-4-[5-(trifluoromethyl)pyridin-2-yl]pyridin-2-yl]methyl)-1-[(4-fluorobenzene)sulfonyl]pyrrolidine-2-carboxamide

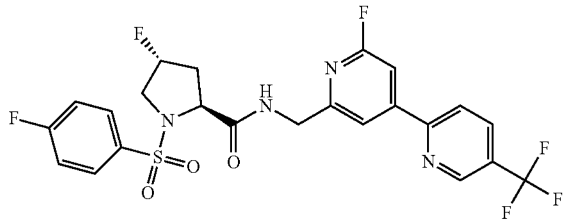 [SMILES: O=C(NCc1cc(-c2ccc(C(F)(F)F)cn2)cc(F)n1)[C@@H]1C[C@@H](F)CN1S(=O)(=O)c1ccc(F)cc1]

Step 1: Preparation of (2,6-dichloropyridin-4-yl)boronic acid

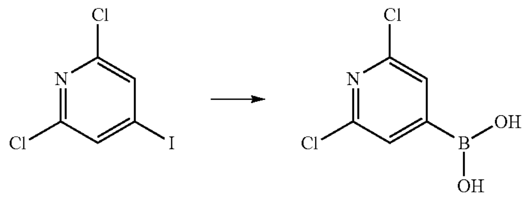 [SMILES: Clc1cc(I)cc(Cl)n1 ; OB(O)c1cc(Cl)nc(Cl)c1]

n-BuLi (3 mL, 2.5 M in hexane, 1.50 equiv) was added dropwise into a solution of 2,6-dichloro-4-iodopyridine (1.40 g, 5.112 mmol, 1.00 equiv) in tetrahydrofuran (20 mL) at −78° C. under nitrogen. The resulting solution was stirred for 30 min at −78° C. Trimethyl borate (580 mg, 5.582 mmol, 1.10 equiv) was added at −78° C. and the reaction was stirred for 1 h at −78° C. The resulting solution was stirred for an additional 12 h at room temperature, quenched by 1.6 g of pinacol and then AcOH (0.6 mL). The solids were filtered out and the liquid was concentrated under vacuum. This resulted in the title compound (1 g, crude) as a yellow solid.

Step 2: Preparation of 2,6-dichloro-4-[5-(trifluoromethyl)pyridin-2-yl]pyridine

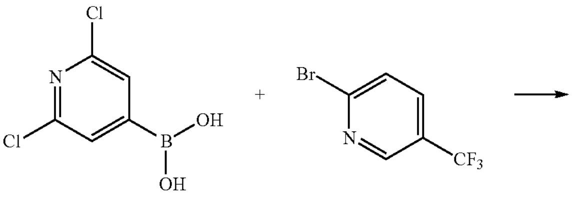

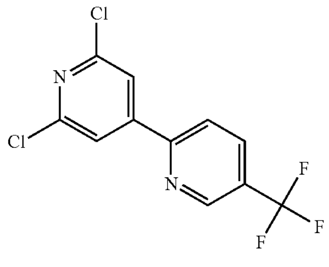

A mixture of 2-bromo-5-(trifluoromethyl)pyridine (800.00 mg, 3.54 mmol, 1.00 equiv), (2,6-dichloropyridin-4-yl)boronic acid (1 g, 5.21 mmol, 1.00 equiv), Pd(dppf)$Cl_2$.$CH_2Cl_2$ (290 mg, 0.36 mmol, 0.10 equiv), and potassium carbonate (1.96 g, 14.18 mmol, 4.00 equiv) in 1,4-dioxane (40 mL)/water(2 mL) was stirred for 12 h at 120° C. under nitrogen. The resulting solution was diluted with ethyl acetate, washed with brine, dried over anhydrous sodium sulfate, and concentrated under vacuum. The residue was purified by flash chromatography on silica gel eluting with ethyl acetate/petroleum ether (1:100). This resulted in the title compound (680 mg, 66%) as a white solid.

Step 3: Preparation of 2-chloro-6-fluoro-4-[5-(trifluoromethyl)pyridin-2-yl]pyridine

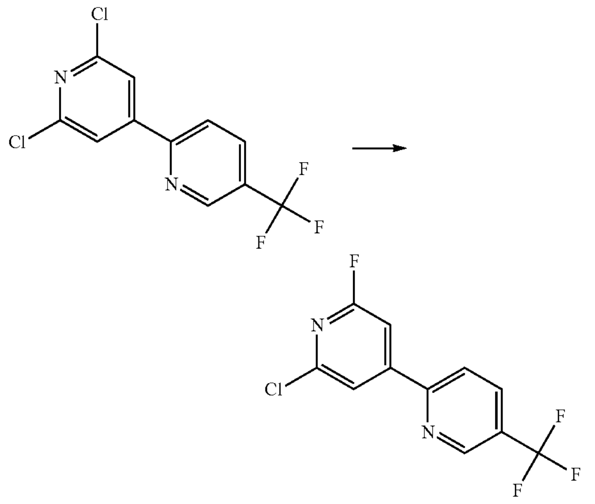

A mixture of 2,6-dichloro-4-[5-(trifluoromethyl)pyridin-2-yl]pyridine (680.00 mg, 2.32 mmol, 1.00 equiv), and KF (134.80 mg, 2.32 mmol, 1.00 equiv) in DMSO (5 mL) was stirred for 6 h at 140° C. The resulting solution was diluted with water and extracted with ethyl acetate. The combined extracts were washed with brine, dried over anhydrous sodium sulfate, and concentrated under vacuum. The residue was purified by flash chromatography on silica gel eluting with ethyl acetate/petroleum ether (1:100). This resulted in the title compound (600 mg, 93%) as a white solid.

Step 4: Preparation of 6-fluoro-4-[5-(trifluoromethyl)pyridin-2-yl]pyridine-2-carbonitrile

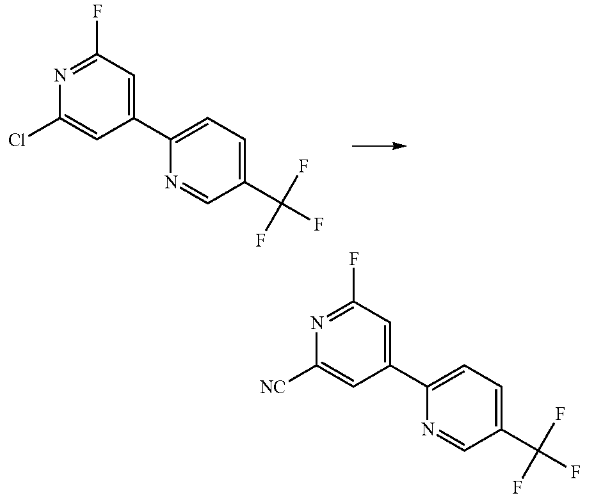

A mixture of 2-chloro-6-fluoro-4-[5-(trifluoromethyl)pyridin-2-yl]pyridine (680.00 mg, 2.46 mmol, 1.00 equiv), $Zn(CN)_2$ (288.71 mg, 2.46 mmol, 1.00 equiv), $Pd_2(dba)_3.CHCl_3$ (250 mg, 0.24 mmol, 0.10 equiv), dppf (410 mg, 0.74 mmol, 0.30 equiv), and DMF (5 mL) was irradiated with microwave for 2 h at 100° C. under nitrogen. The resulting solution was diluted with ethyl acetate, washed with brine, dried over anhydrous sodium sulfate, and concentrated under vacuum. The residue was purified by flash chromatography on silica gel eluting with ethyl acetate/petroleum ether (1:100). This resulted in the title compound (610 mg, 93%) as a white solid.

Step 5: Preparation of [6-fluoro-4-[5-(trifluoromethyl)pyridin-2-yl]pyridin-2-yl]methanamine hydrochloride

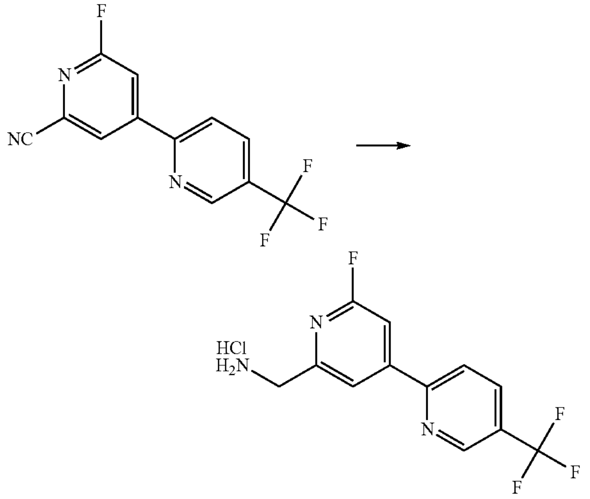

A mixture of 6-fluoro-4-[5-(trifluoromethyl)pyridin-2-yl]pyridine-2-carbonitrile (300 mg, 1.12 mmol, 1.00 equiv), and palladium on carbon (500 mg) in methanol (50 mL) was stirred for 30 min at room temperature under hydrogen. The solids were filtered out and the liquid was concentrated under vacuum to afford the title compound (300 mg, crude) as a yellow solid.

Step 6: tert-butyl (2S,4R)-4-fluoro-2-[([6-fluoro-4-[5-(trifluoromethyl)pyridin-2-yl]pyridin-2-yl]methyl)carbamoyl]pyrrolidine-1-carboxylate

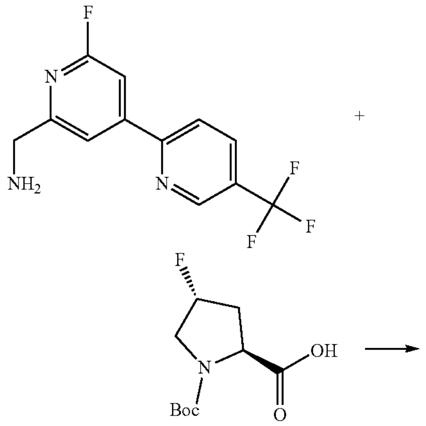

-continued

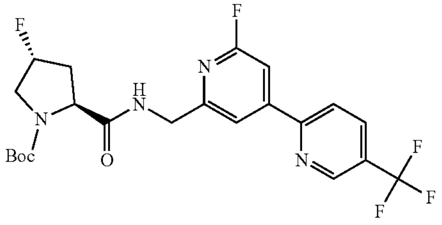

A mixture of (2S,4R)-1-[(tert-butoxy)carbonyl]-4-fluoro-pyrrolidine-2-carboxylic acid (260.00 mg, 1.11 mmol, 1.00 equiv), DIEA (432.22 mg, 3.34 mmol, 3.00 equiv), HATU (635.79 mg, 1.67 mmol, 1.50 equiv), and [6-fluoro-4-[5-(trifluoromethyl)pyridin-2-yl]pyridin-2-yl]methanamine (302.33 mg, 1.11 mmol, 1.00 equiv) in N,N-dimethylformamide (5 mL) was stirred for 2 h at room temperature. The resulting solution was diluted with ethyl acetate, washed with brine, dried over anhydrous sodium sulfate, and concentrated under vacuum. The residue was purified by flash chromatography on silica gel eluting with ethyl acetate/petroleum ether (1:1). This resulted in the title compound (200 mg, 37%) as a white solid.

Step 7: (2S,4R)-4-fluoro-N-([6-fluoro-4-[5-(trifluoromethyl)pyridin-2-yl]pyridin-2-yl]methyl)pyrrolidine-2-carboxamide hydrochloride

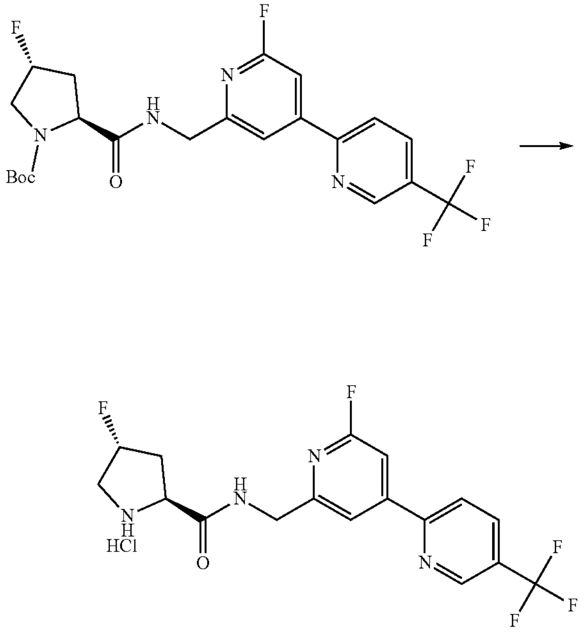

A mixture of tert-butyl (2S,4R)-4-fluoro-2-[([6-fluoro-4-[5-(trifluoromethyl)pyridin-2-yl]pyridin-2-yl]methyl)carbamoyl]pyrrolidine-1-carboxylate (200 mg, 0.41 mmol, 1.00 equiv) and saturated HCl in 1,4-dioxane (30 mL) was stirred for 2 h at room temperature. The resulting mixture was concentrated under vacuum to afford the title compound (150 mg, 94%) as a yellow solid.

Step 8: (2S,4R)-4-fluoro-N-([6-fluoro-4-[5-(trifluoromethyl)pyridin-2-yl]pyridin-2-yl]methyl)-1-[(4-fluorobenzene)sulfonyl]pyrrolidine-2-carboxamide

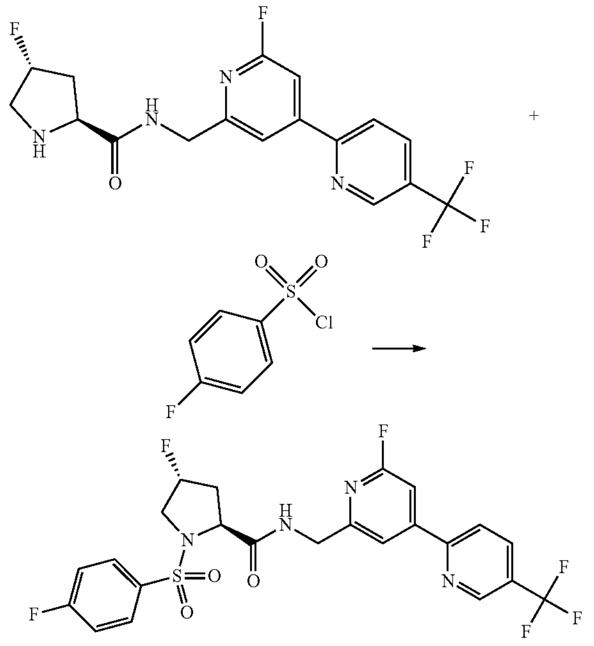

A mixture of (2S,4R)-4-fluoro-N-([6-fluoro-4-[5-(trifluoromethyl)pyridin-2-yl]pyridin-2-yl]methyl)pyrrolidine-2-carboxamide (150.00 mg, 0.39 mmol, 1.00 equiv), triethylamine (117.87 mg, 1.16 mmol, 3.00 equiv), and 4-fluorobenzene-1-sulfonyl chloride (151.13 mg, 0.78 mmol, 2.00 equiv) in dichloromethane (20 mL) was stirred for 12 h at room temperature. The reaction was diluted with water, extracted with dichloromethane, washed with brine, dried over anhydrous sodium sulfate, and concentrated under vacuum. The residue was purified by a silica gel column eluting with ethyl acetate/petroleum ether (1:1). The crude product (100 mg) was re-purified by Prep-HPLC to afford the title compound (54.1 mg, 26%) as a white solid. $^1$H NMR (400 MHz, $CDCl_3$) δ 9.13 (s, 1H), 9.05-9.02 (m, 1H), 8.42-8.34 (m, 2H), 8.07 (s, 1H), 8.01-7.97 (m, 2H), 7.78 (s, 1H), 7.47-7.43 (m, 2H), 5.21 (d, J=52.8 Hz, 2H), 4.46 (d, J=6 Hz, 2H), 4.26-4.22 (m, 1H), 3.72-3.61 (m, 2H), 2.50-2.01 (m, 2H).

Example 50

Preparation of (2S,4R)—N-([3-cyano-1-[4-(trifluoromethyl)phenyl]-1H-pyrazol-4-yl]methyl)-4-fluoro-1-[(4-fluorobenzene)sulfonyl]pyrrolidine-2-carboxamide

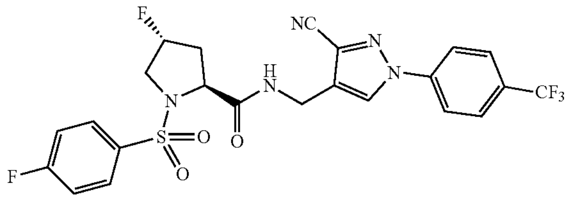 [SMILES: N#Cc1nn(-c2ccc(C(F)(F)F)cc2)cc1CNC(=O)[C@@H]1C[C@@H](F)CN1S(=O)(=O)c1ccc(F)cc1]

Step 1: ethyl 4-methyl-1-[4-(trifluoromethyl)phenyl]-1H-pyrazole-3-carboxylate

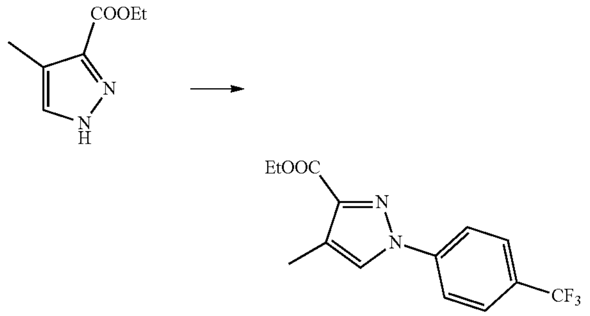

A mixture of ethyl 4-methyl-1H-pyrazole-3-carboxylate (5 g, 32.43 mmol, 1.0 equiv), 1-iodo-4-(trifluoromethyl) benzene (13.25 g, 48.71 mmol, 1.5 equiv), CuI (600 mg, 3.15 mmol, 0.10 equiv), L-proline (750 mg, 6.51 mmol, 0.20 equiv), and potassium carbonate (8.95 g, 64.76 mmol, 2.00 equiv) in DMSO (150 mg) was stirred overnight at 100° C. under nitrogen. The reaction mixture was cooled, diluted with ethyl acetate, washed with brine, dried over anhydrous sodium sulfate, and concentrated under vacuum. The residue was purified by a silica gel column eluting with ethyl acetate/petroleum ether (1:5) to afford the title compound (5.3 g, 55%) as a light yellow solid.

Step 2: ethyl 4-(bromomethyl)-1-[4-(trifluoromethyl)phenyl]-1H-pyrazole-3-carboxylate

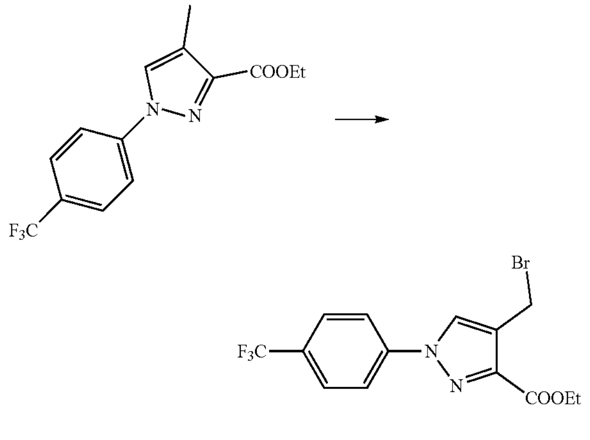

A mixture of ethyl 4-methyl-1-[4-(trifluoromethyl)phenyl]-1H-pyrazole-3-carboxylate (5.78 g, 19.38 mmol, 1.00 equiv), benzoyl benzenecarboperoxoate (469 mg, 1.94 mmol, 0.10 equiv), and 1-bromopyrrolidine-2,5-dione (3.45 g, 19.38 mmol, 1.00 equiv) in $CCl_4$(120 mL) was stirred overnight at 80° C. under nitrogen. The resulting solution was diluted with ethyl acetate, washed with water and brine, dried over anhydrous sodium sulfate, and concentrated under vacuum. The residue was purified by a silica gel column eluting with ethyl acetate/petroleum ether (1:3) to afford the title compound (5 g, 68%) as a yellow solid.

Step 3: ethyl 4-(azidomethyl)-1-[4-(trifluoromethyl) phenyl]-pyrazole 1H-3-carboxylate

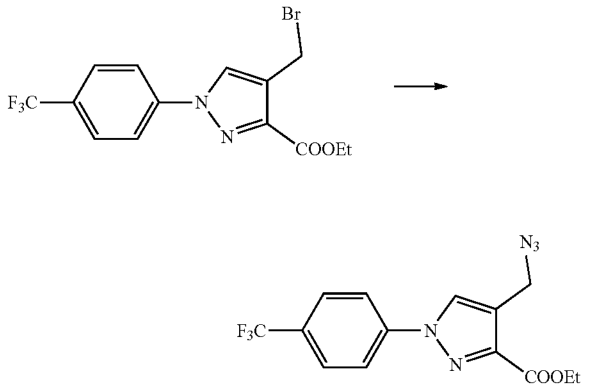

A mixture of ethyl 4-(bromomethyl)-1-[4-(trifluoromethyl)phenyl]-1H-pyrazole-3-carboxylate (5 g, 13.26 mmol, 1.00 equiv) and sodium azide (1 g, 15.38 mmol, 1.20 equiv) in N,N-dimethylformamide (80 mL) was stirred for 2 days at room temperature. The reaction mixture was then quenched by water, extracted with ethyl acetate, washed with water and brine, dried over anhydrous sodium sulfate, and concentrated under vacuum. The residue was purified by a silica gel column eluting with ethyl acetate/petroleum ether (1:10). This resulted in the title compound (1.3 g, 29%) as light yellow oil.

Step 4: ethyl 4-(aminomethyl)-1-[4-(trifluoromethyl)phenyl]-1H-pyrazole-3-carboxylate hydrochloride

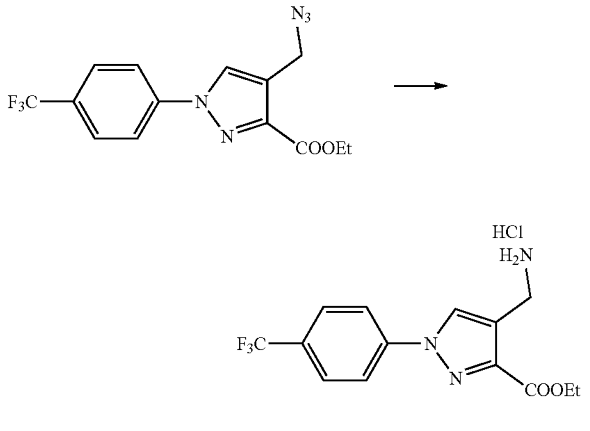

Into a 100-mL round-bottom flask purged and maintained with an atmosphere of H2 was placed ethyl 4-(azidomethyl)-1-[4-(trifluoromethyl)phenyl]-1H-pyrazole-3-carboxylate (1.15 g, 3.39 mmol, 1.00 equiv), ethanol (30 mL), palladium on carbon (500 mg), and hydrogen chloride (2 mL). The resulting solution was stirred for 1 h at room temperature. The solids were filtered out and the liquid was concentrated under vacuum. This resulted in the title compound (1 g, 84%) as a light yellow solid.

Step 5: ethyl 4-([[(2S,4R)-1-[(tert-butoxy)carbonyl]-4-fluoropyrrolidin-2-yl]formamido]methyl)-1-[4-(trifluoromethyl)phenyl]-1H-pyrazole-3-carboxylate

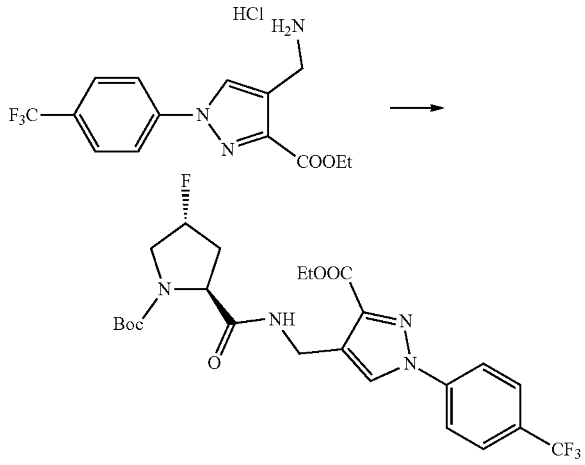

A solution of (2S,4R)-1-[(tert-butoxy)carbonyl]-4-fluoropyrrolidine-2-carboxylic acid (824 mg, 3.53 mmol, 1.30 equiv), HATU (1.55 g, 4.08 mmol, 1.50 equiv), DIEA (1.05 g, 8.12 mmol, 3.00 equiv), and ethyl 4-(aminomethyl)-1-[4-(trifluoromethyl)phenyl]-1H-pyrazole-3-carboxylate hydrochloride (950 mg, 2.72 mmol, 1.00 equiv) in N, N-dimethylformamide (30 mL) was stirred for 1 h at room temperature. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1:3) to afford the title compound (1.35 g, 94%) as a light yellow solid.

Step 6: (2S,4R)-tert-butyl 2-((3-carbamoyl-1-(4-(trifluoromethyl)phenyl)-1H-pyrazol-4-yl)methylcarbamoyl)-4-fluoropyrrolidine-1-carboxylate

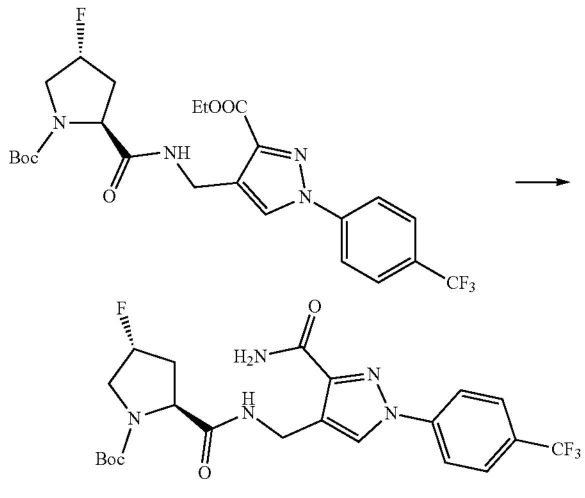

A mixture of ethyl 4-([[(2S,4R)-1-[(tert-butoxy)carbonyl]-4-fluoropyrrolidin-2-yl]formamido]methyl)-1-[4-(trifluoromethyl)phenyl]-1H-pyrazole-3-carboxylate (1.3 g, 2.46 mmol, 1.00 equiv) and $NH_3$/methanol (20 mL, 493.98 mmol, 1.00 equiv) was stirred overnight at 70° C. The reaction mixture was concentrated under vacuum. This resulted in the title compound (1.1 g) as a light yellow solid which was used for the next step without any purification.

Step 7: tert-butyl (2S,4R)-2-[([3-cyano-1-[4-(trifluoromethyl)phenyl]-1H-pyrazol-4-yl]methyl)carbamoyl]-4-fluoropyrrolidine-1-carboxylate

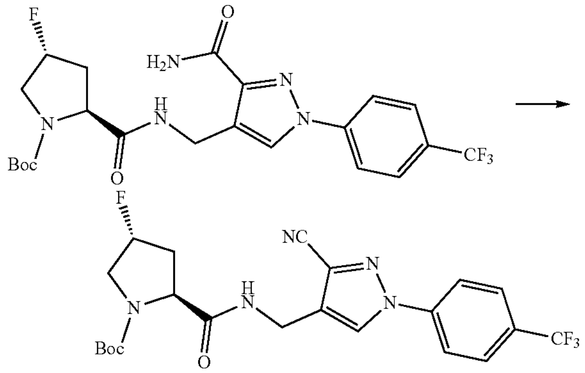

A solution of 4-([[(2S,4R)-1-[(tert-butoxy)carbonyl]-4-fluoropyrrolidin-2-yl]formamido]methyl)-1-[4-(trifluoromethyl)phenyl]-1H-pyrazole-3-carboxylic acid (400 mg, 0.80 mmol, 1.00 equiv), TFAA (452 mg, 2.15 mmol, 2.00 equiv), and TEA (320 mg, 3.16 mmol, 4.00 equiv) in dichloromethane (20 mL) was stirred for 1 h at room temperature. The reaction mixture was diluted with water, extracted with ethyl acetate, dried over anhydrous sodium sulfate, and concentrated under vacuum. The residue was purified by a silica gel column eluting with ethyl acetate/petroleum ether (1:3) to afford the title compound (320 mg, 83%) as a light yellow solid.

Step 8: (2S,4R)—N-([3-cyano-1-[4-(trifluoromethyl)phenyl]-1H-pyrazol-4-yl]methyl)-4-fluoropyrrolidine-2-carboxamide

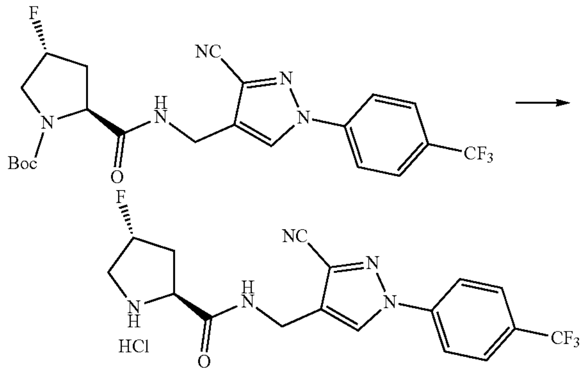

A mixture of tert-butyl (2S,4R)-2-[([3-cyano-1-[4-(trifluoromethyl)phenyl]-1H-pyrazol-4-yl]methyl)carbamoyl]-4-fluoropyrrolidine-1-carboxylate (310 mg, 0.64 mmol, 1.00 equiv) and HCl/1,4-dioxane (20 mL) was stirred for 5 h at room temperature. The solids were collected by filtration to afford the title compound (270 mg) as a white solid which was used for the next step without any further purification.

Step 9: (2S,4R)—N-([3-cyano-1-[4-(trifluoromethyl)phenyl]-1H-pyrazol-4-yl]methyl)-4-fluoro-1-[(4-fluorobenzene)sulfonyl]pyrrolidine-2-carboxamide

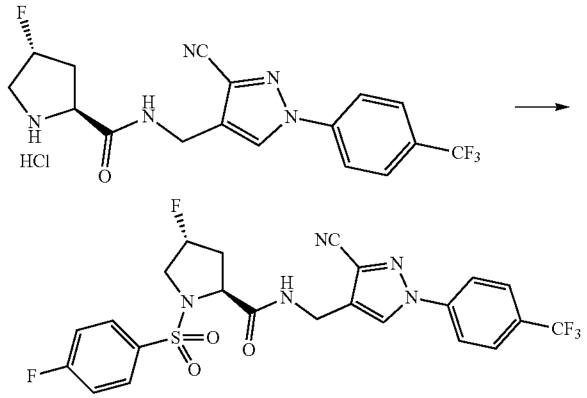

A solution (2S,4R)—N-([3-cyano-1-[4-(trifluoromethyl)phenyl]-1H-pyrazol-4-yl]methyl)-4-fluoropyrrolidine-2-carboxamide hydrochloride (250 mg, 0.598 mmol, 1.00 equiv), TEA (267 mg, 2.639 mmol, 4.00 equiv), 4-dimethylaminopyridine (8 mg, 0.065 mmol, 0.10 equiv), and 4-fluorobenzene-1-sulfonyl chloride (152 mg, 0.781 mmol, 1.20 equiv) in dichloromethane (10 mL) was stirred for 1 h at room temperature. The reaction mixture was diluted with dichloromethane, washed with brine, dried over sodium sulfate, and concentrated under vacuum. The residue was purified by Prep-HPLC to afford the title compound (124.8 mg, 39%) as a white solid.

$^1$H NMR (400 MHz, $CDCl_3$) δ 8.88-8.85 (m, 1H), 8.76 (s, 1H), 8.09-8.06 (m, 2H), 7.97-7.94 (m, 4H), 7.47-7.41 (m, 2H), 5.27-5.09 (d, J=52.5 Hz, 1H), 4.38-4.34 (m, 2H), 4.16-4.10 (m, 1H), 3.71-3.57 (m, 2H), 2.49-2.28 (m, 1H), 2.20-2.35 (m, 1H).

Example 51

5-fluoro-2-(4-fluorophenyl)sulfonyl-N-[[6-[6-(trifluoromethyl)-3-pyridyl]pyrimidin-4-yl]methyl]-2-azabicyclo[2.2.1]heptane-3-carboxamide

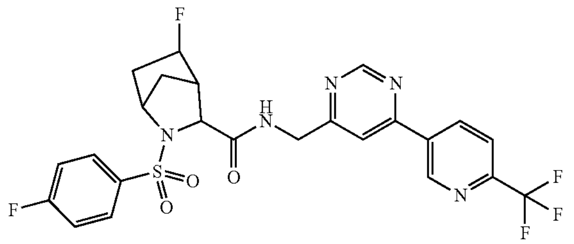 [SMILES: O=C(NCc1cc(-c2ccc(C(F)(F)F)nc2)ncn1)C1C2CC(CC2F)N1S(=O)(=O)c1ccc(F)cc1]

Step 1: Preparation of ethyl 2-azabicyclo[2.2.1]hept-5-ene-3-carboxylate

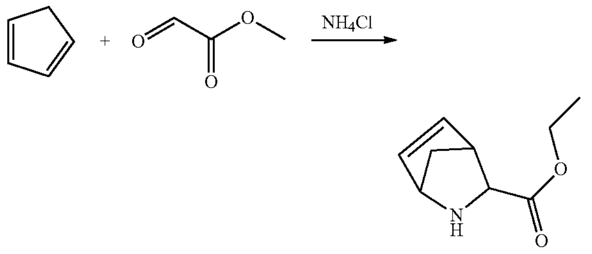

A mixture of cyclopenta-1,3-diene (16.5 g, 249.62 mmol, 1.00 equiv), ethyl 2-oxoacetate (75 mL, 756.70 mmol, 3.00 equiv), and $NH_4Cl$ (200 g, 3.74 mol, 15.00 equiv) in water (800 mL) was stirred for 16 h at room temperature. Sodium bicarbonate (5M) was employed to adjust the pH to 8. The resulting solution was extracted with ethyl acetate, dried over anhydrous sodium sulfate, and concentrated under vacuum. This resulted in the title compound (58 g, crude) as brown oil.

Step 2: Preparation of 2-benzyl 3-ethyl 2-azabicyclo[2.2.1]hept-5-ene-2,3-dicarboxylate

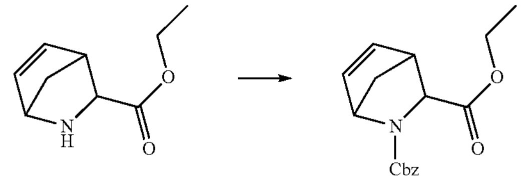 [SMILES: CCOC(=O)C1NC2C=CC1C2 ; CCOC(=O)C1C2C=CC(C2)N1C(=O)OCc1ccccc1]

A mixture of ethyl 2-azabicyclo[2.2.1]hept-5-ene-3-carboxylate (5 g, crude, 29.90 mmol, 1.00 equiv), Cbz-Cl (5 g, 29.31 mmol, 1.00 equiv), and TEA (6 g, 59.29 mmol, 2.00 equiv) in dichloromethane (30 mL) was stirred for 16 h at room temperature. The resulting mixture was concentrated under vacuum. The residue was purified by a silica gel column eluting with ethyl acetate/petroleum ether (1/5) to afford the title compound (1.8 g, 20%) as red oil.

Step 3: Preparation of 2-benzyl 3-ethyl 5-hydroxy-2-aza-bicyclo[2.2.1]heptane-2,3-dicarboxylate

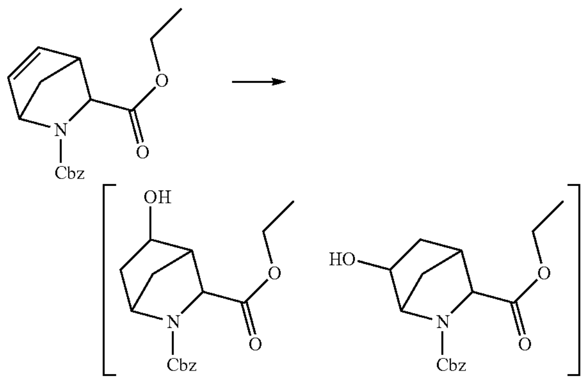

$BH_3$.THF (47.8 mL, 1M in THF, 1.1 equiv) was added dropwise into a mixture of 2-benzyl 3-ethyl 2-aza-bicyclo [2.2.1]hept-5-ene-2,3-dicarboxylate (12 g, 42.4 mmol, 1.00 equiv) in tetrahydrofuran (150 mL) at −78° C. under nitrogen. After 1 h at room temperature sodium hydroxide (10%) (69.6 mL, 148 mmol, 3.50 equiv) and $H_2O_2$ (30%) (22.6 mL, 212 mmol, 5.00 equiv) were added at 0° C. The resulting solution was stirred for 1 h at room temperature, quenched by water, and extracted with ethyl acetate. The combined extracts were washed with brine, dried over anhydrous sodium sulfate, and concentrated under vacuum. The residue was purified by a silica gel column eluting with ethyl acetate/petroleum ether (1/1). This resulted in the title compound (8.2 g, 62%) as yellow oil.

Step 4: Preparation of 2-benzyl 3-ethyl 5-fluoro-2-aza-bicyclo[2.2.1]heptane-2,3-dicarboxylate

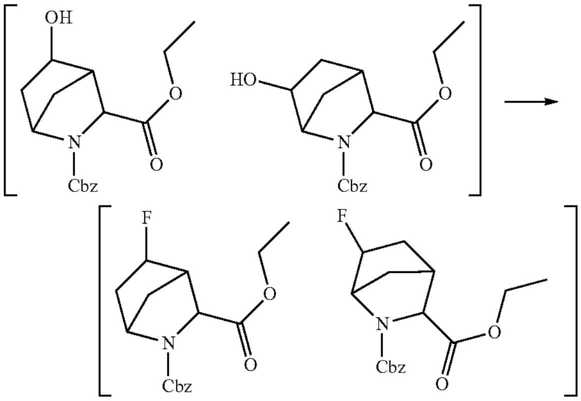

DAST (4.99 g, 31 mmol, 2.2 equiv) was added dropwise into a mixture of 2-benzyl 3-ethyl 5-hydroxy-2-aza-bicyclo [2.2.1]heptane-2,3-dicarboxylate and 2-benzyl 3-ethyl 6-hydroxy-2-aza-bicyclo[2.2.1]heptane-2,3-dicarboxylate (4.5 g, 14.1 mmol, 1.00 equiv) in DCM (100 mL) at −78° C. under nitrogen. The resulting solution was stirred for 5 h at rt, quenched with water, and extracted with dichloromethane. The combined extracts were washed with brine, dried over anhydrous sodium sulfate, and concentrated under vacuum. The residue was purified by a silica gel column eluting with ethyl acetate/petroleum ether (1/5). This resulted in the mixture of the title compounds and 2-benzyl 3-ethyl 6-fluoro-2-aza-bicyclo[2.2.1]heptane-2,3-dicarboxylate (1.2 g, 27%) as yellow oil.

Step 5: Preparation of ethyl 5-fluoro-2-aza-bicyclo [2.2.1]heptane-3-carboxylate

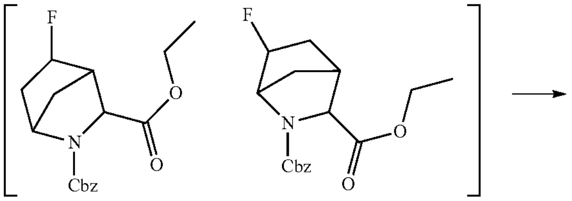

-continued

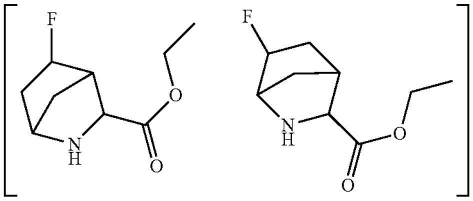

A mixture of 2-benzyl 3-ethyl 6-fluoro-2-aza-bicyclo [2.2.1]heptane-2,3-dicarboxylat and 2-benzyl 3-ethyl 5-fluoro-2-aza-bicyclo[2.2.1]heptane-2,3-dicarboxylate(4.7 g, 15.5 mmol, 1.00 equiv), and palladium on carbon (1.0 g) in methanol (50 mL) was stirred for 16 h at room temperature under hydrogen. The solids were filtered out and the liquid was concentrated under vacuum. This resulted in the title compound and its ethyl 6-fluoro-2-aza-bicyclo[2.2.1] heptane-3-carboxylate(2.5 g, 86%) as yellow oil.

Step 6: Preparation of ethyl 5-fluoro-2-(4-fluorophenylsulfonyl)-2-aza-bicyclo[2.2.1]heptane-3-carboxylate

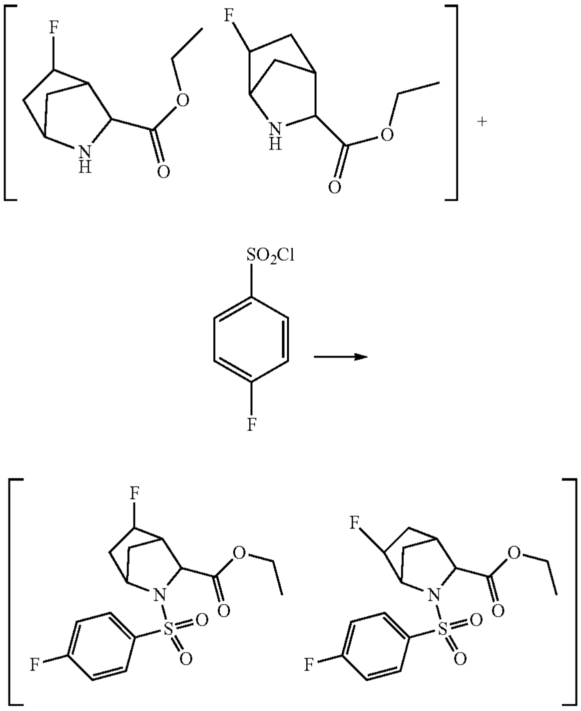

A mixture of two position isomers (2.5 g, 13.3 mmol, 1.00 equiv), TEA (2.7 g, 26.68 mmol, 2.00 equiv), and 4-fluorobenzene-1-sulfonyl chloride (3.1 g, 15.93 mmol, 1.20 equiv) in dichloromethane (50 mL) was stirred for 2 h at room temperature. The resulting mixture was concentrated under vacuum. The residue was purified by a silica gel column eluting with ethyl acetate/petroleum ether (1/5) to afford the mixture of the title compound and ethyl 6-fluoro-2-(4-fluorophenylsulfonyl)-2-aza-bicyclo[2.2.1]heptane-3-carboxylate(2.5 g, 54%) as a yellow solid.

Step 7: Preparation of 5-fluoro-2-(4-fluorophenylsulfonyl)-2-aza-bicyclo[2.2.1]heptane-3-carboxylic acid

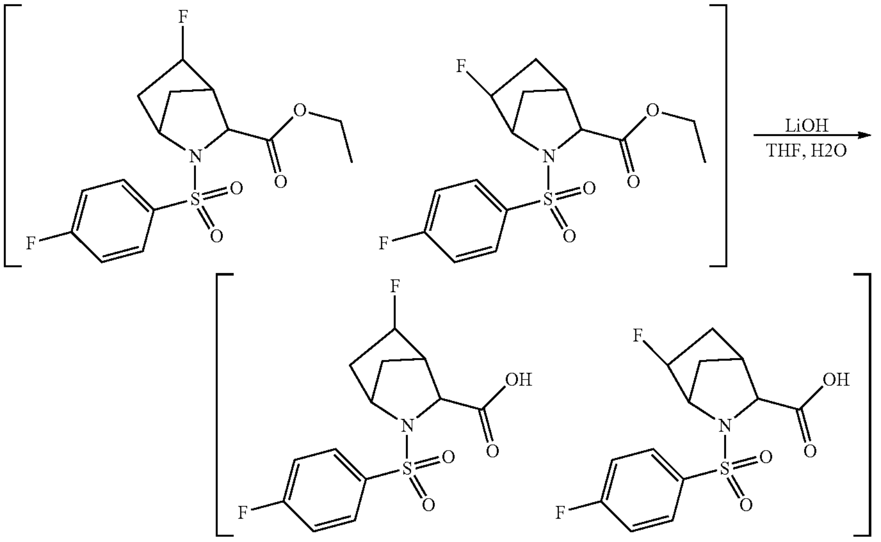

A mixture of ethyl 5-fluoro-2-(4-fluorophenylsulfonyl)-2-aza-bicyclo[2.2.1]heptane-3-carboxylate and ethyl 6-fluoro-2-(4-fluorophenylsulfonyl)-2-aza-bicyclo[2.2.1]heptane-3-carboxylate(2.5 g, 7.24 mmol, 1.00 equiv) in tetrahydrofuran (50 mL) and LiOH (522 mg, 21.80 mmol, 3.00 equiv) in water (50 mL) was stirred for 16 h at room temperature. The pH value of the solution was adjusted to 5 with citric acid. The resulting solution was extracted with ethyl acetate, washed with brine, dried over anhydrous sodium sulfate, and concentrated under vacuum. This resulted in a mixture of the title compound and 6-fluoro-2-(4-fluorophenylsulfonyl)-2-aza-bicyclo[2.2.1]heptane-3-carboxylic acid (2.0 g, 87%) as a yellow solid.

Step 8: Preparation of 5-fluoro-2-(4-fluorophenyl)sulfonyl-N-[[6-[6-(trifluoromethyl)-3-pyridyl]pyrimidin-4-yl]methyl]-2-azabicyclo[2.2.1]heptane-3-carboxamide

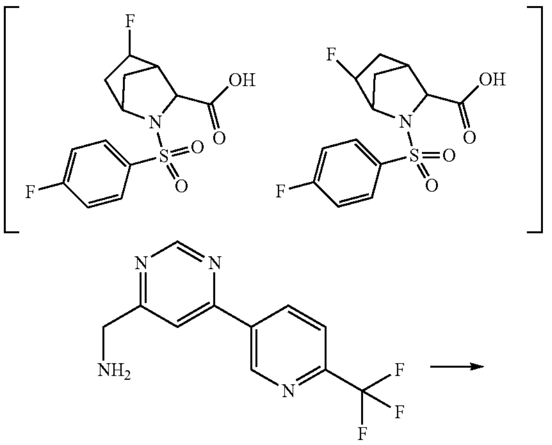

-continued

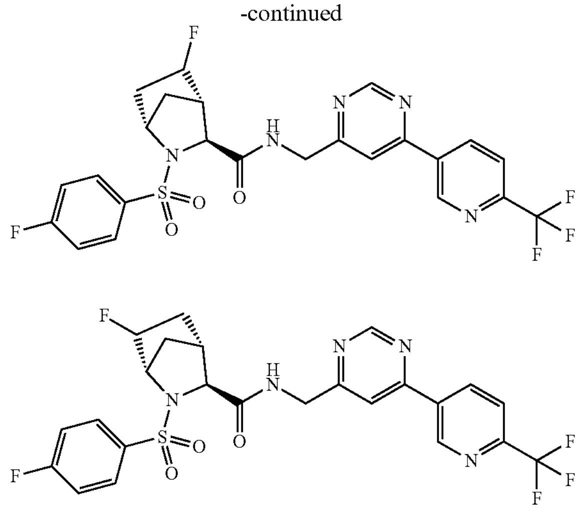

A mixture of 5-fluoro-2-(4-fluorophenylsulfonyl)-2-aza-bicyclo[2.2.1]heptane-3-carboxylic acid and 6-fluoro-2-(4-fluorophenylsulfonyl)-2-aza-bicyclo[2.2.1]heptane-3-carboxylic acid (2.0 g, 6.3 mmol, 1.00 equiv), (6-(6-(trifluoromethyl)pyridin-3-yl)pyrimidin-4-yl)methanaminel (1.6 g, 6.3 mmol, 1.0 equiv), HATU (3.6 g, 9.5 mmol, 1.50 equiv), and DIPEA (1.6 g, 12.6 mmol, 2.0 equiv) in DMF (50 mL) was stirred for 16 h at room temperature. The reaction mixture was diluted with water and extracted with ethyl acetate. The combined extracts were washed with brine, dried over anhydrous sodium sulfate, and concentrated under vacuum. The crude residue was purified by Prep_SFC to afford the title compound (137.3 mg, 3.9%). $t_R$=0.90 min (Lux 3 μm Cellulose-4, 4.6×100 mm, 3 μm, MeOH (0.1% DEA)=30%, 4 ml/min).

$^1$H NMR (300 MHz, DMSO-$d_6$) δ 9.41 (s, 1H), 9.29 (d, J=0.9 Hz, 1H), 8.91 (t, J=6.3 Hz, 1H), 8.73-8.70 (m, 1H), 8.09-7.99 (m, 4H), 7.38 (t, J=9.0 Hz, 2H), 4.85-4.95 (d,

J=59.7 Hz, 1H), 4.47 (t, J=5.1 Hz, 2H), 4.08 (s, 1H), 3.93 (s, 1H), 2.98 (d, J=3.9 Hz, 1H), 2.15 (s, J=9.6 Hz, 1H), 1.79-1.56 (m, 3H).

6-fluoro-2-(4-fluorophenyl)sulfonyl-N-[[6-[6-(trifluoromethyl)-3-pyridyl]pyrimidin-4-yl]methyl]-2-azabicyclo [2.2.1]heptane-3-carboxamide was also isolated (732.9 mg, 20.9%) as a white solid. $t_R$=1.07 min (Lux 3 μm Cellulose-4, 4.6×100 mm, 3 μm, MeOH (0.1% DEA)=30%, 4 ml/min). $^1$H NMR (300 MHz, DMSO-$d_6$) δ 9.42 (s, 1H), 9.29 (s, 1H), 8.91 (t, J=5.7 Hz, 1H), 8.73 (d, J=8.1 Hz, 1H), 8.13-7.99 (m, 4H), 7.38 (t, J=9.0 Hz, 2H), 4.85-4.65 (d, J=59.7 Hz, 1H), 4.54-4.39 (m, 2H), 4.08 (s, 1H), 3.93 (s, 1H), 2.79 (d, J=3.6 Hz, 1H), 2.15 (s, J=9.9 Hz, 1H), 1.91-1.39 (m, 3H).

The F position (5-F or 6-F) for the above two position isomers was arbitrary assigned. The 2-proline stereochemistry is as shown.

Example 52

Preparation of (2S,4R)-4-fluoro-N-(3-fluoro-5-(2-(trifluoromethyl)pyrimidin-5-yl)benzyl)-1-((4-fluorophenyl)sulfonyl)-4-methylpyrrolidine-2-carboxamide

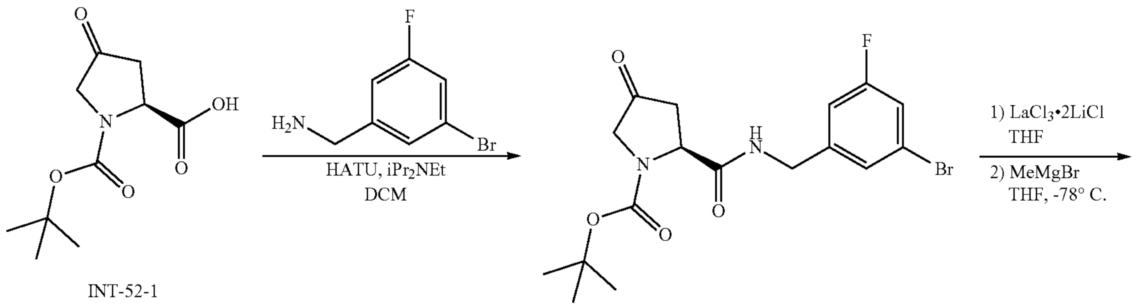

INT-52-1

INT-52-2

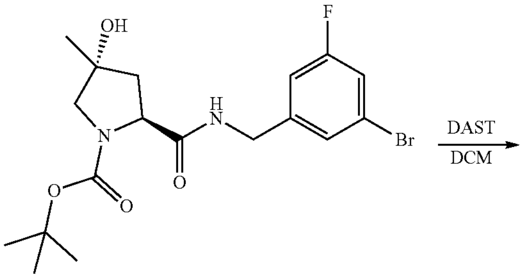

INT-52-3

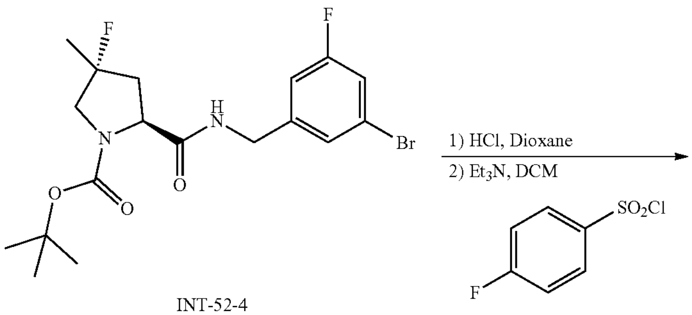

INT-52-4

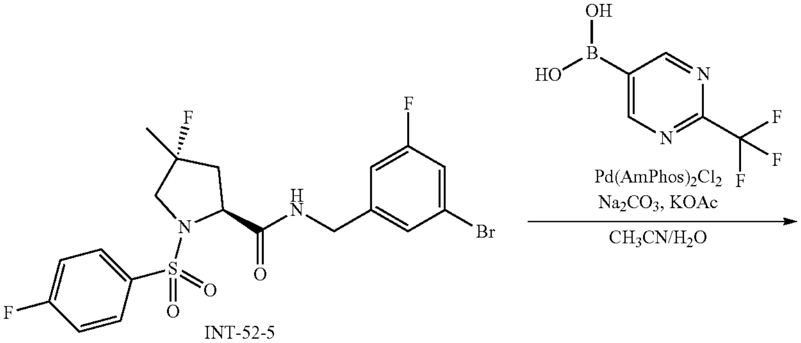

INT-52-5

-continued

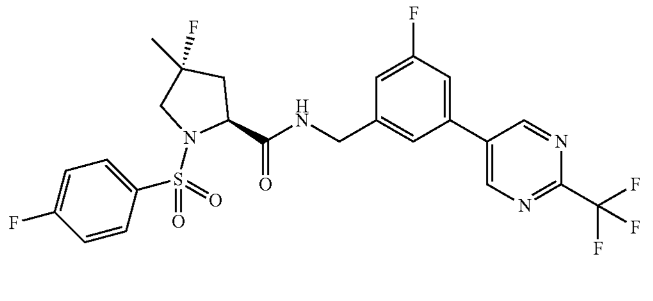 [SMILES: C[C@@]1(F)C[C@@H](C(=O)NCc2cc(F)cc(-c3cnc(C(F)(F)F)nc3)c2)N(S(=O)(=O)c2ccc(F)cc2)C1]

Step 1: (S)-tert-butyl 2-((3-bromo-5-fluorobenzyl) carbamoyl)-4-oxopyrrolidine-1-carboxylate (INT-52-2)

To a round bottomed flask was added (2S)-1-tert-butoxycarbonyl-4-oxo-pyrrolidine-2-carboxylic acid (2.35 g, 10.2 mmol), (3-bromo-5-fluorophenyl)methanamine (2.00 g, 9.31 mmol) and HATU (3.97 g, 10.2 mmol). Dichloromethane (47 mL) was added followed by N,N-diisopropylethylamine (3.25 mL, 18.6 mmol) and the reaction mixture was stirred overnight at room temperature. The reaction was quenched with sat. aq. sodium bicarbonate and extracted with DCM (3×). The combined organic extracts were washed with water (1×), brine (1×) then dried over sodium sulfated, filtered and concentrated in vacuo. The residue was adsorbed onto silica and purified by flash column chromatography with 0-100% EtOAc in Heptane to afford the desired compound as a beige solid (3.47 g, 90%). MS-ESI: $[M+H]^+$ 414.9

Step 2: (2S,4R)-tert-butyl 2-((3-bromo-5-fluorobenzyl)carbamoyl)-4-hydroxy-4-methylpyrrolidine-1-carboxylate (INT-52-3)

To a solution of (S)-tert-butyl 2-((3-bromo-5-fluorobenzyl)carbamoyl)-4-oxopyrrolidine-1-carboxylate (1.94 g, 4.67 mmol) in tetrahydrofuran (40 mL) was added Lanthanum(III) chloride bis(lithium chloride) complex solution 0.6 M in THF (8.6 mL, 5.14 mmol) and the reaction mixture was stirred for 1 h at room temperature. The reaction mixture was then cooled to −78° C. and methylmagnesium bromide (3.0 mol/L) in diethyl ether (7.0 mL, 21.0 mmol) was added dropwise and the reaction mixture was stirred for 30 mins at −78° C. An additional portion of methylmagnesium bromide (3.0 mol/L) in diethyl ether (7.0 mL, 21.0 mmol) was added and the mixture was stirred at −78° C. for an additional 30 min. An additional portion of methylmagnesium bromide (3.0 mol/L) in diethyl ether (7.0 mL, 21.0 mmol) was added and the mixture was stirred at −78° C. for an additional 15 min. The reaction mixture was warmed to room temperature, quenched by the addition of sat. aq. ammonium chloride and extracted with EtOAc (3×). The combined organic layers were washed with brine, dried over sodium sulfate, filtered and concentrated in vacuo. The residue was adsorbed onto silica and purified by flash column chromatography with 0-100% EtOAc in heptane to afford the desired compound as a beige foam (1.29 g, 64%). MS-ESI: $[M-100]^+$ 331.0

Step 3: (2S,4R)-tert-butyl 2-((3-bromo-5-fluorobenzyl)carbamoyl)-4-fluoro-4-methylpyrrolidine-1-carboxylate (INT-52-3)

To a solution of (2S,4R)-tert-butyl 2-((3-bromo-5-fluorobenzyl)carbamoyl)-4-hydroxy-4-methylpyrrolidine-1-carboxylate (337 mg, 0.781 mmol) in dichloromethane (10 mL) cooled to −78° C. was added diethylaminosulfur trifluoride (0.21 mL, 1.56 mmol) and the reaction mixture was stirred at −78° C. for 30 min. The reaction mixture was quenched by the careful addition of sat. aq. ammonium chloride and extracted with DCM (3×). The combined organic layers were dried over sodium sulfate, filtered and concentrated in vacuo. The residue was adsorbed onto silica and purified by flash column chromatography with 0-10% MeOH in DCM to afford the desired compound as a brown solid (314.7 mg, 93%). MS-ESI: $[M+H]^+$ 433.1

Step 4: (2S,4R)—N-(3-bromo-5-fluorobenzyl)-4-fluoro-1-((4-fluorophenyl)sulfonyl)-4-methylpyrrolidine-2-carboxamide (INT-52-5)

To a solution of (2S,4R)-tert-butyl 2-((3-bromo-5-fluorobenzyl)carbamoyl)-4-fluoro-4-methylpyrrolidine-1-carboxylate (315 mg, 0.7270 mmol) in dichloromethane (4 mL) was added hydrochloric acid (4 mol/L) in 1,4-dioxane (1.5 mL, 6.0 mmol). The reaction mixture was stirred at room temp for 2 h then concentrated in vacuo. The crude residue was dissolved in dichloromethane (6 mL) and triethylamine (0.30 mL, 2.2 mmol) and 4-fluorobenzenesulfonyl chloride (156 mg, 0.8005 mmol,) were added and the reaction mixture was stirred at room temperature for 2 h. The reaction mixture was diluted with DCM and water, the layers were separated and the aqueous layer was extracted with DCM (2×). The combined organic layers were dried over sodium sulfate, filtered and concentrated in vacuo. The residue was adsorbed onto silica and purified by flash column chromatography with 0-10% MeOH in DCM to afford the title compound as a pale yellow foam (172.4 mg, 48%). MS-ESI: $[M-H]^-$ 493.1

Step 5: (2S,4R)-4-fluoro-N-(3-fluoro-5-(2-(trifluoromethyl)pyrimidin-5-yl)benzyl)-1-((4-fluorophenyl)sulfonyl)-4-methylpyrrolidine-2-carboxamide To a microwave vial was added (2S)—N-[(3-bromo-5-fluoro-phenyl)methyl]-4-fluoro-1-(4-fluorophenyl)sulfonyl-4-methyl-pyrrolidine-2-carboxamide (60 mg, 0.12 mmol), 2-(trifluoromethyl)pyrimidin-5-ylboronic acid (33 mg, 0.17 mmol), bis(di-tert-butyl(4-dimethylaminophenyl)phosphine)dichloropalladium(II) (6.9 mg, 0.0098 mmol), sodium carbonate (18 mg, 0.17 mmol) and potassium acetate (17 mg, 0.17 mmol). Acetonitrile (0.8 mL) and water (0.16 mL) were added and nitrogen was bubbled through the reaction mixture for 3 mins then heated to 140° C. in the microwave for 30 mins. The reaction mixture was diluted with dichloromethane, filtered through celite, eluting with dichloromethane and the filtrate was concentrated in vacuo. The residue was adsorbed onto silica and purified by flash column chromatography with 0-100% EtOAc in heptane to afford the partially purified product. The residue was further purified by RP-HPLC to yield the title compound as a white solid (43.3 mg, 68%). MS-ESI: $[M+H]^+$ 559.12

$^1H$ NMR (400 MHz, DMSO) δ 9.42 (s, 2H), 8.92 (t, J=6.0 Hz, 1H), 8.02-7.92 (m, 2H), 7.78-7.69 (m, 2H), 7.51-7.40 (m, 2H), 7.40-7.32 (m, 1H), 4.56-4.38 (m, 2H), 4.25-4.16 (m, 1H), 3.71-3.46 (m, 2H), 2.48-2.31 (m, 1H), 2.15-1.94 (m, 1H), 1.38 (d, J=20.7 Hz, 3H).

Example 53

Preparation of (2S,4R)-4-fluoro-1-(4-fluorophenyl)sulfonyl-N-[[4-[2-(trifluoromethyl)pyrimidin-5-yl]-2-pyridyl]methyl]pyrrolidine-2-carboxamide

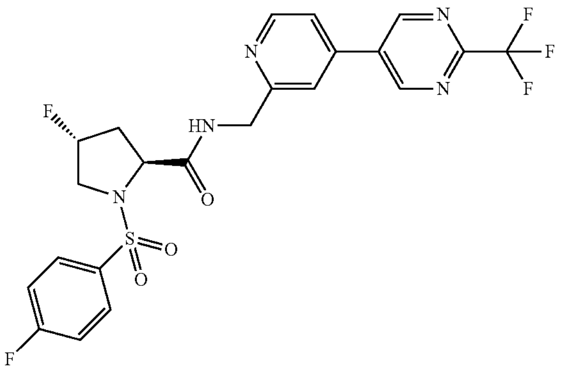 [SMILES: O=C(NCc1cc(-c2cnc(C(F)(F)F)nc2)ccn1)[C@@H]1C[C@@H](F)CN1S(=O)(=O)c1ccc(F)cc1]

Preparation of the title compound follows the same general procedure as Example 48.

1H NMR (400 MHz, DMSO) δ 9.51-9.44 (s, 2H), 9.08-8.98 (t, J=6.0 Hz, 1H), 8.78-8.69 (dd, J=5.2, 0.8 Hz, 1H), 8.04-7.96 (m, 2H), 7.94-7.89 (dd, J=1.7, 0.9 Hz, 1H), 7.89-7.83 (dd, J=5.2, 1.8 Hz, 1H), 7.51-7.40 (m, 2H), 5.30-5.09 (d, J=52.5 Hz, 1H), 4.62-4.46 (m, 2H), 4.29-4.18 (dd, J=9.9, 7.1 Hz, 1H), 3.78-3.57 (m, 2H), 2.43-2.35 (m, 1H), 2.23-2.02 (m, 1H)., LCMS (ESI) m/z:528.11 [M+H]+

Example 54

Preparation of (2S,4R)-4-fluoro-N-(2-fluoro-5-(5-(trifluoromethyl)pyrazin-2-yl)benzyl)-1-((4-fluorophenyl)sulfonyl)pyrrolidine-2-carboxamide

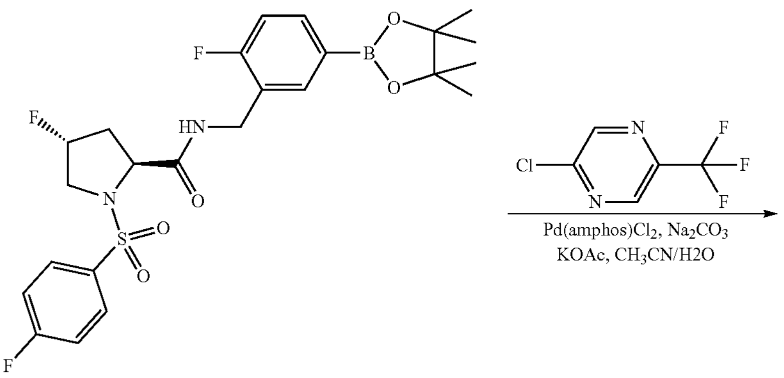

-continued

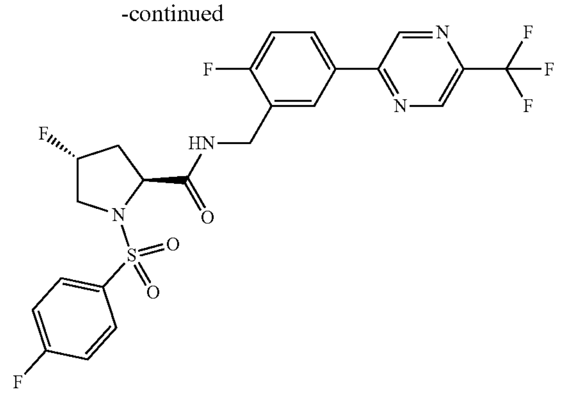

To a microwave vial was added (2S,4R)-4-fluoro-1-(4-fluorophenyl)sulfonyl-N-[[2-fluoro-5-(4,4,5,5-tetramethyl-1,3,2-dioxaborolan-2-yl)phenyl]methyl]pyrrolidine-2-carboxamide 1 (216 mg, 0.41 mmol), 2-chloro-5-(trifluoromethyl)pyrazine (105 mg, 0.58 mmol), Pd $(amphos)Cl_2$ (23 mg, 0.03 mmol), sodium carbonate (61 mg, 0.58 mmol) and potassium acetate (57 mg, 0.58 mmol), acetonitrile (0.8 mL) and water (0.16 mL). The reaction mixture was purged with nitrogen gas for 3 minutes and then heated to 140° C. in the microwave for 30 minutes. Upon cooling to room temperature, the resulting mixture was filtered through a thin layer of celite, washed with water and extracted with ethyl acetate. The combined organic layer was dried over $Na_2SO_4$, filtered and concentrated under reduced pressure. The residue was purified by reverse phase HPLC to afford the title compound (99 mg, 44%) as a white solid. LC/MS (ESI+): m/z 545.5 (M+H).

1H NMR (400 MHz, DMSO-$d_6$) δ 9.42 (d, J=1.5 Hz, 1H), 9.21 (d, J=1.4 Hz, 1H), 8.92 (t, J=5.9 Hz, 1H), 8.36-8.13 (m, 2H), 8.08-7.88 (m, 2H), 7.44 (td, J=8.6, 1.3 Hz, 3H), 4.54-4.35 (m, 2H), 4.22 (dd, J=9.8, 7.2 Hz, 1H), 3.78-3.49 (m, 2H), 2.50-2.27 (m, 2H), 2.09 (dddd, J=42.1, 13.8, 9.8, 3.5 Hz, 1H).

Example 55

Preparation of (2R,3S)—N-[[6-[4-(difluoromethyl)phenyl]pyrimidin-4-yl]methyl]-3-fluoro-1-(4-fluorophenyl)sulfonyl-pyrrolidine-2-carboxamide

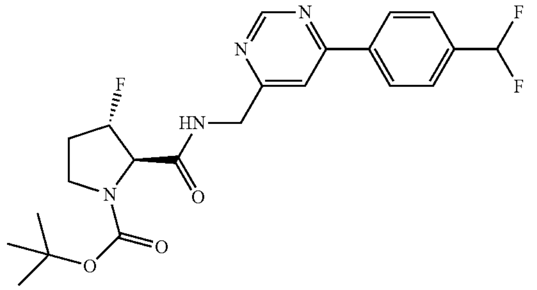 [SMILES: CC(C)(C)OC(=O)N1CC[C@H](F)[C@H]1C(=O)NCc1cc(-c2ccc(C(F)F)cc2)ncn1]

(2R,3S)-tert-butyl 2-(((6-(4-(difluoromethyl)phenyl)pyrimidin-4-yl)methyl)carbamoyl)-3-fluoropyrrolidine-1-carboxylate To a solution of tert-butyl (2S,3R)-2-[[6-[4-(difluoromethyl)phenyl]pyrimidin-4-yl]methylcarbamoyl]-3-hydroxy-pyrrolidine-1-carboxylate (360 mg, 0.8027 mmol) in dichloromethane (16.0 mL) at 0° C. was added dropwise diethylaminosulfur trifluoride (388.1 mg, 0.3187 mL, 2.408 mmol). The reaction was warmed to RT 1 h. The reaction was quenched with water and extracted with EtOAc. The organic layers was dried with sodium sulfate, filtered, and concentrated via rotovap. The crude product was carried to next step. LCMS (ESI) m/z:451.20 [M+H]+

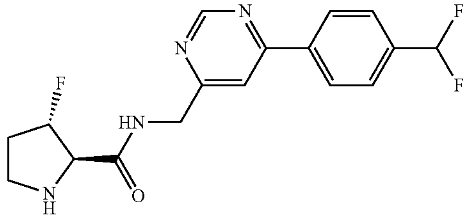 [SMILES: O=C(NCc1cc(-c2ccc(C(F)F)cc2)ncn1)[C@H]1NCC[C@@H]1F]

(2R,3S)—N-((6-(4-(difluoromethyl)phenyl)pyrimidin-4-yl)methyl)-3-fluoropyrrolidine-2-carboxamide A solution of tert-butyl (2R,3S)-2-[[6-[4-(difluoromethyl)phenyl]pyrimidin-4-yl]methylcarbamoyl]-3-fluoro-pyrrolidine-1-carboxylate (361 mg, 0.8015 mmol) in hydrochloric acid (4 mol/L) in 1,4-dioxane (2.00 mL) and 1,4-dioxane (3.00 mL) was stirred at RT 18 h. The reaction was concentrated and carried to next step. LCMS (ESI) m/z:351.05 [M+H]+

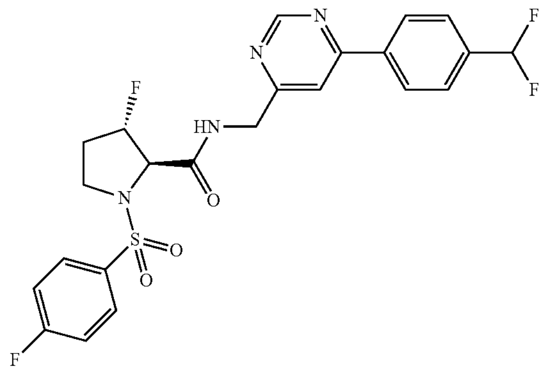 [SMILES: O=C(NCc1cc(-c2ccc(C(F)F)cc2)ncn1)[C@@H]1[C@@H](F)CCN1S(=O)(=O)c1ccc(F)cc1]

(2R,3S)—N-[[6-[4-(difluoromethyl)phenyl]pyrimidin-4-yl]methyl]-3-fluoro-1-(4-fluorophenyl)sulfonyl-pyrrolidine-2-carboxamide To a solution of (2R,3S)—N-[[6-[4-(difluoromethyl)phenyl]pyrimidin-4-yl]methyl]-3-fluoro-pyrrolidine-2-carboxamide (281 mg, 0.8022 mmol) in dichloromethane (8.027 mL) was added triethylamine (2.24 mL, 16.05 mmol) and 4-fluorobenzenesulfonyl chloride (187.5 mg, 0.9632 mmol). The reaction mixture was stirred at RT 1 h. The crude product was concentrated and purified by flash chromatography (MeOH/DCM) then submitted for rHPLC to give 113 mg, 27.69%.

1H NMR (400 MHz, DMSO) δ 9.25-9.21 (d, J=1.3 Hz, 1H), 9.21-9.14 (t, J=6.0 Hz, 1H), 8.40-8.31 (m, 2H), 8.09-8.00 (m, 3H), 7.77-7.70 (dt, J=8.5, 1.1 Hz, 2H), 7.56-7.47 (m, 2H), 7.28-6.96 (m, 1H), 5.32-5.12 (m, 1H), 4.61-4.38 (m, 3H), 3.74-3.63 (ddd, J=9.7, 6.7, 1.9 Hz, 1H), 3.23-3.12 (m, 1H), 2.29-2.08 (m, 2H)., LCMS (ESI) m/z:509.13 [M+H]+

Example 56

Preparation of (2S,4R)-4-fluoro-N-(2-fluoro-5-(2-(trifluoromethyl)pyrimidin-5-yl)benzyl)-1-((4-fluorophenyl)sulfonyl)pyrrolidine-2-carboxamide

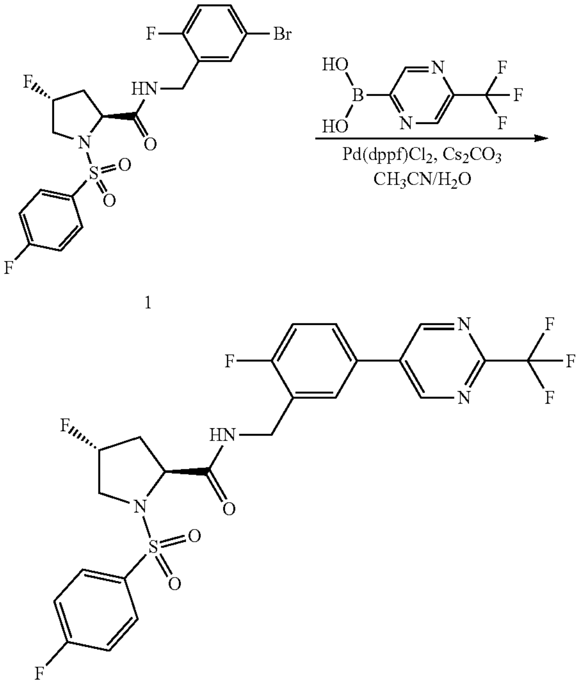

1

Following the same procedure of Example 183, step 4: The title compound (2S,4R)-4-fluoro-N-(2-fluoro-5-(2-(trifluoromethyl)pyrimidin-5-yl)benzyl)-1-((4-fluorophenyl)sulfonyl)pyrrolidine-2-carboxamide (849 mg, 68%) was prepared from (2S,4R)—N-[(5-bromo-2-fluoro-phenyl)methyl]-4-fluoro-1-(4-fluorophenyl)sulfonyl-pyrrolidine-2-carboxamide 1 (1.1 g, 2.3 mmol), [5-(trifluoromethyl)pyrimidin-2-yl]boronic acid (487 mg, 2.5 mmol), cesium carbonate 1 M in water (3.2 mL, 3.2 mmol), Pd(dppf)$Cl_2$ (192 mg, 0.23 mmol) in acetonitrile (4 mL). LC/MS (ESI+): m/z 545.5 (M+H).

1H NMR (400 MHz, DMSO-$d_6$) δ 9.36 (s, 1H), 8.90 (t, J=5.9 Hz, 1H), 8.06-7.79 (m, 3H), 7.45 (td, J=8.8, 1.4 Hz, 2H), 5.19 (d, J=52.6 Hz, 1H), 4.47 (d, J=5.9 Hz, 2H), 4.29-4.10 (m, 1H), 3.75-3.67 (m, 1H), 3.67-3.51 (m, 1H), 2.47-2.29 (m, 1H), 2.09 (dddd, J=42.5, 13.8, 10.0, 3.4 Hz, 1H).

Example 57

Preparation of (2S,4R)-4-fluoro-1-(4-fluorophenyl)sulfonyl-N-[[2-[2-hydroxy-4-(trifluoromethyl)phenyl]-4-pyridyl]methyl]pyrrolidine-2-carboxamide Step 1: (2S,4R)—N-((2-(2-(benzyloxy)-4-(trifluoromethyl)phenyl)pyridin-4-yl)methyl)-4-fluoro-1-((4-fluorophenyl)sulfonyl)pyrrolidine-2-carboxamide

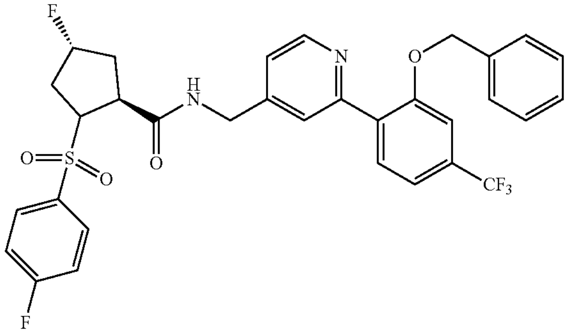 [SMILES: O=C(NCc1ccnc(-c2ccc(C(F)(F)F)cc2OCc2ccccc2)c1)[C@@H]1C[C@@H](F)CC1S(=O)(=O)c1ccc(F)cc1]

The title compound (72 mg, 64%) was prepared following the Suzuki coupling procedure of Example 8, Step 1 from (2S,4R)—N-[(2-bromo-4-pyridyl)methyl]-4-fluoro-1-(4-fluorophenyl)sulfonyl-pyrrolidine-2-carboxamide (82 mg, 0.18 mmol), 2-benzyloxy-4-(trifluoromethyl)phenylboronic acid (69 mg, 0.22 mmol), [1,1'-bis(diphenylphosphino)ferrocene]dichloropalladium(II) (14 mg, 0.02 mmol) and aqueous Cs2CO3 (0.22 mL, 0.22 mmol, 1.0 mol/L) in acetonitrile (4 mL). LCMS (ESI_Formic_MeCN): $[MH^+]$=632.

Step 2: (2S,4R)-4-fluoro-1-(4-fluorophenyl)sulfonyl-N-[[2-[2-hydroxy-4-(trifluoromethyl)phenyl]-4-pyridyl]methyl]pyrrolidine-2-carboxamide

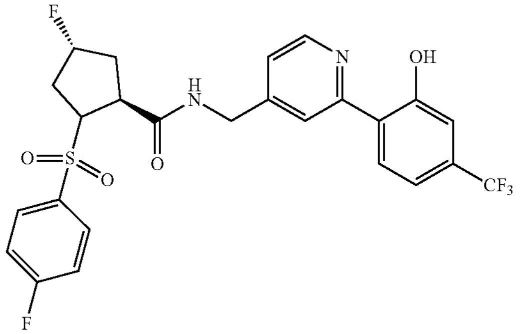 [SMILES: O=C(NCc1ccnc(-c2ccc(C(F)(F)F)cc2O)c1)[C@@H]1C[C@@H](F)CC1S(=O)(=O)c1ccc(F)cc1]

(2S,4R)—N-[[2-[2-benzyloxy-4-(trifluoromethyl)phenyl]-4-pyridyl]methyl]-4-fluoro-1-(4-fluorophenyl)sulfonyl-pyrrolidine-2-carboxamide (36 mg, 0.06 mmol) in methanol (4 ml) was hydrogenated at 1 atm over palladium on carbon (10%) (22 mg) for 2 hours. The mixture was filtered through Celite and the filtrate concentrated in vacuum. The residue was subjected to RP HPLC purification to afford 22 mg (71%) of the title compound.

1H NMR (400 MHz, DMSO-d6) δ 14.70 (s, 1H), 9.02 (t, J=6.0 Hz, 1H), 8.64 (dd, J=5.3, 0.7 Hz, 1H), 8.32-8.22 (m, 2H), 8.06-7.97 (m, 2H), 7.53-7.43 (m, 3H), 7.27-7.21 (m, 1H), 7.20-7.14 (m, 1H), 5.21 (d, J=52.2 Hz, 1H), 4.61-4.44 (m, 2H), 4.21 (dd, J=9.9, 7.1 Hz, 1H), 3.81-3.57 (m, 2H), 2.49-2.36 (m, 1H), 2.11 (dddd, J=42.5, 13.8, 10.0, 3.4 Hz, 1H).

Example 58

Preparation of (2S,4R)-4-fluoro-1-(4-fluorophenyl) sulfonyl-N-[[3-methoxy-1-[5-(trifluoromethyl) pyrazin-2-yl]pyrazol-4-yl]methyl]pyrrolidine-2-carboxamide

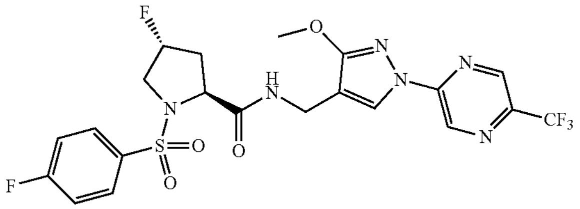 [SMILES: COc1nn(-c2cnc(C(F)(F)F)cn2)cc1CNC(=O)[C@@H]1C[C@@H](F)CN1S(=O)(=O)c1ccc(F)cc1]

Step 1: Preparation of ethyl 3-methoxy-1-[5-(trifluoromethyl)pyrazin-2-yl]-1H-pyrazole-4-carboxylate

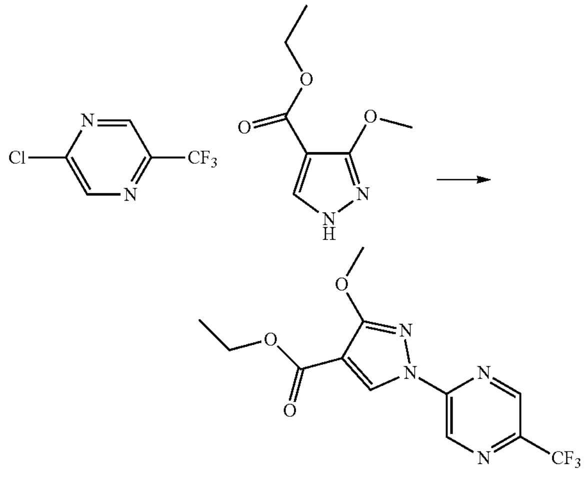

A mixture of ethyl 3-methoxy-1H-pyrazole-4-carboxylate (1.116 g, 6.56 mmol, 1.00 equiv) in N,N-dimethylformamide (60 mL), L-Proline (151 mg, 1.31 mmol, 0.20 equiv), CuI (128 mg, 0.67 mmol, 0.10 equiv), 2-chloro-5-(trifluoromethyl)pyrazine (1.19 g, 6.52 mmol, 1.00 equiv), and potassium carbonate (2.72 g, 19.68 mmol, 3.00 equiv) was stirred overnight at 100° C. under nitrogen. The solids were filtered out. The filtrate was diluted with 500 mL of ethyl acetate, washed with brine, dried over anhydrous sodium sulfate, and concentrated under vacuum. The residue was applied onto a silica gel column eluting with ethyl acetate/petroleum ether (5:100) to afford the title compound (1 g, 48%) as an off-white solid.

Step 2: Preparation of [3-methoxy-1-[5-(trifluoromethyl)pyrazin-2-yl]-1H-pyrazol-4-yl]methanol

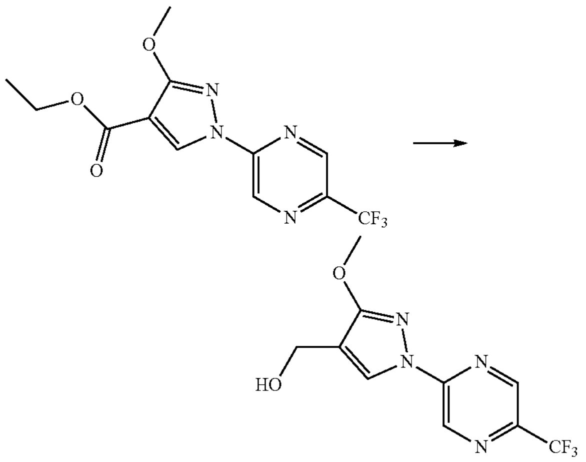

DIBAL-H (6 mL, 6.33 mmol, 2.10 equiv) was added dropwise into a solution of ethyl 3-methoxy-1-[5-(trifluoromethyl)pyrazin-2-yl]-1H-pyrazole-4-carboxylate (950 mg, 3.00 mmol, 1.00 equiv) in dichloromethane (50 mL) at −78° C. under nitrogen. After 3 h at −78° C. the reaction was quenched by methanol, diluted with brine, extracted with dichloromethane, dried over anhydrous sodium sulfate, and concentrated under vacuum. The residue was purified by a silica gel column eluting with ethyl acetate/petroleum ether (10:100) to afford the title compound (600 mg, 73%) as a white solid.

Step 3: Preparation of 2-([3-methoxy-1-[5-(trifluoromethyl)pyrazin-2-yl]-1H-pyrazol-4-yl]methyl)-2,3-dihydro-1H-isoindole-1,3-dione

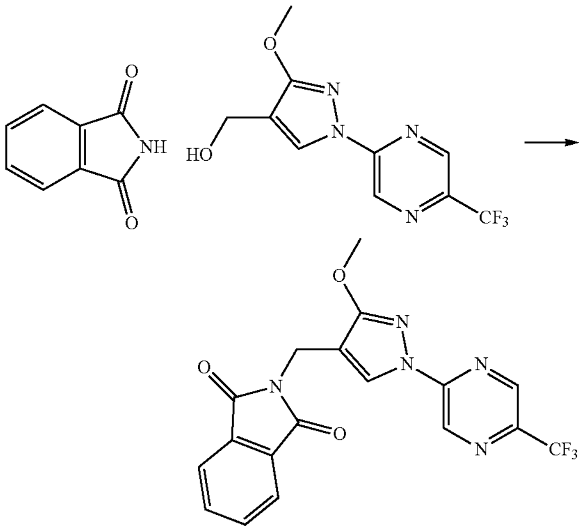

DIAD (267 mg, 1.32 mmol, 1.20 equiv) was added dropwise into a solution of [3-methoxy-1-[5-(trifluoromethyl)pyrazin-2-yl]-1H-pyrazol-4-yl]methanol (300 mg, 1.09 mmol, 1.00 equiv), 2,3-dihydro-1H-isoindole-1,3-dione (242 mg, 1.64 mmol, 1.50 equiv), and $PPh_3$ (577 mg, 2.20 mmol, 2.00 equiv) in tetrahydrofuran (30 mL) at 0° C. under nitrogen. After 5 h at room temperature the resulting mixture was concentrated under vacuum. The residue was purified by a silica gel column eluting with ethyl acetate/petroleum ether (5:100) to afford the title compound (500 mg) as a white solid.

Step 4: Preparation of [3-methoxy-1-[5-(trifluoromethyl)pyrazin-2-yl]-1H-pyrazol-4-yl]methanamine

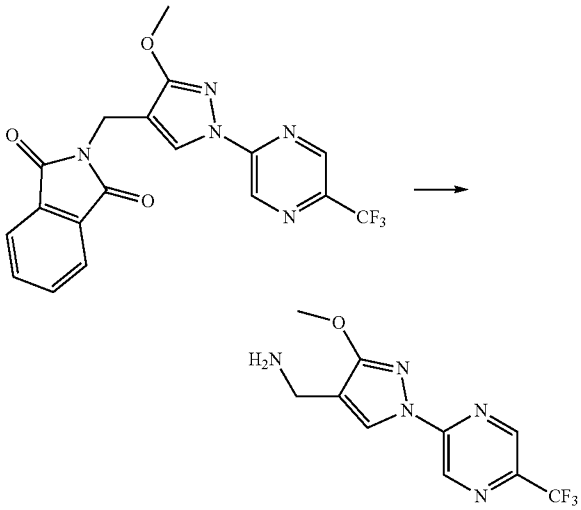 [SMILES: COc1nn(-c2cnc(C(F)(F)F)cn2)cc1CN1C(=O)c2ccccc2C1=O ; COc1nn(-c2cnc(C(F)(F)F)cn2)cc1CN]

A solution of 2-([3-methoxy-1-[5-(trifluoromethyl)pyrazin-2-yl]-1H-pyrazol-4-yl]methyl)-2,3-dihydro-1H-isoindole-1,3-dione (400 mg, 0.99 mmol, 1.00 equiv) and $NH_2NH_2.H_2O$ (1 mL, 20.58 mmol, 41.50 equiv) in methanol (5 mL) was stirred overnight at room temperature. The reaction mixture was concentrated under vacuum and the residue was dissolved in ethyl acetate. The solids were filtered out. The filtrate was concentrated under vacuum to afford the title compound (210 mg, 77%) as light yellow oil.

Step 5: Preparation of tert-butyl (2S,4R)-4-fluoro-2-[([3-methoxy-1-[5-(trifluoromethyl)pyrazin-2-yl]-1H-pyrazol-4-yl]methyl)carbamoyl]pyrrolidine-1-carboxylate

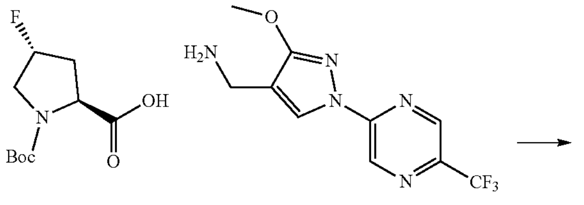

-continued

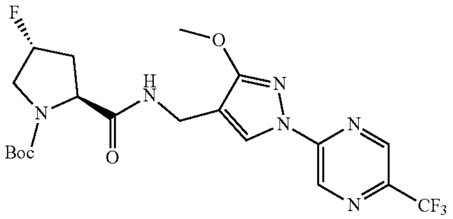

A mixture of [3-methoxy-1-[5-(trifluoromethyl)pyrazin-2-yl]-1H-pyrazol-4-yl]methanamine (210 mg, 0.77 mmol, 1.00 equiv), (2S,4R)-1-[(tert-butoxy)carbonyl]-4-fluoropyrrolidine-2-carboxylic acid (197 mg, 0.84 mmol, 1.10 equiv), HATU (437 mg, 1.15 mmol, 1.50 equiv), and DIEA (248 mg, 1.92 mmol, 2.50 equiv) in N,N-dimethylformamide (5 mL) was stirred overnight at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10) to afford the title compound (190 mg, 51%) as light yellow oil.

Step 6: Preparation of (2S,4R)-4-fluoro-N-([3-methoxy-1-[5-(trifluoromethyl)pyrazin-2-yl]-1H-pyrazol-4-yl]methyl)pyrrolidine-2-carboxamide hydrochloride

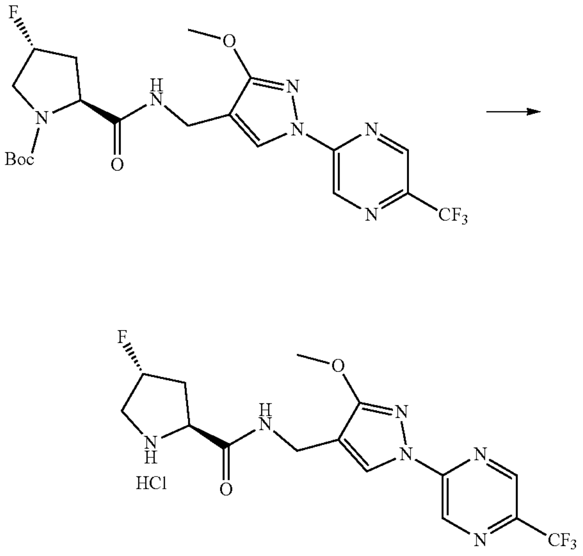

A mixture of tert-butyl (2S,4R)-4-fluoro-2-[([3-methoxy-1-[5-(trifluoromethyl)pyrazin-2-yl]-1H-pyrazol-4-yl]methyl)carbamoyl]pyrrolidine-1-carboxylate (100 mg, 0.205 mmol, 1.00 equiv) and saturated hydrogen chloride in 1,4-dioxane (5 mL) was stirred overnight at room temperature. The resulting mixture was concentrated under vacuum to afford the title compound (79 mg, 91%) as light yellow oil.

Step 7: Preparation of (2S,4R)-4-fluoro-1-(4-fluorophenyl)sulfonyl-N-[[3-methoxy-1-[5-(trifluoromethyl)pyrazin-2-yl]pyrazol-4-yl]methyl]pyrrolidine-2-carboxamide

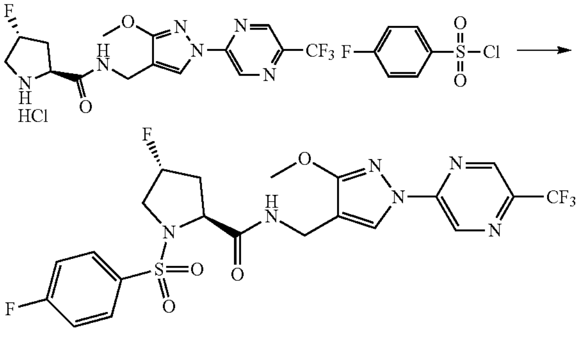

A mixture of (2S,4R)-4-fluoro-N-([3-methoxy-1-[5-(trifluoromethyl)pyrazin-2-yl]-1H-pyrazol-4-yl]methyl)pyrrolidine-2-carboxamide hydrochloride (60 mg, 0.141 mmol, 1.00 equiv), 4-fluorobenzene-1-sulfonyl chloride (36 mg, 0.185 mmol, 1.20 equiv), 4-dimethylaminopyridine (2 mg, 0.016 mmol, 0.20 equiv), and TEA (60 mg, 0.593 mmol, 3.80 equiv) in dichloromethane (5 mL) was stirred overnight at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/5) to afford the title compound (30.6 mg, 38%) as a white solid.

$^1$H NMR (300 MHz, $CDCl_3$) δ 9.16 (s, 1H), 8.61 (s, 1H), 8.37 (s, 1H), 7.88-7.33 (m, 2H), 7.36-7.18 (m, 2H), 5.11-4.94 (d, J=26.1 Hz, 1H), 4.44-4.22 (m, 3H), 4.19 (s, 3H), 3.95-3.38 (m, 1H), 3.69-3.50 (m, 1H), 2.50-2.19 (m, 2H).

Example 59

Preparation of (2S,4R)—N-[[6-[4-(difluoromethyl)-3-fluoro-phenyl]pyrimidin-4-yl]methyl]-4-fluoro-1-(4-fluorophenyl)sulfonyl-pyrrolidine-2-carboxamide

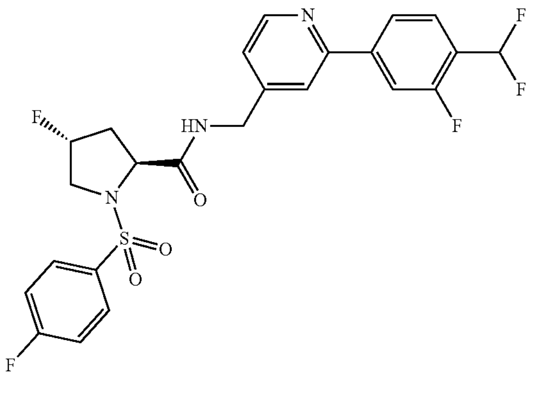 [SMILES: O=C(NCc1ccnc(-c2ccc(C(F)F)c(F)c2)c1)[C@@H]1C[C@@H](F)CN1S(=O)(=O)c1ccc(F)cc1]

Preparation of the title compound follows the same general procedure as Example 42.

1H NMR (400 MHz, DMSO) δ 9.26-9.22 (d, J=1.3 Hz, 1H), 9.15-9.07 (t, J=6.0 Hz, 1H), 8.21-8.09 (m, 3H), 8.07-

8.00 (m, 2H), 7.82-7.74 (t, J=7.7 Hz, 1H), 7.52-7.44 (m, 2H), 7.40-7.11 (m, 1H), 5.31-5.12 (m, 1H), 4.59-4.42 (m, 2H), 4.29-4.22 (dd, J=10.0, 7.1 Hz, 1H), 3.76-3.58 (m, 2H), 2.46-2.36 (m, 1H), 2.24-2.02 (dddd, J=42.6, 13.6, 10.0, 3.3 Hz, 1H)., LCMS (ESI) m/z:527.12 [M+H]+

Example 60

Preparation of (2S,4R)—N-[[2-chloro-6-[6-(difluoromethyl)-3-pyridyl]-4-pyridyl]methyl]-4-fluoro-1-(4-fluorophenyl)sulfonyl-pyrrolidine-2-carboxamide

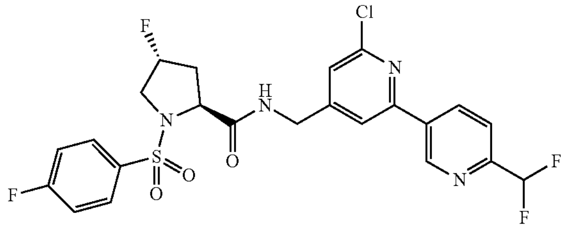 [SMILES: O=C(NCc1cc(Cl)nc(-c2ccc(C(F)F)nc2)c1)[C@@H]1C[C@@H](F)CN1S(=O)(=O)c1ccc(F)cc1]

Preparation of the title compound follows the same general procedure of Example 62.

$^1$H NMR (400 MHz, DMSO) δ 9.36-9.28 (dd, J=2.3, 0.8 Hz, 1H), 9.07-8.97 (t, J=6.0 Hz, 1H), 8.65-8.57 (dd, J=8.2, 2.2 Hz, 1H), 8.14-8.09 (d, J=1.2 Hz, 1H), 8.04-7.96 (m, 2H), 7.86-7.80 (m, 1H), 7.61-7.55 (d, J=1.0 Hz, 1H), 7.52-7.43 (m, 2H), 7.20-6.87 (m, 1H), 5.31-5.10 (d, J=52.4 Hz, 1H), 4.58-4.40 (m, 2H), 4.24-4.13 (dd, J=10.0, 7.1 Hz, 1H), 3.79-3.59 (m, 2H), 2.46-2.36 (m, 1H), 2.22-1.99 (m, 1H)., LCMS (ESI) m/z:543.09 [M+H]+

Example 61

Preparation of (2S,4R)—N-[[2,6-bis[2-(trifluoromethyl)pyrimidin-5-yl]-4-pyridyl]methyl]-4-fluoro-1-(4-fluorophenyl)sulfonyl-pyrrolidine-2-carboxamide

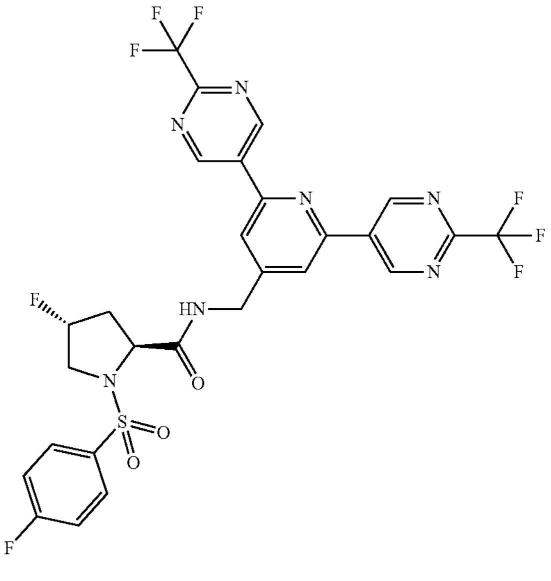 [SMILES: O=C(NCc1cc(-c2cnc(C(F)(F)F)nc2)nc(-c2cnc(C(F)(F)F)nc2)c1)[C@@H]1C[C@@H](F)CN1S(=O)(=O)c1ccc(F)cc1]

Preparation of the title compound follows the same general procedure of Example 62.

1H NMR (400 MHz, DMSO) δ 9.96-9.82 (s, 4H), 9.21-9.09 (t, J=6.0 Hz, 1H), 8.42-8.29 (s, 2H), 8.10-7.98 (m, 2H), 7.55-7.41 (m, 2H), 5.31-5.12 (d, J=52.2 Hz, 1H), 4.72-4.53 (m, 2H), 4.29-4.18 (dd, J=10.1, 7.0 Hz, 1H), 3.80-3.60 (m, 2H), 2.47-2.37 (m, 1H), 2.26-2.03 (m, 1H)., LCMS (ESI) m/z:674.2 [M+H]+

Example 62

Preparation of (2S,4R)—N-[[2-chloro-6-[2-(trifluoromethyl)pyrimidin-5-yl]-4-pyridyl]methyl]-4-fluoro-1-(4-fluorophenyl)sulfonyl-pyrrolidine-2-carboxamide

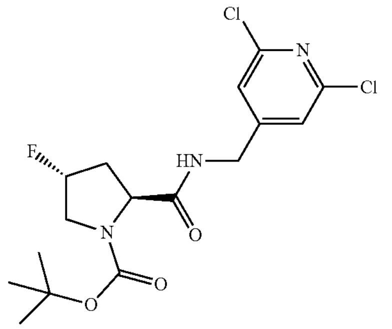 [SMILES: CC(C)(C)OC(=O)N1C[C@H](F)C[C@H]1C(=O)NCc1cc(Cl)nc(Cl)c1]

(2S,4R)-tert-butyl 2-(((2,6-dichloropyridin-4-yl)methyl)carbamoyl)-4-fluoropyrrolidine-1-carboxylate To a solution of (2S,4R)-1-tert-butoxycarbonyl-4-fluoro-pyrrolidine-2-carboxylic acid (500 mg, 2.1437 mmol) and 2,6-dichloropyridine-4-methylamine (426 mg, 2.36 mmol) in N,N-dimethylformamide (8.6 mL) was added N,N-diisopropylethylamine (0.561 mL, 3.2156 mmol) and HATU (998.09 mg, 2.5725 mmol). The reaction mixture was stirred at RT 2 h. The reaction was quenched with water and extracted with EtOAc. The organic layers was dried with sodium sulfate, filtered, and concentrated via rotovap. The crude product was carried to next step. LCMS (ESI) m/z: 392.10 [M+H]+

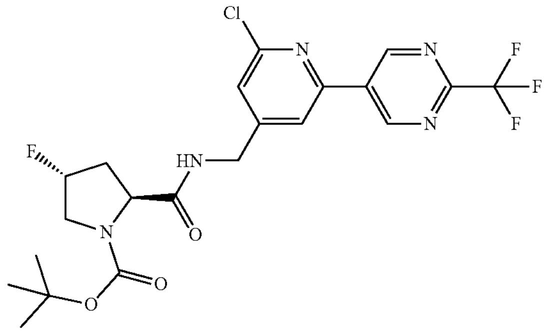 [SMILES: CC(C)(C)OC(=O)N1C[C@H](F)C[C@H]1C(=O)NCc1cc(Cl)nc(-c2cnc(C(F)(F)F)nc2)c1]

(2S,4R)-tert-butyl 2-(((2-chloro-6-(2-(trifluoromethyl)pyrimidin-5-yl)pyridin-4-yl)methyl)carbamoyl)-4-fluoropyrrolidine-1-carboxylate A solution of 5-(4,4,5,5-tetramethyl-1,3,2-dioxaborolan-2-yl)-2-(trifluoromethyl)pyrimidine (0.5 equiv., 0.2295 mmol), tert-butyl (2S,4R)-2-[(2,6-dichloro-4-pyridyl)methylcarbamoyl]-4-fluoro-pyrrolidine-1-carboxylate (180 mg, 0.4589 mmol), cesium carbonate (299.1 mg, 0.07263 mL, 0.9179 mmol) and [1,1'-bis(diphenylphosphino)ferrocene] dichloropalladium(ii) dichloromethane adduct (0.10 equiv., 0.04589 mmol) in acetonitrile (3.0 mL) and water (1.5 mL) was degassed. The reaction mixture was heated at 95° C. for 2 h. The reaction was filtered thru celite. The crude product was purified by flash chromatography (MeOH/DCM) to give 84 mg, 36.3% yield. LCMS (ESI) m/z:504.20 [M+H]+

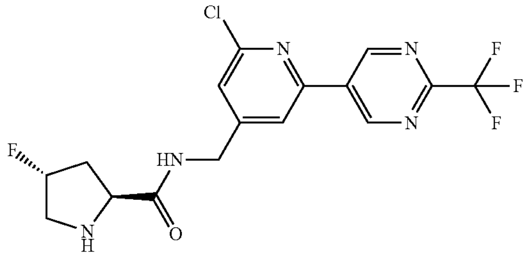 [SMILES: O=C(NCc1cc(Cl)nc(-c2cnc(C(F)(F)F)nc2)c1)[C@@H]1C[C@@H](F)CN1]

(2S,4R)—N-((2-chloro-6-(2-(trifluoromethyl)pyrimidin-5-yl)pyridin-4-yl)methyl)-4-fluoropyrrolidine-2-carboxamide To a solution of tert-butyl (2S,4R)-2-[[2-chloro-6-[2-(trifluoromethyl)pyrimidin-5-yl]-4-pyridyl]methylcarbamoyl]-4-fluoro-pyrrolidine-1-carboxylate (84 mg, 0.1667 mmol) in 1,4-dioxane (860.2 mg, 0.8335 mL, 9.763 mmol) was added hydrochloric acid (4 mol/L) in 1,4-dioxane (438 mg, 0.4167 mL, 1.667 mmol). The reaction mixture was stirred at RT 6 h. The reaction was concentrated and carried to next step. LCMS (ESI) m/z:404.0 [M+H]+

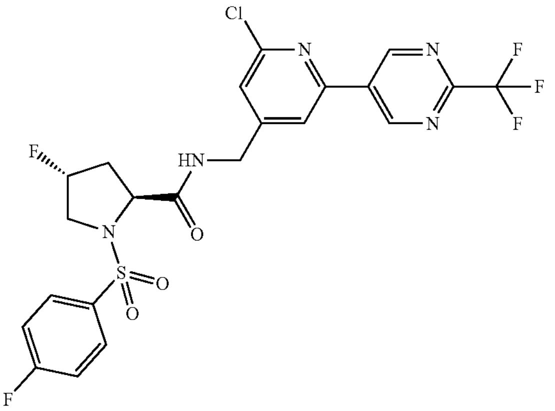 [SMILES: O=C(NCc1cc(Cl)nc(-c2cnc(C(F)(F)F)nc2)c1)[C@@H]1C[C@@H](F)CN1S(=O)(=O)c1ccc(F)cc1]

(2S,4R)—N-[[2-chloro-6-[2-(trifluoromethyl)pyrimidin-5-yl]-4-pyridyl]methyl]-4-fluoro-1-(4-fluorophenyl)sulfonyl-pyrrolidine-2-carboxamide To a solution of (2S,4R)—N-[[2-chloro-6-[2-(trifluoromethyl)pyrimidin-5-yl]-4-pyridyl]methyl]-4-fluoro-pyrrolidine-2-carboxamide (B) in dichloromethane (3.3 mL) was added triethylamine (337.4 mg, 0.465 mL, 3.334 mmol) then 4-fluorobenzenesulfonyl chloride (C, 48.66 mg, 0.2500 mmol). The reaction was stirred at RT 1 h. The reaction was concentrated and submitted for rHPLC 32.1 mg, 34.3% yield.

1H NMR (400 MHz, DMSO) δ 9.64-9.57 (s, 2H), 9.11-9.01 (t, J=6.0 Hz, 1H), 8.23-8.16 (d, J=1.1 Hz, 1H), 8.05-7.97 (m, 2H), 7.70-7.63 (q, J=0.9 Hz, 1H), 7.53-7.43 (m, 2H), 5.30-5.10 (d, J=52.6 Hz, 1H), 4.59-4.41 (m, 2H), 4.23-4.13 (dd, J=10.1, 7.1 Hz, 1H), 3.79-3.58 (m, 2H), 2.47-2.36 (m, 1H), 2.21-1.98 (m, 1H)., LCMS (ESI) m/z: 562.2 [M+H]+

Example 63

(2S,4R)—N-[[6-[4-(difluoromethyl)phenyl]pyrimidin-4-yl]methyl]-4-fluoro-1-(4-fluorophenyl)sulfonyl-pyrrolidine-2-carboxamide

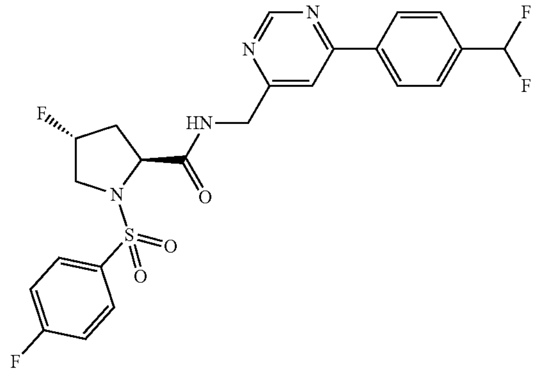 [SMILES: O=C(NCc1cc(-c2ccc(C(F)F)cc2)ncn1)[C@@H]1C[C@@H](F)CN1S(=O)(=O)c1ccc(F)cc1]

Preparation of the title compound follows the same general procedure as Example 42.

1H NMR (400 MHz, DMSO) δ 9.26-9.20 (d, J=1.2 Hz, 1H), 9.12-9.04 (m, 1H), 8.37-8.32 (dd, J=7.7, 1.2 Hz, 1H), 8.17-8.10 (m, 1H), 8.07-8.00 (m, 2H), 7.73-7.67 (d, J=8.2 Hz, 1H), 7.54-7.45 (m, 2H), 7.35-7.28 (m, 1H), 7.26-6.94 (m, 2H), 5.31-5.12 (d, J=52.3 Hz, 1H), 4.60-4.42 (m, 2H), 4.31-4.21 (m, 1H), 3.79-3.59 (m, 2H), 2.46-2.31 (m, 1H), 2.23-2.01 (m, 1H)., LCMS (ESI) m/z:509.2 [M+H]+

Example 64

(2S,4R)—N-[[6-[4-(difluoromethoxy)phenyl]pyrimidin-4-yl]methyl]-4-fluoro-1-(4-fluorophenyl)sulfonyl-pyrrolidine-2-carboxamide

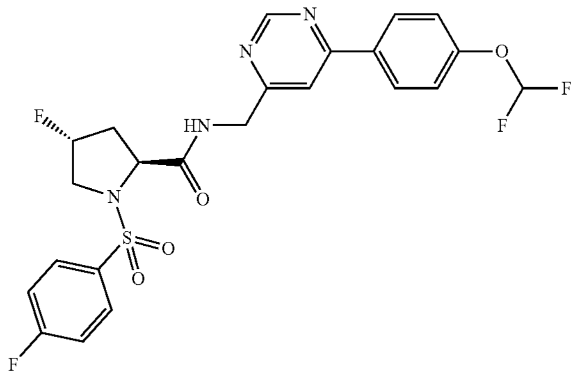 [SMILES: O=C(NCc1cc(-c2ccc(OC(F)F)cc2)ncn1)[C@@H]1C[C@@H](F)CN1S(=O)(=O)c1ccc(F)cc1]

Preparation of the title compound follows the same general procedure as Example 42.

1H NMR (400 MHz, DMSO) δ 9.20-9.14 (d, J=1.2 Hz, 1H), 9.11-9.04 (t, J=6.0 Hz, 1H), 8.33-8.25 (m, 2H), 8.08-8.01 (m, 3H), 7.51-7.44 (m, 2H), 7.32-7.26 (m, 2H), 5.32-5.11 (d, J=52.3 Hz, 1H), 4.50-4.45 (dd, J=5.8, 3.7 Hz, 2H), 4.29-4.21 (m, 1H), 3.76-3.62 (m, 2H), 2.46-2.36 (m, 1H), 2.25-2.01 (m, 1H)., LCMS (ESI) m/z:525.2 [M+H]+

Example 65

(2S,4R)-4-fluoro-N-[[5-fluoro-4-[5-fluoro-6-(trifluoromethyl)-3-pyridyl]-2-pyridyl]methyl]-1-(4-fluorophenyl)sulfonyl-pyrrolidine-2-carboxamide

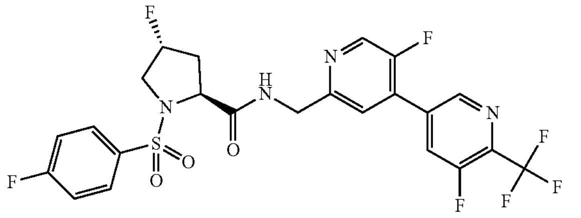 [SMILES: O=C(NCc1cc(-c2cnc(C(F)(F)F)c(F)c2)c(F)cn1)[C@@H]1C[C@@H](F)CN1S(=O)(=O)c1ccc(F)cc1]

Step 1: Preparation of 5-bromo-3-fluoro-2-iodopyridine

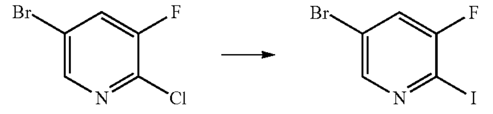 [SMILES: Fc1cc(Br)cnc1Cl ; Fc1cc(Br)cnc1I]

A mixture of 5-bromo-2-chloro-3-fluoropyridine (5.00 g, 23.76 mmol, 1.000 equiv), NaI (10.68 g, 71.25 mmol, 3.0 equiv), and chlorotrimethylsilane (2.58 g, 23.748 mmol, 1.000 equiv) in $CH_3CN$ (20 mL) was stirred for 2 h at 80° C. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (1:100) to afford the title compound (1.5 g, 21%) as a yellow solid.

Step 2: Preparation of 5-bromo-3-fluoro-2-(trifluoromethyl)pyridine

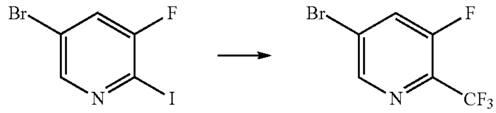 [SMILES: Fc1cc(Br)cnc1I ; Fc1cc(Br)cnc1C(F)(F)F]

A mixture of 5-bromo-3-fluoro-2-iodopyridine (1.20 g, 3.98 mmol, 1.00 equiv), methyl 2,2-difluoro-2-(fluorosulfonyl)acetate (5.35 g, 27.85 mmol, 7.00 equiv), CuI (5.30 g, 27.83 mmol, 7.00 equiv), and DMF (20 mL) was stirred for 12 h at 70° C. under nitrogen. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (1:200) to afford the title compound (200 mg, 21%) as yellow oil.

Step 3. Preparation of [5-fluoro-6-(trifluoromethyl)pyridin-3-yl]boronic acid

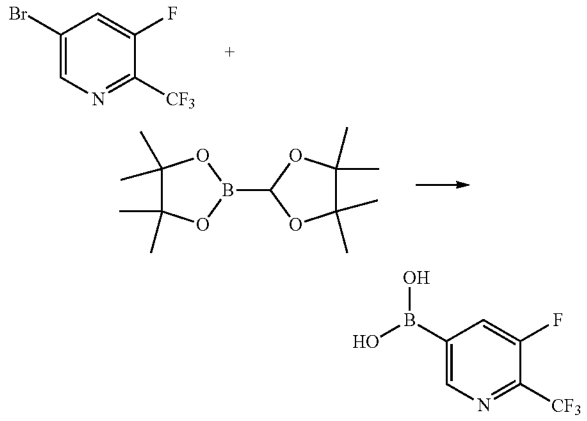

A mixture of 5-bromo-3-fluoro-2-(trifluoromethyl)pyridine (200.00 mg, 0.82 mmol, 1.00 equiv), 4,4,5,5-tetramethyl-2-(tetramethyl-1,3,2-dioxaborolan-2-yl)-1,3,2-dioxaborolane (312.24 mg, 1.23 mmol, 1.50 equiv), $Pd(dppf)Cl_2$ (29.99 mg, 0.04 mmol), and KOAc (241.35 mg, 2.46 mmol, 3.00 equiv) in 1,4-dioxane (5 mL) was stirred for 3 h at 100° C. under nitrogen. The reaction was then quenched by water, extracted with ethyl acetate, washed with brine, dried over anhydrous sodium sulfate, and concentrated under vacuum. This resulted in the title compound (400 mg, crude) as a black solid.

Step 4: (2S,4R)-4-fluoro-N-[[5-fluoro-4-[5-fluoro-6-(trifluoromethyl)-3-pyridyl]-2-pyridyl]methyl]-1-(4-fluorophenyl)sulfonyl-pyrrolidine-2-carboxamide

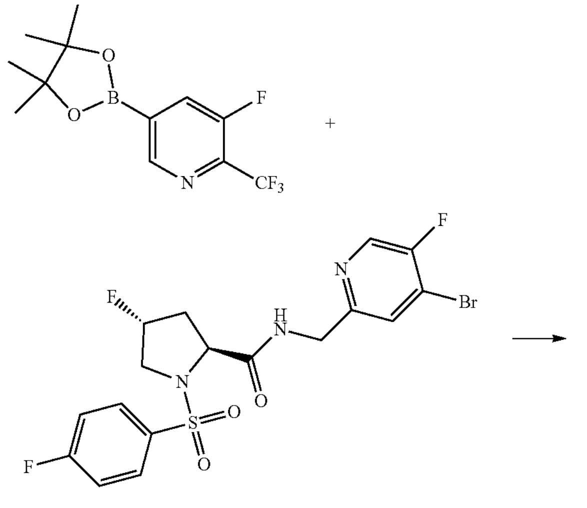

-continued

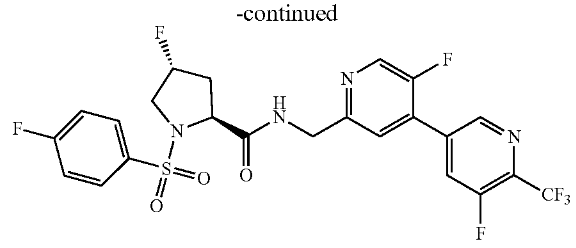

A mixture of (2S,4R)—N-[(4-bromo-5-fluoropyridin-2-yl)methyl]-4-fluoro-1-[(4-fluorobenzene)sulfonyl]pyrrolidine-2-carboxamide (150.00 mg, 0.314 mmol, 1.000 equiv), [5-fluoro-6-(trifluoromethyl)pyridin-3-yl]boronic acid (400 mg, 1.915 mmol, 3.000 equiv), $Pd(dppf)Cl_2$ (22.95 mg, 0.031 mmol, 0.100 equiv), potassium carbonate (130.03 mg, 0.941 mmol, 3.000 equiv), and 1,4-dioxane (20 mL)/water (2 mL) was stirred for 3 h at 100° C. under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether (1:1) to afford the title compound (57.3 mg, 32%) as a white solid.

$^1H$ NMR (300 MHz, DMSO-$d_6$) δ 9.07-9.03 (m, 1H), 8.89 (s, 1H), 8.74 (s, 1H), 8.40 (d, J=11.4 Hz, 1H), 8.00-7.95 (m, 2H), 7.77 (d, J=6.3 Hz, 1H), 7.48-7.42 (m, 2H), 5.19 (d, J=52 Hz, 1H), 4.57-4.42 (m, 2H), 4.23-4.18 (m, 1H), 3.71-3.54 (m, 2H), 2.49-1.99 (m, 2H).

Example 66

(2S,4R)-4-fluoro-1-(4-fluorophenyl)sulfonyl-N-[[5-fluoro-4-[4-(trifluoromethoxy)-1-piperidyl]-2-pyridyl]methyl]pyrrolidine-2-carboxamide

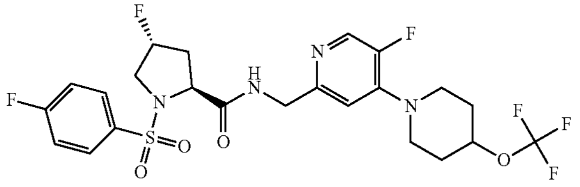 [SMILES: O=C(NCc1cc(N2CCC(OC(F)(F)F)CC2)c(F)cn1)[C@@H]1C[C@@H](F)CN1S(=O)(=O)c1ccc(F)cc1]

Step 1: Preparation of piperidin-4-ol hydrochloride

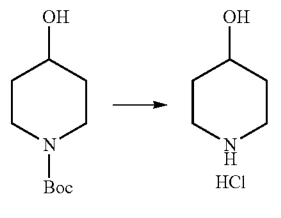 [SMILES: CC(C)(C)OC(=O)N1CCC(O)CC1 ; OC1CCNCC1 ; Cl]

A mixture of tert-butyl 4-hydroxypiperidine-1-carboxylate (5 g, 24.84 mmol, 1.00 equiv) and HCl (saturated solution in 30 mL of 1,4-dioxane) was stirred for 2 h at room temperature. The resulting mixture was concentrated under vacuum to afford the title compound (3.4 g, 99%) as an off-white solid.

Step 2: Preparation of benzyl 4-hydroxypiperidine-1-carboxylate

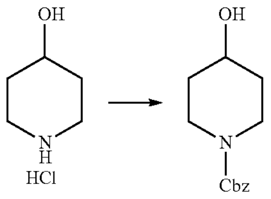 [SMILES: OC1CCNCC1 ; Cl ; O=C(OCc1ccccc1)N1CCC(O)CC1]

Benzyl chloroformate (4.64 g, 27.199 mmol, 1.101 equiv) was added dropwise into a mixture of piperidin-4-ol hydrochloride (3.4 g, 24.71 mmol, 1.0 equiv), sodium hydroxide (2.17 g, 54.25 mmol, 2.2 equiv), and water (55 mL)/1,4-dioxane (55 mL). The resulting solution was stirred for 30 min at room temperature. The mixture was diluted with water. The pH value of the mixture was adjusted to 2 with 1N HCl. The resulting solution was extracted with ethyl acetate, washed with brine, dried over anhydrous sodium sulfate, and concentrated under vacuum. The residue was purified by a silica gel column eluting with ethyl acetate/petroleum ether (1:2). This resulted in the title compound (4.4 g, 76%) as colorless oil.

Step 3: Preparation of benzyl 4-[[(methylsulfanyl)methanethioyl]oxy]piperidine-1-carboxylate

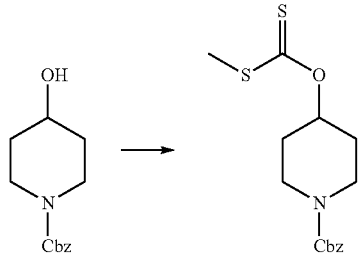 [SMILES: O=C(OCc1ccccc1)N1CCC(O)CC1 ; CSC(=S)OC1CCN(C(=O)OCc2ccccc2)CC1]

Sodium hydride (960 mg, 60% in mineral oil, 2.139 equiv) was added in several batches into a solution of benzyl 4-hydroxypiperidine-1-carboxylate (4.4 g, 18.70 mmol, 1.0 equiv) in N,N-dimethylformamide (50 mL) at 0° C. under nitrogen. After 0.5 h at 0° C. carbon disulfide (5.8 g, 76.174 mmol, 4.07 equiv) was added dropwise. The resulting mixture was stirred for 0.5 h at 0° C. and $CH_3I$ (4.0 g, 28.181 mmol, 1.51 equiv) was then added dropwise. After 1 h at 0° C. the reaction was then quenched by water, extracted with ethyl acetate, washed with brine, dried over anhydrous sodium sulfate, and concentrated under vacuum. The residue was purified by silica gel column eluting with ethyl acetate/petroleum ether (1/10). This resulted in the title compound (3 g, 49%) as colorless oil.

Step 4: Preparation of benzyl 4-(trifluoromethoxy)piperidine-1-carboxylate

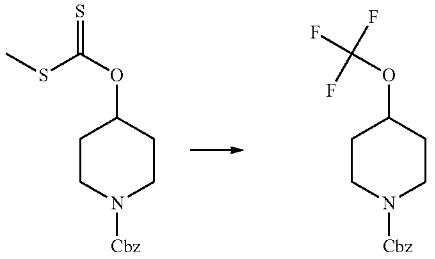 [SMILES: CSC(=S)OC1CCN(C(=O)OCc2ccccc2)CC1 ; O=C(OCc1ccccc1)N1CCC(OC(F)(F)F)CC1]

HF pyridine (20 g, 201.80 mmol, 21.89 equiv) and benzyl 4-[[(methylsulfanyl)methanethioyl]oxy]piperidine-1-carboxylate (3 g, 9.22 mmol, 1.0 equiv) in 10 mL of dichloromethane were added in sequentially into a mixture of 1,3-dibromo-5,5-dimethylimidazolidine-2,4-dione (7.9 g, 27.630 mmol, 2.997 equiv) in dichloromethane (100 mL) at −78° C. under nitrogen. The resulting solution was stirred for 12 h at room temperature. The reaction was then quenched by saturated sodium bicarbonate, extracted with dichloromethane, washed with brine, dried over anhydrous sodium sulfate, and concentrated under vacuum. The residue was purified by a silica gel column eluting with ethyl acetate/petroleum ether (1/10) to afford the title compound (1.5 g, 54%) as light yellow oil.

Step 5: Preparation of 4-(trifluoromethoxy)piperidine

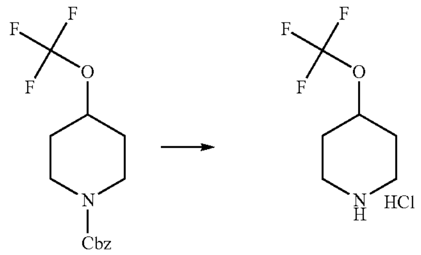 [SMILES: O=C(OCc1ccccc1)N1CCC(OC(F)(F)F)CC1 ; FC(F)(F)OC1CCNCC1 ; Cl]

A mixture of benzyl 4-(trifluoromethoxy)piperidine-1-carboxylate (1.1 g, 3.63 mmol, 1.0 equiv) and palladium on carbon (1 g, 9.397 mmol, 2.591 equiv) in methanol (50 mL) was stirred for 12 h at room temperature. The solids were filtered out and the liquid was concentrated under vacuum. The residue was dissolved with saturated solution of HCl in 1,4-dioxane and concentrated under vacuum. This resulted in the title compound (0.7 g, crude) as a light yellow solid.

Step 6: Preparation of (2S,4R)-4-fluoro-N-([5-fluoro-4-[4-(trifluoromethoxy)piperidin-1-yl]pyridin-2-yl]methyl)-1-[(4-fluorobenzene)sulfonyl]pyrrolidine-2-carboxamide

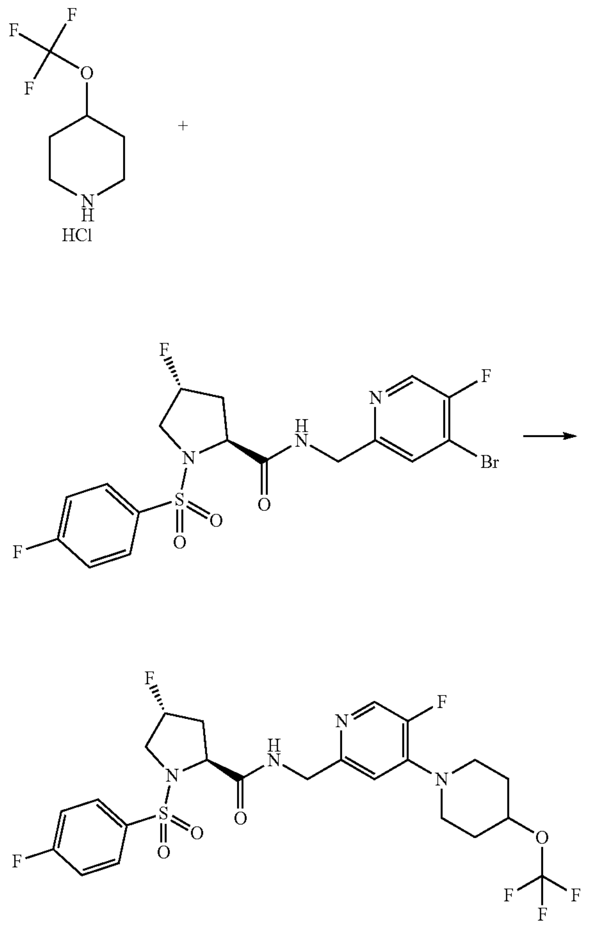

A mixture of 4-(trifluoromethoxy)piperidine hydrochloride (200 mg, 0.973 mmol, 1.0 equiv), potassium carbonate (410 mg, 2.967 mmol, 3.05 equiv), (2S,4R)—N-[(4-bromo-5-fluoropyridin-2-yl)methyl]-4-fluoro-1-[(4-fluorobenzene)sulfonyl]pyrrolidine-2-carboxamide (231 mg, 0.483 mmol, 0.5 equiv), $Pd_2(dba)_3$.CHCl3 (100 mg, 0.097 mmol, 0.099 equiv), and XantPhos (112 mg, 0.194 mmol, 0.2 equiv) in toluene (10 mL) was stirred for 12 h at 100° C. under nitrogen. The reaction mixture was concentrated under vacuum. The residue was dissolved in water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (46.9 mg, 9%) as a white solid.

$^1H$ NMR (300 MHz, $CDCl_3$) δ 8.87-8.86 (m, 1H), 8.19-8.18 (m, 1H), 8.00-7.96 (m, 2H), 7.50-7.44 (m, 2H), 7.01-6.98 (d, J=15 Hz, 1H), 5.27-5.10 (d, J=95 Hz, 1H), 4.69-4.63 (m, 1H), 4.35-4.16 (m, 3H), 3.71-3.53 (m, 4H), 3.21-3.14 (m, 2H), 2.43-2.36 (m, 1H), 2.28-2.10 (m, 1H), 2.01-1.97 (m, 2H), 1.79-1.72 (m, 2H).

Example 67

Preparation of (2S,4R)-4-fluoro-1-(4-fluorophenyl)sulfonyl-N-[[2-[5-(trifluoromethyl)pyrazin-2-yl]-4-pyridyl]methyl]pyrrolidine-2-carboxamide

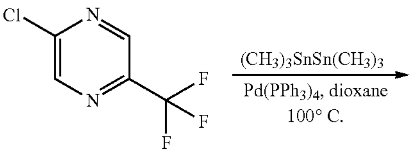

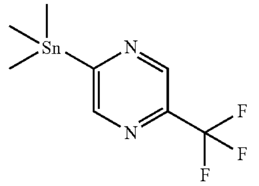

INT-67-1

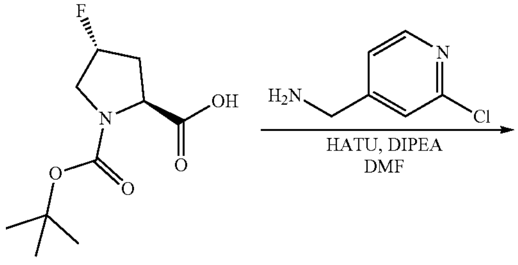

INT-67-2

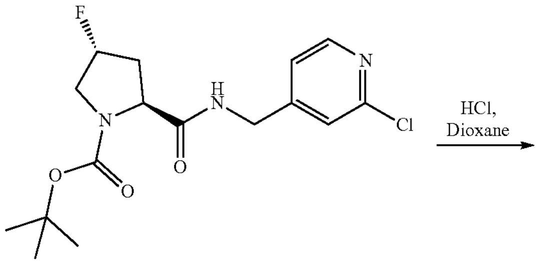

INT-67-3

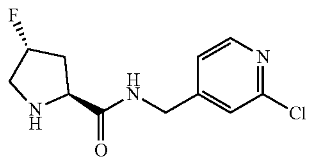

INT-67-4

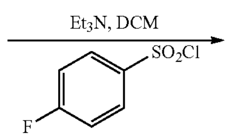

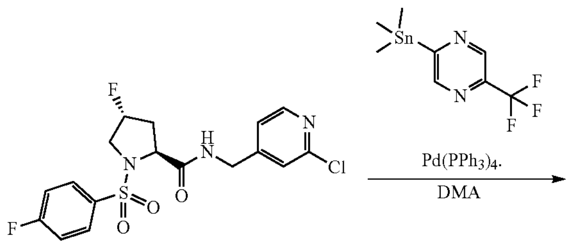

INT-67-5

-continued

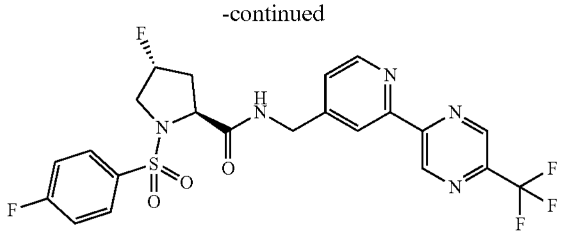

Example 67

Step 1: 2-(trifluoromethyl)-5-(trimethylstannyl)pyrazine (INT-67-1)

To a pressure tube was added 2-chloro-5-(trifluoromethyl)pyrazine (200 mg, 1.1 mmol), hexamethylditin (0.281 mL 1.3 mmol), $Pd(PPh_3)_4$ (318.5 mg, 0.27 mmol) and dioxane (10 mL). The reaction mixture was purged with Nitrogen and heated at 100° C. for 1 hour. The resulting mixture was cooled to room temperature, and filtered through a thin layer of celite. The filter cake was washed with DCM. The filtrate was concentrated in vacuo to give a dark solid. The crude was stored in the refrigerator and used without further purification. (341 mg, 100%). MS-ESI: [M+H]+ 311.9

Step 2: Following the HATU coupling procedure of Example 35, step 1: tert-butyl (2S,4R)-2-[(2-chloro-4-pyridyl)methylcarbamoyl]-4-fluoro-pyrrolidine-1-carboxylate (INT-67-3) (801 mg, 89%) was prepared from (2S,4R)-1-tert-butoxycarbonyl-4-fluoro-pyrrolidine-2-carboxylic acid (450 mg, 1.9 mmol) and (2-chloro-4-pyridyl)methanamine hydrochloride (380 mg, 2.1 mmol), DIPEA (1 mL, 6.4 mmol), HATU (898 mg, 2.3 mmol), DMF (2 mL). MS-ESI: $[M+H]^+$ 358.9

Step 3: Following the boc removal procedure of Example 35, step 3: (2S,4R)—N-[(2-chloro-4-pyridyl)methyl]-4-fluoro-pyrrolidine-2-carboxamide (INT-67-4) (375 mg, 100%) was prepared from tert-butyl (2S,4R)-2-[(2-chloro-4-pyridyl)methylcarbamoyl]-4-fluoro-pyrrolidine-1-carboxylate (500 mg, 1.94 mmol) and 4 N HCl in dioxane (3 mL, 12.4 mmol). MS-ESI: [M+H]+ 258.9

Step 4: Following the sulfonamide formation procedure of Example 35, step 4: (2S,4R)—N-[(2-chloro-4-pyridyl)methyl]-4-fluoro-1-(4-fluorophenyl)sulfonyl-pyrrolidine-2-carboxamide (INT-67-5) (95 mg, 63%) was prepared from (2S,4R)—N-[(2-chloro-4-pyridyl)methyl]-4-fluoro-pyrrolidine-2-carboxamide (INT-67-4) (100 mg, 0.3 mmol), Et3N (0.8 mL, 6 mmol), 4-fluorobenzenesulfonyl chloride (70 mg, 0.36 mmol) in DCM (1 mL). MS-ESI: [M+H]+ 416.5

Step 5: (2S,4R)-4-fluoro-1-(4-fluorophenyl)sulfonyl-N-[[2-fluoro-5-[5-(trifluoromethyl)pyrazin-2-yl]phenyl]methyl]pyrrolidine-2-carboxamide (67)

To a pressure tube was added trimethyl[5-(trifluoromethyl)pyrazin-2-yl]stannane (67 mg, 0.2 mmol), (2S,4R)—N-[(5-chloro-2-fluoro-phenyl)methyl]-4-fluoro-1-(4-fluorophenyl)sulfonyl-pyrrolidine-2-carboxamide (50 mg, 0.11 mmol), $Pd(PPh_3)_4$ (13 mg, 0.011 mmol) and N,N-dimethylacetamide (1 mL). The reaction mixture was purged with Nitrogen and subject to microwave at 150° C. for 30 min. The resulting mixture was cooled to room temperature, and filtered through a thin layer of celite. The crude was purified with reverse phase HPLC and afforded the title compound 67 (30 mg, 53%). MS-ESI: [M+H]+ 528.5

$^1$H NMR (400 MHz, DMSO-$d_6$) δ 9.42 (d, J=2.1 Hz, 1H), 9.29 (d, J=1.3 Hz, 1H), 8.81 (t, J=5.9 Hz, 1H), 8.73 (ddd, J=8.4, 2.3, 0.9 Hz, 1H), 8.17 (d, J=1.3 Hz, 1H), 8.11-7.94 (m, 3H), 7.49-7.19 (m, 2H), 4.67-4.48 (m, 2H), 4.39 (dd, J=17.4, 5.6 Hz, 1H), 2.24-2.10 (m, 1H), 2.02 (td, J=11.5, 6.5 Hz, 1H), 1.84 (ddt, J=12.0, 6.1, 2.7 Hz, 1H), 1.71 (ddd, J=11.8, 6.7, 2.9 Hz, 1H), 1.45 (s, 3H), 1.24 (s, 3H).

Example 68

Preparation of (2R,3S)-3-fluoro-1-(4-fluorophenyl)sulfonyl-N-[[3-fluoro-5-[2-(trifluoromethyl)pyrimidin-5-yl]phenyl]methyl]pyrrolidine-2-carboxamide

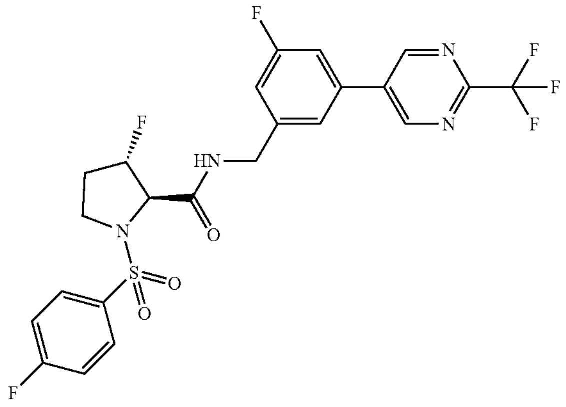 [SMILES: O=C(NCc1cc(F)cc(-c2cnc(C(F)(F)F)nc2)c1)[C@@H]1[C@@H](F)CCN1S(=O)(=O)c1ccc(F)cc1]

Preparation of the title compound follows the same general procedure as Example 55.

1H NMR (400 MHz, DMSO) δ 9.46-9.42 (s, 2H), 9.09-8.99 (t, J=6.0 Hz, 1H), 8.04-7.94 (m, 2H), 7.79-7.72 (dt, J=9.9, 2.1 Hz, 1H), 7.72-7.67 (t, J=1.5 Hz, 1H), 7.54-7.45 (m, 2H), 7.38-7.30 (dt, J=9.6, 1.8 Hz, 1H), 5.29-5.09 (m, 1H), 4.54-4.39 (m, 2H), 4.39-4.30 (d, J=24.6 Hz, 1H), 3.73-3.61 (m, 1H), 3.21-3.11 (m, 1H), 2.22-2.02 (m, 2H)., LCMS (ESI) m/z:545.11 [M+H]+

Example 69

Preparation of (2S,4R)—N-[[4-(2,2-difluoro-6-azaspiro[2.5]octan-6-yl)-5-fluoro-2-pyridyl]methyl]-4-fluoro-1-(4-fluorophenyl)sulfonyl-pyrrolidine-2-carboxamide

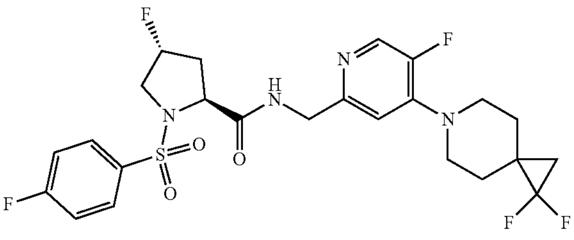 [SMILES: O=C(NCc1cc(N2CCC3(CC2)CC3(F)F)c(F)cn1)[C@@H]1C[C@@H](F)CN1S(=O)(=O)c1ccc(F)cc1]

Step 1: Preparation of tert-butyl 1,1-difluoro-6-azaspiro[2.5]octane-6-carboxylate

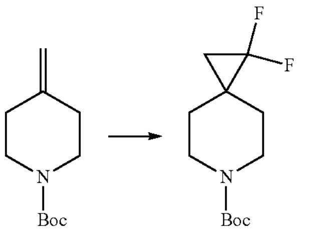 [SMILES: C=C1CCN(C(=O)OC(C)(C)C)CC1 ; CC(C)(C)OC(=O)N1CCC2(CC1)CC2(F)F]

A mixture of tert-butyl 4-methylidenepiperidine-1-carboxylate (1.00 g, 5.07 mmol, 1.00 equiv), NaI (379.91 mg, 2.53 mmol, 0.50 equiv), and trimethyl(trifluoromethyl)silane (1.80 g, 12.66 mmol, 2.50 equiv) in THF (10 mL) was stirred for 12 h at 60° C. under nitrogen. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (1:10) to afford the title compound (1.2 g, 96%) as colorless oil.

Step 2: Preparation of 1,1-difluoro-6-azaspiro[2.5]octane hydrochloride

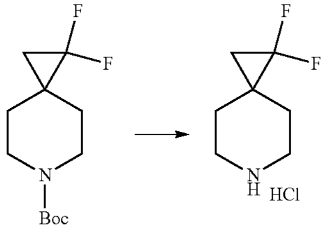 [SMILES: CC(C)(C)OC(=O)N1CCC2(CC1)CC2(F)F ; FC1(F)CC12CCNCC2 ; Cl]

A mixture of tert-butyl 1,1-difluoro-6-azaspiro[2.5]octane-6-carboxylate (1.2 g, 4.85 mmol, 1.00 equiv) and HCl (saturated solution in 20 mL of 1,4-dioxane) was stirred for 2 h at room temperature. The resulting mixture was concentrated under vacuum to afford the title compound (800 mg, 90%) as a white solid.

Step 3: Preparation of (2S,4R)—N-[[4-(2,2-difluoro-6-azaspiro[2.5]octan-6-yl)-5-fluoro-2-pyridyl]methyl]-4-fluoro-1-(4-fluorophenyl)sulfonyl-pyrrolidine-2-carboxamide

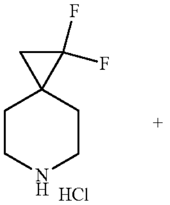

+

-continued

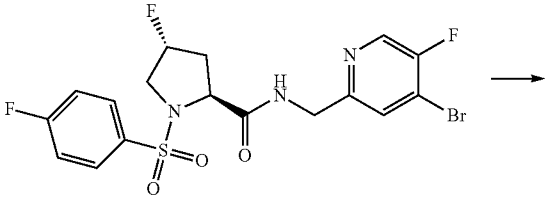

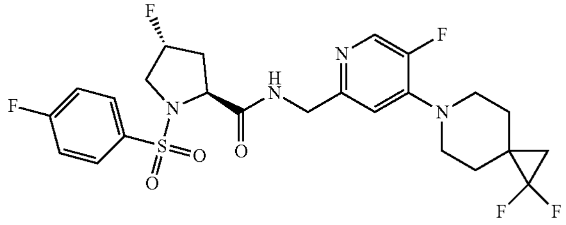

A mixture of (2S,4R)—N-[(4-br-omo-5-fluoropyridin-2-yl)methyl]-4-fluoro-1-[(4-fluorobenzene)sulfonyl]pyrrolidine-2-carboxamide (135.00 mg, 0.28 mmol, 1.00 equiv), 1,1-difluoro-6-azaspiro[2.5]octane hydrochloride (51.83 mg, 0.28 mmol, 1.00 equiv), $Pd_2(dba)_3.CHCl_3$ (58.43 mg, 0.06 mmol, 0.20 equiv), XantPhos (65.33 mg, 0.11 mmol, 0.40 equiv), $Cs_2CO_3$ (275.90 mg, 0.85 mmol, 3.00 equiv), and toluene (5 mL) was stirred for 12 h at 110° C. under nitrogen. The reaction was quenched by water, extracted with ethyl acetate, washed with brine, dried over anhydrous sodium sulfate, and concentrated under vacuum. The residue was purified by a silica gel column eluting with ethyl acetate/petroleum ether (2:1). The crude product was re-purified by Prep-HPLC to afford the title compound (26.5 mg, 17%) as a white solid.

$^1$H NMR (400 MHz, $CDCl_3$) δ 8.15-8.13 (m, 1H), 7.89-7.86 (m, 2H), 7.54 (s, 1H), 7.26-7.19 (m, 2H), 5.87 (d, J=57.2 Hz, 1H), 5.05 (d, J=52 Hz, 1H), 4.66-4.60 (m, 1H), 4.37-4.43 (m, 1H), 4.29-4.25 (m, 1H), 3.88-3.64 (m, 2H), 3.49-3.42 (m, 2H), 3.34-3.28 (m, 2H), 2.60-2.45 (m, 1H), 2.31-2.11 (m, 1H), 1.79-1.74 (m, 4H), 1.16-1.12 (m, 2H).

Example 70

Preparation of (2S,4R)—N-((5-cyano-4-(4-(trifluoromethyl)phenyl)pyridin-2-yl)methyl)-4-fluoro-1-(4-fluorophenylsulfonyl)pyrrolidine-2-carboxamide

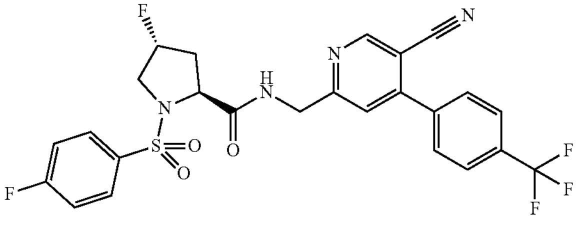 [SMILES: N#Cc1cnc(CNC(=O)[C@@H]2C[C@@H](F)CN2S(=O)(=O)c2ccc(F)cc2)cc1-c1ccc(C(F)(F)F)cc1]

Step 1: Preparation of (2S,4R)—N-((5-cyano-4-(4-(trifluoromethyl)phenyl)pyridin-2-yl)methyl)-4-fluoro-1-(4-fluorophenylsulfonyl)pyrrolidine-2-carboxamide

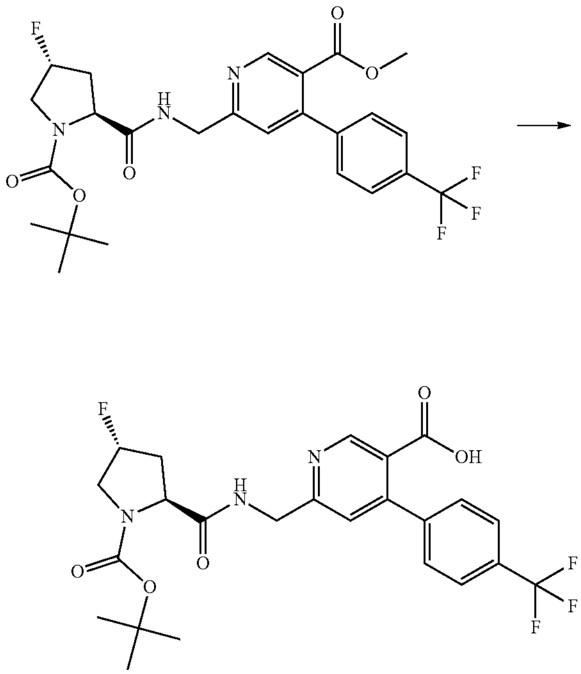 [SMILES: CC(C)(C)OC(=O)N1C[C@H](F)C[C@H]1C(=O)NCc1cc(-c2ccc(C(F)(F)F)cc2)c(C(N)=O)cn1 ; CC(C)(C)OC(=O)N1C[C@H](F)C[C@H]1C(=O)NCc1cc(-c2ccc(C(F)(F)F)cc2)c(C#N)cn1]

A mixture of methyl 6-([[(2S,4R)-1-[(tert-butoxy)carbonyl]-4-fluoropyrrolidin-2-yl]formamido]methyl)-4-[4-(trifluoromethyl)phenyl]pyridine-3-carboxylate (1.4 g, 2.66 mmol, 1.00 equiv) in tetrahydrofuran (20 mL)/water(2 mL) and LiOH (96 mg, 4.01 mmol, 1.50 equiv) in water (2 mL) was stirred for 14 h at room temperature. The reaction was diluted with water and the pH value of the solution was adjusted to 7 with citric acid. The resulting solution was extracted with dichloromethane and concentrated under vacuum. This resulted in the title compound (405 mg, 30%) as a yellow solid.

Step 2: Preparation of tert-butyl (2S,4R)-2-[([5-carbamoyl-4-[4-(trifluoromethyl)phenyl]pyridin-2-yl]methyl)carbamoyl]-4-fluoropyrrolidine-1-carboxylate

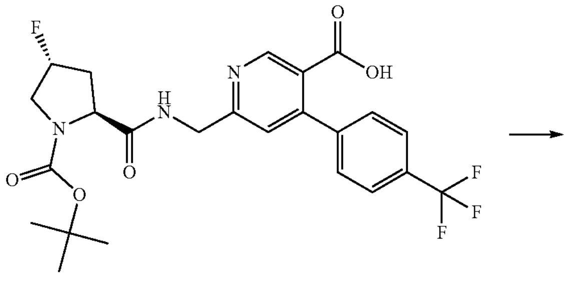

-continued

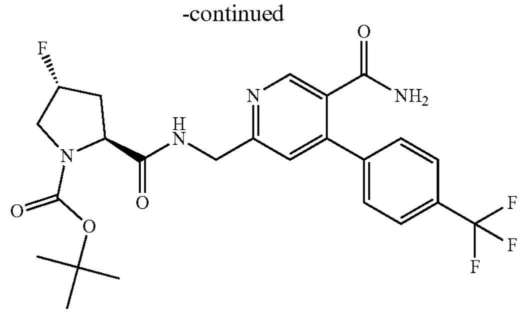

A mixture of 6-([[(2S,4R)-1-[(tert-butoxy)carbonyl]-4-fluoropyrrolidin-2-yl]formamido]methyl)-4-[4-(trifluoromethyl)phenyl]pyridine-3-carboxylic acid (405 mg, 0.79 mmol, 1.00 equiv), $NH_4Cl$ (51 mg, 0.95 mmol, 1.20 equiv), HATU (361 mg, 0.95 mmol, 1.20 equiv), DIEA (307 mg, 2.38 mmol, 3.00 equiv) in tetrahydrofuran (20 mL) was stirred for 14 h at room temperature. The reaction was quenched by water, extracted with ethyl acetate, and concentrated under vacuum. The residue was purified by a silica gel column eluting with ethyl acetate/petroleum ether(3:1) to afford the title compound (190 mg, 47%) as an off-white solid.

Step 3: Preparation of tert-butyl (2S,4R)-2-[([5-cyano-4-[4-(trifluoromethyl)phenyl]pyridin-2-yl]methyl)carbamoyl]-4-fluoropyrrolidine-1-carboxylate

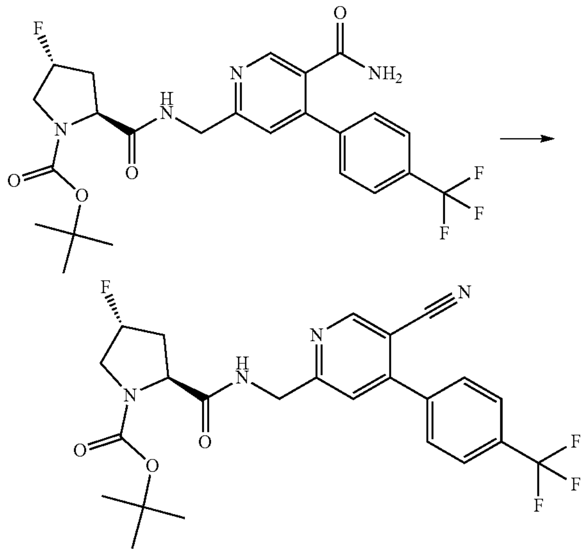

A solution of tert-butyl (2S,4R)-2-[([5-carbamoyl-4-[4-(trifluoromethyl)phenyl]pyridin-2-yl]methyl)carbamoyl]-4-fluoropyrrolidine-1-carboxylate (190 mg, 0.37 mmol, 1.00 equiv), TFAA (157 mg, 0.75 mmol, 2.00 equiv), and TEA (37 mg, 0.37 mmol, 1.00 equiv) in dichloromethane (5 mL) was stirred for 30 seconds at room temperature. The reaction was then quenched by water, extracted with dichloromethane, washed with brine, and concentrated under vacuum. This resulted in the crude product (200 mg) as a yellow solid which was used for the next step without any further purification.

Step 4: Preparation of (2S,4R)—N-([5-cyano-4-[4-(trifluoromethyl)phenyl]pyridin-2-yl]methyl)-4-fluoropyrrolidine-2-carboxamide hydrochloride

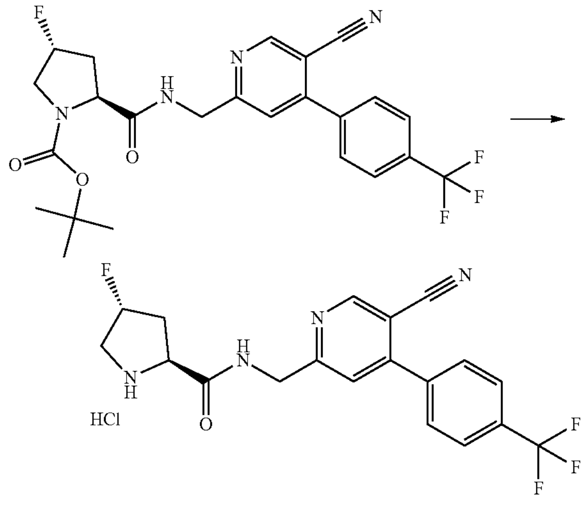

A mixture of tert-butyl (2S,4R)-2-[([5-cyano-4-[4-(trifluoromethyl)phenyl]pyridin-2-yl]methyl)carbamoyl]-4-fluoropyrrolidine-1-carboxylate (200 mg, 0.41 mmol, 1.00 equiv) and TFA (1 mL, 13.46 mmol, 33.20 equiv) in dichloromethane (2 mL) was stirred for 2 min at room temperature. The reaction mixture was concentrated under vacuum. The residue was diluted with 2 mL of hydrogen chloride (6M) and concentrated under vacuum. The resulting solid washed with 2×20 mL of hexane to give the title compound as a crude product.

Step 5: Preparation of (2S,4R)—N-((5-cyano-4-(4-(trifluoromethyl)phenyl)pyridin-2-yl)methyl)-4-fluoro-1-(4-fluorophenyl sulfonyl)pyrrolidine-2-carboxamide

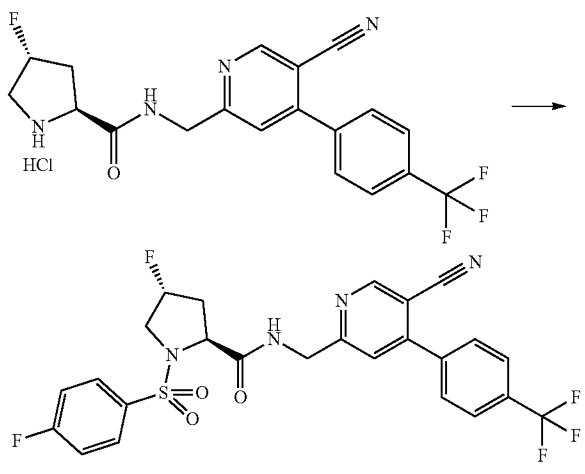

A mixture of 4-fluorobenzene-1-sulfonyl chloride (47.5 mg, 0.24 mmol, 1.20 equiv), (2S,4R)—N-([5-cyano-4-[4-(trifluoromethyl)phenyl]pyridin-2-yl]methyl)-4-fluoropyrrolidine-2-carboxamide (80 mg, 0.10 mmol, 1.00 equiv, 50%), and TEA (62 mg, 0.61 mmol, 3.00 equiv) in dichloromethane (5 mL) was stirred for 1 h at room temperature. The reaction was quenched by water, extracted with dichloromethane, and concentrated under vacuum. The residue was purified by a silica gel column eluting with ethyl acetate/petroleum ether (1:1) to afford the title compound (15.8 mg, 28%) as a white solid.

$^1$H NMR (400 MHz, $CDCl_3$) δ 8.94 (s, 1H), 7.88-7.85 (m, 2H), 7.81-7.77 (m, 4H), 7.66-7.63 (m, 2H), 7.30-7.20 (m, 2H), 5.12-4.99 (d, J=51.2 Hz, 1H), 4.95-24.89 (dd, J=8.0 Hz, J=6.8 Hz, 1H), 4.67-4.61 (dd, J=4.8 Hz, J=5.2 Hz, 1H), 4.30-4.25 (t, J=8.8 Hz, 1H), 3.93-3.84 (m, 1H), 3.75-3.64 (m, 1H), 2.60-2.50 (m, 1H), 2.32-2.00 (m, 1H).

Example 71

Preparation of (2S,4R)—N-[[5-cyano-4-[6-(trifluoromethyl)-3-pyridyl]-2-pyridyl]methyl]-4-fluoro-1-(4-fluorophenyl)sulfonyl-pyrrolidine-2-carboxamide

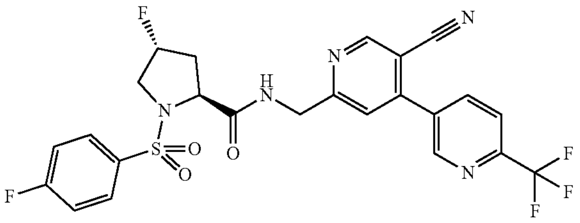 [SMILES: N#Cc1cnc(CNC(=O)[C@@H]2C[C@@H](F)CN2S(=O)(=O)c2ccc(F)cc2)cc1-c1ccc(C(F)(F)F)nc1]

Step 1: Preparation of 6-chloro-4-iodopyridine-3-carboxylic acid

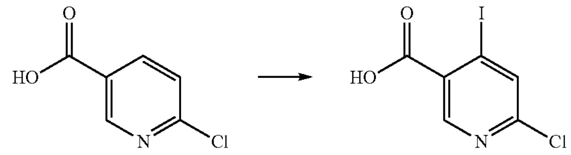 [SMILES: O=C(O)c1ccc(Cl)nc1 ; O=C(O)c1cnc(Cl)cc1I]

n-BuLi (8.8 mL, 2.5 M in hexanes, 2.00 equiv) was added dropwise into a solution of bis(propan-2-yl)amine (2.02 g, 19.96 mmol, 2.00 equiv) in 30 mL of dry THF at −78° C. under nitrogen. The mixture was warmed to −30° C. and stirred for 30 min. A solution of 6-chloropyridine-3-carboxylic acid (1.58 g, 10.03 mmol, 1.00 equiv) in tetrahydrofuran (10 mL) was added dropwise at −78° C. After 1 h $I_2$ (3.07 g, 12.10 mmol, 1.20 equiv) was added at 0° C. After 30 minutes the reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/1) to afford the title compound (1.2 g, 42%) as a yellow solid.

Step 2: Preparation of 6-chloro-4-[6-(trifluoromethyl)pyridin-3-yl]pyridine-3-carboxylic acid

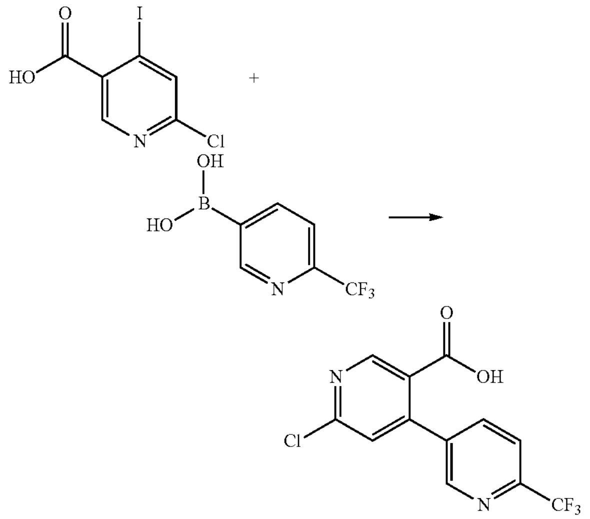

A mixture of 6-chloro-4-iodopyridine-3-carboxylic acid (5 g, 17.64 mmol, 1.00 equiv) in dioxane (100 mL), [6-(trifluoromethyl)pyridin-3-yl]boronic acid (3.17 g, 16.60 mmol, 0.90 equiv), potassium carbonate (6.9 g, 49.93 mmol, 2.80 equiv), Pd(dppf)$Cl_2$ (1 g, 1.37 mmol), and water (20 mL) was stirred for 5 h at 80° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/1). This resulted in the title compound (8.7 g) as a yellow solid.

Step 3: Preparation of methyl 6-chloro-4-[6-(trifluoromethyl)pyridin-3-yl]pyridine-3-carboxylate

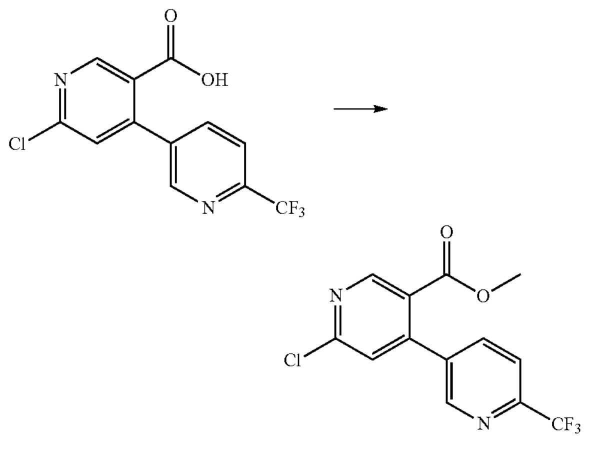

A mixture of 6-chloro-4-[6-(trifluoromethyl)pyridin-3-yl]pyridine-3-carboxylic acid (8.5 g, 28.09 mmol, 1.00 equiv) and thionyl chloride (10 mL, 137.85 mmol, 4.90 equiv) in dichloromethane (50 mL) was stirred for 1 hour at room temperature. The mixture was concentrated under vacuum and the residue was dissolved in methanol (10 mL) and stirred for 30 min. The resulting mixture was concentrated under vacuum. The residue was purified by a silica gel column eluting with ethyl acetate/petroleum ether (1/4) to afford the title compound (2.6 g, 29%) as a yellow solid.

Step 4: Preparation of methyl 6-cyano-4-[6-(trifluoromethyl)pyridin-3-yl]pyridine-3-carboxylate

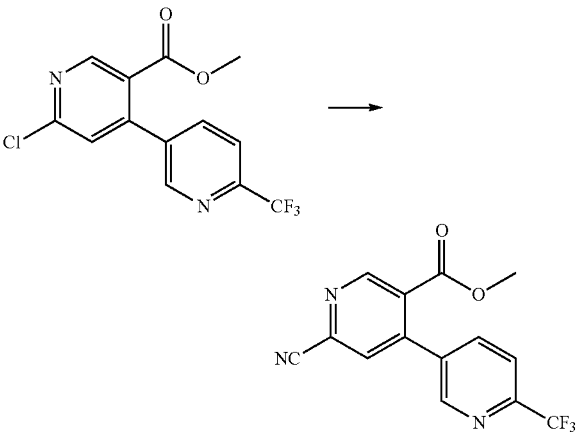

A mixture of methyl 6-chloro-4-[6-(trifluoromethyl)pyridin-3-yl]pyridine-3-carboxylate (1.0 g, 3.16 mmol, 1.00 equiv) in N,N-dimethylformamide (10 mL), $Zn(CN)_2$ (444 mg, 3.78 mmol, 1.20 equiv), $Pd_2(dba)_3$ (200 mg, 0.22 mmol), and dppf (400 mg, 0.72 mmol, 0.20 equiv) was stirred for 3 h at 100° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/1) to afford the title compound (750 mg, 77%) as a yellow solid.

Step 5: Preparation of methyl 6-(aminomethyl)-4-[6-(trifluoromethyl)pyridin-3-yl]pyridine-3-carboxylate hydrochloride

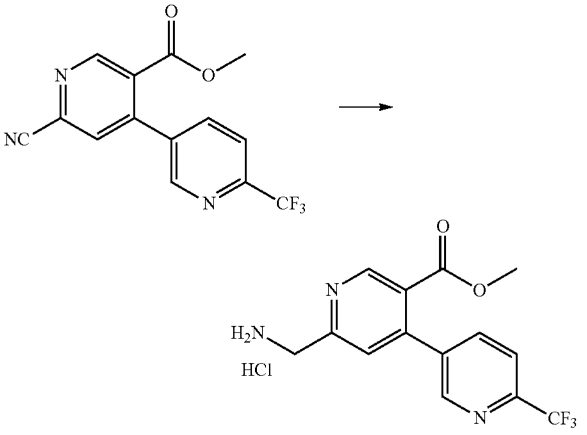

A mixture of methyl 6-cyano-4-[6-(trifluoromethyl)pyridin-3-yl]pyridine-3-carboxylate (750 mg, 2.44 mmol, 1.00 equiv) in methanol (50 mL), conc. HCl (1 mL), and palladium on carbon (750 mg, 7.05 mmol, 2.90 equiv) was stirred for 1 h at room temperature under hydrogen. The solids were filtered out and the liquid was concentrated under vacuum. This resulted in the title compound (700 mg, 92.3%) as a yellow solid.

Step 6: Preparation of methyl 6-([[(2S,4R)-1-[(tert-butoxy)carbonyl]-4-fluoropyrrolidin-2-yl]formamido]methyl)-4-[6-(trifluoromethyl)pyridin-3-yl] pyridine-3-carboxylate

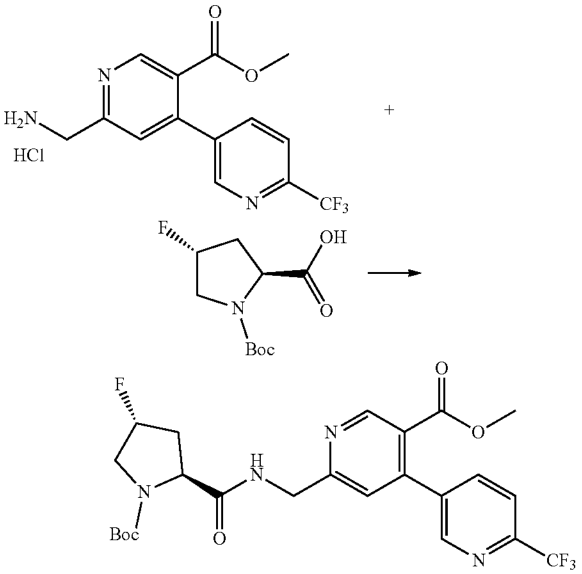

A mixture of methyl 6-(aminomethyl)-4-[6-(trifluoromethyl)pyridin-3-yl]pyridine-3-carboxylate hydrochloride (700 mg, 2.25 mmol, 1.00 equiv) in tetrahydrofuran (50 mL), (2S,4R)-1-[(tert-butoxy)carbonyl]-4-fluoropyrrolidine-2-carboxylic acid (629 mg, 2.70 mmol, 1.20 equiv), HATU (1.28 g, 3.37 mmol, 1.50 equiv), and DIPEA (870 mg, 6.73 mmol, 3.00 equiv) was stirred for 16 h at room temperature. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/1) to afford the title compound (650 mg, 55%) as a yellow solid.

Step 7: Preparation of 6-([[(2S,4R)-1-[(tert-butoxy) carbonyl]-4-fluoropyrrolidin-2-yl]formamido] methyl)-4-[6-(trifluoromethyl)pyridin-3-yl]pyridine-3-carboxylic acid

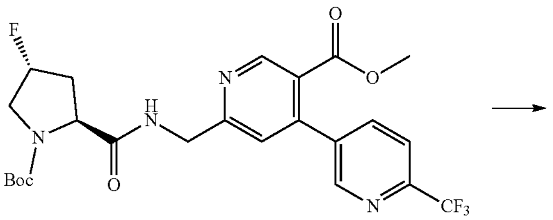

-continued

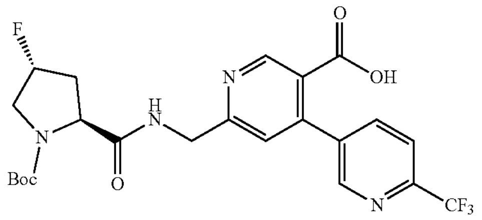

A mixture of methyl 6-([[(2S,4R)-1-[(tert-butoxy)carbonyl]-4-fluoropyrrolidin-2-yl]formamido]methyl)-4-[6-(trifluoromethyl)pyridin-3-yl]pyridine-3-carboxylate (600 mg, 1.14 mmol, 1.00 equiv) in tetrahydrofuran (20 mL), LiOH (96 mg, 4.01 mmol, 3.50 equiv), and water (20 mL) was stirred for 16 h at room temperature. The pH value of the solution was adjusted to 5 with citric acid. The resulting solution was extracted with ethyl acetate. The combined extracts were washed with brine, dried over anhydrous sodium sulfate, and concentrated under vacuum. This resulted in the title compound (480 mg, 82%) as a white solid.

Step 8: Preparation of tert-butyl (2S,4R)-2-[([5-carbamoyl-4-[6-(trifluoromethyl)pyridin-3-yl]pyridin-2-yl]methyl)carbamoyl]-4-fluoropyrrolidine-1-carboxylate

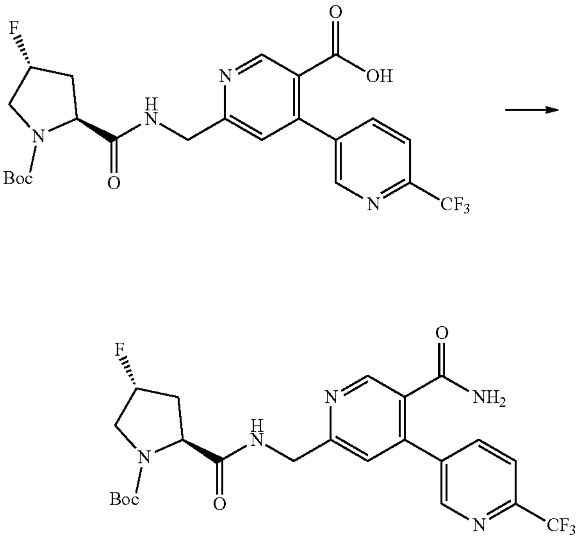

A mixture of 6-([[(2S,4R)-1-[(tert-butoxy)carbonyl]-4-fluoropyrrolidin-2-yl]formamido]methyl)-4-[6-(trifluoromethyl)pyridin-3-yl]pyridine-3-carboxylic acid (480 mg, 0.94 mmol, 1.00 equiv) in tetrahydrofuran (50 mL), $NH_4Cl$ (496 mg, 9.27 mmol, 9.90 equiv), HATU (714 mg, 1.88 mmol, 2.00 equiv), and DIPEA (606 mg, 4.69 mmol, 5.00 equiv) was stirred for 16 h at room temperature. The reaction mixture was diluted with water, extracted with ethyl acetate, washed with brine, dried over anhydrous sodium sulfate, and concentrated under vacuum. This resulted in the title compound (450 mg, 94%) as a white solid.

Step 9: Preparation of tert-butyl (2S,4R)-2-[([5-cyano-4-[6-(trifluoromethyl)pyridin-3-yl]pyridin-2-yl]methyl)carbamoyl]-4-fluoropyrrolidine-1-carboxylate

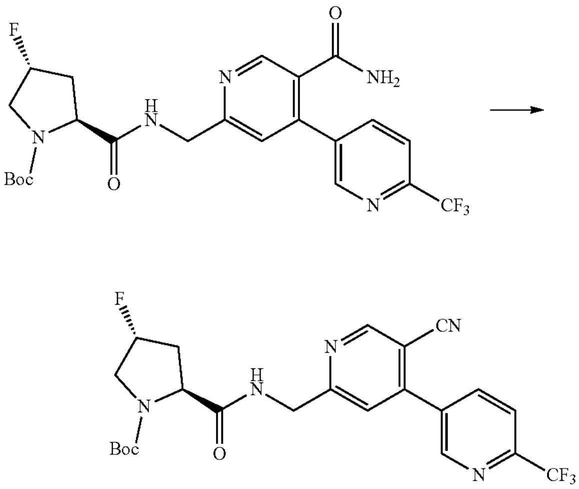

A mixture of tert-butyl (2S,4R)-2-[([5-carbamoyl-4-[6-(trifluoromethyl)pyridin-3-yl]pyridin-2-yl]methyl)carbamoyl]-4-fluoropyrrolidine-1-carboxylate (450 mg, 0.88 mmol, 1.00 equiv) in dichloromethane (5 mL), TFAA (370 mg, 1.76 mmol, 2.00 equiv), and TEA (133 mg, 1.31 mmol, 1.50 equiv) was stirred for 30 min at room temperature. The reaction mixture was diluted with water, extracted with ethyl acetate, washed with brine, dried over anhydrous sodium sulfate, and concentrated under vacuum. The residue was purified by silica gel chromatography eluting with petroleum ether/ethyl acetate (2/1). This resulted in the title compound (410 mg, 94%) as a yellow solid.

Step 10: Preparation of (2S,4R)—N-([5-cyano-4-[6-(trifluoromethyl)pyridin-3-yl]pyridin-2-yl]methyl)-4-fluoropyrrolidine-2-carboxamide hydrochloride

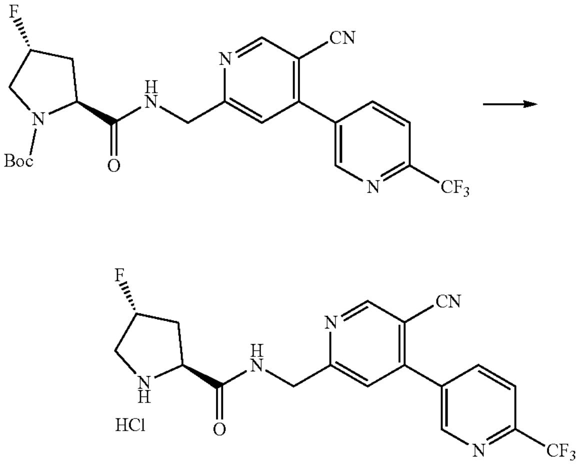

A mixture of tert-butyl (2S,4R)-2-[([5-cyano-4-[6-(trifluoromethyl)pyridin-3-yl]pyridin-2-yl]methyl)carbamoyl]-4-fluoropyrrolidine-1-carboxylate (410 mg, 0.83 mmol, 1.00 equiv) and HCl (saturated solution in 50 mL of 1,4-dioxane) was stirred for 3 h at room temperature. The resulting mixture was concentrated under vacuum. This resulted in the title compound (300 mg, 84%) as a yellow solid.

Step 11: Preparation of (2S,4R)—N-[[5-cyano-4-[6-(trifluoromethyl)-3-pyridyl]-2-pyridyl]methyl]-4-fluoro-1-(4-fluorophenyl)sulfonyl-pyrrolidine-2-carboxamide

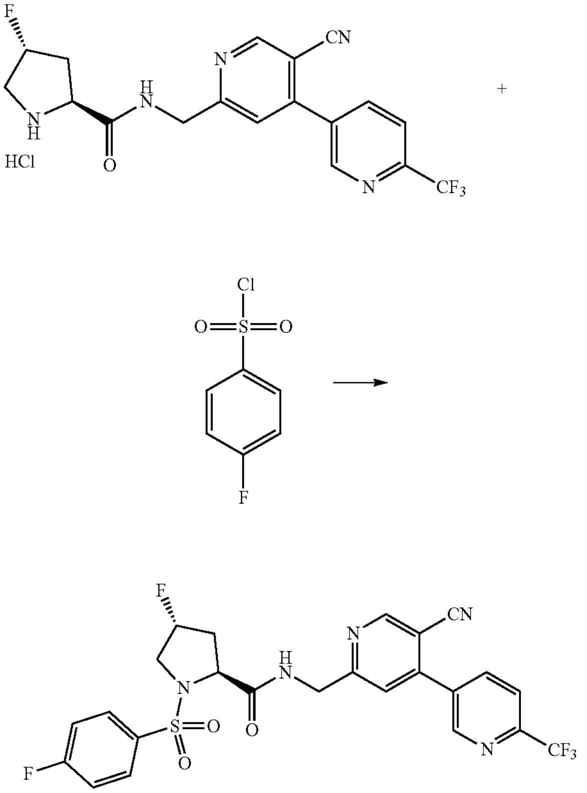

A mixture of (2S,4R)—N-([5-cyano-4-[6-(trifluoromethyl)pyridin-3-yl]pyridin-2-yl]methyl)-4-fluoropyrrolidine-2-carboxamide hydrochloride (300 mg, 0.70 mmol, 1.00 equiv) in dichloromethane (20 mL), TEA (282 mg, 2.79 mmol, 4.00 equiv), and 4-fluorobenzene-1-sulfonyl chloride (204 mg, 1.05 mmol, 1.50 equiv) was stirred for 16 h at room temperature. The reaction mixture was diluted with water, extracted with ethyl acetate, washed with brine, dried over anhydrous sodium sulfate, and concentrated under vacuum. The crude product was purified by silica gel chromatography eluting with ethyl acetate/petroleum ether (1/1). This resulted in the title compound (41.1 mg, 11%) as a white solid.

$^1$H NMR (300 MHz, DMSO-$d_6$) δ 9.17-9.04 (m, 3H), 8.43-8.40 (m, 1H), 8.15 (d, J=8.1 Hz, 1H), 7.97-7.83 (m, 2H), 7.83 (s, 1H), 7.44 (t, J=9.0 Hz, 2H), 5.28-5.10 (d, J=52.2 Hz, 1H), 4.60-4.58 (d, J=6.6 Hz, 2H), 4.23-4.17 (m, 1H), 3.71-3.63 (m, 2H), 2.73-2.08 (m, 2H).

Example 72

Preparation of (2R,3S)-3-fluoro-1-(4-fluorophenyl) sulfonyl-N-[[4-[5-(trifluoromethyl)-2-pyridyl]-2-pyridyl]methyl]pyrrolidine-2-carboxamide

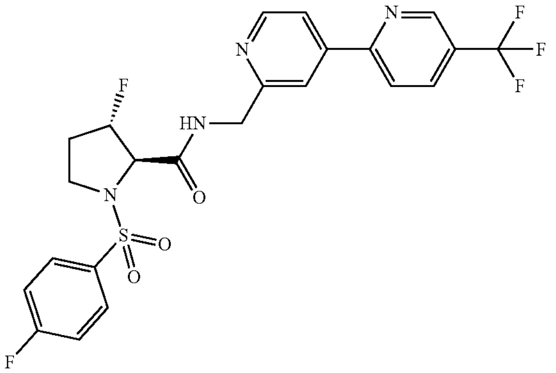 [SMILES: O=C(NCc1cc(-c2ccc(C(F)(F)F)cn2)ccn1)[C@@H]1[C@@H](F)CCN1S(=O)(=O)c1ccc(F)cc1]

Preparation of the title compound follows the same general procedure as Example 55.

1H NMR (400 MHz, DMSO) δ 9.15-9.10 (dt, J=2.0, 1.0 Hz, 1H), 9.11-9.04 (t, J=6.0 Hz, 1H), 8.73-8.69 (dd, J=5.0, 0.9 Hz, 1H), 8.42-8.36 (m, 1H), 8.36-8.29 (m, 1H), 8.07-8.01 (m, 2H), 8.01-7.95 (m, 2H), 7.52-7.43 (m, 2H), 5.27-5.08 (m, 1H), 4.61-4.49 (m, 2H), 4.49-4.38 (d, J=24.1 Hz, 1H), 3.73-3.60 (t, J=9.1 Hz, 1H), 3.25-3.14 (td, J=9.2, 7.0 Hz, 1H), 2.30-2.06 (m, 2H)., LCMS (ESI) m/z:527.12 [M+H]+

Example 73

Preparation of (2S,4R)-4-fluoro-1-(4-fluorophenyl) sulfonyl-N-[[2-[2-(trifluoromethyl)pyrimidin-5-yl]-4-pyridyl]methyl]pyrrolidine-2-carboxamide

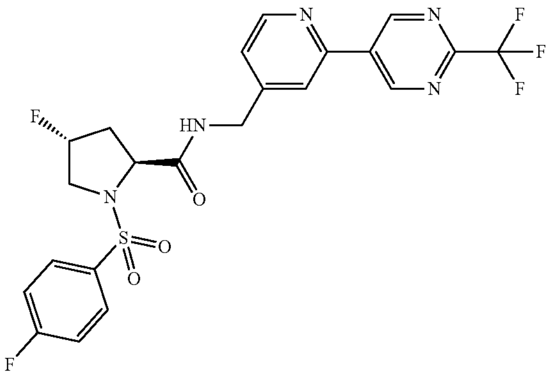 [SMILES: O=C(NCc1ccnc(-c2cnc(C(F)(F)F)nc2)c1)[C@@H]1C[C@@H](F)CN1S(=O)(=O)c1ccc(F)cc1]

Preparation of the title compound follows the same general procedure as Example 48.

1H NMR (400 MHz, DMSO) δ 9.69-9.63 (s, 2H), 9.05-8.97 (t, J=6.0 Hz, 1H), 8.78-8.72 (dd, J=5.1, 0.7 Hz, 1H), 8.20-8.16 (dd, J=1.5, 0.7 Hz, 1H), 8.05-7.97 (m, 2H), 7.54-7.43 (m, 3H), 5.30-5.11 (d, J=52.3 Hz, 1H), 4.59-4.40 (m, 2H), 4.25-4.15 (dd, J=10.0, 7.1 Hz, 1H), 3.79-3.59 (m, 2H), 2.47-2.37 (m, 1H), 2.21-2.00 (m, 1H)., LCMS (ESI) m/z:528.11 [M+H]+

Example 74

Preparation of (2S,4R)-4-fluoro-1-(4-fluorophenyl) sulfonyl-N-[[3-fluoro-5-[5-(trifluoromethyl)-2-piperidyl]phenyl]methyl]pyrrolidine-2-carboxamide

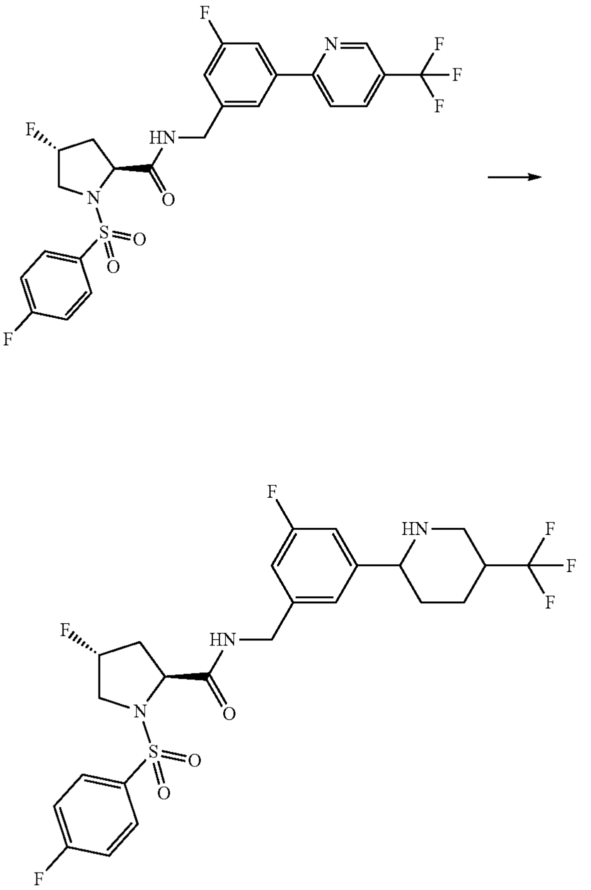

The reaction was carried out on the H-Cube with Rh/C 1.0 mL/min, 80 bar, 100° C. in acetic acid. LCMS showed 50% of desired product. The reaction was concentrated and purified by flash chromatography (EtOAc then MeOH/DCM eluted at 8% MeOH). The product was submitted for rHPLC to give 12.3 mg, 9.358% yield.

1H NMR (400 MHz, DMSO) δ 8.84-8.76 (t, J=6.0 Hz, 1H), 8.01-7.92 (m, 2H), 7.51-7.40 (m, 2H), 7.20-7.14 (d, J=1.8 Hz, 1H), 7.12-6.96 (m, 2H), 5.29-5.08 (d, J=52.6 Hz, 1H), 4.44-4.27 (m, 2H), 4.22-4.11 (m, 1H), 3.79-3.55 (m, 3H), 3.05-2.84 (m, 2H), 2.46-2.28 (m, 2H), 2.17-1.94 (dt, J=43.0, 11.0 Hz, 1H), 1.86-1.63 (m, 4H)., LCMS (ESI) m/z:550.16 [M+H]+

Example 75

Preparation of (2S,4R)—N-[[3-[5-(difluoromethyl)-2-pyridyl]-5-fluoro-phenyl]methyl]-4-fluoro-1-(4-fluorophenyl)sulfonyl-pyrrolidine-2-carboxamide

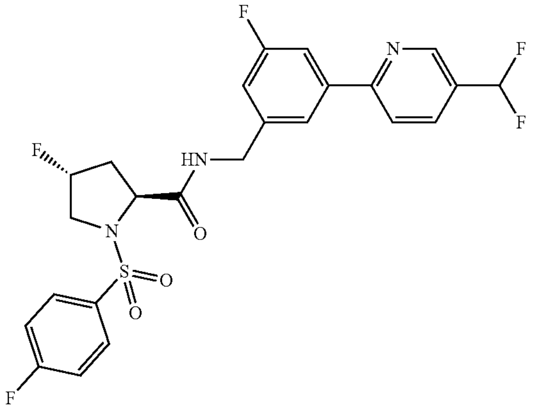 [SMILES: O=C(NCc1cc(F)cc(-c2ccc(C(F)F)cn2)c1)[C@@H]1C[C@@H](F)CN1S(=O)(=O)c1ccc(F)cc1]

Preparation of the title compound follows the same general procedure as Example 48.

1H NMR (400 MHz, DMSO) δ 8.95-8.84 (m, 2H), 8.22-8.15 (m, 1H), 8.13-8.06 (m, 1H), 8.03-7.94 (m, 3H), 7.88-7.79 (ddd, J=10.1, 2.5, 1.5 Hz, 1H), 7.52-7.41 (m, 2H), 7.35-7.04 (m, 2H), 5.31-5.10 (d, J=52.5 Hz, 1H), 4.55-4.38 (m, 2H), 4.25-4.15 (dd, J=9.8, 7.2 Hz, 1H), 3.78-3.57 (m, 2H), 2.47-2.28 (m, 1H), 2.20-1.98 (m, 1H)., LCMS (ESI) m/z:526.12 [M+H]+

Example 76

Preparation of (2S,4R)—N-([3-[6-(difluoromethoxy)pyridin-3-yl]-5-fluorophenyl]methyl)-4-fluoro-1-[(4-fluorobenzene)sulfonyl]pyrrolidine-2-carboxamide

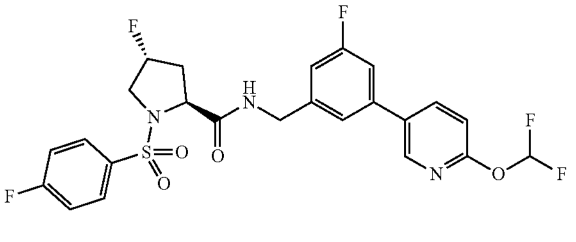 [SMILES: O=C(NCc1cc(F)cc(-c2ccc(OC(F)F)nc2)c1)[C@@H]1C[C@@H](F)CN1S(=O)(=O)c1ccc(F)cc1]

Step 1: Preparation of (2S,4R)—N-([3-[6-(difluoromethoxy)pyridin-3-yl]-5-fluorophenyl]methyl)-4-fluoro-1-[(4-fluorobenzene)sulfonyl]pyrrolidine-2-carboxamide

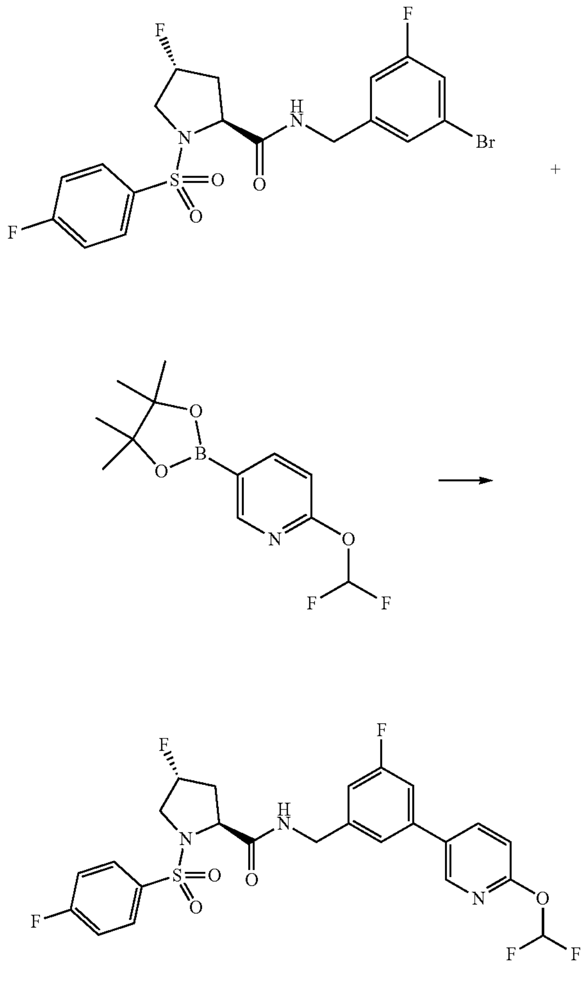

A mixture of (2S,4R)—N-[(3-bromo-5-fluorophenyl)methyl]-4-fluoro-1-[(4-fluorobenzene)sulfonyl]pyrrolidine-2-carboxamide (150 mg, 0.31 mmol, 1.00 equiv) in dioxane (20 mL), 2-(difluoromethoxy)-5-(tetramethyl-1,3,2-dioxaborolan-2-yl)pyridine (94 mg, 0.35 mmol, 1.10 equiv), potassium carbonate (174 mg, 1.26 mmol, 4.00 equiv) in water(4 mL), and Pd(dppf)$Cl_2$ (46 mg, 0.06 mmol, 0.20 equiv) was stirred for 6 h at 60° C. under nitrogen. The solids were filtered out. The liquid was diluted with ethyl acetate, washed with brine, dried over anhydrous sodium sulfate and concentrated under vacuum. The residue was purified by Prep-HPLC to afford the title compound (47.4 mg, 28%) as a white solid.

$^1$H NMR (400 MHz, $CD_3OD$) δ 8.55 (s, 1H), 8.21-8.18 (m, 1H), 8.00-7.97 (m, 2H), 7.56 (s, 1H), 7.41 (s, 1H), 7.36-7.32 (m, 3H), 7.20-7.18 (m, 1H), 7.05-7.03 (m, 1H), 5.21-5.10 (d, J=52 Hz, 1H), 4.55 (s, 2H), 4.28-4.23 (m, 1H), 3.85-3.69 (m, 2H), 2.51-2.49 (m, 1H), 2.21-2.06 (m, 1H).

Example 77

Preparation of (2S,4R)—N-([4-[4-(difluoromethoxy)phenyl]-5-fluoropyridin-2-yl]methyl)-4-fluoro-1-[(4-fluorobenzene)sulfonyl]pyrrolidine-2-carboxamide

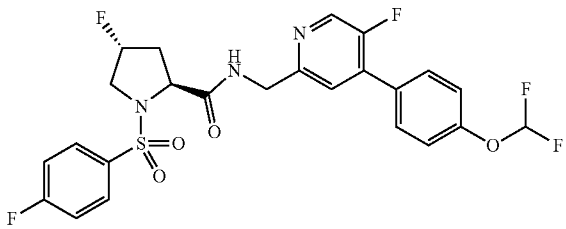 [SMILES: O=C(NCc1cc(-c2ccc(OC(F)F)cc2)c(F)cn1)[C@@H]1C[C@@H](F)CN1S(=O)(=O)c1ccc(F)cc1]

Step 1: Preparation of 2-[4-(difluoromethoxy)phenyl]-4,4,5,5-tetramethyl-1,3,2-dioxaborolane

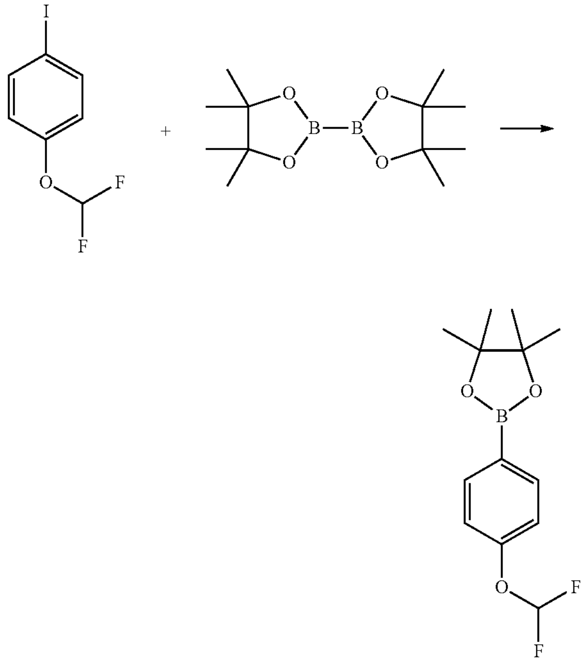

A mixture of 1-(difluoromethoxy)-4-iodobenzene (1.35 g, 5.00 mmol, 1.00 equiv), 4,4,5,5-tetramethyl-2-(tetramethyl-1,3,2-dioxaborolan-2-yl)-1,3,2-dioxaborolane (1.413 g, 5.56 mmol, 1.10 equiv), AcOK (1.47 g, 14.98 mmol, 3.00 equiv), and Pd(dppf)$Cl_2$ (186 mg, 0.25 mmol, 0.05 equiv) in dioxane (30 mL)/water(3 mL) was stirred for 2 h at 95° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:50) to afford the title compound (660 mg, 49%) as colorless oil.

Step 2: Preparation of 2-chloro-4-[4-(difluoromethoxy)phenyl]-5-fluoropyridine

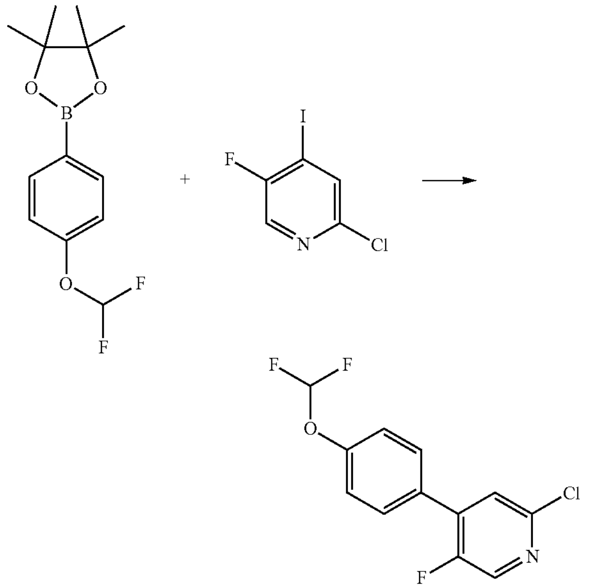

A mixture of 2-[4-(difluoromethoxy)phenyl]-4,4,5,5-tetramethyl-1,3,2-dioxaborolane (600 mg, 2.22 mmol, 1.00 equiv), 2-chloro-5-fluoro-4-iodopyridine (682.7 mg, 2.65 mmol, 1.20 equiv), potassium carbonate (910 mg, 6.58 mmol, 3.00 equiv), and Pd(dppf)$Cl_2$ (82.7 mg, 0.11 mmol, 0.05 equiv) in dioxane (20 mL)/water(2 mL) was stirred for 12 h at 75° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:80). This resulted in the title compound (410 mg, 67%) as a white solid.

Step 3: Preparation of 4-[4-(difluoromethoxy)phenyl]-5-fluoropyridine-2-carbonitrile

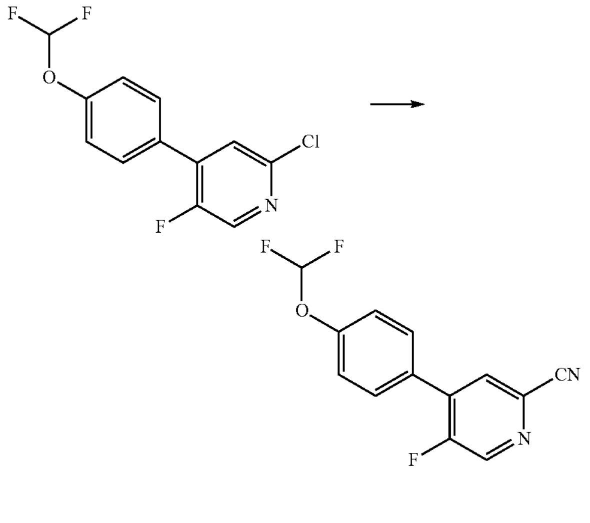

A mixture of 2-chloro-4-[4-(difluoromethoxy)phenyl]-5-fluoropyridine (370 mg, 1.35 mmol, 1.00 equiv), $Zn(CN)_2$ (208.7 mg, 1.78 mmol, 1.50 equiv), dppf (65.8 mg, 0.12 mmol, 0.10 equiv), and $Pd_2(dba)_3CHCl_3$ (61.5 mg, 0.06 mmol, 0.05 equiv) in N,N-dimethylformamide (10 ml) was irradiated with microwave radiation for 2 h at 120° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:12) to afford the title compound (330 mg, 92%) as an off-white solid.

Step 4: Preparation of [4-[4-(difluoromethoxy)phenyl]-5-fluoropyridin-2-yl]methanamine hydrochloride

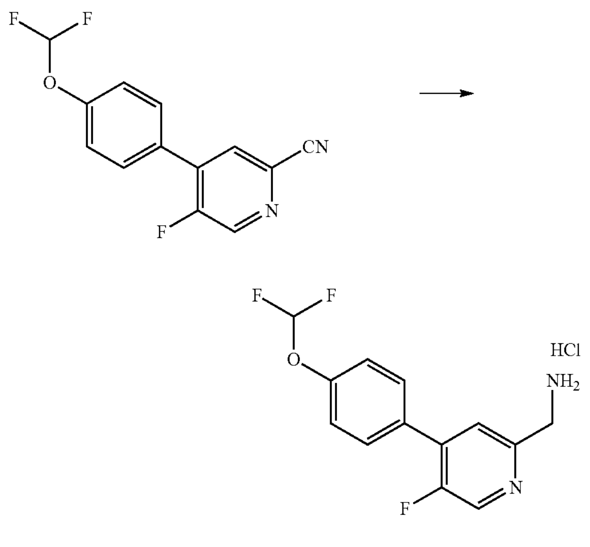

A mixture of 4-[4-(difluoromethoxy)phenyl]-5-fluoropyridine-2-carbonitrile (300 mg, 1.14 mmol, 1.00 equiv), concentrated hydrogen chloride (0.05 mL), palladium on carbon (600 mg) in methanol (30 mL) was stirred for 5 min at room temperature under hydrogen. The solids were filtered out and the filtrate was concentrated under vacuum. This resulted in the title compound (310 mg) as a light yellow solid.

Step 5: Preparation of tert-butyl (2S,4R)-2-[([4-[4-(difluoromethoxy)phenyl]-5-fluoropyridin-2-yl]methyl)carbamoyl]-4-fluoropyrrolidine-1-carboxylate

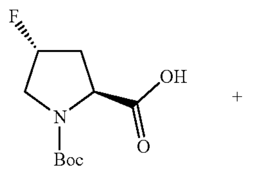

-continued

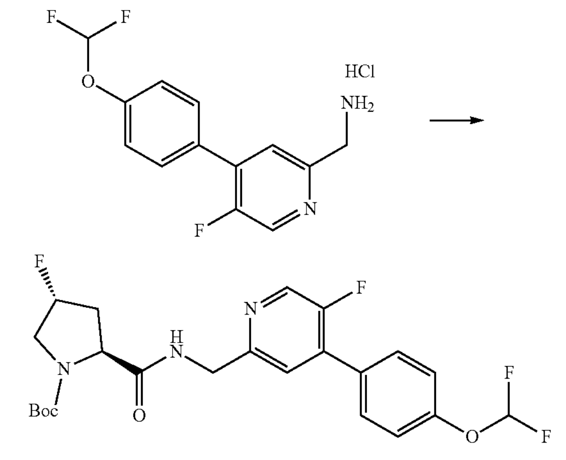

A mixture of (2S,4R)-1-[(tert-butoxy)carbonyl]-4-fluoropyrrolidine-2-carboxylic acid (359 mg, 1.54 mmol, 1.33 equiv), HATU (643.7 mg, 1.69 mmol, 1.46 equiv), DIEA (595.9 mg, 4.61 mmol, 4.00 equiv), and [4-[4-(difluoromethoxy)phenyl]-5-fluoropyridin-2-yl]methanamine hydrochloride (310 mg, 1.16 mmol, 1.00 equiv) in N,N-dimethylformamide (15 mL) was stirred for 2 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:3) to afford the title compound (310 mg, 55%) as orange oil.

Step 6: Preparation of (2S,4R)—N-([4-[4-(difluoromethoxy)phenyl]-5-fluoropyridin-2-yl]methyl)-4-fluoropyrrolidine-2-carboxamide hydrochloride

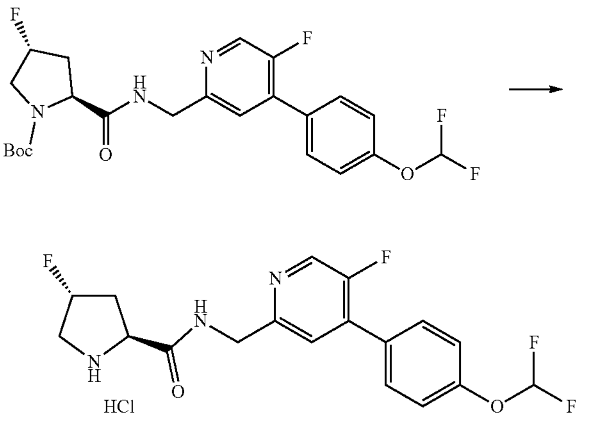

A mixture of tert-butyl (2S,4R)-2-[([4-[4-(difluoromethoxy)phenyl]-5-fluoropyridin-2-yl]methyl)carbamoyl]-4-fluoropyrrolidine-1-carboxylate (310 mg, 0.64 mmol, 1.00 equiv), and saturated hydrogen chloride in dioxane (15 mL) was stirred for 12 h at room temperature. The reaction mixture was concentrated under vacuum to afford the title compound (255 mg, 95%) as a pink solid.

Step 7: Preparation of (2S,4R)—N-([4-[4-(difluoromethoxy)phenyl]-5-fluoropyridin-2-yl]methyl)-4-fluoro-1-[(4-fluorobenzene)sulfonyl]pyrrolidine-2-carboxamide

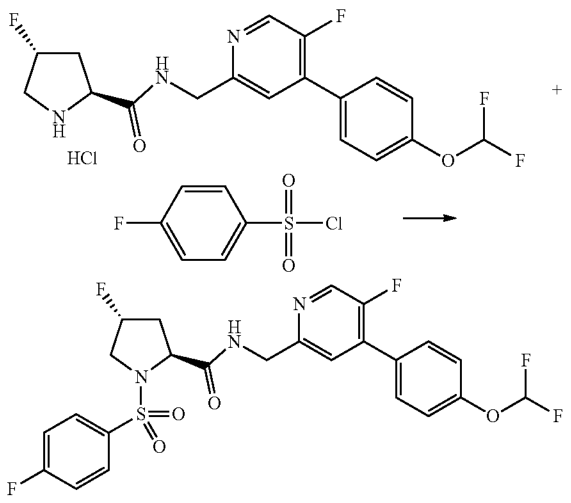

A mixture of 4-fluorobenzene-1-sulfonyl chloride (255 mg, 1.31 mmol, 1.00 equiv), (2S,4R)—N-([4-[4-(difluoromethoxy)phenyl]-5-fluoropyridin-2-yl]methyl)-4-fluoropyrrolidine-2-carboxamide hydrochloride (130.2 mg, 0.31 mmol, 1.10 equiv), TEA (184.8 mg, 1.83 mmol, 3.00 equiv), and 4-dimethylaminopyridine (7.44 mg, 0.06 mmol, 0.10 equiv) in dichloromethane (5 mL) was stirred for 2 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:4). This resulted in the title compound (108.2 mg, 15%) as an off-white solid.

$^1$H NMR (300 MHz, $CD_3OD$) δ 8.46 (s, 1H), 8.00-7.96 (m, 2H), 7.82-7.79 (m, 3H), 7.36-7.22 (m, 3H), 7.16-6.67 (t, J=73.8 Hz, 1H), 5.22-5.05 (d, J=51.6 Hz, 1H), 4.60 (s, 1H), 4.29-4.23 (m, 1H), 3.84-3.66 (m, 2H), 2.51-2.43 (m, 1H), 2.29-2.11 (m, 1H).

Example 78

Preparation of (2S,4R)—N-([5-cyano-2-[4-(trifluoromethyl)phenyl]pyridin-4-yl]methyl)-4-fluoro-1-[(4-fluorobenzene)sulfonyl]pyrrolidine-2-carboxamide

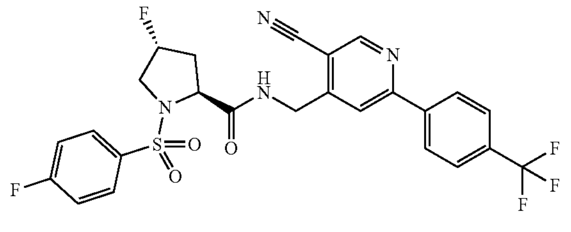 [SMILES: N#Cc1cnc(-c2ccc(C(F)(F)F)cc2)cc1CNC(=O)[C@@H]1C[C@@H](F)CN1S(=O)(=O)c1ccc(F)cc1]

Step 1: Preparation of methyl 4-chloro-6-[4-(trifluoromethyl)phenyl]pyridine-3-carboxylate

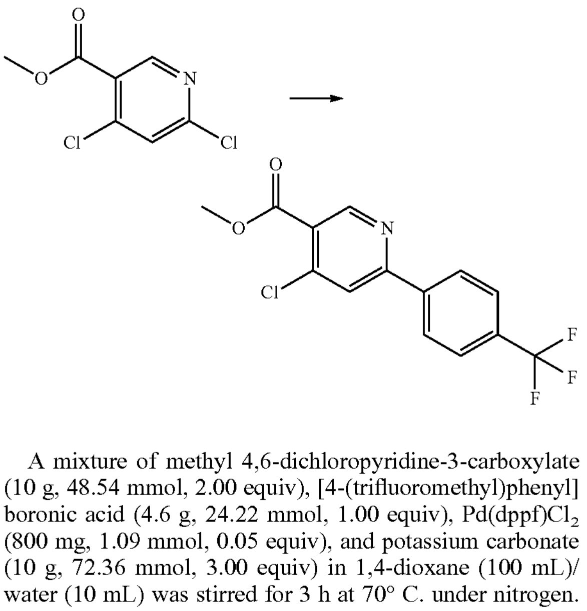

A mixture of methyl 4,6-dichloropyridine-3-carboxylate (10 g, 48.54 mmol, 2.00 equiv), [4-(trifluoromethyl)phenyl]boronic acid (4.6 g, 24.22 mmol, 1.00 equiv), Pd(dppf)$Cl_2$ (800 mg, 1.09 mmol, 0.05 equiv), and potassium carbonate (10 g, 72.36 mmol, 3.00 equiv) in 1,4-dioxane (100 mL)/water (10 mL) was stirred for 3 h at 70° C. under nitrogen. The reaction was then quenched by iced water, extracted with ethyl acetate, washed with brine, and concentrated under vacuum. The residue was purified by a silica gel column eluting with ethyl acetate/petroleum ether (1:10) to afford the title compound (5.6 g, 73%) of as a white solid.

Step 2: Preparation of methyl 4-cyano-6-[4-(trifluoromethyl)phenyl]pyridine-3-carboxylate

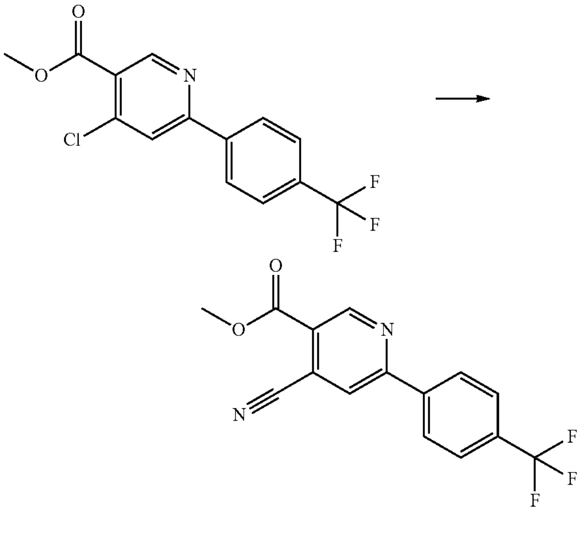

Into a 30-mL sealed tube was placed methyl 4-chloro-6-[4-(trifluoromethyl)phenyl]pyridine-3-carboxylate (2 g, 6.34 mmol, 1.00 equiv), $Zn(CN)_2$ (740 mg, 6.30 mmol, 1.00 equiv), $Pd_2(dba)_3.CHCl_3$ (320 mg, 0.31 mmol, 0.05 equiv), and dppf (350 mg, 0.63 mmol, 0.10 equiv) in N,N-dimethylformamide (10 mL). The reaction mixture was irradiated with microwave for 90 min at 110° C. The reaction was then quenched by water, extracted with ethyl acetate, washed with brine, and concentrated under vacuum. The residue was purified by a silica gel column eluting with ethyl acetate/petroleum ether (1:10) to afford the title compound (0.8 g, 41%) as a yellow solid.

Step 3: Preparation of methyl 4-(aminomethyl)-6-[4-(trifluoromethyl)phenyl]pyridine-3-carboxylate hydrochloride

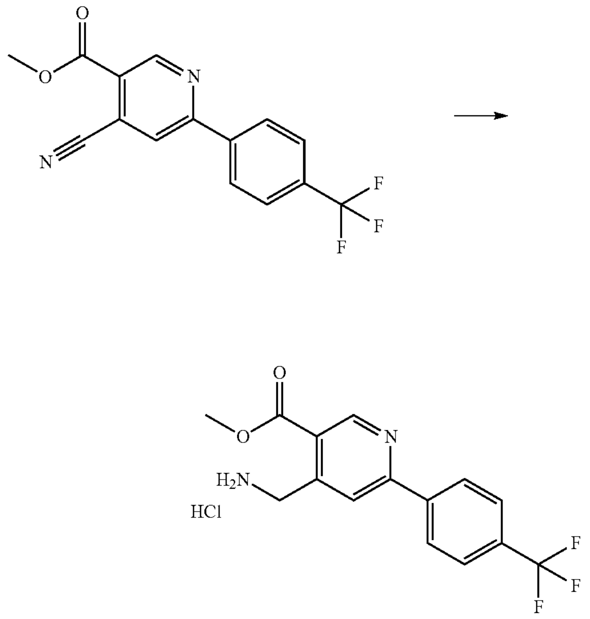

Into a 100-mL round-bottom flask was placed with methyl 4-cyano-6-[4-(trifluoromethyl)phenyl]pyridine-3-carboxylate (150 mg, 0.49 mmol, 1.00 equiv), palladium on carbon (10 mg), methanol (10 mL), and concentrated hydrogen chloride (0.1 mL). The resulting solution was maintained with an atmosphere of $H_2$ and stirred for 1 h at room temperature. The solids were filtered out and the solution was concentrated under vacuum to afford the title compound (147 mg, 87%) as a yellow solid.

Step 4: Preparation of methyl 4-([[(2S,4R)-1-[(tert-butoxy)carbonyl]-4-fluoropyrrolidin-2-yl]formamido]methyl)-6-[4-(trifluoromethyl)phenyl]pyridine-3-carboxylate

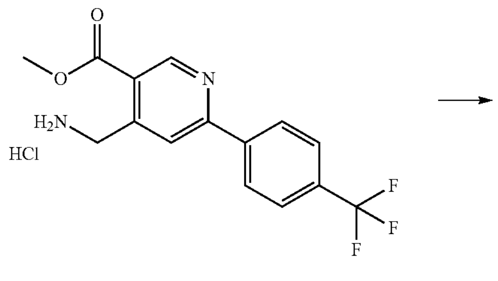

-continued

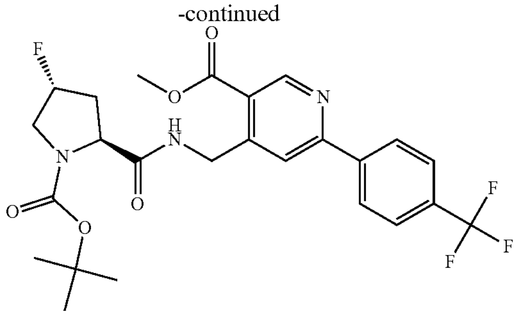

A solution of (2S,4R)-1-[(tert-butoxy)carbonyl]-4-fluoropyrrolidine-2-carboxylic acid (67 mg, 0.29 mmol, 1.00 equiv), methyl 4-(aminomethyl)-6-[4-(trifluoromethyl)phenyl]pyridine-3-carboxylate hydrochloride (100 mg, 0.29 mmol, 1.00 equiv), HATU (131 mg, 0.34 mmol, 1.20 equiv), and DIEA (111 mg, 0.86 mmol, 3.00 equiv) in tetrahydrofuran (5 mL) was stirred for 14 h at room temperature. The reaction was then quenched by water, extracted with ethyl acetate, and concentrated under vacuum. The residue was purified by a silica gel column eluting with ethyl acetate/petroleum ether (2:1) to afford the title compound (100 mg, 66%) as a white solid.

Step 5: Preparation of 4-([[(2S,4R)-1-[(tert-butoxy)carbonyl]-4-fluoropyrrolidin-2-yl]formamido]methyl)-6-[4-(trifluoromethyl)phenyl]pyridine-3-carboxylic acid

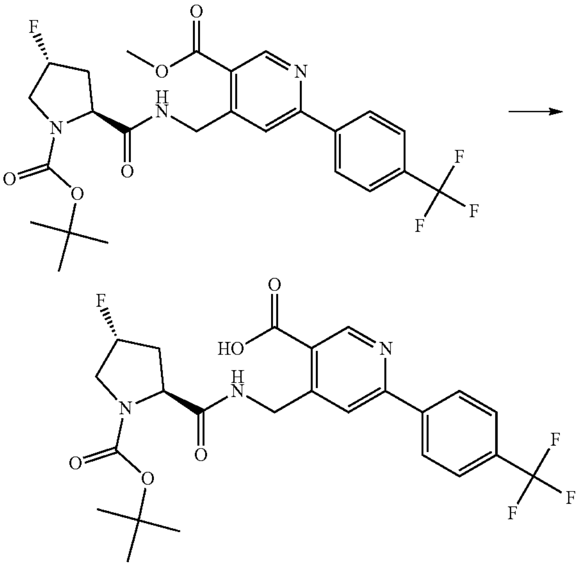

LiOH (46 mg, 1.92 mmol, 2.00 equiv) in water (2 mL) was added dropwise into a stirred solution of methyl 4-([[(2S,4R)-1-[(tert-butoxy)carbonyl]-4-fluoropyrrolidin-2-yl]formamido]methyl)-6-[4-(trifluoromethyl)phenyl]pyridine-3-carboxylate(500 mg, 0.95 mmol, 1.00 equiv) in tetrahydrofuran (10 mL) at 0° C. After being stirred for 14 h at room temperature the reaction was then quenched by water and extracted with ethyl acetate. The aqueous layers were combined and the pH value of the solution was adjusted to 7 with aqueous citric acid. The resulting solution was extracted with 2×100 mL of ethyl acetate and the organic layers were combined and concentrated under vacuum. This resulted in to the title compound (396 mg, 81%) as a yellow solid.

Step 6: Preparation of tert-butyl (2S,4R)-2-[([5-carbamoyl-2-[4-(trifluoromethyl)phenyl]pyridin-4-yl]methyl)carbamoyl]-4-fluoropyrrolidine-1-carboxylate

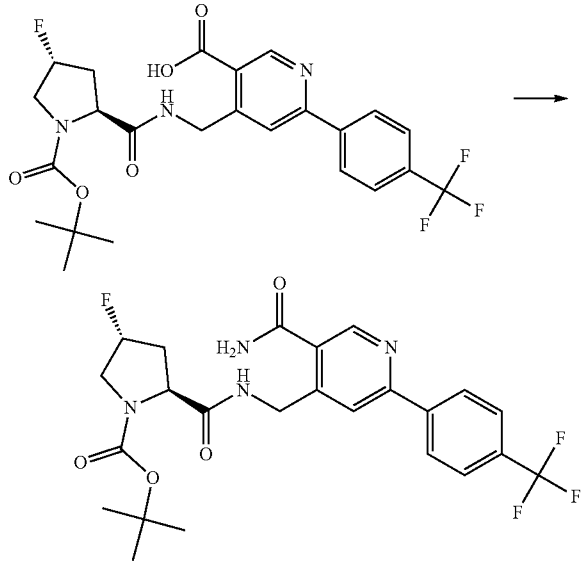

A mixture of 4-([[(2S,4R)-1-[(tert-butoxy)carbonyl]-4-fluoropyrrolidin-2-yl]formamido]methyl)-6-[4-(trifluoromethyl)phenyl]pyridine-3-carboxylic acid (336 mg, 0.66 mmol, 1.00 equiv), $NH_4Cl$ (42 mg, 0.79 mmol, 1.20 equiv), HATU (299 mg, 0.79 mmol, 1.20 equiv), and DIEA (254 mg, 1.97 mmol, 3.00 equiv) in tetrahydrofuran (10 mL) was stirred for 2.5 h at room temperature. The reaction was then quenched by water, extracted with ethyl acetate, and concentrated under vacuum. The residue was purified by a silica gel column eluting with ethyl acetate/petroleum ether (2:1) to afford the title compound (130 mg, 39%) as a yellow solid.

Step 7: Preparation of tert-butyl (2S,4R)-2-[([5-cyano-2-[4-(trifluoromethyl)phenyl]pyridin-4-yl]methyl)carbamoyl]-4-fluoropyrrolidine-1-carboxylate

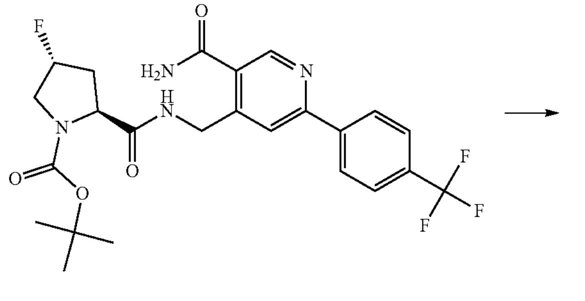

-continued

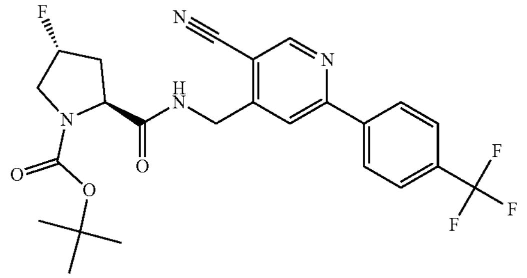

A solution of tert-butyl (2S,4R)-2-[([5-carbamoyl-2-[4-(trifluoromethyl)phenyl]pyridin-4-yl]methyl)carbamoyl]-4-fluoropyrrolidine-1-carboxylate (130 mg, 0.25 mmol, 1.00 equiv), TFAA (107 mg, 0.51 mmol, 2.00 equiv), and TEA (38 mg, 0.38 mmol, 1.50 equiv) in dichloromethane (2 mL) was stirred for 3 h at room temperature. The reaction was then quenched by water, extracted with ethyl acetate, and concentrated under vacuum. The residue was purified by a silica gel column eluting with ethyl acetate/petroleum ether. This resulted in the title compound (74 mg, 59%) as a yellow solid.

Step 8: Preparation of (2S,4R)—N-([5-cyano-2-[4-(trifluoromethyl)phenyl]pyridin-4-yl]methyl)-4-fluoropyrrolidine-2-carboxamide hydrochloride

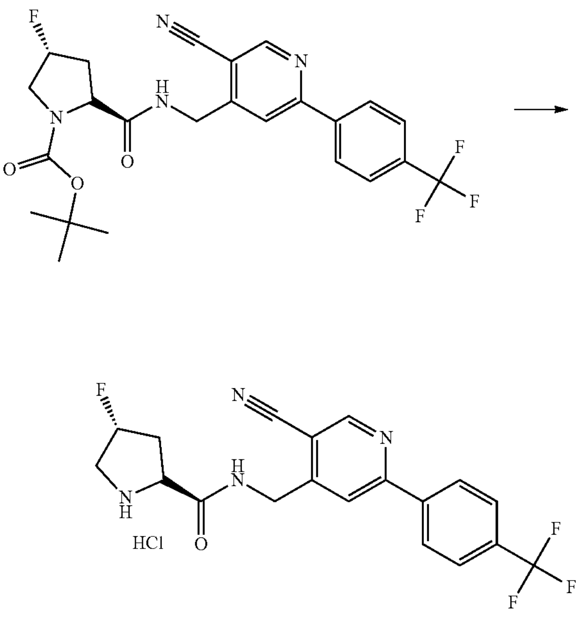

A solution of tert-butyl (2S,4R)-2-[([5-cyano-2-[4-(trifluoromethyl)phenyl]pyridin-4-yl]methyl)carbamoyl]-4-fluoropyrrolidine-1-carboxylate (74 mg, 0.15 mmol, 1.00 equiv), and TFA (2 mL, 26.93 mmol, 179.20 equiv) in dichloromethane (4 mL) was stirred for 1 h at room temperature. The reaction mixture was concentrated under vacuum. The residue was mixed with 0.5 mL of hydrogen chloride (6M) and concentrated under vacuum. This resulted in the title compound (56 mg, 87%) as a white solid.

Step 9: Preparation of (2S,4R)—N-([5-cyano-2-[4-(trifluoromethyl)phenyl]pyridin-4-yl]methyl)-4-fluoro-1-[(4-fluorobenzene)sulfonyl]pyrrolidine-2-carboxamide

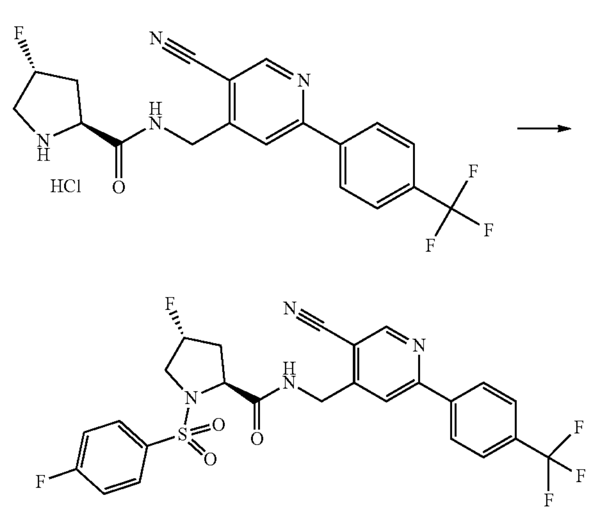

A mixture of 4-fluorobenzene-1-sulfonyl chloride (31 mg, 0.16 mmol, 1.20 equiv), (2S,4R)—N-([5-cyano-2-[4-(trifluoromethyl)phenyl]pyridin-4-yl]methyl)-4-fluoropyrrolidine-2-carboxamide hydrochloride (56 mg, 0.13 mmol, 1.00 equiv), and TEA (40 mg, 0.40 mmol, 3.00 equiv) in dichloromethane (2 mL) was stirred for 14 h at room temperature. The reaction was then quenched by water, extracted with DCM, and concentrated under vacuum. The residue was purified by a silica gel column eluting with ethyl acetate/petroleum ether (1:1) to afford the title compound (25.4 mg, 35%) as a light yellow solid.

$^1$H NMR (400 MHz, $CDCl_3$) δ 8.91 (s, 1H), 8.31-8.28 (d, J=8.4 Hz, 2H), 8.15 (s, 1H), 7.92-7.88 (m, 2H), 7.73-7.70 (d, J=8.4 Hz, 2H), 7.50-7.46 (m, 1H), 7.28-7.26 (d, J=6.6 Hz, 1H), 7.22 (s, 1H), 5.15-4.96 (m, 2H), 4.68-4.57 (d, J=11.2 Hz, 1H), 4.34-4.28 (t, J=8.7 Hz, 1H), 3.97-3.61 (m, 2H), 2.61-2.53 (m, 1H), 2.35-2.12 (m, 1H).

Example 79

Preparation of (2S,4R)—N-([5-cyano-2-[6-(trifluoromethyl)pyridin-3-yl]pyridin-4-yl]methyl)-4-fluoro-1-[(4-fluorobenzene)sulfonyl]pyrrolidine-2-carboxamide

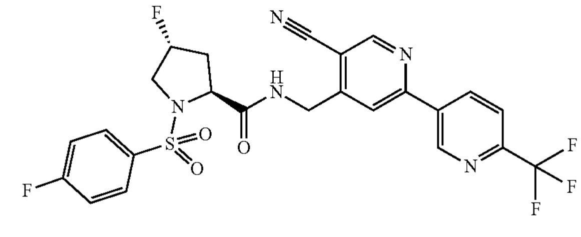 [SMILES: N#Cc1cnc(-c2ccc(C(F)(F)F)nc2)cc1CNC(=O)[C@@H]1C[C@@H](F)CN1S(=O)(=O)c1ccc(F)cc1]

Step 1: Preparation of methyl 4-chloro-6-[6-(trifluoromethyl)pyridin-3-yl]pyridine-3-carboxylate

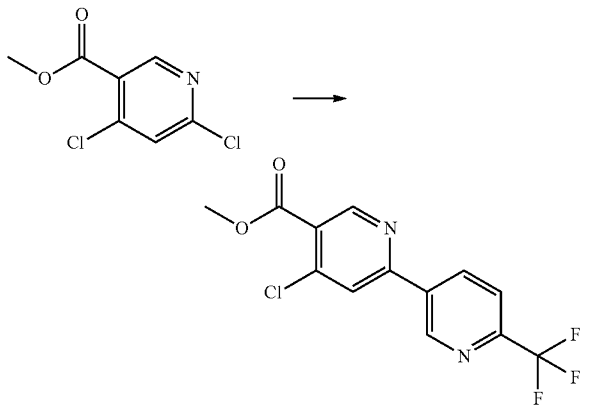

A mixture of methyl 4,6-dichloropyridine-3-carboxylate (5.5 g, 26.70 mmol, 2.00 equiv), [6-(trifluoromethyl)pyridin-3-yl]boronic acid (2.5 g, 13.09 mmol, 1.00 equiv), Pd(dppf)$Cl_2$ (480 mg, 0.66 mmol, 0.05 equiv), and potassium carbonate (5.5 g, 39.80 mmol, 3.00 equiv) in 1,4-dioxane (100 mL)/water (10 mL) was stirred for 3 h at 70° C. The reaction was then quenched by water, extracted with ethyl acetate, washed with brine, and concentrated under vacuum. The residue was purified by a silica gel column eluting with ethyl acetate/petroleum ether (1:3). This resulted in the title compound (2.0 g, 48%) as an off-white solid.

Step 2: Preparation of methyl 4-cyano-6-[6-(trifluoromethyl)pyridin-3-yl]pyridine-3-carboxylate

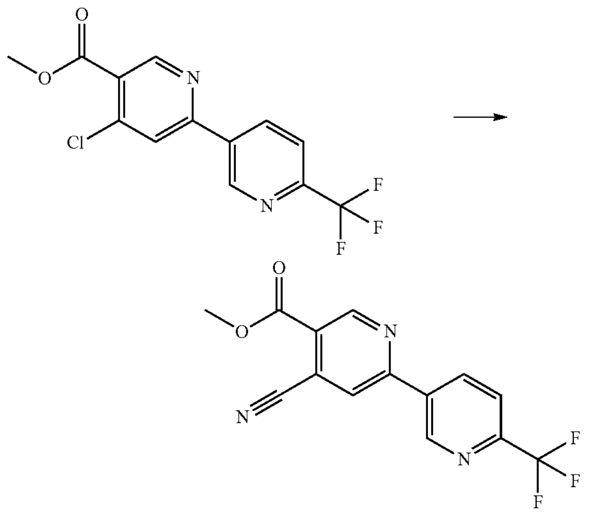

Into a 30-mL sealed tube purged and maintained with an inert atmosphere of nitrogen was placed methyl 4-chloro-6-[6-(trifluoromethyl)pyridin-3-yl]pyridine-3-carboxylate (400 mg, 1.26 mmol, 1.00 equiv), $Zn(CN)_2$ (148 mg, 1.26 mmol, 1.00 equiv), $Pd_2(dba)_3CHCl_3$ (131 mg, 0.13 mmol, 0.10 equiv), and dppf (140 mg, 0.25 mmol, 0.20 equiv) in N,N-dimethylformamide (8 mL). The reaction mixture was irradiated with microwave for 90 min at 105° C. The reaction was then quenched by water, extracted with 2×50 mL of ethyl acetate, and concentrated under vacuum. The residue was purified by a silica gel column eluting with ethyl acetate/petroleum ether (1:10). This resulted in the title compound (342 mg, 88%) as a yellow solid.

Step 3: Preparation of methyl 4-(aminomethyl)-6-[6-(trifluoromethyl)pyridin-3-yl]pyridine-3-carboxylate hydrochloride

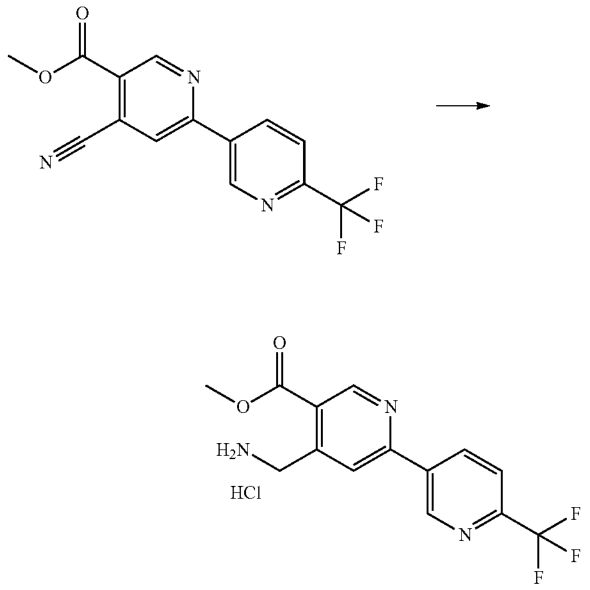

A suspension of methyl 4-cyano-6-[6-(trifluoromethyl)pyridin-3-yl]pyridine-3-carboxylate (200 mg, 0.65 mmol, 1.00 equiv), palladium on carbon (20 mg, 0.19 mmol, 0.30 equiv) in methanol (10 mL)/concentrated aqueous HCl (0.3 mL). was maintained with an atmosphere of $H_2$ and stirred for 1 hour at room temperature. The solids were filtered out and the filtrate was concentrated under vacuum. The resulting mixture was washed with 20 mL of hexane to afford the title compound (224 mg, 99%) as a brown solid.

Step 4: Preparation of methyl 4-([[(2R,4S)-1-[(tert-butoxy)carbonyl]-4-fluoropyrrolidin-2-yl]formamido]methyl)-6-[6-(trifluoromethyl)pyridin-3-yl]pyridine-3-carboxylate

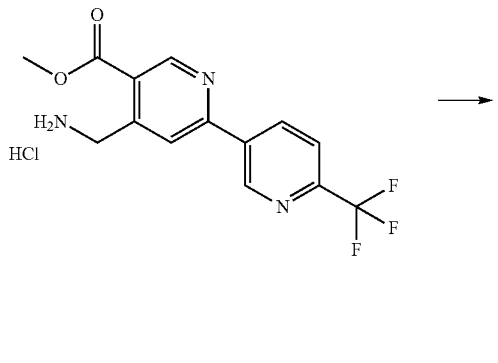

-continued

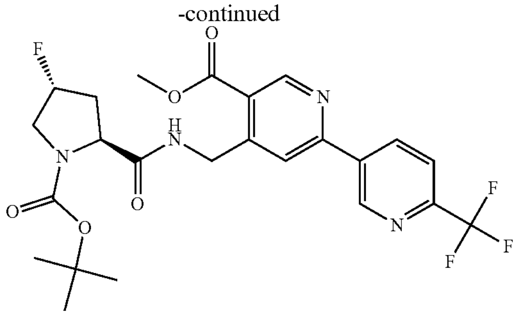

A solution of (2S,4R)-1-[(tert-butoxy)carbonyl]-4-fluoropyrrolidine-2-carboxylic acid (150 mg, 0.64 mmol, 1.00 equiv), methyl 4-(aminomethyl)-6-[6-(trifluoromethyl)pyridin-3-yl]pyridine-3-carboxylate hydrochloride (224 mg, 0.64 mmol, 1.00 equiv), HATU (294 mg, 0.77 mmol, 1.20 equiv), and DIEA (249 mg, 1.93 mmol, 3.00 equiv) in tetrahydrofuran (10 mL) was stirred for 14 h at room temperature. The reaction was then quenched by water, extracted with ethyl acetate, and concentrated under vacuum. The residue was purified by a silica gel column eluting with ethyl acetate/petroleum ether (1:10) to afford the title compound (212 mg, 63%) as a yellow solid.

Step 5: Preparation of 4-([[(2R,4S)-1-[(tert-butoxy)carbonyl]-4-fluoropyrrolidin-2-yl]formamido]methyl)-6-[6-(trifluoromethyl)pyridin-3-yl]pyridine-3-carboxylic acid

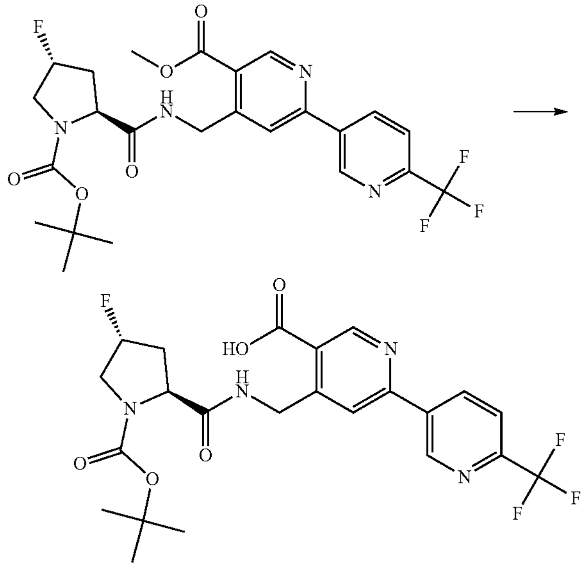

A solution of LiOH (46 mg, 1.92 mmol, 2.00 equiv) in water(2 mL) was added dropwise into a solution of methyl 4-([[(2R,4S)-1-[(tert-butoxy)carbonyl]-4-fluoropyrrolidin-2-yl]formamido]methyl)-6-[6-(trifluoromethyl)pyridin-3-yl]pyridine-3-carboxylate (500 mg, 0.95 mmol, 1.00 equiv) in tetrahydrofuran (10 mL) at 0° C. The resulting solution was stirred for 4 h at room temperature. The reaction was diluted with 50 mL of water. The pH value of the solution was adjusted to 7 with HCl (6M). The resulting solution was extracted with dichloromethane and the organic layers were combined and concentrated under vacuum. This resulted in the title compound (191 mg) as a green solid which was used for the next step without any further purification.

Step 6: Preparation of tert-butyl (2S,4R)-2-[([5-carbamoyl-2-[6-(trifluoromethyl)pyridin-3-yl]pyridin-4-yl]methyl)carbamoyl]-4-fluoropyrrolidine-1-carboxylate

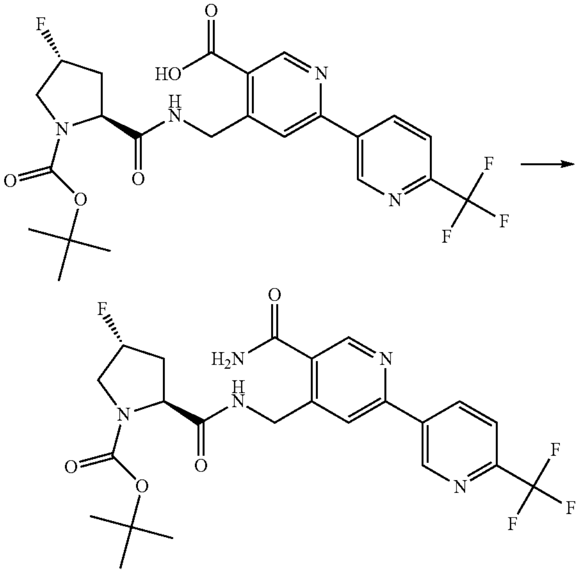

A solution of 4-([[(2S,4R)-1-[(tert-butoxy)carbonyl]-4-fluoropyrrolidin-2-yl]formamido]methyl)-6-[6-(trifluoromethyl)pyridin-3-yl]pyridine-3-carboxylic acid (191 mg, 0.37 mmol, 1.00 equiv), $NH_4Cl$ (30 mg, 0.56 mmol, 1.50 equiv), HATU (171 mg, 0.45 mmol, 1.20 equiv), and DIEA (145 mg, 1.12 mmol, 3.00 equiv) in tetrahydrofuran (20 mL) was stirred for 14 h at room temperature. The reaction was then quenched by 10 mL of water, extracted with ethyl acetate, dried over $Na_2SO_4$, and concentrated under vacuum. The residue was applied onto a silica gel column with ethyl acetate/petroleum ether (7:1). This resulted in 100 mg (52%) of the title compound as a yellow solid.

Step 7: Preparation of tert-butyl (2S,4R)-2-[([5-cyano-2-[6-(trifluoromethyl)pyridin-3-yl]pyridin-4-yl]methyl)carbamoyl]-4-fluoropyrrolidine-1-carboxylate

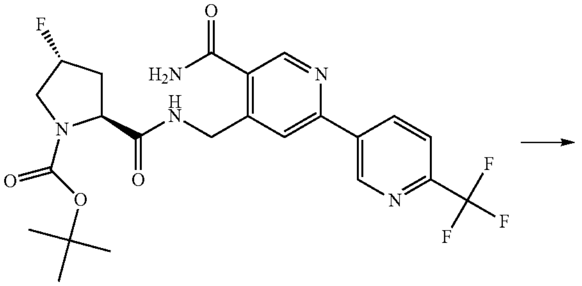

-continued

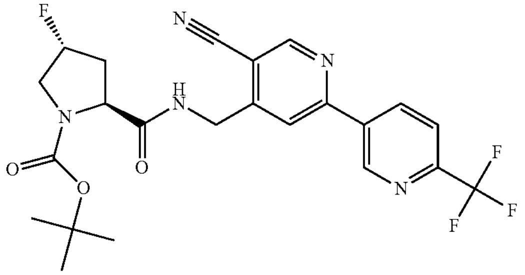

A solution of tert-butyl (2S,4R)-2-[([5-carbamoyl-2-[6-(trifluoromethyl)pyridin-3-yl]pyridin-4-yl]methyl)carbamoyl]-4-fluoropyrrolidine-1-carboxylate (100 mg, 0.20 mmol, 1.00 equiv), TFAA (82 mg, 0.39 mmol, 2.00 equiv), and TEA (20 mg, 0.20 mmol, 1.00 equiv). in dichloromethane (5 mL) was stirred for 14 h at room temperature. The reaction mixture was concentrated under vacuum. The residue was purified by a silica gel column eluting with ethyl acetate/petroleum ether (1:1) to afford the title compound (100 mg) as a yellow solid Step 8: Preparation of (2R,4R)—N-((5-cyano-6'-(trifluoromethyl)-2,3'-bipyridin-4-yl)methyl)-4-fluoropyrrolidine-2-carboxamide hydrochloride

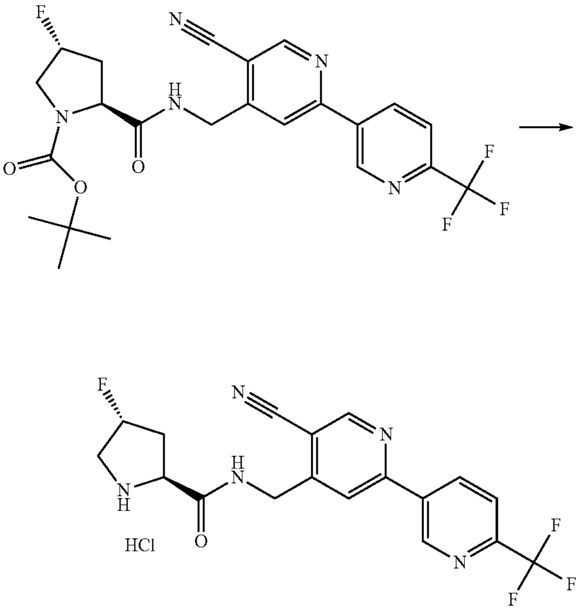

A mixture of (2R,4R)-tert-butyl 2-((5-cyano-6'-(trifluoromethyl)-2,3'-bipyridin-4-yl)methylcarbamoyl)-4-fluoropyrrolidine-1-carboxylate (74 mg, 0.15 mmol, 1.00 equiv) and TFA (2 mL, 26.93 mmol, 179.20 equiv) in dichloromethane (4 mL) was stirred for 1 h at room temperature. The reaction mixture was concentrated under vacuum. The residue was diluted with 0.5 mL of HCl (6M). The resulting mixture was concentrated under vacuum to afford the title compound (56 mg, 87%) as a white solid Step 9: Preparation of (2S,4R)—N-([5-cyano-2-[6-(trifluoromethyl)pyridin-3-yl]pyridin-4-yl]methyl)-4-fluoro-1-[(4-fluorobenzene)sulfonyl]pyrrolidine-2-carboxamide

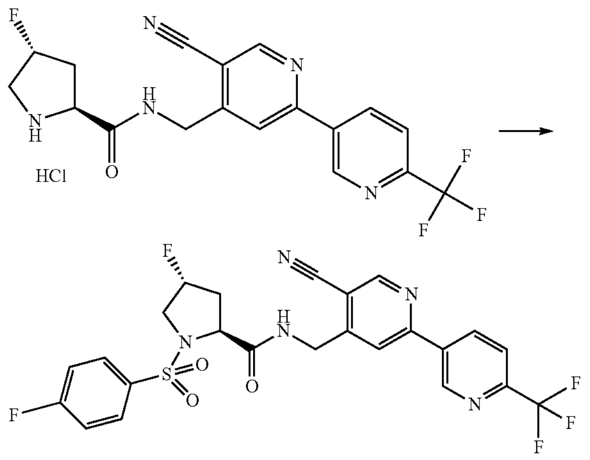

A solution of 4-fluorobenzene-1-sulfonyl chloride (49 mg, 0.25 mmol, 1.20 equiv), (2S,4R)—N-([5-cyano-2-[6-(trifluoromethyl)pyridin-3-yl]pyridin-4-yl]methyl)-4-fluoropyrrolidine-2-carboxamide hydrochloride (91 mg, 0.21 mmol, 1.00 equiv), and TEA (64 mg, 0.63 mmol, 3.00 equiv) in dichloromethane (3 mL) was stirred for 2 h at room temperature. The reaction was quenched by water, extracted with dichloromethane, and concentrated under vacuum. The residue was purified by a silica gel column eluting with ethyl acetate/petroleum ether (1:1) to afford the title compound (15.9 mg, 14%) as a white solid.

$^1$H NMR (400 MHz, $CDCl_3$) δ 9.51 (s, 1H), 8.97 (s, 1H), 8.70-8.68 (dd, J=1.6 Hz, J=1.6 Hz, 1H), 8.25 (s, 1H), 7.94-7.91 (m, 2H), 7.81-7.79 (d, J=8.4 Hz, 1H), 7.51-7.48 (m, 1H), 7.30-7.26 (m, 2H), 5.16-5.03 (m, 2H), 4.64-4.58 (dd, J=4.8 Hz, J=4.8 Hz, 1H), 4.36-4.32 (m, 1H), 3.96-3.80 (m, 1H), 2.66-2.64 (m, 1H), 2.15-2.35 (m, 1H).

Example 80

Preparation of (S)-54(4-fluorophenyl)sulfonyl)-N-((6-(6-(trifluoromethyl)pyridin-3-yl)pyrimidin-4-yl)methyl)-5-azaspiro[2.4]heptane-6-carboxamide

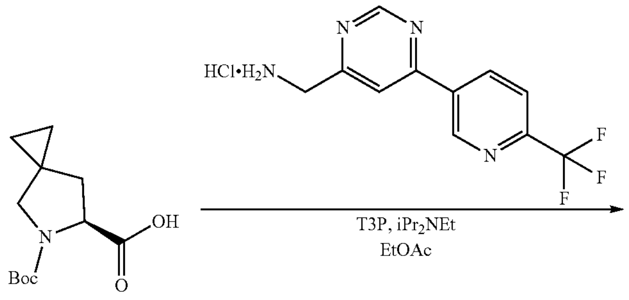

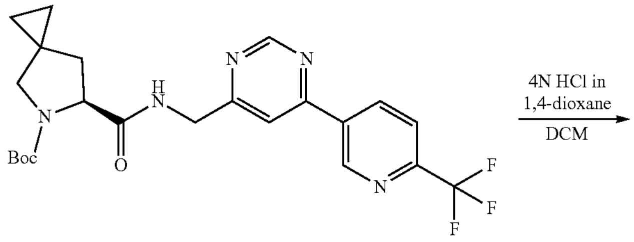

INT-80-12

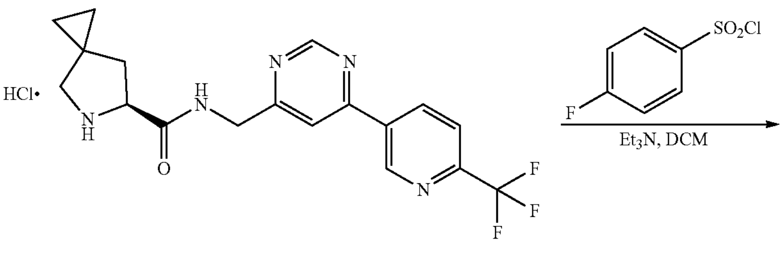

INT-80-13

-continued

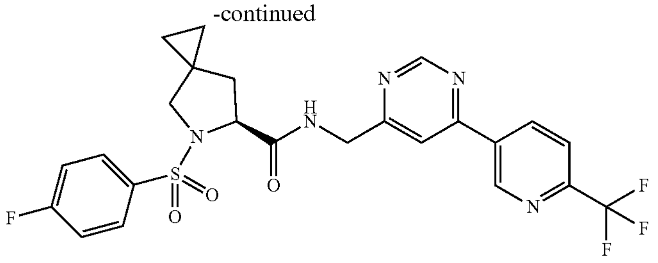

Step 1: (5)-tert-butyl 6-(((6-(6-(trifluoromethyl)pyridin-3-yl)pyrimidin-4-yl)methyl)carbamoyl)-5-azaspiro[2.4]heptane-5-carboxylate (INT-80-12)

To a solution of (5S)-6-tert-butoxycarbonyl-6-azaspiro[2.4]heptane-5-carboxylic acid (200 mg, 0.83 mmol) and [6-[6-(trifluoromethyl)-3-pyridyl]pyrimidin-4-yl]methanamine hydrochloride (265 mg, 0.91 mmol) in ethyl acetate (8.3 mL) was added 2,4,6-tripropyl-1,3,5,2,4,6-trioxatriphosphorinane-2,4,6-trioxide (50 wt %) in ethyl acetate (0.74 mL, 1.24 mmol) and N,N-diisopropylethylamine (0.43 mL, 2.49 mmol) and the reaction mixture was stirred at room temperature overnight. An additional portion of 2,4,6-tripropyl-1,3,5,2,4,6-trioxatriphosphorinane-2,4,6-trioxide (50 wt %) in ethyl acetate (1.48 mL, 2.48 mmol) was added and the reaction mixture was stirred for an additional 72 h. An additional portion of 2,4,6-tripropyl-1,3,5,2,4,6-trioxatriphosphorinane-2,4,6-trioxide (50 wt %) in ethyl acetate (1.48 mL, 2.48 mmol) was added and the reaction mixture was heated to 60° C. The reaction mixture was quenched by the addition of sat. aq. ammonium chloride and extracted with EtOAc (3×). The combined organic layers were washed with brine, dried over sodium sulfate, filtered and concentrated in vacuo. The residue was adsorbed onto silica and purified by flash column chromatography with 0-100% EtOAc in Heptane to afford the desired compound as a brown foam (295 mg, 76%).

MS-ESI: [M+H]+ 478.3

Step 2: (S)—N-((6-(6-(trifluoromethyl)pyridin-3-yl)pyrimidin-4-yl)methyl)-5-azaspiro[2.4]heptane-6-carboxamide (INT-80-13)

To a solution of tert-butyl (5S)-5-[[6-[6-(trifluoromethyl)-3-pyridyl]pyrimidin-4-yl]methylcarbamoyl]-6-azaspiro[2.4]heptane-6-carboxylate (295 mg, 0.62 mmol) in dichloromethane (4 mL) was added hydrochloric acid (4 mol/L) in 1,4-dioxane (2.0 mL, 8.0 mmol) and the reaction mixture was stirred at room temperature for 2 h. The reaction mixture was concentrated in vacuo and used directly without further purification.

MS-ESI: [M−HCl]+ 376.1

Step 3: (5)-5-((4-fluorophenyl)sulfonyl)-N-((6-(6-(trifluoromethyl)pyridin-3-yl)pyrimidin-4-yl)methyl)-5-azaspiro[2.4]heptane-6-carboxamide To crude (S)—N-((6-(6-(trifluoromethyl)pyridin-3-yl)pyrimidin-4-yl)methyl)-5-azaspiro[2.4]heptane-6-carboxamide (122 mg, 0.29 mmol) dissolved in dichloromethane (3 mL) was added triethylamine (0.123 mL, 0.88 mmol) and 4-fluorobenzenesulfonyl chloride (63 mg, 0.32 mmol) at room temperature for 4 h. The reaction mixture was diluted with DCM and water, the layers were separated and the aqueous layer was extracted with DCM (2×). The combined organic layers were dried over sodium sulfate, filtered and concentrated in vacuo. The residue was adsorbed onto silica and purified by flash column chromatography with 0-10% MeOH in DCM to afford the partially purified title compound. The residue was purified by RP-HPLC to yield the title compound (110.6 mg, 70%) as a white solid.

MS-ESI: [M+H]+ 536.14

$^1$H NMR (400 MHz, DMSO) δ 9.49 (d, J=1.8 Hz, 1H), 9.30 (d, J=1.3 Hz, 1H), 8.98 (t, J=6.1 Hz, 1H), 8.84-8.77 (m, 1H), 8.22 (d, J=1.3 Hz, 1H), 8.14-8.08 (m, 1H), 8.08-8.01 (m, 2H), 7.58-7.46 (m, 2H), 4.67-4.56 (m, 1H), 4.51-4.41 (m, 1H), 4.32-4.23 (m, 1H), 3.45 (d, J=10.4 Hz, 1H), 3.19 (d, J=10.5 Hz, 1H), 1.93-1.78 (m, 2H), 0.62-0.52 (m, 1H), 0.52-0.41 (m, 1H), 0.27-0.17 (m, 1H), 0.17-0.06 (m, 1H).

Example 81

Preparation of (2S,4R)-4-fluoro-1-(4-fluorophenyl)sulfonyl-N-[[4-[6-(trifluoromethyl)-3-pyridyl]-2-pyridyl]methyl]pyrrolidine-2-carboxamide

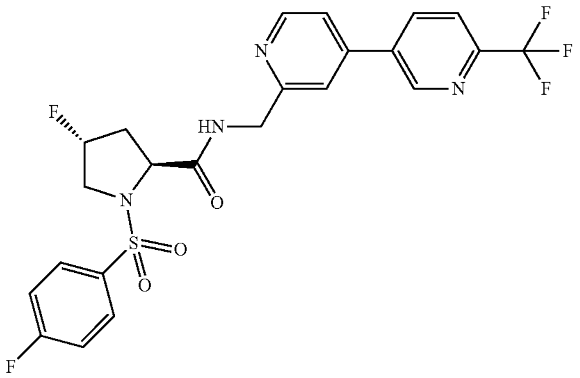 [SMILES: O=C(NCc1cc(-c2ccc(C(F)(F)F)nc2)ccn1)[C@@H]1C[C@@H](F)CN1S(=O)(=O)c1ccc(F)cc1]

Preparation of the title compound follows the same general procedure as Example 48.

1H NMR (400 MHz, DMSO) δ 9.24-9.15 (m, 1H), 9.05-8.96 (t, J=6.0 Hz, 1H), 8.73-8.66 (dd, J=5.1, 0.8 Hz, 1H), 8.51-8.44 (m, 1H), 8.07-7.95 (m, 3H), 7.89-7.84 (dd, J=1.8, 0.8 Hz, 1H), 7.82-7.75 (dd, J=5.2, 1.8 Hz, 1H), 7.51-7.39 (m, 2H), 5.29-5.10 (m, 1H), 4.61-4.45 (m, 2H), 4.29-4.18 (dd, J=9.9, 7.1 Hz, 1H), 3.77-3.57 (m, 2H), 2.47-2.30 (m, 1H), 2.23-2.02 (dddd, J=42.4, 13.8, 9.9, 3.4 Hz, 1H)., LCMS (ESI) m/z:527.12 [M+H]+

Example 82

Preparation of (2S,4R)-4-fluoro-1-(4-fluorophenyl) sulfonyl-N-[[4-[5-(trifluoromethyl)pyrazin-2-yl]-2-pyridyl]methyl]pyrrolidine-2-carboxamide

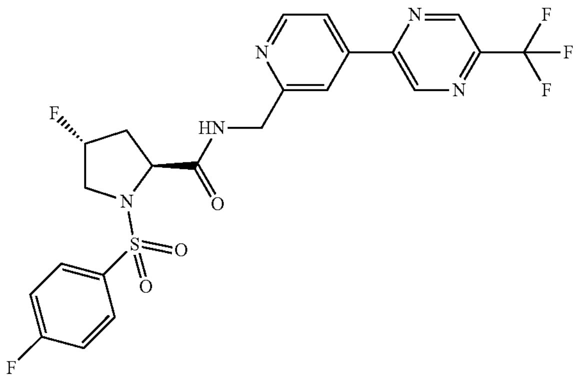 [SMILES: O=C(NCc1cc(-c2cnc(C(F)(F)F)cn2)ccn1)[C@@H]1C[C@@H](F)CN1S(=O)(=O)c1ccc(F)cc1]

Preparation of the title compound follows the same general procedure as Example 48.

1H NMR (400 MHz, DMSO) δ 9.53-9.51 (d, J=1.4 Hz, 1H), 9.33-9.30 (t, J=0.9 Hz, 1H), 9.06-8.98 (t, J=6.0 Hz, 1H), 8.79-8.74 (dd, J=5.2, 0.8 Hz, 1H), 8.17-8.13 (dd, J=1.6, 0.8 Hz, 1H), 8.09-8.05 (dd, J=5.1, 1.7 Hz, 1H), 8.03-7.96 (m, 2H), 7.49-7.39 (m, 2H), 5.31-5.12 (d, J=52.5 Hz, 1H), 4.59-4.51 (d, J=5.9 Hz, 2H), 4.29-4.22 (dd, J=9.8, 7.2 Hz, 1H), 3.75-3.57 (m, 2H), 2.47-2.31 (td, J=16.5, 16.0, 6.8 Hz, 1H), 2.24-2.02 (dddd, J=42.1, 13.8, 9.6, 3.4 Hz, 1H)., LCMS (ESI) m/z:528.11 [M+H]+

Example 83

Preparation of (2S,4R)—N-[[2,6-bis[6-(trifluoromethyl)-3-pyridyl]-4-pyridyl]methyl]-4-fluoro-1-(4-fluorophenyl)sulfonyl-pyrrolidine-2-carboxamide Step 1: (2S,4R)—N-((6,6''-bis(trifluoromethyl)-[3,2':6',3''-terpyridin]-4'-yl)methyl)-4-fluoropyrrolidine-2-carboxamide hydrochloride

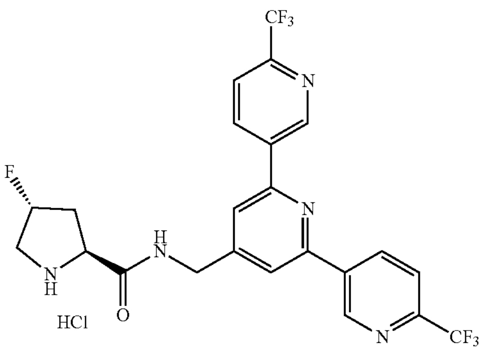 [SMILES: O=C(NCc1cc(-c2ccc(C(F)(F)F)nc2)nc(-c2ccc(C(F)(F)F)nc2)c1)[C@@H]1C[C@@H](F)CN1 ; Cl]

The title compound (60 mg, 98%) was prepared following the Boc deprotection procedure of Example 2, Step 2 from tert-butyl (2S,4R)-2-[[2,6-bis[6-(trifluoromethyl)-3-pyridyl]-4-pyridyl]methylcarbamoyl]-4-fluoro-pyrrolidine-1-carboxylate (68 mg, 0.11 mmol) and 4M HCl in dioxane (4 ml) in DCM (4 ml). LCMS (ESI_Formic_MeCN): $[MH^+]$=514.

Step 2: (2S,4R)—N-[[2,6-bis[6-(trifluoromethyl)-3-pyridyl]-4-pyridyl]methyl]-4-fluoro-1-(4-fluorophenyl)sulfonyl-pyrrolidine-2-carboxamide

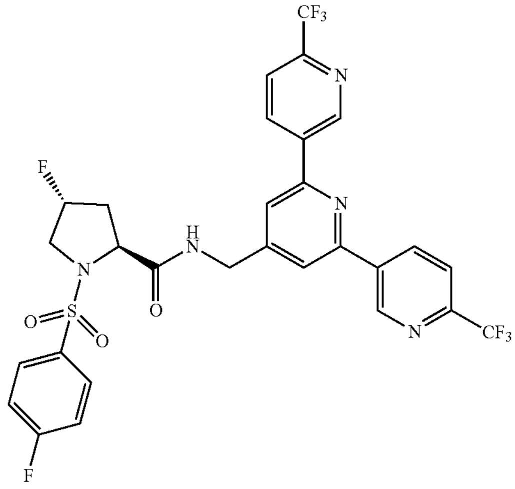 [SMILES: O=C(NCc1cc(-c2ccc(C(F)(F)F)nc2)nc(-c2ccc(C(F)(F)F)nc2)c1)[C@@H]1C[C@@H](F)CN1S(=O)(=O)c1ccc(F)cc1]

The title compound (48 mg, 65%) was prepared following the sulfonamide coupling procedure of Example 2, Step 3 from (2S,4R)—N-[[2,6-bis[6-(trifluoromethyl)-3-pyridyl]-4-pyridyl]methyl]-4-fluoro-pyrrolidine-2-carboxamide hydrochloride (60 mg, 0.11 mmol), 4-fluorobenzenesulfonyl chloride (27 mg, 0.14 mmol) and triethylamine (0.05 mL, 0.4 mmol) in DCM (6 mL).

1H NMR (400 MHz, DMSO-$d_6$) δ 9.58 (dt, J=2.2, 0.7 Hz, 2H), 9.11 (t, J=6.0 Hz, 1H), 8.92-8.85 (m, 2H), 8.23 (d, J=0.8 Hz, 2H), 8.07 (dd, J=8.3, 0.8 Hz, 2H), 8.05-8.00 (m, 2H), 7.51-7.44 (m, 2H), 5.22 (d, J=52.4 Hz, 1H), 4.70-4.52 (m, 2H), 4.24 (dd, J=10.1, 7.1 Hz, 1H), 3.77-3.60 (m, 2H), 2.44 (dd, J=17.2, 7.7 Hz, 2H), 2.24-2.03 (m, 1H).

Example 84

Preparation of (2S,4R)—N-[[2-chloro-6-[6-(trifluoromethyl)-3-pyridyl]-4-pyridyl]methyl]-4-fluoro-1-(4-fluorophenyl)sulfonyl-pyrrolidine-2-carboxamide Step 1: (2S,4R)-tert-butyl 2-(((2,6-dichloropyridin-4-yl)methyl)carbamoyl)-4-fluoropyrrolidine-1-carboxylate

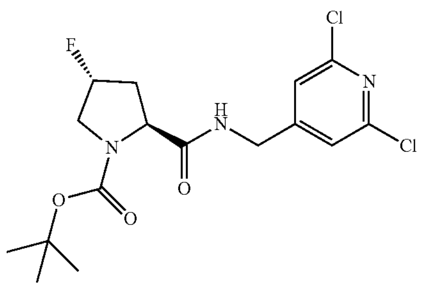 [SMILES: CC(C)(C)OC(=O)N1C[C@H](F)C[C@H]1C(=O)NCc1cc(Cl)nc(Cl)c1]

The title compound (1473 mg, 66%) was prepared following the amide coupling procedure of Example 7, Step 7 from (2,6-dichloro-4-pyridyl)methanamine (1.00 g, 5.65 mmol), (2S,4R)-1-tert-butoxycarbonyl-4-fluoro-pyrrolidine-2-carboxylic acid (1320 mg, 5.66 mmol), HATU (2210 mg, 5.81 mmol) and triethylamine (2.05 mL, 14.7 mmol) in DMF(12 mL). LCMS (ESI_Formic_MeCN): $[MH^+]$=392.

Step 2: (2S,4R)-tert-butyl 2-(((6-chloro-6'-(trifluoromethyl)-[2,3'-bipyridin]-4-yl)methyl)carbamoyl)-4-fluoropyrrolidine-1-carboxylate and (2S,4R)-tert-butyl 2-(((6,6"-bis(trifluoromethyl)-[3,2':6',3"-terpyridin]-4'-yl)methyl)carbamoyl)-4-fluoropyrrolidine-1-carboxylate

A

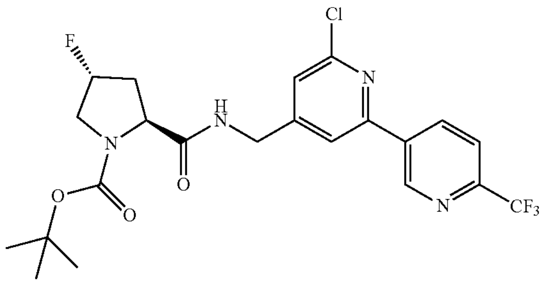

B

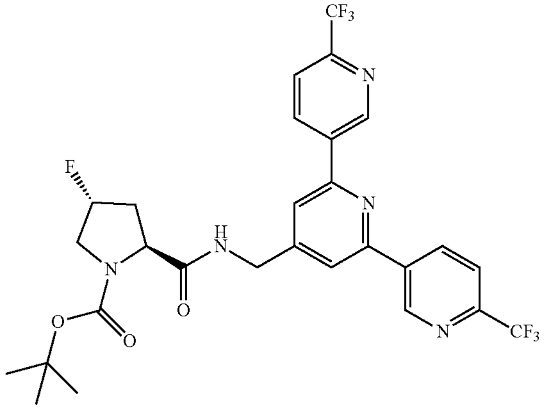

The title compounds were prepared following the Suzuki coupling procedure of Example 8, Step 1 from tert-butyl (2S,4R)-2-[(2,6-dichloro-4-pyridyl)methylcarbamoyl]-4-fluoro-pyrrolidine-1-carboxylate (157 mg, 0.40 mmol), [6-(trifluoromethyl)-3-pyridyl]boronic acid (105 mg, 0.55 mmol), [1,1'-bis(diphenylphosphino)ferrocene]dichloropalladium(II) (31 mg., 0.040 mmol) and 1 M aq Cs2CO3 (0.41 mL, 0.41 mmol, 1.0 mol/L) in acetonitrile (4 ml). Compound A (72 mg, 36%): LCMS (ESI_Formic_MeCN): $[MH^+]$=503. Compound B (68 mg, 28%): LCMS (ESI_Formic_MeCN): $[MH^+]$=614.

Step 3: (2S,4R)—N-((6-chloro-6'-(trifluoromethyl)-[2,3'-bipyridin]-4-yl)methyl)-4-fluoropyrrolidine-2-carboxamide hydrochloride

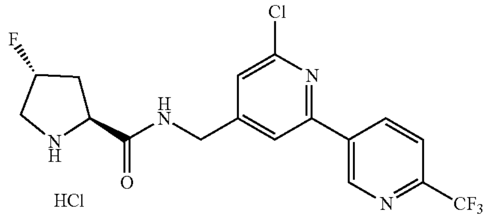 [SMILES: O=C(NCc1cc(Cl)nc(-c2ccc(C(F)(F)F)nc2)c1)[C@@H]1C[C@@H](F)CN1 ; Cl]

The title compound (61 mg, 97%) was prepared following the Boc deprotection procedure of Example 2, Step 2 from tert-butyl (2S,4R)-2-[[2-chloro-6-[6-(trifluoromethyl)-3-pyridyl]-4-pyridyl]methylcarbamoyl]-4-fluoro-pyrrolidine-1-carboxylate (72 mg, 0.1432 mmol) and 4M HCl in dioxane (5 mL) in DCM (5 ml). LCMS (ESI_Formic_MeCN): $[MH^+]$=403.

Step 4: (2S,4R)—N-[[2-chloro-6-[6-(trifluoromethyl)-3-pyridyl]-4-pyridyl]methyl]-4-fluoro-1-(4-fluorophenyl)sulfonyl-pyrrolidine-2-carboxamide

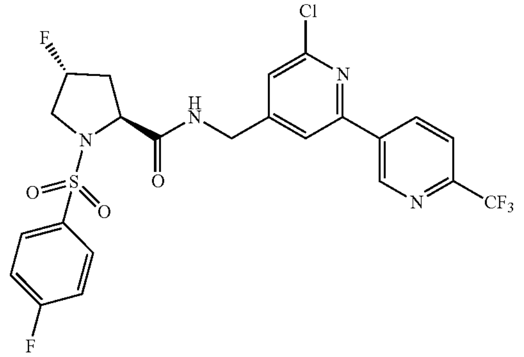 [SMILES: O=C(NCc1cc(Cl)nc(-c2ccc(C(F)(F)F)nc2)c1)[C@@H]1C[C@@H](F)CN1S(=O)(=O)c1ccc(F)cc1]

The title compound (47 mg, 61%) was prepared following the sulfonamide coupling procedure of Example 2, Step 3 from (2S,4R)—N-[[2-chloro-6-[6-(trifluoromethyl)-3-pyridyl]-4-pyridyl]methyl]-4-fluoro-pyrrolidine-2-carboxamide hydrochloride (61 mg, 0.14 mmol), 4-fluorobenzenesulfonyl chloride (33 mg, 0.17 mmol) and triethylamine (0.35 mL, 2.5 mmol) in DCM (5 ml).

1H NMR (400 MHz, DMSO-$d_6$) δ 9.38 (d, J=2.2 Hz, 1H), 9.03 (t, J=6.0 Hz, 1H), 8.71-8.64 (m, 1H), 8.14 (d, J=1.2 Hz, 1H), 8.05 (dd, J=8.3, 0.8 Hz, 1H), 8.03-7.97 (m, 2H), 7.60 (d, J=1.1 Hz, 1H), 7.51-7.43 (m, 2H), 5.20 (d, J=52.6 Hz, 1H), 4.60-4.41 (m, 2H), 4.23-4.14 (m, 1H), 3.79-3.57 (m, 2H), 2.49-2.36 (m, 1H), 2.23-1.98 (m, 1H).

Example 85

Preparation of (2S,4R)-4-fluoro-N-[[3-fluoro-5-[2-oxo-4-(trifluoromethyl)-1-pyridyl]phenyl]methyl]-1-(4-fluorophenyl)sulfonyl-pyrrolidine-2-carboxamide

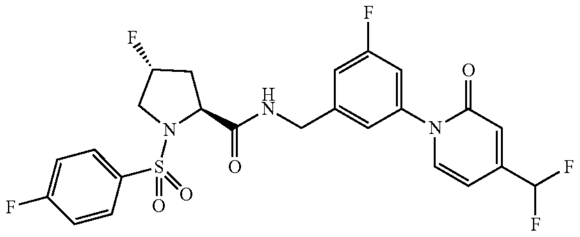 [SMILES: O=C(NCc1cc(F)cc(-n2ccc(C(F)F)cc2=O)c1)[C@@H]1C[C@@H](F)CN1S(=O)(=O)c1ccc(F)cc1]

Preparation of the title compound follows the same general procedure of Example 86.

$^1$H NMR (400 MHz, DMSO) δ 8.93-8.86 (t, J=6.0 Hz, 1H), 7.99-7.92 (m, 2H), 7.92-7.87 (dt, J=7.2, 0.9 Hz, 1H), 7.50-7.41 (m, 2H), 7.37-7.25 (m, 3H), 6.94-6.89 (dq, J=2.0, 1.0 Hz, 1H), 6.56-6.51 (dd, J=7.2, 2.0 Hz, 1H), 5.28-5.09 (m, 1H), 4.50-4.33 (m, 2H), 4.21-4.11 (dd, J=9.9, 7.1 Hz, 1H), 3.73-3.54 (m, 2H), 2.44-2.30 (td, J=15.2, 14.7, 6.1 Hz, 1H), 2.19-1.96 (m, 1H)., LCMS (ESI) m/z:560.11 [M+H]+

Example 86

Preparation of (2S,4R)-4-fluoro-1-(4-fluorophenyl)sulfonyl-N-[[3-fluoro-5-[4-(trifluoromethyl)pyrazol-1-yl]phenyl]methyl]pyrrolidine-2-carboxamide

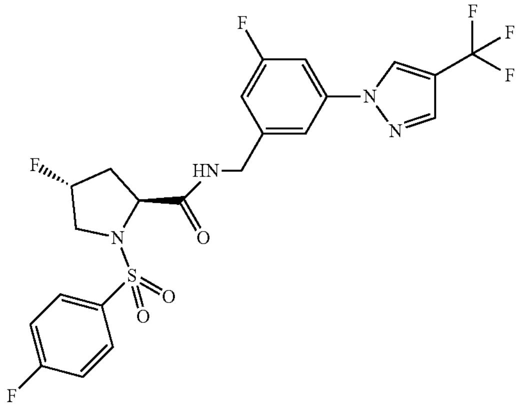 [SMILES: O=C(NCc1cc(F)cc(-n2cc(C(F)(F)F)cn2)c1)[C@@H]1C[C@@H](F)CN1S(=O)(=O)c1ccc(F)cc1]

A solution containing (2S,4R)—N-[(3-bromo-5-fluoro-phenyl)methyl]-4-fluoro-1-(4-fluorophenyl)sulfonyl-pyrrolidine-2-carboxamide (80 mg, 0.1676 mmol), 4-(trifluoromethyl)-1h-pyrazole (48.0 mg, 0.3352 mmol), cuprous iodide (31.92 mg, 0.1676 mmol), N,N'-dimethylethylenediamine (0.036 mL, 0.34 mmol) and potassium carbonate (48.65 mg, 0.3520 mmol) in 1,4-dioxane (1.7 mL) was stirred at 100° C. 18 h. The crude was filtered thru celite and purified by flash chromatography (EtOAc/Heptane_eluted at 80% EtOAc) then submitted for rHPLC to give 60.9 mg, 68.23% yield.

1H NMR (400 MHz, DMSO) δ 9.19-9.14 (t, J=1.0 Hz, 1H), 8.95-8.88 (t, J=6.1 Hz, 1H), 8.28-8.22 (d, J=0.8 Hz, 1H), 8.02-7.93 (m, 2H), 7.77-7.72 (t, J=1.7 Hz, 1H), 7.71-7.65 (dt, J=10.0, 2.2 Hz, 1H), 7.51-7.42 (m, 2H), 7.25-7.18 (ddd, J=9.5, 2.4, 1.3 Hz, 1H), 5.30-5.10 (m, 1H), 4.53-4.36 (m, 2H), 4.22-4.13 (dd, J=9.9, 7.1 Hz, 1H), 3.74-3.56 (m, 2H), 2.45-2.31 (m, 1H), 2.20-1.97 (m, 1H)., LCMS (ESI) m/z:533.11 [M+H]+

Example 87

Preparation of (2S,4R)-4-fluoro-1-(4-fluorophenyl)sulfonyl-N-[[3-fluoro-5-[3-(trifluoromethyl)pyrazol-1-yl]phenyl]methyl]pyrrolidine-2-carboxamide

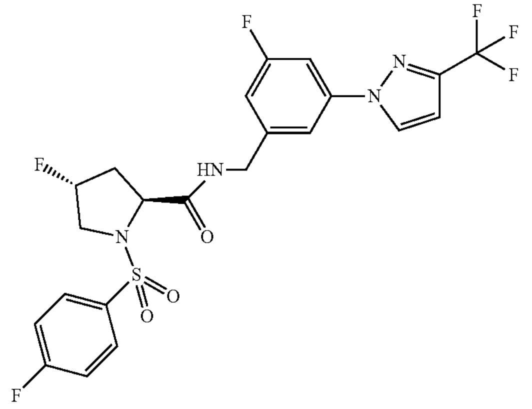 [SMILES: O=C(NCc1cc(F)cc(-n2ccc(C(F)(F)F)n2)c1)[C@@H]1C[C@@H](F)CN1S(=O)(=O)c1ccc(F)cc1]

Preparation of the title compound follows the same general procedure as Example 86.

1H NMR (400 MHz, DMSO) δ 8.95-8.89 (t, J=6.1 Hz, 1H), 8.75-8.71 (dq, J=2.7, 1.0 Hz, 1H), 8.02-7.94 (m, 2H), 7.74-7.65 (m, 2H), 7.50-7.41 (m, 2H), 7.28-7.19 (ddd, J=9.6, 2.3, 1.4 Hz, 1H), 7.10-7.07 (m, 1H), 5.30-5.08 (d, J=52.4 Hz, 1H), 4.53-4.36 (m, 2H), 4.22-4.13 (dd, J=9.8, 7.2 Hz, 1H), 3.75-3.57 (m, 2H), 2.46-2.29 (td, J=16.3, 7.2 Hz, 1H), 2.18-1.98 (m, 1H)., LCMS (ESI) m/z:533.11 [M+H]+

Example 88

Preparation of (2S,4R)—N-[[4-[4-(difluoromethyl)phenyl]-5-fluoro-2-pyridyl]methyl]-4-fluoro-1-(4-fluorophenyl)sulfonyl-pyrrolidine-2-carboxamide

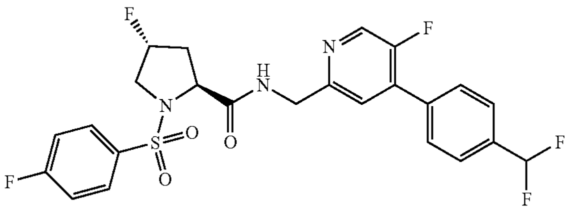 [SMILES: O=C(NCc1cc(-c2ccc(C(F)F)cc2)c(F)cn1)[C@@H]1C[C@@H](F)CN1S(=O)(=O)c1ccc(F)cc1]

Step 1: Preparation of 4-(2-chloro-5-fluoropyridin-4-yl)benzaldehyde

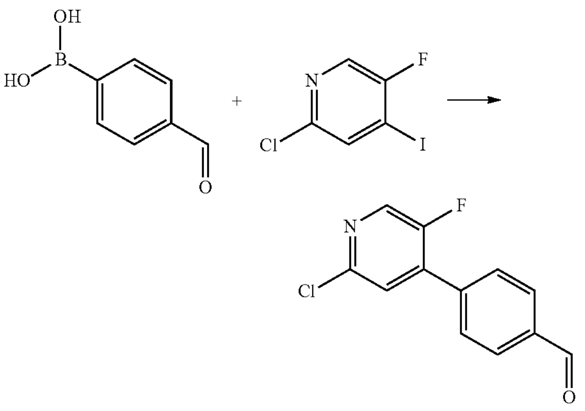

A mixture of (4-formylphenyl)boronic acid (500 mg, 3.33 mmol, 1.00 equiv), 2-chloro-5-fluoro-4-iodopyridine (575 mg, 2.23 mmol, 0.70 equiv), $Pd(dppf)Cl_2$ (80 mg, 0.11 mmol), potassium carbonate (930 mg, 6.73 mmol, 2.00 equiv), and 1,4-dioxane (15 mL)/water(1.5 mL) was stirred for 12 h at 75° C. under nitrogen. The reaction mixture was diluted with ethyl acetate, washed with brine, dried over anhydrous sodium sulfate, and concentrated under vacuum. The residue was purified by a silica gel column eluting with petroleum ether/ethyl acetate (5:1). This resulted in the title compound (520 mg, 66%) as an off-white solid.

Step 2: Preparation of 2-chloro-4-[4-(difluoromethyl)phenyl]-5-fluoropyridine

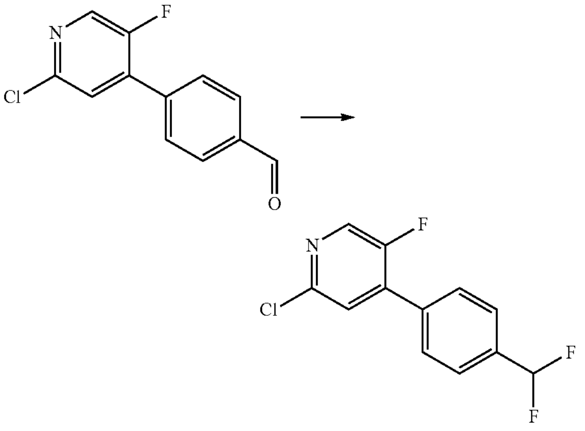

DAST (3.56 g, 22.09 mmol, 10.00 equiv) was added dropwise into a mixture of 4-(2-chloro-5-fluoropyridin-4-yl)benzaldehyde (520 mg, 2.21 mmol, 1.00 equiv) in dichloromethane (130 mL) at −78° C. under nitrogen. The resulting solution was stirred for 12 h at room temperature. The reaction was then quenched by water, extracted with ethyl acetate, washed with saturated solution of sodium bicarbonate and then brine, dried over anhydrous sodium sulfate, and concentrated under vacuum. The residue was purified by a silica gel column eluting with petroleum ether/ethyl acetate (5:1) to afford the title compound (500 mg, 88%) as a white solid.

Step 3: Preparation of 4-[4-(difluoromethyl)phenyl]-5-fluoropyridine-2-carbonitrile

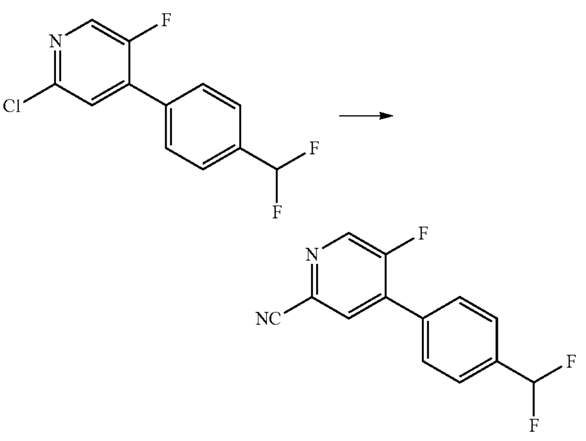

A mixture of 2-chloro-4-[4-(difluoromethyl)phenyl]-5-fluoropyridine (500 mg, 1.94 mmol, 1.00 equiv), $Zn(CN)_2$ (272 mg, 2.32 mmol, 1.20 equiv), $Pd_2(dba)_3CHCl_3$ (200 mg, 0.19 mmol, 0.10 equiv), and dppf (214 mg, 0.39 mmol, 0.20 equiv) in N,N-dimethylformamide (16 mL) was stirred for 1.5 h at 100° C. under nitrogen. The residue was diluted with ethyl acetate, washed with brine, dried over anhydrous sodium sulfate, and concentrated under vacuum. The residue was purified by a silica gel column eluting with petroleum ether/ethyl acetate (10:1). This resulted in the title compound (440 mg, 91%) as a light yellow solid.

Step 4: Preparation of [4-[4-(difluoromethyl)phenyl]-5-fluoropyridin-2-yl]methanamine

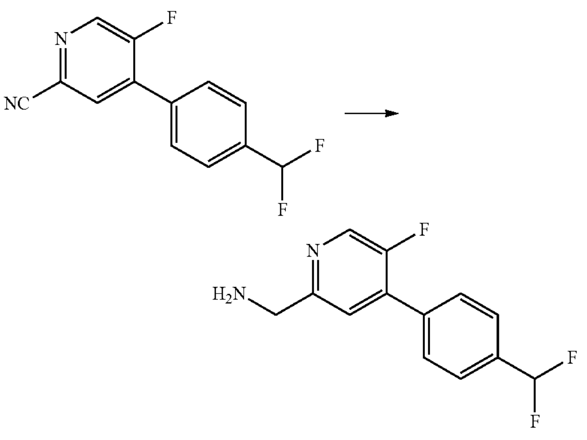

A mixture of 4-[4-(difluoromethyl)phenyl]-5-fluoropyridine-2-carbonitrile (440 mg, 1.77 mmol, 1.00 equiv), methanol (40 mL), and palladium on carbon (400 mg, 3.76 mmol, 2.10 equiv) was stirred for 2 h at room temperature under hydrogen. The solids were filtered out and the liquid was concentrated under vacuum. This resulted in the title compound (420 mg, 94%) as an off-white solid.

Step 5: Preparation of tert-butyl (2S,4R)-2-[([4-[4-(difluoromethyl)phenyl]-5-fluoropyridin-2-yl]methyl)carbamoyl]-4-fluoropyrrolidine-1-carboxylate

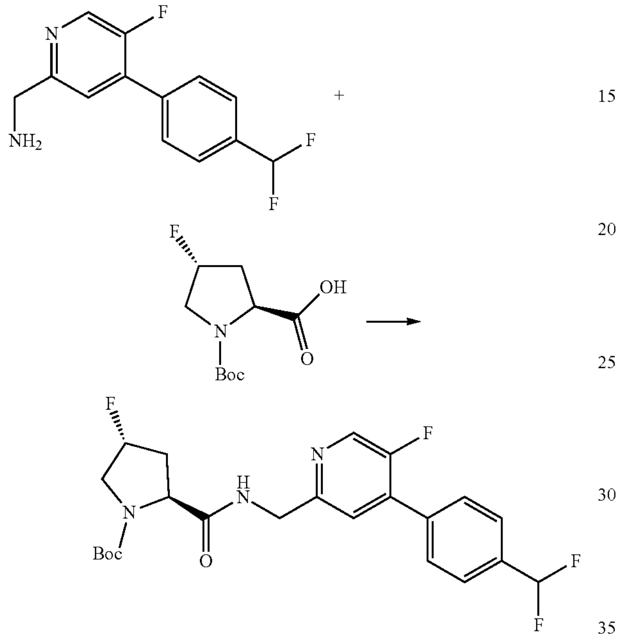

A mixture of (2S,4R)-1-[(tert-butoxy)carbonyl]-4-fluoropyrrolidine-2-carboxylic acid (92 mg, 0.39 mmol, 1.00 equiv), N,N-dimethylformamide (20 mL), DIEA (154 mg, 1.19 mmol, 3.00 equiv), HATU (226 mg, 0.59 mmol, 1.50 equiv), and [4-[4-(difluoromethyl)phenyl]-5-fluoropyridin-2-yl]methanamine (100 mg, 0.40 mmol, 1.00 equiv) was stirred for 12 h at room temperature. The reaction mixture was diluted with ethyl acetate, washed with brine, dried over anhydrous sodium sulfate, and concentrated under vacuum. The residue was purified by a silica gel column eluting with petroleum ether/ethyl acetate (5:1). This resulted in the title compound (120 mg, 65%) as an off-white solid.

Step 6: Preparation of (2S,4R)—N-([4-[4-(difluoromethyl)phenyl]-5-fluoropyridin-2-yl]methyl)-4-fluoropyrrolidine-2-carboxamide hydrochloride

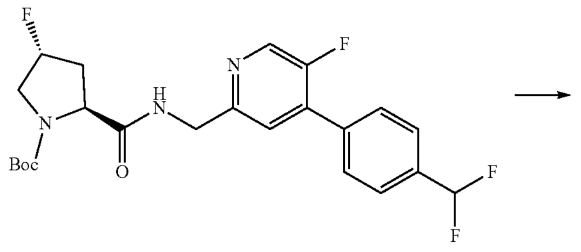

-continued

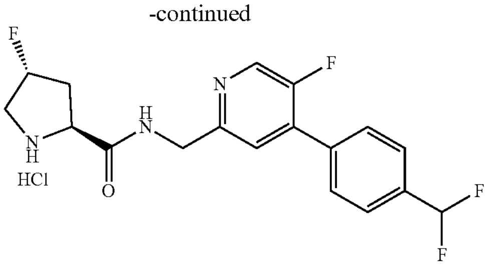

A mixture of tert-butyl (2S,4R)-2-[([4-[4-(difluoromethyl)phenyl]-5-fluoropyridin-2-yl]methyl)carbamoyl]-4-fluoropyrrolidine-1-carboxylate (138 mg, 0.30 mmol, 1.00 equiv) and HCl (saturated solution in 5 ml of dioxane) was stirred for 1 h at room temperature. The resulting mixture was concentrated under vacuum to afford the title compound (120 mg, crude) as an off-white solid.

Step 7: Preparation of (2S,4R)—N-[[4-[4-(difluoromethyl)phenyl]-5-fluoro-2-pyridyl]methyl]-4-fluoro-1-(4-fluorophenyl)sulfonyl-pyrrolidine-2-carboxamide

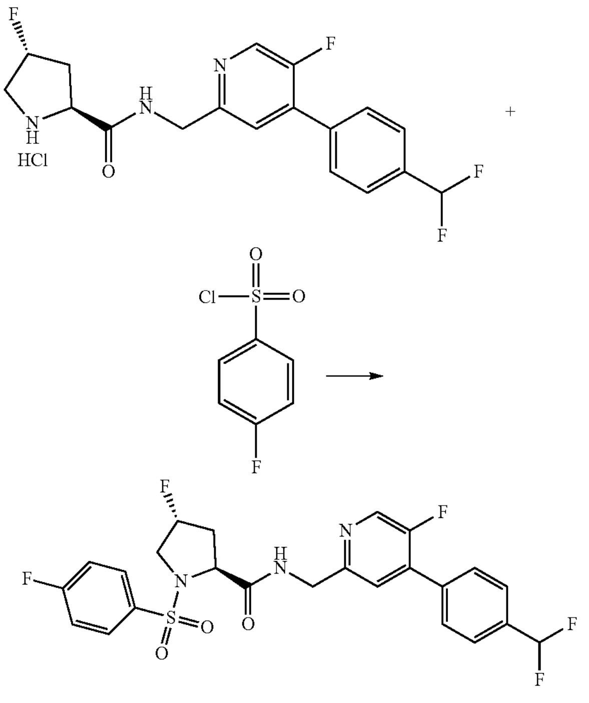

A mixture of (2S,4R)—N-([4-[4-(difluoromethyl)phenyl]-5-fluoropyridin-2-yl]methyl)-4-fluoropyrrolidine-2-carboxamide hydrochloride (120 mg, 0.33 mmol, 1.00 equiv), dichloromethane (10 mL), TEA (99 mg, 0.98 mmol, 3.00 equiv), and 4-fluorobenzene-1-sulfonyl chloride (64 mg, 0.33 mmol, 1.00 equiv) was stirred for 2 h at room temperature. The reaction mixture was diluted with ethyl acetate, washed with brine, dried over anhydrous sodium sulfate, and concentrated under vacuum. The residue was purified by a silica gel column eluting with petroleum ether/ethyl acetate (1:2) to afford the title compound (41.4 mg, 24%) as an off-white solid.

$^1$H NMR (300 MHz, $CDCl_3$) δ 9.01-8.99 (m, 1H), 8.64 (s, 1H), 8.00-7.98 (m, 2H), 7.98-7.97 (m, 2H), 7.81-7.70 (m,

3H), 7.69-7.67 (m, 2H), 7.48-7.43 (m, 3H), 5.28-5.10 (d, J=27 Hz, 1H), 4.50-4.46 (m, 2H), 4.20-4.17 (m, 1H), 3.72-3.59 (m, 2H), 2.46-2.35 (m, 1H), 2.27-2.02 (m, 1H).

Example 89

Preparation of (2S,4R)-4-fluoro-1-(4-fluorophenyl) sulfonyl-N-[[3-fluoro-5-[6-(trifluoromethyl) pyridazin-3-yl]phenyl]methyl]pyrrolidine-2-carboxamide

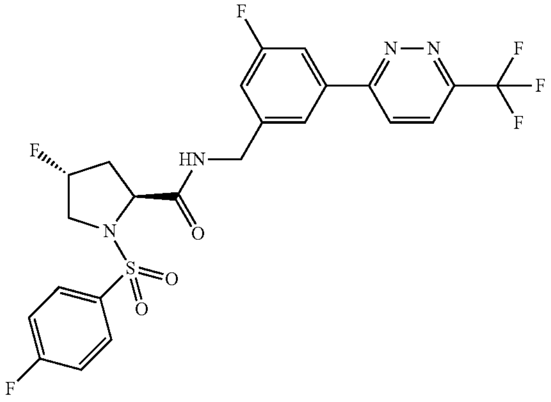 [SMILES: O=C(NCc1cc(F)cc(-c2ccc(C(F)(F)F)nn2)c1)[C@@H]1C[C@@H](F)CN1S(=O)(=O)c1ccc(F)cc1]

The title compound was prepared using the same general procedure as Example 91.

1H NMR (400 MHz, DMSO) δ 8.97-8.90 (t, J=6.0 Hz, 1H), 8.59-8.55 (m, 1H), 8.41-8.37 (d, J=9.0 Hz, 1H), 8.09-8.04 (t, J=1.5 Hz, 1H), 8.01-7.94 (m, 3H), 7.50-7.39 (m, 3H), 5.29-5.10 (d, J=52.4 Hz, 1H), 4.57-4.42 (m, 2H), 4.22-4.14 (dd, J=9.9, 7.1 Hz, 1H), 3.74-3.58 (m, 2H), 2.44-2.30 (m, 1H), 2.20-1.98 (m, 1H)., LCMS (ESI) m/z: 545.2 [M+H]+

Example 90

Preparation of (2S,4R)—N-[[3-[5-(difluoromethyl) pyrazin-2-yl]-5-fluoro-phenyl]methyl]-4-fluoro-1-(4-fluorophenyl)sulfonyl-pyrrolidine-2-carboxamide

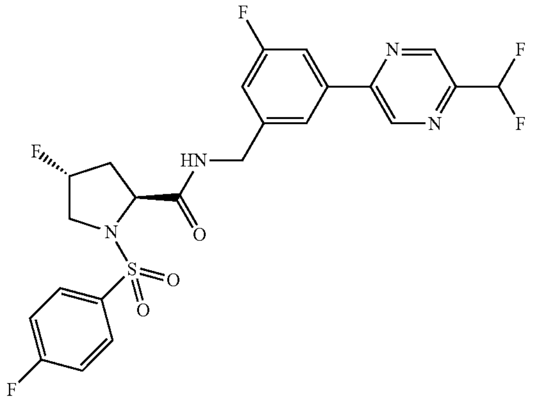 [SMILES: O=C(NCc1cc(F)cc(-c2cnc(C(F)F)cn2)c1)[C@@H]1C[C@@H](F)CN1S(=O)(=O)c1ccc(F)cc1]

The title compound was prepared using the same general procedure as Example 91.

1H NMR (400 MHz, DMSO) δ 9.43-9.40 (d, J=1.4 Hz, 1H), 9.06-9.02 (d, J=1.3 Hz, 1H), 8.96-8.89 (t, J=6.1 Hz, 1H), 8.06-8.02 (t, J=1.5 Hz, 1H), 8.01-7.95 (m, 2H), 7.95-7.88 (dt, J=9.8, 2.0 Hz, 1H), 7.51-7.42 (m, 2H), 7.40-7.33 (dd, J=9.7, 2.1 Hz, 1H), 7.32-7.03 (t, J=54.2 Hz, 1H), 5.30-5.09 (d, J=52.4 Hz, 1H), 4.55-4.40 (m, 2H), 4.24-4.14 (dd, J=9.8, 7.2 Hz, 1H), 3.76-3.71 (q, J=2.0, 1.5 Hz, 1H), 3.70-3.57 (m, 1H), 2.43-2.29 (dt, J=16.5, 7.9 Hz, 1H), 2.20-1.98 (m, 1H)., LCMS (ESI) m/z:527.2 [M+H]+

Example 91

Preparation of (2S,4R)-4-fluoro-1-(4-fluorophenyl) sulfonyl-N-[[3-fluoro-5-[2-(trifluoromethyl)pyrimidin-5-yl]phenyl]methyl]pyrrolidine-2-carboxamide

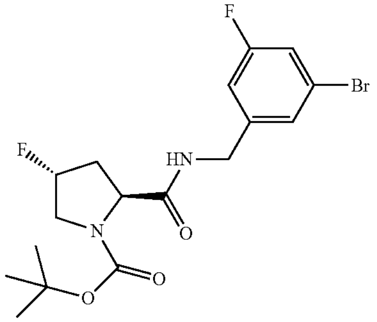 [SMILES: CC(C)(C)OC(=O)N1C[C@H](F)C[C@H]1C(=O)NCc1cc(F)cc(Br)c1]

(2S,4R)-tert-butyl 2-((3-bromo-5-fluorobenzyl)carbamoyl)-4-fluoropyrrolidine-1-carboxylate To a solution of (2S,4R)-1-tert-butoxycarbonyl-4-fluoro-pyrrolidine-2-carboxylic acid (A, 2000 mg, 8.6 mmol) and (3-bromo-5-fluoro-phenyl)methanamine (1.9 g, 9.4 mmol) in N,N-dimethylformamide (34 ml) was added N,N-diisopropylethylamine (2.2 mL, 13 mmol) and HATU (4.0 g, 10 mmol). The reaction mixture was stirred at RT 2 h. The reaction was quenched with water and extracted with EtOAc. The organic layers was dried with sodium sulfate, filtered, and concentrated via rotovap. The crude product was purified by flash chromatography (EtOAc/Heptane_eluted at 50% EtOAc) to give 3.24 g, 90% yield. LCMS (ESI) m/z:419.1 [M+H]+

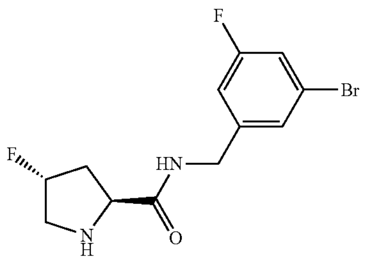 [SMILES: O=C(NCc1cc(F)cc(Br)c1)[C@@H]1C[C@@H](F)CN1]

(2S,4R)—N-(3-bromo-5-fluorobenzyl)-4-fluoropyrrolidine-2-carboxamide

To a solution of tert-butyl (2S,4R)-2-[(3-bromo-5-fluoro-phenyl)methylcarbamoyl]-4-fluoro-pyrrolidine-1-carboxylate (820 mg, 1.956 mmol) in 1,4-dioxane (6.519 mL) was added hydrochloric acid (4 mol/L) in 1,4-dioxane (4.9 mL, 19.56 mmol). The reaction mixture was stirred at RT 6 h.

The reaction was concentrated and carried to next step. LCMS (ESI) m/z:318.9 [M+H]+

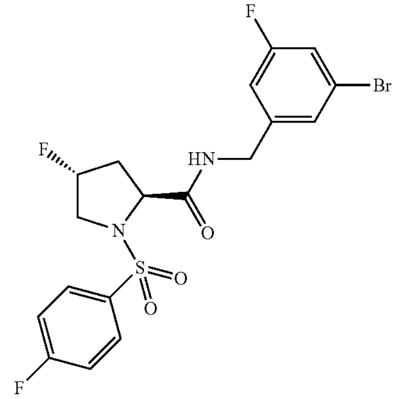 [SMILES: O=C(NCc1cc(F)cc(Br)c1)[C@@H]1C[C@@H](F)CN1S(=O)(=O)c1ccc(F)cc1]

(2S,4R)—N-(3-bromo-5-fluorobenzyl)-4-fluoro-1-((4-fluorophenyl)sulfonyl)pyrrolidine-2-carboxamide To a solution of (2S,4R)—N-[(3-bromo-5-fluoro-phenyl)methyl]-4-fluoro-pyrrolidine-2-carboxamide (624 mg, 1.9553 mmol) in dichloromethane (39 mL) was added triethylamine (5.45 mL, 39.11 mmol) then 4-fluorobenzenesulfonyl chloride (571.0 mg, 2.933 mmol). The reaction was stirred at RT 2 h. The reaction was quenched with water and extracted with EtOAc. The organic layers was dried with sodium sulfate, filtered, and concentrated via rotovap. The crude product was purified by flash chromatography (EtOAc/Heptane_eluted at 65% EtOAc) to give 933.4 mg, 89.46% yield. LCMS (ESI) m/z:477.0 [M+H]+

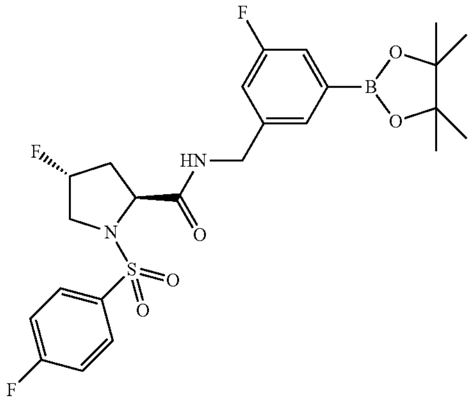 [SMILES: CC1(C)OB(c2cc(F)cc(CNC(=O)[C@@H]3C[C@@H](F)CN3S(=O)(=O)c3ccc(F)cc3)c2)OC1(C)C]

(2S,4R)-4-fluoro-N-(3-fluoro-5-(4,4,5,5-tetramethyl-1,3,2-dioxaborolan-2-yl)benzyl)-1-((4-fluorophenyl)sulfonyl)pyrrolidine-2-carboxamide To a solution of (2S,4R)—N-[(3-bromo-5-fluoro-phenyl)methyl]-4-fluoro-1-(4-fluorophenyl)sulfonyl-pyrrolidine-2-carboxamide (205 mg, 0.4295 mmol) and bis(pinacolato)diboron (166.9 mg, 0.6442 mmol) in 1,4-dioxane (8.60 mL, 100.6 mmol) was added potassium acetate (126.5 mg, 0.0805 mL, 1.288 mmol) and [1,1'-bis(diphenylphosphino)ferrocene]dichloropalladium(II) (31.74 mg, 0.04295 mmol). The reaction mixture was degassed then heated 85° C. 18 h. The reaction was filtered thru celite. The crude was concentrated and carried to next step. LCMS (ESI) m/z:525.1 [M+H]+

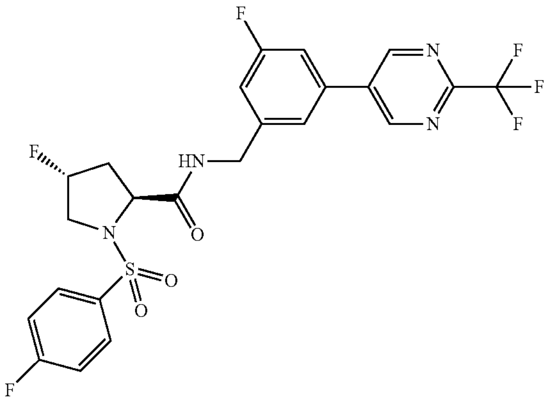 [SMILES: O=C(NCc1cc(F)cc(-c2cnc(C(F)(F)F)nc2)c1)[C@@H]1C[C@@H](F)CN1S(=O)(=O)c1ccc(F)cc1]

(2S,4R)-4-fluoro-1-(4-fluorophenyl)sulfonyl-N-[[3-fluoro-5-[2-(trifluoromethyl)pyrimidin-5-yl]phenyl]methyl]pyrrolidine-2-carboxamide A solution of (2S,4R)-4-fluoro-1-(4-fluorophenyl)sulfonyl-N-[[3-fluoro-5-(4,4,5,5-tetramethyl-1,3,2-dioxaborolan-2-yl)phenyl]methyl]pyrrolidine-2-carboxamide (225 mg, 0.4291 mmol), 5-bromo-2-(trifluoromethyl)pyrimidine (153.9 mg, 0.6442 mmol), [1,1'-bis(diphenylphosphino)ferrocene]dichloropalladium(II) (31.74 mg, 0.04295 mmol) and cesium carbonate (279.9 mg, 0.8590 mmol) in water (2.0 mL) and acetonitrile (4.0 mL) was degassed. The reaction mixture was heated at 95° C. for 2 h. The reaction was filtered thru celite. The crude product was purified by flash chromatography (EtOAc/Hep_eluted at 70% EtOAc) then submitted for rHPLC to give 111.2 mg, 47.55% yield.

1H NMR (400 MHz, DMSO) δ 9.46-9.37 (s, 2H), 8.98-8.89 (t, J=6.0 Hz, 1H), 8.03-7.94 (m, 2H), 7.77-7.70 (m, 2H), 7.51-7.42 (m, 2H), 7.40-7.31 (m, 1H), 5.31-5.09 (m, 1H), 4.56-4.37 (m, 2H), 4.23-4.13 (dd, J=9.9, 7.1 Hz, 1H), 3.77-3.55 (m, 2H), 2.47-2.29 (m, 1H), 2.20-1.98 (m, 1H)., LCMS (ESI) m/z:545.2 [M+H]+

Example 92

Preparation of (2S,4R)—N-[[6-(2,2-difluoro-2H-1,3-benzodioxol-5-yl)pyrimidin-4-yl]methyl]-4-fluoro-1-[(4-fluorobenzene)sulfonyl]pyrrolidine-2-carboxamide

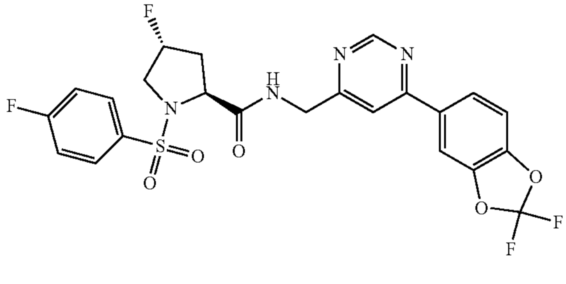 [SMILES: O=C(NCc1cc(-c2ccc3c(c2)OC(F)(F)O3)ncn1)[C@@H]1C[C@@H](F)CN1S(=O)(=O)c1ccc(F)cc1]

Step 1: Preparation of 2-(2,2-difluoro-2H-1,3-benzodioxol-5-yl)-4,4,5,5-tetramethyl-1,3,2-dioxaborolane

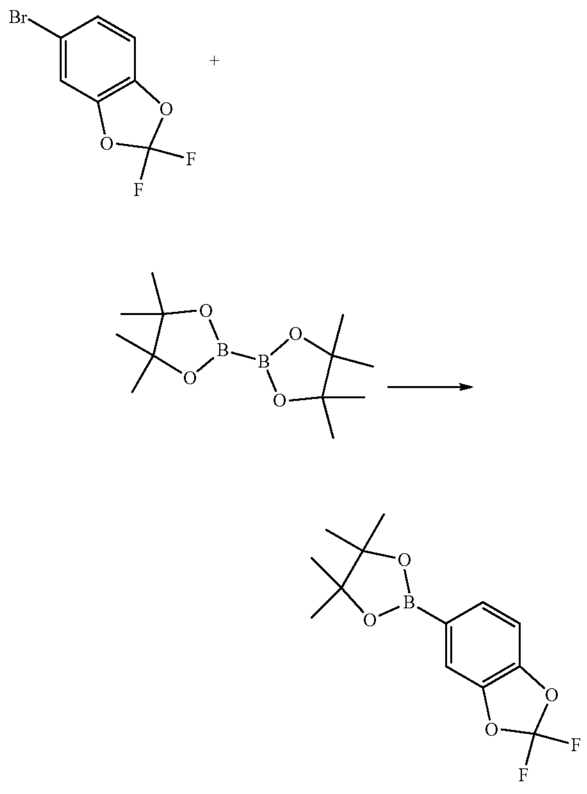

A solution of 5-bromo-2,2-difluoro-2H-1,3-benzodioxole (1 g, 4.22 mmol, 1.00 equiv), 4,4,5,5-tetramethyl-2-(tetramethyl-1,3,2-dioxaborolan-2-yl)-1,3,2-dioxaborolane (1.2 g, 4.73 mmol, 1.10 equiv), $Pd(dppf)Cl_2$ (300 mg, 0.41 mmol, 0.10 equiv), and AcOK (800 mg, 8.15 mmol, 2.00 equiv) in dioxane (20 mL) was stirred overnight at 100° C. The reaction mixture was concentrated under vacuum. The residue was purified by a silica gel column eluting with ethyl acetate/petroleum ether (1:20) to afford the title compound (900 mg, 75%) as yellow oil.

Step 2: Preparation of 4-chloro-6-(2,2-difluoro-2H-1,3-benzodioxol-5-yl)pyrimidine

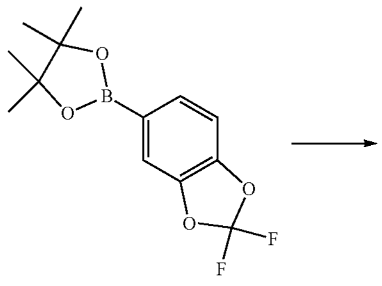

-continued

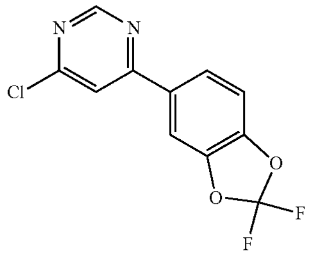

A solution of 2-(2,2-difluoro-2H-1,3-benzodioxol-5-yl)-4,4,5,5-tetramethyl-1,3,2-dioxaborolane (800 mg, 2.82 mmol, 1.00 equiv), 4,6-dichloropyrimidine (640 mg, 4.30 mmol, 1.50 equiv), potassium carbonate (776 mg, 5.61 mmol, 2.00 equiv), and $Pd(PPh_3)_4$ (328 mg, 0.28 mmol, 0.10 equiv) in dioxane (15 mL)/water (3 mL) was stirred overnight at 100° C. The resulting mixture was concentrated under vacuum. The residue was purified by a silica gel column eluting with ethyl acetate/petroleum ether (1:6) to afford the title compound (570 mg, 75%) as a white solid.

Step 3: Preparation of 6-(2,2-difluoro-2H-1,3-benzodioxol-5-yl)pyrimidine-4-carbonitrile

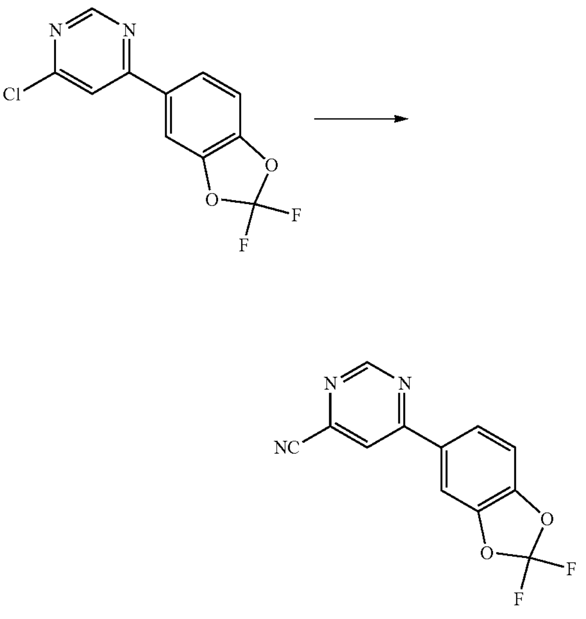

A solution of 4-chloro-6-(2,2-difluoro-2H-1,3-benzodioxol-5-yl)pyrimidine (500 mg, 1.85 mmol, 1.00 equiv), $Pd(PPh_3)_4$ (180 mg, 0.16 mmol, 0.10 equiv), and $Zn(CN)_2$ (330 mg, 2.81 mmol, 1.50 equiv) in N,N-dimethylformamide (8 mL) was stirred for 1 h at 100° C. The reaction mixture was diluted with 100 ml of ethyl acetate, washed with water, dried over sodium sulfate, and concentrated under vacuum. The residue was purified by a silica gel column eluting with ethyl acetate/petroleum ether (1:6). This resulted in the title compound (360 mg, 75%) as a white solid.

Step 4: Preparation of [6-(2,2-difluoro-2H-1,3-benzodioxol-5-yl)pyrimidin-4-yl]methanamine

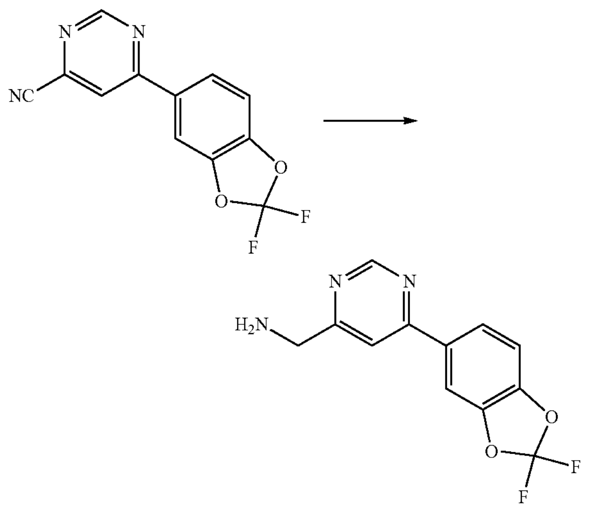

A mixture of 6-(2,2-difluoro-2H-1,3-benzodioxol-5-yl) pyrimidine-4-carbonitrile (340 mg, 1.30 mmol, 1.00 equiv), palladium on carbon (100 mg, 0.94 mmol, 1.00 equiv), and hydrogen chloride (2 drop) in methanol (80 mL) was stirred for 5 min at room temperature under hydrogen. The solids were filtered out and the liquid was concentrated under vacuum. The residue was purified by a silica gel column eluting with DCM:MeOH (100:5) to afford the title compound (220 mg, 64%) as a white solid.

Step 5: Preparation of (2S,4R)—N-[[6-(2,2-difluoro-2H-1,3-benzodioxol-5-yl)pyrimidin-4-yl]methyl]-4-fluoro-1-[(4-fluorobenzene)sulfonyl]pyrrolidine-2-carboxamide

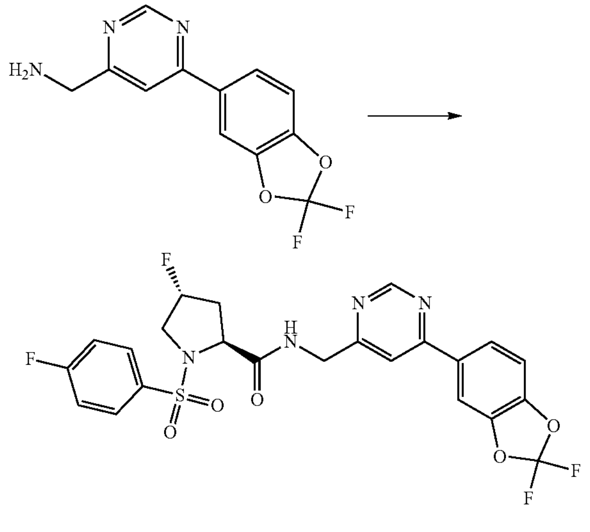

A solution of (2S,4R)-4-fluoro-1-[(4-fluorobenzene) sulfonyl]pyrrolidine-2-carboxylic acid (110 mg, 0.38 mmol, 1.0 equiv), HATU (172 mg, 0.45 mmol, 1.2 equiv), and DIEA (200 mg, 1.55 mmol, 2.00 equiv) in N,N-dimethylformamide (10 mL) was stirred for 10 min at room temperature. Then [6-(2,2-difluoro-2H-1,3-benzodioxol-5-yl) pyrimidin-4-yl]methanamine (100 mg, 0.38 mmol, 1.0 equiv) was added and the resulting solution was stirred for an additional 3 h at room temperature. The resulting solution was diluted with ethyl acetate, washed with water, dried over sodium sulfate, and concentrated under vacuum. The residue was purified by a silica gel column eluting with ethyl acetate to afford the title compound (43.2 mg, 21%) as a white solid. $^1$H NMR (400 MHz, $CDCl_3$) δ 9.20 (s, 1H), 8.06-8.02 (m, 3H), 7.96-7.92 (m, 2H), 7.80 (s, 1H), 7.28-7.23 (m, 2H), 7.18 (d, J=8.4 Hz, 1H), 5.15-5.02 (d, J=51.2 Hz, 1H), 4.95-4.92 (m, 1H), 4.66-4.62 (m, 1H), 4.29 (t, J=8.4 Hz, 1H), 3.88-3.72 (m, 2H), 2.59-2.53 (m, 1H), 2.34-2.17 (m, 1H).

Example 93

Preparation of (2R,3S)-3-fluoro-N-((6-(3-fluoro-4-(trifluoromethyl)phenyl)pyrimidin-4-yl)methyl)-1-(4-fluorophenylsulfonyl)pyrrolidine-2-carboxamide

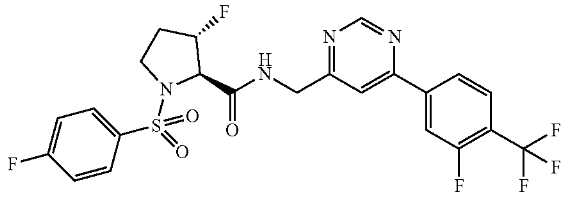 [SMILES: O=C(NCc1cc(-c2ccc(C(F)(F)F)c(F)c2)ncn1)[C@@H]1[C@@H](F)CCN1S(=O)(=O)c1ccc(F)cc1]

Step 1: Preparation of (2S,3R)-tert-butyl 2-((6-(3-fluoro-4-(trifluoromethyl)phenyl)pyrimidin-4-yl) methylcarbamoyl)-3-hydroxypyrrolidine-1-carboxylate

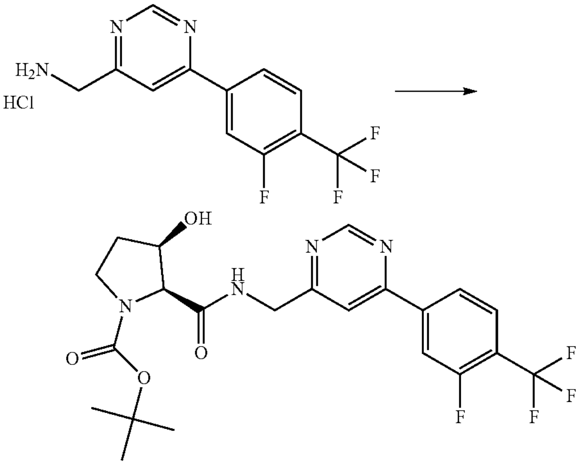

A mixture of (2S,3R)-1-[(tert-butoxy)carbonyl]-3-hydroxypyrrolidine-2-carboxylic acid (209 mg, 0.90 mmol, 1.00 equiv), [6-[3-fluoro-4-(trifluoromethyl)phenyl]pyrimidin-4-yl]methanamine hydrochloride (280 mg, 0.91 mmol, 1.00 equiv), HATU (414 mg, 1.09 mmol, 1.20 equiv), and DIEA (351 mg, 2.72 mmol, 3.00 equiv) in tetrahydrofuran (10 mL) was stirred for 6 h at room temperature. The reaction was then quenched by water. The resulting solution was extracted with 2×50 mL of ethyl acetate and the organic layers were combined and concentrated under vacuum. The residue was purified by a silica gel column eluting with ethyl acetate/petroleum ether (2:1). This resulted in the title compound (270 mg, 62%) as an off-white solid.

Step 2: Preparation of (2R,3S)-tert-butyl 3-fluoro-2-((6-(3-fluoro-4-(trifluoromethyl)phenyl)pyrimidin-4-yl)methylcarbamoyl)pyrrolidine-1-carboxylate

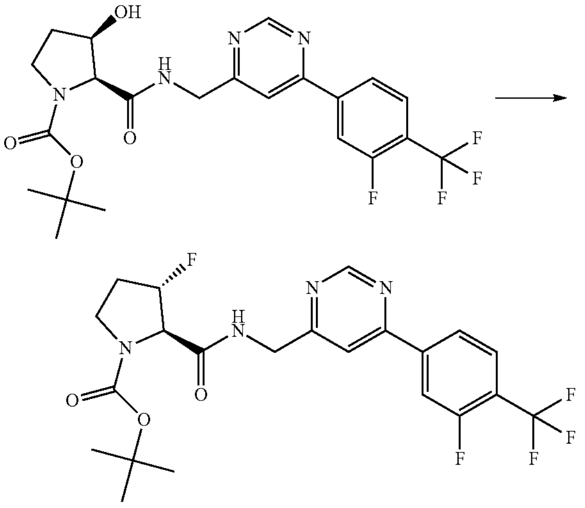

DAST (36.6 mg, 0.23 mmol, 2.20 equiv) was added slowly into a solution of tert-butyl (2S,3R)-2-[([6-[3-fluoro-4-(trifluoromethyl)phenyl]pyrimidin-4-yl]methyl)carbamoyl]-3-hydroxypyrrolidine-1-carboxylate (50 mg, 0.10 mmol, 1.00 equiv) in dichloromethane (5 mL) at 0° C. under nitrogen. The resulting solution was stirred for 10 min at 0° C. in a water/ice bath. The reaction was then quenched by iced water, extracted with 2×50 mL of dichloromethane, washed with 2×10 mL of saturated aqueous $NaHCO_3$, and concentrated under vacuum. The residue was purified by a silica gel column eluting with ethyl acetate/petroleum ether (3:1) to afford the title compound 57 mg (crude) as a brown solid Step 3: Preparation of (2R,3S)-3-fluoro-N-((6-(3-fluoro-4-(trifluoromethyl)phenyl)pyrimidin-4-yl)methyl)pyrrolidine-2-carboxamide hydrochloride

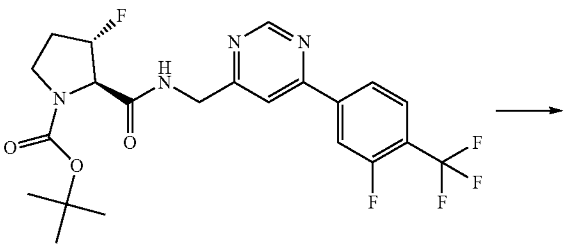

-continued

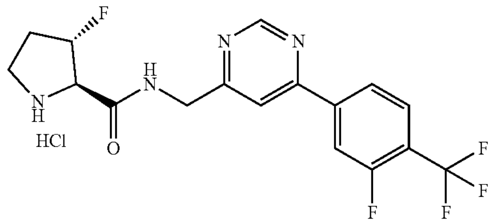

A solution of tert-butyl (2R,3S)-3-fluoro-2-[([6-[3-fluoro-4-(trifluoromethyl)phenyl]pyrimidin-4-yl]methyl)carbamoyl]pyrrolidine-1-carboxylate (57 mg, 0.12 mmol, 1.00 equiv) and saturated hydrogen chloride in 1,4-dioxane (5 mL) was stirred for 14 h at room temperature. The resulting mixture was concentrated under vacuum. This resulted in the title compound (44 mg, 89%) as a brown solid.

Step 4: Preparation of (2R,3S)-3-fluoro-N-((6-(3-fluoro-4-(trifluoromethyl)phenyl)pyrimidin-4-yl)methyl)-1-(4-fluorophenyl sulfonyl)pyrrolidine-2-carboxamide

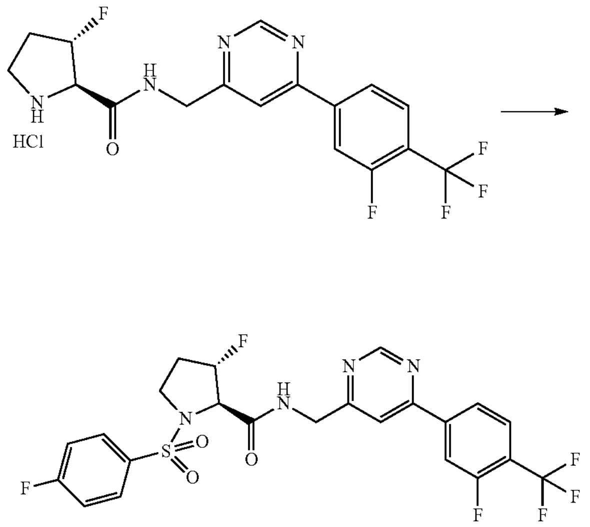

A mixture of 4-fluorobenzene-1-sulfonyl chloride (24 mg, 0.12 mmol, 1.20 equiv), (2R,3S)-3-fluoro-N-([6-[3-fluoro-4-(trifluoromethyl)phenyl]pyrimidin-4-yl]methyl)pyrrolidine-2-carboxamide hydrochloride (44 mg, 0.10 mmol, 1.00 equiv), and TEA (31.5 mg, 0.31 mmol, 3.00 equiv) in dichloromethane (5 mL) was stirred for 14 h at room temperature. The reaction mixture was quenched by water, extracted by ethyl acetate, and concentrated under vacuum. The residue was purified by a silica gel column eluting with ethyl acetate/petroleum ether (3:1) to afford the title compound (21.4 mg, 38%) as a white solid.

$^1H$ NMR (400 MHz, $CDCl_3$) δ 9.25 (s, 1H), 8.10-8.06 (t, J=8.5 Hz, 2H), 7.94-7.91 (m, 3H), 7.78-7.72 (m, 2H), 7.31-7.26 (m, 2H), 5.38-5.25 (d, J=50.8 Hz, 1H), 4.93-4.91 (m, 1H), 4.58-4.53 (m, 1H), 4.43-4.37 (d, J=22.0 Hz, 1H), 3.83 (t, J=8.8 Hz, 1H), 3.35-3.28 (m, 1H), 2.23-2.03 (m, 2H).

Example 94

Preparation of (2S,4R)—N-[[3-[6-(difluoromethyl)-3-pyridyl]-5-fluoro-phenyl]methyl]-4-fluoro-1-(4-fluorophenyl)sulfonyl-pyrrolidine-2-carboxamide

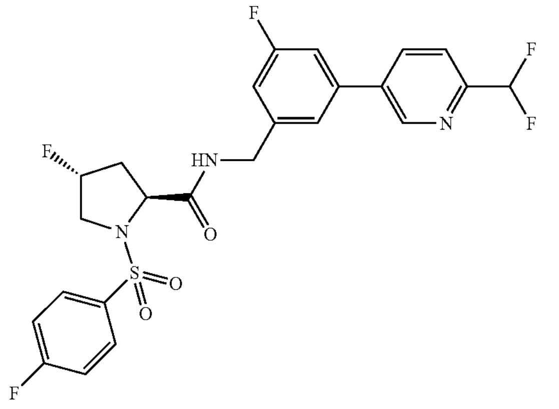 [SMILES: O=C(NCc1cc(F)cc(-c2ccc(C(F)F)nc2)c1)[C@@H]1C[C@@H](F)CN1S(=O)(=O)c1ccc(F)cc1]

Preparation of the title compound follows the same general procedure as Example 48.

1H NMR (400 MHz, DMSO) δ 9.07-9.04 (dd, J=2.3, 0.8 Hz, 1H), 8.93-8.87 (t, J=6.0 Hz, 1H), 8.35-8.30 (dd, J=8.2, 2.3 Hz, 1H), 8.02-7.94 (m, 2H), 7.80-7.75 (m, 1H), 7.65-7.62 (t, J=1.5 Hz, 1H), 7.62-7.56 (ddd, J=10.0, 2.5, 1.6 Hz, 1H), 7.50-7.41 (m, 2H), 7.30-7.23 (ddd, J=9.8, 2.4, 1.5 Hz, 1H), 7.17-6.86 (t, J=54.9 Hz, 1H), 5.30-5.10 (d, J=52.7 Hz, 1H), 4.54-4.37 (m, 2H), 4.23-4.13 (dd, J=9.9, 7.1 Hz, 1H), 3.76-3.56 (m, 2H), 2.46-2.30 (m, 1H), 2.20-1.99 (m, 1H)., LCMS (ESI) m/z:526.12 [M+H]+

Example 95

Preparation of (2S,4R)-4-fluoro-1-(4-fluorophenyl)sulfonyl-N-[[3-fluoro-5-[5-(trifluoromethyl)-2-pyridyl]phenyl]methyl]pyrrolidine-2-carboxamide

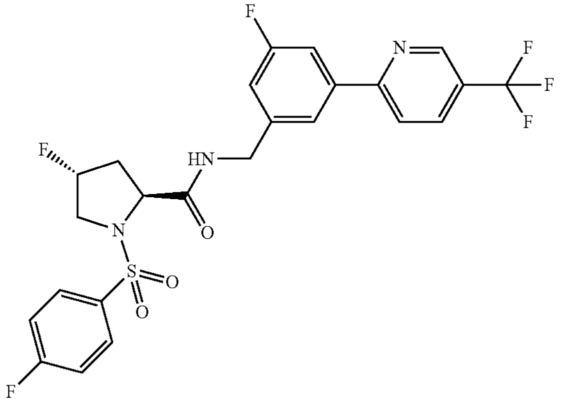 [SMILES: O=C(NCc1cc(F)cc(-c2ccc(C(F)(F)F)cn2)c1)[C@@H]1C[C@@H](F)CN1S(=O)(=O)c1ccc(F)cc1]

Preparation of the title compound follows the same general procedure as Example 91.

1H NMR (400 MHz, DMSO) δ 9.09-9.03 (dt, J=1.9, 0.9 Hz, 1H), 8.95-8.87 (t, J=6.0 Hz, 1H), 8.35-8.29 (m, 1H), 8.28-8.23 (m, 1H), 8.03-7.93 (m, 3H), 7.91-7.83 (ddd, J=10.2, 2.6, 1.6 Hz, 1H), 7.51-7.41 (m, 2H), 7.36-7.28 (ddd, J=9.5, 2.4, 1.3 Hz, 1H), 5.31-5.10 (d, J=52.5 Hz, 1H), 4.54-4.39 (m, 2H), 4.23-4.13 (dd, J=9.8, 7.1 Hz, 1H), 3.79-3.57 (m, 2H), 2.46-2.29 (td, J=16.5, 15.8, 7.1 Hz, 1H), 2.19-1.98 (m, 1H)., LCMS (ESI) m/z:544.11 [M+H]+

Example 96

Preparation of (2S,4R)-4-fluoro-1-(4-fluorophenyl)sulfonyl-N-[[5-methyl-4-[6-(trifluoromethyl)-3-pyridyl]-2-pyridyl]methyl]pyrrolidine-2-carboxamide

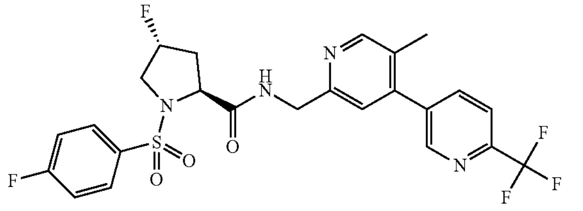 [SMILES: Cc1cnc(CNC(=O)[C@@H]2C[C@@H](F)CN2S(=O)(=O)c2ccc(F)cc2)cc1-c1ccc(C(F)(F)F)nc1]

Step 1: Preparation of 5-methyl-4-[6-(trifluoromethyl)pyridin-3-yl]pyridine-2-carbonitrile

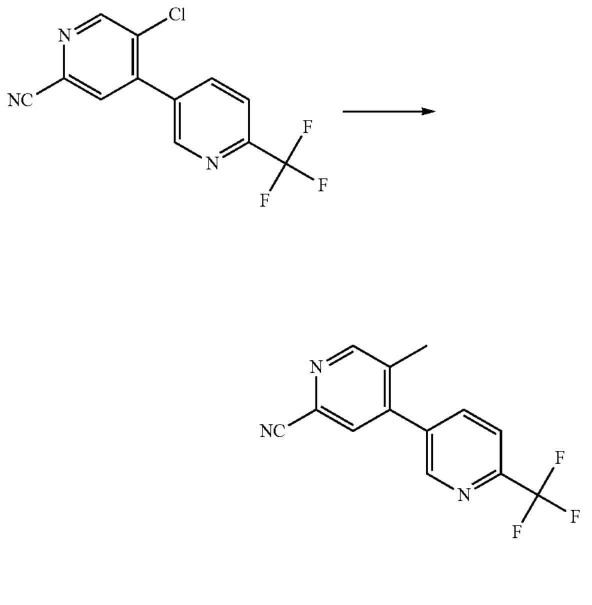

A mixture of 5-chloro-4-[6-(trifluoromethyl)pyridin-3-yl]pyridine-2-carbonitrile (1.08 g, 3.81 mmol, 1.00 equiv) in dioxane (50 mL), $Pd(dppf)Cl_2$ (560 mg, 0.77 mmol, 0.20 equiv), and $Zn(CH_3)_2$ (4.2 mL, 5.72 mmol, 1.30 equiv) was stirred for overnight at 65° C. under nitrogen. The resulting mixture was concentrated under vacuum. The residue was purified by a silica gel column eluting with ethyl acetate/petroleum ether (15:100). This resulted in the title compound (292 mg, 29%) as yellow oil.

Step 2: Preparation of [5-methyl-4-[6-(trifluoromethyl)pyridin-3-yl]pyridin-2-yl]methanamine hydrochloride

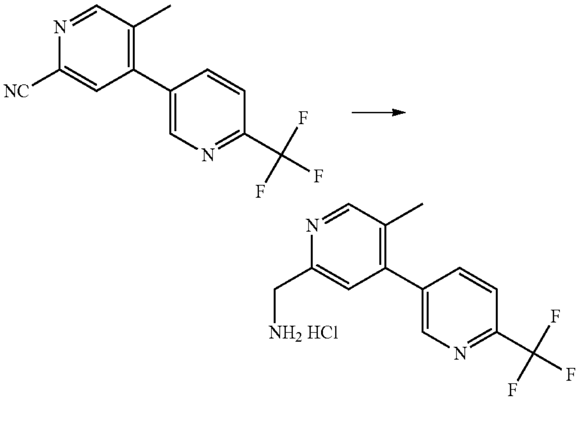

A mixture of 5-methyl-4-[6-(trifluoromethyl)pyridin-3-yl]pyridine-2-carbonitrile (280 mg, 1.06 mmol, 1.00 equiv) in methanol (40 mL), palladium on carbon (50 mg, 0.47 mmol, 0.40 equiv), and concentrated hydrogen chloride (1 mL) was stirred for 10 min at room temperature under hydrogen. The solids were filtered out and the liquid was concentrated under vacuum. This resulted in the title compound (263 mg, 81%) as an off-white solid.

Step 3: Preparation of tert-butyl (2S,4R)-4-fluoro-2-[([5-methyl-4-[6-(trifluoromethyl)pyridin-3-yl]pyridin-2-yl]methyl)carbamoyl]pyrrolidine-1-carboxylate

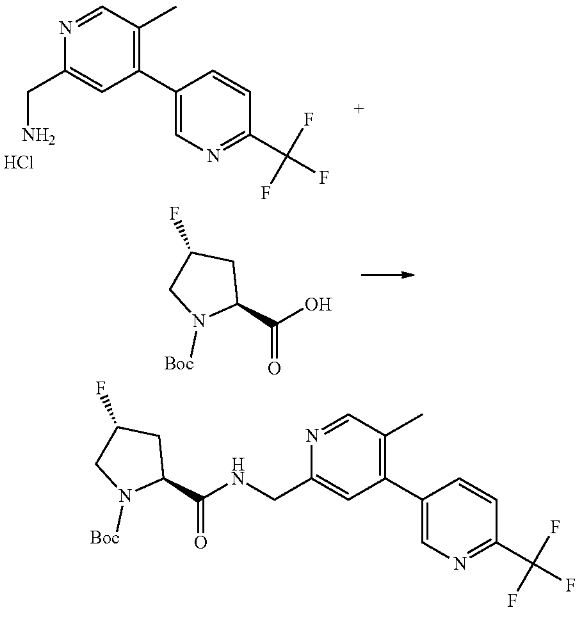

A mixture of [5-methyl-4-[6-(trifluoromethyl)pyridin-3-yl]pyridin-2-yl]methanamine hydrochloride (260 mg, 0.86 mmol, 1.00 equiv) in N,N-dimethylformamide (20 mL), (2S,4R)-1-[(tert-butoxy)carbonyl]-4-fluoropyrrolidine-2-carboxylic acid (200 mg, 0.86 mmol, 1.00 equiv), DIEA (1.11 g, 8.59 mmol, 10.00 equiv), and HATU (392 mg, 1.03 mmol, 1.20 equiv) was stirred for 2 h at room temperature. The reaction was diluted with water, extracted with ethyl acetate, washed with brine, dried over anhydrous sodium sulfate, and concentrated under vacuum. The residue was purified by a silica gel column eluting with dichloromethane/methanol (100:5) to afford the title compound (380 mg, 92%) as brown oil.

Step 4: Preparation of 2S,4R)-4-fluoro-N-([5-methyl-4-[6-(trifluoromethyl)pyridin-3-yl]pyridin-2-yl]methyl)pyrrolidine-2-carboxamide hydrochloride

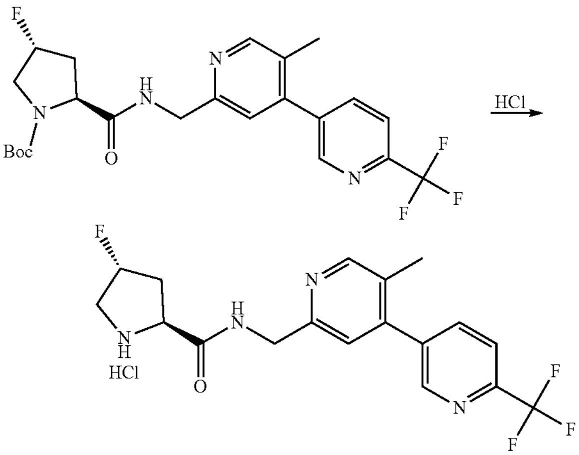

A solution of tert-butyl (2S,4R)-4-fluoro-2-[([5-methyl-4-[6-(trifluoromethyl)pyridin-3-yl]pyridin-2-yl]methyl)carbamoyl]pyrrolidine-1-carboxylate (380 mg, 0.79 mmol, 1.00 equiv) in HCl (saturated solution in 50 mL of 1,4-dioxane) was stirred overnight at room temperature. The resulting mixture was concentrated under vacuum to afford the title compound (285 mg, 86%) as a light brown solid.

Step 5: Preparation of (2S,4R)-4-fluoro-1-(4-fluorophenyl)sulfonyl-N-[[5-methyl-4-[6-(trifluoromethyl)-3-pyridyl]-2-pyridyl]methyl]pyrrolidine-2-carboxamide

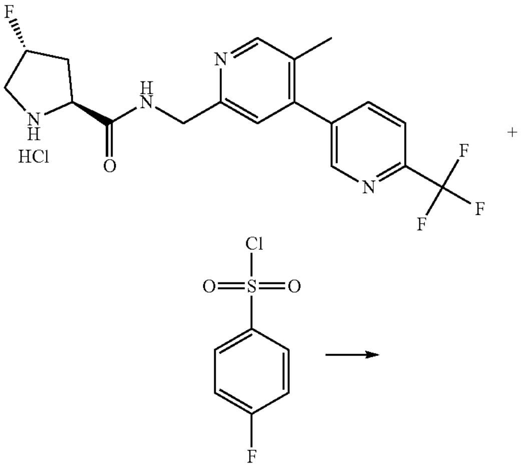

-continued

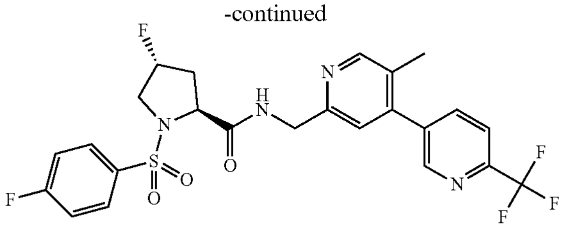

A mixture of (2S,4R)-4-fluoro-N-([5-methyl-4-[6-(trifluoromethyl)pyridin-3-yl]pyridin-2-yl]methyl)pyrrolidine-2-carboxamide hydrochloride (285 mg, 0.680 mmol, 1.000 equiv) in dichloromethane (20 mL), TEA (687 mg, 6.789 mmol, 10.000 equiv), and 4-fluorobenzene-1-sulfonyl chloride (200 mg, 1.028 mmol, 1.500 equiv) was stirred for 2 h at room temperature. The resulting solution was diluted with dichloromethane, washed with brine, dried over anhydrous sodium sulfate, and concentrated under vacuum. The residue was purified by a silica gel column eluting with dichloromethane/methanol (100:10). This resulted in the title compound (71.6 mg, 19%) as a white solid.

$^1$H NMR (300 MHz, $CDCl_3$) δ 8.92-8.83 (m, 2H), 8.52 (s, 1H), 8.18-8.16 (m, 1H), 8.01-7.91 (m, 3H), 7.45-7.40 (m, 3H), 5.27-5.01 (d, J=52.2 Hz, 1H), 4.47-4.44 (m, 2H), 4.23-4.17 (m, 1H), 3.67-3.57 (m, 2H), 2.44-2.41 (m, 1H), 2.38-2.14 (m, 3H), 2.07-2.00 (m, 1H).

Example 97

Preparation of (2R,3S)-3-fluoro-N-([4-fluoro-3-[5-(trifluoromethyl)pyrazin-2-yl]phenyl]methyl)-1-[(4-fluorobenzene)sulfonyl]pyrrolidine-2-carboxamide

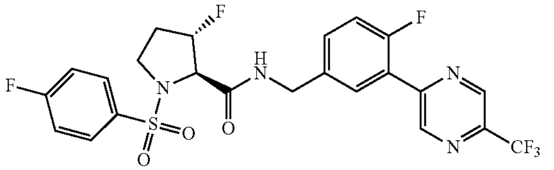 [SMILES: O=C(NCc1ccc(F)c(-c2cnc(C(F)(F)F)cn2)c1)[C@@H]1[C@@H](F)CCN1S(=O)(=O)c1ccc(F)cc1]

Step 1: Preparation of 4-fluoro-3-(5-(trifluoromethyl)pyrazin-2-yl)benzonitrile

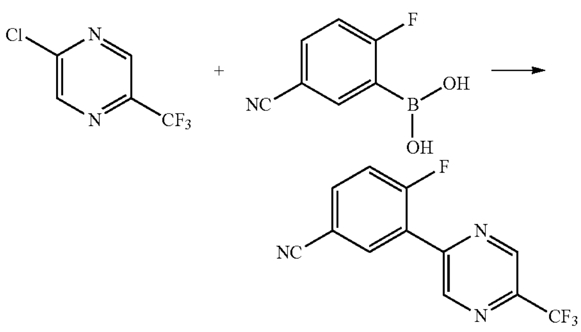

A mixture of (5-cyano-2-fluorophenyl)boronic acid (91 mg, 0.55 mmol, 1.00 equiv), 2-chloro-5-(trifluoromethyl)pyrazine (100 mg, 0.55 mmol, 1.00 equiv), $Pd(PPh_3)_4$ (63 mg, 0.05 mmol, 0.10 equiv), and potassium carbonate (152 mg, 1.10 mmol, 2.00 equiv) in 1,4-dioxane (2 mL)/water(0.4 mL) was stirred overnight at 95° C. under nitrogen. The reaction mixture was diluted with water, extracted with ethyl acetate, dried over anhydrous sodium sulfate, and concentrated under vacuum. The residue was purified by a silica gel column eluting with ethyl acetate/petroleum ether (1:10). This resulted in the title compound (110 mg) as a light yellow solid

Step 2: Preparation of [4-fluoro-3-[5-(trifluoromethyl)pyrazin-2-yl]phenyl]methanamine

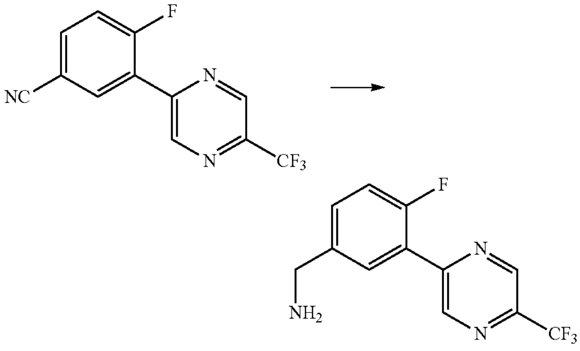

A mixture of 4-fluoro-3-[5-(trifluoromethyl)pyrazin-2-yl]benzonitrile (200 mg, 0.75 mmol, 1.0 equiv), palladium on carbon (50 mg, 0.47 mmol, 1.00 equiv), and HCl (conc.)(1 drop) in methanol (20 mL) was stirred for 20 min at room temperature under hydrogen. The solids were filtered out and the liquid was concentrated under vacuum. This resulted in the title compound (95 mg, 47%) as a brown solid.

Step 3: Preparation of tert-butyl(2S,3R)-2-[([4-fluoro-3-[5-(trifluoromethyl)pyrazin-2-yl]phenyl]methyl)carbamoyl]-3-hydroxypyrrolidine-1-carboxylate

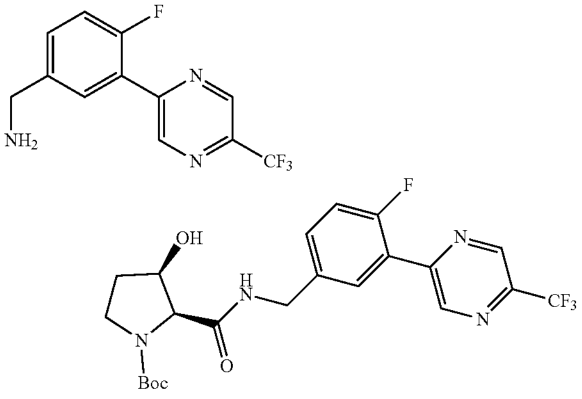

A mixture of (2S,3R)-1-[(tert-butoxy)carbonyl]-3-hydroxypyrrolidine-2-carboxylic acid (90 mg, 0.39 mmol, 1.00 equiv), DIEA (226 mg, 1.75 mmol, 2.00 equiv), and HATU (160 mg, 0.42 mmol, 1.20 equiv) in N,N-dimethylformamide (5 mL) was stirred for 10 min at room temperature. Then [4-fluoro-3-[5-(trifluoromethyl)pyrazin-2-yl]phenyl]

methanamine (95 mg, 0.35 mmol, 1.00 equiv) was added to the reaction mixture. The resulting solution was stirred overnight at room temperature. The reaction solution was diluted with water, extracted with ethyl acetate, dried over anhydrous sodium sulfate, and concentrated under vacuum. This resulted in the title compound (160 mg, 85%) as a light yellow solid.

Step 4: Preparation of tert-butyl (2R,3S)-3-fluoro-2-[([4-fluoro-3-[5-(trifluoromethyl)pyrazin-2-yl]phenyl]methyl)carbamoyl]pyrrolidine-1-carboxylate

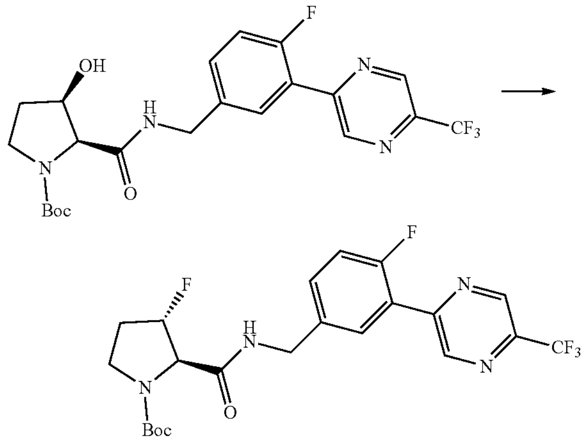

DAST (220 mg, 1.36 mmol, 3.00 equiv) was added dropwise into a stirred solution of tert-butyl (2S,3R)-2-[([4-fluoro-3-[5-(trifluoromethyl)pyrazin-2-yl]phenyl]methyl)carbamoyl]-3-hydroxypyrrolidine-1-carboxylate (220 mg, 0.45 mmol, 1.00 equiv) in dichloromethane (20 mL) at 0° C. The resulting solution was stirred for 5 h at room temperature and quenched by aqueous $NaHCO_3$. The reaction solution was extracted with 100 mL of ethyl acetate, dried over anhydrous sodium sulfate, and concentrated under vacuum. The residue was purified by a silica gel column eluting with ethyl acetate/petroleum ether (1:1) to afford the title compound (65 mg, 29%) as colorless oil.

Step 5: Preparation of (2R,3S)-3-fluoro-N-([4-fluoro-3-[5-(trifluoromethyl)pyrazin-2-yl]phenyl]methyl)pyrrolidine-2-carboxamide hydrochloride

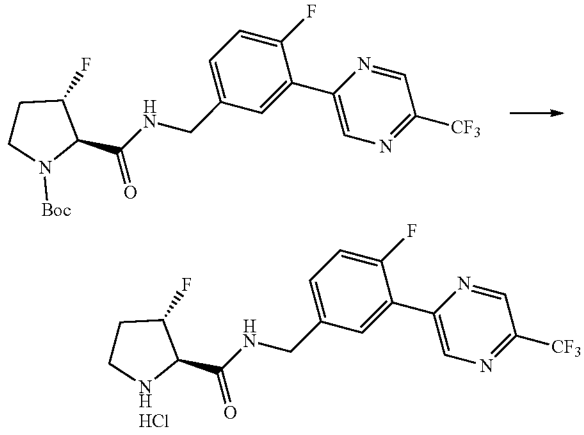

A solution of tert-butyl (2R,3S)-3-fluoro-2-[([4-fluoro-3-[5-(trifluoromethyl)pyrazin-2-yl]phenyl]methyl)carbamoyl]pyrrolidine-1-carboxylate (65 mg, 0.13 mmol, 1.00 equiv) and saturated hydrogen chloride in dioxane (6 mL) was stirred overnight at room temperature and concentrated under vacuum. This resulted in the title compound (60 mg) as a brown solid.

Step 6: Preparation of (2R,3S)-3-fluoro-N-([4-fluoro-3-[5-(trifluoromethyl)pyrazin-2-yl]phenyl]methyl)-1-[(4-fluorobenzene)sulfonyl]pyrrolidine-2-carboxamide

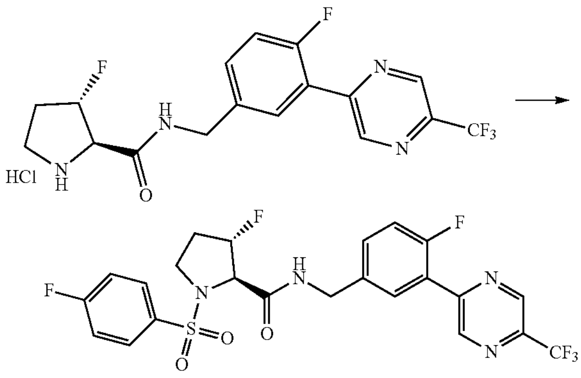

A mixture of (2R,3S)-3-fluoro-N-([4-fluoro-3-[5-(trifluoromethyl)pyrazin-2-yl]phenyl]methyl)pyrrolidine-2-carboxamide hydrochloride (60 mg, 0.14 mmol, 1.00 equiv), TEA (42 mg, 0.42 mmol, 3.00 equiv), and 4-fluorobenzene-1-sulfonyl chloride (30 mg, 0.15 mmol, 1.10 equiv) in dichloromethane (5 mL) was stirred for 3 h at room temperature. The diluted with 50 mL of DCM, washed with water, dried over anhydrous sodium sulfate, and concentrated under vacuum. The residue was purified by a silica gel column eluting with ethyl acetate/petroleum ether (1:2). This resulted in the title compound (23.7 mg, 31%) as a white solid.

$^1H$ NMR (400 MHz, $CDCl_3$) δ 9.23 (s, 1H), 9.02 (s, 1H), 8.01 (dd, J=7.2 Hz, J=2.4 Hz, 1H), 7.87-7.85 (m, 2H), 7.49-7.46 (m, 2H), 7.27-7.22 (m, 3H), 5.44-5.31 (dd, J=50.4 Hz, J=2.4 Hz, 1H), 4.63-4.49 (m, 2H), 4.34-4.29 (d, J=22.0 Hz, 2H), 3.74 (t, J=9.2 Hz, 1H), 3.32-3.26 (m, 1H), 2.16-1.90 (m, 2H).

Example 98

Preparation of (2R,3S)-3-fluoro-N-([3-fluoro-5-[5-(trifluoromethyl)pyrazin-2-yl]phenyl]methyl)-1-[(4-fluorobenzene)sulfonyl]pyrrolidine-2-carboxamide

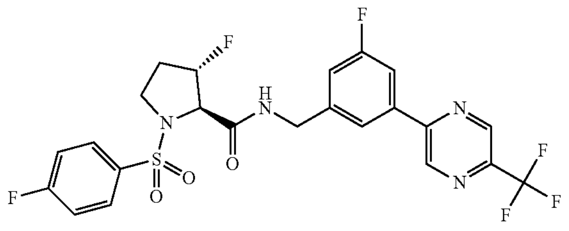 [SMILES: O=C(NCc1cc(F)cc(-c2cnc(C(F)(F)F)cn2)c1)[C@@H]1[C@@H](F)CCN1S(=O)(=O)c1ccc(F)cc1]

Step 1: Preparation of tert-butyl (2S,3R)-2-[([3-fluoro-5-[5-(trifluoromethyl)pyrazin-2-yl]phenyl]methyl)carbamoyl]-3-hydroxypyrrolidine-1-carboxylate

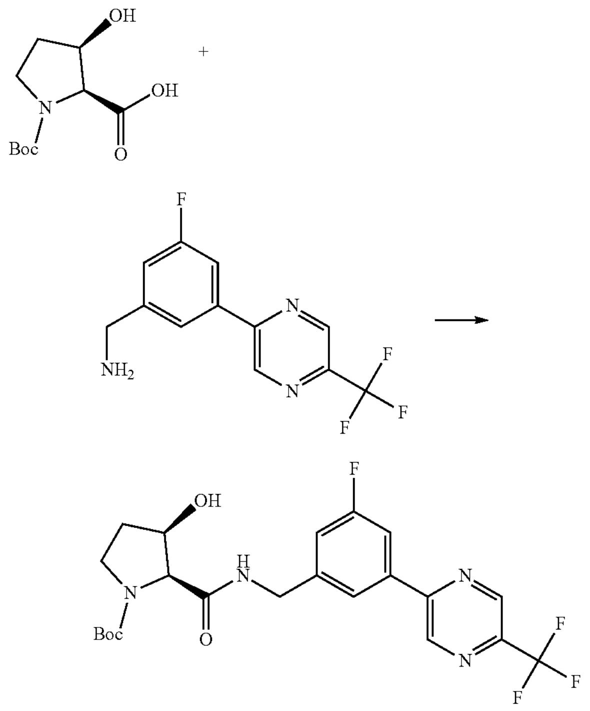

A mixture of (2S,3R)-1-[(tert-butoxy)carbonyl]-3-hydroxypyrrolidine-2-carboxylic acid (358 mg, 1.55 mmol, 1.00 equiv) in N,N-dimethylformamide (30 mL), [3-fluoro-5-[5-(trifluoromethyl)pyrazin-2-yl]phenyl]methanamine (420 mg, 1.55 mmol, 1.00 equiv), DIEA (1 g, 7.74 mmol, 5.00 equiv), and HATU (707 mg, 1.86 mmol, 1.20 equiv) was stirred for overnight at room temperature. The reaction was then diluted with water, extracted with ethyl acetate, washed with brine, dried over anhydrous sodium sulfate, and concentrated under vacuum. The residue was purified by flash chromatography on silica gel eluting with ethyl acetate/petroleum ether (1:1). This resulted in the title compound (400 mg, 53%) as a white solid.

Step 2: Preparation of tert-butyl (2R,3S)-3-fluoro-2-[([3-fluoro-5-[5-(trifluoromethyl)pyrazin-2-yl]phenyl]methyl)carbamoyl]pyrrolidine-1-carboxylate

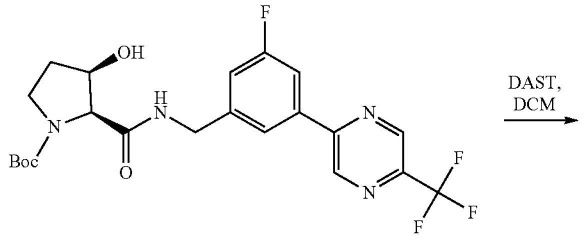

-continued

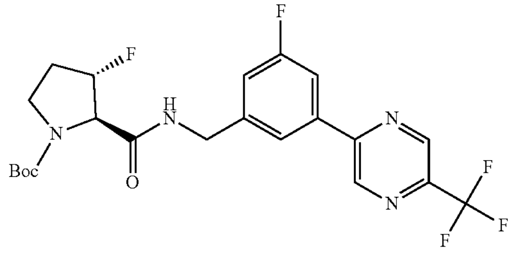

DAST (81 mg, 0.50 mmol, 1.20 equiv) was added dropwise into a solution of tert-butyl (2S,3R)-2-[([3-fluoro-5-[5-(trifluoromethyl)pyrazin-2-yl]phenyl]methyl)carbamoyl]-3-hydroxypyrrolidine-1-carboxylate (200 mg, 0.41 mmol, 1.00 equiv) in dichloromethane (20 mL) at 0° C. under nitrogen. The resulting solution was stirred for 1 h at 5° C. in a water/ice bath. The reaction was then quenched by saturated sodium bicarbonate solution, extracted with dichloromethane, washed with brine, dried over anhydrous sodium sulfate, and concentrated under vacuum. The residue was purified by flash chromatography on silica gel eluting with ethyl acetate/petroleum ether (1:10). This resulted in the title compound (100 mg, 50%) as colorless oil.

Step 3: Preparation of (2R,3S)-3-fluoro-N-[3-fluoro-5-[5-(trifluoromethyl)pyrazin-2-yl]phenyl]pyrrolidine-2-carboxamide hydrochloride

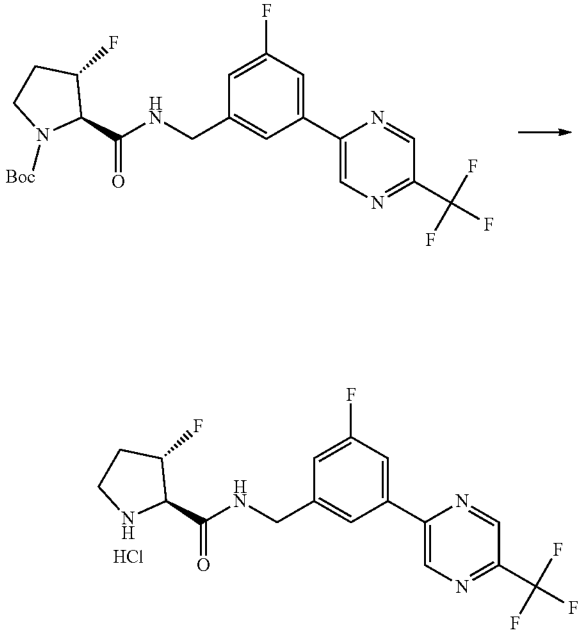

A solution of tert-butyl (2R,3S)-3-fluoro-2-([3-fluoro-5-[5-(trifluoromethyl)pyrazin-2-yl]phenyl]carbamoyl)pyrrolidine-1-carboxylate (100 mg, 0.21 mmol, 1.00 equiv) in saturated HCl (20 mL) in 1,4-dioxane was stirred overnight at room temperature. The resulting mixture was concentrated under vacuum to afford the title compound (75 mg, 87%) as a white solid.

Step 4: Preparation of (2R,3S)-3-fluoro-N-([3-fluoro-5-[5-(trifluoromethyl)pyrazin-2-yl]phenyl]methyl)-1-[(4-fluorobenzene)sulfonyl]pyrrolidine-2-carboxamide

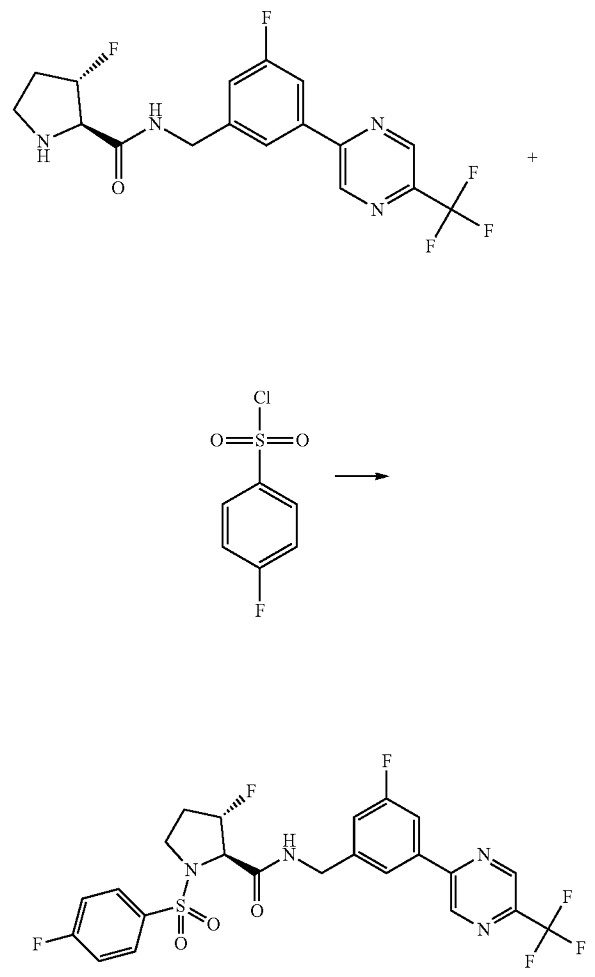

A mixture of (2R,3S)-3-fluoro-N-([3-fluoro-5-[5-(trifluoromethyl)pyrazin-2-yl]phenyl]methyl)pyrrolidine-2-carboxamide hydrochloride (75 mg, 0.18 mmol, 1.00 equiv) in dichloromethane (20 mL), TEA (182 mg, 1.80 mmol, 10.10 equiv), and 4-fluorobenzene-1-sulfonyl chloride (53 mg, 0.27 mmol, 1.50 equiv) was stirred for 2 h at room temperature. The resulting solution was diluted with dichloromethane, washed with brine, dried over anhydrous sodium sulfate, and concentrated under vacuum. The residue was purified by flash chromatography on silica gel eluting with dichloromethane/methanol (10:1) to afford the title compound (32.2 mg, 33%) as a white solid.

$^1$H NMR (400 MHz, DMSO-$d_6$) δ 9.50 (s, 1H), 9.26 (s, 1H), 9.08-9.05 (m, 1H), 8.03 (s, 1H), 8.00-7.95 (m, 3H), 7.51-7.47 (m, 2H), 7.39-7.37 (m, 1H), 5.24-5.11 (d, J=52.4 Hz, 1H), 4.49-4.46 (m, 2H), 4.39-4.33 (m, 1H), 3.70-3.66 (m, 1H), 3.21-3.14 (m, 1H), 2.16-2.10 (m, 2H).

Example 99 and Example 100

Preparation of (2S,3aR,6aS)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide

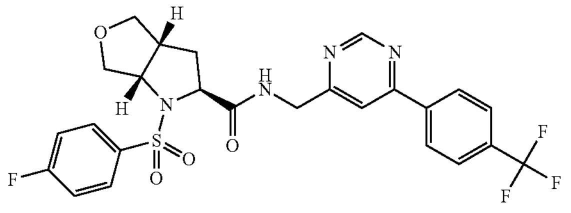 [SMILES: O=C(NCc1cc(-c2ccc(C(F)(F)F)cc2)ncn1)[C@@H]1C[C@H]2COC[C@H]2N1S(=O)(=O)c1ccc(F)cc1]

and (2S,3aS,6aR)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide

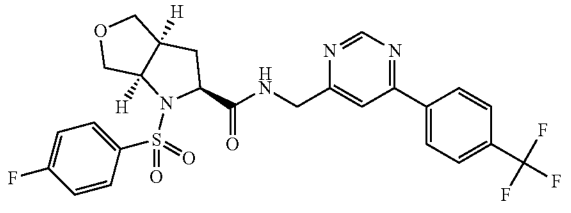 [SMILES: O=C(NCc1cc(-c2ccc(C(F)(F)F)cc2)ncn1)[C@@H]1C[C@@H]2COC[C@@H]2N1S(=O)(=O)c1ccc(F)cc1]

Step 1: Preparation of 3,6-dioxabicyclo[3.1.0]hexane

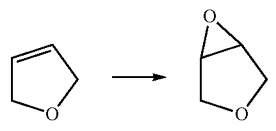 [SMILES: C1=CCOC1 ; C1OCC2OC12]

m-CPBA (88 g, 509.95 mmol, 1.20 equiv) was added in several batches into a solution of 2,5-dihydrofuran (30 g, 428.02 mmol, 1.00 equiv) in dichloromethane (300 mL) at 0° C. After 12 h at room temperature the resulting solution was diluted with saturated $Na_2SO_3$ and stirred for 0.5 h at room temperature. The resulting mixture was washed with saturated sodium bicarbonate and brine, dried over anhydrous sodium sulfate, and concentrated under vacuum at low temperature. This resulted in the title compound (30 g, crude) as colorless oil Step 2: Preparation of (3R,4S)-4-(prop-2-en-1-yl)oxolan-3-ol

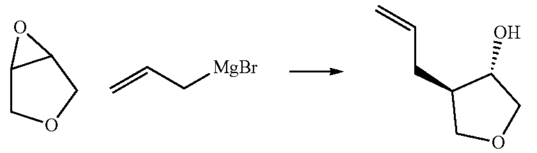

Bromo(prop-2-en-1-yl)magnesium (300 mL, 2.06 mol, 2.00 equiv) was added dropwise into a mixture of 3,6-dioxabicyclo[3.1.0]hexane (12.9 g, 149.84 mmol, 1.00 equiv) and CuI (2.85 g, 14.96 mmol, 0.10 equiv) in tetrahydrofuran (100 mL) at 0-5° C. under nitrogen. The resulting solution was stirred for 3 h at 0° C., quenched by $NH_4Cl$ (aq.), and extracted with ethyl acetate. The combined extracts were washed with brine, dried over anhydrous sodium sulfate, and concentrated under vacuum. The residue was purified by a silica gel column eluting with ethyl acetate/petroleum ether (1:6) to afford the title compound (5 g, 26%) as light yellow oil.

Step 3: Preparation of 4-(prop-2-en-1-yl)oxolan-3-one

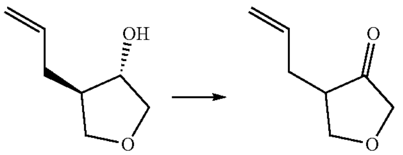

A mixture of (3S,4R)-4-(prop-2-en-1-yl)oxolan-3-ol (3.5 g, 27.31 mmol, 1.00 equiv) and PCC (13 g, 60.31 mmol, 2.00 equiv) in dichloromethane (160 mL) was stirred for 12 h at room temperature. The reaction was then quenched by water, extracted with ethyl acetate, washed with brine, dried over anhydrous sodium sulfate, and concentrated under vacuum. This resulted in the title compound (2.0 g, 58%) as a gray liquid.

Step 4: Preparation of N-[(3Z)-4-(prop-2-en-1-yl)oxolan-3-ylidene]hydroxylamine

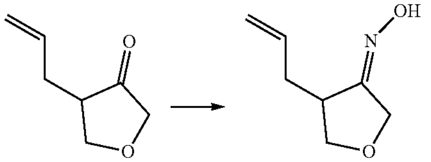

A mixture of 4-(prop-2-en-1-yl)oxolan-3-one (2.25 g, 17.84 mmol, 1.00 equiv), $NH_2OH.HCl$ (2.46 g, 35.40 mmol, 2.00 equiv), and pyridine (1.4 g, 17.48 mmol, 1.00 equiv) in ethanol (50 mL) was stirred for 1.5 h at room temperature. The resulting mixture was concentrated under vacuum. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10) to afford the title compound (1.3 g, 52%) as colorless oil.

Step 5: Preparation of 4-(prop-2-en-1-yl)oxolan-3-amine

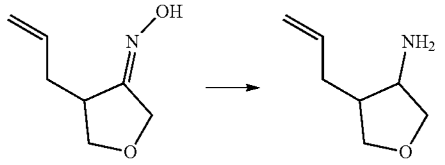

$LiAlH_4$ (1.186 g, 31.25 mmol, 3.00 equiv) was added batch wise into a solution of N-[(3Z)-4-(prop-2-en-1-yl)oxolan-3-ylidene]hydroxylamine (1.17 g, 8.29 mmol, 1.00 equiv) in tetrahydrofuran (25 mL) at 0-5° C. under nitrogen. The resulting solution was stirred for 1 h at room temperature and 2 h at 45° C. The reaction was then quenched by aqueous $Na_2SO_4$. The solids were filtered out and the filtrate was concentrated under vacuum. This resulted in the title compound (1.46 g, crude) as a colorless liquid.

Step 6: Preparation of 4-fluoro-N-[4-(prop-2-en-1-yl)oxolan-3-yl]benzene-1-sulfonamide

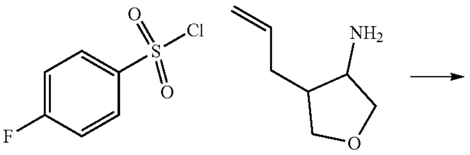

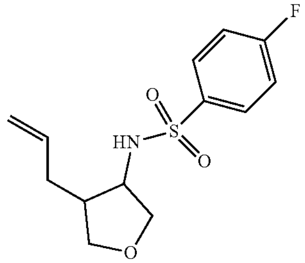

A solution of 4-(prop-2-en-1-yl)oxolan-3-amine (1.35 g, 10.61 mmol, 1.00 equiv), 4-fluorobenzene-1-sulfonyl chloride (1.65 g, 8.48 mmol, 0.80 equiv), TEA (2.14 g, 21.15 mmol, 2.00 equiv), and 4-dimethylaminopyridine (50 mg, 0.41 mmol, 0.05 equiv) in tetrahydrofuran (50 mL) was stirred for 1 h at room temperature. The mixture was diluted with water, extracted with ethyl acetate, washed with brine, dried over anhydrous sodium sulfate, and concentrated under vacuum. The residue was purified by a silica gel column eluting with ethyl acetate/petroleum ether (1:9) to afford the title compound (1.46 g, 48%) as orange oil.

Step 7: Preparation of [1-[(4-fluorobenzene)sulfonyl]-hexahydro-1H-furo[3,4-b]pyrrol-2-yl]methanol

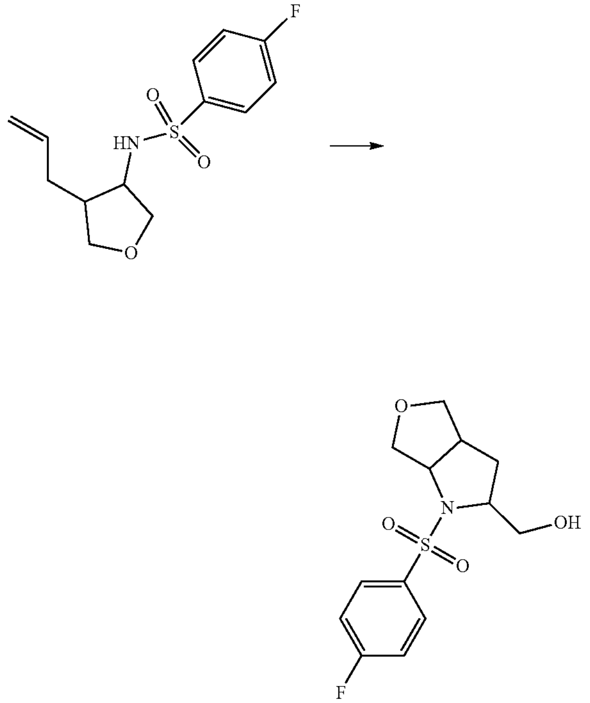 [SMILES: C=CCC1COCC1NS(=O)(=O)c1ccc(F)cc1 ; O=S(=O)(c1ccc(F)cc1)N1C(CO)CC2COCC21]

A mixture of 4-fluoro-N-[4-(prop-2-en-1-yl)oxolan-3-yl]benzene-1-sulfonamide (1.57 g, 5.50 mmol, 1.00 equiv), potassium peroxymonosulfate (6.77 g, 11.01 mmol, 2.00 equiv), and TsOH (105.8 mg, 0.61 mmol, 0.10 equiv) in water (15 mL)/MeCN (30 mL) was stirred for 12 h at 50° C. The reaction mixture was cooled to room temperature, quenched by saturated sodium bicarbonate, extracted with ethyl acetate, washed with brine, dried over anhydrous sodium sulfate, and concentrated under vacuum. The residue was purified by a silica gel column eluting with ethyl acetate/petroleum ether (1:3) to afford the title compound (700 mg, 42%) as light yellow oil Step 8: Preparation of 1-[(4-fluorobenzene)sulfonyl]-hexahydro-1H-furo[3,4-b]pyrrole-2-carboxylic acid as an off-white

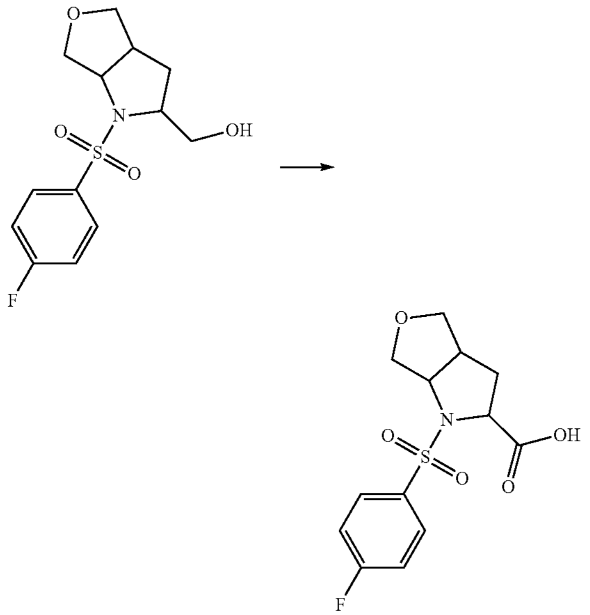

A solution of [1-[(4-fluorobenzene)sulfonyl]-hexahydro-1H-furo[3,4-b]pyrrol-2-yl]methanol (700 mg, 2.32 mmol, 1.00 equiv) in acetone (40 mL) was mixed with a solution of $CrO_3$ (1.163 g, 11.63 mmol, 5.00 equiv) in water(5 mL) containing sulfuric acid (1 mL). The resulting solution was stirred for 2 h at room temperature. The reaction was then quenched by methanol. After 15 min the mixture was poured into 200 mL of brine. The resulting solution was extracted with ethyl acetate. The combined extracts were washed with brine, dried over anhydrous sodium sulfate, and concentrated under vacuum. This resulted in the title compound (630 mg, 86%) as an off-white solid.

Step 9: Preparation of (2S,3aR,6aS)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide And (2R,3aS,6aR)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide

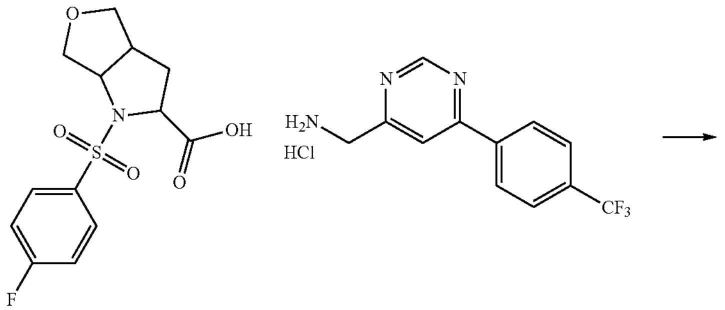

-continued

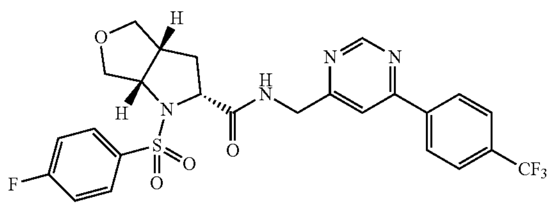

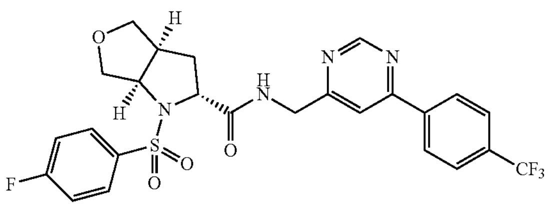

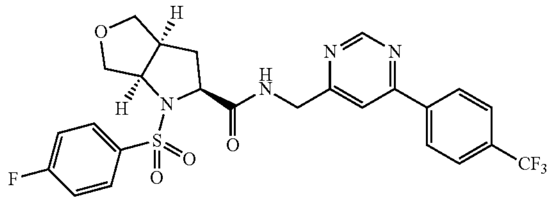

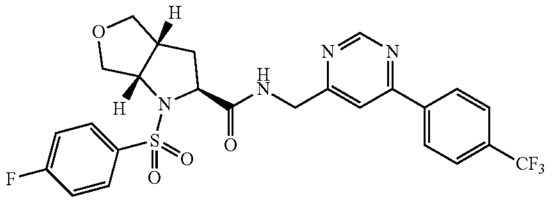

A mixture of 1-[(4-fluorobenzene)sulfonyl]-hexahydro-1H-furo[3,4-b]pyrrole-2-carboxylic acid (600 mg, 1.90 mmol, 1.00 equiv), HATU (794.2 mg, 2.09 mmol, 1.10 equiv), DIEA (735.3 mg, 5.69 mmol, 3.00 equiv), and [6-[4-(trifluoromethyl)phenyl]pyrimidin-4-yl]methanamine hydrochloride (550 mg, 1.90 mmol, 1.00 equiv) in N,N-dimethylformamide (25 mL) was stirred for 2 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:3). The mixture was separated by Chiral-Prep-HPLC to afford (2S,3aR,6aS)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide (47.9 mg, 5%) as a white solid. $t_R$=4.84 min (Repaired IA (CHIRALPAK IA), 0.46×10 cm, 5 μm, Hex(0.1% TEA):EtOH=50:50, 1.0 ml/min).

$^1$H NMR (300 MHz, $CDCl_3$) δ 9.26 (s, 1H), 8.28-8.26 (d, J=6 Hz, 2H), 7.89-7.84 (m, 3H), 7.77-7.74 (d, J=9 Hz, 2H), 7.26-7.11 (m, 3H), 4.68-4.60 (m, 2H), 4.55-4.50 (m, 2H), 4.10-4.06 (m, 1H), 3.73-3.70 (m, 1H), 3.61-3.54 (m, 2H), 3.29-3.19 (m, 1H), 2.42-2.29 (m, 1H), 2.12-2.02 (m, 1H).

(2R,3aS,6aR)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide (51.5 mg, 5%) was also isolated as a white solid. $t_R$=12.96 min (Lux Cellulose-4, 0.46×15 cm, 5 μm, Hex(0.1% TEA):EtOH=50:50, 1.0 ml/min).

$^1$H NMR (300 MHz, $CDCl_3$) δ 9.24 (s, 1H), 8.36-8.34 (d, J=9 Hz, 2H), 8.05 (s, 1H), 7.96-7.91 (m, 2H), 7.87-7.83 (b, 1H), 7.76-7.73 (d, J=9 Hz, 2H), 7.33-7.26 (m, 2H), 4.85-4.64 (m, 2H), 4.42-4.38 (d, J=12 Hz, 1H), 4.33-4.27 (m, 2H), 3.74-3.67 (m, 2H), 2.88-2.79 (m, 1H), 2.36-2.31 (m, 1H), 1.94-1.83 (m, 1H).

(2S,3aS,6aR)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide (36 mg, 3%) was isolated as a white solid. $t_R$=3.27 min (Repaired IA (CHIRALPAK IA), 0.46×10 cm, 5 μm, Hex(0.1% TEA):EtOH=50:50, 1.0 ml/min).

$^1$H NMR (300 MHz, $CDCl_3$) δ 9.25 (s, 1H), 8.28-8.26 (d, J=6 Hz, 2H), 7.89-7.84 (m, 3H), 7.77-7.74 (d, J=9 Hz, 2H), 7.26-7.12 (m, 3H), 4.62-4.61 (m, 2H), 4.56-4.50 (m, 2H), 4.10-4.06 (m, 1H), 3.73-3.70 (m, 1H), 3.58-3.53 (m, 2H), 3.29-3.19 (m, 1H), 2.35-2.28 (m, 1H), 2.12-2.02 (m, 1H).

(2R,3aR,6aS)-1-[(4-fluorobenzene)sulfonyl]-N-([6-[4-(trifluoromethyl)phenyl]pyrimidin-4-yl]methyl)-hexahydro-1H-furo[3,4-b]pyrrole-2-carboxamide (34.3 mg, 3%) was isolated as a white solid. $t_R$=6.60 min (Lux Cellulose-4, 0.46×15 cm, 5 μm, Hex(0.1% TEA):EtOH=50:50, 1.0 ml/min).

$^1$H NMR (300 MHz, $CDCl_3$) δ 9.24 (s, 1H), 8.37-8.34 (d, J=8.5 Hz, 2H), 8.04 (s, 1H), 7.96-7.91 (q, 2H), 7.86-7.83 (m, 1H), 7.76-7.73 (d, J=9 Hz, 2H), 7.33-7.27 (m, 2H), 4.86-4.64 (m, 2H), 4.42-4.38 (d, J=12 Hz, 1H), 4.33-4.27 (m, 2H), 3.74-3.67 (m, 2H), 2.86-2.82 (m, 1H), 2.36-2.31 (m, 1H), 1.94-1.84 (m, 1H).

The stereochemistry for the bicyclic ring of the above compounds was arbitrarily assigned. The 2-proline stereochemistry is as shown.

Example 101

Preparation of (2S,4R)—N-([5-chloro-4-[6-(trifluoromethyl)pyridin-3-yl]pyridin-2-yl]methyl)-4-fluoro-1-[(4-fluorobenzene)sulfonyl]pyrrolidine-2-carboxamide

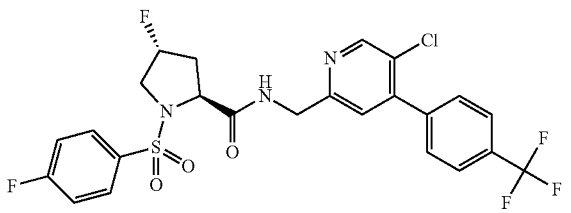 [SMILES: O=C(NCc1cc(-c2ccc(C(F)(F)F)cc2)c(Cl)cn1)[C@@H]1C[C@@H](F)CN1S(=O)(=O)c1ccc(F)cc1]

Step 1: Preparation of 2,5-dichloro-4-[6-(trifluoromethyl)pyridin-3-yl]pyridine

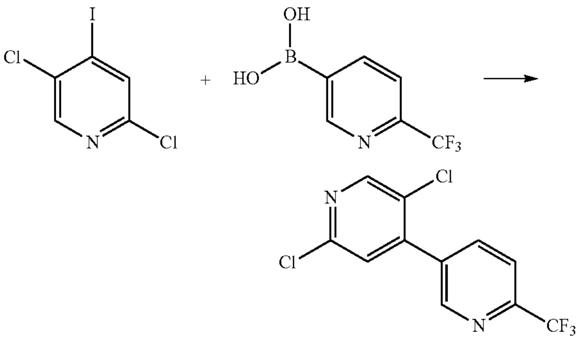

A mixture of 2,5-dichloro-4-iodopyridine (10 g, 36.511 mmol, 1.00 equiv), [6-(trifluoromethyl)pyridin-3-yl]boronic acid (6.7 g, 35.094 mmol, 1.00 equiv), Pd(dppf)$Cl_2$(2.67 g, 3.649 mmol, 0.10 equiv), 1,4-dioxane (250 mL), potassium carbonate (15 g, 108.534 mmol, 3.00 equiv), and water (25 mL) was stirred for 12 h at 80° C. under nitrogen. The solids were filtered out and the solution was concentrated under vacuum. The residue was dissolved in ethyl acetate, washed with brine, dried over anhydrous sodium sulfate, and concentrated under vacuum. The residue was purified by flash chromatography on silica gel eluting with ethyl acetate/petroleum ether (1:20). This resulted in the title compound (9.9 g, 93%) as a white solid.

Step 2: Preparation of methyl 5-chloro-4-[6-(trifluoromethyl)pyridin-3-yl]pyridine-2-carboxylate

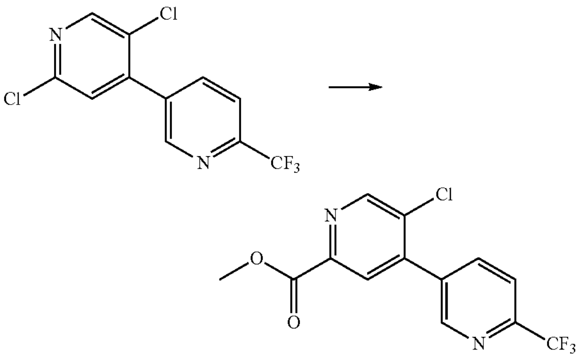

A mixture of 2,5-dichloro-4-[6-(trifluoromethyl)pyridin-3-yl]pyridine (8.8 g, 30.027 mmol, 1.00 equiv), Pd(dppf)$Cl_2$ (2.2 g, 3.007 mmol, 0.10 equiv), methanol (120 mL), TEA (9.1 g, 89.930 mmol, 2.995 equiv) was stirred for 12 h at 60° C. under nitrogen. The solids were filtered out. The resulting solution was extracted with ethyl acetate, washed with brine, dried over anhydrous sodium sulfate, and concentrated under vacuum. The residue was purified by flash chromatography on silica gel eluting with ethyl acetate/petroleum ether (1:10). This resulted in the title compound (4.5 g, 47%) as a white solid.

Step 3: Preparation of [5-chloro-4-[6-(trifluoromethyl)pyridin-3-yl]pyridin-2-yl]methanol

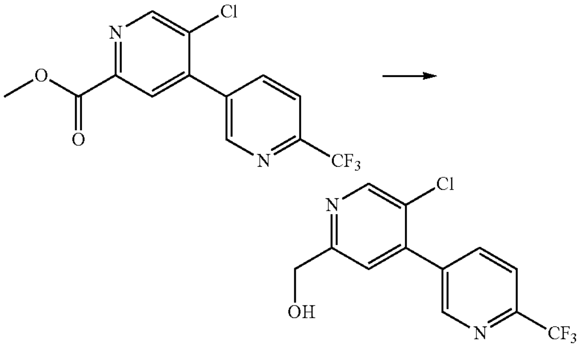

DIBAL-H (47.5 mL, 1M in hexanes, 3.00 equiv) was added dropwise into a solution of methyl 5-chloro-4-[6-(trifluoromethyl)pyridin-3-yl]pyridine-2-carboxylate (5.0 g, 15.790 mmol, 1.00 equiv) in dichloromethane (200 mL) at −70° C. under nitrogen. The resulting solution was stirred for 30 min at −70° C. The reaction was then quenched by methanol at −70° C. and then NaBH4 (0.9 g) was added at 0° C. After 10 min at 0° C. the mixture was then quenched by 1N of HCl at 0° C. The resulting solution was extracted with ethyl acetate, washed with saturated sodium bicarbonate and brine, dried over anhydrous sodium sulfate, and concentrated under vacuum. The residue was purified by flash chromatography on silica gel eluting with ethyl acetate/petroleum ether (1:1). This resulted in the title compound (4.2 g, 92%) as a light yellow solid.

Step 4: Preparation of 2-([5-chloro-4-[6-(trifluoromethyl)pyridin-3-yl]pyridin-2-yl]methyl)-2,3-dihydro-1H-isoindole-1,3-dione

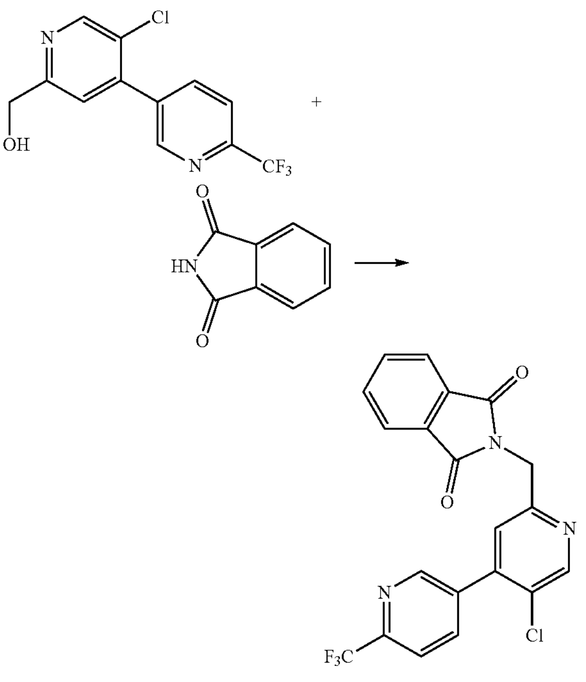

DIAD (6.0 g, 29.672 mmol, 1.992 equiv) was added dropwise into a mixture of [5-chloro-4-[6-(trifluoromethyl)pyridin-3-yl]pyridin-2-yl]methanol (4.3 g, 14.897 mmol, 1.000 equiv), 2,3-dihydro-1H-isoindole-1,3-dione (4.4 g, 29.905 mmol, 2.008 equiv), and $PPh_3$ (7.8 g, 29.739 mmol, 1.996 equiv) in tetrahydrofuran (200 mL) at 0° C. under nitrogen. After 12 h at room temperature the resulting mixture was concentrated under vacuum. The residue was purified by flash chromatography on silica gel eluting with ethyl acetate/petroleum ether (1:10). This resulted in the title compound (6.0 g, 96%) as an off-white solid.

Step 5: Preparation of [5-chloro-4-[6-(trifluoromethyl)pyridin-3-yl]pyridin-2-yl]methanamine

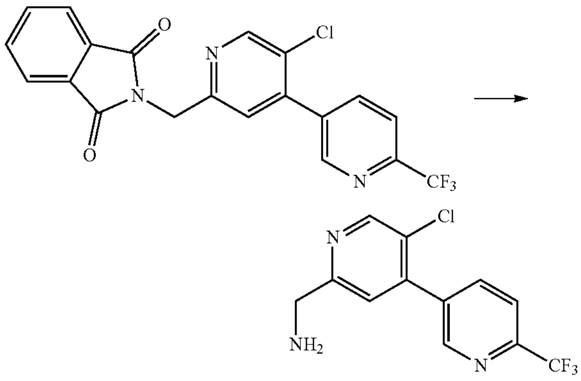

A mixture of 2-([5-chloro-4-[6-(trifluoromethyl)pyridin-3-yl]pyridin-2-yl]methyl)-2,3-dihydro-1H-isoindole-1,3-dione (6.0 g, 14.362 mmol, 1.000 equiv), methanol (150 mL), and $NH_2NH_2.H_2O$ (7.2 g, 143.826 mmol, 10.014 equiv) was stirred for 12 h at room temperature. The resulting mixture was concentrated under vacuum and the residue was dissolved in ethyl acetate. The solids were filtered out and the liquid was concentrated under vacuum. This resulted in the title compound (7.5 g) as a light yellow solid.

Step 6: Preparation of tert-butyl (2S,4R)-2-[([5-chloro-4-[6-(trifluoromethyl)pyridin-3-yl]pyridin-2-yl]methyl)carbamoyl]-4-fluoropyrrolidine-1-carboxylate

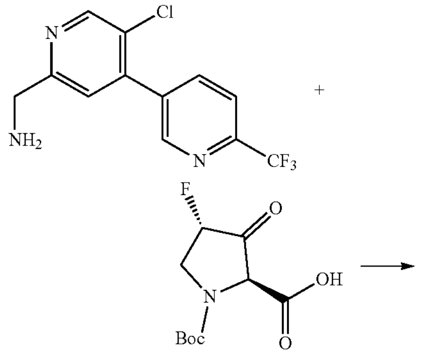

-continued

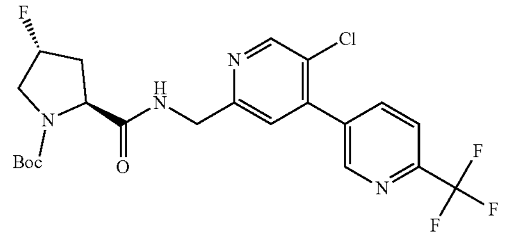

A mixture of (2S,4R)-1-[(tert-butoxy)carbonyl]-4-fluoropyrrolidine-2-carboxylic acid (4.1 g, 17.579 mmol, 1.00 equiv), N,N-dimethylformamide (50 mL), DIEA (4.5 g, 34.818 mmol, 1.98 equiv), HATU (7.9 g, 20.777 mmol, 1.18 equiv), and [5-chloro-4-[6-(trifluoromethyl)pyridin-3-yl]pyridin-2-yl]methanamine (7.5 g, 26.072 mmol, 1.48 equiv) was stirred for 1 h at room temperature. The resulting solution was diluted with ethyl acetate, washed with brine, dried over anhydrous sodium sulfate, and concentrated under vacuum. The residue was purified by flash chromatography on silica gel eluting with ethyl acetate/petroleum ether (1:1). This resulted in the title compound (4.5 g, 51%) as an off-white solid.

Step 7: Preparation of (2S,4R)—N-([5-chloro-4-[6-(trifluoromethyl)pyridin-3-yl]pyridin-2-yl]methyl)-4-fluoropyrrolidine-2-carboxamide

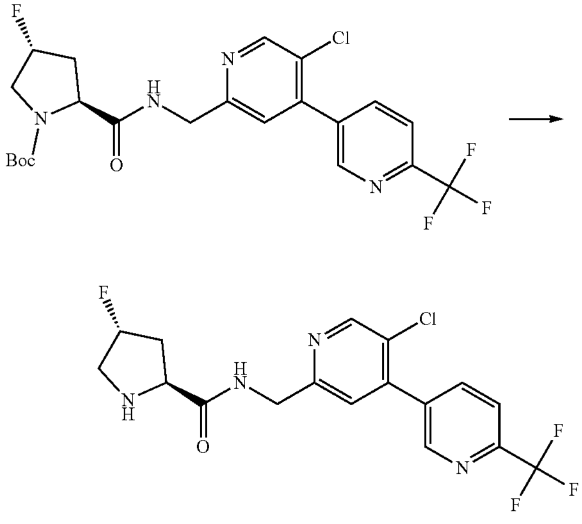

A solution of tert-butyl (2S,4R)-2-[([5-chloro-4-[6-(trifluoromethyl)pyridin-3-yl]pyridin-2-yl]methyl)carbamoyl]-4-fluoropyrrolidine-1-carboxylate (3.5 g, 6.960 mmol, 1.00 equiv) in dichloromethane (100 mL) and trifluoroacetic acid (20 mL) was stirred for 2 h at room temperature. The resulting mixture was concentrated under vacuum. The residue was dissolved in water. The pH value of the solution was adjusted to 8 with saturated sodium bicarbonate. The resulting solution was extracted with ethyl acetate, washed with brine, dried over anhydrous sodium sulfate, and concentrated under vacuum. This resulted in the title compound (2.5 g, 89%) as an off-white solid.

Step 8: (2S,4R)—N-([5-chloro-4-[6-(trifluoromethyl)pyridin-3-yl]pyridin-2-yl]methyl)-4-fluoro-1-[(4-fluorobenzene)sulfonyl]pyrrolidine-2-carboxamide

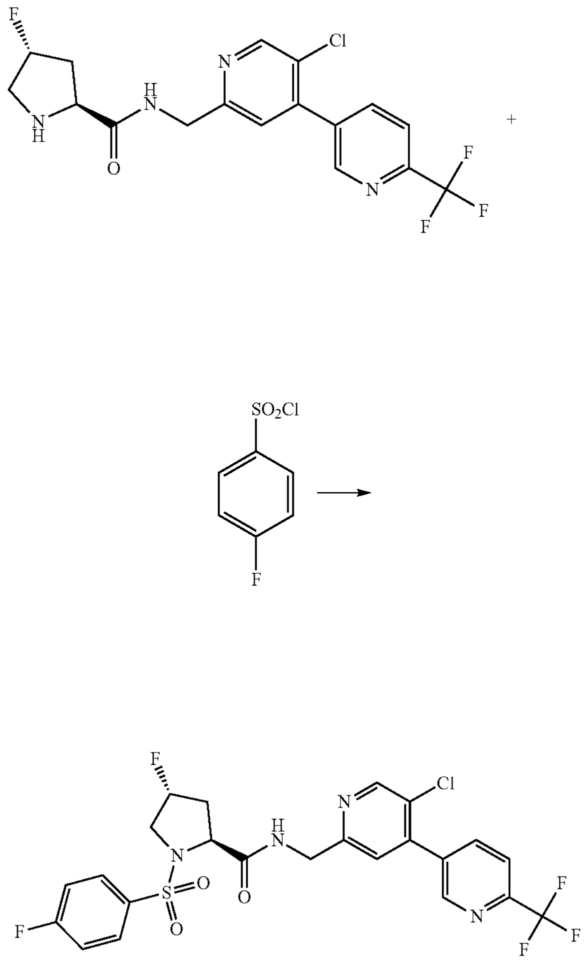

A solution of (2S,4R)—N-([5-chloro-4-[6-(trifluoromethyl)pyridin-3-yl]pyridin-2-yl]methyl)-4-fluoropyrrolidine-2-carboxamide (2.5 g, 6.207 mmol, 1.00 equiv), dichloromethane (100 mL), TEA (1.9 g, 18.777 mmol, 3.025 equiv), and 4-fluorobenzene-1-sulfonyl chloride (1.3 g, 6.680 mmol, 1.08 equiv) was stirred for 12 h at room temperature. The resulting solution was diluted with ethyl acetate, washed with brine, dried over anhydrous sodium sulfate, and concentrated under vacuum. The residue was purified by flash chromatography on silica gel eluting with ethyl acetate/petroleum ether (1/1). The crude product was purified by re-crystallization from ethyl acetate to afford the title compound (2.66 g, 76%) as a white solid.

$^1H$ NMR (400 MHz, $CDCl_3$) δ 8.89 (m, 1H), 8.69 (s, 1H), 8.08-8.06 (m, 1H), 7.89-7.80 (m, 3H), 7.67-7.64 (br, 1H), 7.47 (s, 1H), 7.28-7.21 (m, 2H), 5.13-5.00 (d, J=52 Hz, 1H), 4.86-4.80 (m, 1H), 4.60-4.55 (m, 1H), 4.30-4.26 (m, 1H), 3.94-3.61 (m, 2H), 2.55-2.21 (m, 2H).

Example 102

Preparation of (2S,4R)-4-fluoro-N-([5-fluoro-4-[5-(trifluoromethyl)pyrazin-2-yl]pyridin-2-yl]methyl)-1-[(4-fluorobenzene)sulfonyl]pyrrolidine-2-carboxamide

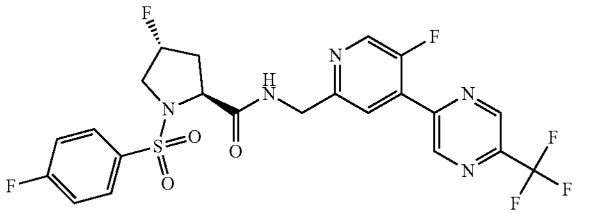 [SMILES: O=C(NCc1cc(-c2cnc(C(F)(F)F)cn2)c(F)cn1)[C@@H]1C[C@@H](F)CN1S(=O)(=O)c1ccc(F)cc1]

Step 1: Preparation of 2-chloro-5-fluoro-4-(tetramethyl-1,3,2-dioxaborolan-2-yl)pyridine

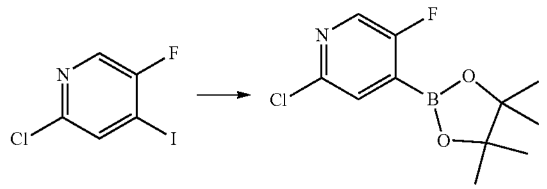 [SMILES: Fc1cnc(Cl)cc1I ; CC1(C)OB(c2cc(Cl)ncc2F)OC1(C)C]

A mixture of 2-chloro-5-fluoro-4-iodopyridine (500 mg, 1.94 mmol, 1.00 equiv), 4,4,5,5-tetramethyl-2-(tetramethyl-1,3,2-dioxaborolan-2-yl)-1,3,2-dioxaborolane (544 mg, 2.14 mmol, 1.10 equiv), KOAc (572 mg, 5.83 mmol, 3.00 equiv), and Pd(dppf)$Cl_2$ (142 mg, 0.19 mmol, 0.10 equiv) in 1,4-dioxane (4 mL) was stirred for 14 h at 100° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:5) to afford the title compound (272 mg) as a yellow solid.

Step 2: Preparation of 2-(2-chloro-5-fluoropyridin-4-yl)-5-(trifluoromethyl)pyrazine

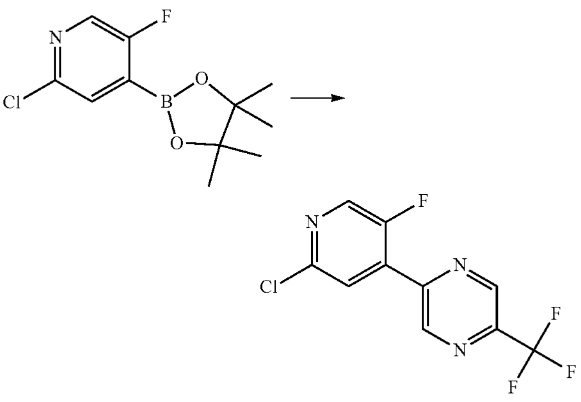

A mixture of (2-chloro-5-fluoropyridin-4-yl)boronic acid (3 g, 17.11 mmol, 3.10 equiv), 2-chloro-5-(trifluoromethyl)pyrazine (1 g, 5.48 mmol, 1.00 equiv), Pd(dppf)$Cl_2$ (200 mg, 0.27 mmol, 0.05 equiv), and potassium carbonate (2.26 g, 16.35 mmol, 3.00 equiv) in water (2 mL)/1,4-dioxane (20 mL) was stirred for 14 h at 75° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10). This resulted in the title compound (500 mg, 33%) as a white solid.

Step 3: Preparation of 5-fluoro-4-[5-(trifluoromethyl)pyrazin-2-yl]pyridine-2-carbonitrile

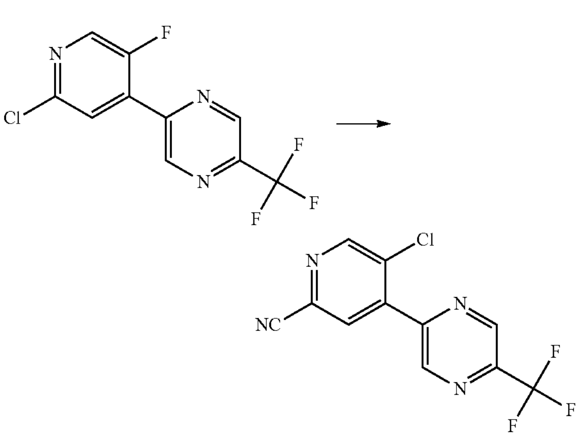

A mixture of 2-(2-chloro-5-fluoropyridin-4-yl)-5-(trifluoromethyl)pyrazine (500 mg, 1.80 mmol, 1.00 equiv), $Zn(CN)_2$ (253 mg, 2.15 mmol, 1.20 equiv), $Pd_2(dba)_3.CHCl_3$ (186 mg, 0.18 mmol, 0.10 equiv), and dppf (200 mg, 0.36 mmol, 0.20 equiv) in 10 mL of N,N-dimethylformamide was irradiated with microwave radiation for 1 h under nitrogen at 100° C. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10) to afford the title compound (250 mg, 52%) as a yellow solid Step 4: Preparation of [5-fluoro-4-[5-(trifluoromethyl)pyrazin-2-yl]pyridin-2-yl]methanamine hydrochloride

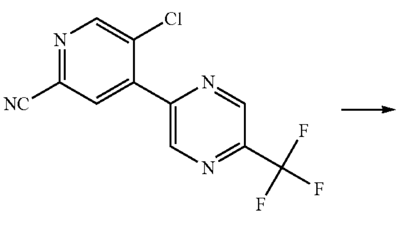

-continued

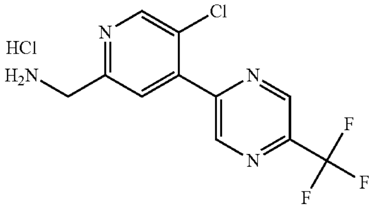

A suspension of 5-fluoro-4-[5-(trifluoromethyl)pyrazin-2-yl]pyridine-2-carbonitrile (200 mg, 0.75 mmol, 1.00 equiv), palladium on carbon (50 mg), and hydrogen chloride (0.5 mL, conc.) in 20 mL of methanol was stirred for 1 min at room temperature under hydrogen. The solids were filtered out. The filtrate was concentrated under vacuum to afford the title compound (120 mg) as a brown solid.

Step 5: Preparation of (2S,4R)-4-fluoro-N-([5-fluoro-4-[5-(trifluoromethyl)pyrazin-2-yl]pyridin-2-yl]methyl)-1-[(4-fluorobenzene)sulfonyl]pyrrolidine-2-carboxamide

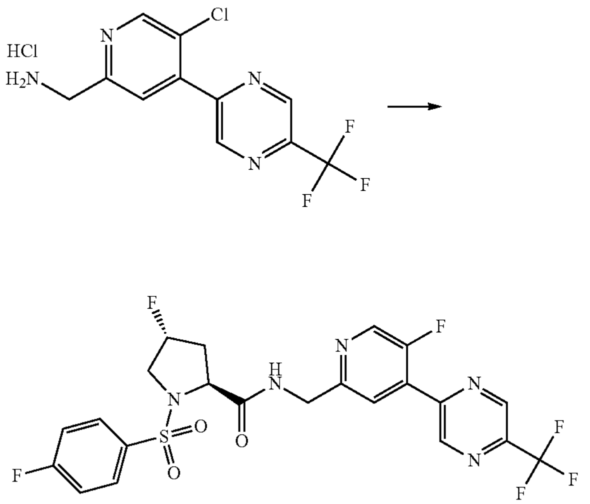

A mixture of (2S,4R)-4-fluoro-1-[(4-fluorobenzene)sulfonyl]pyrrolidine-2-carboxylic acid (47 mg, 0.16 mmol, 1.00 equiv), [5-fluoro-4-[5-(trifluoromethyl)pyrazin-2-yl]pyridin-2-yl]methanamine hydrochloride (50 mg, 0.16 mmol, 1.00 equiv), HATU (74 mg, 0.19 mmol, 1.20 equiv), and DIEA (63 mg, 0.49 mmol, 3.00 equiv) in 3 mL of tetrahydrofuran was stirred for 14 h at room temperature. The mixture was diluted with water and extracted with ethyl acetate. The combined extracts were washed with brine, dried over anhydrous sodium sulfate, and concentrated under vacuum. The crude product was purified by Prep-HPLC to afford the title compound (19.7 mg, 22%) as a white solid.

$^1H$ NMR (300 MHz, $CDCl_3$) δ 9.32 (s, 1H), 9.11 (s, 1H), 8.67 (s, 1H), 8.21 (s, 1H), 8.20-7.90 (m, 3H), 7.29-7.20 (m, 2H), 5.13-5.0 (d, J=39 Hz, 1H), 4.80-4.76 (m, 1H), 4.28-4.24 (t, 1H), 3.92-3.75 (m, 2H), 2.55-2.45 (m, 1H), 2.39-2.22 (m, 1H).

Example 103

Preparation of (2R,3S)-3-fluoro-1-(4-fluorophenylsulfonyl)-N-((3-methoxy-1-(6-(trifluoromethyl) pyridin-3-yl)-1H-pyrazol-4-yl)methyl)pyrrolidine-2-carboxamide

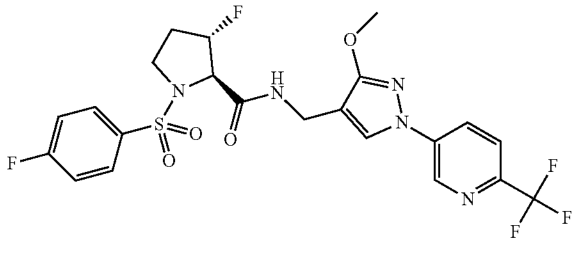 [SMILES: COc1nn(-c2ccc(C(F)(F)F)nc2)cc1CNC(=O)[C@@H]1[C@@H](F)CCN1S(=O)(=O)c1ccc(F)cc1]

Step 1: Preparation of tert-butyl (2S,3S)-3-hydroxy-2-[([3-methoxy-1-[6-(trifluoromethyl)pyridin-3-yl]-1H-pyrazol-4-yl]methyl)carbamoyl]pyrrolidine-1-carboxylate

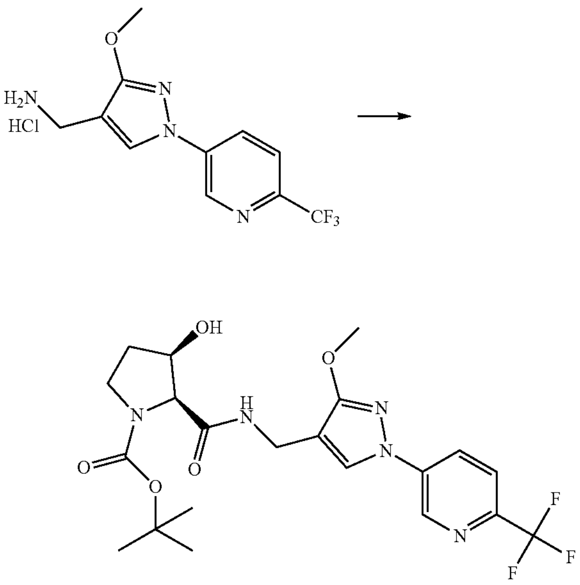

A solution of (2S,3S)-1-[(tert-butoxy)carbonyl]-3-hydroxypyrrolidine-2-carboxylic acid (108 mg, 0.47 mmol, 1.20 equiv), HATU (222 mg, 0.58 mmol, 1.50 equiv), DIEA (151 mg, 1.17 mmol, 3.00 equiv), and [3-methoxy-1-[6-(trifluoromethyl)pyridin-3-yl]-1H-pyrazol-4-yl]methanamine hydrochloride (120 mg, 0.39 mmol, 1.00 equiv) in N,N-dimethylformamide (10 mL) was stirred for 3 h at room temperature. The reaction mixture was diluted with ethyl acetate, washed with brine, dried over anhydrous sodium sulfate, and concentrated under vacuum. The residue was purified by a silica gel column eluting with ethyl acetate/petroleum ether (1:4) to afford the title compound (150 mg, 79%) as a light yellow solid.

Step 2: Preparation of (2R,3S)-3-fluoro-2-[([3-methoxy-1-[6-(trifluoromethyl)pyridin-3-yl]-1H-pyrazol-4-yl]methyl)carbamoyl]pyrrolidine-1-carboxylate

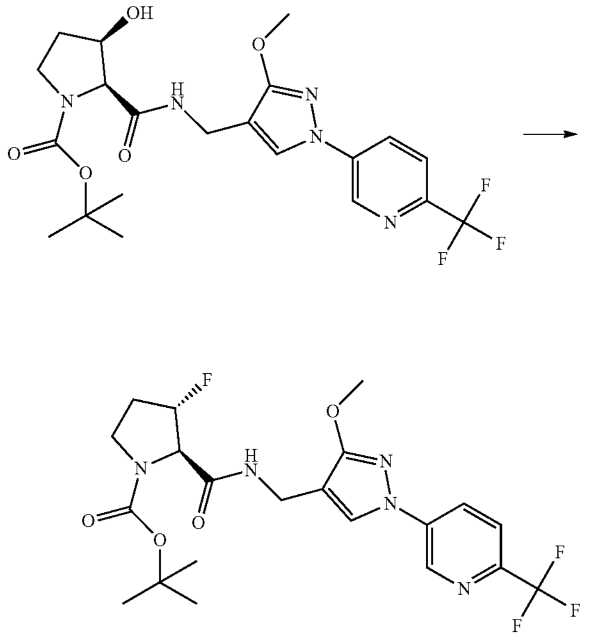 [SMILES: COc1nn(-c2ccc(C(F)(F)F)nc2)cc1CNC(=O)[C@@H]1[C@@H](F)CCN1C(=O)OC(C)(C)C ; COc1nn(-c2ccc(C(F)(F)F)nc2)cc1CNC(=O)[C@H]1NCC[C@@H]1F ; Cl]

DAST (109 mg, 0.48 mmol, 3.00 equiv) was added dropwise into a solution of tert-butyl (2S,3R)-3-hydroxy-2-[([3-methoxy-1-[6-(trifluoromethyl)pyridin-3-yl]-1H-pyrazol-4-yl]methyl)carbamoyl]pyrrolidine-1-carboxylate (110 mg, 0.23 mmol, 1.0 equiv) in dichloromethane (10 mL) at 0° C. under nitrogen. The resulting solution was stirred for 15 min at 0° C. The reaction was quenched by saturated sodium bicarbonate, extracted with dichloromethane, dried over anhydrous sodium sulfate, and concentrated under vacuum. The residue was purified by a silica gel column eluting with ethyl acetate/petroleum ether (1:1) to afford the title compound (65 mg, 59%) as a light yellow solid.

Step 3: Preparation of (2R,3S)-3-fluoro-N-([3-methoxy-1-[6-(trifluoromethyl)pyridin-3-yl]-1H-pyrazol-4-yl]methyl)pyrrolidine-2-carboxamide hydrochloride

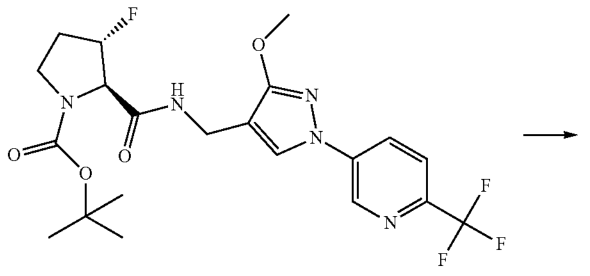

-continued

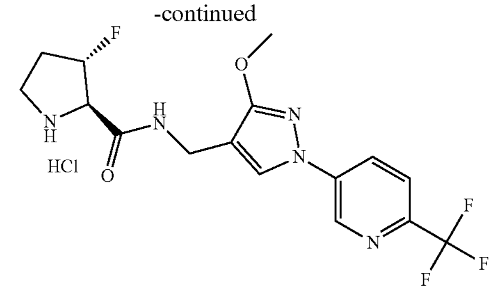

A mixture of tert-butyl (2R,3S)-3-fluoro-2-[([3-methoxy-1-[6-(trifluoromethyl)pyridin-3-yl]-1H-pyrazol-4-yl]methyl)carbamoyl]pyrrolidine-1-carboxylate (65 mg, 0.13 mmol, 1.00 equiv), and saturated HCl in 1,4-dioxane (5 mL). The resulting solution was stirred for 2 h at room temperature. The resulting mixture was concentrated under vacuum to afford the title compound (61 mg) as yellow oil.

Step 4: Preparation of (2R,3S)-3-fluoro-1-(4-fluorophenylsulfonyl)-N-((3-methoxy-1-(6-(trifluoromethyl)pyridin-3-yl)-1H-pyrazol-4-yl)methyl)pyrrolidine-2-carboxamide

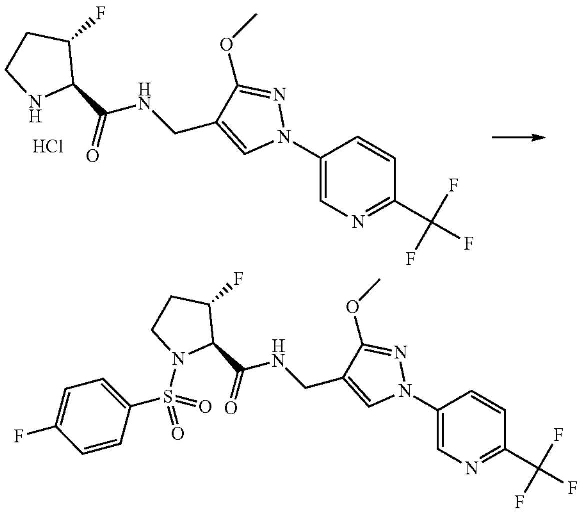

A solution of (2R,3S)-3-fluoro-N-([3-methoxy-1-[6-(trifluoromethyl)pyridin-3-yl]-1H-pyrazol-4-yl]methyl)pyrrolidine-2-carboxamide hydrochloride (50 mg, 0.12 mmol, 1.00 equiv), 4-fluorobenzene-1-sulfonyl chloride (25 mg, 0.13 mmol, 1.10 equiv), 4-dimethylaminopyridine (1 mg, 0.01 mmol, 0.10 equiv), and TEA (30 mg, 0.30 mmol, 1.00 equiv) in dichloromethane (3 mL) was stirred for 2 h at room temperature. The reaction mixture was diluted with dichloromethane, washed with water, dried with $Na_2SO_4$, and concentrated under vacuum. The residue was purified by HPLC-Prep to afford the title compound (29.53 mg) as a white solid.

$^1$H NMR (400 MHz, $CDCl_3$) δ 8.98 (s, 1H), 8.07-8.05 (m, 1H), 7.96 (s, 1H), 7.89-7.86 (m, 2H), 7.73-7.70 (m, 1H), 7.52-7.36 (m, 1H), 7.28-7.23 (m, 2H), 5.38-5.26 (d, J=50.4 Hz, 1H), 4.49-4.44 (m, 1H), 4.32-4.21 (m, 2H), 4.05 (s, 3H), 3.77-3.72 (m, 1H), 3.31-3.24 (m, 1H), 2.15-1.85 (m, 2H).

Example 104

Preparation of (2S,4R)-4-fluoro-N-([6-[3-fluoro-4-(trifluoromethoxy)phenyl]pyrimidin-4-yl]methyl)-1-[(4-fluorobenzene)sulfonyl]pyrrolidine-2-carboxamide

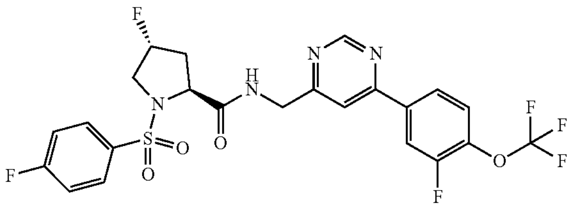 [SMILES: O=C(NCc1cc(-c2ccc(OC(F)(F)F)c(F)c2)ncn1)[C@@H]1C[C@@H](F)CN1S(=O)(=O)c1ccc(F)cc1]

Step 1: Preparation of [3-fluoro-4-(trifluoromethoxy)phenyl]boronic acid

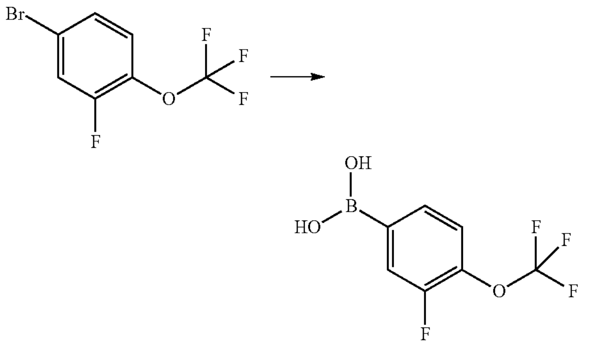

n-BuLi (2.3 mL, 2.5M in hexanes, 1.50 equiv) was added dropwise into a solution of 4-bromo-2-fluoro-1-(trifluoromethoxy)benzene (1 g, 3.86 mmol, 1.00 equiv) in tetrahydrofuran (10 mL) at −78° C. under nitrogen. After 1 h at −78° C. tris(propan-2-yl) borate (1.1 g, 5.85 mmol, 1.50 equiv) was added dropwise at −78° C. The resulting solution was stirred for 14 h at room temperature and quenched by 3N NaOH. The resulting solution was stirred for 30 min at room temperature. The pH value of the solution was adjusted to 7 with 3N aqueous hydrogen chloride. The resulting mixture was extracted with ethyl acetate. The combined extracts were washed with brine, dried over anhydrous sodium sulfate, and concentrated under vacuum. This resulted in the title compound (1.6 g) as yellow oil.

Step 2: Preparation of 4-chloro-6-[3-fluoro-4-(trifluoromethoxy)phenyl]pyrimidine

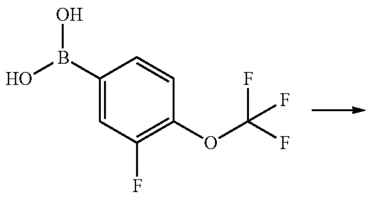

-continued

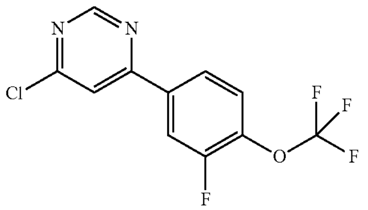

A mixture of [3-fluoro-4-(trifluoromethoxy)phenyl]boronic acid (500 mg, 2.23 mmol, 1.00 equiv), 4,6-dichloropyrimidine (660 mg, 4.43 mmol, 2.00 equiv), $Pd(dppf)Cl_2$ (82 mg, 0.11 mmol, 0.05 equiv), and potassium carbonate (616 mg, 4.46 mmol, 2.00 equiv) in water(1 mL)/1,4-dioxane (10 mL) was stirred for 14 h at 75° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10) to afford the title compound (150 mg, 23%) as a white solid.

Step 3: Preparation of 6-[3-fluoro-4-(trifluoromethoxy)phenyl]pyrimidine-4-carbonitrile

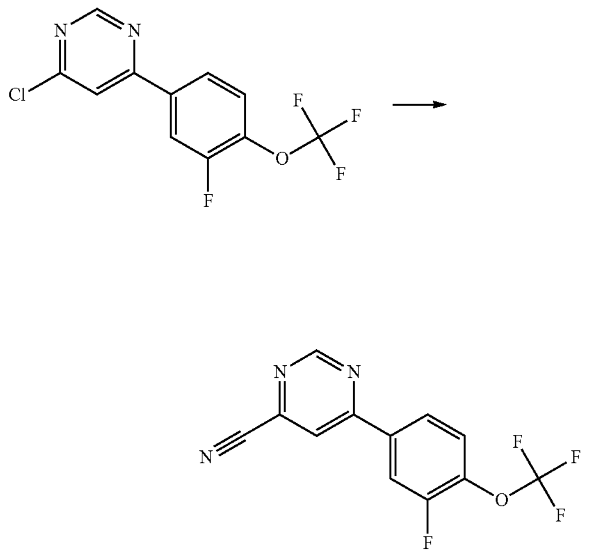

A mixture of 4-chloro-6-[3-fluoro-4-(trifluoromethoxy) phenyl]pyrimidine (150 mg, 0.51 mmol, 1.00 equiv), $Zn(CN)_2$ (72 mg, 0.61 mmol, 1.20 equiv), $Pd_2(dba)_3.CHCl_3$ (53 mg, 0.05 mmol, 0.10 equiv), and dppf (57 mg, 0.10 mmol, 0.20 equiv) in N,N-dimethylformamide (5 mL) was irradiated with microwave radiation for 1 h at 100° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:10). This resulted in the title compound (120 mg, 83%) as a yellow solid.

Step 4: Preparation of [6-[3-fluoro-4-(trifluoromethoxy)phenyl]pyrimidin-4-yl]methanamine hydrochloride

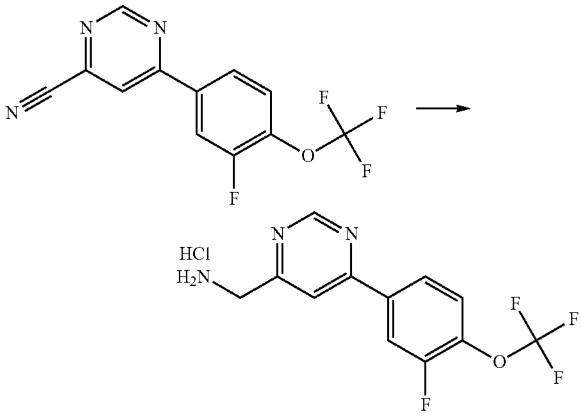

A mixture of 6-[3-fluoro-4-(trifluoromethoxy)phenyl]pyrimidine-4-carbonitrile (120 mg, 0.42 mmol, 1.00 equiv), palladium on carbon (40 mg, 0.38 mmol, 0.90 equiv), and hydrogen chloride(6M, 0.1 mL) in methanol (20 mL) was stirred for 20 min at room temperature under hydrogen. The solids were filtered out. The filtrate was concentrated under vacuum to afford the title compound (133 mg, 97%) as a brown solid.

Step 4: Preparation of (2S,4R)-4-fluoro-N-([6-[3-fluoro-4-(trifluoromethoxy)phenyl]pyrimidin-4-yl]methyl)-1-[(4-fluorobenzene)sulfonyl]pyrrolidine-2-carboxamide

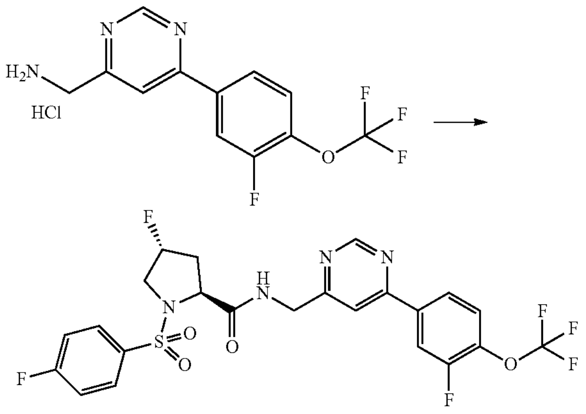

A mixture of (2S,4R)-4-fluoro-1-[(4-fluorobenzene) sulfonyl]pyrrolidine-2-carboxylic acid (119 mg, 0.41 mmol, 1.00 equiv), [6-[3-fluoro-4-(trifluoromethoxy)phenyl]pyrimidin-4-yl]methanamine hydrochloride (133 mg, 0.41 mmol, 1.00 equiv), EDCI (158 mg, 0.82 mmol, 2.00 equiv), HOBT (61 mg, 0.45 mmol, 1.10 equiv), and DIEA (159 mg, 1.23 mmol, 3.00 equiv) in tetrahydrofuran (10 mL) was stirred for 14 h at room temperature. The mixture was diluted with water and extracted with ethyl acetate. The combined extracts were washed with brine, dried over anhydrous sodium sulfate, and concentrated under vacuum.

The crude product was purified by Prep-HPLC to afford the title compound (6.6 mg, 3%) as a white solid.

$^1$H NMR (400 MHz, $CDCl_3$) δ 9.23 (s, 1H), 8.16-8.12 (m, 1H), 8.06-8.02 (m, 2H), 7.96-7.91 (m, 2H), 7.65 (s, 1H), 7.44-7.38 (t, J=8.7 Hz, 1H), 7.28-7.23 (m, 1H), 5.17-4.90 (m, 2H), 4.61-4.54 (dd, J=3.9 Hz, J=3.6 Hz, 1H), 4.35-4.29 (t, J=8.7 Hz, 1H), 3.96-3.66 (m, 2H), 2.61-2.53 (m, 1H), 2.35-2.18 (m, 1H).

Example 105

Preparation of (2S,4R)-4-fluoro-1-[(4-fluorobenzene)sulfonyl]-N-[[2-(methylamino)-6-[4-(trifluoromethyl)phenyl]pyrimidin-4-yl]methyl]pyrrolidine-2-carboxamide

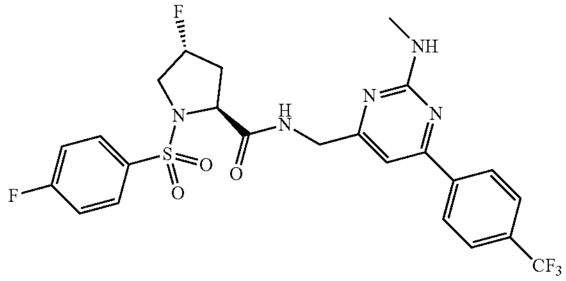 [SMILES: CNc1nc(CNC(=O)[C@@H]2C[C@@H](F)CN2S(=O)(=O)c2ccc(F)cc2)cc(-c2ccc(C(F)(F)F)cc2)n1]

Step 1: Preparation of tert-butyl N-[4-oxo-4-[4-(trifluoromethyl)phenyl]but-2-yn-1-yl]carbamate

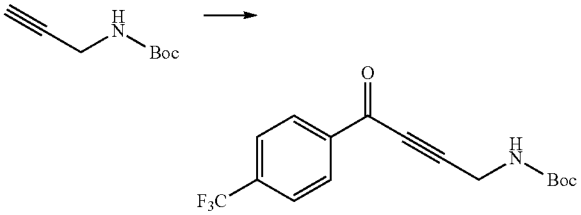

A mixture of tert-butyl N-(prop-2-yn-1-yl)carbamate (5 g, 32.22 mmol, 1.0 equiv), $Pd(PPh_3)_2Cl_2$ (2.25 g, 3.21 mmol, 0.10 equiv), CuI (1.84 g, 9.66 mmol, 0.20 equiv), 4-(trifluoromethyl)benzoyl chloride (6.5 g, 31.17 mmol, 1.00 equiv), and TEA (3.2 g, 31.62 mmol, 1.0 equiv) in THF (150 mL) was stirred for 20 min at room temperature. The solids were filtered out the liquid was concentrated under vacuum. The residue was purified by a silica gel column eluting with ethyl acetate/petroleum ether (1:5). This resulted in the title compound (10 g, 98%) as a brown solid.

Step 2: Preparation of tert-butyl N-[[2-(benzylsulfanyl)-6-[4-(trifluoromethyl)phenyl]pyrimidin-4-yl]methyl]carbamate

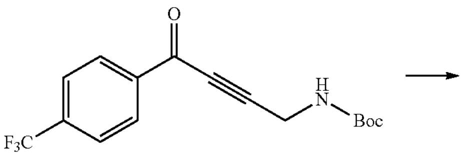

-continued

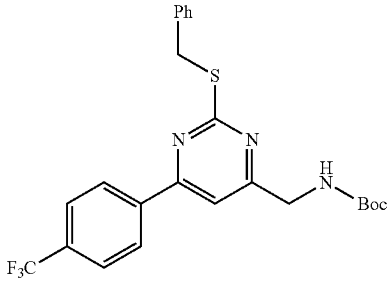

A mixture of tert-butyl N-[4-oxo-4-[4-(trifluoromethyl)phenyl]but-2-yn-1-yl]carbamate (10 g, 30.55 mmol, 1.0 equiv), benzyl carbamimidothioate hydrochloride (6.3 g, 31.08 mmol, 1.00 equiv), and potassium carbonate (6.35 g, 45.95 mmol, 1.50 equiv) in $CH_3CN$ (150 mL) was stirred for 2 h at room temperature. The reaction mixture was diluted with ethyl acetate, washed with water, dried over anhydrous sodium sulfate, and concentrated under vacuum. The residue was purified by a silica gel column eluting with ethyl acetate/petroleum ether (1:5). This resulted in the title compound (7 g, 48%) as a yellow solid.

Step 3: Preparation of [2-(benzylsulfanyl)-6-[4-(trifluoromethyl)phenyl]pyrimidin-4-yl]methanamine hydrochloride

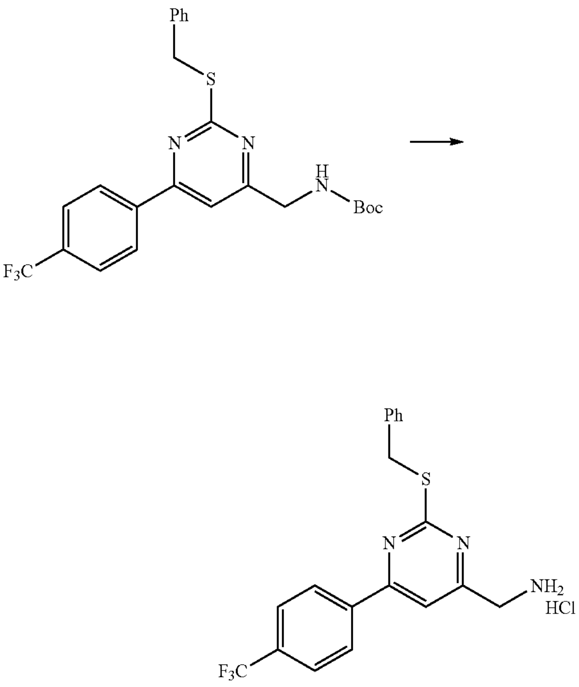

A solution of tert-butyl N-[[2-(benzylsulfanyl)-6-[4-(trifluoromethyl)phenyl]pyrimidin-4-yl]methyl]carbamate (3 g, 6.31 mmol, 1.00 equiv) and saturated HCl in 1,4-dioxane (50 mL) was stirred for overnight at room temperature. The solids were collected by filtration. This resulted in the title compound (2.5 g, 96%) as a light brown solid.

Step 4: Preparation of (2S,4R)—N-[[2-(benzylsulfanyl)-6-[4-(trifluoromethyl)phenyl]pyrimidin-4-yl]methyl]-4-fluoro-1-[(4-fluorobenzene)sulfonyl]pyrrolidine-2-carboxamide

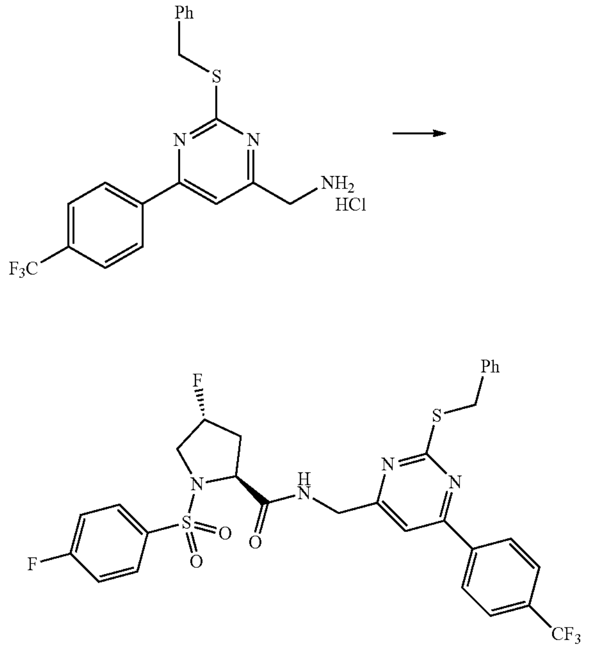

A solution of (2S,4R)-4-fluoro-1-[(4-fluorobenzene)sulfonyl]pyrrolidine-2-carboxylic acid (276.5 mg, 0.95 mmol, 1.00 equiv), HATU (433 mg, 1.14 mmol, 1.20 equiv), DIEA (367.5 mg, 2.84 mmol, 3.0 equiv), and [2,-(benzylsulfanyl)-6-[4(trifluoromethyl)phenyl]pyrimidin-4-yl]methanamine hydrochloride (400 mg, 0.97 mmol, 1.00 equiv) in N,N-dimethylformamide (10 mL) was stirred for 3 h at room temperature. The resulting mixture was diluted with 50 mL of ethyl acetate, washed with brine, dried over anhydrous sodium sulfate, and concentrated under vacuum. The residue was purified by a silica gel column eluting with ethyl acetate/petroleum ether (1:1) to afford the title compound (360 mg, 57%) as light yellow oil.

Step 5: Preparation of (2S,4R)-4-fluoro-1-[(4-fluorobenzene)sulfonyl]-N-[[2-(phenylmethane)sulfonyl-6-[4-(trifluoromethyl)phenyl]pyrimidin-4-yl]methyl]pyrrolidine-2-carboxamide

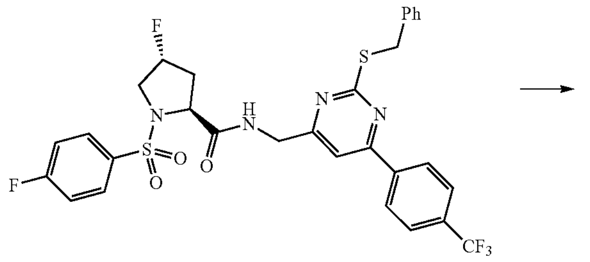

-continued

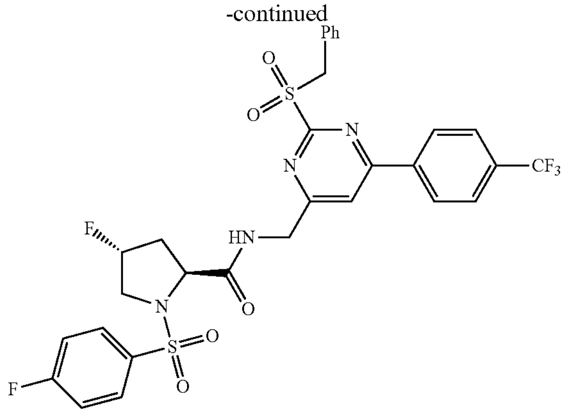

A solution of (2S,4R)—N-[[2-(benzylsulfanyl)-6-[4-(trifluoromethyl)phenyl]pyrimidin-4-yl]methyl]-4-fluoro-1-[(4-fluorobenzene)sulfonyl]pyrrolidine-2-carboxamide (360 mg, 0.55 mmol, 1.00 equiv) and m-CPBA (385 mg, 2.23 mmol, 4.00 equiv) in dichloromethane (30 mL) was stirred for 6 h at room temperature. The resulting mixture was diluted with 50 mL of DCM, washed with aqueous sodium bicarbonate, dried over anhydrous sodium sulfate, and concentrated under vacuum. The residue was purified by a silica gel column eluting with ethyl acetate/petroleum ether (2:3). This resulted in the title compound (260 mg, 69%) as colorless oil.

Step 6: Preparation of (2S,4R)-4-fluoro-1-[(4-fluorobenzene)sulfonyl]-N-[[2-(methylamino)-6-[4-(trifluoromethyl)phenyl]pyrimidin-4-yl]methyl]pyrrolidine-2-carboxamide

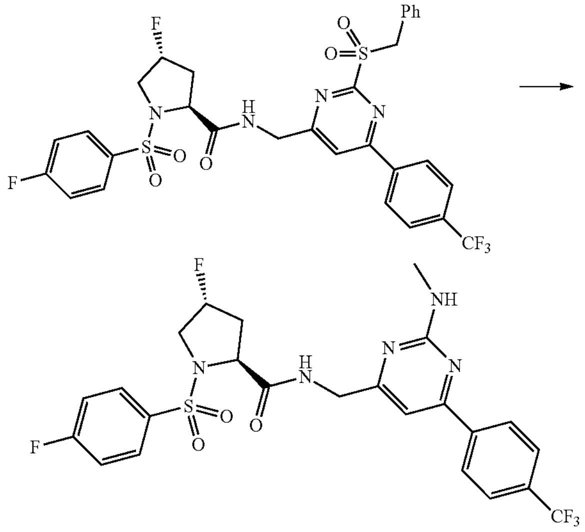

A mixture of (2S,4R)-4-fluoro-1-[(4-fluorobenzene)sulfonyl]-N-[[2-(phenylmethane)sulfonyl-6-[4-(trifluoromethyl)phenyl]pyrimidin-4-yl]methyl]pyrrolidine-2-carboxamide (100 mg, 0.15 mmol, 1.00 equiv) and $CH_3NH_2$ (100 mg, 3.22 mmol, 21.00 equiv) in $CH_3CN$ (15 mL) was stirred for 5 h at room temperature. The reaction mixture was concentrated under vacuum. The crude product was purified by Prep-HPLC to afford the title compound (41.7 mg, 51%) of as a white solid.

$^1H$ NMR (400 MHz, $CDCl_3$) δ 8.25-8.19 (m, 2H), 7.93-7.89 (m, 3H), 7.73-7.71 (m, 2H), 7.25-7.21 (m, 2H), 7.12 (s, 1H), 5.13-5.00 (d, J=52.0 Hz, 1H), 4.67-4.61 (m, 1H), 4.45-4.39 (m, 1H), 4.36-4.32 (m, 1H), 3.96-3.87 (m, 1H), 3.78-3.65 (m, 1H), 3.15 (s, 3H), 2.57-2.48 (m, 1H), 2.41-2.28 (m, 1H).

Example 106

Preparation of (2S,3R,4R)-4-fluoro-1-[(4-fluorobenzene)sulfonyl]-3-methyl-N-([6-[6-(trifluoromethyl)pyridin-3-yl]pyrimidin-4-yl]methyl)pyrrolidine-2-carboxamide

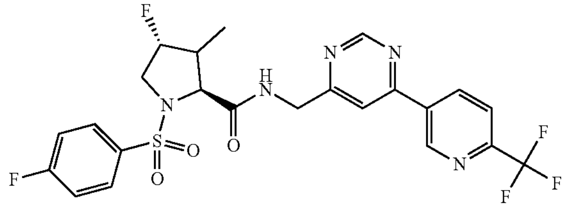 [SMILES: CC1[C@@H](C(=O)NCc2cc(-c3ccc(C(F)(F)F)nc3)ncn2)N(S(=O)(=O)c2ccc(F)cc2)C[C@@H]1F]

Step 1: Preparation of 1-benzyl 2-ethyl (2S,4R)-4-hydroxypyrrolidine-1,2-dicarboxylate

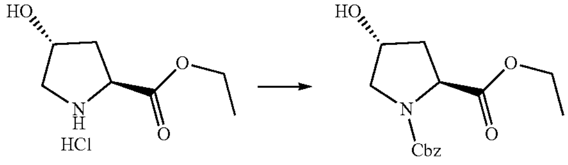 [SMILES: CCOC(=O)[C@@H]1C[C@@H](O)CN1 ; Cl ; CCOC(=O)[C@@H]1C[C@@H](O)CN1C(=O)OCc1ccccc1]

Cbz-Cl (70 g, 410.33 mmol, 2.00 equiv) in dichloromethane (50 mL) was added dropwise into a mixture of ethyl (2S,4R)-4-hydroxypyrrolidine-2-carboxylate hydrochloride (40 g, 204.45 mmol, 1.00 equiv) and TEA (83 g, 820.24 mmol, 4.00 equiv) in dichloromethane (400 mL) at room temperature. The resulting solution was stirred overnight at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (2:1) to afford the title compound (60 g) as light yellow oil.

Step 2: Preparation of 1-benzyl 2-ethyl (2S,4R)-4-[[(4-methylbenzene)sulfonyl]oxy]pyrrolidine-1,2-dicarboxylate

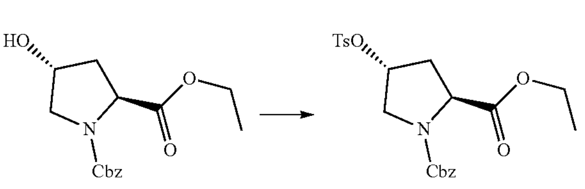 [SMILES: CCOC(=O)[C@@H]1C[C@@H](O)CN1C(=O)OCc1ccccc1 ; CCOC(=O)[C@@H]1C[C@@H](OS(=O)(=O)c2ccc(C)cc2)CN1C(=O)OCc1ccccc1]

4-Methylbenzene-1-sulfonyl chloride (24.0 g, 125.89 mmol, 1.00 equiv) in dichloromethane (200 mL) was added dropwise into a solution of 1-benzyl 2-ethyl (2S,4R)-4-hydroxypyrrolidine-1,2-dicarboxylate (18.6 g, 63.41 mmol, 0.50 equiv), TEA (16.5 g, 163.06 mmol, 1.30 equiv), and 4-dimethylaminopyridine (1.0 g, 8.19 mmol) in dichloromethane (1 L) at room temperature. The resulting solution was stirred for 12 h at 30° C. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/5) to afford the title compound (25 g, 44%) as colorless oil.

Step 3: Preparation of 1-benzyl 2-ethyl (2S,4S)-4-(phenylselanyl)pyrrolidine-1,2-dicarboxylate

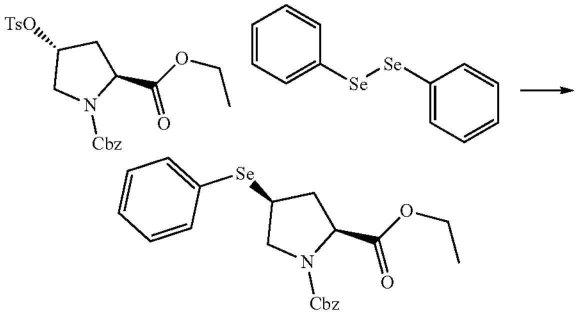

A mixture of (phenyldiselanyl)benzene (109 g, 349.21 mmol, 1.20 equiv) and $NaBH_4$ (13 g, 343.62 mmol, 1.20 equiv) in ethanol (600 mL) was stirred for 30 min at room temperature. To this was added 1-benzyl 2-ethyl (2S,4R)-4-[[(4-methylbenzene)sulfonyl]oxy]pyrrolidine-1,2-dicarboxylate (78 g, 174.30 mmol, 1.00 equiv). The resulting solution was refluxed overnight and concentrated under vacuum. The residue was diluted with ethyl acetate, washed with water, dried over anhydrous sodium sulfate, and concentrated under vacuum. The residue was purified by a silica gel column with ethyl acetate/petroleum ether (1/1) to afford the title compound (32 g, 42%) as colorless oil.

Step 4: Preparation of 1-benzyl 2-ethyl (2S)-2,5-dihydro-1H-pyrrole-1,2-dicarboxylate

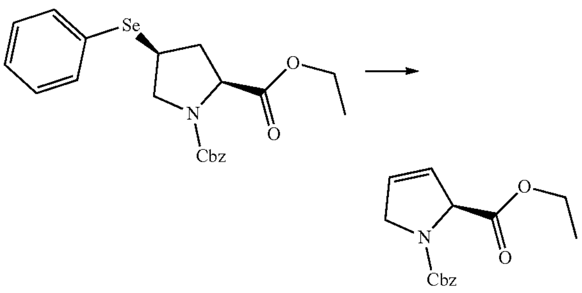

Pyridine (52 mg, 0.66 mmol, 1.40 equiv) and $H_2O_2$ (30%, 131 mg, 3.85 mmol, 2.50 equiv) was added sequentially into a solution of 1-benzyl 2-ethyl (2S,4S)-4-(phenylselanyl)pyrrolidine-1,2-dicarboxylate (200 mg, 0.46 mmol, 1.00 equiv) in DCM (20 mL) at 0° C. The resulting solution was stirred for 2 h at room temperature, diluted with DCM, washed with water, dried over anhydrous sodium sulfate, and concentrated under vacuum. The residue was purified by a silica gel column eluting with ethyl acetate/petroleum ether (1:5). This resulted in the title compound (100 mg, 79%) as colorless oil.

Step 5: Preparation of 3-benzyl 2-ethyl (2S)-6-oxa-3-azabicyclo[3.1.0]hexane-2,3-dicarboxylate

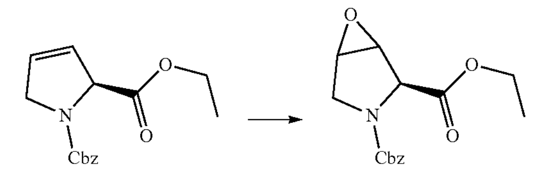 [SMILES: CCOC(=O)[C@@H]1C=CCN1C(=O)OCc1ccccc1 ; CCOC(=O)[C@@H]1C2OC2CN1C(=O)OCc1ccccc1]

m-CPBA (36 g, 208.62 mmol, 6.00 equiv) was added in portions to a stirred solution of 1-benzyl 2-ethyl (2S)-2,5-dihydro-1H-pyrrole-1,2-dicarboxylate (9.5 g, 34.51 mmol, 1.00 equiv) in chloroform (300 mL). The resulting solution was heated to reflux for overnight. The resulting mixture was washed with saturated sodium bicarbonate, dried over anhydrous sodium sulfate, and concentrated under vacuum. The residue was purified by a silica gel column eluting with ethyl acetate/petroleum ether (1:5) to afford the title compound (4 g, 40%) as light yellow oil.

Step 6: Preparation of 1-benzyl 2-ethyl 4-hydroxy-3-methylpyrrolidine-1,2-dicarboxylate

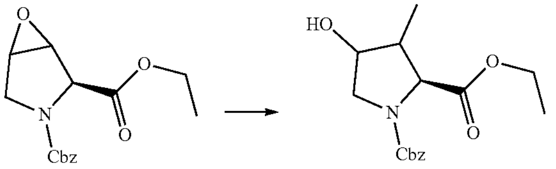 [SMILES: CCOC(=O)[C@@H]1C2OC2CN1C(=O)OCc1ccccc1 ; CCOC(=O)[C@@H]1C(C)C(O)CN1C(=O)OCc1ccccc1]

$CH_3Li$ (20 mL, 5.00 equiv) was added dropwise into a mixture of CuI (2.8 g, 14.70 mmol, 2.40 equiv) in ether (60 mL) at −10° C. under nitrogen. After 20 min at −10° C. a solution of 3-benzyl 2-ethyl 6-oxa-3-azabicyclo[3.1.0]hexane-2,3-dicarboxylate (1.8 g, 6.18 mmol, 1.00 equiv) in ether (13 mL) was added dropwise at −10° C. After 1 h at −10° C. the reaction was quenched by water, extracted with ethyl acetate, dried over sodium sulfate, and concentrated under vacuum. The residue was purified by a silica gel column eluting with petroleum ether/diethyl ether (5:1) to afford the title compound (700 mg, 37%) as light brown oil.

Step 7: Preparation of 1-benzyl 2-ethyl (2S)-4-fluoro-3-methylpyrrolidine-1,2-dicarboxylate

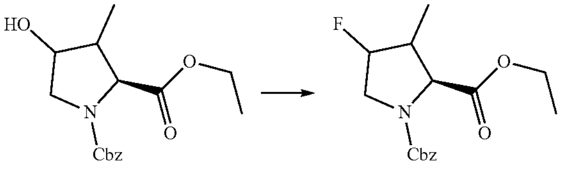 [SMILES: CCOC(=O)[C@@H]1C(C)C(O)CN1C(=O)OCc1ccccc1 ; CCOC(=O)[C@@H]1C(C)C(F)CN1C(=O)OCc1ccccc1]

DAST (8.4 g, 36.68 mmol, 6.00 equiv) was added dropwise into a solution of 1-benzyl 2-ethyl (2S)-4-hydroxy-3-methylpyrrolidine-1,2-dicarboxylate (2.7 g, 8.79 mmol, 1.00 equiv) in dichloromethane (100 mL) at 0° C. under nitrogen. The resulting solution was stirred overnight at room temperature, diluted with DCM, washed with saturated sodium bicarbonate, dried over anhydrous sodium sulfate, and concentrated under vacuum. The residue was applied onto a silica gel column eluting with ethyl acetate/petroleum ether (1:5) to afford the title compound (710 mg, 26%) as colorless oil.

Step 8: Preparation of (2S)-1-[(benzyloxy)carbonyl]-4-fluoro-3-methylpyrrolidine-2-carboxylic acid

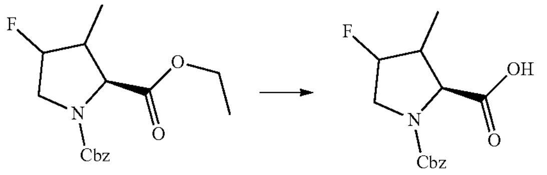 [SMILES: CCOC(=O)[C@@H]1C(C)C(F)CN1C(=O)OCc1ccccc1 ; CC1C(F)CN(C(=O)OCc2ccccc2)[C@@H]1C(=O)O]

A mixture of 1-benzyl 2-ethyl (2S)-4-fluoro-3-methylpyrrolidine-1,2-dicarboxylate (710 mg, 2.30 mmol, 1.00 equiv) and LiOH (276 mg, 11.52 mmol, 5.00 equiv) in methanol (30 ml) was stirred overnight at room temperature. The resulting mixture was concentrated under vacuum. The residue was diluted with water and the pH value of the solution was adjusted to 4 with diluted HCl. The resulting solution was extracted with ethyl acetate, washed with brine, dried over anhydrous sodium sulfate, and concentrated under vacuum. This resulted in the title compound (480 mg, 74%) as crude oil.

Step 9: Preparation of (2S)-4-fluoro-3-methylpyrrolidine-2-carboxylic acid

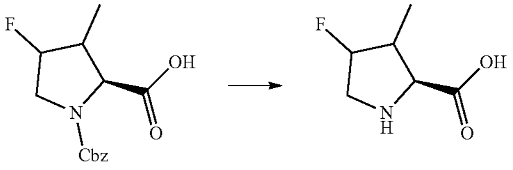

A mixture of (2S)-1-[(benzyloxy)carbonyl]-4-fluoro-3-methylpyrrolidine-2-carboxylic acid (480 mg, 1.71 mmol, 1.00 equiv) and palladium on carbon (50 mg) in methanol (30 mL) was stirred overnight at 35° C. under hydrogen. The solids were filtered out. The filtrate was concentrated under vacuum to afford the title compound (250 mg) as a light brown crude solid.

Step 10: Preparation of (2S)-4-fluoro-1-[(4-fluorobenzene)sulfonyl]-3-methylpyrrolidine-2-carboxylic acid

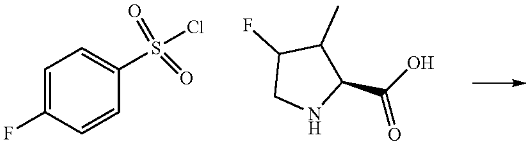

-continued

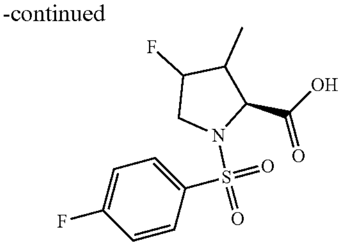

A mixture of (2S)-4-fluoro-3-methylpyrrolidine-2-carboxylic acid (250 mg, 1.70 mmol, 1.00 equiv), TEA (515 mg, 5.09 mmol, 3.00 equiv), and 4-fluorobenzene-1-sulfonyl chloride (330 mg, 1.70 mmol, 1.00 equiv) in dichloromethane (20 mL) was stirred for 3 h at room temperature. The resulting mixture was concentrated under vacuum. The residue was diluted with water. The pH value of the solution was adjusted to 10-11 with aqueous sodium carbonate. The resulting solution was washed with ethyl acetate. The pH value of the aqueous layer was adjusted to 1 by diluted HCl. The resulting solution was extracted with ethyl acetate, dried over anhydrous sodium sulfate, and concentrated under vacuum. This resulted in the title compound (330 mg) as a brown solid which was used for the next step without any further purification Step 11: Preparation of (2R,4R)-4-fluoro-1-[(4-fluorobenzene)sulfonyl]-3-methyl-N-([6-[6-(trifluoromethyl)pyridin-3-yl]pyrimidin-4-yl]methyl)pyrrolidine-2-carboxamide

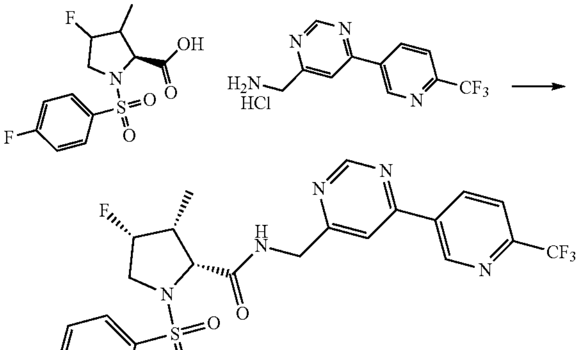

3-Proline Stereochemistry Assumed

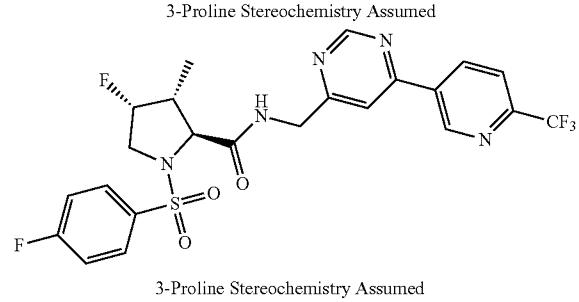

3-Proline Stereochemistry Assumed

A mixture of (2S)-4-fluoro-1-[(4-fluorobenzene)sulfonyl]-3-methylpyrrolidine-2-carboxylic acid (160 g, 524.08 mmol, 1.00 equiv), HATU (239 g, 628.57 mmol, 1.20 equiv), DIEA (135 g, 1.04 mol, 2.00 equiv), and [6-[6-(trifluoromethyl)pyridin-3-yl]pyrimidin-4-yl]methanamine hydrochloride (153 g, 526.37 mmol, 1.00 equiv) in N,N-dimethylformamide (5 mL) was stirred overnight at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (4:1). The crude product was separated by Chiral-Prep-HPLC to afford the title compound (7.3 mg) as a white solid. $t_R$=5.14 min (Lux Cellulose-4, 0.46×5 cm, 3 μm, Hex:EtOH=80:20, 1.0 ml/min).

$^1$H NMR (300 MHz, $CDCl_3$) δ 9.51 (s, 1H), 9.26 (s, 1H), 8.70 (d, J=1.5 Hz, 1H), 8.17 (s, 1H), 7.93-7.89 (m, 2H), 7.80-7.77 (d, J=8.1 Hz, 1H), 7.49 (s, 1H), 7.29-7.23 (m, 2H), 5.04-4.96 (m, 1H), 4.89-4.71 (d, J=52.2 Hz, 1H), 4.53-4.46 (m, 1H), 3.89-3.64 (m, 3H), 2.51-2.34 (m, 1H), 1.19 (d, J=6.6 Hz, 3H).

And (2S,4R)-4-fluoro-1-[(4-fluorobenzene)sulfonyl]-3-methyl-N-([6-[6-(trifluoromethyl)pyridin-3-yl]pyrimidin-4-yl]methyl)pyrrolidine-2-carboxamide (82 mg) was also isolated as a white solid. $t_R$=4.08 min (Lux Cellulose-4, 0.46×5 cm, 3 μm, Hex:EtOH=80:20, 1.0 ml/min).

$^1$H NMR (300 MHz, $CDCl_3$) δ 9.51 (s, 1H), 9.26 (s, 1H), 8.70 (d, J=1.5 Hz, 1H), 8.17 (s, 1H), 7.93-7.89 (m, 2H), 7.80-7.77 (d, J=8.1 Hz, 1H), 7.49 (s, 1H), 7.29-7.23 (m, 2H), 5.04-4.96 (dd, J=17.7 Hz, J=7.2 Hz, 1H), 4.89-4.71 (d, J=52.2 Hz, 1H), 4.53-4.46 (dd, J=18.0 Hz, J=4.2 Hz, 1H), 3.89-3.64 (m, 3H), 2.51-2.34 (m, 1H), 1.19 (d, J=6.6 Hz, 3H).

The 3-proline stereochemistry for the above two compounds was arbitrarily assigned. The 2-proline and 4-proline stereochemistry for the above two compounds is as shown.

Example 107

Preparation of (2S,4R)-4-fluoro-1-[(4-fluorobenzene)sulfonyl]-4-methyl-N-([6-[6-(trifluoromethyl)pyridin-3-yl]pyrimidin-4-yl]methyl)pyrrolidine-2-carboxamide

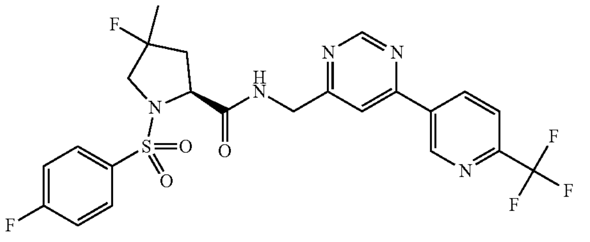 [SMILES: CC1(F)C[C@@H](C(=O)NCc2cc(-c3ccc(C(F)(F)F)nc3)ncn2)N(S(=O)(=O)c2ccc(F)cc2)C1]

Step 1: Preparation of (2S,4R)-1-[(tert-butoxy)carbonyl]-4-hydroxypyrrolidine-2-carboxylic acid

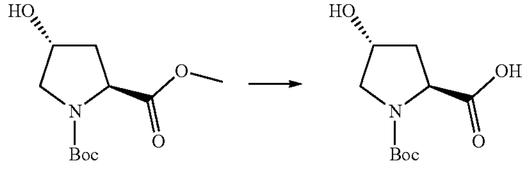 [SMILES: COC(=O)[C@@H]1C[C@@H](O)CN1C(=O)OC(C)(C)C ; CC(C)(C)OC(=O)N1C[C@H](O)C[C@H]1C(=O)O]

A mixture of 1-tert-butyl 2-methyl (2S,4R)-4-hydroxypyrrolidine-1,2-dicarboxylate (6.45 g, 26.30 mmol, 1.00 equiv) and LiOH (3.16 g, 131.95 mmol, 5.00 equiv) in water (50 mL)/methanol (50 mL) was stirred for 1 h at room temperature. The resulting mixture was concentrated under vacuum. The residue was dissolved in water. The resulting solution was extracted with ethyl acetate. The pH value of the water layer was adjusted to 4 with 1M hydrogen chloride. The resulting mixture was extracted with ethyl acetate, washed with brine, dried over anhydrous sodium sulfate, and concentrated under vacuum. This resulted in the title compound (3.5 g, 58%) as colorless syrup which was used for the next step without any further purification.

Step 2: Preparation of (2S,4R)-4-hydroxy-2-[([6-[6-(trifluoromethyl)pyridin-3-yl]pyrimidin-4-yl]methyl)carbamoyl]pyrrolidine-1-carboxylate

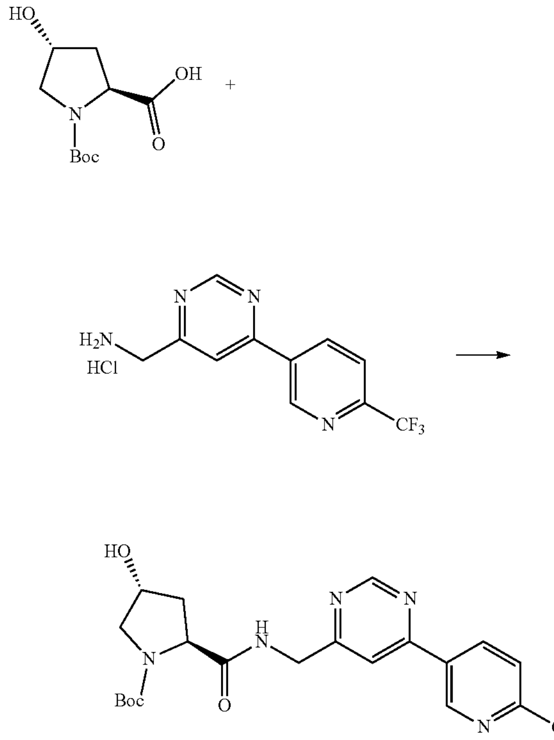

A mixture of (2S,4R)-1-[(tert-butoxy)carbonyl]-4-hydroxypyrrolidine-2-carboxylic acid (3.5 g, 15.14 mmol, 1.00 equiv), HATU (8.6 g, 22.62 mmol, 1.50 equiv), DIEA (7.84 g, 60.66 mmol, 4.00 equiv), and [6-[6-(trifluoromethyl)pyridin-3-yl]pyrimidin-4-yl]methanamine hydrochloride (4.4 g, 15.14 mmol, 1.00 equiv) in N,N-dimethylformamide (300 mL) was stirred for 1 h at room temperature. The reaction was then quenched by water and extracted with ethyl acetate. The combined extracts were washed with brine, dried over anhydrous sodium sulfate, and concentrated under vacuum. The residue was purified by a silica gel column eluting with dichloromethane/methanol (50:1). This resulted in the title compound (6.8 g, 96%) as a light brown solid.

Step 3: Preparation of tert-butyl (2S)-4-oxo-2-[([6-[6-(trifluoromethyl)pyridin-3-yl]pyrimidin-4-yl]methyl)carbamoyl]pyrrolidine-1-carboxylate

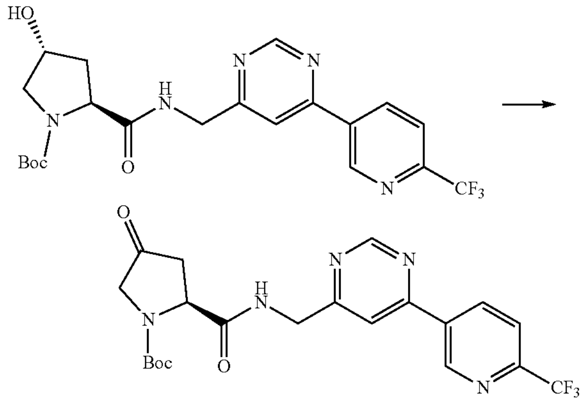

A mixture of tert-butyl (2S,4R)-4-hydroxy-2-[([6-[6-(trifluoromethyl)pyridin-3-yl]pyrimidin-4-yl]methyl)carbamoyl]pyrrolidine-1-carboxylate (1.23 g, 2.63 mmol, 1.00 equiv), Dess-Martin (1.34 g, 3.16 mmol, 1.20 equiv) in dichloromethane (25 mL) was stirred for 12 h at room temperature. The reaction was then quenched by water. The resulting solution was extracted with dichloromethane, washed with saturated sodium bicarbonate solution and then brine, dried over anhydrous sodium sulfate, and concentrated under vacuum. The residue was purified by a silica gel column eluting with ethyl acetate/petroleum ether (1:10). This resulted in the title compound (960 mg, 78%) as a yellow solid.

Step 4: Preparation of tert-butyl (2S)-4-hydroxy-4-methyl-2-[([6-[6-(trifluoromethyl)pyridin-3-yl]pyrimidin-4-yl]methyl)carbamoyl]pyrrolidine-1-carboxylate

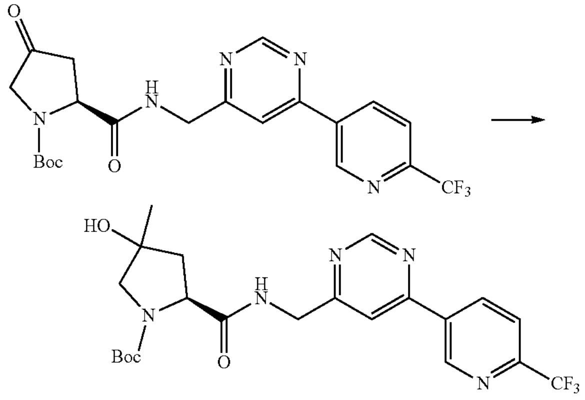

MeMgBr (1.4 mL, 2.00 equiv) was added into a mixture of tert-butyl (2S)-4-oxo-2-[([6-[6-(trifluoromethyl)pyridin-3-yl]pyrimidin-4-yl]methyl)carbamoyl]pyrrolidine-1-carboxylate (960 mg, 2.06 mmol, 1.00 equiv) in tetrahydrofuran (15 mL) at −5° C. under nitrogen. The resulting solution was stirred for 5 h at 0° C., quenched by saturated solution of $NH_4Cl$, and extracted with ethyl acetate. The combined extracts were washed with brine, dried over anhydrous sodium sulfate, and concentrated under vacuum. The residue was purified by a silica gel column eluting with dichloromethane/methanol (50:1) to afford the title compound (250 mg, 25%) as a yellow solid.

Step 5: Preparation of tert-butyl (2S)-4-fluoro-4-methyl-2-[([6-[6-(trifluoromethyl)pyridin-3-yl]pyrimidin-4-yl]methyl)carbamoyl]pyrrolidine-1-carboxylate

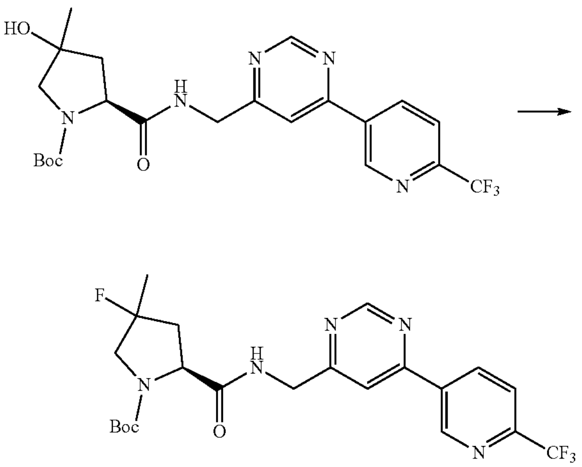

DAST (170.6 mg, 0.74 mmol, 3.00 equiv) was added dropwise into a mixture of tert-butyl (2S)-4-hydroxy-4-methyl-2-[([6-[6-(trifluoromethyl)pyridin-3-yl]pyrimidin-4-yl]methyl)carbamoyl]pyrrolidine-1-carboxylate (170 mg, 0.35 mmol, 1.00 equiv) in dichloromethane (3 mL) at −10° C. under nitrogen. The resulting solution was stirred for 1 h at −10° C., quenched by water, and extracted with dichloromethane. The combined extracts were washed with saturated sodium bicarbonate and brine, dried over anhydrous sodium sulfate, and concentrated under vacuum. This resulted in the title compound (160 mg, 94%) as an orange solid.

Step 6: Preparation of (2S)-4-fluoro-4-methyl-N-([6-[6-(trifluoromethyl)pyridin-3-yl]pyrimidin-4-yl]methyl)pyrrolidine-2-carboxamide hydrochloride

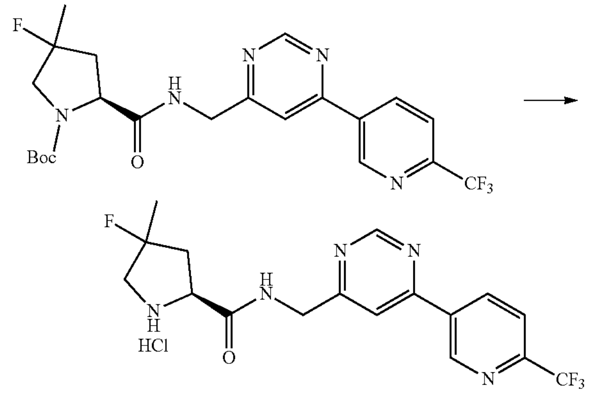

A mixture of tert-butyl (2S)-4-fluoro-4-methyl-2-[([6-[6-(trifluoromethyl)pyridin-3-yl]pyrimidin-4-yl]methyl)carbamoyl]pyrrolidine-1-carboxylate (200 mg, 0.41 mmol, 1.00 equiv) and saturated hydrogen chloride in dioxane (5 mL) was stirred for 3 h at room temperature. The resulting solution was concentrated under vacuum to afford the title compound (186 mg) as an orange solid.

Step 7: Preparation of (2S,4R)-4-fluoro-1-[(4-fluorobenzene)sulfonyl]-4-methyl-N-([6-[6-(trifluoromethyl)pyridin-3-yl]pyrimidin-4-yl]methyl)pyrrolidine-2-carboxamide

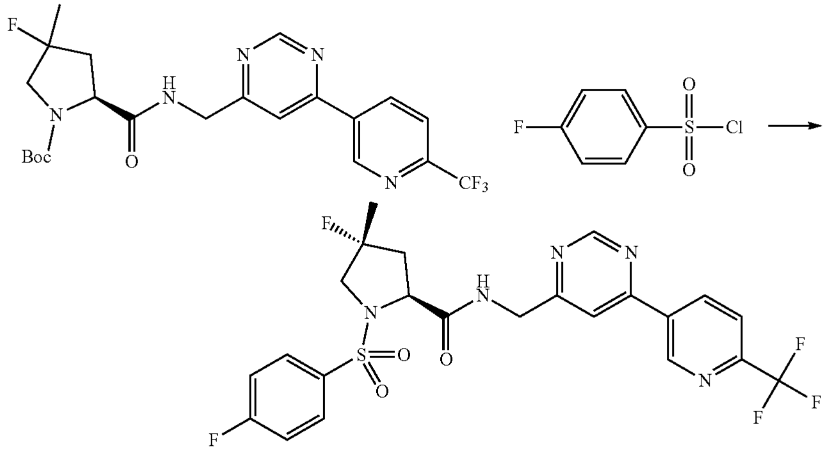

4-Proline Stereochemistry Assumed

A mixture of (2S)-4-fluoro-4-methyl-N-([6-[6-(trifluoromethyl)pyridin-3-yl]pyrimidin-4-yl]methyl)pyrrolidine-2-carboxamide (186 mg, 0.49 mmol, 1.00 equiv), TEA (196 mg, 1.94 mmol, 4.00 equiv), 4-fluorobenzene-1-sulfonyl chloride (113 mg, 0.58 mmol, 1.20 equiv), and 4-dimethylaminopyridine (6 mg, 0.05 mmol, 0.10 equiv) in dichloromethane (5 mL) was stirred for 3 h at room temperature. The reaction mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:3). The crude product was purified by Prep-HPLC to afford the title compound (51.7 mg, 20%) as a white solid. $t_R$=1.94 min (CHIRALPAK IC-3, 0.46×5 cm, 3 μm, Hex:EtOH=70:30, 1.0 ml/min).

$^1$H NMR (300 MHz, DMSO-$d_6$) δ 9.45 (s, 1H), 9.31 (s, 1H), 9.15-9.11 (t, J=6.1 Hz, 1H), 8.81-8.78 (d, J=9.2 Hz, 1H), 8.24 (s, 1H), 8.07-8.01 (m, 3H), 7.50-7.44 (t, 2H), 4.54-4.52 (d, J=6.1 Hz, 2H), 4.28-4.24 (m, 1H), 3.74-2.48 (m, 2H), 2.46-2.39 (m, 1H), 2.19-2.02 (m, 1H), 1.43-1.36 (d, J=9.0 Hz, 3H).

The 4-proline stereochemistry for the above compound was arbitrarily assigned. The 2-proline stereochemistry for the above compound is as shown.

Example 108

Preparation of (2S,4R)-4-fluoro-1-[(4-fluorobenzene)sulfonyl]-N-([5-methoxy-4-[6-(trifluoromethyl) pyridin-3-yl]pyridin-2-yl]methyl)pyrrolidine-2-carboxamide

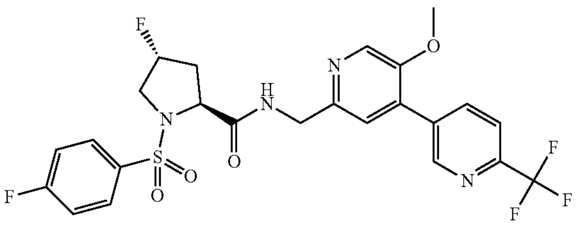 [SMILES: COc1cnc(CNC(=O)[C@@H]2C[C@@H](F)CN2S(=O)(=O)c2ccc(F)cc2)cc1-c1ccc(C(F)(F)F)nc1]

Step 1: Preparation of 2-chloro-4-iodo-5-methoxypyridine

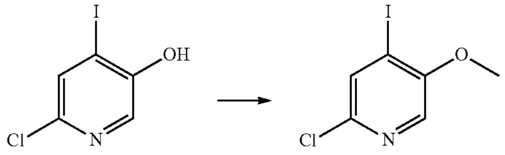

Sodium hydride (1.2 g, 60% in mineral oil, 2.30 equiv) was added in portions to a stirred solution of 6-chloro-4-iodopyridin-3-ol hydrochloride (3.80 g, 13.02 mmol, 1.00 equiv) in N,N-dimethylformamide (30 mL) at 0° C. under nitrogen. After 30 min at 0° C. $CH_3I$ (2.22 g, 15.64 mmol, 1.20 equiv) was added to the solution. The resulting solution was stirred for 12 h at room temperature, quenched by water, extracted with ethyl acetate, washed with brine, dried over anhydrous sodium sulfate, and concentrated under vacuum. The residue was purified by flash chromatography on silica gel eluting with petroleum ether/ethyl acetate (10:1). This resulted in the title compound (2.9 g, 83%) as a white solid.

Step 2: Preparation of 2-chloro-5-methoxy-4-[6-(trifluoromethyl)pyridin-3-yl]pyridine

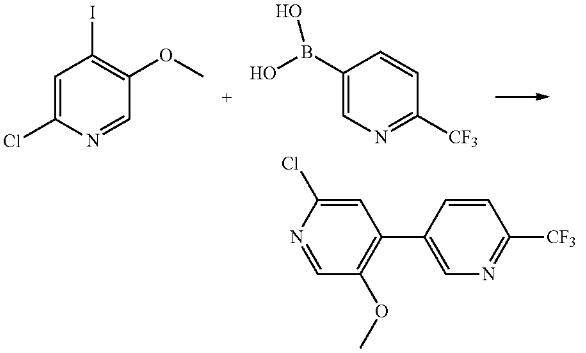

A mixture of 2-chloro-4-iodo-5-methoxypyridine (1 g, 3.71 mmol, 1.00 equiv) in dioxane (30 mL), [6-(trifluoromethyl)pyridin-3-yl]boronic acid (710 mg, 3.72 mmol, 1.00 equiv), $Pd(dppf)Cl_2$ (271 mg, 0.37 mmol, 0.10 equiv), potassium carbonate (1.532 g, 11.08 mmol, 3.00 equiv), and water (3 mL) was stirred for 5 h at 50° C. under nitrogen. The solids were filtered out and the liquid was concentrated under vacuum. The residue was purified by flash chromatography on silica gel eluting with petroleum ether/ethyl acetate (100:3). This resulted in the title compound (510 mg, 48%) as a white solid.

Step 3: Preparation of 5-methoxy-4-[6-(trifluoromethyl)pyridin-3-yl]pyridine-2-carbonitrile

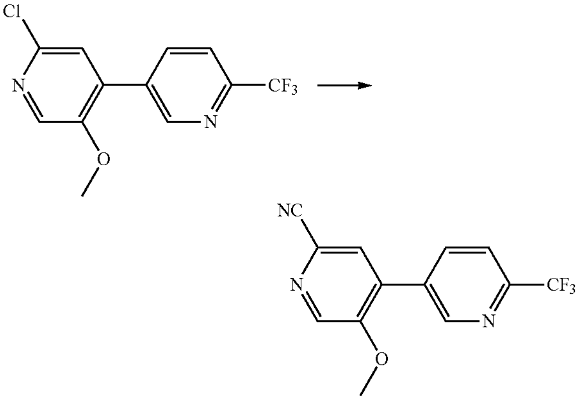

A mixture of 2-chloro-5-methoxy-4-[6-(trifluoromethyl) pyridin-3-yl]pyridine (400 mg, 1.39 mmol, 1.00 equiv) in N,N-dimethylformamide (10 mL), $Zn(CN)_2$ (162 mg, 1.38 mmol, 1.00 equiv), DPPF (77 mg, 0.14 mmol, 0.10 equiv), and $Pd_2(dba)_3$.CHC13 (72 mg, 0.07 mmol, 0.05 equiv) was irradiated with microwave for 1 h at 110° C. under nitrogen. The reaction was then quenched by water, extracted with ethyl acetate, washed with brine, dried over anhydrous sodium sulfate, and concentrated under vacuum. The residue was purified by flash chromatography on silica gel eluting with ethyl acetate/petroleum ether (15:100). This resulted in the title compound (440 mg) as an off-white solid.

Step 4: Preparation of [5-methoxy-4-[6-(trifluoromethyl)pyridin-3-yl]pyridin-2-yl]methanamine hydrochloride

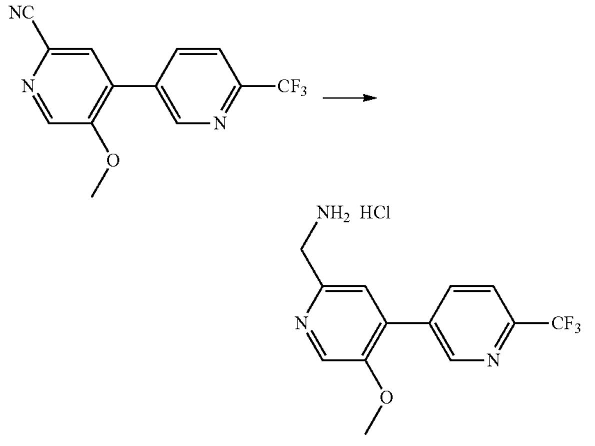

A mixture of 5-methoxy-4-[6-(trifluoromethyl)pyridin-3-yl]pyridine-2-carbonitrile (150 mg, 0.54 mmol, 1.00 equiv), methanol (30 mL), palladium on carbon (30 mg), hydrogen chloride (0.6 mL, concentrated) was stirred for 1 h at room temperature under hydrogen. The solids were filtered out and the liquid was concentrated under vacuum. This resulted in the title compound (325 mg) as a yellow solid.

Step 5: Preparation of (2S,4R)-4-fluoro-1-[(4-fluorobenzene)sulfonyl]-N-([5-methoxy-4-[6-(trifluoromethyl)pyridin-3-yl]pyridin-2-yl]methyl)pyrrolidine-2-carboxamide

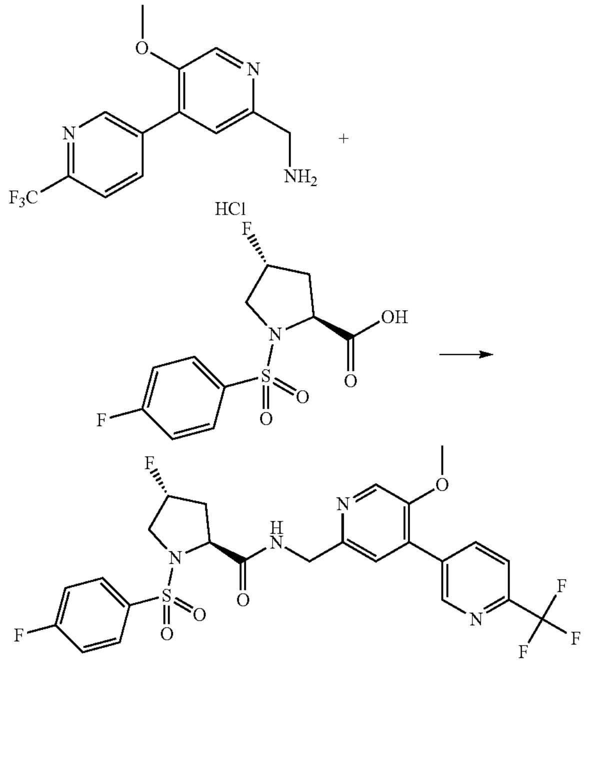

A mixture of (2S,4R)-4-fluoro-1-[(4-fluorobenzene)sulfonyl]pyrrolidine-2-carboxylic acid (291 mg, 1.00 mmol, 1.00 equiv) in N,N-dimethylformamide (30 mL), [5-methoxy-4-[6-(trifluoromethyl)pyridin-3-yl]pyridin-2-yl]methanamine hydrochloride (320 mg, 1.00 mmol, 1.00 equiv), DIEA (1.29 g, 9.98 mmol, 10.00 equiv), and HATU (570 mg, 1.50 mmol, 1.50 equiv) was stirred for overnight at room temperature. The reaction was then quenched by water, extracted with ethyl acetate, washed with brine, dried over anhydrous sodium sulfate, and concentrated under vacuum. The residue was purified by flash chromatography on silica gel eluting with ethyl acetate/petroleum ether (1/10). This resulted in the title compound (55.7 mg, 10%) as a white solid.

$^1$H NMR (300 MHz, DMSO-$d_6$) δ 8.95-8.90 (m, 2H), 8.48 (s, 1H), 8.28-8.25 (m, 1H), 7.99-7.93 (m, 3H), 7.52 (s, 1H), 7.46-7.41 (m, 2H), 5.27-5.01 (d, J=52.8 Hz, 1H), 4.46-4.42 (m, 2H), 4.23-4.17 (m, 1H), 3.93 (s, 3H), 3.70 (s, 1H), 3.62-3.57 (m, 1H), 2.39-2.00 (m, 2H).

Example 109

Preparation of (2S,4R)-4-fluoro-1-(4-fluorophenyl)sulfonyl-N-[[5-methoxy-4-[6-(trifluoromethyl)-3-pyridyl]-2-pyridyl]methyl]-2-methyl-pyrrolidine-2-carboxamide

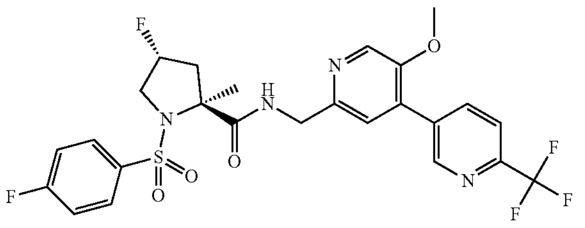 [SMILES: COc1cnc(CNC(=O)[C@]2(C)C[C@@H](F)CN2S(=O)(=O)c2ccc(F)cc2)cc1-c1ccc(C(F)(F)F)nc1]

Step 1: Preparation of (2R,4R)-4-fluoro-1-(4-fluorophenyl)sulfonyl-N-[[5-methoxy-4-[6-(trifluoromethyl)-3-pyridyl]-2-pyridyl]methyl]-2-methyl-pyrrolidine-2-carboxamide

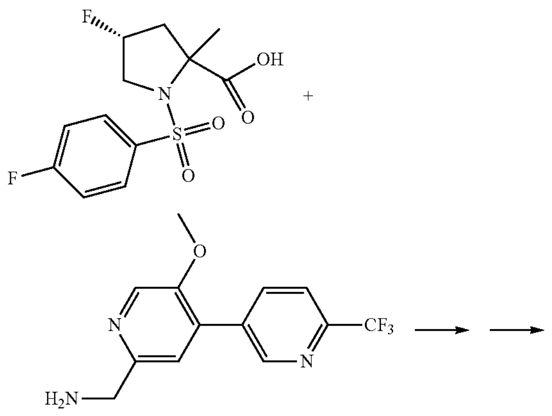

-continued

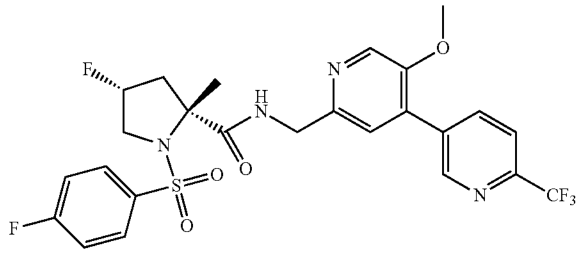

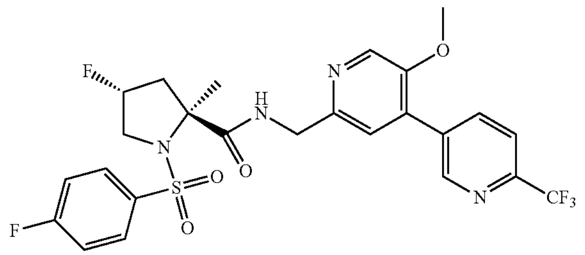

A mixture of [5-methoxy-4-[6-(trifluoromethyl)pyridin-3-yl]pyridin-2-yl]methanamine(150 mg, 0.530 mmol, 1.000 equiv), DMF (5 mL), DIEA (190 mg, 1.470 mmol, 2.776 equiv), HATU (280 mg, 0.736 mmol, 1.391 equiv), and (4R)-4-fluoro-1-[(4-fluorobenzene)sulfonyl]-2-methylpyrrolidine-2-carboxylic acid (157 mg, 0.514 mmol, 0.971 equiv) was stirred for 2 h at room temperature. The reaction was then quenched by water, extracted with ethyl acetate, washed with brine, dried over sodium sulfate, and concentrated under vacuum. The residue was purified a silica gel column eluting with petroleum ether/ethyl acetate (1:1). The crude product (200 mg) was re-purified by Chiral-Prep-HPLC eluting with Hex and ethanol (hold 20.0% ethanol in 20 min) to afford the title compound (89.5 mg, 30%) as a white solid. $t_R$=2.68 min (CHIRALPAK IC, 4.6×100 mm, 5 μm, MeOH (0.1%)=10% to 50% in 4.0 min, hold 2.0 min at 50%, 4 ml/min).

$^1$H NMR (300 MHz, $CD_3OD$) δ 8.96 (s, 1H), 8.40 (s, 1H), 8.33 (d, J=1.5 Hz, 1H), 8.00-7.96 (m, 2H), 7.88 (d, J=8.4 Hz, 1H), 7.65 (s, 1H), 7.37-7.31 (m, 2H), 5.20 (d, J=52.8 Hz, 1H), 4.86-4.49 (m, 2H), 4.07-3.95 (m, 4H), 3.73-3.57 (m, 1H), 2.67-2.60 (m, 1H), 2.27-2.08 (m, 2H), 1.58 (s, 3H).

(2S,4R)-4-fluoro-1-(4-fluorophenyl)sulfonyl-N-[[5-methoxy-4-[6-(trifluoromethyl)-3-pyridyl]-2-pyridyl]methyl]-2-methyl-pyrrolidine-2-carboxamide (37.1 mg, 12%) was also isolated as a white solid. $t_R$=2.46 min (CHIRALPAK IC, 4.6×100 mm, 5 μm, MeOH (0.1%)=10% to 50% in 4.0 min, hold 2.0 min at 50%, 4 ml/min).

$^1$H NMR (300 MHz, $CD_3OD$) δ 8.97 (s, 1H), 8.40 (s, 1H), 8.32-8.28 (m, 1H), 7.94-7.90 (m, 2H), 7.82 (d, J=8.4 Hz, 1H), 7.73 (s, 1H), 7.30-7.24 (m, 2H), 5.20 (d, J=52.8 Hz, 1H), 4.64-4.51 (m, 2H), 3.99 (s, 3H), 3.86-3.75 (m, 1H), 2.60-2.27 (m, 1H), 1.75 (s, 3H).

Example 110

Preparation of (2S,4R)-4-cyano-1-[(4-fluorobenzene)sulfonyl]-N-([3-methoxy-1-[4-(trifluoromethyl)phenyl]-1H-pyrazol-4-yl]methyl)pyrrolidine-2-carboxamide

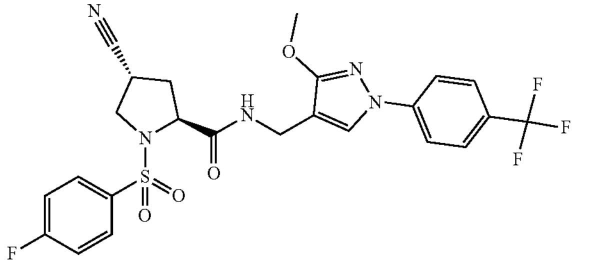 [SMILES: COc1nn(-c2ccc(C(F)(F)F)cc2)cc1CNC(=O)[C@@H]1C[C@@H](C#N)CN1S(=O)(=O)c1ccc(F)cc1]

Step 1: Preparation of (2S,4S)-1-[(tert-butoxy)carbonyl]-4-hydroxypyrrolidine-2-carboxylic acid

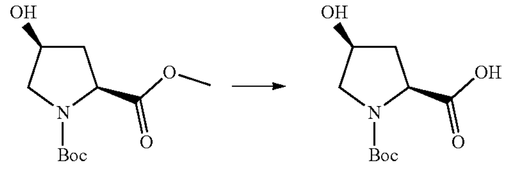 [SMILES: COC(=O)[C@@H]1C[C@H](O)CN1C(=O)OC(C)(C)C ; CC(C)(C)OC(=O)N1C[C@@H](O)C[C@H]1C(=O)O]

A mixture of 1-tert-butyl 2-methyl (2S,4S)-4-hydroxypyrrolidine-1,2-dicarboxylate (5 g, 20.39 mmol, 1.00 equiv), methanol (100 mL), water (20 mL), and sodium hydroxide (2.85 g, 71.26 mmol, 3.50 equiv) was stirred for 12 h at 20° C. The resulting solution was concentrated and dissolved in water. The pH value of the solution was adjusted to 3-4 with 5% of HCl, extracted with ethyl acetate, dried over anhydrous sodium sulfate, and concentrated under vacuum. This resulted in the title compound (2.4 g, 51%) as a white solid.

Step 2: Preparation of tert-butyl (2S,4S)-4-hydroxy-2-[([3-methoxy-1-[4-(trifluoromethyl)phenyl]-1H-pyrazol-4-yl]methyl)carbamoyl]pyrrolidine-1-carboxylate

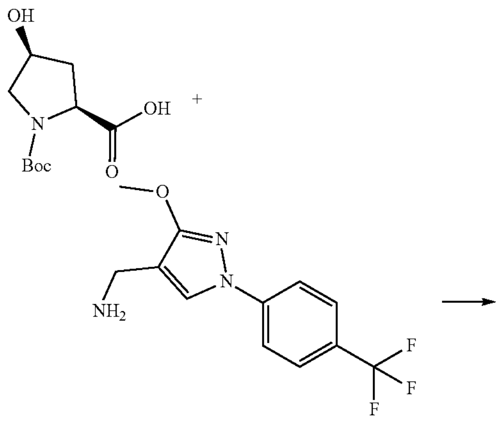

-continued

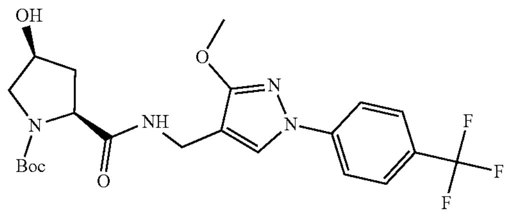

A mixture of (2S,4S)-1-[(tert-butoxy)carbonyl]-4-hydroxypyrrolidine-2-carboxylic acid (500 mg, 2.16 mmol, 1.00 equiv), dichloromethane (20 mL), EDCI (412.5 mg, 2.15 mmol, 1.00 equiv), HOBT (292.5 mg, 2.16 mmol, 1.00 equiv), and 3-methoxy-1-[4-(trifluoromethyl)phenyl]-1H-pyrazol-4-ylmethanamine (600 mg, 2.21 mmol, 1.00 equiv) was stirred for 1 h at 20° C. The resulting solution was diluted with water, extracted with dichloromethane, dried over sodium sulfate, and concentrated under vacuum. The residue was purified by flash chromatography on silica gel eluting with dichloromethane/methanol (20/1). This resulted in the title compound (630 mg, 60%) as a white solid.

Step 3: Preparation of (2S,4S)-4-hydroxy-N-([3-methoxy-1-[4-(trifluoromethyl)phenyl]-1H-pyrazol-4-yl]methyl)pyrrolidine-2-carboxamide

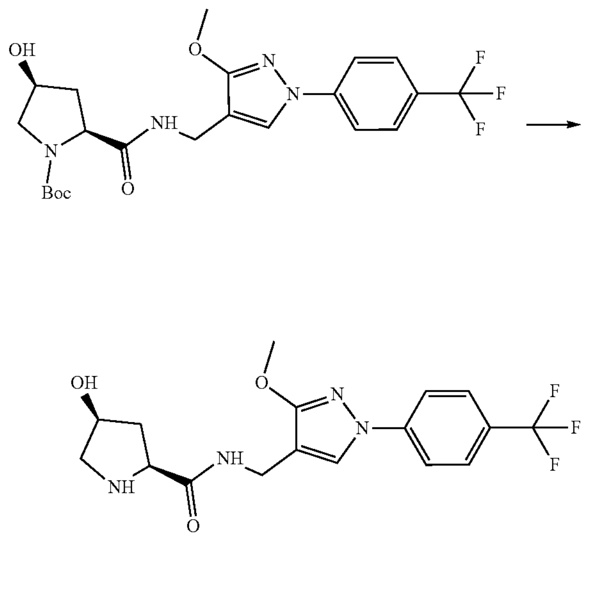

A solution of tert-butyl (2S,4S)-4-hydroxy-2-[([3-methoxy-1-[4-(trifluoromethyl)phenyl]-1H-pyrazol-4-yl]methyl)carbamoyl]pyrrolidine-1-carboxylate (1.6 g, 3.30 mmol, 1.00 equiv) in dichloromethane (20 mL)/trifluoroacetic acid (4 mL) was stirred for 12 h at 20° C. The resulting mixture was concentrated under vacuum. The residue was dissolved in water. The pH value of the solution was adjusted to 8-9 with sodium bicarbonate. The resulting solution was extracted with ethyl acetate, dried over anhydrous sodium sulfate, and concentrated under vacuum. This resulted in the title compound (1.2 g, 95%) as a yellow solid.

Step 4: Preparation of (2S,4S)-1-[(4-fluorobenzene)sulfonyl]-4-hydroxy-N-([3-methoxy-1-[4-(trifluoromethyl)phenyl]-1H-pyrazol-4-yl]methyl)pyrrolidine-2-carboxamide

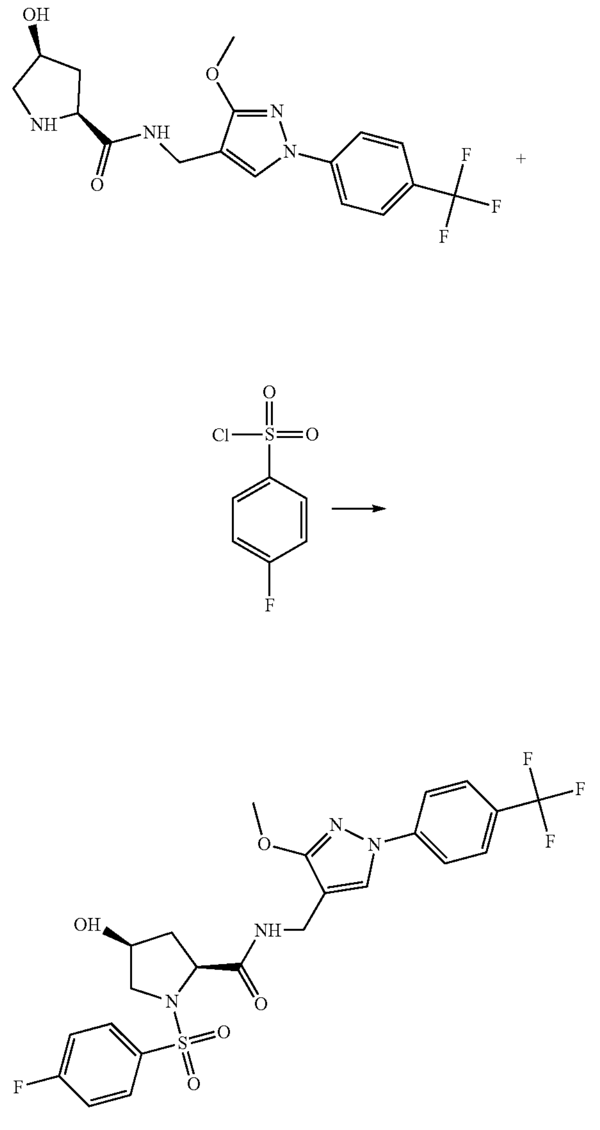

A solution of (2S,4S)-4-hydroxy-N-([3-methoxy-1-[4-(trifluoromethyl)phenyl]-1H-pyrazol-4-yl]methyl)pyrrolidine-2-carboxamide (1.2 g, 3.12 mmol, 1.00 equiv), dichloromethane (60 mL), TEA (630 mg, 6.23 mmol, 2.00 equiv), and 4-fluorobenzene-1-sulfonyl chloride (606 mg, 3.11 mmol, 1.00 equiv) was stirred for 12 h at 20° C. The resulting solution was diluted with water, extracted with ethyl acetate, dried over anhydrous sodium sulfate, and concentrated under vacuum. The residue was purified by flash chromatography on silica gel eluting with ethyl acetate/petroleum ether (1:1). This resulted in the title compound (1.1 g, 65%) as a white solid.

Step 5: Preparation of (3S,5S)-1-[(4-fluorobenzene)sulfonyl]-5-[([3-methoxy-1-[4-(trifluoromethyl)phenyl]-1H-pyrazol-4-yl]methyl)carbamoyl]pyrrolidin-3-yl 4-methylbenzene-1-sulfonate

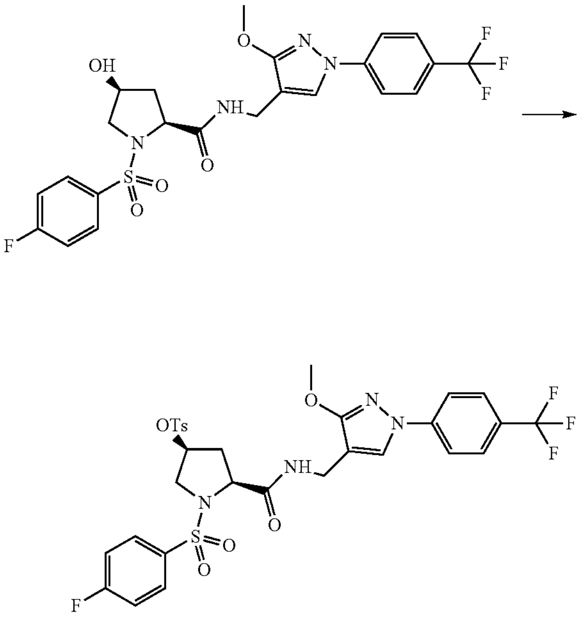

A mixture of (2S,4S)-1-[(4-fluorobenzene)sulfonyl]-4-hydroxy-N-([3-methoxy-1-[4-(trifluoromethyl)phenyl]-1H-pyrazol-4-yl]methyl)pyrrolidine-2-carboxamide (1.1 g, 2.03 mmol, 1.00 equiv), TEA (615 mg, 6.08 mmol, 3.00 equiv), Tesco (578 mg, 3.03 mmol, 1.50 equiv), and 4-dimethylaminopyridine (25 mg, 0.20 mmol, 0.10 equiv) in dichloromethane (20 mL) was stirred for 24 h at 20° C. The resulting solution was diluted with water and extracted with ethyl acetate. The combined extracts were dried over anhydrous sodium sulfate and concentrated under vacuum. The residue was purified by flash chromatography on silica gel eluting with ethyl acetate/petroleum ether (1/10) to afford the title compound (1 g, 71%) as a white solid.

Step 6: Preparation of (2S,4R)-4-cyano-1-[(4-fluorobenzene)sulfonyl]-N-([3-methoxy-1-[4-(trifluoromethyl)phenyl]-1H-pyrazol-4-yl]methyl)pyrrolidine-2-carboxamide

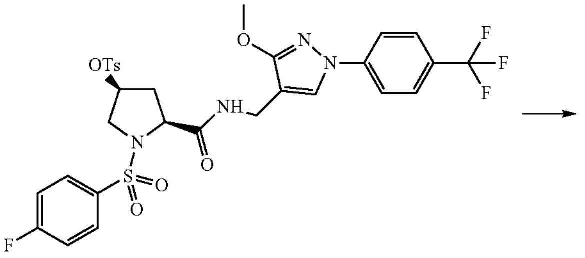

-continued

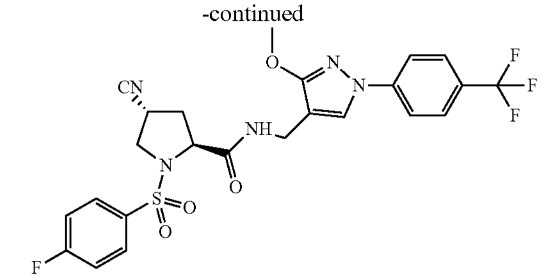

A mixture of (3S,5S)-1-[(4-fluorobenzene)sulfonyl]-5-[([3-methoxy-1-[4-(trifluoromethyl)phenyl]-1H-pyrazol-4-yl]methyl)carbamoyl]pyrrolidin-3-yl 4-methylbenzene-1-sulfonate (1.1 g, 1.58 mmol, 1.00 equiv), DMSO (6 mL), and NaCN (93 mg, 1.90 mmol, 1.20 equiv) was stirred for 48 h at 50° C. The resulting solution was diluted with ethyl acetate, washed with brine, dried over anhydrous sodium sulfate, and concentrated under vacuum. The residue was purified by flash chromatography on silica gel eluting with ethyl acetate/petroleum ether (1/1). The crude product was purified by Prep-HPLC to afford the title compound (43.1 mg, 5%) as a white solid.

$^1$H NMR (400 MHz, $CDCl_3$) δ 7.90-7.85 (m, 3H), 7.71-7.64 (m, 4H), 7.31-7.26 (s, 2H), 4.35-4.23 (m, 3H), 4.05 (s, 3H), 3.87-3.83 (m, 1H), 3.40-3.35 (m, 1H), 3.18-3.14 (m, 1H), 2.69-2.65 (m, 1H), 1.93-1.87 (m, 1H).

Example 111

Preparation of (2R,3S)-3-fluoro-1-(4-fluorophenyl)sulfonyl-N-[[6-[4-(trifluoromethoxy)phenyl]pyrimidin-4-yl]methyl]pyrrolidine-2-carboxamide

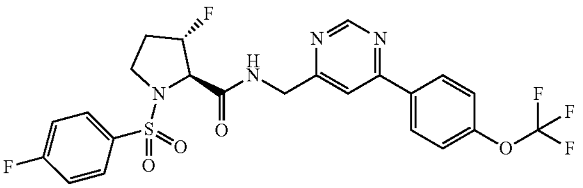 [SMILES: O=C(NCc1cc(-c2ccc(OC(F)(F)F)cc2)ncn1)[C@@H]1[C@@H](F)CCN1S(=O)(=O)c1ccc(F)cc1]

Step 1: Preparation of 4-chloro-6-[4-(trifluoromethoxy)phenyl]pyrimidine

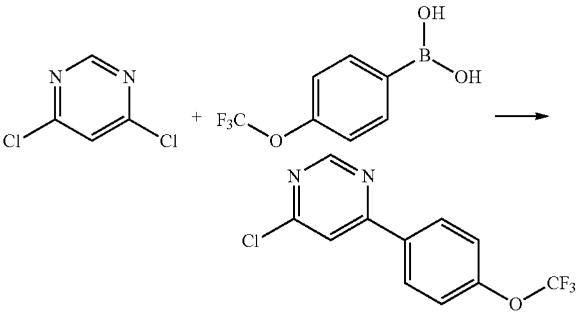

A mixture of [4-(trifluoromethoxy)phenyl]boronic acid (5 g, 24.28 mmol, 1.00 equiv) in 1,4-dioxane (50 mL), water (10 mL), 4,6-dichloropyrimidine (3.59 g, 24.10 mmol, 1.00 equiv), potassium carbonate (6.67 g, 48.26 mmol, 1.00 equiv), and Pd(dppf)$Cl_2$ (1.2 g, 1.64 mmol, 1.00 equiv) was stirred for 3 h at 80° C. under nitrogen. The reaction mixture was diluted with water and extracted with ethyl acetate. The combined extracts were washed with brine, dried over anhydrous sodium sulfate, and concentrated under vacuum. The crude residue was purified by recrystallized from ethyl acetate/petroleum ether (1/10) to afford the title compound (3.6 g, 54%) as a white solid.

Step 2: Preparation of 6-[4-(trifluoromethoxy)phenyl]pyrimidine-4-carbonitrile

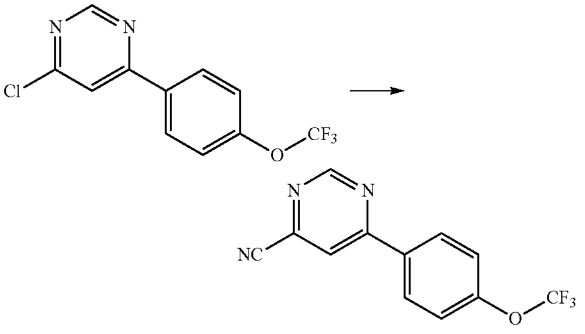

A mixture of 4-chloro-6-[4-(trifluoromethoxy)phenyl]pyrimidine (500 mg, 1.82 mmol, 1.00 equiv), $Zn(CN)_2$ (256 mg, 2.18 mmol, 1.20 equiv), dppf (150 mg, 0.27 mmol, 0.30 equiv), and $Pd_2(dba)_3$ (100 mg, 0.11 mmol, 0.20 equiv) in N,N-dimethylformamide (5 mL) was irradiated with microwave for 3 h at 100° C. under nitrogen. The reaction mixture was diluted with water and extracted with ethyl acetate. The combined extracts were washed with brine, dried over anhydrous sodium sulfate, and concentrated under vacuum. The residue was purified by flash chromatography on silica gel eluting with ethyl acetate/petroleum ether (1/10). This resulted in the title compound (200 mg, 41%) as yellow oil.

Step 3: Preparation of [6-[4-(trifluoromethoxy)phenyl]pyrimidin-4-yl]methanamine hydrochloride

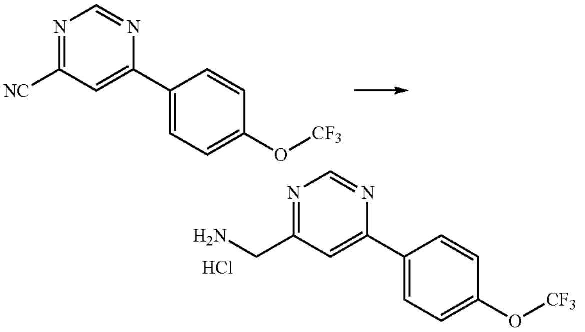

A mixture of 6-[4-(trifluoromethoxy)phenyl]pyrimidine-4-carbonitrile (200 mg, 0.75 mmol, 1.00 equiv), palladium on carbon (100 mg, 0.94 mmol, 1.00 equiv), ethanol (10 mL), and concentrated hydrogen chloride (0.2 mL) was stirred for 10 min at room temperature under hydrogen. The solids were filtered out and the liquid was concentrated under vacuum. This resulted in the title compound (65 mg, 32%) as a yellow solid.

Step 4: Preparation of (2R,3S)-3-fluoro-1-(4-fluorophenyl)sulfonyl-N-[[6-[4-(trifluoromethoxy)phenyl]pyrimidin-4-yl]methyl]pyrrolidine-2-carboxamide

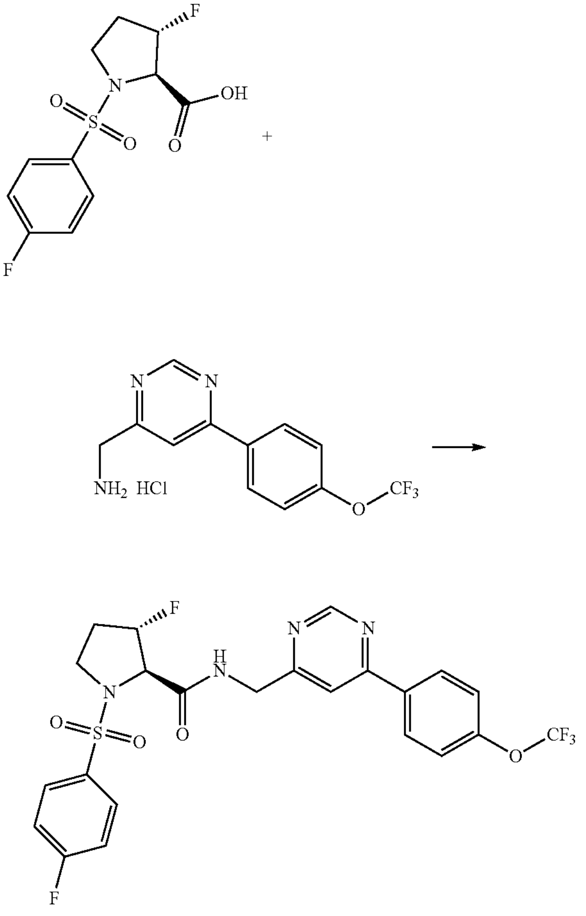

A mixture of [6-[4-(trifluoromethoxy)phenyl]pyrimidin-4-yl]methanamine hydrochloride (65 mg, 0.24 mmol, 1.00 equiv), (2R,3S)-3-fluoro-1-[(4-fluorobenzene)sulfonyl]pyrrolidine-2-carboxylic acid (70 mg, 0.24 mmol, 1.00 equiv), DIPEA (93 mg, 0.72 mmol, 3.00 equiv), and HATU (182 mg, 0.48 mmol, 2.00 equiv) in tetrahydrofuran (10 mL) was stirred for 16 h at room temperature. The reaction mixture was diluted with water and extracted with ethyl acetate. The combined extracts were washed with brine, dried over anhydrous sodium sulfate, and concentrated under vacuum. The crude product was purified by chromatograph on a silica gel eluting with ethyl acetate/petroleum ether (1/1). This resulted in the title compound (23 mg, 18%) as a white solid.

$^1H$ NMR (300 MHz, DMSO-$d_6$) δ 9.21-9.17 (m, 2H), 8.35 (d, J=6.6 Hz, 1H), 8.05-8.01 (m, 3H), 7.54-7.49 (m, 4H), 5.33-5.15 (d, J=52.2 Hz, 1H), 4.57-4.40 (m, 3H), 3.71-3.66 (t, J=6.6 Hz, 1H), 3.33-3.15 (m, 1H), 2.27-2.01 (m, 2H).

Example 112

Preparation of (2S,4R)—N-[[3-cyano-5-[6-(trifluoromethyl)-3-pyridyl]phenyl]methyl]-4-fluoro-1-(4-fluorophenyl)sulfonyl-pyrrolidine-2-carboxamide

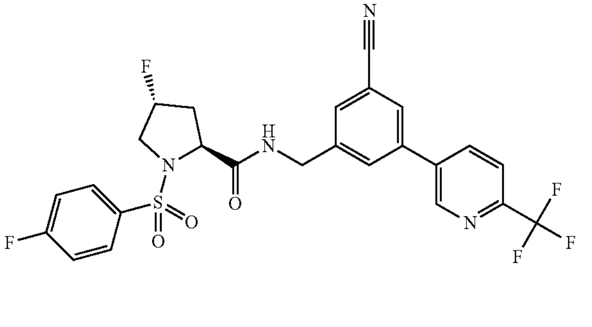 [SMILES: N#Cc1cc(CNC(=O)[C@@H]2C[C@@H](F)CN2S(=O)(=O)c2ccc(F)cc2)cc(-c2ccc(C(F)(F)F)nc2)c1]

Step 1: Preparation of (3-bromo-5-iodophenyl)methanol

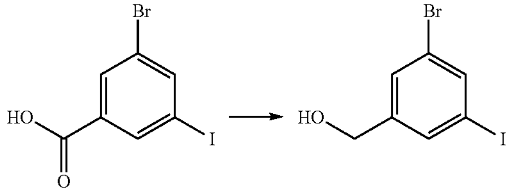 [SMILES: O=C(O)c1cc(Br)cc(I)c1 ; OCc1cc(Br)cc(I)c1]

$BH_3$.THF (51 mL, 1 mol/L in THF) dropwise was added dropwise into a solution of 3-bromo-5-iodobenzoic acid (10 g, 30.59 mmol, 1.00 equiv) in THF (50 mL) at 0° C. under nitrogen. The resulting solution was stirred for 12 h at room temperature. The reaction was then quenched by water at 0° C. The resulting solution was extracted with ethyl acetate, washed with brine, dried over anhydrous sodium sulfate, and concentrated under vacuum. This resulted in the title compound (8.5 g, 89%) as an off-white solid.

Step 2: Preparation of 1-bromo-3-(chloromethyl)-5-iodobenzene

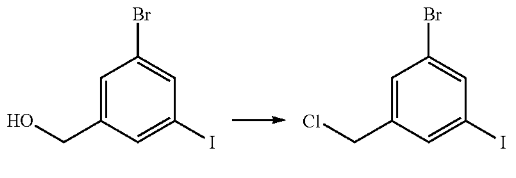 [SMILES: OCc1cc(Br)cc(I)c1 ; ClCc1cc(Br)cc(I)c1]

A mixture of (3-bromo-5-iodophenyl)methanol (3.00 g, 9.59 mmol, 1.00 equiv), dichloromethane (20 mL), and sulfuryl dichloride (2.20 g, 19.21 mmol, 2.00 equiv) was stirred for 1 h at 0° C. The resulting solution was diluted with water and extracted with dichloromethane. The combined extracts were washed with brine, dried over anhydrous sodium sulfate, and concentrated under vacuum. The residue was purified by a silica gel column eluting with ethyl acetate/petroleum ether (1:10). This resulted in the title compound (2 g, 63%) as a white solid.

Step 3: Preparation of 2-[(3-bromo-5-iodophenyl)methyl]-2,3-dihydro-1H-isoindole-1,3-dione

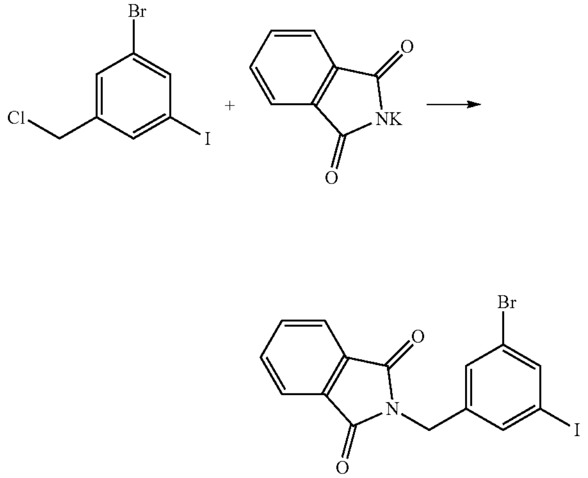

A mixture of 1-bromo-3-(chloromethyl)-5-iodobenzene (2.00 g, 6.04 mmol, 1.00 equiv) and 2-potassium-2,3-dihydro-1H-isoindole-1,3-dione (1.68 g, 9.07 mmol, 1.50 equiv) in DMF (15 mL) was stirred for 12 h at room temperature. The reaction mixture was diluted with water. The solids were collected by filtration to afford the title compound (2.5 g, 94%) as a white solid.

Step 4: Preparation of (3-bromo-5-iodophenyl)methanamine

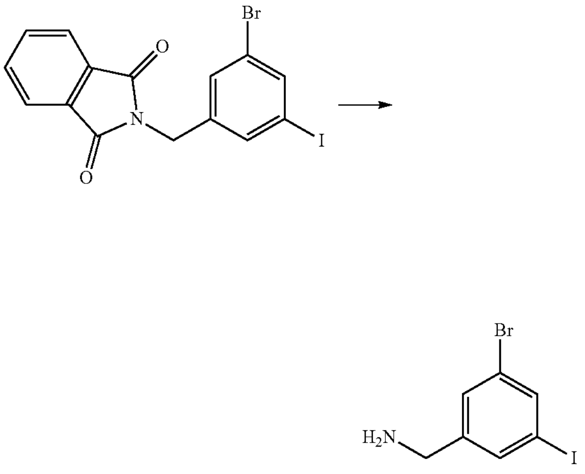

A mixture of 2-[(3-bromo-5-iodophenyl)methyl]-2,3-dihydro-1H-isoindole-1,3-dione (3.00 g, 6.79 mmol, 1.00 equiv), methanol (50 mL), and $NH_2NH_2.H_2O$ (3.40 g, 67.92 mmol, 10.00 equiv) was stirred for 12 h at 50° C. The solids were filtered out and the liquid was concentrated under vacuum. The residue was purified by a silica gel column eluting with dichloromethane/methanol (20:1). This resulted in the title compound (2 g, 94%) as yellow oil.

Step 5: Preparation of (2S,4R)—N-[(3-bromo-5-iodophenyl)methyl]-4-fluoro-1-[(4-fluorobenzene)sulfonyl]pyrrolidine-2-carboxamide

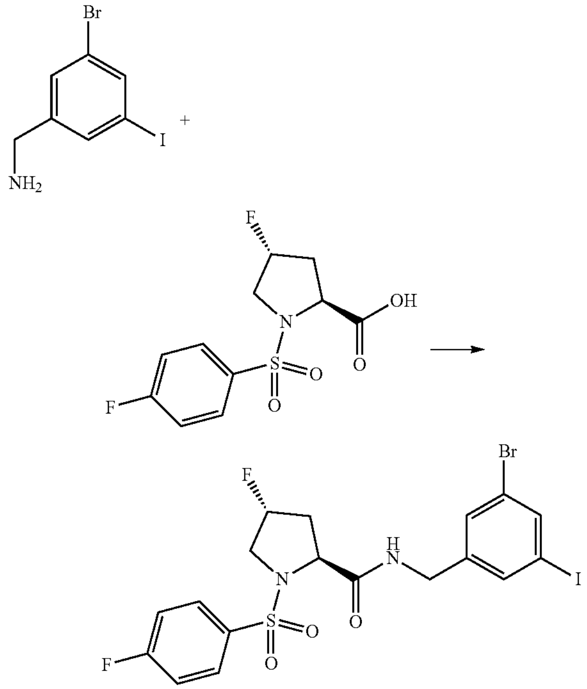

A mixture of (2S,4R)-4-fluoro-1-[(4-fluorobenzene)sulfonyl]pyrrolidine-2-carboxylic acid (780.00 mg, 2.68 mmol, 1.00 equiv), DMF (10.01 mL), HATU (1527.34 mg, 4.02 mmol, 1.50 equiv), DIEA (1038.31 mg, 8.03 mmol, 3.00 equiv), and (3-bromo-5-iodophenyl)methanamine (1002.44 mg, 3.21 mmol, 1.20 equiv) was stirred for 12 h at room temperature. The resulting solution was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:1). This resulted in the title compound (1.2 g, 77%) as a white solid.

Step 6: Preparation of (2S,4R)—N-([3-bromo-5-[6-(trifluoromethyl)pyridin-3-yl]phenyl]methyl)-4-fluoro-1-[(4-fluorobenzene)sulfonyl]pyrrolidine-2-carboxamide

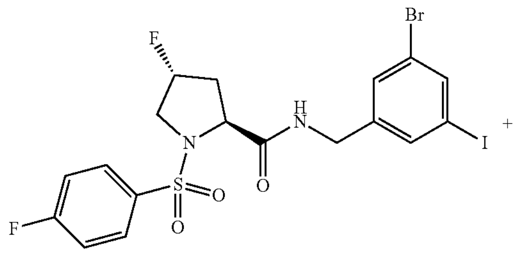

-continued

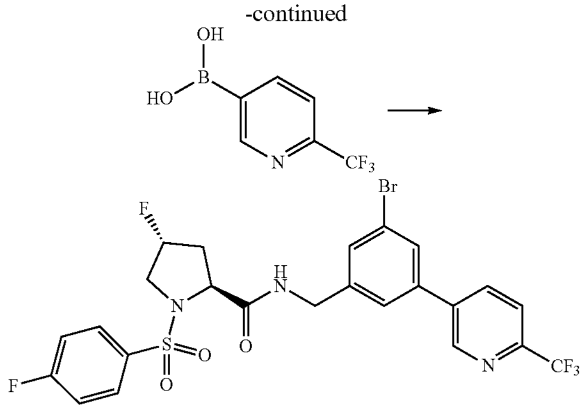

A mixture of [6-(trifluoromethyl)pyridin-3-yl]boronic acid (130.50 mg, 0.68 mmol, 1.00 equiv), (2S,4R)—N-[(3-bromo-5-iodophenyl)methyl]-4-fluoro-1-[(4-fluorobenzene)sulfonyl]pyrrolidine-2-carboxamide (400.01 mg, 0.68 mmol, 1.00 equiv), $Pd(dppf)Cl_2$ (50.02 mg, 0.07 mmol, 0.10 equiv), potassium carbonate (380 mg, 2.75 mmol, 4.00 equiv), and 1,4-dioxane (15 mL)/water(3 mL) was stirred for 12 h at 50° C. under nitrogen. The resulting solution was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:1). This resulted in the title compound (260 mg, 63%) as a light yellow solid.

Step 7: Preparation of (2S,4R)—N-[[3-cyano-5-[6-(trifluoromethyl)-3-pyridyl]phenyl]methyl]-4-fluoro-1-(4-fluorophenyl)sulfonyl-pyrrolidine-2-carboxamide

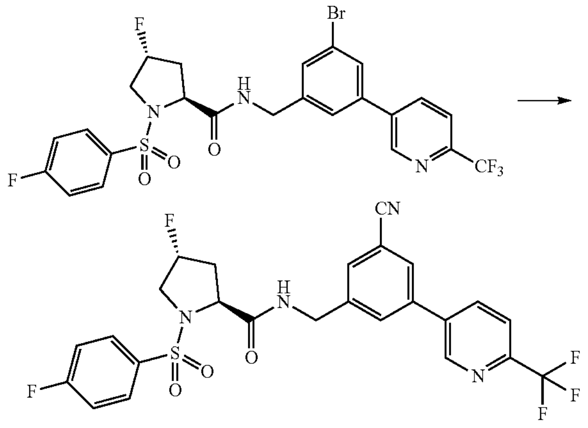

A mixture of (2S,4R)—N-([3-bromo-5-[6-(trifluoromethyl)pyridin-3-yl]phenyl]methyl)-4-fluoro-1-[(4fluorobenzene)su-lfonyl]-pyrrolidine-2-carboxamide (220 mg, 0.36 mmol, 1.00 equiv), DMF (3 mL), dppf (55 mg, 0.10 mmol, 0.30 equiv), $Zn(CN)_2$ (43 mg, 0.37 mmol, 1.00 equiv), and $Pd_2(dba)_3$ (33 mg, 0.04 mmol, 0.10 equiv) was irradiated with microwave radiation for 2 h at 100° C. under nitrogen. The resulting solution was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:1). The crude product (200 mg) was purified by Prep-HPLC to afford the title compound (92 mg, 46%) as a white solid.

$^{1}$H NMR (300 MHz, $CDCl_3$) δ 8.97 (s, 1H), 8.14-8.11 (m, 1H), 7.90-7.71 (m, 7H), 7.43 (s, 1H), 7.26-7.21 (m, 2H), 5.05 (d, J=52.5 Hz, 1H), 4.87-4.80 (m, 1H), 4.48-4.42 (m, 1H), 4.30-4.24 (m, 1H), 3.96-3.84 (m, 1H), 3.72-3.49 (m, 1H), 2.61-2.41 (m, 1H), 2.35-2.00 (m, 1H).

Example 113

Preparation of (2S,4R)-4-fluoro-N-((6-(2-fluoro-4-(trifluoromethyl)phenyl)pyrimidin-4-yl)methyl)-1-(4-fluorophenylsulfonyl)pyrrolidine-2-carboxamide

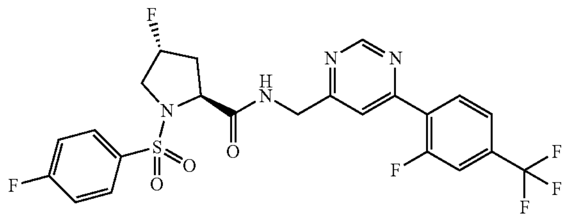 [SMILES: O=C(NCc1cc(-c2ccc(C(F)(F)F)cc2F)ncn1)[C@@H]1C[C@@H](F)CN1S(=O)(=O)c1ccc(F)cc1]

Step 1: Preparation of 4-chloro-6-[2-fluoro-4-(trifluoromethyl)phenyl]pyrimidine

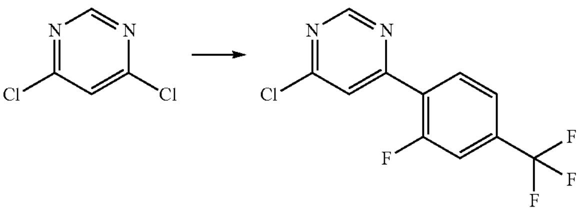 [SMILES: Clc1cc(Cl)ncn1 ; Fc1cc(C(F)(F)F)ccc1-c1cc(Cl)ncn1]

A mixture of [2-fluoro-4-(trifluoromethyl)phenyl]boronic acid (1 g, 4.81 mmol, 1.00 equiv), 4,6-dichloropyrimidine (2 g, 13.42 mmol, 3.00 equiv), potassium carbonate (1.66 g, 12.01 mmol, 2.50 equiv), and Pd(dppf)$Cl_2$ (180 mg, 0.25 mmol, 0.05 equiv) in 1,4-dioxane (15 mL)/water(1 mL) was stirred overnight at 100° C. under nitrogen. The reaction mixture was cooled to room temperature, quenched with water, extracted with ethyl acetate, washed with brine, dried over anhydrous sodium sulfate, and concentrated under vacuum. The residue was purified by a silica gel column eluting with ethyl acetate/petroleum ether (1:1) to afford the title compound (0.7 g, 53%) as a brown solid.

Step 2: Preparation of 6-[2-fluoro-4-(trifluoromethyl)phenyl]pyrimidine-4-carbonitrile

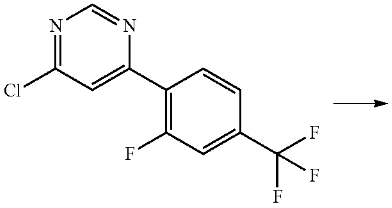

-continued

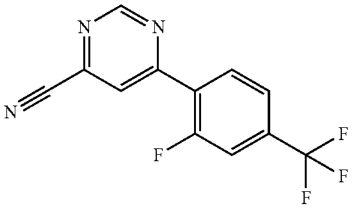

A mixture of 4-chloro-6-[2-fluoro-4-(trifluoromethyl)phenyl]pyrimidine (2.2 g, 7.95 mmol, 1.00 equiv), $Zn(CN)_2$ (564 mg, 4.80 mmol, 0.60 equiv), $Pd_2(dba)_3.CHCl_3$ (414 mg, 0.40 mmol, 0.05 equiv), dppf (446 mg, 0.80 mmol, 0.10 equiv), and Zn (50 mg, 0.76 mmol, 0.10 equiv) in DMA (15 mL) was irradiated with microwave radiation for 1 h at 125° C. under nitrogen. The resulting mixture was cooled to room temperature, quenched by water, extracted with ethyl acetate, washed with brine, dried over anhydrous sodium sulfate, and concentrated under vacuum. The residue was purified by a silica gel column eluting with ethyl acetate/petroleum ether (1:1) to afford the title compound (730 mg, 34%) as a brown solid.

Step 3: Preparation of [6-[2-fluoro-4-(trifluoromethyl)phenyl]pyrimidin-4-yl]methanamine

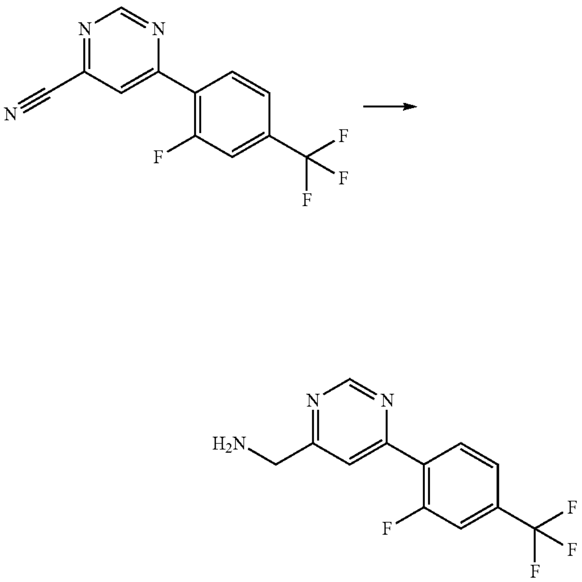

A mixture of 6-[2-fluoro-4-(trifluoromethyl)phenyl]pyrimidine-4-carbonitrile (300 mg, 1.12 mmol, 1.00 equiv) in ethyl acetate (5 mL), methanol (5 mL, 123.49 mmol, 110.00 equiv), and $Pd(OH)_2/C$ (200 mg, 1.42 mmol, 1.30 equiv) was stirred for 15 h at room temperature under hydrogen. The solids were filtered out and the liquid was concentrated under vacuum to afford the title compound 280 mg) as a brown oil.

Step 4: Preparation of (2S,4R)-4-fluoro-N-((6-(2-fluoro-4-(trifluoromethyl)phenyl)pyrimidin-4-yl)methyl)-1-(4-fluorophenylsulfonyl)pyrrolidine-2-carboxamide

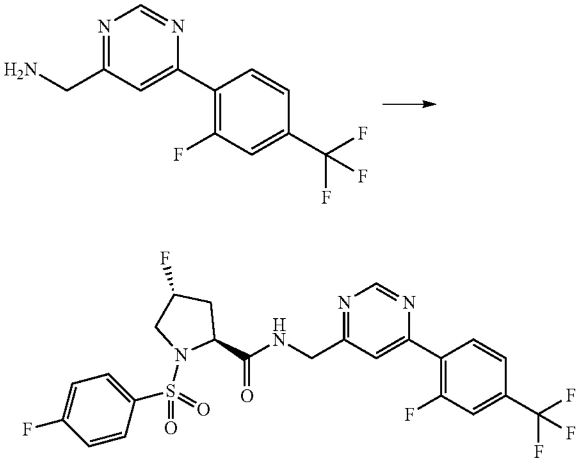

A solution of [6-[2-fluoro-4-(trifluoromethyl)phenyl]pyrimidin-4-yl]methanamine (280 mg, 1.03 mmol, 1.00 equiv), (2S,4R)-4-fluoro-1-[(4-fluorobenzene)sulfonyl]pyrrolidine-2-carboxylic acid (300 mg, 1.03 mmol, 1.00 equiv), EDCI (297 mg, 1.55 mmol, 1.50 equiv), HOBT (153 mg, 1.13 mmol, 1.10 equiv), and DIEA (267 mg, 2.07 mmol, 2.00 equiv) in tetrahydrofuran (10 mL) was stirred for 10 h at room temperature. The reaction was then quenched by water, extracted with ethyl acetate, washed with brine, and concentrated under vacuum. The crude product was purified by Prep-HPLC to afford the title compound (28.4 mg, 5%) as a white solid.

$^1$H NMR (300 MHz, $CDCl_3$) δ 9.41 (s, 1H), 8.35-8.29 (t, J=7.7 Hz, 1H), 7.94-7.88 (m, 3H), 7.79 (s, 1H), 7.62-7.59 (d, J=7.5 Hz, 1H), 7.49-7.46 (d, J=11.4 Hz, 1H), 7.31-7.20 (m, 2H), 5.16-4.99 (d, J=52.2 Hz, 1H), 4.77-4.66 (s, 2H), 4.33-4.27 (t, J=8.5 Hz, 1H), 3.97-3.49 (m, 2H), 2.60-2.46 (m, 1H), 2.42-2.04 (m, 1H).

Example 114

Preparation of (2S,4R)-4-fluoro-N-([6-[3-fluoro-4-(trifluoromethyl)phenyl]pyrimidin-4-yl]methyl)-1-[(4-fluorobenzene)sulfonyl]pyrrolidine-2-carboxamide

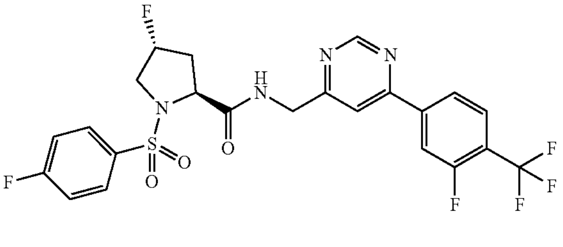 [SMILES: O=C(NCc1cc(-c2ccc(C(F)(F)F)c(F)c2)ncn1)[C@@H]1C[C@@H](F)CN1S(=O)(=O)c1ccc(F)cc1]

Step 1: Preparation of 6-[3-fluoro-4-(trifluoromethyl)phenyl]pyrimidine-4-carbonitrile

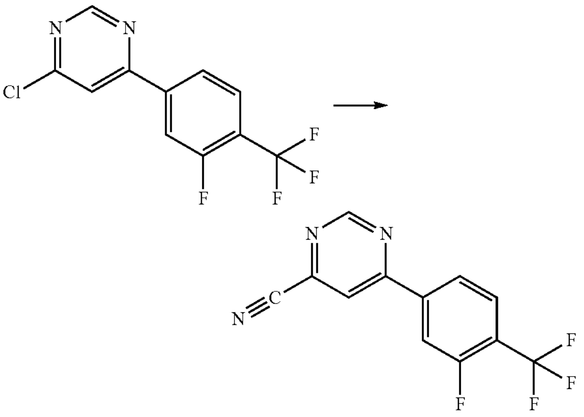

A mixture of 4-chloro-6-[3-fluoro-4-(trifluoromethyl)phenyl]pyrimidine (200 mg, 0.72 mmol, 1.00 equiv), dppf (80 mg, 0.14 mmol, 0.20 equiv), $Zn(CN)_2$ (124 mg, 1.06 mmol, 1.50 equiv), and $Pd_2(dba)_3.CHCl_3$ (72 mg, 0.07 mmol, 0.10 equiv) in N,N-dimethylformamide (4 mL) was irradiated with microwave radiation for 2 h at 100° C. under nitrogen. The reaction was then quenched by water. The resulting solution was extracted with ethyl acetate, washed with brine, and concentrated under vacuum. The residue was purified by a silica gel column eluting with ethyl acetate/petroleum ether (1:10) to afford the title compound (160 mg, 80%) as a yellow solid.

Step 2: Preparation of [6-[3-fluoro-4-(trifluoromethyl)phenyl]pyrimidin-4-yl]methanamine

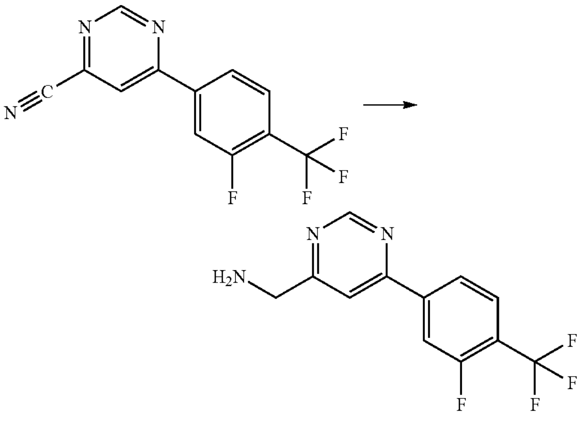

Into a 100-mL round-bottom flask was placed 6-[3-fluoro-4-(trifluoromethyl)phenyl]pyrimidine-4-carbonitrile (160 mg, 0.60 mmol, 1.00 equiv), palladium on carbon (160 mg, 1.50 mmol, 2.50 equiv), methanol (5 mL), and ethyl acetate (5 mL). The resulting solution was maintained with an atmosphere of H2 for 10 min at room temperature. Then the solids were filtered out and the liquid was concentrated under vacuum. This resulted in the title compound (120 mg, 74%) as a yellow solid.

Step 3: Preparation of (2S,4R)-4-fluoro-N-([6-[3-fluoro-4-(trifluoromethyl)phenyl]pyrimidin-4-yl]methyl)-1-[(4-fluorobenzene)sulfonyl]pyrrolidine-2-carboxamide

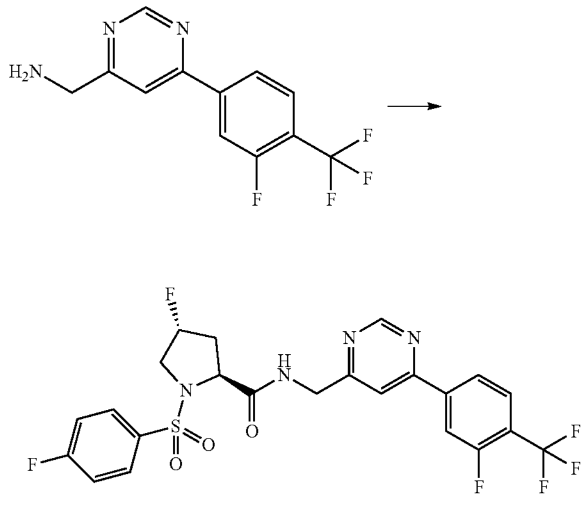

A solution of [6-[3-fluoro-4-(trifluoromethyl)phenyl]pyrimidin-4-yl]methanamine (120 mg, 0.44 mmol, 1.00 equiv), (2S,4R)-4-fluoro-1-[(4-fluorobenzene)sulfonyl]pyrrolidine-2-carboxylic acid (128 mg, 0.44 mmol, 1.00 equiv), EDCI (170 mg, 0.89 mmol, 2.00 equiv), HOBT (65.7 mg, 0.49 mmol, 1.10 equiv), and DIEA (114 mg, 0.88 mmol, 2.00 equiv) in tetrahydrofuran (4 mL) was stirred for 13 h at room temperature. The reaction was then quenched by water/ice, extracted with ethyl acetate, and concentrated under vacuum. The crude product was purified by Prep-HPLC to afford the title compound (34.7 mg, 14%) as a white solid.

$^1$H NMR (300 MHz, $CDCl_3$) δ 9.21 (s, 1H), 8.19-8.08 (m, 3H), 7.95-7.86 (m, 2H), 7.74-7.64 (m, 2H), 7.28-7.23 (m, 2H), 5.17-4.91 (m, 2H), 4.54-4.53 (d, J=4.2 Hz, 1H), 4.36-4.30 (t, J=8.5 Hz, 1H), 3.95-3.65 (m, 2H), 2.66-2.56 (m, 1H), 2.34-2.13 (m, 1H).

Example 115

Preparation of (2R,3S)-3-fluoro-1-(4-fluorophenyl)sulfonyl-N-[[5-fluoro-4-[6-(trifluoromethyl)-3-pyridyl]-2-pyridyl]methyl]pyrrolidine-2-carboxamide

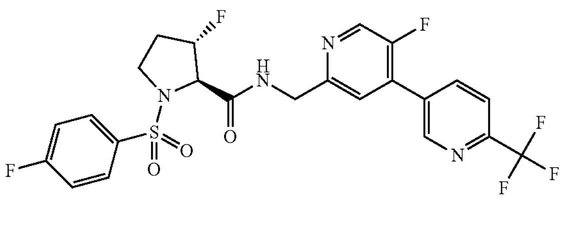 [SMILES: O=C(NCc1cc(-c2ccc(C(F)(F)F)nc2)c(F)cn1)[C@@H]1[C@@H](F)CCN1S(=O)(=O)c1ccc(F)cc1]

Step 1: Preparation of 1-tert-butyl 2-methyl (3S)-3-fluoropyrrolidine-1,2-dicarboxylate

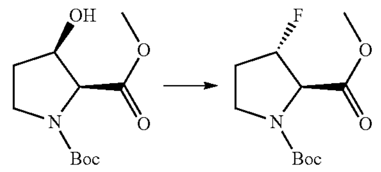 [SMILES: COC(=O)[C@@H]1[C@H](O)CCN1C(=O)OC(C)(C)C ; COC(=O)[C@@H]1[C@@H](F)CCN1C(=O)OC(C)(C)C]

A mixture of 1-tert-butyl 2-methyl (3R)-3-hydroxypyrrolidine-1,2-dicarboxylate (760 mg, 3.10 mmol, 1.00 equiv) in dichloromethane (20 mL, 314.60 mmol, 1.00 equiv) was added DAST (1.1 g, 4.80 mmol, 3.00 equiv) dropwise with stirring at −78° C. under nitrogen. The resulting solution was stirred overnight at room temperature. The reaction was then quenched by water, extracted with dichloromethane, washed with brine, dried over anhydrous sodium sulfate, and concentrated under vacuum. The residue was purified by a silica gel column eluting with ethyl acetate/petroleum ether (1:1) to afford the title compound (420 mg, 55%) as brown oil.

Step 2: Preparation of methyl (3S)-3-fluoropyrrolidine-2-carboxylate hydrochloride

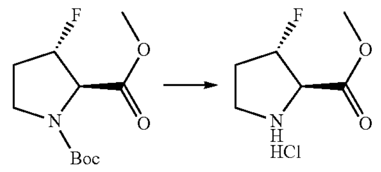

A mixture of 1-tert-butyl 2-methyl (3S)-3-fluoropyrrolidine-1,2-dicarboxylate (420 mg, 1.70 mmol, 1.00 equiv) and HCl (saturated solution in 10 mL of 1,4-dioxane) was stirred for 3 h at room temperature. The reaction was concentrated under vacuum to afford the title compound (320 mg, crude) as brown oil.

Step 3: Preparation of methyl (3S)-3-fluoro-1-[(4-fluorobenzene)sulfonyl]pyrrolidine-2-carboxylate

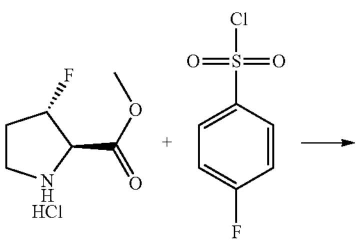

-continued

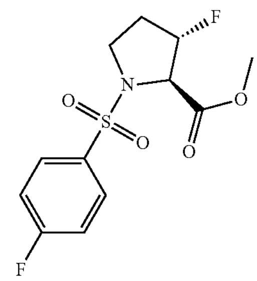

A mixture of methyl (3S)-3-fluoropyrrolidine-2-carboxylate hydrochloride (320 mg, 2.17 mmol, 1.00 equiv) in dichloromethane (20 mL), TEA (661 mg, 6.53 mmol, 3.00 equiv), and 4-fluorobenzene-1-sulfonyl chloride (844 mg, 4.34 mmol, 2.00 equiv) was stirred for 16 hours at room temperature. The reaction mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:1) to afford the title compound (520 mg, 78%) as a brown solid.

Step 4: (3S)-3-fluoro-1-[(4-fluorobenzene)sulfonyl]pyrrolidine-2-carboxylic acid

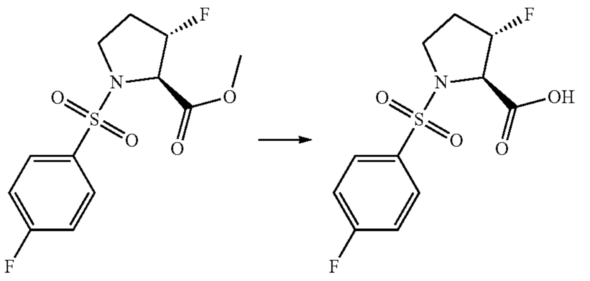 [SMILES: COC(=O)[C@@H]1[C@@H](F)CCN1S(=O)(=O)c1ccc(F)cc1 ; O=C(O)[C@@H]1[C@@H](F)CCN1S(=O)(=O)c1ccc(F)cc1]

A mixture of methyl (3S)-3-fluoro-1-[(4-fluorobenzene)sulfonyl]pyrrolidine-2-carboxylate (200 mg, 0.66 mmol, 1.00 equiv) in 1,4-dioxane (2 mL) and sulfuric acid (50%) (10 mL, 187.61 mmol, 1.00 equiv) was stirred for 1 h at 100° C. The reaction mixture was diluted with water, extracted with ethyl acetate, washed with brine, dried over anhydrous sodium sulfate, and concentrated under vacuum. This resulted in the title compound (228 mg, crude) as yellow oil.

Step 5: Preparation of (2R,3S)-3-fluoro-1-(4-fluorophenyl)sulfonyl-N-[[5-fluoro-4-[6-(trifluoromethyl)-3-pyridyl]-2-pyridyl]methyl]pyrrolidine-2-carboxamide

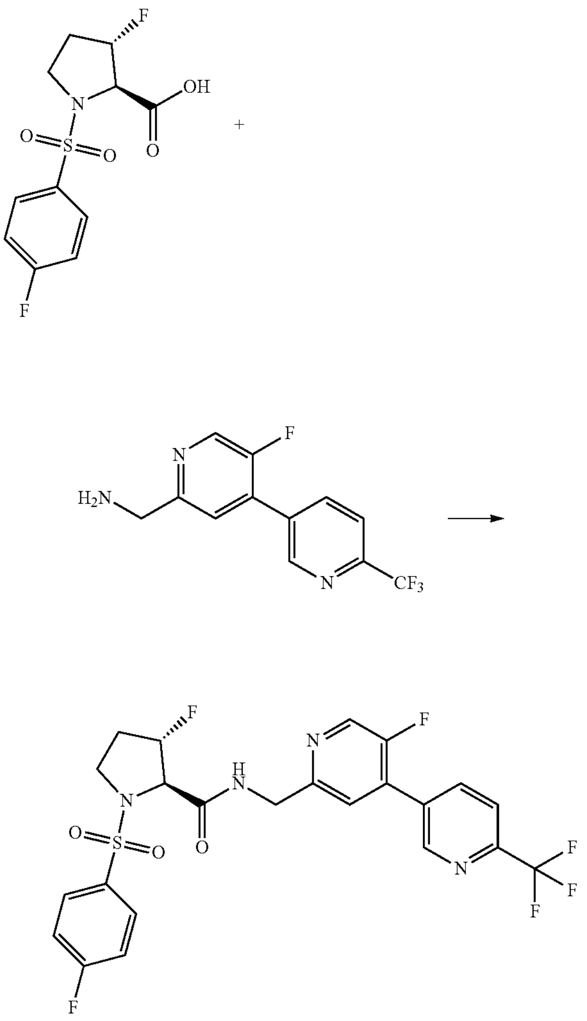

A mixture of [5-fluoro-4-[6-(trifluoromethyl)pyridin-3-yl]pyridin-2-yl]methanamine (100 mg, 0.37 mmol, 1.00 equiv) in DMF (10 mL), (3S)-3-fluoro-1-[(4-fluorobenzene)sulfonyl]pyrrolidine-2-carboxylic acid (92 mg, 0.32 mmol, 1.00 equiv), DIPEA (133 mg, 1.03 mmol, 3.00 equiv), and HATU (258 mg, 0.68 mmol, 2.00 equiv) was stirred for 16 h at room temperature. The reaction mixture was diluted with water, extracted with ethyl acetate, washed with brine, dried over anhydrous sodium sulfate, and concentrated under vacuum. The residue was purified by flash chromatography on silica gel eluting with petroleum ether/ethyl acetate (1/1). This resulted in the title compound (45.2 mg, 23%) as a white solid.

$^1H$ NMR (300 MHz, DMSO-$d_6$) δ 9.11-9.09 (m, 1H), 8.73 (d, J=1.8 Hz, 1H), 8.40 (d, J=7.8 Hz, 1H), 8.11 (d, J=8.1 Hz, 1H), 7.99-7.95 (m, 2H), 7.71 (d, J=6 Hz, 1H), 7.51 (t, J=8.7 Hz, 2H), 5.27-5.10 (d, J=51.6 Hz, 1H), 4.59-4.35 (m, 3H), 3.68-3.62 (m, 1H), 3.21-3.12 (m, 1H), 2.27-2.08 (m, 2H).

Example 116

Preparation of (2S,4R)-4-fluoro-1-(4-fluorophenyl)sulfonyl-N-[[3-methoxy-5-[6-(trifluoromethyl)-3-pyridyl]phenyl]methyl]pyrrolidine-2-carboxamide

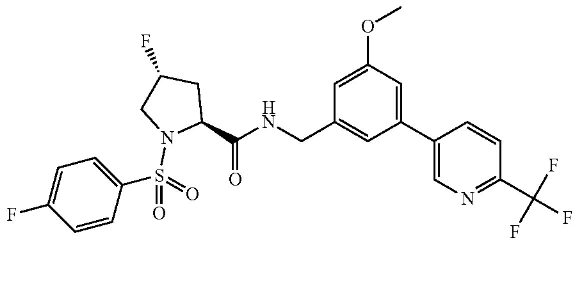 [SMILES: COc1cc(CNC(=O)[C@@H]2C[C@@H](F)CN2S(=O)(=O)c2ccc(F)cc2)cc(-c2ccc(C(F)(F)F)nc2)c1]

Step 1: Preparation of 1-bromo-3-(bromomethyl)-5-methoxybenzene

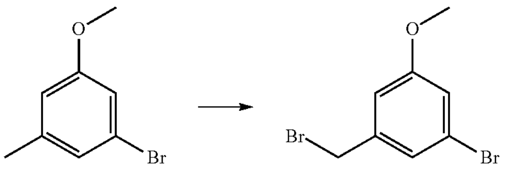

A mixture of NBS (5.31 g, 29.83 mmol, 1.20 equiv), AIBN (2.04 g, 12.42 mmol, 0.50 equiv), $CCl_4$ (100 mL), and 1-bromo-3-methoxy-5-methylbenzene (5.00 g, 24.87 mmol, 1.00 equiv) was stirred for 12 h at 80° C. under nitrogen. The reaction was then quenched by water, extracted with dichloromethane, washed with brine, dried over anhydrous sodium sulfate, and concentrated under vacuum. The residue was purified by a silica gel column eluting with ethyl acetate/petroleum ether (1:100) to afford the title compound (6 g, 86%) as a light yellow solid.

Step 2: Preparation of 2-[(3-bromo-5-methoxyphenyl)methyl]-2,3-dihydro-1H-isoindole-1,3-dione

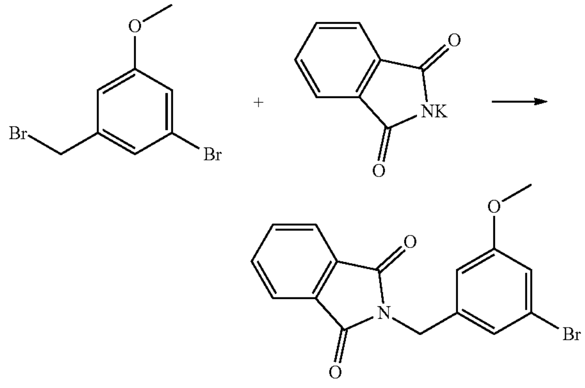

A mixture of 2-potassium-2,3-dihydro-1H-isoindole-1,3-dione (5.95 g, 32.12 mmol, 1.00 equiv), DMF (30 ml), and 1-bromo-3-(bromomethyl)-5-methoxybenzene (6 g, 21.43 mmol, 1.00 equiv) was stirred for 12 h at 50° C. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1:20) to afford the title compound (5 g, 45%) as a white solid.

Step 3: Preparation of (3-bromo-5-methoxyphenyl)methanamine

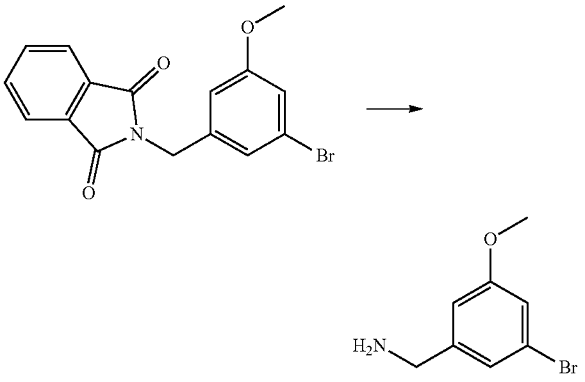

A mixture of 2-[(3-bromo-5-methoxyphenyl)methyl]-2,3-dihydro-1H-isoindole-1,3-dione (4.90 g, 14.15 mmol, 1.00 equiv), methanol (50 mL), and $NH_2NH_2.H_2O$ (7.09 g, 141.63 mmol, 10.00 equiv) was stirred for 3 h at 50° C. The resulting mixture was concentrated under vacuum. The residue was dissolved in ethyl acetate. The solids were filtered out and the filtrate was concentrated under vacuum to afford the title compound (3 g, 98%) as yellow oil.

Step 4: Preparation of (2S,4R)—N-[(3-bromo-5-methoxyphenyl)methyl]-4-fluoro-1-[(4-fluorobenzene)sulfonyl]pyrrolidine-2-carboxamide

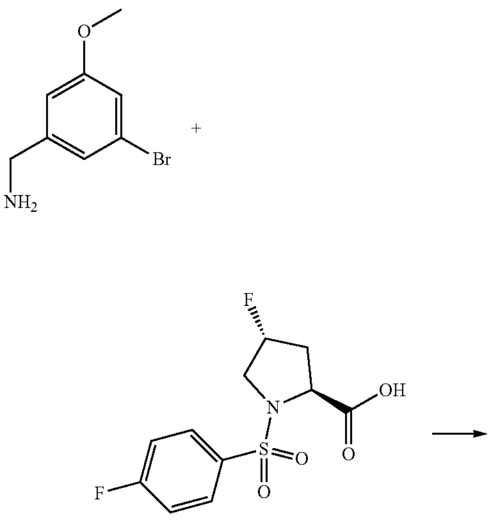

-continued

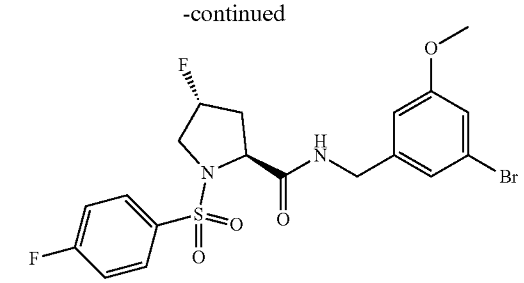

A mixture (2S,4R)-4-fluoro-1-[(4-fluorobenzene)sulfonyl]pyrrolidine-2-carboxylic acid (1.00 g, 3.43 mmol, 1.00 equiv), N,N-dimethylformamide (20 mL), HATU (1.96 g, 5.15 mmol, 1.50 equiv), DIEA (1.33 g, 10.29 mmol, 3.00 equiv), and (3-bromo-5-methoxyphenyl)methanamine (890 mg, 4.12 mmol, 1.20 equiv) was stirred for 12 h at room temperature. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1:1) to afford the title compound (1 g, 60%) as a yellow solid.

Step 5: Preparation of (2S,4R)-4-fluoro-1-(4-fluorophenyl)sulfonyl-N-[[3-methoxy-5-[6-(trifluoromethyl)-3-pyridyl]phenyl]methyl]pyrrolidine-2-carboxamide

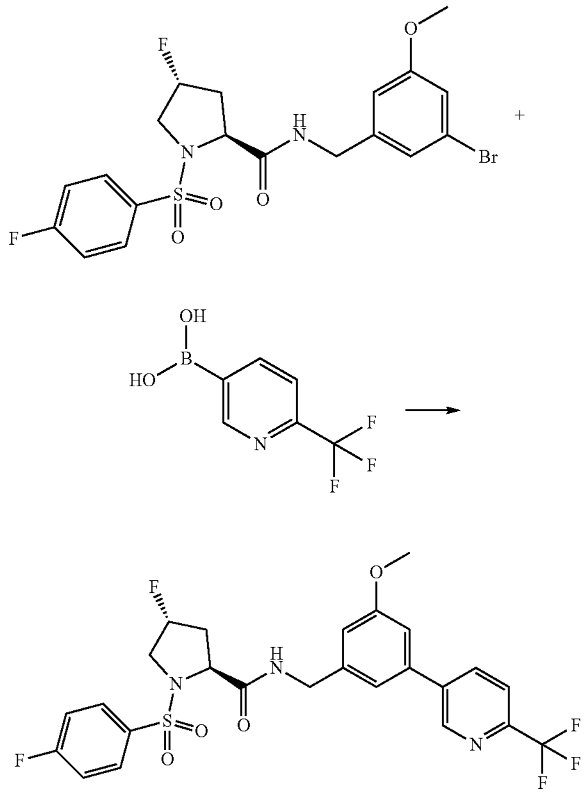

A mixture of (2S,4R)—N-[(3-bromo-5-methoxyphenyl)methyl]-4-fluoro-1-[(4-fluorobenzene)sulfonyl]pyrrolidine-2-carboxamide (500 mg, 1.02 mmol, 1.00 equiv), [6-(trifluoromethyl)pyridin-3-yl]boronic acid (400 mg, 2.10 mmol, 2.10 equiv), Pd(dppf)$Cl_2$ (80 mg, 0.11 mmol, 0.10 equiv), potassium carbonate (560 mg, 4.05 mmol, 4.00 equiv), and 1,4-dioxane (20 mL)/water (4 mL) was stirred for 12 h at 100° C. under nitrogen. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (2:1). The crude product (230 mg) was purified by Prep-HPLC to afford the title compound (152 mg, 27%) as a white solid.

$^1$H NMR (300 MHz, $CDCl_3$) δ 8.94 (s, 1H), 8.08 (d, J=8.1 Hz, 1H), 7.89-7.85 (m, 2H), 7.73 (d, J=8.1 Hz, 1H), 7.29-7.18 (m, 4H), 7.02 (d, J=9.3 Hz, 2H), 5.04 (d, J=51.3 Hz, 1H), 4.76-4.71 (m, 1H), 4.46-4.40 (m, 1H), 4.31-4.28 (m, 1H), 3.94-3.82 (m, 4H), 3.70-3.52 (m, 1H), 2.55-2.47 (m, 1H), 2.34-2.19 (m, 1H).

Example 117

Preparation of (2S,4R)—N-([3,5-difluoro-4-[6-(trifluoromethyl)pyridin-3-yl]pyridin-2-yl]methyl)-4-fluoro-1-[(4-fluorobenzene)sulfonyl]pyrrolidine-2-carboxamide

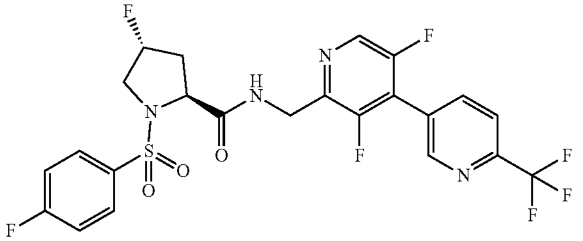 [SMILES: O=C(NCc1ncc(F)c(-c2ccc(C(F)(F)F)nc2)c1F)[C@@H]1C[C@@H](F)CN1S(=O)(=O)c1ccc(F)cc1]

Step 1: Preparation of 3,5-difluoro-4-iodopyridine-2-carbonitrile

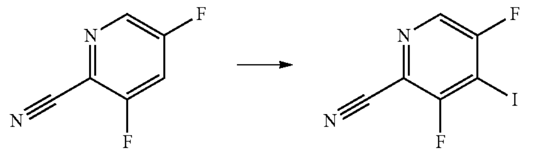 [SMILES: N#Cc1ncc(F)cc1F ; N#Cc1ncc(F)c(I)c1F]

LDA (841.14 mg, 7.85 mmol, 1.10 equiv) was added dropwise into a solution of 3,5-difluoropyridine-2-carbonitrile (1.00 g, 7.14 mmol, 1.00 equiv) in tetrahydrofuran (15 mL). at −78° C. under nitrogen. After being stirred for 30 min at −78° C. a solution of $I_2$ (1.81 g, 7.13 mmol, 1.00 equiv) in tetrahydrofuran (8 mL) was added dropwise. The resulting reaction was stirred at −78° C. for 40 minutes, quenched by water, extracted with ethyl acetate, washed with brine, dried over anhydrous sodium sulfate, and concentrated under vacuum. The residue was purified by a silica gel column eluting with ethyl acetate/petroleum ether (1:5) to afford the title compound (920 mg, 48%) as a yellow solid.

Step 2: Preparation of 3,5-difluoro-4-[6-(trifluoromethyl)pyridin-3-yl]pyridine-2-carbonitrile

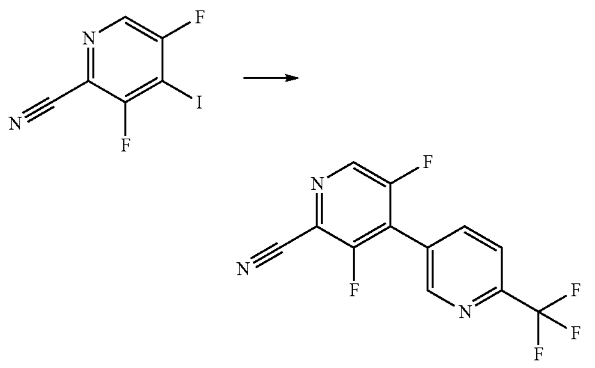

A mixture of 3,5-difluoro-4-iodopyridine-2-carbonitrile (650.00 mg, 2.44 mmol, 1.00 equiv), [6-(trifluoromethyl)pyridin-3-yl]boronic acid (1399.64 mg, 7.33 mmol, 3.00 equiv), $Pd(dppf)Cl_2.CH_2Cl_2$ (99.78 mg, 0.12 mmol), and sodium carbonate (518.01 mg, 4.89 mmol, 2.00 equiv) in water(4.5 mL)/toluene (40 mL) was stirred overnight at 70° C. under nitrogen. The reaction was then quenched by water, extracted with dichloromethane, and washed with brine. The organic layer was dried over anhydrous sodium sulfate and concentrated under vacuum. The residue was purified by a silica gel column eluting with ethyl acetate/petroleum ether (1:4) to afford the title compound (220 mg, 32%) as a white solid Step 3: Preparation of [3,5-difluoro-4-[6-(trifluoromethyl)pyridin-3-yl]pyridin-2-yl]methanamine

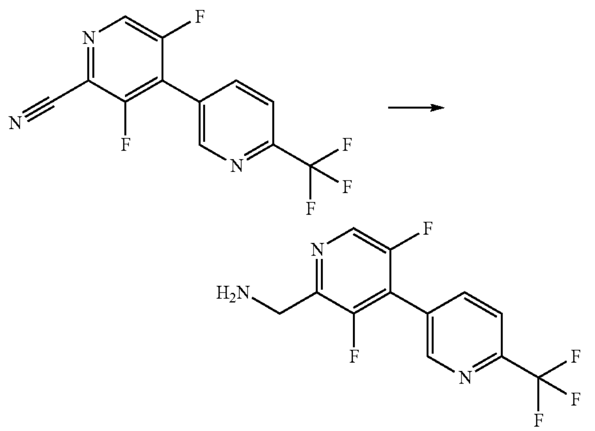

Into a 25-mL round-bottom flask was placed 3,5-difluoro-4-[6-(trifluoromethyl)pyridin-3-yl]pyridine-2-carbonitrile (20 mg, 0.07 mmol, 1.00 equiv), methanol (15 mL), palladium on carbon (20 mg, 0.19 mmol, 2.70 equiv), and concentrated hydrogen chloride (0.05 mL). To the above mixture hydrogen gas was introduced. The resulting solution was stirred for 15 min at 25° C. The solids were filtered out and the liquid was concentrated under vacuum. This resulted in the title compound (20 mg) as a light yellow solid.

Step 4: Preparation of (2S,4R)—N-([3,5-difluoro-4-[6-(trifluoromethyl)pyridin-3-yl]pyridin-2-yl]methyl)-4-fluoro-1-[(4-fluorobenzene)sulfonyl]pyrrolidine-2-carboxamide

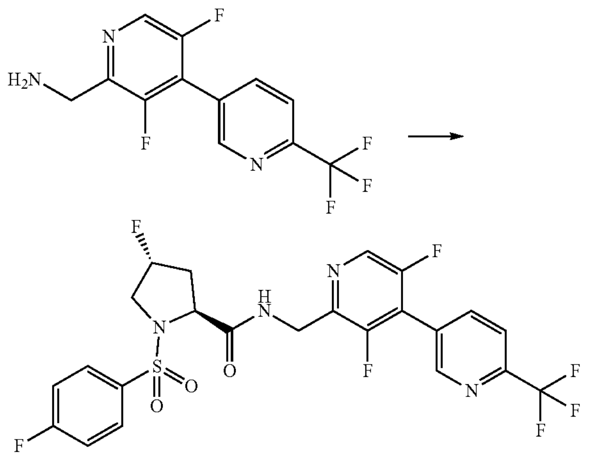

A solution of [3,5-difluoro-4-[6-(trifluoromethyl)pyridin-3-yl]pyridin-2-yl]methanamine (50 mg, 0.17 mmol, 1.00 equiv), (2S,4R)-4-fluoro-1-[(4-fluorobenzene)sulfonyl]pyrrolidine-2-carboxylic acid (50.3 mg, 0.17 mmol, 1.00 equiv), EDCI (66.4 mg, 0.35 mmol, 2.00 equiv), HOBT (25.7 mg, 0.19 mmol, 1.10 equiv), and DIEA (44.6 mg, 0.35 mmol, 2.00 equiv) in tetrahydrofuran (5 mL) was stirred for 10 h at room temperature. The reaction mixture was then quenched with water. The resulting solution was extracted with ethyl acetate and concentrated under vacuum. The residue was purified by a silica gel column eluting with ethyl acetate/petroleum ether (1:5) to afford the title compound (10 mg, 10%) as an off-white solid.

$^1$H NMR (300 MHz, $CDCl_3$) δ 8.91 (s, 1H), 8.52 (s, 1H), 8.10-8.07 (d, J=8.1 Hz, 1H), 7.92-7.81 (m, 4H), 7.23-7.20 (d, J=8.4 Hz, 2H), 5.16-4.99 (d, J=52.2 Hz, 1H), 4.75 (s, 2H), 4.33-4.27 (t, J=8.4 Hz, 1H), 3.99-3.86 (m, 1H), 2.53-2.26 (m, 2H).

Example 118

Preparation of (2S,4R)-4-fluoro-1-[(4-fluorobenzene)sulfonyl]-N-([6-methoxy-4-[6-(trifluoromethyl)pyridin-3-yl]pyridin-2-yl]methyl)pyrrolidine-2-carboxamide

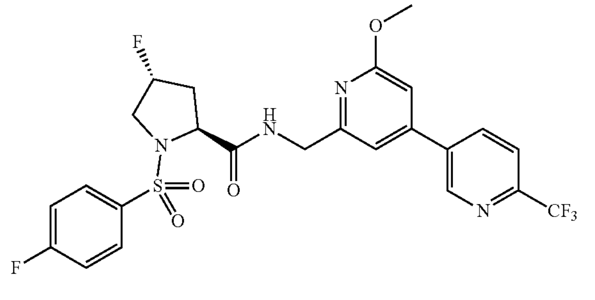 [SMILES: COc1cc(-c2ccc(C(F)(F)F)nc2)cc(CNC(=O)[C@@H]2C[C@@H](F)CN2S(=O)(=O)c2ccc(F)cc2)n1]

Step 1: Preparation of (2S,4R)-4-fluoro-1-[(4-fluorobenzene)sulfonyl]-N-([6-methoxy-4-[6-(trifluoromethyl)pyridin-3-yl]pyridin-2-yl]methyl)pyrrolidine-2-carboxamide

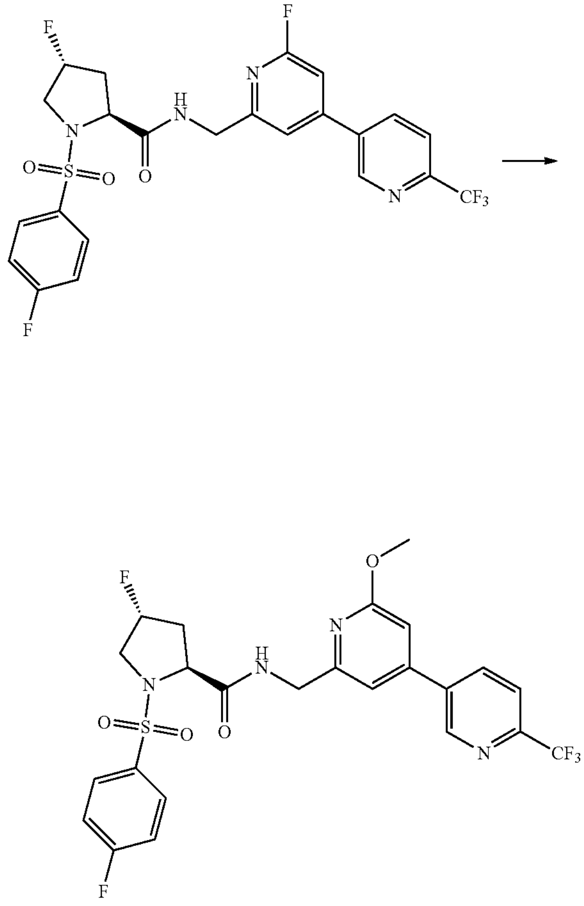 [SMILES: O=C(NCc1cc(-c2ccc(C(F)(F)F)nc2)cc(F)n1)[C@@H]1C[C@@H](F)CN1S(=O)(=O)c1ccc(F)cc1 ; COc1cc(-c2ccc(C(F)(F)F)nc2)cc(CNC(=O)[C@@H]2C[C@@H](F)CN2S(=O)(=O)c2ccc(F)cc2)n1]

A mixture of (2S,4R)-4-fluoro-N-([6-fluoro-4-[6-(trifluoromethyl)pyridin-3-yl]pyridin-2-yl]methyl)-1-[(4-fluorobenzene)sulfonyl]pyrrolidine-2-carboxamide (55 mg, 0.10 mmol, 1.00 equiv), methanol (5 mL, 123.49 mmol, 1222.50 equiv), and MeONa (6 mg, 0.11 mmol, 1.10 equiv) was stirred overnight at 60° C. The reaction mixture was concentrated under vacuum, dissolved in water, and extracted with ethyl acetate. The combined extracts were dried over anhydrous sodium sulfate and concentrated under vacuum. The crude product (48.6 mg) was purified by Prep-HPLC to afford the title compound (12.5 mg, 22%) as a white solid.

$^1H$ NMR (400 MHz, $CD_3OD$) δ 9.11 (s, 1H), 8.45-8.43 (m, 1H), 8.03-7.99 (m, 2H), 7.90-7.88 (m, 1H), 7.56 (s, 1H), 7.37-7.32 (m, 2H), 7.09 (s, 1H), 5.22-5.09 (d, J=52 Hz, 1H), 4.63-4.53 (m, 2H), 4.35-4.30 (m, 1H), 4.02 (s, 3H), 3.90-3.70 (m, 2H), 2.54-2.16 (m, 2H).

Example 119

Preparation of (2S,4R)-4-fluoro-N-([2-fluoro-6-[6-(trifluoromethyl)pyridin-3-yl]pyridin-4-yl]methyl)-1-[(4-fluorobenzene)sulfonyl]pyrrolidine-2-carboxamide

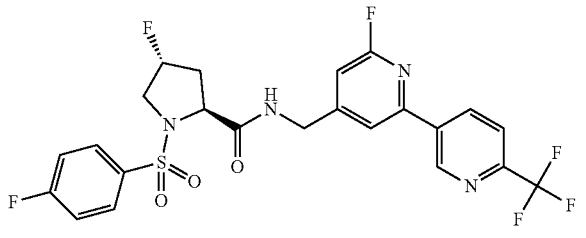 [SMILES: O=C(NCc1cc(F)nc(-c2ccc(C(F)(F)F)nc2)c1)[C@@H]1C[C@@H](F)CN1S(=O)(=O)c1ccc(F)cc1]

Step 1: Preparation of 2-chloro-6-[6-(trifluoromethyl)pyridin-3-yl]pyridine-4-carbonitrile

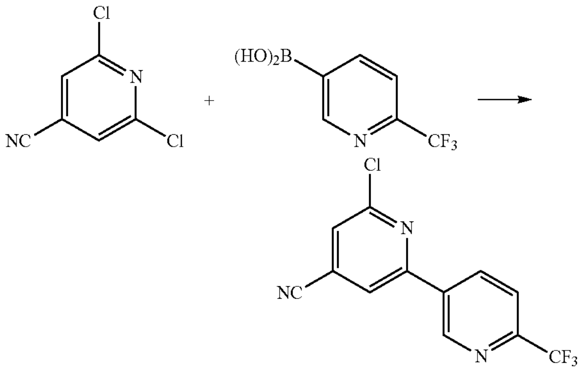

A mixture of 2,6-dichloropyridine-4-carbonitrile (5.00 g, 28.90 mmol, 1.00 equiv), [6-(trifluoromethyl)pyridin-3-yl]boronic acid (1.82 g, 9.53 mmol, 0.30 equiv), Pd(dppf)$Cl_2$.$CH_2Cl_2$ (1.18 g, 1.44 mmol, 0.05 equiv), sodium carbonate (6.13 g, 57.84 mmol, 2.00 equiv), and water (12 mL)/1,4-dioxane (100 mL) was stirred for 1 h at 70° C. under nitrogen. The resulting mixture was concentrated under vacuum. The mixture was diluted with water, extracted with ethyl acetate, washed with brine, dried over anhydrous sodium sulfate, and concentrated under vacuum. The residue was purified by flash chromatography on silica gel eluting with ethyl acetate/petroleum ether (1/10) to afford the title compound (2.6 g, 32%) as a white solid.

Step 2: Preparation of 2-fluoro-6-[6-(trifluoromethyl)pyridin-3-yl]pyridine-4-carbonitrile

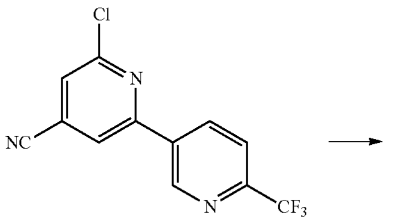

-continued

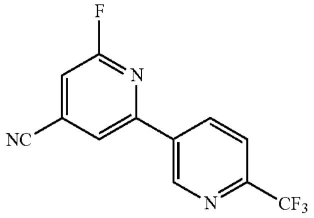

A mixture of 2-chloro-6-[6-(trifluoromethyl)pyridin-3-yl]pyridine-4-carbonitrile (1.5 g, 5.29 mmol, 1.00 equiv), KF (928 mg, 15.97 mmol, 4.00 equiv), and 30 mL of DMSO was stirred for 5 h at 110° C. under nitrogen. The reaction was then quenched by water, extracted with ethyl acetate, washed with brine, concentrated under vacuum, and dried over anhydrous sodium sulfate. The residue was purified by flash chromatography on silica gel eluting with ethyl acetate/petroleum ether (1/10) to afford the title compound (1.1 g, 78%) as a white solid.

Step 3: Preparation of [2-fluoro-6-[6-(trifluoromethyl)pyridin-3-yl]pyridin-4-yl]methanamine hydrochloride

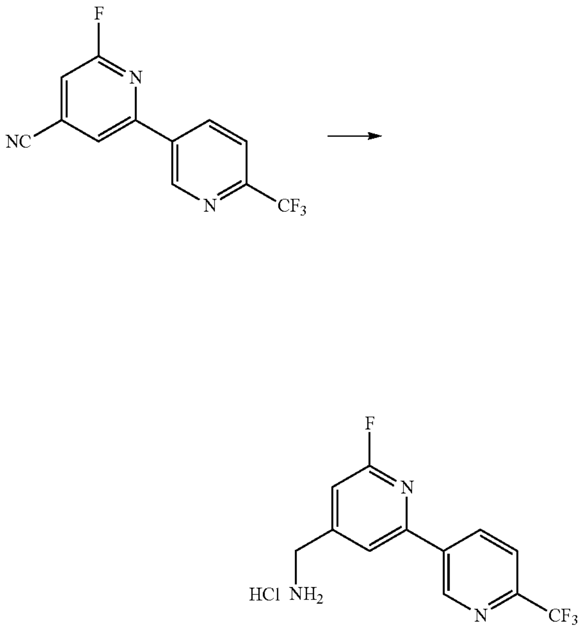

A mixture of 2-fluoro-6-[6-(trifluoromethyl)pyridin-3-yl]pyridine-4-carbonitrile (3 g, 11.23 mmol, 1.00 equiv), palladium on carbon (500 mg), and hydrogen chloride (2 mL) in 60 mL of tetrahydrofuran was stirred for 12 h under hydrogen at 40° C. The solids were filtered out and the liquid was concentrated under vacuum. This resulted in the title compound (3 g, 87%) as a light yellow solid.

Step 4: Preparation of tert-butyl (2S,4R)-4-fluoro-2-[([2-fluoro-6-[6-(trifluoromethyl)pyridin-3-yl]pyridin-4-yl]methyl)carbamoyl]pyrrolidine-1-carboxylate

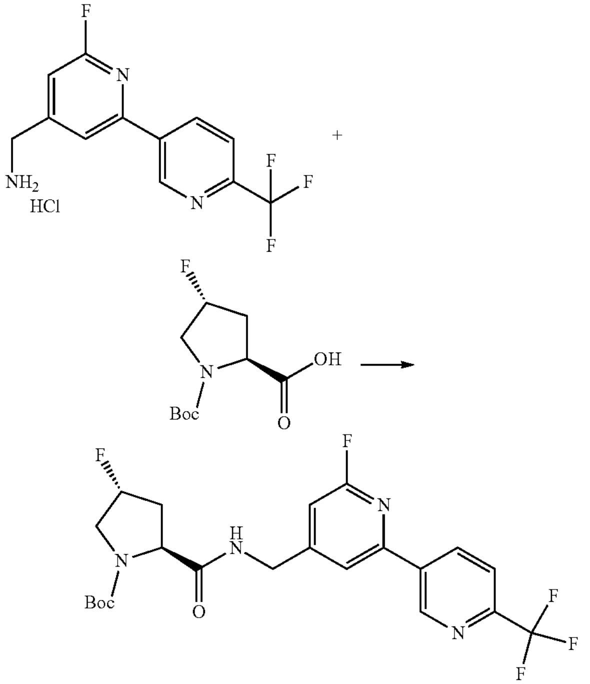 [SMILES: NCc1cc(F)nc(-c2ccc(C(F)(F)F)nc2)c1 ; Cl ; CC(C)(C)OC(=O)N1C[C@H](F)C[C@H]1C(=O)O ; CC(C)(C)OC(=O)N1C[C@H](F)C[C@H]1C(=O)NCc1cc(F)nc(-c2ccc(C(F)(F)F)nc2)c1]

A mixture of (2S,4R)-1-[(tert-butoxy)carbonyl]-4-fluoropyrrolidine-2-carboxylic acid (3 g, 12.86 mmol, 1.00 equiv), HOBT (1.74 g, 12.88 mmol, 1.10 equiv), EDCI (4.47 g, 23.32 mmol, 2.00 equiv), DIEA (3.02 g, 23.37 mmol, 2.00 equiv), and [2-fluoro-6-[6-(trifluoromethyl)pyridin-3-yl]pyridin-4-yl]methanamine hydrochloride (3.6 g, 11.70 mmol, 1.00 equiv) in 300 mL of tetrahydrofuran was stirred for 2 h at room temperature. The resulting mixture was diluted with ethyl acetate, washed with brine, dried over anhydrous sodium sulfate, and concentrated under vacuum. The residue was purified by flash chromatography on silica gel eluting with ethyl acetate/petroleum ether (1:2). This resulted in the title compound (4 g, 64%) as a light yellow solid.

Step 5: Preparation of (2S,4R)-4-fluoro-N-([2-fluoro-6-[6-(trifluoromethyl)pyridin-3-yl]pyridin-4-yl]methyl)pyrrolidine-2-carboxamide hydrochloride

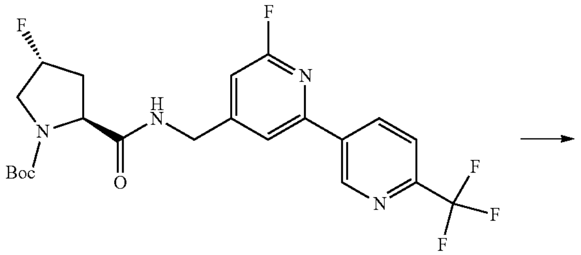

-continued

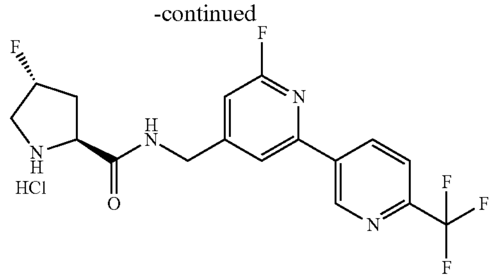

A mixture of tert-butyl (2S,4R)-4-fluoro-2-[([2-fluoro-6-[6-(trifluoromethyl)pyridin-3-yl]pyridin-4-yl]methyl)carbamoyl]pyrrolidine-1-carboxylate (4 g, 8.22 mmol, 1.00 equiv) in 100 mL HCl (a saturated solution in 1,4-dioxane) was stirred for 2 h at 40° C. The solids were collected by filtration and washed with hexane to afford the title compound (4 g) as a light yellow solid.

Step 6: Preparation of (2S,4R)-4-fluoro-N-([2-fluoro-6-[6-(trifluoromethyl)pyridin-3-yl]pyridin-4-yl]methyl)-1-[(4-fluorobenzene)sulfonyl]pyrrolidine-2-carboxamide

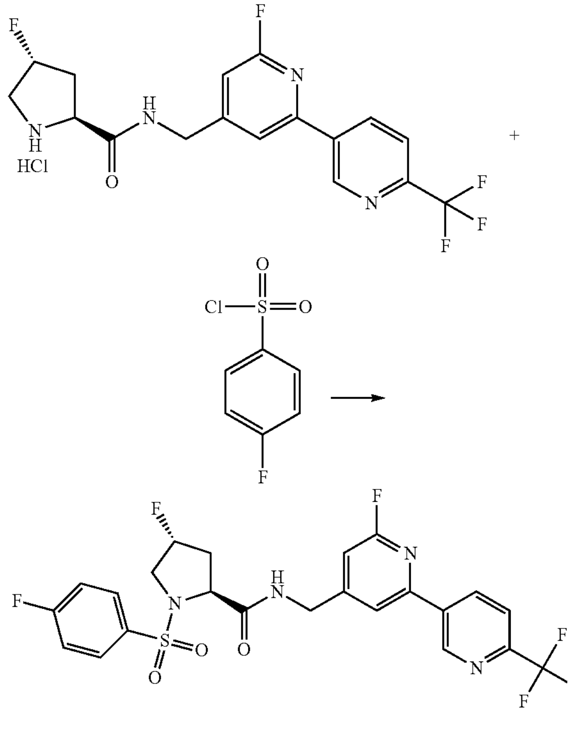

A mixture of (2S,4R)-4-fluoro-N-([2-fluoro-6-[6-(trifluoromethyl)pyridin-3-yl]pyridin-4-yl]methyl)pyrrolidine-2-carboxamide hydrochloride (4 g, 9.46 mmol, 1.00 equiv), 4-dimethylaminopyridine (115 mg, 0.94 mmol, 0.10 equiv), TEA (3.83 g, 37.85 mmol, 4.00 equiv), and 4-fluorobenzene-1-sulfonyl chloride (2.2 g, 11.30 mmol, 1.20 equiv) in 200 mL of dichloromethane was stirred for 3 h at 40° C. The resulting solution was diluted with dichloromethane, washed with brine, dried over sodium sulfate, and concentrated under vacuum. The residue was purified by flash chromatography on silica gel eluting with ethyl acetate/petroleum ether (1:1) to afford the title compound (1.204 g, 23%) as a white solid.

$^1$H NMR (400 MHz, $CDCl_3$) δ 9.35 (s, 1H), 8.58-8.56 (m, 1H), 7.92-7.88 (m, 2H), 7.83 (s, 1H), 7.78-7.76 (d, J=8.4 Hz, 1H), 7.49 (s, 1H), 7.27-7.23 (m, 2H), 6.97 (s, 1H), 5.13-4.99 (d, J=51.6 Hz, 1H), 4.89-4.83 (m, 1H), 4.47-4.42 (m, 1H), 4.32-4.28 (m, 1H), 3.96-3.87 (m, 1H), 3.74-3.59 (m, 1H), 2.60-2.58 (m, 1H), 2.31-2.12 (m, 1H).

Example 120

Preparation of (2S,4R)-4-fluoro-1-(4-fluorophenyl)sulfonyl-N-[[6-fluoro-4-[6-(trifluoromethyl)-3-pyridyl]-2-pyridyl]methyl]pyrrolidine-2-carboxamide

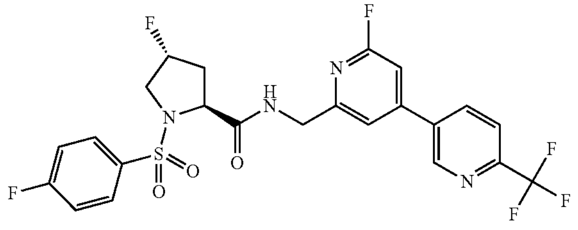 [SMILES: O=C(NCc1cc(-c2ccc(C(F)(F)F)nc2)cc(F)n1)[C@@H]1C[C@@H](F)CN1S(=O)(=O)c1ccc(F)cc1]

Step 1: Preparation of (2S,4R)-4-fluoro-1-(4-fluorophenyl)sulfonyl-N-[[6-fluoro-4-[6-(trifluoromethyl)-3-pyridyl]-2-pyridyl]methyl]pyrrolidine-2-carboxamide

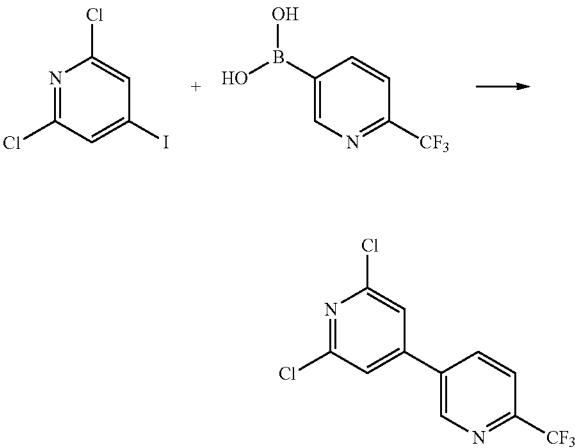

A mixture of 2,6-dichloro-4-iodopyridine (7.00 g, 25.56 mmol, 1.00 equiv), [6-(trifluoromethyl)pyridin-3-yl]boronic acid (4.88 g, 25.56 mmol, 1.00 equiv), 1,4-dioxane (100 mL), sodium carbonate (5.42 g, 51.14 mmol, 2.00 equiv), and water (2 mL) was stirred overnight at 100° C. under nitrogen. The reaction was diluted with water, extracted with ethyl acetate, washed with brine, dried over anhydrous sodium sulfate, and concentrated under vacuum. The residue was purified by a silica gel column eluting with ethyl acetate/petroleum ether (1/20) to afford the title compound (6.5 g, 87%) as a light yellow solid.

Step 2: Preparation of 6-chloro-4-[6-(trifluoromethyl)pyridin-3-yl]pyridine-2-carbonitrile

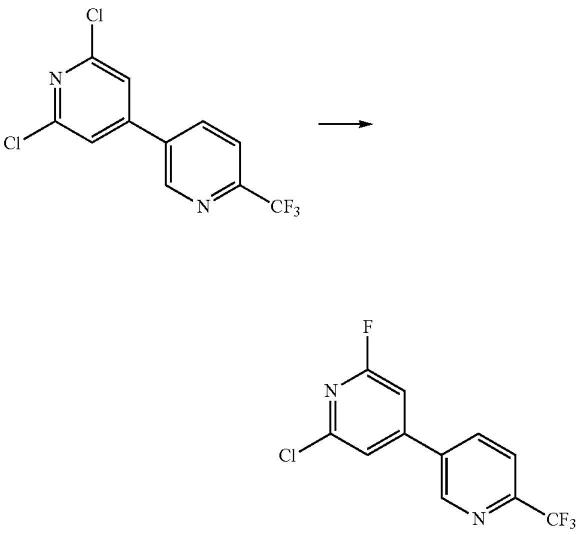

A mixture of 2,6-dichloro-4-[6-(trifluoromethyl)pyridin-3-yl]pyridine (5.00 g, 17.06 mmol, 1.00 equiv), DMSO (15 mL, 211.18 mmol, 12.40 equiv), and KF (990 mg, 17.04 mmol, 1.00 equiv) was stirred overnight at 150° C. in an oil bath. The reaction was cooled to room temperature, diluted with water, extracted with of ethyl acetate, washed with brine, dried oven anhydrous sodium sulfate, and concentrated under vacuum. The residue was purified by a silica gel column eluting with ethyl acetate/petroleum ether (1/20) to afford the title compound (3.8 g, 81%) as a white solid.

Step 3: Preparation of 6-fluoro-4-[6-(trifluoromethyl)pyridin-3-yl]pyridine-2-carbonitrile

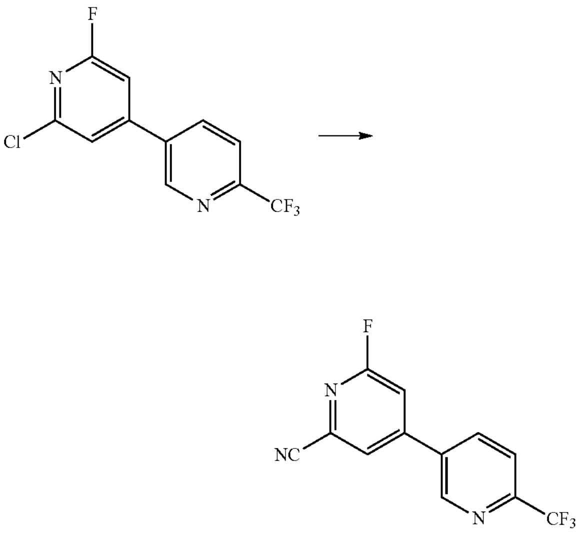

A mixture of 6-chloro-4-[6-(trifluoromethyl)pyridin-3-yl]pyridine-2-carbonitrile (1 g, 3.53 mmol, 1.00 equiv), $Zn(CN)_2$ (420 mg, 3.58 mmol, 1.00 equiv), Zn (20 mg, 0.31 mmol, 0.09 equiv), $Pd_2(dba)_3.CHCl_3$ (190 mg, 0.18 mmol, 0.05 equiv), dppf (100 mg, 0.18 mmol, 0.05 equiv), and DMA (4 mL, 43.02 mmol, 12.20 equiv) was irradiated with microwave radiation for 1 h at 125° C. under nitrogen. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (1/20) to afford the title compound (410 mg) as a white solid.

Step 4: Preparation of [6-fluoro-4-[6-(trifluoromethyl)pyridin-3-yl]pyridin-2-yl]methanamine hydrochloride

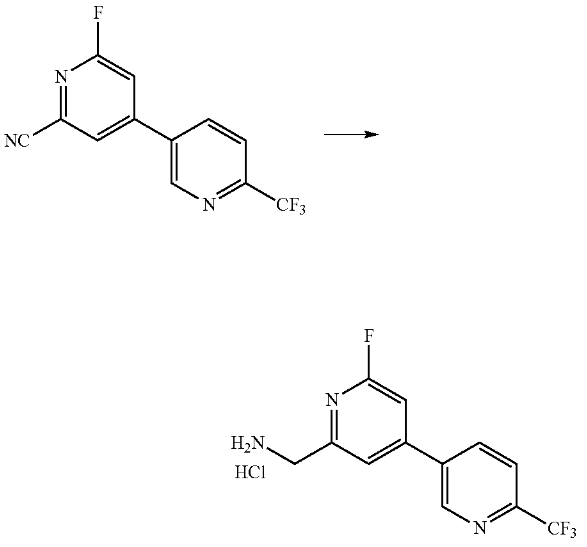

A mixture of 6-fluoro-4-[6-(trifluoromethyl)pyridin-3-yl]pyridine-2-carbonitrile (200 mg, 0.75 mmol, 1.00 equiv), tetrahydrofuran (30 mL), palladium on carbon (200 mg, 1.88 mmol, 2.50 equiv), and concentrated hydrogen chloride (0.1 mL) was stirred for 8 h at 25° C. The solids were filtered out. The filtrate was concentrated under vacuum to afford the title compound (200 mg) as a light yellow solid which was used for the next step without any further purification.

Step 5: Preparation of (2S,4R)-4-fluoro-1-(4-fluorophenyl)sulfonyl-N-[[6-fluoro-4-[6-(trifluoromethyl)-3-pyridyl]-2-pyridyl]methyl]pyrrolidine-2-carboxamide

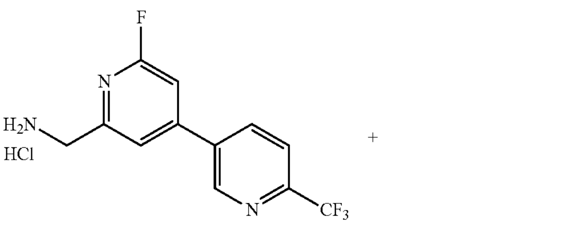

-continued

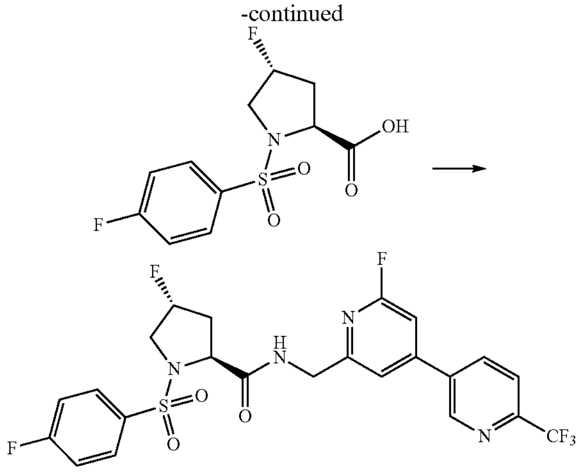

A mixture of (2S,4R)-4-fluoro-1-[(4-fluorobenzene)sulfonyl]pyrrolidine-2-carboxylic acid (214.79 mg, 0.74 mmol, 1.00 equiv), [6-fluoro-4-[6-(trifluoromethyl)pyridin-3-yl]pyridin-2-yl]methanamine hydrochloride (200.00 mg, 0.74 mmol, 1.00 equiv), tetrahydrofuran (10 mL), HOBT (109.61 mg, 0.81 mmol, 1.10 equiv), EDCI (282.73 mg, 1.47 mmol, 2.00 equiv), and DIEA (190.61 mg, 1.47 mmol, 2.00 equiv) was stirred overnight at 25° C. The reaction mixture was diluted with water, extracted with ethyl acetate, washed with brine, dried over anhydrous sodium sulfate, and concentrated under vacuum. The crude product (50.8 mg) was purified by Prep-HPLC to afford the title compound (21.2 mg, 5%) as a white solid.

$^{1}$H NMR (400 MHz, $CD_3OD$) δ 9.18 (s, 1H), 8.52-8.49 (m, 2H), 8.04-8.00 (m, 2H), 8.00-7.91 (m, 2H), 7.43 (s, 1H), 7.38-7.33 (m, 2H), 5.23-5.10 (d, J=52 Hz, 1H), 4.65-4.54 (m, 2H), 4.33-4.29 (m, 1H), 3.86-3.71 (m, 2H), 2.54-2.53 (m, 1H), 2.30-2.16 (m, 1H).

Example 121

Preparation of (2S,4R)-4-fluoro-N-([5-fluoro-4-[3-(trifluoromethyl)-8-azabicyclo[3.2.1]octan-8-yl]pyridin-2-yl]methyl)-1-[(4-fluorobenzene)sulfonyl]pyrrolidine-2-carboxamide

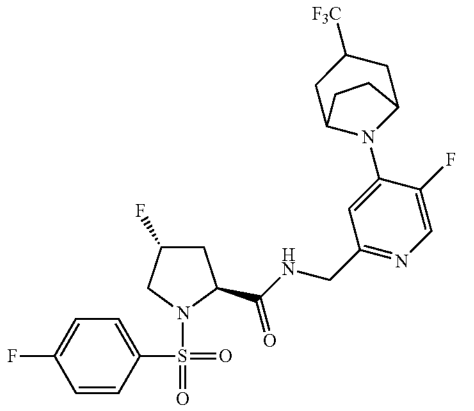 [SMILES: O=C(NCc1cc(N2C3CCC2CC(C(F)(F)F)C3)c(F)cn1)[C@@H]1C[C@@H](F)CN1S(=O)(=O)c1ccc(F)cc1]

Step 1: Preparation of tert-butyl 3-(trifluoromethyl)-3-[(trimethylsilyl)oxy]-8-azabicyclo[3.2.1]octane-8-carboxylate

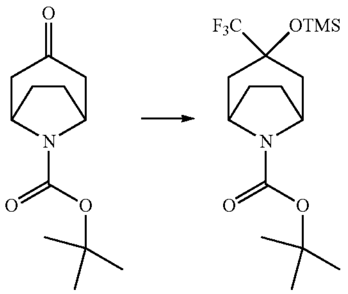

A solution of tert-butyl 3-oxo-8-azabicyclo[3.2.1]octane-8-carboxylate (20 g, 88.78 mmol, 1.00 equiv), trimethyl (trifluoromethyl)silane (38 g, 267.24 mmol, 3.00 equiv), and TBAF (4 mL, 61.02 mmol, 1.00 equiv) in tetrahydrofuran (180 ml) was stirred for 1 day at 60° C. and concentrated under vacuum. The residue was purified by a silica gel column eluting with ethyl acetate/petroleum ether (1:10) to afford the title compound (19 g, 58%) as yellow oil.

Step 2: Preparation of tert-butyl 3-hydroxy-3-(trifluoromethyl)-8-azabicyclo[3.2.1]octane-8-carboxylate

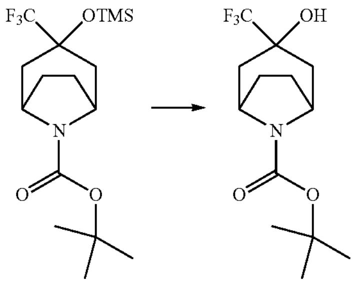

A mixture of tert-butyl 3-(trifluoromethyl)-3-[(trimethylsilyl)oxy]-8-azabicyclo[3.2.1]octane-8-carboxylate (7.0 g, 19.05 mmol, 1.0 equiv) and potassium methaneperoxoate (4 g, 28.73 mmol, 1.50 equiv) in methanol (100 mL) was stirred for 30 min at room temperature and concentrated under vacuum. The resulting solution was diluted with 50 mL of ethyl acetate, washed with brine, dried over anhydrous sodium sulfate, and concentrated under vacuum. This resulted in the title compound (6 g) as a light yellow solid.

Step 3: Preparation of 3-(trifluoromethyl)-8-azabicyclo[3.2.1]oct-2-ene

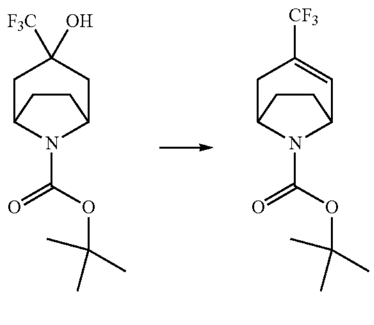 [SMILES: CC(C)(C)OC(=O)N1C2CCC1CC(O)(C(F)(F)F)C2 ; CC(C)(C)OC(=O)N1C2C=C(C(F)(F)F)CC1CC2]

Thionyl chloride (7 g, 58.84 mmol, 6.00 equiv) and pyridine (4.7 g, 59.42 mmol, 6.0 equiv) was added dropwise into a solution of tert-butyl 3-hydroxy-3-(trifluoromethyl)-8-azabicyclo[3.2.1]octane-8-carboxylate (3 g, 10.16 mmol, 1.00 equiv), 4-dimethylaminopyridine (122 mg, 0.10 equiv) in 1,4-dioxane (100 mL) at 0° C. The resulting solution was heated to 60° C. for 12 h, quenched with sodium bicarbonate solution (200 ml), extracted with ethyl acetate, dried over anhydrous sodium sulfate, and concentrated under vacuum. The residue was purified by a silica gel column eluting with ethyl acetate/petroleum ether (1:10) to afford the title compound (900 mg, 50%) as a light yellow solid Step 4: Preparation of tert-butyl 3-(trifluoromethyl)-8-azabicyclo[3.2.1]octane-8-carboxylate

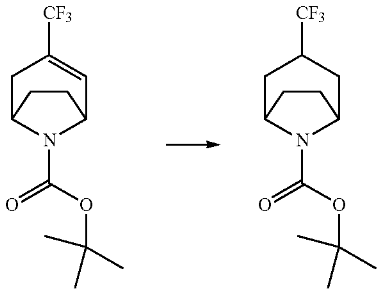 [SMILES: CC(C)(C)OC(=O)N1C2C=C(C(F)(F)F)CC1CC2 ; CC(C)(C)OC(=O)N1C2CCC1CC(C(F)(F)F)C2]

Into a 100-mL round-bottom flask purged and maintained with an atmosphere of $H_2$ was placed tert-butyl 3-(trifluoromethyl)-8-azabicyclo[3.2.1]oct-2-ene-8-carboxylate (900 mg, 3.25 mmol, 1.00 equiv), and palladium on carbon (30 mg) in methanol (15 mL). The resulting solution was stirred overnight at room temperature. The solids were filtered out and the liquid was concentrated under vacuum. This resulted in the title compound (800 mg, 88%) as light yellow oil Step 5: Preparation of 3-(trifluoromethyl)-8-azabicyclo[3.2.1]octane hydrochloride

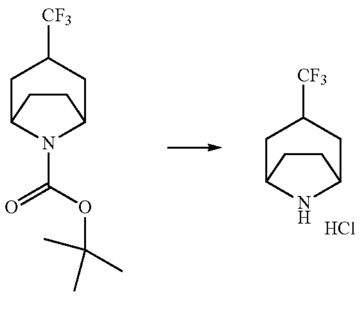 [SMILES: CC(C)(C)OC(=O)N1C2CCC1CC(C(F)(F)F)C2 ; FC(F)(F)C1CC2CCC(C1)N2 ; Cl]

A solution of tert-butyl 3-(trifluoromethyl)-8-azabicyclo[3.2.1]octane-8-carboxylate (800 mg, 2.86 mmol, 1.00 equiv) and saturated HCl in 1,4-dioxane (20 mL) was stirred for 2 h at room temperature and concentrated under vacuum. This resulted in the title compound (400 mg, 65%) as a white solid Step 6: Preparation of 8-(2-chloro-5-fluoropyridin-4-yl)-3-(trifluoromethyl)-8-azabicyclo[3.2.1]octane

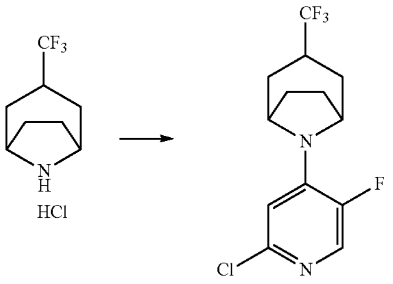 [SMILES: FC(F)(F)C1CC2CCC(C1)N2 ; Cl ; Fc1cnc(Cl)cc1N1C2CCC1CC(C(F)(F)F)C2]

Into a 20-mL sealed tube purged and maintained with an inert atmosphere of nitrogen was placed 3-(trifluoromethyl)-8-azabicyclo[3.2.1]octane hydrochloride (400 mg, 1.85 mmol, 1.00 equiv), 2-chloro-5-fluoro-4-iodopyridine (860 mg, 3.34 mmol, 1.80 equiv), $Pd_2(dba)_3CHCl_3$ (385 mg, 0.37 mmol, 0.20 equiv), Xantphos (400 mg, 0.69 mmol, 0.40 equiv), $Cs_2CO_3$ (1.8 g, 5.52 mmol, 3.00 equiv), and methylbenzene (6 mL). The resulting solution was stirred overnight at 110° C. and concentrated under vacuum. The residue was applied onto a silica gel column with ethyl acetate/petroleum ether (1:1). This resulted in 580 mg of the title compound as a light brown solid Step 7: Preparation of 5-fluoro-4-[3-(trifluoromethyl)-8-azabicyclo[3.2.1]octan-8-yl]pyridine-2-carbonitrile

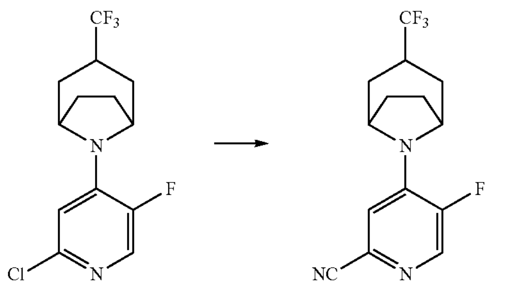 [SMILES: Fc1cnc(Cl)cc1N1C2CCC1CC(C(F)(F)F)C2 ; N#Cc1cc(N2C3CCC2CC(C(F)(F)F)C3)c(F)cn1]

Into a 20-mL sealed tube purged and maintained with an inert atmosphere of nitrogen was placed 8-(2-chloro-5-fluoropyridin-4-yl)-3-(trifluoromethyl)-8-azabicyclo[3.2.1]octane (760 mg, 2.46 mmol, 1.00 equiv), $Pd_2(dba)_3CHCl_3$ (248 mg, 0.24 mmol, 0.10 equiv), dppf (265 mg, 0.48 mmol, 0.20 equiv), zinc dicarbonitrile (282 mg, 2.40 mmol, 1.00 equiv), Zn (15.5 mg, 0.24 mmol, 0.10 equiv), and DMA (8 mL). The resulting solution was stirred overnight at 110° C., diluted with 20 mL of water, extracted with ethyl acetate, dried over anhydrous sodium sulfate, and concentrated under vacuum. The residue was purified by a silica gel column eluting with ethyl acetate/petroleum ether (1:3) to afford the title compound (120 mg, 16%) as a white solid.

Step 8: Preparation of [5-fluoro-4-[3-(trifluoromethyl)-8-azabicyclo[3.2.1]octan-8-yl]pyridin-2-yl]methanamine hydrochloride

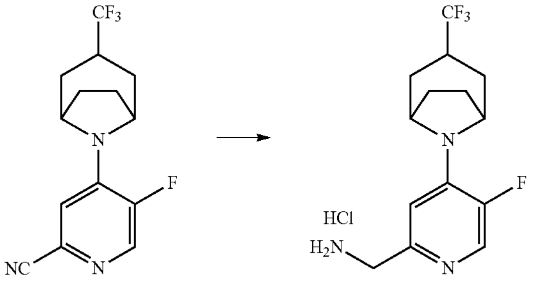 [SMILES: N#Cc1cc(N2C3CCC2CC(C(F)(F)F)C3)c(F)cn1 ; Cl ; NCc1cc(N2C3CCC2CC(C(F)(F)F)C3)c(F)cn1]

Into a 50-mL round-bottom flask purged and maintained with an inert atmosphere of $H_2$ was placed 5-fluoro-4-[3-(trifluoromethyl)-8-azabicyclo[2.2.1]octan-8-yl]pyridine-2-carbonitrile (120 mg, 0.40 mmol, 1.00 equiv), methanol (20 mL), palladium on carbon (100 mg), and hydrogen chloride (0.5 mL). The resulting solution was stirred for 20 min at room temperature. The solids were filtered out and the liquid was concentrated under vacuum. This resulted in the title compound 120 mg (88%) as a light brown solid.

Step 9: Preparation of (2S,4R)-4-fluoro-N-([5-fluoro-4-[3-(trifluoromethyl)-8-azabicyclo[3.2.1]octan-8-yl]pyridin-2-yl]methyl)-1-[(4-fluorobenzene)sulfonyl]pyrrolidine-2-carboxamide

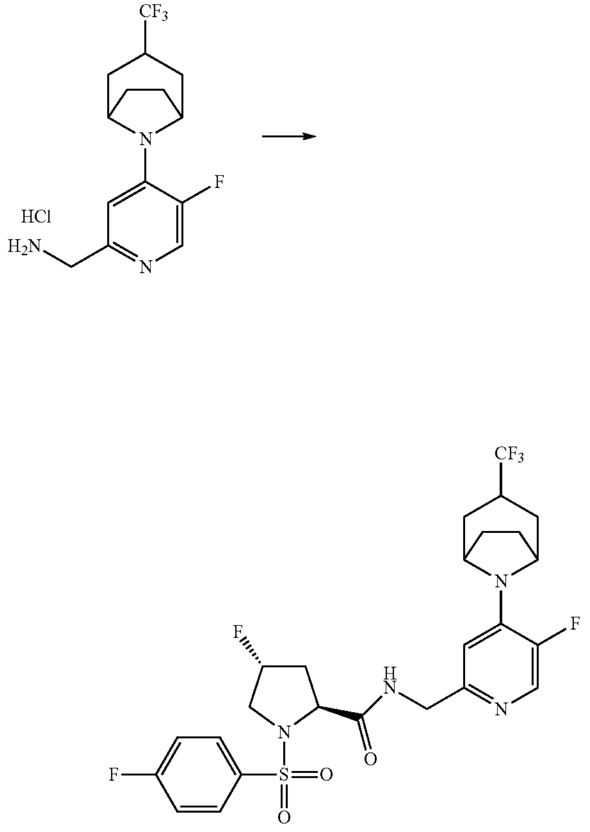

A solution of (2S,4R)-4-fluoro-1-[(4-fluorobenzene)sulfonyl]pyrrolidine-2-carboxylic acid (170 mg, 0.58 mmol, 1.50 equiv), HATU (227 mg, 0.60 mmol, 1.50 equiv), DIEA (154 mg, 1.19 mmol, 3.00 equiv), and [5-fluoro-4-[3-(trifluoromethyl)-8-azabicyclo[3.2.1]octan-8-yl]pyridin-2-yl]methanamine hydrochloride (120 mg, 0.35 mmol, 1.00 equiv) in N,N-dimethylformamide (3 mL) was stirred for 2 h at room temperature. The resulting mixture was diluted with ethyl acetate, washed with brine, dried over sodium sulfate, and concentrated under vacuum. The crude product was purified by Prep-HPLC to afford the title compound 56.8 mg (28%) of as a white solid.

$^1H$ NMR (300 MHz, DMSO-$d_6$) δ 8.86-8.84 (m, 1H), 8.15-8.13 (d, J=6.0 Hz, 1H), 8.01-7.96 (m, 2H), 7.49-7.43 (t, J=9.0 Hz, 2H), 6.92-6.89 (d, J=8.1 Hz, 2H), 5.27-5.10 (d, J=51.3 Hz, 1H), 4.53 (s, 2H), 4.39-4.16 (m, 3H), 3.71 (s, 1H), 3.61-3.59 (m, 1H), 2.95 (s, 1H), 2.42-2.35 (m, 1H), 2.14-2.07 (s, 1H), 2.00-1.96 (m, 2H), 1.90-1.85 (m, 2H), 1.83-1.60 (m, 4H).

Example 122

Preparation of (2S,4R)-4-fluoro-1-(4-fluorophenyl)sulfonyl-N-[[3-fluoro-5-[5-(trifluoromethyl)pyrazin-2-yl]phenyl]methyl]pyrrolidine-2-carboxamide

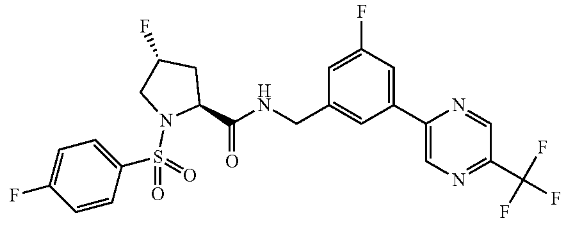 [SMILES: O=C(NCc1cc(F)cc(-c2cnc(C(F)(F)F)cn2)c1)[C@@H]1C[C@@H](F)CN1S(=O)(=O)c1ccc(F)cc1]

Step 1: Preparation of ethyl 3-bromo-5-fluorobenzoate

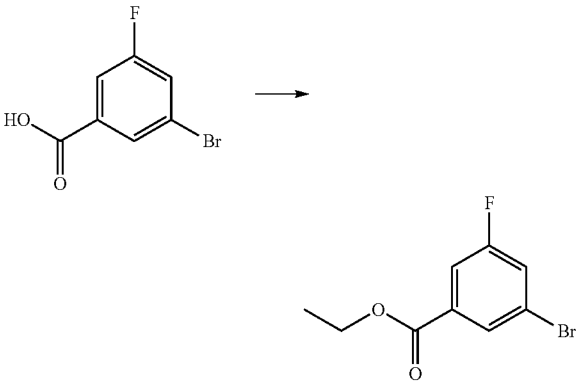

A mixture of 3-bromo-5-fluorobenzoic acid (2 g, 9.13 mmol, 1.00 equiv), ethanol (40 mL), and sulfuric acid (3 mL) was stirred overnight at 85° C. in an oil bath. The reaction mixture was diluted with water, extracted with ethyl acetate, washed with brine, dried over anhydrous sodium sulfate, and concentrated under vacuum. This resulted in the title compound (1.9 g, 84%) as a light brown solid.

Step 2: Preparation of ethyl 3-fluoro-5-(tetramethyl-1,3,2-dioxaborolan-2-yl)benzoate

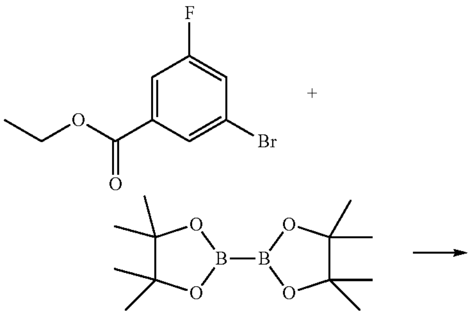

-continued

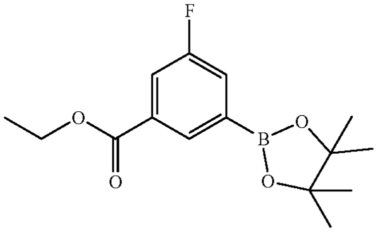

A mixture of ethyl 3-bromo-5-fluorobenzoate (800 mg, 3.24 mmol, 1.00 equiv) in dioxane (30 mL), 4,4,5,5-tetramethyl-2-(tetramethyl-1,3,2-dioxaborolan-2-yl)-1,3,2-dioxaborolane (1.24 g, 4.88 mmol, 1.50 equiv), AcOK (959 mg, 9.77 mmol, 3.00 equiv), and Pd(dppf)$Cl_2$ (477 mg, 0.65 mmol, 0.20 equiv) was stirred overnight at 90° C. under nitrogen. The reaction mixture was diluted with water, extracted with ethyl acetate, washed with brine, dried over anhydrous sodium sulfate, and concentrated under vacuum. This resulted in the title compound (700 mg, crude) as a black crude solid.

Step 3: Preparation of ethyl 3-fluoro-5-[5-(trifluoromethyl)pyrazin-2-yl]benzoate

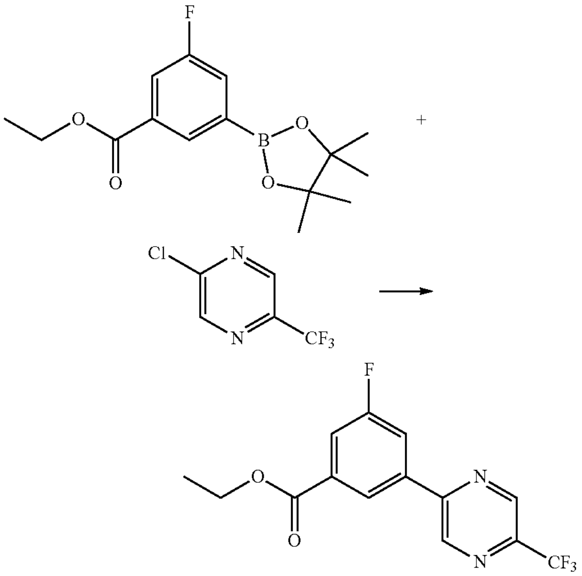

A mixture of ethyl 3-fluoro-5-(tetramethyl-1,3,2-dioxaborolan-2-yl)benzoate (700 mg, 2.38 mmol, 1.00 equiv) in dioxane (15 mL), 2-chloro-5-(trifluoromethyl)pyrazine (437 mg, 2.39 mmol, 1.00 equiv), Pd(dppf)Cl2 (352 mg, 0.48 mmol, 0.20 equiv), and $Cs_2CO_3$ (2.35 g, 7.21 mmol, 3.00 equiv) was stirred overnight at 90° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1:100) to afford the title compound (300 mg, 40%) as an off-white solid.

Step 4: Preparation of [3-fluoro-5-[5-(trifluoromethyl)pyrazin-2-yl]phenyl]methanol

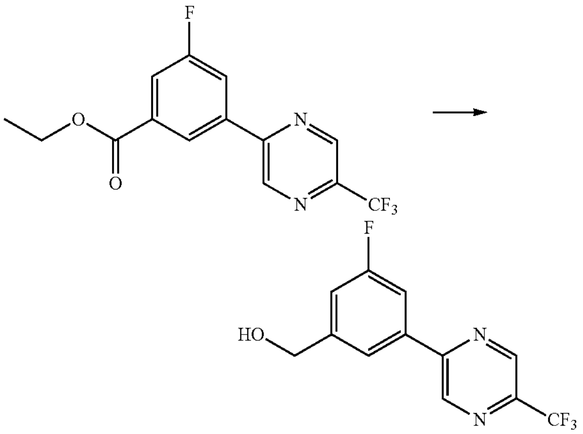

$LiAlH_4$ (73 mg, 1.92 mmol, 2.00 equiv) was added in several batches into a solution of ethyl 3-fluoro-5-[5-(trifluoromethyl)pyrazin-2-yl]benzoate (300 mg, 0.95 mmol, 1.00 equiv) in tetrahydrofuran (15 mL) at 0° C. under nitrogen. After 10 min at 0° C. the reaction was quenched by water. The solids were filtered out and the filtrate was concentrated under vacuum. The residue was purified by a silica gel column eluting with ethyl acetate/petroleum ether (7:100) to afford the title compound (160 mg, 62%) as an off-white solid.

Step 5: Preparation of 2-([3-fluoro-5-[5-(trifluoromethyl)pyrazin-2-yl]phenyl]methyl)-2,3-dihydro-1H-isoindole-1,3-dione

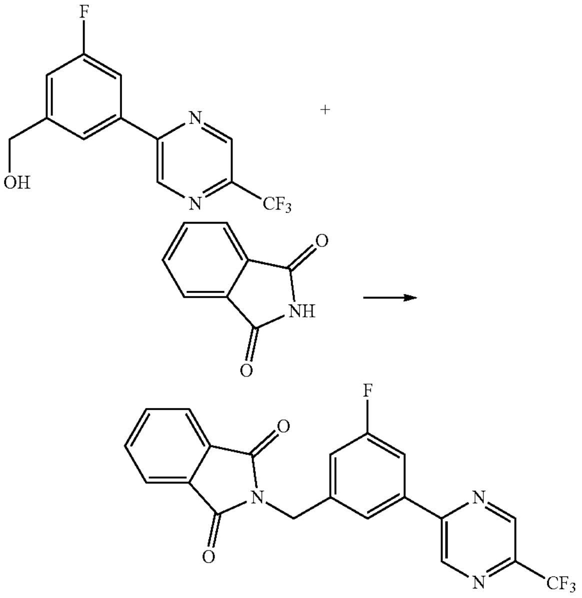

DIAD (134 mg, 0.66 mmol, 1.20 equiv) was added dropwise into a solution of [3-fluoro-5-[5-(trifluoromethyl)pyrazin-2-yl]phenyl]methanol (150 mg, 0.55 mmol, 1.00 equiv), 2,3-dihydro-1H-isoindole-1,3-dione (98 mg, 0.67 mmol, 1.20 equiv), and $PPh_3$ (288 mg, 1.10 mmol, 2.00 equiv) in 10 mL of THF at 0° C. under nitrogen. The resulting solution was stirred overnight at room temperature. The resulting mixture was concentrated under vacuum. The residue was purified by a silica gel column eluting with ethyl acetate/petroleum ether (7:100) to afford the title compound (230 mg) as a white solid.

Step 6: Preparation of [3-fluoro-5-[5-(trifluoromethyl)pyrazin-2-yl]phenyl]methanamine

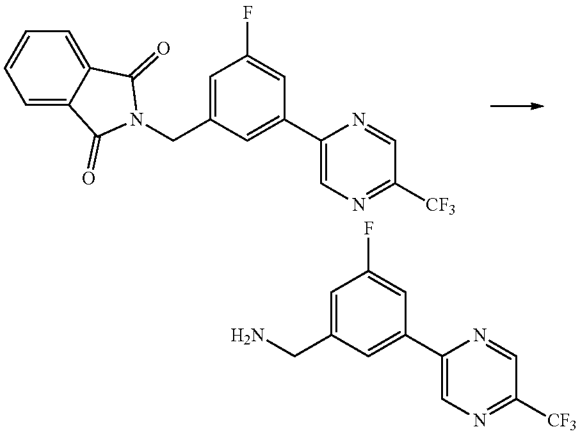

A solution of 2-([3-fluoro-5-[5-(trifluoromethyl)pyrazin-2-yl]phenyl]methyl)-2,3-dihydro-1H-isoindole-1,3-dione (230 mg, 0.57 mmol, 1.00 equiv) in ethanol (7 mL) and $NH_2NH_2H_2O$ (7 mL, 144.03 mmol, 251.30 equiv) was stirred overnight at 60° C. The resulting mixture was concentrated under vacuum. The residue was purified by a silica gel column eluting with dichloromethane/methanol (100:10) to afford the title compound (100 mg, 64%) as an off-white solid.

Step 7: Preparation of (2S,4R)-4-fluoro-1-(4-fluorophenyl)sulfonyl-N-[[3-fluoro-5-[5-(trifluoromethyl)pyrazin-2-yl]phenyl]methyl]pyrrolidine-2-carboxamide

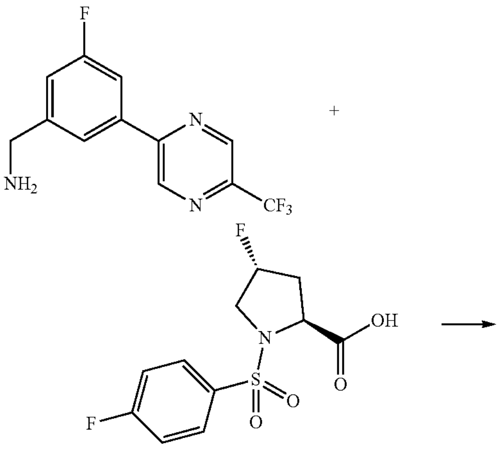

-continued

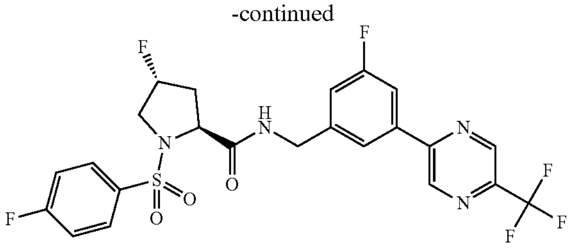

A mixture of [3-fluoro-5-[5-(trifluoromethyl)pyrazin-2-yl]phenyl]methanamine (104 mg, 0.38 mmol, 1.00 equiv), (2S,4R)-4-fluoro-1-[(4-fluorobenzene)sulfonyl]pyrrolidine-2-carboxylic acid (168 mg, 0.58 mmol, 1.50 equiv), N,N-dimethylformamide (5 mL), DIEA (150 mg, 1.16 mmol, 3.00 equiv), and HATU (220 mg, 0.58 mmol, 1.50 equiv) was stirred overnight at room temperature. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (20:100) to afford the title compound (15.7 mg, 8%) as a white solid.

$^1$H NMR (300 MHz, $CD_3OD$) δ 9.39-9.38 (m, 1H), 9.07 (s, 1H), 8.07 (s, 1H), 8.00-7.88 (m, 3H), 7.37-7.30 (m, 3H), 5.50-5.22 (d, J=83.1 Hz, 1H), 4.58 (s, 2H), 4.29-4.23 (m, 1H), 3.85-3.70 (m, 2H), 2.60-2.40 (m, 1H), 2.39-2.04 (m, 1H).

Example 123

Preparation of (1R,3S,5R)-2-(4-fluorophenyl)sulfonyl-N-[[6-[6-(trifluoromethyl)-3-pyridyl]pyrimidin-4-yl]methyl]-2-azabicyclo[3.1.0]hexane-3-carboxamide

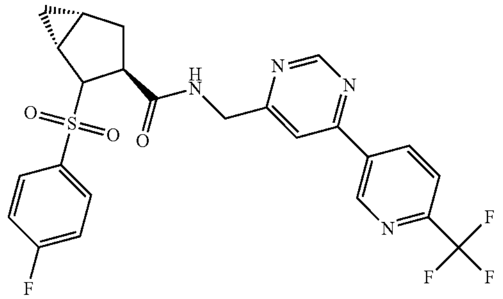 [SMILES: O=C(NCc1cc(-c2ccc(C(F)(F)F)nc2)ncn1)[C@@H]1C[C@H]2C[C@H]2C1S(=O)(=O)c1ccc(F)cc1]

Step 1: Preparation of (5S)-5-[[(tert-butyldiphenylsily)oxy]methyl]pyrrolidin-2-one

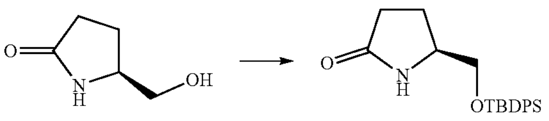

A mixture of (5S)-5-(hydroxymethyl)pyrrolidin-2-one (20 g, 173.72 mmol, 1.00 equiv), 1H-imidazole (26 g, 381.92 mmol, 2.20 equiv), 4-dimethylaminopyridine (2.12 g, 17.35 mmol, 0.10 equiv), and TBDPS-Cl (50 g, 181.91 mmol, 1.00 equiv) in dichloromethane (800 mL) was stirred overnight at room temperature. The reaction mixture was diluted with water, extracted with ethyl acetate, washed with brine, dried over anhydrous sodium sulfate, and concentrated under vacuum. This resulted in the title compound (62.7 g, crude) as a colorless crystal.

Step 2: Preparation of tert-butyl (2S)-2-[[(tert-butyldiphenylsilyl)oxy]methyl]-5-oxopyrrolidine-1-carboxylate

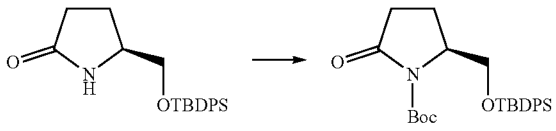

A mixture of (5S)-5-[[(tert-butyldiphenylsilyl)oxy]methyl]pyrrolidin-2-one (62.7 g, 177.35 mmol, 1.00 equiv), 4-dimethylaminopyridine (24 g, 196.45 mmol, 1.10 equiv), and di-tert-butyl dicarbonate (38.6 g, 176.86 mmol, 1.00 equiv) in acetonitrile (800 mL) was stirred for 16 h at room temperature. The reaction mixture was diluted with water, extracted with ethyl acetate, washed with brine, dried over anhydrous sodium sulfate, and concentrated under vacuum. The residue was purified by a silica gel column eluting with petroleum ether/ethyl acetate (50:1) to afford the title compound (45 g, 56%) as a white solid.

Step 3: Preparation of tert-butyl (2S)-2-[[(tert-butyldiphenylsilyl)oxy]methyl]-2,3-dihydro-1H-pyrrole-1-carboxylate

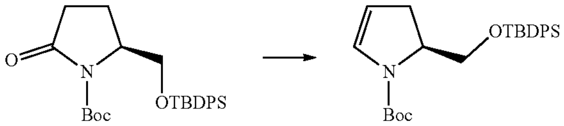

Lithium triethylborohydride (23 mL, 217.10 mmol, 9.80 equiv) was added dropwise into a solution of tert-butyl (2S)-2-[[(tert-butyldiphenylsilyl)oxy]methyl]-5-oxopyrrolidine-1-carboxylate (10.05 g, 22.15 mmol, 1.00 equiv) in toluene (36 mL) at −50° C. under nitrogen. After 30 min DIEA (16.5 mL, 99.84 mmol, 4.50 equiv), 4-dimethylaminopyridine (34 mg, 0.28 mmol), and $Tf_2O$ (3.6 mL, 21.31 mmol, 1.00 equiv) was added sequentially at −50° C. The resulting solution was stirred overnight at 20° C. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (3:100) to afford the title compound (4.321 g, 45%) as yellow oil.

Step 4: Preparation of tert-butyl (3S)-3-[[(tert-butyldiphenylsilyl)oxy]methyl]-2-azabicyclo[3.1.0]hexane-2-carboxylate

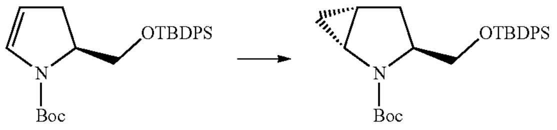

Diethylzinc (8.3 mL, 67.19 mmol, 1.10 equiv) was added dropwise into a solution of tert-butyl (2S)-2-[[(tert-butyldiphenylsilyl)oxy]methyl]-2,3-dihydro-1H-pyrrole-1-carboxylate (3.3 g, 7.54 mmol, 1.00 equiv) in dichloromethane (30 mL) at 0° C. To this was added diiodomethane (3.04 g, 11.35 mmol, 1.50 equiv) dropwise with stirring at 0° C. After 30 min at 0° C. the resulting solution was stirred for 4 h at 20° C. The pH value of the solution was adjusted to 8 with saturated sodium carbonate solution. The resulting solution was extracted with dichloromethane, washed with brine, dried over anhydrous sodium sulfate, and concentrated under vacuum. The residue was purified by a silica gel column eluting with ethyl acetate/petroleum ether (1:50) to afford the title compound (2 g, 59%) as colorless oil.

Step 5: Preparation of tert-butyl (3S)-3-(hydroxymethyl)-2-azabicyclo[3.1.0]hexane-2-carboxylate

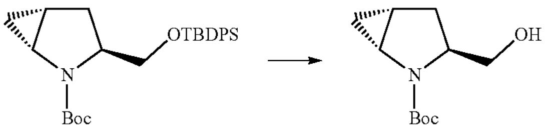

A mixture of tert-butyl (3S)-3-[[(tert-butyldiphenylsilyl)oxy]methyl]-2-azabicyclo[3.1.0]hexane-2-carboxylate (1.6 g, 3.54 mmol, 1.00 equiv) in tetrahydrofuran (20 mL) and TBAF (3.5 mL, 13.39 mmol, 1.00 equiv) was stirred for overnight at room temperature. The resulting mixture was concentrated under vacuum. The residue was purified by a silica gel column eluting with ethyl acetate/petroleum ether (1:10) to afford the title compound (900 mg) as colorless oil.

Step 6: Preparation of (3S)-2-[(tert-butoxy)carbonyl]-2-azabicyclo[3.1.0]hexane-3-carboxylicacid

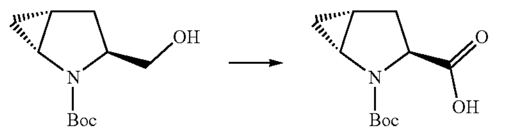 [SMILES: CC(C)(C)OC(=O)N1[C@H](CO)C[C@H]2C[C@H]21 ; CC(C)(C)OC(=O)N1[C@@H]2C[C@@H]2C[C@H]1C(=O)O]

A mixture of tert-butyl (3S)-3-(hydroxymethyl)-2-azabicyclo[3.1.0]hexane-2-carboxylate (900 mg, 4.22 mmol, 1.00 equiv) in $CH_3CN$ (10 mL)/$CCl_4$ (10 mL), $NaIO_4$ (2.72 g, 12.72 mmol, 3.00 equiv) in water (10 mL), and $RuCl_3.H_2O$ (44 mg, 0.20 mmol) was stirred for overnight at room temperature. The reaction mixture was diluted with water, extracted with ethyl acetate, washed with brine, dried over anhydrous sodium sulfate, and concentrated under vacuum. This resulted in the title compound (620 mg, 65%) as a brown solid.

Step 7: Preparation of tert-butyl (3S)-3-[([6-[6-(trifluoromethyl)pyridin-3-yl]pyrimidin-4-yl]methyl)carbamoyl]-2-azabicyclo[3.1.0]hexane-2-carboxylate

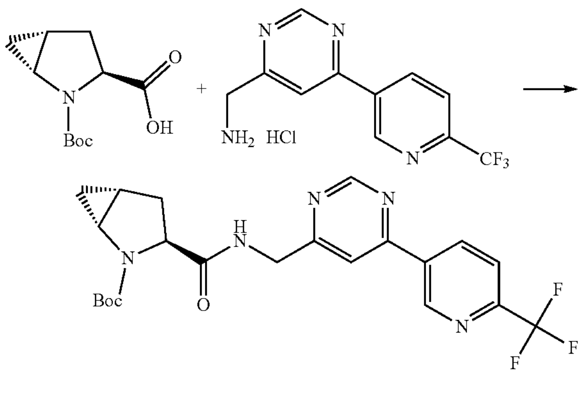

A mixture of (3S)-2-[(tert-butoxy)carbonyl]-2-azabicyclo[3.1.0]hexane-3-carboxylic acid (620 mg, 2.73 mmol, 1.00 equiv) in N,N-dimethylformamide (20 mL), [6-[6-(trifluoromethyl)pyridin-3-yl]pyrimidin-4-yl]methanamine hydrochloride (955 mg, 3.29 mmol, 1.20 equiv), DIEA (3.52 g, 27.24 mmol, 10.00 equiv), and HATU (1.246 g, 3.28 mmol, 1.20 equiv) was stirred overnight at room temperature. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (30:100) to afford the title compound (700 mg, 55%) as a yellow solid.

Step 8: Preparation of (3S)—N-([6-[6-(trifluoromethyl)pyridin-3-yl]pyrimidin-4-yl]methyl)-2-azabicyclo[3.1.0]hexane-3-carboxamide hydrochloride

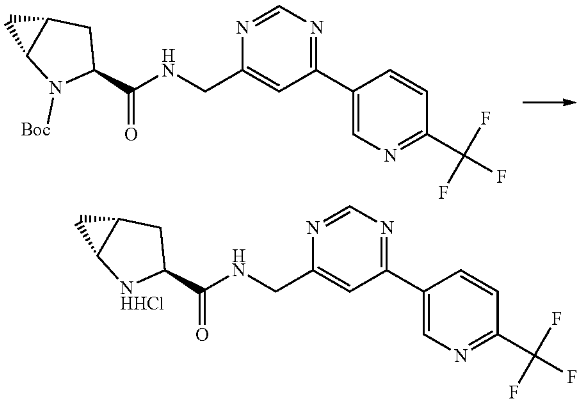

A mixture of tert-butyl (3S)-3-[([6-[6-(trifluoromethyl)pyridin-3-yl]pyrimidin-4-yl]methyl)carbamoyl]-2-azabicyclo[3.1.0]hexane-2-carboxylate (700 mg, 1.51 mmol, 1.00 equiv) and HCl (saturated solution in 50 mL of 1,4-dioxane) was stirred for 20 min at room temperature. The resulting mixture was concentrated under vacuum to afford the title compound (790 mg, crude) as a yellow solid.

Step 9: Preparation of (1R,3S,5R)-2-(4-fluorophenyl)sulfonyl-N-[[6-[6-(trifluoromethyl)-3-pyridyl]pyrimidin-4-yl]methyl]-2-azabicyclo[3.1.0]hexane-3-carboxamide

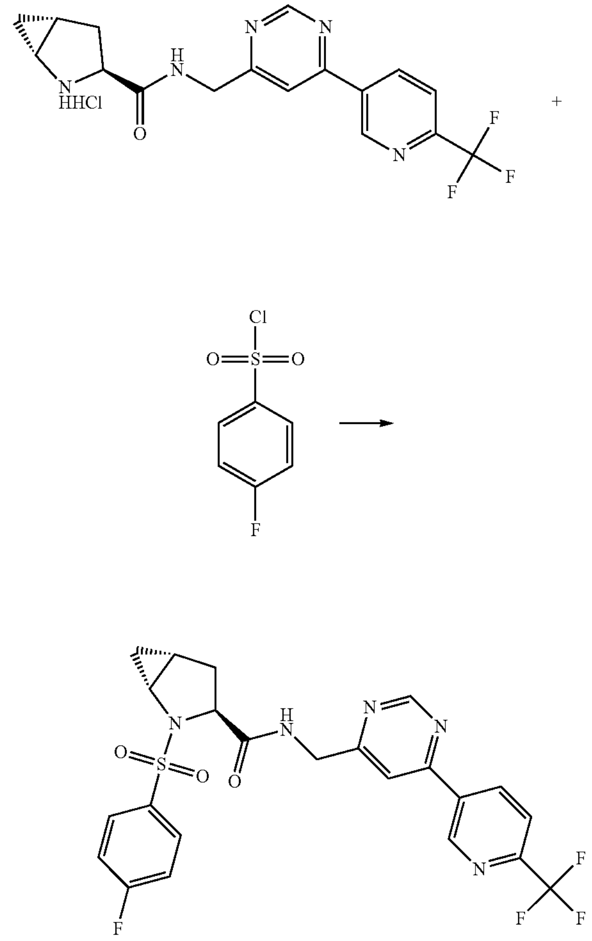

A mixture of (3S)-2-[(4-fluorobenzene)sulfonyl]-N-([6-[6-(trifluoromethyl)pyridin-3-yl]pyrimidin-4-yl]methyl)-2-azabicyclo[3.1.0]hexane-3-carboxamide (700 mg, 1.34 mmol, 1.00 equiv) in dichloromethane (40 mL), triethylamine (884 mg, 8.74 mmol, 5.00 equiv), 4-dimethylaminopyridine (43 mg, 0.35 mmol, 0.30 equiv), and 4-fluorobenzene-1-sulfonyl chloride (683 mg, 3.51 mmol, 2.60 equiv) was stirred for 2 h at room temperature. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (35:100) to afford the title compound (328.3 mg, 47%) as a white solid.

$^1$H NMR (400 MHz, $CD_3OD$) δ 9.47 (s, 1H), 9.30-9.29 (m, 1H), 8.94-8.90 (m, 1H), 8.80-8.77 (m, 1H), 8.26-8.25 (m, 1H), 8.10-8.01 (m, 1H), 8.01-7.97 (m, 2H), 7.57-7.51 (m, 2H), 4.52-4.48 (m, 2H), 3.60-3.54 (m, 1H), 3.39-3.32 (m, 1H), 2.30-2.15 (m, 2H), 1.67-1.66 (m, 1H), 0.38-0.35 (m, 1H), −0.41-−0.39 (m, 1H).

Example 124

Preparation of (3R,6S)-1,1-difluoro-5-[(4-fluorobenzene)sulfonyl]-N-([6-[6-(trifluoromethyl)pyridin-3-yl]pyrimidin-4-yl]methyl)-5-azaspiro[2.4]heptane-6-carboxamide

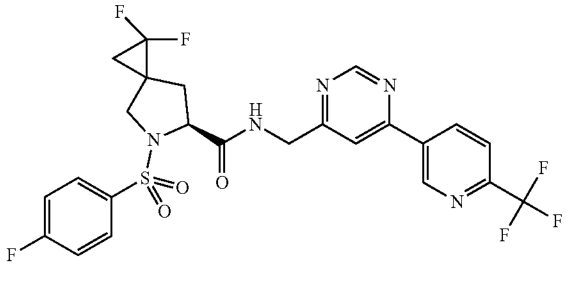 [SMILES: O=C(NCc1cc(-c2ccc(C(F)(F)F)nc2)ncn1)[C@@H]1CC2(CN1S(=O)(=O)c1ccc(F)cc1)CC2(F)F]

Step 1: Preparation of 5-tert-butyl 6-methyl (6S)-1,1-difluoro-5-azaspiro[2.4]heptane-5,6-dicarboxylate

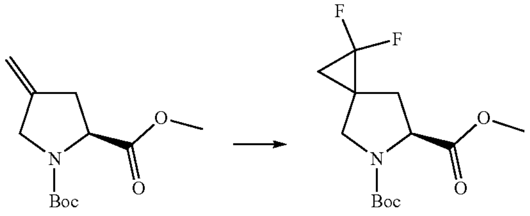

A mixture of NaI (87.14 mg, 0.50 equiv), 1-tert-butyl 2-methyl (2S)-4-methylidenepyrrolidine-1,2-dicarboxylate (280 mg, 1.16 mmol, 1.00 equiv), and TMS-$CF_3$ (412.5 mg, 2.50 equiv) in tetrahydrofuran (10 mL) was stirred for 12 h at 60° C. under nitrogen. The reaction was then quenched by saturated $NH_4Cl$ solution. The resulting solution was extracted with ethyl acetate, washed with saturated $Na_2S_2O_3$ and then brine, dried over anhydrous sodium sulfate, and concentrated under vacuum. This resulted in the title compound (400 mg, crude) as orange oil.

Step 2: Preparation of (6S)-5-[(tert-butoxy)carbonyl]-1,1-difluoro-5-azaspiro[2.4]heptane-6-carboxylic acid

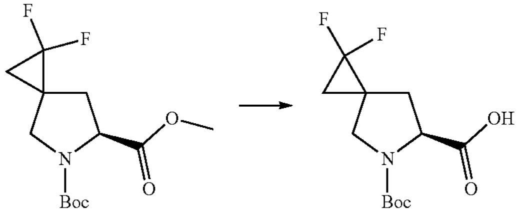 [SMILES: COC(=O)[C@@H]1CC2(CN1C(=O)OC(C)(C)C)CC2(F)F ; CC(C)(C)OC(=O)N1CC2(C[C@H]1C(=O)O)CC2(F)F]

A mixture of 5-tert-butyl 6-methyl (6S)-1,1-difluoro-5-azaspiro[2.4]heptane-5,6-dicarboxylate (400 mg, 1.37 mmol, 1.00 equiv) and LiOH (164.95 mg, 6.89 mmol, 5.00 equiv) in water(5 mL)/methanol (2 mL) was stirred for 2 h at 0-5° C. The mixture was diluted with water and extracted with ethyl acetate. The pH value of the water layer was adjusted to 5 with hydrogen chloride (10%). The resulting solution was extracted with ethyl acetate, washed with brine, dried over anhydrous sodium sulfate, and concentrated under vacuum. This resulted in the title compound (240 mg, 63%) as orange oil.

Step 3: Preparation of tert-butyl (6S)-1,1-difluoro-6-[([6-[6-(trifluoromethyl)pyridin-3-yl]pyrimidin-4-yl]methyl)carbamoyl]-5-azaspiro[2.4]heptane-5-carboxylate

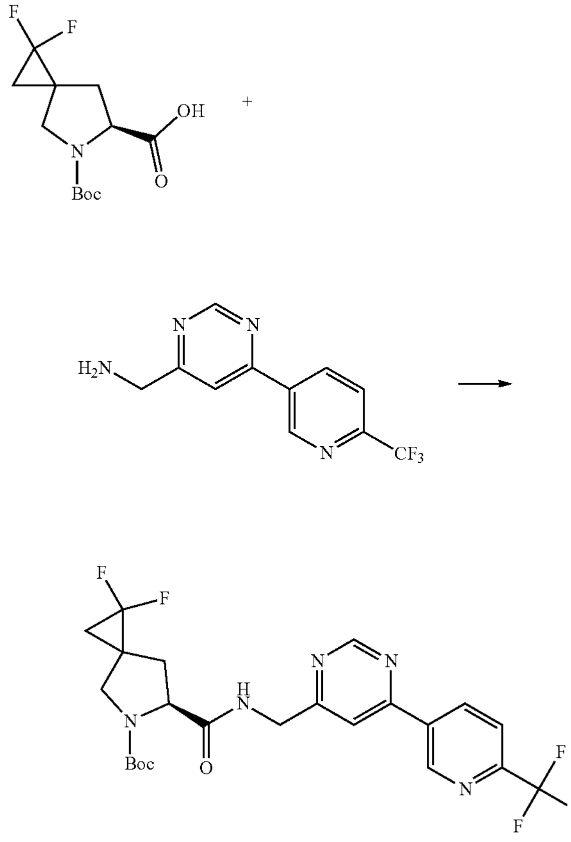

A mixture of (6S)-5-[(tert-butoxy)carbonyl]-1,1-difluoro-5-azaspiro[2.4]heptane-6-carboxylic acid (247 mg, 0.89 mmol, 1.00 equiv), HATU (508 mg, 1.34 mmol, 1.50 equiv), DIEA (460.2 mg), and [6-[6-(trifluoromethyl)pyridin-3-yl]pyrimidin-4-yl]methanamine hydrochloride (271.7 mg, 0.93 mmol, 1.20 equiv) in N,N-dimethylformamide (15 mL) was stirred for 1 h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:3) to afford the title compound (230 mg) as a light yellow solid.

Step 4: Preparation of (6S)-1,1-difluoro-N-([6-[6-(trifluoromethyl)pyridin-3-yl]pyrimidin-4-yl]methyl)-5-azaspiro[2.4]heptane-6-carboxamide

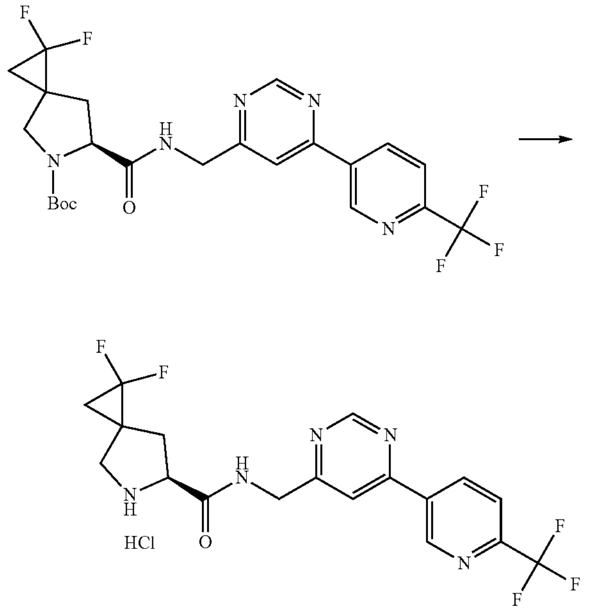

A mixture of tert-butyl (6S)-1,1-difluoro-6-[([6-[6-(trifluoromethyl)pyridin-3-yl]pyrimidin-4-yl]methyl)carbamoyl]-5-azaspiro[2.4]heptane-5-carboxylate (230 mg, 0.45 mmol, 1.00 equiv) and saturated hydrogen chloride in dioxane (3 mL) was stirred for 12 h at room temperature. The resulting solution was concentrated under vacuum to afford the title compound (200 mg, crude) as an orange solid.

Step 5: Preparation of (3R,6S)-1,1-difluoro-5-[(4-fluorobenzene)sulfonyl]-N-([6-[6-(trifluoromethyl)pyridin-3-yl]pyrimidin-4-yl]methyl)-5-azaspiro[2.4]heptane-6-carboxamide

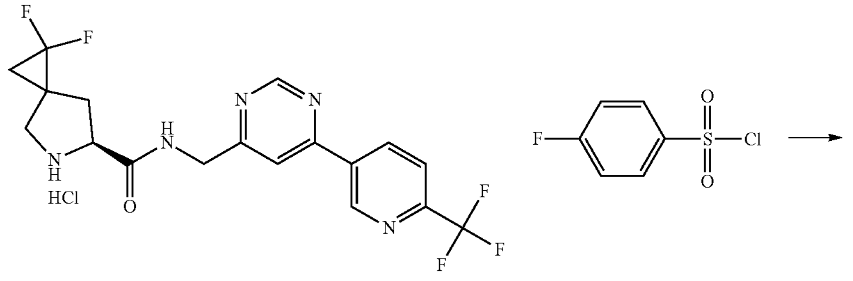

-continued

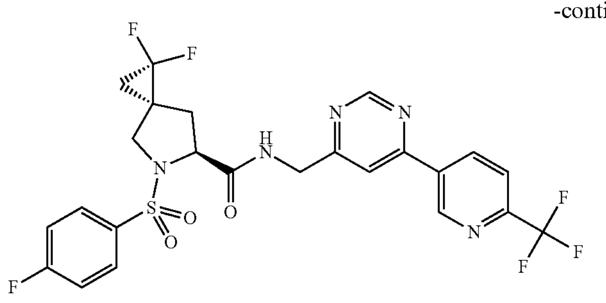

4-Proline Stereochemstry Assumed

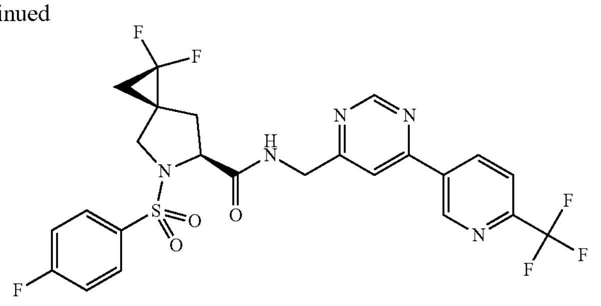

4-Proline Stereochemstry Assumed

A mixture of (6S)-1,1-difluoro-N-([6-[6-(trifluoromethyl)pyridin-3-yl]pyrimidin-4-yl]methyl)-5-azaspiro[2.4]heptane-6-carboxamide hydrochloride (200 mg, 0.44 mmol, 1.00 equiv), triethylamine (179.78 mg, 1.78 mmol, 4.00 equiv), 4-fluorobenzene-1-sulfonyl chloride (103.7 mg, 0.53 mmol, 1.20 equiv), and 4-dimethylaminopyridine (5.43 mg, 0.04 mmol, 0.10 equiv) in dichloromethane (10 mL) was stirred for 12 h at room temperature. The reaction was then quenched by water and extracted with ethyl acetate. The organic layers were combined, washed with brine, dried over anhydrous sodium sulfate, and concentrated under vacuum. The crude product was purified by Prep-HPLC to afford the title compound (42.7 mg, 17%) as a white solid. $t_R$=1.14 min (Repaired IC (CHIRALPAK IC), 0.46×10 cm, 5 μm, MeOH (0.1% DEA)=2%, 4 ml/min).

$^1$H NMR (300 MHz, $CDCl_3$) δ 9.48 (s, 1H), 9.29 (s, 1H), 8.70-8.67 (m, 1H), 8.03 (s, 1H), 7.96-7.91 (m, 2H), 7.91-7.84 (m, 1H), 7.75-7.71 (m, 1H), 7.34-7.26 (m, 2H), 4.99-4.91 (m, 1H), 4.64-4.56 (m, 1H), 4.39-4.34 (m, 1H), 3.61 (s, 2H), 2.25-2.01 (m, 2H), 1.40-1.34 (m, 2H).

And (3S,6S)-1,1-difluoro-5-[(4-fluorobenzene)sulfonyl]-N-([6-[6-(trifluoromethyl)pyridin-3-yl]pyrimidin-4-yl]methyl)-5-azaspiro[2.4]heptane-6-carboxamide was also isolated (27.3 mg, 11%) as a white solid. $t_R$=1.45 min (Repaired IC (CHIRALPAK IC), 0.46×10 cm, 5 μm, MeOH (0.1% DEA)=2%, 4 ml/min).

$^1$H NMR (300 MHz, $CDCl_3$) δ 9.47 (s, 1H), 9.30 (s, 1H), 8.99 (m, 1H), 8.79-8.77 (d, J=6 Hz, 1H), 8.15-8.03 (m, 4H), 7.53-7.47 (m, 2H), 4.53-4.45 (m, 3H), 3.61-3.32 (m, 2H), 2.03 (s, 2H), 1.48-1.44 (m, 2H).

The stereochemistry for position 4 of the prolines was arbitrarily assigned. The stereochemistry for position 2 of the prolines is as shown.

Example 125

Preparation of (2S,4R)-4-fluoro-1-[(4-fluorobenzene)sulfonyl]-N-([3-methoxy-1-[6-(trifluoromethyl)pyridin-3-yl]-1H-pyrazol-4-yl]methyl)-2-methylpyrrolidine-2-carboxamide

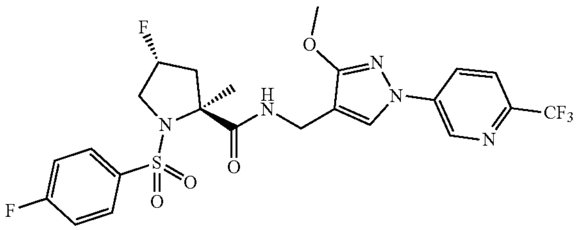 [SMILES: COc1nn(-c2ccc(C(F)(F)F)nc2)cc1CNC(=O)[C@]1(C)C[C@@H](F)CN1S(=O)(=O)c1ccc(F)cc1]

Step 1: Preparation of (2S,4R)-4-fluoro-1-[(4-fluorobenzene)sulfonyl]-N-([3-methoxy-1-[6-(trifluoromethyl)pyridin-3-yl]-1H-pyrazol-4-yl]methyl)-2-methylpyrrolidine-2-carboxamide

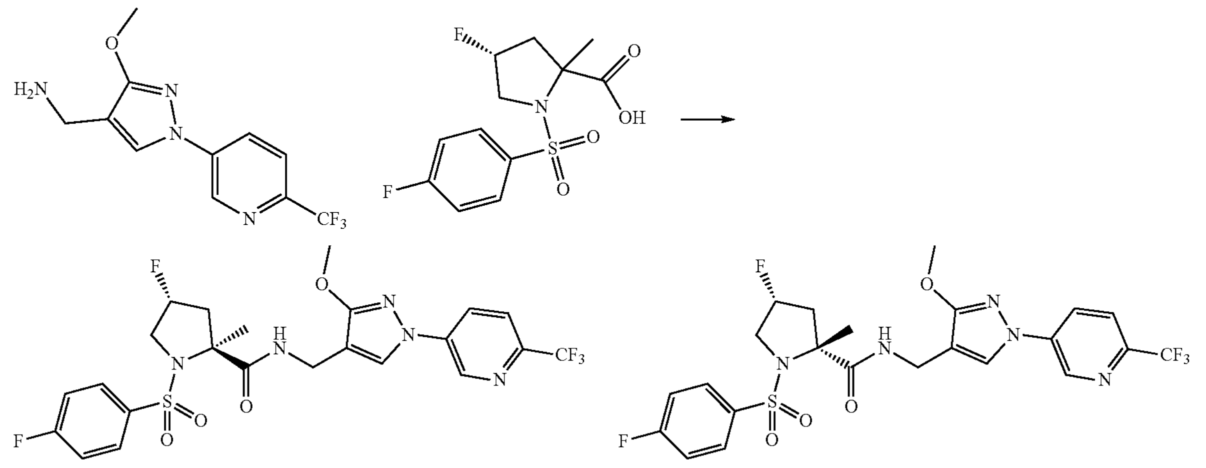

A mixture of (2R,4R)-4-fluoro-1-[(4-fluorobenzene)sulfonyl]-2-methylpyrrolidine-2-carboxylic acid (360 mg, 1.18 mmol, 1.00 equiv), HATU (673 mg, 1.77 mmol, 1.50 equiv), DIEA (456 mg, 3.53 mmol, 3.00 equiv), and [3-methoxy-1-[6-(trifluoromethyl)pyridin-3-yl]-1H-pyrazol-4-yl]methanamine (250 mg, 0.92 mmol, 0.80 equiv) in N,N-dimethylformamide (15 mL) was stirred for 3 h at room temperature. The reaction was then quenched by water and extracted with ethyl acetate. The combined extracts were washed with brine, dried over anhydrous sodium sulfate, and concentrated under vacuum. The residue was purified by a silica gel column eluting with ethyl acetate/petroleum ether (1:5). The crude product was purified by Chiral-Prep-HPLC to afford the title compound (39.8 mg, 6%) as a white solid. $t_R$=2.42 min (Lux 3 μm, Cellulose-4, 0.46×5 cm, 3 μm, Hex:EtOH=70:30, 1.0 ml/min).

$^1$H NMR (400 MHz, $CDCl_3$) δ 8.98 (s, 1H), 8.06-8.04 (m, 2H), 7.93-7.89 (m, 2H), 7.70-7.68 (d, J=6.0 Hz, 1H), 7.24-7.17 (m, 2H), 7.05 (s, 1H), 5.23-5.05 (m, 1H), 4.45-4.25 (m, 2H), 4.04 (s, 3H), 3.91-3.63 (m, 2H), 2.77-2.58 (m. 1H), 2.33-2.27 (m, 1H), 1.70 (s, 3H).

(2R,4R)-4-fluoro-1-[(4-fluorobenzene)sulfonyl]-N-([3-methoxy-1-[6-(trifluoromethyl)pyridin-3-yl]-1H-pyrazol-4-yl]methyl)-2-methylpyrrolidine-2-carboxamide was also isolated (110 mg, 17%) as a white solid. $t_R$=3.56 min (Lux 3 μm, Cellulose-4, 0.46×5 cm, 3 μm, Hex:EtOH=70:30, 1.0 ml/min).

$^1$H NMR (400 MHz, $CDCl_3$) δ 8.96 (s, 1H), 8.07-8.02 (m, 2H), 7.91-7.86 (m, 2H), 7.70-7.67 (d, J=6 Hz, 1H), 7.26-7.20 (m, 3H), 5.22-5.03 (m, 1H), 4.48-4.24 (m, 2H), 4.07-3.96 (m, 4H), 3.52-3.36 (m, 1H), 2.95-2.83 (m, 1H), 2.05-1.86 (m, 1H), 1.64 (s, 3H).

Example 126

Preparation of (2S,4R)-4-fluoro-1-(4-fluorophenyl)sulfonyl-N-[[5-fluoro-4-[6-(trifluoromethyl)-3-pyridyl]-2-pyridyl]methyl]-2-methyl-pyrrolidine-2-carboxamide

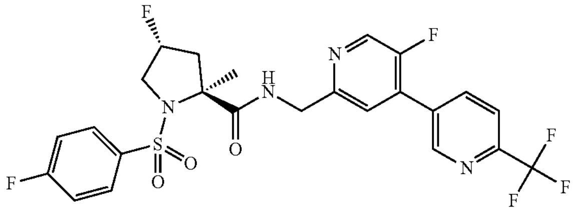 [SMILES: C[C@@]1(C(=O)NCc2cc(-c3ccc(C(F)(F)F)nc3)c(F)cn2)C[C@@H](F)CN1S(=O)(=O)c1ccc(F)cc1]

Step 1: Preparation of (2R,4R)-4-fluoro-1-(4-fluorophenyl)sulfonyl-N-[[5-fluoro-4-[6-(trifluoromethyl)-3-pyridyl]-2-pyridyl]methyl]-2-methyl-pyrrolidine-2-carboxamide

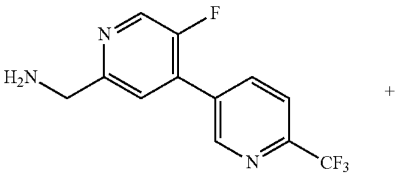

-continued

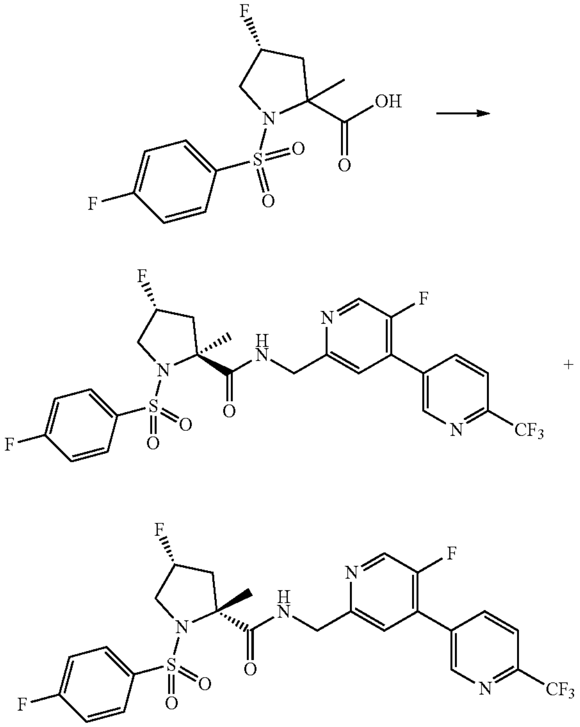

A mixture of [5-fluoro-4-[6-(trifluoromethyl)pyridin-3-yl]pyridin-2-yl]methanamine (100.00 mg, 0.37 mmol, 1.00 equiv), (4R)-4-fluoro-1-[(4-fluorobenzene)sulfonyl]-2-methylpyrrolidine-2-carboxylic acid (112.57 mg, 0.37 mmol, 1.00 equiv), HOBT (54.80 mg, 0.41 mmol, 1.10 equiv), EDCI (141.37 mg, 0.74 mmol, 2.00 equiv), and DIEA (95.31 mg, 0.74 mmol, 2.00 equiv) in THF (5 mL) was stirred for 12 h at 25° C. The reaction mixture was diluted with water, extracted with ethyl acetate, washed with brine, dried over anhydrous sodium sulfate, and concentrated under vacuum. The crude product (100.9 mg) was purified by Prep-HPLC to afford (2S,4R)-4-fluoro-N-([5-fluoro-4-[6-(trifluoromethyl)pyridin-3-yl]pyridin-2-yl]methyl)-1-[(4-fluorobenzene)sulfonyl]-2-methylpyrrolidine-2-carboxamide (41.9 mg, 20%) as a white solid. $t_R$=1.68 min (CHIRALPAK AD-H, 0.46×15 cm, 5 μm, MeOH (0.1% DEA)=30%, 4 ml/min).

$^1$H NMR (400 MHz, $CD_3OD$) δ 9.06 (s, 1H), 8.60-8.59 (d, J=4 Hz, 1H), 8.42-8.40 (m, 1H), 8.03-7.96 (m, 3H), 7.88-7.87 (d, J=4 Hz, 1H), 7.39-7.35 (m, 2H), 5.36-5.18 (d, J=72 Hz, 1H), 4.79-4.75 (d, J=16 Hz, 1H), 4.58-4.54 (d, J=16 Hz, 1H), 4.18-4.05 (m, 1H), 3.83-3.62 (m, 1H), 2.78-2.62 (m, 1H), 2.13-2.28 (m, 1H), 1.60 (s, 3H).

(2R,4R)-4-fluoro-N-([5-fluoro-4-[6-(trifluoromethyl)pyridin-3-yl]pyridin-2-yl]methyl)-1-[(4-fluorobenzene)sulfonyl]-2-methylpyrrolidine-2-carboxamide (20.9 mg, 10%) was also isolated from the reaction as a white solid. $t_R$=2.12 min (CHIRALPAK AD-H, 0.46×15 cm, 5 μm, MeOH (0.1% DEA)=30%, 4 ml/min).

$^1$H NMR (400 MHz, $CD_3OD$) δ 9.09 (s, 1H), 8.60-8.59 (d, J=4 Hz, 1H), 8.41-8.39 (d, J=8 Hz, 1H), 7.98-7.90 (m, 4H), 7.32-7.27 (m, 2H), 5.35-5.34 (d, J=4 Hz, 1H), 4.89-4.58 (m, 2H), 3.92-3.76 (m, 2H), 2.70-2.32 (m, 2H), 1.78 (s, 1H).

Example 127

Preparation of (2S,4R)-4-fluoro-1-[(4-fluorobenzene)sulfonyl]-N-([2-methoxy-6-[6-(trifluoromethyl)pyridin-3-yl]pyrimidin-4-yl]methyl)pyrrolidine-2-carboxamide

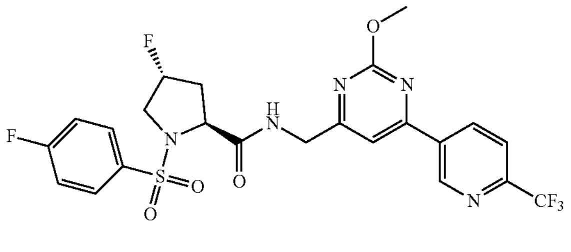 [SMILES: COc1nc(CNC(=O)[C@@H]2C[C@@H](F)CN2S(=O)(=O)c2ccc(F)cc2)cc(-c2ccc(C(F)(F)F)nc2)n1]

Step 1: Preparation of [2-(benzylsulfanyl)-6-[6-(trifluoromethyl)pyridin-3-yl]pyrimidin-4-yl]methanamine hydrochloride

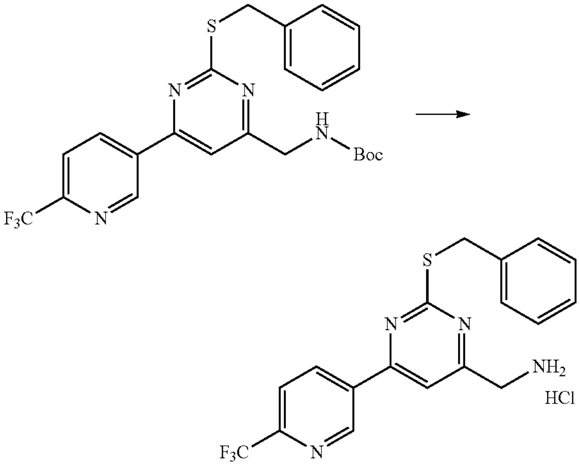

A mixture of tert-butyl N-[[2-(benzylsulfanyl)-6-[6-(trifluoromethyl)pyridin-3-yl]pyrimidin-4-yl]methyl]carbamate (1.2 g, 2.52 mmol, 1.00 equiv) and saturated HCl in 50 mL of 1,4-dioxane was stirred for 3 h at room temperature. The solids were collected by filtration to afford the title compound (850 mg, 82%) as a gray solid.

Step 2: Preparation of (1S,4R)—N-[[2-(benzylsulfanyl)-6-[6-(trifluoromethyl)pyridin-3-yl]pyrimidin-4-yl]methyl]-4-fluoro-2-[(4-fluorobenzene)sulfonyl]cyclopentane-1-carboxamide hydrochloride

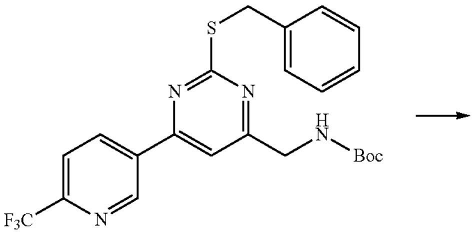

-continued

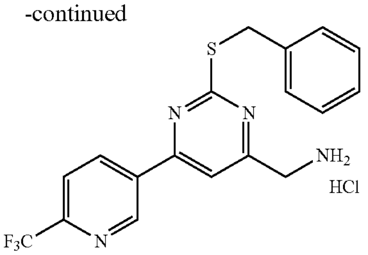

A solution of (1S,4R)-4-fluoro-2-[(4-fluorobenzene)sulfonyl]cyclopentane-1-carboxylic acid (300 mg, 1.03 mmol, 1.00 equiv), HATU (470 mg, 1.24 mmol, 1.00 equiv), and DIEA (266 mg, 2.06 mmol, 2.00 equiv) in N,N-dimethylformamide (8 mL) was stirred for 10 min at room temperature. [2-(Benzylsulfanyl)-6-[6-(trifluoromethyl)pyridin-3-yl]pyrimidin-4-yl]methanamine hydrochloride (424 mg, 1.03 mmol, 1.00 equiv) was added and the resulting solution was stirred overnight at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1:1). This resulted in the title compound (320 mg, 48%) as light brown oil.

Step 3: Preparation of (1S,4R)-4-fluoro-2-[(4-fluorobenzene)sulfonyl]-N-[[2-(phenylmethane)sulfonyl-6-[6-(trifluoromethyl)pyridin-3-yl]pyrimidin-4-yl]methyl]cyclopentane-1-carboxamide

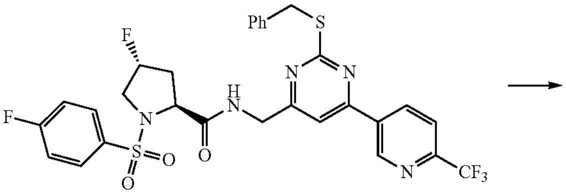

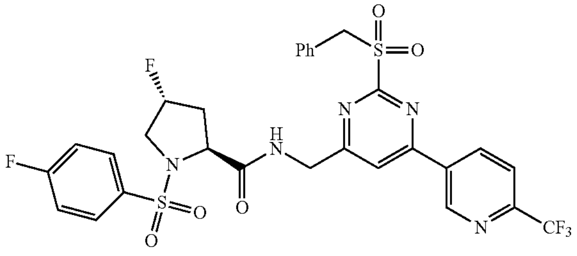

m-CPBA (340 mg, 1.97 mmol, 4.00 equiv) was added in portions into a solution of (1S,4R)—N-[[2-(benzylsulfanyl)-6-[6-(trifluoromethyl)pyridin-3-yl]pyrimidin-4-yl]methyl]-4-fluoro-2-[(4-fluorobenzene)sulfonyl]cyclopentane-1-carboxamide (320 mg, 0.49 mmol, 1.00 equiv) in dichloromethane (50 mL) at room temperature. After 4 h at room temperature the resulting solution was diluted with dichloromethane, washed with saturated sodium bicarbonate, dried over sodium sulfate, and concentrated under vacuum. The residue was purified by a silica gel column eluting with ethyl acetate/petroleum ether (2:1) to afford the title compound (250 mg, 74%) as a yellow solid.

Step 4: Preparation of (2S,4R)-4-fluoro-1-[(4-fluorobenzene)sulfonyl]-N-([2-methoxy-6-[6-(trifluoromethyl)pyridin-3-yl]pyrimidin-4-yl]methyl)pyrrolidine-2-carboxamide

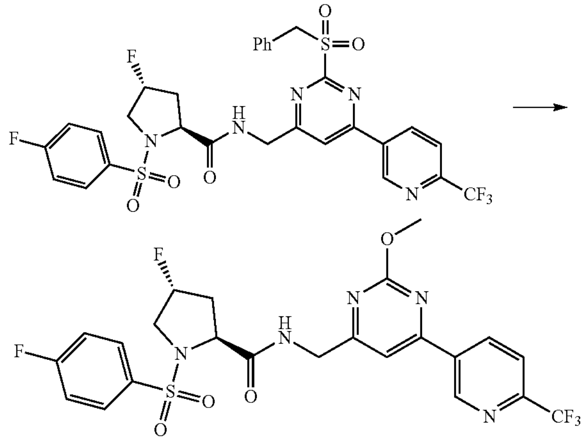

Sodium methylate (60 mg, 2.00 equiv) was added in several batches into a solution of (2S,4R)-4-fluoro-1-[(4-fluorobenzene)sulfonyl]-N-[[2-(phenylmethane)sulfonyl-6-[6-(trifluoromethyl)pyridin-3-yl]pyrimidin-4-yl]methyl] pyrrolidine-2-carboxamide (250 mg, 0.37 mmol, 1.00 equiv) in methanol (20 mL) at 0° C. The resulting solution was stirred for 30 min at room temperature and concentrated under vacuum. The residue was purified by a silica gel column eluting with ethyl acetate/petroleum ether (2:1) to afford the title compound (91.7 mg, 45%) as a pink solid.

$^1$H NMR (300 MHz, DMSO-$d_6$) δ 9.46 (s, 1H), 9.10 (t, J=5.8 Hz, 1H), 8.78 (d, J=8.4 Hz, 1H), 8.09-8.00 (m, 3H), 7.88 (s, 1H), 7.47 (t, J=8.8 Hz, 2H), 5.29-5.12 (d, J=52.0 Hz, 1H), 4.46 (d, J=6.0 Hz, 2H), 4.27-4.22 (dd, J=9.9 Hz, J=7.2 Hz, 1H), 4.04 (s, 3H), 3.75 (s, 1H), 3.71-3.58 (m, 1H), 2.51-2.37 (m, 1H), 2.24-2.01 (m, 1H).

Example 128

Preparation of (2S,4R)—N-[[4-(4,4-difluoro-1-piperidyl)-5-fluoro-2-pyridyl]methyl]-4-fluoro-1-(4-fluorophenyl)sulfonyl-pyrrolidine-2-carboxamide

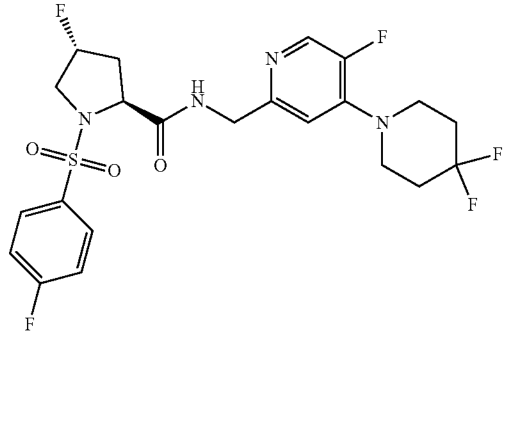 [SMILES: O=C(NCc1cc(N2CCC(F)(F)CC2)c(F)cn1)[C@@H]1C[C@@H](F)CN1S(=O)(=O)c1ccc(F)cc1]

Step 1: Preparation of tert-butyl 4,4-difluoropiperidine-1-carboxylate

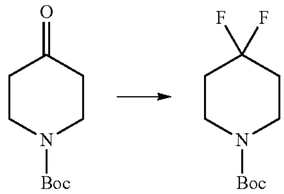 [SMILES: CC(C)(C)OC(=O)N1CCC(=O)CC1 ; CC(C)(C)OC(=O)N1CCC(F)(F)CC1]

BAST (222.4 g, 1.01 mol, 20.00 equiv) was added dropwise into a solution of tert-butyl 4-oxopiperidine-1-carboxylate (10 g, 50.19 mmol, 1.00 equiv) in dichloromethane (200 mL) at 0° C. under nitrogen. The resulting solution was stirred overnight at 25° C. The reaction was then quenched by saturated sodium bicarbonate, extracted with dichloromethane, washed with brine, dried over sodium sulfate, and concentrated under vacuum. The residue was purified by a silica gel column eluting with ethyl acetate/petroleum ether (1/10). This resulted in the title compound (9.7 g, 87%) as a light yellow solid.

Step 2: Preparation of 4,4-difluoropiperidine hydrochloride

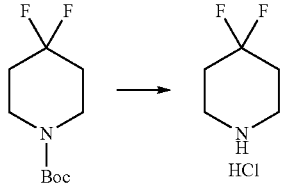 [SMILES: CC(C)(C)OC(=O)N1CCC(F)(F)CC1 ; FC1(F)CCNCC1 ; Cl]

A mixture of tert-butyl 4,4-difluoropiperidine-1-carboxylate (5 g, 22.60 mmol, 1.00 equiv) and hydrogen chloride (saturated solution in 150 mL of 1,4-dioxane) was stirred for 6 h at 25° C. The resulting mixture was concentrated under vacuum to afford the title compound (4.2 g, crude) as a yellow solid.

Step 3: Preparation of 2-chloro-4-(4,4-difluoropiperidin-1-yl)-5-fluoropyridine

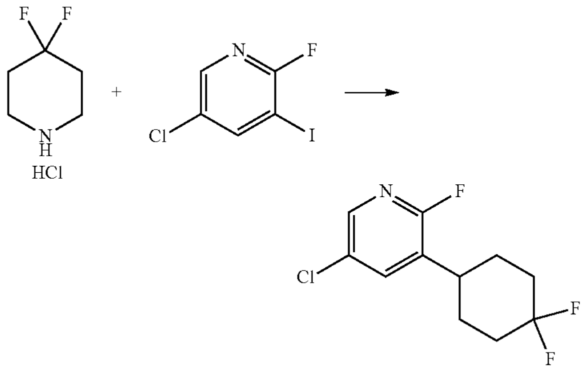

A mixture of 2-chloro-5-fluoro-4-iodopyridine (813 mg, 3.16 mmol, 1.00 equiv), 4,4-difluoropiperidine hydrochloride (500 mg, 3.17 mmol, 1.00 equiv), XantPhos (183 mg, 0.32 mmol, 0.10 equiv), $Cs_2CO_3$ (3.1 g, 9.51 mmol, 3.00 equiv), and $Pd_2(dba)_3CHCl_3$ (164 mg, 0.16 mmol, 0.05 equiv) in toluene (20 mL) was stirred overnight at 100° C. under nitrogen. The resulting mixture was concentrated under vacuum. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (200 mg, 25%) as a yellow solid.

Step 4: Preparation of 4-(4,4-difluoropiperidin-1-yl)-5-fluoropyridine-2-carbonitrile

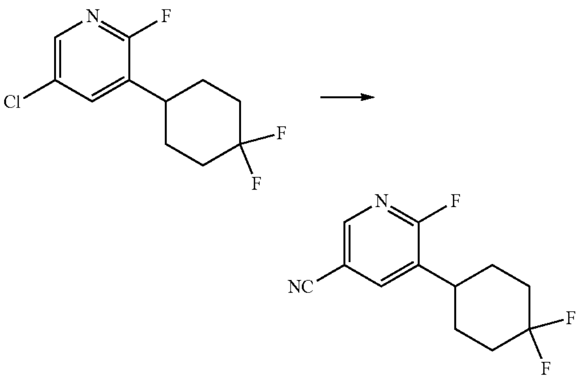

A mixture of 2-chloro-4-(4,4-difluoropiperidin-1-yl)-5-fluoropyridine (150 mg, 0.60 mmol, 1.00 equiv), $Pd_2(dba)_3.CHCl_3$ (10.3 mg, 0.01 mmol, 0.05 equiv), $Zn(CN)_2$ (23.3 mg, 0.20 mmol, 1.00 equiv), dppf (11 mg, 0.02 mmol, 0.10 equiv), Zn (1.3 mg, 0.02 mmol, 0.10 equiv), and DMA (2 mL) was irradiated with microwave radiation for 1.5 h at 125° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/4) to afford the title compound (180 mg) as a yellow solid.

Step 5: [4-(4,4-difluoropiperidin-1-yl)-5-fluoropyridin-2-yl]methanamine hydrochloride

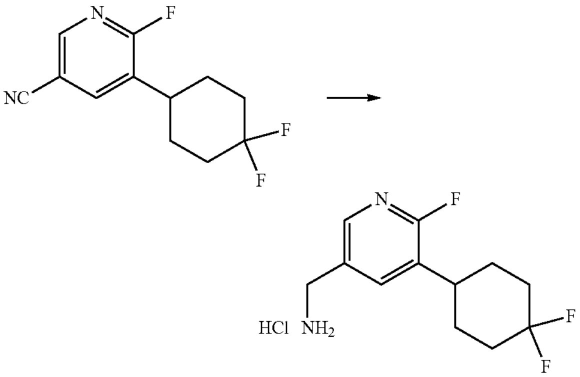

A mixture of 4-(4,4-difluoropiperidin-1-yl)-5-fluoropyridine-2-carbonitrile (180 mg, 0.75 mmol, 1.00 equiv), methanol (20 mL), palladium on carbon (180 mg, 1.69 mmol, 1.00 equiv), and concentrated hydrogen chloride (0.2 mL) was stirred for 20 min at 25° C. under hydrogen. The solids were filtered out. The resulting solution was concentrated under vacuum to afford the title compound (180 mg, 98%) as a white solid.

Step 6: Preparation of (2S,4R)—N-[[4-(4,4-difluoro-1-piperidyl)-5-fluoro-2-pyridyl]methyl]-4-fluoro-1-(4-fluorophenyl)sulfonyl-pyrrolidine-2-carboxamide

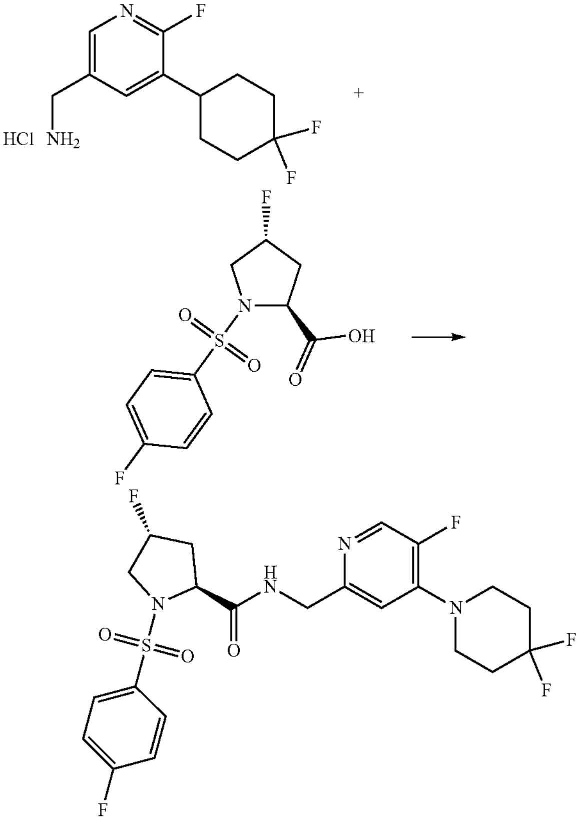

A mixture of [4-(4,4-difluoropiperidin-1-yl)-5-fluoropyridin-2-yl]methanamine hydrochloride (180 mg, 0.73 mmol, 1.00 equiv), (2S,4R)-4-fluoro-1-[(4-fluorobenzene)sulfonyl]pyrrolidine-2-carboxylic acid (213.8 mg, 0.73 mmol, 1.00 equiv), EDCI (282.1 mg, 1.47 mmol, 2.00 equiv), HOBt (109.1 mg, 0.81 mmol, 1.10 equiv), and DIEA (189.6 mg, 1.47 mmol, 12.00 equiv) in tetrahydrofuran (10 mL) was stirred overnight at 25° C. The reaction mixture was diluted with water, extracted with ethyl acetate, washed with brine, dried over anhydrous sodium sulfate, and concentrated under vacuum. The crude product (150 mg) was purified by Prep-HPLC to afford the title compound (39.2 mg, 10%) as a white solid.

$^1H$ NMR (300 MHz, $CDCl_3$) δ 8.09-8.01 (m, 1H), 8.00-7.97 (m, 2H), 7.38-7.32 (m, 2H), 7.19-7.17 (m, 1H), 5.21-5.14 (d, J=52.0 Hz, 1H), 4.52-4.39 (m, 2H), 4.27-4.21 (m, 1H), 3.83-3.74 (m, 2H), 3.70-3.54 (m, 4H), 2.62-2.42 (m, 1H), 2.27-2.00 (m, 5H).

Example 129

Preparation of (2S,4R)—N-[[4-(6-azaspiro[2.5]octan-6-yl)-5-fluoro-2-pyridyl]methyl]-4-fluoro-1-(4-fluorophenyl)sulfonyl-pyrrolidine-2-carboxamide

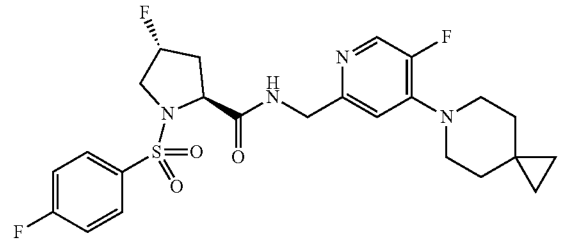 [SMILES: O=C(NCc1cc(N2CCC3(CC2)CC3)c(F)cn1)[C@@H]1C[C@@H](F)CN1S(=O)(=O)c1ccc(F)cc1]

Step 1: Preparation of 6-(2-chloro-5-fluoropyridin-4-yl)-6-azaspiro[2.5]octane

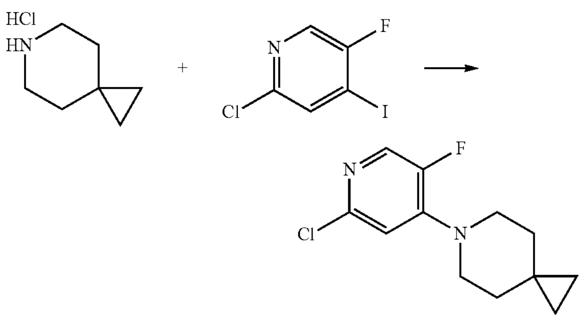

A mixture of 6-azaspiro[2.5]octane hydrochloride (1.00 g, 6.77 mmol, 1.00 equiv), 2-chloro-5-fluoro-4-iodopyridine (1.74 g, 6.76 mmol, 1.00 equiv), $Pd_2(dba)_3.CHCl_3$ (350 mg, 0.34 mmol, 0.05 equiv), BINAP (420 mg, 0.67 mmol, 0.10 equiv), and t-BuONa (1.95 g, 20.29 mmol, 3.00 equiv) in toluene (20 mL) was stirred for overnight at 100° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (480 mg, 29%) as a light yellow solid.

Step 2: Preparation of 4-(4-cyclopropylpiperidin-1-yl)-5-fluoropyridine-2-carbonitrile

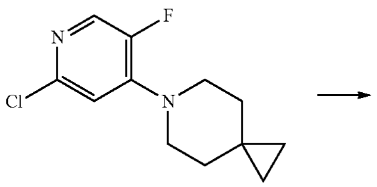

-continued

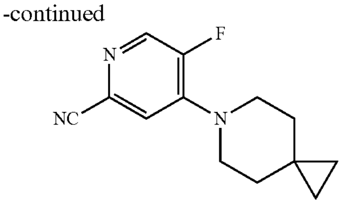

A mixture of 2-chloro-4-(4-cyclopropylpiperidin-1-yl)-5-fluoropyridine (480.00 mg, 1.88 mmol, 1.00 equiv), $Pd_2(dba)_3.CHCl_3$ (103 mg, 0.10 mmol, 0.05 equiv), $Zn(CN)_2$ (140 mg, 1.19 mmol, 0.60 equiv), dppf (104.46 mg, 0.19 mmol, 0.10 equiv), Zn (12.33 mg, 0.19 mmol, 0.10 equiv), and DMA (5 mL, 53.78 mmol, 28.50 equiv) was irradiated with microwave radiation for 1 h at 100° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (170 mg, 37%) as a light yellow solid.

Step 3: Preparation of (4-[6-azaspiro[2.5]octan-6-yl]-5-fluoropyridin-2-yl)methanamine hydrochloride

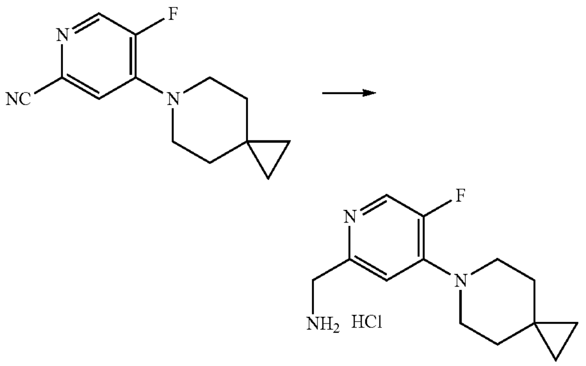

A mixture of 4-[6-azaspiro[2.5]octan-6-yl]-5-fluoropyridine-2-carbonitrile (140 mg, 0.61 mmol, 1.00 equiv), methanol (5 mL, 123.49 mmol, 204.00 equiv), palladium on carbon (140 mg, 1.32 mmol, 2.20 equiv), and concentrated hydrogen chloride (0.1 mL) was stirred for 15 min at 25° C. under hydrogen. The resulting mixture was concentrated under vacuum to afford the title compound (140 mg, 98%) as a light yellow solid.

Step 4: Preparation of (2S,4R)—N-[[2-(6-azaspiro[2.5]octan-6-yl)-5-fluoro-2-pyridyl]methyl]-4-fluoro-1-(4-fluorophenyl)sulfonyl-pyrrolidine-2-carboxamide

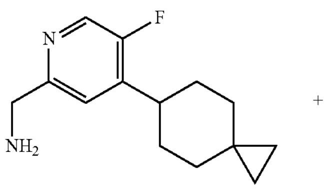

-continued

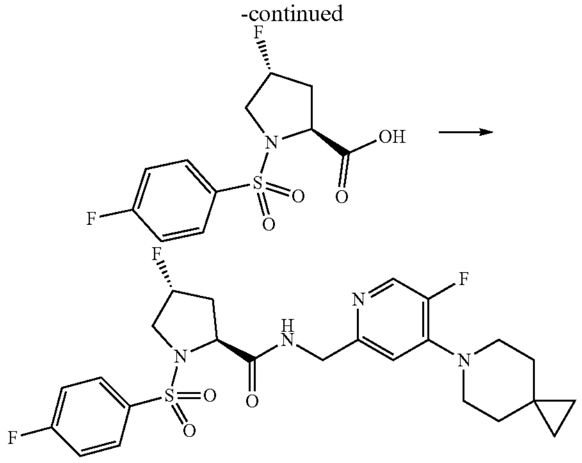

A mixture of (4-[6-azaspiro[2.5]octan-6-yl]-5-fluoropyridin-2-yl)methanamine (140.00 mg, 0.59 mmol, 1.00 equiv), (2S,4R)-4-fluoro-1-[(4-fluorobenzene)sulfonyl]pyrrolidine-2-carboxylic acid (225.29 mg, 0.77 mmol, 1.30 equiv), EDCI (228.12 mg, 1.19 mmol, 2.00 equiv), HOBT (88.44 mg, 0.65 mmol, 1.10 equiv), and DIEA (153.80 mg, 1.19 mmol, 2.00 equiv) in THF (5 mL) was stirred overnight at 25° C. The reaction mixture was diluted with water, extracted with ethyl acetate, washed with brine, dried over anhydrous sodium sulfate, and concentrated under vacuum. The crude product (43.9 mg) was purified by Prep-HPLC to afford the title compound (28.4 mg, 9%) as a white solid. $^1$H NMR (400 MHz, $CD_3OD$) δ 8.04-7.98 (m, 3H), 7.38-7.33 (m, 2H), 7.16-7.14 (d, J=8 Hz, 1H), 5.20-5.07 (d, J=52 Hz, 1H), 4.46 (s, 2H), 4.28-4.24 (m, 1H), 3.83-3.68 (m, 2H), 3.49-3.46 (m, 4H), 2.54-2.46 (m, 1H), 2.26-2.12 (m, 1H), 1.51-1.49 (m, 4H), 0.37 (s, 4H).

Example 130

Preparation of (2S,4R)-4-fluoro-1-(4-fluorophenyl)sulfonyl-N-[[5-(trifluoromethyl)-4-[4-(trifluoromethyl)-1-piperidyl]-2-pyridyl]methyl]pyrrolidine-2-carboxamide

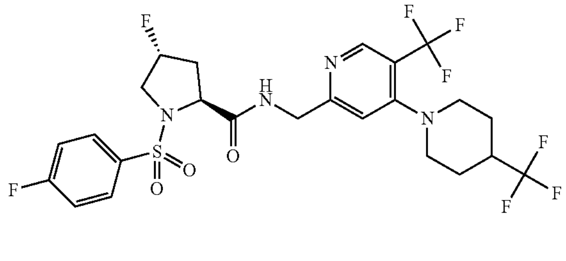 [SMILES: O=C(NCc1cc(N2CCC(C(F)(F)F)CC2)c(C(F)(F)F)cn1)[C@@H]1C[C@@H](F)CN1S(=O)(=O)c1ccc(F)cc1]

Step 1: Preparation of 2-chloro-5-(trifluoromethyl)-4-[4-(trifluoromethyl)piperidin-1-yl]pyridine

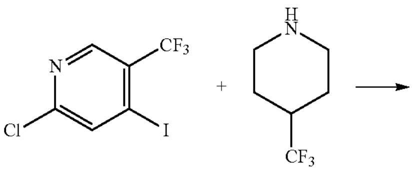

-continued

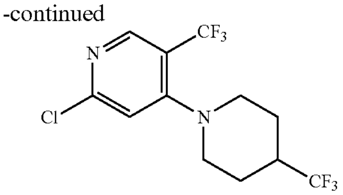

A mixture of 2-chloro-4-iodo-5-(trifluoromethyl)pyridine (1.00 g, 3.25 mmol, 1.00 equiv), 4-(trifluoromethyl)piperidine (500 mg, 3.26 mmol, 1.00 equiv), $Pd(dppf)Cl_2.CH_2Cl_2$ (130 mg, 0.16 mmol, 0.05 equiv), and $Cs_2CO_3$ (2.12 g, 6.51 mmol, 2.00 equiv) in toluene (10.00 mL) was stirred overnight at 100° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (700 mg, 65%) as a yellow solid.

Step 2: Preparation of 5-(trifluoromethyl)-4-[4-(trifluoromethyl)piperidin-1-yl]pyridine-2-carbonitrile

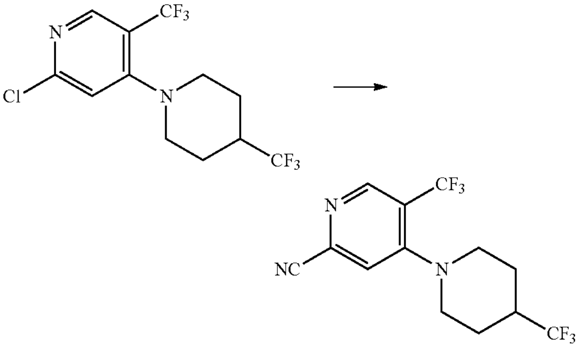

A mixture of 2-chloro-5-(trifluoromethyl)-4-[4-(trifluoromethyl)piperidin-1-yl]pyridine (700.00 mg, 2.10 mmol, 1.00 equiv), $Pd_2(dba)_3.CHCl_3$ (108.90 mg, 0.11 mmol, 0.05 equiv), $Zn(CN)_2$ (148.27 mg, 1.26 mmol, 0.60 equiv), dppf (116.65 mg, 0.21 mmol, 0.10 equiv), Zn (13.76 mg, 0.21 mmol, 0.10 equiv), and DMA (5.01 mL) was irradiated with microwave radiation for 1 h at 125° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (450 mg, 66%) as a white solid.

Step 3: Preparation of [5-(trifluoromethyl)-4-[4-(trifluoromethyl)piperidin-1-yl]pyridin-2-yl]methanamine hydrochloride

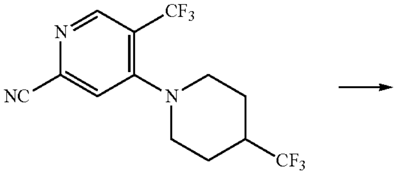

-continued

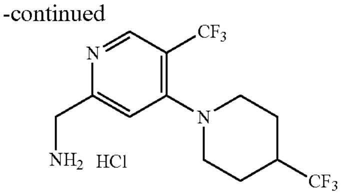

A mixture of 5-(trifluoromethyl)-4-[4-(trifluoromethyl) piperidin-1-yl]pyridine-2-carbonitrile (120 mg, 0.37 mmol, 1.00 equiv), palladium on carbon (120 mg, 1.13 mmol, 3.00 equiv), and concentrated hydrogen chloride (0.1 mL) in methanol (10 mL) was stirred for 10 min at 25° C. under hydrogen. The resulting mixture was concentrated under vacuum to afford the title compound (130 mg, crude) as a white solid.

Step 4: Preparation of (2S,4R)-4-fluoro-1-(4-fluorophenyl)sulfonyl-N-[[5-(trifluoromethyl)-4-[4-(trifluoromethyl)-1-piperidyl]-2-pyridyl]methyl]pyrrolidine-2-carboxamide

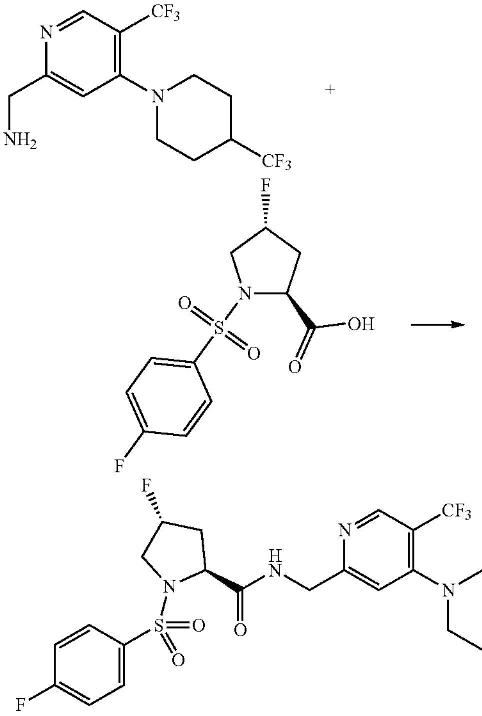

A mixture of [5-(trifluoromethyl)-4-[4-(trifluoromethyl) piperidin-1-yl]pyridin-2-yl]methanamine (100.00 mg, 0.31 mmol, 1.00 equiv), (2S,4R)-4-fluoro-1-[(4-fluorobenzene) sulfonyl]pyrrolidine-2-carboxylic acid (115.70 mg, 0.40 mmol, 1.30 equiv), EDCI (117.15 mg, 0.61 mmol, 2.00 equiv), HOBT (45.42 mg, 0.34 mmol, 1.10 equiv), and DIEA (78.98 mg, 0.61 mmol, 2.00 equiv) in tetrahydrofuran (5 mL) was stirred overnight at 25° C. The reaction mixture was diluted with water, extracted with ethyl acetate, washed with brine, dried over anhydrous sodium sulfate, and concentrated under vacuum. The crude product (58 mg) was purified by Prep-HPLC to afford the title compound (43.4 mg, 24%) as a white solid.

$^1$H NMR (400 MHz, $CD_3OD$) δ 8.42 (s, 1H), 8.05-8.00 (m, 2H), 7.40-7.35 (m, 3H), 5.24-5.18 (d, J=18 Hz, 2H), 4.57-4.56 (m, 2H), 4.31-4.26 (m, 1H), 3.86 (s, 1H), 3.68-3.63 (m, 3H), 3.02 (m, 2H), 2.68-2.12 (m, 3H), 1.97-1.93 (d, J=12 Hz, 2H), 1.73-1.72 (m, 2H).

Example 131

Preparation of (2S,4R)-4-fluoro-1-(4-fluorophenyl) sulfonyl-N-[[4-[5-(trifluoromethyl)-2-pyridyl]-2-pyridyl]methyl]pyrrolidine-2-carboxamide

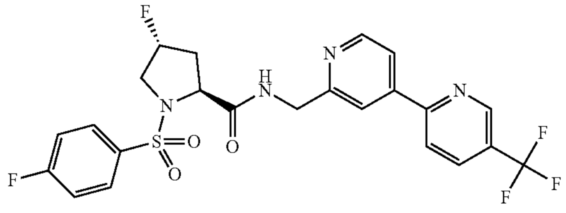 [SMILES: O=C(NCc1cc(-c2ccc(C(F)(F)F)cn2)ccn1)[C@@H]1C[C@@H](F)CN1S(=O)(=O)c1ccc(F)cc1]

Step 1: Preparation of 4-(tetramethyl-1,3,2-dioxaborolan-2-yl)pyridine-2-carbonitrile

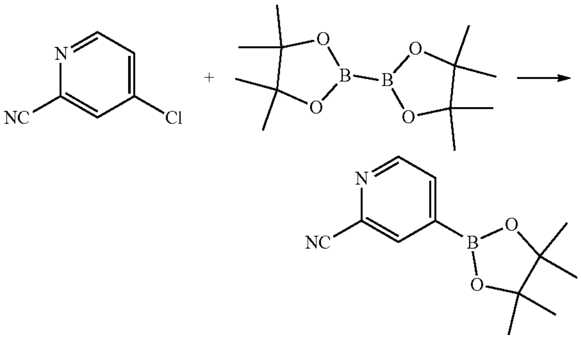

A mixture of 4-chloropyridine-2-carbonitrile (5 g, 36.09 mmol, 1.00 equiv), 4,4,5,5-tetramethyl-2-(tetramethyl-1,3,2-dioxaborolan-2-yl)-1,3,2-dioxaborolane (13.8 g, 54.34 mmol, 1.50 equiv), KOAc (11 g, 112.08 mmol, 3.10 equiv), and Pd(dppf)$Cl_2$ (1.33 g, 1.82 mmol) in dioxane (40 mL) was stirred for 6 h at 100° C. under nitrogen. The reaction mixture was diluted with water, extracted with ethyl acetate, washed with brine, dried over anhydrous sodium sulfate, and concentrated under vacuum. This resulted in the title compound (16 g, crude) as black oil.

Step 2: Preparation of 4-[5-(trifluoromethyl)pyridin-2-yl]pyridine-2-carbonitrile

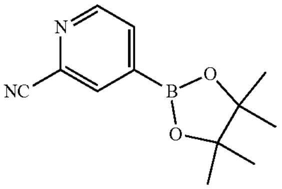

+

-continued

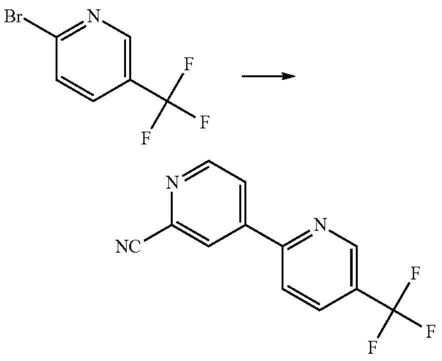

A mixture of 4-(tetramethyl-1,3,2-dioxaborolan-2-yl)pyridine-2-carbonitrile (1.6 g, 6.95 mmol, 3.10 equiv), 2-bromo-5-(trifluoromethyl)pyridine (500 mg, 2.21 mmol, 1.00 equiv), Pd(dppf)$Cl_2$ (170 mg, 0.23 mmol, 0.10 equiv), and potassium carbonate (921 mg, 6.66 mmol, 3.00 equiv) in dioxane (40 mL)/water (2 mL) was stirred for 12 h at 100° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1:20) to afford the title compound (380 mg, 69%) as a white solid.

Step 3: Preparation of [4-[5-(trifluoromethyl)pyridin-2-yl]pyridin-2-yl]methanamine hydrochloride

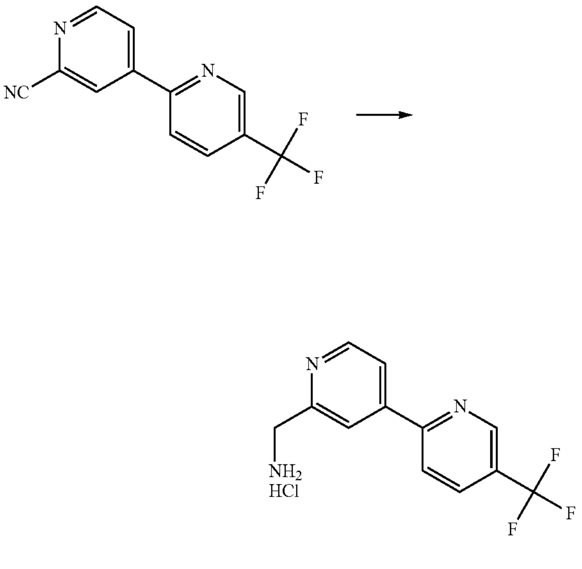

A mixture of 4-[5-(trifluoromethyl)pyridin-2-yl]pyridine-2-carbonitrile (200 mg, 0.80 mmol, 1.00 equiv), palladium on carbon (100 mg, 0.94 mmol, 1.20 equiv), and concentrated hydrogen chloride (0.1 mL) in ethanol (10 mL) was stirred for 30 min at room temperature under hydrogen. The solids were filtered out. The filtrate was concentrated under vacuum to afford the title compound (240 mg, crude) as a white solid.

Step 4: Preparation of (2S,4R)-4-fluoro-1-(4-fluorophenyl)sulfonyl-N-[[4-[5-(trifluoromethyl)-2-pyridyl]-2-pyridyl]methyl]pyrrolidine-2-carboxamide

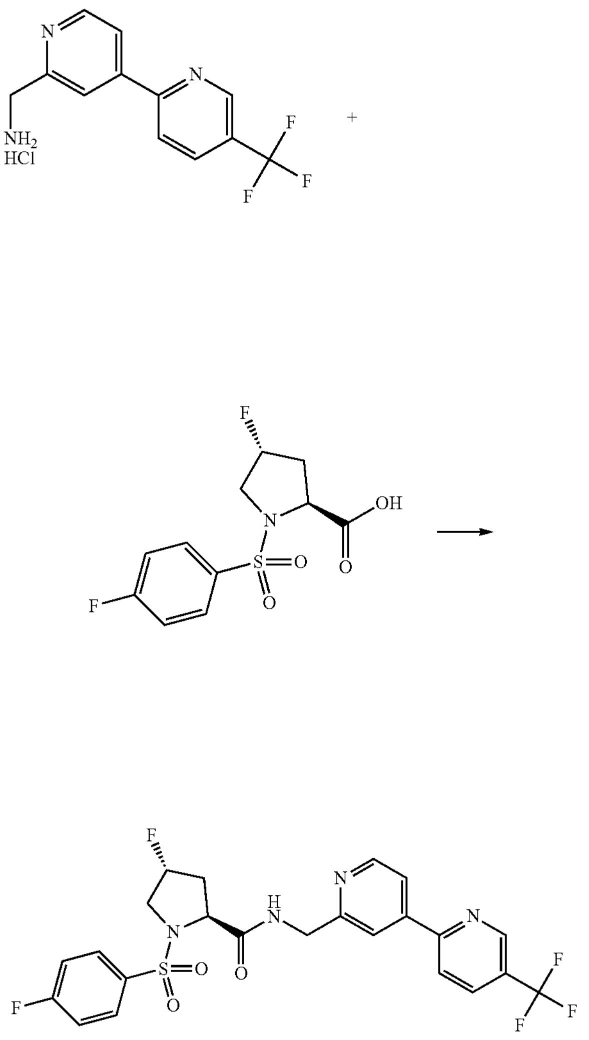

A mixture of (2S,4R)-4-fluoro-1-[(4-fluorobenzene)sulfonyl]pyrrolidine-2-carboxylic acid (150.00 mg, 0.51 mmol, 1.00 equiv), DIEA (266.23 mg, 2.06 mmol, 4.00 equiv), HATU (293.72 mg, 0.77 mmol, 1.50 equiv), and [4-[5-(trifluoromethyl)pyridin-2-yl]pyridin-2-yl]methanamine hydrochloride (223.77 mg, 0.77 mmol, 1.50 equiv) in N,N-dimethylformamide (5 mL) was stirred for 12 h at room temperature. The reaction mixture was diluted with water, extracted with ethyl acetate, washed with brine, dried over anhydrous sodium sulfate, and concentrated under vacuum. The residue was purified by a silica gel column eluting with dichloromethane/methanol (20:1) to afford the title compound (78.2 mg, 29%) as a white solid.

$^1$H NMR (400 MHz, DMSO-$d_6$) δ 9.11 (s, 1H), 9.02-9.01 (m, 1H), 8.71 (d, J=4.8 Hz, 1H), 8.83-8.22 (m, 2H), 8.09-7.98 (m, 4H), 7.47-7.43 (m, 2H), 5.21 (d, J=52.8 Hz, 2H), 4.53-4.24 (m, 3H), 3.76-3.58 (m, 2H), 2.50-2.33 (m, 1H), 2.22-2.04 (m, 1H).

Example 132

Preparation of (2S,4R)-4-fluoro-1-[(4-fluorobenzene)sulfonyl]-N-([3-methoxy-1-[2-(trifluoromethyl)pyrimidin-5-yl]-1H-pyrazol-4-yl]methyl)pyrrolidine-2-carboxamide

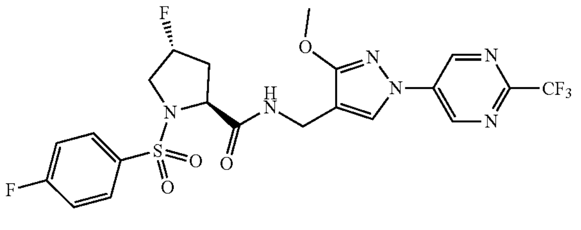 [SMILES: COc1nn(-c2cnc(C(F)(F)F)nc2)cc1CNC(=O)[C@@H]1C[C@@H](F)CN1S(=O)(=O)c1ccc(F)cc1]

Step 1: Preparation of 5-bromo-2-(trifluoromethyl)pyrimidine

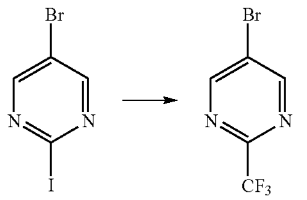 [SMILES: Brc1cnc(I)nc1 ; FC(F)(F)c1ncc(Br)cn1]

A mixture of 5-bromo-2-iodopyrimidine (10 g, 35.10 mmol, 1.00 equiv), trimethyl(trifluoromethyl)silane (20 g, 140.65 mmol, 4.00 equiv), KF (4.1 g, 70.57 mmol, 2.00 equiv), and CuI (13 g, 68.26 mmol, 2.00 equiv) in NMP (80 mL) was stirred overnight at 70° C. under nitrogen. The reaction was quenched by 200 mL of ammonia hydroxide, extracted with ethyl acetate, dried over anhydrous sodium sulfate, and concentrated under vacuum. The residue was purified by a silica gel column eluting with petroleum ether to afford the title compound 1.1 g (14%) of 5-bromo-2-(trifluoromethyl)pyrimidine as a light yellow solid.

Step 2: Preparation of ethyl 3-methoxy-1-[2-(trifluoromethyl)pyrimidin-5-yl]-1H-pyrazole-4-carboxylate

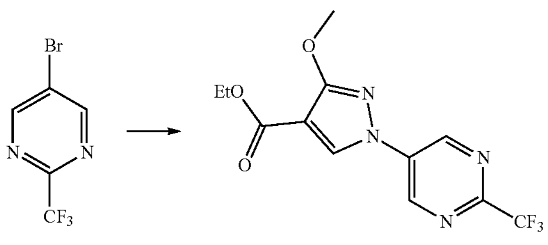 [SMILES: FC(F)(F)c1ncc(Br)cn1 ; CCOC(=O)c1cn(-c2cnc(C(F)(F)F)nc2)nc1OC]

A mixture of CuI (88 mg, 0.46 mmol, 0.10 equiv), L-proline (108 mg, 0.94 mmol, 0.20 equiv), potassium carbonate (1.3 g, 9.41 mmol, 2.00 equiv), ethyl 3-methoxy-1H-pyrazole-4-carboxylate (800 mg, 4.70 mmol, 1.00 equiv), and 5-bromo-2-(trifluoromethyl)pyrimidine (1.28 g, 5.64 mmol, 1.20 equiv) in DMSO (5 mL) was stirred overnight at 100° C. under nitrogen. The reaction mixture was diluted with 40 mL of water, extracted with ethyl acetate, dried over anhydrous sodium sulfate, and concentrated under vacuum. The residue was purified by a silica gel column eluting with ethyl acetate/petroleum ether (1:5) to afford the title compound (580 mg, 39%) as a white solid.

Step 3: Preparation of 3-methoxy-1-[2-(trifluoromethyl)pyrimidin-5-yl]-1H-pyrazole-4-carboxylic acid

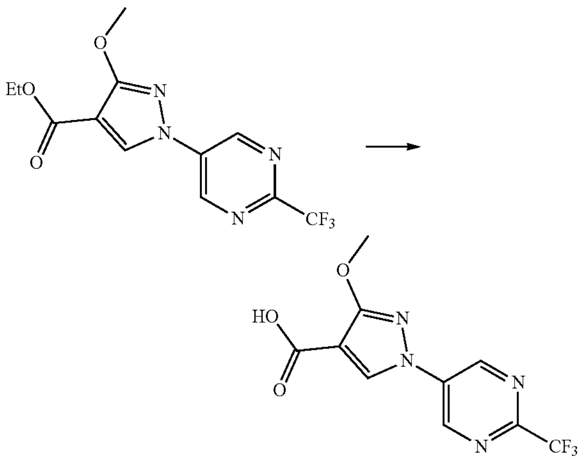

A mixture of ethyl 3-methoxy-1-[2-(trifluoromethyl)pyrimidin-5-yl]-1H-pyrazole-4-carboxylate (150 mg, 0.47 mmol, 1.0 equiv) and LiOH (22 mg, 0.92 mmol, 2.0 equiv) in THF (5 mL)/water (2 mL) was stirred for 2 h at 50° C. and diluted with 30 mL of water. The pH value of the solution was adjusted to 2 with diluted HCl. The resulting solution was extracted with ethyl acetate, dried over anhydrous sodium sulfate, and concentrated under vacuum. This resulted in the title compound (120 mg, 88%) as a white solid.

Step 4: Preparation of 3-methoxy-1-[2-(trifluoromethyl)pyrimidin-5-yl]-1H-pyrazole-4-carboxamide

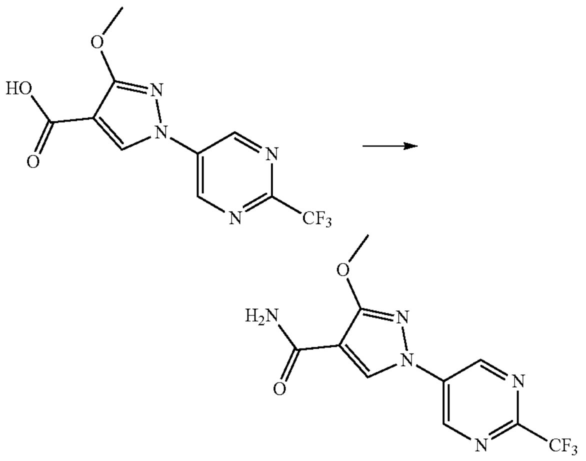

A mixture of 3-methoxy-1-[2-(trifluoromethyl)pyrimidin-5-yl]-1H-pyrazole-4-carboxylic acid (400 mg, 1.39 mmol, 1.0 equiv), HATU (792 mg, 2.08 mmol, 1.5 equiv), DIEA (540 mg, 4.18 mmol, 3.0 equiv), and $NH_4Cl$ (110 mg, 2.06 mmol, 1.5 equiv) in N,N-dimethylformamide (20 ml) was stirred for 1 h at room temperature. The reaction was diluted with 30 mL of water, extracted with ethyl acetate, dried over anhydrous sodium sulfate, and concentrated under vacuum. The residue was purified by a silica gel column eluting with ethyl acetate/petroleum ether (1:3). This resulted in the title compound (300 mg, 75%) as a white solid.

Step 5: Preparation of 3-methoxy-1-[4-(trifluoromethyl)phenyl]-1H-pyrazole-4-carbonitrile

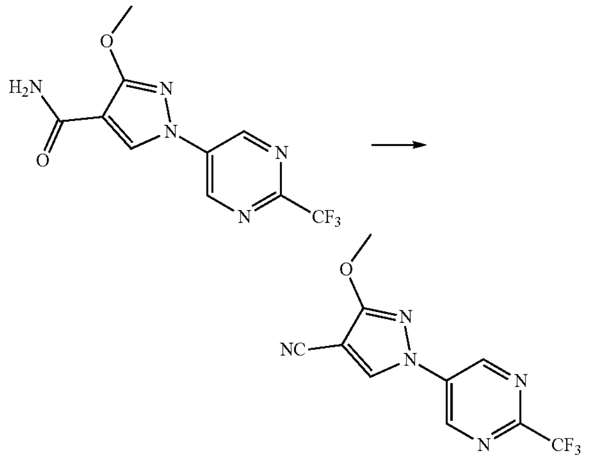

A mixture of 3-methoxy-1-[4-(trifluoromethyl)phenyl]-1H-pyrazole-4-carboxamide (300 mg, 1.05 mmol, 1.00 equiv), pyridine (347 mg, 4.39 mmol, 4.00 equiv), and $Tf_2O$ (620 mg, 2.20 mmol, 2.00 equiv) in dichloromethane (30 mL) was stirred for 2 h at room temperature. The reaction was diluted with 30 mL of water, extracted with dichloromethane, dried over anhydrous sodium sulfate, and concentrated under vacuum. This resulted in the title compound 170 mg (60%) as a brown solid.

Step 6: Preparation of (3-methoxy-1-(2-(trifluoromethyl)pyrimidin-5-yl)-1H-pyrazol-4-yl)methanamine hydrochloride

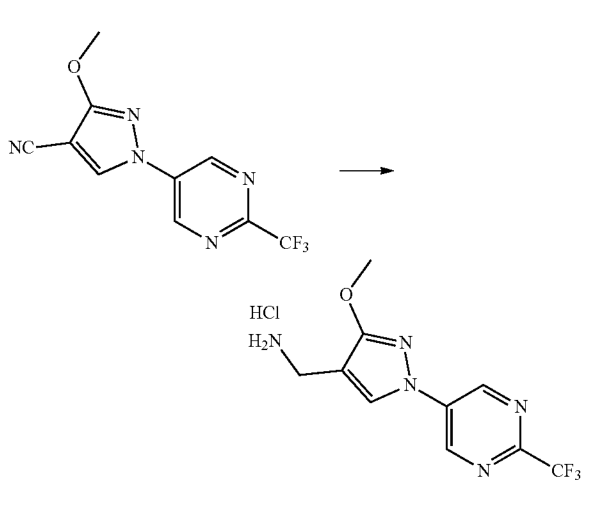

Into a 100-mL round-bottom flask purged and maintained with an inert atmosphere of $H_2$ was placed 3-methoxy-1-[2-(trifluoromethyl)pyrimidin-5-yl]-1H-pyrazole-4-carbonitrile (170 mg, 0.63 mmol, 1.00 equiv), methanol (30 mL), hydrogen chloride (0.5 mL, 13.71 mmol, 1.00 equiv), and palladium on carbon (40 mg, 0.38 mmol, 1.00 equiv). After 30 min at room temperature the solids were filtered out. The liquid was concentrated under vacuum to afford the title compound (120 mg, 70%) of as a light yellow solid.

Step 7: Preparation of (2S,4R)-4-fluoro-1-[(4-fluorobenzene)sulfonyl]-N-([3-methoxy-1-[2-(trifluoromethyl)pyrimidin-5-yl]-1H-pyrazol-4-yl]methyl) pyrrolidine-2-carboxamide

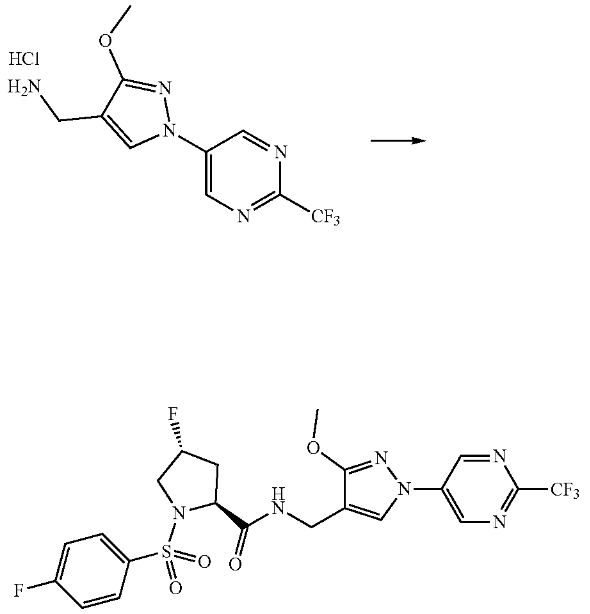

A mixture of (2S,4R)-4-fluoro-1-[(4-fluorobenzene) sulfonyl]pyrrolidine-2-carboxylic acid (253 mg, 0.87 mmol, 1.50 equiv), HATU (330 mg, 0.87 mmol, 1.50 equiv), and DIEA (224 mg, 1.73 mmol, 3.00 equiv) in N,N-dimethylformamide (3 mL) was stirred for 15 min at room temperature and then (3-methoxy-1-(2-(trifluoromethyl)pyrimidin-5-yl)-1H-pyrazol-4-yl)methanamine hydrochloride (160 mg, 0.59 mmol, 1.0 equiv) was added. The resulting solution was stirred overnight at room temperature, diluted with ethyl acetate, washed with brine, dried over anhydrous magnesium sulfate, and concentrated under vacuum. The crude product was purified by Pre-HPLC to afford the title compound 20 mg (6%) of as a white solid $^1H$ NMR (300 MHz, $CDCl_3$) δ 9.32 (s, 1H), 8.65-8.62 (m, 1H), 8.48 (s, 1H), 7.97-7.79 (m, 2H), 7.47-7.42 (m, 2H), 5.24-5.11 (d, J=52.4 Hz, 1H), 4.18-4.05 (m, 3H), 3.99 (s, 3H), 3.69-3.58 (m, 2H), 2.40-2.22 (m, 1H), 2.18-1.95 (m, 1H).

Example 133

Preparation of (2S,4R)—N-[[6-[4-(difluoromethyl)-1-bicyclo[2.2.2]octanyl]pyrimidin-4-yl]methyl]-4-fluoro-1-(4-fluorophenyl)sulfonyl-pyrrolidine-2-carboxamide

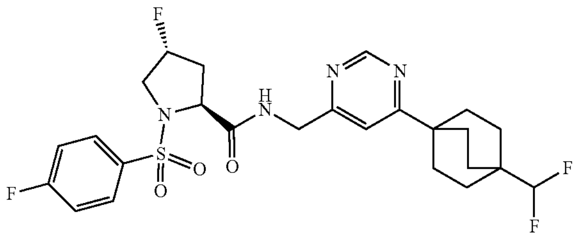 [SMILES: O=C(NCc1cc(C23CCC(C(F)F)(CC2)CC3)ncn1)[C@@H]1C[C@@H](F)CN1S(=O)(=O)c1ccc(F)cc1]

Step 1: Preparation of methyl 4-[2-acetyl-3-(tert-butoxy)-3-oxopropanoyl]bicyclo[2.2.2]octane-1-carboxylate

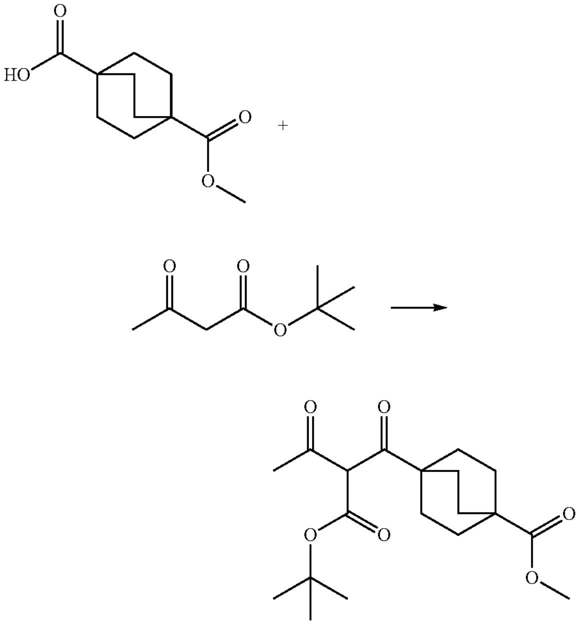

PrMgBr (71 mL, 575.75 mmol, 1M in THF, 1.50 equiv) was added dropwise into a solution of tert-butyl 3-oxobutanoate (11.2 g, 70.80 mmol, 1.50 equiv) in tetrahydrofuran (150 mL) at 0° C. under nitrogen. After 2 h at 0° C. the chloride (prepared by refluxing 4-(methoxycarbonyl)bicyclo[2.2.2]octane-1-carboxylic acid (10 g, 47.12 mmol, 1.00 equiv) in thionyl chloride (50 mL) for 3h) in 50 mL of THF at 0° C. The resulting solution was stirred for 12 h at room temperature. The reaction was then quenched by saturated solution of $NH_4Cl$, extracted with ethyl acetate, washed with brine, dried over anhydrous sodium sulfate, and concentrated under vacuum. This resulted in the title compound (10 g, crude) as yellow oil.

Step 2: Preparation of methyl 4-(3-oxobutanoyl)bicyclo[2.2.2]octane-1-carboxylate

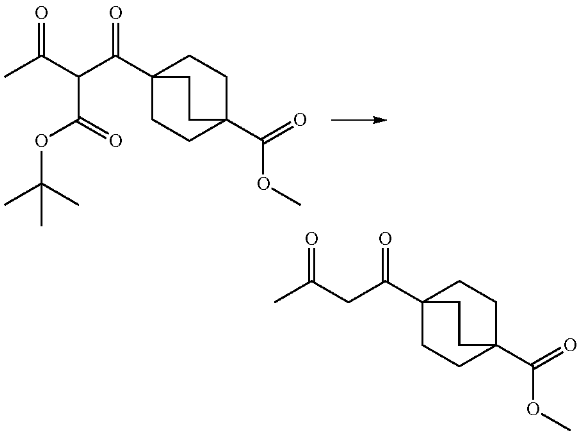

A solution of methyl 4-[2-acetyl-3-(tert-butoxy)-3-oxopropanoyl]bicyclo[2.2.2]octane-1-carboxylate (10 g, 28.38 mmol, 1.00 equiv) and 2,2,2-trifluoroacetaldehyde (20 mL) in DCM (100 mL) was stirred for 12 h at room temperature. The pH value of the solution was adjusted to 8 to 9 with sodium bicarbonate. The resulting solution was extracted with ethyl acetate. The combined extracts were washed with brine, dried over anhydrous sodium sulfate, and concentrated under vacuum. The residue was purified by a silica gel column eluting with ethyl acetate/petroleum ether (1/10) to afford the title compound (4.8 g, 67%) as a light yellow solid.

Step 3: Preparation of methyl 4-(6-methylpyrimidin-4-yl)bicyclo[2.2.2]octane-1-carboxylate

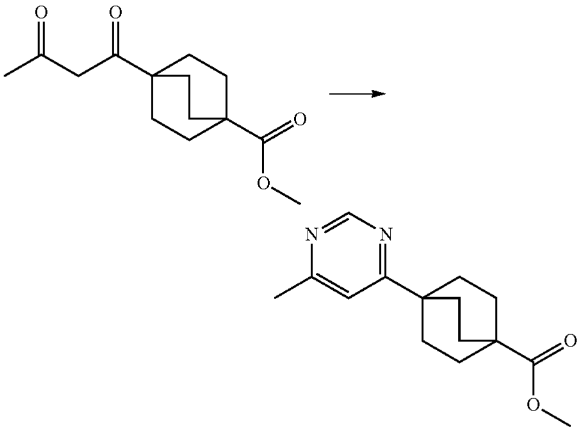

A solution of methyl 4-(3-oxobutanoyl)bicyclo[2.2.2]octane-1-carboxylate (4.8 g, 19.02 mmol, 1.00 equiv) in formamide (50 mL) was irradiated with microwave radiation for 3 h at 180° C. in 5 batches. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (1/20) to afford the title compound (1.5 g, 30%) as a light yellow solid.

Step 4: Preparation of [4-(6-methylpyrimidin-4-yl) bicyclo[2.2.2]octan-1-yl]methanol

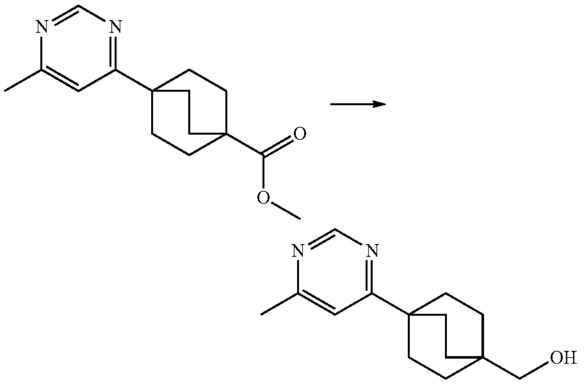

DIBAL-H (17 mL, 119.53 mmol, 1M in hexanes, 3.00 equiv) was added dropwise into a solution of methyl 4-(6-methylpyrimidin-4-yl)bicyclo[2.2.2]octane-1-carboxylate (1.5 g, 5.76 mmol, 1.00 equiv) in dichloromethane (150 mL) at −78° C. under nitrogen. The resulting solution was stirred for 3 h at −78° C. The reaction was then quenched by sodium hydroxide (1N). The solids were filtered out. The filtrate was dried over anhydrous sodium sulfate and concentrated under vacuum. This resulted in the title compound (1.1 g, 82%) as a white solid.

Step 5: Preparation of 4-(6-methylpyrimidin-4-yl) bicyclo[2.2.2]octane-1-carbaldehyde

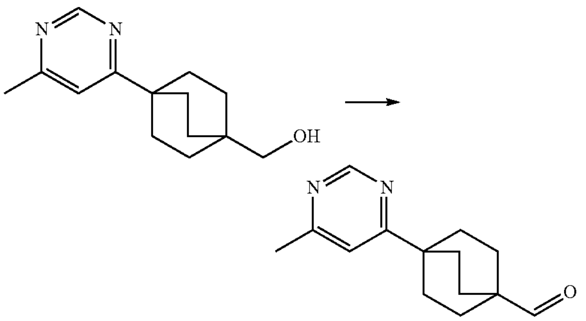

A mixture of [4-(6-methylpyrimidin-4-yl)bicyclo[2.2.2] octan-1-yl]methanol (1.1 g, 4.73 mmol, 1.00 equiv) and DMP (2.0 g, 4.72 mmol, 1.00 equiv) in dichloromethane (150 mL) was stirred for 1 h at room temperature. The solids were filtered out. The resulting solution was diluted with $CH_2Cl_2$, washed with saturated sodium bicarbonate and brine, dried over anhydrous sodium sulfate, and concentrated under vacuum. The residue was purified by a silica gel column eluting with ethyl acetate/petroleum ether (1/10) to afford the title compound (875 mg, 80%) as a light yellow solid.

Step 6: Preparation of 4-[4-(difluoromethyl)bicyclo [2.2.2]octan-1-yl]-6-methylpyrimidine

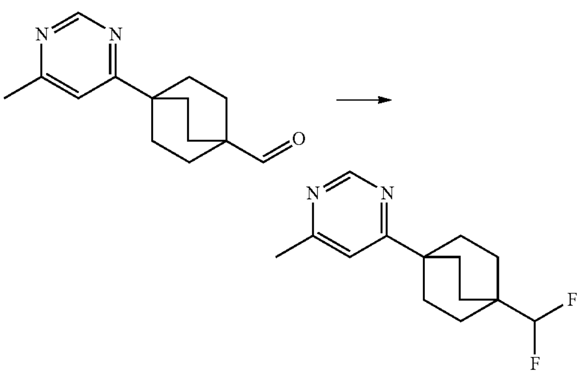

DAST (8.67 g, 37.86 mmol, 10.00 equiv) was added dropwise into a solution of 4-(6-methylpyrimidin-4-yl)bicyclo[2.2.2]octane-1-carbaldehyde (875 mg, 3.80 mmol, 1.00 equiv) in dichloromethane (200 mL) at −78° C. under nitrogen. The resulting solution was stirred for 12 h at room temperature. The reaction was then quenched by saturated sodium bicarbonate and extracted with ethyl acetate. The combined extracts were washed with brine, dried over anhydrous sodium sulfate, and concentrated under vacuum. The residue was purified by a silica gel column eluting with ethyl acetate/petroleum ether (1/4) to afford the title compound (750 mg, 78%) as a light yellow solid.

Step 7: Preparation of 4-(bromomethyl)-6-[4-(difluoromethyl)bicyclo[2.2.2]octan-1-yl]pyrimidine

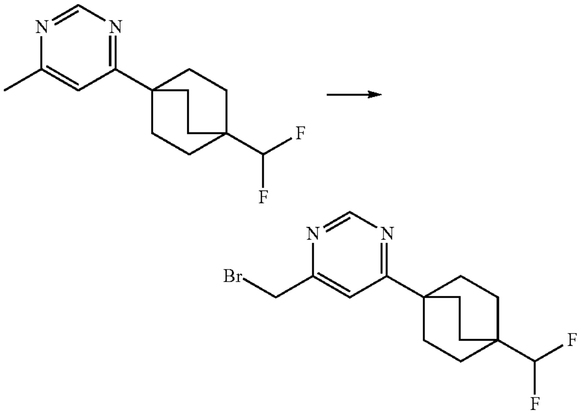

BPO (152 mg, 0.59 mmol, 0.20 equiv) was added in portions into a mixture of 4-[4-(difluoromethyl)bicyclo [2.2.2]octan-1-yl]-6-methylpyrimidine (750 mg, 2.97 mmol, 1.00 equiv) and NBS (530 mg, 2.98 mmol, 1.00 equiv) in $CCl_4$ (50 mL) at room temperature under nitrogen. The resulting solution was heated to 80° C. After 6 h at 80° C. the reaction mixture was cooled to room temperature. The reaction mixture was then diluted with water and extracted with ethyl acetate. The combined extracts were washed with brine, dried over anhydrous sodium sulfate, and concentrated under vacuum. This resulted in the title compound (750 mg, crude) as yellow oil.

Step 8: Preparation of 2-([6-[4-(difluoromethyl) bicyclo[2.2.2]octan-1-yl]pyrimidin-4-yl]methyl)-2,3-dihydro-1H-isoindole-1,3-dione

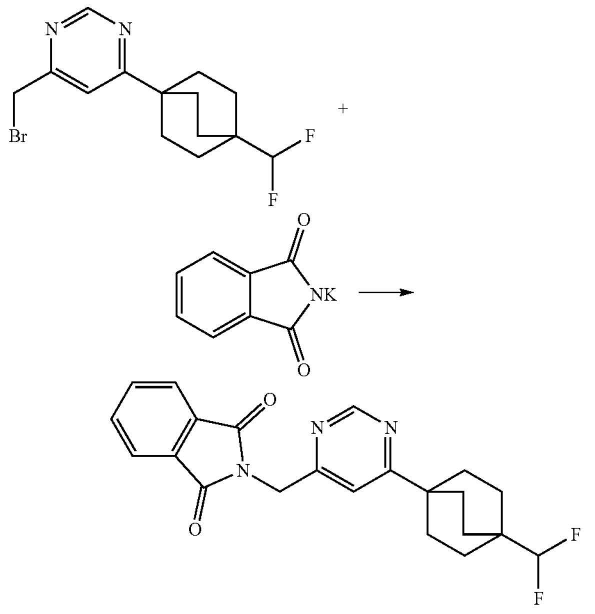

A mixture of 4-(bromomethyl)-6-[4-(difluoromethyl)bicyclo[2.2.2]octan-1-yl]pyrimidine (550 mg, 1.66 mmol, 1.00 equiv) and 2-potassium-2,3-dihydro-1H-isoindole-1,3-dione (307 mg, 1.66 mmol, 1.00 equiv) in N,N-dimethylformamide (5 mL) was stirred for 12 h at room temperature. The reaction mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/1) to afford the title compound (180 mg) as an off-white solid.

Step 9: Preparation of [6-[4-(difluoromethyl)bicyclo [2.2.2]octan-1-yl]pyrimidin-4-yl]methanamine

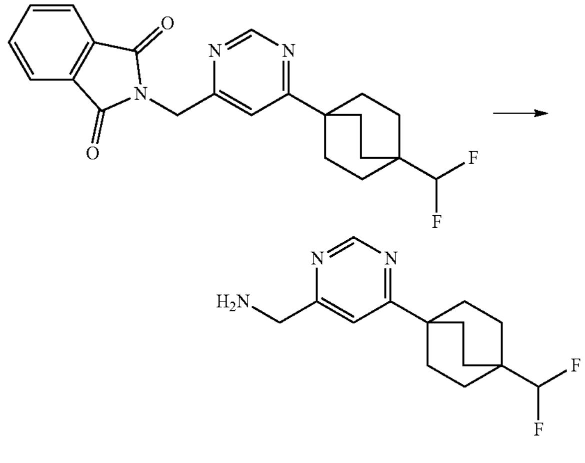

A mixture of 2-([6-[4-(difluoromethyl)bicyclo[2.2.2]octan-1-yl]pyrimidin-4-yl]methyl)-2,3-dihydro-1H-isoindole- 1,3-dione (180 mg, 0.45 mmol, 1.00 equiv) and hydrazine hydrate (227 mg, 4.53 mmol, 10.00 equiv) in methanol (10 mL) was stirred for 12 h at room temperature. The resulting mixture was concentrated under vacuum. The residue was dissolved in ethyl acetate. The solids were filtered out and the filtrate was concentrated under vacuum. This resulted in the title compound (100 mg, 83%) as a yellow solid which was used for the next step without any further purification.

Step 10: Preparation of (2S,4R)—N-[[6-[4-(difluoromethyl)-1-bicyclo[2.2.2]octanyl]pyrimidin-4-yl] methyl]-4-fluoro-1-(4-fluorophenyl)sulfonyl-pyrrolidine-2-carboxamide

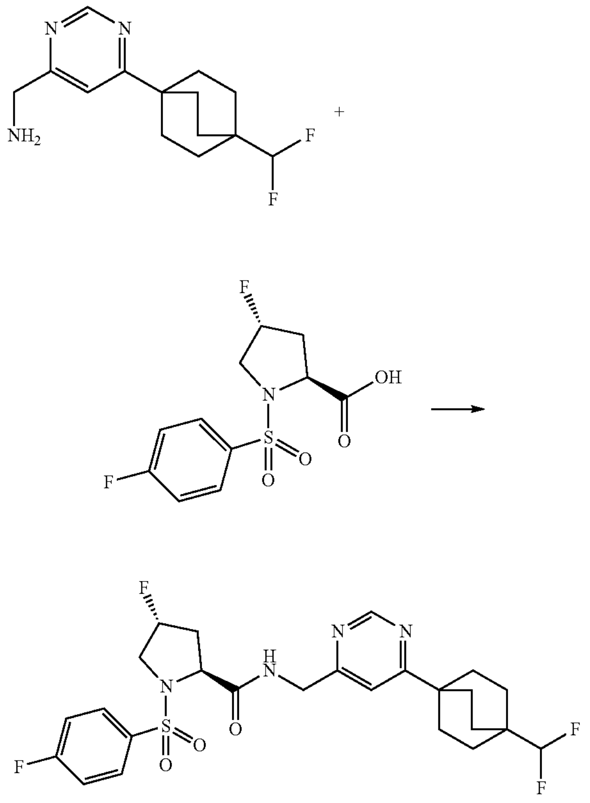

A solution of (2S,4R)-4-fluoro-1-[(4-fluorobenzene) sulfonyl]pyrrolidine-2-carboxylic acid (218 mg, 0.75 mmol, 2.00 equiv), DIEA (145 mg, 1.12 mmol, 3.00 equiv), HATU (285 mg, 0.75 mmol, 2.00 equiv), and [6-[4-(difluoromethyl)bicyclo[2.2.2]octan-1-yl]pyrimidin-4-yl]methanamine (100 mg, 0.37 mmol, 1.00 equiv) in N,N-dimethylformamide (3 mL) was stirred for 1 h at room temperature. The reaction mixture was diluted with water, extracted with ethyl acetate, washed with brine, dried over anhydrous sodium sulfate, and concentrated under vacuum. The crude product was purified by Prep-HPLC to afford the title compound (38.7 mg, 19%) as a white solid.

$^1$H NMR (300 MHz, $CD_3OD$) δ 8.95 (s, 1H), 8.04-8.00 (m, 2H), 7.72 (s, 1H), 7.39-7.34 (m, 2H), 5.67-5.29 (t, J=56.9 Hz, 1H), 5.23-5.05 (d, J=52.2 Hz, 1H), 4.59-4.46 (m, 2H), 4.28-4.25 (m, 1H), 3.84-3.70 (m, 2H), 2.52-2.11 (m, 2H), 2.04-1.94 (m, 6H), 1.68-1.63 (m, 6H).

Example 134

Preparation of (2S,4R)-4-fluoro-1-[(3-fluorobenzene)sulfonyl]-N-([3-methoxy-1-[4-(trifluoromethyl)phenyl]-1H-pyrazol-4-yl]methyl)pyrrolidine-2-carboxamide

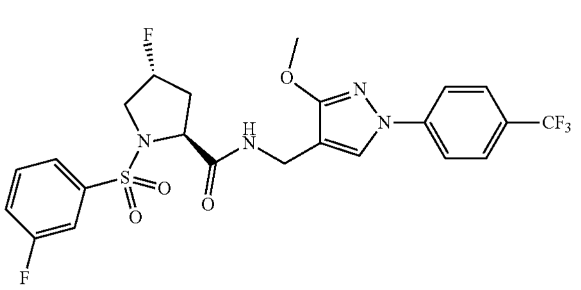 [SMILES: COc1nn(-c2ccc(C(F)(F)F)cc2)cc1CNC(=O)[C@@H]1C[C@@H](F)CN1S(=O)(=O)c1cccc(F)c1]

Step 1: Preparation of (2S,4R)-4-fluoro-1-[(3-fluorobenzene)sulfonyl]-N-([3-methoxy-1-[4-(trifluoromethyl)phenyl]-1H-pyrazol-4-yl]methyl)pyrrolidine-2-carboxamide

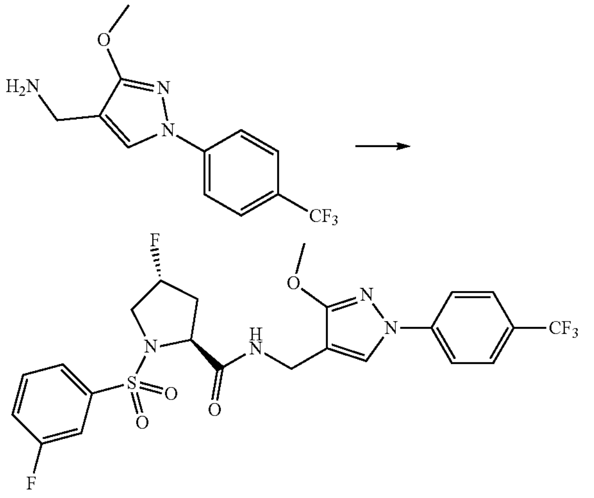

A mixture of (1S,4R)-4-fluoro-2-[(3-fluorobenzene)sulfonyl]cyclopentane-1-carboxylic acid (384 mg, 1.32 mmol, 1.50 equiv), HATU (501 mg, 1.32 mmol, 1.50 equiv), DIEA (227 mg, 1.76 mmol, 2.00 equiv), and [3-methoxy-1-[4-(trifluoromethyl)phenyl]-1H-pyrazol-4-yl]methanamine (240 mg, 0.88 mmol, 1.00 equiv) in N,N-dimethylformamide (20 mL) was stirred overnight at room temperature. The mixture was diluted with water, extracted with ethyl acetate. The combined extracts were washed with brine, dried over anhydrous sodium sulfate, and concentrated under vacuum. The crude product was purified by Prep-HPLC to afford the title compound (60.4 mg, 13%) as a light yellow solid.

$^1$H NMR (400 MHz, DMSO-$d_6$) δ 8.62-8.61 (m, 1H), 8.36 (s, 1H), 7.88-7.54 (m, 8H), 5.25-5.12 (d, J=52.4 Hz, 1H), 4.21-4.05 (m, 3H), 3.96 (s, 3H), 3.76-3.54 (m, 2H), 2.37-2.29 (m, 1H), 2.15-1.95 (m, 1H).

Example 135

Preparation of (2S,4R)-4-fluoro-1-[(4-fluorobenzene)sulfonyl]-N-([3-methoxy-1-[4-(trifluoromethyl)phenyl]-1H-pyrazol-4-yl]methyl)pyrrolidine-2-carboxamide

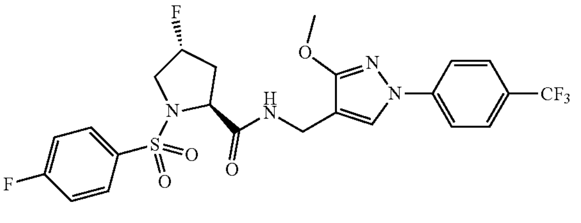 [SMILES: COc1nn(-c2ccc(C(F)(F)F)cc2)cc1CNC(=O)[C@@H]1C[C@@H](F)CN1S(=O)(=O)c1ccc(F)cc1]

Step 1: Preparation of 1-tert-butyl 4-ethyl 3-hydroxy-1H-pyrazole-1,4-dicarboxylate

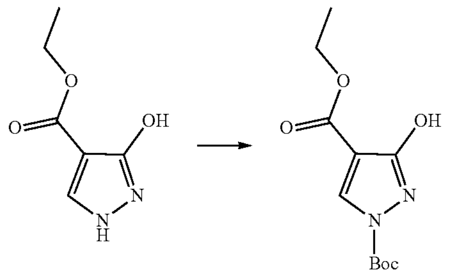 [SMILES: CCOC(=O)c1c[nH]nc1O ; CCOC(=O)c1cn(C(=O)OC(C)(C)C)nc1O]

A mixture of ethyl 3-hydroxy-1H-pyrazole-4-carboxylate (15 g, 96.07 mmol, 1.00 equiv), 4-dimethylaminopyridine (587 mg, 4.80 mmol, 0.05 equiv), triethylamine (29 g, 286.59 mmol, 3.00 equiv), and $Boc_2O$ (42 g, 192.4 mmol, 2.0 equiv) in tetrahydrofuran (180 mL) was stirred overnight at room temperature and concentrated under vacuum. The residue was purified by a silica gel column eluting with ethyl acetate/petroleum ether (1:3) to afford the title compound (20 g, 81%) as a white solid.

Step 2: Preparation of 1-tert-butyl 4-ethyl 3-methoxy-1H-pyrazole-1,4-dicarboxylate

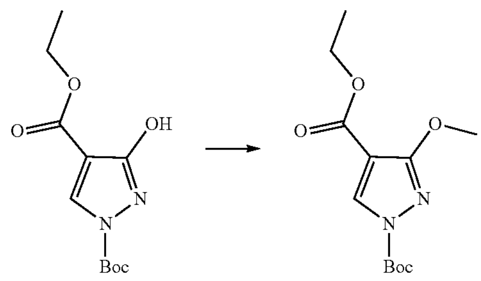 [SMILES: CCOC(=O)c1cn(C(=O)OC(C)(C)C)nc1O ; CCOC(=O)c1cn(C(=O)OC(C)(C)C)nc1OC]

Into a 250-mL round-bottom flask was placed 1-tert-butyl 4-ethyl 3-hydroxy-1H-pyrazole-1,4-dicarboxylate (1.8 g, 7.02 mmol, 1.00 equiv), $CH_3CN$ (60 mL, 1.14 mol, 100.00 equiv), and potassium carbonate (3.86 g, 27.93 mmol, 4.00 equiv). Iodomethane (3.0 g, 21.14 mmol, 3.0 equiv) was added dropwise at 0° C. After 3 h at room temperature the solid was filtered out. The liquid was concentrated under vacuum. The residue was purified by a silica gel column eluting with ethyl acetate/petroleum ether (1:1) to afford the title compound (600 mg, 32%) as colorless oil.

Step 3: Preparation of ethyl 3-methoxy-1H-pyrazole-4-carboxylate

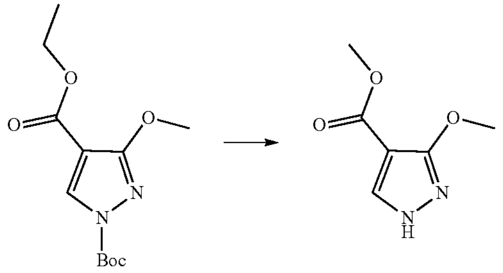 [SMILES: CCOC(=O)c1cn(C(=O)OC(C)(C)C)nc1OC ; COC(=O)c1c[nH]nc1OC]

A mixture of 1-tert-butyl 4-ethyl 3-methoxy-1H-pyrazole-1,4-dicarboxylate (16 g, 59.20 mmol, 1.00 equiv) and saturated hydrogen chloride in 1,4-dioxane (200 mL) was stirred for 5 h at room temperature and concentrated under vacuum. The resulting solution was diluted with 20 mL of water and the pH value of the solution was adjusted to 8 by sodium bicarbonate. The resulting solution was extracted with ethyl acetate, dried over anhydrous sodium sulfate, and concentrated under vacuum. This resulted in the title compound (7 g, 69%) as brown oil.

Step 4: Preparation of ethyl 3-methoxy-1-[4-(trifluoromethyl)phenyl]-1H-pyrazole-4-carboxylate

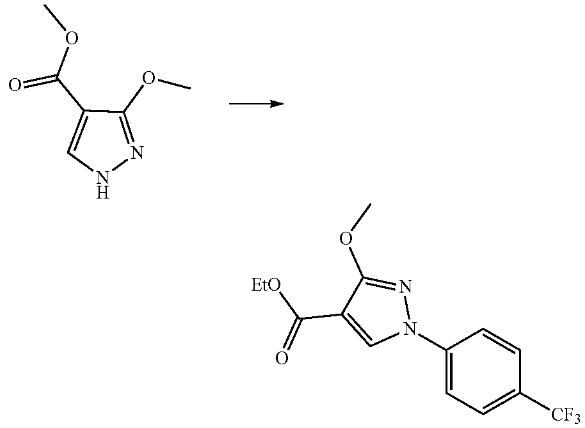

A mixture of CuI (95 mg, 0.50 mmol, 0.10 equiv), L-proline (115 mg, 1.00 mmol, 0.20 equiv), potassium carbonate (1.38 g, 9.99 mmol, 2.00 equiv), ethyl 3-methoxy-1H-pyrazole-4-carboxylate (850 mg, 5.00 mmol, 1.00 equiv), and 1-bromo-4-(trifluoromethyl)benzene (2.04 g, 7.50 mmol, 1.50 equiv) in DMSO (10 mL) was stirred overnight at 100° C. under nitrogen. The reaction was diluted with water, extracted with ethyl acetate, dried over anhydrous sodium sulfate, and concentrated under vacuum. This resulted in the title compound (1.06 g, 68%) as a white solid.

Step 5: Preparation of [3-methoxy-1-[4-(trifluoromethyl)phenyl]-1H-pyrazol-4-yl]methanol

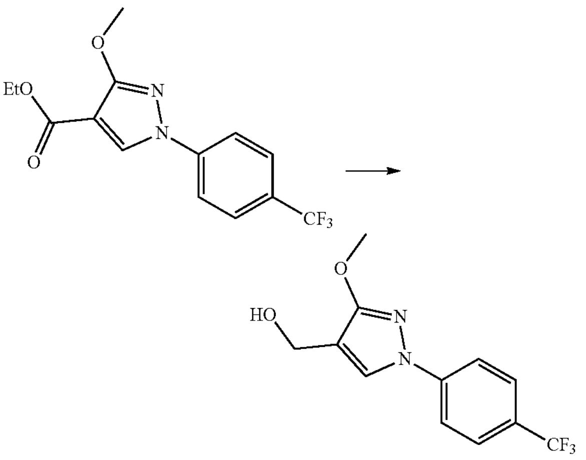

$LiAlH_4$ (385 mg, 10.14 mmol, 3.0 equiv) was added batch wise into a solution of ethyl 3-methoxy-1-[4-(trifluoromethyl)phenyl]-1H-pyrazole-4-carboxylate (1.06 g, 3.37 mmol, 1.00 equiv) in tetrahydrofuran (20 mL) at 0° C. under nitrogen. The resulting solution was stirred for 1.5 h at 0° C., quenched by water, extracted with ethyl acetate, dried over anhydrous sodium sulfate, and concentrated under vacuum. This resulted in the title compound (800 mg, 87%) as a light yellow solid.

Step 6: Preparation of 3-methoxy-1-[4-(trifluoromethyl)phenyl]-1H-pyrazole-4-carbaldehyde

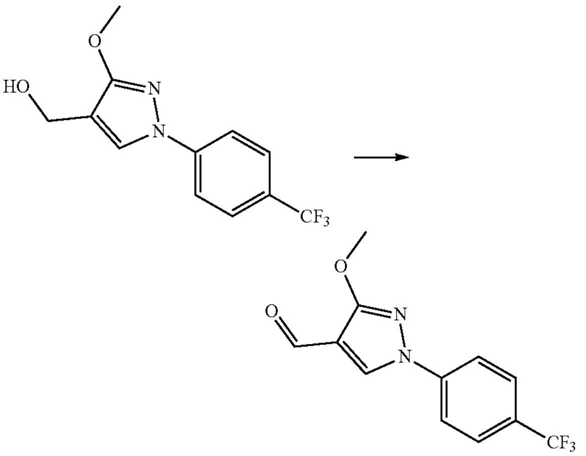

A solution of [3-methoxy-1-[4-(trifluoromethyl)phenyl]-1H-pyrazol-4-yl]methanol (580 mg, 2.13 mmol, 1.00 equiv) and PCC (916 mg, 4.25 mmol, 2.0 equiv) in dichloromethane (20 mL) was stirred for 3 h at room temperature and concentrated under vacuum. The residue was purified by a silica gel column eluting with ethyl acetate/petroleum ether (1:3) to afford the title compound (500 mg, 87%) as a light yellow solid.

Step 7: Preparation of (E)-N-([3-methoxy-1-[4-(trifluoromethyl)phenyl]-1H-pyrazol-4-yl]methylidene) hydroxylamine

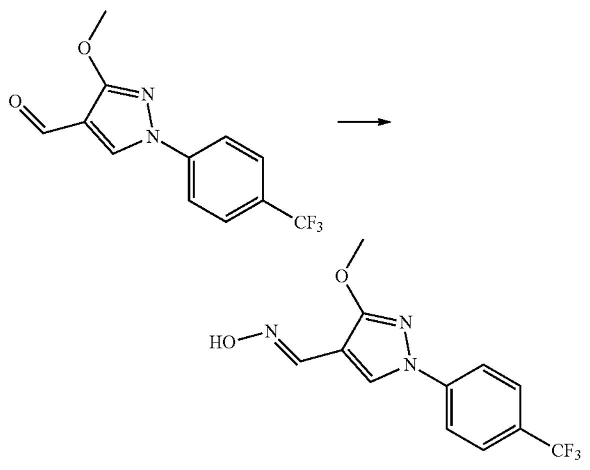

A mixture of 3-methoxy-1-[4-(trifluoromethyl)phenyl]-1H-pyrazole-4-carbaldehyde (500 mg, 1.85 mmol, 1.00 equiv), hydroxylamine hydrochloride (383 mg, 5.51 mmol, 3.00 equiv), and sodium acetate (759 mg, 9.25 mmol, 5.00 equiv) in ethanol (20 mL) was stirred for 40 min at room temperature and concentrated under vacuum. The residue was diluted with water, extracted with ethyl acetate, dried over anhydrous sodium sulfate, and concentrated under vacuum. This resulted in the title compound (520 mg, 99%) as a yellow solid.

Step 8: Preparation of [3-methoxy-1-[4-(trifluoromethyl)phenyl]-1H-pyrazol-4-yl]methanamine

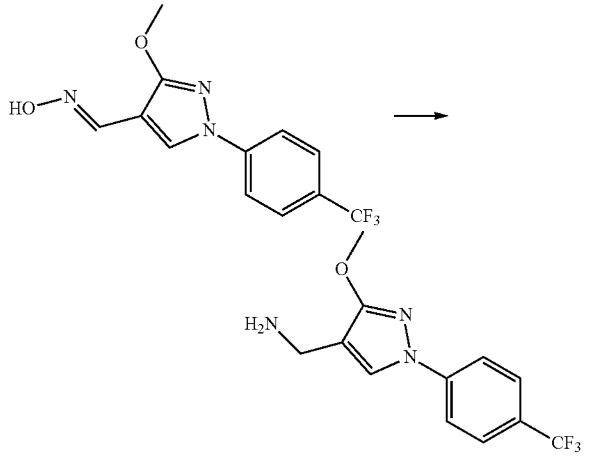

Into a 250-mL round-bottom flask purged and maintained with an atmosphere of $H_2$ was placed Raney Ni (50 mg, 0.58 mmol, 1.00 equiv), methanol (10 mL), and (E)-N-([3-methoxy-1-[4-(trifluoromethyl)phenyl]-1H-pyrazol-4-yl] methylidene)hydroxylamine (520 mg, 1.82 mmol, 1.00 equiv). After 30 min at room temperature the solids were filtered out. The liquid was concentrated under vacuum to afford the title compound (480 mg) as a greenish solid.

Step 9: Preparation of (2S,4R)-4-fluoro-1-[(4-fluorobenzene)sulfonyl]-N-([3-methoxy-1-[4-(trifluoromethyl)phenyl]-1H-pyrazol-4-yl]methyl)pyrrolidine-2-carboxamide

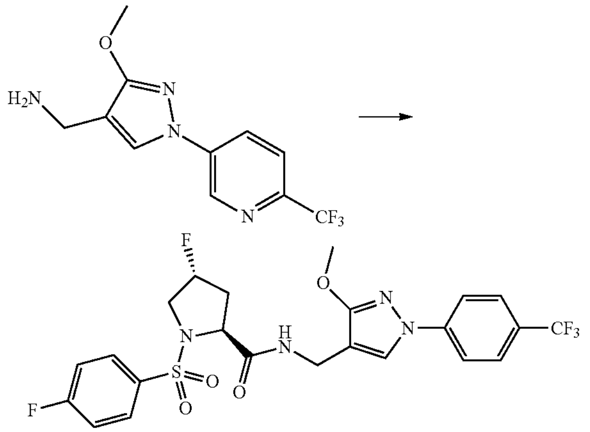

A mixture of (2S,4R)-4-fluoro-1-[(4-fluorobenzene) sulfonyl]pyrrolidine-2-carboxylic acid (384 mg, 1.32 mmol, 1.50 equiv), HATU (501 mg, 1.32 mmol, 1.50 equiv), DIEA (227 mg, 1.76 mmol, 2.00 equiv), and [3-methoxy-1-[4-(trifluoromethyl)phenyl]-1H-pyrazol-4-yl]methanamine (240 mg, 0.88 mmol, 1.00 equiv) in N,N-dimethylformamide (20 mL) was stirred overnight at room temperature. The reaction was diluted with 20 mL of water, extracted with ethyl acetate, dried over anhydrous sodium sulfate, and concentrated under vacuum. The residue was purified by a silica gel column eluting with ethyl acetate/petroleum ether (1:6). The crude product was purified by Prep-HPLC to afford the title compound (53.8 mg, 11%) as a white solid.

$^1$H NMR (300 MHz, $CDCl_3$) δ 8.61-8.58 (m, 1H), 8.35 (s, 1H), 7.98-7.94 (m, 2H), 7.87-7.80 (m, 4H), 7.47-7.42 (m, 2H), 5.24-5.11 (d, J=52.8 Hz, 1H), 4.16-4.05 (m, 3H), 3.96 (s, 3H), 3.68-3.55 (m, 2H), 2.38-2.28 (m, 1H), 2.15-1.90 (m, 1H).

Example 136

Preparation of (2R,3S)-3-fluoro-1-(4-fluorophenylsulfonyl)-N-((6-(6-(trifluoromethyl)pyridin-3-yl) pyrimidin-4-yl)methyl)pyrrolidine-2-carboxamide Step 1: Preparation of tert-butyl (2S,3R)-3-hydroxy-2-[([6-[6-(trifluoromethyl)pyridin-3-yl]pyrimidin-4-yl]methyl)carbamoyl]pyrrolidine-1-carboxylate

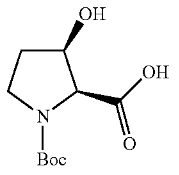

+

-continued

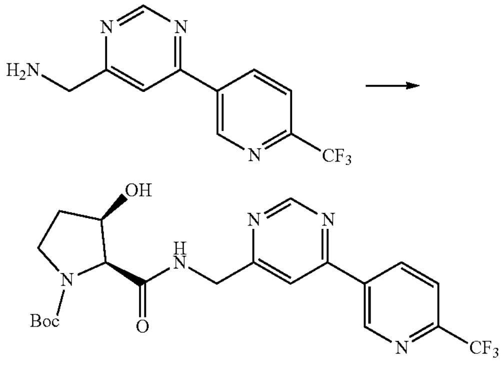

A mixture of (2S,3R)-1-[(tert-butoxy)carbonyl]-3-hydroxypyrrolidine-2-carboxylic acid (200 mg, 0.86 mmol, 1.00 equiv), DMF (10 mL), HATU (493.6 mg, 1.30 mmol, 1.50 equiv), DIEA (446.9 mg, 3.46 mmol, 4.00 equiv), [6-[6-(trifluoromethyl)pyridin-3-yl]pyrimidin-4-yl]methanamine hydrochloride (302.3 mg, 1.04 mmol, 1.20 equiv) was stirred for 3 h at room temperature. The reaction was then quenched by the addition of water, extracted with ethyl acetate. The organic layers combined, washed with water and brine, dried over anhydrous sodium sulfate and concentrated to afford the title compound 400 mg (99%) as orange oil.

Step 2: Preparation of tert-butyl (2R,3S)-3-fluoro-2-[([6-[6-(trifluoromethyl)pyridin-3-yl]pyrimidin-4-yl]methyl)carbamoyl]pyrrolidine-1-carboxylate

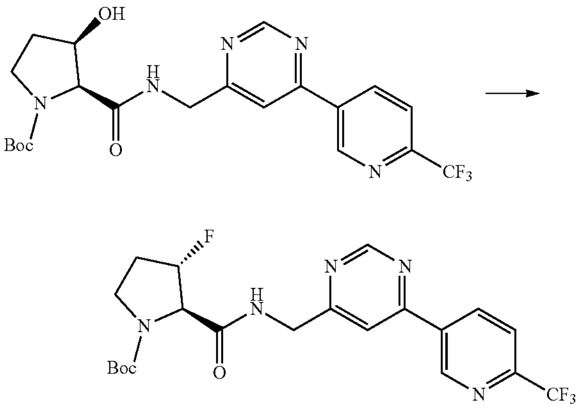

DAST (204 mg, 0.89 mmol, 3.00 equiv) was added dropwise into a solution of tert-butyl(2S,3R)-3-hydroxy-2-[([6-[6-(trifluoromethyl)pyridin-3-yl]pyrimidin-4-yl]methyl)carbamoyl]pyrrolidine-1-carboxylate (200 mg, 0.43 mmol, 1.00 equiv) in 10 mL of DCM at 0° C. The resulting solution was stirred for an additional 30 min at room temperature, quenched by the addition of water, extracted with ethyl acetate. The organic layers combined, dried over anhydrous sodium sulfate and concentrated. The residue was applied onto a silica gel column with dichloromethane/methanol (40:1) to afford the title compound 85 mg (42%) as a orange solid.

Step 3: Preparation of (2R,3S)-3-fluoro-N-([6-[6-(trifluoromethyl)pyridin-3-yl]pyrimidin-4-yl]methyl)pyrrolidine-2-carboxamide hydrochloride

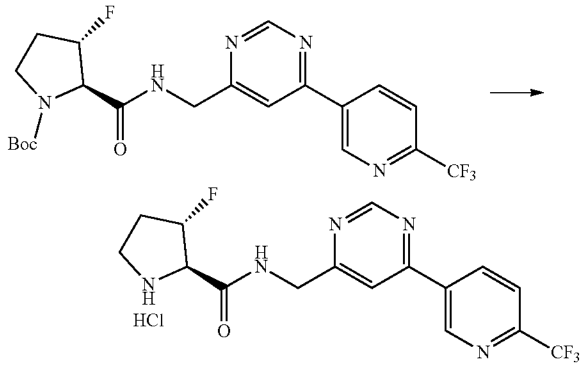

A mixture of tert-butyl (2R,3S)-3-fluoro-2-[([6-[6-(trifluoromethyl)pyridin-3-yl]pyrimidin-4-yl]methyl)carbamoyl]pyrrolidine-1-carboxylate (85 mg, 0.18 mmol, 1.00 equiv), HCl in dioxane (10 mL, 1 mol/L) was stirred for 3 h at room temperature. The resulting solution was diluted with ethyl acetate. The solids were collected by filtration to afford the title compound 70 mg (95%) as a orange solid.

Step 4: Preparation of (2R,3S)-3-fluoro-1-[(4-fluorobenzene)sulfonyl]-N-([6-[6-(trifluoromethyl)pyridin-3-yl]pyrimidin-4-yl]methyl)pyrrolidine-2-carboxamide

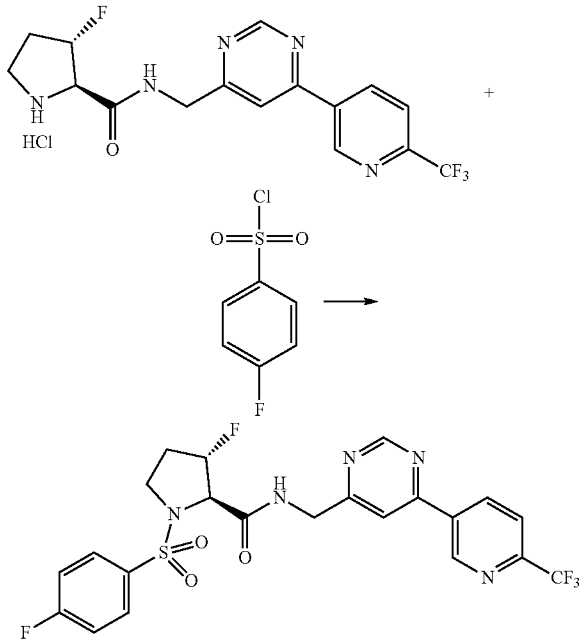

A mixture of (2R,3S)-3-fluoro-N-([6-[6-(trifluoromethyl)pyridin-3-yl]pyrimidin-4-yl]methyl)pyrrolidine-2-carboxamide hydrochloride (70 mg, 0.17 mmol, 1.00 equiv), TEA (51.5 mg, 0.51 mmol, 3.00 equiv), 4-fluorobenzene-1-sulfonyl chloride (39.6 mg, 0.20 mmol, 1.10 equiv), 4-dimethylaminopyridine (2.1 mg, 0.02 mmol, 0.10 equiv) in DCM (3 mL) was stirred for 3 h at room temperature. The reaction was quenched by the addition of water, extracted with ethyl acetate. The organic layers combined, dried over anhydrous sodium sulfate and concentrated. The residue was applied onto a silica gel column with ethyl acetate/petroleum ether (1:1) to afford the title compound 40 mg (44%) as a light yellow solid. NMR (400 MHz, $CDCl_3$) δ 9.49 (s, 1H), 9.28 (s, 1H), 8.70-8.68 (d, J=8.4 Hz, 1H), 7.99 (s, 1H), 7.94-7.91 (m, 2H), 7.84-7.80 (m, 2H), 7.31-7.27 (t, J=8.4 Hz, 2H), 5.38-5.26 (d, J=48 Hz, 1H), 4.96-4.90 (m, 1H), 4.59-4.53 (m, 1H), 4.43-4.38 (d, J=22.4 Hz, 1H), 3.86-3.81 (t, J=8.8 Hz 1H), 3.34-3.27 (m, 1H), 2.26-2.03 (m, 2H).

Example 137

Preparation of (2S,4R)—N-([3-chloro-1-[4-(trifluoromethyl)phenyl]-1H-pyrazol-4-yl]methyl)-4-fluoro-1-[(4-fluorobenzene)sulfonyl]pyrrolidine-2-carboxamide

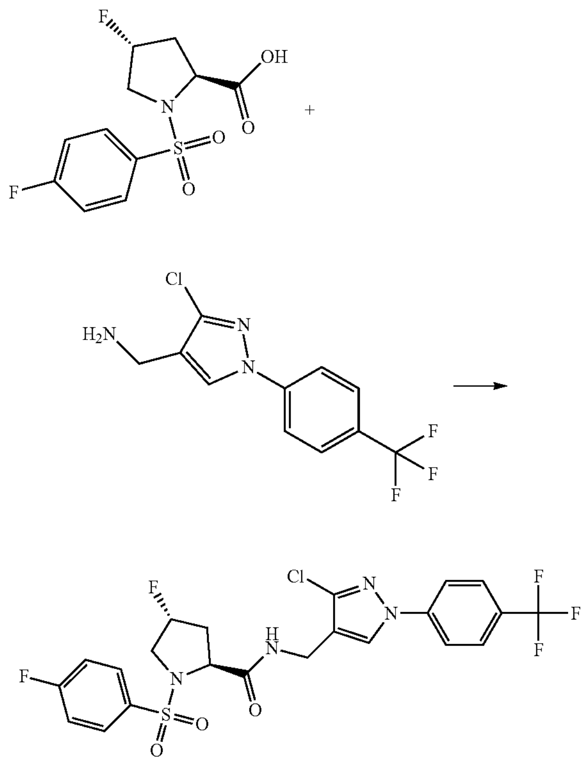

A mixture of (2S,4R)-4-fluoro-1-[(4-fluorobenzene)sulfonyl]-pyrrolidine-2-carboxylic acid (100 mg, 0.34 mmol), DMF (2 mL), DIPEA (132 mg, 1.02 mmol), HATU (194 mg, 0.51 mmol) and [3-chloro-1-[4-(trifluoromethyl)phenyl]-1H-pyrazol-4-yl]methanamine (187 mg, 0.68 mmol) was stirred for 2 h at room temperature. The reaction mixture was purified directly by Prep-HPLC to afford the title compound (38 mg, 20%) as a white solid. $^1H$ NMR (400 MHz, $CD_3OD$) •8.45 (s, 1H), 8.00-7.79 (m, 6H), 7.42-7.31 (m, 2H), 5.14 (d, J=52 Hz, 1H), 4.37 (s, 2H), 4.30-4.19 (m, 1H), 3.87-3.69 (m, 3H), 2.52-2.43 (m, 1H), 2.25-2.08 (m, 1H).

Example 138

Preparation of (2S,4R)-4-fluoro-1-(4-fluorophenylsulfonyl)-2-methyl-N-((6-(4-(trifluoromethyl)phenyl)pyrimidin-4-yl)methyl)pyrrolidine-2-carboxamide

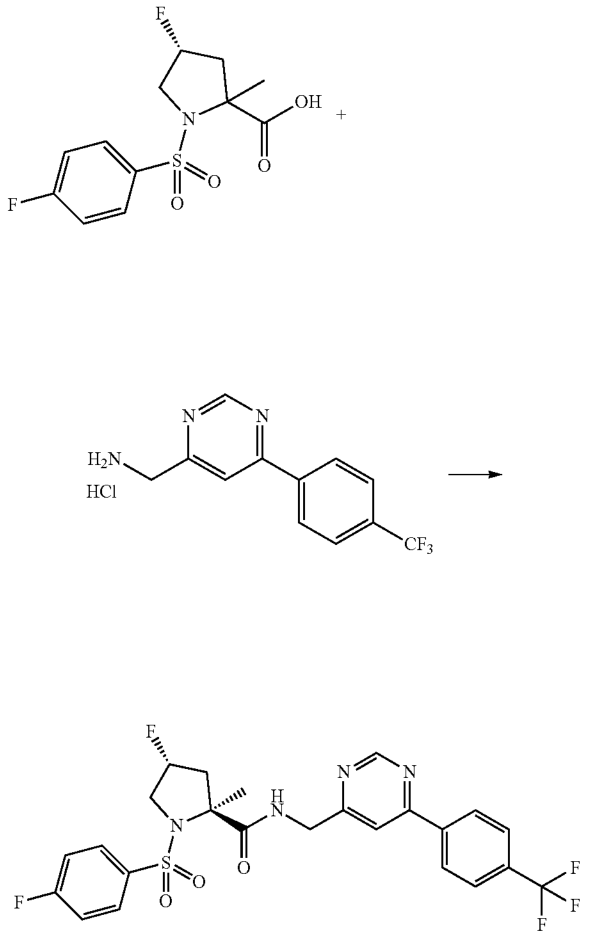

A mixture of (4R)-4-fluoro-1-[(4-fluorobenzene)sulfonyl]-2-methylpyrrolidine-2-carboxylic acid (125 mg, 0.41 mmol), DMF (4 mL), HATU (234 mg, 0.62 mmol), DIPEA (212 mg, 1.64 mmol) and [6-[4-(trifluoromethyl)phenyl]pyrimidin-4-yl]methanamine hydrochloride (106 mg, 0.37 mmol) was stirred for 12 h at room temperature. The mixture was diluted with water, extracted with EtOAc, washed with brine, dried over anhydrous $Na_2SO_4$ and concentrated. The residue was purified by flash chromatography on silica gel eluting with EtOAc/petroleum ether (1:1).

Faster eluting isomer (24.8 mg) assigned by potency SAR as (2S,4R)-4-fluoro-1-(4-fluorophenylsulfonyl)-2-methyl-N-((6-(4-(trifluoromethyl)phenyl)pyrimidin-4-yl)methyl)pyrrolidine-2-carboxamide: $^1H$ NMR (300 MHz, $CD_3OD$) δ 9.19 (d, J=1.2 Hz, 1H), 8.45 (d, J=7.8 Hz, 2H), 8.34 (s, 1H), 8.05-8.01 (m, 2H), 7.77 (d, J=8.4 Hz, 2H), 7.32 (t, J=8.7 Hz, 2H), 5.30 (d, J=51.9 Hz, 1H), 4.71-4.51 (m, 2H), 3.94-3.90 (m, 1H), 3.82 (d, J=2.4 Hz, 1H), 2.72-2.34 (m, 2H), 1.82 (s, 3H Example 139

(2S,4R)-4-fluoro-1-(4-fluorophenyl)sulfonyl-N-[[3-fluoro-5-[6-(trifluoromethyl)-3-pyridyl]phenyl]methyl]pyrrolidine-2-carboxamide

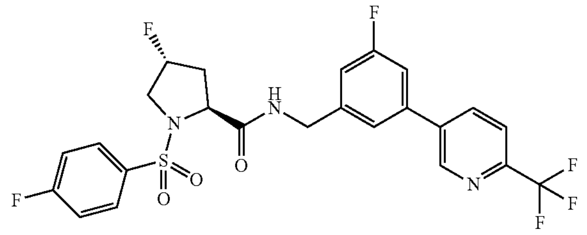 [SMILES: O=C(NCc1cc(F)cc(-c2ccc(C(F)(F)F)nc2)c1)[C@@H]1C[C@@H](F)CN1S(=O)(=O)c1ccc(F)cc1]

Step 1: Preparation of 3-fluoro-5-[6-(trifluoromethyl)pyridin-3-yl]benzonitrile

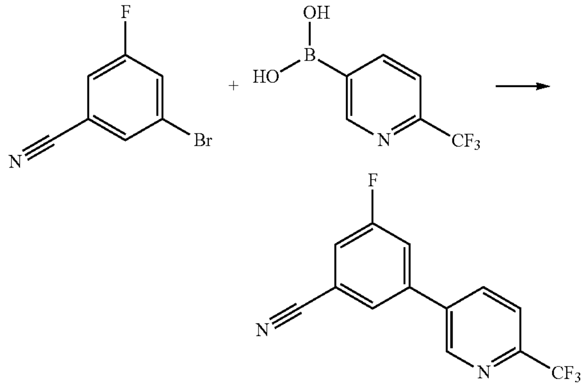

A mixture of 3-bromo-5-fluorobenzonitrile (10 g, 50.00 mmol, 1.00 equiv), [6-(trifluoromethyl)pyridin-3-yl]boronic acid (9.6 g, 50.28 mmol, 1.00 equiv), potassium carbonate (27.6 g, 199.70 mmol, 4.00 equiv), and $Pd(dppf)Cl_2$ (3.67 g, 5.02 mmol, 0.10 equiv) in dioxane (400 mL)/water(80 mL) was stirred overnight at 100° C. under nitrogen. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (10:100) to afford the title compound (11.4 g, 86%) as a light yellow solid.

Step 2: Preparation of [3-fluoro-5-[6-(trifluoromethyl)pyridin-3-yl]phenyl]methanamine hydrochloride

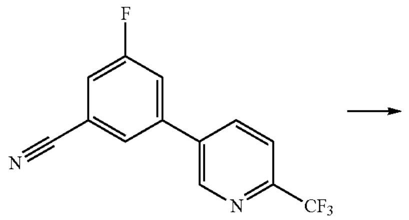

-continued

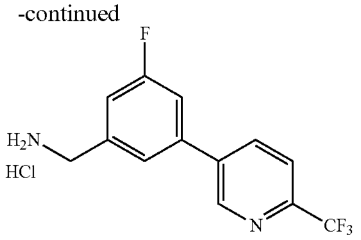

A mixture of 3-fluoro-5-[6-(trifluoromethyl)pyridin-3-yl]benzonitrile (3 g, 11.27 mmol, 1.00 equiv), palladium on carbon (1 g, 9.40 mmol, 0.80 equiv), and concentrated HCl (10 mL) in methanol (200 mL)/tetrahydrofuran (100 mL) was stirred for 1.5 h at room temperature under hydrogen. The solids were filtered out and the filtrate was concentrated under vacuum. This resulted in the title compound (4 g, crude) as a yellow solid.

Step 3: Preparation of (2S,4R)-4-fluoro-1-(4-fluorophenyl)sulfonyl-N-[[3-fluoro-5-[6-(trifluoromethyl)-3-pyridyl]phenyl]methyl]pyrrolidine-2-carboxamide

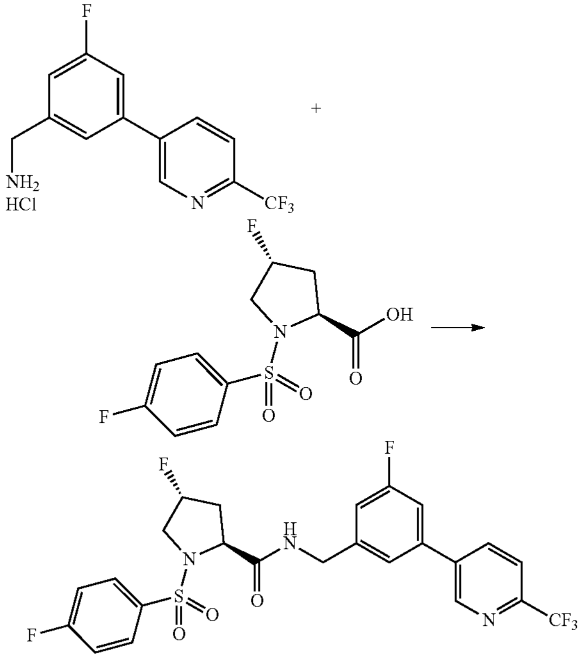

A mixture of [3-fluoro-5-[6-(trifluoromethyl)pyridin-3-yl]phenyl]methanamine hydrochloride (8 g, 26.09 mmol, 1.00 equiv), (2S,4R)-4-fluoro-1-[(4-fluorobenzene)sulfonyl]pyrrolidine-2-carboxylic acid (7.6 g, 26.09 mmol, 1.00 equiv), DIEA (34 g, 263.07 mmol, 10.10 equiv), and HATU (14.8 g, 38.92 mmol, 1.50 equiv) in N,N-dimethylformamide (300 mL) was stirred overnight at room temperature. The reaction mixture was diluted with water, extracted with ethyl acetate, washed with brine, dried over anhydrous sodium sulfate, and concentrated under vacuum. The residue was purified by a silica gel column eluting with ethyl acetate/petroleum ether (30:100) to afford the title compound (2.7672 g, 20%) as a white solid.

$^1H$ NMR (300 MHz, DMSO-$d_6$) δ 9.14 (s, 1H), 8.95-8.91 (m, 1H), 8.43-8.40 (m, 1H), 8.01-7.95 (m, 3H), 7.66-7.62

(m, 2H), 7.50-7.43 (m, 2H), 7.32-7.29 (m, 1H), 5.28-5.11 (m, 1H), 4.55-4.54 (m, 2H), 4.22-4.16 (m, 1H), 3.73-3.60 (m, 2H), 2.42-2.37 (m, 1H), 2.16-2.02 (m, 1H).

Example 140

Preparation of (2S,4R)-4-fluoro-N-((5'-fluoro-6-(trifluoromethyl)-3,4'-bipyridin-2'-yl)methyl)-1-(4-fluorophenylsulfonyl)pyrrolidine-2-carboxamide Step 1: Preparation of 2'-chloro-5'-fluoro-6-(trifluoromethyl)-3,4'-bipyridine

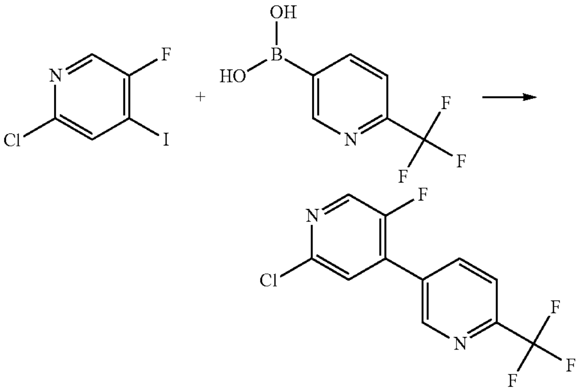

A mixture of 2-chloro-5-fluoro-4-iodopyridine (2.57 g, 9.98 mmol), [6-(trifluoromethyl)pyridin-3-yl]boronic acid (2.00 g, 10.48 mmol), $Pd(dppf)Cl_2.CH_2Cl_2$ (407.63 mg, 0.50 mmol), sodium carbonate (2.12 g, 20.00 mmol) in water (10 mL) and toluene (25 mL) was stirred for overnight at 90° C. under nitrogen. The reaction mixture was concentrated under reduced pressure, diluted with water, extracted with dichloromethane, and separated. The combined organic layers were washed with brine, dried ($Na_2SO_4$) and concentrated under reduced pressure. The residue was purified by flash chromatography on silica gel eluting with EtOAc/petroleum ether (1:5) to afford the title compound (2.31 g) as colorless oil.

Step 2: Preparation of 5'-fluoro-6-(trifluoromethyl)-3,4'-bipyridine-2'-carbonitrile

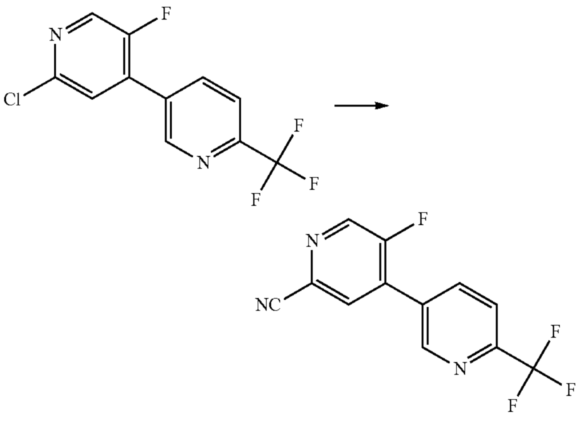

A mixture of 2-chloro-5-fluoro-4-[6-(trifluoromethyl)pyridin-3-yl]pyridine (1 g, 3.62 mmol), $Pd_2(dba)_3.CHCl_3$ (187 mg, 0.18 mmol), $Zn(CN)_2$ (254 mg, 2.16 mmol), DPPF (200 mg, 0.36 mmol), and Zn (24 mg, 0.37 mmol) in DMA (10 mL) was irradiated with microwave radiation for 1 h at 125° C. under nitrogen. The reaction was then quenched with water, extracted with EtOAc. The organic layers were combined and washed with brine, dried ($Na_2SO_4$) and concentrated under reduced pressure. The residue was purified by flash chromatography on silica gel eluting with EtOAc/petroleum ether (1:5) to afford the title compound (860 mg) as a yellow solid.

Step 3: Preparation of (5'-fluoro-6-(trifluoromethyl)-3,4'-bipyridin-2'-yl)methanamine

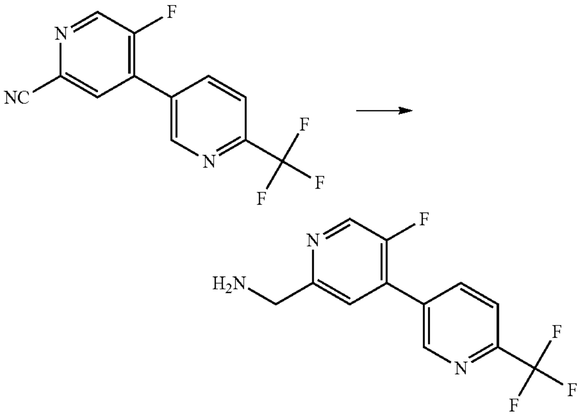

A mixture of 5-fluoro-4-[6-(trifluoromethyl)pyridin-3-yl]pyridine-2-carbonitrile (250 mg, 0.94 mmol), Raney Ni (100 mg, 1.17 mmol) in methanol (10 mL) was stirred for 1 h at room temperature under an atmosphere of hydrogen. The solids were filtered off and the filtrate was concentrated under reduced pressure to afford the crude title compound (250 mg) as brown oil, which was used in the next step without any further purification.

Step 4: Preparation of (2S,4R)-4-fluoro-N-((5'-fluoro-6-(trifluoromethyl)-3,4'-bipyridin-2'-yl)methyl)-1-(4-fluorophenylsulfonyl)pyrrolidine-2-carboxamide

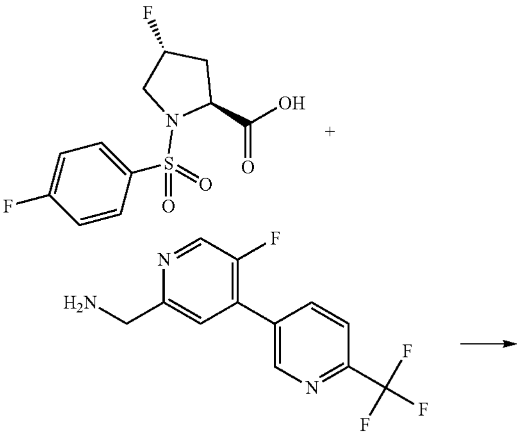

-continued

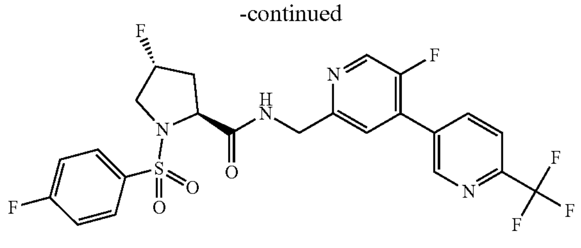

A mixture of [5-fluoro-4-[6-(trifluoromethyl)pyridin-3-yl]pyridin-2-yl]methanamine (141 mg, 0.52 mmol), HATU (231 mg, 0.61 mmol), DIPEA (157 mg, 1.21 mmol), (3R, 4R)-4-fluoro-1-[(4-fluorobenzene)sulfonyl]pyrrolidine-3-carboxylic acid (110 mg, 0.38 mmol) in DMF (5 mL) was stirred overnight at 25° C. The reaction mixture was quenched with water, extracted with $CH_2Cl_2$. The combined organic layers were washed with brine, dried ($Na_2SO_4$) and concentrated under reduced pressure. The residue was purified by Prep-HPLC to afford the title compound (32.4 mg) as a white solid. 1H NMR (300 MHz, $CD_3OD$) δ 9.41 (s, 1H), 8.72 (d, J=9.9 Hz, 2H), 8.58 (d, J=1.2 Hz, 1H), 8.28 (d, J=5.7 Hz, 1H), 8.04-7.99 (m, 2H), 7.86 (d, J=8.4 Hz, 1H), 7.37-7.31 (m, 2H), 5.16 (d, J=51.9 Hz, 1H), 4.74-4.56 (m, 2H), 4.33-4.27 (m, 1H), 3.86-3.67 (m, 2H), 2.54-2.52 (m, 1H), 2.30-2.12 (m, 1H).

Example 141

Preparation of (2S,4R)-4-fluoro-N-((5-fluoro-6'-(trifluoromethyl)-2,3'-bipyridin-4-yl)methyl)-1-(4-fluorophenylsulfonyl)pyrrolidine-2-carboxamide

Step 1: Preparation of 5-fluoro-6'-(trifluoromethyl)-2,3'-bipyridine-4-carbaldehyde

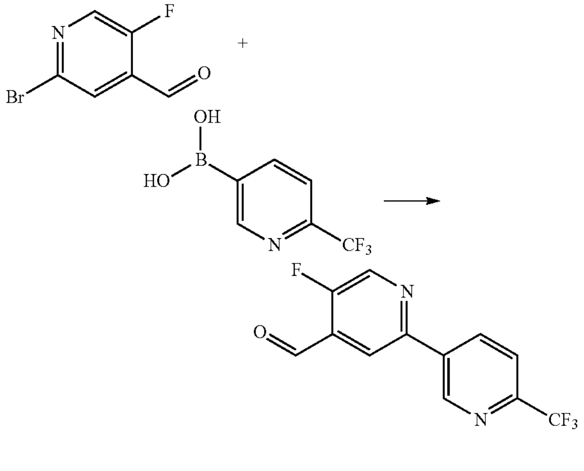

A mixture of 2-bromo-5-fluoropyridine-4-carbaldehyde (300 mg, 1.47 mmol), [6-(trifluoromethyl)pyridin-3-yl]boronic acid (420 mg, 2.20 mmol), $Pd(dppf)Cl_2.CH_2Cl_2$ (60 mg, 0.07 mmol), $Cs_2CO_3$ (1.44 g, 0.09 mmol) in water (2 mL) and 1,4-Dioxane (6 mL) was stirred overnight at 90° C. in an oil bath under nitrogen. The resulting mixture was quenched with water, extracted with $CH_2Cl_2$ and separated. The combined organic layers were washed with brine, dried ($Na_2SO_4$) and concentrated under reduce pressure. The residue was purified by flash chromatography on silica gel with EtOAc/petroleum ether (12:88) to afford the title compound (110 mg) as a light yellow solid.

Step 2: Preparation of (5-fluoro-6'-(trifluoromethyl)-2,3'-bipyridin-4-yl)methanamine

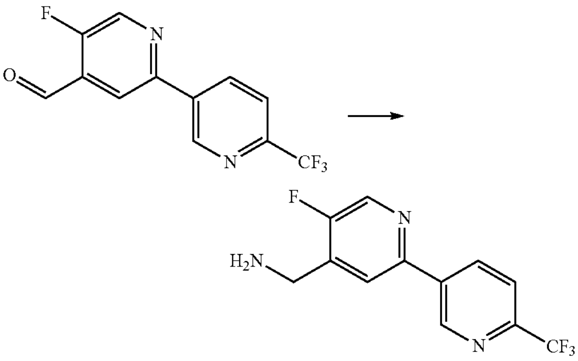

A mixture of 5-fluoro-2-[6-(trifluoromethyl)pyridin-3-yl]pyridine-4-carbaldehyde (363 mg, 1.34 mmol), $NH_2OH.HCl$ (187 mg, 2.69 mmol) in ethanol (15 mL) and water (3 mL) was stirred for 30 min at 25° C. Then concentrated HCl (0.08 mL, 36%), Pd/C (300 mg, 10%) was added and the reaction mixture was stirred for 50 min at 25° C. under an atmosphere of hydrogen gas. The solids were filtered off and the filtrate was concentrated under reduced pressure. The resulting mixture was diluted with $H_2O$, and adjusted to pH ~7-8 with 5 N $NaHCO_3$, extracted with EtOAc. The combined organic layers were washed with brine, dried ($Na_2SO_4$) and concentrated under reduced pressure to afford the crude title compound (300 mg) as yellow oil, which was used in the next step without any further purification.

Step 3: Preparation of (2S,4R)-4-fluoro-N-((5-fluoro-6'-(trifluoromethyl)-2,3'-bipyridin-4-yl)methyl)-1-(4-fluorophenylsulfonyl)pyrrolidine-2-carboxamide

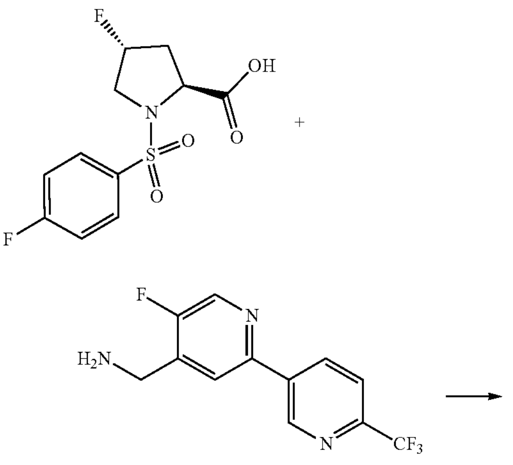

-continued

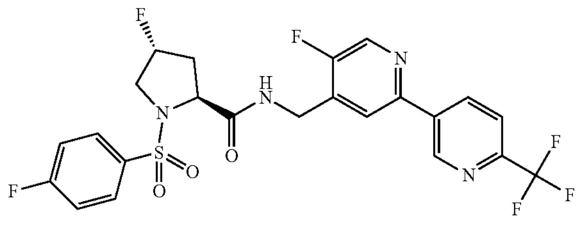

A mixture of (2S,4R)-4-fluoro-1-[(4-fluorobenzene)sulfonyl]pyrrolidine-2-carboxylic acid (129 mg, 0.44 mmol), HATU (169 mg, 0.44 mmol), DIPEA (143 mg, 1.11 mmol), [5-fluoro-2-[6-(trifluoromethyl)pyridin-3-yl]pyridin-4-yl]methanamine (100 mg, 0.37 mmol) in DMF (2 mL) was stirred for overnight at 25° C. The reaction mixture was quenched with water, extracted with dichloromethane. The combined organic layers were washed with brine, dried ($Na_2SO_4$) and concentrated under reduced pressure. The residue was purified by flash chromatography on silica gel eluting with EtOAc/petroleum ether (6:4). The crude product was recrystallized from methanol to afford the title compound (67 mg) as an off-white solid. 1H NMR (300 MHz, $CD_3OD$) δ 9.08 (s, 1H), 8.61 (d, J=3 Hz, 1H), 8.43 (d, J=6 Hz, 1H), 8.02-7.92 (m, 4H), 7.38-7.32 (m, 2H), 5.16 (d, J=54 Hz, 1H), 4.65 (s, 2H), 4.31-4.26 (m, 1H), 3.86-3.68 (m, 2H). 2.54-2.52 (m, 1H), 2.32-2.06 (m, 1H).

Example 142

Preparation of (2S,4R)-4-fluoro-1-(4-fluorophenylsulfonyl)-2-methyl-N-((6-(6-(trifluoromethyl)pyridin-3-yl)pyrimidin-4-yl)methyl)pyrrolidine-2-carboxamide

Step 1: Preparation of 1-tert-Butyl 2-methyl (2S,4R)-4-fluoropyrrolidine-1,2-dicarboxylate

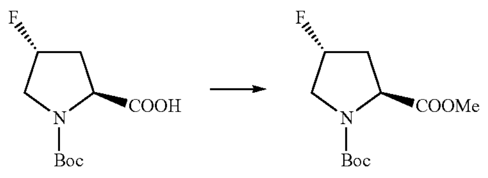 [SMILES: CC(C)(C)OC(=O)N1C[C@H](F)C[C@H]1C(=O)O ; COC(=O)[C@@H]1C[C@@H](F)CN1C(=O)OC(C)(C)C]

A mixture of (2S,4R)-1-[(tert-butoxy)carbonyl]-4-fluoropyrrolidine-2-carboxylic acid (2 g, 8.57 mmol), potassium carbonate (5.9 g, 42.69 mmol), THF (80 mL) and $CH_3I$ (6.1 g, 42.98 mmol) was stirred for 12 h at room temperature. The solids were filtered off and the filtrate was concentrated under reduced pressure. The residue was purified by flash chromatography on silica gel eluting with EtOAc/petroleum ether (1:5) to afford the title compound (800 mg, 38%) as colorless oil.

Step 2: Preparation of 1-tert-butyl 2-methyl (4R)-4-fluoro-2-methylpyrrolidine-1,2-dicarboxylate

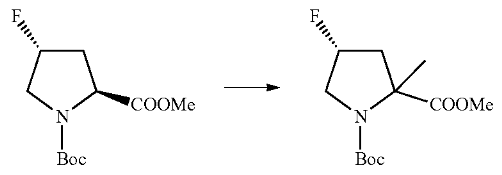 [SMILES: COC(=O)[C@@H]1C[C@@H](F)CN1C(=O)OC(C)(C)C ; COC(=O)C1(C)C[C@@H](F)CN1C(=O)OC(C)(C)C]

A 1 M solution of LiHMDS (4.85 mL, 4.85 mmol) was added dropwise into a mixture of 1-tert-butyl 2-methyl (2S,4R)-4-fluoropyrrolidine-1,2-dicarboxylate (400 mg, 1.62 mmol) in THF (20 mL) with stirring at −78° C. under nitrogen. The reaction solution was stirred for 30 min at −78° C. To this was added $CH_3I$ (690 mg, 4.86 mmol) dropwise at −78° C. The reaction mixture stirred for 12 h at room temperature, quenched with water, extracted with EtOAc, dried over anhydrous $Na_2SO_4$ and concentrated. The residue was purified by flash chromatography on silica gel eluting with EtOAc/petroleum ether (1:5) to afford the title compound (360 mg, 85%) as colorless oil.

Step 3: Preparation of 4R-4-fluoro-2-methylpyrrolidine-2-carboxylic acid hydrochloride

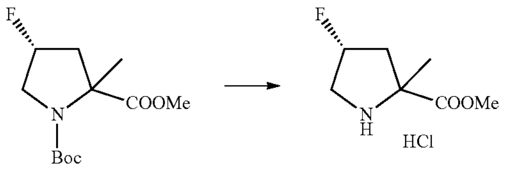 [SMILES: COC(=O)C1(C)C[C@@H](F)CN1C(=O)OC(C)(C)C ; COC(=O)C1(C)C[C@@H](F)CN1 ; Cl]

A mixture of 1-tert-butyl 2-methyl (4R)-4-fluoro-2-methylpyrrolidine-1,2-dicarboxylate (360 mg, 1.38 mmol) and HCl in dioxane (10 mL, 1 mol/L) was stirred for 2 h at room temperature. The mixture was concentrated to afford the crude product (315 mg) as a light yellow solid, which was used in the next step without any further purification.

Step 4: Preparation of methyl (4R)-4-fluoro-1-[(4-fluorobenzene)sulfonyl]-2-methylpyrrolidine-2-carboxylate

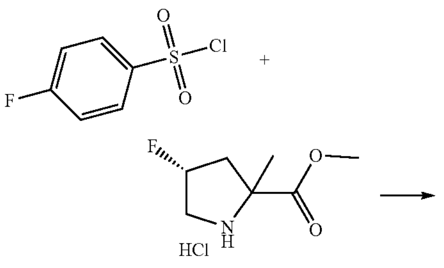

-continued

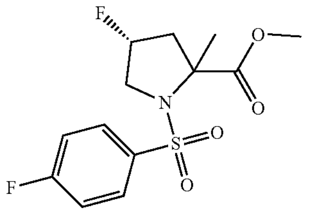

A mixture of 4R-4-fluoro-2-methylpyrrolidine-2-carboxylate hydrochloride (315 mg, 1.60 mmol), triethylamine (485 mg, 4.80 mmol), dichloromethane (20 mL) and 4-fluorobenzene-1-sulfonyl chloride (310 mg, 1.60 mmol) was stirred for 12 h at room temperature. The reaction was diluted with dichloromethane, washed with brine, dried over anhydrous $Na_2SO_4$ and concentrated. The residue was purified by flash chromatography on silica gel eluting with EtOAc/petroleum ether (1:4) to afford the title compound (380 mg) as colorless oil, which was used in the next step without any further purification.

Step 5: Preparation of (4R)-4-fluoro-1-[(4-fluorobenzene)sulfonyl]-2-methylpyrrolidine-2-carboxylic acid

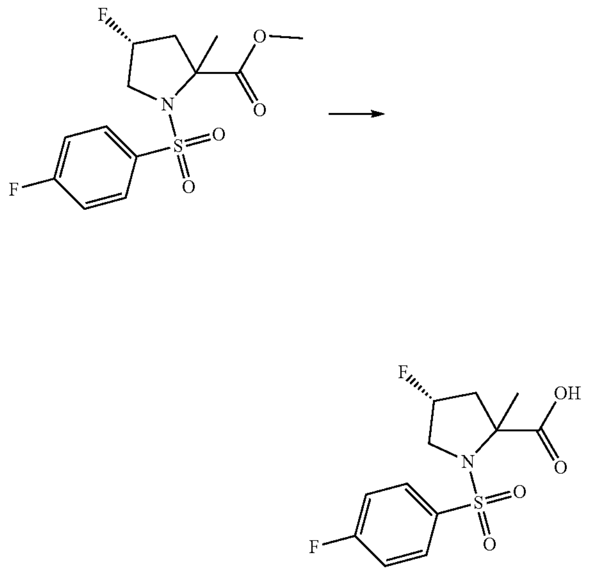

A mixture of methyl (4R)-4-fluoro-1-[(4-fluorobenzene) sulfonyl]-2-methylpyrrolidine-2-carboxylate (380 mg, 1.19 mmol), LiOH (58 mg, 2.42 mmol), methanol (8 mL), water (2 mL) was stirred for 12 h at room temperature. The reaction mixture was concentrated, dissolved in water, extracted with ether. The aqueous layers was acidified with 3 N HCl (pH 2-3), extracted with EtOAc, dried over anhydrous $Na_2SO_4$ and concentrated to afford the title compound (260 mg, 72%) as yellow oil, which was used in the next step without any further purification.

Step 6: (2S,4R)-4-fluoro-1-(4-fluorophenylsulfonyl)-2-methyl-N-((6-(6-(trifluoromethyl)pyridin-3-yl)pyrimidin-4-yl)methyl)pyrrolidine-2-carboxamide

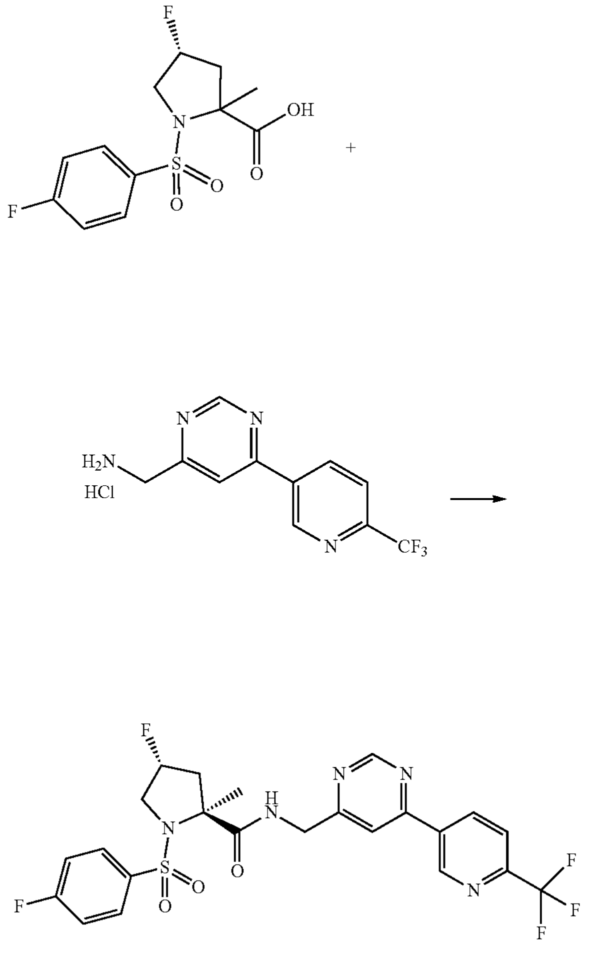

A mixture of (4R)-4-fluoro-1-[(4-fluorobenzene)sulfonyl]-2-methylpyrrolidine-2-carboxylic acid (125 mg, 0.41 mmol), DMF (4 mL), HATU (228 mg, 0.60 mmol), DIPEA (206 mg, 1.59 mmol) and [6-[6-(trifluoromethyl)pyridin-3-yl]pyrimidin-4-yl]methanamine hydrochloride (104 mg, 0.36 mmol) was stirred for 12 h at room temperature. The mixture was diluted with water, extracted with EtOAc. The combined organic layers were washed with brine, dried over anhydrous $Na_2SO_4$ and concentrated. The residue was purified by flash chromatography on silica gel eluting with EtOAc/petroleum ether (1:1 to 2:1).

Slower eluting isomer (72.7 mg) assigned by potency SAR as (2S,4R)-4-fluoro-1-(4-fluorophenylsulfonyl)-2-methyl-N-((6-(6-(trifluoromethyl)pyridin-3-yl)pyrimidin-4-yl)methyl)pyrrolidine-2-carboxamide: 1H NMR (300 MHz, $CD_3OD$) δ 9.50 (s, 1H), 9.20 (s, 1H), 8.83 (d, J=8.4 Hz, 1H), 8.31 (s, 1H), 8.06-7.98 (m, 3H), 7.37 (t, J=17.4 Hz, 2H), 5.26 (d, J=51 Hz, 1H), 4.80 (d, J=15 Hz, 1H), 4.54 (d, J=17.4 Hz, 1H), 4.19-4.07 (m, 1H), 3.76-3.60 (m, 1H), 2.76-2.64 (m, 1H), 2.33-2.14 (m, 1H), 1.61 (s, 3H).

Example 143

Preparation of (2S,4R)-4-fluoro-1-(4-fluorophenylsulfonyl)-N-((6-(4-(trifluoromethyl)phenyl)pyrimidin-4-yl)methyl)pyrrolidine-2-carboxamide

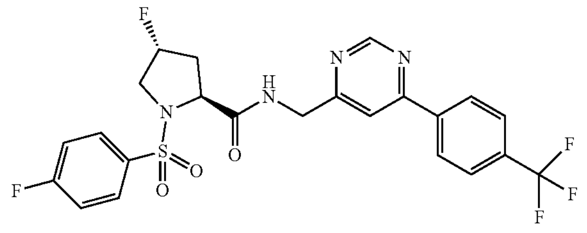 [SMILES: O=C(NCc1cc(-c2ccc(C(F)(F)F)cc2)ncn1)[C@@H]1C[C@@H](F)CN1S(=O)(=O)c1ccc(F)cc1]

The title compound was prepared by the procedures described in Example 198, step 1 using (2S,4R)-1-(tert-butoxycarbonyl)-4-fluoropyrrolidine-2-carboxylic acid and (6-(4-(trifluoromethyl)phenyl)pyrimidin-4-yl)methanamine (obtained following Example 145, steps 1, 2, 3, and standard deprotonation of the HCl salt) and Example 198, steps 2 and 3 (107 mg): 1H NMR (400 MHz, DMSO-$d_6$) δ 9.25 (s, 1H), 9.11 (t, J=5.7 Hz, 1H), 8.40 (d, J=8.1 Hz, 2H), 8.15 (s, 1H), 8.07-7.99 (m, 2H), 7.88 (d, J=8.1 Hz, 2H), 7.47 (t, J=8.6 Hz, 2H), 5.21 (d, J=52.4 Hz, 1H), 4.51 (d, J=5.8 Hz, 2H), 4.31-4.22 (m, 1H), 3.78-3.59 (m, 2H), 2.48-2.38 (m, 1H), 2.23-2.05 (m, 1H).

Example 144

Preparation of (2S,4R)-4-fluoro-N-((5-fluoro-4-(4-(trifluoromethyl)piperidin-1-yl)pyridin-2-yl)methyl)-1-(4-fluorophenylsulfonyl)pyrrolidine-2-carboxamide Step 1: Preparation of 2-chloro-5-fluoro-4-(4-(trifluoromethyl)piperidin-1-yl)pyridine

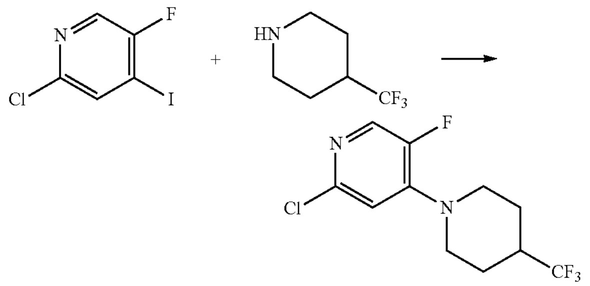

A mixture of 2-chloro-5-fluoro-4-iodopyridine (1.5 g, 5.83 mmol), 4-(trifluoromethyl)piperidine (890 mg, 5.81 mmol), $Pd_2(dba)_3.CHCl_3$ (300 mg, 0.29 mmol), BINAP (360 mg, 0.58 mmol), t-BuONa (1.4 g, 14.57 mmol) in Toluene (15 mL) was irradiated with microwave radiation for 1 h at 125° C. under nitrogen and quenched by water (50 mL), extracted with dichloromethane, and the organic layers was combined and dried over anhydrous sodium sulfate and concentrated under reduced pressure. The residue was purified by flash chromatography on silica gel with ethyl acetate/petroleum ether (1:5) to afford the title compound (960 mg) as a yellow solid.

Step 2: Preparation of 5-fluoro-4-(4-(trifluoromethyl)piperidin-1-yl)picolinonitrile

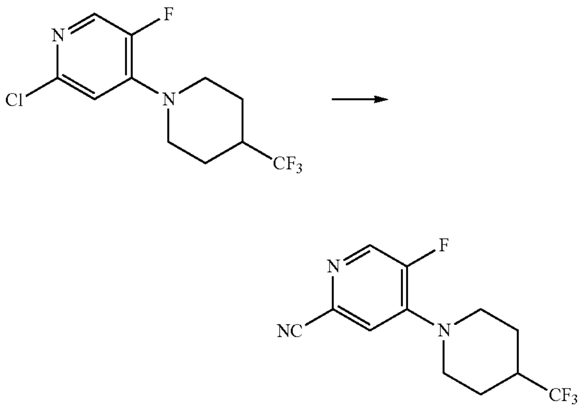

A mixture of 2-chloro-5-fluoro-4-[4-(trifluoromethyl)piperidin-1-yl]pyridine (400 mg, 1.42 mmol), $Pd_2(dba)_3.CHCl_3$ (72 mg, 0.07 mmol), $Zn(CN)_2$ (100 mg, 0.85 mmol), Dppf (80 mg, 0.14 mmol), Zn (8 mg, 0.12 mmol) in DMA (10 mL) was irradiated with microwave radiation for 1 h at 125° C. under nitrogen and quenched by water (100 mL), extracted with dichloromethane, dried over anhydrous sodium sulfate and concentrated under reduced pressure. The residue was purified by flash chromatography on silica gel with ethyl acetate/petroleum ether (1:5) to afford the title compound (350 mg) as a yellow solid.

Step 3: Preparation of (5-fluoro-4-(4-(trifluoromethyl)piperidin-1-yl)pyridin-2-yl)methanamine

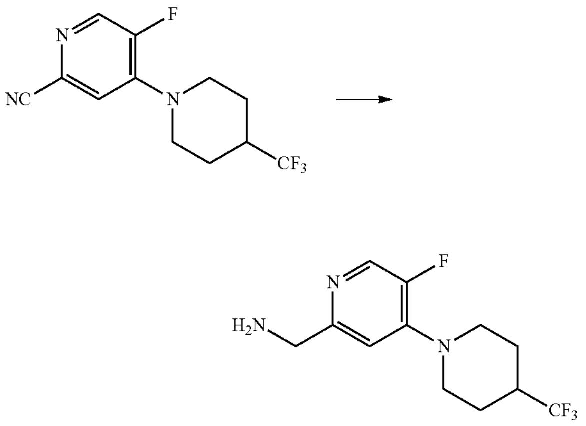

A mixture of 5-fluoro-4-[4-(trifluoromethyl)piperidin-1-yl]pyridine-2-carbonitrile (200 mg, 0.73 mmol), 10% Pd/C (50 mg), conc.HCl (0.25 mL) in methanol (10 mL) was stirred for 1 h at room temperature under an atmosphere of hydrogen gas. The solids were filtered out and the filtrate was concentrated under reduced pressure to afford the crude title compound as a brown solid, which was used in the next step without any further purification.

Step 4: Preparation of (2S,4R)-4-fluoro-N-((5-fluoro-4-(4-(trifluoromethyl)piperidin-1-yl)pyridin-2-yl)methyl)-1-(4-fluorophenylsulfonyl)pyrrolidine-2-carboxamide

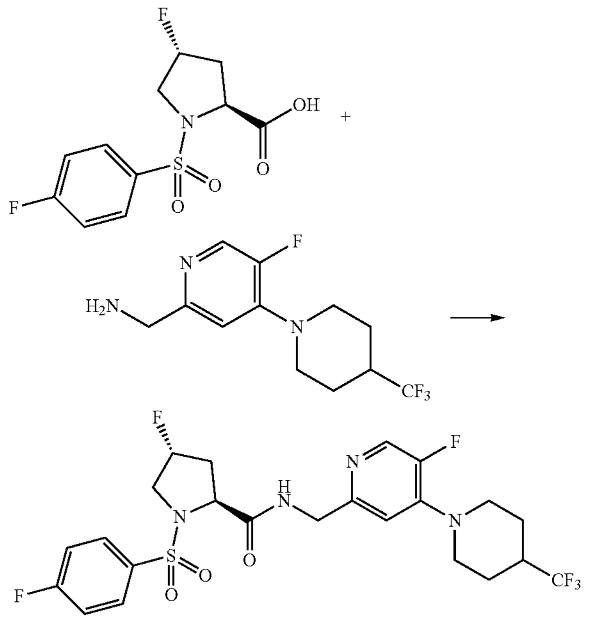

A mixture of (2S,4R)-4-fluoro-1-[(4-fluorobenzene)sulfonyl]pyrrolidine-2-carboxylic acid (315 mg, 1.08 mmol), HATU (410 mg, 1.08 mmol), DIEA (0.8 mL, 4.84 mmol), [5-fluoro-4-[4-(trifluoromethyl)piperidin-1-yl]pyridin-2-yl]methanamine (250 mg, 0.90 mmol) in DMF (4 mL) was stirred overnight at room temperature. The resulting mixture was purified by Prep-HPLC with the following conditions (1#Waters 2767-1): Column, X Bridge C18; mobile phase, Mobile Phase A: Water/0.05% $NH_4HCO_3$, Mobile Phase B: ACN=30% increasing to ACN=70% within 10 min; Detector, UV 254 nm to afford the title compound (28.2 mg) as a white solid. $^1H$ NMR (400 MHz, $CD_3OD$) δ 8.09 (s, 1H), 8.03-7.99 (m, 2H), 7.39-7.34 (m, 2H), 7.18-7.16 (d, J=7.6 Hz, 2H), 5.21-5.07 (d, J=52.4 Hz, 1H), 4.47 (s, 2H), 4.28-4.24 (m, 1H), 4.04-4.01 (d, J=12.8 Hz, 2H), 3.83-3.70 (m, 2H), 3.00-2.94 (t, J=12.8 Hz, 2H), 2.51-2.40 (m, 2H), 2.25-2.12 (m, 1H), 1.94-1.91 (d, J=12.8 Hz, 2H), 1.71-1.65 (m, 2H).

Example 145

Preparation of (2S,4R)-4-fluoro-1-(4-fluorophenylsulfonyl)-N-((6-(4-(trifluoromethoxy)phenyl)pyrimidin-4-yl)methyl)pyrrolidine-2-carboxamide Step 1: Preparation of 4-chloro-6-[4-(trifluoromethoxy)phenyl]pyrimidine

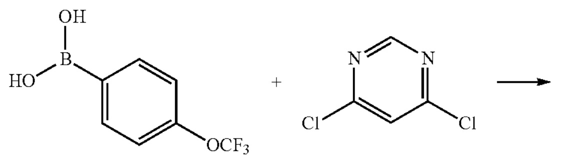

-continued

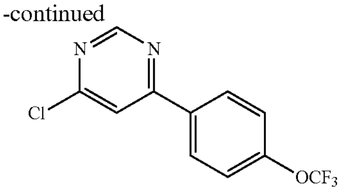

A mixture of 4,6-dichloropyrimidine (2.17 g, 14.57 mmol), [4-(trifluoromethoxy)phenyl]boronic acid (1 g, 4.86 mmol), Pd(dppf)$Cl_2$ (731 mg, 1.00 mmol), potassium carbonate (5 g, 36.18 mmol), dioxane (40 mL) and water (4 mL) was stirred for 12 h at 100° C. under nitrogen. The mixture was diluted with EtOAc, washed with brine, dried and concentrated. The residue was purified by flash chromatography on silica gel eluting with EtOAc/petroleum ether (1/50) to afford the title compound (1.1 g, 82%) as a white solid.

Step 2: Preparation of 6-[4-(trifluoromethoxy)phenyl]pyrimidine-4-carbonitrile

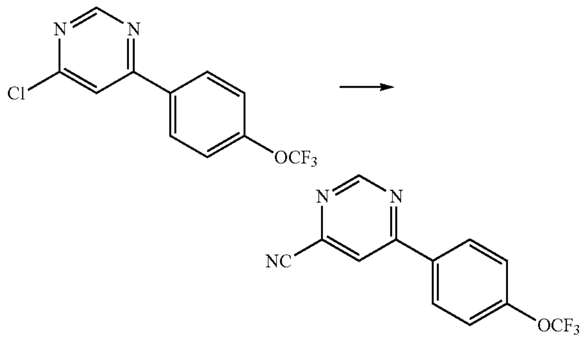

A mixture of 4-chloro-6-[4-(trifluoromethoxy)phenyl]pyrimidine (820 mg, 2.99 mmol), $Zn(CN)_2$ (421 mg, 3.58 mmol), Pd(PPh3)4 (347 mg, 0.30 mmol), DMF (6 mL) was stirred for 9 h at 100° C. under nitrogen. The reaction was cooled, diluted with water (30 mL), extracted with EtOAc. The combined organic layers were washed with brine, dried over anhydrous $Na_2SO_4$ and concentrated. The residue was purified by flash chromatography on silica gel eluting with EtOAc/petroleum ether (1/50) to afford the title compound (320 mg, 40%) as a white solid.

Step 3: Preparation of (6-(4-(trifluoromethoxy)phenyl)pyrimidin-4-yl)methanamine hydrochloride

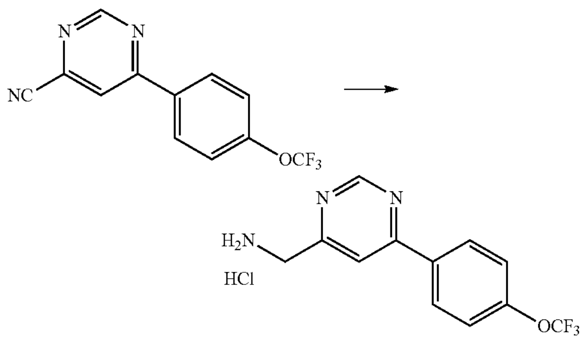

A mixture of 6-[4-(trifluoromethoxy)phenyl]pyrimidine-4-carbonitrile (160 mg, 0.60 mmol), ethanol (10 mL), concentrated HCl solution (0.02 mL), 10% Palladium on carbon (100 mg) was stirred for 10 min at room temperature under an atmosphere of hydrogen gas. The solids were filtered off and the filtrate was concentrated to afford the crude product (200 mg) as a solid, which was used in the next step without any further purification.

Step 4: Preparation of (2S,4R)-4-fluoro-1-(4-fluorophenylsulfonyl)-N-((6-(4-(trifluoromethoxy)phenyl)pyrimidin-4-yl)methyl)pyrrolidine-2-carboxamide

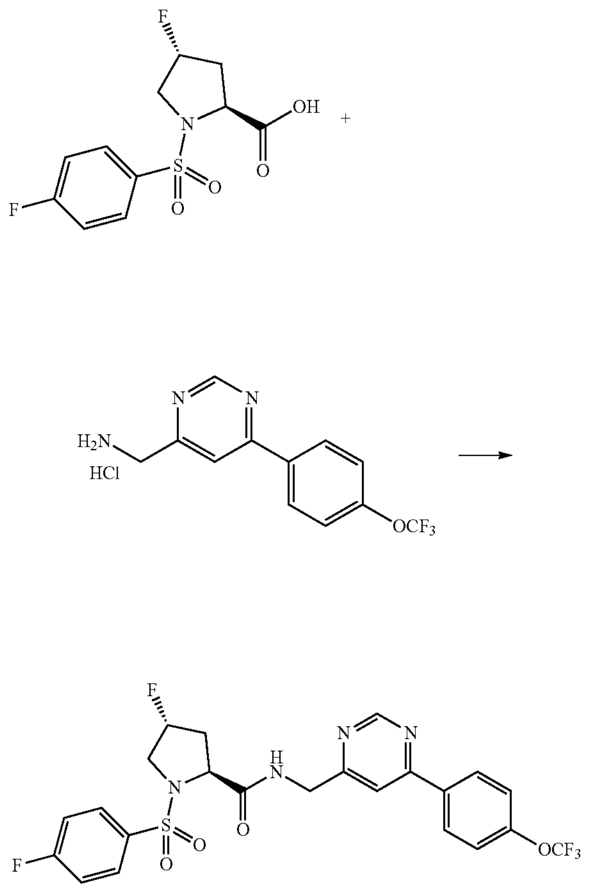

A mixture of (2S,4R)-4-fluoro-1-[(4-fluorobenzene)sulfonyl]pyrro-lidine-2-carboxylic acid (150 mg, 0.51 mmol), DMF (4 mL), DIPEA (263 mg, 2.03 mmol), HATU (294 mg, 0.77 mmol) and [6-[4-(trifluoromethoxy)phenyl]pyrimidin-4-yl]methanamine (200 mg, 0.74 mmol) was stirred for 12 h at room temperature. The crude solution was purified directly by Prep-HPLC to afford the title compound (51 mg, 13%) as a white solid. $^1$H NMR (300 MHz, $CD_3OD$) δ 9.15 (s, 1H), 8.41 (d, J=8.7 Hz, 6H), 8.25 (s, 1H), 8.08-8.03 (m, 2H), 7.40-7.34 (m, 4H), 5.17 (d, J=51.6 Hz, 1H), 4.63 (d, J=4.8 Hz, 2H), 4.37-4.31 (m, 1H), 3.88-3.75 (m, 2H), 2.61-2.48 (m, 1H), 2.35-2.11 (m, 1H).

Example 146

Preparation of (2S,4R)—N-([3-chloro-1-[6-(trifluoromethyl)pyridin-3-yl]-1H-pyrazol-4-yl]methyl)-4-fluoro-1-[(4-fluorobenzene)sulfonyl]pyrrolidine-2-carboxamide

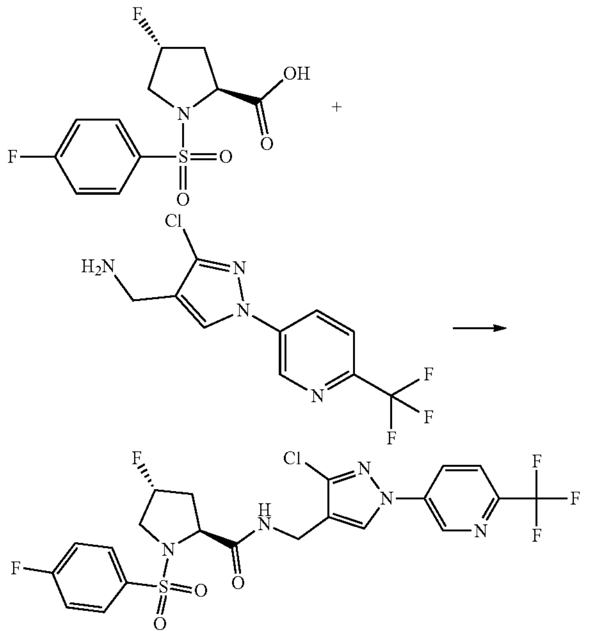

A mixture of (2S,4R)-4-fluoro-1-[(4-fluorobenzene)sulfonyl]-pyrrolidine-2-carboxylic acid (48 mg, 0.16 mmol), DIPEA (63 mg, 0.49 mmol), DMF (3 mL), HATU (94 mg, 0.25 mmol) and [3-chloro-1-[6-(trifluoromethyl)pyridin-3-yl]-1H-pyrazol-4-yl]methanamine (46 mg, 0.17 mmol) was stirred for 2 h at room temperature. The reaction mixture was purified directly by Prep-HPLC to afford the title compound (40 mg, 44%) as a white solid. $^1$H NMR (300 MHz, $CD_3OD$) δ 9.16 (s, 1H), 8.55 (s, 1H), 8.33-8.37 (m, 1H), 7.94-8.02 (m, 3H), 7.32-7.38 (m, 2H), 5.15 (d, J=52.5 Hz, 1H), 4.39 (s, 2H), 4.25-4.19 (m, 1H), 3.85-3.67 (m, 2H), 2.53-2.42 (m, 1H), 2.29-2.10 (m, 1H).

Example 147

Preparation of (2S,4R)-4-fluoro-1-(4-fluorophenylsulfonyl)-N-((6-(4-(trifluoromethylthio)phenyl)pyrimidin-4-yl)methyl)pyrrolidine-2-carboxamide

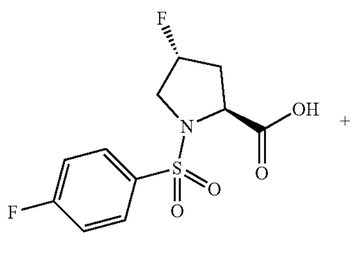

-continued

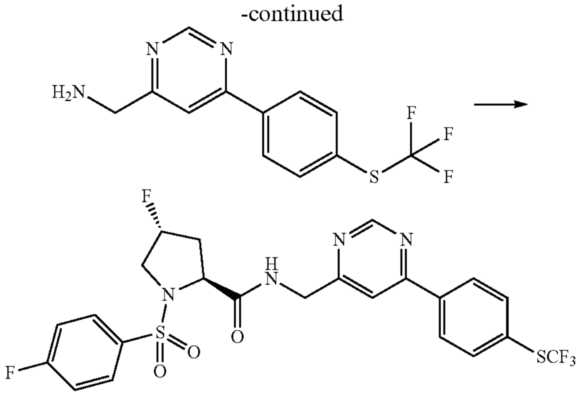

A mixture of (2S,4R)-4-fluoro-1-[(4-fluorobenzene) sulfonyl]pyrrolidine-2-carboxylic acid (102 mg, 0.35 mmol), DMF(5 mL), DIPEA (136 mg, 1.05 mmol), HATU (200 mg, 0.53 mmol) and (6-[4-[(trifluoromethyl)sulfanyl] phenyl]pyrimidin-4-yl)methanamine (100 mg, 0.35 mmol) was stirred for 1 h at room temperature. The crude solution was purified directly by Prep-HPLC high to afford the title compound (75.4 mg, 39%) as a white solid. $^1$H NMR (300 MHz, $CD_3OD$) δ 9.16 (s, 1H), 8.39 (d, J=8.4 Hz, 2H), 8.27 (s, 1H), 8.07-8.01 (m, 2H), 7.79 (d, J=8.4 Hz, 2H), 7.38-7.32 (m, 2H), 5.16 (d, J=51.9 Hz, 1H), 4.63 (d, J=4.2 Hz, 2H), 4.32 (dd, J=10.2, 7.2 Hz, 1H), 3.87-3.9 (m, 2H), 2.57-2.15 (m, 2H).

Example 148

Preparation of (2S,4R)-4-fluoro-1-(4-fluorophenylsulfonyl)-N-((6-(4-(trifluoromethyl)cyclohex-1-enyl)pyrimidin-4-yl)methyl)pyrrolidine-2-carboxamide Step 1: Preparation of [6-[4-(trifluoromethyl)cyclohex-1-en-1-yl]pyrimidin-4-yl]methanol

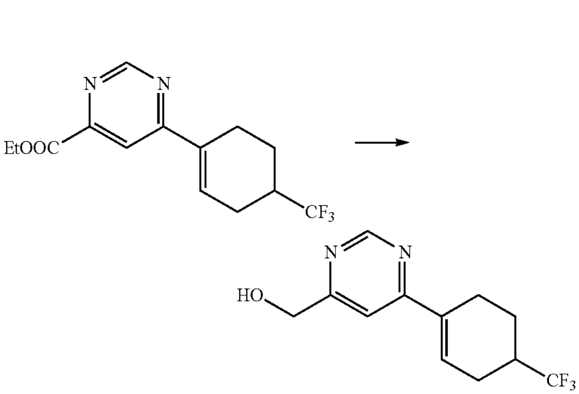

$NaBH_4$ (76 mg, 2.01 mmol) was added portionwise to a solution of ethyl 6-[4-(trifluoromethyl) cyclohex-1-en-1-yl] pyrimidine-4-carboxylate (300 mg, 1.00 mmol) in methanol (10 mL) with stirring. The resulting mixture was stirred for 2 h at 25° C., and concentrated under reduced pressure. The residue was purified by flash chromatography on silica gel eluting with EtOAc/petroleum ether (1:1) to afford the title compound (254 mg) as a white solid.

Step 2: Preparation of 2-([6-[4-(trifluoromethyl) cyclohex-1-en-1-yl]pyrimidin-4-yl]methyl)-2,3-dihydro-1H-isoindole-1,3-dione

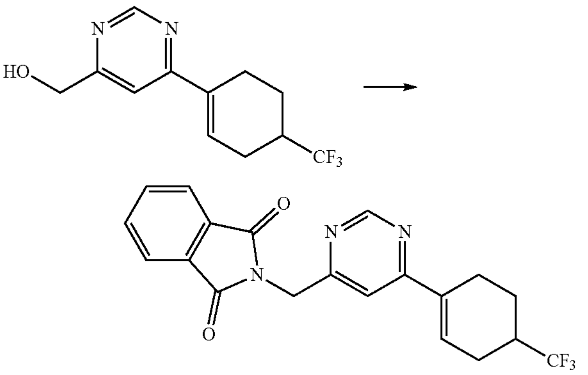

DIAD (235 mg, 1.16 mmol) was added dropwise to a solution of [6-[4-(trifluoromethyl)cyclohex-1-en-1-yl]pyrimidin-4-yl]methanol (150 mg, 0.58 mmol), 2,3-dihydro-1H-isoindole-1,3-dione (94 mg, 0.64 mmol), $PPh_3$ (305 mg, 1.16 mmol) in THF (10 mL) at 0° C. with stirring. The resulting mixture was stirred for 2 h at 25° C., then diluted with water, extracted with dichloromethane. The organic layers were combined and washed with brine, dried over anhydrous $Na_2SO_4$ and concentrated under reduced pressure. The residue was purified by flash chromatography on silica gel eluting with EtOAc/petroleum ether (1:1) to afford the title compound (425 mg) as a white solid.

Step 3: Preparation of [6-[4-(trifluoromethyl)cyclohex-1-en-1-yl]pyrimidin-4-yl]methanamine

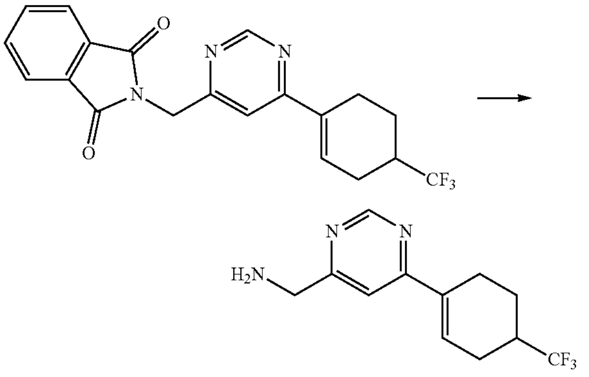

A mixture of 2-([6-[4-(trifluoromethyl)cyclohex-1-en-1-yl]pyrimidin-4-yl]methyl)-2,3-dihydro-1H-isoindole-1,3-dione (425 mg, 1.10 mmol), hydrazine hydrate (80%) (0.5 mL) in methanol (10 mL) was stirred for 3 h at 25° C., and concentrated under reduced pressure. The residue was dissolved in EtOAc, and the solids were filtered out. The filtrate was concentrated under reduced pressure to afford the crude title compound (210 mg) as a white solid, which was used in the next step without any further purification.

Step 4: Preparation of (2S,4R)-4-fluoro-1-(4-fluorophenylsulfonyl)-N-((6-(4-(trifluoromethyl)cyclohex-1-enyl)pyrimidin-4-yl)methyl)pyrrolidine-2-carboxamide

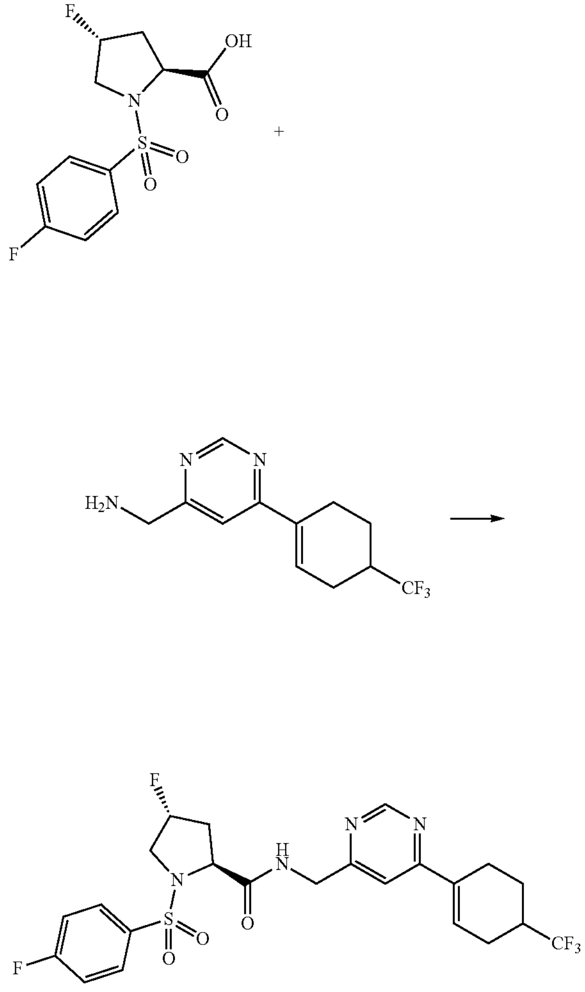

A mixture of [6-[4-(trifluoromethyl) cyclohex-1-en-1-yl] pyrimidin-4-yl]methanamine (284 mg, 1.10 mmol), HATU (465.8 mg, 1.23 mmol), DIPEA (317 mg, 2.45 mmol) in DMF (5 mL) was stirred for 10 min at 25° C. Then (2S,4R)-4-fluoro-1-[(4-fluorobenzene)sulfonyl]pyrrolidine-2-carboxylic acid (210 mg, 0.72 mmol) was added and the resulting mixture was a stirred overnight at 25° C. The reaction mixture was then quenched with water, extracted with dichloromethane. The combined organic layers were washed with brine (2×10 mL), dried over anhydrous $Na_2SO_4$ and concentrated under reduced pressure. The crude product (120 mg) was purified by Prep-HPLC to afford the title compound (25.8 mg) as a white solid. $^1H$ NMR (300 MHz, $CD_3OD$) δ 8.99 (s, 1H), 8.04 (q, J=6 Hz, 2H), 7.84 (s, 1H), 7.38 (t, J=9 Hz, 2H), 7.15 (s, 1H), 5.16 (d, J=51 Hz, 1H), 4.88-4.86 (d, J=6 Hz, 2H), 4.31 (t, J=9 Hz, 1H), 3.86-3.72 (m, 2H), 2.84 (m, 1H), 2.59-2.47 (m, 4H), 2.32-2.14 (m, 3H), 1.67-1.61 (m, 1H).

Example 149

Preparation of ((2S,4R)-4-fluoro-1-(4-fluorophenylsulfonyl)-N-((6-((1r, 4S)-4-(trifluoromethyl)cyclohexyl)pyrimidin-4-yl)methyl)pyrrolidine-2-carboxamide

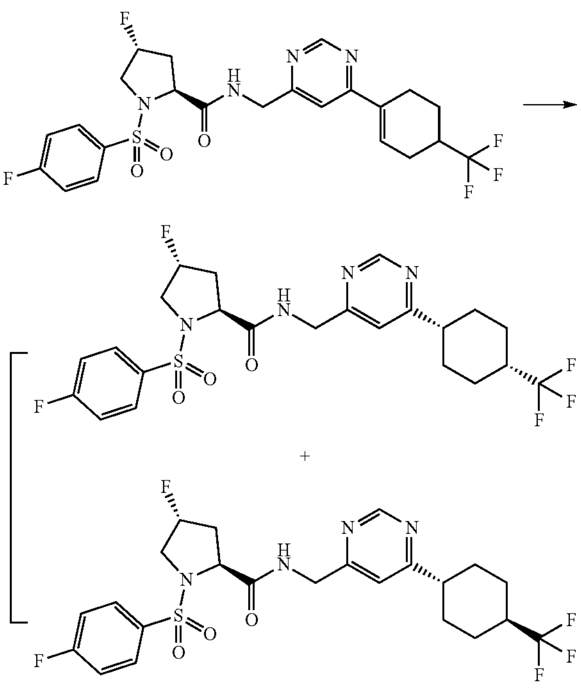

A mixture of (2S,4R)-4-fluoro-1-[(4-fluorobenzene) sulfonyl]-N-([6-[4-(trifluoromethyl)cyclohex-1-en-1-yl]pyrimidin-4-yl]methyl)pyrrolidine-2-carboxamide (180 mg, 0.34 mmol), 10% $Pd(OH)_2/C$ (30 mg) in methanol (20 mL) was stirred for 15 min at 25° C. under an atmosphere of hydrogen gas. The solids were filtered off and the filtrate was concentrated under reduced pressure. The residue (260 mg) was purified by Prep-HPLC to afford a mixture of cis/trans-isomers (120 mg). The isomers were separated by Chiral-Prep-HPLC eluting with Hex and IPA (hold 30.0% IPA in 20 min). Faster eluting isomer (33.6 mg) arbitrarily assigned as trans isomer (2S,4R)-4-fluoro-1-[(4-fluorobenzene) sulfonyl]-N-([6-[(1r,4S)-4-(trifluoromethyl) cyclohexyl]pyrimidin-4-yl]methyl) pyrrolidine-2-carboxamide: $^1H$ NMR (300 MHz, $CD_3OD$) δ 8.97 (s, 1H), 8.04 (q, J=6 Hz, 2H), 7.71 (s, 1H), 7.37 (t, J=9 Hz, 2H), 5.16 (d, J=54 Hz, 1H), 4.54 (s, 2H), 4.32 (t, J=9 Hz, 1H), 3.86-3.72 (m, 2H), 2.72 (t, J=3 Hz, 1H), 2.51 (m, 1H), 2.27-2.04 (m, 6H), 1.74-1.53 (m, 2H), 1.50-1.44 (m, 2H).

Slower eluting isomer (18 mg), arbitrarily assigned as cis isomer (2S,4R)-4-fluoro-1-[(4-fluorobenzene)sulfonyl]-N-([6-[(1s,4R)-4-(trifluoromethyl)cyclohexyl]pyrimidin-4-yl] methyl)pyrrolidine-2-carboxamide: $^1H$ NMR (300 MHz, $CD_3OD$) δ 9.02 (s, 1H), 8.01 (q, J=6 Hz, 2H), 7.74 (s, 1H), 7.36 (t, J=9 Hz, 2H), 5.15 (d, J=54 Hz, 1H), 4.56 (d, J=3 Hz, 2H), 4.27 (t, J=9 Hz, 1H), 3.86-3.72 (m, 2H), 3.03-3.00 (m, 1H), 2.53-2.51 (m, 1H), 2.35-2.06 (m, 5H), 1.88-1.61 (m, 6H).

Example 150

Preparation of (2S,4R)-1-(3,4-difluorophenylsulfonyl)-4-fluoro-N-((6-(4-(trifluoromethyl)phenyl)pyrimidin-4-yl)methyl)pyrrolidine-2-carboxamide

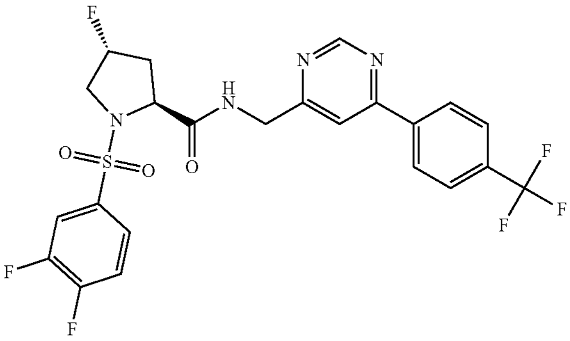 [SMILES: O=C(NCc1cc(-c2ccc(C(F)(F)F)cc2)ncn1)[C@@H]1C[C@@H](F)CN1S(=O)(=O)c1ccc(F)c(F)c1]

The title compound was prepared by the procedures described in Example 198, step 1 using (2S,4R)-1-(tert-butoxycarbonyl)-4-fluoropyrrolidine-2-carboxylic acid and (6-(4-(trifluoromethyl)phenyl)pyrimidin-4-yl)methanamine, and Example 198, steps 2 and 3 using 3,4-difluorobenzene-1-sulfonyl chloride as a white solid. $^1$H NMR (300 MHz, $CDCl_3$) δ 9.29 (s, 1H), 8.33 (d, J=8.1 Hz, 2H), 8.08 (s, 1H), 7.82-7.61 (m, 5H), 7.41-7.33 (m, 1H), 5.11 (d, J=51.9 Hz, 1H), 4.95-4.88 (m, 1H), 4.71-4.65 (m, 1H), 4.33 (dd, J=7.4 Hz, J=9.9 Hz, 1H), 3.94-3.69 (m, 2H), 2.67-2.53 (m, 1H), 2.40-2.23 (m, 1H).

Example 151

Preparation of (2S,4R)—N-([3-cyclopropyl-1-[6-(trifluoromethyl)pyridin-3-yl]-1H-pyrazol-4-yl]methyl)-4-fluoro-1-[(4-fluorobenzene)sulfonyl]pyrrolidine-2-carboxamide Step 1: Preparation of 2-(cyclopropanecarbonyl)-3-ethoxyprop-2-enenitrile

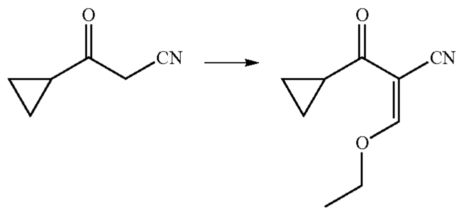

A mixture of 3-cyclopropyl-3-oxopropanenitrile (5.5 g, 50.40 mmol), (diethoxymethoxy)ethane (74.7 g, 504.05 mmol), acetic anhydride (60 mL, 634.74 mmol) was stirred for 2 h at 150° C. The mixture was cooled, concentrated under reduced pressure. The residue was recrystallized from ethanol to afford the title compound (6 g, 72%) as a light yellow solid.

Step 2: Preparation of 3-cyclopropyl-1H-pyrazole-4-carbonitrile

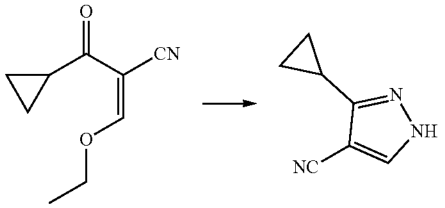

A mixture of 2(cyclopropanecarbonyl)-3-ethoxyprop-2-enenitrile (2 g, 12.11 mmol), hydrazine hydrate (85%) (6.1 g, 121.85 mmol) and ethanol (20 mL) was stirred for 10 min at room temperature. The mixture was concentrated under reduced pressure. The residue was re-crystallized from toluene to afford the title compound (1 g, 62%) as a yellow solid.

Step 3: Preparation of 3-cyclopropyl-1-[6-(trifluoromethyl)pyridin-3-yl]-1H-pyrazole-4-carbonitrile

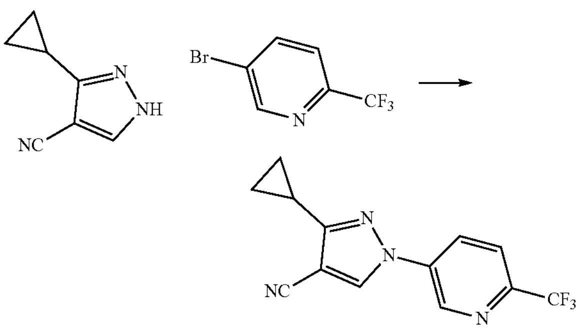

A mixture of 3-cyclopropyl-1H-pyrazole-4-carbonitrile (1 g, 7.51 mmol), 5-bromo-2-(trifluoromethyl)pyridine (2.88 g, 12.74 mmol), CuI (143 mg, 0.75 mmol), L-proline (173 mg, 1.50 mmol), potassium carbonate (2.28 g, 16.50 mmol) and DMSO (50 mL) was stirred for 12 h at 100° C. under nitrogen. The mixture was cooled, diluted with EtOAc, washed with brine, dried over anhydrous $Na_2SO_4$ and concentrated under reduced pressure. The residue was purified by flash chromatography on a silica gel eluting with petroleum ether/EtOAc (50/1) to afford the title compound (1.1 g, 53%) as a white solid.

Step 4: Preparation of [3-cyclopropyl-1-[6-(trifluoromethyl)pyridin-3-yl]-1H-pyrazol-4-yl]methanamine

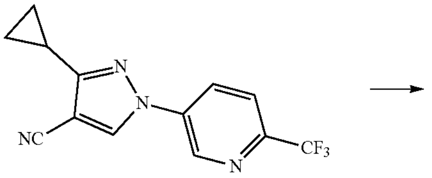

-continued

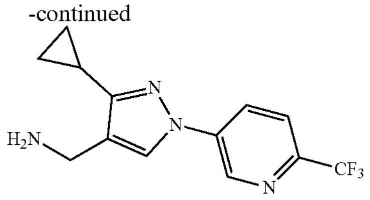

A mixture of 3-cyclopropyl-1-[6-(trifluoromethyl)pyridin-3-yl]-1H-pyrazole-4-carbonitrile (1 g, 3.59 mmol), methanol (50 mL) and Raney Ni (500 mg, 5.84 mmol) was stirred for 15 min at room temperature under an atmosphere of hydrogen gas. The solids were filtered off, and the filtrate was concentrated under reduced pressure to afford the title compound (900 mg) as a white solid, which was used in the next step without any further purification.

Step 5: Preparation of (2S,4R)—N-([3-cyclopropyl-1-[6-(trifluoromethyl)pyridin-3-yl]-1H-pyrazol-4-yl]methyl)-4-fluoro-1-[(4-fluorobenzene)sulfonyl]pyrrolidine-2-carboxamide

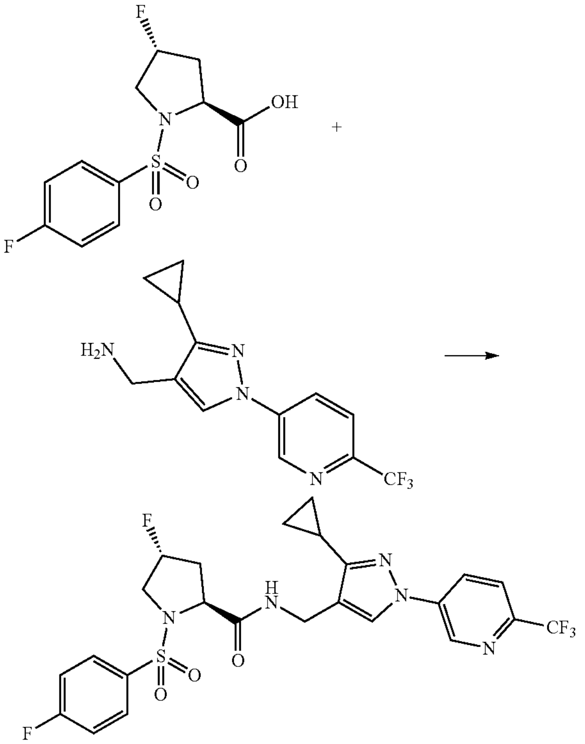

A mixture of (2S,4R)-4-fluoro-1-[(4-fluorobenzene)sulfonyl]pyrrolidine-2-carboxylic acid (80 mg, 0.27 mmol), DMF (5 mL), DIPEA (106.8 mg, 0.83 mmol), HATU (156.6 mg, 0.41 mmol) and 3-cyclopropyl-1-[6-(trifluoromethyl)pyridin-3-yl]-1H-pyrazol-4-ylmethanamine (77.55 mg, 0.27 mmol) was stirred for 1 h at room temperature. The crude solution was purified directly by Prep-HPLC to afford the title compound (50 mg, 33%) as a white solid. $^1$H-NMR (300 MHz, DMSO-$d_6$) δ 9.14 (s, 1H), 8.66 (s, 1H), 8.49 (s, 1H), 8.32 (d, J=7.8 Hz, 1H), 8.02-7.96 (m, 3H), 7.74 (m, 1H), 5.27-5.10 (m, 1H), 4.33-4.30 (m, 2H), 4.19-4.14 (m, 1H), 3.71-3.67 (m, 1H), 3.62-3.58 (m, 1H), 2.51 (m, 1H), 2.42-2.29 (m, 1H), 2.18-1.94 (m, 1H), 0.96-0.90 (m, 4H).

Example 152

Preparation of (2S,4R)-4-fluoro-1-(4-fluorophenylsulfonyl)-N-((2-methyl-6-(6-(trifluoromethyl)pyridin-3-yl)pyrimidin-4-yl)methyl)pyrrolidine-2-carboxamide Step 1: Preparation of 4-chloro-2-methyl-6-[6-(trifluoromethyl)pyridin-3-yl]pyrimidine

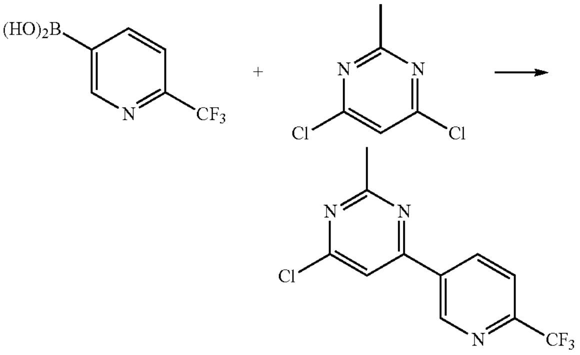

A mixture of 4,6-dichloro-2-methylpyrimidine (1 g, 6.13 mmol), [6-(trifluoromethyl)pyridin-3-yl]boronic acid (229 mg, 1.20 mmol), potassium carbonate (2.07 g, 14.98 mmol), dioxane (50 mL), water (2 mL) and Pd(dppf)$Cl_2$ (320 mg, 0.44 mmol) was irradiated with microwave radiation for 3 h at 100° C. under nitrogen. The mixture was diluted with EtOAc (150 mL), washed with brine (3x50 mL), dried over anhydrous $Na_2SO_4$ and concentrated. The residue was purified by flash chromatography on silica gel eluting with EtOAc/petroleum ether (1/10) to afford the title compound (1.1 g, 66%) as a white solid.

Step 2: Preparation of 2-methyl-6-[6-(trifluoromethyl)pyridin-3-yl]pyrimidine-4-carbonitrile

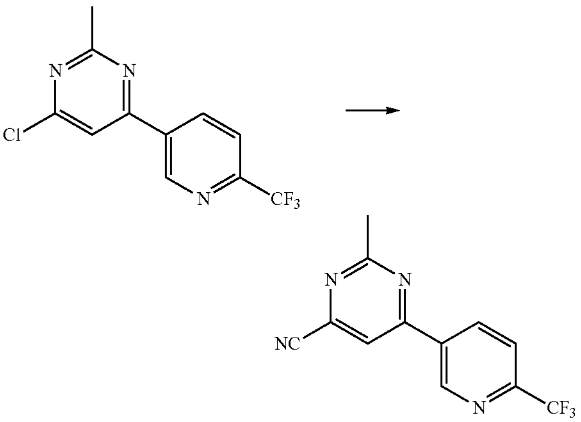

A mixture of 4-chloro-2-methyl-6-[6-(trifluoromethyl)pyridin-3-yl]pyrimidine (300 mg, 1.10 mmol), DMF (5 mL), $Zn(CN)_2$ (128.7 mg, 1.10 mmol), dppf (60.9 mg, 0.11 mmol) and $Pd_2(dba)3CHCl3$ (113.9 mg, 0.11 mmol) was irradiated with microwave radiation for 3 h at 120° C. under nitrogen. The mixture was diluted with EtOAc (100 mL), washed with brine (3×), dried over anhydrous $Na_2SO_4$ and concentrated. The residue was purified by flash chromatography on silica gel eluting with EtOAc/petroleum ether (1/10) to afford the title compound (250 mg, 86%) as a white solid.

Step 3: Preparation of [2-methyl-6-[6-(trifluoromethyl)pyridin-3-yl]pyrimidin-4-yl]methanamine hydrogen chloride

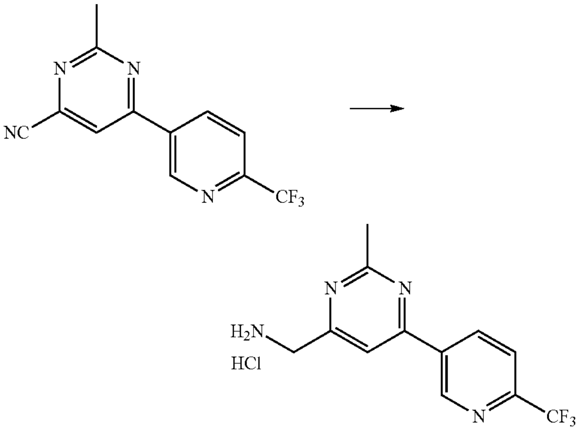

A mixture of 2-methyl-6-[6-(trifluoromethyl)pyridin-3-yl]pyrimidine-4-carbonitrile (250 mg, 0.94 mmol), ethanol (20 mL), concentrated HCl (0.2 mL) and 10% Palladium carbon (200 mg) was stirred for 5 min at room temperature under an atmosphere of hydrogen gas. The solids were filtered off and the filtrate was concentrated to afford the crude product (200 mg) as a black solid, which was used in the next step without any further purification.

Step 4: Preparation of (2S,4R)-4-fluoro-1-(4-fluorophenylsulfonyl)-N-((2-methyl-6-(6-(trifluoromethyl)pyridin-3-yl)pyrimidin-4-yl)methyl)pyrrolidine-2-carboxamide

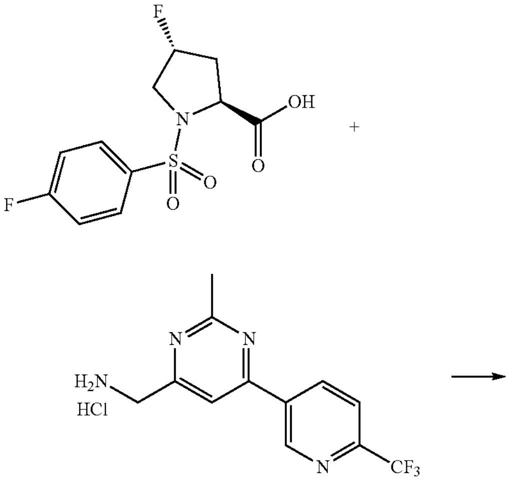

-continued

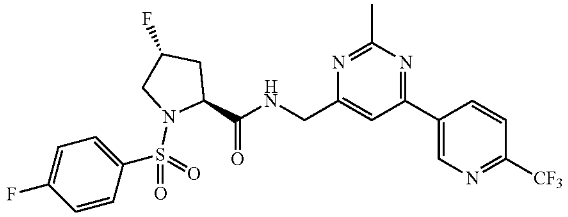

A mixture of (2S,4R)-4-fluoro-1-[(4-fluorobenzene)sulfonyl]pyrrolidine-2-carboxylic acid (107.7 mg, 0.37 mmol), DMF (5 mL), DIPEA (144.4 mg, 1.12 mmol), HATU (212.8 mg, 0.56 mmol) and [2-methyl-6-[6-(trifluoromethyl)pyridin-3-yl]pyrimidin-4-yl]methanamine hydrogen chloride (112 mg, 0.37 mmol) was stirred for 1 h at room temperature. The crude solution was purified directly by Prep-HPLC to afford the title compound (32.9 mg, 16%) as a white solid. $^1H$ NMR (300 MHz, DMSO-$d_6$) δ 9.46 (s, 1H), 8.69 (d, J=7.2 Hz, 1H), 7.94-7.91 (m, 3H), 7.89 (d, J=8.1 Hz, 1H), 7.61 (s, 1H), 7.28-7.23 (m, 1H), 5.09 (d, J=52.2 Hz, 1H), 4.94-4.89 (m, 1H), 4.50-4.45 (m, 1H), 4.37-4.31 (m, 1H), 3.96-3.62 (m, 2H), 2.83 (s, 3H), 2.64-2.54 (m, 1H), 2.34-1.52 (m, 1H).

Example 153

Preparation of (2S,4R)-4-fluoro-1-[(4-fluorobenzene)sulfonyl]-N-([3-methoxy-1-[6-(trifluoromethyl)pyridin-3-yl]-1H-pyrazol-4-yl]methyl)pyrrolidine-2-carboxamide

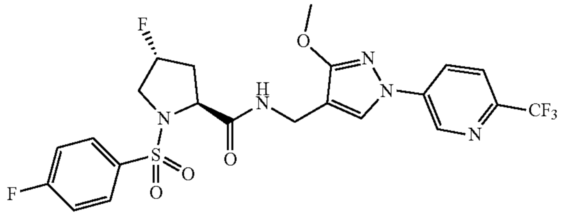 [SMILES: COc1nn(-c2ccc(C(F)(F)F)nc2)cc1CNC(=O)[C@@H]1C[C@@H](F)CN1S(=O)(=O)c1ccc(F)cc1]

Step 1: Preparation of ethyl 3-methoxy-1-[6-(trifluoromethyl)pyridin-3-yl]-1H-pyrazole-4-carboxylate

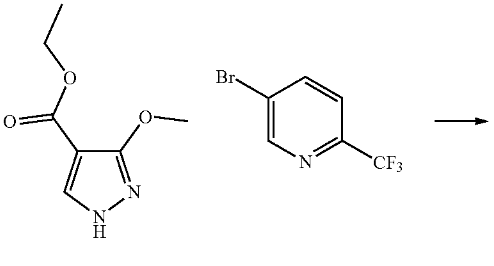

-continued

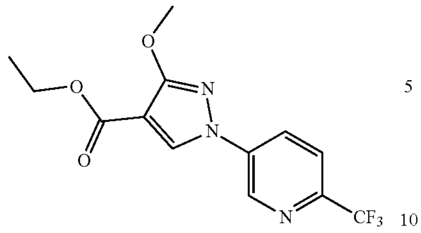

A mixture of CuI (122.93 mg, 0.65 mmol, 0.10 equiv), L-proline (148.8 mg, 1.29 mmol, 0.20 equiv), potassium carbonate (1.786 g, 12.92 mmol, 2.00 equiv), ethyl 3-methoxy-1H-pyrazole-4-carboxylate (1.1 g, 6.46 mmol, 1.00 equiv), and 5-bromo-2-(trifluoromethyl)pyridine (2.185 g, 9.67 mmol, 1.50 equiv) in DMSO (60 mL) was stirred overnight at 100° C. under nitrogen. The reaction solution was diluted with water and extracted with ethyl acetate. The combined extracts were washed with brine, dried over anhydrous sodium sulfate, and concentrated under vacuum. The residue was purified by a silica gel column with ethyl acetate/petroleum ether (1:6) to afford the title compound (790 mg, 39%) as a white solid.

Step 2: Preparation of [3-methoxy-1-[6-(trifluoromethyl)pyridin-3-yl]-1H-pyrazol-4-yl]methano

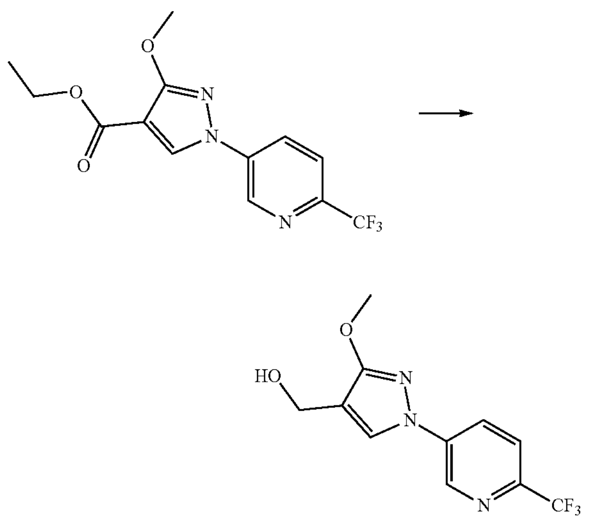

$LiAlH_4$ (190.61 mg, 5.02 mmol, 1.50 equiv) was added in several batches into a solution of ethyl 3-methoxy-1-[6-(trifluoromethyl)pyridin-3-yl]-1H-pyrazole-4-carboxylate (790 mg, 2.51 mmol, 1.00 equiv) in tetrahydrofuran (10 mL) at 0° C. The resulting solution was stirred for 30 min at 0° C. The reaction was then quenched by water and the solids were filtered out. The resulting solution was extracted with ethyl acetate and the organic layers were combined. The organic was washed with brine, dried over anhydrous sodium sulfate, and concentrated under vacuum. The residue was purified by a silica gel column eluting with ethyl acetate/petroleum ether (1:12) to afford the title compound (462 mg, 67%) as a yellow solid.

Step 3: Preparation of 3-methoxy-1-[6-(trifluoromethyl)pyridin-3-yl]-1H-pyrazole-4-carbaldehyde

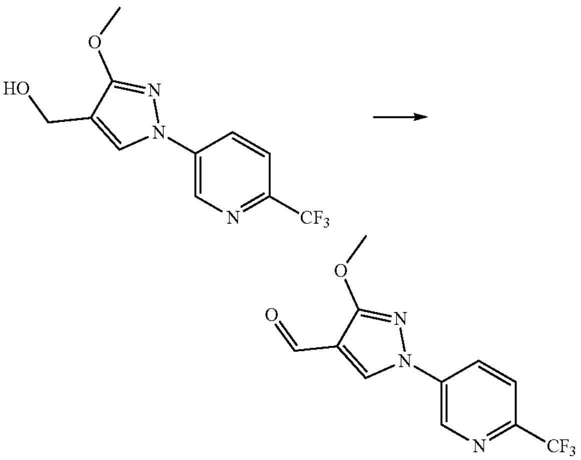

A mixture of [3-methoxy-1-[6-(trifluoromethyl)pyridin-3-yl]-1H-pyrazol-4-yl]methanol (460 mg, 1.68 mmol, 1.00 equiv) and PCC (714.43 mg, 3.31 mmol, 2.00 equiv) in dichloromethane (20 mL) was stirred for 1 h at room temperature. The resulting mixture was concentrated under vacuum. The residue was purified by a silica gel column eluting with ethyl acetate/petroleum ether (1:12) to afford the title compound (283 mg, 62%) as a light yellow solid.

Step 4: Preparation of [3-methoxy-1-[6-(trifluoromethyl)pyridin-3-yl]-1H-pyrazol-4-yl]methanamine

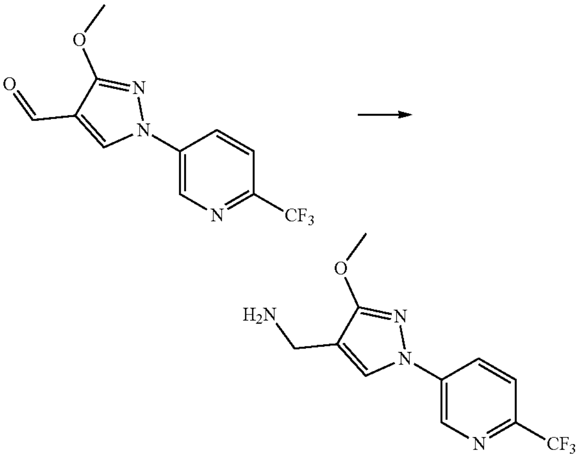

A mixture of 3-methoxy-1-[6-(trifluoromethyl)pyridin-3-yl]-1H-pyrazole-4-carbaldehyde (450 mg, 1.66 mmol, 1.00 equiv), ethanol (20 mL), water (1 mL), and hydroxylamine hydrochloride (229.15 mg, 3.30 mmol, 2.00 equiv) was stirred for 2 h at room temperature. Then the flask was purged and maintained with $H_2$ (g). Concentrated hydrogen chloride (0.1 mL) and Pd/C (300 mg, 10%) were added to the above mixture. The resulting solution was stirred for 15 min at room temperature. The solids were filtered out and the filtrate was concentrated under vacuum. The resulting solution was diluted with water. The pH value of the solution was adjusted to 8 with sodium bicarbonate. The resulting solution was extracted with ethyl acetate, dried over anhydrous sodium sulfate, and concentrated under vacuum. This resulted in the title compound (280 mg, 62%) as a gray solid.

Step 5: Preparation of (2S,4R)-4-fluoro-1-[(4-fluorobenzene)sulfonyl]-N-([3-methoxy-1-[6-(trifluoromethyl)pyridin-3-yl]-1H-pyrazol-4-yl]methyl) pyrrolidine-2-carboxamide

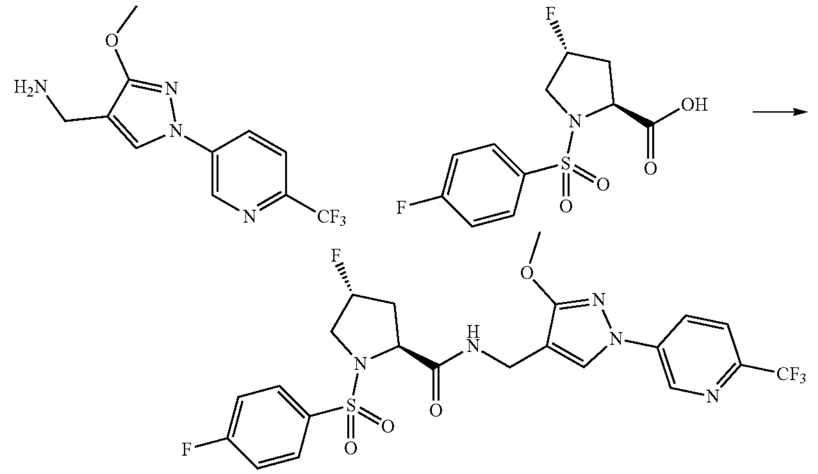

A mixture of (2S,4R)-4-fluoro-1-[(4-fluorobenzene) sulfonyl]pyrrolidine-2-carboxylic acid (64.13 mg, 0.22 mmol, 1.20 equiv), HATU (104.89 mg, 0.28 mmol, 1.50 equiv), DIEA (71.21 mg, 0.55 mmol, 3.00 equiv), and [3-methoxy-1-[6-(trifluoromethyl)pyridin-3-yl]-1H-pyrazol-4-yl]methanamine (50 mg, 0.18 mmol, 1.00 equiv) in N,N-dimethylformamide (5 mL) was stirred for 45 min at room temperature. The reaction was then quenched by water. The solids were collected by filtration. The crude product was purified by Prep-HPLC to afford the title compound (41.5 mg, 41%) as a white solid.

$^1$H NMR (400 MHz, $CDCl_3$) δ 8.57-8.51 (m, 2H), 8.02-7.88 (m, 6H), 7.47-7.41 (t, 2H), 4.42-4.36 (m, 1H), 4.15-4.05 (m, 5H), 3.57-3.51 (t, 1H), 3.42-3.35 (m, 1H).

Example 154

Preparation of (2S,4R)-4-fluoro-1-(4-fluorophenylsulfonyl)-N-((6-(6-(trifluoromethyl)pyridin-3-yl) pyrimidin-4-yl)methyl)pyrrolidine-2-carboxamide Step 1: (2S,4R)-tert-butyl 4-fluoro-2-((6-(6-(trifluoromethyl)pyridin-3-yl)pyrimidin-4-yl)methylcarbamoyl)pyrrolidine-1-carboxylate

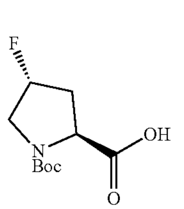

+

-continued

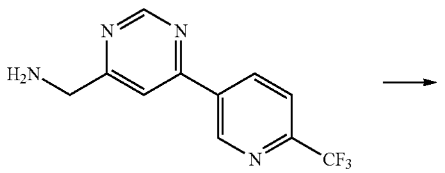

-continued

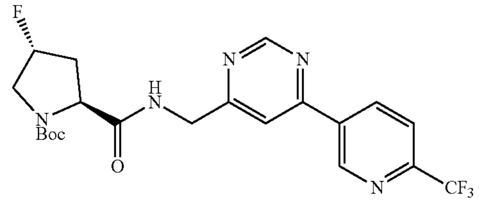

(2S,4R)-tert-butyl 4-fluoro-2-((6-(6-(trifluoromethyl) pyridin-3-yl)pyrimidin-4-yl)methylcarbamoyl)pyrrolidine-1-carboxylate was prepared by the procedure described in Example 198, step 1 using (2S,4R)-1-(tert-butoxycarbonyl)-4-fluoropyrrolidine-2-carboxylic acid.

Step 2: (2S,4R)-4-fluoro-2-((6-(6-(trifluoromethyl) pyridin-3-yl)pyrimidin-4-yl)methylcarbamoyl)pyrrolidinium chloride

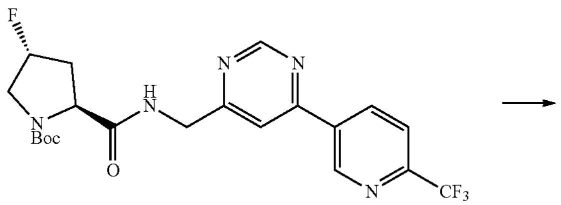

-continued

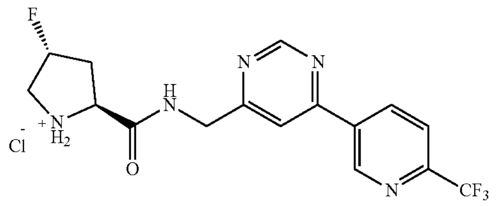

(2S,4R)-4-fluoro-N-((6-(6-(trifluoromethyl)pyridin-3-yl)pyrimidin-4-yl)methyl)pyrrolidine-2-carboxamide was prepared by the procedure described in Example 198, step 2.

Step 3: (2S,4R)-4-fluoro-1-(4-fluorophenylsulfonyl)-N-((6-(6-(trifluoromethyl)pyridin-3-yl)pyrimidin-4-yl)methyl)pyrrolidine-2-carboxamide

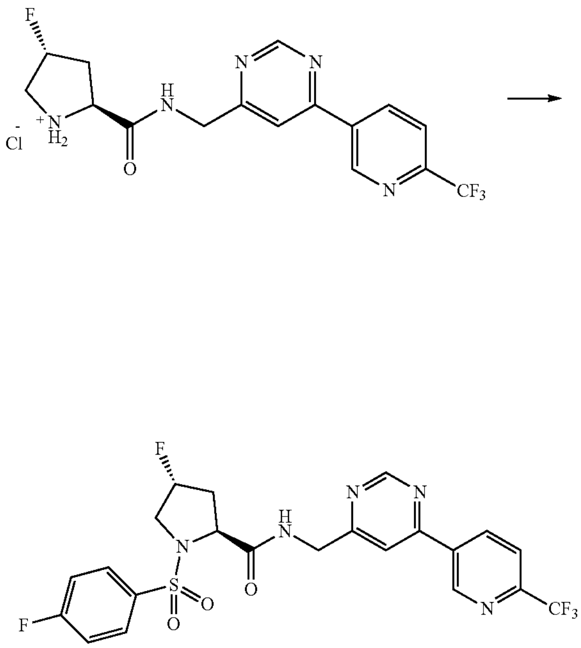

The title compound was prepared by the procedure described in Example 198, step 3 (29 mg): $^1$H NMR (400 MHz, DMSO-$d_6$) δ 9.48 (d, J=1.9 Hz, 1H), 9.30 (d, J=1.2 Hz, 1H), 9.11 (t, J=5.9 Hz, 1H), 8.79 (dd, J=8.3 Hz, J=1.7 Hz, 1H), 8.23 (s, 1H), 8.08 (d, J=8.3 Hz, 1H), 8.05-7.98 (m, 2H), 7.47 (t, J=8.8 Hz, 2H), 5.21 (d, J=52.4 Hz, 1H), 4.53 (d, J=5.9 Hz, 2H), 4.25 (dd, J=9.8, 7.2 Hz, 1H), 3.79-3.60 (m, 2H), 2.46-2.37 (m, 1H), 2.25-2.04 (m, 1H).

Example 155

Preparation of (2S,4R)—N-((6-(4-cyclopropylphenyl)pyrimidin-4-yl)methyl)-4-fluoro-1-(4-fluorophenylsulfonyl)pyrrolidine-2-carboxamide

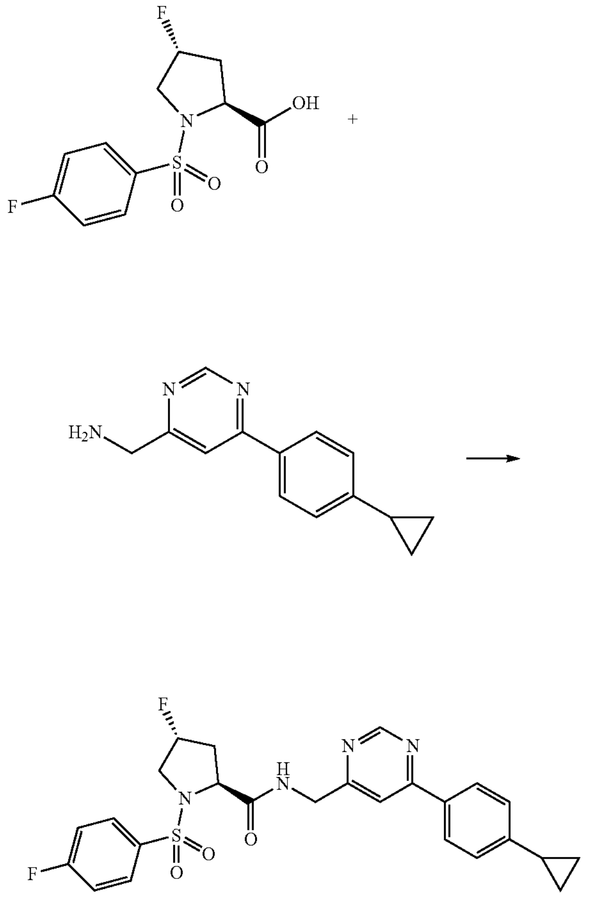

A mixture of (2S,4R)-4-fluoro-1-[(4-fluorobenzene)sulfonyl]pyrrolidine-2-carboxylic acid (155.2 mg, 0.53 mmol), HATU (253.3 mg, 0.67 mmol), DIPEA (172 mg, 1.33 mmol), [6-(4-cyclopropylphenyl)pyrimidin-4-yl]methanamine (100 mg, 0.44 mmol) in DMF (5 mL) was stirred overnight at 25° C. The reaction mixture was quenched with water (20 mL), extracted with $CH_2Cl_2$ (3×) and separated. The combined organic layers were washed with brine (20 mL), dried over anhydrous $Na_2SO_4$ and concentrated under reduced pressure. The residue was purified by Prep-HPLC to afford the title compound (36.4 mg) as a white solid. $^1$H NMR (400 MHz, $CD_3OD$) δ 8.94 (s, 1H), 8.04 (d, J=8 Hz, 3H), 7.94-7.90 (m, 2H), 7.26-7.21 (m, 2H), 7.05 (d, J=8.4 Hz, 2H), 5.06 (d, J=52 Hz, 1H), 4.48 (dd, J=17.6 Hz, J=8.8 Hz, 2H), 4.23-4.18 (m, 1H), 3.76-3.63 (m, 2H), 2.43-2.39 (m, 1H), 2.17-2.04 (m, 1H), 1.86-1.81 (m, 1H), 0.92-0.90 (m, 2H), 0.65-0.63 (m, 2H).

Example 156

Preparation of (2S,4R)-1-(3,4-difluorophenylsulfonyl)-4-fluoro-N-((6-(6-(trifluoromethyl)pyridin-3-yl)pyrimidin-4-yl)methyl)pyrrolidine-2-carboxamide

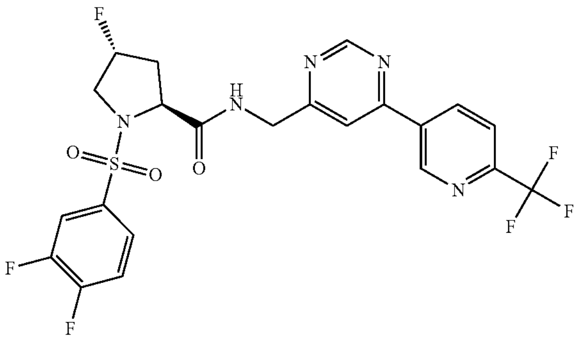 [SMILES: O=C(NCc1cc(-c2ccc(C(F)(F)F)nc2)ncn1)[C@@H]1C[C@@H](F)CN1S(=O)(=O)c1ccc(F)c(F)c1]

The title compound was prepared by the procedures described in Example 198, step 1 using (2S,4R)-1-(tert-butoxycarbonyl)-4-fluoropyrrolidine-2-carboxylic acid and (6-(6-(trifluoromethyl)pyridin-3-yl)pyrimidin-4-yl)methanamine, Example 198, step 2 and Example 198, step 3 using 3,4-difluorobenzene-1-sulfonyl chloride as a light yellow solid. $^1$H NMR (300 MHz, $CDCl_3$) δ 9.52 (s, 1H), 9.28 (s, 1H), 8.70 (d, J=7.8 Hz, 1H), 8.09 (s, 1H), 7.83-7.68 (m, 3H), 7.61-7.58 (m, 1H), 7.42-7.33 (m, 1H), 5.11 (d, J=51.6 Hz, 1H), 4.99-4.92 (m, 1H), 4.62-4.55 (m, 1H), 4.35 (t, J=9 Hz, 1H), 3.95-3.64 (m, 2H), 2.65-2.57 (m, 1H), 2.37-2.02 (m, 1H).

Example 157

Preparation of (2R,3S)-3-fluoro-1-(4-fluorophenyl)sulfonyl-N-[[4-[2-(trifluoromethyl)pyrimidin-5-yl]-2-pyridyl]methyl]pyrrolidine-2-carboxamide

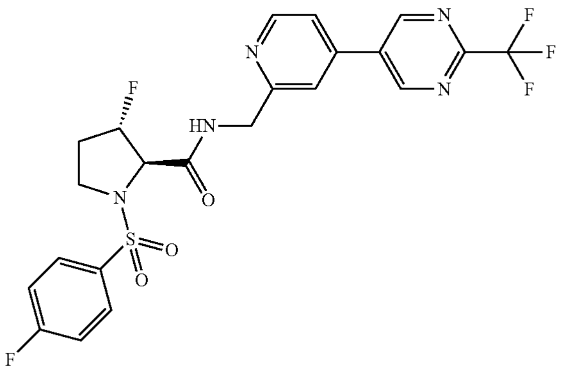 [SMILES: O=C(NCc1cc(-c2cnc(C(F)(F)F)nc2)ccn1)[C@@H]1[C@@H](F)CCN1S(=O)(=O)c1ccc(F)cc1]

Preparation of the title compound follows the same general procedure as Example 55.

1H NMR (400 MHz, DMSO) δ 9.52-9.47 (s, 2H), 9.15-9.06 (t, J=6.0 Hz, 1H), 8.77-8.71 (dd, J=4.8, 1.2 Hz, 1H), 8.05-7.96 (m, 2H), 7.90-7.83 (m, 2H), 7.54-7.45 (m, 2H), 5.30-5.12 (m, 1H), 4.64-4.46 (m, 2H), 4.46-4.37 (m, 1H), 3.71-3.62 (ddd, J=9.8, 5.6, 2.1 Hz, 1H), 3.21-3.12 (m, 1H), 2.29-2.05 (m, 2H)., LCMS (ESI) m/z:528.2 [M+H]+

Example 158

Preparation of (2S,4R)—N-[[2-chloro-5-[2-(trifluoromethyl)pyrimidin-5-yl]phenyl]methyl]-4-fluoro-1-(4-fluorophenyl)sulfonyl-pyrrolidine-2-carboxamide

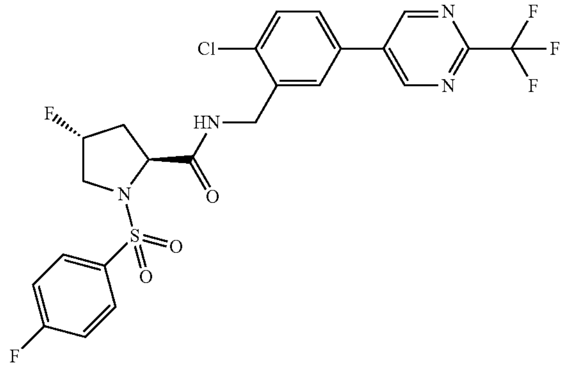 [SMILES: O=C(NCc1cc(-c2cnc(C(F)(F)F)nc2)ccc1Cl)[C@@H]1C[C@@H](F)CN1S(=O)(=O)c1ccc(F)cc1]

Preparation of the title compound follows the same general procedure as Example 48.

1H NMR (400 MHz, DMSO) δ 9.39-9.36 (s, 2H), 9.00-8.92 (t, J=5.9 Hz, 1H), 8.02-7.94 (m, 3H), 7.90-7.85 (dd, J=8.3, 2.3 Hz, 1H), 7.72-7.68 (d, J=8.3 Hz, 1H), 7.49-7.40 (m, 2H), 5.29-5.09 (d, J=52.2 Hz, 1H), 4.51-4.46 (d, J=5.9 Hz, 2H), 4.27-4.19 (dd, J=10.0, 7.1 Hz, 1H), 3.73-3.56 (m, 2H), 2.46-2.35 (m, 1H), 2.21-2.00 (m, 1H)., LCMS (ESI) m/z:561.2 [M+H]+

Example 159

Preparation of (2S,4R)-4-fluoro-1-(4-fluorophenyl)sulfonyl-N-[[2-[4-(trifluoromethoxy)phenyl]-4-pyridyl]methyl]pyrrolidine-2-carboxamide

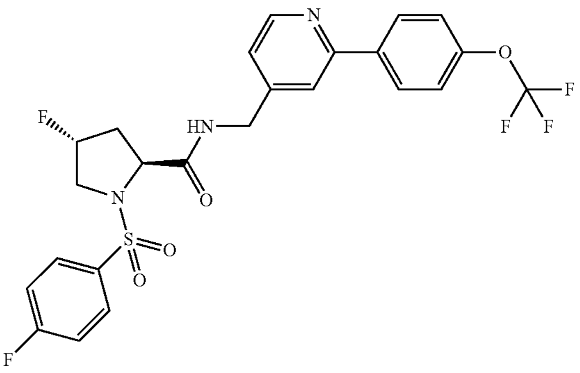 [SMILES: O=C(NCc1ccnc(-c2ccc(OC(F)(F)F)cc2)c1)[C@@H]1C[C@@H](F)CN1S(=O)(=O)c1ccc(F)cc1]

Preparation of the title compound follows the same general procedure as Example 48.

1H NMR (400 MHz, DMSO) δ 8.98-8.91 (t, J=6.0 Hz, 1H), 8.64-8.59 (dd, J=5.0, 0.8 Hz, 1H), 8.25-8.19 (m, 2H), 8.03-7.96 (m, 2H), 7.96-7.93 (dd, J=1.6, 0.9 Hz, 1H), 7.52-7.41 (m, 5H), 7.36-7.31 (dd, J=5.0, 1.5 Hz, 1H), 5.31-5.11 (d, J=52.3 Hz, 1H), 4.55-4.37 (m, 2H), 4.25-4.16 (dd, J=9.9, 7.1 Hz, 1H), 3.76-3.57 (m, 2H), 2.47-2.35 (m, 1H), 2.21-2.00 (m, 1H)., LCMS (ESI) m/z:542.2 [M+H]+

Example 160

Preparation of (2S,4R)—N-[[2-[4-(difluoromethoxy)phenyl]-4-pyridyl]methyl]-4-fluoro-1-(4-fluorophenyl)sulfonyl-pyrrolidine-2-carboxamide

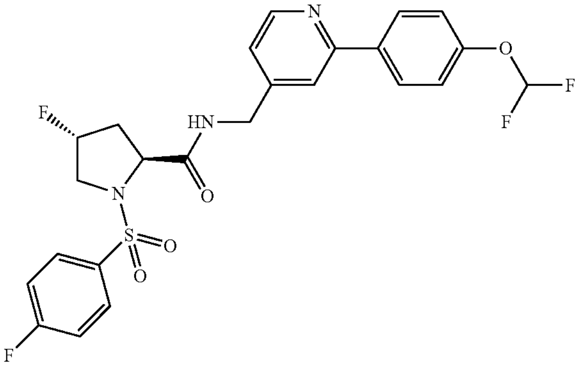 [SMILES: O=C(NCc1ccnc(-c2ccc(OC(F)F)cc2)c1)[C@@H]1C[C@@H](F)CN1S(=O)(=O)c1ccc(F)cc1]

Preparation of the title compound follows the same general procedure as Example 48.

1H NMR (400 MHz, DMSO) δ 8.99-8.88 (t, J=6.0 Hz, 1H), 8.62-8.56 (dd, J=5.0, 0.7 Hz, 1H), 8.20-8.12 (m, 2H), 8.04-7.96 (m, 2H), 7.94-7.89 (dd, J=1.6, 0.8 Hz, 1H), 7.53-7.45 (m, 2H), 7.45-7.13 (m, 1H), 7.31-7.22 (m, 3H), 5.31-5.10 (m, 1H), 4.53-4.36 (m, 2H), 4.26-4.16 (dd, J=9.9, 7.1 Hz, 1H), 3.78-3.58 (m, 2H), 2.47-2.35 (m, 1H), 2.20-1.98 (dddd, J=42.5, 13.7, 9.9, 3.4 Hz, 1H)., LCMS (ESI) m/z:524.2 [M+14]+

Example 161

Preparation of (2S,4R)-4-fluoro-N-(2-fluoro-5-(6-(trifluoromethyl)pyridin-3-yl)benzyl)-1-((4-fluorophenyl)sulfonyl)pyrrolidine-2-carboxamide

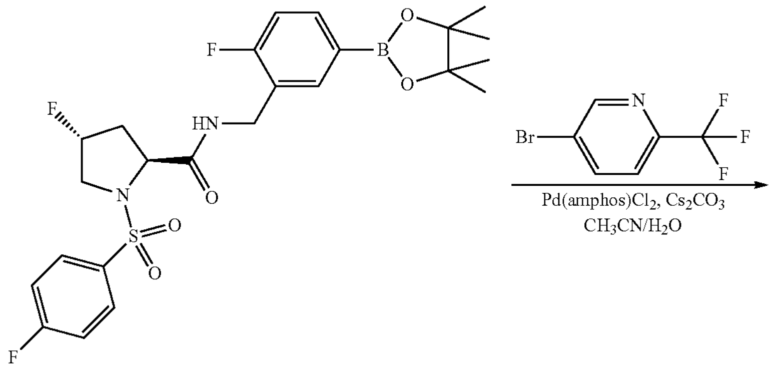

1

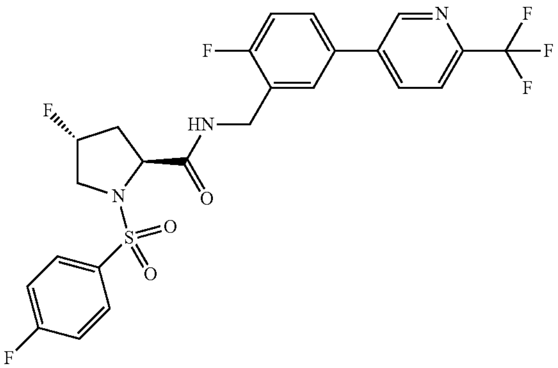

Following the same procedure of Example 163, step 2: The title compound (2S,4R)-4-fluoro-1-(4-fluorophenyl) sulfonyl-N-[[2-fluoro-5-[6-(trifluoromethyl)-3-pyridyl]phenyl]methyl]pyrrolidine-2-carboxamide (39 mg, 60%) was prepared from (2S,4R)-4-fluoro-1-(4-fluorophenyl)sulfonyl-N-[[2-fluoro-5-(4,4,5,5-tetramethyl-1,3,2-dioxaborolan-2-yl)phenyl]methyl]pyrrolidine-2-carboxamide 1 (62 mg, 0.12 mmol), 2-bromo-5-(trifluoromethyl)pyridine (37 mg, 0.17 mmol), cesium carbonate 1 M in water (0.16 mL, 0.16 mmol), Pd(amphos)$Cl_2$ (7 mg, 0.009 mmol) in acetonitrile (1 mL). LC/MS (ESI+): m/z 544.2 (M+H).

1H NMR (400 MHz, DMSO-$d_6$) δ 9.08 (d, J=2.2 Hz, 1H), 8.89 (t, J=5.9 Hz, 1H), 8.44-8.20 (m, 1H), 8.07-7.93 (m, 2H), 7.93-7.72 (m, 2H), 7.56-7.29 (m, 3H), 5.12 (t, J=2.7 Hz, 1H), 4.46 (d, J=5.8 Hz, 2H), 4.21 (dd, J=9.9, 7.1 Hz, 1H), 3.79-3.50 (m, 2H), 2.47-2.29 (m, 1H), 2.08 (dddd, J=42.5, 13.8, 9.9, 3.4 Hz, 1H).

Example 162

Preparation of (2S,4R)-4-fluoro-N-(2-fluoro-5-(5-(trifluoromethyl)pyridin-2-yl)benzyl)-1-((4-fluorophenyl)sulfonyl)pyrrolidine-2-carboxamide

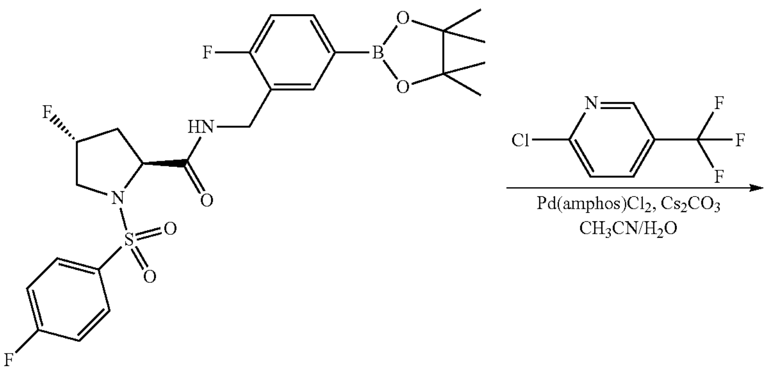

1

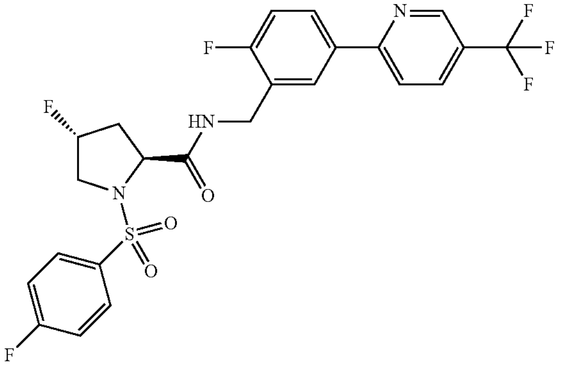

Following the same procedure of Example 163, step 2: The title compound (2S,4R)-4-fluoro-1-(4-fluorophenyl) sulfonyl-N-[[2-fluoro-5-[5-(trifluoromethyl)-2-pyridyl]phenyl]methyl]pyrrolidine-2-carboxamide (15 mg, 14%) was prepared from (2S)-4-fluoro-1-(4-fluorophenyl)sulfonyl-N-[[2-fluoro-5-(4,4,5,5-tetramethyl-1,3,2-dioxaborolan-2-yl) phenyl]methyl]pyrrolidine-2-carboxamide 1 (108 mg, 0.21 mmol), 2-chloro-5-(trifluoromethyl)pyridine (52 mg, 0.29 mmol), cesium carbonate 1 M in water (0.6 mL, 0.6 mmol), Pd(amphos)$Cl_2$ (11 mg, 0.016 mmol) in acetonitrile (1 mL). LC/MS (ESI+): m/z 544.2 (M+H).

1H NMR (400 MHz, DMSO-$d_6$) δ 9.02 (dq, J=2.5, 1.0 Hz, 1H), 8.87 (t, J=5.8 Hz, 1H), 8.28-8.11 (m, 3H), 8.01-7.92 (m, 2H), 7.48-7.41 (m, 2H), 7.38 (dd, J=9.8, 8.6 Hz, 1H), 5.37-5.04 (m, 1H), 4.55-4.37 (m, 2H), 4.30-4.13 (m, 1H), 3.81-3.49 (m, 2H), 2.46-2.28 (m, 1H), 2.08 (dddd, J=42.1, 13.8, 9.8, 3.7 Hz, 1H).

Example 163

Preparation of (2S,4R)-4-fluoro-N-(2-fluoro-5-(6-(trifluoromethyl)pyridazin-3-yl)benzyl)-1-((4-fluorophenyl)sulfonyl)pyrrolidine-2-carboxamide

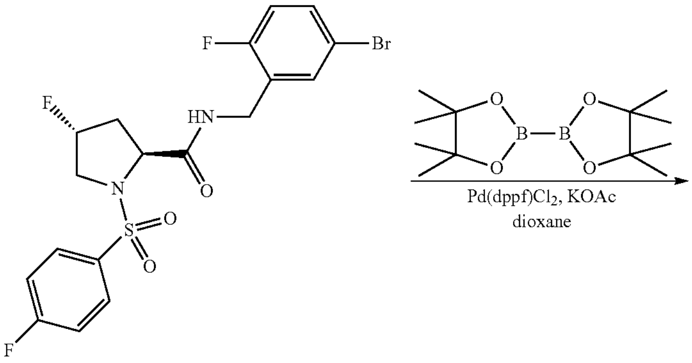

1

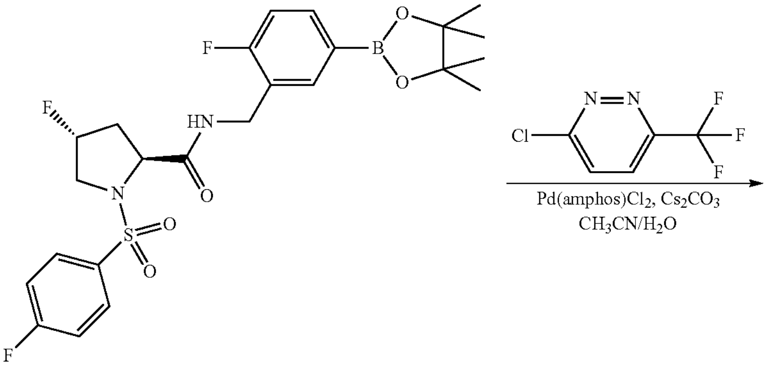

2

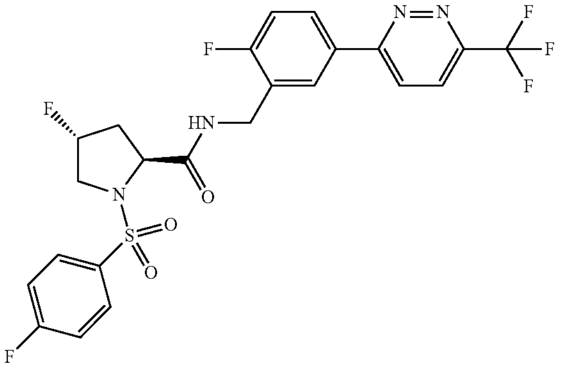

Step 1: (2S,4R)-4-fluoro-1-(4-fluorophenyl)sulfonyl-N-[[2-fluoro-5-(4,4,5,5-tetramethyl-1,3,2-dioxaborolan-2-yl)phenyl]methyl]pyrrolidine-2-carboxamide 2

To a microwave vial was added (2S,4R)—N-[(5-bromo-2-fluoro-phenyl)methyl]-4-fluoro-1-(4-fluorophenyl)sulfonyl-pyrrolidine-2-carboxamide 1 (prepared following the same procedure of Example 177, step 1-3) (1.2 g, 2.5 mmol), Pd(dppf)$Cl_2$ (210 mg, 0.25 mmol), bis(pinacolato)diboron (960 mg, 3.8 mmol), potassium acetate (740 mg, 7.5 mmol) and dioxane (5 mL). The reaction mixture was purged with nitrogen gas for 3 minutes and then heated to 85° C. in the microwave for 16 hours. Upon cooling to room temperature, the resulting mixture was diluted with DCM, filtered through a thin layer of celite, and concentrated under reduced pressure to afford the crude product 2 (1.3, 100%).

LC/MS (ESI+): m/z 525.5 (M+H).

Step 2: (2S,4R)-4-fluoro-1-(4-fluorophenyl)sulfonyl-N-[[2,-fluoro-5-[6-(trifluoromethyl)pyridazin-3-yl]phenyl]methyl]pyrrolidine-2-carboxamide To a microwave vial was added (2S)-4-fluoro-1-(4-fluorophenyl)sulfonyl-N-[[2-fluoro-5-(4,4,5,5-tetramethyl-1,3,2-dioxaborolan-2-yl)phenyl]methyl]pyrrolidine-2-carboxamide 2 (108 mg, 0.2059 mmol), 3-chloro-6-(trifluoromethyl)pyridazine (52.63 mg, 0.2883 mmol), cesium carbonate 1 M in water (0.6 mL, 0.6 mmol), acetonitrile (0.8 mL) and Pd(amphos)$Cl_2$ (11.67 mg, 0.016 mmol) were added and the reaction mixture was purged with nitrogen gas for 3 minutes and then heated to 140° C. in the microwave for 30 minutes. Upon cooling to room temperature, the resulting mixture was filtered through a thin layer of celite, washed with water and extracted with ethyl acetate. The combined organic layer was dried over $Na_2SO_4$, filtered and concentrated under reduced pressure. The residue was purified by reverse phase HPLC to afford the title compound (39 mg, 25%) as a white solid.

LC/MS (ESI+): m/z 545.2 (M+H).

1H NMR (400 MHz, DMSO-d6) δ 8.89 (t, J=5.9 Hz, 1H), 8.49 (d, J=9.2 Hz, 1H), 8.33 (d, J=9.0 Hz, 1H), 8.26 (ddd, J=10.6, 5.8, 2.5 Hz, 2H), 8.04-7.89 (m, 2H), 7.56-7.32 (m, 3H), 5.35-5.02 (m, 1H), 4.62-4.36 (m, 2H), 4.21 (dd, J=9.8, 7.2 Hz, 1H), 3.82-3.64 (m, 1H), 3.58 (dd, J=13.4, 2.7 Hz, 1H), 2.39 (dt, J=17.5, 8.8 Hz, 1H), 2.08 (dddd, J=42.0, 13.8, 9.7, 3.5 Hz, 1H).

Example 164

Preparation of (2S,4R)—N-(2-cyano-5-(2-(trifluoromethyl)pyrimidin-5-yl)benzyl)-4-fluoro-1-((4-fluorophenyl)sulfonyl)pyrrolidine-2-carboxamide

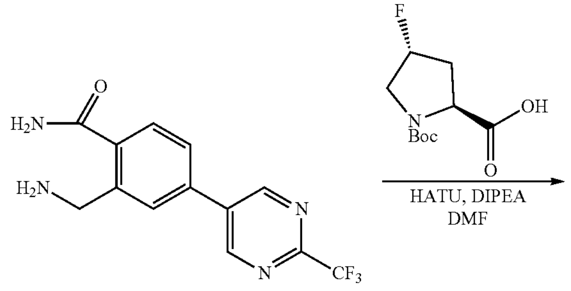

1

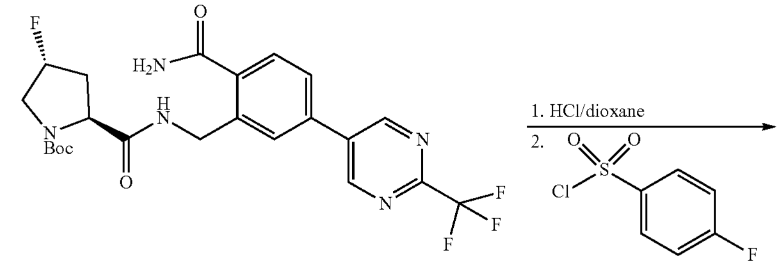

2

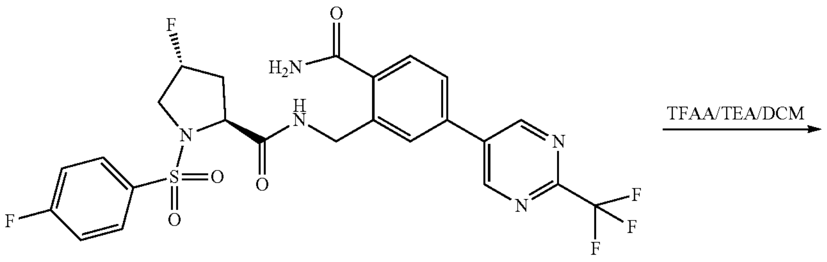

3

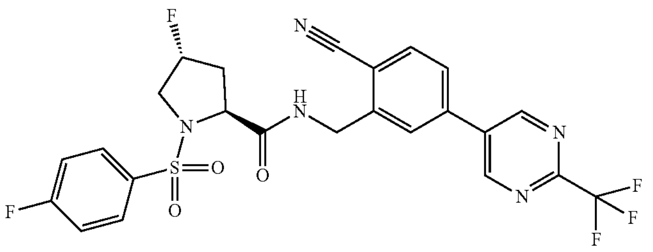

2-(aminomethyl)-4-[2-(trifluoromethyl)pyrimidin-5-yl] benzamide 1 was prepared following the same procedure of Example 176, step 1 to 5.

Following the same HATU coupling procedure of Example 176, step 6: (2S,4R)-tert-butyl 2-(2-carbamoyl-5-(2-(trifluoromethyl)pyrimidin-5-yl)benzylcarbamoyl)-4-fluoropyrrolidine-1-carboxylate 2 (387 mg, 75%) was prepared from (2S,4R)-1-tert-butoxycarbonyl-4-fluoro-pyrrolidine-2-carboxylic acid (259.9 mg, 1.11 mmol) and 2-(aminomethyl)-4-[2-(trifluoromethyl)pyrimidin-5-yl]benzamide 1 (300 mg, 1.01 mmol), DIPEA (0.530 mL, 3.04 mmol), HATU (471.6 mg, 1.2 mmol) in DMF (4 mL). LC/MS (ESI+): m/z 512.5 (M+H).

Following the same procedure of Example 176, step 7: (2S,4R)—N-[[2-carbamoyl-5-[2-(trifluoromethyl)pyrimidin-5-yl]phenyl]methyl]-4-fluoro-1-(4-fluorophenyl)sulfonyl-pyrrolidine-2-carboxamide 3 (180 mg, 52%) was prepared from (2S,4R)-tert-butyl 2-(2-carbamoyl-5-(2-(trifluoromethyl)pyrimidin-5-yl)benzylcarbamoyl)-4-fluoropyrrolidine-1-carboxylate 2 (387 mg, 0.76 mmol), 4 N HCl in dioxane (1.9 mL, 7.6 mmol) followed by the reaction with $Et_3N$ (1.7 mL, 12.15 mmol), 4-fluorobenzenesulfonyl chloride (142 mg, 0.73 mmol) in DCM (1 mL).

LC/MS (ESI+): m/z 570.5 (M+H).

Following the same procedure of Example 176, step 8: The title compound (129 mg, 78%) was prepared from (2S,4R)—N-[[2-carbamoyl-5-[2-(trifluoromethyl)pyrimidin-5-yl]phenyl]methyl]-4-fluoro-1-(4-fluorophenyl)sulfonyl-pyrrolidine-2-carboxamide 3 (180 mg, 0.3 mmol), trifluoroacetic anhydride (0.08 mL, 0.6 mmol), $Et_3N$ (0.04 mL, 0.32 mmol) in DCM (5 mL). LC/MS (ESI+): m/z 552.5 (M+H).

1H NMR (400 MHz, DMSO-$d_6$) δ 9.43 (s, 2H), 9.09 (t, J=5.8 Hz, 1H), 8.11-8.05 (m, 2H), 8.03 (dd, J=8.0, 1.9 Hz, 1H), 8.01-7.94 (m, 2H), 7.57-7.31 (m, 2H), 5.34-5.07 (m, 1H), 4.69-4.52 (m, 2H), 4.20 (dd, J=10.0, 7.1 Hz, 1H), 3.79-3.70 (m, 1H), 3.70-3.53 (m, 1H), 2.41 (td, J=16.3, 15.8, 6.7 Hz, 1H), 2.24-2.00 (m, 1H).

Example 165

Preparation of (2S,4R)—N-((2-chloro-6-(4-(difluoromethoxy)phenyl)pyridin-4-yl)methyl)-4-fluoro-1-((4-fluorophenyl)sulfonyl)pyrrolidine-2-carboxamide

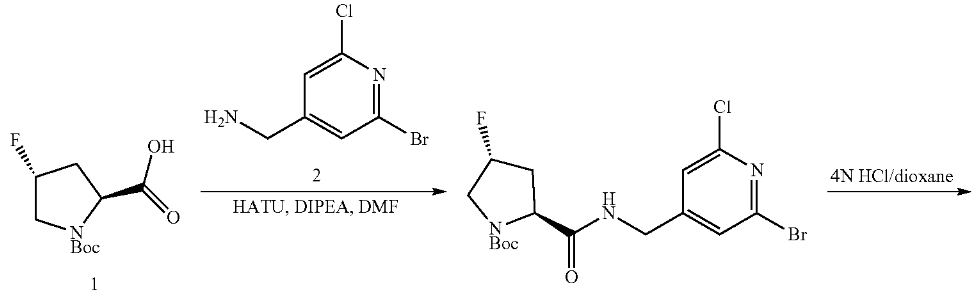

3

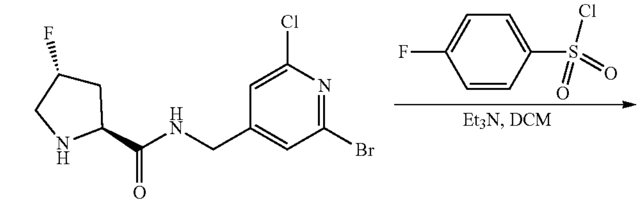

4

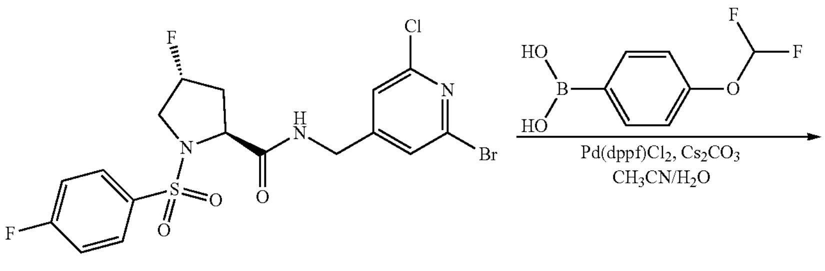

5

-continued

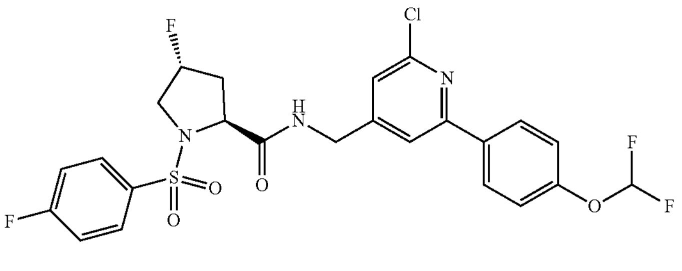

Following the HATU coupling procedure of Example 183, step 1: tert-butyl (2S,4R)-2-[(2-bromo-6-chloro-4-pyridyl)methylcarbamoyl]-4-fluoro-pyrrolidine-1-carboxylate 3 (4 g, 93%) was prepared from (2S,4R)-1-tert-butoxycarbonyl-4-fluoro-pyrrolidine-2-carboxylic acid 1 (2.3 g, 9.9 mmol) and (2-bromo-6-chloro-4-pyridyl)methanamine 2 (2.4 g, 11 mmol), DIPEA (5.2 mL, 30 mmol), HATU (4.6 g, 12 mmol) in DMF (39 mL). LC/MS (ESI+): m/z 437.7 (M+H).

Following the same procedure of Example 183, step 2: (2S,4R)—N-[(2-bromo-6-chloro-4-pyridyl)methyl]-4-fluoro-pyrrolidine-2-carboxamide 4 (2.3 g, 100%) was prepared from tert-butyl (2S,4R)-2-[(2-bromo-6-chloro-4-pyridyl)methylcarbamoyl]-4-fluoro-pyrrolidine-1-carboxylate 3 (3 g, 6.9 mmol) and 4 N HCl in dioxane (8.6 mL, 34 mmol). LC/MS (ESI+): m/z 337.7 (M+H).

Following the same procedure of Example 183, step 3: (2S,4R)—N-[(2-bromo-6-chloro-4-pyridyl)methyl]-4-fluoro-1-(4-fluorophenyl)sulfonyl-pyrrolidine-2-carboxamide 5 (2.2 g, 60%) was prepared from tert-butyl (2S,4R)-2-[(2-bromo-6-chloro-4-pyridyl)methylcarbamoyl]-4-fluoro-pyrrolidine-1-carboxylate 4 (2.5 g, 7.4 mmol), $Et_3N$ (21 mL, 0.148 mol), 4-fluorobenzenesulfonyl chloride (1.7 g, 8.9 mmol) in DCM (10 mL). LC/MS (ESI+): m/z 495.7 (M+H).

Following the same procedure of Example 183, step 4: The title compound (2S,4R)—N-[[2-chloro-6-[4-(difluoromethoxy)phenyl]-4-pyridyl]methyl]-4-fluoro-1-(4-fluorophenyl)sulfonyl-pyrrolidine-2-carboxamide (18 mg, 28%) was prepared from (2S,4R)—N-[(2-bromo-6-chloro-4-pyridyl)methyl]-4-fluoro-1-(4-fluorophenyl)sulfonyl-pyrrolidine-2-carboxamide 5 (54 mg, 0.11 mmol), [5-(trifluoromethyl)pyrimidin-2-yl]boronic acid (30 mg, 0.16 mmol), cesium carbonate 1 M in water (0.16 mL, 0.16 mmol), $Pd(dppf)Cl_2$ (11 mg, 0.016 mmol) in acetonitrile (1 mL). LC/MS (ESI+): m/z 558.2 (M+H).

1H NMR (400 MHz, DMSO-$d_6$) δ 9.08 (d, J=2.2 Hz, 1H), 8.89 (t, J=5.9 Hz, 1H), 8.44-8.20 (m, 1H), 8.07-7.93 (m, 2H), 7.93-7.72 (m, 2H), 7.56-7.29 (m, 3H), 5.12 (t, J=2.7 Hz, 1H), 4.46 (d, J=5.8 Hz, 2H), 4.21 (dd, J=9.9, 7.1 Hz, 1H), 3.79-3.50 (m, 2H), 2.47-2.29 (m, 1H), 2.08 (dddd, J=42.5, 13.8, 9.9, 3.4 Hz, 1H).

Example 166

Preparation of (2R,3S)—N-([5-cyano-2-[6-(trifluoromethyl)pyridin-3-yl]pyridin-4-yl]methyl)-3-fluoro-1-[(4-fluorobenzene)sulfonyl]pyrrolidine-2-carboxamide

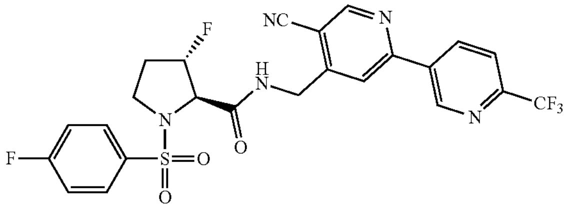 [SMILES: N#Cc1cnc(-c2ccc(C(F)(F)F)nc2)cc1CNC(=O)[C@@H]1[C@@H](F)CCN1S(=O)(=O)c1ccc(F)cc1]

Step 1: Preparation of 4-([[(2S,3R)-1-[(tert-butoxy)carbonyl]-3-hydroxypyrrolidin-2-yl]formamido]methyl)-6-[6-(trifluoromethyl)pyridin-3-yl]pyridine-3-carboxylate

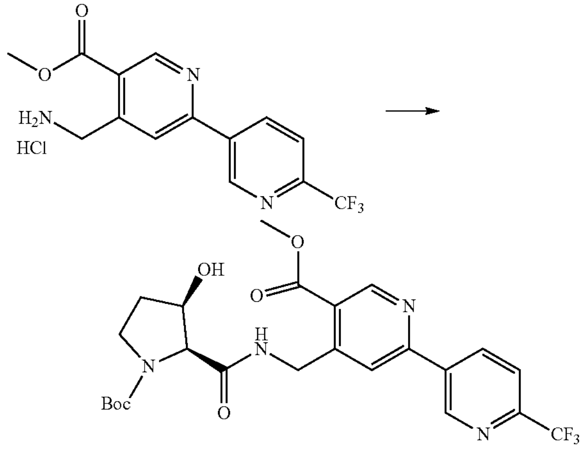

A solution of (2S,3R)-1-[(tert-butoxy)carbonyl]-3-hydroxypyrrolidine-2-carboxylic acid (318 mg, 1.38 mmol, 1.00 equiv), DIEA (356 mg, 2.75 mmol, 2.00 equiv), HATU (525 mg, 1.38 mmol, 1.00 equiv), and methyl 4-(aminomethyl)-6-[6-(trifluoromethyl)pyridin-3-yl]pyridine-3-carboxylate (430 mg, 1.38 mmol, 1.00 equiv) in DMF (10 mL) was stirred for 1 h at 20° C. The resulting solution was diluted with ethyl acetate, washed with water, dried over anhydrous sodium sulfate, and concentrated under vacuum. The residue was purified by a silica gel column eluting with DCM/MeOH (10:1) to afford the title compound (450 mg, 62%) as a white solid.

Step 2: Preparation of 4-([[(2S,3R)-1-[(tert-butoxy)carbonyl]-3-hydroxypyrrolidin-2-yl]formamido]methyl)-6-[6-(trifluoromethyl)pyridin-3-yl]pyridine-3-carboxylic acid

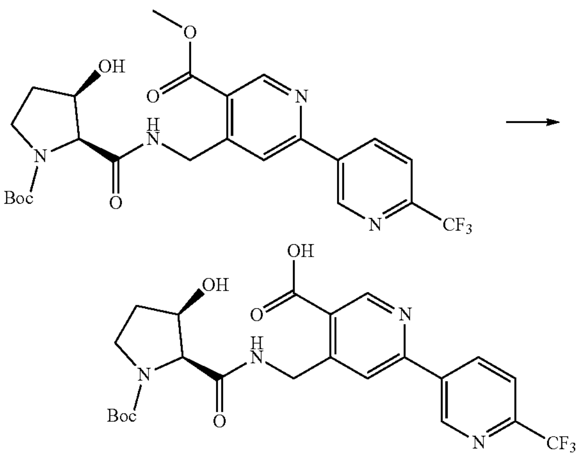

A solution of methyl 4-([[(2S,3R)-1-[(tert-butoxy)carbonyl]-3-hydroxypyrrolidin-2-yl]formamido]methyl)-6-[6-(trifluoromethyl)pyridin-3-yl]pyridine-3-carboxylate (280 mg, 0.53 mmol, 1.00 equiv) and LiOH (64 mg, 2.67 mmol, 5.00 equiv) in THF (2 mL)/water (2 mL) was stirred for 4 h at room temperature. The resulting solution was diluted with water. The pH value of the solution was adjusted to 4 with AcOH, extracted with ethyl acetate, washed with water and brine, dried over anhydrous sodium sulfate, and concentrated under vacuum. This resulted in 180 mg (66%) of the title compound as a yellow solid.

Step 3: Preparation of tert-butyl (2S,3R)-2-[([5-carbamoyl-2-[6-(trifluoromethyl)pyridin-3-yl]pyridin-4-yl]methyl)carbamoyl]-3-hydroxypyrrolidine-1-carboxylate

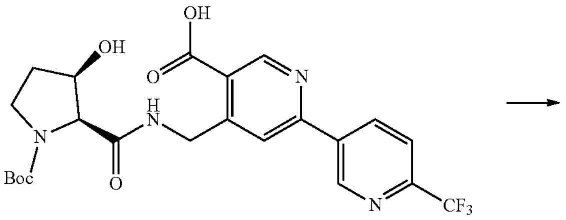

-continued

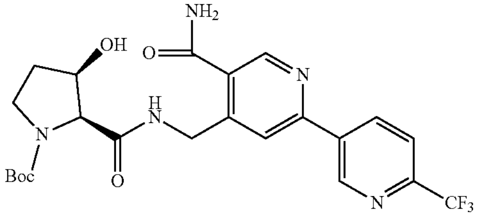

A solution of 4-([[(2S,3R)-1-[(tert-butoxy)carbonyl]-3-hydroxypyrrolidin-2-yl]formamido]methyl)-6-[6-(trifluoromethyl)pyridin-3-yl]pyridine-3-carboxylic acid (180 mg, 0.35 mmol, 1.00 equiv), HATU (147 mg, 0.39 mmol, 1.10 equiv), DIEA (182 mg, 1.41 mmol, 4.00 equiv), and $NH_4Cl$ (20.58 mg, 0.38 mmol, 1.10 equiv) in DMF (5 mL) was stirred for 3 h at room temperature. The reaction was quenched with water, extracted with ethyl acetate, dried over anhydrous sodium sulfate, and concentrated under vacuum. This resulted in 155 mg (86%) of the title compound as brown oil.

Step 4

Preparation of tert-butyl (2R,3S)-2-[([5-carbamoyl-2-[6-(trifluoromethyl)pyridin-3-yl]pyridin-4-yl]methyl)carbamoyl]-3-fluoropyrrolidine-1-carboxylate

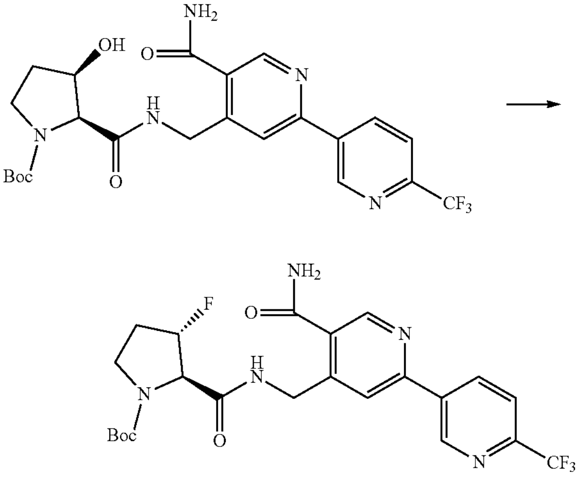

DAST (237.2 mg, 1.47 mmol, 5.00 equiv) was added to the solution of tert-butyl (2S,3R)-2-[([5-carbamoyl-2-[6-(trifluoromethyl)pyridin-3-yl]pyridin-4-yl]methyl)carbamoyl]-3-hydroxypyrrolidine-1-carboxylate (150 mg, 0.29 mmol, 1.00 equiv) in chloroform (2 mL) dropwise at 0° C. The resulting solution was stirred for 2 h at room temperature and then quenched with of water, extracted with dichloromethane, washed with sodium bicarbonate/water, dried over anhydrous sodium sulfate, and concentrated under vacuum. The residue was purified by a silica gel column eluting with ethyl acetate/petroleum ether (3/2) to afford the title compound (50 mg, 33%) as a yellow solid.

Step 5: Preparation of tert-butyl (2R,3S)-2-[([5-cyano-2-[6-(trifluoromethyl)pyridin-3-yl]pyridin-4-yl]methyl)carbamoyl]-3-fluoropyrrolidine-1-carboxylate

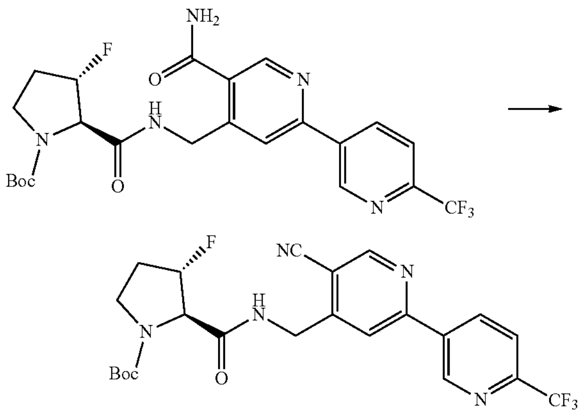

A solution of tert-butyl (2R,3S)-2-[([5-carbamoyl-2-[6-(trifluoromethyl)pyridin-3-yl]pyridin-4-yl]methyl)carbamoyl]-3-fluoropyrrolidine-1-carboxylate (40 mg, 0.08 mmol, 1.00 equiv), TFAA (32.8 mg, 0.16 mmol, 2.00 equiv), and TEA (12 mg, 0.12 mmol, 1.50 equiv) in dichloromethane (3 mL) was stirred for 15 min at room temperature. The reaction was then quenched with water, extracted with dichloromethane, washed with saturated sodium bicarbonate and brine, dried over anhydrous sodium sulfate, and concentrated under vacuum. This resulted in 50 mg (crude) of the title compound as orange oil.

Step 6: Preparation of (2R,3S)—N-([5-cyano-2-[6-(trifluoromethyl)pyridin-3-yl]pyridin-4-yl]methyl)-3-fluoropyrrolidine-2-carboxamide hydrochloride

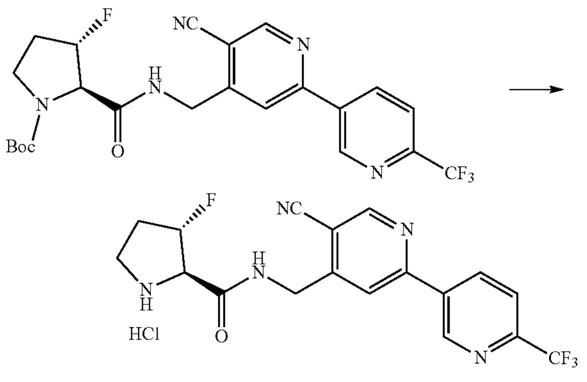

A mixture of tert-butyl (2R,3S)-2-[([5-cyano-2-[6-(trifluoromethyl)pyridin-3-yl]pyridin-4-yl]methyl)carbamoyl]-3-fluoropyrrolidine-1-carboxylate (50 mg, 0.10 mmol, 1.00 equiv) and saturated hydrogen chloride in 1,4-dioxane (3 mL) was stirred for 0.5 h at room temperature. The solids were collected by filtration. This resulted in 40 mg (92%) of the title compound as a dark red solid.

Step 7: Preparation of (2R,3S)—N-([5-cyano-2-[6-(trifluoromethyl)pyridin-3-yl]pyridin-4-yl]methyl)-3-fluoro-1-[(4-fluorobenzene)sulfonyl]pyrrolidine-2-carboxamide

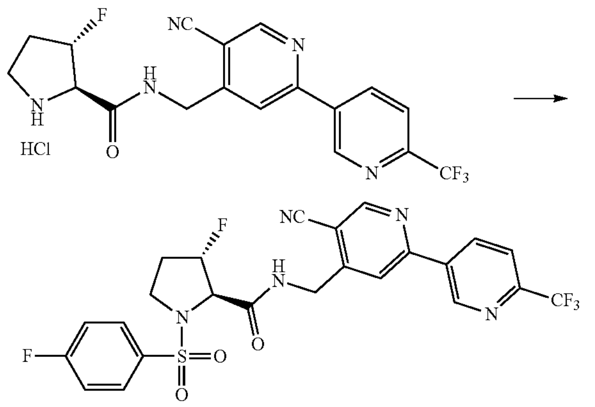

4-Fluorobenzene-1-sulfonyl chloride (19.9 mg, 102.20 mmol, 1.10 equiv) was added into a solution of (2R,3S)—N-([5-cyano-2-[6-(trifluoromethyl)pyridin-3-yl]pyridin-4-yl]methyl)-3-fluoropyrrolidine-2-carboxamide hydrochloride (40 mg, 93.06 mmol, 1.00 equiv), and TEA (28 mg, 276.70 mmol, 3.00 equiv) in dichloromethane (5 mL). This was stirred for 2 h at room temperature. The reaction was then quenched with water, extracted with dichloromethane, dried over anhydrous sodium sulfate, and concentrated under vacuum. The residue was purified by a silica gel column eluting with ethyl acetate/petroleum ether (3:2) to afford the title compound 12.6 mg (crude) of as a pink solid.

$^1$H NMR (300 MHz, $CDCl_3$) δ 9.48 (s, 1H), 8.95 (s, 1H), 8.68-8.65 (d, J=8.1 Hz, J=1.2 Hz, 1H), 8.11 (s, 1H), 7.93-7.89 (m, 2H), 7.82-7.79 (d, J=8.1 Hz, 1H), 7.70 (t, J=6.0 Hz, 1H), 7.32-7.26 (m, 2H), 5.39-5.22 (dd, J=49.8 Hz, J=1.8 Hz, 1H), 5.11-5.02 (dd, J=17.4 Hz, J=7.8 Hz, 1H), 4.61 (dd, J=17.7 Hz, J=4.8 Hz, 1H), 4.41-4.33 (d, J=23.1 Hz, 1H), 3.83 (t, J=8.4 Hz, 1H), 3.34-3.25 (m, 1H), 2.23-1.98 (m, 2H).

Example 167

Preparation of (2S,4R)-4-fluoro-N-((5-fluoro-4-(2-(trifluoromethyl)pyrimidin-5-yl)pyridin-2-yl)methyl)-1-(4-fluorophenylsulfonyl)pyrrolidine-2-carboxamide

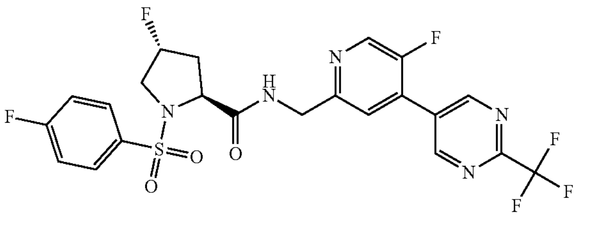 [SMILES: O=C(NCc1cc(-c2cnc(C(F)(F)F)nc2)c(F)cn1)[C@@H]1C[C@@H](F)CN1S(=O)(=O)c1ccc(F)cc1]

Step 1: Preparation of [5-fluoro-2-([[(2S,4R)-4-fluoro-1-[(4-fluorobenzene)sulfonyl]pyrrolidin-2-yl]formamido]methyl)pyridin-4-yl]boronic acid

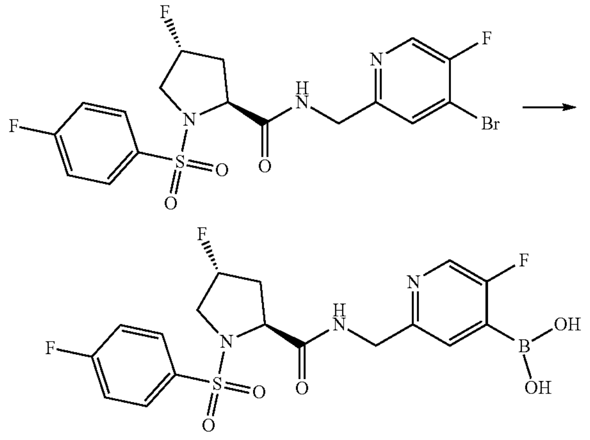

A mixture of (2S,4R)—N-[(4-bromo-5-fluoropyridin-2-yl)methyl]-4-fluoro-1-[(4-fluorobenzene)sulfonyl]pyrrolidine-2-carboxamide (300 mg, 0.63 mmol, 1.00 equiv), 4,4,5,5-tetramethyl-2-(tetramethyl-1,3,2-dioxaborolan-2-yl)-1,3,2-dioxaborolane (238 mg, 0.94 mmol, 1.50 equiv), KOAc (184 mg, 1.87 mmol, 3.00 equiv), and Pd(dppf)$Cl_2$ (46 mg, 0.06 mmol, 0.10 equiv) in 1,4-dioxane (20 mL) was stirred for 12 h at 75° C. under nitrogen. The solids were filtered out. The filtrate was diluted with water and extracted with ethyl acetate. The combined extracts were washed with brine, dried over anhydrous sodium sulfate, and concentrated under vacuum. This resulted in the title compound (500 mg, crude) as brown oil.

Step 2: Preparation of (2S,4R)-4-fluoro-N-((5-fluoro-4-(2-(trifluoromethyl)pyrimidin-5-yl)pyridin-2-yl)methyl)-1-(4-fluorophenylsulfonyl)pyrrolidine-2-carboxamide

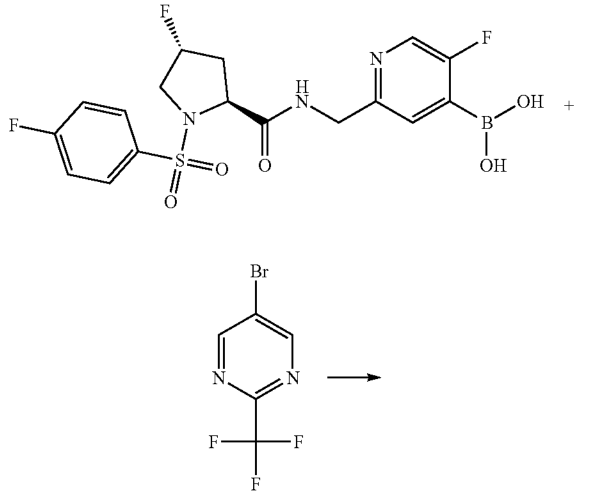

-continued

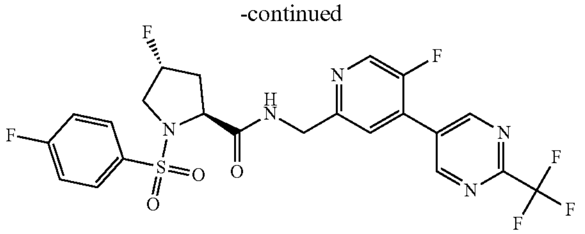

A mixture of [5-fluoro-2-([[(2S,4R)-4-fluoro-1-[(4-fluorobenzene)sulfonyl]pyrrolidin-2-yl]formamido]methyl)pyridin-4-yl]boronic acid (278 mg, 0.627 mmol, 1.00 equiv), 5-bromo-2-(trifluoromethyl)pyrimidine (284 mg, 1.251 mmol, 2.00 equiv), potassium carbonate (260 mg, 1.881 mmol, 3.00 equiv), and Pd(dppf)$Cl_2$ (46 mg, 0.063 mmol, 0.100 equiv) in 1,4-dioxane (20 mL)/water (2 mL) was stirred for 4 h at 70° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/1). The crude product (100 mg) was purified by Prep-HPLC to afford the titled compound (35.5 mg, 10%) as a white solid.

$^1$H NMR (300 MHz, $CDCl_3$) δ 9.23 (s, 2H), 8.61 (s, 1H), 7.90-7.86 (m, 2H), 7.72-7.70 (d, J=6 Hz, 1H), 7.58-7.54 (t, J=5.86 Hz, 1H), 7.26-7.24 (d, J=7.2 Hz, 2H), 5.15-4.92 (m, 2H), 4.56-4.48 (m, 1H), 4.32-4.26 (t, J=8.7 Hz, 1H), 3.94-3.59 (m, 2H), 2.60-2.54 (m, 1H), 2.32-2.01 (m, 1H).

Example 168

Preparation of (2R,3S)-3-fluoro-1-(4-fluorophenyl)sulfonyl-N-[[2-[2-(trifluoromethyl)pyrimidin-5-yl]-4-pyridyl]methyl]pyrrolidine-2-carboxamide

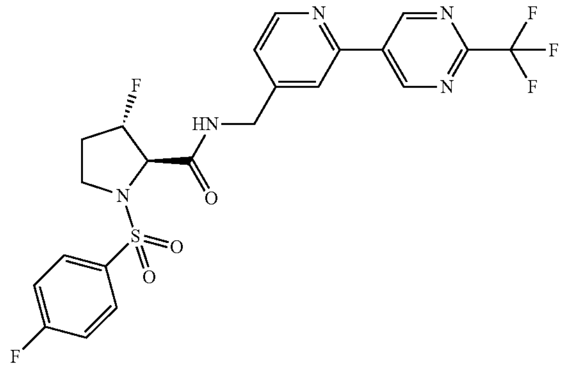 [SMILES: O=C(NCc1ccnc(-c2cnc(C(F)(F)F)nc2)c1)[C@@H]1[C@@H](F)CCN1S(=O)(=O)c1ccc(F)cc1]

Preparation of the title compound follows the same general procedure as Example 55.

1H NMR (400 MHz, DMSO) δ 9.69-9.65 (s, 2H), 9.16-9.09 (t, J=6.0 Hz, 1H), 8.77-8.73 (m, 1H), 8.17-8.12 (s, 1H), 8.06-7.98 (m, 2H), 7.55-7.45 (m, 3H), 5.30-5.13 (m, 1H), 4.59-4.42 (m, 2H), 4.42-4.33 (d, J=24.3 Hz, 1H), 3.75-3.64 (ddd, J=9.4, 7.5, 2.3 Hz, 1H), 3.24-3.12 (ddd, J=10.8, 9.1, 7.3 Hz, 1H), 2.25-2.05 (m, 2H)., LCMS (ESI) m/z:527.2 [M+H]+

Example 169

Preparation of (2S,4R)-4-fluoro-1-[(4-fluorobenzene)sulfonyl]-N-([5-methyl-2-[2-(trifluoromethyl)pyrimidin-5-yl]pyridin-4-yl]methyl)pyrrolidine-2-carboxamide

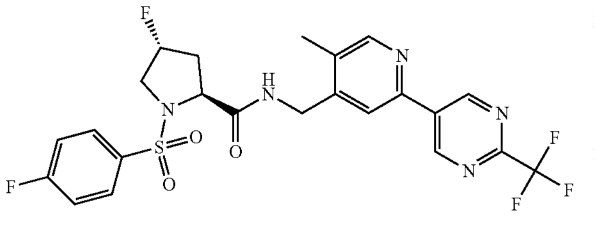 [SMILES: Cc1cnc(-c2cnc(C(F)(F)F)nc2)cc1CNC(=O)[C@@H]1C[C@@H](F)CN1S(=O)(=O)c1ccc(F)cc1]

Step 1: Preparation of 5-(tetramethyl-1,3,2-dioxaborolan-2-yl)-2-(trifluoromethyl)pyrimidine

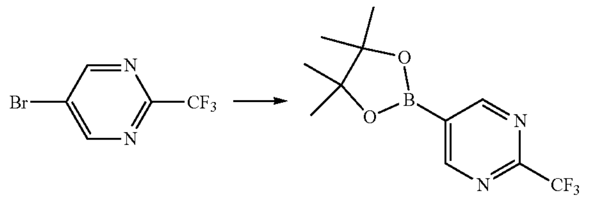 [SMILES: FC(F)(F)c1ncc(Br)cn1 ; CC1(C)OB(c2cnc(C(F)(F)F)nc2)OC1(C)C]

A mixture of 5-bromo-2-(trifluoromethyl)pyrimidine (10.0 g, 44.056 mmol, 1.0 equiv), 4,4,5,5-tetramethyl-2-(tetramethyl-1,3,2-dioxaborolan-2-yl)-1,3,2-dioxaborolane (11.19 g, 44.066 mmol, 1.0 equiv), and $Pd(OAc)_2$ (100 mg, 0.445 mmol) in DMF (100 mL) was stirred for 12 h at 70° C. under nitrogen. The reaction mixture was then quenched with water, extracted with ethyl acetate, washed with brine, dried over anhydrous sodium sulfate, and concentrated under vacuum. This resulted in the title compound (10 g, 83%) as black oil.

Step 2: Preparation of methyl 5-chloro-2-[2-(trifluoromethyl)pyrimidin-5-yl]pyridine-4-carboxylate

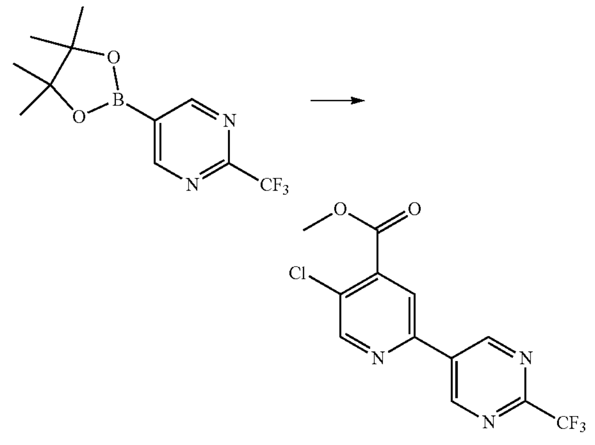

A mixture of 5-(tetramethyl-1,3,2-dioxaborolan-2-yl)-2-(trifluoromethyl)pyrimidine (3 g, 10.95 mmol, 1.00 equiv), methyl 2,5-dichloropyridine-4-carboxylate (6 g, 29.12 mmol, 1.00 equiv), $Pd(dppf)Cl_2$ (1.55 g, 2.12 mmol, 0.20 equiv), and potassium carbonate (8.78 g, 63.53 mmol, 5.80 equiv) in dioxane (100 mL)/water(5 mL) was stirred for 12 h at 60° C. under nitrogen. The reaction mixture was concentrated under vacuum. The residue purified by a silica gel column eluting with ethyl acetate/petroleum ether (1:10) to afford the title compound (1.4 g, 40%) as a white solid.

Step 3: Preparation of methyl 5-methyl-2-[2-(trifluoromethyl)pyrimidin-5-yl]pyridine-4-carboxylate

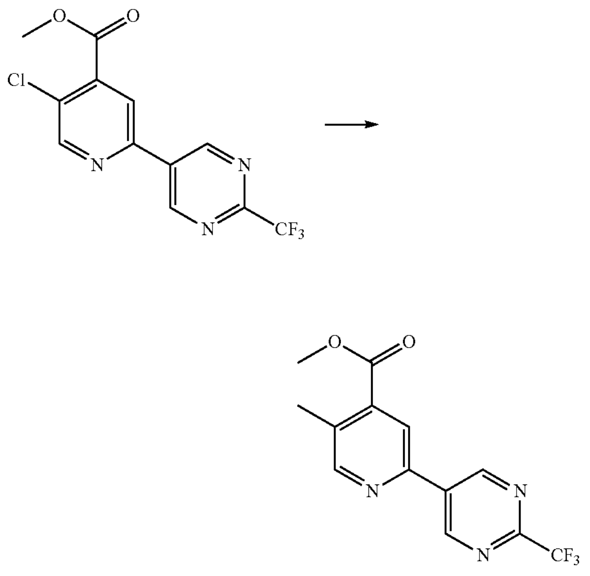 [SMILES: COC(=O)c1cc(-c2cnc(C(F)(F)F)nc2)ncc1Cl ; COC(=O)c1cc(-c2cnc(C(F)(F)F)nc2)ncc1C]

A mixture of methyl 5-chloro-2-[2-(trifluoromethyl)pyrimidin-5-yl]pyridine-4-carboxylate (600.00 mg, 1.89 mmol, 1.00 equiv), $Pd(dppf)Cl_2$ (230.35 mg, 0.315 mmol, 0.200 equiv), and $Zn(CH_3)_2$ (4.8 ml, 3.000 equiv, 1.2 mol/L in toluene) in dioxane (20 mL) was stirred for 12 h at 65° C. under nitrogen. The reaction mixture was concentrated under vacuum. The residue was purified by a silica gel column eluting with ethyl acetate/petroleum ether (1:10) to afford the title compound (400 mg, 71%) as a white solid.

Step 4: Preparation of [5-methyl-2-[2-(trifluoromethyl)pyrimidin-5-yl]pyridin-4-yl]methanol

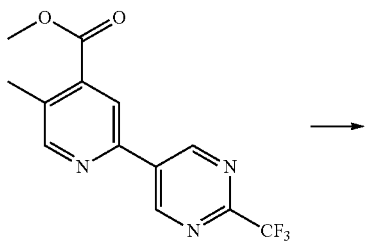

-continued

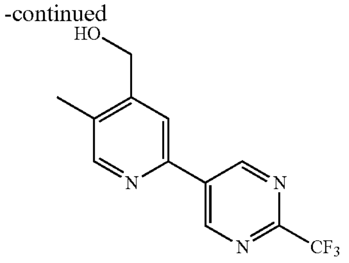

DIBAl-H (4 mL, 1 mol/L in hexanes, 3.000 equiv) was added dropwise into a solution of methyl 5-methyl-2-[2-(trifluoromethyl)pyrimidin-5-yl]pyridine-4-carboxylate (380.00 mg, 1.278 mmol, 1.000 equiv) in THF (20 mL) at −78° C. under nitrogen. The resulting solution was stirred for 30 min at −78° C. The resulting solution was stirred for 12 h at room temperature and quenched by methanol. The pH value of the solution was adjusted to 9 with sodium hydroxide (1 mol/L). The resulting solution was extracted with ethyl acetate, washed with brine, dried over anhydrous sodium sulfate, and concentrated under vacuum. The residue was purified by a silica gel column eluting with ethyl acetate/petroleum ether (1:1). This resulted in the title compound (250 mg, 73%) as a white solid.

Step 5: Preparation of 2-([5-methyl-2-[2-(trifluoromethyl)pyrimidin-5-yl]pyridin-4-yl]methyl)-2,3-dihydro-1H-isoindole-1,3-dione

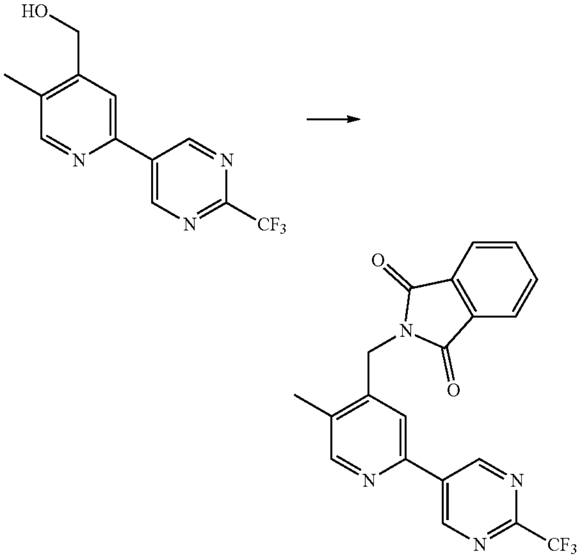

DIAD (300.43 mg, 1.486 mmol, 2.0 equiv) was added dropwise into a solution of [5-methyl-2-[2-(trifluoromethyl)pyrimidin-5-yl]pyridin-4-yl]methanol (200.0 mg, 0.743 mmol, 1.0 equiv), $PPh_3$ (389.69 mg, 1.486 mmol, 2.0 equiv), and 2,3-dihydro-1H-isoindole-1,3-dione (131.16 mg, 0.891 mmol, 1.2 equiv) in THF (20 mL) at 0° C. under nitrogen. The resulting solution was stirred for 10 min at 0° C. and 12 h at room temperature. The mixture was concentrated under vacuum. The solid was washed with ethyl acetate to afford the title compound (400 mg) as a white solid.

Step 6: Preparation of [5-methyl-2-[2-(trifluoromethyl)pyrimidin-5-yl]pyridin-4-yl]methanamine

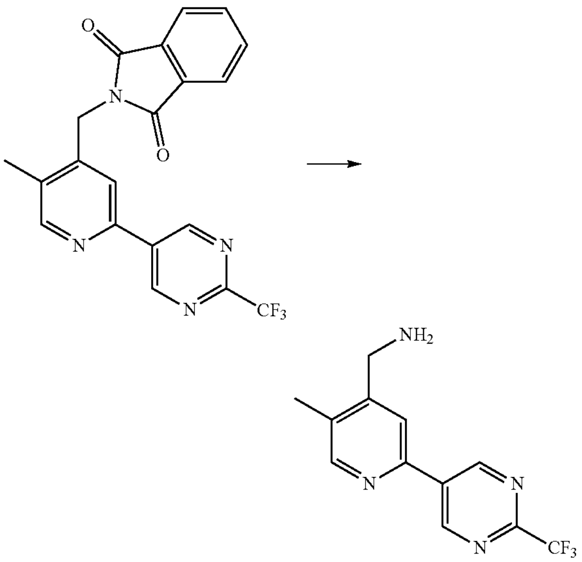

A mixture of 2-([5-methyl-2-[2-(trifluoromethyl)pyrimidin-5-yl]pyridin-4-yl]methyl)-2,3-dihydro-1H-isoindole-1,3-dione (400.00 mg, 1.004 mmol, 1.000 equiv) and $NH_2NH_2.H_2O$ (502.69 mg, 10.042 mmol, 10.000 equiv) in methanol (40 mL) was stirred for 12 h at 60° C. The reaction mixture was concentrated under vacuum. The resulting solution was diluted with ethyl acetate and the solids were filtered out. The liquid was concentrated under vacuum to afford the title compound (200 mg, 74%) as a white solid.

Step 7: Preparation of tert-butyl (2S,4R)-4-fluoro-2-[([5-methyl-2-[2-(trifluoromethyl)pyrimidin-5-yl]pyridin-4-yl]methyl)carbamoyl]pyrrolidine-1-carboxylate

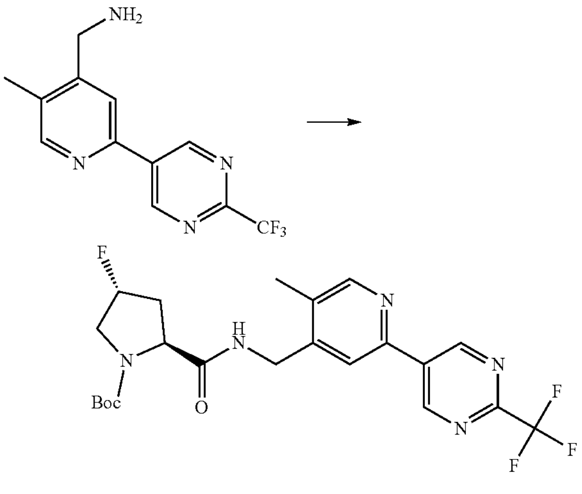

A solution of (2S,4R)-1-[(tert-butoxy)carbonyl]-4-fluoropyrrolidine-2-carboxylic acid (130.43 mg, 0.559 mmol, 1.000 equiv), HATU (318.95 mg, 0.839 mmol, 1.500 equiv), DIEA (216.83 mg, 1.678 mmol, 3.000 equiv), and [5-methyl-2-[2-(trifluoromethyl)pyrimidin-5-yl]pyridin-4-yl]methanamine (150.0 mg, 0.559 mmol, 1.0 equiv) in DMF (5 mL) was stirred for 2 h at room temperature. The reaction mixture was diluted with ethyl acetate, washed with brine, dried over anhydrous sodium sulfate, and concentrated under vacuum. The residue was purified by a silica gel column eluting with ethyl acetate/petroleum ether (1:1) to afford the title compound (200 mg, 74%) as a white solid.

Step 8: Preparation of (2S,4R)-4-fluoro-N-((5-methyl-2-(2-(trifluoromethyl)pyrimidin-5-yl)pyridin-4-yl)methyl)pyrrolidine-2-carboxamide hydrochloride

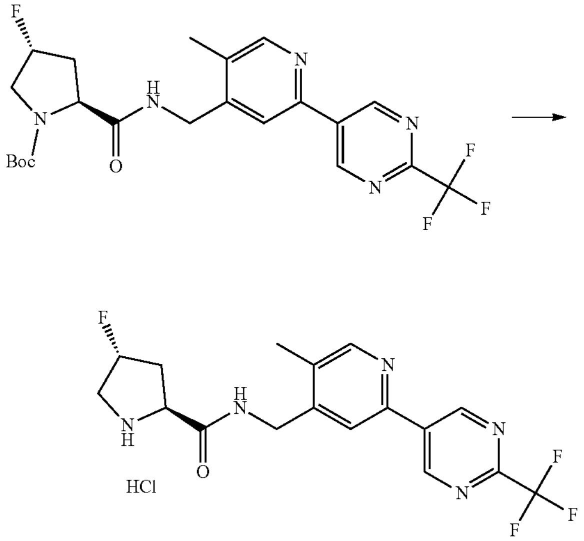 [SMILES: Cc1cnc(-c2cnc(C(F)(F)F)nc2)cc1CNC(=O)[C@@H]1C[C@@H](F)CN1C(=O)OC(C)(C)C ; Cc1cnc(-c2cnc(C(F)(F)F)nc2)cc1CNC(=O)[C@@H]1C[C@@H](F)CN1 ; Cl]

A mixture of tert-butyl (2S,4R)-4-fluoro-2-[([5-methyl-2-[2-(trifluoromethyl)pyrimidin-5-yl]pyridin-4-yl]methyl)carbamoyl]pyrrolidine-1-carboxylate (200 mg, 0.414 mmol, 1.000 equiv) and saturated HCl in dioxane (20 mL) was stirred for 2 h at room temperature. The reaction mixture was concentrated under vacuum. This resulted in the title compound (150 mg, 95%) as a white solid.

Step 9: Preparation of (2S,4R)-4-fluoro-1-[(4-fluorobenzene)sulfonyl]-N-([5-methyl-2-[2-(trifluoromethyl)pyrimidin-5-yl]pyridin-4-yl]methyl)pyrrolidine-2-carboxamide

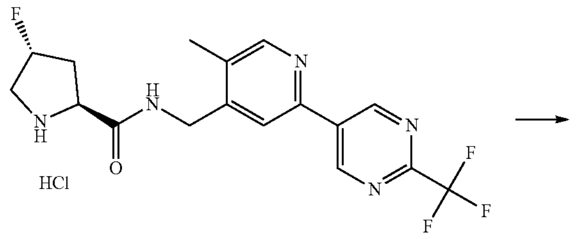

-continued

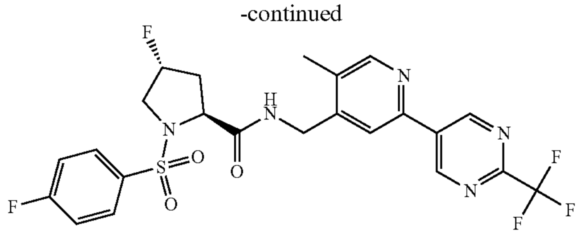

A solution of (2S,4R)-4-fluoro-N-((5-methyl-2-(2-(trifluoromethyl)pyrimidin-5-yl)pyridin-4-yl)methyl)pyrrolidine-2-carboxamide hydrochloride (200.00 mg, 0.522 mmol, 1.0 equiv), triethylamine (158.38 mg, 1.565 mmol, 3.0 equiv), and 4-fluorobenzene-1-sulfonyl chloride (203.07 mg, 1.04 mmol, 2.0 equiv) in DCM (10 mL) was stirred for 12 h at room temperature. The reaction was then quenched by water, extracted with dichloromethane, dried over anhydrous sodium sulfate, and concentrated under vacuum. The residue was purified by a silica gel column eluting with ethyl acetate/petroleum ether (1:1). The crude product (200 mg) was re-purified by Flash-Prep-HPLC to afford the title compound (105.5 mg, 37%) as a white solid.

$^1$H NMR (300 MHz, $CDCl_3$) δ 9.65 (s, 2H), 8.51 (s, 1H), 8.04 (s, 1H), 7.92-7.88 (m, 2H), 7.46-7.43 (m, 1H), 7.28-7.23 (m, 2H), 5.05 (d, J=51.2 Hz, 1H), 4.89-4.83 (m, 2H), 4.36-4.32 (m, 2H), 3.95-3.86 (m, 1H), 3.74-3.60 (m, 1H), 2.63-2.61 (m, 1H), 2.39 (s, 3H), 2.28-2.00 (m, 1H).

Example 170

Preparation of (2S,4R)-4-fluoro-1-(4-fluorophenylsulfonyl)-N-((6'-(2-methoxyethoxy)-6-(trifluoromethyl)-3,4'-bipyridin-2'-yl)methyl)pyrrolidine-2-carboxamide

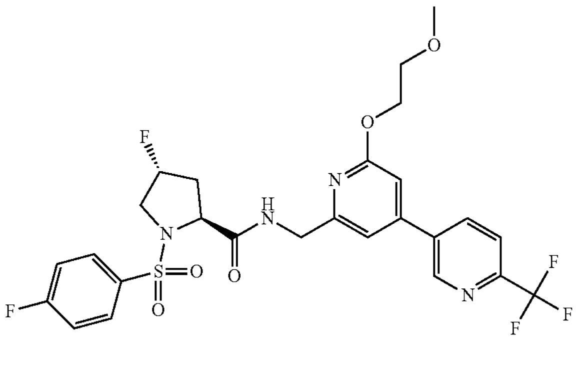 [SMILES: COCCOc1cc(-c2ccc(C(F)(F)F)nc2)cc(CNC(=O)[C@@H]2C[C@@H](F)CN2S(=O)(=O)c2ccc(F)cc2)n1]

Step 1: Preparation of 2,6-dichloro-4-[6-(trifluoromethyl)pyridin-3-yl]pyridine

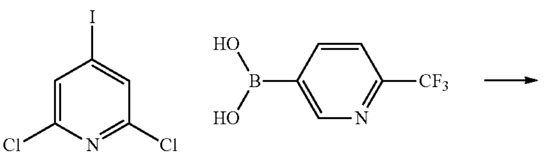

-continued

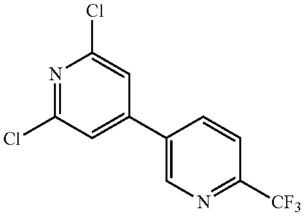

A mixture of Pd(dppf)$Cl_2$ (534 mg, 0.73 mmol, 0.10 equiv), potassium carbonate (2 g, 14.47 mmol, 2.00 equiv), 2,6-dichloro-4-iodopyridine (2 g, 7.30 mmol, 1.00 equiv), and [6-(trifluoromethyl)pyridin-3-yl]boronic acid (1.39 g, 7.28 mmol, 1.00 equiv) in 1,4-dioxane (80 mL)/water(8 mL) was stirred for 12 h at 60° C. under nitrogen. The solids were filtered out. The filtrate was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/50) to afford the title compound (1.9 g, 89%) as a solid.

Step 2: Preparation of 2-chloro-6-(2-methoxyethoxy)-4-[6-(trifluoromethyl)pyridin-3-yl]pyridine

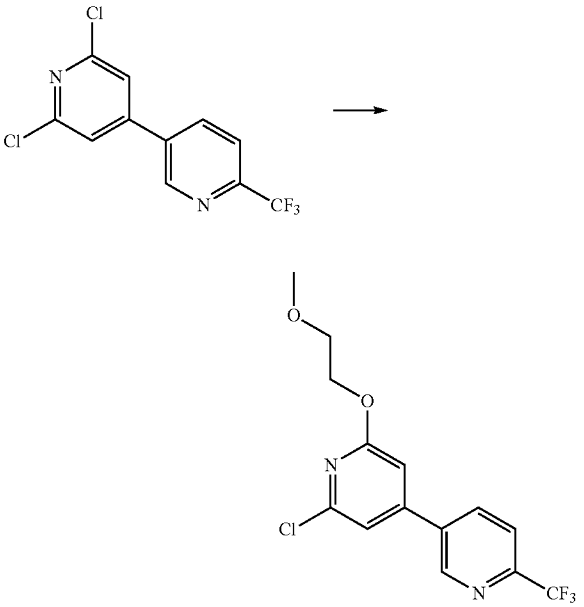 [SMILES: FC(F)(F)c1ccc(-c2cc(Cl)nc(Cl)c2)cn1 ; COCCOc1cc(-c2ccc(C(F)(F)F)nc2)cc(Cl)n1]

A solution of 2,6-dichloro-4-[6-(trifluoromethyl)pyridin-3-yl]pyridine (900 mg, 3.07 mmol, 1.00 equiv) and 1-methoxy-2-(sodiooxy)ethane (1.7 mL, 2.7 mmol/mL in 2-methoxyethan-1-ol, 1.50 equiv) in 2-methoxyethan-1-ol (18 mL) was stirred for 12 h at 60° C. The mixture was diluted with water and extracted with ethyl acetate. The combined extracts were washed with brine, dried over anhydrous sodium sulfate, and concentrated under vacuum. This resulted in the title compound (948 mg, 93%) as a white solid which was used for the next step without any further purification.

Step 3: Preparation of 6-(2-methoxyethoxy)-4-[6-(trifluoromethyl)pyridin-3-yl]pyridine-2-carbonitrile

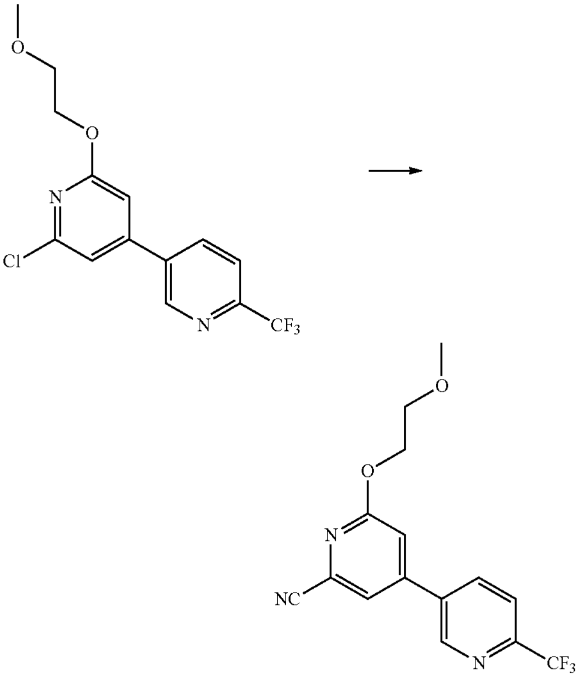

A mixture of 2-chloro-6-(2-methoxyethoxy)-4-[6-(trifluoromethyl)pyridin-3-yl]pyridine (400 mg, 1.202 mmol, 1.00 equiv), dppf (133 mg, 0.241 mmol, 0.20 equiv), $Zn(CN)_2$ (282 mg, 2.401 mmol, 2.0 equiv), and $Pd_2(dba)_3CHCl_3$ (62 mg, 0.060 mmol, 0.050 equiv) in N,N-dimethylformamide (8 mL) was irradiated with microwave radiation for 1 h at 100° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/5) to afford the title compound (350 mg, 90%) as a solid.

Step 4: Preparation of [6-(2-methoxyethoxy)-4-[6-(trifluoromethyl)pyridin-3-yl]pyridin-2-yl]methanamine hydrochloride

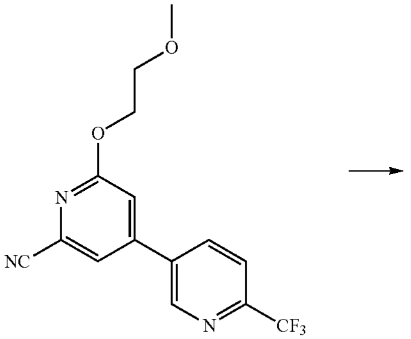

-continued

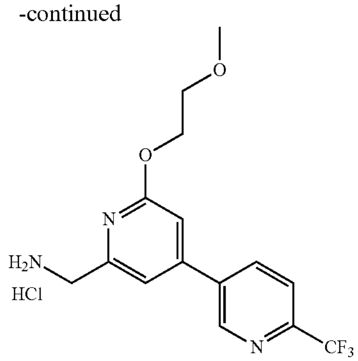

A mixture of 6-(2-methoxyethoxy)-4-[6-(trifluoromethyl) pyridin-3-yl]pyridine-2-carbonitrile (1 g, 3.093 mmol, 1.00 equiv), concentrated hydrogen chloride (4 mL), and palladium on carbon (2 g) in methanol (200 mL) was stirred for 7 min at room temperature under hydrogen. The solids were filtered out. The filtrate was concentrated under vacuum to afford the title compound (1.43 g, crude) as a yellow solid.

Step 5: Preparation of tert-butyl (2R,4S)-4-fluoro-2-([[6-(2-methoxyethoxy)-4-[6-(trifluoromethyl)pyridin-3-yl]pyridin-2-yl]methyl]carbamoyl)pyrrolidine-1-carboxylate

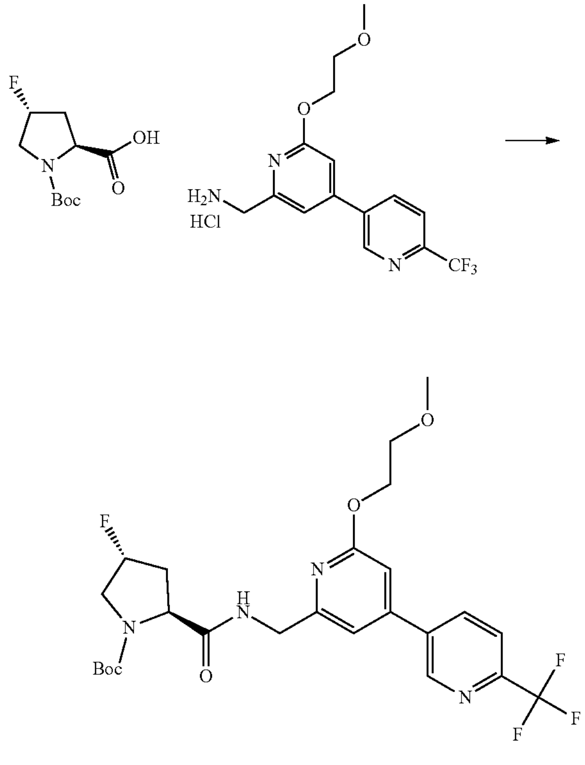

A mixture of (2S,4R)-1-[(tert-butoxy)carbonyl]-4-fluoro-pyrrolidine-2-carboxylic acid (235 mg, 1.008 mmol, 1.00 equiv), DIEA (355 mg, 2.747 mmol, 2.73 equiv), HATU (418 mg, 1.099 mmol, 1.09 equiv), and 6-(2-methoxy-ethoxy)-4-[6-(trifluoromethyl)pyridin-3-yl]pyridin-2-yl] methanamine (300 mg, 0.917 mmol, 0.91 equiv) in N,N-dimethylformamide (8 mL) was stirred for 10 min at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/1) to afford the title compound (450 mg, 82%) as a white solid.

Step 6: Preparation of 4-fluoro-N-[[6-(2-methoxyethoxy)-4-[6-(trifluoromethyl)pyridin-3-yl]pyridin-2-yl]methyl]-1H-pyrrole-2-carboxamide

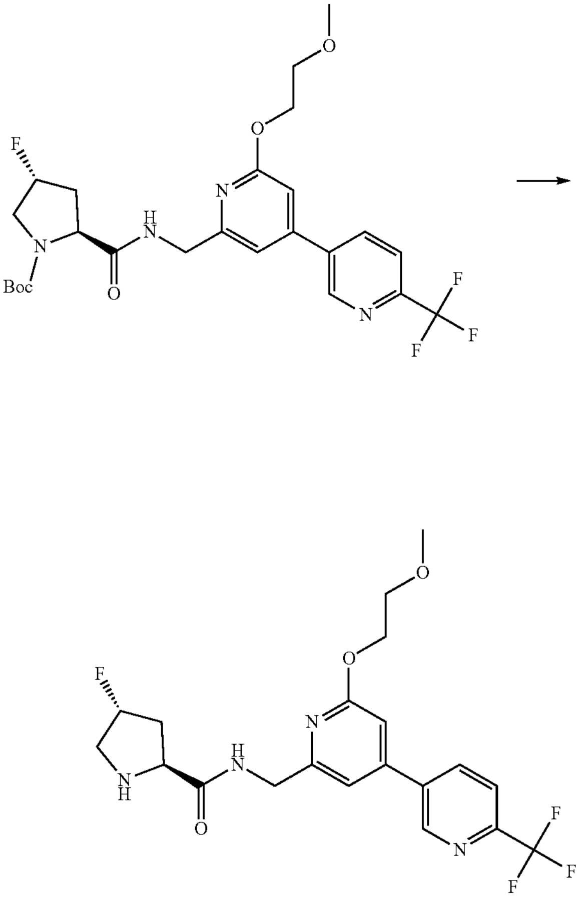

A solution of tert-butyl 4-fluoro-2-([[6-(2-methoxyethoxy)-4-[6-(trifluoromethyl)pyridin-3-yl]pyridin-2-yl] methyl]carbamoyl)-1H-pyrrole-1-carboxylate (450 mg, 0.836 mmol, 1.000 equiv) and trifluoroacetic acid (4 mL) in dichloromethane (20 mL) was stirred for 1 h at 25° C. The resulting mixture was concentrated under vacuum. The residue was dissolved in water. The pH value of the mixture was adjusted to 8 with saturated solution of sodium bicarbonate. The resulting mixture was extracted with ethyl acetate. The combined extracts were washed with brine, dried over anhydrous sodium sulfate and concentrated under vacuum. This resulted in the title compound (270 mg, 75%) as light yellow oil.

Step 7: Preparation of (2S,4R)-4-fluoro-1-(4-fluorophenylsulfonyl)-N-((6'-(2-methoxyethoxy)-6-(trifluoromethyl)-3,4'-bipyridin-2'-yl)methyl)pyrrolidine-2-carboxamide

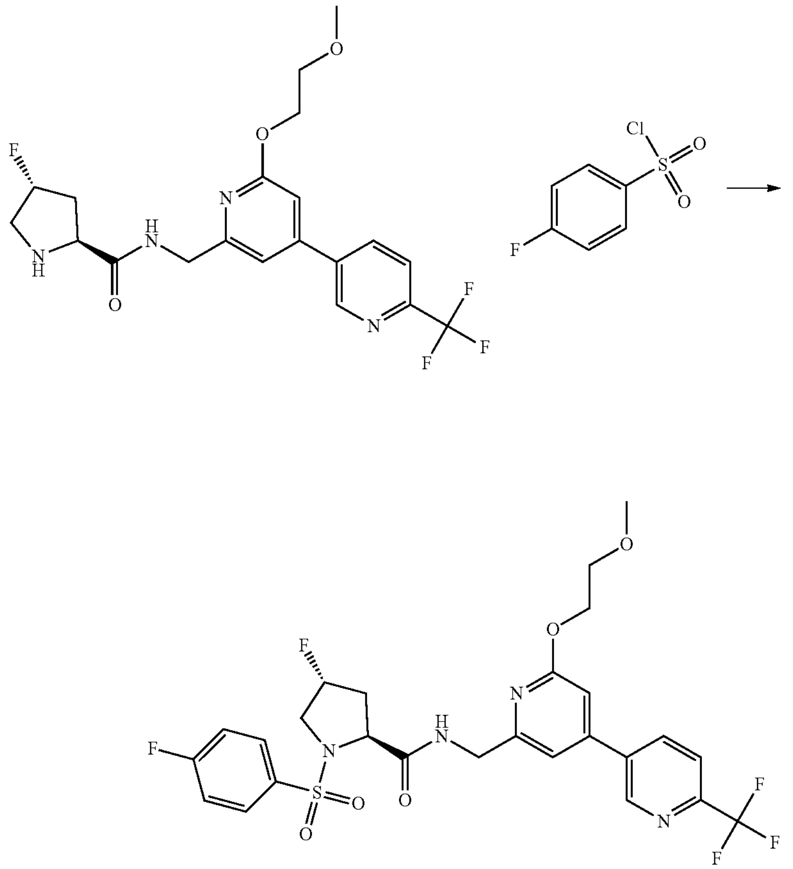

A mixture of 4-fluoro-N-[[6-(2-methoxyethoxy)-4-[6-(trifluoromethyl)pyridin-3-yl]pyridin-2-yl]methyl]-1H-pyrrole-2-carboxamide (270 mg, 0.616 mmol, 1.000 equiv), triethylamine (178 mg), and 4-fluorobenzene-1-sulfonyl chloride (138 mg, 0.709 mmol, 0.703 equiv) in dichloromethane (30 mL) was stirred for 12 h at 25° C. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/1). The crude product (300 mg) was purified by Prep-HPLC to afford the title compound (99 mg) as a white solid.

$^1H$ NMR (300 MHz, $CDCl_3$) δ 8.97 (s, 1H), 8.13-8.10 (m, 1H), 7.93-7.87 (m, 3H), 7.79-7.77 (m, 1H), 7.27-7.19 (m, 3H), 6.98 (s, 1H), 5.11-4.98 (d, J=52 Hz, 1H), 4.98-4.63 (m, 3H), 4.53-4.48 (m, 1H), 4.35-4.30 (m, 1H), 3.96-3.87 (m, 1H), 3.82-3.80 (m, 2H), 3.71-3.58 (m, 1H), 3.47 (s, 3H), 2.67-2.20 (m, 2H).

Example 171

Preparation of (2S,4R)-4-fluoro-1-(4-fluorophenyl)sulfonyl-N-[[2-fluoro-5-[2-(trifluoromethyl)pyrimidin-5-yl]-3-pyridyl]methyl]pyrrolidine-2-carboxamide

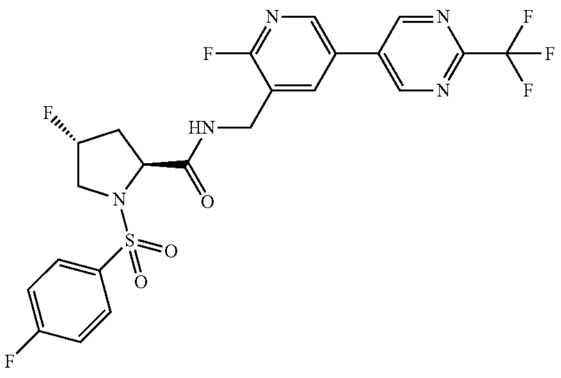

Preparation of the title compound follows the same general procedure as Example 48.

1H NMR (400 MHz, DMSO) δ 9.45-9.37 (d, J=2.3 Hz, 2H), 9.06-8.95 (dq, J=6.2, 2.8 Hz, 1H), 8.76-8.67 (t, J=2.5 Hz, 1H), 8.47-8.38 (dt, J=9.1, 2.6 Hz, 1H), 8.03-7.93 (ddd, J=8.2, 5.1, 2.4 Hz, 2H), 7.51-7.41 (td, J=8.9, 2.5 Hz, 2H), 5.30-5.07 (m, 1H), 4.52-4.38 (m, 2H), 4.24-4.13 (ddd, J=9.7, 7.2, 2.4 Hz, 1H), 3.76-3.55 (m, 2H), 2.46-2.30 (td, J=16.8, 16.3, 7.2 Hz, 1H), 2.20-1.98 (m, 1H)., LCMS (ESI) m/z: 546.2 [M+H]+

Example 172

Preparation of (1R,4S,5S)-3-(4-fluorophenyl)sulfonyl-N-[[2-[2-(trifluoromethyl)pyrimidin-5-yl]-4-pyridyl]methyl]-3-azabicyclo[3.1.0]hexane-4-carboxamide

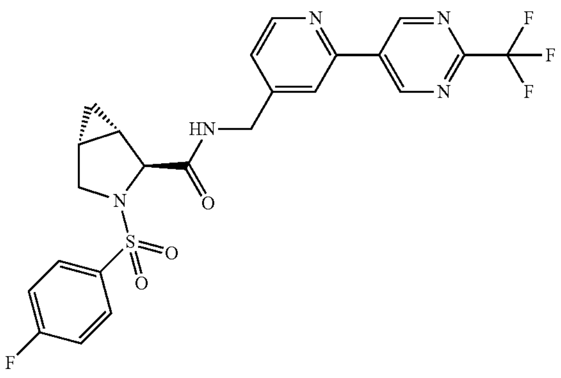 [SMILES: O=C(NCc1ccnc(-c2cnc(C(F)(F)F)nc2)c1)[C@@H]1[C@H]2C[C@H]2CN1S(=O)(=O)c1ccc(F)cc1]

Preparation of the title compound follows the same general procedure as Example 48.

1H NMR (400 MHz, DMSO) δ 9.68-9.63 (s, 2H), 8.92-8.85 (t, J=6.0 Hz, 1H), 8.77-8.71 (d, J=5.0 Hz, 1H), 8.17-8.10 (s, 1H), 7.97-7.89 (m, 2H), 7.51-7.42 (m, 3H), 4.58-4.38 (qd, J=16.7, 6.0 Hz, 2H), 4.24-4.21 (s, 1H), 3.82-3.71 (dd, J=10.4, 3.4 Hz, 1H), 3.54-3.45 (d, J=10.5 Hz, 1H), 1.68-1.51 (dtd, J=7.5, 5.9, 5.2, 3.7 Hz, 2H), 0.59-0.48 (td, J=7.8, 5.3 Hz, 1H), −0.77-−0.89 (q, J=4.4 Hz, 1H)., LCMS (ESI) m/z:522.2 [M+H]+

Example 173

Preparation of (2S,4R)-4-fluoro-1-(4-fluorophenyl)sulfonyl-N-[[3-fluoro-5-[2-(trifluoromethyl)thiazol-4-yl]phenyl]methyl]pyrrolidine-2-carboxamide

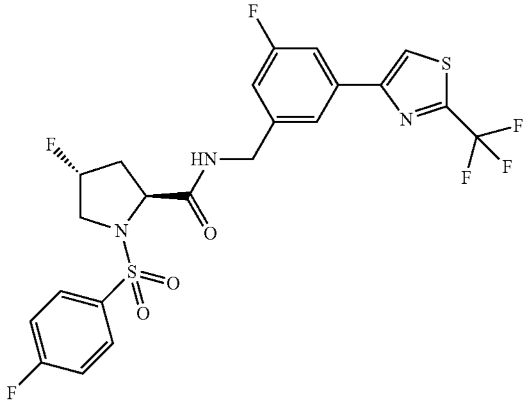 [SMILES: O=C(NCc1cc(F)cc(-c2csc(C(F)(F)F)n2)c1)[C@@H]1C[C@@H](F)CN1S(=O)(=O)c1ccc(F)cc1]

Preparation of the title compound follows the same general procedure as Example 91.

1H NMR (400 MHz, DMSO) δ 8.96-8.90 (t, J=6.1 Hz, 1H), 8.65-8.59 (q, J=0.9 Hz, 1H), 8.02-7.94 (m, 2H), 7.83-7.78 (t, J=1.5 Hz, 1H), 7.72-7.66 (ddd, J=9.4, 2.5, 1.6 Hz, 1H), 7.50-7.42 (m, 2H), 7.40-7.34 (ddd, J=9.7, 2.4, 1.4 Hz, 1H), 5.29-5.09 (m, 1H), 4.54-4.38 (m, 2H), 4.23-4.13 (dd, J=9.9, 7.1 Hz, 1H), 3.75-3.57 (m, 2H), 2.47-2.31 (m, 1H), 2.20-1.97 (m, 1H)., LCMS (ESI) m/z:550.2 [M+H]+

Example 174

Preparation of (2S,4R)-4-fluoro-1-(4-fluorophenyl)sulfonyl-N-[[3-fluoro-5-[2-(trifluoromethyl)thiazol-5-yl]phenyl]methyl]pyrrolidine-2-carboxamide

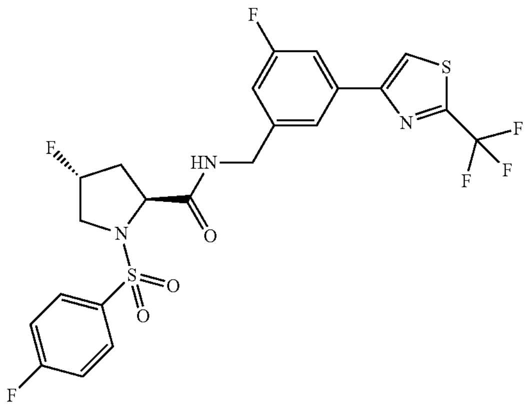 [SMILES: O=C(NCc1cc(F)cc(-c2csc(C(F)(F)F)n2)c1)[C@@H]1C[C@@H](F)CN1S(=O)(=O)c1ccc(F)cc1]

Preparation of the title compound follows the same general procedure as Example 91.

1H NMR (400 MHz, DMSO) δ 8.96-8.89 (t, J=6.0 Hz, 1H), 8.61-8.58 (q, J=1.1 Hz, 1H), 8.03-7.95 (m, 2H), 7.69-7.62 (m, 1H), 7.62-7.58 (t, J=1.5 Hz, 1H), 7.51-7.43 (m, 2H), 7.32-7.25 (ddd, J=9.7, 2.4, 1.4 Hz, 1H), 5.29-5.10 (dd, J=50.1, 3.0 Hz, 1H), 4.54-4.34 (m, 2H), 4.23-4.14 (dd, J=10.0, 7.1 Hz, 1H), 3.76-3.57 (m, 2H), 2.47-2.34 (m, 1H), 2.19-1.98 (m, 1H)., LCMS (ESI) m/z:550.2 [M+H]+

Example 175

Preparation of (2S,4R)-4-fluoro-1-(4-fluorophenyl) sulfonyl-N-[[3-fluoro-5-[4-(trifluoromethyl)thiazol-2-yl]phenyl]methyl]pyrrolidine-2-carboxamide

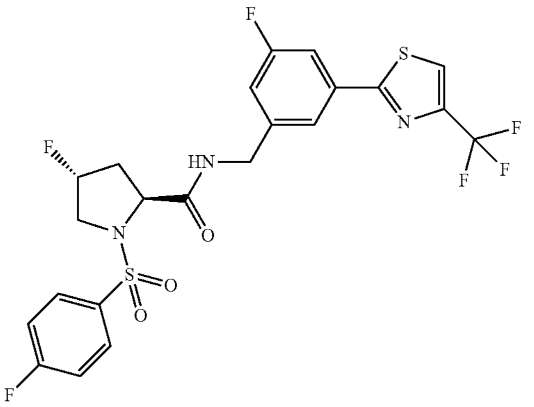 [SMILES: O=C(NCc1cc(F)cc(-c2nc(C(F)(F)F)cs2)c1)[C@@H]1C[C@@H](F)CN1S(=O)(=O)c1ccc(F)cc1]

Preparation of the title compound follows the same general procedure as Example 91.

1H NMR (400 MHz, DMSO) δ 8.92-8.86 (t, J=6.0 Hz, 1H), 8.65-8.62 (s, 1H), 8.01-7.94 (m, 2H), 7.82-7.79 (t, J=1.5 Hz, 1H), 7.74-7.68 (ddd, J=9.9, 2.5, 1.5 Hz, 1H), 7.49-7.41 (m, 2H), 7.26-7.20 (ddd, J=9.7, 2.4, 1.4 Hz, 1H), 5.28-5.10 (d, J=52.6 Hz, 1H), 4.50-4.37 (m, 2H), 4.22-4.15 (dd, J=9.8, 7.1 Hz, 1H), 3.74-3.56 (m, 2H), 2.46-2.33 (m, 1H), 2.20-1.98 (m, 1H)., LCMS (ESI) m/z:550.2 [M+H]+

Example 176

Preparation of (1S,2S,5R)—N-(2-cyano-5-(2-(trifluoromethyl)pyrimidin-5-yl)benzyl)-3-((4-fluorophenyl)sulfonyl)-3-azabicyclo[3.1.0]hexane-2-carboxamide

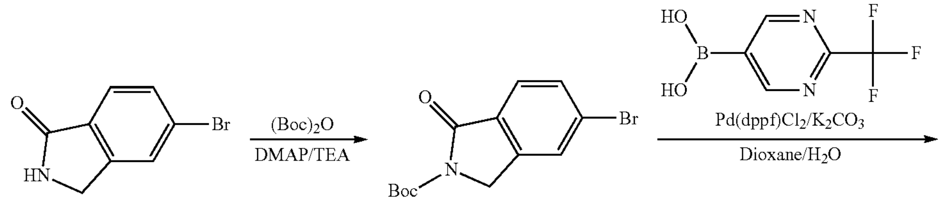

1 2

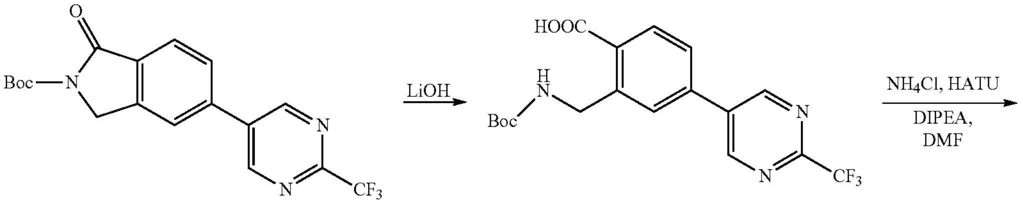

3 4

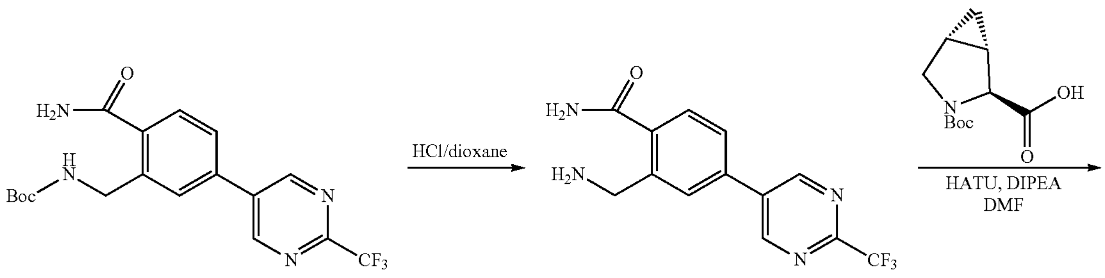

5 6

-continued

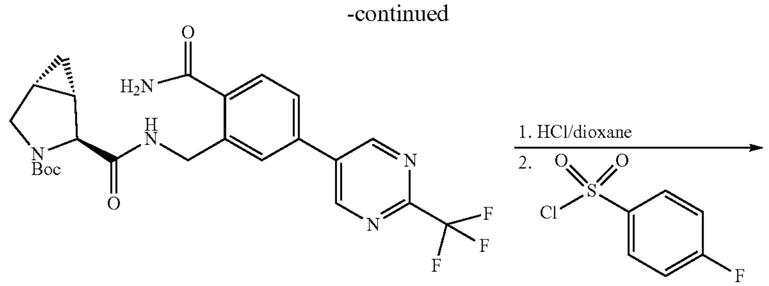

7

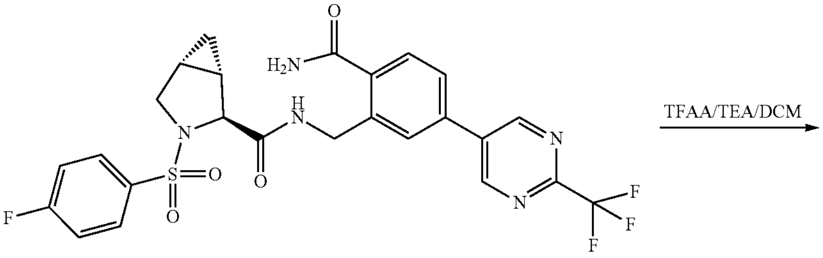

8

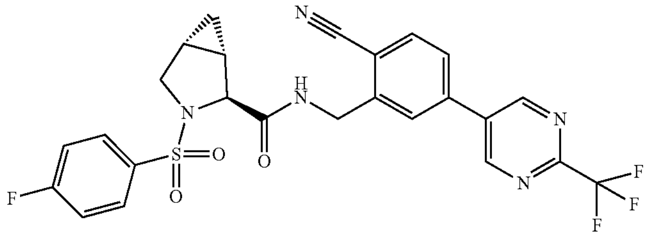

Step 1: tert-butyl 5-bromo-1-oxo-isoindoline-2-carboxylate 2A mixture of 5-bromoisoindolin-1-one 1 (5 g, 23.6 mmol), THF (50 mL), 4-dimethylaminopyridine (288 mg, 2.36 mmol) and di-tert-butyl dicarbonate (8 g, 35.4 mmol) was stirred for overnight at room temperature. The resulting mixture was concentrated under reduced pressure, diluted with ethyl acetate, washed with 10% citric acid. The organic layer was dried over $Na_2SO_4$, filtered and concentrated under reduced pressure. The residue was purified by flash chromatography on silica gel, eluting with ethyl acetate/heptane (1:1) to afford the compound 2 (7.1 g, 96%) as a white solid. LC/MS (ESI+): m/z 313.2 (M+H).

Step 2: tert-butyl 1-oxo-5-[2-(trifluoromethyl)pyrimidin-5-yl]isoindoline-2-carboxylate 3

To a microwave vial was added tert-butyl 5-bromo-1-oxo-isoindoline-2-carboxylate 2 (800 mg, 2.6 mmol), [5-(trifluoromethyl)pyrimidin-2-yl]boronic acid (584 mg, 3.1 mmol), potassium carbonate (1.1 g, 7.7 mmol), water (0.5 mL, 30 mmol) and Pd(dppf)$Cl_2$ (214 mg, 0.26 mmol) in dioxane (5 mL). The reaction mixture was purged with nitrogen gas for 3 minutes and then heated to 120° C. in the microwave for 30 minutes. Upon cooling to room temperature, the resulting mixture was filtered through a thin layer of celite, washed with water and extracted with ethyl acetate. The combined organic layer was dried over $Na_2SO_4$, filtered and concentrated. The residue was purified by flash chromatography on silica gel, eluting with ethyl acetate/heptane (1:1) to afford the title compound 3 (700 mg, 72%) as a white solid. LC/MS (ESI+): m/z 380.3 (M+H).

Step 3: 2-[(tert-butoxycarbonylamino)methyl]-4-[2-(trifluoromethyl)pyrimidin-5-yl]benzoic acid 4 tert-butyl 1-oxo-5-[2-(trifluoromethyl)pyrimidin-5-yl]isoindoline-2-carboxylate 3 (200 mg, 0.53 mmol), lithium hydroxide 1 M in water (1 mL) and THF (1 mL) was stirred for 12 h at room temperature. The resulting solution was concentrated under reduced pressure, acidified by 10% aqueous citric acid to pH=5 and extracted with ethyl acetate twice. The combined organic layer was washed with brine, dried over $Na_2SO_4$, filtered and concentrated to afford the crude product 4 which was used without further purification. LC/MS (ESI+): m/z 398.4 (M+H).

Step 4: tert-butyl N-[[2-carbamoyl-5-[2-(trifluoromethyl)pyrimidin-5-yl]phenyl]methyl]carbamate 5

2-[(tert-butoxycarbonylamino)methyl]-4-[2-(trifluoromethyl)pyrimidin-5-yl]benzoic acid 4 (300 mg, 0.75 mmol) in THF (10 mL) was treated with HATU (351 mg, 0.91 mmol), DIPEA (1.5 mL, 8.3 mmol) followed by $NH_4Cl$ (485 mg, 9.1 mmol). The resulting solution was washed with saturated sodium bicarbonate and extracted with ethyl acetate twice. The combined organic layer was dried over sodium sulfate and concentrated. The residue was purified by flash chromatography on silica gel, eluting with ethyl acetate/heptane (1:1) to afford the compound 5 (250 mg, 84%) as a white solid. LC/MS (ESI+): m/z 397.4 (M+H).

Step 5: 2-(aminomethyl)-4-[2-(trifluoromethyl)pyrimidin-5-yl]benzamide 6 tert-butyl N-[[2-carbamoyl-5-[2-(trifluoromethyl)pyrimidin-5-yl]phenyl]methyl]carbamate 5 (400 mg, 1 mmol) was treated with 4N HCl in dioxane (1.8 mL, 7.4 mmol), and stirred at room temperature for 30 minutes. The reaction was concentrated to dry and the crude product 6 was used in the next step without further purification. LC/MS (ESI+): m/z 297.4 (M+H).

Step 6: tert-butyl (1R,4S,5S)-4-[[2-carbamoyl-5-[2-(trifluoromethyl)pyrimidin-5-yl]phenyl]methylcarbamoyl]-3-azabicyclo[3.1.0]hexane-3-carboxylate 7

To a solution of (1R,4S,5S)-3-tert-butoxycarbonyl-3-azabicyclo[3.1.0]hexane-4-carboxylic acid (278 mg, 1.23 mmol) and 2-(aminomethyl)-4-[2-(trifluoromethyl)pyrimidin-5-yl]benzamide 6 (330 mg, 1.11 mmol) in DMF (1 mL) was added DIPEA (0.58 mL, 3.3 mmol) and HATU (518.6 mg, 1.34 mmol). The reaction mixture was stirred for 1 h at room temperature. The resulting mixture was diluted with ethyl acetate, washed with water, brine, dried over sodium sulfate, filtered and concentrated under reduced pressure. The residue was purified by flash chromatography on silica gel column, eluting with ethyl acetate/Heptane (1:1) to afford the compound 7 (499 mg, 88%) as a white solid. LC/MS (ESI+): m/z 506.5 (M+H).

Step 7: (1R,4S,5S)—N-[[2-carbamoyl-5-[2-(trifluoromethyl)pyrimidin-5-yl]phenyl]methyl]-3-azabicyclo[3.1.0]hexane-4-carboxamide 8 tert-butyl (1R,4S,5S)-4-[[2-carbamoyl-5-[2-(trifluoromethyl)pyrimidin-5-yl]phenyl]methylcarbamoyl]-3-azabicyclo[3.1.0]hexane-3-carboxylate 7 (387 mg, 0.7656 mmol) was treated with 4N HCl in dioxane (1.9 mL, 7.6 mmol), and stirred at room temperature for 30 minutes. The reaction was concentrated to dry and the crude product (310 mg, 0.76 mmol) was treated with $Et_3N$ (2 mL, 1.415.369 mmol) in DCM (1 mL), followed by 4-fluorobenzenesulfonyl chloride (179 mg, 0.92 mmol). The reaction was stirred for overnight at room temperature. The reaction mixture was concentrated under reduced pressure. The residue was purified by flash chromatography on silica gel, eluting with ethyl acetate/heptane (1:1) to afford the compound 8 (180 mg, 40%) as yellow solid. LC/MS (ESI+): m/z 564.5 (M+H).

Step 8: (1R,4S,5S)—N-[[2-cyano-5-[2-(trifluoromethyl)pyrimidin-5-yl]phenyl]methyl]-3-(4-fluorophenyl)sulfonyl-3-azabicyclo[3.1.0]hexane-4-carboxamide (1R,4S,5S)—N-[[2-carbamoyl-5-[2-(trifluoromethyl)pyrimidin-5-yl]phenyl]methyl]-3-(4-fluorophenyl)sulfonyl-3-azabicyclo[3.1.0]hexane-4-carboxamide 8 (180 mg, 0.32 mmol) was treated with trifluoroacetic anhydride (0.09 mL, 0.64 mmol) and triethylamine (0.04 mL, 0.32 mmol) in DCM (5 mL). The reaction mixture was stirred for overnight at room temperature. The resulting solution was concentrated and purified with reverse phase HPLC to afford the title compound (54 mg, 31%). LC/MS (ESI+): m/z 546.2 (M+H).

$^1$H NMR (400 MHz, DMSO-$d_6$) δ 9.43 (s, 2H), 8.95 (t, J=5.8 Hz, 1H), 8.09 (d, J=8.1 Hz, 1H), 8.06-7.95 (m, 2H), 7.95-7.79 (m, 2H), 7.59-7.38 (m, 2H), 4.65 (dd, J=16.0, 6.1 Hz, 1H), 4.52 (dd, J=16.0, 5.5 Hz, 1H), 4.22 (s, 1H), 3.74 (dd, J=10.4, 3.7 Hz, 1H), 3.47 (d, J=10.4 Hz, 1H), 1.59 (tdd, J=9.6, 7.0, 3.8 Hz, 2H), 0.54 (td, J=7.8, 5.3 Hz, 1H), −0.84 (q, J=4.4 Hz, 1H).

Example 177

Preparation of (2S,4R)-4-fluoro-N-((4-fluoro-4'-(trifluoromethyl)-[1,1'-biphenyl]-3-yl)methyl)-1-((4-fluorophenyl)sulfonyl)pyrrolidine-2-carboxamide

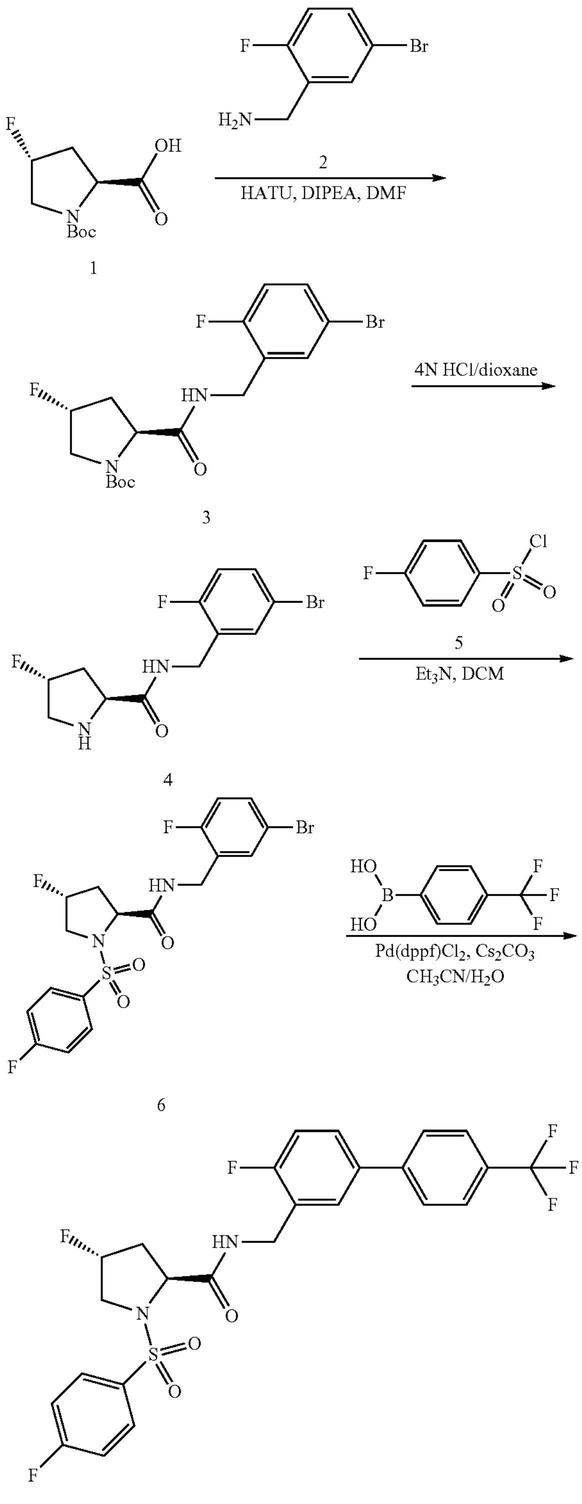

Following the HATU coupling procedure of Example 35, step 1: tert-butyl (2S,4R)-2-[(5-bromo-2-fluoro-phenyl)

methylcarbamoyl]-4-fluoro-pyrrolidine-1-carboxylate 3 (801 mg, 89%) was prepared from (2S,4R)-1-tert-butoxycarbonyl-4-fluoro-pyrrolidine-2-carboxylic acid 1 (500 mg, 2.14 mmol) and (5-bromo-2-fluorophenyl)methanamine 2 (567 mg, 2.55 mmol), DIPEA (1.12 mL, 6.4 mmol), HATU (998 mg, 2.57 mmol), DMF (8 mL). LC/MS (ESI+): m/z 420.3 (M+H).

Following the same procedure of Example 35, step 3: (2S,4R)—N-[(5-bromo-2-fluoro-phenyl)methyl]-4-fluoro-pyrrolidine-2-carboxamide 4 (609 mg, 100%) was prepared from tert-butyl (2S,4R)-2-[(5-bromo-2-fluoro-phenyl)methylcarbamoyl]-4-fluoro-pyrrolidine-1-carboxylate 3 (801 mg, 1.9 mmol) and 4 N HCl in dioxane (3.8 mL, 15.2 mmol). LC/MS (ESI+): m/z 320.3 (M+H).

Following the same procedure of Example 35, step 4: (2S,4R)—N-[(5-bromo-2-fluoro-phenyl)methyl]-4-fluoro-1-(4-fluorophenyl)sulfonyl-pyrrolidine-2-carboxamide 6 (710 mg, 70%) was prepared from (2S,4R)—N-[(5-bromo-2-fluoro-phenyl)methyl]-4-fluoro-pyrrolidine-2-carboxamide 4 (680 mg, 2.1 mmol), $Et_3N$ (6 mL, 42.6 mmol), 4-fluorobenzenesulfonyl chloride (710 mg, 1.5 mmol) in DCM (1 mL). LC/MS (ESI+): m/z 478.3 (M+H).

Following the same procedure of Example 183, step 4: The title compound (2S,4R)-4-fluoro-1-(4-fluorophenyl)sulfonyl-N-[[2-fluoro-5-[4-(trifluoromethyl)phenyl]phenyl]methyl]pyrrolidine-2-carboxamide (48 mg, 39%) was prepared from (2S,4R)—N-[(5-bromo-2-fluoro-phenyl)methyl]-4-fluoro-1-(4-fluorophenyl)sulfonyl-pyrrolidine-2-carboxamide 6 (110 mg, 0.23 mmol), [4-(trifluoromethyl)phenyl]boronic acid (48 mg, 0.25 mmol), cesium carbonate 1 M in water (0.32 mL, 0.32 mmol), Pd(dppf)$Cl_2$ (19 mg, 0.023 mmol) in acetonitrile (1 mL). LC/MS (ESI+): m/z 543.2 (M+H).

1H NMR (400 MHz, DMSO-$d_6$) δ 8.86 (t, J=5.8 Hz, 1H), 8.07-7.93 (m, 2H), 7.89 (d, J=7.9 Hz, 2H), 7.82 (dd, J=7.2, 2.5 Hz, 1H), 7.75 (d, J=8.3 Hz, 2H), 7.72-7.64 (m, 1H), 7.53-7.40 (m, 2H), 7.34 (dd, J=9.9, 8.5 Hz, 1H), 5.38-4.97 (m, 1H), 4.45 (d, J=5.8 Hz, 2H), 4.22 (dd, J=9.8, 7.1 Hz, 1H), 3.79-3.65 (m, 1H), 3.65 (s, 1H), 2.43-2.29 (m, 1H).

Example 178

Preparation of (2S,4R)—N-[[2-[2-amino-6-(trifluoromethyl)-3-pyridyl]-4-pyridyl]methyl]-4-fluoro-1-(4-fluorophenyl)sulfonyl-pyrrolidine-2-carboxamide

Step 1: (2S,4R)-tert-butyl 2-(((2-bromopyridin-4-yl)methyl)carbamoyl)-4-fluoropyrrolidine-1-carboxylate

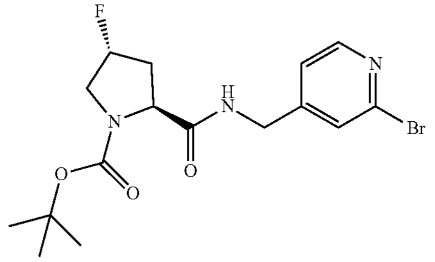 [SMILES: CC(C)(C)OC(=O)N1C[C@H](F)C[C@H]1C(=O)NCc1ccnc(Br)c1]

The title compound (4812 mg, 98%) was prepared following the amide coupling procedure of Example 35, Step 1 from (2-bromo-4-pyridyl)methanamine (2020 mg, 10.800 mmol), (2S,4R)-1-tert-butoxycarbonyl-4-fluoro-pyrrolidine-2-carboxylic acid (2771 mg, 11.88 mmol), HATU (4610 mg, 11.88 mmol) and triethylamine (3.31 mL, 23.7 mmol) in N,N-dimethylformamide (25 mL). LC/MS (ESI+): m/z 402 (M+H).

Step 2: (2S,4R)—N-((2-bromopyridin-4-yl)methyl)-4-fluoropyrrolidine-2-carboxamide

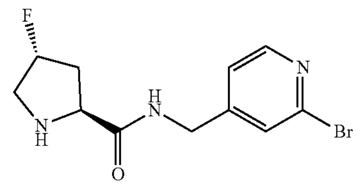 [SMILES: O=C(NCc1ccnc(Br)c1)[C@@H]1C[C@@H](F)CN1]

Trifluoroacetic acid (8 ml) was added dropwise to a solution of tert-butyl (2S,4R)-2-[(2-bromo-4-pyridyl)methylcarbamoyl]-4-fluoro-pyrrolidine-1-carboxylate (1010 mg, 2.51 mmol) in DCM (12 ml) mixture. The mixture was stirred for 2 hours, concentrated in vacuum, the residue diluted with sat aq $NaHCO_3$ and extracted with ethyl acetate. The organic extracts were washed with brine, dried over $Na_2SO_4$ and concentrated to afford 422 mg (56%). The residue was used without further purification. LC/MS (ESI+): m/z 302 (M+H).

Step 3: (2S,4R)—N-((2-bromopyridin-4-yl)methyl)-4-fluoro-1-((4-fluorophenyl)sulfonyl)pyrrolidine-2-carboxamide

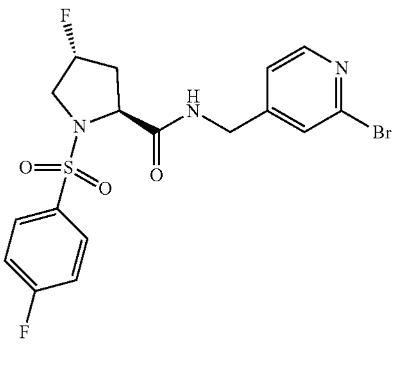 [SMILES: O=C(NCc1ccnc(Br)c1)[C@@H]1C[C@@H](F)CN1S(=O)(=O)c1ccc(F)cc1]

The title compound (369 mg, 57%) was prepared following the sulfonamide coupling procedure of Example 35, Step 4 from (2S,4R)—N-[(2-bromo-4-pyridyl)methyl]-4-fluoro-pyrrolidine-2-carboxamide (422 mg, 1.40 mmol), 4-fluorobenzenesulfonyl chloride (300 mg, 1.54 mmol) and triethylamine (0.30 mL, 2.2 mmol) in 9 ml of DMF/DCM mixture (2:1). LC/MS (ESI+): m/z 460 (M+H).

Step 4: ((2S,4R)-4-fluoro-N-((2'-fluoro-6'-(trifluoromethyl)-[2,3'-bipyridin]-4-yl)methyl)-1-((4-fluorophenyl)sulfonyl)pyrrolidine-2-carboxamide

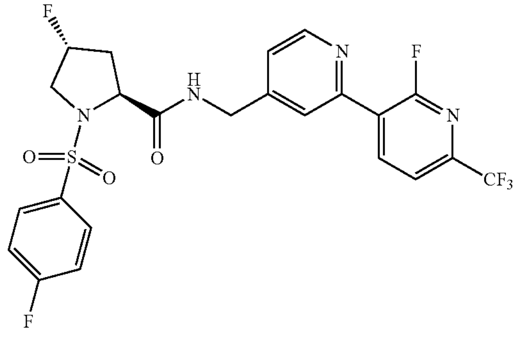 [SMILES: O=C(NCc1ccnc(-c2ccc(C(F)(F)F)nc2F)c1)[C@@H]1C[C@@H](F)CN1S(=O)(=O)c1ccc(F)cc1]

The title compound (174 mg, 40%) was prepared following the Suzuki coupling procedure of Example 42, Step 1 from (2S,4R)—N-[(2-bromo-4-pyridyl)methyl]-4-fluoro-1-(4-fluorophenyl)sulfonyl-pyrrolidine-2-carboxamide (369 mg, 0.80 mmol), [2-fluoro-6-(trifluoromethyl)-3-pyridyl] boronic acid (402 mg, 1.92 mmol), [1,1'-bis(diphenylphosphino)ferrocene]dichloropalladium(II) (112 mg, 0.15 mmol) and aqueous Cs2CO3 (1.6 mL, 1.60 mmol, 1.0 mol/L) in acetonitrile (10 mL). LCMS (ESI_Formic_MeCN): [$MH^+$]=545.

Step 5: (2S,4R)—N-[[2-[2-amino-6-(trifluoromethyl)-3-pyridyl]-4-pyridyl]methyl]-4-fluoro-1-(4-fluorophenyl)sulfonyl-pyrrolidine-2-carboxamide

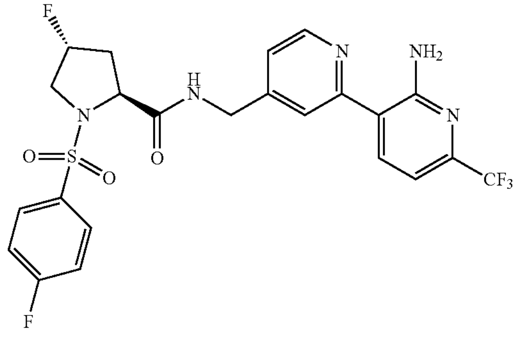 [SMILES: Nc1nc(C(F)(F)F)ccc1-c1cc(CNC(=O)[C@@H]2C[C@@H](F)CN2S(=O)(=O)c2ccc(F)cc2)ccn1]

A mixture of (2S,4R)-4-fluoro-1-(4-fluorophenyl)sulfonyl-N-[[2-[2-fluoro-6-(trifluoromethyl)-3-pyridyl]-4-pyridyl]methyl]pyrrolidine-2-carboxamide (80 mg, 0.13 mmol) in DMSO (2 ml) was saturated with ammonia (gas) and then heated at 80° C. in a sealed vial for 24 hours. The mixture was degassed in vacuum and submitted for RP HPLC purification to afford 51 mg (71%) of the title product.

1H NMR (400 MHz, DMSO-d6) δ 8.96 (t, J=6.0 Hz, 1H), 8.63 (dd, J=5.1, 0.7 Hz, 1H), 8.29-8.21 (m, 1H), 8.04-7.88 (m, 5H), 7.52-7.43 (m, 2H), 7.37 (dd, J=5.2, 1.5 Hz, 1H), 7.00 (d, J=7.8 Hz, 1H), 5.32-5.09 (m, 1H), 4.57-4.38 (m, 2H), 4.20 (dd, J=9.9, 7.1 Hz, 1H), 3.80-3.57 (m, 2H), 2.48-2.35 (m, 1H), 2.10 (dddd, J=42.5, 13.9, 10.0, 3.4 Hz, 1H).

Example 179

Preparation of (2S,4R)-4-fluoro-1-(4-fluorophenyl) sulfonyl-N-[[2-[2-(methylamino)-6-(trifluoromethyl)-3-pyridyl]-4-pyridyl]methyl]pyrrolidine-2-carboxamide

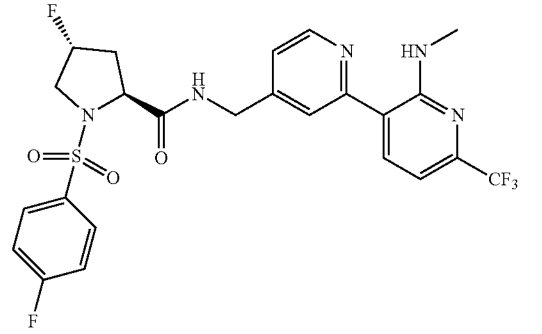 [SMILES: CNc1nc(C(F)(F)F)ccc1-c1cc(CNC(=O)[C@@H]2C[C@@H](F)CN2S(=O)(=O)c2ccc(F)cc2)ccn1]

A mixture of (2S,4R)-4-fluoro-1-(4-fluorophenyl)sulfonyl-N-[[2-[2-fluoro-6-(trifluoromethyl)-3-pyridyl]-4-pyridyl]methyl]pyrrolidine-2-carboxamide (80 mg, 0.15 mmol) and methylamine in tetrahydrofuran (1.0 mL, 2.0 mmol, 2 mol/L) in dimethyl sulfoxide (2 mL) was heated in a sealed vial at 80° C. for 3 hours. The mixture was degassed in vacuum and submitted for a RP HPLC purification to afford 46 mg (56%) of the title compound.

1H NMR (400 MHz, DMSO-$d_6$) δ 9.34 (q, J=4.8 Hz, 1H), 8.96 (t, J=6.0 Hz, 1H), 8.63 (dd, J=5.2, 0.7 Hz, 1H), 8.28-8.21 (m, 1H), 8.05-7.95 (m, 3H), 7.52-7.43 (m, 2H), 7.39 (dd, J=5.2, 1.5 Hz, 1H), 6.97 (d, J=7.8 Hz, 1H), 5.32-5.10 (m, 1H), 4.56-4.39 (m, 2H), 4.20 (dd, J=9.9, 7.1 Hz, 1H), 3.80-3.56 (m, 2H), 2.98 (d, J=4.7 Hz, 3H), 2.42 (dddd, J=20.0, 14.7, 6.6, 2.0 Hz, 1H), 2.22-1.97 (m, 1H).

Example 180

Preparation of (2S,4R)-4-fluoro-1-(4-fluorophenyl) sulfonyl-N-[[5-fluoro-2-[2-(trifluoromethyl)pyrimidin-5-yl]-4-pyridyl]methyl]pyrrolidine-2-carboxamide

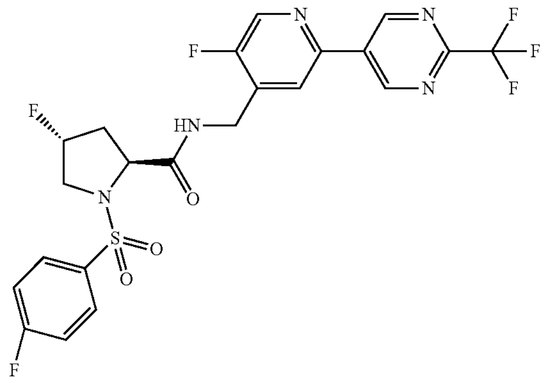 [SMILES: O=C(NCc1cc(-c2cnc(C(F)(F)F)nc2)ncc1F)[C@@H]1C[C@@H](F)CN1S(=O)(=O)c1ccc(F)cc1]

Preparation of the title compound follows the same general procedure as Example 48.

1H NMR (400 MHz, DMSO) δ 9.63-9.57 (s, 2H), 9.11-9.04 (t, J=5.9 Hz, 1H), 8.81-8.74 (d, J=1.3 Hz, 1H), 8.28-

8.21 (d, J=5.7 Hz, 1H), 8.06-7.99 (m, 2H), 7.52-7.44 (m, 2H), 5.30-5.11 (m, 1H), 4.60-4.50 (d, J=5.8 Hz, 2H), 4.27-4.19 (dd, J=10.0, 7.1 Hz, 1H), 3.76-3.57 (m, 2H), 2.47-2.36 (m, 1H), 2.21-2.00 (m, 1H)., LCMS (ESI) m/z:546.2 [M+H]+

Example 181

Preparation of (1R,5S)-4-(4-fluorophenyl)sulfonyl-N-[[3-fluoro-5-[2-(trifluoromethyl)pyrimidin-5-yl]phenyl]methyl]-4-azabicyclo[3.1.0]hexane-5-carboxamide

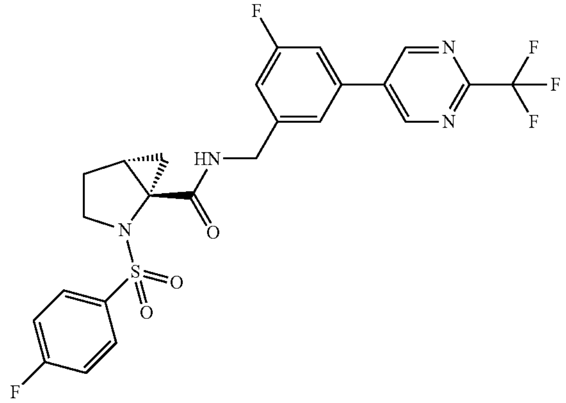 [SMILES: O=C(NCc1cc(F)cc(-c2cnc(C(F)(F)F)nc2)c1)[C@]12C[C@H]1CCN2S(=O)(=O)c1ccc(F)cc1]

Preparation of the title compound follows the same general procedure as Example 48.

1H NMR (400 MHz, DMSO) δ 9.47-9.39 (s, 2H), 8.75-8.68 (dd, J=6.8, 5.3 Hz, 1H), 7.95-7.87 (m, 2H), 7.82-7.77 (t, J=1.5 Hz, 1H), 7.76-7.69 (ddd, J=9.8, 2.3, 1.4 Hz, 1H), 7.56-7.48 (m, 2H), 7.44-7.36 (ddd, J=9.7, 2.3, 1.3 Hz, 1H), 4.70-4.59 (dd, J=16.0, 6.8 Hz, 1H), 4.40-4.27 (dd, J=16.2, 5.4 Hz, 1H), 3.74-3.62 (ddd, J=10.5, 9.0, 3.1 Hz, 1H), 2.99-2.87 (dt, J=10.4, 8.3 Hz, 1H), 2.24-2.10 (dtd, J=12.6, 8.9, 5.7 Hz, 1H), 1.87-1.72 (m, 2H), 1.50-1.43 (dd, J=9.0, 5.9 Hz, 1H), 0.31-0.22 (t, J=5.9 Hz, 1H)., LCMS (ESI) m/z:539.2 [M+H]+

Example 182

Preparation of (1R,5S)-4-(4-fluorophenyl)sulfonyl-N-[[2-fluoro-5-[2-(trifluoromethyl)pyrimidin-5-yl]phenyl]methyl]-4-azabicyclo[3.1.0]hexane-5-carboxamide

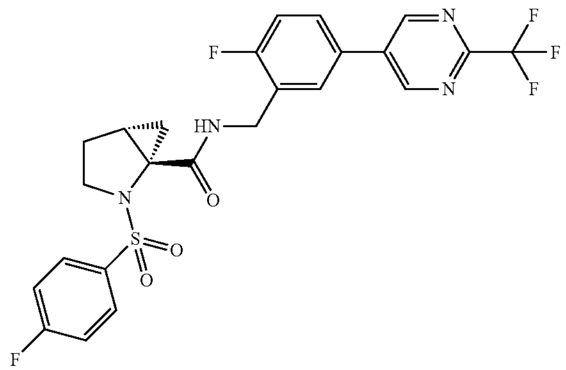 [SMILES: O=C(NCc1cc(-c2cnc(C(F)(F)F)nc2)ccc1F)[C@]12C[C@H]1CCN2S(=O)(=O)c1ccc(F)cc1]

Preparation of the title compound follows the same general procedure as Example 48.

1H NMR (400 MHz, DMSO) δ 9.40-9.35 (s, 2H), 8.71-8.66 (dd, J=6.8, 5.2 Hz, 1H), 8.10-8.04 (dd, J=7.2, 2.4 Hz, 1H), 7.95-7.85 (m, 3H), 7.56-7.47 (m, 2H), 7.47-7.40 (dd, J=9.9, 8.6 Hz, 1H), 4.75-4.64 (dd, J=16.1, 6.8 Hz, 1H), 4.36-4.26 (dd, J=16.1, 5.3 Hz, 1H), 3.74-3.62 (ddd, J=10.6, 9.2, 3.1 Hz, 1H), 3.00-2.88 (dt, J=10.5, 8.5 Hz, 1H), 2.24-2.11 (dtd, J=13.0, 9.1, 5.9 Hz, 1H), 1.88-1.74 (m, 2H), 1.52-1.42 (dd, J=9.0, 5.9 Hz, 1H), 0.33-0.23 (t, J=6.0 Hz, 1H)., LCMS (ESI) m/z:539.2 [M+H]+

Example 183

Preparation of (1S,2S,5R)—N-(2-fluoro-5-(2-(trifluoromethyl)pyrimidin-5-yl)benzyl)-3-((4-fluorophenyl)sulfonyl)-3-azabicyclo[3.1.0]hexane-2-carboxamide

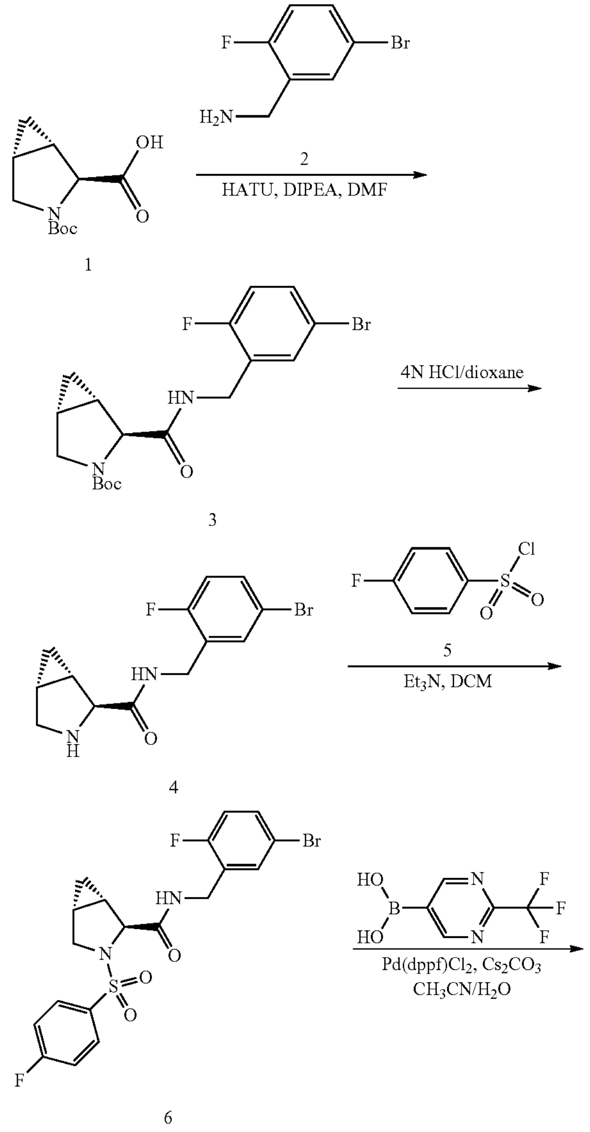

-continued

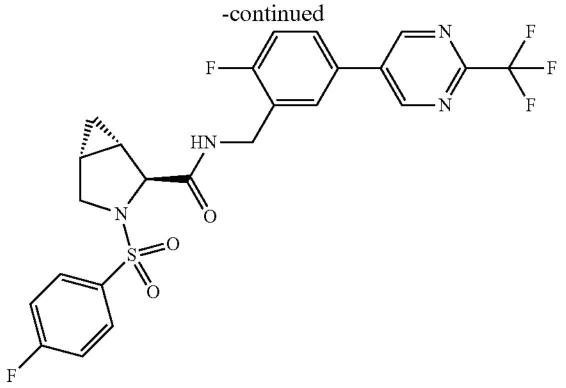

Step 1: tert-butyl (1R,4S,5S)-4-[(5-bromo-2-fluoro-phenyl)methylcarbamoyl]-3-azabicyclo[3.1.0]hexane-3-carboxylate 3

To a solution of (1R,4S,5S)-3-tert-butoxycarbonyl-3-azabicyclo[3.1.0]hexane-4-carboxylic acid 1 (31 mg, 0.13 mmol), (5-bromo-2-fluoro-phenyl)methanamine hydrochloride 2 (36 mg, 0.15 mmol) and DIPEA (0.07 mL, 0.4 mmol) in DMF (0.5 mL) was added HATU (63.5 mg, 0.16 mmol). The reaction mixture was stirred for 1 h at room temperature. The resulting mixture was diluted with ethyl acetate, washed with water, brine, dried over sodium sulfate, filtered, and concentrated under reduced pressure. The residue was purified by flash chromatography on silica gel column, eluting with ethyl acetate/Heptane (1:1) to afford the compound 3 (30 mg, 53%) as a clear oil. LC/MS (ESI+): m/z 414 (M+H).

Step 2: (1R,4S,5S)—N-[(5-bromo-2-fluoro-phenyl)methyl]-3-azabicyclo[3.1.0]hexane-4-carboxamide 4

A solution of tert-butyl (1R,4S,5S)-4-[(5-bromo-2-fluoro-phenyl)methylcarbamoyl]-3-azabicyclo[3.1.0]hexane-3-carboxylate 3 (30 mg, 0.072 mmol) in dioxane (5 mL) was treated with 4N HCl in dioxane (0.46 mL, 1.9 mmol). The reaction was stirred for 30 minutes at room temperature. The resulting mixture was concentrated under reduced pressure to afford the crude product 4 which was used without further purification. LC/MS (ESI+): m/z 314 (M+H).

Step 3: (1R,4S,5S)—N-[(5-bromo-2-fluoro-phenyl)methyl]-3-(4-fluorophenyl)sulfonyl-3-azabicyclo[3.1.0]hexane-4-carboxamide 6

(1R,4S,5S)—N-[(5-bromo-2-fluoro-phenyl)methyl]-3-azabicyclo[3.1.0]hexane-4-carboxamide 4 (23 mg, 0.07 mmol) in DCM (1 mL) was treated with $Et_3N$ (0.2 mL, 1.5 mmol) followed by 4-fluorobenzenesulfonyl chloride 5 (17 mg, 0.09 mmol). The reaction was stirred for overnight at room temperature. The resulting mixture was concentrated under reduced pressure. The residue was purified by flash chromatography on silica gel, eluting with ethyl acetate/heptane (1:1) to afford the compound 6 (26 mg, 75%) as a clear oil. LC/MS (ESI+): m/z 472 (M+H).

Step 4: (1R,4S,5S)-3-(4-fluorophenyl)sulfonyl-N-[[2-fluoro-5-[2-(trifluoromethyl)pyrimidin-5-yl]phenyl]methyl]-3-azabicyclo[3.1.0]hexane-4-carboxamide To a microwave vial was added (1R,4S,5S)—N-[(5-bromo-2-fluoro-phenyl)methyl]-3-(4-fluorophenyl)sulfonyl-3-azabicyclo[3.1.0]hexane-4-carboxamide 6 (35 mg, 0.07 mmol), [5-(trifluoromethyl)pyrimidin-2-yl]boronic acid (15.7 mg, 0.08 mmol), cesium carbonate 1 M in water (0.10 mL, 0.10 mmol), Pd(dppf)$Cl_2$ (0.1 equiv., 0.01 mmol) and acetonitrile (0.8 mL). The reaction mixture was purged with nitrogen gas for 3 minutes and then heated to 140° C. in the microwave for 30 minutes. Upon cooling to room temperature, the resulting mixture was filtered through a thin layer of celite, washed with water and extracted with ethyl acetate. The combined organic layer was dried over $Na_2SO_4$, filtered and concentrated under reduced pressure. The residue was purified by flash chromatography on silica gel, eluting with ethyl acetate/heptane (3:1) to afford the title compound (24 mg, 60%) as a white solid. LC/MS (ESI+): m/z 539.2 (M+H).

1H NMR (400 MHz, DMSO-$d_6$) δ 9.36 (s, 2H), 8.77 (t, J=5.9 Hz, 1H), 8.02-7.75 (m, 4H), 7.57-7.28 (m, 3H), 4.60-4.31 (m, 2H), 4.22 (s, 1H), 3.72 (td, J=9.9, 3.6 Hz, 1H), 3.47 (d, J=10.4 Hz, 1H), 1.69-1.40 (m, 2H), 0.60-0.45 (m, 1H), −0.82 (dt, J=5.1, 4.0 Hz, 1H).

Example 184

Preparation of (2S,4R)—N-([5-chloro-2-[2-(trifluoromethyl)pyrimidin-5-yl]pyridin-4-yl]methyl)-4-fluoro-1-[(4-fluorobenzene)sulfonyl]pyrrolidine-2-carboxamide

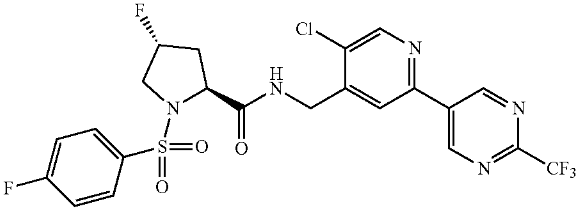 [SMILES: O=C(NCc1cc(-c2cnc(C(F)(F)F)nc2)ncc1Cl)[C@@H]1C[C@@H](F)CN1S(=O)(=O)c1ccc(F)cc1]

Step 1: Preparation of (2,5-dichloropyridin-4-yl)methanol

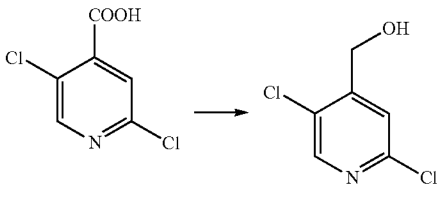 [SMILES: O=C(O)c1cc(Cl)ncc1Cl ; OCc1cc(Cl)ncc1Cl]

A solution of 2,5-dichloropyridine-4-carboxylic acid (2.00 g, 10.417 mmol, 1.0 equiv) and $BH_3$-THF (30 mL, 3.0 equiv, 1 mol/L in THF) in tetrahydrofuran (100 mL) was stirred for 30 min at 0° C. and 2 h at room temperature. The reaction was then quenched by water, extracted ethyl acetate, washed with brine and concentrated under vacuum. The residue was purified by a silica gel column eluting with ethyl acetate/petroleum ether (1:3) to afford the title compound (1.5 g, 81%) as a white solid.

Step 2: Preparation of 2-[(2,5-dichloropyridin-4-yl)methyl]-2,3-dihydro-1H-isoindole-1,3-dione

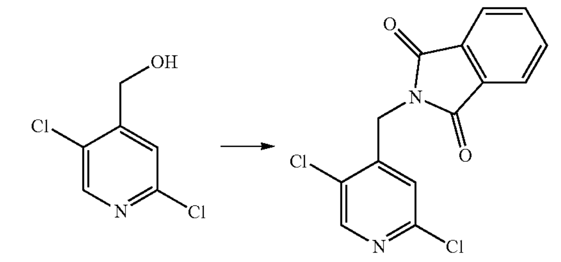 [SMILES: OCc1cc(Cl)ncc1Cl ; O=C1c2ccccc2C(=O)N1Cc1cc(Cl)ncc1Cl]

DIAD (3.18 g, 15.726 mmol, 2.0 equiv) was added dropwise into a solution of (2,5-dichloropyridin-4-yl)methanol (1.40 g, 7.864 mmol, 1.0 equiv), $PPh_3$ (4125.47 mg, 15.729 mmol, 2.0 equiv), and 2,3-dihydro-1H-isoindole-1,3-dione (1735.66 mg, 11.797 mmol, 1.5 equiv) in tetrahydrofuran (50 mL) at 0° C. under nitrogen. The resulting solution was stirred for 2 h at 0° C. and quenched by water. The resulting solution was extracted with ethyl acetate, washed with brine, dried over $Na_2SO_4$, and concentrated under vacuum. The residue was purified by a silica gel column eluting with ethyl acetate/petroleum ether (1:5) to afford the title compound (1.4 g, 58%) as a yellow solid.

Step 3: Preparation of 2-([5-chloro-2-[2-(trifluoromethyl)pyrimidin-5-yl]pyridin-4-yl]methyl)-2,3-dihydro-1H-isoindole-1,3-dione

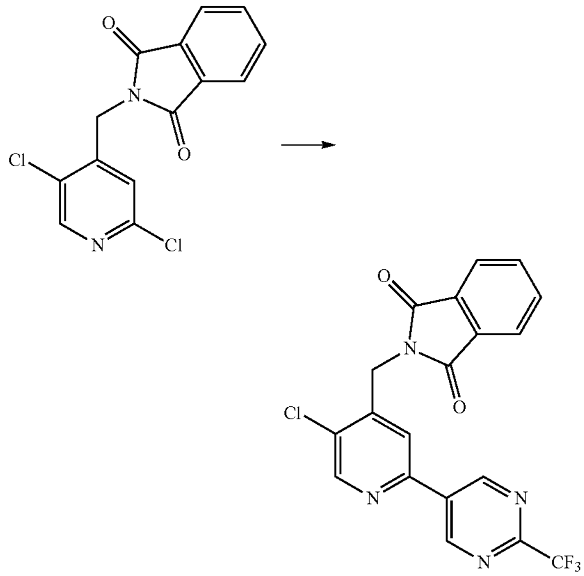

A mixture of 2-[(2,5-dichloropyridin-4-yl)methyl]-2,3-dihydro-1H-isoindole-1,3-dione (1.40 g, 4.558 mmol, 1.0 equiv), 5-(tetramethyl-1,3,2-dioxaborolan-2-yl)-2-(trifluoromethyl)pyrimidine (1.25 g, 4.561 mmol, 1.0 equiv), Pd(dppf)$Cl_2$ (330 mg, 0.451 mmol, 0.1 equiv), and potassium carbonate (1.89 g, 13.675 mmol, 3.000 equiv) in dioxane (100 mL)/water(5 mL) was stirred for 12 h at 60° C. under nitrogen. The reaction mixture was diluted with ethyl acetate, washed with brine, dried over anhydrous sodium sulfate, and concentrated under vacuum. The residue was purified by a silica gel column eluting with dichloromethane/petroleum ether (20:1) to afford the title compound (700 mg, 37%) as a white solid.

Step 4: Preparation of [5-chloro-2-[2-(trifluoromethyl)pyrimidin-5-yl]pyridin-4-yl]methanamine

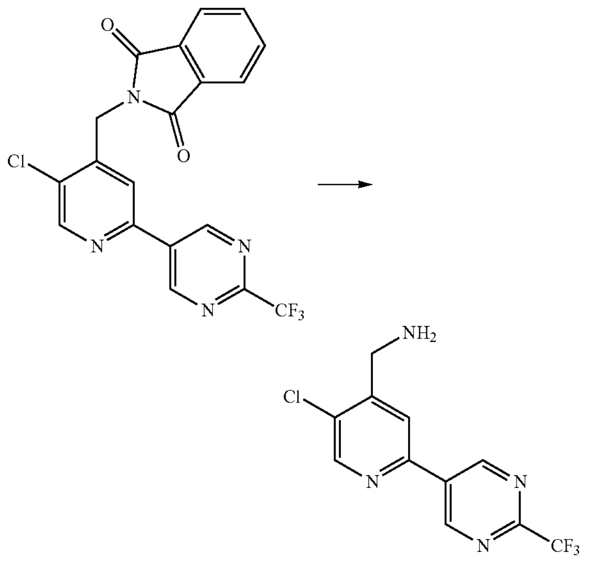

A mixture of 2-([5-chloro-2-[2-(trifluoromethyl)pyrimidin-5-yl]pyridin-4-yl]methyl)-2,3-dihydro-1H-isoindole-1,3-dione (300.00 mg, 0.716 mmol, 1.0 equiv) and $NH_2NH_2.H_2O$ (358.64 mg, 7.164 mmol, 10.0 equiv) in methanol (20 mL) was stirred for 12 h at 50° C. The reaction mixture was concentrated under vacuum. The solution was diluted with ethyl acetate and the solids were filtered out. The solution was concentrated under vacuum to afford the title compound (200 mg, 97%) as a gray solid.

Step 5: Preparation of tert-butyl (2S,4R)-2-[([5-chloro-2-[2-(trifluoromethyl)pyrimidin-5-yl]pyridin-4-yl]methyl)carbamoyl]-4-fluoropyrrolidine-1-carboxylate

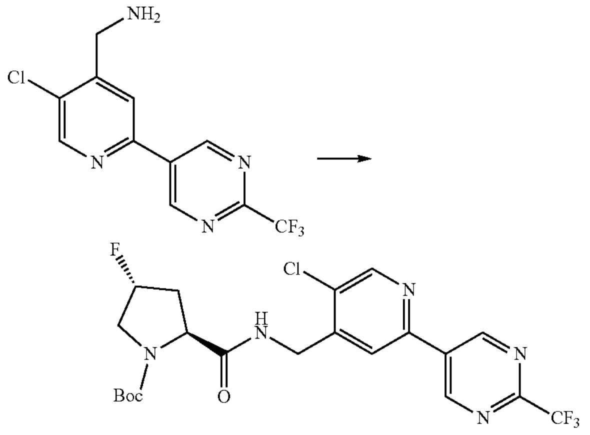

A solution of (2S,4R)-1-[(tert-butoxy)carbonyl]-4-fluoropyrrolidine-2-carboxylic acid (161.60 mg, 0.693 mmol, 1.0 equiv), DIEA (268.64 mg, 2.079 mmol, 3.0 equiv), and HATU (316.14 mg, 0.831 mmol, 1.2 equiv) in DMF (5 mL) was stirred for 30 min at room temperature. [5-Chloro-2-[2-(trifluoromethyl)pyrimidin-5-yl]pyridin-4-yl]methanamine (200.00 mg, 0.693 mmol, 1.0 equiv) was then added to the solution. The resulting solution was stirred for 12 h at room temperature. The reaction mixture was diluted with ethyl acetate, washed with brine, dried over anhydrous sodium sulfate, and concentrated under vacuum. The residue was purified by a silica gel column eluting with ethyl acetate/petroleum ether (1:3) to afford the title compound (250 mg, 72%) as a white solid.

Step 6: Preparation of (2S,4R)—N-((5-chloro-2-(2-(trifluoromethyl)pyrimidin-5-yl)pyridin-4-yl)methyl)-4-fluoropyrrolidine-2-carboxamide hydrochloride

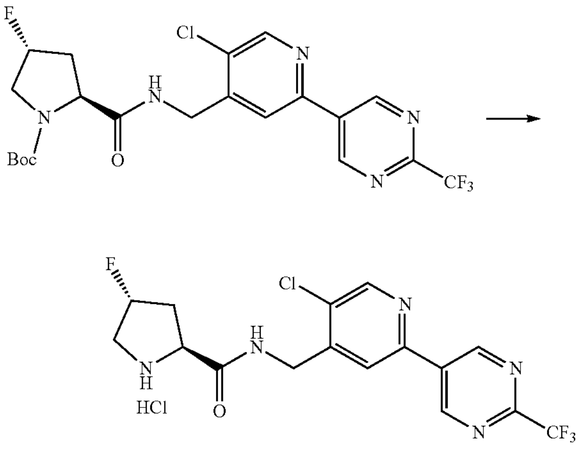

A mixture of tert-butyl (2S,4R)-2-[([5-chloro-2-[2-(trifluoromethyl)pyrimidin-5-yl]pyridin-4-yl]methyl)carbamoyl]-4-fluoropyrrolidine-1-carboxylate (250 mg, 0.496 mmol, 1.000 equiv) and saturated HCl in dioxane(20 mL) was stirred for 12 h at room temperature. The reaction mixture was concentrated under vacuum. This resulted in the title compound (200 mg, 100%) as a white solid.

Step 7: Preparation of (2S,4R)—N-([5-chloro-2-[2-(trifluoromethyl)pyrimidin-5-yl]pyridin-4-yl]methyl)-4-fluoro-1-[(4-fluorobenzene)sulfonyl]pyrrolidine-2-carboxamide

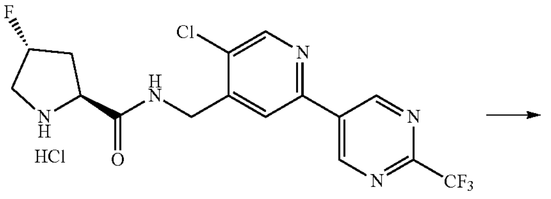

-continued

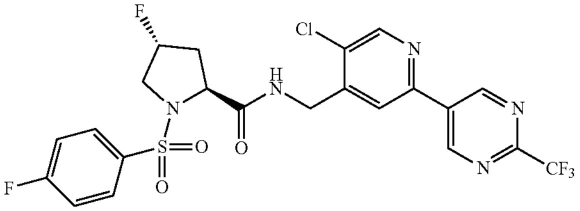

A solution of (2S,4R)—N-((5-chloro-2-(2-(trifluoromethyl)pyrimidin-5-yl)pyridin-4-yl)methyl)-4-fluoropyrrolidine-2-carboxamide hydrochloride (300.00 mg, 0.743 mmol, 1.0 equiv), triethylamine (225.56 mg, 2.229 mmol, 3.0 equiv), and 4-fluorobenzene-1-sulfonyl chloride (289.20 mg, 1.486 mmol, 2.0 equiv) in dichloromethane (20 mL) was stirred for 12 h at room temperature. The reaction mixture was then quenched by water, extracted with dichloromethane, washed with brine, dried over anhydrous sodium sulfate, and concentrated under vacuum. The residue was purified by a silica gel column eluting with ethyl acetate/petroleum ether (1:1) to afford the title compound (33.5 mg, 8%) as a white solid.

$^1H$ NMR (300 MHz, $CDCl_3$) δ 9.65 (s, 2H), 8.69 (s, 1H), 8.18 (s, 1H), 7.91-7.88 (m, 2H), 7.41 (s, 1H), 7.29-7.23 (m, 2H), 5.15-4.96 (m, 2H), 4.45-4.31 (m, 2H), 3.95-3.60 (m, 2H), 2.70-2.57 (m, 1H), 2.15-2.07 (m, 1H).

Example 185

Preparation of 5-fluoro-N-((5-fluoro-2-(2-(trifluoromethyl)pyrimidin-5-yl)pyridin-4-yl)methyl)-2-(4-fluorophenylsulfonyl)-2-aza-bicyclo[2.2.1]heptane-3-carboxamide

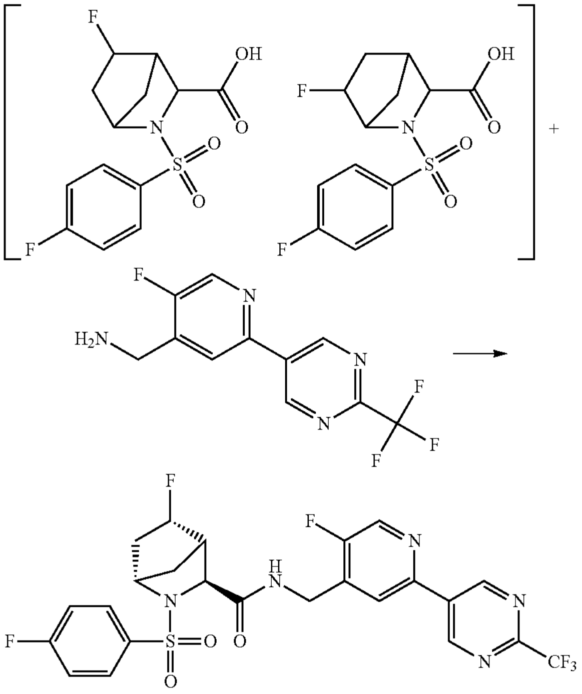

-continued

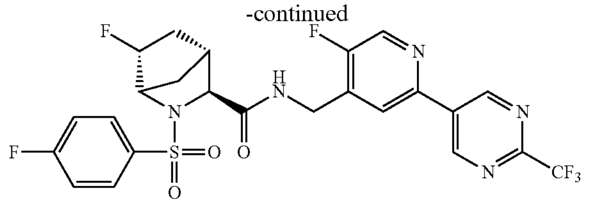

A solution of 5-fluoro-2-[(4-fluorobenzene)sulfanyl]-2-azabicyclo[2.2.1]heptane-3-carboxylic acid and 6-fluoro-2-[(4-fluorobenzene)sulfonyl]-2-azabicyclo[2.2.1]heptane-3-carboxylic acid (150 mg, 0.473 mmol, 1.74 equiv), [5-fluoro-2-[2-(trifluoromethyl)pyrimidin-5-yl]pyridin-4-yl]methanamine (74 mg, 0.272 mmol, 1.00 equiv), DIEA (121 mg, 0.936 mmol, 3.44 equiv), and HATU (270 mg, 0.710 mmol, 2.61 equiv) in tetrahydrofuran (20 mL) was stirred for 12h at room temperature. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1:15). This resulted in the title compound (6.7 mg, 4%) as a white solid. $t_R$=2.09 min (Lux Cellulose-4, 0.46x5 cm, 3 μm, Hex:EtOH=50:50, 1.0 ml/min).

$^1$H NMR (300 MHz, $CD_3OD$) δ 9.58 (s, 2H), 8.59 (s, 1H), 8.28 (d, J=5.7 Hz, 1H), 8.04-8.00 (m, 2H), 7.34-7.29 (m, 2H), 5.18-5.00 (m, 1H), 4.77-4.51 (m, 2H), 4.44 (s, 1H), 4.23 (s, 1H), 3.01 (d, J=3.9 Hz, 1H), 2.25 (d, J=10.8 Hz, 1H), 1.90-1.77 (m, 1H), 1.57 (d, J=11.4 Hz, 1H), 1.46-1.28 (m, 1H).

6-Fluoro-N-([5-fluoro-2-[2-(trifluoromethyl)pyrimidin-5-yl]pyridin-4-yl]methyl)-2-[(4-fluorobenzene)sulfonyl]-2-azabicyclo[2.2.1]heptane-3-carboxamide (7.1 mg, 5%) was also isolated as a white solid. $t_R$=2.76 min (Lux Cellulose-4, 0.46x5 cm, 3 μm, Hex:EtOH=50:50, 1.0 ml/min).

$^1$H NMR (300 MHz, $CD_3OD$) δ 9.58 (s, 2H), 8.60 (s, 1H), 8.28 (d, J=5.7 Hz, 1H), 8.04-8.00 (m, 2H), 7.34-7.26 (m, 2H), 5.19-4.99 (m, 1H), 4.77-4.51 (m, 2H), 4.44 (s, 1H), 4.23 (s, 1H), 3.02 (d, J=4.2 Hz, 1H), 2.25 (d, J=10.2 Hz, 1H), 2.00-1.77 (m, 1H), 1.57 (d, J=11.4 Hz, 1H), 1.41-1.21 (m, 1H).

The F position (5-F or 6-F) for the above two position isomers was arbitrary assigned. The 2-proline stereochemistry is as shown.

Example 186

Preparation of (2S,5S)-1-(4-fluorophenylsulfonyl)-5-methyl-N-((2-(2-(trifluoromethyl)pyrimidin-5-yl)pyridin-4-yl)methyl)pyrrolidine-2-carboxamide

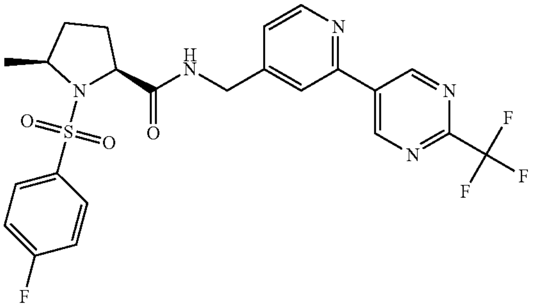 [SMILES: C[C@H]1CC[C@@H](C(=O)NCc2ccnc(-c3cnc(C(F)(F)F)nc3)c2)N1S(=O)(=O)c1ccc(F)cc1]

Step 1: Preparation of 2-([2-[2-(trifluoromethyl)pyrimidin-5-yl]pyridin-4-yl]methyl)-2,3-dihydro-1H-isoindole-1,3-dione

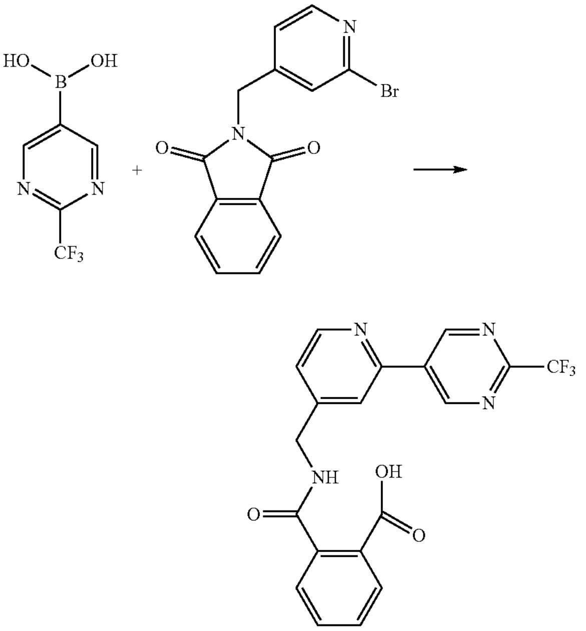 [SMILES: OB(O)c1cnc(C(F)(F)F)nc1 ; O=C1c2ccccc2C(=O)N1Cc1ccnc(Br)c1 ; O=C(O)c1ccccc1C(=O)NCc1ccnc(-c2cnc(C(F)(F)F)nc2)c1]

A mixture of $Pd(dppf)Cl_2$ (1.15 g, 1.572 mmol, 0.10 equiv), potassium carbonate (4.35 g, 31.475 mmol, 2.00 equiv), 2-[(2-bromopyridin-4-yl)methyl]-2,3-dihydro-1H-isoindole-1,3-dione (5 g, 15.77 mmol, 1.00 equiv), and bis(propan-2-yl) [2-(trifluoromethyl)pyrimidin-5-yl]boronate (4.35 g, 15.757 mmol, 1.00 equiv) in dioxane (80 mL)/water (8 mL) was stirred for 12 h at 70° C. under nitrogen. The solids were filtered out and the filtrate was diluted in water. The aqueous layer was extracted with ethyl acetate. The pH value of the aqueous solution was adjusted to 3-4 with 1N HCl. The resulting solution was extracted with ethyl acetate. The combined extracts were washed with brine, dried over anhydrous sodium sulfate, and concentrated under vacuum. This resulted in the title compound (10 g, crude) as a yellow solid.

Step 2: Preparation of [2-[2-(trifluoromethyl)pyrimidin-5-yl]pyridin-4-yl]methanamine

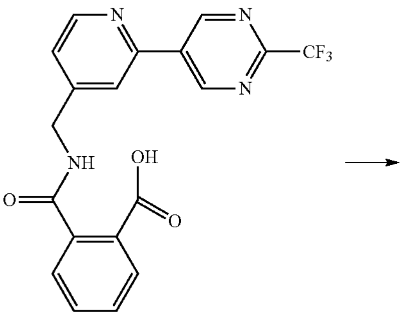

-continued

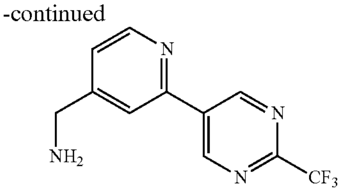

A solution of 2-([2-[2-(trifluoromethyl)pyrimidin-5-yl] pyridin-4-yl]methyl)-2,3-dihydro-1H-isoindole-1,3-dione (10 g, 26.021 mmol, 1.00 equiv) and $NH_2NH_2.H_2O$ (13 g, 259.686 mmol, 9.98 equiv) in ethanol (150 mL) was stirred for 12 h at 80° C. The resulting mixture was concentrated under vacuum. The reaction was diluted in water. The pH value of the aqueous solution was adjusted to 3-4 with 1N HCl. The resulting solution was extracted with ethyl acetate. The pH value of the solution was adjusted to 8 with sodium bicarbonate. The resulting solution was extracted with ethyl acetate. The combined extracts were washed with brine, dried over anhydrous sodium sulfate, and concentrated under vacuum. This resulted in the title compound (1 g, crude) as a yellow solid.

Step 3: Preparation of (2S,5S)-1-(4-fluorophenylsulfonyl)-5-methyl-N-((2-(2-(trifluoromethyl) pyrimidin-5-yl)pyridin-4-yl)methyl)pyrrolidine-2-carboxamide

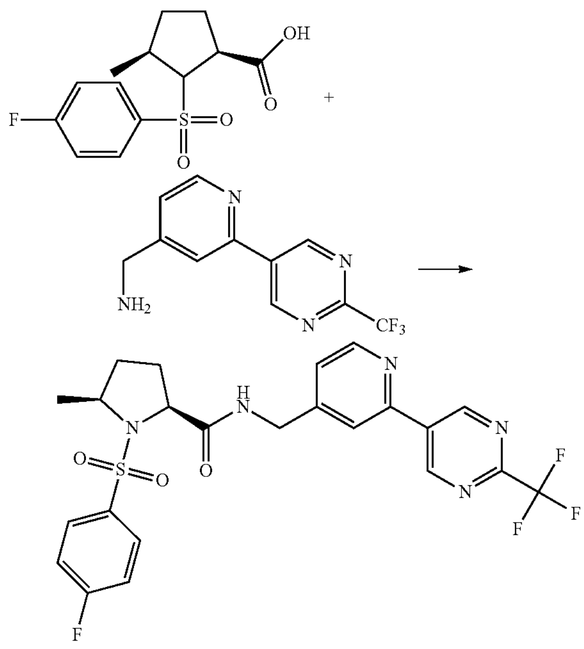

A solution of (2S,5S)-1-[(4-fluorobenzene)sulfonyl]-5-methylpyrrolidine-2-carboxylic acid (140 mg, 0.487 mmol, 0.67 equiv), DIEA (189 mg, 1.462 mmol, 2.0 equiv), HATU (222 mg, 0.584 mmol, 0.8 equiv), and [2-[2-(trifluoromethyl)pyrimidin-5-yl]pyridin-4-yl]methanamine (186 mg, 0.732 mmol, 1.00 equiv) in N,N-dimethylformamide (10 mL) was stirred for 30 min at 25° C. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/1). The crude product (568 mg) was purified by Prep-HPLC to afford the title compound (136 mg) as a white solid.

$^1$H NMR (300 MHz, $CDCl_3$) δ 9.59 (s, 2H), 8.74-8.72 (s, 1H), 7.95-7.89 (m, 3H), 7.54 (s, 1H), 7.36-7.26 (m, 3H), 4.94-4.86 (m, 1H), 4.48-4.41 (m, 1H), 4.19-4.15 (m, 1H), 3.73-3.67 (m, 1H), 2.22-2.15 (s, 1H), 1.81-1.71 (m, 2H), 1.70-1.46 (m, 4H).

Example 187

Preparation of (2S,4R)-4-fluoro-N-(2-fluoro-5-(2-(trifluoromethyl)pyrimidin-5-yl)benzyl)-1-((4-fluorophenyl)sulfonyl)-4-methylpyrrolidine-2-carboxamide

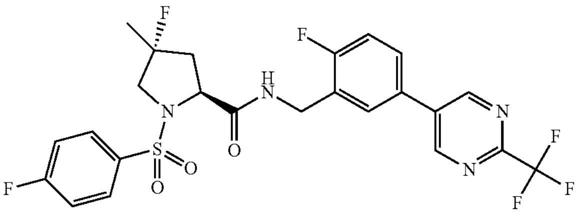 [SMILES: C[C@@]1(F)C[C@@H](C(=O)NCc2cc(-c3cnc(C(F)(F)F)nc3)ccc2F)N(S(=O)(=O)c2ccc(F)cc2)C1]

Preparation of the title compound follow the same general procedure as Example 52.

MS-ESI: $[M+H]^+$ 559.2

$^1$H NMR (400 MHz, DMSO) δ 9.36 (s, 2H), 8.89 (t, J=5.9 Hz, 1H), 8.00-7.93 (m, 3H), 7.92-7.87 (m, 1H), 7.52-7.39 (m, 3H), 4.47 (d, J=5.8 Hz, 2H), 4.27-4.18 (m, 1H), 3.70-3.45 (m, 2H), 2.45-2.30 (m, 1H), 2.14-1.93 (m, 1H), 1.37 (d, J=20.7 Hz, 3H).

Example 188

Preparation of (2S,4R)-4-fluoro-1-(4-fluorophenyl) sulfonyl-N-[[2-methoxy-6-[2-(trifluoromethyl)pyrimidin-5-yl]-4-pyridyl]methyl]pyrrolidine-2-carboxamide

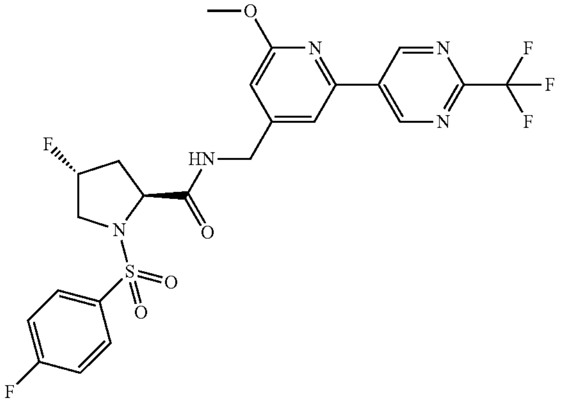 [SMILES: COc1cc(CNC(=O)[C@@H]2C[C@@H](F)CN2S(=O)(=O)c2ccc(F)cc2)cc(-c2cnc(C(F)(F)F)nc2)n1]

Preparation of the title compound follows the same general procedure as Example 48.

1H NMR (400 MHz, DMSO) δ 9.69-9.63 (s, 2H), 9.00-8.93 (t, J=6.0 Hz, 1H), 8.03-7.96 (m, 2H), 7.82-7.79 (d, J=1.1 Hz, 1H), 7.52-7.44 (m, 2H), 6.97-6.92 (q, J=1.0 Hz,

1H), 5.29-5.10 (d, J=52.3 Hz, 1H), 4.53-4.36 (m, 2H), 4.23-4.16 (dd, J=10.0, 7.1 Hz, 1H), 4.03-3.98 (s, 3H), 3.75-3.58 (m, 2H), 2.46-2.36 (m, 1H), 2.21-1.99 (m, 1H)., LCMS (ESI) m/z:558.2 [M+H]+

Example 189

Preparation of (2S,4R)—N-([5-cyano-2-[2-(trifluoromethyl)pyrimidin-5-yl]pyridin-4-yl]methyl)-4-fluoro-1-[(4-fluorobenzene)sulfonyl]pyrrolidine-2-carboxamide

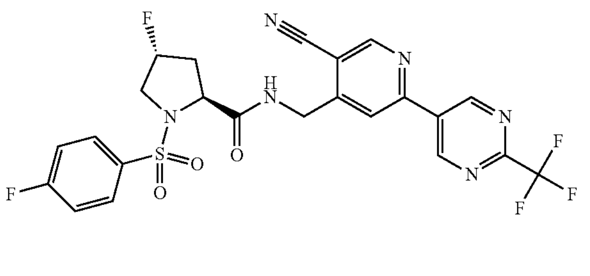 [SMILES: N#Cc1cnc(-c2cnc(C(F)(F)F)nc2)cc1CNC(=O)[C@@H]1C[C@@H](F)CN1S(=O)(=O)c1ccc(F)cc1]

Step 1: Preparation of (2S,4R)—N-([5-cyano-2-[2-(trifluoromethyl)pyrimidin-5-yl]pyridin-4-yl]methyl)-4-fluoro-1-[(4-fluorobenzene)sulfonyl]pyrrolidine-2-carboxamide

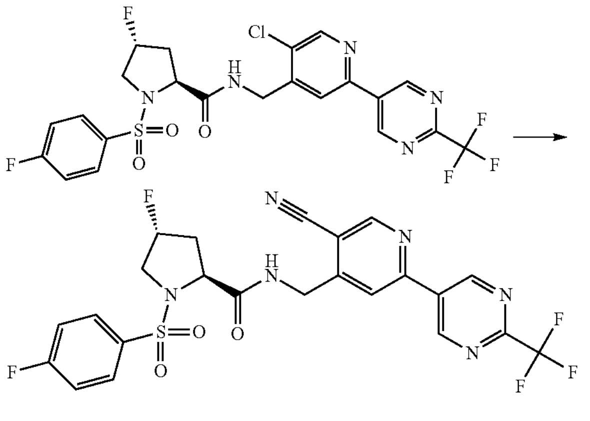

A mixture of (2S,4R)—N-([5-chloro-2-[2-(trifluoromethyl)pyrimidin-5-yl]pyridin-4-yl]methyl)-4-fluoro-1-[(4-fluorobenzene)sulfonyl]pyrrolidine-2-carboxamide (150 mg, 0.267 mmol, 1.0 equiv), $Zn(CN)_2$ (32 mg, 0.272 mmol, 1.02\equiv), $Pd_2(dba)_3.CHCl_3$ (28 mg, 0.027 mmol, 0.10 equiv), and dppf (45 mg, 0.081 mmol, 0.31 equiv) in DMF (15 mL) was irradiated with microwave for 1 h at 150° C. under nitrogen. The reaction mixture was diluted with ethyl acetate, washed with brine, dried over anhydrous sodium sulfate, and concentrated under vacuum. The residue was purified by a silica gel column eluting with ethyl acetate/petroleum ether (1:1). The crude product (100 mg) was re-purified by Flash-Prep-HPLC to afford the title compound (44.5 mg, 30%) as a pink solid.

$^1$H NMR (400 MHz, $CDCl_3$) δ 9.65 (s, 2H), 8.96 (s, 1H), 8.32 (s, 1H), 7.92-7.88 (m, 2H), 7.52-7.49 (m, 1H), 7.29-7.24 (m, 2H), 5.17-5.01 (m, 2H), 4.58-4.52 (m, 1H), 4.34-4.30 (m, 1H), 3.91-3.65 (m, 2H), 2.66-2.60 (m, 1H), 2.25-2.12 (m, 1H).

Example 190

Preparation of (2S,4R)-4-fluoro-N-([3-fluoro-5-[2-(2-methoxyethoxy)-6-(trifluoromethyl)pyridin-3-yl]phenyl]methyl)-1-[(4-fluorobenzene)sulfonyl]pyrrolidine-2-carboxamide

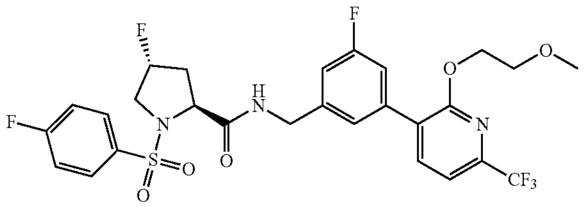 [SMILES: COCCOc1nc(C(F)(F)F)ccc1-c1cc(F)cc(CNC(=O)[C@@H]2C[C@@H](F)CN2S(=O)(=O)c2ccc(F)cc2)c1]

Step 1: Preparation of 3-bromo-2-chloro-6-(trifluoromethyl)pyridine

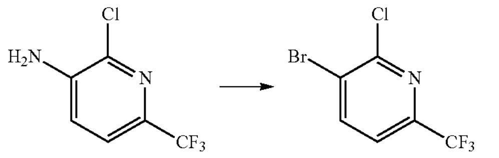 [SMILES: Nc1ccc(C(F)(F)F)nc1Cl ; FC(F)(F)c1ccc(Br)c(Cl)n1]

2-Chloro-6-(trifluoromethyl)pyridin-3-amine (3 g, 15.263 mmol, 1.000 equiv) was added into a mixture of $CuBr_2$ (6.8 g, 30.445 mmol, 2.000 equiv) and t-BuONO (3.1 g, 30.062 mmol, 2.000 equiv) in $CH_3CN$ (100 mL). The resulting solution was stirred for 2 h at room temperature. The reaction mixture was diluted with water, extracted with diethyl ether, dried over sodium sulfate, and concentrated under vacuum. This resulted in the title compound (3 g, 75%) as a brown liquid.

Step 2: Preparation of 3-bromo-2-(2-methoxyethoxy)-6-(trifluoromethyl)pyridine

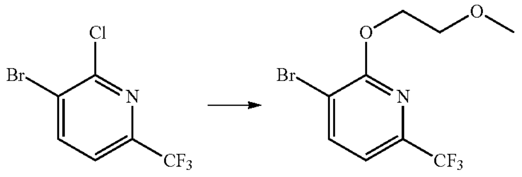 [SMILES: FC(F)(F)c1ccc(Br)c(Cl)n1 ; COCCOc1nc(C(F)(F)F)ccc1Br]

A mixture of 3-bromo-2-chloro-6-(trifluoromethyl)pyridine (3 g, 11.519 mmol, 1.00 equiv) and 1-methoxy-2-(sodiooxy)ethane (1.2 g, 12.235 mmol, 1.10 equiv) in 2-methoxyethan-1-ol (30 mL) was stirred overnight at room temperature. The reaction mixture was then quenched with water, extracted with diethyl ether, dried over sodium sulfate, and concentrated under vacuum. This resulted in the title compound (4 g) as a red liquid which was used for the next step without any further purification.

Step 3: Preparation of methyl 3-fluoro-5-[2-(2-methoxyethoxy)-6-(trifluoromethyl)pyridin-3-yl]benzoate

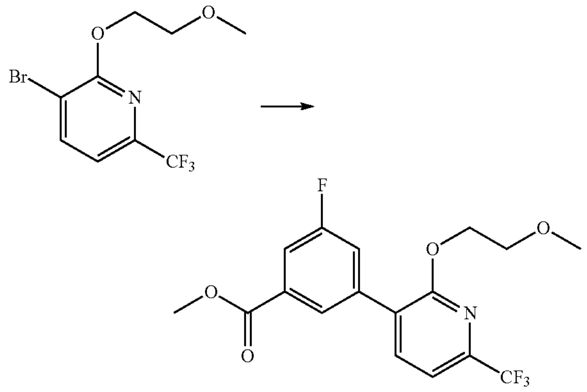

A mixture of 3-bromo-2-(2-methoxyethoxy)-6-(trifluoromethyl)pyridine (1.6 g, 5.33 mmol, 1.0 equiv), methyl 3-fluoro-5-(tetramethyl-1,3,2-dioxaborolan-2-yl)benzoate (1.5 g, 5.36 mmol, 1.0 equiv), potassium carbonate (1.5 g, 10.85 mmol, 2.0 equiv), and $Pd(dppf)Cl_2$ (390 mg, 0.533 mmol, 0.10 equiv) in dioxane (50 mL) was stirred overnight at 90° C. under nitrogen. The reaction mixture was diluted with water, extracted with ethyl acetate, dried over sodium sulfate, and concentrated under vacuum. The residue was purified by a silica gel column eluting with ethyl acetate/petroleum ether (1:10) to afford the title compound (1.9 g, 95%) as brown oil.

Step 4: Preparation of [3-fluoro-5-[2-(2-methoxyethoxy)-6-(trifluoromethyl)pyridin-3-yl]phenyl]methanol

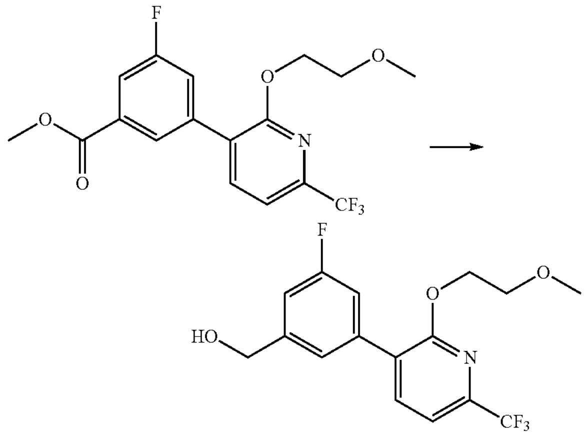

$LiAlH_4$ (360 mg, 9.485 mmol, 2.000 equiv) was added in several batches into a solution of methyl 3-fluoro-5-[2-(2-methoxyethoxy)-6-(trifluoromethyl)pyridin-3-yl]benzoate (1.8 g, 4.822 mmol, 1.000 equiv) in tetrahydrofuran (50 mL) at 0° C. under nitrogen. The resulting solution was stirred for 2 h at 0° C. and quenched by water. The solids were filtered out and the liquid was concentrated under vacuum. This resulted in 1.5 g of the title compound as a light yellow solid.

Step 5: Preparation of 2-([3-fluoro-5-[2-(2-methoxyethoxy)-6-(trifluoromethyl)pyridin-3-yl]phenyl]methyl)-2,3-dihydro-1H-isoindole-1,3-dione

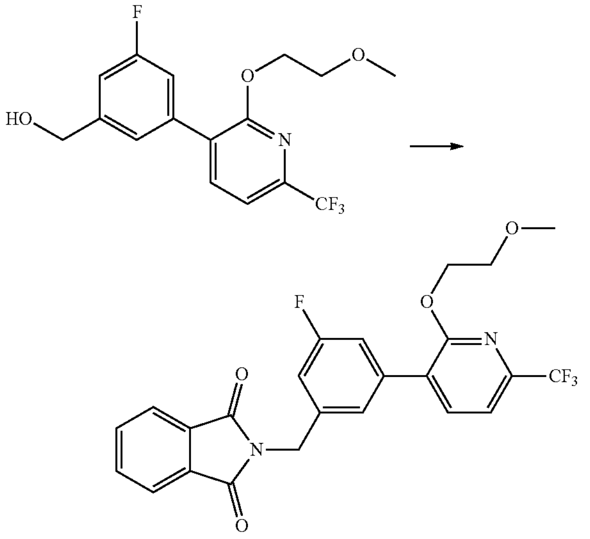

DIAD (1.6 g, 7.913 mmol, 2.000 equiv) was added dropwise into a solution of [3-fluoro-5-[2-(2-methoxyethoxy)-6-(trifluoromethyl)pyridin-3-yl]phenyl]methanol (1.4 g, 4.055 mmol, 1.000 equiv), 2,3-dihydro-1H-isoindole-1,3-dione (1.2 g, 8.156 mmol, 2.000 equiv), and $PPh_3$ (2.1 g, 8.007 mmol, 2.000 equiv) in tetrahydrofuran (50 mL) at 0° C. under nitrogen. The resulting solution was stirred for 2 h at room temperature and concentrated under vacuum. The residue was purified by a silica gel column eluting with ethyl acetate/petroleum ether (1:5) to afford the title compound (1.3 g, 68%) as a white solid.

Step 6: Preparation of [3-fluoro-5-[2-(2-methoxyethoxy)-6-(trifluoromethyl)pyridin-3-yl]phenyl]methanamine

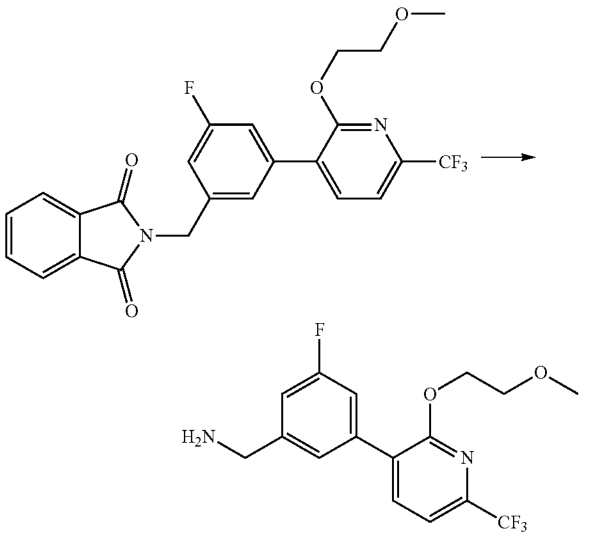

A mixture of 2-([3-fluoro-5-[2-(2-methoxyethoxy)-6-(trifluoromethyl)pyridin-3-yl]phenyl]methyl)-2,3-dihydro-1H-isoindole-1,3-dione (1.2 g, 2.53 mmol, 1.0 equiv) and $NH_2NH_2.H_2O$ (2 mL, 41.150 mmol, 10.0 equiv) in methanol (10 mL) was stirred overnight at room temperature. The reaction mixture was concentrated under vacuum, diluted with water, extracted with dichloromethane, dried over sodium sulfate, and concentrated under vacuum. This resulted in the title compound (750 mg, 86%) as light yellow oil.

Step 7: Preparation of tert-butyl (4R)-4-fluoro-2-[([3-fluoro-5-[2-(2-methoxyethoxy)-6-(trifluoromethyl)pyridin-3-yl]phenyl]methyl)carbamoyl]pyrrolidine-1-carboxylate

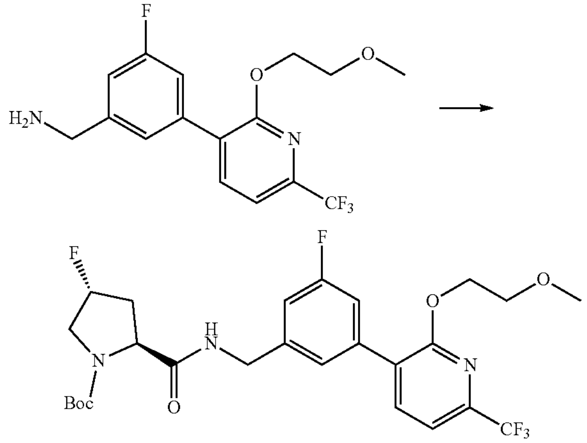

A solution of (2S,4R)-1-[(tert-butoxy)carbonyl]-4-fluoropyrrolidine-2-carboxylic acid (68 mg, 0.292 mmol, 1.000 equiv), HATU (132 mg, 0.347 mmol, 1.200 equiv), [3-fluoro-5-[2-(2-methoxyethoxy)-6-(trifluoromethyl)pyridin-3-yl]phenyl]methanamine (100 mg, 0.290 mmol, 1.000 equiv), and DIEA (75 mg, 0.580 mmol, 2.000 equiv) in N,N-dimethylformamide (5 mL) was stirred for 2 h at room temperature. The reaction mixture was diluted with water, extracted with ethyl acetate, dried over anhydrous sodium sulfate, and concentrated under vacuum. This resulted in the title compound (180 mg) as light yellow oil.

Step 8: Preparation of (2S,4R)-4-fluoro-N-([3-fluoro-5-[2-(2-methoxyethoxy)-6-(trifluoromethyl)pyridin-3-yl]phenyl]methyl)pyrrolidine-2-carboxamide hydrochloride

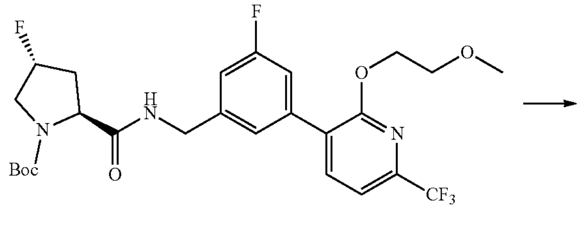

-continued

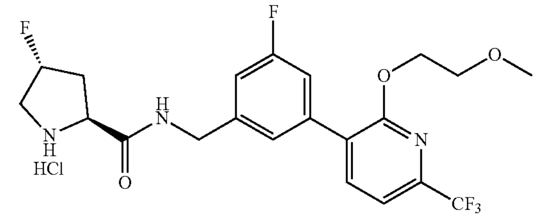

A mixture of tert-butyl (4R)-4-fluoro-2-[([3-fluoro-5-[2-(2-methoxyethoxy)-6-(trifluoromethyl)pyridin-3-yl]phenyl]methyl)carbamoyl]pyrrolidine-1-carboxylate (180 mg, 0.322 mmol, 1.000 equiv) and hydrogen chloride in dioxane (10 mL) was stirred overnight at room temperature. The product was precipitated by the addition of hexane. The solids were collected by filtration to afford the title compound (160 mg) as a brown solid.

Step 9: Preparation of (2S,4R)-4-fluoro-N-([3-fluoro-5-[2-(2-methoxyethoxy)-6-(trifluoromethyl)pyridin-3-yl]phenyl]methyl)-1-[(4-fluorobenzene)sulfonyl]pyrrolidine-2-carboxamide

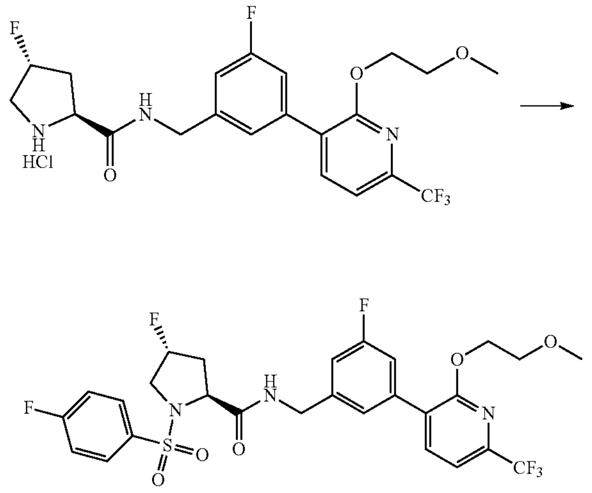

A solution of (2S,4R)-4-fluoro-N-([3-fluoro-5-[2-(2-methoxyethoxy)-6-(trifluoromethyl)pyridin-3-yl]phenyl]methyl)pyrrolidine-2-carboxamide hydrochloride (160 mg, 0.32 mmol, 1.000 equiv), DIEA (125 mg, 0.967 mmol, 3.0 equiv), and 4-fluorobenzene-1-sulfonyl chloride (69 mg, 0.355 mmol, 1.1 equiv) in dichloromethane (20 mL) was stirred for 2 h at room temperature. The reaction mixture was concentrated under vacuum. The residue was purified by a silica gel column eluting with ethyl acetate/petroleum ether (1:1). The crude product was purified by Prep-HPLC to afford the tile compound (50.3 mg, 25%) as a white solid.

$^1H$ NMR (400 MHz, $CDCl_3$) δ 7.79-7.84 (m, 3H), 7.40-7.22 (m, 6H), 7.11 (d, J=12.0 Hz, 1H), 5.12-4.99 (d, J=52.0 Hz, 1H), 4.68-4.60 (m, 3H), 4.53-4.48 (dd, J=15.2 Hz, J=5.2 Hz, 1H), 4.29 (t, J=8.4 Hz, 1H), 3.96-3.87 (m, 1H), 3.78 (t, J=4.8 Hz, 1H), 3.70-3.56 (m, 1H), 3.43 (s, 3H), 2.60-2.47 (m, 1H), 2.40-2.20 (m, 1H).

Example 191

Preparation of (2R,3S)-3-fluoro-1-[(4-fluorobenzene)sulfonyl]-N-([6-methyl-4-[2-(trifluoromethyl)pyrimidin-5-yl]pyridin-2-yl]methyl)pyrrolidine-2-carboxamide

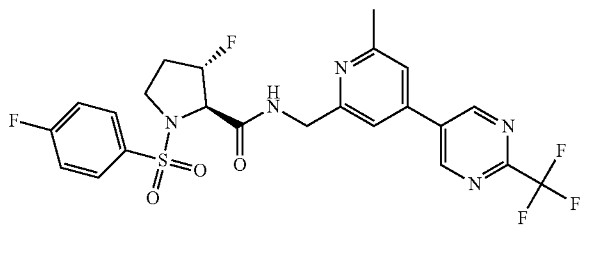 [SMILES: Cc1cc(-c2cnc(C(F)(F)F)nc2)cc(CNC(=O)[C@@H]2[C@@H](F)CCN2S(=O)(=O)c2ccc(F)cc2)n1]

Step 1: Preparation of 5-(2,6-dichloropyridin-4-yl)-2-(trifluoromethyl)pyrimidine

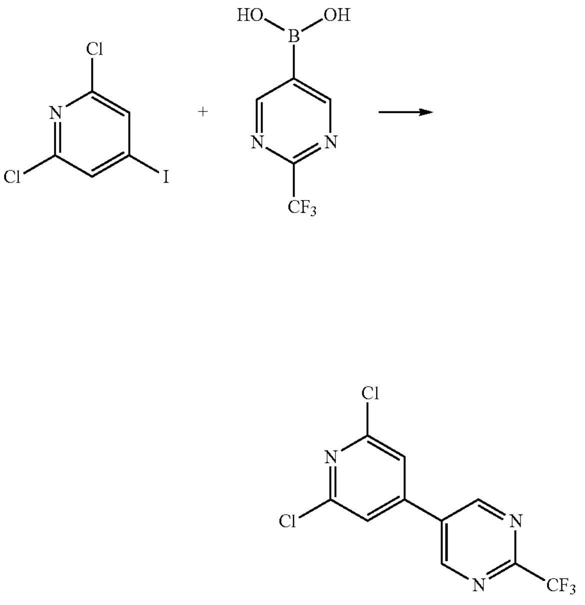

A mixture of 2,6-dichloro-4-iodopyridine (8.61 g, 31.43 mmol, 1.00 equiv), 5-(tetramethyl-1,3,2-dioxaborolan-2-yl)-2-(trifluoromethyl)pyrimidine (7.85 g, 28.64 mmol, 1.00 equiv), potassium carbonate (11.9 g, 86.10 mmol, 1.00 equiv), and Pd(dppf)$Cl_2$(1.05 g, 1.43 mmol, 1.00 equiv) in dioxane (150 mL)/water(10 mL) was stirred for 12 h at 60° C. under nitrogen. The reaction solution was diluted with ethyl acetate, washed with brine, dried over anhydrous sodium sulfate, and concentrated under vacuum. The residue was purified by a silica gel column eluting with ethyl acetate/petroleum ether (1:20) to afford the title compound (6 g, 65%) as an off-white solid.

Step 2: Preparation of 5-(2,6-dimethylpyridin-4-yl)-2-(trifluoromethyl)pyrimidine

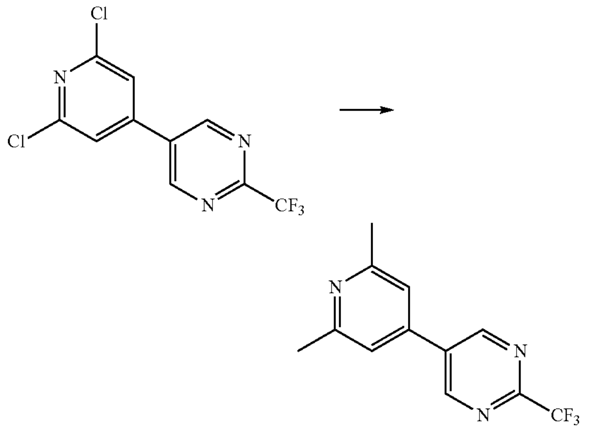

A mixture of 5-(2,6-dichloropyridin-4-yl)-2-(trifluoromethyl)pyrimidine (1.7 g, 5.78 mmol, 1.00 equiv), Pd(dppf)$Cl_2$ (423 mg, 0.57 mmol, 0.10 equiv), and dimethylzinc (21.7 mL, 1.2 M in toluene, 4.50 equiv) in dioxane (100 mL) was stirred for 12 h at 60° C. under nitrogen. The resulting mixture was concentrated under vacuum. The residue was purified by a silica gel column eluting with ethyl acetate/petroleum ether (1:5) to afford the title compound (770 mg, 53%) as a light yellow solid.

Step 3: Preparation of 2,6-dimethyl-4-[2-(trifluoromethyl)pyrimidin-5-yl]pyridin-1-ium-1-olate

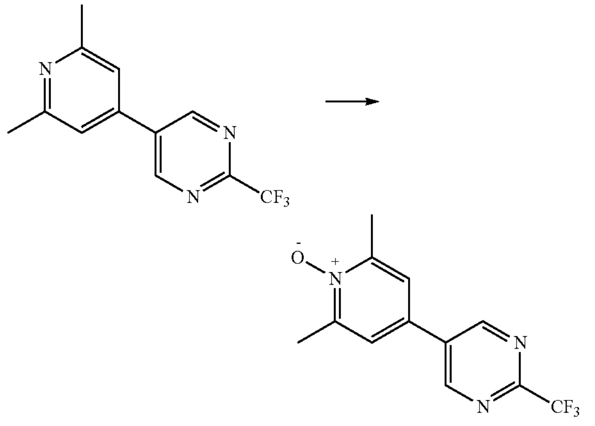

A solution of m-CPBA (578 mg, 3.34 mmol, 1.10 equiv) in ethyl acetate(5 mL) was added dropwise with stirring into the solution of 5-(2,6-dimethylpyridin-4-yl)-2-(trifluoromethyl)pyrimidine (770 mg, 3.04 mmol, 1.00 equiv) in dichloromethane (50 mL) at 0° C. The resulting solution was stirred for 12 h at room temperature. The reaction was then quenched with saturated of sodium bicarbonate, extracted with ethyl acetate, washed with brine, dried over anhydrous sodium sulfate, and concentrated under vacuum. The residue was purified by a silica gel column eluting with dichloromethane/methanol (50/1) to afford the title compound (750 mg, 92%) as a light yellow solid.

Step 4: Preparation of [6-methyl-4-[2-(trifluoromethyl)pyrimidin-5-yl]pyridin-2-yl]methyl acetate

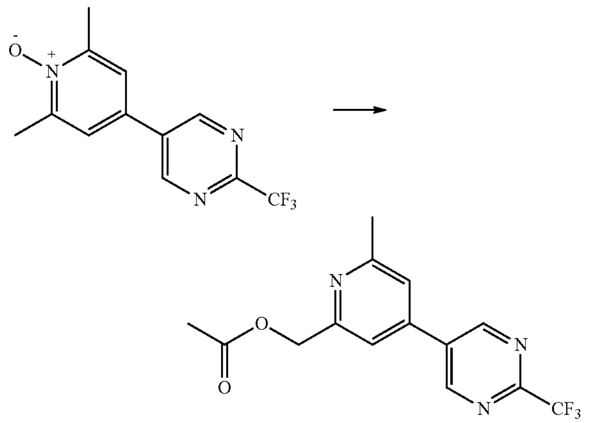

A solution of 2,6-dimethyl-4-[2-(trifluoromethyl)pyrimidin-5-yl]pyridin-1-ium-1-olate(750 mg, 2.78 mmol, 1.00 equiv) in acetic anhydride (15 mL) was heated to reflux for 1 h. The reaction mixture was cooled and poured into ice water. The pH value of the solution was adjusted to 8 with saturated of sodium bicarbonate, extracted with ethyl acetate, washed with brine, dried over anhydrous sodium sulfate, and concentrated under vacuum. The residue was purified by a silica gel column eluting with dichloromethane/methanol (20/1) to afford the title compound (650 mg, 75%) as an off-white solid.

Step 5: Preparation of [6-methyl-4-[2-(trifluoromethyl)pyrimidin-5-yl]pyridin-2-yl]methanol

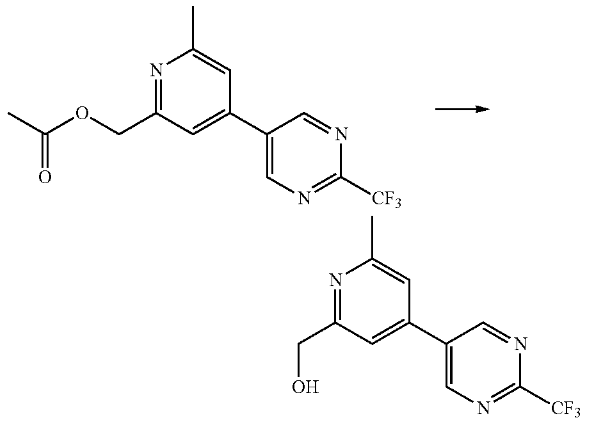

A solution of [6-methyl-4-[2-(trifluoromethyl)pyrimidin-5-yl]pyridin-2-yl]methyl acetate (650 mg, 2.08 mmol, 1.00 equiv) and hydrogen chloride (15 mL, 493.67 mmol, 1.00 equiv) in ethanol (15 mL) was heated to reflux for 2 h. The reaction solution was diluted with water. The pH value of the solution was adjusted to 8 with saturated of sodium bicarbonate, extracted with ethyl acetate, washed with brine, dried over anhydrous sodium sulfate, and concentrated under vacuum. The residue was purified by a silica gel column eluting with dichloromethane/methanol (20/1) to afford the title compound (340 mg, 60%) as a light yellow solid.

Step 6: Preparation of 2-([6-methyl-4-[2-(trifluoromethyl)pyrimidin-5-yl]pyridin-2-yl]methyl)-2,3-dihydro-1H-isoindole-1,3-dione

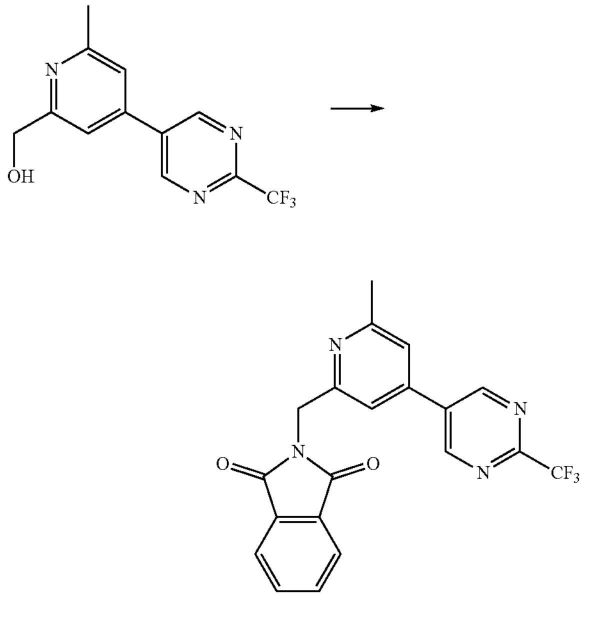

DIAD (511 mg, 2.52 mmol, 2.00 equiv) was added to the solution of [6-methyl-4-[2-(trifluoromethyl)pyrimidin-5-yl]pyridin-2-yl]methanol (340 mg, 1.26 mmol, 1.00 equiv), 2,3-dihydro-1H-isoindole-1,3-dione (372 mg, 2.52 mmol, 2.00 equiv), and $PPh_3$ (662 mg, 2.52 mmol, 1.99 equiv) in THF (50 mL) dropwise at 0° C. The resulting solution was stirred for 12 h at room temperature. The resulting mixture was concentrated under vacuum. The residue was purified by a silica gel column eluting with acetate/petroleum ether (1/1) to afford the title compound (300 mg, 60%) as a white solid.

Step 7: Preparation of 6-methyl-4-[2-(trifluoromethyl)pyrimidin-5-yl]pyridin-2-amine

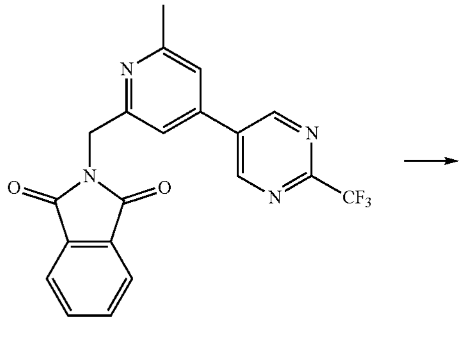

-continued

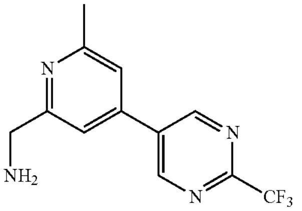

A solution of 2-[6-methyl-4-[2-(trifluoromethyl)pyrimidin-5-yl]pyridin-2-yl]-2,3-dihydro-1H-isoindole-1,3-dione (600 mg, 1.56 mmol, 1.00 equiv) and $NH_2NH_2.H_2O$ (754 mg, 15.06 mmol, 9.64 equiv) in methanol (15 mL) was stirred for 12 h at 25° C. The resulting mixture was concentrated under vacuum. The residue was dissolved with ethyl acetate and the solid were filtered out. The filtrate was concentrated under vacuum. This resulted in 686 mg (crude) of the title compound as oil.

Step 8: Preparation of tert-butyl (2S,3R)-3-hydroxy-2-[([6-methyl-4-[2-(trifluoromethyl)pyrimidin-5-yl]pyridin-2-yl]methyl)carbamoyl]pyrrolidine-1-carboxylate

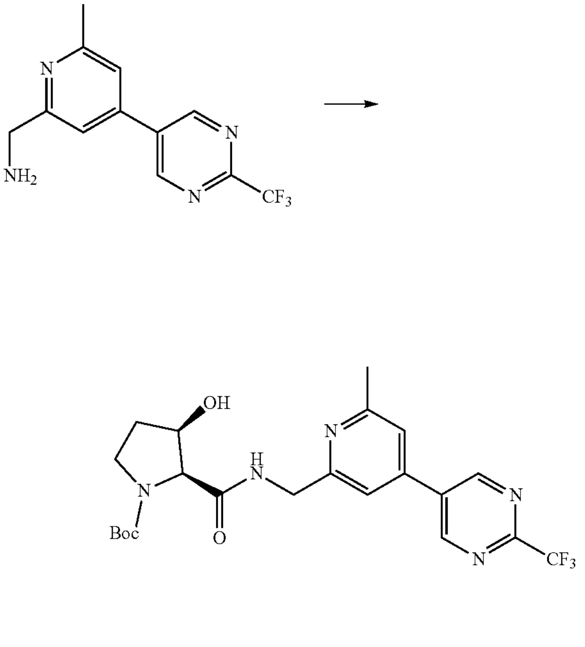

A solution of (2S,3R)-1-[(tert-butoxy)carbonyl]-3-hydroxypyrrolidine-2-carboxylic acid (97 mg, 0.41 mmol, 1.19 equiv), DIEA (136 mg, 1.05 mmol, 3.00 equiv), HATU (213 mg, 0.56 mmol, 1.59 equiv), and [6-methyl-4-[2-(trifluoromethyl)pyrimidin-5-yl]pyridin-2-yl]methanamine(94 mg, 0.35 mmol, 1.00 equiv) in DMF (5 mL) was stirred for 30 min at 25° C. The reaction solution was diluted with ethyl acetate, washed with brine, dried over anhydrous sodium sulfate, and concentrated under vacuum. This resulted in 168 mg (crude) of the title compound as a solid.

Step 9: Preparation of tert-butyl (2R,3S)-3-fluoro-2-[([6-methyl-4-[2-(trifluoromethyl)pyrimidin-5-yl]pyridin-2-yl]methyl)carbamoyl]pyrrolidine-1-carboxylate

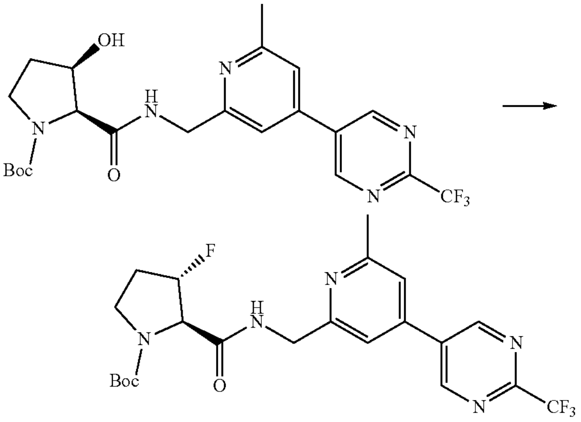

DAST (112 mg, 0.69 mmol, 1.99 equiv) was added to a solution of tert-butyl (2S,3R)-3-hydroxy-2-[([6-methyl-4-[2-(trifluoromethyl)pyrimidin-5-yl]pyridin-2-yl]methyl)carbamoyl]pyrrolidine-1-carboxylate (168 mg, 0.34 mmol, 1.00 equiv) in dichloromethane (20 mL) dropwise at 0° C. and the reaction was stirred for 2 h at room temperature. The reaction was then quenched by sodium bicarbonate/water, extracted with of ethyl acetate, dried over anhydrous sodium sulfate, and concentrated under vacuum. This resulted in 65 mg (39%) of the title compound as a white solid.

Step 10: Preparation of (2R,3S)-3-fluoro-N-((6-methyl-4-(2-(trifluoromethyl)pyrimidin-5-yl)pyridin-2-yl)methyl)pyrrolidine-2-carboxamide hydrochloride

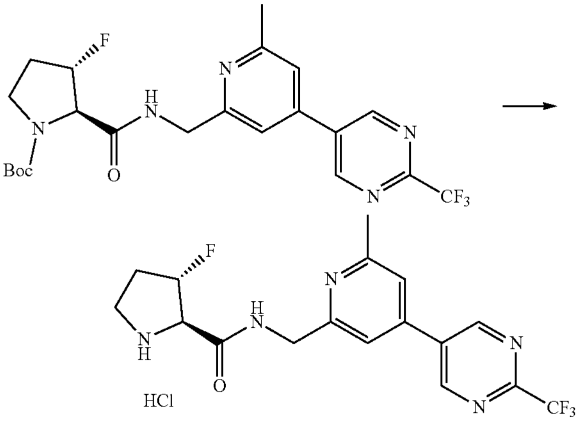

A mixture of tert-butyl (2R,3S)-3-fluoro-2-[([6-methyl-4-[2-(trifluoromethyl)pyrimidin-5-yl]pyridin-2-yl]methyl)carbamoyl]pyrrolidine-1-carboxylate (65 mg, 0.13 mmol, 1.00 equiv) and saturated hydrogen chloride in 1,4-dioxane (5 mL) was stirred for 2h at room temperature. The resulting mixture was concentrated under vacuum to afford the title compound (120 mg) as a crude solid.

Step 11: Preparation of (2R,3S)-3-fluoro-1-[(4-fluorobenzene)sulfonyl]-N-([6-methyl-4-[2-(trifluoromethyl)pyrimidin-5-yl]pyridin-2-yl]methyl)pyrrolidine-2-carboxamide

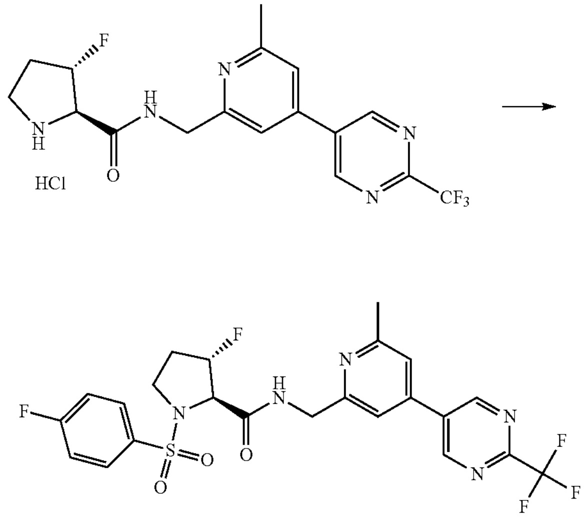

4-Fluorobenzene-1-sulfonyl chloride (84 mg, 0.43 mmol, 1.51 equiv) was added into the solution of (2R,3S)-3-fluoro-N-([6-methyl-4-[2-(trifluoromethyl)pyrimidin-5-yl]pyridin-2-yl]methyl)pyrrolidine-2-carboxamide hydrochloride (120 mg, 0.28 mmol, 1.00 equiv) and TEA (87 mg, 0.86 mmol, 3.00 equiv) in dichloromethane(20 mL). The reaction mixture was stirred for 12h at room temperature. The resulting solution was diluted with ethyl acetate, washed with brine, dried over anhydrous sodium sulfate and concentrated under vacuum. This resulted in the title compound (24.4 mg, 16%) as a white solid.

$^1$H NMR (400 MHz, $CDCl_3$) δ 9.18 (s, 2H), 7.98-7.88 (m, 3H), 7.60-7.50 (m, 1H), 7.34-7.23 (m, 2H), 6.91 (m, 1H), 5.39-5.22 (d, J=51.0 Hz, 1H), 4.94-4.86 (m, 1H), 4.60-4.55 (m, 1H), 4.41-4.33 (m, 1H), 3.84-3.70 (m, 1H), 3.33-3.24 (m, 1H), 2.72-2.62 (s, 3H), 2.20-1.95 (m, 2H).

Example 192

Preparation of (2S,4R)—N-([5-chloro-4-[2-(trifluoromethyl)pyrimidin-5-yl]pyridin-2-yl]methyl)-4-fluoro-1-[(4-fluorobenzene)sulfonyl]pyrrolidine-2-carboxamide

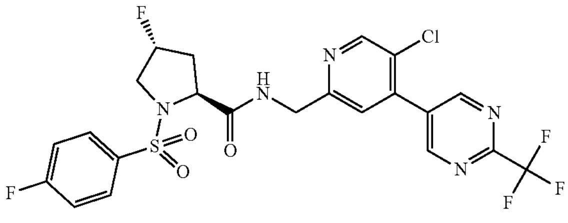 [SMILES: O=C(NCc1cc(-c2cnc(C(F)(F)F)nc2)c(Cl)cn1)[C@@H]1C[C@@H](F)CN1S(=O)(=O)c1ccc(F)cc1]

Step 1: Preparation of 5-(2,5-dichloropyridin-4-yl)-2-(trifluoromethyl)pyrimidine

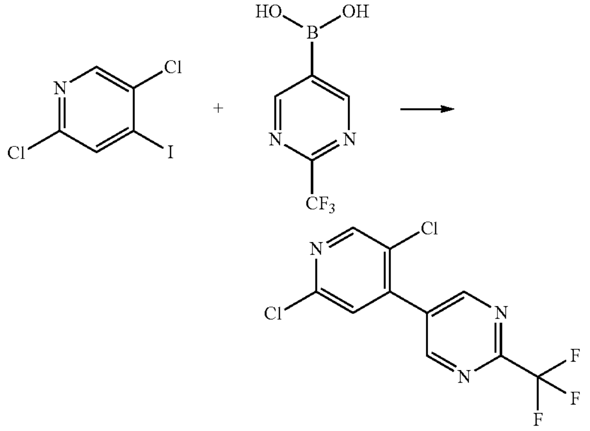

A mixture of 2,5-dichloro-4-iodopyridine (3.86 g, 14.09 mmol, 1.00 equiv), 5-(tetramethyl-1,3,2-dioxaborolan-2-yl)-2-(trifluoromethyl)pyrimidine (4.26 g, 15.54 mmol, 1.10 equiv), potassium carbonate (5.83 g, 42.19 mmol, 2.99 equiv), and Pd(dppf)$Cl_2$ (516 mg, 0.70 mmol, 0.05 equiv) in dioxane (50 mL)/water (5 mL) was stirred for 12 h at 60° C. under nitrogen. The solids were filtered out. The filtrate was diluted with ethyl acetate, washed with brine, dried over anhydrous sodium sulfate, and concentrated under vacuum. The residue was purified by a silica gel column eluting with acetate/petroleum ether (1/100) to afford the title compound (2.2 g, 53%) as a yellow solid.

Step 2: Preparation of methyl 5-chloro-4-[2-(trifluoromethyl)pyrimidin-5-yl]pyridine-2-carboxylate

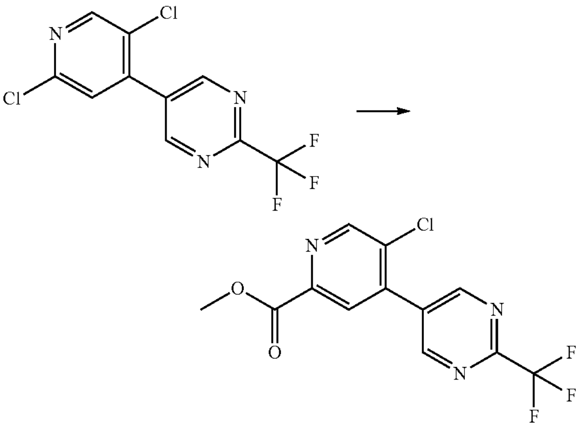

A mixture of 5-(2,5-dichloropyridin-4-yl)-2-(trifluoromethyl)pyrimidine (2.19 g, 7.47 mmol, 1.00 equiv), Pd(dppf) $Cl_2$ (549 mg, 0.75 mmol, 0.10 equiv), and TEA (2.27 g, 22.47 mmol, 3.00 equiv) in methanol (50 mL) was stirred for 12 h at 60° C. under carbon monoxide. The reaction solution was diluted with ethyl acetate, washed with water and brine, dried over anhydrous sodium sulfate, and concentrated under vacuum. The residue was purified by a silica gel column eluting with acetate/petroleum ether (1/100) to afford the title compound (1.2 g, 52%) as a pink solid.

Step 3: Preparation of 5-chloro-4-[2-(trifluoromethyl)pyrimidin-5-yl]pyridine-2-carbaldehyde

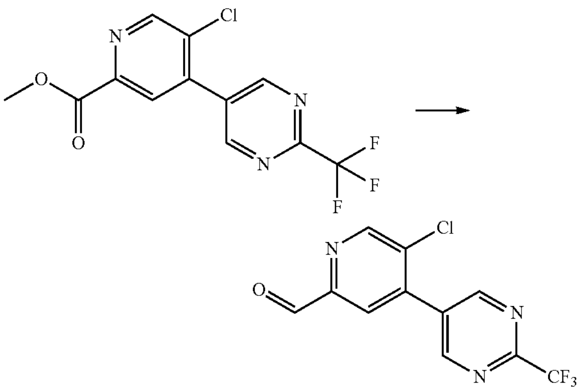

DIBAL-H (4.5 mL, 31.64 mmol, 3.00 equiv) was added to the solution methyl 5-chloro-4-[2-(trifluoromethyl)pyrimidin-5-yl]pyridine-2-carboxylate(482 mg, 1.51 mol, 1.00 equiv) in dichloromethane (200 mL) dropwise at −78° C. under nitrogen, and stirred for 20 min at −78° C. The reaction was then quenched with methanol. The resulting solution was diluted with ethyl acetate, washed with water and brine, dried over anhydrous sodium sulfate, and concentrated under vacuum. The residue was purified by a silica gel column eluting with acetate/petroleum ether (1/20) to afford the title compound 344 mg (crude) as a light yellow solid.

Step 4: Preparation of [5-chloro-4-[2-(trifluoromethyl)pyrimidin-5-yl]pyridin-2-yl]methanol

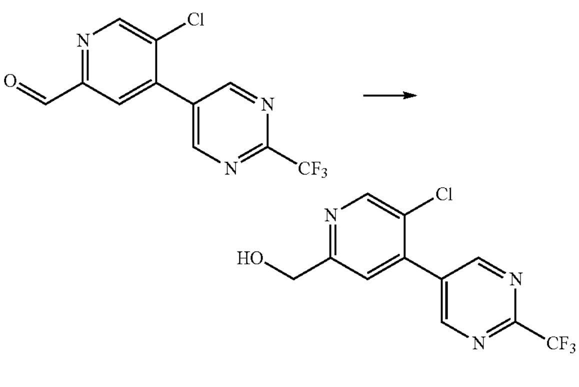

$NaBH_4$ (18 mg, 0.47 mmol, 0.39 equiv) was added into the solution of 5-chloro-4-[2-(trifluoromethyl)pyrimidin-5-yl]pyridine-2-carbaldehyde (344 mg, 1.19 mmol, 1.00 equiv) in methanol (200 mL) batch wise at −20° C. and stirred for 30 min. The reaction mixture was quenched with saturated $NH_4Cl$, extracted with ethyl acetate, dried over anhydrous sodium sulfate, and concentrated under vacuum. The residue was purified by a silica gel column eluting with acetate/petroleum ether (1/1) to afford the title compound (330 mg, 95%) as a brown solid.

Step 5: Preparation of 2-([5-chloro-4-[2-(trifluoromethyl)pyrimidin-5-yl]pyridin-2-yl]methyl)-2,3-dihydro-1H-isoindole-1,3-dione

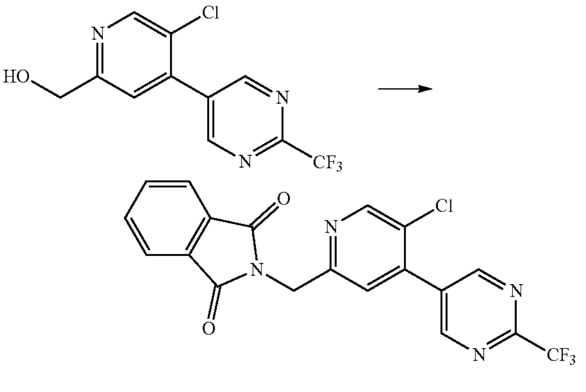

DIAD (490 mg, 2.42 mmol, 2.00 equiv) was added to a solution of [5-chloro-4-[2-(trifluoromethyl)pyrimidin-5-yl]pyridin-2-yl]methanol (350 mg, 1.20 mmol, 1.00 equiv), 2,3-dihydro-1H-isoindole-1,3-dione (356 mg, 2.42 mmol, 2.00 equiv), and $PPh_3$ (634 mg, 2.41 mmol, 2.00 equiv) in tetrahydrofuran (200 mL) dropwise at 0° C. The resulting solution was stirred for 12 hours at room temperature. The resulting solution was diluted with ethyl acetate, washed with water and brine, dried over anhydrous sodium sulfate, and concentrated under vacuum. The residue was purified by a silica gel column eluting with acetate/petroleum ether (1/5) to afford the title compound 800 mg (crude) as yellow oil.

Step 6: Preparation of [5-chloro-4-[2-(trifluoromethyl)pyrimidin-5-yl]pyridin-2-yl]methanamine

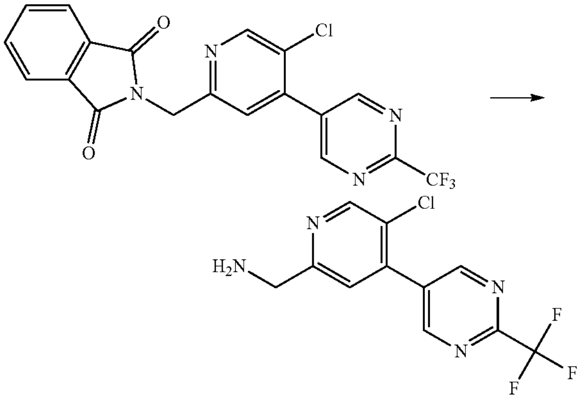

A solution of 2-([5-chloro-4-[2-(trifluoromethyl)pyrimidin-5-yl]pyridin-2-yl]methyl)-2,3-dihydro-1H-isoindole-1,3-dione (800 mg, 1.91 mmol, 1.00 equiv), $NH_2NH_2.H_2O$ (957 mg, 19.17 mmol, 10.00 equiv) in methanol (60 mL) was stirred for 3 h at 60° C. The resulting mixture was concentrated under vacuum. The residue was dissolved with ethyl acetate. The solids were filtered out. The filtrate was concentrated under vacuum. This resulted in 700 mg (crude) of the title compound as yellow oil.

Step 7: Preparation of tert-butyl (2S,4R)-2-[([5-chloro-4-[2-(trifluoromethyl)pyrimidin-5-yl]pyridin-2-yl]methyl)carbamoyl]-4-fluoropyrrolidine-1-carboxylate

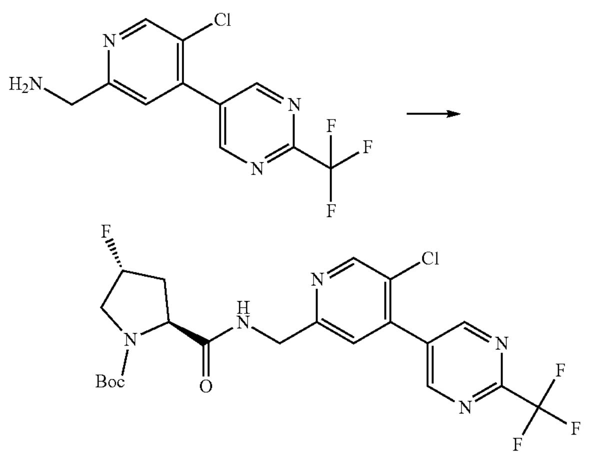

A solution of (2S,4R)-1-[(tert-butoxy)carbonyl]-4-fluoropyrrolidine-2-carboxylic acid (690 mg, 2.95 mmol, 1.23 equiv), HATU (1.091 g, 2.86 mmol, 1.20 equiv), DIEA (618 mg, 4.78 mmol, 2.00 equiv), and [5-chloro-4-[2-(trifluoromethyl)pyrimidin-5-yl]pyridin-2-yl]methanamine (690 mg, 2.39 mmol, 1.00 equiv) in DMF (15 mL) was stirred for 2 h at room temperature. The resulting solution was diluted with ethyl acetate, washed with water and brine, dried over anhydrous sodium sulfate, and concentrated under vacuum. The residue was purified by a silica gel column eluting with acetate/petroleum ether (1/5) to afford the title compound (800 mg, 66%) as a yellow solid.

Step 8: Preparation of (2S,4R)—N-([5-chloro-4-[2-(trifluoromethyl)pyrimidin-5-yl]pyridin-2-yl]methyl)-4-fluoropyrrolidine-2-carboxamide hydrochloride

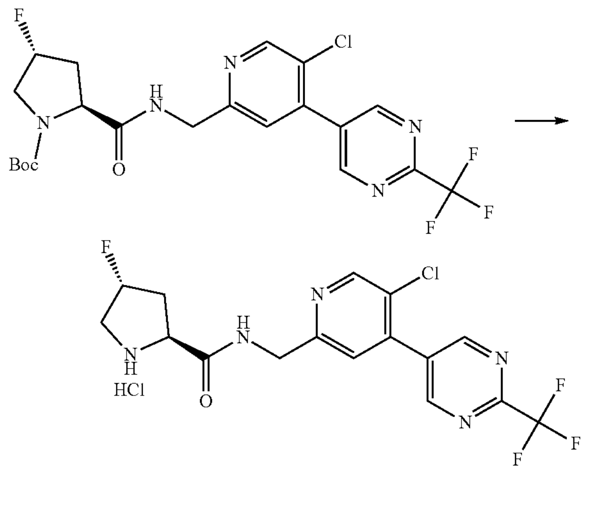

A mixture of (2S,4R)-2-[([5-chloro-4-[2-(trifluoromethyl)pyrimidin-5-yl]pyridin-2-yl]methyl)carbamoyl]-4-fluoropyrrolidine-1-carboxylate (210 mg, 0.41 mmol, 1.00 equiv) and saturated hydrogen chloride in 1,4-dioxane (50 mL) was stirred for 12 hours at room temperature. The resulting mixture was concentrated under vacuum. This resulted in 168 mg (92%) of the title compound as light yellow oil.

Step 9: Preparation of (2S,4R)—N-([5-chloro-4-[2-(trifluoromethyl)pyrimidin-5-yl]pyridin-2-yl]methyl)-4-fluoro-1-[(4-fluorobenzene)sulfonyl]pyrrolidine-2-carboxamide

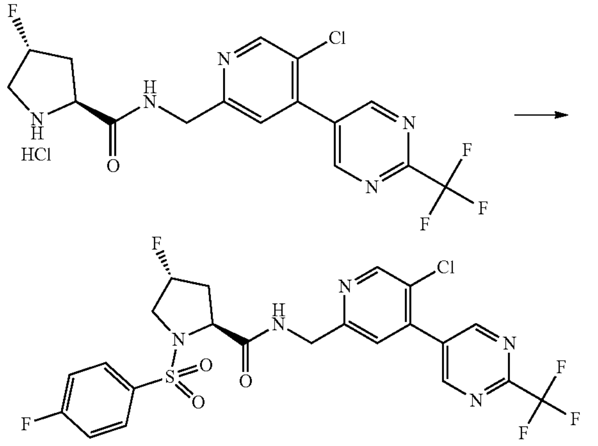

4-Fluorobenzene-1-sulfonyl chloride (180 mg, 0.92 mmol, 2.42 equiv) was added to the solution of (2S,4R)—N-([5-chloro-4-[2-(trifluoromethyl)pyrimidin-5-yl]pyridin-2-yl]methyl)-4-fluoropyrrolidine-2-carboxamide hydrochloride (168 mg, 0.38 mmol, 1.00 equiv), and TEA (200 mg, 1.97 mmol, 5.17 equiv) in dichloromethane (30 mL), and stirred for 4 h at room temperature. The resulting solution was diluted with ethyl acetate, washed with brine, dried over anhydrous sodium sulfate, and concentrated under vacuum. The crude product (200 mg) was purified by Prep-HPLC to give the title compound (32.3 mg, 15%) as a white solid.

$^1$H NMR (400 MHz, $CDCl_3$) δ 9.10 (s, 2H), 8.73 (s, 1H), 7.87-7.84 (m, 2H), 7.58 (s, 1H), 7.55 (s, 1H), 7.23 (s, 1H), 7.21 (s, 1H), 5.12-4.99 (d, J=52.0 Hz, 1H), 4.94-4.88 (m, 1H), 4.57-4.52 (m, 1H), 4.29-4.25 (t, J=8.4 Hz, 1H), 3.91-3.61 (m, 2H), 2.61-2.51 (m, 1H), 2.31-2.15 (m, 1H).

Example 193

Preparation of (2S,4R,5S)-4-fluoro-1-[(4-fluorobenzene)sulfonyl]-5-methyl-N-([2-[2-(trifluoromethyl)pyrimidin-5-yl]pyridin-4-yl]methyl)pyrrolidine-2-carboxamide

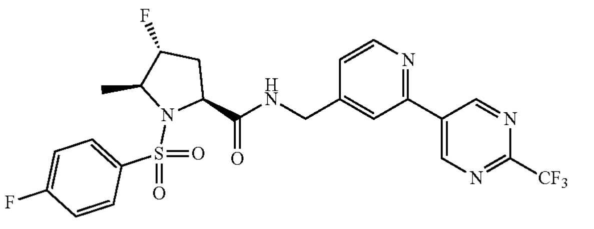 [SMILES: C[C@H]1[C@H](F)C[C@@H](C(=O)NCc2ccnc(-c3cnc(C(F)(F)F)nc3)c2)N1S(=O)(=O)c1ccc(F)cc1]

Step 1: Preparation of 1-tert-butyl 2-methyl (2S,4S)-4-[(tert-butyldimethylsilyl)oxy]pyrrolidine-1,2-dicarboxylate

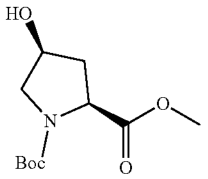

A solution of 2-methyl (2S,4S)-4-hydroxypyrrolidine-1,2-dicarboxylate (10 g, 40.77 mmol, 1.00 equiv), Imidazole (2.78 g, 40.83 mmol, 1.10 equiv), and tert-butyl(chloro)dimethylsilane(6.7 g, 44.45 mmol, 1.10 equiv) in DMF (100 mL) was stirred overnight at room temperature. The resulting solution was diluted with ethyl acetate, washed with water and of brine, dried over anhydrous sodium sulfate, and concentrated under vacuum. The residue was purified by a silica gel column eluting with acetate/petroleum ether (1/8) to afford the title compound (16 g) as colorless oil.

Step 2: Preparation of 1-tert-butyl 2-methyl (2S,4S)-4-[(tert-butyldimethylsilyl)oxy]-5-oxopyrrolidine-1,2-dicarboxylate

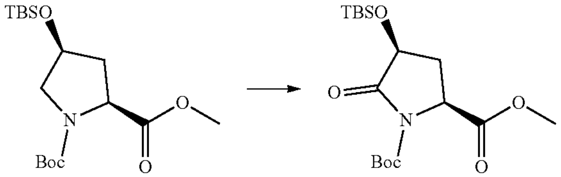 [SMILES: COC(=O)[C@@H]1C[C@H](O[Si](C)(C)C(C)(C)C)CN1C(=O)OC(C)(C)C ; COC(=O)[C@@H]1C[C@H](O[Si](C)(C)C(C)(C)C)C(=O)N1C(=O)OC(C)(C)C]

A mixture of $NaIO_4$ (7.43 g, 34.73 mmol, 2.50 equiv) and ruthenium(IV) oxide (370 mg, 2.78 mmol, 0.20 equiv) in water (107 mL) was stirred for 5 min at room temperature. To this was added the solution of 1-tert-butyl 2-methyl (2S,4S)-4-[(tert-butyldimethylsilyl)oxy]pyrrolidine-1,2-dicarboxylate (5 g, 13.90 mmol, 1.00 equiv) in ethyl acetate (60 mL) and the reaction was stirred for 3 h at room temperature. The resulting solution was diluted with ethyl acetate, washed with $NaHSO_3$/water and brine, dried over anhydrous sodium sulfate, and concentrated under vacuum. The residue was purified by a silica gel column eluting with acetate/petroleum ether (1/8) to afford the title compound (3.3 g, 64%) as colorless oil.

Step 3: Preparation of methyl (2S,4S)-1-tert-butyl 2-methyl 4-(tert-butyldimethylsilyloxy)-5-hydroxy-5-methylpyrrolidine-1,2-dicarboxylate

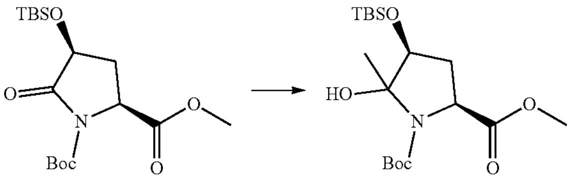 [SMILES: COC(=O)[C@@H]1C[C@H](O[Si](C)(C)C(C)(C)C)C(=O)N1C(=O)OC(C)(C)C ; COC(=O)[C@@H]1C[C@H](O[Si](C)(C)C(C)(C)C)C(C)(O)N1C(=O)OC(C)(C)C]

Bromo(methyl)magnesium (3.48 mL, 87.55 mmol, 1.20 equiv) was added to the solution of 1-tert-butyl 2-methyl (2S,4S)-4-[(tert-butyldimethylsilyl)oxy]-5-oxopyrrolidine-1,2-dicarboxylate (3.25 g, 8.70 mmol, 1.00 equiv) in THF (50 mL) dropwise at −40° C. and stirred for 2h at −40° C. The reaction was then quenched with saturated $NH_4Cl$, extracted with ethyl acetate, washed with water and of brine, dried over anhydrous sodium sulfate, and concentrated under vacuum. The residue was purified by a silica gel column eluting with ethyl acetate/petroleum ether (1/8) to afford the title compound (1.1 g, 32%) as light yellow oil.

Step 4: Preparation of methyl 4-[(tert-butyldimethylsilyl)oxy]-5-methyl-3,4-dihydro-2H-pyrrole-2-carboxylate

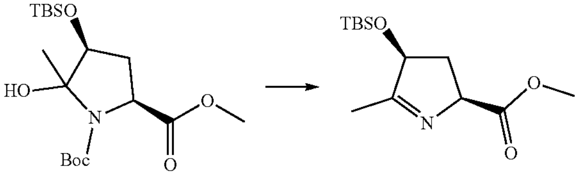

A solution of methyl (2S,4S)-1-tert-butyl 2-methyl 4-(tert-butyldimethylsilyloxy)-5-hydroxy-5-methylpyrrolidine-1,2-dicarboxylate (6 g, 15.40 mmol, 1.00 equiv) and TFA (5 mL, 67.31 mmol, 1.00 equiv) in dichloromethane (50 mL) was stirred for 5 h at room temperature. The resulting mixture was concentrated under vacuum. This resulted in 6 g of the title compound as brown oil.

Step 5: Preparation of methyl (2S,4S,5S)-4-[(tert-butyldimethylsilyl)oxy]-5-methylpyrrolidine-2-carboxylate

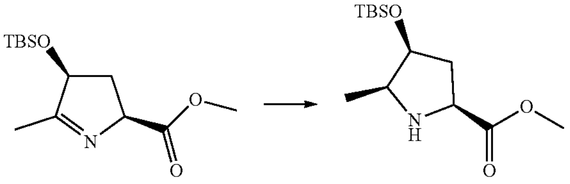

A mixture of methyl (2S,4S)-4-[(tert-butyldimethylsilyl)oxy]-5-methyl-3,4-dihydro-2H-pyrrole-2-carboxylate (6 g, 22.10 mmol, 1.00 equiv) and palladium carbon (500 mg) in methanol (100 mL) was stirred for 2 h at room temperature under $H_2$. The solids were filtered out. The resulting mixture was concentrated under vacuum. This resulted in 5.6 g (93%) of as yellow oil.

Step 6: Preparation of 1-tert-butyl 2-methyl (2S,4S,5S)-4-[(tert-butyldimethylsilyl)oxy]-5-methylpyrrolidine-1,2-dicarboxylate

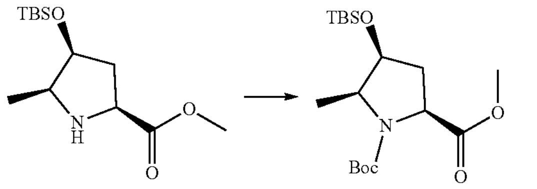

A solution of methyl (2S,4S,5S)-4-[(tert-butyldimethylsilyl)oxy]-5-methylpyrrolidine-2-carboxylate (5.5 g, 20.11 mmol, 1.00 equiv), TEA (8.13 g, 80.34 mmol, 4.00 equiv), 4-dimethylaminopyridine (245 mg, 2.00 mmol, 0.10 equiv), di-tert-butyl dicarbonate (13.16 g, 60.29 mmol, 3.00 equiv) in THF (250 mL) was stirred overnight at 50° C. The resulting mixture was concentrated under vacuum. The residue was purified by a silica gel column eluting with ethyl acetate/petroleum ether (1/10) to afford the title compound (3 g, 40%) as light yellow oil.

Step 7: Preparation of (2S,4S,5S)-1-[(tert-butoxy)carbonyl]-4-[(tert-butyldimethylsilyl)oxy]-5-methylpyrrolidine-2-carboxylic acid

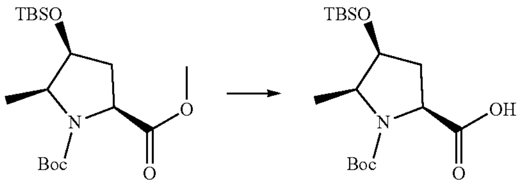

A solution of 1-tert-butyl 2-methyl (2S,4S,5S)-4-[(tert-butyldimethylsilyl)oxy]-5-methylpyrrolidine-1,2-dicarboxylate (20 mg, 0.05 mmol, 1.00 equiv) and LiOH (3 mg, 0.12 mmol, 2.00 equiv) in methanol (2 mL)/water (0.2 mL) was stirred for 5 h at 40° C. The resulting solution was diluted with water. The pH value of the solution was adjusted to 4 with acetic acid. The resulting solution was extracted with dichloromethane, dried over anhydrous sodium sulfate, and concentrated under vacuum. This resulted in 20 mg (crude) of the title compound as yellow oil.

Step 8: Preparation of tert-butyl (2S,3S,5S)-3-[(tert-butyldimethylsilyl)oxy]-2-methyl-5-[([2-[2-(trifluoromethyl)pyrimidin-5-yl]pyridin-4-yl]methyl)carbamoyl]pyrrolidine-1-carboxylate

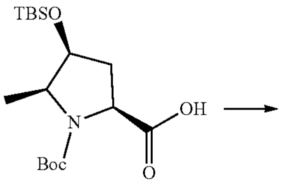

-continued

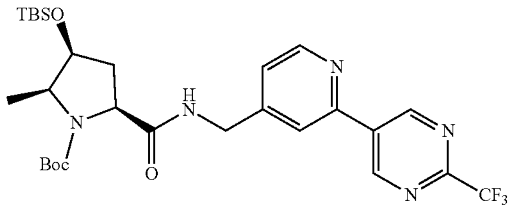

A solution of (2S,4S,5S)-1-[(tert-butoxy)carbonyl]-4-[(tert-butyldimethylsilyl)oxy]-5-methylpyrrolidine-2-carboxylic acid (400 mg, 1.11 mmol, 1.00 equiv), HATU (880 mg, 2.31 mmol, 1.50 equiv), DIEA(600 mg, 4.64 mmol, 3.00 equiv), and 2-[2-(trifluoromethyl)pyrimidin-5-yl]pyridin-4-ylmethanamine(464 mg, 1.82 mmol, 1.20 equiv) in DMF (10 mL) was stirred for 1 h at room temperature. The resulting solution was diluted with ethyl acetate, washed with water and brine, dried over anhydrous sodium sulfate, and concentrated under vacuum. The residue was purified by a silica gel column eluting with ethyl acetate/petroleum ether (1/3) to afford the title compound (360 mg, 54%) as light yellow oil.

Step 9: Preparation of tert-butyl (2S,3S,5S)-3-hydroxy-2-methyl-5-[([2-[2-(trifluoromethyl)pyrimidin-5-yl]pyridin-4-yl]methyl)carbamoyl]pyrrolidine-1-carboxylate

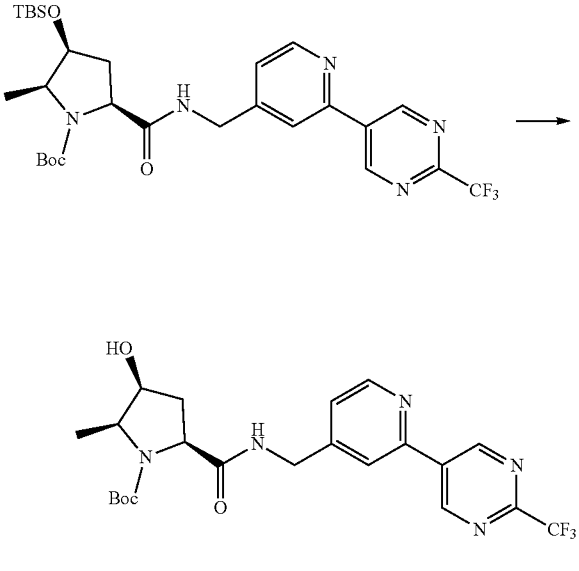

A solution of tert-butyl (2S,3S,5S)-3-[(tert-butyldimethylsilyl)oxy]-2-methyl-5-[([2-[2-(trifluoromethyl)pyrimidin-5-yl]pyridin-4-yl]methyl)carbamoyl]pyrrolidine-1-carboxylate (360 mg, 0.60 mmol, 1.00 equiv) and TBAF (1.34 mL, 5.12 mmol, 1.00 equiv) in THF (10 mL) was stirred for 1 h at room temperature. The resulting mixture was concentrated under vacuum. The residue was purified by a silica gel column eluting with ethyl acetate/petroleum ether (2/1) to afford the title compound (300 mg, crude) as a white solid.

Step 10: Preparation of tert-butyl (2S,3R,5S)-3-fluoro-2-methyl-5-[([2-[2-(trifluoromethyl)pyrimidin-5-yl]pyridin-4-yl]methyl)carbamoyl]pyrrolidine-1-carboxylate

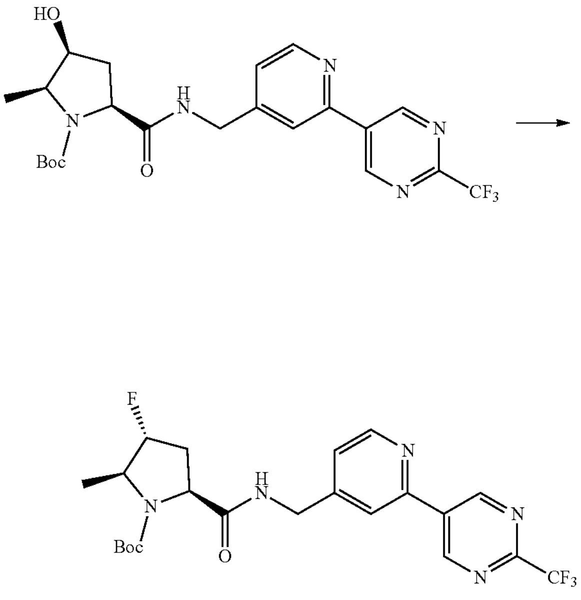

DAST (424 mg, 2.63 mmol, 3.00 equiv) was added to the solution of tert-butyl (2S,3S,5S)-3-hydroxy-2-methyl-5-[([2-[2-(trifluoromethyl)pyrimidin-5-yl]pyridin-4-yl]methyl)carbamoyl]pyrrolidine-1-carboxylate (300 mg, 0.62 mmol, 1.00 equiv) in dichloromethane (10 mL) dropwise at 0° C. and stirred overnight at room temperature. The reaction was then quenched with water, extracted with dichloromethane, dried over anhydrous sodium sulfate, and concentrated under vacuum. The residue was purified by a silica gel column eluting with ethyl acetate/petroleum ether (2/1) to afford the title compound (110 mg, 37%) as a light yellow solid.

Step 11: Preparation of (2S,4R,5S)-4-fluoro-5-methyl-N-([2-[2-(trifluoromethyl)pyrimidin-5-yl]pyridin-4-yl]methyl)pyrrolidine-2-carboxamide hydrochloride

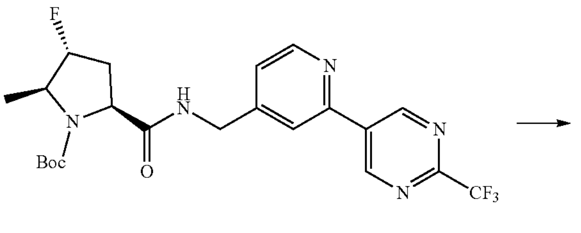

-continued

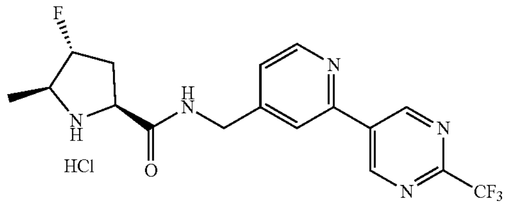

A mixture of tert-butyl (2S,3R,5S)-3-fluoro-2-methyl-5-[([2-[2-(trifluoromethyl)pyrimidin-5-yl]pyridin-4-yl]methyl)carbamoyl]pyrrolidine-1-carboxylate (110 mg, 0.22 mmol, 1.00 equiv) and saturated hydrogen chloride in 1,4-dioxane (20 mL) was stirred overnight at room temperature. The resulting mixture was concentrated under vacuum. This resulted in 105 mg (crude) of the title compound as a light yellow solid.

Step 12: Preparation of (2S,4R,5S)-4-fluoro-1-[(4-fluorobenzene)sulfonyl]-5-methyl-N-([2-[2-(trifluoromethyl)pyrimidin-5-yl]pyridin-4-yl]methyl)pyrrolidine-2-carboxamide

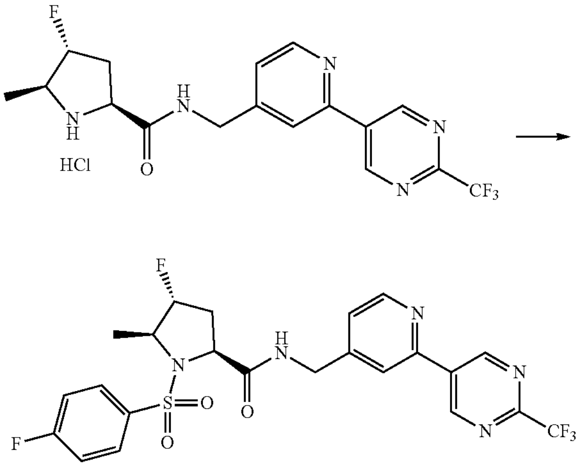

4-Fluorobenzene-1-sulfonyl chloride (73 mg, 0.37 mmol, 1.20 equiv) was added to a solution of (2S,4R,5S)-4-fluoro-5-methyl-N-([2-[2-(trifluoromethyl)pyrimidin-5-yl]pyridin-4-yl]methyl)pyrrolidine-2-carboxamide hydrochloride (105 mg, 0.25 mmol, 1.00 equiv) and sodium bicarbonate (41.5 mg, 0.49 mmol, 2.00 equiv) in THF (8 mL)/water (8 mL). This was stirred for 1 h at room temperature. The resulting solution was extracted with ethyl acetate, washed with water and brine, dried over anhydrous sodium sulfate, and concentrated under vacuum. The crude product was purified by Prep-HPLC to give the title compound (16.9 mg, 12%) as a white solid.

$^1$H NMR (400 MHz, $CDCl_3$) δ 9.65 (s, 2H), 8.80 (s, 1H), 8.13 (s, 1H), 7.93-7.90 (m, 2H), 7.54-7.51 (m, 2H), 7.28-7.25 (m, 1H), 5.03-4.99 (m, 1H), 4.82-4.68 (d, J=51.6 Hz, 1H), 4.50-4.32 (m, 1H), 4.30-4.27 (m, 1H), 4.15-4.08 (m, 1H), 2.65-2.55 (m, 1H), 2.39-2.23 (m, 1H), 1.48-1.38 (m, 3H).

Example 194

Preparation of (2S)-1-(4-fluorophenyl)sulfonyl-5,5-dimethyl-N-[[6-[6-(trifluoromethyl)-3-pyridyl]pyrimidin-4-yl]methyl]pyrrolidine-2-carboxamide

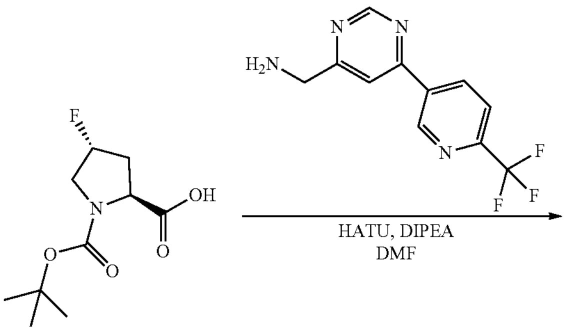

INT-194-1

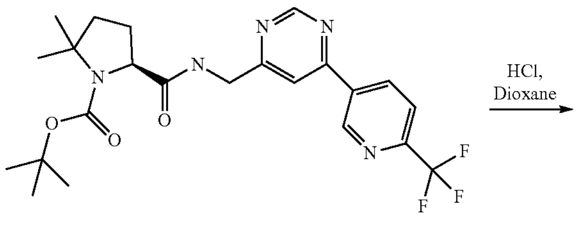

INT-194-2

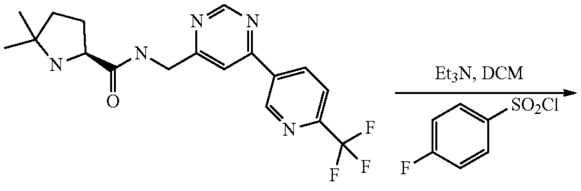

INT-194-3

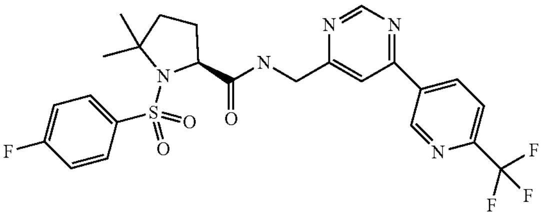

194

Step 1: Following the HATU coupling procedure of Example 35, step 1: tert-butyl (5S)-2,2-dimethyl-5-[[6-[6-(trifluoromethyl)-3-pyridyl]pyrimidin-4-yl]methylcarbamoyl]pyrrolidine-1-carboxylate (INT-194-2) (320 mg, 81%) was prepared from (2S)-1-tert-butoxycarbonyl-5,5-dimethyl-pyrrolidine-2-carboxylic acid (200 mg, 0.8 mmol) and [6-[6-(trifluoromethyl)-3-pyridyl]pyrimidin-4-yl]methanamine (230 mg, 0.9 mmol), DIPEA (0.4 mL, 2.5 mmol), HATU (383 mg, 0.99 mmol) in DMF (2 mL). MS-ESI: [M+H]+ 480.5

Step 2: Following the boc removal procedure of Example 35, step 3: (2S)-5,5-dimethyl-N-[[6-[6-(trifluoromethyl)-3-pyridyl]pyrimidin-4-yl]methyl]pyrrolidine-2-carboxamide hydrochloride (INT-194-3) (250 mg, 81%) was prepared from tert-butyl (5S)-2,2-dimethyl-5-[[6-[6-(trifluoromethyl)-3-pyridyl]pyrimidin-4-yl]methylcarbamoyl]pyrrolidine-1-carboxylate (387 mg, 0.8 mmol) and 4 N HCl in dioxane (2 mL, 8 mmol). MS-ESI: $[M+H]^+$ 380.5

Step 3: Following the sulfonamide formation procedure of Example 35, step 4: The title compound 194 (2S)-1-(4-fluorophenyl)sulfonyl-5,5-dimethyl-N-[[6-[6-(trifluoromethyl)-3-pyridyl]pyrimidin-4-yl]methyl]pyrrolidine-2-carboxamide (162 mg, 37%) was prepared from (2S)-5,5-dimethyl-N-[[6-[6-(trifluoromethyl)-3-pyridyl]pyrimidin-4-yl]methyl]pyrrolidine-2-carboxamide hydrochloride (INT194-3) (306 mg, 0.8 mmol), $Et_3N$ (2.25 mL, 16 mmol), 4-fluorobenzenesulfonyl chloride (188 mg, 0.97 mmol) in DCM (1 mL). MS-ESI: $[M+H]^+$ 538.5

$^1H$ NMR (400 MHz, DMSO-$d_6$) δ 9.42 (d, J=2.1 Hz, 1H), 9.29 (d, J=1.3 Hz, 1H), 8.81 (t, J=5.9 Hz, 1H), 8.73 (ddd, J=8.4, 2.3, 0.9 Hz, 1H), 8.17 (d, J=1.3 Hz, 1H), 8.11-7.94 (m, 3H), 7.49-7.19 (m, 2H), 4.67-4.48 (m, 2H), 4.39 (dd, J=17.4, 5.6 Hz, 1H), 2.24-2.10 (m, 1H), 2.02 (td, J=11.5, 6.5 Hz, 1H), 1.84 (ddt, J=12.0, 6.1, 2.7 Hz, 1H), 1.71 (ddd, J=11.8, 6.7, 2.9 Hz, 1H), 1.45 (s, 3H), 1.24 (s, 3H).

Example 195

Preparation of (2S,4R)-4-fluoro-1-(4-fluorophenyl)sulfonyl-N-[[5-[2-trifluoromethyl)pyrimidin-5-yl]-3-pyridyl]methyl]pyrrolidine-2-carboxamide

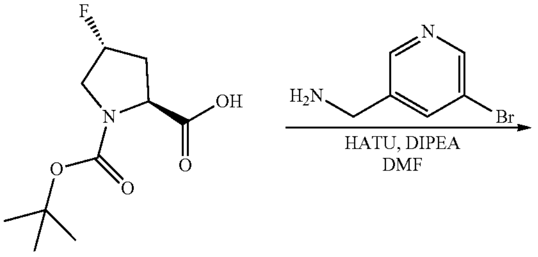

INT-195-1

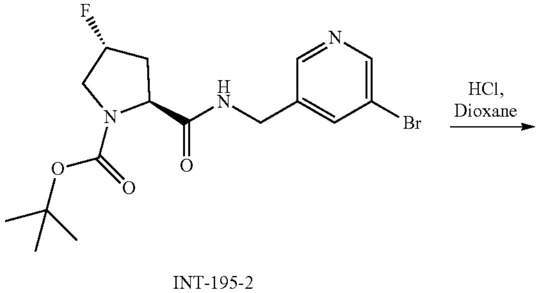

INT-195-2

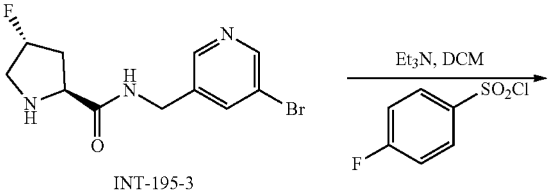

INT-195-3

-continued

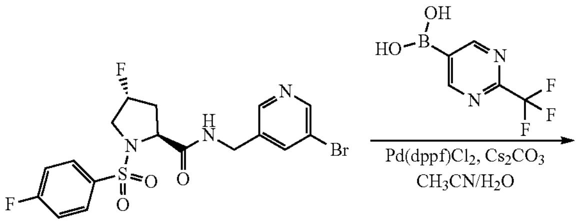

INT-195-4

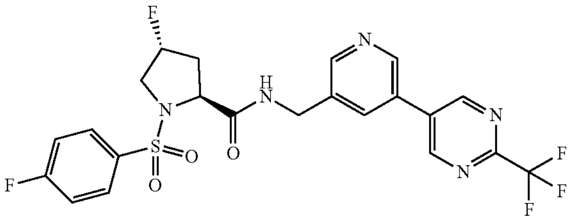

195

Step 1: Following the HATU coupling procedure of Example 35, step 1: tert-butyl (2S,4R)-2-[(5-bromo-3-pyridyl)methylcarbamoyl]-4-fluoro-pyrrolidine-1-carboxylate (INT-195-2) (280 mg, 32%) was prepared from (2S,4R)-1-tert-butoxycarbonyl-4-fluoro-pyrrolidine-2-carboxylic acid (500 mg, 2.1 mmol) and (5-bromo-3-pyridyl)methanamine (441 mg, 2.4 mmol), DIPEA (1.1 mL, 6.4 mmol), HATU (998 mg, 2.6 mmol) in DMF (2 mL). MS-ESI: $[M+H]^+$ 403.3

Step 2: Following the boc removal procedure of Example 35, step 3: (2S,4R)—N-[(5-bromo-3-pyridyl)methyl]-4-fluoro-pyrrolidine-2-carboxamide (INT-195-3) (210 mg, 100%) was prepared from tert-butyl (2S,4R)-2-[(5-bromo-3-pyridyl)methylcarbamoyl]-4-fluoro-pyrrolidine-1-carboxylate (INT-195-2) (280 mg, 0.7 mmol) and 4 N HCl in dioxane (1.7 mL, 7 mmol). MS-ESI: $[M+H]^+$ 303.3

Step 3: Following the sulfonamide formation procedure of Example 35, step 4: (2S,4R)—N-[(5-bromo-3-pyridyl)methyl]-4-fluoro-1-(4-fluorophenyl)sulfonyl-pyrrolidine-2-carboxamide (INT-195-4) (200 mg, 63%) was prepared from (2S,4R)—N-[(5-bromo-3-pyridyl)methyl]-4-fluoro-pyrrolidine-2-carboxamide (INT-195-3) (210 mg, 0.7 mmol), $Et_3N$ (1.9 mL, 14 mmol), 4-fluorobenzenesulfonyl chloride (162 mg, 0.8 mmol) in DCM (1 mL). MS-ESI: $[M+H]^+$ 461.3

Step 4: Following the same Suzuki coupling procedure of Example 42, step 1: The title compound 195 (2S,4R)-4-fluoro-1-(4-fluorophenyl)sulfonyl-N-[[5-[2-(trifluoromethyl)pyrimidin-5-yl]-3-pyridyl]methyl]pyrrolidine-2-carboxamide (62 mg, 54%) was prepared from (2S,4R)—N-[(5-bromo-3-pyridyl)methyl]-4-fluoro-1-(4-fluorophenyl)sulfonyl-pyrrolidine-2-carboxamide (INT-195-4) (100 mg, 0.22 mmol), [5-(trifluoromethyl)pyrimidin-2-yl]boronic acid (46 mg, 0.24 mmol), cesium carbonate 1 M in water (0.3 mL, 0.3 mmol), Pd(dppf)$Cl_2$ (18 mg, 0.02 mmol) in acetonitrile (1 mL). MS-ESI: $[M+H]^+$ 528.5

$^1$H NMR (400 MHz, DMSO-$d_6$) δ 9.53-9.37 (m, 2H), 9.07-8.97 (m, 1H), 8.70 (d, J=2.0 Hz, 1H), 8.23 (t, J=2.2 Hz, 1H), 8.05-7.87 (m, 2H), 7.56-7.33 (m, 2H), 5.19 (d, J=52.8 Hz, 1H), 4.63-4.33 (m, 2H), 4.25-4.09 (m, 1H), 3.78-3.67 (m, 1H), 3.64 (dd, J=14.9, 2.4 Hz, 1H), 2.49-2.28 (m, 1H), 2.07 (s, 1H).

Example 196

Preparation of (2S,4R)-4-fluoro-1-(4-fluorophenylsulfonyl)-N-((5-methoxy-2-(2-(trifluoromethyl)pyrimidin-5-yl)pyridin-4-yl)methyl)pyrrolidine-2-carboxamide

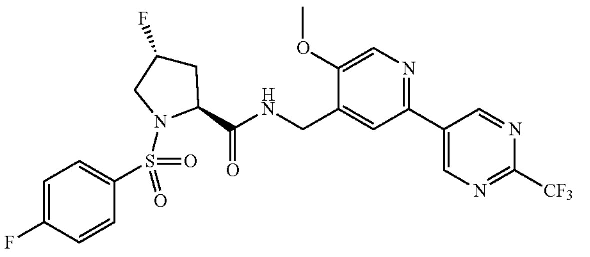 [SMILES: COc1cnc(-c2cnc(C(F)(F)F)nc2)cc1CNC(=O)[C@@H]1C[C@@H](F)CN1S(=O)(=O)c1ccc(F)cc1]

Step 1: Preparation of 2-[(2-bromo-5-fluoropyridin-4-yl)methyl]-2,3-dihydro-1H-isoindole-1,3-dione

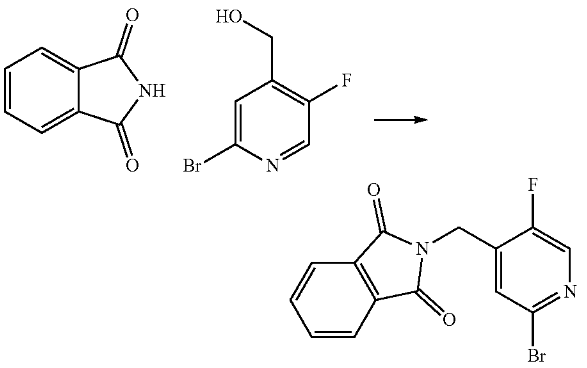

DIAD (1.57 g, 7.76 mmol, 2.00 equiv) was added dropwise into a solution of 2,3-dihydro-1H-isoindole-1,3-dione (690 mg, 4.69 mmol, 1.20 equiv), (2-bromo-5-fluoropyridin-4-yl)methanol (800.00 mg, 3.88 mmol, 1.00 equiv), and $PPh_3$ (2.04 g, 7.78 mmol, 2.00 equiv) in tetrahydrofuran (40 mL) at 0° C. under nitrogen. The resulting solution was stirred for 12 h at room temperature. The resulting mixture was concentrated under vacuum. The residue was purified by a silica gel column with ethyl acetate/petroleum ether (1:5) to afford the title compound (500 mg, 38%) as a white solid.

Step 2: Preparation of 2-([5-fluoro-2-[2-(trifluoromethyl)pyrimidin-5-yl]pyridin-4-yl]methyl)-2,3-dihydro-1H-isoindole-1,3-dione

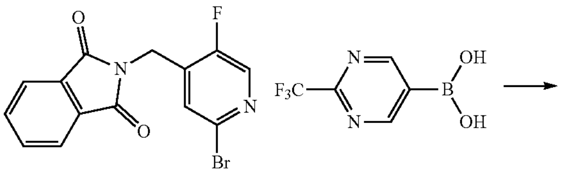

-continued

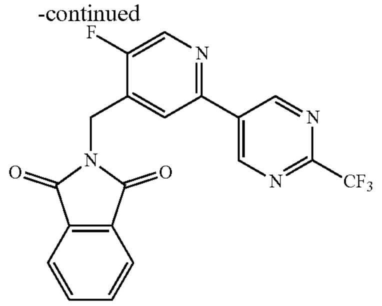

A mixture of Pd(dppf)$Cl_2$ (196 mg, 0.268 mmol, 0.10 equiv), potassium carbonate (741 mg, 5.362 mmol, 2.0 equiv), 2-[(2-bromo-5-fluoropyridin-4-yl)methyl]-2,3-dihydro-1H-isoindole-1,3-dione (900 mg, 2.686 mmol, 1.0 equiv), and bis(propan-2-yl) [2-(trifluoromethyl)pyrimidin-5-yl]boronate (3.3 g, 11.954 mmol, 4.45 equiv) in 1,4-dioxane (25 mL)/water(2.5 mL) was stirred for 12 h at 70° C. under nitrogen. The mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/5) to afford the title compound (1 g, 91%) as a yellow solid.

Step 3: Preparation of 2-[([5-methoxy-2-[2-(trifluoromethyl)pyrimidin-5-yl]pyridin-4-yl]methyl)carbamoyl]benzoic acid

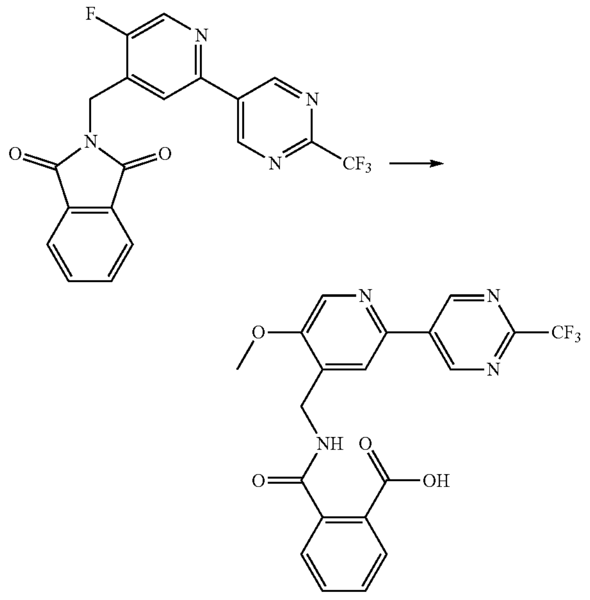

A solution of 2-([5-fluoro-2-[2-(trifluoromethyl)pyrimidin-5-yl]pyridin-4-yl]methyl)-2,3-dihydro-1H-isoindole-1,3-dione (250 mg, 0.621 mmol, 1.00 equiv) and MeONa (340 mg, 6.294 mmol, 10.128 equiv) in methanol (50 mL) was stirred for 5 h at 85° C. The resulting mixture was concentrated under vacuum and diluted with water. The pH value of the solution was adjusted to 3-5 with 1N hydrogen chloride. The resulting solution was extracted with ethyl acetate. The combined extracts were washed with brine, dried over anhydrous sodium sulfate, and concentrated under vacuum. This resulted in the title compound (250 mg, 93%) as a white solid.

Step 4: Preparation of [5-methoxy-2-[2-(trifluoromethyl)pyrimidin-5-yl]pyridin-4-yl]methanamine

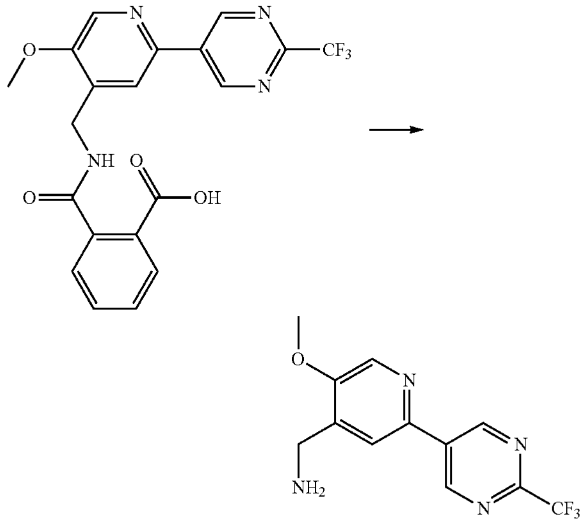

A solution of 2-[([5-methoxy-2-[2-(trifluoromethyl)pyrimidin-5-yl]pyridin-4-yl]methyl)carbamoyl]benzoic acid (250 mg, 0.578 mmol, 1.00 equiv) and $NH_2NH_2.H_2O$ (300 mg, 5.993 mmol, 10.36 equiv) in ethanol (30 mL) was stirred for 12 h at 80° C. The resulting mixture was concentrated under vacuum and diluted with water. The pH value of the solution was adjusted to 3-5 with 1N hydrogen chloride. The resulting solution was extracted with ethyl acetate. The pH value of the aqueous solution was adjusted to 8 with sodium bicarbonate. The resulting solution was extracted with ethyl acetate. The combined extracts were dried over anhydrous sodium sulfate and concentrated under vacuum. This resulted in the title compound (120 mg, 73%) as a solid.

Step 5: Preparation of tert-butyl (2S,4R)-4-fluoro-2-[([5-methoxy-2-[2-(trifluoromethyl)pyrimidin-5-yl]pyridin-4-yl]methyl)carbamoyl]pyrrolidine-1-carboxylate

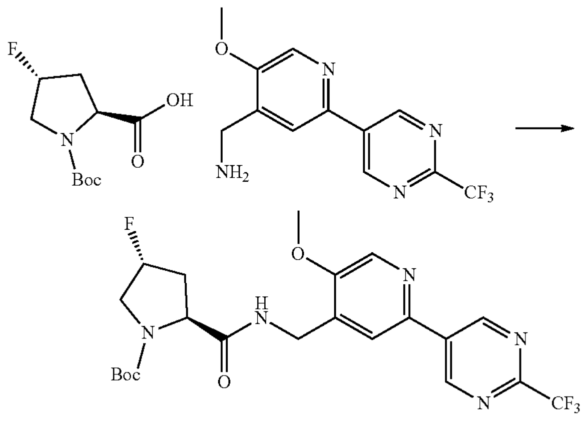

A solution of (2S,4R)-1-[(tert-butoxy)carbonyl]-4-fluoropyrrolidine-2-carboxylic acid (108 mg, 0.463 mmol, 1.097 equiv), DIEA (164 mg, 1.269 mmol, 3.0 equiv), HATU (193 mg, 0.508 mmol, 1.202 equiv), and [5-methoxy-2-[2-(trifluoromethyl)pyrimidin-5-yl]pyridin-4-yl]methanamine (120 mg, 0.422 mmol, 1.000 equiv) in N,N-dimethylformamide (8 mL) was stirred for 30 min at 25° C. The reaction mixture was diluted with water and extracted with ethyl acetate. The combined extracts were washed with brine, dried over anhydrous sodium sulfate, and concentrated under vacuum. The residue was purified by a silica gel column eluting with ethyl acetate/petroleum ether (1/5). This resulted in the title compound (180 mg, 85%) as light yellow oil.

Step 6: Preparation of (2S,4R)-4-fluoro-N-([5-methoxy-2-[2-(trifluoromethyl)pyrimidin-5-yl]pyridin-4-yl]methyl)pyrrolidine-2-carboxamide

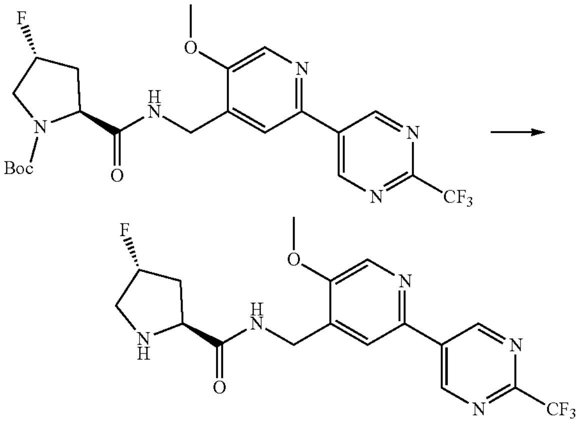

A solution of tert-butyl (2S,4R)-4-fluoro-2-[([5-methoxy-2-[2-(trifluoromethyl)pyrimidin-5-yl]pyridin-4-yl]methyl)carbamoyl]pyrrolidine-1-carboxylate (120 mg, 0.24 mmol, 1.00 equiv) and trifluoroacetic acid (4 mL) in dichloromethane (20 mL) was stirred for 30 min at 25° C. The resulting mixture was concentrated under vacuum. The residue was dissolved in water. The pH value of the solution was adjusted to 7-9 with aqueous sodium bicarbonate. The resulting solution was extracted with ethyl acetate. The combined extracts were washed with brine, dried over anhydrous sodium sulfate, and concentrated under vacuum. This resulted in the title compound (140 mg, crude) as a light yellow solid.

Step 7: Preparation of (2S,4R)-4-fluoro-1-(4-fluorophenylsulfonyl)-N-((5-methoxy-2-(2-(trifluoromethyl)pyrimidin-5-yl)pyridin-4-yl)methyl)pyrrolidine-2-carboxamide

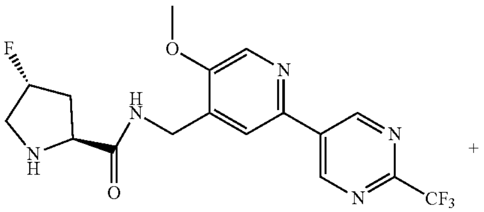

-continued

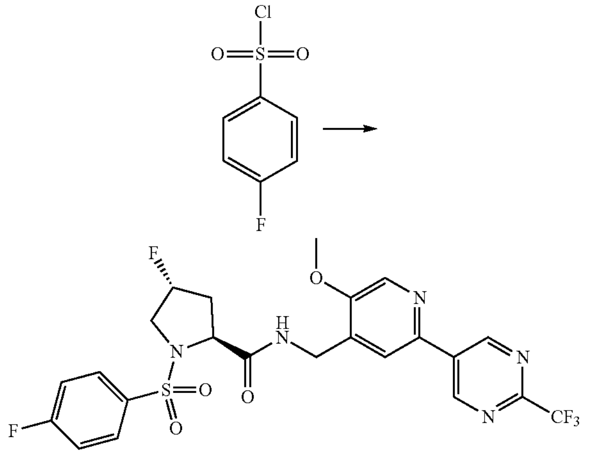

A solution of (2S,4R)-4-fluoro-N-([5-methoxy-2-[2-(trifluoromethyl)pyrimidin-5-yl]pyridin-4-yl]methyl)pyrrolidine-2-carboxamide (225 mg, 0.563 mmol, 1.00 equiv), TEA (171 mg, 1.690 mmol, 3.0 equiv), and 4-fluorobenzene-1-sulfonyl chloride (132 mg, 0.678 mmol, 1.20 equiv) in dichloromethane (25 mL) was stirred for 12 h at 25° C. The mixture was diluted with water and extracted with ethyl acetate. The combined extracts were washed with brine, dried over anhydrous sodium sulfate, and concentrated under vacuum. The crude product was purified by Prep-HPLC to afford the title compound (20.7 mg) as a white solid.

$^1$H NMR (300 MHz, $CDCl_3$) δ 9.55 (s, 1H), 8.41 (s, 1H), 8.07 (s, 1H), 7.88-7.91 (m, 2H), 7.44-7.52 (s, 1H), 7.23-7.26 (m, 2H), 4.99-5.12 (d, J=51.2 Hz, 1H), 4.83-4.90 (m, 1H), 4.29-4.39 (m, 2H), 4.07 (s, 3H), 3.84-3.93 (m, 1H), 3.61-3.73 (m, 1H), 2.55-2.61 (m, 1H), 2.13-2.26 (m, 1H).

Example 197

Preparation of (2S)—N-([3-chloro-1-[4-(trifluoromethyl)phenyl]-1H-pyrazol-4-yl]methyl)-1-[(4-fluorobenzene)sulfonyl]azetidine-2-carboxamide

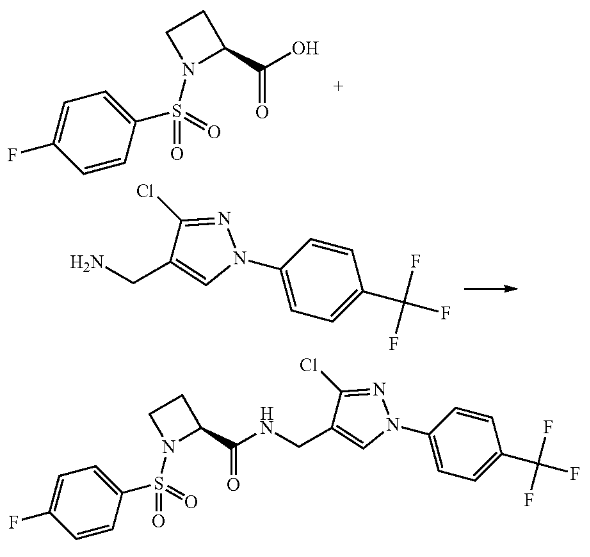

A mixture of (2S)-1-[(4-fluorobenzene)sulfonyl]azetidine-2-carboxylic acid (62 mg, 0.24 mmol, 1.20 equiv), HATU (114 mg, 0.30 mmol, 1.50 equiv), DIEA (77 g, 595.78 mmol, 3.00 equiv), and [3-chloro-1-[4-(trifluoromethyl)phenyl]-1H-pyrazol-4-yl]methanamine (55 mg, 0.20 mmol, 1.00 equiv) in N,N-dimethylformamide (2 mL) was stirred for 1 h at room temperature. The resulting solution was diluted with water, extracted with ethyl acetate, washed with brine, dried over anhydrous sodium sulfate, and concentrated under vacuum. The crude product (100 mg) was purified by Prep-HPLC to afford the title compound (63.3 mg, 61%) as a white solid.

$^1$H NMR (400 MHz, DMSO-$d_6$) δ 8.59 (s, 1H), 8.55-8.52 (t, J=5.4 Hz, 1H), 8.00-7.88 (m, 6H), 7.55-7.51 (t, J=8.8 Hz, 2H), 4.31-4.21 (m, 2H), 3.73-3.71 (m, 1H), 3.58-3.55 (m, 1H), 2.21-2.14 (m, 2H).

Example 198

Preparation of (S)-1-(4-fluorophenylsulfonyl)-2-methyl-N-((6-(6-(trifluoromethyl)pyridin-3-yl)pyrimidin-4-yl)methyl)azetidine-2-carboxamide

Step 1: Preparation of tert-butyl 2-methyl-2-((6-(6-(trifluoromethyl)pyridin-3-yl)pyrimidin-4-yl)methylcarbamoyl)azetidine-1-carboxylate

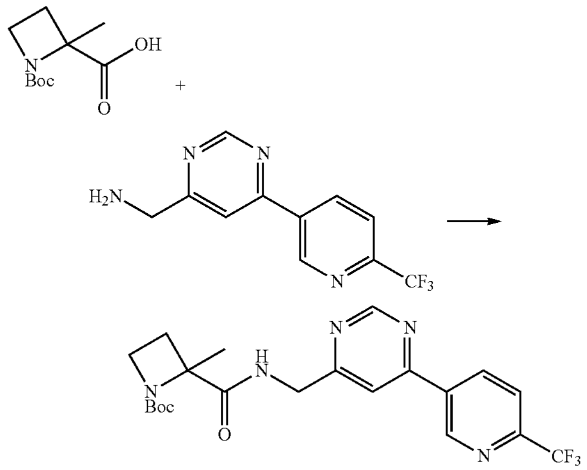

A mixture of 1-(tert-butoxycarbonyl)-2-methylazetidine-2-carboxylic acid (0.1 g, 0.51 mmol), (6-(6-(trifluoromethyl)pyridin-3-yl)pyrimidin-4-yl)methanamine (0.13 mg, 0.51 mmol), $iPr_2NEt$ (0.17 mL, 0.98 mmol), PyAOP (0.29 mg, 0.54 mmol) and 4-DMAP (0.006 mg, 0.05 mmol) in DMF (3 mL) was stirred at room temperature for 3 h. The mixture was washed with saturated aqueous $NaHCO_3$ solution and brine, and extracted with EtOAc (2×). The combined organic layers were dried ($Na_2SO_4$) filtered, passed through a silica gel plug washing with EtOAc, and concentrated to provide crude tert-butyl 2-methyl-2-((6-(6-(trifluoromethyl)pyridin-3-yl)pyrimidin-4-yl)methylcarbamoyl) azetidine-1-carboxylate, which was used in the next step without any further purification.

Step 2: Preparation of 2-methyl-2-((6-(6-(trifluoromethyl)pyridin-3-yl)pyrimidin-4-yl)methylcarbamoyl)azetidinium chloride

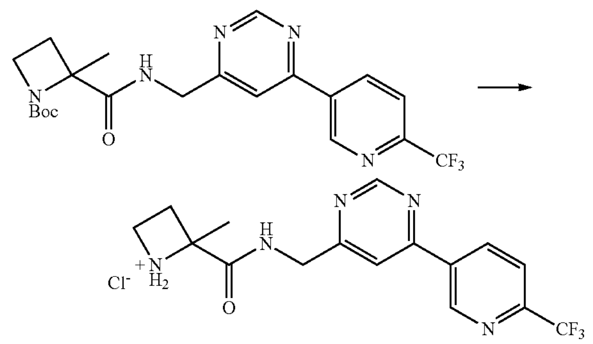

To a solution of crude tert-butyl 2-methyl-2-((6-(6-(trifluoromethyl)pyridin-3-yl)pyrimidin-4-yl)methylcarbamoyl) azetidine-1-carboxylate (0.22 g, 0.49 mmol), in $CH_2Cl_2$ (2 mL) was added 4 N HCl in dioxane (1 mL, 4 mmol) and the mixture stirred at room temperature for 3 h. The mixture was concentrated under reduced pressure to provide 2-methyl-2-((6-(6-(trifluoromethyl)pyridin-3-yl)pyrimidin-4-yl)methylcarbamoyl)azetidinium chloride as a crude salt, which was used in the next step without any further purification.

Step 3: Preparation of (S)-1-(4-fluorophenylsulfonyl)-2-methyl-N-((6-(6-(trifluoromethyl)pyridin-3-yl)pyrimidin-4-yl)methyl)azetidine-2-carboxamide

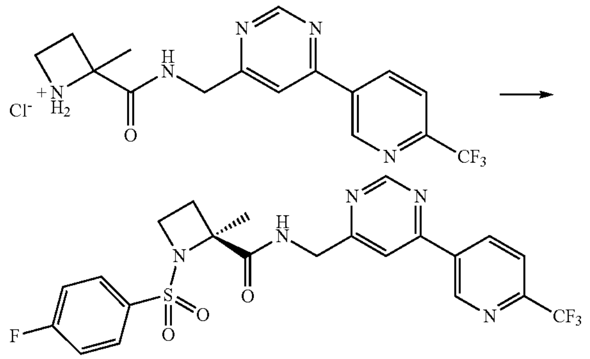

A mixture of crude 2-methyl-2-((6-(6-(trifluoromethyl) pyridin-3-yl)pyrimidin-4-yl)methylcarbamoyl)azetidinium chloride (0.085 g, 0.22 mmol), 4-fluorobenzene-1-sulfonyl chloride (0.047 mg, 0.24 mmol), and $Et_3N$ (0.15 mL, 1.1 mmol) in $CH_2Cl_2$ (2 mL) was stirred at room temperature for 12 h. The mixture was diluted with water and extracted with $CH_2Cl_2$ (2×). The combined organic layers were dried ($Na_2SO_4$), filtered, and concentrated. The resulting residue was purified by chiral SFC affording the title compound (22 mg) as the slower eluting isomer: $^1$H NMR (400 MHz, DMSO-$d_6$) δ 9.48 (d, J=1.9 Hz, 1H), 9.32 (d, J=1.2 Hz, 1H), 8.79 (dd, J=8.2, 1.7 Hz, 1H), 8.74 (t, J=5.9 Hz, 1H), 8.18 (d, J=0.9 Hz, 1H), 8.11 (d, J=8.2 Hz, 1H), 8.03-7.95 (m, 2H), 7.54-7.43 (m, 2H), 4.66 (dd, J=17.4 Hz, J=6.4 Hz, 1H), 4.49 (dd, J=17.4, J=5.4 Hz, 1H), 3.97-3.86 (m, 1H), 3.82-3.74 (m, 1H), 2.10-1.98 (m, 1H), 1.54 (s, 3H).

Example 199

Preparation of (2S)—N-([3-chloro-1-[6-(trifluoromethyl)pyridin-3-yl]-1H-pyrazol-4-yl]methyl)-1-[(4-fluorobenzene)sulfonyl]azetidine-2-carboxamide

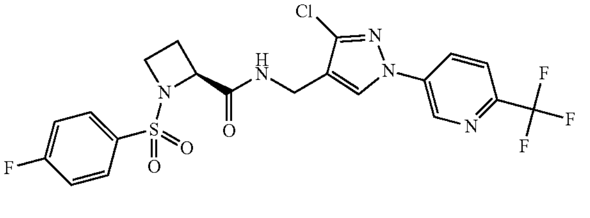

Step 1: Preparation of (2S)-1-[(4-fluorobenzene)sulfonyl]azetidine-2-carboxylic acid

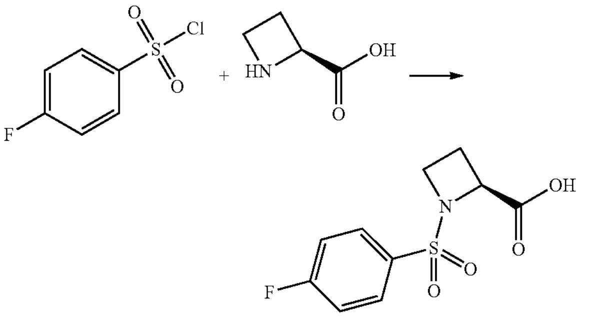

4-Fluorobenzene-1-sulfonyl chloride (2.14 g, 11.00 mmol, 1.00 equiv) was added into a solution of (2S)-azetidine-2-carboxylic acid (1 g, 9.89 mmol, 1.10 equiv) in saturated aqueous sodium hydroxide (6 mL)/tetrahydrofuran (6 mL) at 0° C. The resulting mixture was stirred for 18 h at room temperature. The mixture was extracted with ether. The pH value of the aqueous solution was adjusted to 3 with 2 M hydrogen chloride. The resulting mixture was extracted with ethyl acetate, washed with brine, dried over anhydrous sodium sulfate, and concentrated under vacuum. This resulted in the title compound (1.7 g, 60%) as a white solid.

Step 2: Preparation of (2S)—N-([3-chloro-1-[6-(trifluoromethyl)pyridin-3-yl]-1H-pyrazol-4-yl]methyl)-1-[(4-fluorobenzene)sulfonyl]azetidine-2-carboxamide

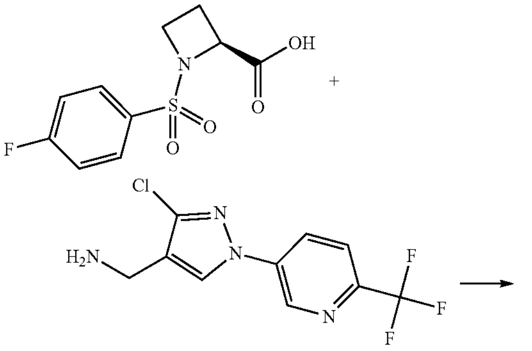

-continued

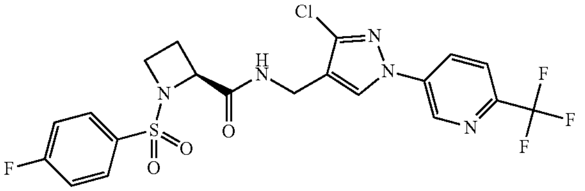 [SMILES: O=C(NCc1cn(-c2ccc(C(F)(F)F)nc2)nc1Cl)[C@@H]1CCN1S(=O)(=O)c1ccc(F)cc1]

A mixture of (2S)-1-[(4-fluorobenzene)sulfonyl]azetidine-2-carboxylic acid (62 mg, 0.24 mmol, 1.20 equiv), HATU (114 mg, 0.30 mmol, 1.50 equiv), DIEA (77 mg, 0.60 mmol, 3.00 equiv), and [3-chloro-1-[6-(trifluoromethyl)pyridin-3-yl]-1H-pyrazol-4-yl]methanamine (55 mg, 0.20 mmol, 1.00 equiv) in N,N-dimethylformamide (2 mL) was stirred for 1 h at room temperature. The resulting solution was diluted with water, extracted with ethyl acetate, washed with brine, dried over anhydrous sodium sulfate, and concentrated under vacuum. The crude product (100 mg) was purified by Prep-HPLC to afford the title compound (40.2 mg, 39%) as a white solid.

$^1$H NMR (400 MHz, DMSO-$d_6$) δ 9.21 (s, 1H), 8.67 (s, 1H), 8.56-8.53 (m, 1H), 8.44-8.41 (m, 1H), 8.09-8.07 (d, J=8.4 Hz, 1H), 7.98-7.93 (m, 2H), 7.55-7.49 (m, 2H), 4.31-4.22 (m, 3H), 3.73-3.70 (m, 1H), 3.61-3.52 (m, 1H), 2.27-2.11 (m, 2H).

Example 200

Preparation of (2S,4R)-1-[(4-fluorobenzene)sulfonyl]-4-methyl-N-([6-[6-(trifluoromethyl)pyridin-3-yl]pyrimidin-4-yl]methyl)azetidine-2-carboxamide

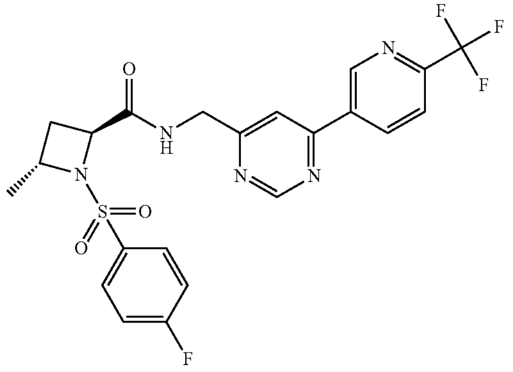 [SMILES: C[C@@H]1C[C@@H](C(=O)NCc2cc(-c3ccc(C(F)(F)F)nc3)ncn2)N1S(=O)(=O)c1ccc(F)cc1]

Step 1: Preparation of methyl 1-[(4-fluorobenzene)sulfonyl]-4-methylazetidine-2-carboxylate

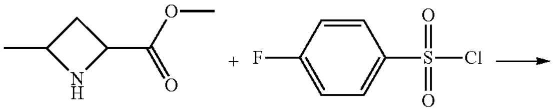

-continued

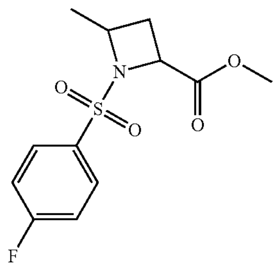

4-Fluorobenzene-1-sulfonyl chloride (312 mg, 1.60 mmol, 1.20 equiv) was added into a solution of methyl 4-methylazetidine-2-carboxylate (400 mg, 3.10 mmol, 1.00 equiv), 4-dimethylaminopyridine (240 mg, 1.96 mmol, 0.70 equiv), and TEA (0.8 mL, 5.76 mmol, 4.00 equiv) in dichloromethane (12 mL) at room temperature. The reaction was stirred for 12 h at room temperature. The mixture was diluted with water, extracted with dichloromethane, washed with brine, dried over anhydrous sodium sulfate, and concentrated under vacuum. The residue was purified by a silica gel column eluting with ethyl acetate/petroleum ether (1:5) to afford the title compound (220 mg, 25%) as orange oil.

Step 2: Preparation of 1-[(4-fluorobenzene)sulfonyl]-4-methylazetidine-2-carboxylic acid

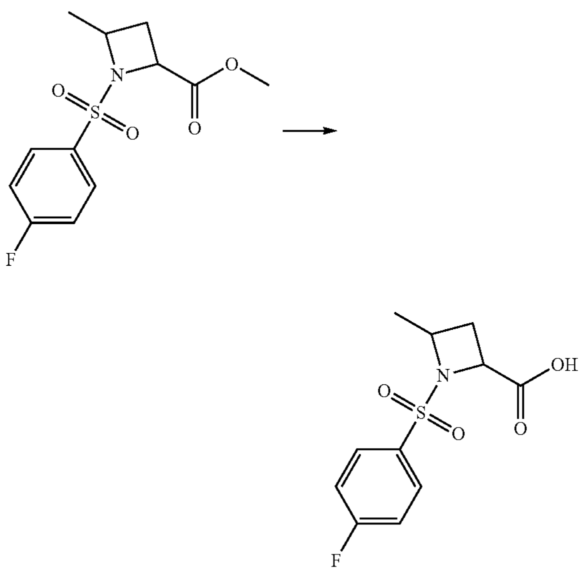

A mixture of methyl 1-[(4-fluorobenzene)sulfonyl]-4-methylazetidine-2-carboxylate (180 mg, 0.63 mmol, 1.00 equiv) and LiOH (15 mg, 0.63 mmol, 1.00 equiv) in methanol (15 mL)/$H_2O$ (1.5 mL) was stirred for 12 h at room temperature. The mixture was concentrated under vacuum. The residue was dissolved in water. The pH value of the solution was adjusted to 3 with 1 M hydrogen chloride. The resulting mixture was extracted with ethyl acetate, washed with brine, dried over anhydrous sodium sulfate, and concentrated under vacuum. This resulted in the title compound (0.12 g, 70%) as a white solid.

Step 3: Preparation of (2S,4R)-1-[(4-fluorobenzene)sulfonyl]-4-methyl-N-([6-[6-(trifluoromethyl)pyridin-3-yl]pyrimidin-4-yl]methyl)azetidine-2-carboxamide

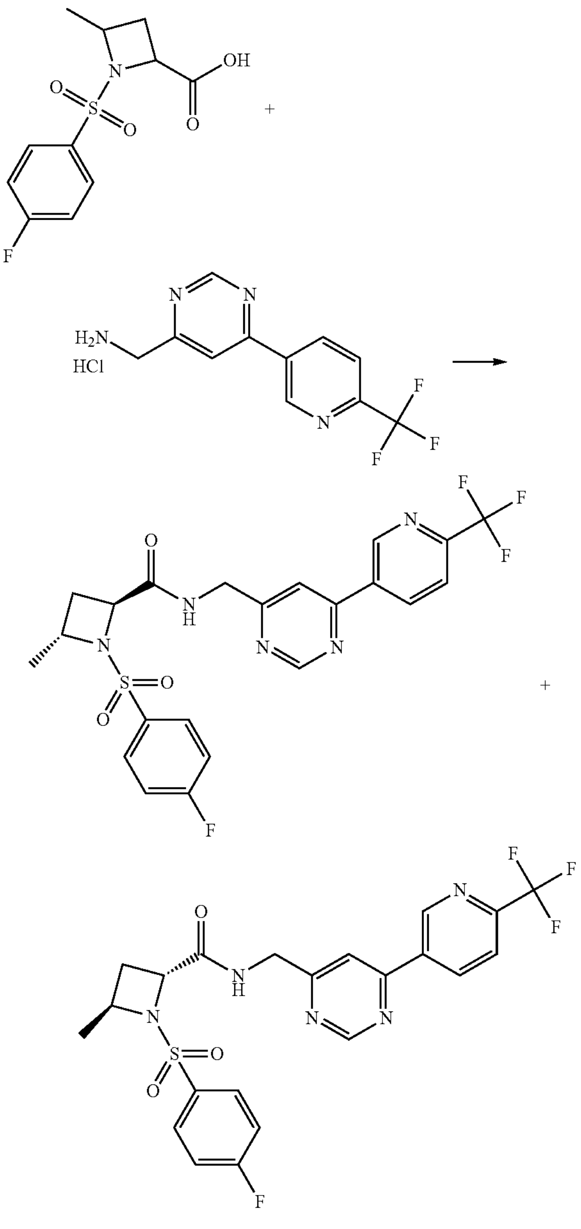

A solution of 1-[(4-fluorobenzene)sulfonyl]-4-methylazetidine-2-carboxylic acid (123 mg, 0.45 mmol, 1.00 equiv), [6-[6-(trifluoromethyl)pyridin-3-yl]pyrimidin-4-yl]methanamine hydrochloride (198 mg, 0.68 mmol, 1.50 equiv), DIEA (290 mg, 2.24 mmol, 5.00 equiv), and HATU (259 mg, 0.68 mmol, 1.50 equiv) in N,N-dimethylformamide (4 mL) was stirred overnight at room temperature. The reaction was diluted with water, extracted with ethyl acetate, washed with brine, dried over anhydrous sodium sulfate, and concentrated under vacuum. The residue was purified by a silica gel column eluting with ethyl acetate/petroleum ether (30:100). The crude product was purified by Chiral-Prep-HPLC to afford the title compound (96.9 mg, 42%) as a white solid. $t_R$=5.32 min (Lux Cellulose-4, 0.46×5 cm, 3 μm, Hex:EtOH=80:20, 1.0 ml/min).

$^1$H NMR (300 MHz, DMSO-$d_6$) δ 9.47 (m, 1H), 9.31-9.30 (m, 1H), 9.08-9.04 (m, 1H), 8.79-8.76 (m, 1H), 8.18 (s, 1H), 8.10-8.07 (m, 1H), 7.91-7.86 (m, 2H), 7.43-7.38 (m, 2H), 4.77-4.72 (m, 1H), 4.51-4.45 (m, 3H), 2.37-2.31 (m, 1H), 2.11-2.06 (m, 1H), 1.28-1.26 (m, 3H).

And (2R,4S)-1-[(4-fluorobenzene)sulfonyl]-4-methyl-N-([6-[6-(trifluoromethyl)pyridin-3-yl]pyrimidin-4-yl]methyl)azetidine-2-carboxamide (94.4 mg, 41%) was also isolated as a white solid. $t_R$=6.48 min (Lux Cellulose-4, 0.46×5 cm, 3 μm, Hex:EtOH=80:20, 1.0 ml/min).

$^1$H NMR (300 MHz, DMSO-$d_6$) δ 9.47 (m, 1H), 9.31-9.30 (m, 1H), 9.08-9.04 (m, 1H), 8.79-8.76 (m, 1H), 8.18 (s, 1H), 8.10-8.07 (m, 1H), 7.91-7.87 (m, 2H), 7.44-7.38 (m, 2H), 4.77-4.72 (m, 1H), 4.57-4.43 (m, 3H), 2.39-2.31 (m, 1H), 2.11-2.03 (m, 1H), 1.28-1.26 (m, 3H).

Example 201

Preparation of (S)-1-(4-fluorophenylsulfonyl)-N-((6-(6-(trifluoromethyl)pyridin-3-yl)pyrimidin-4-yl)methyl)azetidine-2-carboxamide

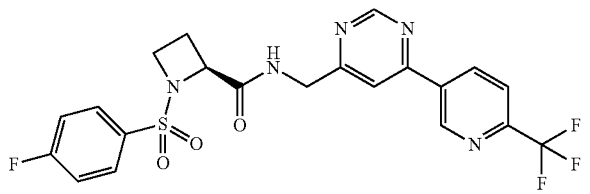 [SMILES: O=C(NCc1cc(-c2ccc(C(F)(F)F)nc2)ncn1)[C@@H]1CCN1S(=O)(=O)c1ccc(F)cc1]

Preparation of the title compound follows the same general procedure as Example 198.

LCMS: m/z=496 (ret time: 4.78)

$^1$H NMR (400 MHz, DMSO) δ 9.49 (d, J=1.9 Hz, 1H), 9.30 (d, J=1.2 Hz, 1H), 8.96 (t, J=5.5 Hz, 1H), 8.80 (dd, J=8.3, 1.9 Hz, 1H), 8.16 (d, J=0.9 Hz, 1H), 8.09 (d, J=8.3 Hz, 1H), 8.05-7.98 (m, 2H), 7.56 (t, J=8.8 Hz, 2H), 4.56 (ddd, J=40.0, 17.3, 6.0 Hz, 2H), 4.42-4.35 (m, 1H), 3.81-3.73 (m, 1H), 3.59 (dd, J=16.9, 8.5 Hz, 1H), 2.34-2.15 (m, 2H), LCMS (ESI) m/z: 496 [M+H]+

TABLE 4

MS Data for Exemplified Compounds.

| Example | LC/MS (ESI+): m/z (M + H) |
|---|---|
| 38 | 552.1 |
| 39 | 524.1 |
| 40 | 560.1 |
| 41 | 524.1 |
| 42 | 529.11 |
| 43 | 542.13 |
| 44 | 574.1 |
| 45 | 559.12 |
| 46 | 557.13 |
| 47 | 559.12 |
| 48 | 542.13 |
| 49 | 545.1 |
| 50 | 540.1 |
| 51 | 554.1 |
| 52 | 559.12 |
| 53 | 528.11 |
| 54 | 545.11 |

TABLE 4-continued

MS Data for Exemplified Compounds.

| Example | LC/MS (ESI+): m/z (M + H) |
|---|---|
| 55 | 509.13 |
| 56 | 545.11 |
| 57 | 542.12 |
| 58 | 547.1 |
| 59 | 527.12 |
| 60 | 543.09 |
| 61 | 674.2 |
| 62 | 562.2 |
| 63 | 509.2 |
| 64 | 525.2 |
| 65 | 563.1 |
| 66 | 567.1 |
| 67 | 528.11 |
| 68 | 545.11 |
| 69 | 545.1 |
| 70 | 551.1 |
| 71 | 552.1 |
| 72 | 527.12 |
| 73 | 528.11 |
| 74 | 550.16 |
| 75 | 526.12 |
| 76 | 542.1 |
| 77 | 542.1 |
| 78 | 551.1 |
| 79 | 552.1 |
| 80 | 536.14 |
| 81 | 527.12 |
| 82 | 528.11 |
| 83 | 672.13 |
| 84 | 561.07 |
| 85 | 560.11 |
| 86 | 533.11 |
| 87 | 533.11 |
| 88 | 526.1 |
| 89 | 545.2 |
| 90 | 527.2 |
| 91 | 545.2 |
| 92 | 539.1 |
| 93 | 545.1 |
| 94 | 526.12 |
| 95 | 544.11 |
| 96 | 541.1 |
| 97 | 545.1 |
| 98 | 545.1 |
| 99 | 551.1 |
| 100 | 551.1 |
| 101 | 561.1 |
| 102 | 546.1 |
| 103 | 546.1 |
| 104 | 561.1 |
| 105 | 556.1 |
| 106 | 542.1 |
| 107 | 542.1 |
| 108 | 557.1 |
| 109 | 571.1 |
| 110 | 552.1 |
| 111 | 543.1 |
| 112 | 551.1 |
| 113 | 545.1 |
| 114 | 545.1 |
| 115 | 545.1 |
| 116 | 556.1 |
| 117 | 563.1 |
| 118 | 557.1 |
| 119 | 545.1 |
| 120 | 545.1 |
| 121 | 577.1 |
| 122 | 545.1 |
| 123 | 522.1 |
| 124 | 572.1 |
| 125 | 560.1 |
| 126 | 559.1 |
| 127 | 558.1 |
| 128 | 519.1 |
| 129 | 509.1 |

TABLE 4-continued

| MS Data for Exemplified Compounds. | |
|---|---|
| Example | LC/MS (ESI+): m/z (M + H) |
| 130 | 601.1 |
| 131 | 527.1 |
| 132 | 547.1 |
| 133 | 541.2 |
| 134 | 545.1 |
| 135 | 545.1 |
| 136 | 528.1 |
| 137 | 549.1 |
| 138 | 541.1 |
| 139 | 544.1 |
| 140 | 545.1 |
| 141 | 545.1 |
| 142 | 542.1 |
| 143 | 527.2 |
| 144 | 551.1 |
| 145 | 543.1 |
| 146 | 550.1 |
| 147 | 559.1 |
| 148 | 531.1 |
| 149 | 533.2 |
| 150 | 545.1 |
| 151 | 556.1 |
| 152 | 542.1 |
| 153 | 546.1 |
| 154 | 528.2 |
| 155 | 499.2 |
| 156 | 546.1 |
| 157 | 528.2 |
| 158 | 561.2 |
| 159 | 542.2 |
| 160 | 524.2 |
| 161 | 544.2 |
| 162 | 543.2 |
| 163 | 545.2 |
| 164 | 552.2 |
| 165 | 558.2 |
| 166 | 552.1 |
| 167 | 546.1 |
| 168 | 527.2 |
| 169 | 542.1 |
| 170 | 601.1 |
| 171 | 546.2 |
| 172 | 522.2 |
| 173 | 550.2 |
| 174 | 550.2 |
| 175 | 550.2 |
| 176 | 546.2 |
| 177 | 543.2 |
| 178 | 542.2 |
| 179 | 556.2 |
| 180 | 546.2 |

TABLE 4-continued

| MS Data for Exemplified Compounds. | |
|---|---|
| Example | LC/MS (ESI+): m/z (M + H) |
| 181 | 539.2 |
| 182 | 539.2 |
| 183 | 539.2 |
| 184 | 562.1 |
| 185 | 572.1 |
| 186 | 524.1 |
| 187 | 559.2 |
| 188 | 558.2 |
| 189 | 553.1 |
| 190 | 618.1 |
| 191 | 542.1 |
| 192 | 562.1 |
| 193 | 542.1 |
| 194 | 538.5 |
| 195 | 528.5 |
| 196 | 558.1 |
| 197 | 517.1 |
| 198 | 510.2 |
| 199 | 518.1 |
| 200 | 510. |
| 201 | 496 |

IC50 Determinations of Exemplified Compounds.

IC50s (effective concentration) of compounds on the human and rat TRPA1 channels were determined using a FLIPR Tetra instrument. CHO cells expressing TRPA1 were plated into 384-well plates, incubated overnight at 37C, and loaded with BD calcium indicator dye for 1 hr at 37° C. followed by 15 minutes. at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 20 minutes at room temperature prior to adding agonist. Following this incubation, ~EC80 concentration of cinnamaldehyde (75 uM for human TRPA1 and 45 uM for rat TRPA1) was added to active the channels and block of cinnamaldehyde induced calcium influx was measured.

IC50s were fit with a standard Hill function, keeping the Hill coefficient (n) fixed to 1.5. Fixing the Hill coefficient will generally reduce variability of the IC50 determination. The IC50s were individually examined to make sure the MIN and MAX points were set correctly prior to validation of the results. Data for representative compounds of formula I and II is provided in Table 5 below.

TABLE 5

| $IC_{50}$ Determinations of Exemplified Compounds. | | |
|---|---|---|
| Example Number | Structure | hTRPA1 AUC $IC_{50}$ (μM) |
| 38 | 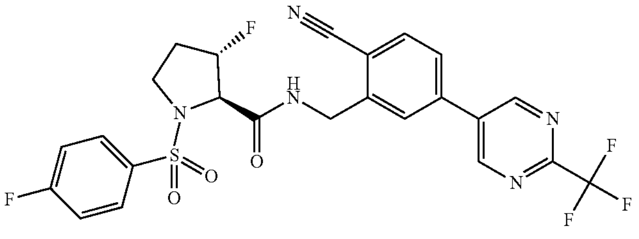 [SMILES: N#Cc1ccc(-c2cnc(C(F)(F)F)nc2)cc1CNC(=O)[C@@H]1[C@@H](F)CCN1S(=O)(=O)c1ccc(F)cc1] | 0.014 |

TABLE 5-continued
| IC$_{50}$ Determinations of Exemplified Compounds. | | |
|---|---|---|
| Example Number | Structure | hTRPA1 AUC IC$_{50}$ (μM) |
| 39 | 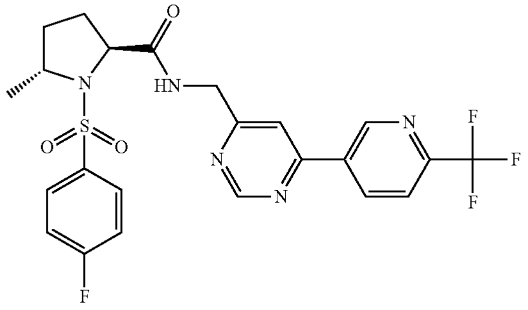 [SMILES: C[C@@H]1CC[C@@H](C(=O)NCc2cc(-c3ccc(C(F)(F)F)nc3)ncn2)N1S(=O)(=O)c1ccc(F)cc1] | 0.045 |
| 40 | 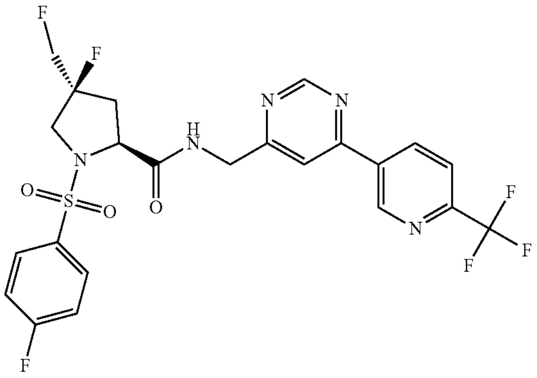 [SMILES: O=C(NCc1cc(-c2ccc(C(F)(F)F)nc2)ncn1)[C@@H]1C[C@@](F)(CF)CN1S(=O)(=O)c1ccc(F)cc1] | 0.291 |
| 41 | 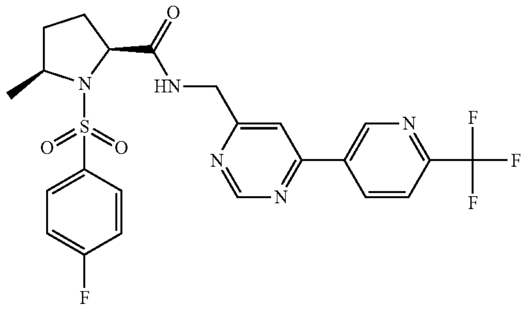 [SMILES: C[C@H]1CC[C@@H](C(=O)NCc2cc(-c3ccc(C(F)(F)F)nc3)ncn2)N1S(=O)(=O)c1ccc(F)cc1] | 0.005 |
| 42 | 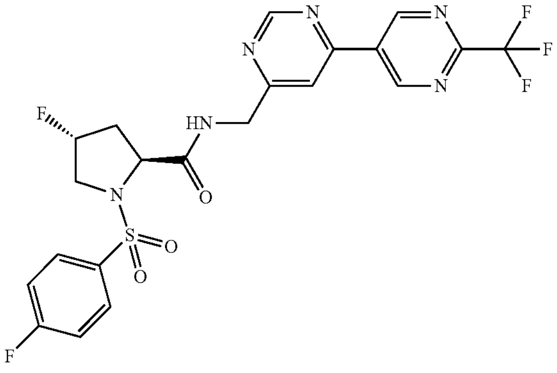 [SMILES: O=C(NCc1cc(-c2cnc(C(F)(F)F)nc2)ncn1)[C@@H]1C[C@@H](F)CN1S(=O)(=O)c1ccc(F)cc1] | 0.251 |

TABLE 5-continued
| IC$_{50}$ Determinations of Exemplified Compounds. | | |
|---|---|---|
| Example Number | Structure | hTRPA1 AUC IC$_{50}$ (μM) |
| 43 | 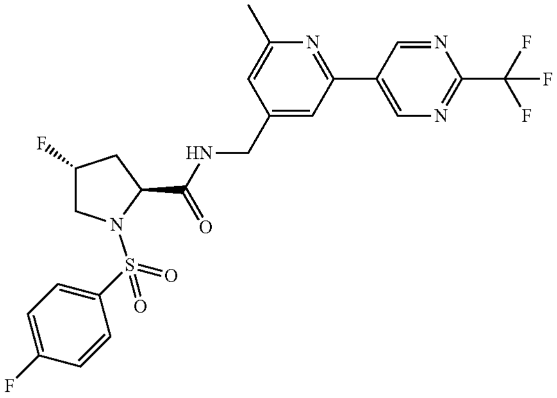 [SMILES: Cc1cc(CNC(=O)[C@@H]2C[C@@H](F)CN2S(=O)(=O)c2ccc(F)cc2)cc(-c2cnc(C(F)(F)F)nc2)n1] | 0.047 |
| 44 | 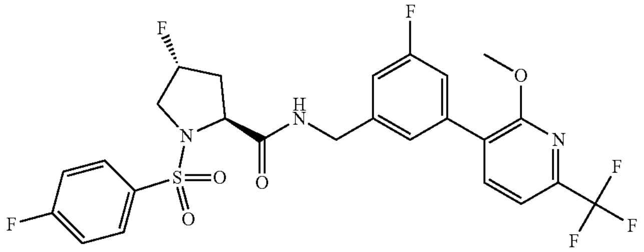 [SMILES: COc1nc(C(F)(F)F)ccc1-c1cc(F)cc(CNC(=O)[C@@H]2C[C@@H](F)CN2S(=O)(=O)c2ccc(F)cc2)c1] | 0.048 |
| 45 | 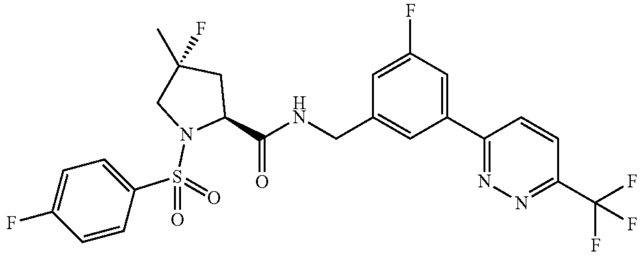 [SMILES: C[C@@]1(F)C[C@@H](C(=O)NCc2cc(F)cc(-c3ccc(C(F)(F)F)nn3)c2)N(S(=O)(=O)c2ccc(F)cc2)C1] | 0.024 |
| 46 | 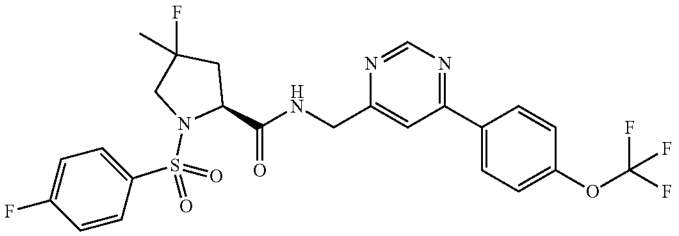 [SMILES: CC1(F)C[C@@H](C(=O)NCc2cc(-c3ccc(OC(F)(F)F)cc3)ncn2)N(S(=O)(=O)c2ccc(F)cc2)C1] | 0.020 |
| 47 | 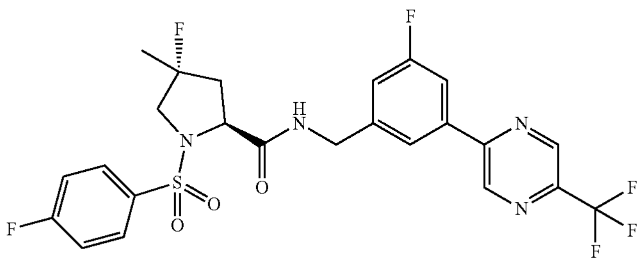 [SMILES: C[C@@]1(F)C[C@@H](C(=O)NCc2cc(F)cc(-c3cnc(C(F)(F)F)cn3)c2)N(S(=O)(=O)c2ccc(F)cc2)C1] | 0.011 |

TABLE 5-continued
| IC$_{50}$ Determinations of Exemplified Compounds. | | |
|---|---|---|
| Example Number | Structure | hTRPA1 AUC IC$_{50}$ (μM) |
| 48 | 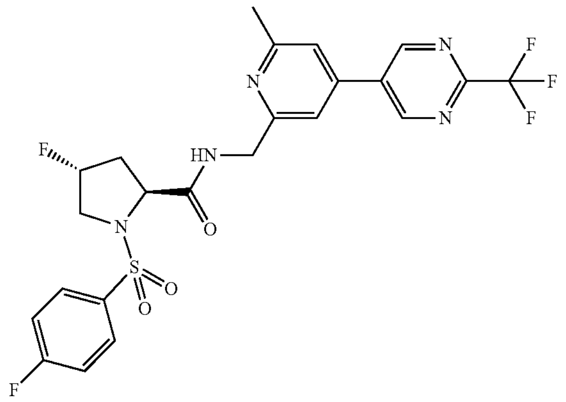 [SMILES: Cc1cc(-c2cnc(C(F)(F)F)nc2)cc(CNC(=O)[C@@H]2C[C@@H](F)CN2S(=O)(=O)c2ccc(F)cc2)n1] | 0.152 |
| 49 | 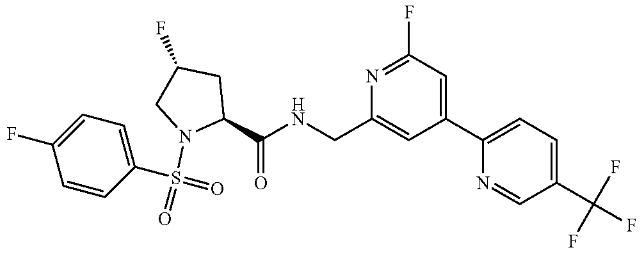 [SMILES: O=C(NCc1cc(-c2ccc(C(F)(F)F)cn2)cc(F)n1)[C@@H]1C[C@@H](F)CN1S(=O)(=O)c1ccc(F)cc1] | 0.009 |
| 50 | 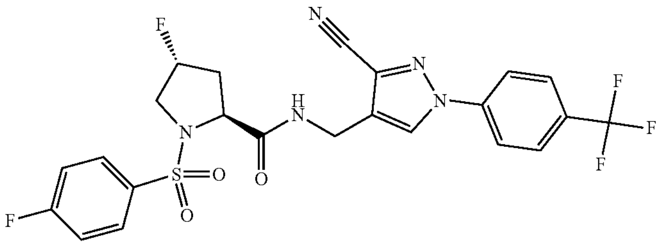 [SMILES: N#Cc1nn(-c2ccc(C(F)(F)F)cc2)cc1CNC(=O)[C@@H]1C[C@@H](F)CN1S(=O)(=O)c1ccc(F)cc1] | 0.060 |
| 51 | 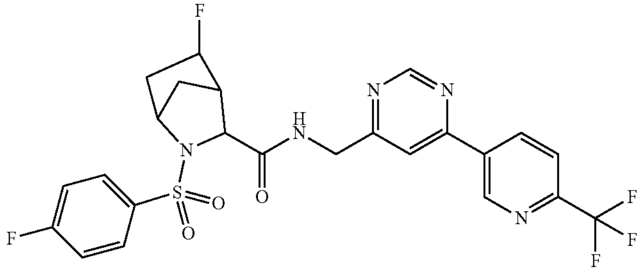 [SMILES: O=C(NCc1cc(-c2ccc(C(F)(F)F)nc2)ncn1)C1C2CC(CC2F)N1S(=O)(=O)c1ccc(F)cc1] | 0.052 |
| 52 | 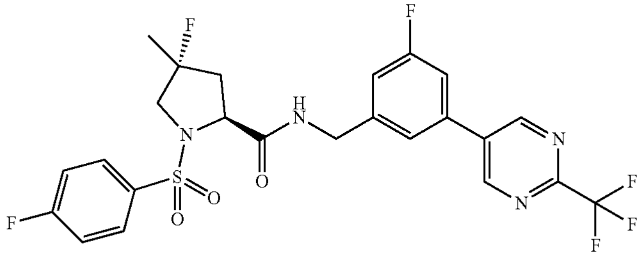 [SMILES: C[C@@]1(F)C[C@@H](C(=O)NCc2cc(F)cc(-c3cnc(C(F)(F)F)nc3)c2)N(S(=O)(=O)c2ccc(F)cc2)C1] | 0.016 |

TABLE 5-continued
IC$_{50}$ Determinations of Exemplified Compounds.
| Example Number | Structure | hTRPA1 AUC IC$_{50}$ (μM) |
|---|---|---|
| 53 | 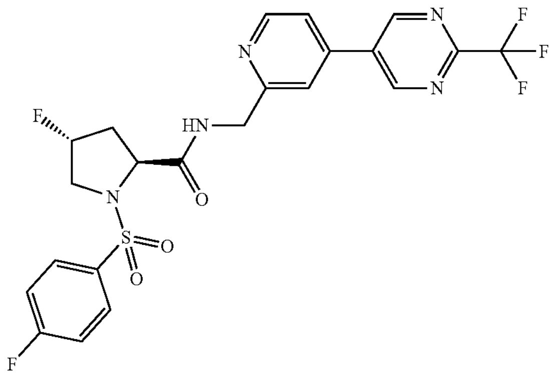 [SMILES: O=C(NCc1cc(-c2cnc(C(F)(F)F)nc2)ccn1)[C@@H]1C[C@@H](F)CN1S(=O)(=O)c1ccc(F)cc1] | 0.411 |
| 54 | 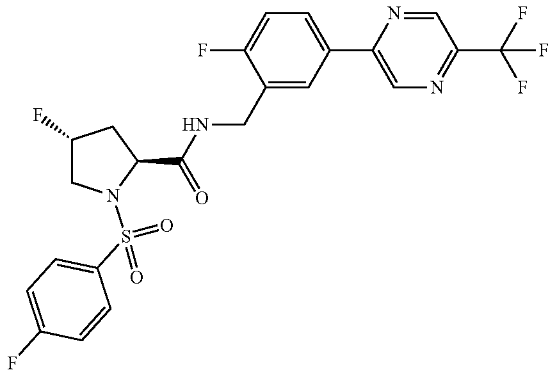 [SMILES: O=C(NCc1cc(-c2cnc(C(F)(F)F)cn2)ccc1F)[C@@H]1C[C@@H](F)CN1S(=O)(=O)c1ccc(F)cc1] | 0.013 |
| 55 | 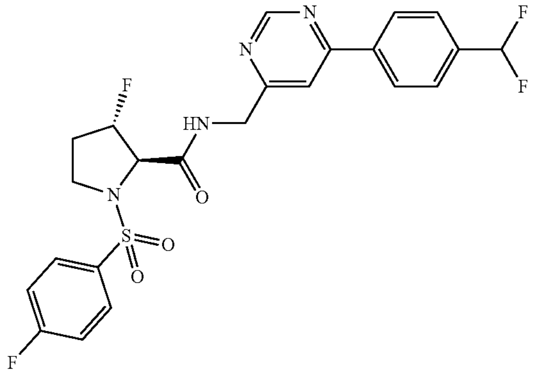 [SMILES: O=C(NCc1cc(-c2ccc(C(F)F)cc2)ncn1)[C@@H]1[C@@H](F)CCN1S(=O)(=O)c1ccc(F)cc1] | 0.033 |
| 56 | 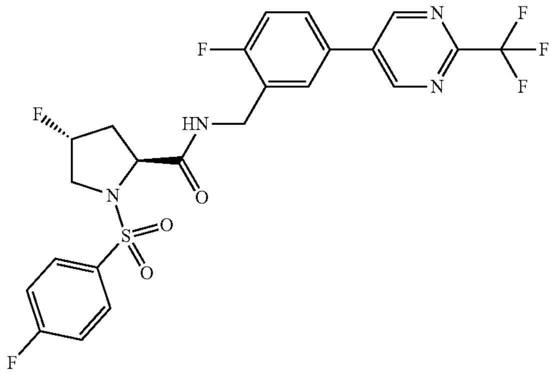 [SMILES: O=C(NCc1cc(-c2cnc(C(F)(F)F)nc2)ccc1F)[C@@H]1C[C@@H](F)CN1S(=O)(=O)c1ccc(F)cc1] | 0.011 |

TABLE 5-continued
| IC$_{50}$ Determinations of Exemplified Compounds. | | |
|---|---|---|
| Example Number | Structure | hTRPA1 AUC IC$_{50}$ (μM) |
| 57 | 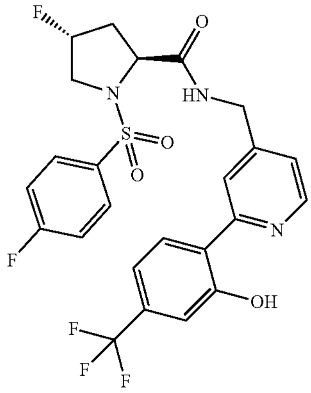 [SMILES: O=C(NCc1ccnc(-c2ccc(C(F)(F)F)cc2O)c1)[C@@H]1C[C@@H](F)CN1S(=O)(=O)c1ccc(F)cc1] | 0.005 |
| 58 | 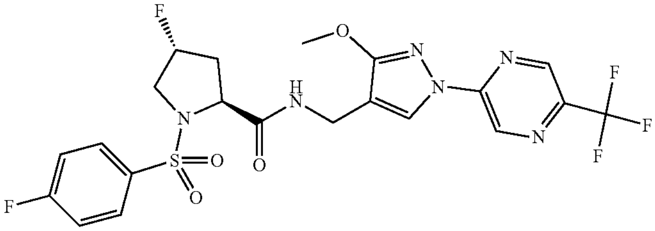 [SMILES: COc1nn(-c2cnc(C(F)(F)F)cn2)cc1CNC(=O)[C@@H]1C[C@@H](F)CN1S(=O)(=O)c1ccc(F)cc1] | 0.014 |
| 59 | 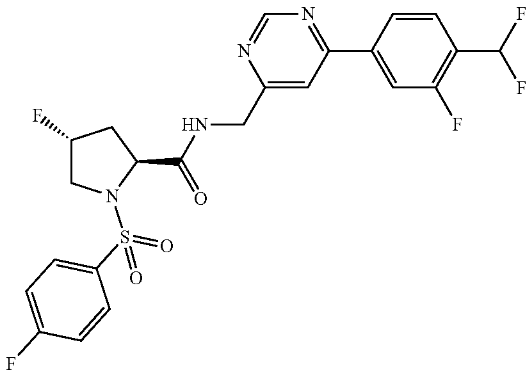 | 0.029 |
| 60 | 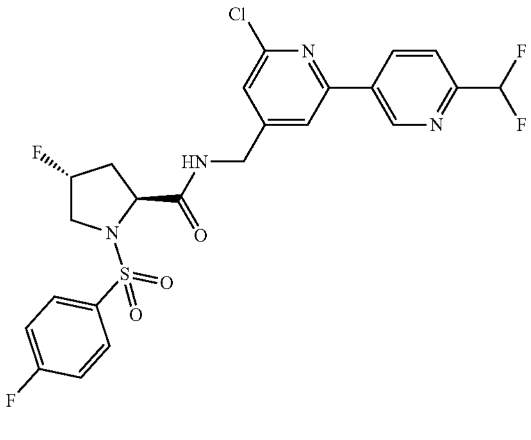 [SMILES: O=C(NCc1cc(Cl)nc(-c2ccc(C(F)F)nc2)c1)[C@@H]1C[C@@H](F)CN1S(=O)(=O)c1ccc(F)cc1] | 0.055 |

TABLE 5-continued
| IC$_{50}$ Determinations of Exemplified Compounds. | | |
|---|---|---|
| Example Number | Structure | hTRPA1 AUC IC$_{50}$ (μM) |
| 61 | 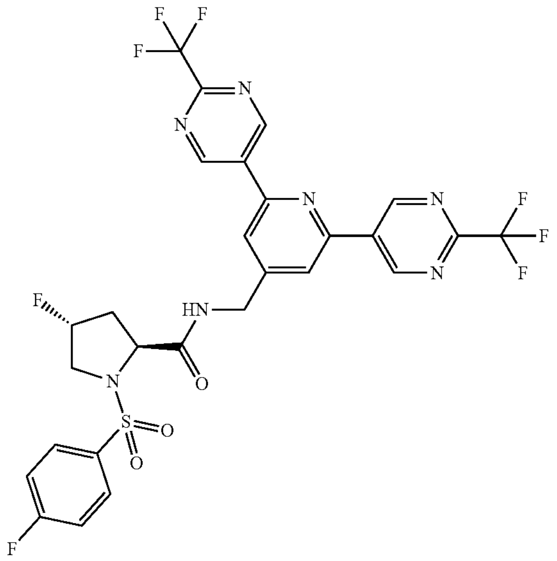 [SMILES: O=C(NCc1cc(-c2cnc(C(F)(F)F)nc2)nc(-c2cnc(C(F)(F)F)nc2)c1)[C@@H]1C[C@@H](F)CN1S(=O)(=O)c1ccc(F)cc1] | 0.071 |
| 62 | 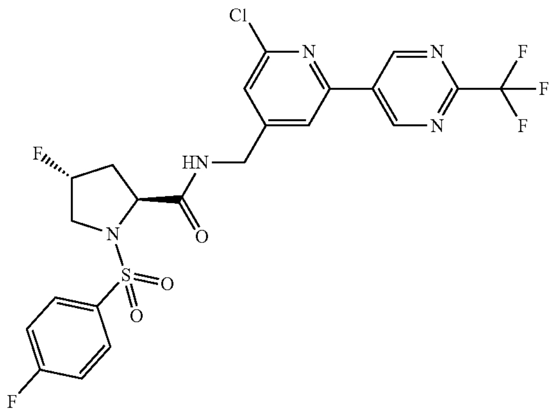 [SMILES: O=C(NCc1cc(Cl)nc(-c2cnc(C(F)(F)F)nc2)c1)[C@@H]1C[C@@H](F)CN1S(=O)(=O)c1ccc(F)cc1] | 0.014 |
| 63 | 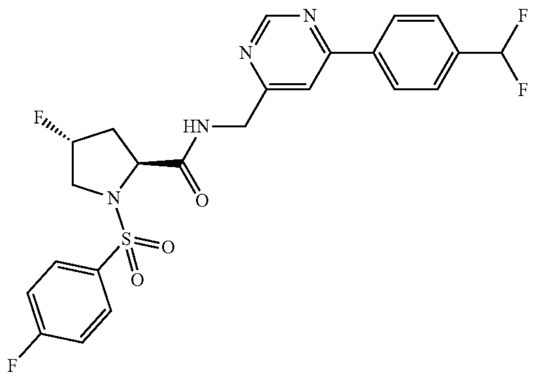 [SMILES: O=C(NCc1cc(-c2ccc(C(F)F)cc2)ncn1)[C@@H]1C[C@@H](F)CN1S(=O)(=O)c1ccc(F)cc1] | 0.318 |

TABLE 5-continued
| IC$_{50}$ Determinations of Exemplified Compounds. | | |
|---|---|---|
| Example Number | Structure | hTRPA1 AUC IC$_{50}$ (μM) |
| 64 | 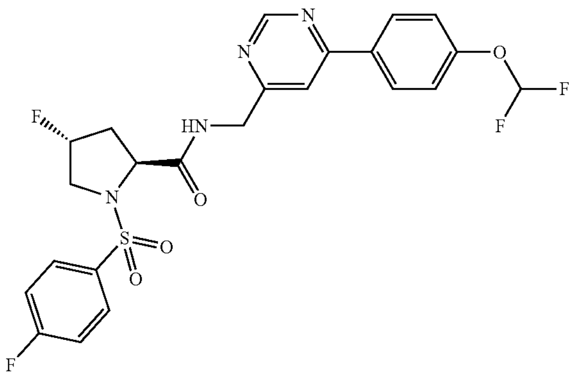 [SMILES: O=C(NCc1cc(-c2ccc(OC(F)F)cc2)ncn1)[C@@H]1C[C@@H](F)CN1S(=O)(=O)c1ccc(F)cc1] | 0.041 |
| 65 | 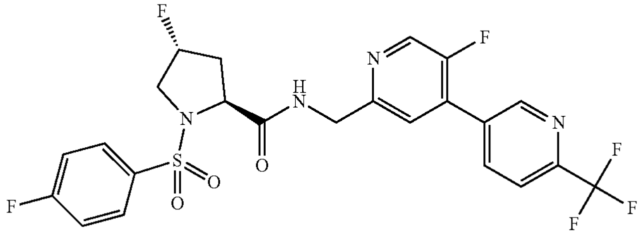 [SMILES: O=C(NCc1cc(-c2ccc(C(F)(F)F)nc2)c(F)cn1)[C@@H]1C[C@@H](F)CN1S(=O)(=O)c1ccc(F)cc1] | 0.040 |
| 66 | 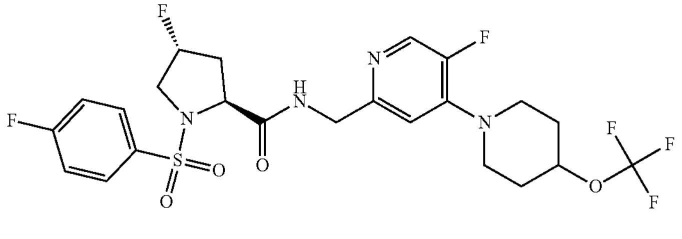 [SMILES: O=C(NCc1cc(N2CCC(OC(F)(F)F)CC2)c(F)cn1)[C@@H]1C[C@@H](F)CN1S(=O)(=O)c1ccc(F)cc1] | 0.022 |
| 67 | 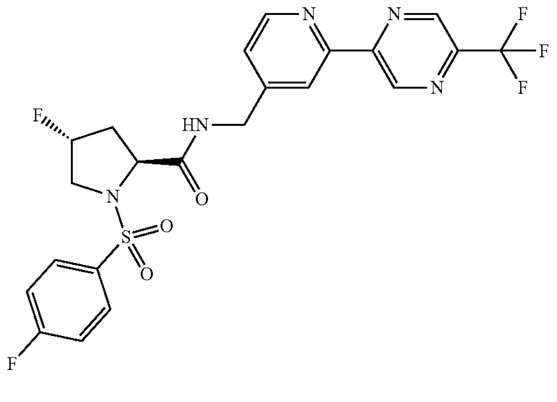 [SMILES: O=C(NCc1ccnc(-c2cnc(C(F)(F)F)cn2)c1)[C@@H]1C[C@@H](F)CN1S(=O)(=O)c1ccc(F)cc1] | 0.290 |

TABLE 5-continued
| IC$_{50}$ Determinations of Exemplified Compounds. | | |
|---|---|---|
| Example Number | Structure | hTRPA1 AUC IC$_{50}$ (μM) |
| 68 | 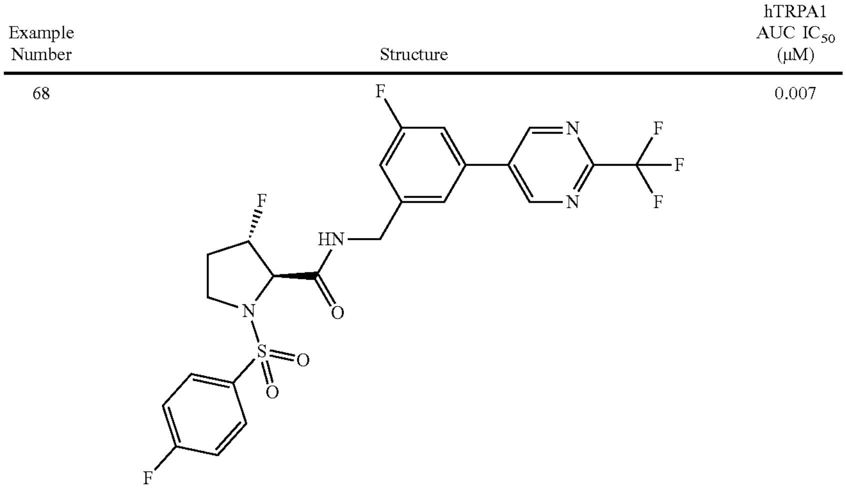 | 0.007 |
| 69 | 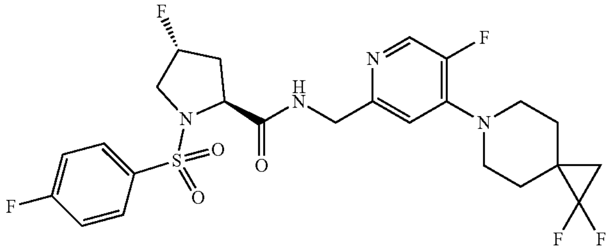 [SMILES: O=C(NCc1cc(N2CCC3(CC2)CC3(F)F)c(F)cn1)[C@@H]1C[C@@H](F)CN1S(=O)(=O)c1ccc(F)cc1] | 0.014 |
| 70 | 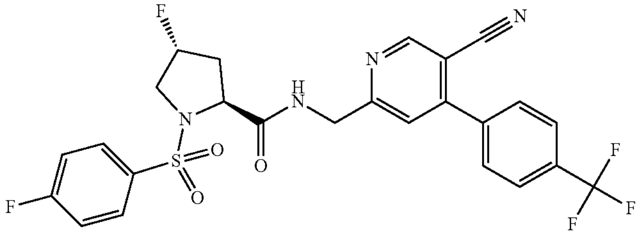 [SMILES: N#Cc1cnc(CNC(=O)[C@@H]2C[C@@H](F)CN2S(=O)(=O)c2ccc(F)cc2)cc1-c1ccc(C(F)(F)F)cc1] | 0.023 |
| 71 | 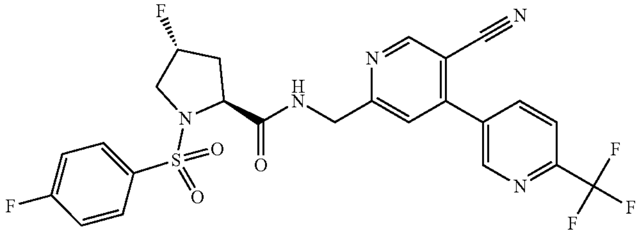 [SMILES: N#Cc1cnc(CNC(=O)[C@@H]2C[C@@H](F)CN2S(=O)(=O)c2ccc(F)cc2)cc1-c1ccc(C(F)(F)F)nc1] | 0.176 |
| 72 | 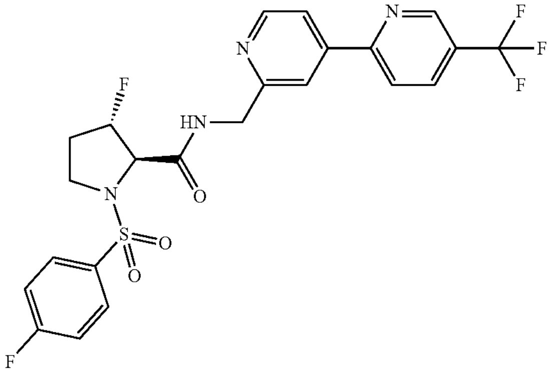 [SMILES: O=C(NCc1cc(-c2ccc(C(F)(F)F)cn2)ccn1)[C@@H]1[C@@H](F)CCN1S(=O)(=O)c1ccc(F)cc1] | 0.007 |

TABLE 5-continued
| IC$_{50}$ Determinations of Exemplified Compounds. | | |
|---|---|---|
| Example Number | Structure | hTRPA1 AUC IC$_{50}$ (μM) |
| 73 | 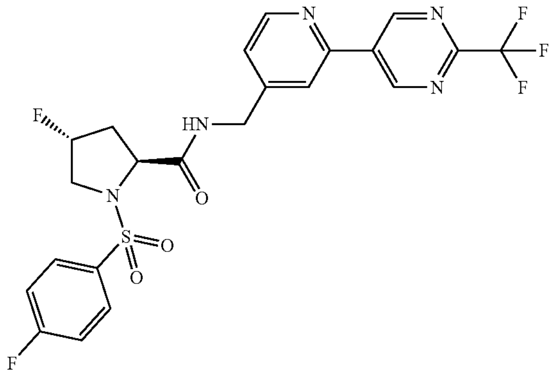 | 0.129 |
| 74 | 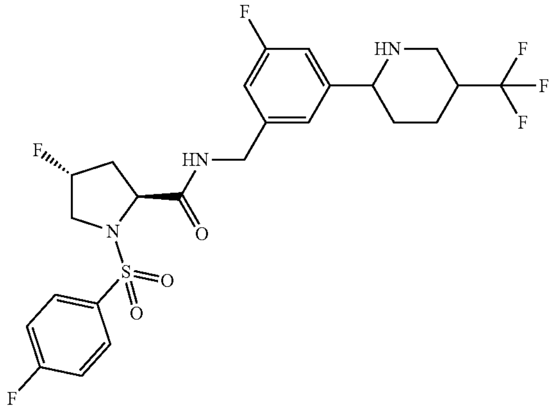 [SMILES: O=C(NCc1cc(F)cc(C2CCC(C(F)(F)F)CN2)c1)[C@@H]1C[C@@H](F)CN1S(=O)(=O)c1ccc(F)cc1] | 0.192 |
| 75 | 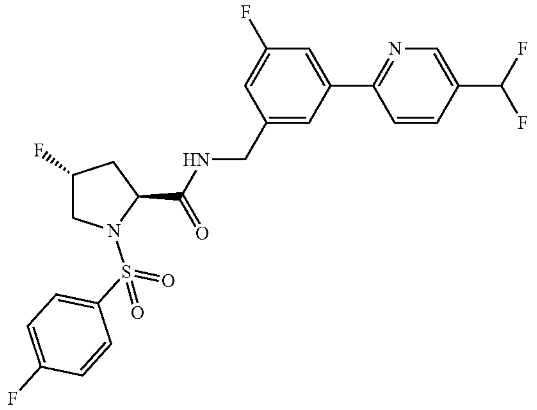 [SMILES: O=C(NCc1cc(F)cc(-c2ccc(C(F)F)cn2)c1)[C@@H]1C[C@@H](F)CN1S(=O)(=O)c1ccc(F)cc1] | 0.031 |
| 76 | 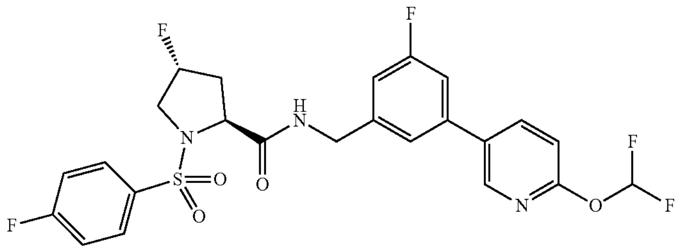 [SMILES: O=C(NCc1cc(F)cc(-c2ccc(OC(F)F)nc2)c1)[C@@H]1C[C@@H](F)CN1S(=O)(=O)c1ccc(F)cc1] | 0.039 |

TABLE 5-continued
| IC$_{50}$ Determinations of Exemplified Compounds. | | |
|---|---|---|
| Example Number | Structure | hTRPA1 AUC IC$_{50}$ (μM) |
| 77 | 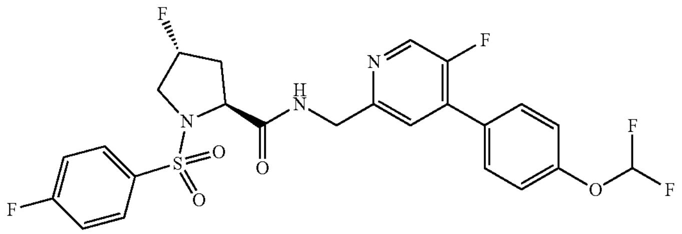 [SMILES: O=C(NCc1cc(-c2ccc(OC(F)F)cc2)c(F)cn1)[C@@H]1C[C@@H](F)CN1S(=O)(=O)c1ccc(F)cc1] | 0.053 |
| 78 | 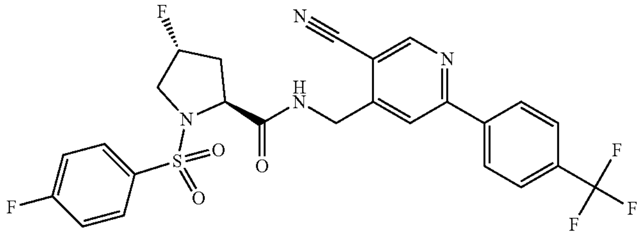 [SMILES: N#Cc1cnc(-c2ccc(C(F)(F)F)cc2)cc1CNC(=O)[C@@H]1C[C@@H](F)CN1S(=O)(=O)c1ccc(F)cc1] | 0.007 |
| 79 | 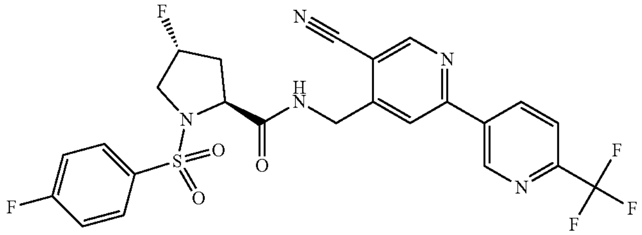 [SMILES: N#Cc1cnc(-c2ccc(C(F)(F)F)nc2)cc1CNC(=O)[C@@H]1C[C@@H](F)CN1S(=O)(=O)c1ccc(F)cc1] | 0.009 |
| 80 | 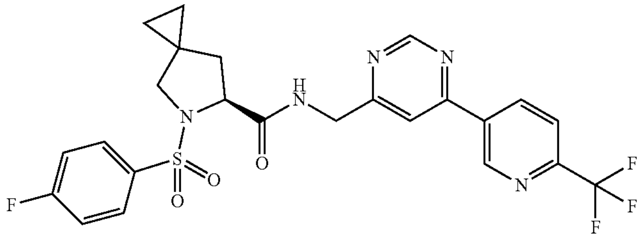 [SMILES: O=C(NCc1cc(-c2ccc(C(F)(F)F)nc2)ncn1)[C@@H]1CC2(CC2)CN1S(=O)(=O)c1ccc(F)cc1] | 0.044 |
| 81 | 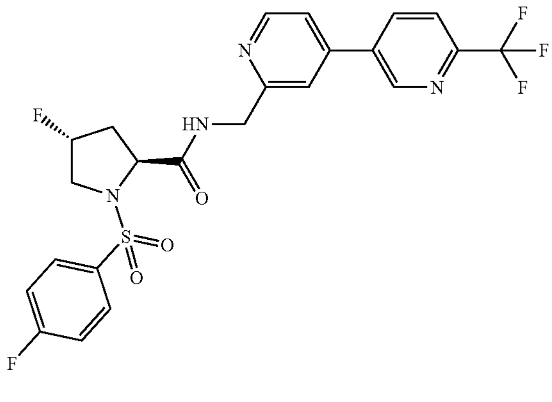 | 0.187 |

TABLE 5-continued
| IC$_{50}$ Determinations of Exemplified Compounds. | | |
|---|---|---|
| Example Number | Structure | hTRPA1 AUC IC$_{50}$ (μM) |
| 82 | 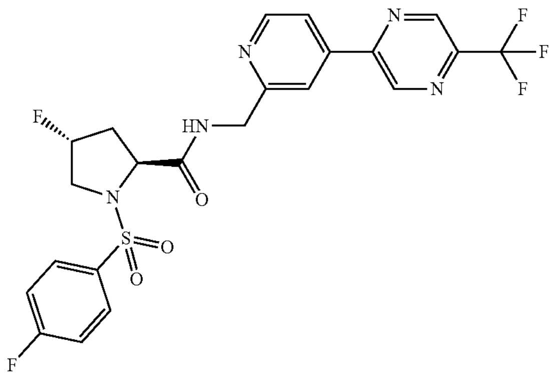 [SMILES: O=C(NCc1cc(-c2cnc(C(F)(F)F)cn2)ccn1)[C@@H]1C[C@@H](F)CN1S(=O)(=O)c1ccc(F)cc1] | 0.189 |
| 83 | 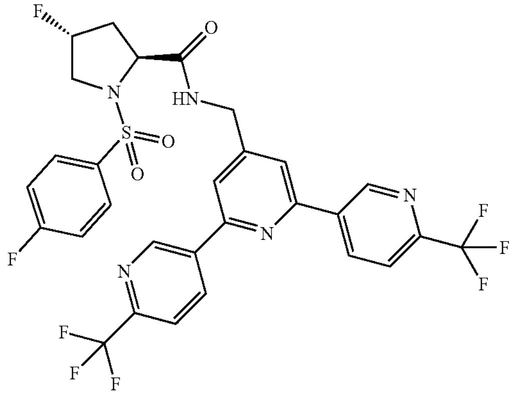 [SMILES: O=C(NCc1cc(-c2ccc(C(F)(F)F)nc2)nc(-c2ccc(C(F)(F)F)nc2)c1)[C@@H]1C[C@@H](F)CN1S(=O)(=O)c1ccc(F)cc1] | 0.0546 |
| 84 | 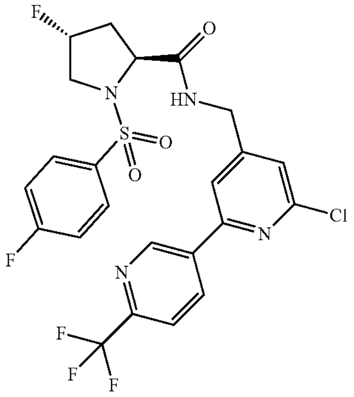 [SMILES: O=C(NCc1cc(Cl)nc(-c2ccc(C(F)(F)F)nc2)c1)[C@@H]1C[C@@H](F)CN1S(=O)(=O)c1ccc(F)cc1] | 0.014 |

TABLE 5-continued
| IC$_{50}$ Determinations of Exemplified Compounds. | | |
|---|---|---|
| Example Number | Structure | hTRPA1 AUC IC$_{50}$ (μM) |
| 85 | 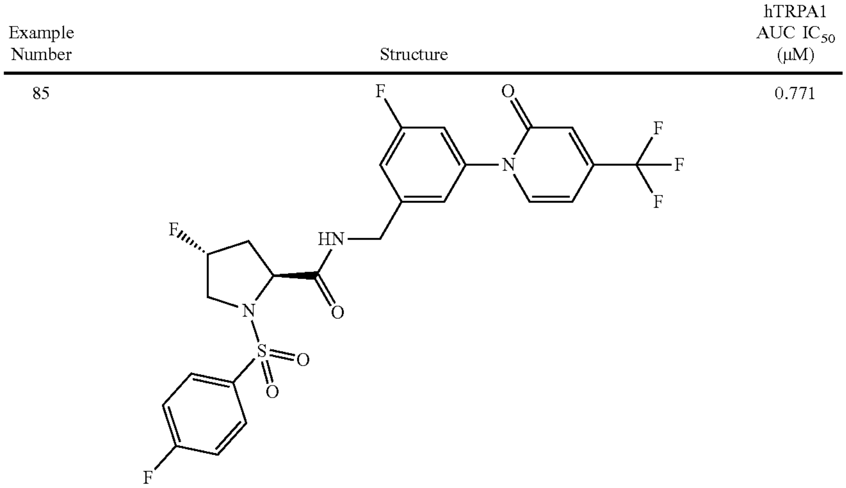 | 0.771 |
| 86 | 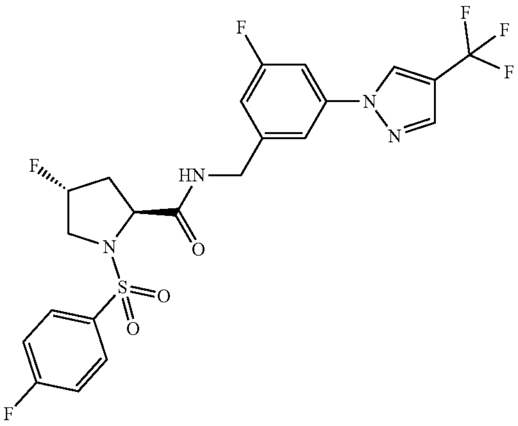 [SMILES: O=C(NCc1cc(F)cc(-n2cc(C(F)(F)F)cn2)c1)[C@@H]1C[C@@H](F)CN1S(=O)(=O)c1ccc(F)cc1] | 0.119 |
| 87 | 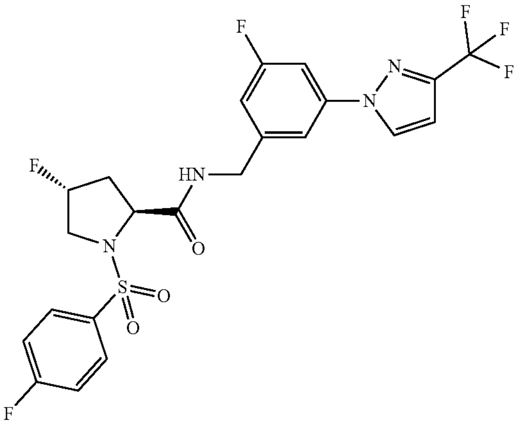 [SMILES: O=C(NCc1cc(F)cc(-n2ccc(C(F)(F)F)n2)c1)[C@@H]1C[C@@H](F)CN1S(=O)(=O)c1ccc(F)cc1] | 0.103 |
| 88 | 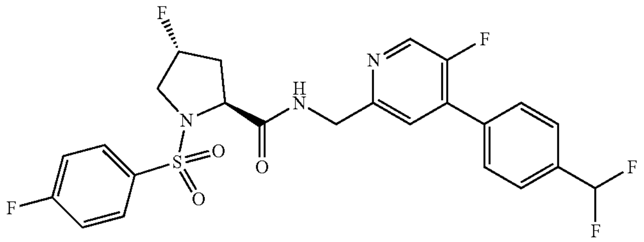 [SMILES: O=C(NCc1cc(-c2ccc(C(F)F)cc2)c(F)cn1)[C@@H]1C[C@@H](F)CN1S(=O)(=O)c1ccc(F)cc1] | 0.041 |

TABLE 5-continued
| IC50 Determinations of Exemplified Compounds. | | |
|---|---|---|
| Example Number | Structure | hTRPA1 AUC $IC_{50}$ (μM) |
| 89 | 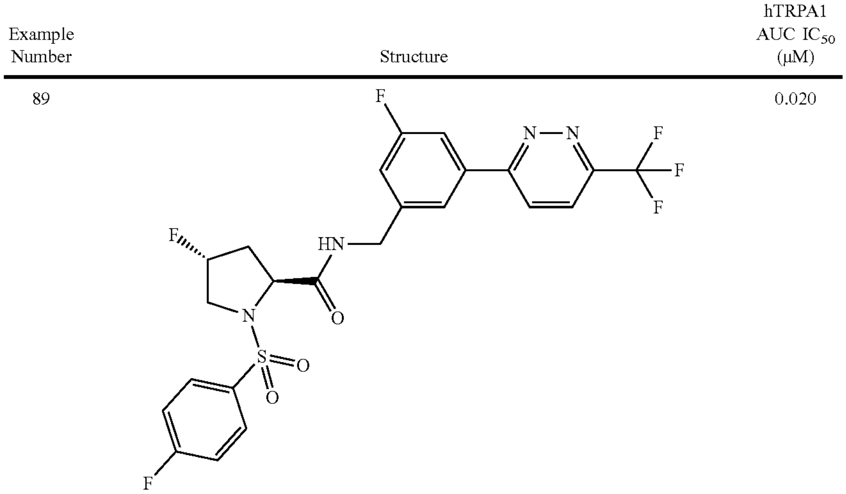 | 0.020 |
| 90 | 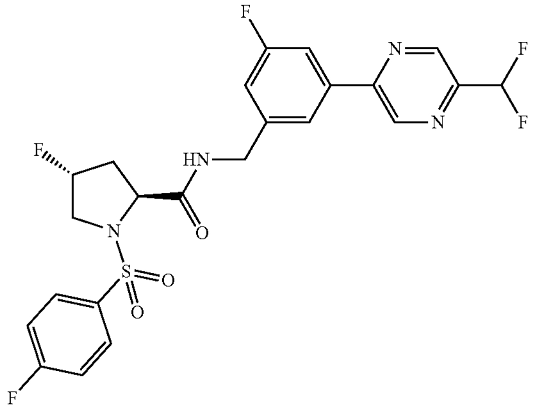 [SMILES: O=C(NCc1cc(F)cc(-c2cnc(C(F)F)cn2)c1)[C@@H]1C[C@@H](F)CN1S(=O)(=O)c1ccc(F)cc1] | 0.062 |
| 91 | 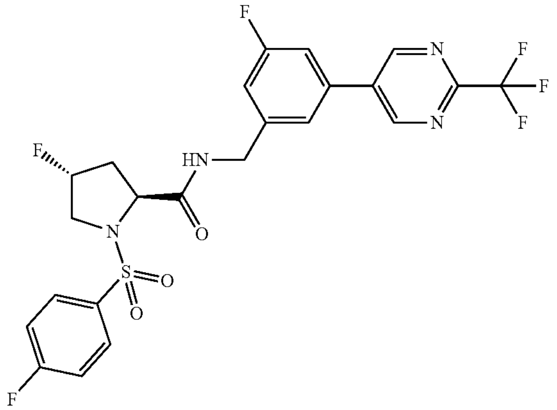 | 0.014 |
| 92 | 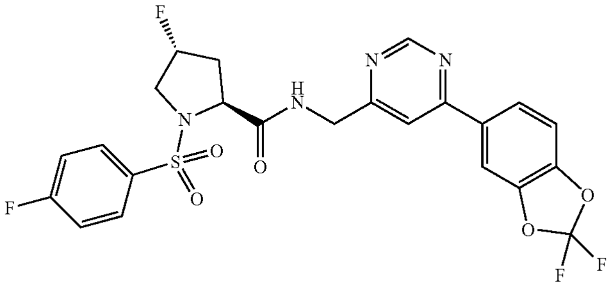 [SMILES: O=C(NCc1cc(-c2ccc3c(c2)OC(F)(F)O3)ncn1)[C@@H]1C[C@@H](F)CN1S(=O)(=O)c1ccc(F)cc1] | 0.087 |

TABLE 5-continued
IC$_{50}$ Determinations of Exemplified Compounds.
| Example Number | Structure | hTRPA1 AUC IC$_{50}$ (μM) |
|---|---|---|
| 93 | 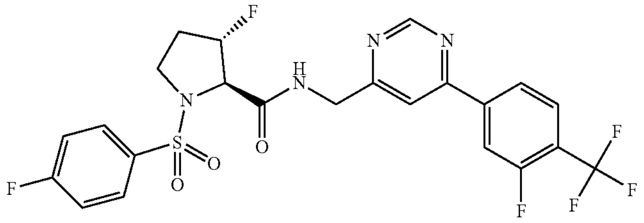 [SMILES: O=C(NCc1cc(-c2ccc(C(F)(F)F)c(F)c2)ncn1)[C@@H]1[C@@H](F)CCN1S(=O)(=O)c1ccc(F)cc1] | 0.014 |
| 94 | 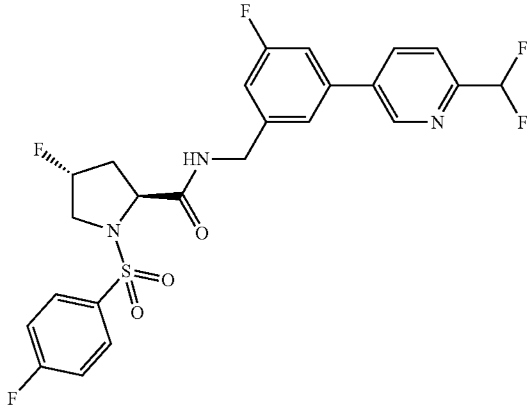 [SMILES: O=C(NCc1cc(F)cc(-c2ccc(C(F)F)nc2)c1)[C@@H]1C[C@@H](F)CN1S(=O)(=O)c1ccc(F)cc1] | 0.029 |
| 95 | 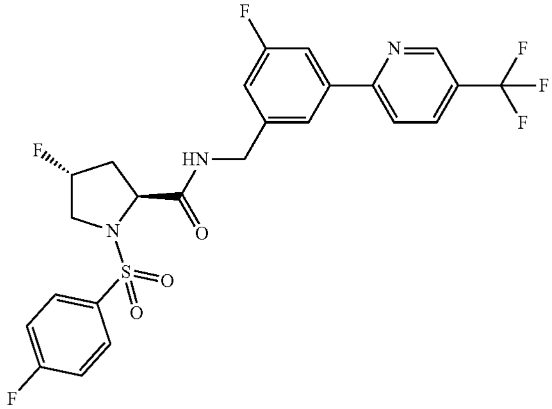 [SMILES: O=C(NCc1cc(F)cc(-c2ccc(C(F)(F)F)cn2)c1)[C@@H]1C[C@@H](F)CN1S(=O)(=O)c1ccc(F)cc1] | 0.012 |
| 96 | 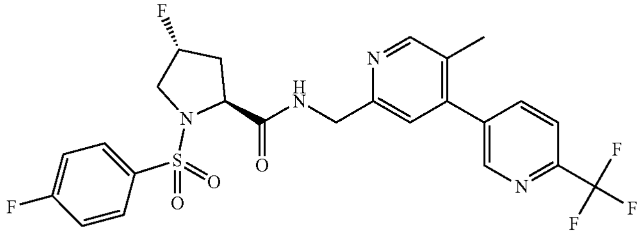 [SMILES: Cc1cnc(CNC(=O)[C@@H]2C[C@@H](F)CN2S(=O)(=O)c2ccc(F)cc2)cc1-c1ccc(C(F)(F)F)nc1] | 0.162 |
| 97 | 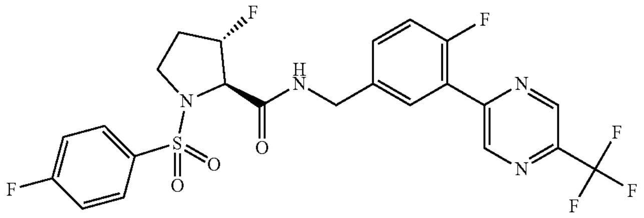 [SMILES: O=C(NCc1ccc(F)c(-c2cnc(C(F)(F)F)cn2)c1)[C@@H]1[C@@H](F)CCN1S(=O)(=O)c1ccc(F)cc1] | 0.024 |

TABLE 5-continued
IC$_{50}$ Determinations of Exemplified Compounds.
| Example Number | Structure | hTRPA1 AUC IC$_{50}$ (μM) |
|---|---|---|
| 98 | 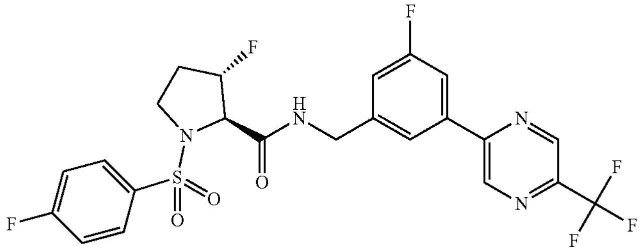 [SMILES: O=C(NCc1cc(F)cc(-c2cnc(C(F)(F)F)cn2)c1)[C@@H]1[C@@H](F)CCN1S(=O)(=O)c1ccc(F)cc1] | 0.004 |
| 99 | 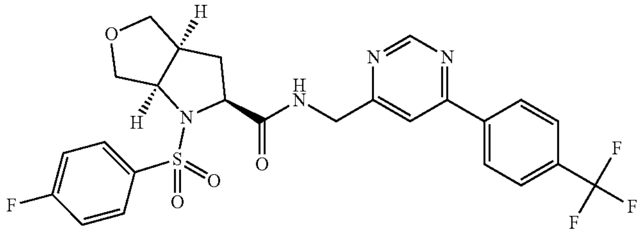 [SMILES: O=C(NCc1cc(-c2ccc(C(F)(F)F)cc2)ncn1)[C@@H]1C[C@@H]2COC[C@@H]2N1S(=O)(=O)c1ccc(F)cc1] | 0.428 |
| 100 | 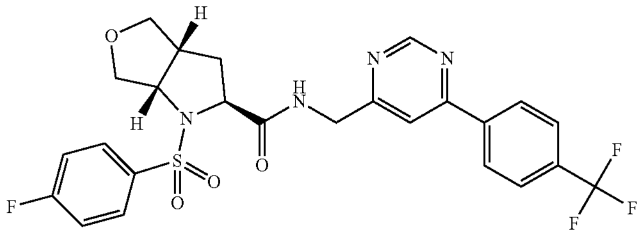 [SMILES: O=C(NCc1cc(-c2ccc(C(F)(F)F)cc2)ncn1)[C@@H]1C[C@H]2COC[C@H]2N1S(=O)(=O)c1ccc(F)cc1] | 0.449 |
| 101 | 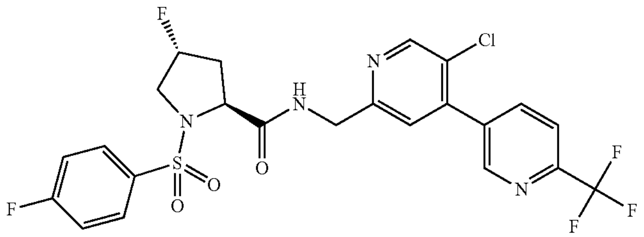 | 0.033 |
| 102 | 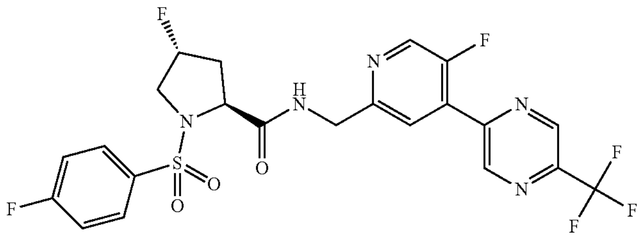 [SMILES: O=C(NCc1cc(-c2cnc(C(F)(F)F)cn2)c(F)cn1)[C@@H]1C[C@@H](F)CN1S(=O)(=O)c1ccc(F)cc1] | 0.066 |
| 103 | 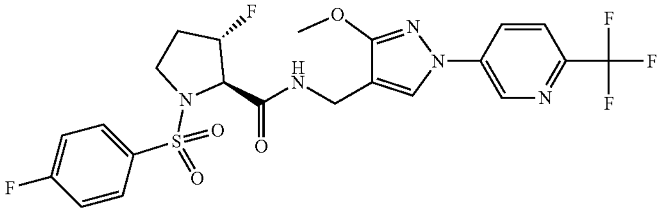 [SMILES: COc1nn(-c2ccc(C(F)(F)F)nc2)cc1CNC(=O)[C@@H]1[C@@H](F)CCN1S(=O)(=O)c1ccc(F)cc1] | 0.026 |

TABLE 5-continued
IC$_{50}$ Determinations of Exemplified Compounds.
| Example Number | Structure | hTRPA1 AUC IC$_{50}$ (μM) |
|---|---|---|
| 104 | 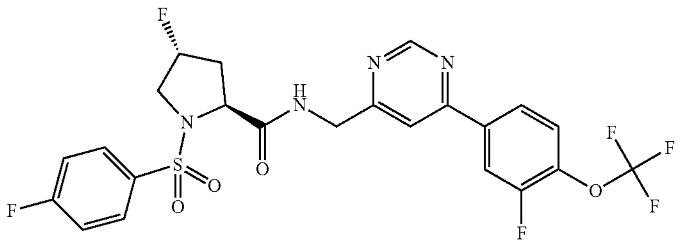 [SMILES: O=C(NCc1cc(-c2ccc(OC(F)(F)F)c(F)c2)ncn1)[C@@H]1C[C@@H](F)CN1S(=O)(=O)c1ccc(F)cc1] | 0.072 |
| 105 | 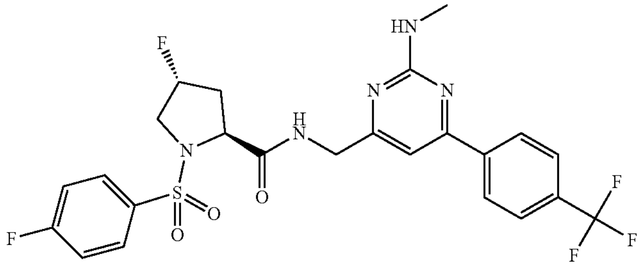 [SMILES: CNc1nc(CNC(=O)[C@@H]2C[C@@H](F)CN2S(=O)(=O)c2ccc(F)cc2)cc(-c2ccc(C(F)(F)F)cc2)n1] | 0.128 |
| 106 | 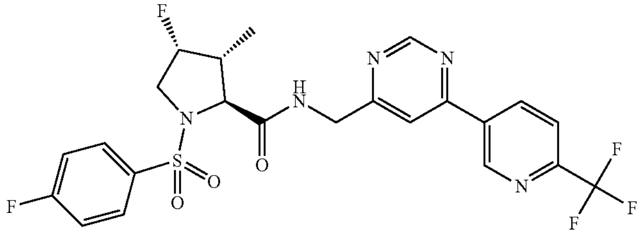 [SMILES: C[C@@H]1[C@@H](C(=O)NCc2cc(-c3ccc(C(F)(F)F)nc3)ncn2)N(S(=O)(=O)c2ccc(F)cc2)C[C@@H]1F] | 0.28 |
| 107 | 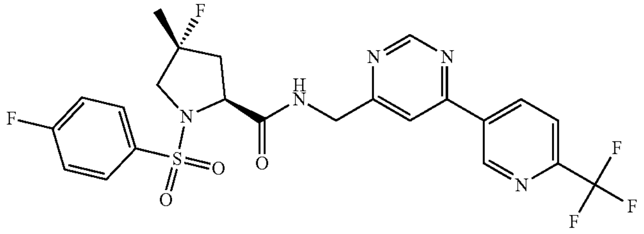 [SMILES: C[C@@]1(F)C[C@@H](C(=O)NCc2cc(-c3ccc(C(F)(F)F)nc3)ncn2)N(S(=O)(=O)c2ccc(F)cc2)C1] | 0.090 |
| 108 | 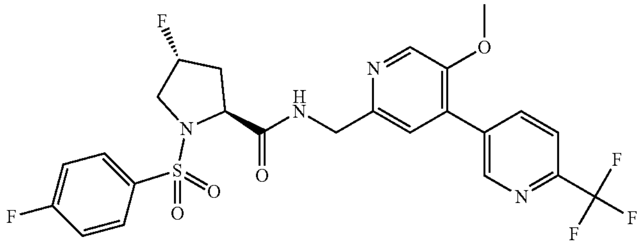 [SMILES: COc1cnc(CNC(=O)[C@@H]2C[C@@H](F)CN2S(=O)(=O)c2ccc(F)cc2)cc1-c1ccc(C(F)(F)F)nc1] | 0.256 |
| 109 | 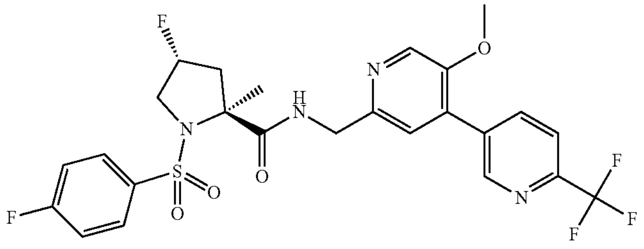 [SMILES: COc1cnc(CNC(=O)[C@]2(C)C[C@@H](F)CN2S(=O)(=O)c2ccc(F)cc2)cc1-c1ccc(C(F)(F)F)nc1] | 0.164 |

TABLE 5-continued
IC$_{50}$ Determinations of Exemplified Compounds.
| Example Number | Structure | hTRPA1 AUC IC$_{50}$ (μM) |
|---|---|---|
| 110 | 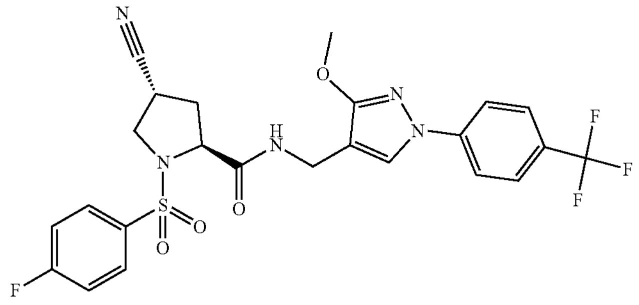 [SMILES: COc1nn(-c2ccc(C(F)(F)F)cc2)cc1CNC(=O)[C@@H]1C[C@@H](C#N)CN1S(=O)(=O)c1ccc(F)cc1] | 0.165 |
| 111 | 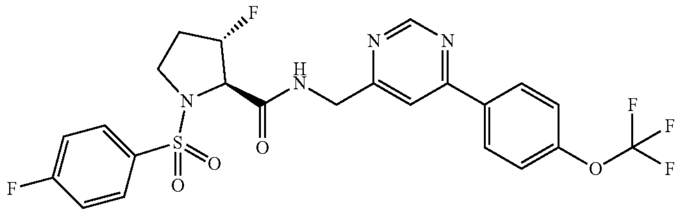 [SMILES: O=C(NCc1cc(-c2ccc(OC(F)(F)F)cc2)ncn1)[C@@H]1[C@@H](F)CCN1S(=O)(=O)c1ccc(F)cc1] | 0.007 |
| 112 | 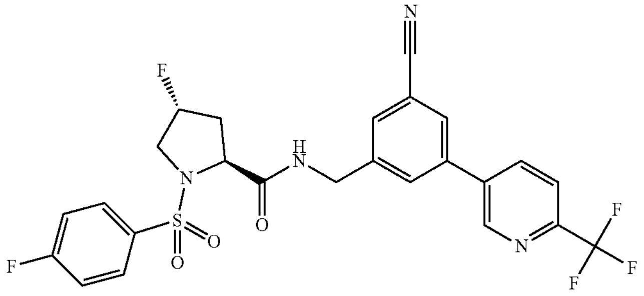 [SMILES: N#Cc1cc(CNC(=O)[C@@H]2C[C@@H](F)CN2S(=O)(=O)c2ccc(F)cc2)cc(-c2ccc(C(F)(F)F)nc2)c1] | 0.048 |
| 113 | 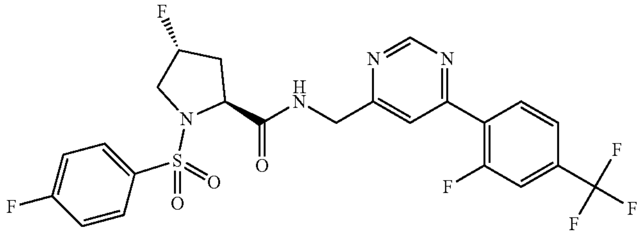 [SMILES: O=C(NCc1cc(-c2ccc(C(F)(F)F)cc2F)ncn1)[C@@H]1C[C@@H](F)CN1S(=O)(=O)c1ccc(F)cc1] | 0.161 |
| 114 | 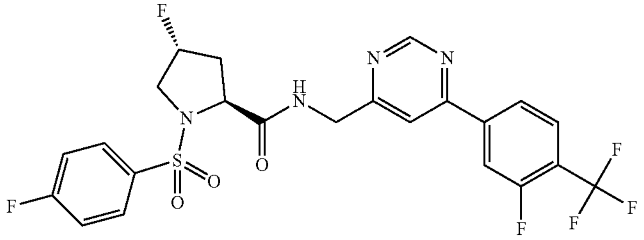 [SMILES: O=C(NCc1cc(-c2ccc(C(F)(F)F)c(F)c2)ncn1)[C@@H]1C[C@@H](F)CN1S(=O)(=O)c1ccc(F)cc1] | 0.026 |

TABLE 5-continued
IC$_{50}$ Determinations of Exemplified Compounds.
| Example Number | Structure | hTRPA1 AUC IC$_{50}$ (μM) |
|---|---|---|
| 115 | 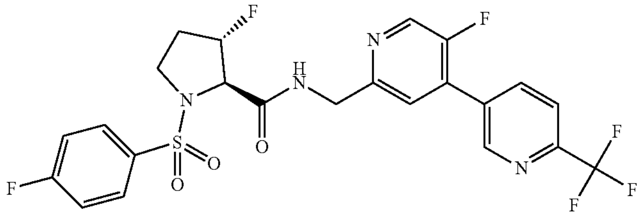 [SMILES: O=C(NCc1cc(-c2ccc(C(F)(F)F)nc2)c(F)cn1)[C@@H]1[C@@H](F)CCN1S(=O)(=O)c1ccc(F)cc1] | 0.013 |
| 116 | 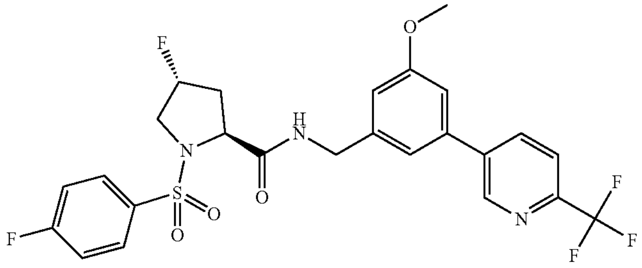 [SMILES: COc1cc(CNC(=O)[C@@H]2C[C@@H](F)CN2S(=O)(=O)c2ccc(F)cc2)cc(-c2ccc(C(F)(F)F)nc2)c1] | 0.047 |
| 117 | 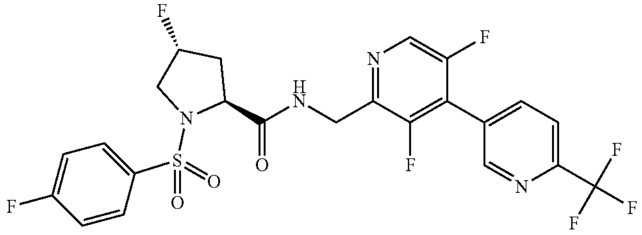 [SMILES: O=C(NCc1ncc(F)c(-c2ccc(C(F)(F)F)nc2)c1F)[C@@H]1C[C@@H](F)CN1S(=O)(=O)c1ccc(F)cc1] | 0.224 |
| 118 | 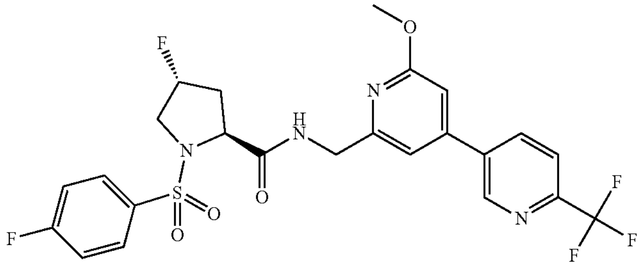 [SMILES: COc1cc(-c2ccc(C(F)(F)F)nc2)cc(CNC(=O)[C@@H]2C[C@@H](F)CN2S(=O)(=O)c2ccc(F)cc2)n1] | 0.037 |
| 119 | 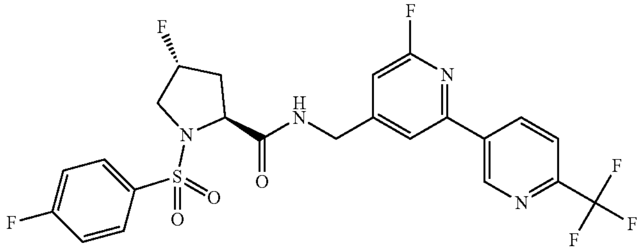 [SMILES: O=C(NCc1cc(F)nc(-c2ccc(C(F)(F)F)nc2)c1)[C@@H]1C[C@@H](F)CN1S(=O)(=O)c1ccc(F)cc1] | 0.052 |
| 120 | 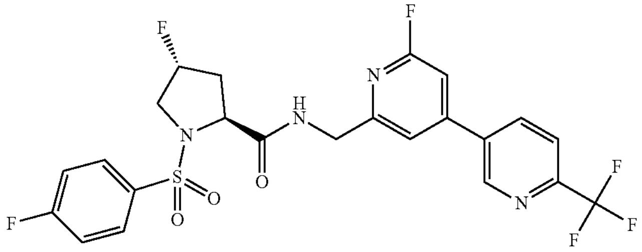 [SMILES: O=C(NCc1cc(-c2ccc(C(F)(F)F)nc2)cc(F)n1)[C@@H]1C[C@@H](F)CN1S(=O)(=O)c1ccc(F)cc1] | 0.049 |

TABLE 5-continued
| IC$_{50}$ Determinations of Exemplified Compounds. | | |
|---|---|---|
| Example Number | Structure | hTRPA1 AUC IC$_{50}$ (μM) |
| 121 | 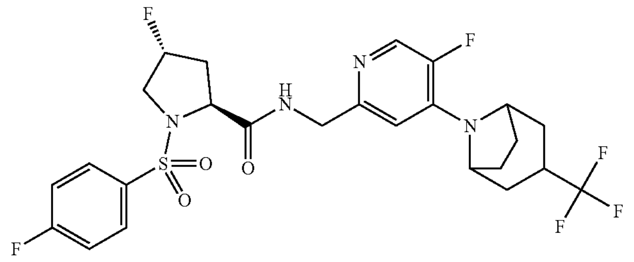 [SMILES: O=C(NCc1cc(N2C3CCC2CC(C(F)(F)F)C3)c(F)cn1)[C@@H]1C[C@@H](F)CN1S(=O)(=O)c1ccc(F)cc1] | 0.741 |
| 122 | 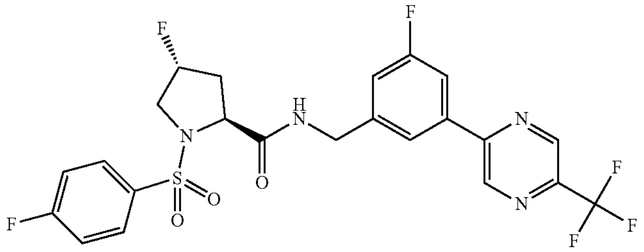 [SMILES: O=C(NCc1cc(F)cc(-c2cnc(C(F)(F)F)cn2)c1)[C@@H]1C[C@@H](F)CN1S(=O)(=O)c1ccc(F)cc1] | 0.014 |
| 123 | 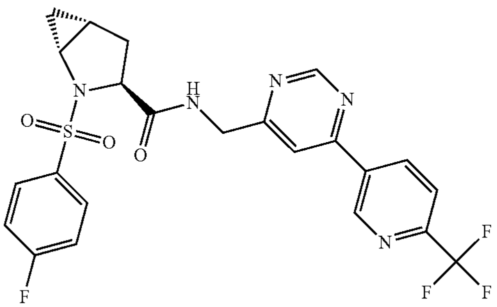 [SMILES: O=C(NCc1cc(-c2ccc(C(F)(F)F)nc2)ncn1)[C@@H]1C[C@H]2C[C@H]2N1S(=O)(=O)c1ccc(F)cc1] | 0.156 |
| 124 | 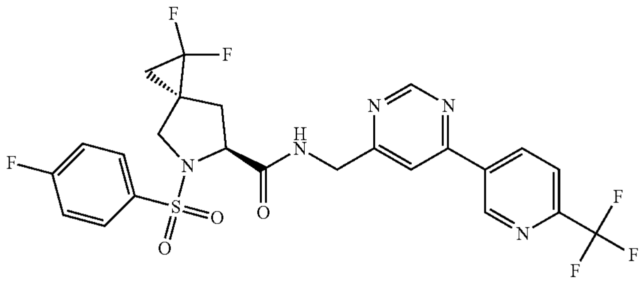 [SMILES: O=C(NCc1cc(-c2ccc(C(F)(F)F)nc2)ncn1)[C@@H]1C[C@]2(CN1S(=O)(=O)c1ccc(F)cc1)CC2(F)F] | 0.113 |
| 125 | 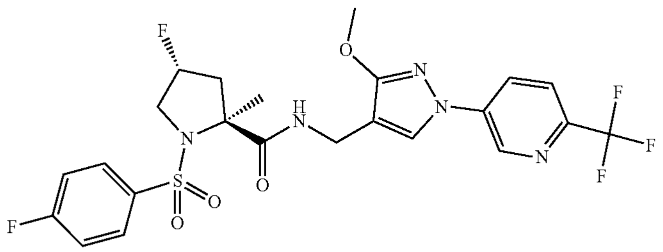 [SMILES: COc1nn(-c2ccc(C(F)(F)F)nc2)cc1CNC(=O)[C@]1(C)C[C@@H](F)CN1S(=O)(=O)c1ccc(F)cc1] | 0.009 |

TABLE 5-continued
| IC$_{50}$ Determinations of Exemplified Compounds. | | |
|---|---|---|
| Example Number | Structure | hTRPA1 AUC IC$_{50}$ (μM) |
| 126 | 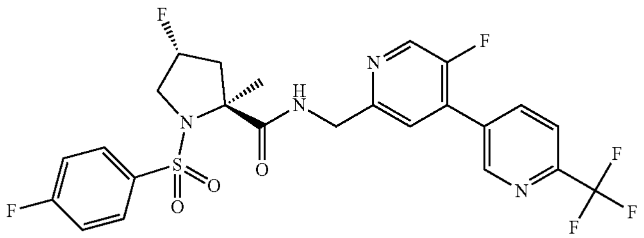 [SMILES: C[C@@]1(C(=O)NCc2cc(-c3ccc(C(F)(F)F)nc3)c(F)cn2)C[C@@H](F)CN1S(=O)(=O)c1ccc(F)cc1] | 0.025 |
| 127 | 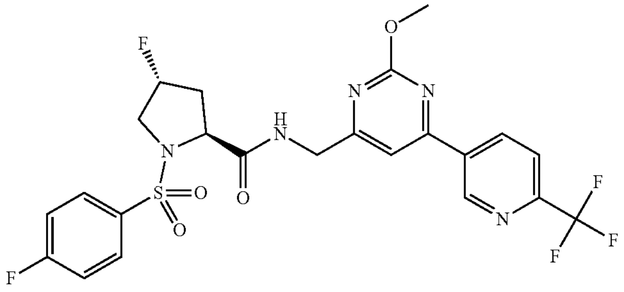 [SMILES: COc1nc(CNC(=O)[C@@H]2C[C@@H](F)CN2S(=O)(=O)c2ccc(F)cc2)cc(-c2ccc(C(F)(F)F)nc2)n1] | 0.097 |
| 128 | 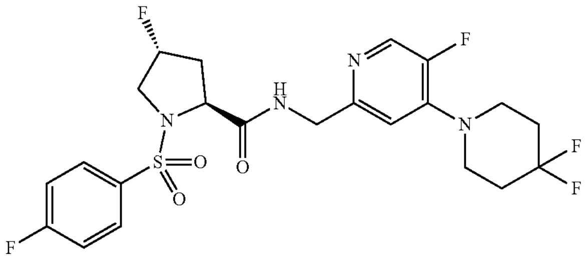 [SMILES: O=C(NCc1cc(N2CCC(F)(F)CC2)c(F)cn1)[C@@H]1C[C@@H](F)CN1S(=O)(=O)c1ccc(F)cc1] | 0.404 |
| 129 | 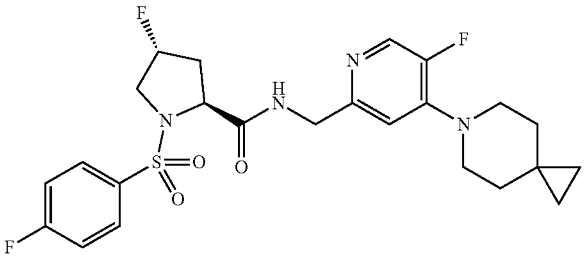 [SMILES: O=C(NCc1cc(N2CCC3(CC2)CC3)c(F)cn1)[C@@H]1C[C@@H](F)CN1S(=O)(=O)c1ccc(F)cc1] | 0.099 |
| 130 | 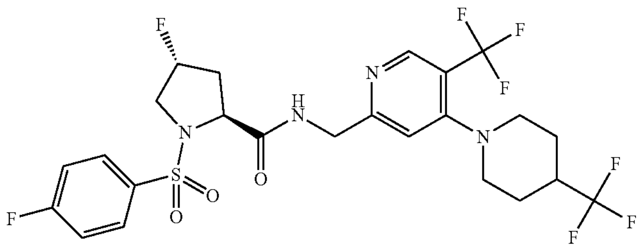 [SMILES: O=C(NCc1cc(N2CCC(C(F)(F)F)CC2)c(C(F)(F)F)cn1)[C@@H]1C[C@@H](F)CN1S(=O)(=O)c1ccc(F)cc1] | 0.052 |

TABLE 5-continued
IC$_{50}$ Determinations of Exemplified Compounds.
| Example Number | Structure | hTRPA1 AUC IC$_{50}$ (μM) |
|---|---|---|
| 131 | 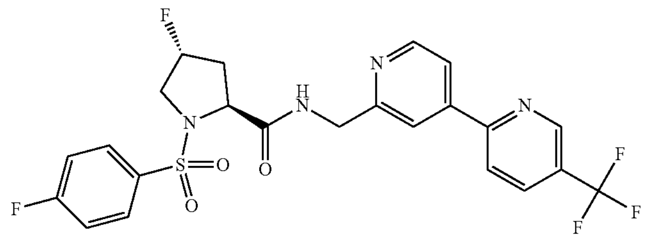 [SMILES: O=C(NCc1cc(-c2ccc(C(F)(F)F)cn2)ccn1)[C@@H]1C[C@@H](F)CN1S(=O)(=O)c1ccc(F)cc1] | 0.102 |
| 132 | 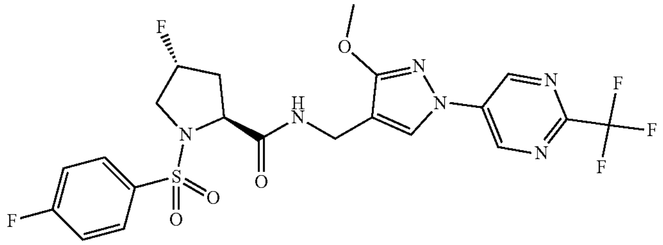 [SMILES: COc1nn(-c2cnc(C(F)(F)F)nc2)cc1CNC(=O)[C@@H]1C[C@@H](F)CN1S(=O)(=O)c1ccc(F)cc1] | 0.126 |
| 133 | 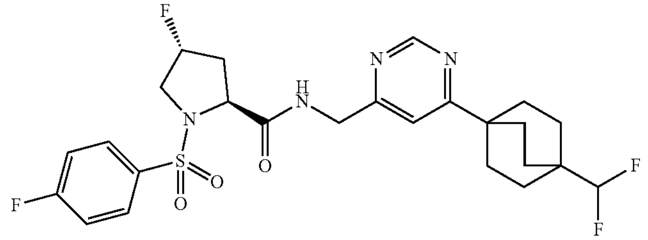 [SMILES: O=C(NCc1cc(C23CCC(C(F)F)(CC2)CC3)ncn1)[C@@H]1C[C@@H](F)CN1S(=O)(=O)c1ccc(F)cc1] | 0.059 |
| 134 | 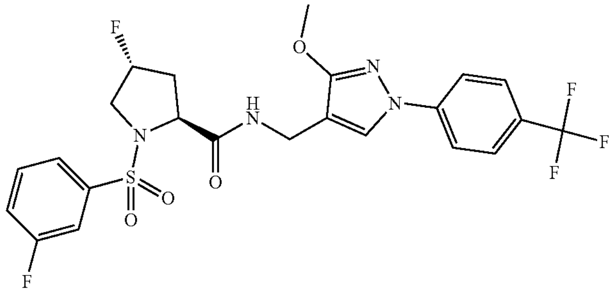 [SMILES: COc1nn(-c2ccc(C(F)(F)F)cc2)cc1CNC(=O)[C@@H]1C[C@@H](F)CN1S(=O)(=O)c1cccc(F)c1] | 0.023 |
| 135 | 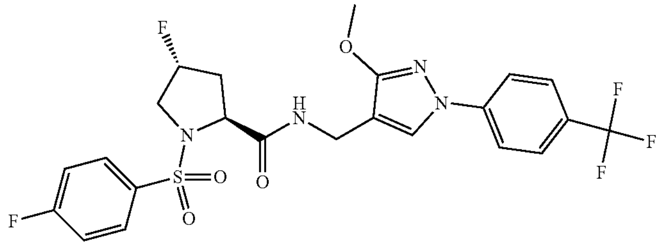 [SMILES: COc1nn(-c2ccc(C(F)(F)F)cc2)cc1CNC(=O)[C@@H]1C[C@@H](F)CN1S(=O)(=O)c1ccc(F)cc1] | 0.011 |
| 136 | 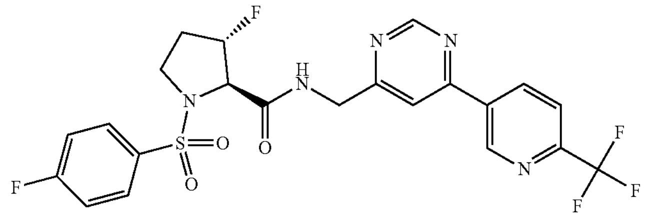 [SMILES: O=C(NCc1cc(-c2ccc(C(F)(F)F)nc2)ncn1)[C@@H]1[C@@H](F)CCN1S(=O)(=O)c1ccc(F)cc1] | 0.021 |

TABLE 5-continued
| Example Number | Structure | hTRPA1 AUC $IC_{50}$ (μM) |
| --- | --- | --- |
| | $IC_{50}$ Determinations of Exemplified Compounds. | |
| 137 | 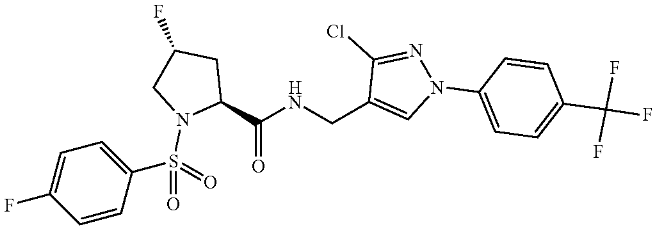 [SMILES: O=C(NCc1cn(-c2ccc(C(F)(F)F)cc2)nc1Cl)[C@@H]1C[C@@H](F)CN1S(=O)(=O)c1ccc(F)cc1] | 0.078 |
| 138 | 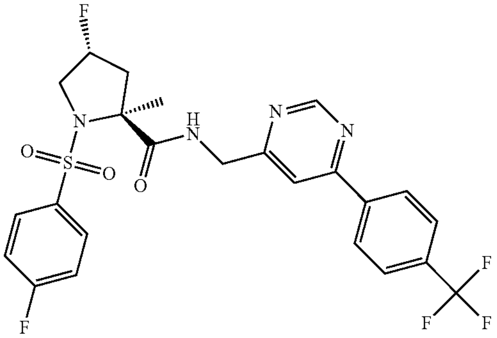 [SMILES: C[C@@]1(C(=O)NCc2cc(-c3ccc(C(F)(F)F)cc3)ncn2)C[C@@H](F)CN1S(=O)(=O)c1ccc(F)cc1] | 0.025 |
| 139 | 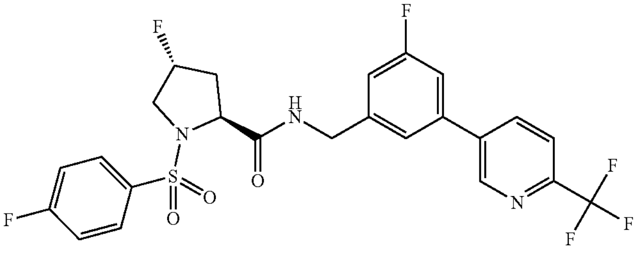 | 0.016 |
| 140 | 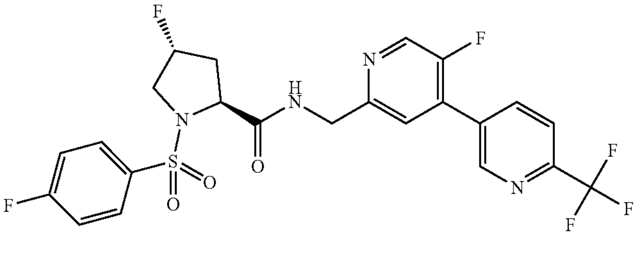 [SMILES: O=C(NCc1cc(-c2ccc(C(F)(F)F)nc2)c(F)cn1)[C@@H]1C[C@@H](F)CN1S(=O)(=O)c1ccc(F)cc1] | 0.020 |
| 141 | 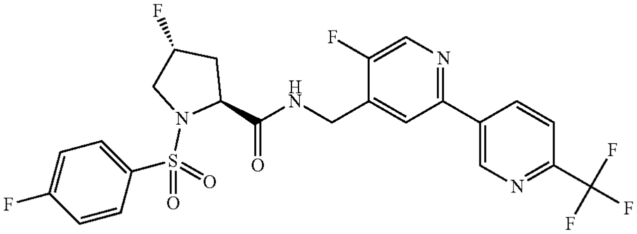 [SMILES: O=C(NCc1cc(-c2ccc(C(F)(F)F)nc2)ncc1F)[C@@H]1C[C@@H](F)CN1S(=O)(=O)c1ccc(F)cc1] | 0.068 |

TABLE 5-continued
$IC_{50}$ Determinations of Exemplified Compounds.
| Example Number | Structure | hTRPA1 AUC $IC_{50}$ (μM) |
|---|---|---|
| 142 | 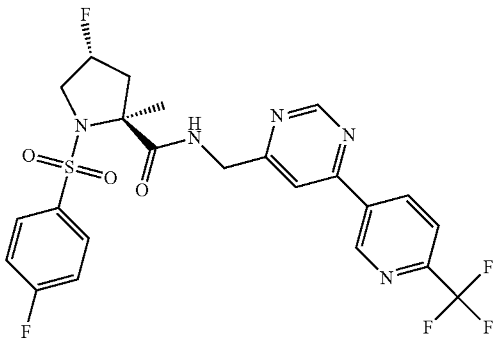 [SMILES: C[C@@]1(C(=O)NCc2cc(-c3ccc(C(F)(F)F)nc3)ncn2)C[C@@H](F)CN1S(=O)(=O)c1ccc(F)cc1] | 0.092 |
| 143 | 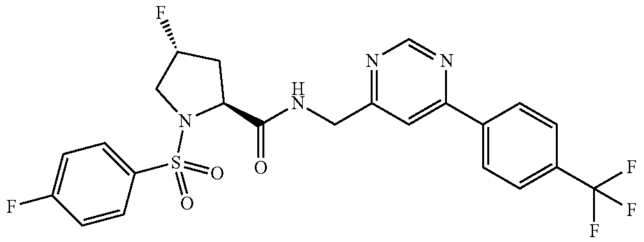 [SMILES: O=C(NCc1cc(-c2ccc(C(F)(F)F)cc2)ncn1)[C@@H]1C[C@@H](F)CN1S(=O)(=O)c1ccc(F)cc1] | 0.015 |
| 144 | 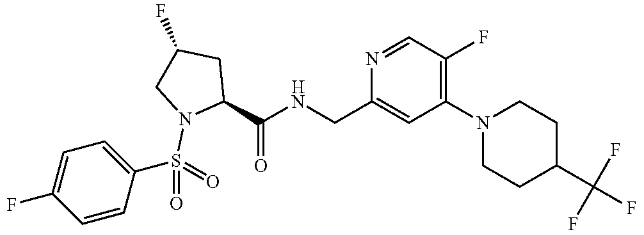 [SMILES: O=C(NCc1cc(N2CCC(C(F)(F)F)CC2)c(F)cn1)[C@@H]1C[C@@H](F)CN1S(=O)(=O)c1ccc(F)cc1] | 0.056 |
| 145 | 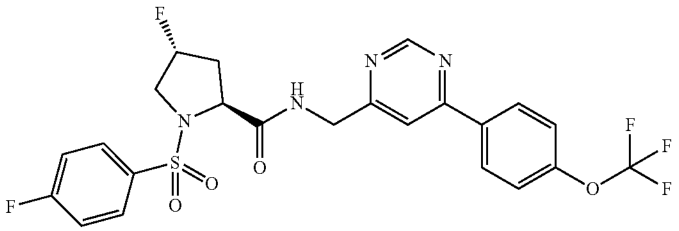 [SMILES: O=C(NCc1cc(-c2ccc(OC(F)(F)F)cc2)ncn1)[C@@H]1C[C@@H](F)CN1S(=O)(=O)c1ccc(F)cc1] | 0.021 |
| 146 | 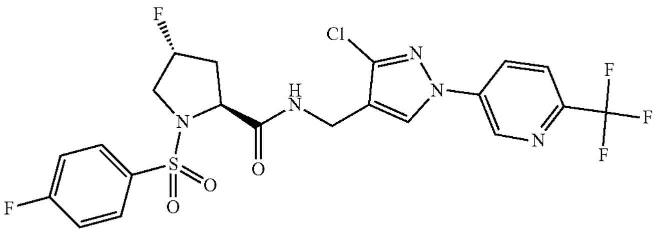 [SMILES: O=C(NCc1cn(-c2ccc(C(F)(F)F)nc2)nc1Cl)[C@@H]1C[C@@H](F)CN1S(=O)(=O)c1ccc(F)cc1] | 0.078 |

TABLE 5-continued
| IC$_{50}$ Determinations of Exemplified Compounds. | | |
|---|---|---|
| Example Number | Structure | hTRPA1 AUC IC$_{50}$ (μM) |
| 147 | 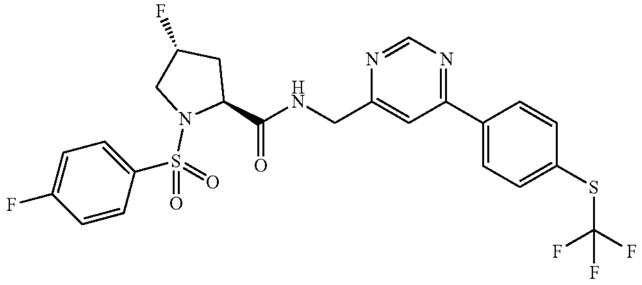 [SMILES: O=C(NCc1cc(-c2ccc(SC(F)(F)F)cc2)ncn1)[C@@H]1C[C@@H](F)CN1S(=O)(=O)c1ccc(F)cc1] | 0.049 |
| 148 | 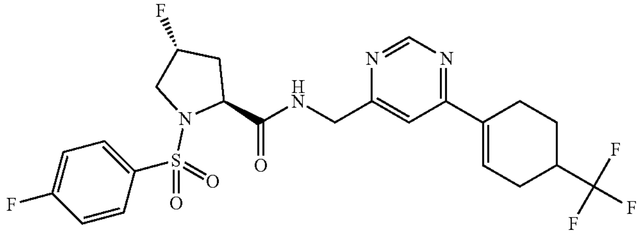 [SMILES: O=C(NCc1cc(C2=CCC(C(F)(F)F)CC2)ncn1)[C@@H]1C[C@@H](F)CN1S(=O)(=O)c1ccc(F)cc1] | 0.046 |
| 149 | 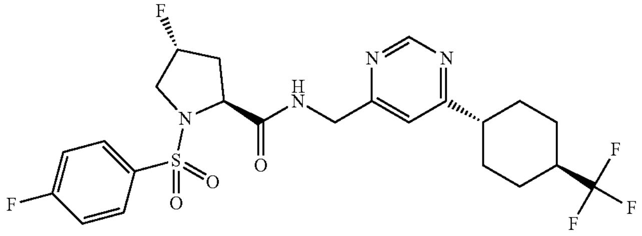 [SMILES: O=C(NCc1cc([C@H]2CC[C@H](C(F)(F)F)CC2)ncn1)[C@@H]1C[C@@H](F)CN1S(=O)(=O)c1ccc(F)cc1] | 0.034 |
| 150 | 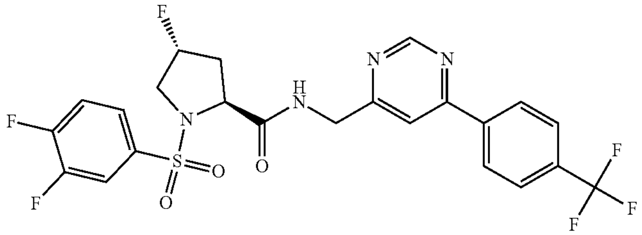 [SMILES: O=C(NCc1cc(-c2ccc(C(F)(F)F)cc2)ncn1)[C@@H]1C[C@@H](F)CN1S(=O)(=O)c1ccc(F)c(F)c1] | 0.046 |
| 151 | 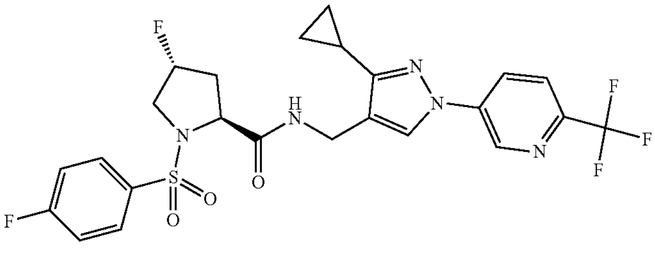 [SMILES: O=C(NCc1cn(-c2ccc(C(F)(F)F)nc2)nc1C1CC1)[C@@H]1C[C@@H](F)CN1S(=O)(=O)c1ccc(F)cc1] | 0.161 |
| 152 | 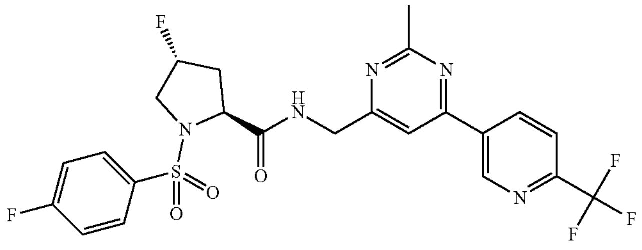 [SMILES: Cc1nc(CNC(=O)[C@@H]2C[C@@H](F)CN2S(=O)(=O)c2ccc(F)cc2)cc(-c2ccc(C(F)(F)F)nc2)n1] | 0.163 |

TABLE 5-continued
| Example Number | Structure | hTRPA1 AUC $IC_{50}$ (μM) |
|---|---|---|
| | $IC_{50}$ Determinations of Exemplified Compounds. | |
| 153 | 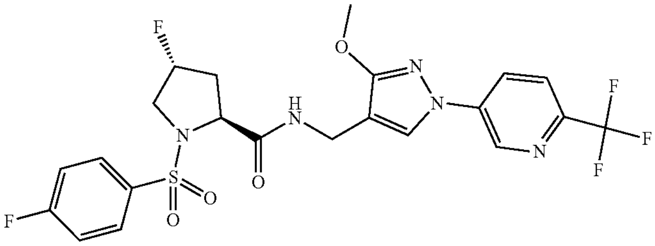 [SMILES: COc1nn(-c2ccc(C(F)(F)F)nc2)cc1CNC(=O)[C@@H]1C[C@@H](F)CN1S(=O)(=O)c1ccc(F)cc1] | 0.068 |
| 154 | 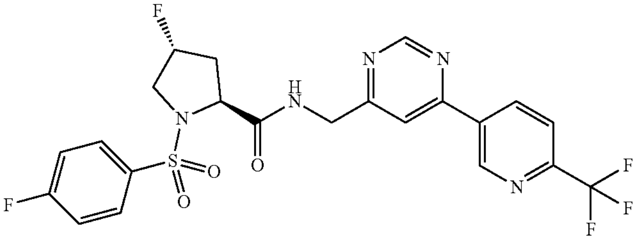 [SMILES: O=C(NCc1cc(-c2ccc(C(F)(F)F)nc2)ncn1)[C@@H]1C[C@@H](F)CN1S(=O)(=O)c1ccc(F)cc1] | 0.097 |
| 155 | 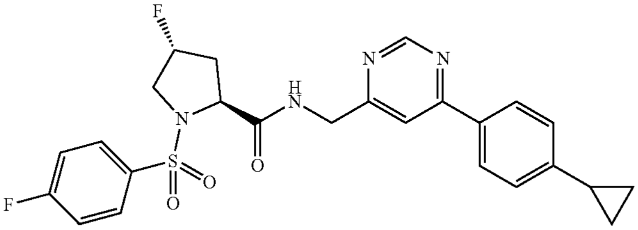 [SMILES: O=C(NCc1cc(-c2ccc(C3CC3)cc2)ncn1)[C@@H]1C[C@@H](F)CN1S(=O)(=O)c1ccc(F)cc1] | 0.134 |
| 156 | 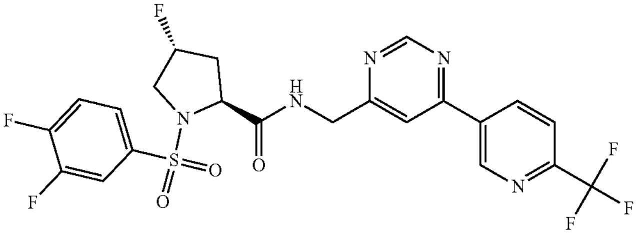 | 0.109 |
| 157 | 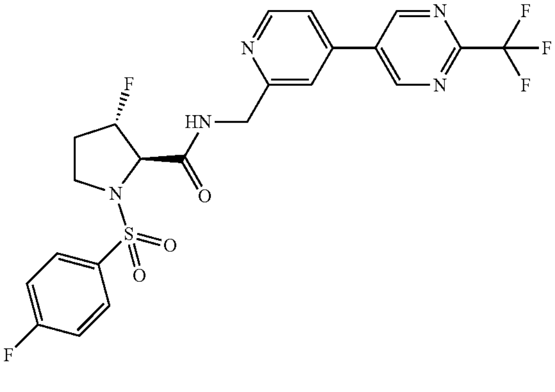 [SMILES: O=C(NCc1cc(-c2cnc(C(F)(F)F)nc2)ccn1)[C@@H]1[C@@H](F)CCN1S(=O)(=O)c1ccc(F)cc1] | 0.103 |

TABLE 5-continued
| IC$_{50}$ Determinations of Exemplified Compounds. | | |
|---|---|---|
| Example Number | Structure | hTRPA1 AUC IC$_{50}$ (μM) |
| 158 | 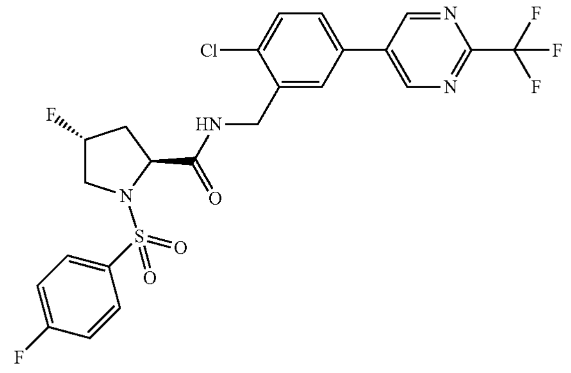 [SMILES: O=C(NCc1cc(-c2cnc(C(F)(F)F)nc2)ccc1Cl)[C@@H]1C[C@@H](F)CN1S(=O)(=O)c1ccc(F)cc1] | 0.004 |
| 159 | 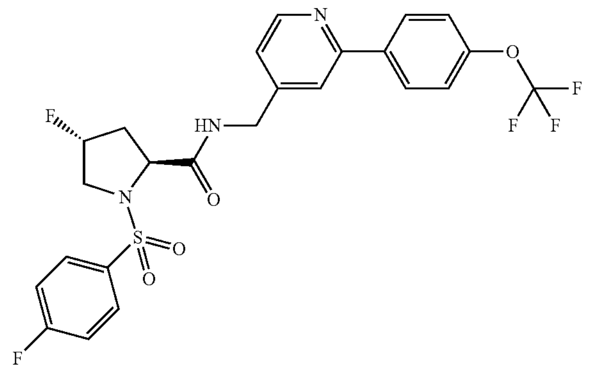 [SMILES: O=C(NCc1ccnc(-c2ccc(OC(F)(F)F)cc2)c1)[C@@H]1C[C@@H](F)CN1S(=O)(=O)c1ccc(F)cc1] | 0.018 |
| 160 | 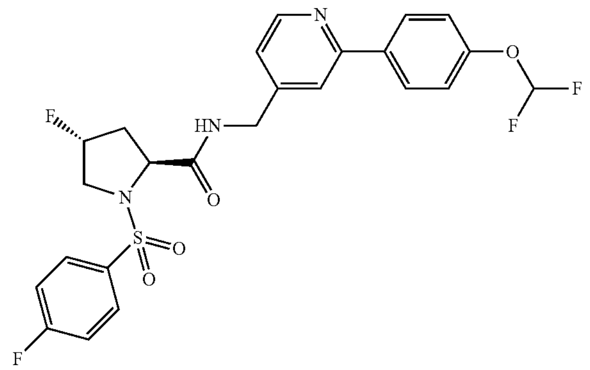 [SMILES: O=C(NCc1ccnc(-c2ccc(OC(F)F)cc2)c1)[C@@H]1C[C@@H](F)CN1S(=O)(=O)c1ccc(F)cc1] | 0.086 |
| 161 | 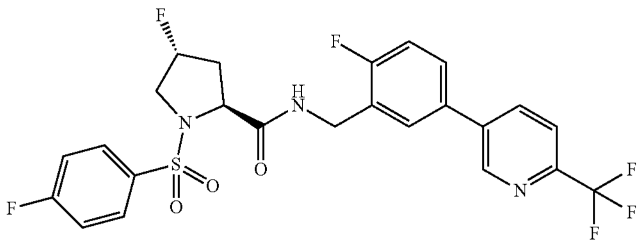 [SMILES: O=C(NCc1cc(-c2ccc(C(F)(F)F)nc2)ccc1F)[C@@H]1C[C@@H](F)CN1S(=O)(=O)c1ccc(F)cc1] | 0.009 |

TABLE 5-continued
| Example Number | Structure | hTRPA1 AUC $IC_{50}$ (μM) |
| --- | --- | --- |
| IC50 Determinations of Exemplified Compounds. | | |
| 162 | 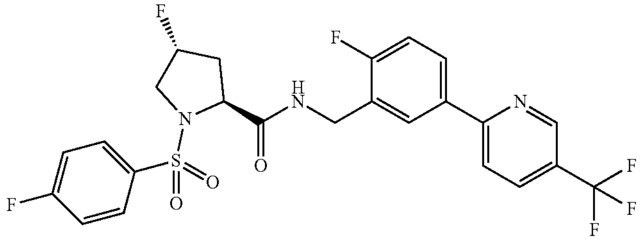 [SMILES: O=C(NCc1cc(-c2ccc(C(F)(F)F)cn2)ccc1F)[C@@H]1C[C@@H](F)CN1S(=O)(=O)c1ccc(F)cc1] | 0.011 |
| 163 | 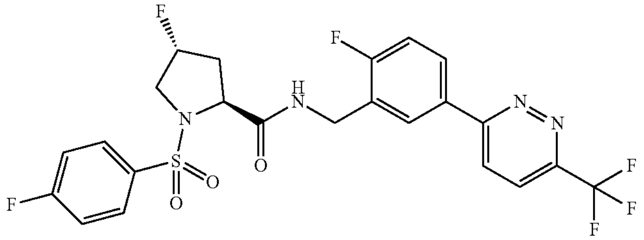 [SMILES: O=C(NCc1cc(-c2ccc(C(F)(F)F)nn2)ccc1F)[C@@H]1C[C@@H](F)CN1S(=O)(=O)c1ccc(F)cc1] | 0.043 |
| 164 | 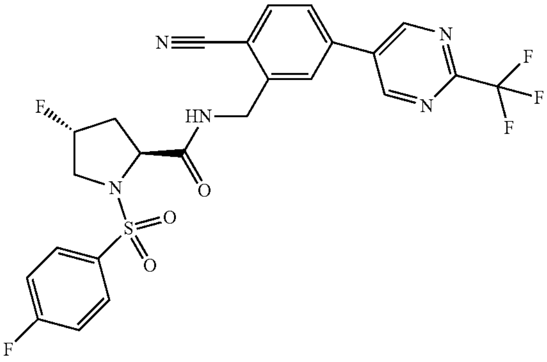 [SMILES: N#Cc1ccc(-c2cnc(C(F)(F)F)nc2)cc1CNC(=O)[C@@H]1C[C@@H](F)CN1S(=O)(=O)c1ccc(F)cc1] | 0.032 |
| 165 | 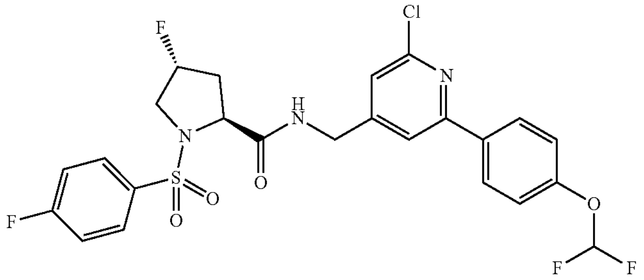 [SMILES: O=C(NCc1cc(Cl)nc(-c2ccc(OC(F)F)cc2)c1)[C@@H]1C[C@@H](F)CN1S(=O)(=O)c1ccc(F)cc1] | 0.066 |
| 166 | 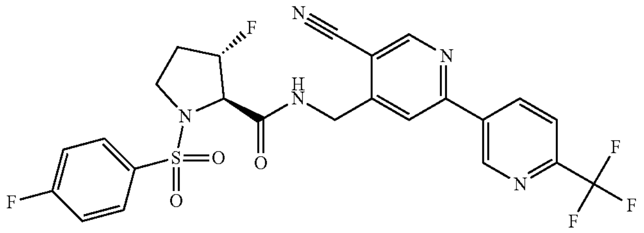 [SMILES: N#Cc1cnc(-c2ccc(C(F)(F)F)nc2)cc1CNC(=O)[C@@H]1[C@@H](F)CCN1S(=O)(=O)c1ccc(F)cc1] | 0.013 |

TABLE 5-continued
| IC$_{50}$ Determinations of Exemplified Compounds. | | |
|---|---|---|
| Example Number | Structure | hTRPA1 AUC IC$_{50}$ (μM) |
| 167 | 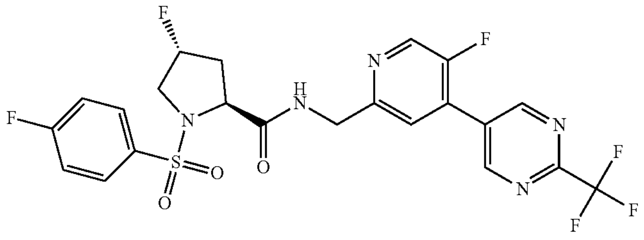 [SMILES: O=C(NCc1cc(-c2cnc(C(F)(F)F)nc2)c(F)cn1)[C@@H]1C[C@@H](F)CN1S(=O)(=O)c1ccc(F)cc1] | 0.038 |
| 168 | 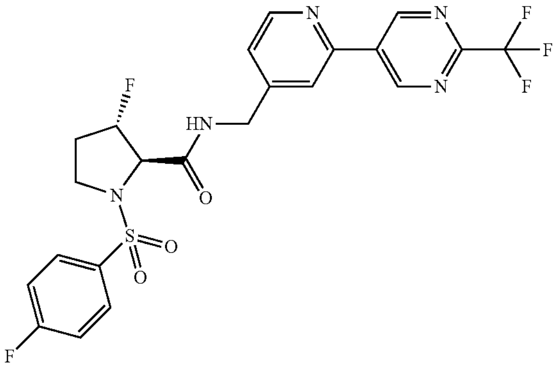 [SMILES: O=C(NCc1ccnc(-c2cnc(C(F)(F)F)nc2)c1)[C@@H]1[C@@H](F)CCN1S(=O)(=O)c1ccc(F)cc1] | 0.075 |
| 169 | 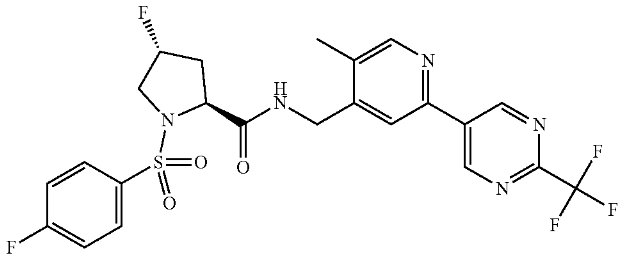 [SMILES: Cc1cnc(-c2cnc(C(F)(F)F)nc2)cc1CNC(=O)[C@@H]1C[C@@H](F)CN1S(=O)(=O)c1ccc(F)cc1] | 0.116 |
| 170 | 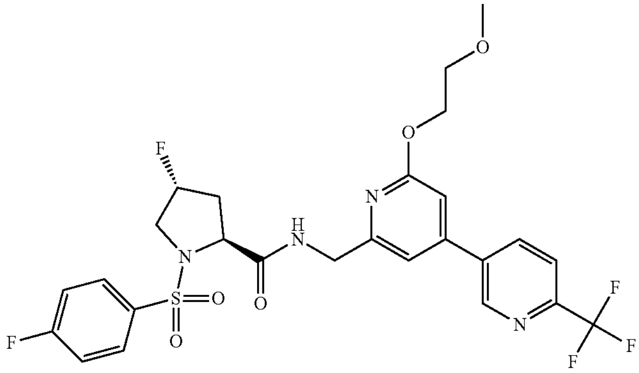 [SMILES: COCCOc1cc(-c2ccc(C(F)(F)F)nc2)cc(CNC(=O)[C@@H]2C[C@@H](F)CN2S(=O)(=O)c2ccc(F)cc2)n1] | 0.089 |

TABLE 5-continued
| Example Number | Structure | hTRPA1 AUC $IC_{50}$ (μM) |
|---|---|---|
| $IC_{50}$ Determinations of Exemplified Compounds. | | |
| 171 | 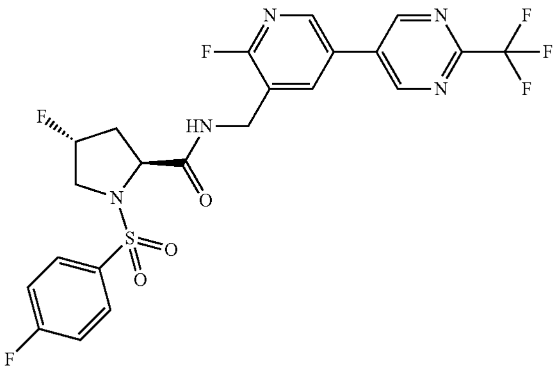 [SMILES: O=C(NCc1cc(-c2cnc(C(F)(F)F)nc2)cnc1F)[C@@H]1C[C@@H](F)CN1S(=O)(=O)c1ccc(F)cc1] | 0.211 |
| 172 | 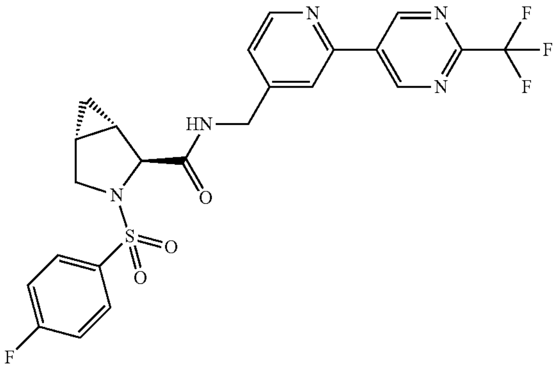 [SMILES: O=C(NCc1ccnc(-c2cnc(C(F)(F)F)nc2)c1)[C@@H]1[C@H]2C[C@H]2CN1S(=O)(=O)c1ccc(F)cc1] | 0.038 |
| 173 | 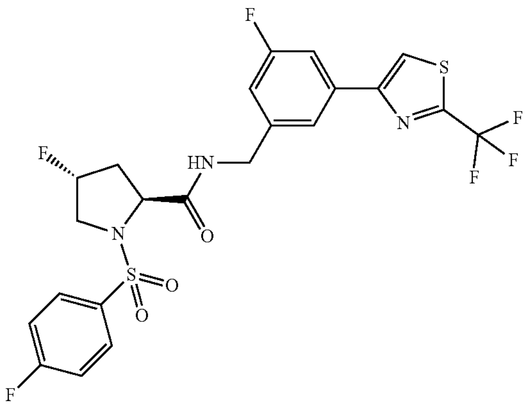 [SMILES: O=C(NCc1cc(F)cc(-c2csc(C(F)(F)F)n2)c1)[C@@H]1C[C@@H](F)CN1S(=O)(=O)c1ccc(F)cc1] | 0.111 |

TABLE 5-continued
IC$_{50}$ Determinations of Exemplified Compounds.
| Example Number | Structure | hTRPA1 AUC IC$_{50}$ (μM) |
|---|---|---|
| 174 | 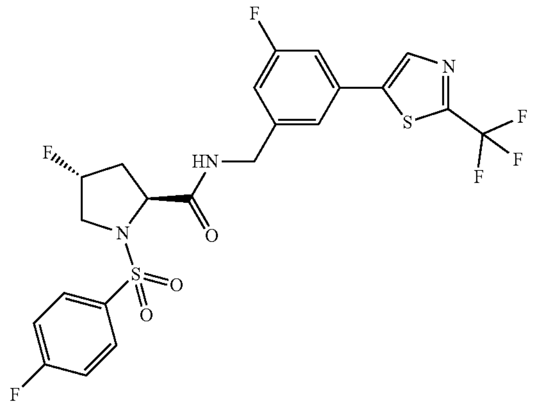 [SMILES: O=C(NCc1cc(F)cc(-c2cnc(C(F)(F)F)s2)c1)[C@@H]1C[C@@H](F)CN1S(=O)(=O)c1ccc(F)cc1] | 0.012 |
| 175 | 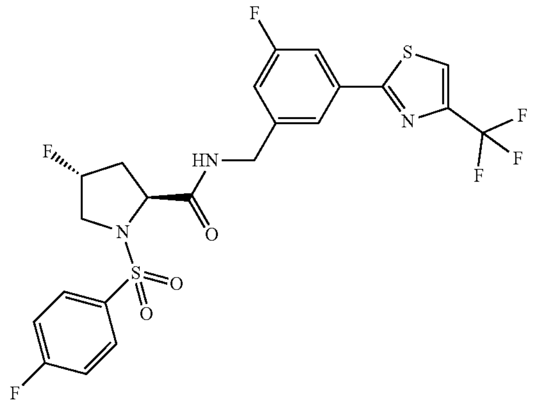 [SMILES: O=C(NCc1cc(F)cc(-c2nc(C(F)(F)F)cs2)c1)[C@@H]1C[C@@H](F)CN1S(=O)(=O)c1ccc(F)cc1] | 0.086 |
| 176 | 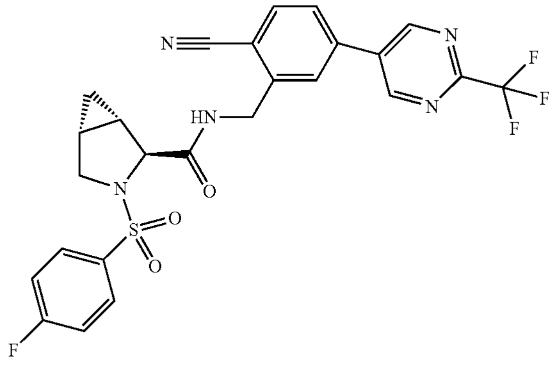 [SMILES: N#Cc1ccc(-c2cnc(C(F)(F)F)nc2)cc1CNC(=O)[C@@H]1[C@H]2C[C@H]2CN1S(=O)(=O)c1ccc(F)cc1] | 0.008 |
| 177 | 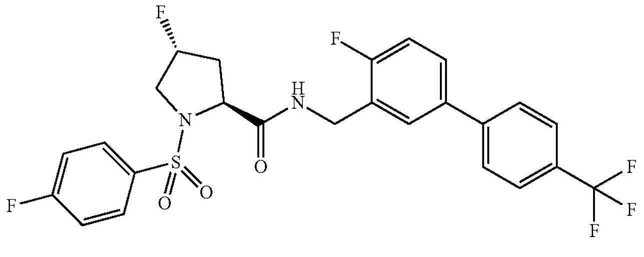 [SMILES: O=C(NCc1cc(-c2ccc(C(F)(F)F)cc2)ccc1F)[C@@H]1C[C@@H](F)CN1S(=O)(=O)c1ccc(F)cc1] | 0.005 |

TABLE 5-continued
| IC$_{50}$ Determinations of Exemplified Compounds. | | |
|---|---|---|
| Example Number | Structure | hTRPA1 AUC IC$_{50}$ (μM) |
| 178 | 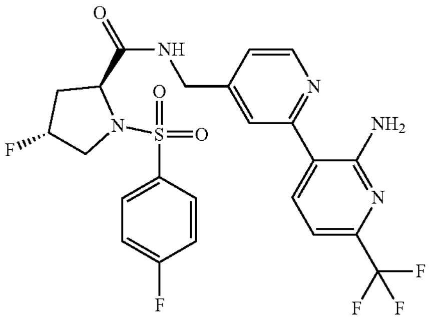 [SMILES: Nc1nc(C(F)(F)F)ccc1-c1cc(CNC(=O)[C@@H]2C[C@@H](F)CN2S(=O)(=O)c2ccc(F)cc2)ccn1] | 0.175 |
| 179 | 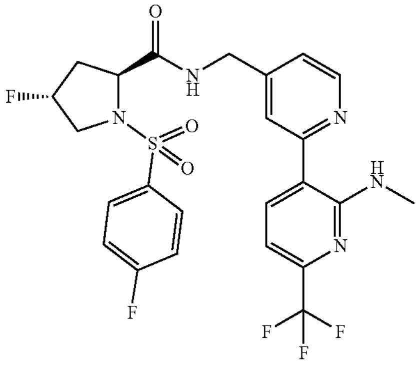 [SMILES: CNc1nc(C(F)(F)F)ccc1-c1cc(CNC(=O)[C@@H]2C[C@@H](F)CN2S(=O)(=O)c2ccc(F)cc2)ccn1] | 0.062 |
| 180 | 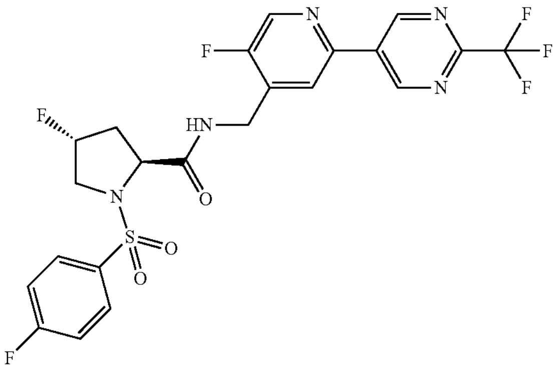 | 0.026 |
| 181 | 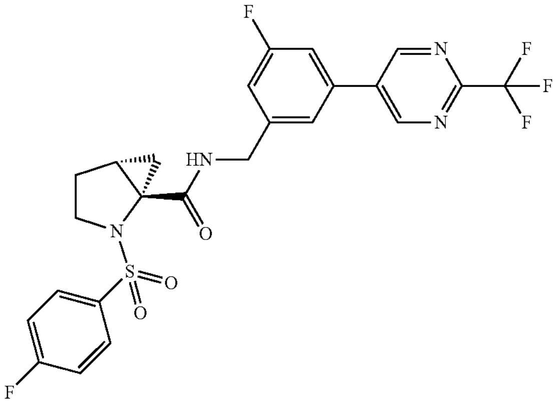 [SMILES: O=C(NCc1cc(F)cc(-c2cnc(C(F)(F)F)nc2)c1)[C@]12C[C@H]1CCN2S(=O)(=O)c1ccc(F)cc1] | 0.010 |

TABLE 5-continued
| Example Number | Structure | hTRPA1 AUC $IC_{50}$ (μM) |
|---|---|---|
| IC50 Determinations of Exemplified Compounds. | | |
| 182 | 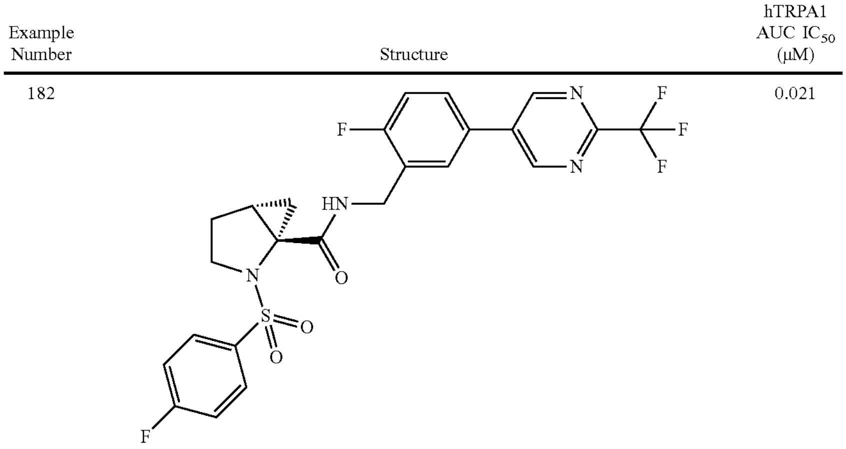 | 0.021 |
| 183 | 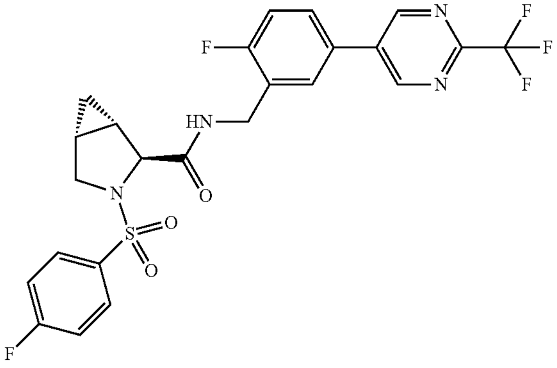 [SMILES: O=C(NCc1cc(-c2cnc(C(F)(F)F)nc2)ccc1F)[C@@H]1[C@H]2C[C@H]2CN1S(=O)(=O)c1ccc(F)cc1] | 0.003 |
| 184 | 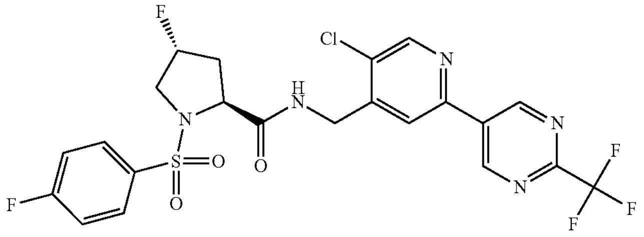 [SMILES: O=C(NCc1cc(-c2cnc(C(F)(F)F)nc2)ncc1Cl)[C@@H]1C[C@@H](F)CN1S(=O)(=O)c1ccc(F)cc1] | 0.010 |
| 185 | 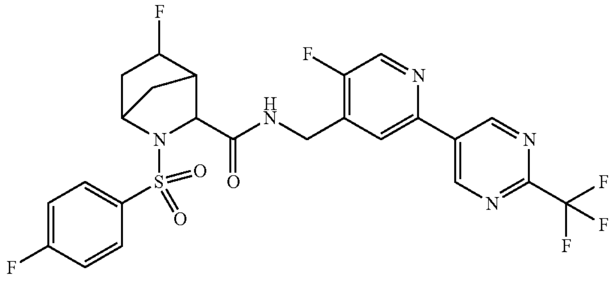 [SMILES: O=C(NCc1cc(-c2cnc(C(F)(F)F)nc2)ncc1F)C1C2CC(CC2F)N1S(=O)(=O)c1ccc(F)cc1] | 0.155 |
| 186 | Chiral 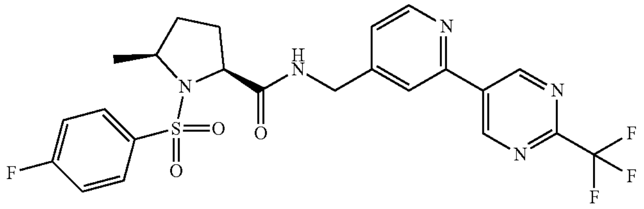 | 0.004 |

TABLE 5-continued
| IC$_{50}$ Determinations of Exemplified Compounds. | | |
|---|---|---|
| Example Number | Structure | hTRPA1 AUC IC$_{50}$ (μM) |
| 187 | 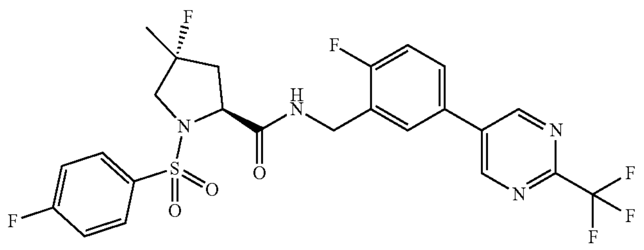 [SMILES: C[C@@]1(F)C[C@@H](C(=O)NCc2cc(-c3cnc(C(F)(F)F)nc3)ccc2F)N(S(=O)(=O)c2ccc(F)cc2)C1] | 0.006 |
| 188 | 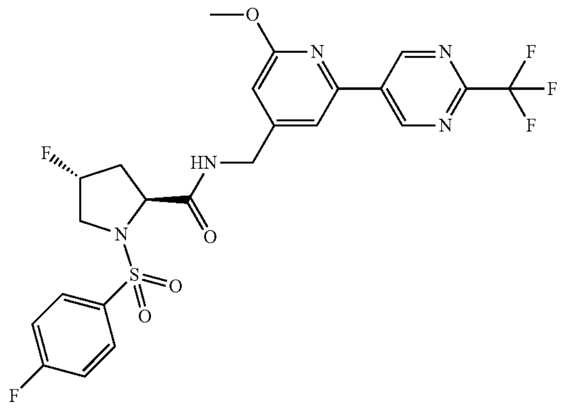 [SMILES: COc1cc(CNC(=O)[C@@H]2C[C@@H](F)CN2S(=O)(=O)c2ccc(F)cc2)cc(-c2cnc(C(F)(F)F)nc2)n1] | 0.008 |
| 189 | 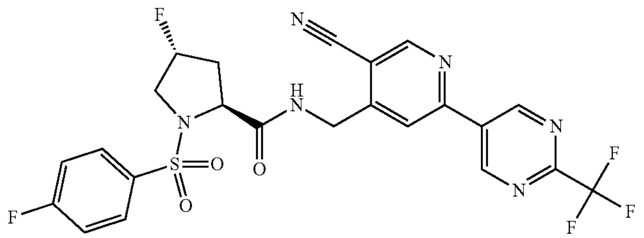 [SMILES: N#Cc1cnc(-c2cnc(C(F)(F)F)nc2)cc1CNC(=O)[C@@H]1C[C@@H](F)CN1S(=O)(=O)c1ccc(F)cc1] | 0.055 |
| 190 | 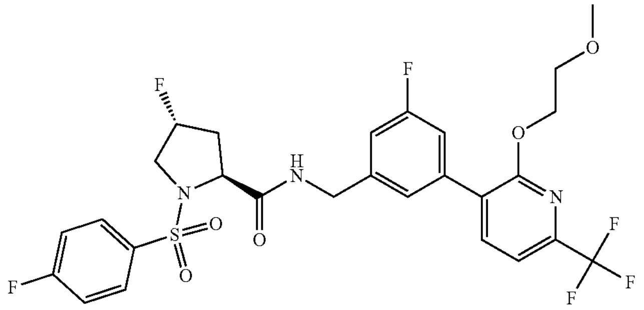 [SMILES: COCCOc1nc(C(F)(F)F)ccc1-c1cc(F)cc(CNC(=O)[C@@H]2C[C@@H](F)CN2S(=O)(=O)c2ccc(F)cc2)c1] | 0.052 |
| 191 | 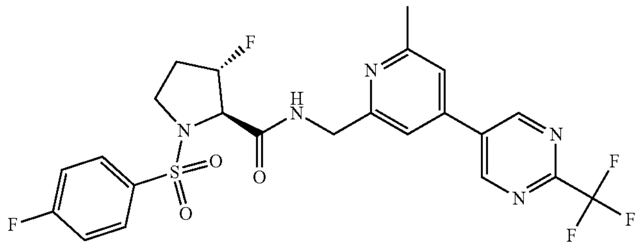 [SMILES: Cc1cc(-c2cnc(C(F)(F)F)nc2)cc(CNC(=O)[C@@H]2[C@@H](F)CCN2S(=O)(=O)c2ccc(F)cc2)n1] | 0.027 |

TABLE 5-continued
IC$_{50}$ Determinations of Exemplified Compounds.
| Example Number | Structure | hTRPA1 AUC IC$_{50}$ (μM) |
|---|---|---|
| 192 | 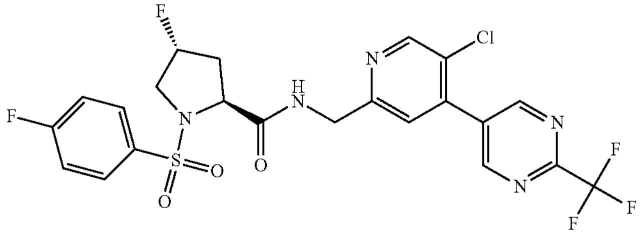 [SMILES: O=C(NCc1cc(-c2cnc(C(F)(F)F)nc2)c(Cl)cn1)[C@@H]1C[C@@H](F)CN1S(=O)(=O)c1ccc(F)cc1] | 0.042 |
| 193 | 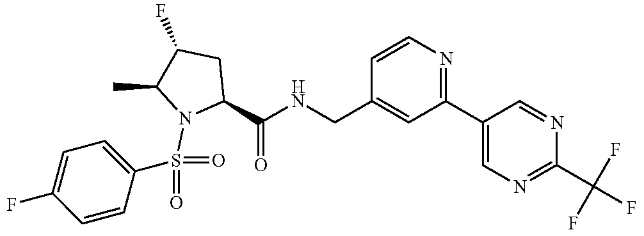 [SMILES: C[C@H]1[C@H](F)C[C@@H](C(=O)NCc2ccnc(-c3cnc(C(F)(F)F)nc3)c2)N1S(=O)(=O)c1ccc(F)cc1] | 0.015 |
| 194 | 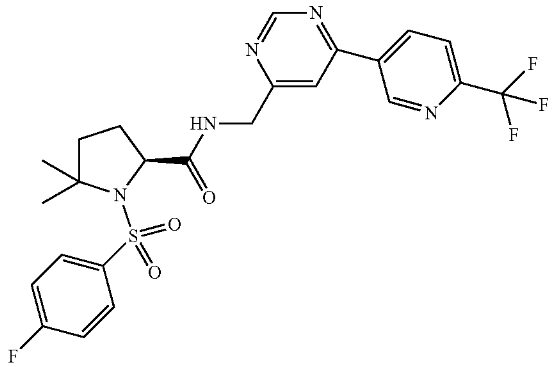 [SMILES: CC1(C)CC[C@@H](C(=O)NCc2cc(-c3ccc(C(F)(F)F)nc3)ncn2)N1S(=O)(=O)c1ccc(F)cc1] | 0.381 |
| 195 | 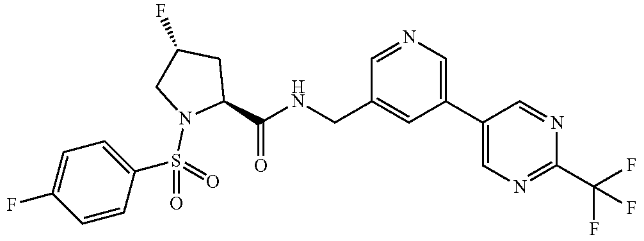 [SMILES: O=C(NCc1cncc(-c2cnc(C(F)(F)F)nc2)c1)[C@@H]1C[C@@H](F)CN1S(=O)(=O)c1ccc(F)cc1] | 0.795 |
| 196 | 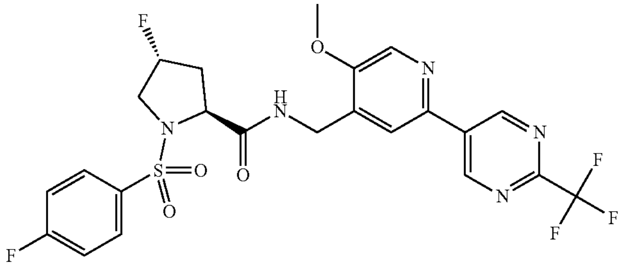 [SMILES: COc1cnc(-c2cnc(C(F)(F)F)nc2)cc1CNC(=O)[C@@H]1C[C@@H](F)CN1S(=O)(=O)c1ccc(F)cc1] | 0.134 |

TABLE 5-continued
| IC$_{50}$ Determinations of Exemplified Compounds. | | |
|---|---|---|
| Example Number | Structure | hTRPA1 AUC IC$_{50}$ (μM) |
| 197 | 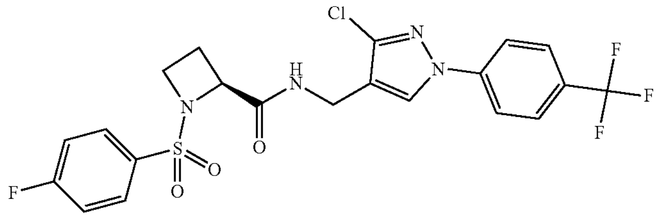 [SMILES: O=C(NCc1cn(-c2ccc(C(F)(F)F)cc2)nc1Cl)[C@@H]1CCN1S(=O)(=O)c1ccc(F)cc1] | 0.015 |
| 198 | 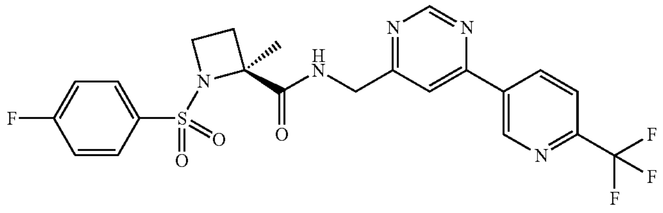 [SMILES: C[C@@]1(C(=O)NCc2cc(-c3ccc(C(F)(F)F)nc3)ncn2)CCN1S(=O)(=O)c1ccc(F)cc1] | 0.059 |
| 199 | 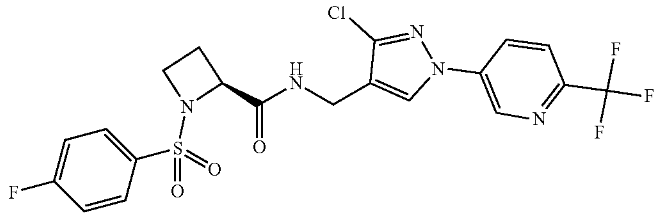 [SMILES: O=C(NCc1cn(-c2ccc(C(F)(F)F)nc2)nc1Cl)[C@@H]1CCN1S(=O)(=O)c1ccc(F)cc1] | 0.138 |
| 200 | 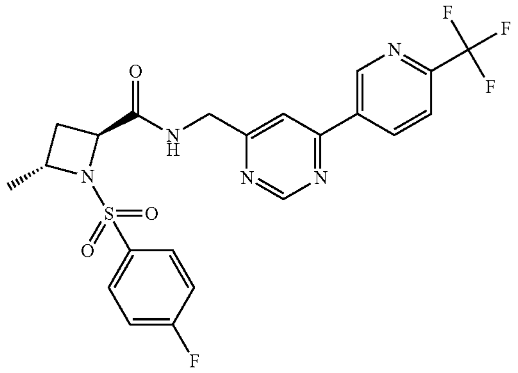 [SMILES: C[C@@H]1C[C@@H](C(=O)NCc2cc(-c3ccc(C(F)(F)F)nc3)ncn2)N1S(=O)(=O)c1ccc(F)cc1] | 0.333 |
| 201 | 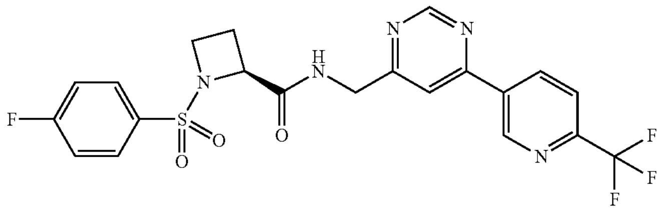 [SMILES: O=C(NCc1cc(-c2ccc(C(F)(F)F)nc2)ncn1)[C@@H]1CCN1S(=O)(=O)c1ccc(F)cc1] | 0.268 |

It is to be understood that the invention is not limited to the particular embodiments of the invention described above, as variations of the particular embodiments may be made and still fall within the scope of the appended claims. All documents cited to or relied upon herein are expressly incorporated by reference.
We claim:
1.
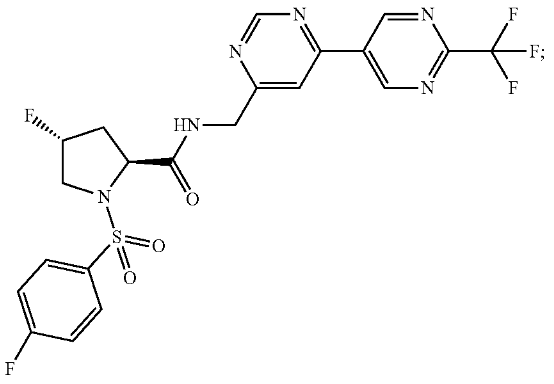
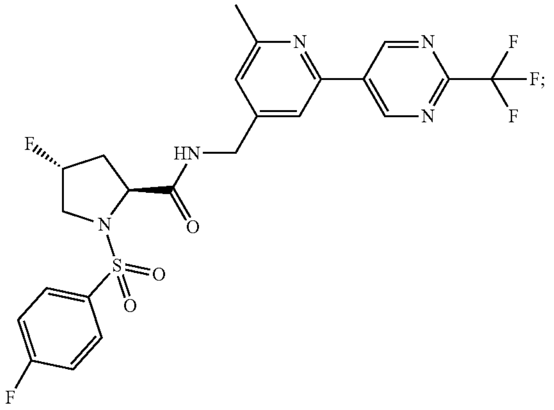
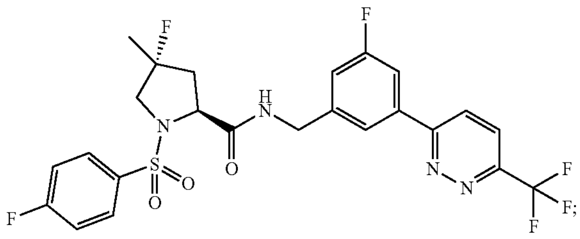
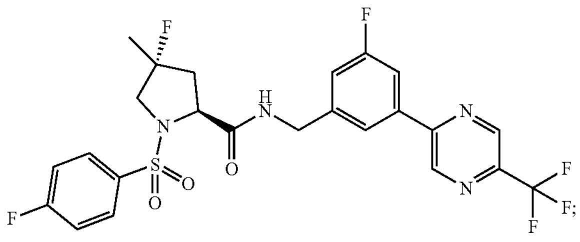
-continued
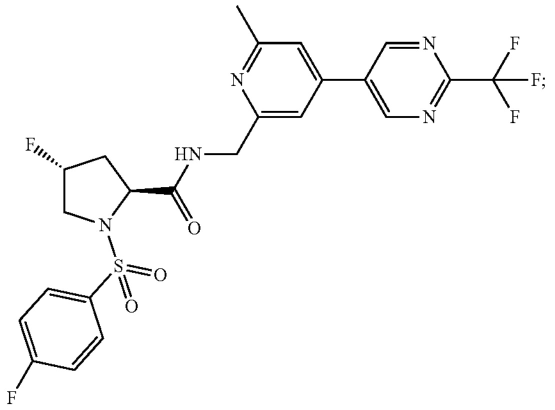
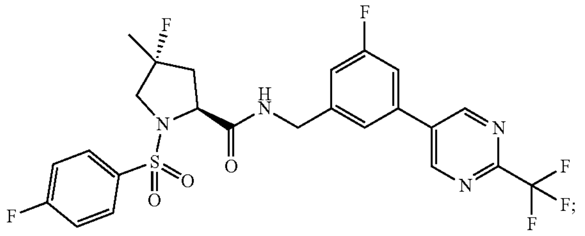
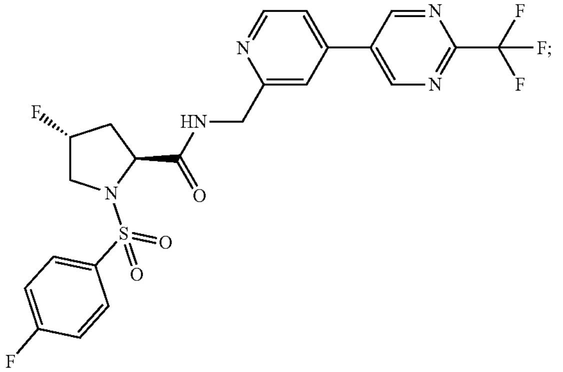
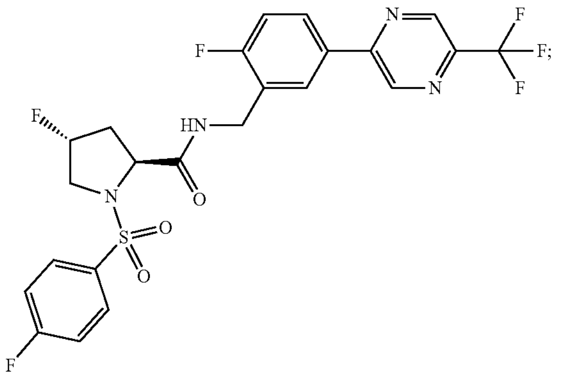

-continued
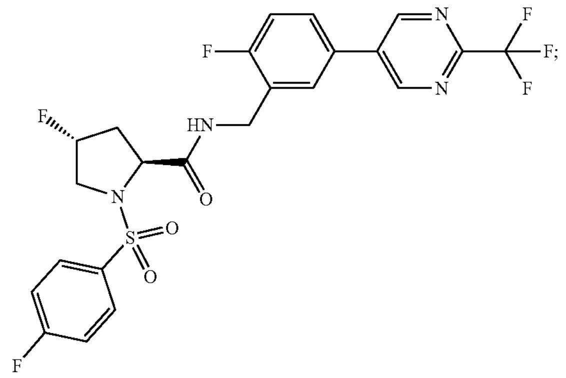
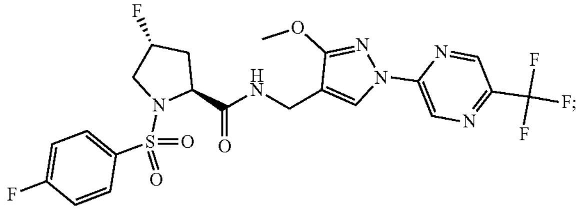
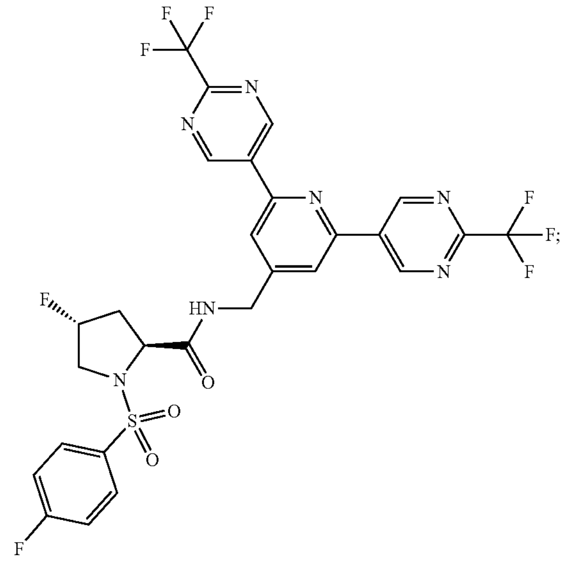
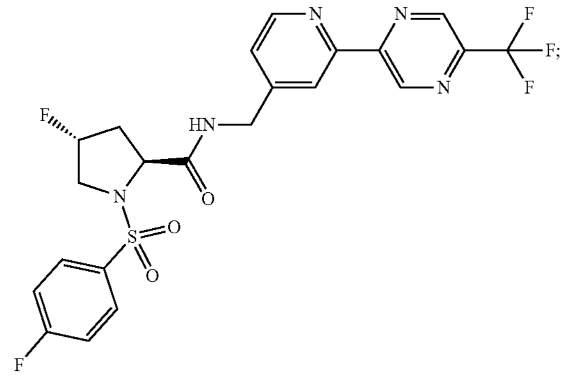
-continued
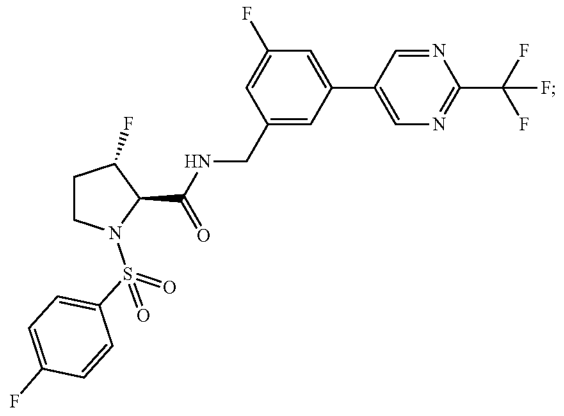
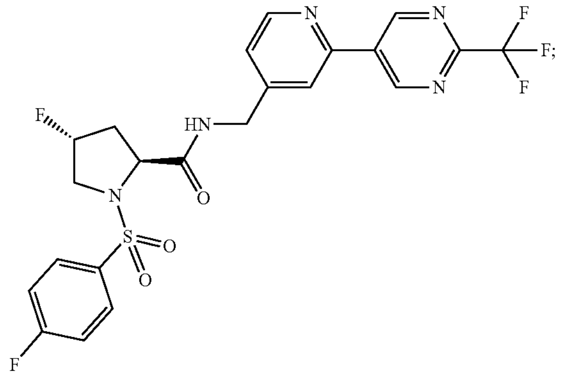
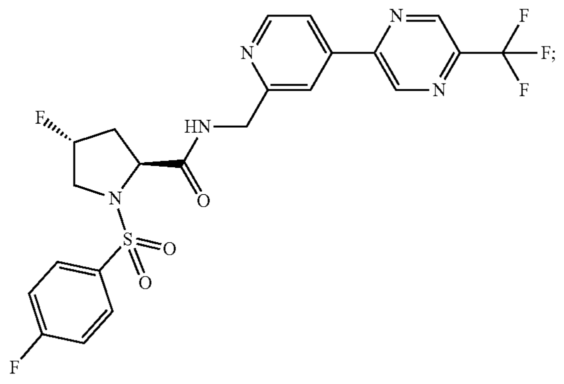
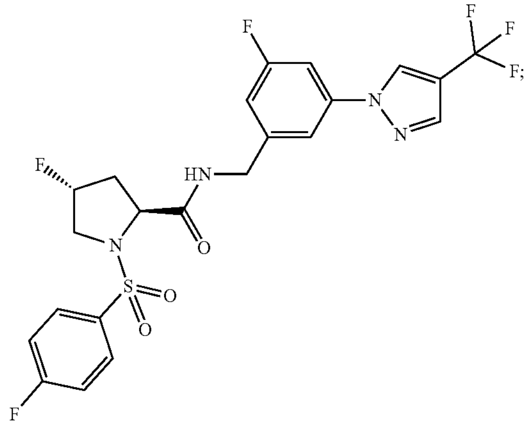

-continued
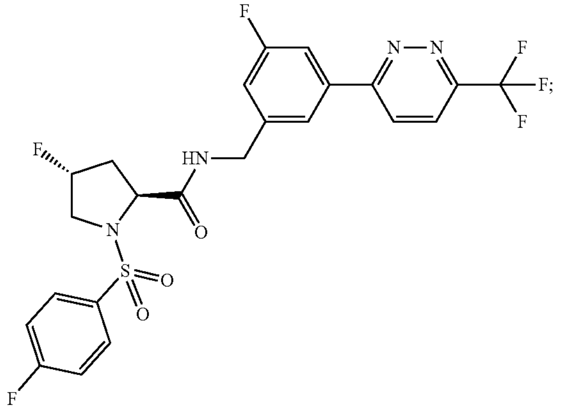
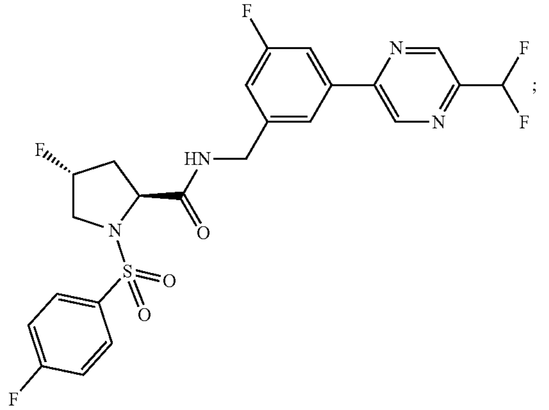
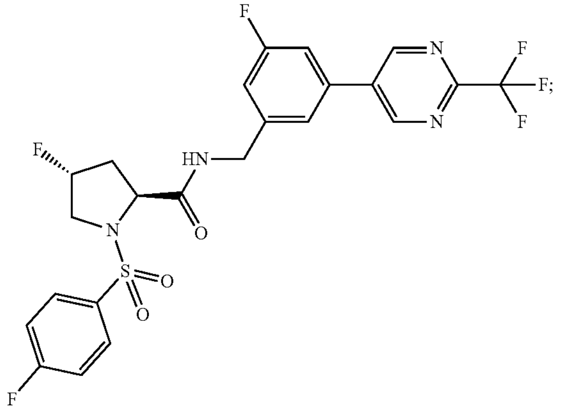
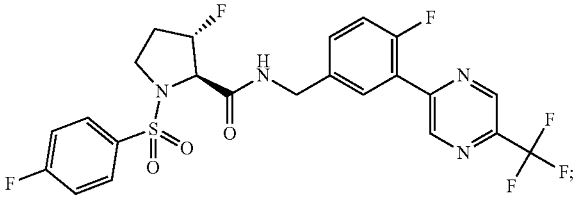
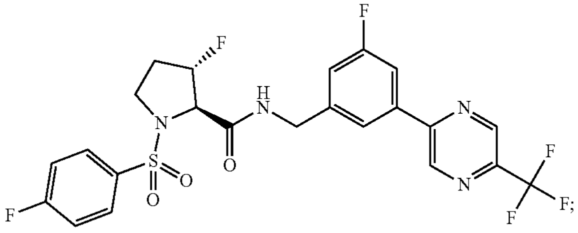
-continued
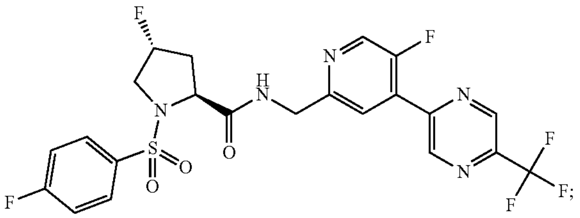
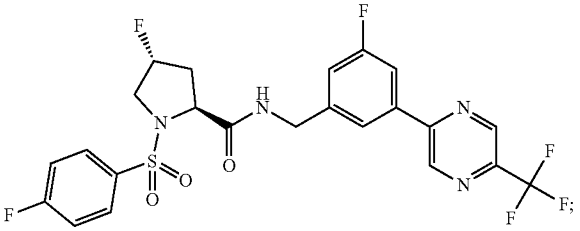
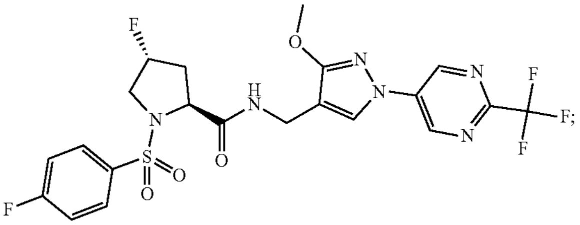
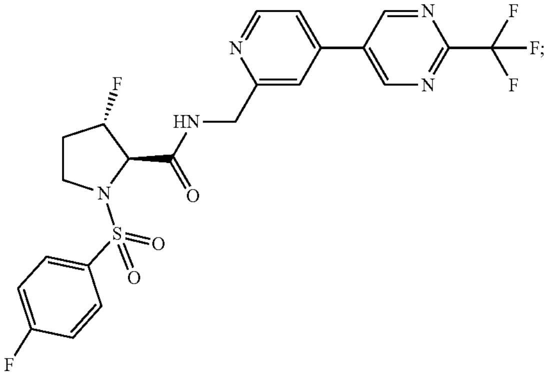
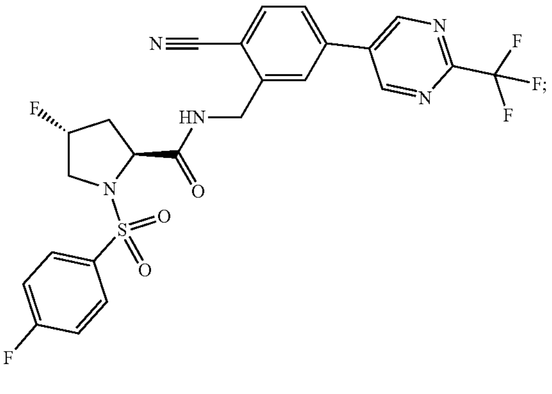
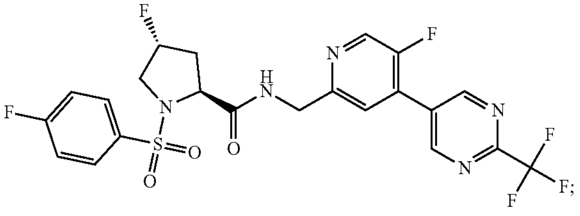

-continued
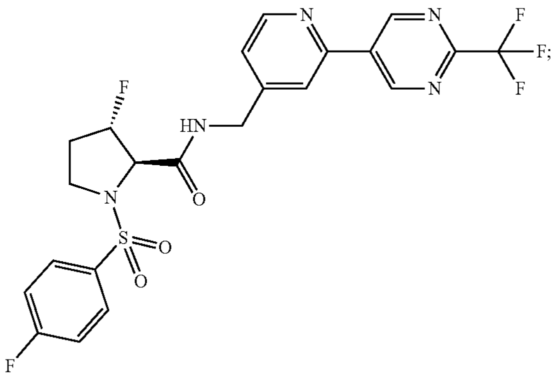
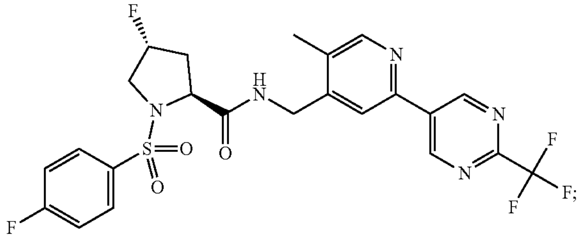
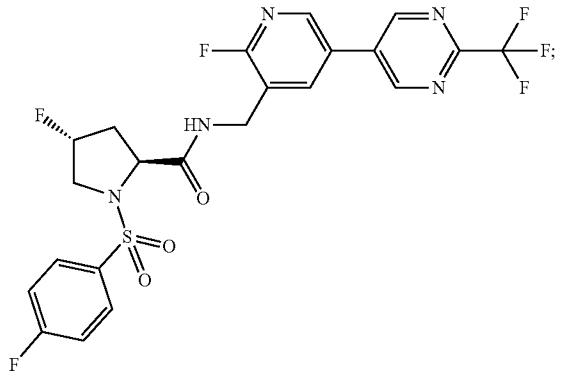
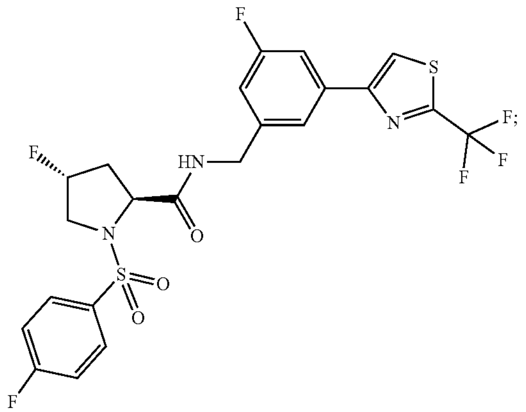
-continued
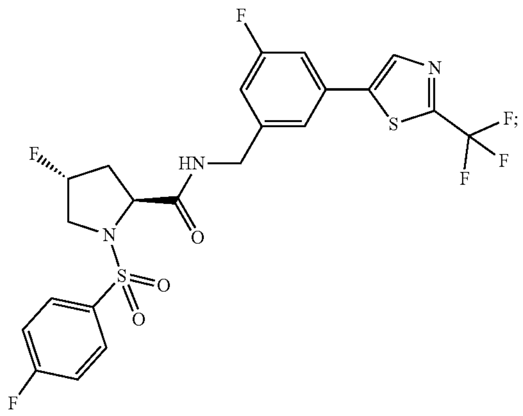
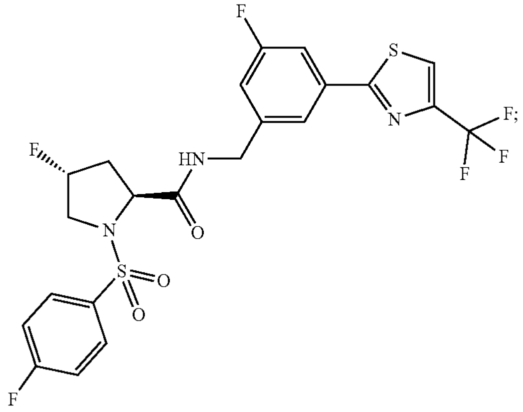
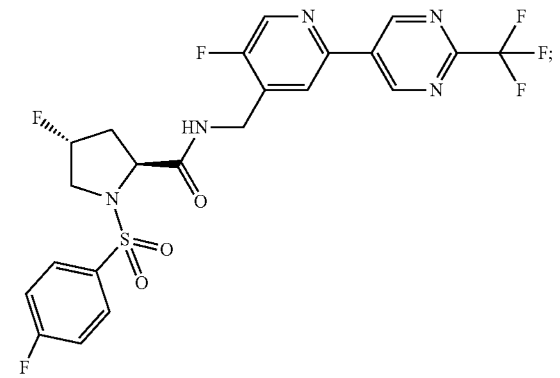
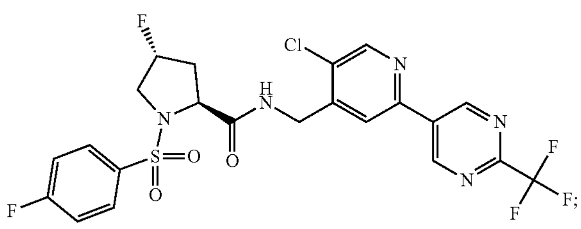

-continued
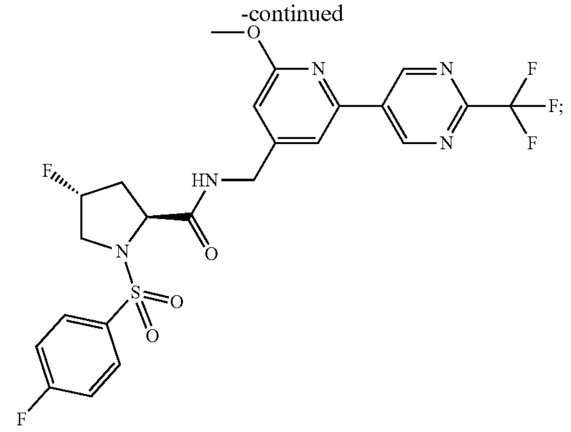
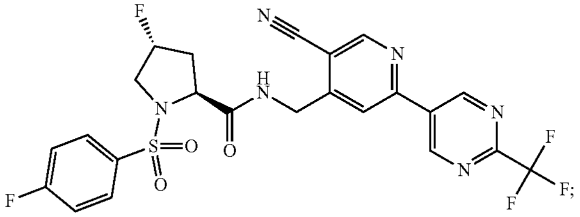
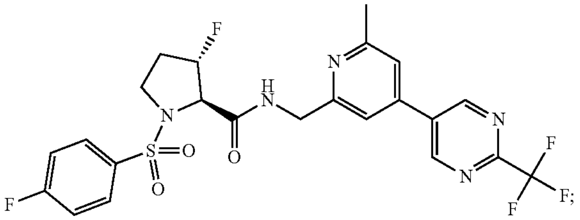
-continued
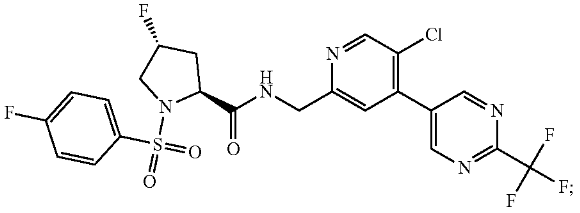
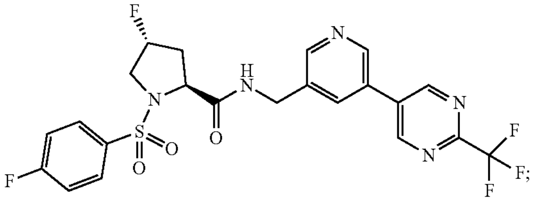
and
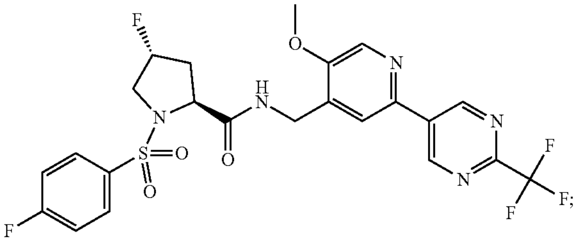
or a pharmaceutically acceptable salt thereof.
* * * * *